(12) United States Patent      (10) Patent No.: US 9,650,642 B2
Woods et al.      (45) Date of Patent: May 16, 2017

(54) GENETICALLY MODIFIED CYANOBACTERIA FOR THE PRODUCTION OF ETHANOL

(75) Inventors: R. Paul Woods, Naples, FL (US); Craig R. Smith, Naples, FL (US); Dan Kramer, Berlin (DE); Heike Enke, Berlin (DE); Ulf Duhring, Fredersdorf (DE); Kerstin Baier, Kleinmachnow (DE); Marianne Grundel, Berlin (DE); Wolfgang Lockau, Berlin (DE); Karl Ziegler, Zeuthen (DE); Christine Oesterhelt, Berlin (DE); John Coleman, Toronto (CA)

(73) Assignee: Algenol Biotech LLC, Fort Myers, FL (US)

( * ) Notice: Subject to any disclaimer, the term of this patent is extended or adjusted under 35 U.S.C. 154(b) by 2248 days.

(21) Appl. No.: 12/368,060

(22) Filed: Feb. 9, 2009

(65) Prior Publication Data

US 2010/0068776 A1    Mar. 18, 2010

Related U.S. Application Data

(60) Provisional application No. 61/065,292, filed on Feb. 8, 2008.

(51) Int. Cl.
| | |
|---|---|
| *C12P 7/06* | (2006.01) |
| *C12N 1/21* | (2006.01) |
| *C12N 15/82* | (2006.01) |
| *C12N 15/74* | (2006.01) |

(52) U.S. Cl.
CPC ......... *C12N 15/8243* (2013.01); *C12N 15/74* (2013.01); *C12P 7/065* (2013.01); *Y02E 50/17* (2013.01)

(58) Field of Classification Search
USPC ............ 435/252.3, 161, 69.1, 440, 183, 232
See application file for complete search history.

(56) References Cited

U.S. PATENT DOCUMENTS

| | | |
|---|---|---|
| 5,000,000 A | 3/1991 | Ingram et al. |
| 5,270,175 A | 12/1993 | Moll |
| 6,306,639 B1 | 10/2001 | Woods et al. |
| 6,699,696 B2 | 3/2004 | Woods et al. |
| 7,314,974 B2 | 1/2008 | Cao et al. |
| 8,163,516 B2 | 4/2012 | Dehring et al. |
| 2009/0155871 A1 | 6/2009 | Fu et al. |
| 2009/0203070 A1 | 8/2009 | Devroe et al. |
| 2010/0003739 A1 | 1/2010 | Duhring et al. |
| 2010/0068776 A1 | 3/2010 | Woods et al. |
| 2010/0297736 A1 | 11/2010 | Duhring et al. |
| 2011/0008861 A1 | 1/2011 | Berry et al. |
| 2012/0142066 A1 | 6/2012 | Baier et al. |

FOREIGN PATENT DOCUMENTS

| | | |
|---|---|---|
| EP | 1854889 | 11/2007 |
| WO | 9839457 | 9/1998 |
| WO | 2009/062190 | 5/2009 |
| WO | 2009078712 | 6/2009 |
| WO | 2009/098089 | 8/2009 |
| WO | 2011/018116 | 2/2011 |

OTHER PUBLICATIONS

Branden et al., Introduction to Protein Structure, Garland Publishing Inc., New York, p. 247, 1991.*
Witkowski et al., Biochemistry 38:11643-11650, 1999.*
Seffernick et al., J. Bacteriol. 183(8):2405-2410, 2001.*
Wahlund et al., Am. Chem. Soc. Div. Fuel Chem. 41:1403-1406, 1996.*
Spreitzer et al., Annu. Rev. Plant Biol. 53:449-475, 2002.*
Amichay et al., Plant Molecular Biology 23:465-476, 1993.*
Onizuka et al., Plant Cell Physiology 45(10):1390-1395, 2004.*
Duhring et al., PNAS 103(18):7054-7058, 2006.*
Kaneko et al., GenBank accession No. BA000022, May 20, 2006.*
Deng et al., Ethanol Synthesis by Genetic Engineering in Cyanobacteria, Feb. 1999, 523-528, vol. 65 No. 2, Applied and Environmental Microbiology.
Juntarajumnong et al., Two-component Signal Transduction in *Synechocystis* sp. PCC 6803 under Phosphate Limitation: Role of Acetyl Phosphate, Sep. 2007, pp. 708-714, vol. 40 No. 5, Journal of Biochemistry and Molecular Biology.
Kaneko et al., Sequence Analysis of the Genome of the Unicellular Cyanobacterium *Synechocystis* sp. Strain PCC 6803. II Sequence Determination of the Entire Genome and Assignment of Potential Protein-coding Regions, 1993, pp. 109-136, vol. 3, DNA Research.
International Search Report: International Publication No. WO 2009/098089 A3, Applicant/Inventors Baier et al.
Fu et al., "Genome-scale Modeling of *Synechocystis* sp. PCC 6803 and Prediction of Pathway Insertion," Journal of Chemical Technology & Biotechnology 84:473-483 (2009).
International Preliminary Report on Patentability and Written Opinion for PCT/EP2009/000892 dated Aug. 10, 2010.
Bowie et al., "Deciphering the Message in Protein Sequences: Tolerance to Amino Acid Substitution," Science 247:1306-1310 (1990).
Broun et al., "Catalytic Plasticity of Fatty Acid Modification Enzymes Underlying Chemical Diversity of Plant Lipids," Science 282:1315-1317 (1998).
Chica et al., "Semi-rational Approaches to Engineering Enzyme Activity: Combining the Benefits of Directed Evolution and Rational Design," Curr. Opin. Biotechnol. 16:378-384 (2005).
Devos et al., "Practical Limits of Function Prediction," Proteins: Structure, Function, and Genetics 41:98-107 (2000).
Dias et al., "Antisense Oligonucleotides: Basic Concepts and Mechanisms," Mol. Cancer Therap. 1:347-355 (2002).
Guo et al., "Protein Tolerance to Random Amino Acid Change," Proc. Nat. Acad. Sci. 101:9205-9210 (2004).
Kisselev, et al., "Polypeptide Release Factors in Prokaryotes and Eukaryotes: Same Function, Different Structure," Structure 10:8-9 (2002).

(Continued)

*Primary Examiner* — Delia Ramirez

(57) ABSTRACT

The invention provides novel compositions of matter for the production of ethanol from carbon dioxide and water. Particularly, the invention provides photoautotrophic organisms having a first and second genetic modification, wherein the first genetic modification improves the ethanol production from organisms having the second genetic modification.

12 Claims, 376 Drawing Sheets

(56) References Cited

OTHER PUBLICATIONS

Kurreck, et al., "Antisense Technologies," Eur. Jour. Biochem. 270:1628-1644 (2003).
Sen et al., "Developments in Directed Evolution for Improving Enzyme Functions," Appl. Biochem. Biotechnol. 143:212-223 (2007).
Whisstock et al., "Prediction of Protein Function from Protein Sequence," Q. Rev. Biophysics 36:307-340 (2003).
Wishart et al., "A Single Mutation Converts a Novel Phosphotyrosine Binding Domain into a Dual-specificity Phosphatase," Jour. Biol. Chem. 270:26782-26785 (1995).
Tous et al., "Conditional Expression of RNase P in the Cyanobacterium Synechocystis sp. PCC6803 Allows Detection of Precursor RNAs," Jour. Biol. Chem. 276:29059-29066 (2001).
Nakamura et al., "CyanoBase, the Genome Database for Synechocystis sp. Strain PCC6803: Status for the Year 2000," Nucleic Acids Research 28:72 (2000).
Gfeller et al.,"Fermentative Metabolism of Chlamydomonas reinhardtii," Plant Physiology 75:212-218 (1984).
Duran et al., "The Efficient Functioning of Photosynthesis and Respiration in Synechocystis sp. PCC 6803 Strictly Requires the Presence of either Cytochrome c6 or Plastocyanin," Journal of Biological Chemistry 279:7229-7233 (2004).
Singh et al., "The Heat Shock Response in the Cyanobacterium Synechocystis sp. Strain PCC 6803 and Regulation of Gene Expression by HrcA and SigB," Arch Microbiol. 186:273-286 (2006).
Imamura et al., "Antagonistic Dark/light-induced SigB/SigD, Group 2 Sigma Factors, Expression Through Redox Potential and their Roles in Cyanobacteria," FEBS Lett. 554:357-362 (2003).
Imamura et al., "Growth Phase-dependent Activation of Nitrogen-related Genes by a Control Network of Group 1 and Group 2 Sigma Factors in a Cyanobacterium," Jour. Biol. Chem. 281:2668-2675 (2006).
Samartzidou et al., "Transcriptional and Posttranscriptional Control of mRNA from IrtA, a Light-repressed Transcript in Synechococcus sp. PCC 7002," Plant Physiol. 117:225-234 (1998).
Agrawal et al., "Light-dependent and Rhythmic psbA Transcripts in Homologous/heterologous Cyanobacterial Cells," Biochem. Biophys. Res. Commun. 255:47-53 (1999).
Mohamed et al., "Influence of Light on Accumulation of Photosynthesis-specific Transcripts in the Cyanobacterium Synechocystis 6803," Plant Mol. Biol. 13:693-700 (1989).
Herranen et al., "Regulation of Photosystem I Reaction Center Genes in Synechocystis sp. Strain PCC 6803 During Light Acclimation," Plant Cell Physiol. 46:1484-1493 (2005).
Muramatsu et al., "Characterization of High-light-responsive Promoters of the psaAB Genes in Synechocystis sp. PCC 6803," Plant Cell Physiol. 47:878-890 (2006).

Marin et al., "Gene Expression Profiling Reflects Physiological Processes in Salt Acclimation of Synechocystis sp. strain PCC 6803," Plant Physiol. 136:3290-3300 (2004).
Marin et al., "Salt-dependent Expression of Glucosylglycerol-phosphate Synthase, Involved in Osmolyte Synthesis in the Cyanobacterium Synechocystis sp. Strain PCC 6803," Jour. Bacteriol. 184:2870-2877 (2002).
Qi et al., "Application of the Synechococcus nirA Promoter to Establish an Inducible Expression System for Engineering the Synechocystis Tocopherol Pathway," Appl. Environ. Microbiol. 71:5678-5684 (2005).
Maeda et al., "Cis-acting Sequences Required for NtcB-dependent, Nitrite-responsive Positive Regulation of the Nitrate Assimilation Operon in the Cyanobacterium Synechococcus sp. Strain PCC 7942," Jour. Bacteriol. 180:4080-4088 (1998).
Ghassemian et al., "Cloning, Sequencing and Transcriptional Studies of the Genes for Cytochrome c-553 and Plastocyanin from Anabaena sp. PCC 7120," Microbiology 140:1151-1159 (1994).
Buikema et al., "Expression of the Anabaena hetR gene from a Copper-regulated Promoter Leads to Heterocyst Differentiation under Repressing Conditions," Proc. Natl. Acad. Sci. U S A. 98:2729-2734 (2001).
Fang et al., "Expression of the Heat Shock Gene hsp16.6 and Promoter Analysis in the Cyanobacterium, Synechocystis sp. PCC 6803," Curr Microbiol. 49:192-198 (2004).
Suzuki et al., "The Heat Shock Response of Synechocystis sp. PCC 6803 Analyzed by Transcriptomics and Proteomics," Jour. Exp. Bot 57:1573-1578 (2006).
He et al., "The High Light-inducible Polypeptides in Synechocystis PCC6803. Expression and Function in High Light," Jour. Biol. Chem. 276:306-314 (2001).
Kappell et al., "The Response Regulator RpaB Binds the High Light Regulatory 1 Sequence Upstream of the High-light-inducible hliB Gene from the Cyanobacterium Synechocystis PCC 6803," Arch. Microbiol. 187:337-342 (2007).
Mary et al., "Effects of High Light on Transcripts of Stress-associated Genes for the Cyanobacteria Synechocystis sp. PCC 6803 and Prochlorococcus MED4 and MIT9313," Microbiology 150:1271-1281 (2004).
International Preliminary Report and Written Opinion for PCT/EP2009/060526 dated Feb. 14, 2012.
Van der Oost et al., "Fermentation Metabolism of the Unicellular/Cyanobacterium Cyanothece PCC 7822," Archives of Microbiology 152:415-419 (1989).
Beutler et al., "Two and One Carbon Compounds: Ethanol" in: Methods of Enzymatic Analysis (Bergmeyer, H.U. ed.) 3rd ed. vol. 6:598-606, Verlag Chemie, Weinheim, Germany (1984).
Häusler et al., "Determination of Low-abundant Metabolites in Plant Extracts by NAD(P)H Fluorescence with a Microtiter Plate Reader," Anal. Biochem. 281:1-8 (2000).
Iwaki et al., "Expression of Foreign Type I Ribulose-1,5-bisphosphate Carboxylase/oxygenase (EC 4.1.1.39) Stimulates Photosynthesis in Cyanobacterium Synechocystis PCC7942 cells," Photosynthesis Research 88:287-297 (2006).

* cited by examiner

MKILFVAAEVSPLAKVGGMGDVVGSLPKVLHQLGHDVRVFMPYYGFIGDKIDVPKEPVWK
GEAMFQQFAVYQSYLPDTKIPLYLFGHPAFDSRRIYGGDDEAWRFTFFSNGAAEFAWNHW
KPEIIHCHDWHTGMIPVWMHQSPDIATVFTIHNLAYQGPWRGLLETMTWCPWYMQGDNVM
AAAIQFANRVTTVSPTYAQQIQTPAYGEKLEGLLSYLSGNLVGILNGIDTEIYNPAEDRF
ISNVFDADSLDKRVKNKIAIQEETGLEINRNAMVVGIVARLVEQKGIDLVIQILDRFMSY
TDSQLIILGTGDRHYETQLWQMASRFPGRMAVQLLHNDALSRRVYAGADVFLMPSRFEPC
GLSQLMAMRYGCIPIVRRTGGLVDTVSFYDPINEAGTGYCFDRYEPLDCFTAMVRAWEGF
RFKADWQKLQQRAMRADFSWYRSAGEYIKVYKGVVGKPEELSPMEEEKIAELTASYR
(SEQ ID NO:1)

Figure 4A

MYIVQIASECAPVIKAGGLGDVIYGLSRELELRGHCVELILPMYDCMRYDHIWGLHDAYR

NLEVPWYGSSIFCDVFCGWVHGRLCFFIQPKSSDNFFNRGHYYGALDDHMRFAFFSKAAM

EFLLRSNKRPDIIHCHDWQTGLVPVLLYEIYRFHGMDHQRVCYTIHNFKHQGIAGANILH

ATGLNNDSYYFSYDRLQDNFNPNAINFMKGGIVYSNYVNTVSPHHAWEARFSDISCGLGH

TLEIHQQKFGGILNGLDYEVWNPEIDPLLASNFSVKTFGDKAKNKQALRERLLLETDDKK

PMLCFIGRLDGQKGVHLVHHSIYYALSQGAQFVLLGSATEPNLSKWFWHEKQHLNDNPNV

HLELGFDEELAHLIYGAADIIVVPSNYEPCGLTQMIGLRYGAVPVVRGVGGLVNTVFDRD

YDQNHPPEKRNGFVFYQPDEYALETALSRAIALYKDDPVAFKTLALQGMAYDYSWNKPGL

QYVEAYEYIRA (SEQ ID NO:2)

Figure 4B

```
   1 TCGCGCGTTT CGGTGATGAC GGTGAAAACC TCTGACACAT GCAGCTCCCG
  51 GAGACGGTCA CAGCTTGTCT GTAAGCGGAT GCCGGGAGCA GACAAGCCCG
 101 TCAGGGCGCG TCAGCGGGTG TTGGCGGGTG TCGGGGCTGG CTTAACTATG
 151 CGGCATCAGA GCAGATTGTA CTGAGAGTGC ACCATATGCG GTGTGAAATA
 201 CCGCACAGAT GCGTAAGGAG AAAATACCGC ATCAGGCGCC ATTCGCCATT
 251 CAGGCTGCGC AACTGTTGGG AAGGGCGATC GGTGCGGGCC TCTTCGCTAT
 301 TACGCCAGCT GGCGAAAGGG GGATGTGCTG CAAGGCGATT AAGTTGGGTA
 351 ACGCCAGGGT TTTCCCAGTC ACGACGTTGT AAAACGACGG CCAGTGAATT
 401 CGAGCTCGGT ACCAACTAAA GTCTGCCCGC ATGGCCCGTT GCTGTAATTT
 451 TTGCCAATCT GCCTTGAAAC GGAAACCCTC CCAGGCCCGC ACCATGGCCG
 501 TAAAGCAATC CAGGGGTTCA TAACGGTCAA AGCAATAGCC GGTGCCGGCT
 551 TCATTGATAG GATCGTAGAA GGATACCGTA TCCACCAAAC CCCCTGTCCG
 601 CCGCACAATG GGGATACAGC CATAACGCAT GGCCATCAAT TGACTCAGCC
 651 CACAGGGCTC AAAGCGAGAA GGCATTAAAA ACACATCCGC CCCGGCATAG
 701 ACTCGACGGG AAAGGGCATC GTTGTGGAGT AATTGCACCG CCATCCGCCC
 751 AGGAAATCGG GAAGCCATCT GCCAAAGTTG GGTTTCGTAA TGGCGATCGC
 801 CAGTGCCGAG GATAATTAAC TGGGAATCGG TGTAGGACAT GAAGCGGTCA
 851 AGGATCTGAA TCACCAAATC AATCCCCTTT TGTTCCACCA AGCGAGCCAC
 901 TATACCCACG TAAGAGGTTC CAACTTTCAC CATAATGAAA TAAGATCACT
 951 ACCGGGCGTA TTTTTTGAGT TATCGAGATT TTCAGGAGCT AAGGAAGCTA
1001 AAATGGAGAA AAAAATCACT GGATATACCA CCGTTGATAT ATCCCAATGG
1051 CATCGTAAAG AACATTTTGA GGCATTTCAG TCAGTTGCTC AATGTACCTA
1101 TAACCAGACC GTTCAGCTGG ATATTACGGC CTTTTTAAAG ACCGTAAAGA
1151 AAAATAAGCA CAAGTTTTAT CCGGCCTTTA TTCACATTCT TGCCCGCCTG
1201 ATGAATGCTC ATCCGGAATT CCGTATGGCA ATGAAAGACG GTGAGCTGGT
1251 GATATGGGAT AGTGTTCACC CTTGTTACAC CGTTTTCCAT GAGCAAACTG
1301 AAACGTTTTC ATCGCTCTGG AGTGAATACC ACGACGATTT CCGGCAGTTT
1351 CTACACATAT ATTCGCAAGA TGTGGCGTGT TACGGTGAAA ACCTGGCCTA
1401 TTTCCCTAAA GGGTTTATTG AGAATATGTT TTTCGTCTCA GCCAATCCCT
1451 GGGTGAGTTT CACCAGTTTT GATTTAAACG TGGCCAATAT GGACAACTTC
1501 TTCGCCCCCG TTTTCACCAT GGGCAAATAT TATACGCAAG GCGACAAGGT
1551 GCTGATGCCG CTGGCGATTC AGGTTCATCA TGCCGTCTGT GATGGCTTCC
1601 ATGTCGGCAG AATGCTTAAT GAATTACAAC AGTACTGCGA TGAGTGGCAG
1651 GGCGGGGCGT AATTTTTTTA AGGCAGTTAT TGGTGCCCTT AAACGCCTGG
```

Figure 4E(1)

```
1701 TGCTACGCCT GAATAAGTGA TAATAAGCGG ATGAATGGCA GAAATTCGAA
1751 AGCAAATTCG ACCCGGTCGT CGGTTCAGGG CAGGGTCGTT AAATAGCCGC
1801 TTATGTCTAT TGCTGGTTTA CCGGTTTATT GACTACCGGA AGCAGTGTGA
1851 CCGTGTGCTT CTCAAATGCC TGAGGCCAGT TTGCTCAGGC TCTCCCCGTG
1901 GAGGTAATAA TTGACGATAT GATCATTTAT TCTGCCTCCC AGAGCCTGAT
1951 AAAAACGGTT AGCGCTTCGT TAATACAGAT GTAGGTGTTC CACAGGGTAG
2001 CCAGCAGCAT CCTGCGATGC ATGGCATTAC GATTAATTTC TAACCCCGTT
2051 TCCTCCTGGA TGGCAATTTT ATTTTTCACC CGCTTGTCCA AACTGTCCGC
2101 ATCGAAAACA TTGCTGATAA AGCGGTCTTC CGCCGGGTTG TAAATCTCCG
2151 TATCAATACC GTTGAGAATA CCGACTAAAT TACCACTCAG GTAGGACAAT
2201 AACCCTTCCA GCTTTTCCCC ATAGGCCGGG GTTTGGATCT GTTGGGCATA
2251 GGTGGGAGAA ACGGTAGTCA CCCGATTGGC AAATTGAATC GCCGCCGCCA
2301 TCACATTGTC TCCCTGCATG TACCAAGGAC ACCAAGTCAT AGTTTCAAGC
2351 AAGCCCCGCC AGGGCCCTTG GTAAGCAAGA TTATGGATGG TGAAAACGGT
2401 GGCGATGTCT GGGGACTGAT GCATCCAAAC AGGGATCATG CCAGTGTGCC
2451 AATCATGGCA ATGGATAATT TCCGGCTTCC AATGGTTCCA GGCAAATTCA
2501 GCTGCCCCGT TAGAAAAAAA AGTGAACCGC CACGCCTCGT CATCTCCGCC
2551 ATAGATCCTT CGGGAGTCGA AAGCTGGATG GCCGAACAAG TAGAGAGGAA
2601 TTTTGGTGTC CGGTAGATAG GACTGGTAAA CAGCAAACTG CTGGAACATG
2651 GCTTCCCCTT TCCAGACCGG CTCCTTGGGC ACATCAATCT TGTCGCCGAT
2701 GAAACCGTAG TAGGGCATGA AGACACGGAC ATCATGGCCC AACTGATGCA
2751 GAACTTTAGG CAGGGAACCC ACCACATCCC CCATGCCACC TACCTTTGCT
2801 AGGGGGGATA CTTCCGCCGC CACAAATAAA AGCTTGGCGT AATCATGGTC
2851 ATAGCTGTTT CCTGTGTGAA ATTGTTATCC GCTCACAATT CCACACAACA
2901 TACGAGCCGG AAGCATAAAG TGTAAAGCCT GGGGTGCCTA ATGAGTGAGC
2951 TAACTCACAT TAATTGCGTT GCGCTCACTG CCCGCTTTCC AGTCGGGAAA
3001 CCTGTCGTGC CAGCTGCATT AATGAATCGG CCAACGCGCG GGGAGAGGCG
3051 GTTTGCGTAT TGGGCGCTCT TCCGCTTCCT CGCTCACTGA CTCGCTGCGC
3101 TCGGTCGTTC GGCTGCGGCG AGCGGTATCA GCTCACTCAA AGGCGGTAAT
3151 ACGGTTATCC ACAGAATCAG GGGATAACGC AGGAAAGAAC ATGTGAGCAA
3201 AAGGCCAGCA AAAGGCCAGG AACCGTAAAA AGGCCGCGTT GCTGGCGTTT
3251 TTCCATAGGC TCCGCCCCCC TGACGAGCAT CACAAAAATC GACGCTCAAG
3301 TCAGAGGTGG CGAAACCCGA CAGGACTATA AAGATACCAG GCGTTTCCCC
3351 CTGGAAGCTC CCTCGTGCGC TCTCCTGTTC CGACCCTGCC GCTTACCGGA
3401 TACCTGTCCG CCTTTCTCCC TTCGGGAAGC GTGGCGCTTT CTCATAGCTC
3451 ACGCTGTAGG TATCTCAGTT CGGTGTAGGT CGTTCGCTCC AAGCTGGGCT
3501 GTGTGCACGA ACCCCCCGTT CAGCCCGACC GCTGCGCCTT ATCCGGTAAC
```

Figure 4E(2)

```
3551 TATCGTCTTG AGTCCAACCC GGTAAGACAC GACTTATCGC CACTGGCAGC
3601 AGCCACTGGT AACAGGATTA GCAGAGCGAG GTATGTAGGC GGTGCTACAG
3651 AGTTCTTGAA GTGGTGGCCT AACTACGGCT ACACTAGAAG GACAGTATTT
3701 GGTATCTGCG CTCTGCTGAA GCCAGTTACC TTCGGAAAAA GAGTTGGTAG
3751 CTCTTGATCC GGCAAACAAA CCACCGCTGG TAGCGGTGGT TTTTTTGTTT
3801 GCAAGCAGCA GATTACGCGC AGAAAAAAAG GATCTCAAGA AGATCCTTTG
3851 ATCTTTTCTA CGGGGTCTGA CGCTCAGTGG AACGAAAACT CACGTTAAGG
3901 GATTTTGGTC ATGAGATTAT CAAAAAGGAT CTTCACCTAG ATCCTTTTAA
3951 ATTAAAAATG AAGTTTTAAA TCAATCTAAA GTATATATGA GTAAACTTGG
4001 TCTGACAGTT ACCAATGCTT AATCAGTGAG GCACCTATCT CAGCGATCTG
4051 TCTATTTCGT TCATCCATAG TTGCCTGACT CCCCGTCGTG TAGATAACTA
4101 CGATACGGGA GGGCTTACCA TCTGGCCCCA GTGCTGCAAT GATACCGCGA
4151 GACCCACGCT CACCGGCTCC AGATTTATCA GCAATAAACC AGCCAGCCGG
4201 AAGGGCCGAG CGCAGAAGTG GTCCTGCAAC TTTATCCGCC TCCATCCAGT
4251 CTATTAATTG TTGCCGGGAA GCTAGAGTAA GTAGTTCGCC AGTTAATAGT
4301 TTGCGCAACG TTGTTGCCAT TGCTACAGGC ATCGTGGTGT CACGCTCGTC
4351 GTTTGGTATG GCTTCATTCA GCTCCGGTTC CCAACGATCA AGGCGAGTTA
4401 CATGATCCCC CATGTTGTGC AAAAAAGCGG TTAGCTCCTT CGGTCCTCCG
4451 ATCGTTGTCA GAAGTAAGTT GGCCGCAGTG TTATCACTCA TGGTTATGGC
4501 AGCACTGCAT AATTCTCTTA CTGTCATGCC ATCCGTAAGA TGCTTTTCTG
4551 TGACTGGTGA GTACTCAACC AAGTCATTCT GAGAATAGTG TATGCGGCGA
4601 CCGAGTTGCT CTTGCCCGGC GTCAATACGG GATAATACCG CGCCACATAG
4651 CAGAACTTTA AAAGTGCTCA TCATTGGAAA ACGTTCTTCG GGGCGAAAAC
4701 TCTCAAGGAT CTTACCGCTG TTGAGATCCA GTTCGATGTA ACCCACTCGT
4751 GCACCCAACT GATCTTCAGC ATCTTTTACT TTCACCAGCG TTTCTGGGTG
4801 AGCAAAAACA GGAAGGCAAA ATGCCGCAAA AAAGGGAATA AGGGCGACAC
4851 GGAAATGTTG AATACTCATA CTCTTCCTTT TTCAATATTA TTGAAGCATT
4901 TATCAGGGTT ATTGTCTCAT GAGCGGATAC ATATTTGAAT GTATTTAGAA
4951 AAATAAACAA ATAGGGGTTC CGCGCACATT TCCCCGAAAA GTGCCACCTG
5001 ACGTCTAAGA AACCATTATT ATCATGACAT TAACCTATAA AAATAGGCGT
5051 ATCACGAGGC CCTTTCGTC (SEQ ID NO:3)
```

Figure 4E(3)

```
   1 TCGCGCGTTT CGGTGATGAC GGTGAAAACC TCTGACACAT GCAGCTCCCG
  51 GAGACGGTCA CAGCTTGTCT GTAAGCGGAT GCCGGGAGCA GACAAGCCCG
 101 TCAGGGCGCG TCAGCGGGTG TTGGCGGGTG TCGGGCTGG  CTTAACTATG
 151 CGGCATCAGA GCAGATTGTA CTGAGAGTGC ACCATATGCG GTGTGAAATA
 201 CCGCACAGAT GCGTAAGGAG AAAATACCGC ATCAGGCGCC ATTCGCCATT
 251 CAGGCTGCGC AACTGTTGGG AAGGGCGATC GGTGCGGGCC TCTTCGCTAT
 301 TACGCCAGCT GGCGAAAGGG GGATGTGCTG CAAGGCGATT AAGTTGGGTA
 351 ACGCCAGGGT TTTCCCAGTC ACGACGTTGT AAAACGACGG CCAGTGAATT
 401 CTCCTCCAGT GCTTGCAAGG GAGGGGCAAT ATAGGAAAAT ACAATCAACT
 451 CGATCGCCGT CGAGCCGAAG TCGAGTAAAA ACCGCTATCA GGAGCCTCTA
 501 TGTACATCGT TCAAATTGCC TCAGAATGCG CCCCCGTCAT TAAGGCTGGG
 551 GGATTGGGGG ATGTTATTTA CGGCCTAAGC CGTGAATTGG AACTGCGGGG
 601 CCATTGCGTC GAGCTAATCC TACCCATGTA CGATTGCATG CGCTATGACC
 651 ACATCTGGGG TTTACACGAT GCTTACCGCA ACCTAGAGGT GCCCTGGTAT
 701 GGAAGCTCAA TCTTCTGTGA TGTTTTTTGT GGCTGGGTTC ACGGTAGGCT
 751 CTGCTTCTTC ATTCAGCCCA AATCTTCTGA TAACTTTTTC AATCGGGGTC
 801 ATTATTATGG CGCTCTAGAC GACCATATGC GCTTTGCCTT TTTCTCCAAG
 851 GCGGCCATGG AGTTTTTGCT ACGCAGTAAC AAACGCCCAG ACATTATCCA
 901 CTGCCACGAT TGGCAAACGG GACTGGTGCC GGTGTTGTTG TATGAAATTT
 951 ACCGTTTCCA TGGCATGGAC CATCAACGGG TTTGTTACAC CATCCACAAT
1001 TTCAAACACC AGGGTATTGC TGGAGCCAAT ATTCTCCACG CCACTGGGCT
1051 CAATAATGAC AGTTATTATT TCAGCTACGA TCGCCTGCAG GATAATTTCA
1101 ATCCCAATGC GATTAACTTC ATGAAGGGGG GCATTGTCGA CCTGCAGGGG
1151 GGGGGGGGAA AGCCACGTTG TGTCTCAAAA TCTCTGATGT TACATTGCAC
1201 AAGATAAAAA TATATCATCA TGAACAATAA AACTGTCTGC TTACATAAAC
1251 AGTAATACAA GGGGTGTTAT GAGCCATATT CAACGGGAAA CGTCTTGCTC
1301 GAGGCCGCGA TTAAATTCCA ACATGGATGC TGATTTATAT GGGTATAAAT
1351 GGGCTCGCGA TAATGTCGGG CAATCAGGTG CGACAATCTA TCGATTGTAT
1401 GGGAAGCCCG ATGCGCCAGA GTTGTTTCTG AAACATGGCA AAGGTAGCGT
1451 TGCCAATGAT GTTACAGATG AGATGGTCAG ACTAAACTGG CTGACGGAAT
1501 TTATGCCTCT TCCGACCATC AAGCATTTTA TCCGTACTCC TGATGATGCA
1551 TGGTTACTCA CCACTGCGAT CCCCGGGAAA ACAGCATTCC AGGTATTAGA
1601 AGAATATCCT GATTCAGGTG AAAATATTGT TGATGCGCTG GCAGTGTTCC
1651 TGCGCCGGTT GCATTCGATT CCTGTTTGTA ATTGTCCTTT TAACAGCGAT
```

Figure 4H(1)

```
1701 CGCGTATTTC GTCTCGCTCA GGCGCAATCA CGAATGAATA ACGGTTTGGT
1751 TGATGCGAGT GATTTTGATG ACGAGCGTAA TGGCTGGCCT GTTGAACAAG
1801 TCTGGAAAGA AATGCATAAG CTTTTGCCAT TCTCACCGGA TTCAGTCGTC
1851 ACTCATGGTG ATTTCTCACT TGATAACCTT ATTTTTGACG AGGGGAAATT
1901 AATAGGTTGT ATTGATGTTG GACGAGTCGG AATCGCAGAC CGATACCAGG
1951 ATCTTGCCAT CCTATGGAAC TGCCTCGGTG AGTTTTCTCC TTCATTACAG
2001 AAACGGCTTT TTCAAAAATA TGGTATTGAT AATCCTGATA TGAATAAATT
2051 GCAGTTTCAT TTGATGCTCG ATGAGTTTTT CTAATCAGAA TTGGTTAATT
2101 GGTTGTAACA CTGGCAGAGC ATTACGCTGA CTTGACGGGA CGGCGGCTTT
2151 GTTGAATAAA TCGAACTTTT GCTGAGTTGA AGGATCAGAT CACGCATCTT
2201 CCCGACAACG CAGACCGTTC CGTGGCAAAG CAAAAGTTCA AAATCACCAA
2251 CTGGTCCACC TACAACAAAG CTCTCATCAA CCGTGGCTCC CTCACTTTCT
2301 GGCTGGATGA TGGGGCGATT CAGGCCTGGT ATGAGTCAGC AACACCTTCT
2351 TCACGAGGCA GACCTCAGCG CCCCCCCCCC CCTGCAGGTC TACTCCAACT
2401 ATGTCAACAC CGTTTCCCCC CACCATGCTT GGGAAGCCCG TTTTTCCGAT
2451 ATTTCCTGTG GCTTGGGCCA TACCCTGGAA ATCCATCAGC AAAAATTCGG
2501 CGGTATTTTG AACGGTTTGG ATTACGAAGT GTGGAACCCA GAAATTGATC
2551 CTTTACTGGC GAGTAACTTC AGTGTCAAAA CCTTTGGCGA TAAGGCAAAA
2601 AATAAGCAAG CGTTACGGGA AAGATTACTG TTAGAAACGG ATGATAAAAA
2651 ACCCATGCTC TGCTTTATTG GCCGCTTGGA TGGACAAAAA GGTGTGCACT
2701 TGGTGCATCA CTCCATCTAC TACGCCCTCA GCCAGGGAGC GCAATTTGTC
2751 CTGCTCGGCT CCGCCACCGA ACCCAATCTG AGCAAATGGT TCTGGCATGA
2801 AAAACAACAT CTCAACGATA ACCCCAATGT CCATCTAGAG TTGGGCTTTG
2851 ACGAGGAGCT GGCCCACTTA ATTTACGGAG CGGCGGACAT TATTGTGGTG
2901 CCCAGTAACT ACGAACCCTG TGGTTTGACC CAAATGATTG GTCTGCGTTA
2951 TGGGGCCGTT CCGGTGGTGC GGGGAGTAGG CGGTTTGGTA AATACTGTTT
3001 TCGACCGGGA TTATGACCAG AACCATCCCC CGGAGAAACG TAATGGTTTT
3051 GTTTTCTATC AACCGGATGA GTATGCCCTG GAAACGGCCC TCAGTCGGGC
3101 GATCGCCTTG TATAAGGATG ATCCCGTGGC TTTTAAAACC TTGGCCTTGC
3151 AGGGCATGGC CTACGACTAC TCTTGGAATA AACCAGGGCT CCAATATGTG
3201 GAAGCCTACG AATACATCCG GGCTTAACAC CTCGGGTTTG TAACAGTTTC
3251 GTTACACTAG TTCAGAGGCG GAGTCAAAGC AGTTGGTCAG AATAAGCTTG
3301 GCGTAATCAT GGTCATAGCT GTTTCCTGTG TGAAATTGTT ATCCGCTCAC
3351 AATTCCACAC AACATACGAG CCGGAAGCAT AAAGTGTAAA GCCTGGGGTG
3401 CCTAATGAGT GAGCTAACTC ACATTAATTG CGTTGCGCTC ACTGCCCGCT
3451 TTCCAGTCGG GAAACCTGTC GTGCCAGCTG CATTAATGAA TCGGCCAACG
```

Figure 4H(2)

```
3501 CGCGGGGAGA GGCGGTTTGC GTATTGGGCG CTCTTCCGCT TCCTCGCTCA
3551 CTGACTCGCT GCGCTCGGTC GTTCGGCTGC GGCGAGCGGT ATCAGCTCAC
3601 TCAAAGGCGG TAATACGGTT ATCCACAGAA TCAGGGGATA ACGCAGGAAA
3651 GAACATGTGA GCAAAAGGCC AGCAAAAGGC CAGGAACCGT AAAAAGGCCG
3701 CGTTGCTGGC GTTTTTCCAT AGGCTCCGCC CCCCTGACGA GCATCACAAA
3751 AATCGACGCT CAAGTCAGAG GTGGCGAAAC CCGACAGGAC TATAAAGATA
3801 CCAGGCGTTT CCCCCTGGAA GCTCCCTCGT GCGCTCTCCT GTTCCGACCC
3851 TGCCGCTTAC CGGATACCTG TCCGCCTTTC TCCCTTCGGG AAGCGTGGCG
3901 CTTTCTCATA GCTCACGCTG TAGGTATCTC AGTTCGGTGT AGGTCGTTCG
3951 CTCCAAGCTG GGCTGTGTGC ACGAACCCCC CGTTCAGCCC GACCGCTGCG
4001 CCTTATCCGG TAACTATCGT CTTGAGTCCA ACCCGGTAAG ACACGACTTA
4051 TCGCCACTGG CAGCAGCCAC TGGTAACAGG ATTAGCAGAG CGAGGTATGT
4101 AGGCGGTGCT ACAGAGTTCT TGAAGTGGTG GCCTAACTAC GGCTACACTA
4151 GAAGGACAGT ATTTGGTATC TGCGCTCTGC TGAAGCCAGT TACCTTCGGA
4201 AAAAGAGTTG GTAGCTCTTG ATCCGGCAAA CAAACCACCG CTGGTAGCGG
4251 TGGTTTTTTT GTTTGCAAGC AGCAGATTAC GCGCAGAAAA AAAGGATCTC
4301 AAGAAGATCC TTTGATCTTT TCTACGGGGT CTGACGCTCA GTGGAACGAA
4351 AACTCACGTT AAGGGATTTT GGTCATGAGA TTATCAAAAA GGATCTTCAC
4401 CTAGATCCTT TTAAATTAAA AATGAAGTTT TAAATCAATC TAAAGTATAT
4451 ATGAGTAAAC TTGGTCTGAC AGTTACCAAT GCTTAATCAG TGAGGCACCT
4501 ATCTCAGCGA TCTGTCTATT TCGTTCATCC ATAGTTGCCT GACTCCCCGT
4551 CGTGTAGATA ACTACGATAC GGGAGGGCTT ACCATCTGGC CCCAGTGCTG
4601 CAATGATACC GCGAGACCCA CGCTCACCGG CTCCAGATTT ATCAGCAATA
4651 AACCAGCCAG CCGGAAGGGC CGAGCGCAGA AGTGGTCCTG CAACTTTATC
4701 CGCCTCCATC CAGTCTATTA ATTGTTGCCG GGAAGCTAGA GTAAGTAGTT
4751 CGCCAGTTAA TAGTTTGCGC AACGTTGTTG CCATTGCTAC AGGCATCGTG
4801 GTGTCACGCT CGTCGTTTGG TATGGCTTCA TTCAGCTCCG GTTCCCAACG
4851 ATCAAGGCGA GTTACATGAT CCCCCATGTT GTGCAAAAAA GCGGTTAGCT
4901 CCTTCGGTCC TCCGATCGTT GTCAGAAGTA AGTTGGCCGC AGTGTTATCA
4951 CTCATGGTTA TGGCAGCACT GCATAATTCT CTTACTGTCA TGCCATCCGT
5001 AAGATGCTTT TCTGTGACTG GTGAGTACTC AACCAAGTCA TTCTGAGAAT
5051 AGTGTATGCG GCGACCGAGT TGCTCTTGCC CGGCGTCAAT ACGGGATAAT
5101 ACCGCGCCAC ATAGCAGAAC TTTAAAAGTG CTCATCATTG GAAAACGTTC
5151 TTCGGGGCGA AAACTCTCAA GGATCTTACC GCTGTTGAGA TCCAGTTCGA
5201 TGTAACCCAC TCGTGCACCC AACTGATCTT CAGCATCTTT TACTTTCACC
5251 AGCGTTTCTG GGTGAGCAAA AACAGGAAGG CAAAATGCCG CAAAAAAGGG
```

Figure 4H(3)

```
5301 AATAAGGGCG ACACGGAAAT GTTGAATACT CATACTCTTC CTTTTTCAAT
5351 ATTATTGAAG CATTTATCAG GGTTATTGTC TCATGAGCGG ATACATATTT
5401 GAATGTATTT AGAAAAATAA ACAAATAGGG GTTCCGCGCA CATTTCCCCG
5451 AAAAGTGCCA CCTGACGTCT AAGAAACCAT TATTATCATG ACATTAACCT
5501 ATAAAAATAG GCGTATCACG AGGCCCTTTC GTC (SEQ ID NO:4)
```

Figure 4H(4)

MEIGVPKEIKDQEFRVGLTPSSVRALLSQGHQVFVEEGAGVGSGFPDGAYAKAGAELVATA
KEAWNRELVVKVKEPLPEEYEYLTLPKLLFTYLHLAAERTLTEALIKSGITAIAYETVELA
DGQLPLLAPMSRIAGRLAVQMGAHYLEKQQGGRGVLLGGVPGVKAGQVTILGGGVVGTEAA
KMAIGLGAMVTILDINVDRLNQLGELFGSRVDLRYSNASQIEDLLPHTDLLIGAVLITGKR
APVLVSRQEVEQMLPGAVIMDVAIDQGGCVETLRVTSHSQPSYIEAEVVHVGIPNMPGATP
WTATQALNNSTLRYVLKLANLGEQAWENDLPLAKGVNVQAGKLVQGAVKTVFPDL (SEQ
ID NO:5)

Figure 5A

```
   1 GGGATTGGCT GACCCCCAGT AGTGTACGGG CATTGCTGAG CCAGGGCCAT
  51 CAAGTATTTG TGGAAGAAGG GGCCGGAGTC GGGTCTGGCT TCCCCGATGG
 101 AGCCTACGCA AAGGCGGGAG CTGAGTTAGT TGCCACTGCC AAAGAGGCTT
 151 GGAACAGGGA ATTGGTGGTG AAAGTGAAAG AGCCTCTCCC TGAAGAGTAT
 201 GAATATTTAA CTTTGCCTAA GTTGTTGTTC ACTTATCTCC ATTTGGCAGC
 251 GGAACGTACC CTCACCGAAG CTCTAATTAA ATCTGGCATT ACGGCGATCG
 301 CCTATGAAAC GGTGGAATTG GCTGATGGTC AATTGCCATT GTTGGCCCCC
 351 ATGAGCCGCA TTGCCGGACG ATTGGCGGTG CAGATGGGTG CCCATTATTT
 401 GGAAAAACAA CAGGGAGGCC GGGGAGTTCT GTTGGGAGGC GTACCCGGAG
 451 TCAAGGCCGG ACAAGTAACT ATCCTCGGCG GTGGCGTAGT CGGTACAGAG
 501 GCGGCCAAAA TGGCGATCGG ACTGGGGGCC ATGGTGACCA TCCTAGACAT
 551 CAATGTAGAC CGTTTAAACC AATTGGGAGA ACTGTTCGGT TCCCGAATTC
 601 CCCGGATCCG TCGACCTGCA GGGGGGGGGG GGCGCTGAGG TCTGCCTCGT
 651 GAAGAAGGTG TTGCTGACTC ATACCAGGCC TGAATCGCCC CATCATCCAG
 701 CCAGAAAGTG AGGGAGCCAC GGTTGATGAG AGCTTTGTTG TAGGTGGACC
 751 AGTTGGTGAT TTTGAACTTT TGCTTTGCCA CGGAACGGTC TGCGTTGTCG
 801 GGAAGATGCG TGATCTGATC CTTCAACTCA GCAAAGTTC GATTTATTCA
 851 ACAAAGCCGC CGTCCCGTCA AGTCAGCGTA ATGCTCTGCC AGTGTTACAA
 901 CCAATTAACC AATTCTGATT AGAAAAACTC ATCGAGCATC AAATGAAACT
 951 GCAATTTATT CATATCAGGA TTATCAATAC CATATTTTTG AAAAAGCCGT
1001 TTCTGTAATG AAGGAGAAAA CTCACCGAGG CAGTTCCATA GGATGGCAAG
1051 ATCCTGGTAT CGGTCTGCGA TTCCGACTCG TCCAACATCA ATACAACCTA
1101 TTAATTTCCC CTCGTCAAAA ATAAGGTTAT CAAGTGAGAA ATCACCATGA
1151 GTGACGACTG AATCCGGTGA GAATGGCAAA AGCTTATGCA TTTCTTTCCA
1201 GACTTGTTCA ACAGGCCAGC CATTACGCTC GTCATCAAAA TCACTCGCAT
1251 CAACCAAACC GTTATTCATT CGTGATTGCG CCTGAGCGAG ACGAAATACG
1301 CGATCGCTGT TAAAAGGACA ATTACAAACA GGAATCGAAT GCAACCGGCG
1351 CAGGAACACT GCCAGCGCAT CAACAATATT TCACCTGAA TCAGGATATT
1401 CTTCTAATAC CTGGAATGCT GTTTTCCCGG GGATCGCAGT GGTGAGTAAC
1451 CATGCATCAT CAGGAGTACG GATAAAATGC TTGATGGTCG AAGAGGCAT
1501 AAATTCCGTC AGCCAGTTTA GTCTGACCAT CTCATCTGTA ACATCATTGG
1551 CAACGCTACC TTTGCCATGT TTCAGAAACA ACTCTGGCGC ATCGGGCTTC
```

Figure 5C(1)

```
1601 CCATACAATC GATAGATTGT CGCACCTGAT TGCCCGACAT TATCGCGAGC
1651 CCATTTATAC CCATATAAAT CAGCATCCAT GTTGGAATTT AATCGCGGCC
1701 TCGAGCAAGA CGTTTCCCGT TGAATATGGC TCATAACACC CCTTGTATTA
1751 CTGTTTATGT AAGCAGACAG TTTTATTGTT CATGATGATA TATTTTTATC
1801 TTGTGCAATG TAACATCAGA GATTTTGAGA CACAACGTGG CTTTCCCCCC
1851 CCCCCCTGCA GGTCGACGGA TCCGGGGAAT TCGGGTGGAT CTGCGCTACA
1901 GCAATGCCAG CCAAATCGAA GACCTGTTGC CCCATACAGA TTTGCTCATC
1951 GGCGCAGTAT TGATCACAGG CAAGCGGGCC CCAGTGTTGG TTTCCCGCCA
2001 GGAAGTGGAG CAAATGTTGC CAGGGGCGGT GATTATGGAT GTGGCGATCG
2051 ACCAAGGGGG CTGTGTGGAG ACTTTGCGGG TAACTTCTCA TAGTCAACCC
2101 AGTTACATCG AAGCAGAAGT AGTTCATGTG GGCATTCCCA ATATGCCAGG
2151 AGCCACTCCC TGGACAGCAA CCCAAGCGTT GAATAATAGT ACATTGCGCT
2201 ATGTGTTGAA ATTGGCCAAT CTGGGGGAAC AGGCTTGGGA AAATGATTTG
2251 CCGTTGGCGA AAGGAGTCAA TGTTCAAGCC GGAAAATAAT CA (SEQ ID NO:6)
```

Figure 5C(2)

```
MCCWQSRGLLVKRVLAIILGGGAGTRLYPLTKLRAKPAVPLAGKYRLIDIPVSNCINSEI
VKIYVLTQFNSASLNRHISRAYNFSGFQEGFVEVLAAQQTKDNPDWFQGTADAVRQYLWL
FREWDVDEYLILSGDHLYRMDYAQFVKRHRETNADITLSVVPVDDRKAPELGLMKIDAQG
RITDFSEKPQGEALRAMQVDTSVLGLSAEKAKLNPYIASMGIYVFKKEVLHNLLEKYEGA
TDFGKEIIPDSASDHNLQAYLFDDYWEDIGTIEAFYEANLALTKQPSPDFSFYNEKAPIY
TRGRYLPPTKMLNSTVTESMIGEGCMIKQCRIHHSVLGIRSRIESDCTIEDTLVMGNDFY
ESSSERDTLKARGEIAAGIGSGTTIRRAIIDKNARIGKNVMIVNKENVQEANREELGFYI
RNGIVVVIKNVTIADGTVI (SEQ ID NO:7)
```

Figure 6A

```
   1 GGGATTGTTG TTGGCAATCG AGAGGTCTGC TTGTGAAACG TGTCTTAGCG
  51 ATTATCCTGG GCGGTGGGGC CGGGACCCGC CTCTATCCTT TAACCAAACT
 101 CAGAGCCAAA CCCGCAGTTC CCTTGGCCGG AAAGTATCGC CTCATCGATA
 151 TTCCCGTCAG TAATTGCATC AACTCAGAAA TCGTTAAAAT TTACGTCCTT
 201 ACCCAGTTTA ATTCCGCCTC CCTTAACCGT CACATCAGCC GGGCCTATAA
 251 TTTTTCCGGC TTCCAAGAAG GATTTGTGGA AGTCCTCGCC GCCCAACAAA
 301 CCAAAGATAA TCCTGATTGG TTTCAGGGCA CTGCTGATGC GGTACGGCAA
 351 TACCTCTGGT TGTTTAGGGA ATGGGACGTA GATGAATATC TTATTCTGTC
 401 CGGCGACCAT CTCTACCGCA TGGATTACGC CCAATTTGTT AAAAGACACC
 451 GGGAAACCAA TGCCGACATA ACCCTTTCCG TTGTGCCCGT GGATGACAGA
 501 AAGGCACCCG AGCTGGGCTT AATGAAAATC GACGCCCAGG GCAGAATTAC
 551 TGACTTTTCT GAAAAGCCCC AGGGGGAAGC CCTCCGGGCC ATGCAGGTGG
 601 ACACCAGCGT TTTGGGCCTA AGTGCGGAGA AGGCTAAGCT TAATCCTTAC
 651 ATTGCCTCCA TGGGCATTTA CGTTTTCAAG AAGGAAGTAT TGCACAACCT
 701 CCTGGAAAAA TATGAAGGGG CAACGGACTT TGGCAAAGAA ATCATTCCTG
 751 ATTCAGCCAG TGATCACAAT CTGCAAGCCT ATCTCTTTGA TGACTATTGG
 801 GAAGACATTG GTACCATTGA AGCCTTCTAT GAGGCTAATT TAGCCCTGAC
 851 CAAACAACCT AGTCCCGACT TTAGTTTTTA TAACGAAAAA GCCCCCATCT
 901 ATACCAGGGG TCGTTATCTT CCCCCCACCA AAATGTTGAA TTCCCCGGAT
 951 CCGTCGACCT GCAGGGGGGG GGGGCGCTG AGGTCTGCCT CGTGAAGAAG
1001 GTGTTGCTGA CTCATACCAG GCCTGAATCG CCCCATCATC CAGCCAGAAA
1051 GTGAGGGAGC CACGGTTGAT GAGAGCTTTG TTGTAGGTGG ACCAGTTGGT
1101 GATTTTGAAC TTTTGCTTTG CCACGGAACG GTCTGCGTTG TCGGGAAGAT
1151 GCGTGATCTG ATCCTTCAAC TCAGCAAAAG TTCGATTTAT TCAACAAAGC
1201 CGCCGTCCCG TCAAGTCAGC GTAATGCTCT GCCAGTGTTA CAACCAATTA
1251 ACCAATTCTG ATTAGAAAAA CTCATCGAGC ATCAAATGAA ACTGCAATTT
1301 ATTCATATCA GGATTATCAA TACCATATTT TTGAAAAAGC CGTTTCTGTA
1351 ATGAAGGAGA AAACTCACCG AGGCAGTTCC ATAGGATGGC AAGATCCTGG
1401 TATCGGTCTG CGATTCCGAC TCGTCCAACA TCAATACAAC CTATTAATTT
1451 CCCCTCGTCA AAAATAAGGT TATCAAGTGA GAAATCACCA TGAGTGACGA
1501 CTGAATCCGG TGAGAATGGC AAAAGCTTAT GCATTTCTTT CCAGACTTGT
1551 TCAACAGGCC AGCCATTACG CTCGTCATCA AAATCACTCG CATCAACCAA
1601 ACCGTTATTC ATTCGTGATT GCGCCTGAGC GAGACGAAAT ACGCGATCGC
1651 TGTTAAAAGG ACAATTACAA ACAGGAATCG AATGCAACCG GCGCAGGAAC
1701 ACTGCCAGCG CATCAACAAT ATTTTCACCT GAATCAGGAT ATTCTTCTAA
1751 TACCTGGAAT GCTGTTTTCC CGGGGATCGC AGTGGTGAGT AACCATGCAT
```

Figure 6C(1)

```
1801 CATCAGGAGT ACGGATAAAA TGCTTGATGG TCGGAAGAGG CATAAATTCC
1851 GTCAGCCAGT TTAGTCTGAC CATCTCATCT GTAACATCAT TGGCAACGCT
1901 ACCTTTGCCA TGTTTCAGAA ACAACTCTGG CGCATCGGGC TTCCCATACA
1951 ATCGATAGAT TGTCGCACCT GATTGCCCGA CATTATCGCG AGCCCATTTA
2001 TACCCATATA AATCAGCATC CATGTTGGAA TTTAATCGCG GCCTCGAGCA
2051 AGACGTTTCC CGTTGAATAT GGCTCATAAC ACCCCTTGTA TTACTGTTTA
2101 TGTAAGCAGA CAGTTTTATT GTTCATGATG ATATATTTTT ATCTTGTGCA
2151 ATGTAACATC AGAGATTTTG AGACACAACG TGGCTTTCCC CCCCCCCCCT
2201 GCAGGTCGAC GGATCCGGGG AATTCCACCG TGACGGAATC CATGATCGGG
2251 GAAGGTTGCA TGATTAAGCA ATGTCGCATC CACCACTCAG TTTTAGGCAT
2301 TCGCAGTCGC ATTGAATCTG ATTGCACCAT TGAGGATACT TTGGTGATGG
2351 GCAATGATTT CTACGAATCT TCATCAGAAC GAGACACCCT CAAAGCCCGG
2401 GGGGAAATTG CCGCTGGCAT AGGTTCCGGC ACCACTATCC GCCGAGCCAT
2451 CATCGACAAA AATGCCCGCA TCGGCAAAAA CGTCATGATT GTCAACAAGG
2501 AAAATGTCCA GGAGGCTAAT CA (SEQ ID NO:8)
```

Figure 6C(2)

```
   1 AATTCGTGAT TACCCCATCA TCATACGAAG CCAGGGACAG TTTACTCAGC
  51 GGCAGTTTCC GACCTTTGCC ATTTCGGTTA TCCGTACCCC CACAGTGATC
 101 TGACAACTCA GCTCCGAATC CCAACGGCGA TCGCCATTCT TGCTTGGGGC
 151 ATTAAAACCC GCTGGTTAGC CGGAATTTCC GTCCAGATTC CCTTTCCAGA
 201 TGTCCCCCTC GGTTCTAAAC TTGACTTCGA AGTGTGTTGT TGGCAATCGA
 251 GAGGTCTGCT TGTGAAACGT GTCTTAGCGA TTATCCTGGG CGGTGGGGCC
 301 GGGACCCGCC TCTATCCTTT AACCAAACTC AGAGCCAAAC CCGCAGTTCC
 351 CTTGGCCGGA AAGTATCGCC TCATCGATAT TCCCGTCAGT AATTGCATCA
 401 ACTCAGAAAT CGTTAAAATT TACGTCCTTA CCCAGTTTAA TTCCGCCTCC
 451 CTTAACCGTC ACATCAGCCG GGCCTATAAT TTTTCCGGCT TCCAAGAAGG
 501 ATTTGTGGAA GTCCTCGCCG CCCAACAAAC CAAAGATAAT CCTGATTGGT
 551 TTCAGGGCAC TGCTGATGCG GTACGGCAAT ACCTCTGGTT GTTTAGGGAA
 601 TGGGACGTAG ATGATACGTG CTGCTGAAGT TGCCCGCAAC AGAGAGTGGA
 651 ACCAACCGGT GATACCACGA TACTATGACT GAGAGTCAAC GCCATGAGCG
 701 GCCTCATTTC TTATTCTGAG TTACAACAGT CCGCACCGCT GTCCGGTAGC
 751 TCCTTCCGGT GGGCGCGGGG CATGACTATC GTCGCCGCAC TTATGACTGT
 801 CTTCTTTATC ATGCAACTCG TAGGACAGGT GCCGGCAGCG CCCAACAGTC
 851 CCCCGGCCAC GGGGCCTGCC ACCATACCCA CGCCGAAACA AGCGCCCTGC
 901 ACCATTATGT TCCGGATCTG CATCGCAGGA TGCTGCTGGC TACCCTGTGG
 951 AACACCTACA TCTGTATTAA CGAAGCGCTA ACCGTTTTTA TCAGGCTCTG
1001 GGAGGCAGAA TAAATGATCA TATCGTCAAT TATTACCTCC ACGGGGAGAG
1051 CCTGAGCAAA CTGGCCTCAG GCATTTGAGA AGCACACGGT CACACTGCTT
1101 CCGGTAGTCA ATAAACCGGT AAACCAGCAA TAGACATAAG CGGCTATTTA
1151 ACGACCCTGC CCTGAACCGA CGACCGGGTC GAATTTGCTT TCGAATTTCT
1201 GCCATTCATC CGCTTATTAT CACTTATTCA GGCGTAGCAC CAGGCGTTTA
1251 AGGGCACCAA TAACTGCCTT AAAAAAATTA CGCCCCGCCC TGCCACTCAT
1301 CGCAGTACTG TTGTAATTCA TTAAGCATTC TGCCGACATG GAAGCCATCA
1351 CAGACGGCAT GATGAACCTG AATCGCCAGC GGCATCAGCA CCTTGTCGCC
1401 TTGCGTATAA TATTTGCCCA TGGTGAAAAC GGGGGCGAAG AAGTTGTCCA
1451 TATTGGCCAC GTTTAAATCA AAACTGGTGA AACTCACCCA GGGATTGGCT
1501 GAGACGAAAA ACATATTCTC AATAAACCCT TTAGGGAAAT AGGCCAGGTT
1551 TTCACCGTAA CACGCCACAT CTTGCGAATA TATGTGTAGA AACTGCCGGA
1601 AATCGTCGTG GTATTCACTC CAGAGCGATG AAAACGTTTC AGTTTGCTCA
1651 TGGAAAACGG TGTAACAAGG GTGAACACTA TCCCATATCA CCAGCTCACC
```

Figure 6E(1)

```
1701 GTCTTTCATT GCCATACGGA ATTCCGGATG AGCATTCATC AGGCGGGCAA
1751 GAATGTGAAT AAAGGCCGGA TAAAACTTGT GCTTATTTTT CTTTACGGTC
1801 TTTAAAAAGG CCGTAATATC CAGCTGAACG GTCTGGTTAT AGGTACATTG
1851 AGCAACTGAC TGAAATGCCT CAAAATGTTC TTTACGATGC CATTGGGATA
1901 TATCAACGGT GGTATATCCA GTGATTTTTT TCTCCATTTT AGCTTCCTTA
1951 GCTCCTGAAA ATCTCGATAA CTCAAAAAAT ACGCCCGGTA GTGATCTTAT
2001 TTCATTATGG TGAAAGTTGG AACCTCTTAC GTGATATCTT ATTCTGTCCG
2051 GCGACCATCT CTACCGCATG GATTACGCCC AATTTGTTAA AAGACACCGG
2101 GAAACCAATG CCGACATAAC CCTTTCCGTT GTGCCCGTGG ATGACAGAAA
2151 GGCACCCGAG CTGGGCTTAA TGAAAATCGA CGCCCAGGGC AGAATTACTG
2201 ACTTTTCTGA AAAGCCCCAG GGGGAAGCCC TCCGGGCCAT GCAGGTGGAC
2251 ACCAGCGTTT TGGGCCTAAG TGCGGAGAAG CTAAGCTTA ATCCTTACAT
2301 TGCCTCCATG GGCATTTACG TTTTCAAGAA GGAAGTATTG CACAACCTCC
2351 TGGAAAAATA TGAAGGGGCA ACGGACTTTG GCAAAGAAAT CATTCCTGAT
2401 TCAGCCAGTG ATCACAATCT GCAAGCCTAT CTCTTTGATG ACTATTGGGA
2451 AGACATTGGT ACCATTGAAG CCTTCTATGA GGCTAATTTA GCCCTGACCA
2501 AACAACCTAG TCCCGACTTT AGTTTTTATA ACGAAAAAGC CCCCATCTAT
2551 ACCAGGGGTC GTTATCTTCC CCCCACCAAA ATGTTG (SEQ ID NO:9)
```

Figure 6E(2)

MVSSVVEKTSVAHKETALILWFEEVGTHDVGLVGGKNSSLGEMIQQLTNKGVNVPSGFAT
TAYAYRYFIQEAGLEQKLRDLFTDLDVNDMANLQERGHLARQLILDTPFPQNLQTAIAEA
YGAMCERYGQKMGRTGVDVAVRSSATAEDLPEASFAGQQETYLNVHSLSCVLESCHKCFA
SLFTDRAISYRHHNGFDHFAVALSVGVQKMVRSDLATSGVMFSIDTETGFKNAALITAAY
GLGENVVQGAVNPDEYFVFKPTLKEGFKPILEKRLGSKAIKMVYDVGGSKLTKNVEVAEP
EREKYCINDEEILQLARWACIIEDHYSGVRGVYTPMDIEWAKDGQTGELFIVQARPETVQ
SQKSANVIKTYELKDHSQVLATGRSVGAAIGQGKAQVIRNVSQINQFRPGEVLITNRTDP
DWEPIMKQASAIVTNQGGKTCHAAIIAREMGIPAIVGCGDATDTIKTGEDVTICCSEGDE
GSVYSGILNYEVHETELSNLPRTKTQILMNVGNPEQAFGFASYPADGVGLARLEFIIANH
IKAHPLALMKFDELEDPLAKAEIAELTKLYAGDRPRFFVDKLAHGIAMIAAAFYPKPVVV
RMSDFKSNEYANLLGGRQFEPKEENPMIGWRGASRYYDPNYREAYALECQALKRVRDEMG
LTNVIPMIPFCRTPDEGRKVIAEMAKHGLKQGKNGLEIYVMCELPSNVILADEFSEVFDG
FSIGSNDLTQLTLGLDRDSSLVAHLFDERNLGVKRMVKMAIETAKANGRKIGICGQAPSD
YPEFAEFLVELGIDSISLNPDSVLKTVLRIAEVEKALG (SEQ ID NO:10)

Figure 7A

```
   1 GGGATTTTCA CTGACCGGGC TATTTCCTAT CGCCATCACA ATGGTTTTGA
  51 CCATTTTGCG GTGGCCCTAT CGGTGGGCGT ACAAAAGATG GTGCGTTCTG
 101 ATCTGGCCAC CTCCGGGGTG ATGTTTTCCA TTGATACGGA AACGGGTTTC
 151 AAAAATGCCG CTCTGATTAC TGCCGCCTAT GGCCTAGGGG AAAATGTGGT
 201 GCAAGGGGCG GTTAACCCCG ATGAATATTT TGTGTTTAAA CCTACTTTGA
 251 AAGAGGGTTT TAAACCAATT CTGGAAAAAC GTTTGGGTAG TAAAGCTATC
 301 AAAATGGTCT ATGACGTGGG CGGTTCCAAA CTGACCAAAA ATGTGGAAGT
 351 AGCGGAGCCG GAACGGGAAA AATATTGCAT TAATGATGAA GAAATTCTCC
 401 AATTAGCCCG CTGGGCCTGC ATCATTGAAG ACCATTATTC TGGGGTGCGG
 451 GGAGTTTATA CCCCCATGGA TATTGAATGG GCTAAGGATG GGCAAACGGG
 501 GGAATTGTTC ATTGTCCAAG CCCGCCCAGA AACGGTGCAG TCGCAAAAAT
 551 CCGCCAATGT GATTAAAACC TATGAGTTAA AAGATCACAG CCAAGTGTTA
 601 GCCACGGGCC GCAGTGTGGG GGCGGCGATC GGCCAGGGTA AAGCCCAGGT
 651 AATTCGCAAT GTGTCCCAAA TCAATCAGTT TCGTCCCGGC GAGGTGTTAA
 701 TCACCAACCG CACTGACCCG GATTGGGAAC CGATTATGAA ACAGGCTTCG
 751 GCGATCGTCA CTAACCAGGG GGGGAAAACC TGCCACGCCG CAATTATTGC
 801 CCGAATTCCC CGGATCCGTC GACCTGCAGG GGGGGGGGGG CGCTGAGGTC
 851 TGCCTCGTGA AGAAGGTGTT GCTGACTCAT ACCAGGCCTG AATCGCCCCA
 901 TCATCCAGCC AGAAAGTGAG GGAGCCACGG TTGATGAGAG CTTTGTTGTA
 951 GGTGGACCAG TTGGTGATTT TGAACTTTTG CTTTGCCACG GAACGGTCTG
1001 CGTTGTCGGG AAGATGCGTG ATCTGATCCT TCAACTCAGC AAAAGTTCGA
1051 TTTATTCAAC AAAGCCGCCG TCCCGTCAAG TCAGCGTAAT GCTCTGCCAG
1101 TGTTACAACC AATTAACCAA TTCTGATTAG AAAAACTCAT CGAGCATCAA
1151 ATGAAACTGC AATTTATTCA TATCAGGATT ATCAATACCA TATTTTTGAA
1201 AAAGCCGTTT CTGTAATGAA GGAGAAAACT CACCGAGGCA GTTCCATAGG
1251 ATGGCAAGAT CCTGGTATCG GTCTGCGATT CCGACTCGTC AACATCAAT
1301 ACAACCTATT AATTTCCCCT CGTCAAAAAT AAGGTTATCA AGTGAGAAAT
1351 CACCATGAGT GACGACTGAA TCCGGTGAGA ATGGCAAAAG CTTATGCATT
1401 TCTTTCCAGA CTTGTTCAAC AGGCCAGCCA TTACGCTCGT CATCAAAATC
1451 ACTCGCATCA ACCAAACCGT TATTCATTCG TGATTGCGCC TGAGCGAGAC
1501 GAAATACGCG ATCGCTGTTA AAAGGACAAT TACAAACAGG AATCGAATGC
1551 AACCGGCGCA GGAACACTGC CAGCGCATCA ACAATATTTT CACCTGAATC
1601 AGGATATTCT TCTAATACCT GGAATGCTGT TTTCCCGGGG ATCGCAGTGG
1651 TGAGTAACCA TGCATCATCA GGAGTACGGA TAAAATGCTT GATGGTCGGA
```

Figure 7C(1)

```
1701 AGAGGCATAA ATTCCGTCAG CCAGTTTAGT CTGACCATCT CATCTGTAAC
1751 ATCATTGGCA ACGCTACCTT TGCCATGTTT CAGAAACAAC TCTGGCGCAT
1801 CGGGCTTCCC ATACAATCGA TAGATTGTCG CACCTGATTG CCCGACATTA
1851 TCGCGAGCCC ATTTATACCC ATATAAATCA GCATCCATGT TGGAATTTAA
1901 TCGCGGCCTC GAGCAAGACG TTTCCCGTTG AATATGGCTC ATAACACCCC
1951 TTGTATTACT GTTTATGTAA GCAGACAGTT TTATTGTTCA TGATGATATA
2001 TTTTTATCTT GTGCAATGTA ACATCAGAGA TTTTGAGACA CAACGTGGCT
2051 TTCCCCCCCC CCCCTGCAGG TCGACGGATC CGGGGAATTC GGGAAATGGG
2101 TATTCCGGCG ATTGTGGGTT GTGGAGATGC CACCGACACA ATCAAAACCG
2151 GGGAAGATGT CACCATCTGT TGCTCCGAAG GGGATGAAGG TTCGGTTTAC
2201 AGCGGCATTT TGAACTATGA AGTTCACGAA ACGGAACTGT CCAATTTGCC
2251 CCGCACCAAG ACTCAAATTT TGATGAATGT GGGTAACCCA GAACAGGCCT
2301 TTGGATTTGC TAGTTATCCC GCCGATGGCG TGGGTCTAGC CCGGTTGGAA
2351 TTTATCATTG CTAACCACAT TAAGGCTCAC CCCCTCGCCC TGATGAAATT
2401 TGATGAGTTG GAAGATCCCT TGGCCAAGGC AGAAATTGCC GAACTAACCA
2451 AACTCTATGC TGGCGATCGC CCCCGGTTCT TTGTGGACAA ATTGGCCCAT
2501 GGTATTGCCA TGATTGCGGC GGCGTTCTAT CCCAAACCTG TGGTGGTGCG
2551 GATGTCGGAT TTTAAATCCA ATGAATACGC TAACCTCCTG GGTGGTCGTC
2601 AGTTTGAGCC GAAGGAAGAA AACCCCATGA TCGGTTGGCG GGGCGCTTCC
2651 CGTTACTACG ATCCCAATTA CCGAGAAGCC TACGCTTTGG AATGCCAAGC
2701 TCTGAAACGA GTGCGGGACG AAATGGGTTT AACCAACGTC ATTCCCATGA
2751 TTCCCTTCTG TCGTACCCCC GATGAAGGTC GCAAAGTTAT TGCGGAAATG
2801 GCTAAACATG GCTTGAAACA AGGGAAAAAC GGCTTGGAAA TCTACGTTAT
2851 GTGTGAATTG CCCAGTAACG TCATTCTGGC CGATGAATTT AGCGAGGTAT
2901 TTGACGGCTT CTCCATTGGC TCCAATGATT TAACCCAATT AACTTTAGGT
2951 TTAGACCGGG ATTCTTCCCT CGTTGCCCAT CTGTTTGATG AACGCAATCT
3001 AGGGGTCAAA CGGATGGTCA AAATGGCCAT TGAAACGGCG AAAGCTAACG
3051 GTCGCAAAAT CGGTATCTGT GGCCAAGAAT CA (SEQ ID NO:11)
```

Figure 7C(2)

```
MKIAFFSSKAYDRQFFQQANHPHQREMVFFDAQLNLDTAILAEDCPVICLFVNDQAPAPV
LEKLAAQGTKLIALRSAGYNNVDLKTAADLGLKVVHVPSYSPHAVAEHTVGLILALNRKL
YRAYNRVRDDNFSLEGLLGFDLHGTTVGVIGTGKIGLAFAQIMNGFGCHLLGYDAFPNDK
FTAIGQALYVSLNELLAHSDIISLHCPLLPETHYLINTNTIAQMKPGVMLINTSRGHLID
TQAVIQGIKSHKIGFLGIDVYEEEEELFFTDHSDTIIQDDTFQLLQSFPNVMITAHQGFF
THNALQTIAATTLANIAEFEQNKPLTYQVICPH (SEQ ID NO:12)
```

Figure 8A

```
   1 CGGGCCCCCC CTCGAGGTCG ACGGTATCGA TAAGCTTGAT ATCCCTGGGA
  51 GCGGAGACCT TTAAGCTCAA ATTTGGTCAT CGAGGGCTCA ATCAACCCTG
 101 TGGCCTGGAG CAACAGGTGG AAATTACCAG CCAGAACCAT GGTTTTGCGG
 151 TGACGGAAGG TTCCCTGGCC GAAGAAGTGG AAATTACCCA TTTCAACCTC
 201 AACGATAAAA CGGTGGCGGG GCTACGCCAT AAAGAATTGC CCTTTTTCTC
 251 GGTGCAGTAC CACCCGGAGG CCAGCCCTGG ACCCCATGAT GCCGATTATC
 301 TGTTCGAGAA GTTCGTCAAG TTGATGCGAC AACAAAAGGC AGAAGTCGCC
 351 GGTTAGTAAA ACCTAGTAAC AGCTACGATT TATCGTACTA TCGATCACCA
 401 AGGTAGTGCC GTTAATACTA TCGTTGCTTC ATTTTTAGGA AAAATATCTG
 451 GTAATAAAAG CTAAAAAAT TTAACGTTAT CTTTAGTTAA CATTGATATT
 501 TTCTAACCTT AATGGGGACA GATTACTTGG TAAGTTAAAG GTTTATTCTG
 551 CTCAAATTCA GCAATATTTG CCAGTGTCGT TGCGGCAATG GTTTGCAGAG
 601 CGTTGTGGGT AAAGAATCCC TGATGAGCTG TGATCCGTCG ACCTGCAGGG
 651 GGGGGGGGGC GCTGAGGTCT GCCTCGTGAA GAAGGTGTTG CTGACTCATA
 701 CCAGGCCTGA ATCGCCCCAT CATCCAGCCA GAAAGTGAGG GAGCCACGGT
 751 TGATGAGAGC TTTGTTGTAG GTGGACCAGT TGGTGATTTT GAACTTTTGC
 801 TTTGCCACGG AACGGTCTGC GTTGTCGGGA AGATGCGTGA TCTGATCCTT
 851 CAACTCAGCA AAAGTTCGAT TTATTCAACA AAGCCGCCGT CCCGTCAAGT
 901 CAGCGTAATG CTCTGCCAGT GTTACAACCA ATTAACCAAT TCTGATTAGA
 951 AAAACTCATC GAGCATCAAA TGAAACTGCA ATTTATTCAT ATCAGGATTA
1001 TCAATACCAT ATTTTTGAAA AAGCCGTTTC TGTAATGAAG GAGAAAACTC
1051 ACCGAGGCAG TTCCATAGGA TGGCAAGATC CTGGTATCGG TCTGCGATTC
1101 CGACTCGTCC AACATCAATA CAACCTATTA ATTTCCCCTC GTCAAAAATA
1151 AGGTTATCAA GTGAGAAATC ACCATGAGTG ACGACTGAAT CCGGTGAGAA
1201 TGGCAAAAGC TTATGCATTT CTTTCCAGAC TTGTTCAACA GGCCAGCCAT
1251 TACGCTCGTC ATCAAAATCA CTCGCATCAA CCAAACCGTT ATTCATTCGT
1301 GATTGCGCCT GAGCGAGACG AAATACGCGA TCGCTGTTAA AAGGACAATT
1351 ACAAACAGGA ATCGAATGCA ACCGGCGCAG GAACACTGCC AGCGCATCAA
1401 CAATATTTTC ACCTGAATCA GGATATTCTT CTAATACCTG GAATGCTGTT
1451 TTCCCGGGGA TCGCAGTGGT GAGTAACCAT GCATCATCAG GAGTACGGAT
1501 AAAATGCTTG ATGGTCGGAA GAGGCATAAA TTCCGTCAGC CAGTTTAGTC
1551 TGACCATCTC ATCTGTAACA TCATTGGCAA CGCTACCTTT GCCATGTTTC
1601 AGAAACAACT CTGGCGCATC GGGCTTCCCA TACAATCGAT AGATTGTCGC
1651 ACCTGATTGC CCGACATTAT CGCGAGCCCA TTTATACCCA TATAAATCAG
```

Figure 8D(1)

```
1701 CATCCATGTT GGAATTTAAT CGCGGCCTCG AGCAAGACGT TTCCCGTTGA
1751 ATATGGCTCA TAACACCCCT TGTATTACTG TTTATGTAAG CAGACAGTTT
1801 TATTGTTCAT GATGATATAT TTTTATCTTG TGCAATGTAA CATCAGAGAT
1851 TTTGAGACAC AACGTGGCTT TCCCCCCCCC CCCTGCAGGT CGACGGATCT
1901 GCGGCTGTTT TGAGGTCAAC ATTATTATAG CCCGCACTGC GCAGAGCGAT
1951 TAATTTTGTG CCCTGGGCAG CTAACTTTTC TAGCACCGGG GCAGGAGCTT
2001 GGTCATTAAC GAAGAGGCAA ATAACGGGGC AATCCTCCGC TAAAATAGCG
2051 GTATCAAGGT TGAGTTGGGC ATCAAAAAAG ACCATTTCCC GTTGATGGGG
2101 GTGGTTTGCT TGTTGGAAAA ATTGACGATC ATAGGCTTTA CTGCTAAAAA
2151 AAGCGATTTT CATGACGATT ATGGGAAGTA GTTTAGAACG TGTTTGGAAA
2201 GTTTTATTCC GCCCCCTAAA TCCCCCAATA ATGGGGTACT TTCACCCAGC
2251 TTCACCCCAA ATTTGGGGGC CAGGGGGGCT TGTTAAACAG GCTCTTAGAG
2301 CACTATTTAG TCAAGGGTAT TTTTTCCAAT CTTAAAAGAA ATTTTCTGAT
2351 TCTTCCTGCA TTTGTATTAT TTAATACTCC CCTAGCTCTG GCGATTGCCG
2401 TAGCGGTAGA TATTGACTCA CACTGGGGCA ACTGTAGGGT TTGGCCTCCA
2451 ACTCCTGTGT TTGGCTGTGA TGCATTTTCA GCTTCCCTTT AGCTAGAGCG
2501 GCCGCCACCG CGGTGGAGCT (SEQ ID NO:13)
```

Figure 8D(2)

MKFLILNAGSSSQKSCLYELTGDRLPETIPEPLWEAFIDWTVLANQGRLTVETAGQKQVI
ILETGDRQQGIARMLDTLVTGDDAVLKSLAEIDLVGHRVVHGGTDHAEATLITPEVQQAI
ADLIPLAPAHNPAHLEGIEAISALLVLGEVPQIAVFDTAFHRTIPTPAAEYPIPQAWTNL
GIRRYGFHGTSHKYCAQKTAEILGKPLADLKLITCHIGNGASLTAIKNGVSIDTTMGFTP
LEGLMMGARSGSIDPAILLFLQETQGLTPAEINTTLNKKSGLLGVSGLSADLRTILQAKA
EGNEQAQLAYVMYIHRFRSCLGQMIASLEGLDTLVFTAGVGENAATVRADVCQAFEFLGL
KLDPELNNRSPRDTVISHSDSLVTVLIVHTEEDWAIAQDCWHWWHSQGQRKQS (SEQ ID
NO:14)

Figure 9A

```
   1 CTAGTAGTGC AGAAATTTTG AGCGATCTGG AAGCCACCAT TGCCTACGCC
  51 CAAACTTTAC CCAACGTTAA ACCGGAAGAA GTAGGATTAA TTGGTTTTTG
 101 TTTTGGTGGT TGGATTGTCT ATTTAGGGGC TAGTTTACCC ACAGTCAAGG
 151 CCACGGCTTC CTTTTACGGC GCGGGTATTC CCCATTGGGC TCCAGGGACA
 201 GCGGAACCGC CCATTACCTA TACCGATAAA ATTCAGGGCA CTTTATACGC
 251 CTTCTTCGGC TTGGAAGATA CCAGCATTCC CATGGCAGAT ACGGAGCAGA
 301 TTGAACAGGC TTTAACCAAG TATCAGGTGA ACCATAAAAT TTTCCGTTAC
 351 CCAGGCGCAG ACCATGGCTT TTTCTGTGAC CAAAGGGCTA GCTATAACGC
 401 CGAAGCGGCC GCCGATGCTT GGCAAAAAGT GAAACAACTT TTCCAAACCG
 451 AATTGAAATG AAATTCCTGA TTCTCAATGC CGGTTCCAGC AGTCAAAAAA
 501 GTTGTCTTTA TGAGCTGACT GGCGATCGCC TACCGAGAC GATACCGGAG
 551 CCCTTATGGG AGGCTTTCAT TGATTGGACG GTGTTGGCAA ATCAGGGGCG
 601 GTTGACCTGC AGGGGGGGGG GGGCGCTGAG GTCTGCCTCG TGAAGAAGGT
 651 GTTGCTGACT CATACCAGGC CTGAATCGCC CCATCATCCA GCCAGAAAGT
 701 GAGGGAGCCA CGGTTGATGA GAGCTTTGTT GTAGGTGGAC CAGTTGGTGA
 751 TTTTGAACTT TTGCTTTGCC ACGGAACGGT CTGCGTTGTC GGGAAGATGC
 801 GTGATCTGAT CCTTCAACTC AGCAAAAGTT CGATTTATTC AACAAAGCCG
 851 CCGTCCCGTC AAGTCAGCGT AATGCTCTGC CAGTGTTACA ACCAATTAAC
 901 CAATTCTGAT TAGAAAAACT CATCGAGCAT CAAATGAAAC TGCAATTTAT
 951 TCATATCAGG ATTATCAATA CCATATTTTT GAAAAAGCCG TTTCTGTAAT
1001 GAAGGAGAAA ACTCACCGAG GCAGTTCCAT AGGATGGCAA GATCCTGGTA
1051 TCGGTCTGCG ATTCCGACTC GTCCAACATC AATACAACCT ATTAATTTCC
1101 CCTCGTCAAA AATAAGGTTA TCAAGTGAGA AATCACCATG AGTGACGACT
1151 GAATCCGGTG AGAATGGCAA AAGCTTATGC ATTTCTTTCC AGACTTGTTC
1201 AACAGGCCAG CCATTACGCT CGTCATCAAA ATCACTCGCA TCAACCAAAC
1251 CGTTATTCAT TCGTGATTGC GCCTGAGCGA GACGAAATAC GCGATCGCTG
1301 TTAAAAGGAC AATTACAAAC AGGAATCGAA TGCAACCGGC GCAGGAACAC
1351 TGCCAGCGCA TCAACAATAT TTTCACCTGA ATCAGGATAT TCTTCTAATA
1401 CCTGGAATGC TGTTTTCCCG GGGATCGCAG TGGTGAGTAA CCATGCATCA
1451 TCAGGAGTAC GGATAAAATG CTTGATGGTC GGAAGAGGCA TAAATTCCGT
1501 CAGCCAGTTT AGTCTGACCA TCTCATCTGT AACATCATTG GCAACGCTAC
1551 CTTTGCCATG TTTCAGAAAC AACTCTGGCG CATCGGGCTT CCCATACAAT
1601 CGATAGATTG TCGCACCTGA TTGCCCGACA TTATCGCGAG CCCATTTATA
1651 CCCATATAAA TCAGCATCCA TGTTGGAATT TAATCGCGGC CTCGAGCAAG
```

Figure 9D(1)

```
1701 ACGTTTCCCG TTGAATATGG CTCATAACAC CCCTTGTATT ACTGTTTATG
1751 TAAGCAGACA GTTTTATTGT TCATGATGAT ATATTTTTAT CTTGTGCAAT
1801 GTAACATCAG AGATTTTGAG ACACAACGTG GCTTTCCCCC CCCCCCCTGC
1851 AGGTCAACCC CGGCGGAAAT TAACACCACC CTCAATAAAA AATCCGGTTT
1901 GCTCGGAGTC TCTGGGCTGT CGGCGGATCT TCGTACCATT TTGCAGGCCA
1951 AAGCAGAGGG TAATGAACAA GCTCAATTGG CTTATGTCAT GTATATCCAT
2001 CGCTTCCGGA GTTGTTTGGG GCAAATGATT GCTTCCTTGG AAGGTTTGGA
2051 TACGTTGGTG TTTACCGCCG GGTGGGGGA AAATGCCGCC ACTGTGCGGG
2101 CAGATGTTTG CCAAGCTTTT GAATTTCTAG GTTTAAAACT TGATCCAGAG
2151 TTGAATAACC GATCGCCAAG GGATACTGTC ATTTCTCACT CCGACTCCTT
2201 GGTGACGGTG TTGATTGTCC ACACCGAAGA AGATTGGGCG ATCGCCCAGG
2251 ATTGTTGGCA CTGGTGGCAT AGCCAGGGAC AGAGAAAGCA ATCGTAAATT
2301 GCGAAAATGT TAGAAAATGG CTGTGAAGAT AAATGTTGAA TTAGGCTAAA
2351 TTTCCTTGGC TAGAGTCCGC ATCCGCCAAC ACGTCAACCC CCTCAGTGAA
2401 AAATATCGGC AGGTGTTGGC CTGTCCCGAT TGGGCCACCG TTTATGACGA
2451 TGTCCAACGA CCATTGCATC TAGATATTGG CTGTGCCCGG GGTCGCTTTC
2501 CCCTCAAAAT GGCTCAACAA CACCCCGACT GGAATTTTTT AGGGGTGGAA
2551 ATCCGTCAAC CCTTGGTGCT AGAGGCCAAC GAAACCGGCG ATCGTCTGGG
2601 GTTAAAAAAT CTCCATTACC TGTTTGGCAA CATCAATGTG GAGCCAGAAA
2651 AATTCTTTTC CGCCTTTCCC CCCACTCTGC AACGGGTCAG CATCCAATTT
2701 CCCGATCCCT GGTTTAAGCA ACGACATAAT AAACGCCGAG TGGCCCAACC
2751 AGAA (SEQ ID NO:15)
```

Figure 9D(2)

```
MTSSLYLSTTEARSGKSLVVLGILDLILKKTTRIAYFRPIIQDPVNGKHDNNIILVLENF
RLQQTYTDSFGLYFHEAVSLASDGAIDQVLDRILAKYRHLADQVDFILCEGSDYLGEESA
FEFDLNTTIAKMLNCPILLLGNAMGNTIADSLQPIDMALNSYDQESCQVVGVIINRVQPE
LATEIQAQLEQRYGDRPMVLGTIPQDIMLKSLRLREIVSGLNAQVLSGADLLDNLVYHHL
VVAMHIAHALHWLHEKNTLIITPGDRGDIILGVMQAHRSLNYPSIAGILLTADYHPEPAI
MKLIEGLPDAPPLLLTSTHTHETSARLETLHPALSPTDNYKIRHSIALFQQQIDGEKLLN
YLKTIRSKGITPKLFLYNLVQAATAAQRHIVLPEGEEIRILKAAASLINHGIVRLTLLGN
IEAIEQTVKINHIDLDLSKVRLINPKTSPDRERYAETYYQLRKHKGVTLAMARDILTDIS
YFGTMMVHLGEADGMVSGSVNTTQHTVRPALQIIKTQPGFSLVSSVFFMCLEDRVLVYGD
CAVNPDPNAEQLAEIALTSAATAKNFGIEPRVALLSYSSGSSGQGADVEKVRQATAIAKE
REPDLALEGPIQYDAAVDSTVAAQKMPGSAVAGKATVFIFPDLNTGNNTYKAVQRETKAI
AIGPILQGLNKPVNDLSRGCLVEDIINTVVITALQVK (SEQ ID NO:16)
```

Figure 10A

```
   1 TTGGCCAAAA AACAAGGTTT ACTGGGTTTT ACCGCTGATG TTTTACTGGA
  51 AAATCGAGCC ATGTTGCATC TATTTGAGAA GATGAACTTT CGCATGGAAC
 101 GACGTATGAG CGAAGGGGTT TACGAATTAA AAATGTTTTT TAGTTGAGCC
 151 GTCTTCTTTC TGCTAATTTA TTGAAGGAAT TTTTGATGCT GGCGTTAGTA
 201 ATTTTACCGC TTCTTAGATT TATTAAAATC TCGTCATAAA ACTTTACTGA
 251 CTAGCGGTTT ATTTTCTGGC TAAAAGCGCT ATCACTTAAG TAGGTGGAAT
 301 TGGCAGATTT GTAGTAGTTG ATACTTAACT TTTTAGGGAA TATCGCTGTG
 351 GGAAAAATCG AGATCATTTT CCCAGAAAAA TCATTGCTGG ATACGTTGAG
 401 GTTATTTAAA TTATGACGAG TTCCCTTTAT TTAAGCACCA CCGAAGCCCG
 451 CAGCGGTAAA TCTCTAGTAG TATTGGGCAT TTTAGACTTA ATTCTCAAAA
 501 AAACCACCCG TATTGCCTAT TTTCGTCCCA TTATTCAAGA CCCAGTTAAT
 551 GGCAAACATG ATAACAACAT TATTCTGGTG CTGGAAAATT TTCGTCTCCA
 601 ACAAACCTAT ACCGATTCCT TTGGTTTGTA TTTCCATGAA GCGGTGAGTT
 651 TAGCCTCCGA TGGAGCTATT GATCAGGTAT TAGACCGAAT TTTGGCTAAA
 701 TATCGCCATT TGGCAGATCA AGTAGATTTT ATTCTCTGTG AAGGCTCAGA
 751 CTATTTGGGG GAGGAATCGG CTTTTGAATT TGATCTCAAC ACCACGATCG
 801 CCAAGATGTT GAACTGCCCC ATTTTGCTGT TGGGCAATGC CATGGGCAAC
 851 ACCATTGCCG ATAGTTTGCA ACCCATCGAT TTTCCATGGC AGCTGAGAAT
 901 ATTGTAGGAG ATCTTCTAGA AAGATCCTGT GACGGAAGTT AACTTCGCAG
 951 AATAAATAAA TCCTGGTGTC CCTGTTGATA CCGGGAAGCC CTGGGCCAAC
1001 TTTTGGCGAA AATGAGACGT TGATCGGCAC GTAAGAGGTT CCAACTTTCA
1051 CCATAATGAA ATAAGATCAC TACCGGGCGT ATTTTTTGAG TTATCGAGAT
1101 TTTCAGGAGC TAAGGAAGCT AAAATGGAGA AAAAAATCAC TGGATATACC
1151 ACCGTTGATA TATCCCAATG GCATCGTAAA GAACATTTTG AGGCATTTCA
1201 GTCAGTTGCT CAATGTACCT ATAACCAGAC CGTTCAGCTG GATATTACGG
1251 CCTTTTTAAA GACCGTAAAG AAAAATAAGC ACAAGTTTTA TCCGGCCTTT
1301 ATTCACATTC TTGCCCGCCT GATGAATGCT CATCCGGAAT TCCGTATGGC
1351 AATGAAAGAC GGTGAGCTGG TGATATGGGA TAGTGTTCAC CCTTGTTACA
1401 CCGTTTTCCA TGAGCAAACT GAAACGTTTT CATCGCTCTG GAGTGAATAC
1451 CACGACGATT TCCGGCAGTT TCTACACATA TATTCGCAAG ATGTGGCGTG
1501 TTACGGTGAA AACCTGGCCT ATTTCCCTAA AGGGTTTATT GAGAATATGT
1551 TTTTCGTCTC AGCCAATCCC TGGGTGAGTT TCACCAGTTT TGATTTAAAC
1601 GTGGCCAATA TGGACAACTT CTTCGCCCCC GTTTTCACCA TGGGCAAATA
1651 TTATACGCAA GGCGACAAGG TGCTGATGCC GCTGGCGATT CAGGTTCATC
```

Figure 10D(1)

```
1701 ATGCCGTTTG TGATGGCTTC CATGTCGGCA GAATGCTTAA TGAATTACAA
1751 CAGTACTGCG ATGAGTGGCA GGGCGGGGCG TAATTTTTTT AAGGCAGTTA
1801 TTGGTGCCCT TAAACGCCTG GTTGCTACGC CTGAATAAGT GATAATAAGC
1851 GGTTGACTGG CAGAAATTCG ATCTTGCTGA AAAACTCGAG CCATCCGGAA
1901 GATCTGGCGG CCGCTCTCCC TATAGTGAGT CGTATTACGC CGGATGGATA
1951 TGGTGTTCAG GCACAAGTGT TAAAGCAGTT GATTTTATTC ACTATGATGA
2001 AAAAAACAAT GAATGGAACC TGCTCCAAGT TAAAAATAGA GATAATACCG
2051 AAAACTCATC GAGTAGTAAG ATTAGAGATA ATACAACAAT AAAAAAATGG
2101 TTTAGAACTT ACTCACAGCG TGATGCTACT AATTGGGACA ATTTTCCAGA
2151 TGAAGTATCA TCTAAGAATT TAAATGAAGA AGACTTCAGA GCTTTTGTTA
2201 AAAATTATTT GGCAAAAATA ATATAATTCG GCTGCAGATT ACCATCCCGA
2251 ACCGGCCATT ATGAAACTAA TTGAAGGGCT ACCCGACGCC CCTCCCCTGT
2301 TGCTGACTAG CACCCACACC CATGAAACTT CCGCCCGTTT GGAAACTCTC
2351 CACCCTGCCC TGAGCCCTAC GGATAATTAT AAAATTCGCC ACAGTATTGC
2401 GCTGTTTCAA CAACAAATTG ATGGGGAGAA ATTACTCAAT TACCTTAAAA
2451 CCATCCGCAG TAAAGGTATT ACCCCAAAC TGTTTCTCTA CAATTTAGTT
2501 CAAGCCGCCA CCGCCGCCCA ACGACATATT GTCCTACCGG AAGGGGAAGA
2551 AATTCGTATT CTCAAGGCGG CCGCTAGCTT AATTAACCAC GGCATTGTCC
2601 GTTTGACTTT ACTCGGTAAC ATTGAGGCGA TCGAGCAAAC GGTAAAAATT
2651 AATCACATTG ACTTAGATTT GAGCAAAGTT CGCCTCATTA ATCCTAAAAC
2701 TAGCCCAGAC CGAGAGCGCT ACGCCGAAAC CTATTACCAG CTACGTAAAC
2751 ATAAGGGGGT AACCCTGGCC ATGGCTCGGG ATATCCTCAC CGATATTTCC
2801 TATTTTGGAA CGATGATGGT GCATTTGGGA GAGGCCGATG GCATGGTTTC
2851 TGGCTCCGTC AATACCACCC AACATACCGT GCGTCCTGCT TTACAAATTA
2901 TTAAAACCCA GCCAGGTTTT TCCTTGGTTT CTTCAGTCTT TTTTATGTGT
2951 TTAGAAGACC GAGTTTTGGT CTATGGAGAT TGTGCTGTTA ATCCCGATCC
3001 CAATGCAGAA CAGTTAGCAG AAATTGCCCT TACTTCTGCG GCTACGGCCA
3051 AGAATTTTGG CATTGAGCCC AGGGTAGCTC TATTGTCCTA TTCTTCCGGT
3101 TCTTCTGGGC AAGGGGCCGA TGTGGAAAAA GTGCGGCAAG CCACGGCGAT
3151 CGCCAAGGAA AGAGAGCCAG ATTTAGCATT GGAAGGGCCG ATCCAGTATG
3201 ATGCGGCGGT GGATTCCACA GTGGCGGCCC AAAAAATGCC TGGGTCAGCG
3251 GTGGCGGGTA AAGCAACGGT GTTTATTTTT CCCGATTTAA ATACCGGTAA
3301 CAATACTTAC AAGGCAGTGC AAAGAGAAAC AAAGGCGATC GCCATTGGCC
3351 CCATTTTACA AGGATTAAAT AAACCAGTTA ATGATCTAAG TCGGGGTTGT
```

Figure 10D(2)

```
3401 TTAGTGGAGG ATATTATTAA TACGGTGGTA ATTACAGCTT TGCAAGTTAA
3451 ATAATTTTAC TCTTAATTAG TTAAAATGAT CCCTTGAATT ACCTTGATTT
3501 TGCCCTCCAA ACTACCAATA GCTGGGCCGA AAATTGGCAT CATTTAAAAT
3551 CACCAACGTG TCCCCGGACG GAGCTAGCAC AAACAGACCC TTACCATAGG
3601 CATAGCTGAC CACTTCTTGG CTTAACACCA TGGCTGCCAC TGCACCTAAA
3651 GCTT (SEQ ID NO:17)
```

Figure 10D(3)

```
MFLLFFIVHWLKIMLPFFAQVGLEENLHETLDFTEKFLSGLENLQGLNEDDIQVGFTPKE
AVYQEDKVILYRFQPVVENPLPIPVLIVYALVNRPYMVDLQEGRSLVANLLKLGLDVYLI
DWGYPSRGDRWLTLEDYLSGYLNNCVDIICQRSQQEKITLLGVCQGGTFSLCYASLFPDK
VKNLVVMVAPVDFEQPGTLLNARGGCTLGAEAVDIDLMVDAMGNIPGDYLNLEFLMLKPL
QLGYQKYLDVPDIMGDEAKLLNFLRMEKWIFDSPDQAGETYRQFLKDFYQQNKLIKGEVM
IGDRLVDLHNLTMPILNLYAEKDHLVAPASSLALGDYLPENCDYTVQSFPVGHIGMYVSG
KVQRDLPPAIAHWLSERQ (SEQ ID NO:18)
```

Figure 11A

```
   1  TCTAGATAAT TCACCATCAA TGTTTTTACT ATTTTTTATC GTTCATTGGT
  51  TAAAAATTAT GTTGCCTTTT TTTGCTCAGG TGGGGTTAGA AGAAAATCTC
 101  CATGAAACCC TAGATTTTAC TGAAAAATTT CTCTCTGGCT TGGAAAATTT
 151  GCAGGGTTTG AATGAAGATG ACATCCAGGT GGGCTTTACC CCCAAAGAAG
 201  CAGTTTACCA GGAAGATAAG GTTATTCTTT ACCGTTTCCA ACCGGTGGTG
 251  GAAAATCCCT TACCTATCCC GGTTTTAATT GTTTACGCCC TGGTAAATCG
 301  CCCCTACATG GTGGATTTGC AGGAAGGACG CTCCCTGGTG GCCAACCTCC
 351  TCAAACTGGG TTTGGACGTG TATTTAATTG ATTGGGGTTA TCCCTCCCGG
 401  GGCGATCGTT GGATCCGTCG ACCTGCAGGG GGGGGGGGGC GCTGAGGTCT
 451  GCCTCGTGAA GAAGGTGTTG CTGACTCATA CCAGGCCTGA ATCGCCCCAT
 501  CATCCAGCCA GAAAGTGAGG GAGCCACGGT TGATGAGAGC TTTGTTGTAG
 551  GTGGACCAGT TGGTGATTTT GAACTTTTGC TTTGCCACGG AACGGTCTGC
 601  GTTGTCGGGA AGATGCGTGA TCTGATCCTT CAACTCAGCA AAAGTTCGAT
 651  TTATTCAACA AAGCCGCCGT CCCGTCAAGT CAGCGTAATG CTCTGCCAGT
 701  GTTACAACCA ATTAACCAAT TCTGATTAGA AAAACTCATC GAGCATCAAA
 751  TGAAACTGCA ATTTATTCAT ATCAGGATTA TCAATACCAT ATTTTTGAAA
 801  AAGCCGTTTC TGTAATGAAG GAGAAAACTC ACCGAGGCAG TTCCATAGGA
 851  TGGCAAGATC CTGGTATCGG TCTGCGATTC CGACTCGTCC AACATCAATA
 901  CAACCTATTA ATTTCCCCTC GTCAAAAATA AGGTTATCAA GTGAGAAATC
 951  ACCATGAGTG ACGACTGAAT CCGGTGAGAA TGGCAAAAGC TTATGCATTT
1001  CTTTCCAGAC TTGTTCAACA GGCCAGCCAT TACGCTCGTC ATCAAAATCA
1051  CTCGCATCAA CCAAACCGTT ATTCATTCGT GATTGCGCCT GAGCGAGACG
1101  AAATACGCGA TCGCTGTTAA AAGGACAATT ACAAACAGGA ATCGAATGCA
1151  ACCGGCGCAG GAACACTGCC AGCGCATCAA CAATATTTTC ACCTGAATCA
1201  GGATATTCTT CTAATACCTG GAATGCTGTT TTCCCGGGGA TCGCAGTGGT
1251  GAGTAACCAT GCATCATCAG GAGTACGGAT AAAATGCTTG ATGGTCGGAA
1301  GAGGCATAAA TTCCGTCAGC CAGTTTAGTC TGACCATCTC ATCTGTAACA
1351  TCATTGGCAA CGCTACCTTT GCCATGTTTC AGAAACAACT CTGGCGCATC
1401  GGGCTTCCCA TACAATCGAT AGATTGTCGC ACCTGATTGC CCGACATTAT
1451  CGCGAGCCCA TTTATACCCA TATAAATCAG CATCCATGTT GGAATTTAAT
1501  CGCGGCCTCG AGCAAGACGT TTCCCGTTGA ATATGGCTCA TAACACCCCT
```

Figure 11C(1)

```
1551  TGTATTACTG TTTATGTAAG CAGACAGTTT TATTGTTCAT GATGATATAT
1601  TTTTATCTTG TGCAATGTAA CATCAGAGAT TTTGAGACAC AACGTGGCTT
1651  TCCCCCCCCC CCCTGCAGGT CGACGGATCC TCTTAACCTA GAATTTCTCA
1701  TGCTTAAACC CCTGCAATTA GGTTACCAAA AGTATCTTGA TGTGCCCGAT
1751  ATTATGGGGG ATGAAGCGAA ATTGTTAAAC TTTCTACGCA TGGAAAAATG
1801  GATTTTTGAT AGTCCCGATC AAGCGGGGA AACTTACCGT CAATTCCTCA
1851  AGGATTTTTA TCAACAAAAT AAATTGATCA AAGGGGAAGT GATGATTGGC
1901  GATCGCCTGG TGGATCTGCA TAATTTGACC ATGCCCATAT TGAATTTATA
1951  TGCGGAAAAA GACCACTTGG TGGCCCCTGC TTCTTCCCTA GCTTTGGGGG
2001  ACTATTTGCC GGAAAACTGT GACTACACCG TCCAATCTTT CCCCGTGGGT
2051  CATATTGGCA TGTATGTCAG TGGTAAAGTA CAACGGGATC TGCCCCCGGC
2101   GATCGCCCAT TGGCTATCGA T (SEQ ID NO:19)
```

Figure 11C(2)

MKKVLAIILGGGAGTRLYPLTKLRAKPAVPVAGKYRLIDIPVSNCINSEIFKIYVLTQFN
SASLNRHIARTYNFSGFSEGFVEVLAAQQTPENPNWFQGTADAVRQYLWMLQEWDVDEFL
ILSGDHLYRMDYRLFIQRHRETNADITLSVIPIDDRRASDFGLMKIDNSGRVIDFSEKPK
GEALTKMRVDTTVLGLTPEQAASQPYIASMGIYVFKKDVLIKLLKEALERTDFGKEIIPD
AAKDHNVQAYLFDDYWEDIGTIEAFYNANLALTQQPMPPFSFYDEEAPIYTRARYLPPTK
LLDCHVTESIIGEGCILKNCRIQHSVLGVRSRIETGCMIEESLLMGADFYQASVERQCSI
DKGDIPVGIGPDTIIRRAIIDKNARIGHDVKIINKDNVQEADRESQGFYIRSGIVVVLKN
AVITDGTII (SEQ ID NO:20)

Figure 11D

```
   1 gagctctgtt aacagtcaac agtcatttca caaattaagg caagattaag
  51 aaaatactgt aaccattaac atatctaata tttttaatca tgagtgcaaa
 101 ttaatacagt ggaaattgtt ttctgatcaa tggctgcacg atacgtcacc
 151 agtaaggttt tttaaaattc attcaagata atctttgatc cccccttacc
 201 agctgccaca gacagtccta aactgtaggt gggagttgaa aggcagttgg
 251 gagaaatctt gtgaaaaaag tcttagcaat tattcttggt ggtggtgcgg
 301 gtactcgcct ttacccacta accaaactcc gcgctaaacc ggcagtacca
 351 gtggcaggga ataccgcct aatagatatc cctgtcagta actgcattaa
 401 ttcggaaatt tttaaaatct acgtattaac acaatttaac tcagcttctc
 451 tcaatcgcca cattgcccgt acctacaact ttagtggttt tagcgagggt
 501 tttgtggaag tgctggccgc ccagcagaca ccagagaacc ctaactggtt
 551 ccaaggtaca gccgatgctg tacgtcagta tctctggatg ttacaagagt
 601 gggacgtaga tgaatttttg atcctgtcgg gggatcacct gtaccggatg
 651 gactatcgcc tatttatcca gcgccatcta gaggatcccc aaatggcaaa
 701 ttatttatga cggtaggctt aatagcctgt aaaaatttgt aacaatattt
 751 tttgttttg caataaacaa aaacaaatgc ctccgattag aaatcggagg
 801 cattgtttgc ttgaaaatca agacaggacg gaaaaccgtt ttcctgtttt
 851 gaaattagaa agcgctcagg aagagttctt caacttcttt ctgatcaccc
 901 tgacgcgggt tggtcagagc acaagcatct ttcagagcgt ggtcagcaag
 951 aagcggcaca tcttctttct tagcacccag ctcggtcaga tttgctggaa
1001 taccaatgga agcagccaga tcgcgaacag cctgaatggt ggcttctgcg
1051 ccttctttat caccgagatt ggcgatatcg agacccatag caacaccaac
1101 gtctttcaga cgaccagcaa cgacagaggc gttataagcc agaacatgcg
1151 gaagcagaac agcgttgcag acaccatgcg gcaggttgta gtagccgccc
1201 aactggtgag ccatagcatg gacataacca agcgaagcgt tgttgaaggc
1251 cataccagcg aggaattggg cataagccat agcttcacga gctggcatat
1301 ccttaccgtt gtcgcaagcg gtcttcagat tcttagcgat catggacgca
1351 gccttcaagg cgcaagcatc ggtgatcgga gtagctgccg ttgaagaata
1401 agcttcaaat gcgtgggtca gagcatccat accggtggcg gcggtcaggc
1451 cttttggcat accaaccatc aacagaggat cgttgacgga aaccatcggg
1501 gtaacgtgac ggtcaacaat ggccatctta acgtgacgga cttcatcagt
1551 gatgatgcag aaacgcgtca tttcagaagc cgtaccagcc gtcgtgttga
1601 ttgacatcaa aggcagggca ggtttcttag atttgtcgat accttcgtag
```

Figure 11F(1)

```
1651 tctttgactt caccaccatt ggttgcgacc agagcgatgg ctttggcgca
1701 gtcatgggga gaaccaccac cgagggagat gacgaagtct gaattgttat
1751 ccttcaggat cttaaggcct tccagaactg cggtaacagt cgggttcggc
1801 ataacgccat cataaacagc agaattaata ccctgtgctt tcaacaggtc
1851 agcaacctgc ttcacaacac cggatttgtt catgaaagca tcagaaacga
1901 tcagcgcatt tttaaagccg ctgccgttaa gatccttgat tgctttttca
1951 agcgaacctt cgcccatttc gttgacgaaa ggaatataaa aagttgaaga
2001 agccatagct ataacctcac cctacatact agtttgggta ccgagctcga
2051 attgatcccc aaaaactaga ggagcttgtt aacaggctta cggctgttgg
2101 cggcagcaac gcgcttaccc catttgacca attcttcagt gcagtcttca
2151 cgaccgatga agcattcgat cagggttggg ccgtcggtgt ttgccagagc
2201 aaccttgata gcttctgcca gttcgccacc ggttttagcc ttcaggcctt
2251 taccagcacc gctgtcataa ccaccgttac cgttgaacac ttccatcaga
2301 ccggcataat cccagttctt gatgttgttg tacggaccat catggatcat
2351 aacttcgatg gtgtaaccat agttattgat caagaagatg ataaccggca
2401 gtttcaggcg aaccatctga gcgacttcct gagccgtcag ctggaaggaa
2451 ccatcaccaa ccatgaggat gttgcgacgt tccggagcac cgacggcata
2501 accgaaggcg gcaggaacgg accaaccgat gtgaccccac tgcatttcat
2551 attcaacgcg agcaccgttc gggagcttca tgcgctgagc attgaaccaa
2601 gagtcaccgg tttcagcaat aaccgtcgtg ttcggggtca gaagagcttc
2651 gacctgacgg gcgatttctg cgttgaccaa cggagcactc ggatcagccg
2701 gagcggcttt cttcagttca cctgcattga gggatttgaa gaagtccaaa
2751 gcaccggttt tcttggaaac tttctgagcc aaacgggtca gatagtcttt
2801 cagatgaacg ctggggaagc gaacgccgtt aacgacgaca gaacgcggtt
2851 cagcgagaac cagtttctta ggatcaggaa tatccgtcca accagtggtg
2901 gagtagtcgt tgaagacagg agccagagcg ataaccgcat cggcttcttt
2951 catcgtcttt tcaacgcccg gatagctgac ttcaccccat gaggtaccga
3001 tgtaatgcgg gtttcttct gggaagaagc ttttgcagc agccatggta
3051 gcaactgcgc caccgagagc atcagcaaat tgacagcag cttcttcagc
3101 accagctgcg cgcagcttgc tgccgacgag gacggcaact ttgtcgcggt
3151 tggcgatgaa tttcagggtt tcttcaaccg ctgcattcaa agaagcttcg
```

Figure 11F(2)

```
3201 tcgctggctt cgtcattgaa caatgcgctt gccggtccag gagcggcgca
3251 gggcatggaa gcaatgttgc aagcgatttc gagataaacc ggcttcttct
3301 cacgaagagc agttttaatc acgtgatcga ttttagccgg agcttcttct
3351 ggggtgtaaa tcgcttcagc tgcggccgtg atgttcttgg ccatttccaa
3401 ctgatagtga tagtcggttt tgccaagagc gtgatgcaac acgtgaccag
3451 cagcgtgatc attgttgttc ggagcaccgg agatcaggat aaccggaagg
3501 ttttctgcat aggcgccacc gatagcatca aatgcggaaa gcgcaccgac
3551 gctgtaggta acgacggctg ctgctgcgcc tttggcacga cataaccttc
3601 ctgcactgaa accgcagttc agttcgttac agcaataaac ctgctccatg
3651 tttttgttca aaagcaggtt gtcaagaagg acgaggttgt agtcgcccgc
3701 gactgcgaag tgatgcttga gaccaatctg gacaagccgc tccgctaaat
3751 aggtaccgac agtataagaa ttcatggcgt tctcctaacc tgtagtttta
3801 ttttcttat ttcattttaa ataaaatcga caccaaatat gacaatctgt
3851 catacttcgg gcaaattttt tttgagatcg cgataaatcc agggaaaaat
3901 gctctgcgat cgctaaaaat cactataatt acatggcact aaaaaactta
3951 tggctaaaaa tacatcaata tatgcagcca gagcgacaaa ttaaattttt
4001 tatttatgtg atgtagataa aagatatctt tccctatac ccctacactc
4051 tccttcaagt catagaggcg cggagattgc ccaattttat tagctgtgta
4101 ctcagtacct cagcaaaaaa gtcgacatat gtttctcggc aaaaattaat
4151 tatcgattgg ctggaacctg gtcaaaccag gcttttcat ccattggaaa
4201 agcgattttg atcatctagg gtcaggagca aagatccccg gtgggcgaag
4251 aactccagca tgagatcccc gcgctggagg atcatccagc cggcgtcccg
4301 gaaaacgatt ccgaagccca acctttcata gaaggcggcg gtggaatcga
4351 aatctcgtga tggcaggttg ggcgtcgctt ggtcggtcat ttcgaacccc
4401 agagtcccgc tcagaagaac tcgtcaagaa ggcgatagaa ggcgatgcgc
4451 tgcgaatcgg gagcggcgat accgtaaagc acgaggaagc ggtcagccca
4501 ttcgccgcca agctcttcag caatatcacg ggtagccaac gctatgtcct
4551 gatagcggtc cgccacaccc agccggccac agtcgatgaa tccagaaaag
4601 cggccatttt ccaccatgat attcggcaag caggcatcgc catgggtcac
4651 gacgagatcc tcgccgtcgg gcatgcgcgc cttgagcctg gcgaacagtt
4701 cggctggcgc gagcccctga tgctcttcgt ccagatcatc ctgatcgaca
4751 agaccggctt ccatccgagt acgtgctcgc tcgatgcgat gtttcgcttg
```

Figure 11F(3)

```
4801 gtggtcgaat gggcaggtag ccggatcaag cgtatgcagc cgccgcattg
4851 catcagccat gatggatact ttctcggcag gagcaaggtg agatgacagg
4901 agatcctgcc ccggcacttc gcccaatagc agccagtccc ttcccgcttc
4951 agtgacaacg tcgagcacag ctgcgcaagg aacgcccgtc gtggccagcc
5001 acgatagccg cgctgcctcg tcctgcagtt cattcagggc accggacagg
5051 tcggtcttga caaaaagaac cgggcgcccc tgcgctgaca gccggaacac
5101 ggcggcatca gagcagccga ttgtctgttg tgcccagtca tagccgaata
5151 gcctctccac ccaagcggcc ggagaacctg cgtgcaatcc atcttgttca
5201 atcatgcgaa acgatcctca tcctgtctct tgatcagatc cgtccttgtt
5251 attcaacagt ataacatgtc ttatacgccc gtgtcaacca atattcattg
5301 agatcctcta gacgagtcat tgatttcagt gaaaaaccca agggcgaagc
5351 cttaaccaaa atgcgtgttg ataccacggt tttaggcttg acaccagaac
5401 aggcggcatc acagccttac attgcctcga tggggattta cgtatttaaa
5451 aaagacgttt tgatcaagct gttgaaggaa gctttagaac gtactgattt
5501 cggcaaagaa attattcctg atgccgccaa agatcacaac gttcaagctt
5551 acctattcga tgactactgg aagatattg ggacaatcga agctttttat
5601 aacgccaatt tagcgttaac tcagcagccc atgccgccct ttagcttcta
5651 cgatgaagaa gcacctattt atacccgcgc tcgttactta ccacccacaa
5701 aactattaga ttccacgtt acagaatcaa tcattggcga aggctgtatt
5751 ctgaaaaact gtcgcattca acactcagta ttgggagtgc gatcgcgtat
5801 tgaaactggc tgcatgatcg aagaatcttt actcatgggt gccgacttct
5851 accaagcttc agtggaacgc cagtgcagca tcgataaagg agacatccct
5901 gtaggcatcg ctcgag (SEQ ID NO:21)
```

Figure 11F(4)

MKKVLAIILGGGAGTRLYPLTKLRAKPAVPVAGKYRLIDIPVSNCINSEIFKIYVLTQFN
SASLNRHIARTYNFSGFSEGFVEVLAAQQTPENPNWFQGTADAVRQYLWMLQEWDVDEFL
ILSGDHLYRMDYRLFIQRHRETNADITLSVIPIDDRRASDFGLMKIDNSGRVIDFSEKPK
GEALTKMRVDTTVLGLTPEQAASQPYIASMGIYVFKKDVLIKLLKESLERTDFGKEIIPD
ASKDHNVQAYLFDDYWEDIGTIEAFYNANLALTQQPMPPFSFYDEEAPIYTRARYLPPTK
LLDCHVTESIIGEGCILKNCRIQHSVLGVRSRIETGCVIEESLLMGADFYQASVERQCSI
DKGDIPVGIGPDTIIRRAIIDKNARIGHDVKIINKDNVQEADRESQGFYIRSGIVVVLKN
AVITDGTII (SEQ ID NO:22)

Figure 11G

MAETLLFAALRQALDEEMGRDVNVLVLGEDVGLYGGSYKVTKDLYEKYGEMRVLDTPIAE
NSFTGMAVGAAMTGLRPVIEGMNMGFLLLAFNQIANNAGMLRYTSGGNYQIPMVIRGPGG
VGRQLGAEHSQRLEAYFHAVPGLKIVACSTPYNAKGLLKAAIRDNNPVLFFEHVLLYNLK
ENLPDYEYIVPLDKAEVVRPGKDVTILTYSRMRHHCLQALKTLEKEGYDPEIIDLISLKP
FDMETISASVKKTHRVIIVEECMKTGGIGAELIALINDHLFDELDGPVVRLSSQDIPTPY
NGMLERLTIVQPPQIVDAVKAIIG (SEQ ID NO:23)

Figure 12A

```
  1 CGATATAATT TCCGGGTCGT AGCCTTCTTT TTCCAAAGTT TTTAGTGCCT
 51 GTAAACAATG GTGACGCATG CGGGAATAGG TCAAAATAGT GACATCCTTA
101 CCGGGGCGCA CCACTTCGGC TTTATCCAGA GGCACAATAT ATTCGTAGTC
151 GGGTAAGTTT TCTTTCAAGT TGTACAAAAG TACGTGCTCA AAAAATAACA
201 CTGGGTTATT ATCCCGAATG GCTGCCGCTC GGTTGCCGCC GGGCGTTTTT
251 TATTCCA (SEQ ID NO:24)
```

Figure 12C

```
   1 ATATGGCTGA GACCCTACTG TTTGCCGCCC TACGCCAAGC CCTTGACGAA
  51 GAAATGGGAC GGGATGTCAA CGTCCTTGTG CTGGGAGAAG ATGTGGGACT
 101 CTATGGCGGT TCCTATAAGG TAACCAAGGA TTTGTACGAG AAGTATGGCG
 151 AAATGCGGGT GCTGGATACG CCCATCGCCG AAAACAGTTT TACCGGCATG
 201 GCGGTGGGGG CGGCCATGAC AGGATTGCGC CCAGTCATTG AAGGCATGAA
 251 TATGGGTTTT CTTCTGCTGG CGTTTAACCA AATTGCCAAT AATGCGGGGA
 301 TGTTGCGCTA TACCTCCGGC GGCAATTACC AAATTCCCAT GGTTATCCGT
 351 GGTCCTGGGG GCGTAGGTCG GCAATTAGGG GCAGAACATT CCCAACGGTT
 401 GGAGGCCTAT TTCCATGCGG TGCCGGGGTT AAAAATTGTG GCTTGCTCCA
 451 CCCCCTATAA CGCCAAGGGA TTGCTCAAAG CAGCCATTCG GGATAATAAC
 501 CCAGTGTTAT TTTTTGAGCA CGTACTTTTG TACAACTTGA AAGAAAACTT
 551 ACCCGACTAC GAATATATTG TGCCTCTGGA TAAAGCCGAA GTGGTGCGCC
 601 CCGGTAAGGA TGTCACTATT TTGACCTATT CCCGCATGCG TCACCATTGT
 651 TTACAGGCAC TAAAAACTTT GGAAAAAGAA GGCTACGACC CGGAAATTAT
 701 TGATTTGATT TCCCTCAAGC CTTTTGACAT GGAAACCATC AGCGCTTCGG
 751 TGAAGAAAAC CCATCGGGTC ATTATTGTCG AAGAATGTAT GAAAACCGGA
 801 GGCATCGGCG CTGAGCTCAT TGCCCTAATC AATGATCATC TCTTTGATGA
 851 GTTAGATGGG CCGGTGGTGC GCCTTTCTTC CCAAGATATT CCCACTCCCT
 901 ACAACGGTAT GTTGGAACGA CTGACCATTG TGCAACCGCC CCAAATTGTG
 951 GACGCAGTTA AGGCGATCAT CGGCTAATTG GCCTCAAAAC AGTACCCCTT
1001 GCCGTAAACG GAATTAATCA GGCGGGGGGC ATTGGGCTGT TCAATTTTGC
1051 GCCGCAGTAA TCGCACCAGG GCCGCCAGCA CGTTACTACT GGGGGGGCTT
1101 TCGCCGGGCC AAAGGTGGGA ATAGATCT (SEQ ID NO:25)
```

Figure 12E

```
   1 GGGATTAATC GACATCCACC CTTGTCCCCT GACTAAAATC TCCGCTATGG
  51 TGGCCAGCCA GTGTGTCAAA ATACTAGATT GTTGTGCCCC GATCGCCCTT
 101 GCTTGGTTTG CCTACACCGG ACCAACAAGG AGAGATGCGG CGGCGGTCTA
 151 AATTGTTATT AAAAACTAAG TTTTCCCCCA GAAATCATGG CTGAGACCCT
 201 ACTGTTTGCC GCCCTACGCC AAGCCCTTGA CGAAGAAATG GGACGGGATG
 251 TCAACGTCCT TGTGCTGGGA GAAGATGTGG GACTCTATGG CGGTTCCTAT
 301 AAGGTAACCA AGGATTTGTA CGAGAAGTAT GGCGAAATGC GGGTGCTGGA
 351 TACGCCCATC GCCGAAAACA GTTTTACCGG CATGGCGGTG GGGGCGGCCA
 401 TGACAGGATT GCGCCCAGTC ATTGAAGGCA TGAATATGGG TTTTCTTCTG
 451 CTGGCGTTTA ACCAAATTGC CAATAATGCG GGATGTTGC GCTATACCTC
 501 CGGCGGCAAT TACCAAATTC CCATGGTTAT CCGTGGTCCT GGGGGCGTAG
 551 GTCGGCAATT AGGGGCAGAA CATTCCCAAC GGTTGGAGGG AATTCCCCGG
 601 ATCCGTCGAC CTGCAGGGGG GGGGGGGCGC TGAGGTCTGC CTCGTGAAGA
 651 AGGTGTTGCT GACTCATACC AGGCCTGAAT CGCCCCATCA TCCAGCCAGA
 701 AAGTGAGGGA GCCACGGTTG ATGAGAGCTT TGTTGTAGGT GGACCAGTTG
 751 GTGATTTTGA ACTTTTGCTT TGCCACGGAA CGGTCTGCGT TGTCGGGAAG
 801 ATGCGTGATC TGATCCTTCA ACTCAGCAAA AGTTCGATTT ATTCAACAAA
 851 GCCGCCGTCC CGTCAAGTCA GCGTAATGCT CTGCCAGTGT TACAACCAAT
 901 TAACCAATTC TGATTAGAAA AACTCATCGA GCATCAAATG AAACTGCAAT
 951 TTATTCATAT CAGGATTATC AATACCATAT TTTTGAAAAA GCCGTTTCTG
1001 TAATGAAGGA GAAAACTCAC CGAGGCAGTT CCATAGGATG CAAGATCCT
1051 GGTATCGGTC TGCGATTCCG ACTCGTCCAA CATCAATACA ACCTATTAAT
1101 TTCCCCTCGT CAAAATAAG GTTATCAAGT GAGAAATCAC CATGAGTGAC
1151 GACTGAATCC GGTGAGAATG GCAAAAGCTT ATGCATTTCT TTCCAGACTT
1201 GTTCAACAGG CCAGCCATTA CGCTCGTCAT CAAAATCACT CGCATCAACC
1251 AAACCGTTAT TCATTCGTGA TTGCGCCTGA GCGAGACGAA ATACGCGATC
1301 GCTGTTAAAA GGACAATTAC AAACAGGAAT CGAATGCAAC CGGCGCAGGA
1351 ACACTGCCAG CGCATCAACA ATATTTTCAC CTGAATCAGG ATATTCTTCT
1401 AATACCTGGA ATGCTGTTTT CCCGGGGATC GCAGTGGTGA GTAACCATGC
1451 ATCATCAGGA GTACGGATAA AATGCTTGAT GGTCGGAAGA GGCATAAATT
1501 CCGTCAGCCA GTTTAGTCTG ACCATCTCAT CTGTAACATC ATTGGCAACG
1551 CTACCTTTGC CATGTTTCAG AAACAACTCT GGCGCATCGG GCTTCCCATA
1601 CAATCGATAG ATTGTCGCAC CTGATTGCCC GACATTATCG CGAGCCCATT
1651 TATACCCATA TAAATCAGCA TCCATGTTGG AATTTAATCG CGGCCTCGAG
```

Figure 12G(1)

```
1701 CAAGACGTTT CCCGTTGAAT ATGGCTCATA ACACCCCTTG TATTACTGTT
1751 TATGTAAGCA GACAGTTTTA TTGTTCATGA TGATATATTT TTATCTTGTG
1801 CAATGTAACA TCAGAGATTT TGAGACACAA CGTGGCTTTC CCCCCCCCCC
1851 CTGCAGGTCG ACGGATCCGG GGAATTCCCT ATTTCCATGC GGTGCCGGGG
1901 TTAAAAATTG TGGCTTGCTC CACCCCCTAT AACGCCAAGG GATTGCTCAA
1951 AGCAGCCATT CGGGATAATA ACCCAGTGTT ATTTTTTGAG CACGTACTTT
2001 TGTACAACTT GAAAGAAAAC TTACCCGACT ACGAATATAT TGTGCCTCTG
2051 GATAAAGCCG AAGTGGTGCG CCCCGGTAAG GATGTCACTA TTTTGACCTA
2101 TTCCCGCATG CGTCACCATT GTTTACAGGC ACTAAAAACT TTGGAAAAAG
2151 AAGGCTACGA CCCGGAAATT ATTGATTTGA TTTCCCTCAA GCCTTTTGAC
2201 ATGGAAACCA TCAGCGCTTC GGTGAAGAAA ACCCATCGGG TCATTATTGT
2251 CGAAGAATGT ATGAAAACCG GAGGCATCGG CGCTGAGCTC ATTGCCCTAA
2301 TCAATGATCA TCTCTTTGAT GAGTTAGATG GGCCGGTGGT GCGCCTTTCT
2351 TCCCAAGATA TTCCCACTCC CTACAACGGT ATGTTGGAAC GACTGACCAT
2401 TGTGCAACCG CCCCAAATTG TGGACGCAGT TAAGGCAATC A (SEQ ID NO:26)
```

Figure 12G(2)

```
   1 GGGCGAATTG GGCCCGACGT CGCATGCTCC CGGCCGCCAT GGCCGCGGGA
  51 T*ATCACTAGT GCGGCCGCCT GCAGGTCGAC CATATGGGAG AGCTCCCAAC
 101 GCGTTGGATG CATAGCTTGA GTATTCTATA GTGTCACCTA AATAGCTTGG
 151 CGTAATCATG GTCATAGCTG TTTCCTGTGT GAAATTGTTA TCCGCTCACA
 201 ATTCCACACA ACATACGAGC CGGAAGCATA AAGTGTAAAG CCTGGGGTGC
 251 CTAATGAGTG AGCTAACTCA CATTAATTGC GTTGCGCTCA CTGCCCGCTT
 301 TCCAGTCGGG AAACCTGTCG TGCCAGCTGC ATTAATGAAT CGGCCAACGC
 351 GCGGGGAGAG GCGGTTTGCG TATTGGGCGC TCTTCCGCTT CCTCGCTCAC
 401 TGACTCGCTG CGCTCGGTCG TTCGGCTGCG GCGAGCGGTA TCAGCTCACT
 451 CAAAGGCGGT AATACGGTTA TCCACAGAAT CAGGGGATAA CGCAGGAAAG
 501 AACATGTGAG CAAAAGGCCA GCAAAAGGCC AGGAACCGTA AAAAGGCCGC
 551 GTTGCTGGCG TTTTTCCATA GGCTCCGCCC CCCTGACGAG CATCACAAAA
 601 ATCGACGCTC AAGTCAGAGG TGGCGAAACC CGACAGGACT ATAAAGATAC
 651 CAGGCGTTTC CCCCTGGAAG CTCCCTCGTG CGCTCTCCTG TTCCGACCCT
 701 GCCGCTTACC GGATACCTGT CCGCCTTTCT CCCTTCGGGA AGCGTGGCGC
 751 TTTCTCATAG CTCACGCTGT AGGTATCTCA GTTCGGTGTA GGTCGTTCGC
 801 TCCAAGCTGG GCTGTGTGCA CGAACCCCCC GTTCAGCCCG ACCGCTGCGC
 851 CTTATCCGGT AACTATCGTC TTGAGTCCAA CCCGGTAAGA CACGACTTAT
 901 CGCCACTGGC AGCAGCCACT GGTAACAGGA TTAGCAGAGC GAGGTATGTA
 951 GGCGGTGCTA CAGAGTTCTT GAAGTGGTGG CCTAACTACG GCTACACTAG
1001 AAGAACAGTA TTTGGTATCT GCGCTCTGCT GAAGCCAGTT ACCTTCGGAA
1051 AAAGAGTTGG TAGCTCTTGA TCCGGCAAAC AAACCACCGC TGGTAGCGGT
1101 GGTTTTTTTG TTTGCAAGCA GCAGATTACG CGCAGAAAAA AAGGATCTCA
1151 AGAAGATCCT TTGATCTTTT CTACGGGGTC TGACGCTCAG TGGAACGAAA
1201 ACTCACGTTA AGGGATTTTG GTCATGAGAT TATCAAAAAG GATCTTCACC
1251 TAGATCCTTT TAAATTAAAA ATGAAGTTTT AAATCAATCT AAAGTATATA
1301 TGAGTAAACT TGGTCTGACA GTTACCAATG CTTAATCAGT GAGGCACCTA
1351 TCTCAGCGAT CTGTCTATTT CGTTCATCCA TAGTTGCCTG ACTCCCCGTC
1401 GTGTAGATAA CTACGATACG GGAGGGCTTA CCATCTGGCC CCAGTGCTGC
1451 AATGATACCG CGAGACCCAC GCTCACCGGC TCCAGATTTA TCAGCAATAA
1501 ACCAGCCAGC CGGAAGGGCC GAGCGCAGAA GTGGTCCTGC AACTTTATCC
1551 GCCTCCATCC AGTCTATTAA TTGTTGCCGG GAAGCTAGAG TAAGTAGTTC
1601 GCCAGTTAAT AGTTTGCGCA ACGTTGTTGC CATTGCTACA GGCATCGTGG
```

Figure 13B(1)

```
1651 TGTCACGCTC GTCGTTTGGT ATGGCTTCAT TCAGCTCCGG TTCCCAACGA
1701 TCAAGGCGAG TTACATGATC CCCCATGTTG TGCAAAAAAG CGGTTAGCTC
1751 CTTCGGTCCT CCGATCGTTG TCAGAAGTAA GTTGGCCGCA GTGTTATCAC
1801 TCATGGTTAT GGCAGCACTG CATAATTCTC TTACTGTCAT GCCATCCGTA
1851 AGATGCTTTT CTGTGACTGG TGAGTACTCA ACCAAGTCAT TCTGAGAATA
1901 GTGTATGCGG CGACCGAGTT GCTCTTGCCC GGCGTCAATA CGGGATAATA
1951 CCGCGCCACA TAGCAGAACT TTAAAAGTGC TCATCATTGG AAAACGTTCT
2001 TCGGGGCGAA AACTCTCAAG GATCTTACCG CTGTTGAGAT CCAGTTCGAT
2051 GTAACCCACT CGTGCACCCA ACTGATCTTC AGCATCTTTT ACTTTCACCA
2101 GCGTTTCTGG GTGAGCAAAA ACAGGAAGGC AAAATGCCGC AAAAAAGGGA
2151 ATAAGGGCGA CACGGAAATG TTGAATACTC ATACTCTTCC TTTTTCAATA
2201 TTATTGAAGC ATTTATCAGG GTTATTGTCT CATGAGCGGA TACATATTTG
2251 AATGTATTTA GAAAAATAAA CAAATAGGGG TTCCGCGCAC ATTTCCCCGA
2301 AAAGTGCCAC CTGATGCGGT GTGAAATACC GCACAGATGC GTAAGGAGAA
2351 AATACCGCAT CAGGAAATTG TAAGCGTTAA TATTTTGTTA AAATTCGCGT
2401 TAAATTTTTG TTAAATCAGC TCATTTTTTA ACCAATAGGC CGAAATCGGC
2451 AAAATCCCTT ATAAATCAAA AGAATAGACC GAGATAGGGT TGAGTGTTGT
2501 TCCAGTTTGG AACAAGAGTC CACTATTAAA GAACGTGGAC TCCAACGTCA
2551 AAGGGCGAAA AACCGTCTAT CAGGGCGATG GCCCACTACG TGAACCATCA
2601 CCCTAATCAA GTTTTTTGGG GTCGAGGTGC CGTAAAGCAC TAAATCGGAA
2651 CCCTAAAGGG AGCCCCCGAT TTAGAGCTTG ACGGGGAAAG CCGGCGAACG
2701 TGGCGAGAAA GGAAGGGAAG AAAGCGAAAG GAGCGGGCGC TAGGGCGCTG
2751 GCAAGTGTAG CGGTCACGCT GCGCGTAACC ACCACACCCG CCGCGCTTAA
2801 TGCGCCGCTA CAGGGCGCGT CCATTCGCCA TTCAGGCTGC GCAACTGTTG
2851 GGAAGGGCGA TCGGTGCGGG CCTCTTCGCT ATTACGCCAG CTGGCGAAAG
2901 GGGGATGTGC TGCAAGGCGA TTAAGTTGGG TAACGCCAGG GTTTTCCCAG
2951 TCACGACGTT GTAAAACGAC GGCCAGTGAA TTGTAATACG ACTCACTATA (SEQ ID
NO:27)
```

Figure 13B(2)

```
   1 GCGCCCAATA CGCAAACCGC CTCTCCCCGC GCGTTGGCCG ATTCATTAAT
  51 GCAGCTGGCA CGACAGGTTT CCCGACTGGA AAGCGGGCAG TGAGCGCAAC
 101 GCAATTAATG TGAGTTAGCT CACTCATTAG GCACCCCAGG CTTTACACTT
 151 TATGCTTCCG GCTCGTATGT TGTGTGGAAT TGTGAGCGGA TAACAATTTC
 201 ACACAGGAAA CAGCTATGAC CATGATTACG CCAAGCTCTA ATACGACTCA
 251 CTATAGGGAA AGCTCGGTAC CACGCATGCT GCAGACGCGT TACGTATCGG
 301 ATCCAGAATT CGTGATATCT GAATTCGTCG ACAAGCTTCT CGAGCCTAGG
 351 CTAGCTCTAG ACCACACGTG TGGGGCCCG AGCTCGCGGC CGCTGTATTC
 401 TATAGTGTCA CCTAAATGGC CGCACAATTC ACTGGCCGTC GTTTTACAAC
 451 GTCGTGACTG GGAAAACCCT GGCGTTACCC AACTTAATCG CCTTGCAGCA
 501 CATCCCCCTT TCGCCAGCTG GCGTAATAGC GAAGAGGCCC GCACCGATCG
 551 CCCTTCCCAA CAGTTGCGCA GCCTGAATGG CGAATGGAAA TTGTAAGCGT
 601 TAATATTTTG TTAAAATTCG CGTTAAATTT TTGTTAAATC AGCTCATTTT
 651 TTAACCAATA GGCCGAAATC GGCAAAATCC CTTATAAATC AAAAGAATAG
 701 ACCGAGATAG GGTTGAGTGT TGTTCCAGTT TGGAACAAGA GTCCACTATT
 751 AAAGAACGTG GACTCCAACG TCAAAGGGCG AAAAACCGTC TATCAGGGCG
 801 ATGGCCCACT ACGTGAACCA TCACCCTAAT CAAGTTTTTT GGGGTCGAGG
 851 TGCCGTAAAG CACTAAATCG GAACCCTAAA GGGAGCCCCC GATTTAGAGC
 901 TTGACGGGGA AAGCCGGCGA ACGTGGCGAG AAAGGAAGGG AAGAAAGCGA
 951 AAGGAGCGGG CGCTAGGGCG CTGGCAAGTG TAGCGGTCAC GCTGCGCGTA
1001 ACCACCACAC CCGCCGCGCT TAATGCGCCG CTACAGGGCG CGTCAGGTGG
1051 CACTTTTCGG GGAAATGTGC GCGGAACCCC TATTTGTTTA TTTTTCTAAA
1101 TACATTCAAA TATGTATCCG CTCATGAGAC AATAACCCTG ATAAATGCTT
1151 CAATAATATT GAAAAAGGAA GAGTATGAGT ATTCAACATT TCCGTGTCGC
1201 CCTTATTCCC TTTTTTGCGG CATTTGCCT TCCTGTTTTT GCTCACCCAG
1251 AAACGCTGGT GAAAGTAAAA GATGCTGAAG ATCAGTTGGG TGCACGAGTG
1301 GGTTACATCG AACTGGATCT CAACAGCGGT AAGATCCTTG AGAGTTTTCG
1351 CCCCGAAGAA CGTTTTCCAA TGATGAGCAC TTTTAAAGTT CTGCTATGTG
1401 GCGCGGTATT ATCCCGTATT GACGCCGGGC AAGAGCAACT CGGTCGCCGC
1451 ATACACTATT CTCAGAATGA CTTGGTTGAG TACTCACCAG TCACAGAAAA
1501 GCATCTTACG GATGGCATGA CAGTAAGAGA ATTATGCAGT GCTGCCATAA
1551 CCATGAGTGA TAACACTGCG GCCAACTTAC TTCTGACAAC GATCGGAGGA
1601 CCGAAGGAGC TAACCGCTTT TTTGCACAAC ATGGGGGATC ATGTAACTCG
1651 CCTTGATCGT TGGGAACCGG AGCTGAATGA AGCCATACCA AACGACGAGC
```

Figure 14B(1)

```
1701 GTGACACCAC GATGCCTGTA GCAATGGCAA CAACGTTGCG CAAACTATTA
1751 ACTGGCGAAC TACTTACTCT AGCTTCCCGG CAACAATTAA TAGACTGGAT
1801 GGAGGCGGAT AAAGTTGCAG GACCACTTCT GCGCTCGGCC CTTCCGGCTG
1851 GCTGGTTTAT TGCTGATAAA TCTGGAGCCG GTGAGCGTGG GTCTCGCGGT
1901 ATCATTGCAG CACTGGGGCC AGATGGTAAG CCCTCCCGTA TCGTAGTTAT
1951 CTACACGACG GGGAGTCAGG CAACTATGGA TGAACGAAAT AGACAGATCG
2001 CTGAGATAGG TGCCTCACTG ATTAAGCATT GGTAACTGTC AGACCAAGTT
2051 TACTCATATA TACTTTAGAT TGATTTAAAA CTTCATTTTT AATTTAAAAG
2101 GATCTAGGTG AAGATCCTTT TTGATAATCT CATGAACAAT AAAACTGTCT
2151 GCTTACATAA ACAGTAATAC AAGGGGTGTT ATGAGCCATA TTCAACGGGA
2201 AACGTCTTGC TCTAGGCCGC GATTAAATTC CAACATGGAT GCTGATTTAT
2251 ATGGGTATAA ATGGGCTCGC GATAATGTCG GGCAATCAGG TGCGACAATC
2301 TATCGATTGT ATGGAAGCC CGATGCGCCA GAGTTGTTTC TGAAACATGG
2351 CAAAGGTAGC GTTGCCAATG ATGTTACAGA TGAGATGGTC AGACTAAACT
2401 GGCTGACGGA ATTTATGCCT CTTCCGACCA TCAAGCATTT TATCCGTACT
2451 CCTGATGATG CATGGTTACT CACCACTGCG ATCCCCGGGA AAACAGCATT
2501 CCAGGTATTA GAAGAATATC CTGATTCAGG TGAAAATATT GTTGATGCGC
2551 TGGCAGTGTT CCTGCGCCGG TTGCATTCGA TTCCTGTTTG TAATTGTCCT
2601 TTTAACAGCG ATCGCGTATT TCGTCTCGCT CAGGCGCAAT CACGAATGAA
2651 TAACGGTTTG GTTGATGCGA GTGATTTTGA TGACGAGCGT AATGGCTGGC
2701 CTGTTGAACA AGTCTGGAAA GAAATGCATA AACTTTTGCC ATTCTCACCG
2751 GATTCAGTCG TCACTCATGG TGATTTCTCA CTTGATAACC TTATTTTTGA
2801 CGAGGGGAAA TTAATAGGTT GTATTGATGT TGGACGAGTC GGAATCGCAG
2851 ACCGATACCA GGATCTTGCC ATCCTATGGA ACTGCCTCGG TGAGTTTTCT
2901 CCTTCATTAC AGAAACGGCT TTTTCAAAAA TATGGTATTG ATAATCCTGA
2951 TATGAATAAA TTGCAGTTTC ATTTGATGCT CGATGAGTTT TTCTAAGAAT
3001 TAATTCATGA CCAAAATCCC TTAACGTGAG TTTTCGTTCC ACTGAGCGTC
3051 AGACCCCGTA GAAAAGATCA AAGGATCTTC TTGAGATCCT TTTTTTCTGC
3101 GCGTAATCTG CTGCTTGCAA ACAAAAAAAC CACCGCTACC AGCGGTGGTT
3151 TGTTTGCCGG ATCAAGAGCT ACCAACTCTT TTTCCGAAGG TAACTGGCTT
3201 CAGCAGAGCG CAGATACCAA ATACTGTCCT TCTAGTGTAG CCGTAGTTAG
3251 GCCACCACTT CAAGAACTCT GTAGCACCGC CTACATACCT CGCTCTGCTA
3301 ATCCTGTTAC CAGTGGCTGC TGCCAGTGGC GATAAGTCGT GTCTTACCGG
3351 GTTGGACTCA AGACGATAGT TACCGGATAA GGCGCAGCGG TCGGGCTGAA
```

Figure 14B(2)

```
3401 CGGGGGGTTC GTGCACACAG CCCAGCTTGG AGCGAACGAC CTACACCGAA
3451 CTGAGATACC TACAGCGTGA GCTATGAGAA AGCGCCACGC TTCCCGAAGG
3501 GAGAAAGGCG GACAGGTATC CGGTAAGCGG CAGGGTCGGA ACAGGAGAGC
3551 GCACGAGGGA GCTTCCAGGG GGAAACGCCT GGTATCTTTA TAGTCCTGTC
3601 GGGTTTCGCC ACCTCTGACT TGAGCGTCGA TTTTTGTGAT GCTCGTCAGG
3651 GGGGCGGAGC CTATGGAAAA ACGCCAGCAA CGCGGCCTTT TTACGGTTCC
3701 TGGCCTTTTG CTGGCCTTTT GCTCACATGT TCTTTCCTGC GTTATCCCCT
3751 GATTCTGTGG ATAACCGTAT TACCGCCTTT GAGTGAGCTG ATACCGCTCG
3801 CCGCAGCCGA ACGACCGAGC GCAGCGAGTC AGTGAGCGAG GAAGCGGAAG
3851 A (SEQ ID NO:28)
```

Figure 14B(3)

```
   1  CTAAATTGTA AGCGTTAATA TTTTGTTAAA ATTCGCGTTA AATTTTTGTT
  51  AAATCAGCTC ATTTTTTAAC CAATAGGCCG AAATCGGCAA AATCCCTTAT
 101  AAATCAAAAG AATAGACCGA GATAGGGTTG AGTGTTGTTC CAGTTTGGAA
 151  CAAGAGTCCA CTATTAAAGA ACGTGGACTC CAACGTCAAA GGGCGAAAAA
 201  CCGTCTATCA GGGCGATGGC CCACTACGTG AACCATCACC CTAATCAAGT
 251  TTTTTGGGGT CGAGGTGCCG TAAAGCACTA AATCGGAACC CTAAAGGGAG
 301  CCCCCGATTT AGAGCTTGAC GGGGAAAGCC GGCGAACGTG GCGAGAAAGG
 351  AAGGGAAGAA AGCGAAAGGA GCGGGCGCTA GGGCGCTGGC AAGTGTAGCG
 401  GTCACGCTGC GCGTAACCAC CACACCCGCC GCGCTTAATG CGCCGCTACA
 451  GGGCGCGTCC CATTCGCCAT TCAGGCTGCG CAACTGTTGG GAAGGGCGAT
 501  CGGTGCGGGC CTCTTCGCTA TTACGCCAGC TGGCGAAAGG GGGATGTGCT
 551  GCAAGGCGAT TAAGTTGGGT AACGCCAGGG TTTTCCCAGT CACGACGTTG
 601  TAAAACGACG GCCAGTGAGC GCGCGTAATA CGACTCACTA TAGGGCGAAT
 651  TGGGTACCGG GCCCCCCCTC GAGGTCGACG GTATCGATAA GCTTGATATC
 701  GAATTCCTGC AGCCCGGGGG ATCCACTAGT TCTAGAGCGG CCGCCACCGC
 751  GGTGGAGCTC CAGCTTTTGT TCCCTTTAGT GAGGGTTAAT TGCGCGCTTG
 801  GCGTAATCAT GGTCATAGCT GTTTCCTGTG TGAAATTGTT ATCCGCTCAC
 851  AATTCCACAC AACATACGAG CCGGAAGCAT AAAGTGTAAA GCCTGGGGTG
 901  CCTAATGAGT GAGCTAACTC ACATTAATTG CGTTGCGCTC ACTGCCCGCT
 951  TTCCAGTCGG GAAACCTGTC GTGCCAGCTG CATTAATGAA TCGGCCAACG
1001  CGCGGGGAGA GGCGGTTTGC GTATTGGGCG CTCTTCCGCT TCCTCGCTCA
1051  CTGACTCGCT GCGCTCGGTC GTTCGGCTGC GGCGAGCGGT ATCAGCTCAC
1101  TCAAAGGCGG TAATACGGTT ATCCACAGAA TCAGGGGATA ACGCAGGAAA
1151  GAACATGTGA GCAAAAGGCC AGCAAAAGGC CAGGAACCGT AAAAAGGCCG
1201  CGTTGCTGGC GTTTTTCCAT AGGCTCCGCC CCCCTGACGA GCATCACAAA
1251  AATCGACGCT CAAGTCAGAG GTGGCGAAAC CCGACAGGAC TATAAAGATA
1301  CCAGGCGTTT CCCCCTGGAA GCTCCCTCGT GCGCTCTCCT GTTCCGACCC
1351  TGCCGCTTAC CGGATACCTG TCCGCCTTTC TCCCTTCGGG AAGCGTGGCG
1401  CTTTCTCATA GCTCACGCTG TAGGTATCTC AGTTCGGTGT AGGTCGTTCG
1451  CTCCAAGCTG GGCTGTGTGC ACGAACCCCC CGTTCAGCCC GACCGCTGCG
1501  CCTTATCCGG TAACTATCGT CTTGAGTCCA ACCCGGTAAG ACACGACTTA
1551  TCGCCACTGG CAGCAGCCAC TGGTAACAGG ATTAGCAGAG CGAGGTATGT
1601  AGGCGGTGCT ACAGAGTTCT TGAAGTGGTG GCCTAACTAC GGCTACACTA
1651  GAAGGACAGT ATTTGGTATC TGCGCTCTGC TGAAGCCAGT TACCTTCGGA
1701  AAAAGAGTTG GTAGCTCTTG ATCCGGCAAA CAAACCACCG CTGGTAGCGG
1751  TGGTTTTTTT GTTTGCAAGC AGCAGATTAC GCGCAGAAAA AAAGGATCTC
```

Figure 15B(1)

```
1801  AAGAAGATCC TTTGATCTTT TCTACGGGGT CTGACGCTCA GTGGAACGAA
1851  AACTCACGTT AAGGGATTTT GGTCATGAGA TTATCAAAAA GGATCTTCAC
1901  CTAGATCCTT TTAAATTAAA AATGAAGTTT TAAATCAATC TAAAGTATAT
1951  ATGAGTAAAC TTGGTCTGAC AGTTACCAAT GCTTAATCAG TGAGGCACCT
2001  ATCTCAGCGA TCTGTCTATT TCGTTCATCC ATAGTTGCCT GACTCCCCGT
2051  CGTGTAGATA ACTACGATAC GGGAGGGCTT ACCATCTGGC CCCAGTGCTG
2101  CAATGATACC GCGAGACCCA CGCTCACCGG CTCCAGATTT ATCAGCAATA
2151  AACCAGCCAG CCGGAAGGGC CGAGCGCAGA AGTGGTCCTG CAACTTTATC
2201  CGCCTCCATC CAGTCTATTA ATTGTTGCCG GGAAGCTAGA GTAAGTAGTT
2251  CGCCAGTTAA TAGTTTGCGC AACGTTGTTG CCATTGCTAC AGGCATCGTG
2301  GTGTCACGCT CGTCGTTTGG TATGGCTTCA TTCAGCTCCG GTTCCCAACG
2351  ATCAAGGCGA GTTACATGAT CCCCCATGTT GTGCAAAAAA GCGGTTAGCT
2401  CCTTCGGTCC TCCGATCGTT GTCAGAAGTA AGTTGGCCGC AGTGTTATCA
2451  CTCATGGTTA TGGCAGCACT GCATAATTCT CTTACTGTCA TGCCATCCGT
2501  AAGATGCTTT TCTGTGACTG GTGAGTACTC AACCAAGTCA TTCTGAGAAT
2551  AGTGTATGCG GCGACCGAGT TGCTCTTGCC CGGCGTCAAT ACGGGATAAT
2601  ACCGCGCCAC ATAGCAGAAC TTTAAAAGTG CTCATCATTG GAAAACGTTC
2651  TTCGGGGCGA AAACTCTCAA GGATCTTACC GCTGTTGAGA TCCAGTTCGA
2701  TGTAACCCAC TCGTGCACCC AACTGATCTT CAGCATCTTT TACTTTCACC
2751  AGCGTTTCTG GGTGAGCAAA AACAGGAAGG CAAAATGCCG CAAAAAAGGG
2801  AATAAGGGCG ACACGGAAAT GTTGAATACT CATACTCTTC CTTTTTCAAT
2851  ATTATTGAAG CATTTATCAG GGTTATTGTC TCATGAGCGG ATACATATTT
2901  GAATGTATTT AGAAAAATAA ACAAATAGGG GTTCCGCGCA CATTTCCCCG
2951   AAAAGTGCCA C (SEQ ID NO:29)
```

Figure 15B(2)

```
   1 tcgcgcgttt cggtgatgac ggtgaaaacc tctgacacat gcagctcccg gagacggtca
  61 cagcttgtct gtaagcggat gccgggagca gacaagcccg tcagggcgcg tcagcgggtg
 121 ttggcgggtg tcggggctgg cttaactatg cggcatcaga gcagattgta ctgagagtgc
 181 accatatgcg gtgtgaaata ccgcacagat gcgtaaggag aaaataccgc atcaggcgcc
 241 attcgccatt caggctgcgc aactgttggg aagggcgatc ggtgcgggcc tcttcgctat
 301 tacgccagct ggcgaaaggg ggatgtgctg caaggcgatt aagttgggta acgccagggt
 361 tttcccagtc acgacgttgt aaaacgacgg ccagtgaatt cgagctcggt acccggggat
 421 cctctagagt cgacctgcag gcatgcaagc ttggcgtaat catggtcata gctgtttcct
 481 gtgtgaaatt gttatccgct cacaattcca cacaacatac gagccggaag cataaagtgt
 541 aaagcctggg gtgcctaatg agtgagctaa ctcacattaa ttgcgttgcg ctcactgccc
 601 gctttccagt cgggaaacct gtcgtgccag ctgcattaat gaatcggcca acgcgcgggg
 661 agaggcggtt tgcgtattgg gcgctcttcc gcttcctcgc tcactgactc gctgcgctcg
 721 gtcgttcggc tgcggcgagc ggtatcagct cactcaaagg cggtaatacg gttatccaca
 781 gaatcagggg ataacgcagg aaagaacatg tgagcaaaag gccagcaaaa ggccaggaac
 841 cgtaaaaagg ccgcgttgct ggcgtttttc cataggctcc gcccccctga cgagcatcac
 901 aaaaatcgac gctcaagtca gaggtggcga aacccgacag gactataaag ataccaggcg
 961 tttccccctg gaagctccct cgtgcgctct cctgttccga ccctgccgct taccggatac
1021 ctgtccgcct ttctcccttc gggaagcgtg gcgctttctc atagctcacg ctgtaggtat
1081 ctcagttcgg tgtaggtcgt tcgctccaag ctgggctgtg tgcacgaacc cccgttcag
1141 cccgaccgct gcgccttatc cggtaactat cgtcttgagt ccaacccggt aagacacgac
1201 ttatcgccac tggcagcagc cactggtaac aggattagca gagcgaggta tgtaggcggt
1261 gctacagagt tcttgaagtg gtggcctaac tacggctaca ctagaaggac agtatttggt
1321 atctgcgctc tgctgaagcc agttaccttc ggaaaaagag ttggtagctc ttgatccggc
1381 aaacaaacca ccgctggtag cggtggtttt tttgtttgca agcagcagat tacgcgcaga
1441 aaaaaggat ctcaagaaga tcctttgatc ttttctacgg ggtctgacgc tcagtggaac
1501 gaaaactcac gttaagggat tttggtcatg agattatcaa aaaggatctt cacctagatc
1561 cttttaaatt aaaaatgaag ttttaaatca atctaaagta tatatgagta aacttggtct
1621 gacagttacc aatgcttaat cagtgaggca cctatctcag cgatctgtct atttcgttca
1681 tccatagttg cctgactccc cgtcgtgtag ataactacga tacgggaggg cttaccatct
1741 ggccccagtg ctgcaatgat accgcgagac ccacgctcac cggctccaga tttatcagca
1801 ataaaccagc cagccggaag ggccgagcgc agaagtggtc ctgcaacttt atccgcctcc
1861 atccagtcta ttaattgttg ccgggaagct agagtaagta gttcgccagt taatagtttg
1921 cgcaacgttg ttgccattgc tacaggcatc gtggtgtcac gctcgtcgtt tggtatggct
1981 tcattcagct ccggttccca acgatcaagg cgagttacat gatccccat gttgtgcaaa
2041 aaagcggtta gctccttcgg tcctccgatc gttgtcagaa gtaagttggc cgcagtgtta
2101 tcactcatgg ttatggcagc actgcataat tctcttactg tcatgccatc cgtaagatgc
2161 ttttctgtga ctggtgagta ctcaaccaag tcattctgag aatagtgtat gcggcgaccg
2221 agttgctctt gcccggcgtc aatacgggat aataccgcgc cacatagcag aactttaaaa
```

Figure 16B(1)

```
2281 gtgctcatca ttggaaaacg ttcttcgggg cgaaaactct caaggatctt accgctgttg
2341 agatccagtt cgatgtaacc cactcgtgca cccaactgat cttcagcatc ttttactttc
2401 accagcgttt ctgggtgagc aaaaacagga aggcaaaatg ccgcaaaaaa gggaataagg
2461 gcgacacgga aatgttgaat actcatactc ttccttttc aatattattg aagcatttat
2521 cagggttatt gtctcatgag cggatacata tttgaatgta tttagaaaaa taaacaaata
2581 ggggttccgc gcacatttcc ccgaaaagtg ccacctgacg tctaagaaac cattattatc
2641 atgacattaa cctataaaaa taggcgtatc acgaggccct ttcgtc (SEQ ID NO:30)
```

Figure 16B(2)

BglII - 3156 - A'GATC_T Ndel - 3051 - CA'TA_TG

```
   1 CACCTAAATT GTAAGCGTTA ATATTTTGTT AAAATTCGCG TTAAATTTTT
  51 GTTAAATCAG CTCATTTTTT AACCAATAGG CCGAAATCGG CAAAATCCCT
 101 TATAAATCAA AAGAATAGAC CGAGATAGGG TTGAGTGTTG TTCCAGTTTG
 151 GAACAAGAGT CCACTATTAA AGAACGTGGA CTCCAACGTC AAAGGGCGAA
 201 AAACCGTCTA TCAGGGCGAT GGCCCACTAC GTGAACCATC ACCCTAATCA
 251 AGTTTTTTGG GGTCGAGGTG CCGTAAAGCA CTAAATCGGA ACCCTAAAGG
 301 GAGCCCCCGA TTTAGAGCTT GACGGGGAAA GCCGGCGAAC GTGGCGAGAA
 351 AGGAAGGGAA GAAAGCGAAA GGAGCGGGCG CTAGGGCGCT GGCAAGTGTA
 401 GCGGTCACGC TGCGCGTAAC CACCACACCC GCCGCGCTTA ATGCGCCGCT
 451 ACAGGGCGCG TCCCATTCGC CATTCAGGCT GCGCAACTGT TGGGAAGGGC
 501 GATCGGTGCG GGCCTCTTCG CTATTACGCC AGCTGGCGAA AGGGGGATGT
 551 GCTGCAAGGC GATTAAGTTG GGTAACGCCA GGGTTTTCCC AGTCACGACG
 601 TTGTAAAACG ACGGCCAGTG AATTGTAATA CGACTCACTA TAGGGCGAAT
 651 TGGAGGCCAG TGCTGGAGGA ATATGATTTT GTCATCCTCG ACTGTGCCCC
 701 TGGTTATAAT CTGTTGACCC GCAGTGGCAT TGCGGCCAGC GACTTTTATC
 751 TGTTGCCGGC TCGTCCTGAA CCCCTATCGG TGGTGGGGAT GCAGTTACTG
 801 GAAAGAAGAA TTGAGAAACT GAAGGAAAGC CATAAGGCCT CCGATGATCC
 851 CCTGAATATC AATCTGATCG GAGTGGTGTT TATTCTGTCC GGCGGCGGTT
 901 TGATGAGTCG CTACTATAAC CAGGTAATGC GGCGGGTACA AACGGATTTC
 951 ACCCCGGGAC AACTTTTTCA GCAGTCCATT CCCATGGATG TCAATGTGGC
1001 TAAGGCAGTG GATAGCTTTA TGCCGGTGGT TACCTCCATG CCCAATACGG
1051 CGGGTTCAAA AGCTTTTATT AAATTAACCC AGGAATTTTT ACAGAAAGTA
1101 GAAGCTTTTG GCTAAAGCAA AGCCCCCATT GATTAACAAC GGGAGGGGTA
1151 CCGAGGTGCT GCTGAAGTTG CCCGCAACAG AGAGTGGAAC CAACCGGTGA
1201 TACCACGATA CTATGACTGA GAGTCAACGC CATGAGCGGC CTCATTTCTT
1251 ATTCTGAGTT ACAACAGTCC GCACCGCTGT CCGGTAGCTC CTTCCGGTGG
1301 GCGCGGGGCA TGACTATCGT CGCCGCACTT ATGACTGTCT TCTTTATCAT
1351 GCAACTCGTA GGACAGGTGC CGGCAGCGCC CAACAGTCCC CCGGCCACGG
1401 GGCCTGCCAC CATACCCACG CCGAAACAAG CGCCCTGCAC CATTATGTTC
1451 CGGATCTGCA TCGCAGGATG CTGCTGGCTA CCCTGTGGAA CACCTACATC
1501 TGTATTAACG AAGCGCTAAC CGTTTTTATC AGGCTCTGGG AGGCAGAATA
1551 AATGATCATA TCGTCAATTA TTACCTCCAC GGGGAGAGCC TGAGCAAACT
1601 GGCCTCAGGC ATTTGAGAAG CACACGGTCA CACTGCTTCC GGTAGTCAAT
1651 AAACCGGTAA ACCAGCAATA GACATAAGCG GCTATTTAAC GACCCTGCCC
1701 TGAACCGACG ACCGGGTCGA ATTTGCTTTC GAATTTCTGC CATTCATCCG
1751 CTTATTATCA CTTATTCAGG CGTAGCACCA GGCGTTTAAG GGCACCAATA
```

Figure 17B(1)

```
1801 ACTGCCTTAA AAAAATTACG CCCCGCCCTG CCACTCATCG CAGTACTGTT
1851 GTAATTCATT AAGCATTCTG CCGACATGGA AGCCATCACA GACGGCATGA
1901 TGAACCTGAA TCGCCAGCGG CATCAGCACC TTGTCGCCTT GCGTATAATA
1951 TTTGCCCATG GTGAAAACGG GGGCGAAGAA GTTGTCCATA TTGGCCACGT
2001 TTAAATCAAA ACTGGTGAAA CTCACCCAGG GATTGGCTGA GACGAAAAAC
2051 ATATTCTCAA TAAACCCTTT AGGGAAATAG GCCAGGTTTT CACCGTAACA
2101 CGCCACATCT TGCGAATATA TGTGTAGAAA CTGCCGGAAA TCGTCGTGGT
2151 ATTCACTCCA GAGCGATGAA AACGTTTCAG TTTGCTCATG GAAAACGGTG
2201 TAACAAGGGT GAACACTATC CCATATCACC AGCTCACCGT CTTTCATTGC
2251 CATACGGAAT TCCGGATGAG CATTCATCAG GCGGCAAGA ATGTGAATAA
2301 AGGCCGGATA AAACTTGTGC TTATTTTTCT TTACGGTCTT TAAAAAGGCC
2351 GTAATATCCA GCTGAACGGT CTGGTTATAG GTACATTGAG CAACTGACTG
2401 AAATGCCTCA AAATGTTCTT TACGATGCCA TTGGGATATA TCAACGGTGG
2451 TATATCCAGT GATTTTTTC TCCATTTTAG CTTCCTTAGC TCCTGAAAAT
2501 CTCGATAACT CAAAAAATAC GCCCGGTAGT GATCTTATTT CATTATGGTG
2551 AAAGTTGGAA CCTCTTACCT CGGTACCCCT CATCGGGGC TGTGTTGGCC
2601 GAGACGGCAC TGAGGATTTT ACTCTCCATG GCATTCCAAG GAATATCTAC
2651 CCAACTCACC TGCTCCGGCG GATTGTTCCG CTCAAAAGTA CTAATCAAGT
2701 CGTCAAAATA CTTATTAAAT TTGGCTGCA ATTGCATAGT CCAAAAGCTG
2751 ACTTTCCCCT CCATGCTCTG GGGGAATTG CTCTGGCAAC TGATTAATCC
2801 ACTGAGCAAC AGCCCAAGAC ACGCAAACAA AAACCAACGT CTTGGCGATC
2851 GCCATCGGCA CCATGAAACC ATCGTAAAAG CTGGGGAAAG AATAAAAAAC
2901 AGTGGTTCAG GAATTGCATT GCCATGGCCA CTTCACAAAC CTAGCCAATT
2951 TTAGCTTGAC CGCAACTTTG ACAGATTGTC TTTTGACTTT GCCTGGACCG
3001 CCTCCCATAA TACCTTCGCG TCTTGAAGAC TTTATCCTTG AAAGGAGAAC
3051 ATATGTTTCT CGGCAAAAAT TAATTATCGA TTGGCTGGAA CCTGGTCAAA
3101 CCAGGGCTTT TCATCCATTG GAAAAGCGAT TTTGATCATC TAGGGTCAGG
3151 AGCAAAGATC TGATCAAATA TTGATCATTT ATTAGGAAAG CTGAACTTTC
3201 ACCACTTTAT TTTTGGCTTC CTCTACTTTG GCAAAGTCA AAGTTAGGAT
3251 ACCGGCATCG TAATTAGCTT TAACTTCTGT GTTTTGGATT GCTCCAGGTA
3301 CAGGAATAAC CCGGCGGAAA CTGCCATAGC GGAACTCTGT GCGCCGCACC
3351 CCATCTTTTT CGGTGCTATG GGTATCCTGG CGATCGCCGC TGACGGTCAC
3401 CGCATCCCTG GCGGCTTGGA TGTCCAAATT ATCGGGGTCC ATGCCAGGTA
3451 ATTCTAGTTT GAGCACATAG GCTTCTTCAG TTTCAGTTAG TTCTGCTTTA
3501 GGATTAAACC CTTGGCGATC GCCGTGGCGG TCCGTAGGGA CAAAAACTTC
3551 TTCAAACAGT TGGTTCATCT GCTGCTGGAA ATTATCCATT TCCCGCAGGG
3601 GATTGTAAAG AATGAGAGAC ATAATGTTAA CTCCTGATGT GTGGAAGGAA
```

Figure 17B(2)

```
3651 TTGATTACCC TTGAATGGTT CTATCTTAAA ATTTCCCCTT CCAGGTTAGA
3701 TTCGGTTTTC AGGAAAGAAG GTGGGGGGAT TGCCGAAATT ACATTTCTAG
3751 CCGCAATTTT TAGTAAAAAA AAGATGAGTT TTTACCTCAC CTTAAGTAAA
3801 TATTTGAGTG GCAAAACAAA ATGGTAAAAA TAGCTAAGCT TCCACCGCCC
3851 TATGGATTTT TGGAAGGAAG TCTTAGGTTG TGAAAAACTA TAAAAACCAA
3901 CCATAGGAAT GGAGACCTTT ACCCAACAAG TTGACCCCTA GGTAACAAAT
3951 CCAAACCACC GTAAAACCGC TGGCGGCCAA AATAGCGGGC TTGCGGCCTT
4001 GCCAACCTTT GGTAATGCGG GCATGGAGAT AGGCGGCAAA TACTAGCCAG
4051 GTGATTAGGG CCCGGTACCC AGCTTTTGTT CCCTTTAGTG AGGGTTAATT
4101 TCGAGCTTGG CGTAATCATG GTCATAGCTG TTTCCTGTGT GAAATTGTTA
4151 TCCGCTCACA ATTCCACACA ACATACGAGC CGGAAGCATA AAGTGTAAAG
4201 CCTGGGGTGC CTAATGAGTG AGCTAACTCA CATTAATTGC GTTGCGCTCA
4251 CTGCCCGCTT TCCAGTCGGG AAACCTGTCG TGCCAGCTGC ATTAATGAAT
4301 CGGCCAACGC GCGGGGAGAG GCGGTTTGCG TATTGGGCGC TCTTCCGCTT
4351 CCTCGCTCAC TGACTCGCTG CGCTCGGTCG TTCGGCTGCG GCGAGCGGTA
4401 TCAGCTCACT CAAAGGCGGT AATACGGTTA TCCACAGAAT CAGGGGATAA
4451 CGCAGGAAAG AACATGTGAG CAAAAGGCCA GCAAAAGGCC AGGAACCGTA
4501 AAAAGGCCGC GTTGCTGGCG TTTTTCCATA GGCTCCGCCC CCCTGACGAG
4551 CATCACAAAA ATCGACGCTC AAGTCAGAGG TGGCGAAACC CGACAGGACT
4601 ATAAAGATAC CAGGCGTTTC CCCCTGGAAG CTCCCTCGTG CGCTCTCCTG
4651 TTCCGACCCT GCCGCTTACC GGATACCTGT CCGCCTTTCT CCCTTCGGGA
4701 AGCGTGGCGC TTTCTCATAG CTCACGCTGT AGGTATCTCA GTTCGGTGTA
4751 GGTCGTTCGC TCCAAGCTGG GCTGTGTGCA CGAACCCCCC GTTCAGCCCG
4801 ACCGCTGCGC CTTATCCGGT AACTATCGTC TTGAGTCCAA CCCGGTAAGA
4851 CACGACTTAT CGCCACTGGC AGCAGCCACT GGTAACAGGA TTAGCAGAGC
4901 GAGGTATGTA GGCGGTGCTA CAGAGTTCTT GAAGTGGTGG CCTAACTACG
4951 GCTACACTAG AAGGACAGTA TTTGGTATCT GCGCTCTGCT GAAGCCAGTT
5001 ACCTTCGGAA AAAGAGTTGG TAGCTCTTGA TCCGGCAAAC AAACCACCGC
5051 TGGTAGCGGT GGTTTTTTTG TTTGCAAGCA GCAGATTACG CGCAGAAAAA
5101 AAGGATCTCA AGAAGATCCT TTGATCTTTT CTACGGGGTC TGACGCTCAG
5151 TGGAACGAAA ACTCACGTTA AGGGATTTTG GTCATGAGAT TATCAAAAAG
5201 GATCTTCACC TAGATCCTTT TAAATTAAAA ATGAAGTTTT AAATCAATCT
5251 AAAGTATATA TGAGTAAACT TGGTCTGACA GTTACCAATG CTTAATCAGT
5301 GAGGCACCTA TCTCAGCGAT CTGTCTATTT CGTTCATCCA TAGTTGCCTG
5351 ACTCCCCGTC GTGTAGATAA CTACGATACG GGAGGGCTTA CCATCTGGCC
```

Figure 17B(3)

```
5401 CCAGTGCTGC AATGATACCG CGAGACCCAC GCTCACCGGC TCCAGATTTA
5451 TCAGCAATAA ACCAGCCAGC CGGAAGGGCC GAGCGCAGAA GTGGTCCTGC
5501 AACTTTATCC GCCTCCATCC AGTCTATTAA TTGTTGCCGG GAAGCTAGAG
5551 TAAGTAGTTC GCCAGTTAAT AGTTTGCGCA ACGTTGTTGC CATTGCTACA
5601 GGCATCGTGG TGTCACGCTC GTCGTTTGGT ATGGCTTCAT TCAGCTCCGG
5651 TTCCCAACGA TCAAGGCGAG TTACATGATC CCCCATGTTG TGCAAAAAAG
5701 CGGTTAGCTC CTTCGGTCCT CCGATCGTTG TCAGAAGTAA GTTGGCCGCA
5751 GTGTTATCAC TCATGGTTAT GGCAGCACTG CATAATTCTC TTACTGTCAT
5801 GCCATCCGTA AGATGCTTTT CTGTGACTGG TGAGTACTCA ACCAAGTCAT
5851 TCTGAGAATA GTGTATGCGG CGACCGAGTT GCTCTTGCCC GGCGTCAATA
5901 CGGGATAATA CCGCGCCACA TAGCAGAACT TTAAAAGTGC TCATCATTGG
5951 AAAACGTTCT TCGGGGCGAA AACTCTCAAG GATCTTACCG CTGTTGAGAT
6001 CCAGTTCGAT GTAACCCACT CGTGCACCCA ACTGATCTTC AGCATCTTTT
6051 ACTTTCACCA GCGTTTCTGG GTGAGCAAAA ACAGGAAGGC AAAATGCCGC
6101 AAAAAAGGGA ATAAGGGCGA CACGGAAATG TTGAATACTC ATACTCTTCC
6151 TTTTTCAATA TTATTGAAGC ATTTATCAGG GTTATTGTCT CATGAGCGGA
6201 TACATATTTG AATGTATTTA GAAAAATAAA CAAATAGGGG TTCCGCGCAC
6251 ATTTCCCCGA AAAGTGC (SEQ ID NO:31)
```

Figure 17B(4)

```
MVSLTPNPSYSVSLLLELPNHAGTLASVTQAIADAGGSFGQISLIESNLKLTRREIAVDA
SSSEHAEKIIGAVKALDNVKLLKVSDRTFDLHRQGKISVVSRIPLTSQSDLAMAYTPGVG
RICRAIAEDPEKVYSLTIKSNTVAVVTDGSAVLGLGNLGPEAALPVMEGKAMLFKEFAQL
DAFPICLDTQDTEEIIRTVKAIAPVFGGVNLEDIAAPRCFEIEARLKKELNIPVFHDDQH
GTAIVTLAALLNALKFVGKAMAAVRIVINGAGAAGLAIAELLKESGATDIWICDSKGIVG
KHRTDLNSKKQSFAVDAEGTLADAMAGADVFLGVSAPGVVTKEMVQSMAKDPIVFAMANP
IPEIQPELIQEDAAVIATGRSDYPNQINNVLAFPGVFRGAIDCRASIITTTMCIEAAKAI
ASLVHSNTLDSEHIIPSVFDNRVATTVASAVQLAARNEGVAGQ (SEQ ID NO:32)
```

Figure 18A

```
  1 T███GTTAGC CTCACCCCCA ATCCGAGTTA TAGCGTCAGC CTACTGTTGG
 51 AACTCCCCAA CCACGCCGGA ACTTTGGCCA GCGTTACCCA GGCGATCGCC
101 GATGCGGGGG GCAGTTTTGG GCAAATTTCC CTGATTGAGA GTAACTTAAA
151 ACTCACCCGG CGGGAAATTG CGGTGGATGC TTCCAGCAGT GAGCACGCCG
201 AAAAAATTAT TGGGGCAGTG AAAGCTCTGG ATAATGTCAA ATTGCTGAAG
251 GTGTCCGATC GCACCTTTGA TTTACACCGT CAGGGCAAAA TTAGCGTGGT
301 TAGTCGCATT CCCCTCACCT CCCAATCGGA TTTGGCCATG GCCTATACCC
351 CAGGGGTGGG GCGCATCTGT CGGGCGATCG CCGAAGATCC GGAAAAGGTT
401 TATTCCCTGA CCATTAAAAG CAATACGGTG GCGGTGGTGA CCGATGGCAG
451 TGCGGTGTTG GGGTTGGGTA ACCTGGGGCC GGAAGCGGCT TTACCAGTGA
501 TGGAAGGCAA GGCCATGTTA TTCAAGGAAT TTGCCCAACT GGACGCTTTT
551 CCCATCTGTT TGGATACCCA GGATACGGAG GAAATTATTC GCACCGTCAA
601 GGCGATCGCC CCGGTGTTTG GCGGCGTAAA TTTGGAAGAC ATTGCCGCTC
651 CCCGGTGTTT TGAAATTGAA GCCCGGCTGA AAAAGAATT AAATATTCCT
701 GTATTTCACG ATGATCAGCA CGGCACCGCC ATTGTTACCC TGGCCGCTTT
751 GTTAAATGCC CTCAAATTTG TTGGTAAAGC CATGGCCGCT GTCCGCATTG
801 TCATCAACGG CGCTGGGGCT GCTGGGTTGG CGATCGCCGA ATTGCTCAAG
851 GAATCCGGAG CCACCGATAT TTGGATTTGC GACTCCAAGG GCATTGTGGG
901 CAAACATCGC ACCGATTTAA ACAGCAAAAA ACAGAGCTTT GCGGTGGATG
951 CGGAAGGGAC TTTAGCCGAT GCTATGGCTG GAGCTGATGT GTTTTTAGGG
1001 GTGAGTGCGC CGGGGGTAGT GACCAAGGAA ATGGTGCAAT CCATGGCCAA
1051 GGACCCGATT GTGTTTGCCA TGGCCAACCC TATCCCCGAA ATTCAGCCGG
1101 AATTAATCCA AGAGGATGCG GCGGTTATTG CCACGGGGCG CAGTGATTAC
1151 CCCAACCAAA TTAACAATGT GCTTGCCTTT CCGGGGGTTT TCCGGGGAGC
1201 CATTGACTGT AGAGCTAGCA TTATTACCAC CACCATGTGC ATCGAAGCGG
1251 CCAAGGCGAT CGCCTCTTTG GTGCACAGCA ACACCCTAGA TAGTGAGCAT
1301 ATTATTCCTT CGGTTTTTGA CAATCGGGTC GCCACTACCG TAGCCAGTGC
1351 AGTGCAGTTG GCCGCCCGCA ATGAAGGGGT GGCCGGTCAA ███TTAATCG
1401 GGAATTGTTA AACCTTTACT GGTCAACCAT TCCTGATTGT AAAGACGGGA
1451 TTGGTAACGG GCTCCTCCGT CACAAAGTAC GGTAACAATG GTATGCCCCG
1501 GCCCAAGTTT TTTGGCCAAT TGGTAAGCCG CTCCCACATT AATAT (SEQ ID
NO:33)
```

Figure 18C

MNILEYAPIACQSWQVTVVGAGNVGRTLAQRLVQQNVANVVLLDIVPGLPQGIALDLMAA
QSVEEYDSKIIGTNEYEATAGSDVVVITAGLPRRPGMSRDDLLGKNANIVAQGAREALRY
SPNAILIVVTNPLDVMTYLAWKVTGLPSQRVMGMAGVLDSARLKAFIAMKLGACPSDINT
LVLGGHGDLMLPLPRYCTVSGVPITELIPPQTIEELVERTRNGGAEIAALLQTGTAYYAP
ASSAAVMVESILRNQSRILPAATYLDGAYGLKDIFLGVPCRLGCRGVEDILEVQLTPEEK
AALHLSAEAVRLNIDVALAMVSDG (SEQ ID NO:34)

Figure 19A

```
   1 TATGAATATT TTGGAGTATG CTCCGATCGC CTGTCAGTCC TGGCAGGTTA
  51 CCGTGGTCGG CGCTGGCAAT GTGGGGCGGA CCCTTGCCCA GAGGTTAGTG
 101 CAGCAAAATG TCGCCAACGT AGTTTTGTTG GACATTGTGC CAGGCTTACC
 151 CCAGGGCATT GCCTTGGATT TGATGGCCGC CCAGAGCGTG GAGGAATACG
 201 ACAGCAAAAT CATTGGCACC AATGAATACG AGGCCACCGC CGGCTCCGAT
 251 GTGGTGGTAA TTACCGCTGG TCTACCCGC AGGCCCGGCA TGAGTCGGGA
 301 TGATTTGTTG GGCAAAAACG CCAACATTGT GGCCCAGGGG GCCCGGGAAG
 351 CATTGCGTTA TTCCCCCAAC GCCATTTTGA TTGTGGTCAC CAATCCCCTG
 401 GATGTAATGA CCTATTTGGC CTGGAAAGTA ACTGGTTTAC CTTCCCAACG
 451 GGTTATGGGC ATGGCGGGGG TGTTGGACTC GGCTCGGCTC AAGGCCTTCA
 501 TTGCGATGAA ATTAGGGGCC TGTCCTTCTG ATATCAACAC CTTAGTGCTG
 551 GGCGGGCACG GAGATTTGAT GCTGCCCTTG CCACGATACT GCACCGTCAG
 601 CGGGGTTCCC ATTACCGAAT TAATACCCCC CCAAACCATT GAAGAGTTGG
 651 TGGAGCGTAC CCGTAACGGT GGGGCTGAAA TTGCCGCCTT ACTACAAACG
 701 GGCACAGCCT ATTATGCGCC GGCCTCTTCC GCTGCGGTGA TGGTGGAGTC
 751 CATTTTACGC AATCAGTCTA GAATTCTCCC CGCCGCCACC TACCTTGATG
 801 GTGCCTATGG ATTGAAGGAC ATTTTCCTTG GAGTGCCCTG CCGTTTGGGG
 851 TGTCGAGGAG TGGAAGATAT TCTCGAAGTG CAATTAACCC CTGAAGAAAA
 901 AGCTGCCCTC CATCTTTCTG CAGAAGCAGT TCGCCTTAAT ATTGATGTGG
 951 CGTTGGCCAT GGTTAGCGAC GGTTAACACG ATAACGGACA GTGCCAATAC
1001 CGTTTTTTCA CCGAGGTTAG GGCTTAT (SEQ ID NO:35)
```

Figure 19C

```
   1 TATGGTTAGC CTCACCCCCA ATCCGAGTTA TAGCGTCAGC CTACTGTTGG
  51 AACTCCCCAA CCACGCCGGA ACTTTGGCCA GCGTTACCCA GGCGATCGCC
 101 GATGCGGGGG GCAGTTTTGG GCAAATTTCC CTGATTGAGA GTAACTTAAA
 151 ACTCACCCGG CGGGAAATTG CGGTGGATGC TTCCAGCAGT GAGCACGCCG
 201 AAAAAATTAT TGGGGCAGTG AAAGCTCTGG ATAATGTCAA ATTGCTGAAG
 251 GTGTCCGATC GCACCTTTGA TTTACACCGT CAGGGCAAAA TTAGCGTGGT
 301 TAGTCGCATT CCCCTCACCT CCCAATCGGA TTTGGCCATG GCCTATACCC
 351 CAGGGGTGGG GCGCATCTGT CGGGCGATCG CCGAAGATCC GGAAAAGGTT
 401 TATTCCCTGA CCATTAAAAG CAATACGGTG GCGGTGGTGA CCGATGGCAG
 451 TGCGGTGTTG GGGTTGGGTA ACCTGGGGCC GGAAGCGGCT TTACCAGTGA
 501 TGGAAGGCAA GGCCATGTTA TTCAAGGAAT TGCCCAACT GGACGCTTTT
 551 CCCATCTGTT TGGATACCCA GGATACGGAG GAAATTATTC GCACCGTCAA
 601 GGCGATCGCC CCGGTGTTTG GCGGCGTAAA TTTGGAAGAC ATTGCCGCTC
 651 CCCGGTGTTT TGAAATTGAA GCCCGGCTGA AAAAAGAATT AAATATTCCT
 701 GTATTTCACG ATGATCAGCA CGGCACCGCC ATTGTTACCC TGGCCGCTTT
 751 GTTAAATGCC CTCAAATTTG TTGGTAAAGC CATGGCCGCT GTCCGCATTG
 801 TCATCAACGG CGCTGGGGCT GCTGGGTTGG CGATCGCCGA ATTGCTCAAG
 851 GAATCCGGAG CCACCGATAT TTGGATTTGC GACTCCAAGG GCATTGTGGG
 901 CAAACATCGC ACCGATTTAA ACAGCAAAAA ACAGAGCTTT GCGGTGGATG
 951 CGGAAGGGAC TTTAGCCGAT GCTATGGCTG GAGCTGATGT GTTTTTAGGG
1001 GTGAGTGCGC CGGGGGTAGT GACCAAGGAA ATGGTGCAAT CCATGGCCAA
1051 GGACCCGATT GTGTTTGCCA TGGCCAACCC TATCCCCGAA ATTCAGCCGG
1101 AATTAATCCA AGAGGATGCG GCGGTTATTG CCACGGGGCG CAGTGATTAC
1151 CCCAACCAAA TTAACAATGT GCTTGCCTTT CCGGGGGTTT TCCGGGGAGC
1201 CATTGACTGT AGAGCTAGCA TTATTACCAC CACCATGTGC ATCGAAGCGG
1251 CCAAGGCGAT CGCCTCTTTG GTGCACAGCA ACACCCTAGA TAGTGAGCAT
1301 ATTATTCCTT CGGTTTTTGA CAATCGGGTC GCCACTACCG TAGCCAGTGC
1351 AGTGCAGTTG GCCGCCCGCA ATGAAGGGGT GGCCGGTCAA TAGTTAATCG
1401 GGAATTGTTA AACCTTTACT GGTCAACCAT TCCTGATTGT AAAGACGGGA
1451 TTGGTAACGG GCTCCTCCGT CACAAAGTAC GGTAACAATG GTATGCCCCG
1501 GCCCAAGTTT TTTGGCCAAT TGGTAAGCCG CTCCCACATT AATATCGATT
1551 TTTCTCCACC ATCAACACCC GGAGGGTGC C____AATATT TTGGAGTATG
1601 CTCCGATCGC CTGTCAGTCC TGGCAGGTTA CCGTGGTCGG CGCTGGCAAT
1651 GTGGGGCGGA CCCTTGCCCA GAGGTTAGTG CAGCAAAATG TCGCCAACGT
```

Figure 19E(1)

```
1701 AGTTTTGTTG GACATTGTGC CAGGCTTACC CCAGGGCATT GCCTTGGATT
1751 TGATGGCCGC CCAGAGCGTG GAGGAATACG ACAGCAAAAT CATTGGCACC
1801 AATGAATACG AGGCCACCGC CGGCTCCGAT GTGGTGGTAA TTACCGCTGG
1851 TCTACCCCGC AGGCCCGGCA TGAGTCGGGA TGATTTGTTG GGCAAAAACG
1901 CCAACATTGT GGCCCAGGGG GCCCGGGAAG CATTGCGTTA TTCCCCCAAC
1951 GCCATTTTGA TTGTGGTCAC CAATCCCCTG GATGTAATGA CCTATTTGGC
2001 CTGGAAAGTA ACTGGTTTAC CTTCCCAACG GGTTATGGGC ATGGCGGGGG
2051 TGTTGGACTC GGCTCGGCTC AAGGCCTTCA TTGCGATGAA ATTAGGGGCC
2101 TGTCCTTCTG ATATCAACAC CTTAGTGCTG GGCGGGCACG GAGATTTGAT
2151 GCTGCCCTTG CCACGATACT GCACCGTCAG CGGGGTTCCC ATTACCGAAT
2201 TAATACCCCC CCAAACCATT GAAGAGTTGG TGGAGCGTAC CCGTAACGGT
2251 GGGGCTGAAA TTGCCGCCTT ACTACAAACG GCACAGCCT ATTATGCGCC
2301 GGCCTCTTCC GCTGCGGTGA TGGTGGAGTC CATTTTACGC AATCAGTCTA
2351 GAATTCTCCC CGCCGCCACC TACCTTGATG GTGCCTATGG ATTGAAGGAC
2401 ATTTTCCTTG GAGTGCCCTG CCGTTTGGGG TGTCGAGGAG TGGAAGATAT
2451 TCTCGAAGTG CAATTAACCC CTGAAGAAAA AGCTGCCCTC CATCTTTCTG
2501 CAGAAGCAGT TCGCCTTAAT ATTGATGTGG CGTTGGCCAT GGTTAGCGAC
2551 GGTTAACACG ATAACGGACA GTGCCAATAC CGTTTTTTCA CCGAGGTTAG
2601 GGCTTA (SEQ ID NO:36)
```

Figure 19E(2)

MRPLSHRTKIVATIGPASSSVEVIRQMVDAGMNVARLNFSHGSYEDHATMVRLLRSVEQE
MDTPITLLQDLQGPKIRIGQLPGGEKQLREGEKVSLVPVEIGDRHPGAVGIDYPHLATEA
KVGERILLDDGLLEMKVVSIQDPEVICEVVTGGILKSRKGVNLPGLVLTLPSMTTKDKQD
LEFGLSQGIDWVSLSFVRKGEDIHTLKQFLAERGHPDLPVIAKIEKPQAIDNLEEIVAVS
NGIMVARGDLGVEVNPEKVPRLQKEIIRRCNVRAIPVITATQMLDSMIQNSRPTRAEASD
VANAILDGTDAVMLSGESAVGQYPVKSVQMLRKIAEETEVGLHLVNNPPIENTETHALSE
ALVVIDGILDLKYIVTFTTSGFTSLLASNQRPSVPVIAFTPSEKVYHSLNLVWGIIPFLI
NEEFDTFEDLIQQAEVLLRDRKMVEKGDQLLIMAGIPTKIPRGTNFLKIHRIS (SEQ ID
NO:37)

Figure 20A

```
   1 TCGACTACCC ATTGGGGGCT GAGCGGCCCA GCGGTGTTAA AGCTATCTGC
  51 CTGGGGAGCA AGACAATTAC AGGCATCGGG TTATGACCAT TCCCTCTGGA
 101 TCAACTGGCT GCCTAAAGTG ACTCCCCTGG AATCCATGGC CCAATGGCGA
 151 GCAACAAAGC AAAGCCATCC CCGCAAACAA ATCGCTAACT TTACCGCCAC
 201 TGCTTTACCT AAACGACTTT GGCAGAGGTT GACGACCCAG GCTGGTATTA
 251 AACCGGGGCA ATGTTGGGCC GATTTTTCCA AGGTTCAGGA GCGACAACTA
 301 ACAGAGAATA TCCACCGCTA CCACTGTCAG ATCAAAGGTA AAGGGGTGTT
 351 CAAAGAAGAA TTTGTCACCT GTGGGGGCAT TACCCTCAAG GAAGTGGATT
 401 TTAAGACCAT GGCTAGCCGT TGTTGCCCTG GATTATATTT TGCCGGGGAA
 451 ATCCTCGACG TAGATGGTAT TACCGGCGGT TTTAATTTTC AAAATGCCTG
 501 GACTACGGCT TGGTTGGCGG CCCAGGGGAT GGCGGCTCCA TAACATTCCC
 551 TTAATTCCTC CTCAGTAAGT TGGACTAAAA TTCCAGTGCC AGCCCTGATT
 601 AACCCGGTGA AGTTTATGAG ACCCCTAAGT CATCGCACCA AAATTGTGGC
 651 CACCATTGGC CCCGCCAGTA GTTCGGTAGA GGTGATACGT CAGATGGTGG
 701 ATGCGGGCAT GAATGTGGCC CGGCTGAATT TTTCCCACGG TAGTTATGAG
 751 GACCATGCCA CCATGGTTCG CCTACTACGG TCAGTGGAGC AGGAAATGGA
 801 CACCCCCATT ACCCTTTTGC AAGATTTACA GGGGCCCAAA ATTCGGATTG
 851 GTCAGTTGCC GGGGGGAGAA AAGCAACTGC GGGAAGGGGA AAAAGTTTCT
 901 TTGGTGCCGG TGGAAATTGG CGATCGCCAT CCTGGAGCGG TGGGCATTGA
 951 CTATCCCCAT TTGGCGACGG AGGCAAAAGT AGGGGAAAGA ATTTTATTGG
1001 ACGATGGTTT ACTGGAAATG AAAGTTGTGT CCATTCAAGA TCCAGAGGTA
1051 ATTTGTGAAG TGGTGACCGG GGGCATCCTC AAAAGTCGCA AAGGGGTCAA
1101 TCTACCGGGT TTAGTCCTAA CCCTACCTTC CATGACGACC AAAGACAAGC
1151 AAGACTTAGA ATTTGGTTTG AGCCAAGGCA TTGACTGGGT TTCCCTTAGT
1201 TTTGTCCGCA AAGGGGAAGA TATCCACACC CTTAAACAAT TTCTCGCTGA
1251 ACGGGGCCAT CCTGATCTGC CGGTCATTGC CAAAATTGAA AAACCCCAGG
1301 CGATCGATAA TCTAGAAGAA ATCGTGGCAG TTTCCAACGG CATTATGGTG
1351 GCCAGGGGGG ATCTGGGGGT GGAAGTAAAC CCAGAAAAGG TTCCCCGTTT
1401 GCAAAAGGAA ATTATTCGGC GCTGTAACGT GCGGGCCATT CCGGTCATCA
1451 CCGCTACCCA AATGCTAGAT AGCATGATTC AAAATTCCCG ACCCACCAGG
1501 GCGGAAGCCA GTGACGTGGC CAACGCTATT TTGGACGGCA CCGATGCGGT
1551 GATGTTATCG GGGGAATCGG CAGTGGGACA ATATCCCGTT AAATCAGTGC
1601 AAATGTTGCG AAAAATTGCC GAAGAGACGG AAGTGGGTCT ACATCTTGTT
1651 AATAATCCCC AATAGAAAA TACGGAAACC CATGCCCTAA GTGAAGCGTT
```

Figure 20C(1)

```
1701 AGTGGTAATT GACGGAATTC TAGATTTAAA ATACATTGTC ACGTTCACCA
1751 CCTCAGGTTT TACTTCTCTC CTCGCTTCCA ACCAAAGACC GTCGGTGCCG
1801 GTGATTGCTT TCACTCCCTC AGAAAAGGTT TACCATAGCC TCAACTTAGT
1851 TTGGGGTATT ATTCCCTTTT TAATTAACGA AGAATTTGAC ACCTTTGAGG
1901 ATTTAATCCA ACAGGCGGAG GTACTACTGC GGGATAGAAA AATGGTGGAA
1951 AAGGGCGATC AGTTGCTAAT CATGGCGGGA ATTCCCACTA AAATACCCAG
2001 GGGCACTAAT TTCCTCAAGA TTCACCGTAT TTCTTAAAAC CTATGCCTCA
2051 AATCCATAGT TGCTGGACAA GGATTCTACA CTACTGTTTT CAGGAAGTAT
2101 ACTTGGAATA ATTTCTAGAA AATAGCAAAA TTATGTCATT ATTCCCTCTT
2151 TTAACCGCTT TGTTAGGGAT TATGCCCGCA AACACCATTG AACAAGTTCC
2201 TGCTGTTGTT GAAGCTGAAG CTCGTCCTTT TCTGGTTAGC CAAGCTAACA
2251 GCGCAGATAT TTTGGTGAAA CTCCCCCGAC CCCAGGGTAG TCCCAAGAAT
2301 GTAGGTAGCA TGTTCATGGC CAATGCCTAT GGACAACAGG GCCTAAATTC (SEQ ID
NO:38)
```

Figure 20C(2)

```
   1 TCGACTCTAG AGGATCCCCG GGTACCCCTC ATCGGGGGCT GTGTTGGCCG
  51 AGACGGCACT GAGGATTTTA CTCTCCATGG CATTCCAAGG AATATCTACC
 101 CAACTCACCT GCTCCGGCGG ATTGTTCCGC TCAAAAGTAC TAATCAAGTC
 151 GTCAAAATAC TTATTAAATT TTGGCTGCAA TTGCATAGTC CAAAAGCTGA
 201 CTTTCCCCTC CATGCTCTGG GGGAATTGC TCTGGCAACT GATTAATCCA
 251 CTGAGCAACA GCCCAAGACA CGCAAACAAA AACCAACGTC TTGGCGATCG
 301 CCATCGGCAC CATGAAACCA TCGTAAAAGC TGGGGAAAGA ATAAAAAACA
 351 GTGGTTCAGG AATTGCATTG CCATGGCCAC TTCACAAACC TAGCCAATTT
 401 TAGCTTGACC GCAACTTTGA CAGATTGTCT TTTGACTTTG CCTGGACCGC
 451 CTCCCATAAT ACCTTCGCGT CTTGAAGACT TTATCCTTGA AAGGAGAACA
 501 TATGAGACCC CTAAGTCATC GCACCAAAAT TGTGGCCACC ATTGGCCCCG
 551 CCAGTAGTTC GGTAGAGGTG ATACGTCAGA TGGTGGATGC GGGCATGAAT
 601 GTGGCCCGGC TGAATTTTTC CCACGGTAGT TATGAGGACC ATGCCACCAT
 651 GGTTCGCCTA CTACGGTCAG TGGAGCAGGA AATGGACACC CCCATTACCC
 701 TTTTGCAAGA TTTACAGGGG CCCAAAATTC GGATTGGTCA GTTGCCGGGG
 751 GGAGAAAAGC AACTGCGGGA AGGGGAAAAA GTTTCTTTGG TGCCGGTGGA
 801 AATTGGCGAT CGCCATCCTG GAGCGGTGGG CATTGACTAT CCCCATTTGG
 851 CGACGGAGGC AAAAGTAGGG GAAAGAATTT TATTGGACGA TGGTTTACTG
 901 GAAATGAAAG TTGTGTCCAT TCAAGATCCA GAGGTAATTT GTGAAGTGGT
 951 GACCGGGGGC ATCCTCAAAA GTCGCAAAGG GGTCAATCTA CCGGGTTTAG
1001 TCCTAACCCT ACCTTCCATG ACGACCAAAG ACAAGCAAGA CTTAGAATTT
1051 GGTTTGAGCC AAGGCATTGA CTGGGTTTCC CTTAGTTTTG TCCGCAAAGG
1101 GGAAGATATC CACACCCTTA AACAATTTCT CGCTGAACGG GGCCATCCTG
1151 ATCTGCCGGT CATTGCCAAA ATTGAAAAAC CCCAGGCGAT CGATAATCTA
1201 GAAGAAATCG TGGCAGTTTC CAACGGCATT ATGGTGGCCA GGGGGGATCT
1251 GGGGGTGGAA GTAAACCCAG AAAAGGTTCC CCGTTTGCAA AAGGAAATTA
1301 TTCGGCGCTG TAACGTGCGG GCCATTCCGG TCATCACCGC TACCCAAATG
1351 CTAGATAGCA TGATTCAAAA TTCCCGACCC ACCAGGGCGG AAGCCAGTGA
1401 CGTGGCCAAC GCTATTTTGG ACGGCACCGA TGCGGTGATG TTATCGGGGG
1451 AATCGGCAGT GGGACAATAT CCCGTTAAAT CAGTGCAAAT GTTGCGAAAA
1501 ATTGCCGAAG AGACGGAAGT GGGTCTACAT CTTGTTAATA ATCCCCCAAT
1551 AGAAAATACG GAAACCCATG CCCTAAGTGA AGCGTTAGTG GTAATTGACG
1601 GAATTCTAGA TTTAAAATAC ATTGTCACGT TCACCACCTC AGGTTTTACT
1651 TCTCTCCTCG CTTCCAACCA AAGACCGTCG GTGCCGGTGA TTGCTTTCAC
```

Figure 20E(1)

```
1701 TCCCTCAGAA AAGGTTTACC ATAGCCTCAA CTTAGTTTGG GGTATTATTC
1751 CCTTTTTAAT TAACGAAGAA TTTGACACCT TTGAGGATTT AATCCAACAG
1801 GCGGAGGTAC TACTGCGGGA TAGAAAAATG GTGGAAAAGG GCGATCAGTT
1851 GCTAATCATG GCGGGAATTC CCACTAAAAT ACCCAGGGGC ACTAATTTCC
1901 TCAAGATTCA CCGTATTTCT TAAAACCTAT GCCTCAAATC CATAGTTGCT
1951 GGACAAGGAT TCTACACTAC TGTTTTCAGG AAGTATACTT GGAATAATTT
2001 CTAGAAAATA GCAAAATTAT GTCATTATTC CCTCTTTTAA CCGCTTTGTT
2051 AGGGATTATG CCCGCAAACA CCATTGAACA AGTTCCTGCT GTTGTTGAAG
2101 CTGAAGCTCG TCCTTTTCTG GTTAGCCAAG CTAACAGCGC AGATATTTTG
2151 GTGAAACTCC CCCGACCCCA GGGTAGTCCC AAGAATGTAG GTAGCATGTT
2201 CATGGCCAAT GCCTATGGAC AACAGGGCCT AAATTC (SEQ ID NO:39)
```

Figure 20E(2)

MQTSPLPRRTKIVATIGPATQSKEVLRQLIQAGATTFRLNFSHGDHAYHQQSIRLIRQIA
FELNQPVGILQDLQGPKIRVGKFLNDAGSVQLKNGDPYTLTSRPVECTETISSISYEYLA
DEVPSGARILLDDGKLEMLVEEVDTVARDLHCRVIVGGTLSSNKGVNFPGVCLSVKAMTD
KDKEDLMFGLDQGVDWVALSFVRNPQDIDEIKGLIAAAGKSVPVIAKIEKHEAIKDMQAV
LEKCDGVMVARGDLGVELPAEDVPILQKKLIATANRLGIPVITATQMLDSMVNSPRPTRA
EVSDVANAILDGTDAVMLSNETAIGKFPVEAVAIMAKIAERIEQEDINPSQAEASRTSIP
NAISSAVSQIAETLNAAAIMSLTKTGSTARHVSKFRPKTPILAVTPHVDVSRQLQLVWGV
KPLLVLDLPSTSQTFQAAINVAQENHFLRDGDLVVMTAGTLQGVAGSTDLIKVEVVKAIL
GRGVGIGQGAVSGRARVASRPQAIAQFTQGEILVVPSTNADCVDMMRRAAGIITEEESLT
SHAAIIGLRLGVPVIVGFKGATQKIRDGAIVTIDAQKGLIYSGALPPVSKG (SEQ ID
NO:40)

Figure 21A

```
   1 TCGACCGGCA AACAAATCCA GCGGAAAATA ACCGTAGGTT CCCGCTAAGG
  51 TATCATCCTC CGCCTGACAG GAAATTAATA CTCCCCGATA ATCCCCGTCA
 101 TAACTGTCGA GATAAAAGCG CAGGGATTGG CTCTGGCATT TCAAATACAC
 151 TGGCCCTTCA ATGGTTTTAC CTGGTTCCAT GGCGATCGCC TCTCCGTAAT
 201 CCAACCCCTG TAGATATTGC CCCAAAGCAT TTTCCGCACT AGCTTGGTCG
 251 TCGGCACAAA TGCCAAAATT TTCCGCTTCA CTCTGGCCAC AAATCCAGAC
 301 AATGGCTTGG CGTAAATCTT CCCTTTCCTG GTCATTCTGG GGAATACGGA
 351 TTTCTAAACG ACTGTAATCC TTTAACAACG TCAACTGAGC GGAAGCATTC
 401 ATAGCAAACC CATCAAACTG TGCAGACTAT TGGGAAAAAT TGCCCAAAGC
 451 CCAGCCTACC ATCGTTGGCC CTGTAAGCCG ATGCAACTGA AACGGCGATC
 501 GTGGCGGATA ATGAGAATAT TTCCCTAACA CCGCTTAAAA GCAGACGGCC
 551 TTAACTATTA TATTTAACTG CCCCTAATTT CAGCCCATTA TGCAAACGTC
 601 TCCCCTTCCC CGTCGTACCA AAATCGTCGC TACCATTGGC CCCGCGACCC
 651 AAAGCAAGGA AGTGCTGAGA CAACTGATCC AAGCCGGTGC TACCACTTTC
 701 CGCCTCAATT TTTCCCACGG AGACCACGCT TACCACCAAC AAAGTATCCG
 751 TTTGATTCGC CAGATTGCCT TTGAACTGAA CCAACCAGTG GGCATTCTCC
 801 AGGATTTACA GGGGCCAAAG ATTCGGGTGG GCAAATTTCT CAATGATGCC
 851 GGCTCTGTGC AACTCAAAAA CGGTGATCCC TATACCCTCA CCAGTCGCCC
 901 GGTGGAATGT ACGGAAACCA TTAGTTCCAT TAGCTACGAA TATTTAGCCG
 951 ACGAAGTACC TTCTGGGGCA AGAATTTTGC TCGACGACGG CAAACTGGAA
1001 ATGTTGGTGG AGGAAGTGGA CACTGTTGCC CGGGATCTCC ACTGTCGGGT
1051 GATTGTGGGG GGAACCCTTT CCAGCAATAA AGGGGTTAAT TTTCCCGGGG
1101 TCTGCCTTTC CGTTAAGGCC ATGACCGATA AAGATAAGGA AGATTTGATG
1151 TTCGGGCTGG ACCAAGGGGT GGACTGGGTG GCCCTGAGTT TTGTTCGTAA
1201 TCCCCAGGAT ATTGATGAGA TTAAGGGGTT AATTGCGGCG GCAGGGAAAT
1251 CCGTGCCGGT AATCGCCAAA ATTGAGAAGC ACGAAGCGAT TAAGGATATG
1301 CAGGCGGTGC TGGAAAAATG TGACGGTGTC ATGGTGGCCC GGGGGGACTT
1351 GGGGGTAGAA CTACCCGCAG AAGATGTACC TATTTTGCAA AAGAAACTCA
1401 TTGCCACTGC TAACCGGTTG GGCATTCCTG TCATTACTGC TACCCAAATG
1451 TTGGACAGTA TGGTCAACAG CCCCCGACCT ACTAGGGCTG AAGTGTCCGA
1501 CGTGGCCAAT GCCATCCTCG ATGGTACCGA TGCGGTGATG CTCTCCAACG
1551 AAACGGCGAT CGGTAAATTT CCCGTGGAAG CAGTGGCTAT TATGGCCAAA
1601 ATTGCGGAGC GCATTGAACA GGAAGATATC AATCCTTCCC AAGCGGAAGC
1651 CAGTCGCACT TCTATTCCCA ATGCTATTTC CAGCGCCGTT AGCCAGATTG
```

Figure 21C(1)

```
1701 CGGAAACCCT CAACGCGGCG GCTATTATGT CTTTGACTAA GACCGGATCC
1751 ACCGCCCGCC ATGTGTCAAA GTTCCGCCCC AAAACCCCCA TTCTGGCCGT
1801 TACGCCCCAT GTGGATGTGT CCCGTCAGTT GCAGTTGGTG TGGGGAGTTA
1851 AGCCCCTGTT GGTATTGGAT TTACCTTCCA CCAGCCAAAC GTTCCAAGCC
1901 GCCATTAACG TGGCCCAGGA AAACCATTTT CTCCGGGATG GAGATTTGGT
1951 GGTGATGACC GCCGGGACAT TGCAGGGAGT TGCCGGTTCG ACGGATTTAA
2001 TCAAAGTGGA AGTGGTCAAG GCCATTCTTG GTCGGGGTGT AGGTATTGGC
2051 CAAGGAGCTG TAAGTGGCCG GGCCAGGGTT GCCAGTCGTC CCCAGGCGAT
2101 CGCCCAATTT ACCCAGGGAG AAATTTTAGT AGTTCCCTCT ACCAACGCTG
2151 ATTGTGTGGA CATGATGCGA CGGGCGGCGG GCATTATCAC CGAAGAAGAA
2201 AGCCTGACTA GCCATGCGGC CATTATTGGT TTGCGGCTGG GGGTGCCGGT
2251 CATTGTGGGT TTTAAAGGCG CTACCCAAAA GATTCGAGAT GGAGCCATTG
2301 TCACCATCGA TGCCCAAAAA GGACTGATTT ATTCCGGTGC ATTACCCCCG
2351 GTGTCCAAAG GATAGGGAAT AATTAGGGAC CCAGTAACAG GGCGAGAACA
2401 GGAAGCATCA TCCCAATGGA GTTCCCATTC CCCACCCCCT GGAACAGTAA
2451 CATTTTGGTA GAATCAACGG GGTTCTTTTC CCGACGTAAT TTAGTCCTTT
2501 GCAGAAAAAA TCTTCCCTTA AATCCCGCTA CTGGCTGTTA ATCCCTATA
2551 TTCGTCCCCA TCGGCGGACT ATTGGGCTGG CTTTCCTCTG TACTCTGCTA
2601 TTCACTGTTT TTTGGCCCAC (SEQ ID NO:41)
```

Figure 21C(2)

```
   1 TCGACTCTAG AGGATCCCCG GGTACCCCTC ATCGGGGGCT GTGTTGGCCG
  51 AGACGGCACT GAGGATTTTA CTCTCCATGG CATTCCAAGG AATATCTACC
 101 CAACTCACCT GCTCCGGCGG ATTGTTCCGC TCAAAAGTAC TAATCAAGTC
 151 GTCAAAATAC TTATTAAATT TTGGCTGCAA TTGCATAGTC CAAAAGCTGA
 201 CTTTCCCCTC CATGCTCTGG GGGAATTGC TCTGGCAACT GATTAATCCA
 251 CTGAGCAACA GCCCAAGACA CGCAAACAAA AACCAACGTC TTGGCGATCG
 301 CCATCGGCAC CATGAAACCA TCGTAAAAGC TGGGGAAAGA ATAAAAAACA
 351 GTGGTTCAGG AATTGCATTG CCATGGCCAC TTCACAAACC TAGCCAATTT
 401 TAGCTTGACC GCAACTTTGA CAGATTGTCT TTTGACTTTG CCTGGACCGC
 451 CTCCCATAAT ACCTTCGCGT CTTGAAGACT TTATCCTTGA AGGAGAACA
 501 TATGCAAACG TCTCCCCTTC CCCGTCGTAC CAAAATCGTC GCTACCATTG
 551 GCCCCGCGAC CCAAAGCAAG GAAGTGCTGA GACAACTGAT CCAAGCCGGT
 601 GCTACCACTT TCCGCCTCAA TTTTTCCCAC GGAGACCACG CTTACCACCA
 651 ACAAAGTATC CGTTTGATTC GCCAGATTGC CTTTGAACTG AACCAACCAG
 701 TGGGCATTCT CCAGGATTTA CAGGGGCCAA AGATTCGGGT GGGCAAATTT
 751 CTCAATGATG CCGGCTCTGT GCAACTCAAA AACGGTGATC CCTATACCCT
 801 CACCAGTCGC CCGGTGGAAT GTACGGAAAC CATTAGTTCC ATTAGCTACG
 851 AATATTTAGC CGACGAAGTA CCTTCTGGGG CAAGAATTTT GCTCGACGAC
 901 GGCAAACTGG AAATGTTGGT GGAGGAAGTG GACACTGTTG CCCGGGATCT
 951 CCACTGTCGG GTGATTGTGG GGGAACCCT TTCCAGCAAT AAAGGGGTTA
1001 ATTTTCCCGG GGTCTGCCTT TCCGTTAAGG CCATGACCGA TAAAGATAAG
1051 GAAGATTTGA TGTTCGGGCT GGACCAAGGG GTGGACTGGG TGGCCCTGAG
1101 TTTTGTTCGT AATCCCCAGG ATATTGATGA GATTAAGGGG TTAATTGCGG
1151 CGGCAGGGAA ATCCGTGCCG GTAATCGCCA AAATTGAGAA GCACGAAGCG
1201 ATTAAGGATA TGCAGGCGGT GCTGGAAAAA TGTGACGGTG TCATGGTGGC
1251 CCGGGGGGAC TTGGGGGTAG AACTACCCGC AGAAGATGTA CCTATTTTGC
1301 AAAAGAAACT CATTGCCACT GCTAACCGGT TGGGCATTCC TGTCATTACT
1351 GCTACCCAAA TGTTGGACAG TATGGTCAAC AGCCCCGAC CTACTAGGGC
1401 TGAAGTGTCC GACGTGGCCA ATGCCATCCT CGATGGTACC GATGCGGTGA
1451 TGCTCTCCAA CGAAACGGCG ATCGGTAAAT TTCCCGTGGA AGCAGTGGCT
1501 ATTATGGCCA AAATTGCGGA GCGCATTGAA CAGGAAGATA TCAATCCTTC
1551 CCAAGCGGAA GCCAGTCGCA CTTCTATTCC CAATGCTATT TCCAGCGCCG
1601 TTAGCCAGAT TGCGGAAACC CTCAACGCGG CGGCTATTAT GTCTTTGACT
```

Figure 21E(1)

```
1651 AAGACCGGAT CCACCGCCCG CCATGTGTCA AAGTTCCGCC CCAAAACCCC
1701 CATTCTGGCC GTTACGCCCC ATGTGGATGT GTCCCGTCAG TTGCAGTTGG
1751 TGTGGGGAGT TAAGCCCCTG TTGGTATTGG ATTTACCTTC CACCAGCCAA
1801 ACGTTCCAAG CCGCCATTAA CGTGGCCCAG GAAAACCATT TTCTCCGGGA
1851 TGGAGATTTG GTGGTGATGA CCGCCGGGAC ATTGCAGGGA GTTGCCGGTT
1901 CGACGGATTT AATCAAAGTG GAAGTGGTCA AGGCCATTCT TGGTCGGGGT
1951 GTAGGTATTG GCCAAGGAGC TGTAAGTGGC CGGGCCAGGG TTGCCAGTCG
2001 TCCCCAGGCG ATCGCCCAAT TTACCCAGGG AGAAATTTTA GTAGTTCCCT
2051 CTACCAACGC TGATTGTGTG GACATGATGC GACGGGCGGC GGGCATTATC
2101 ACCGAAGAAG AAAGCCTGAC TAGCCATGCG GCCATTATTG GTTTGCGGCT
2151 GGGGGTGCCG GTCATTGTGG GTTTTAAAGG CGCTACCCAA AAGATTCGAG
2201 ATGGAGCCAT TGTCACCATC GATGCCCAAA AAGGACTGAT TTATTCCGGT
2251 GCATTACCCC CGGTGTCCAA AGGATAGGGA ATAATTAGGG ACCCAGTAAC
2301 AGGGCGAGAA CAGGAAGCAT CATCCCAATG GAGTTCCCAT TCCCCACCCC
2351 CTGGAACAGT AACATTTTGG TAGAATCAAC GGGGTTCTTT TCCCGACGTA
2401 ATTTAGTCCT TTGCAGAAAA AATCTTCCCT TAAATCCCGC TACTGGCTGT
2451 TAATCCCCTA TATTCGTCCC CATCGGCGGA CTATTGGGCT GGCTTTCCTC
2501 TGTACTCTGC TATTCACTGT TTTTTGGCCC AC (SEQ ID NO:42)
```

Figure 21E(2)

MKKTKIVCTIGPKTESEEMLAKMLDAGMNVMRLNFSHGDYAEHGQRIQNLRNVMSKTGKT
AAILLDTKGPEIRTMKLEGGNDVSLKAGQTFTFTTDKSVIGNSEMVAVTYEGFTTDLSVG
NTVLVDDGLIGMEVTAIEGNKVICKVLNNGDLDENKGVNLPGVSIALPALAEKDKQDLIF
GCEQGVDFVAASFIRKRSDVIEIREHLKAHGGENIHIISKIENQEGLNNFDEILEASDGI
MVARGDLGVEIPVEEVIFAQKMMIEKCIRARKVVITATQMLDSMIKNPRPTRAEAGDVAN
AILDGTDAVMLSGESAKGKYPLEAVSIMATICERTDRVMNSRLEFNNDNRKLRITEAVCR
GAVETAEKLDAPLIVVATQGGKSARAVRKYFPDATILALTTNEKTAHQLVLSKGVVPQLV
KEITSTDDFYRLGKELALQSGLAHKGDVVVMVSGALVPSGTTNTASVHVL (SEQ ID
NO:43)

Figure 22B

```
MTAIVSIHGRQVVDSRGNPTVEVDVTLEDGSFGRAAVPSGASTGVHEAVELRDGDKTRWG
GKGVTKAVHAVNNEIANAIIGLEAEDQELIDQTMIKLDGTPNKGKFGANAILGVSLAVAK
AAAEARGLPLYRYVGGTAAHVLPVPMMNIVNGGMHADNPIDFQEFMIAPVGASSINEAVR
IGTEVFHTLKKELSAKGMNTNVGDEGGFAPSLDSASSALDFIVDSISKAGYKPGEDVFIA
LDAASSEFYNKDQNIYDLKGEGRKLTSAQLVDYYVELCGKYPIYSIEDGLAEDDFEGWKI
LTEKLGDKVQLVGDDLFVTNVKRLSDGIERGIANSLLVKFNQIGSLSETLAAVNMANDAS
YTAVMSHRSGETEDTTIADLAVATNCGQIKTGSLCRSERIAKYNQLMRIEEELGSVAKYA
GRSVLRKAK (SEQ ID NO:44)
```

Figure 22C

MPTLVLSRHGQSEWNLENRFTGWWDVNLTEQGVQEATAGGKALAEKGFEFDIAFTSVLTR
AIKTTNLILEAGKTLWVPTEKDWRLNERHYGGLTGLNKAETAAKHGEEQVHIWRRSYGVP
PPPMEKGSKFDLSGDRRYDGVKIPETESLKDTVARVLPYWEERIAPELKAGKRVLIGAHG
NSLRALVKHLSKLSDEEIVKFELPTGQPLVYELNDDLTPKDRYFLNER (SEQ ID
NO:45)

Figure 22D

```
   1 CCCGGGATCT CTAGAAAGTT TCGGACTCAG TAGACCTAAG TACAGAGTGA
  51 TGTCAACGCC TTCAAGCTAG ACGGGAGGCG GCTTTTGCCA TGGTTCAGCG
 101 ATCGCTCCTC ATCTTCAATA AGCAGGGCAT GAGCCAGCGT TAAGCAAATC
 151 AAATCAAATC TCGCTTCTGG GCTTCAATAA ATGGTTCCGA TTGATGATAG
 201 GTTGATTCAT GAGGAATCTA AGGCTTAATT CTCCACAAAA GAATTAAGCG
 251 TCCGTCGCAA CGGAATGCTC CGCTGGACTT GCGCTGTGGG ACTGCAGCTT
 301 TACAGGCTCC CCCTGCCAGA AATCCTGAAT CGTCGAGCAT ATCTGACATA
 351 TCTCTAGGGA GAGACGACAT GTCGACGATT AATTTCAGCG TATAATGCGC
 401 GCCAATTGAC TCTTGAATGG TTTCAGCACT TTGGACTGTA GAACTCAACG
 451 ACTCAAAAAC AGGCACTCAC GTTGGGCTGA GACACAAGCA CACATTCCTC
 501 TGCACGCTTT TTCGATGTCA CCTATCCTTA GAGCGAGGCA CCACCACTTT
 551 CGTAATACCG GATTCGCTTT CCGGCAGTGC GCCCAGAAAG CAAGTTTCTC
 601 CCATCCTTCT CAACTTAAAG ACTAAGACTG TCATGAAAAA GACCAAAATT
 651 GTTTGCACCA TCGGACCGAA AACCGAATCT GAAGAGATGT TAGCTAAAAT
 701 GCTGGACGCT GGCATGAACG TTATGCGTCT GAACTTCTCT CATGGTGACT
 751 ATGCAGAACA CGGTCAGCGC ATTCAGAATC TGCGCAACGT GATGAGCAAA
 801 ACTGGTAAAA CCGCCGCTAT CCTGCTTGAT ACCAAAGGTC CGGAAATCCG
 851 CACCATGAAA CTGGAAGGCG GTAACGACGT TTCTCTGAAA GCTGGTCAGA
 901 CCTTTACTTT CACCACTGAT AAATCTGTTA TCGGCAACAG CGAAATGGTT
 951 GCGGTAACGT ATGAAGGTTT CACTACTGAC CTGTCTGTTG CAACACCGT
1001 ACTGGTTGAC GATGGTCTGA TCGGTATGGA AGTTACCGCC ATTGAAGGTA
1051 ACAAAGTTAT CTGTAAAGTG CTGAACAACG GTGACCTGGA CGAAAACAAA
1101 GGTGTGAACC TGCCTGGCGT TTCCATTGCT CTGCCAGCAC TGGCTGAAAA
1151 AGACAAACAG GACCTGATCT TTGGTTGCGA ACAAGGCGTA GACTTTGTTG
1201 CTGCTTCCTT TATTCGTAAG CGTTCTGACG TTATCGAAAT CCGTGAGCAC
1251 CTGAAAGCGC ACGGCGGCGA AAACATCCAC ATCATCTCCA AAATCGAAAA
1301 CCAGGAAGGC CTCAACAACT TCGACGAAAT CCTCGAAGCC TCTGACGGCA
1351 TCATGGTTGC GCGTGGCGAC CTGGGTGTAG AAATCCCGGT AGAAGAAGTT
1401 ATCTTCGCCC AGAAGATGAT GATCGAAAAA TGTATCCGTG CACGTAAAGT
1451 CGTTATCACT GCGACCCAGA TGCTGGATTC CATGATCAAA AACCCACGCC
1501 CGACTCGCGC AGAAGCCGGT GACGTTGCAA ACGCCATCCT CGACGGTACT
1551 GACGCAGTGA TGCTGTCTGG TGAATCCGCA AAAGGTAAAT ACCCGCTGGA
1601 AGCGGTTTCT ATCATGGCGA CCATCTGCGA ACGTACCGAC GCGGTGATGA
1651 ACAGCCGTCT CGAGTTCAAC AATGACAACC GTAAACTGCG CATTACCGAA
```

Figure 22E(1)

```
1701 GCGGTATGCC GTGGTGCCGT CGAAACTGCT GAAAAACTGG ATGCTCCGCT
1751 GATCGTGGTT GCTACTCAGG GCGGTAAATC TGCTCGCGCA GTACGTAAAT
1801 ACTTCCCGGA TGCCACCATC CTGGCACTGA CCACTAACGA AAAAACGGCT
1851 CATCAGTTGG TACTGAGCAA AGGCGTTGTG CCGCAGCTTG TTAAAGAGAT
1901 CACTTCTACT GATGATTTCT ACCGTCTGGG TAAAGAACTG GCTCTGCAGA
1951 GCGGTCTGGC ACACAAAGGT GACGTTGTAG TTATGGTTTC TGGTGCACTG
2001 GTACCGAGCG GCACTACTAA CACCGCATCT GTTCACGTCC TGTAATAAGC
2051 TTCATTGACG GACTGAGTTC AAAAAGAGAC TCGTCTAAAA GATTTTAAGA
2101 AAGGTTTCGA TATGACAGCT ATTGTCAGTA TCCATGGCCG TCAGGTTGTC
2151 GACAGCCGCG GTAACCCGAC CGTTGAAGTT GATGTTACGC TTGAAGATGG
2201 CAGCTTCGGC CGCGCCGCAG TGCCGTCAGG TGCTTCTACC GGCGTTCATG
2251 AAGCTGTTGA ACTTCGTGAT GGCGACAAAA CCCGTTGGGG TGGTAAAGGC
2301 GTTACCAAAG CTGTTCACGC TGTAAACAAC GAAATTGCTA ACGCAATTAT
2351 TGGTCTGGAA GCCGAAGATC AGGAACTGAT CGACCAGACG ATGATCAAGC
2401 TCGATGGCAC CCCGAACAAG GGTAAATTCG GTGCTAACGC TATCCTCGGT
2451 GTCAGCTTGG CTGTTGCTAA AGCTGCTGCT GAAGCTCGCG GTCTCCCGCT
2501 TTACCGTTAT GTTGGTGGTA CGGCAGCTCA CGTTCTTCCG GTTCCGATGA
2551 TGAACATCGT TAACGGTGGT ATGCACGCTG ACAACCCCAT CGATTTCCAG
2601 GAATTCATGA TTGCTCCGGT TGGCGCCAGC TCTATCAATG AAGCTGTCCG
2651 CATCGGTACC GAAGTTTTCC ATACCCTGAA AAAAGAACTG TCTGCTAAAG
2701 GCATGAACAC CAACGTCGGT GACGAAGGTG GTTTCGCTCC TAGCCTTGAC
2751 AGTGCTTCTT CTGCTCTGGA CTTCATCGTC GATTCCATCT CCAAAGCCGG
2801 TTATAAGCCG GGCGAAGATG TGTTCATCGC TCTCGATGCA GCTTCCTCCG
2851 AGTTCTACAA CAAAGATCAG AACATCTACG ATCTTAAGGG TGAAGGCCGT
2901 AAACTGACCT CCGCTCAGCT CGTTGATTAC TATGTCGAAC TCTGCGGCAA
2951 ATATCCGATC TATTCCATCG AAGATGGTCT GGCCGAAGAT GACTTCGAAG
3001 GCTGGAAGAT CCTTACCGAA AAGCTCGGTG ACAAAGTTCA GTTGGTCGGT
3051 GACGATCTGT TCGTGACCAA CGTGAAGCGT CTTTCTGATG GTATCGAACG
3101 CGGTATCGCC AACTCGCTGC TCGTGAAGTT TAACCAGATC GGTTCTTTGT
3151 CTGAAACGCT CGCAGCCGTT AACATGGCTA ACGACGCTTC TTACACGGCT
3201 GTTATGTCTC ACCGTTCCGG TGAAACCGAA GACACCACGA TTGCTGACCT
3251 CGCTGTTGCC ACCAACTGCG GTCAGATCAA GACCGGTAGC CTTTGCCGTT
3301 CCGAACGTAT CGCTAAATAC AATCAGCTGA TGCGCATCGA AGAAGAACTG
3351 GGTTCGGTTG CTAAATATGC TGGCCGTTCG GTTCTTAGAA AAGCCAAATA
3401 AGAATCACAG CTAGAACCGA GCTCACATAA CGAAGAGATA TTGAAAAGGA
```

Figure 22E(2)

```
3451 GTGGAATATG CCCACGCTCG TTTTGTCCCG TCACGGACAG TCCGAATGGA
3501 ACCTTGAAAA CCGTTTCACC GGTTGGTGGG ATGTTAACCT GACTGAACAG
3551 GGTGTTCAGG AAGCAACGGC CGGTGGTAAA GCTCTGGCTG AAAAGGGTTT
3601 TGAATTCGAT ATCGCTTTCA CCAGCGTTCT GACCCGCGCC ATCAAAACCA
3651 CCAATCTTAT TCTCGAAGCC GGTAAAACCC TTTGGGTTCC GACCGAAAAA
3701 GATTGGCGTT TGAATGAACG TCACTATGGT GGTCTGACCG GTCTGAACAA
3751 GGCTGAAACC GCCGCTAAAC ATGGTGAAGA ACAGGTTCAT ATTTGGCGCC
3801 GTTCTTATGG CGTTCCGCCG CCCCGATGG AAAAAGGCAG CAAGTTCGAT
3851 CTGTCTGGCG ATCGCCGTTA TGATGGTGTC AAGATTCCTG AAACGGAAAG
3901 CCTGAAAGAC ACCGTTGCTC GCGTGCTGCC TTATTGGGAA GAACGCATTG
3951 CCCCTGAACT GAAGGCTGGC AAGCGCGTCC TGATCGGTGC GCATGGTAAC
4001 TCACTGCGCG CTCTCGTTAA GCATCTGTCG AAATTGTCGG ACGAAGAAAT
4051 CGTCAAATTC GAATTGCCCA CCGGTCAGCC GTTGGTCTAC GAATTGAATG
4101 ATGATCTGAC TCCGAAAGAT CGTTACTTCC TTAACGAACG TTAATAGCCT
4151 TGGGCTTTTA AAGCCTTTTG GTTTGTTAAC CGTTTTTTCG GCCAGAGTTT
4201 TCTCTGGCCG AAAATTTATG TCTATCCCTT TGTTTTTCTA TCCCCATCAC
4251 CTCGGTTTTG TTGGATCCAC TAGT (SEQ ID NO:46)
```

Figure 22E(3)

MLSKVPATIEEIAAREILDSRGRPTIEAEVRLESGAHGIAQVPSGASTGSFEAHELRDGDP
KRYDGKGVEKAVRNVTEKIAPVVEGLDAFDQMAVDQAMIDRDGTDNKKELGANAILGVSLA
TAKAAAAELAIPLYRYLGGPLANVLPVPMMNVINGGAHADNNVDFQEFMIMPVGAETFKEA
LRWGAEVFAVLGKVLKERKLLSGGVGDEGGYAPNLTSNQQALDILIEAIEQAGYKPGSQIA
LAMDIAASEFFKNGQYEYDGGSHSPQEFIDYQAKLVSQYPIVSIEDGLHEDDWESWKGLTT
SLGTKTQLVGDDLMVTNPVRLQKSIDLGVANAILIKLNQIGTLSETLETISLATRHSYRSV
ISHRSGETEDTTIADLAVATRVGQIKTGSLCRSERVAKYNRLLRIEDELGDRAVYAPKIGL
GPKHS (SEQ ID NO:47)

Figure 23A

```
   1  gtcgactcta gaggatcccc gggtacccct catcgggggc tgtgttggcc
  51  gagacggcac tgaggatttt actctccatg gcattccaag gaatatctac
 101  ccaactcacc tgctccggcg gattgttccg ctcaaaagta ctaatcaagt
 151  cgtcaaaata cttattaaat tttggctgca attgcatagt ccaaaagctg
 201  actttcccct ccatgctctg gggggaattg ctctggcaac tgattaatcc
 251  actgagcaac agcccaagac acgcaaacaa aaaccaacgt cttggcgatc
 301  gccatcggca ccatgaaacc atcgtaaaag ctggggaaag aataaaaaac
 351  agtggttcag gaattgcatt gccatggcca cttcacaaac ctagccaatt
 401  ttagcttgac cgcaactttg acagattgtc ttttgacttt gcctggaccg
 451  cctcccataa taccttcgcg tcttgaagac tttatccttg aaggagaac
 501  atatggagct cttaagtaaa gtccccgcca ccattgaaga aatcgccgcc
 551  cgggaaattt tagactccag gggtcgcccc accatcgaag cggaagtccg
 601  gctggaaagt ggggcccacg gcattgccca ggtgcccagt ggtgcttcca
 651  caggcagttt tgaagcccat gaattgcggg acggagaccc caaacgctat
 701  gacgggaaag gggtagaaaa agcagtacgg aacgtgacag aaaaaattgc
 751  cccggtggtg gaaggcctgg atgccttcga tcaaatggcg gtggatcagg
 801  ccatgattga ccgggatgga acggacaata aaaagaatt gggggccaat
 851  gccattttgg gggtttcttt agccaccgct aaggccgccg ccgctgagct
 901  agccattccc ctctaccgct acctgggagg cccctggct aacgtactgc
 951  cggtaccgat gatgaacgtg attaacggtg gggcccatgc cgacaataac
1001  gtcgattttc aggaattcat gatcatgccg gtgggggcag aaacctttaa
1051  agaagctctg cgctgggggg cggaagtttt cgctgtgttg ggcaaagtgt
1101  tgaaagaacg aaaactgctc tccggtgggg tggggacga agggggttat
1151  gctcccaatt tgacctcgaa tcaacaggcc ctagatattc tcatcgaggc
1201  gattgaacaa gctggttaca aacccggtag tcaaattgcc ttggccatgg
1251  acattgccgc cagtgaattt ttcaaaaatg gtcagtatga atacgacggt
1301  ggttcccatt ctccccagga attcatcgac tatcaggcca agctagtgag
1351  tcaatatccc attgtctcca ttgaagacgg tttgcacgaa gacgattggg
1401  aaagttggaa gggtttaacc acttccctgg gcaccaaaac ccagttggtg
1451  ggggatgact tgatggtgac caacccggtg cgtctgcaaa aatccattga
1501  tttgggagtt gccaacgcca ttttgatcaa actcaatcaa atcggcactt
1551  tgagcgaaac tttagagacc atttccctag ctactcgcca tagttaccgt
```

Figure 23C(1)

```
1601  tctgttattt cccatcgctc cggtgaaacg gaggacacca cgatcgccga
1651  cttggccgtg gccaccaggg tagggcaaat taaaaccggt tccctttgtc
1701  gttctgagcg ggttgctaaa tataaccgtt tactccgcat tgaagatgaa
1751  cttggcgatc gggccgttta tgcccctaaa attggcctgg gtcccaaaca
1801  ttcttaaaaa gtgttttaaa gttccctag cccaagggtt ggggttactt
1851  cgggagataa tcaaaccatt gccaacaggt tcttttggtt aggttgttgc
1901  ttaggattgt ctaaaattcc tcagtttttt attcaagact taatttttcc
1951  catggttacc ctaccggtga actgtgggaa ttttatgcc taacccgttc
2001  taagccaagg aagcaatgac ctcgag (SEQ ID NO:48)
```

Figure 23C(2)

```
MATRVIIVRHGQSTYNAEKRIQGRSNLSVLTDKGKADAQKVGQTLNSLAIDKIYCSPLRR
AKETAQIIQASFAHPPELIPSENLLEVNLPLWEKMTKDDVAHQYPEQYRLWHEAPDQLAM
TVDGAEYYPVAALYAQAQRFWQDVLTDAAGQTLLIVAHNGINRCLLMSAIGMPASHYQRL
QQSNCNINVLNFSGGWGDPVQLESLNQTAHMGVPLPPPRKDNNRLRLLLIRHGETQWNRE
GRFQGIRDIPLNDNGRHQAQKAAEFLKDVPINLGISSPMARPKETAEIILQYHPSIELDL
QPELAEICHGLWEGKLETEIEAEYPGLLQQWKDAPATVQMPEGENLQQVWDRAIACWQDR
VKFYSQGDGSTVGIVVAHDAINKVILAYLLGLTPAHFWQVKQGNGGVSVIDYPQGLDKPP
VIQAINLMGHLGTVLDKTAAGAL (SEQ ID NO:49)
```

Figure 24A

```
   1  gtcgactcta gaggatcccc gggtacccct catcggggc tgtgttggcc
  51  gagacggcac tgaggatttt actctccatg gcattccaag gaatatctac
 101  ccaactcacc tgctccggcg gattgttccg ctcaaaagta ctaatcaagt
 151  cgtcaaaata cttattaaat tttggctgca attgcatagt ccaaaagctg
 201  actttcccct ccatgctctg gggggaattg ctctggcaac tgattaatcc
 251  actgagcaac agcccaagac acgcaaacaa aaaccaacgt cttggcgatc
 301  gccatcggca ccatgaaacc atcgtaaaag ctggggaaag aataaaaaac
 351  agtggttcag gaattgcatt gccatggcca cttcacaaac ctagccaatt
 401  ttagcttgac cgcaactttg acagattgtc ttttgacttt gcctggaccg
 451  cctcccataa taccttcgcg tcttgaagac tttatccttg aaaggagaac
 501  atatggagct caccaaagac gatgtggccc accaatatcc cgaacaatat
 551  cgtctctggc acgaagcacc ggatcaattg gccatgaccg tagatggagc
 601  ggaatattac cccgttgcgg ctctctatgc ccaggcccaa agatttggc
 651  aggatgtgtt aaccgatgcg gcgggacaaa ccctgctgat tgtggcccac
 701  aatggcatca atcgttgcct gttaatgagc gccattggta tgcccgcttc
 751  ccattaccaa cgcctgcaac agtccaactg caatattaat gtgttgaatt
 801  ttagtggtgg ctggggcgat ccggtgcaac tggaatcctt gaatcaaacc
 851  gcccatatgg gggtacctct gccacctccc cgcaaggata taatcgtct
 901  gcggttactg cttatccgcc atggggaaac ccaatggaat cgggaaggac
 951  ggttccaagg tattcgggat attcccctca atgacaatgg ccgccatcaa
1001  gcccaaaaag cggcggaatt cctcaaagat gtgcccatta acctaggcat
1051  tagcagtccc atggctcggc caaggaaac ggcggagatt attctgcaat
1101  atcacccaag catagagttg gatttacagc cggaattggc ggaaatttgc
1151  catggcctgt gggaaggcaa gctagaaacg gaaattgaag cggaatatcc
1201  cggattattg caacagtgga agatgcccc cgccacagtg cagatgccgg
1251  aagggggaaaa tttacaacag gtctgggacc gggcgatcgc ctgttggcag
1301  gaccgggtca aattctatag ccaggggat ggttccacag tgggcattgt
1351  ggtggcccat gatgccatca acaaggtgat tttggcttat tgttgggtc
1401  ttactcccgc tcacttttgg caagttaaac agggtaatgg cggggtgagc
1451  gtcattgact atccccaggg tctagataag cccccagtta ttcaagccat
1501  taatttgatg ggccatttgg gcacagtgtt ggataaaacc gccgccggag
```

Figure 24C(1)

```
1551  ccctatagtc ctgtccatag ccaattatcc ccccatttgt tccctaactc
1601  ttgtttgcta tgactcactt tggtttgctc tgtccagcaa cgacgggtca
1651  tctcaatacc atgttgccct tgggtaagga actgcaacag cggggtcata
1701  ctcgag (SEQ ID NO:50)
```

Figure 24C(2)

```
   1  ctgcaggtcg actctagagg atccccgggt acccctcatc gggggctgtg
  51  ttggccgaga cggcactgag gattttactc tccatggcat tccaaggaat
 101  atctacccaa ctcacctgct ccggcggatt gttccgctca aaagtactaa
 151  tcaagtcgtc aaaatactta ttaaattttg gctgcaattg catagtccaa
 201  aagctgactt tcccctccat gctctggggg gaattgctct ggcaactgat
 251  taatccactg agcaacagcc caagacacgc aaacaaaaac caacgtcttg
 301  gcgatcgcca tcggcaccat gaaaccatcg taaaagctgg ggaaagaata
 351  aaaaacagtg gttcaggaat tgcattgcca tggccacttc acaaacctag
 401  ccaattttag cttgaccgca actttgacag attgtctttt gactttgcct
 451  ggaccgcctc ccataatacc ttcgcgtctt gaagacttta tccttgaaag
 501  gagaacatat gagaccccta agtcatcgca ccaaaattgt ggccaccatt
 551  ggccccgcca gtagttcggt agaggtgata cgtcagatgg tggatgcggg
 601  catgaatgtg gcccggctga attttcccca cggtagttat gaggaccatg
 651  ccaccatggt tcgcctacta cggtcagtgg agcaggaaat ggacacccc
 701  attcccttt tgcaagattt acagggggccc aaaattcgga ttggtcagtt
 751  gccggggggga gaaaagcaac tgcgggaagg ggaaaaagtt tctttggtgc
 801  cggtggaaat tggcgatcgc catcctggag cggtgggcat tgactatccc
 851  catttggcga cggaggcaaa agtaggggaa agaattttat tggacgatgg
 901  tttactggaa atgaaagttg tgtccattca agatccagag gtaatttgtg
 951  aagtggtgac cgggggcatc ctcaaaagtc gcaaggggt caatctaccg
1001  ggtttagtcc taaccctacc ttccatgacg accaaagaca agcaagactt
1051  agaatttggt ttgagccaag gcattgactg ggtttccctt agttttgtcc
1101  gcaaggggga agatatccac acccttaaac aatttctcgc tgaacggggc
1151  catcctgatc tgccggtcat tgccaaaatt gaaaaacccc aggcgatcga
1201  taatctagaa gaaatcgtgg cagtttccaa cggcattatg gtggccaggg
1251  gggatctggg ggtggaagta aacccagaaa aggttccccg tttgcaaaag
1301  gaaattattc ggcgctgtaa cgtgcgggcc attccggtca tcaccgctac
1351  ccaaatgcta gatagcatga ttcaaaattc ccgacccacc agggcggaag
1401  ccagtgacgt ggccaacgct attttggacg gcaccgatgc ggtgatgtta
1451  tcgggggaat cggcagtggg acaatatccc gttaaatcag tgcaaatgtt
1501  gcgaaaaatt gccgaagaga cggaagtggg tctacatctt gttaataatc
1551  ccccaataga aaatacggaa acccatgccc taagtgaagc gttagtggta
```

Figure 24F(1)

```
1601  attgacggaa ttctagattt aaaatacatt gtcacgttca ccacctcagg
1651  ttttacttct ctcctcgctt ccaaccaaag accgtcggtg ccggtgattg
1701  ctttcactcc ctcagaaaag gtttaccata gcctcaactt agtttggggt
1751  attattccct ttttaattaa cgaagaattt gacacctttg aggatttaat
1801  ccaacaggcg gaggtactac tgcgggatag aaaaatggtg gaaaagggcg
1851  atcagttgct aatcatggcg ggaattccca ctaaaatacc caggggcact
1901  aatttcctca agattcaccg tatttcttaa gagctcgtgt ttggagcatt
1951  acacaccgat gttaagtaaa gtccccgcca ccattgaaga aatcgccgcc
2001  cgggaaattt tagactccag gggtcgcccc accatcgaag cggaagtccg
2051  gctggaaagt ggggcccacg gcattgccca ggtgcccagt ggtgcttcca
2101  caggcagttt tgaagcccat gaattgcggg acggagaccc caaacgctat
2151  gacgggaaag gggtagaaaa agcagtacgg aacgtgacag aaaaaattgc
2201  cccggtggtg gaaggcctgg atgccttcga tcaaatggcg gtggatcagg
2251  ccatgattga ccgggatgga acggacaata aaaaagaatt gggggccaat
2301  gccatttttgg gggtttcttt agccaccgct aaggccgccg ccgctgagct
2351  agccattccc ctctaccgct acctgggagg cccctggct aacgtactgc
2401  cggtaccgat gatgaacgtg attaacggtg gggcccatgc cgacaataac
2451  gtcgattttc aggaattcat gatcatgccg gtgggggcag aaacctttaa
2501  agaagctctg cgctgggggg cggaagtttt cgctgtgttg ggcaaagtgt
2551  tgaaagaacg aaaactgctc tccggtgggg tgggggacga aggggttat
2601  gctcccaatt tgacctcgaa tcaacaggcc ctagatattc tcatcgaggc
2651  gattgaacaa gctggttaca aacccggtag tcaaattgcc ttggccatgg
2701  acattgccgc cagtgaattt ttcaaaaatg gtcagtatga atacgacggt
2751  ggttcccatt ctccccagga attcatcgac tatcaggcca agctagtgag
2801  tcaatatccc attgtctcca ttgaagacgg tttgcacgaa gacgattggg
2851  aaagttggaa gggtttaacc acttccctgg gcaccaaaac ccagttggtg
2901  ggggatgact tgatggtgac caacccggtg cgtctgcaaa aatccattga
2951  tttgggagtt gccaacgcca ttttgatcaa actcaatcaa atcggcactt
3001  tgagcgaaac tttagagacc atttccctag ctactcgcca tagttaccgt
3051  tctgttattt cccatcgctc cggtgaaacg gaggacacca cgatcgccga
3101  cttggccgtg gccaccaggg tagggcaaat taaaaccggt tccctttgtc
3151  gttctgagcg ggttgctaaa tataaccgtt tactccgcat tgaagatgaa
3201  cttggcgatc gggccgttta tgcccctaaa attggcctgg gtcccaaaca
```

Figure 24F(2)

```
3251  ttcttaaaaa gatctgcccc tctgggaaaa aatgaccaaa gacgatgtgg
3301  cccaccaata tcccgaacaa tatcgtctct ggcacgaagc accggatcaa
3351  ttggccatga ccgtagatgg agcggaatat taccccgttg cggctctcta
3401  tgcccaggcc caaagatttt ggcaggatgt gttaaccgat gcggcgggac
3451  aaaccctgct gattgtggcc cacaatggca tcaatcgttg cctgttaatg
3501  agcgccattg gtatgcccgc ttcccattac caacgcctgc aacagtccaa
3551  ctgcaatatt aatgtgttga attttagtgg tggctggggc gatccggtgc
3601  aactggaatc cttgaatcaa accgcccata tgggggtacc tctgccacct
3651  ccccgcaagg ataataatcg tctgcggtta ctgcttatcc gccatgggga
3701  aacccaatgg aatcgggaag gacggttcca aggtattcgg gatattcccc
3751  tcaatgacaa tggccgccat caagcccaaa aagcggcgga attcctcaaa
3801  gatgtgccca ttaacctagg cattagcagt cccatggctc ggcccaagga
3851  aacggcggag attattctgc aatatcaccc aagcatagag ttggatttac
3901  agccggaatt ggcggaaatt tgccatggcc tgtgggaagg caagctagaa
3951  acggaaattg aagcggaata tcccggatta ttgcaacagt ggaaagatgc
4001  ccccgccaca gtgcagatgc cggaagggga aaatttacaa caggtctggg
4051  accggcgat cgcctgttgg caggaccggg tcaaattcta tagccagggg
4101  gatggttcca cagtgggcat tgtggtggcc catgatgcca tcaacaaggt
4151  gattttggct tatttgttgg gtcttactcc cgctcacttt tggcaagtta
4201  aacagggtaa tggcggggtg agcgtcattg actatcccca gggtctagat
4251  aagcccccag ttattcaagc cattaatttg atgggccatt tgggcacagt
4301  gttggataaa accgccgccg gagccctata gtcctgtcca tagccaatta
4351  tccccccatt tgttccctaa ctcttgtttg ctatgactca ctttggtttg
4401  ctctgtccag caacgacggg tcatctcaat accatgttgc ccttgggtaa
4451  ggaactgcaa cagcggggtc atactcgag (SEQ ID NO:51)
```

Figure 24F(3)

```
   1  ctgcaggtcg actctagagg atccccgggt accccctcatc gggggctgtg
  51  ttggccgaga cggcactgag gattttactc tccatggcat tccaaggaat
 101  atctacccaa ctcacctgct ccggcggatt gttccgctca aaagtactaa
 151  tcaagtcgtc aaaatactta ttaaattttg gctgcaattg catagtccaa
 201  aagctgactt tcccctccat gctctggggg gaattgctct ggcaactgat
 251  taatccactg agcaacagcc caagacacgc aaacaaaaac caacgtcttg
 301  gcgatcgcca tcggcaccat gaaaccatcg taaaagctgg ggaaagaata
 351  aaaaacagtg gttcaggaat tgcattgcca tggccacttc acaaacctag
 401  ccaattttag cttgaccgca actttgacag attgtctttt gactttgcct
 451  ggaccgcctc ccataatacc ttcgcgtctt gaagacttta tccttgaaag
 501  gagaacatat gcaaacgtct ccccttcccc gtcgtaccaa aatcgtcgct
 551  accattggcc ccgcgaccca aagcaaggaa gtgctgagac aactgatcca
 601  agccggtgct accactttcc gcctcaattt ttcccacgga gaccacgctt
 651  accaccaaca aagtatccgt ttgattcgcc agattgcctt tgaactgaac
 701  caaccagtgg gcattctcca ggatttacag gggccaaaga ttcgggtggg
 751  caaatttctc aatgatgccg gctctgtgca actcaaaaac ggtgatccct
 801  ataccctcac cagtcgcccg gtggaatgta cggaaaccat tagttccatt
 851  agctacgaat atttagccga cgaagtacct tctggggcaa gaattttgct
 901  cgacgacggc aaactggaaa tgttggtgga ggaagtggac actgttgccc
 951  gggatctcca ctgtcgggtg attgtggggg gaacccttc cagcaataaa
1001  ggggttaatt ttcccggggt ctgcctttcc gttaaggcca tgaccgataa
1051  agataaggaa gatttgatgt tcgggctgga ccaaggggtg gactgggtgg
1101  ccctgagttt tgttcgtaat ccccaggata ttgatgagat taaggggtta
1151  attgcggcgg cagggaaatc cgtgccggta atcgccaaaa ttgagaagca
1201  cgaagcgatt aaggatatgc aggcggtgct ggaaaaatgt gacggtgtca
1251  tggtggcccg gggggacttg ggggtagaac tacccgcaga agatgtacct
1301  attttgcaaa agaaactcat tgccactgct aaccggttgg gcattcctgt
1351  cattactgct acccaaatgt tggacagtat ggtcaacagc ccccgaccta
1401  ctagggctga agtgtccgac gtggccaatg ccatcctcga tggtaccgat
1451  gcggtgatgc tctccaacga aacggcgatc ggtaaatttc ccgtggaagc
1501  agtggctatt atggccaaaa ttgcggagcg cattgaacag gaagatatca
```

Figure 24G(1)

```
1551  atccttccca  agcggaagcc  agtcgcactt  ctattcccaa  tgctatttcc
1601  agcgccgtta  gccagattgc  ggaaaccctc  aacgcggcgg  ctattatgtc
1651  tttgactaag  accggatcca  ccgcccgcca  tgtgtcaaag  ttccgcccca
1701  aaaccccat   tctggccgtt  acgcccatg   tggatgtgtc  ccgtcagttg
1751  cagttggtgt  ggggagttaa  gccctgttg   gtattggatt  taccttccac
1801  cagccaaacg  ttccaagccg  ccattaacgt  ggcccaggaa  aaccattttc
1851  tccgggatgg  agatttggtg  gtgatgaccg  ccgggacatt  gcagggagtt
1901  gccggttcga  cggatttaat  caaagtggaa  gtggtcaagg  ccattcttgg
1951  tcggggtgta  ggtattggcc  aaggagctgt  aagtggccgg  gccagggttg
2001  ccagtcgtcc  ccaggcgatc  gcccaattta  cccagggaga  aattttagta
2051  gttccctcta  ccaacgctga  ttgtgtggac  atgatgcgac  gggcggcggg
2101  cattatcacc  gaagaagaaa  gcctgactag  ccatgcggcc  attattggtt
2151  tgcggctggg  ggtgccggtc  attgtgggtt  ttaaaggcgc  tacccaaaag
2201  attcgagatg  gagccattgt  caccatcgat  gcccaaaaag  gactgattta
2251  ttccggtgca  ttaccccgg   tgtccaaagg  ataggggagct  cgtgtttgga
2301  gcattacaca  ccgatgttaa  gtaaagtccc  cgccaccatt  gaagaaatcg
2351  ccgcccggga  aattttagac  tccaggggtc  gccccaccat  cgaagcggaa
2401  gtccggctgg  aaagtggggc  ccacggcatt  gcccaggtgc  ccagtggtgc
2451  ttccacaggc  agttttgaag  cccatgaatt  gcgggacgga  gaccccaaac
2501  gctatgacgg  gaaaggggta  gaaaaagcag  tacggaacgt  gacagaaaaa
2551  attgccccgg  tggtggaagg  cctggatgcc  ttcgatcaaa  tggcggtgga
2601  tcaggccatg  attgaccggg  atggaacgga  caataaaaaa  gaattggggg
2651  ccaatgccat  tttgggggtt  tctttagcca  ccgctaaggc  cgccgccgct
2701  gagctagcca  ttcccctcta  ccgctacctg  ggaggccccc  tggctaacgt
2751  actgccggta  ccgatgatga  acgtgattaa  cggtggggcc  catgccgaca
2801  ataacgtcga  ttttcaggaa  ttcatgatca  tgccggtggg  ggcagaaacc
2851  tttaaagaag  ctctgcgctg  ggggcggaa   gttttcgctg  tgttgggcaa
2901  agtgttgaaa  gaacgaaaac  tgctctccgg  tggggtgggg  gacgaagggg
2951  gttatgctcc  caatttgacc  tcgaatcaac  aggccctaga  tattctcatc
3001  gaggcgattg  aacaagctgg  ttacaaaccc  ggtagtcaaa  ttgccttggc
3051  catggacatt  gccgccagtg  aattttcaa   aaatggtcag  tatgaatacg
3101  acggtggttc  ccattctccc  caggaattca  tcgactatca  ggccaagcta
3151  gtgagtcaat  atcccattgt  ctccattgaa  gacggtttgc  acgaagacga
```

Figure 24G(2)

```
3201   ttgggaaagt tggaagggtt taaccacttc cctgggcacc aaaacccagt
3251   tggtggggga tgacttgatg gtgaccaacc cggtgcgtct gcaaaaatcc
3301   attgatttgg gagttgccaa cgccattttg atcaaactca atcaaatcgg
3351   cactttgagc gaaactttag agaccatttc cctagctact cgccatagtt
3401   accgttctgt tatttcccat cgctccggtg aaacggagga caccacgatc
3451   gccgacttgg ccgtggccac cagggtaggg caaattaaaa ccggttccct
3501   ttgtcgttct gagcgggttg ctaaatataa ccgtttactc cgcattgaag
3551   atgaacttgg cgatcgggcc gtttatgccc ctaaaattgg cctgggtccc
3601   aaacattctt aaaaagatct gcccctctgg gaaaaaatga ccaaagacga
3651   tgtggcccac caatatcccg aacaatatcg tctctggcac gaagcaccgg
3701   atcaattggc catgaccgta gatggagcgg aatattaccc cgttgcggct
3751   ctctatgccc aggcccaaag attttggcag gatgtgttaa ccgatgcggc
3801   gggacaaacc ctgctgattg tggcccacaa tggcatcaat cgttgcctgt
3851   taatgagcgc cattggtatg cccgcttccc attaccaacg cctgcaacag
3901   tccaactgca atattaatgt gttgaatttt agtggtggct ggggcgatcc
3951   ggtgcaactg gaatccttga atcaaaccgc ccatatgggg gtacctctgc
4001   cacctccccg caaggataat aatcgtctgc ggttactgct tatccgccat
4051   ggggaaaccc aatggaatcg ggaaggacgg ttccaaggta ttcgggatat
4101   tcccctcaat gacaatggcc gccatcaagc ccaaaaagcg gcggaattcc
4151   tcaaagatgt gcccattaac ctaggcatta gcagtcccat ggctcggccc
4201   aaggaaacgg cggagattat tctgcaatat cacccaagca tagagttgga
4251   tttacagccg gaattggcgg aaatttgcca tggcctgtgg gaaggcaagc
4301   tagaaacgga aattgaagcg gaatatcccg gattattgca acagtggaaa
4351   gatgcccccg ccacagtgca gatgccggaa ggggaaaatt tacaacaggt
4401   ctgggaccgg gcgatcgcct gttggcagga ccgggtcaaa ttctatagcc
4451   aggggggatgg ttccacagtg ggcattgtgg tggcccatga tgccatcaac
4501   aaggtgattt tggcttattt gttgggtctt actcccgctc acttttggca
4551   agttaaacag ggtaatggcg gggtgagcgt cattgactat ccccagggtc
4601   tagataagcc cccagttatt caagccatta atttgatggg ccatttgggc
4651   acagtgttgg ataaaaccgc cgccggagcc ctatagtcct gtccatagcc
4701   aattatcccc ccatttgttc cctaactctt gtttgctatg actcactttg
4751   gtttgctctg tccagcaacg acgggtcatc tcaataccat gttgcccttg
4801   ggtaaggaac tgcaacagcg gggtcatact cgag (SEQ ID NO:52)
```

Figure 24G(3)

```
MGSTLVGKCTSLGVFSMVTSPFSLSPFGQARSTVTGNPLDPTELNQMHGFWRAANYLAVGM
IYLRDNPLLREPLQPEQIKHRLLGHWGSSPGISFLYTHLNRIIRKFDQDMLYMVGPGHGAP
GFLGPCYLEGSYSRFFAECSEDEDGMKRFFKQFSFPGGIGSHCTPETPGSIHEGGELGYCL
SHAYGAAFDNPNLIVVGLAGDGESETGPLATSWHSNKFINPIRDGAVLPVLHLNGYKINNP
SVLSRISHEELKALFEGYGYTPYFVEGSDPESMHQAMAATLDHCVSEIHQIQQEARSTGIA
VRPRWPMVVMRTPKGWTGPDYVDGHKVEGFWRSHQVPMGGMHENPAHLQQLEAWMRSYKPE
ELFDEQGTLKPGFKAIAPEGDKRLGSTPYANGGLLRRGLKMPDFRQYGIDVDQPGTIEAPN
TAPLGVFLRDVMANNMTNFRLFGPDENSSNKLHAVYEVSKKFWIAEYLEEDQDGGELSPDG
RVMEMLSEHTLEGWLEAYLLTGRHGFFATYESFAHVITSMVNQHAKWLDICRHLNWRADIS
SLNILMTSTVWRQDHNGFTHQDPGFLDVILNKSPDVVRIYLPPDVNSLLSVADHCLQSKNY
INIIVCDKQAHLQYQDMTSAIRNCTKGVDIWEWASNDAGTEPDVVMAAAGDIPTKEALAAT
AMLRQFFPNLRIRFVSVIDLLKLQPESEHPHGLSDRDFDSLFTTDKPIIFNFHAYPWLIHR
LTYRRTNHGNLHVRGYKEKGNINTPMDLAIQNQIDRFSLAIDVIDRLPQLRVAGAHIKEML
KDMQIDCTNYAYEHGIDMPEIVNWRWPL (SEQ ID NO:53)
```

Figure 25A

```
   1  ctgcaggtcg actctagagg atccccgggt accectcatc gggggctgtg
  51  ttggccgaga cggcactgag gattttactc tccatggcat tccaaggaat
 101  atctacccaa ctcacctgct ccggcggatt gttccgctca aaagtactaa
 151  tcaagtcgtc aaaatactta ttaaattttg gctgcaattg catagtccaa
 201  aagctgactt tccectccat gctctggggg gaattgctct ggcaactgat
 251  taatccactg agcaacagcc caagacacgc aaacaaaaac caacgtcttg
 301  gcgatcgcca tcggcaccat gaaaccatcg taaaagctgg ggaaagaata
 351  aaaaacagtg gttcaggaat tgcattgcca tggccacttc acaaacctag
 401  ccaattttag cttgaccgca actttgacag attgtctttt gactttgcct
 451  ggaccgcctc ccataatacc ttcgcgtctt gaagacttta tccttgaaag
 501  gagaacatat ggttacatcc cccttttccc ttagtccctt tggtcaagct
 551  agatccaccg tcactggcaa tccccttgac ccgacagaac ttaaccaaat
 601  gcacggtttt tggcgggcag ccaactactt ggcagtgggc atgatttatc
 651  tgcgggataa tcccettttg cgggaaccgc ttcaaccgga acagatcaag
 701  catcgcctgt tgggtcactg gggttctagt cccggcatta gttttctcta
 751  cacccatctc aaccgcatta tcaggaaatt tgaccaggat atgctgtaca
 801  tggtggggcc tggccacggc gcaccaggct ttttggggcc ctgctaccta
 851  gaagggagct attctcgctt ttttgccgag tgtagtgaag atgaggacgg
 901  catgaagcgc tttttcaaac aatttteett tcccggtggc attggcagtc
 951  attgcactcc cgaaacccct ggttccatcc acgaggggg agaattgggc
1001  tactgcctat cccatgccta tggcgctgcc tttgataatc ccaatttaat
1051  tgtggtcggt ttagcggggg atggggagtc ggaaacaggc cccttggcta
1101  cctcctggca ttccaataag tttattaacc cgattcggga tggggcagtt
1151  ttaccggttc tgcatctcaa tgggtacaag attaacaatc caagtgtttt
1201  atctcgcatt agccatgaag aattaaaggc tttatttgaa ggttacggtt
1251  atacccccta ctttgttgaa ggctctgacc cggaatctat gcaccaagcc
1301  atggcagcca cgttggatca ttgtgtgagc gaaattcatc aaatccaaca
1351  agaagctcgt agtacgggca ttgccgtgcg ccccgttgg cccatggttg
1401  tgatgcggac tcccaaggga tggacggggc ctgactatgt tgatggccat
1451  aaggtagaag gttttggcg atcgcaccaa gttcccatgg ggggcatgca
1501  cgagaatcca gcccatttgc aacagttgga agcttggatg cggagttata
```

Figure 25C(1)

```
1551  agccggaaga attgttcgac gagcaaggta ctttaaaacc gggatttaag
1601  gcgatcgccc cggagggaga taagcgttta ggctctactc cctacgccaa
1651  tggtggtttg ttacggcggg gtttgaaaat gccggacttt cgtcaatatg
1701  gtattgatgt ggaccaacca ggcaccatcg aagcccctaa tactgcaccc
1751  ctgggagtat ttctgcggga tgtgatggcc aacaacatga ccaatttccg
1801  cctgtttggc cccgatgaaa atagttccaa taaactccat gccgtctacg
1851  aggttagcaa aaaattctgg attgctgaat atctagaaga agaccaggat
1901  gggggggaat taagtcccga tggtcgggtg atggaaatgt taagcgagca
1951  caccttagaa ggttggttag aggcctatct tttaaccggg cgtcacggct
2001  ttttcgccac ctatgaatcc tttgcccatg tgatcacttc catggttaac
2051  caacacgcta aatggttgga tatttgtcga cacctcaact ggcgggcaga
2101  tatttcctcg ttaaatatct tgatgacgtc caccgtgtgg cgacaggatc
2151  acaacgggtt tacccaccaa gatcccggtt ttctcgatgt cattctcaat
2201  aaaagccccg atgtggtgcg aatttattta ccccccgatg ttaattctct
2251  gctttccgta gcggaccatt gtttacagag caaaaactac atcaacatca
2301  tcgtttgcga taagcaagcc cacctgcaat accaggacat gacttccgct
2351  atccgtaact gcactaaagg ggtggacatt tgggaatggg ccagtaatga
2401  tgccggtacg gaaccggatg tggtgatggc agcggcgggg gatattccca
2451  ccaaagaggc cttggcggcc acagccatgc taaggcaatt ttttcctaat
2501  ctgagaattc gctttgtcag cgtgattgat ttgctcaaac tgcaaccgga
2551  atcggagcat ccccatggcc tgagcgatcg ggatttgac tccctcttta
2601  ccaccgataa accgattatt tttaacttcc acgcctatcc ctggttaatt
2651  catcggttga cctatcgacg gactaaccat ggcaatctcc atgtgcgggg
2701  ctacaaggaa aagggcaaca tcaacacccc catggattta gcgattcaaa
2751  accagattga ccgtttcagc ctcgccattg atgtgatcga tcgcctgccc
2801  caattgcggg tggccggagc ccacatcaag gaaatgctca aggatatgca
2851  gattgactgc accaactacg cctacgaaca cggcattgat atgccagaaa
2901  tcgttaattg gcgctggccc ctctagacct taactaaaat ccctgacatc
2951  gttctagttt ctgttccaat aggttagcta ggccatgggg acaacgctg
3001  gtccagcaaa attttggcag aagctagagc aaagttgggg agcttttccc
```

Figure 25C(2)

```
3051  gttaaagatc ggcaaaggtt tccctgcca gtaagccagc attaattttg
3101  ttggtgacca gttcccggta catggctagt tcctgggata gtaattcata
3151  ccggggcttg gagtggagtg ccaaggcctt aatgttggat tcttcttcct
3201  tggtgaccac accatcggcc acggcctgct cgag (SEQ ID NO:54)
```

Figure 25C(3)

```
MTSSLYLSTTEARSGKSLVVLGILDLILKKTTRIAYFRPIIQDPVNGKHDNNIILVLENF
RLQQTYTDSFGLYFHEAVSLASDGAIDQVLDRILAKYRHLADQVDFILCEGSDYLGEESA
FEFDLNTTIAKMLNCPILLLGNAMGNTIADSLQPIDMALNSYDQESCQVVGVIINRVQPE
LATEIQAQLEQRYGDRPMVLGTIPQDIMLKSLRLREIVSGLNAQVLSGADLLDNLVYHHL
VVAMHIAHALHWLHEKNTLIITPGDRGDIILGVMQAHRSLNYPSIAGILLTADYHPEPAI
MKLIEGLPDAPPLLLTSTHTHETSARLETLHPALSPTDNYKIRHSIALFQQQIDGEKLLN
YLKTIRSKGITPKLFLYNLVQAATAAQRHIVLPEGEEIRILKAAASLINHGIVRLTLLGN
IEAIEQTVKINHIDLDLSKVRLINPKTSPDRERYAETYYQLRKHKGVTLAMARDILTDIS
YFGTMMVHLGEADGMVSGSVNTTQHTVRPALQIIKTQPGFSLVSSVFFMCLEDRVLVYGD
CAVNPDPNAEQLAEIALTSAATAKNFGIEPRVALLSYSSGSSGQGADVEKVRQATAIAKE
REPDLALEGPIQYDAAVDSTVAAQKMPGSAVAGKATVFIFPDLNTGNNTYKAVQRETKAI
AIGPILQGLNKPVNDLSRGCLVEDIINTVVITALQVK (SEQ ID NO:55)
```

Figure 26A

```
   1  gtcgactcta gaggatcccc gggtacccct catcggggc  tgtgttggcc
  51  gagacggcac tgaggatttt actctccatg gcattccaag gaatatctac
 101  ccaactcacc tgctccggcg gattgttccg ctcaaaagta ctaatcaagt
 151  cgtcaaaata cttattaaat tttggctgca attgcatagt ccaaaagctg
 201  actttcccct ccatgctctg gggggaattg ctctggcaac tgattaatcc
 251  actgagcaac agcccaagac acgcaaacaa aaaccaacgt cttggcgatc
 301  gccatcggca ccatgaaacc atcgtaaaag ctggggaaag aataaaaaac
 351  agtggttcag gaattgcatt gccatggcca cttcacaaac ctagccaatt
 401  ttagcttgac cgcaactttg acagattgtc ttttgacttt gcctggaccg
 451  cctcccataa taccttcgcg tcttgaagac tttatccttg aaaggagaac
 501  atatgacgag ttccctttat ttaagcacca ccgaagcccg cagcggtaaa
 551  tctctagtag tattgggcat tttagactta attctcaaaa aaaccacccg
 601  tattgcctat tttcgtccca ttattcaaga cccagttaat ggcaaacatg
 651  ataacaacat tattctggtg ctggaaaatt ttcgtctcca acaaacctat
 701  accgattcct ttggtttgta tttccatgaa gcggtgagtt tagcctccga
 751  tggagctatt gatcaggtat tagaccgaat tttggctaaa tatcgccatt
 801  tggcagatca agtagatttt attctctgtg aaggctcaga ctatttgggg
 851  gaggaatcgg cttttgaatt tgatctcaac accacgatcg ccaagatgtt
 901  gaactgcccc attttgctgt tgggcaatgc catgggcaac accattgccg
 951  atagtttgca acccatcgat atggccctga atagctatga ccaagagtct
1001  tgtcaggtgg tggggtaat cattaaccga gtgcagcccg aattagccac
1051  agaaattcaa gcccaactgg aacagcgtta tggcgatcgc ccgatggtgt
1101  tgggcactat tccccaggac attatgctca aaagtctgcg cctgagggaa
1151  attgtcagcg ggctcaatgc ccaagtactc agcggtgcgg atttgctcga
1201  taacttggtc tatcaccatt tagtggtggc gatgcacatt gcccacgccc
1251  tccattggtt gcacgaaaaa aatacccta ttattacccc tggcgatcgg
1301  ggcgacatca ttctgggggt gatgcaggcc caccgctccc tcaactatcc
1351  cagcattgcc ggtattttgc tcactgcaga ttaccatccc gaaccggcca
1401  ttatgaaact aattgaaggg ctacccgacg cccctcccct gttgctgact
1451  agcacccaca cccatgaaac ttccgcccgt ttggaaactc tccaccctgc
1501  cctgagccct acggataatt ataaaattcg ccacagtatt gcgctgtttc
1551  aacaacaaat tgatggggag aaattactca attaccttaa aaccatccgc
```

Figure 26C(1)

```
1601  agtaaaggta ttaccccaa  actgtttctc tacaatttag ttcaagccgc
1651  caccgccgcc caacgacata ttgtcctacc ggaaggggaa gaaattcgta
1701  ttctcaaggc ggccgctagc ttaattaacc acggcattgt ccgtttgact
1751  ttactcggta acattgaggc gatcgagcaa acggtaaaaa ttaatcacat
1801  tgacttagat ttgagcaaag ttcgcctcat taatcctaaa actagcccag
1851  accgagagcg ctacgccgaa acctattacc agctacgtaa acataagggg
1901  gtaaccctgg ccatggctcg ggatatcctc accgatattt cctattttgg
1951  aacgatgatg gtgcatttgg gagaggccga tggcatggtt tctggctccg
2001  tcaataccac ccaacatacc gtgcgtcctg ctttacaaat tattaaaacc
2051  cagccaggtt tttccttggt ttcttcagtc ttttttatgt gtttagaaga
2101  ccgagttttg gtctatggag attgtgctgt taatcccgat cccaatgcag
2151  aacagttagc agaaattgcc cttacttctg cggctacggc caagaatttt
2201  ggcattgagc ccagggtagc tctattgtcc tattcttccg gttcttctgg
2251  gcaaggggcc gatgtggaaa aagtgcggca agccacggcg atcgccaagg
2301  aaagagagcc agatttagca ttggaagggc cgatccagta tgatgcggcg
2351  gtggattcca cagtggcggc ccaaaaaatg cctgggtcag cggtggcggg
2401  taaagcaacg gtgtttattt ttcccgattt aaataccggt aacaatactt
2451  acaaggcagt gcaaagagaa acaaaggcga tcgccattgg ccccatttta
2501  caaggattaa ataaaccagt taatgatcta agtcggggtt gtttagtgga
2551  ggatattatt aatacggtgg taattacagc tttgcaagtt aaataatttt
2601  actcttaatt agttaaaatg atcccttgaa ttaccttgat tttgccctcc
2651  aaactaccaa tagctgggcc gaaaattggc atcatttaaa atcaccaacg
2701  tgtccccgga cggagctagc acaaacagac ccttaccata ggcatagctg
2751  accacttctt ggcttaacac catggctgcc actgcaccta aagctttaac
2801  atcccggtag cggggcataa actgtttgaa tttacccaac cgttccagat
2851  gctcgag (SEQ ID NO:56)
```

Figure 26C(2)

```
   1  cccgggtacc cctcatcggg ggctgtgttg gccgagacgg cactgaggat
  51  tttactctcc atggcattcc aaggaatatc tacccaactc acctgctccg
 101  gcggattgtt ccgctcaaaa gtactaatca agtcgtcaaa atacttatta
 151  aattttggct gcaattgcat agtccaaaag ctgactttcc cctccatgct
 201  ctgggggggaa ttgctctggc aactgattaa tccactgagc aacagcccaa
 251  gacacgcaaa caaaaaccaa cgtcttggcg atcgccatcg gcaccatgaa
 301  accatcgtaa aagctgggga aagaataaaa aacagtggtt caggaattgc
 351  attgccatgg ccacttcaca aacctagcca attttagctt gaccgcaact
 401  ttgacagatt gtcttttgac tttgcctgga ccgcctccca taataccttc
 451  gcgtcttgaa gactttatcc ttgaaaggag aacatatggt tacatccccc
 501  ttttccctta gtccctttgg tcaagctaga tccaccgtca ctggcaatcc
 551  ccttgacccg acagaactta accaaatgca cggttttttgg cgggcagcca
 601  actacttggc agtgggcatg atttatctgc gggataatcc ccttttgcgg
 651  gaaccgcttc aaccggaaca gatcaagcat cgcctgttgg gtcactgggg
 701  ttctagtccc ggcattagtt ttctctacac ccatctcaac cgcattatca
 751  ggaaatttga ccaggatatg ctgtacatgg tggggcctgg ccacggcgca
 801  ccaggctttt tggggccctg ctacctagaa gggagctatt ctcgcttttt
 851  tgccgagtgt agtgaagatg aggacggcat gaagcgcttt ttcaaacaat
 901  tttccttttcc cggtggcatt ggcagtcatt gcactcccga aacccctggt
 951  tccatccacg agggggggaga attgggctac tgcctatccc atgcctatgg
1001  cgctgccttt gataatccca atttaattgt ggtcggttta gcggggggatg
1051  gggagtcgga aacaggcccc ttggctacct cctggcattc caataagttt
1101  attaacccga ttcgggatgg ggcagtttta ccggttctgc atctcaatgg
1151  gtacaagatt aacaatccaa gtgttttatc tcgcattagc catgaagaat
1201  taaaggcttt atttgaaggt tacggttata cccctactt tgttgaaggc
1251  tctgacccgg aatctatgca ccaagccatg gcagccacgt tggatcattg
1301  tgtgagcgaa attcatcaaa tccaacaaga agctcgtagt acgggcattg
1351  ccgtgcgccc ccgttggccc atggttgtga tgcggactcc caaggggatgg
1401  acggggcctg actatgttga tggccataag gtagaaggtt tttggcgatc
1451  gcaccaagtt cccatggggg gcatgcacga gaatccagcc catttgcaac
1501  agttggaagc ttggatgcgg agttataagc cggaagaatt gttcgacgag
1551  caaggtactt taaaaccggg atttaaggcg atcgccccgg agggagataa
```

Figure 26E(1)

```
1601  gcgtttaggc tctactccct acgccaatgg tggtttgtta cggcggggtt
1651  tgaaaatgcc ggactttcgt caatatggta ttgatgtgga ccaaccaggc
1701  accatcgaag cccctaatac tgcacccctg ggagtatttc tgcgggatgt
1751  gatggccaac aacatgacca atttccgcct gtttggcccc gatgaaaata
1801  gttccaataa actccatgcc gtctacgagg ttagcaaaaa attctggatt
1851  gctgaatatc tagaagaaga ccaggatggg ggggaattaa gtcccgatgg
1901  tcggtgatg gaaatgttaa gcgagcacac cttagaaggt tggttagagg
1951  cctatctttt aaccgggcgt cacggctttt tcgccaccta tgaatccttt
2001  gcccatgtga tcacttccat ggttaaccaa cacgctaaat ggttggatat
2051  ttgtcgacac ctcaactggc gggcagatat ttcctcgtta aatatcttga
2101  tgacgtccac cgtgtggcga caggatcaca acgggtttac ccaccaagat
2151  cccggttttc tcgatgtcat tctcaataaa agccccgatg tggtgcgaat
2201  ttatttaccc cccgatgtta attctctgct ttccgtagcg gaccattgtt
2251  tacagagcaa aaactacatc aacatcatcg tttgcgataa gcaagcccac
2301  ctgcaatacc aggacatgac ttccgctatc cgtaactgca ctaaaggggt
2351  ggacatttgg gaatgggcca gtaatgatgc cggtacggaa ccggatgtgg
2401  tgatggcagc ggcgggggat attcccacca agaggccttt ggcggccaca
2451  gccatgctaa ggcaattttt tcctaatctg agaattcgct ttgtcagcgt
2501  gattgatttg ctcaaactgc aaccggaatc ggagcatccc catggcctga
2551  gcgatcggga ttttgactcc ctctttacca ccgataaacc gattattttt
2601  aacttccacg cctatccctg gttaattcat cggttgacct atcgacggac
2651  taaccatggc aatctccatg tgcggggcta caaggaaaag ggcaacatca
2701  acaccccat ggatttagcg attcaaaacc agattgaccg tttcagcctc
2751  gccattgatg tgatcgatcg cctgccccaa ttgcgggtgg ccggagccca
2801  catcaaggaa atgctcaagg atatgcagat tgactgcacc aactacgcct
2851  acgaacacgg cattgatatg ccagaaatcg ttaattggcg ctggccctc
2901  tagaccttaa ctaaaatccc tgacatcgtt ctagtttctg ttccaatagg
2951  ttagctaggc catgggggac aacagatctg gatacgttga ggttatttaa
3001  attatgacga gttccctta tttaagcacc accgaagccc gcagcggtaa
3051  atctctagta gtattgggca ttttagactt aattctcaaa aaaaccaccc
3101  gtattgccta ttttcgtccc attattcaag acccagttaa tggcaaacat
3151  gataacaaca ttattctggt gctggaaaat tttcgtctcc aacaaaccta
3201  taccgattcc tttggtttgt atttccatga agcggtgagt ttagcctccg
```

```
3251  atggagctat tgatcaggta ttagaccgaa ttttggctaa atatcgccat
3301  ttggcagatc aagtagattt tattctctgt gaaggctcag actatttggg
3351  ggaggaatcg gcttttgaat ttgatctcaa caccacgatc gccaagatgt
3401  tgaactgccc cattttgctg ttgggcaatg ccatgggcaa caccattgcc
3451  gatagtttgc aacccatcga tatggccctg aatagctatg accaagagtc
3501  ttgtcaggtg gtggggtaa tcattaaccg agtgcagccc gaattagcca
3551  cagaaattca agcccaactg gaacagcgtt atggcgatcg cccgatggtg
3601  ttgggcacta ttccccagga cattatgctc aaaagtctgc gcctgaggga
3651  aattgtcagc gggctcaatg cccaagtact cagcggtgcg gatttgctcg
3701  ataacttggt ctatcaccat ttagtggtgg cgatgcacat tgcccacgcc
3751  ctccattggt tgcacgaaaa aaatacccta attattaccc ctggcgatcg
3801  gggcgacatc attctggggg tgatgcaggc ccaccgctcc ctcaactatc
3851  ccagcattgc cggtattttg ctcactgcag attaccatcc cgaaccggcc
3901  attatgaaac taattgaagg gctacccgac gcccctcccc tgttgctgac
3951  tagcacccac acccatgaaa cttccgcccg tttggaaact ctccaccctg
4001  ccctgagccc tacggataat tataaaattc gccacagtat tgcgctgttt
4051  caacaacaaa ttgatgggga gaaattactc aattaccta aaaccatccg
4101  cagtaaaggt attacccca aactgtttct ctacaattta gttcaagccg
4151  ccaccgccgc ccaacgacat attgtcctac cggaagggga agaaattcgt
4201  attctcaagg cggccgctag cttaattaac cacggcattg tccgtttgac
4251  tttactcggt aacattgagg cgatcgagca aacggtaaaa attaatcaca
4301  ttgacttaga tttgagcaaa gttcgcctca ttaatcctaa aactagccca
4351  gaccgagagc gctacgccga aacctattac cagctacgta aacataaggg
4401  ggtaaccctg gccatggctc gggatatcct caccgatatt tcctattttg
4451  gaacgatgat ggtgcatttg ggagaggccg atggcatggt ttctggctcc
4501  gtcaatacca cccaacatac cgtgcgtcct gctttacaaa ttattaaaac
4551  ccagccaggt ttttccttgg tttcttcagt cttttttatg tgtttagaag
4601  accgagtttt ggtctatgga gattgtgctg ttaatcccga tcccaatgca
4651  gaacagttag cagaaattgc ccttacttct gcggctacgg ccaagaattt
4701  tggcattgag cccagggtag ctctattgtc ctattcttcc ggttcttctg
4751  ggcaagggc cgatgtggaa aaagtgcggc aagccacggc gatcgccaag
4801  gaaagagagc cagatttagc attggaaggg ccgatccagt atgatgcggc
4851  ggtggattcc acagtggcgg cccaaaaaat gcctgggtca gcggtggcgg
```

Figure 26E(3)

```
4901  gtaaagcaac ggtgtttatt tttcccgatt taaataccgg taacaatact
4951  tacaaggcag tgcaaagaga aacaaaggcg atcgccattg gccccatttt
5001  acaaggatta aataaaccag ttaatgatct aagtcggggt tgtttagtgg
5051  aggatattat taatacggtg gtaattacag ctttgcaagt taaataattt
5101  tactcttaat tagttaaaat gatcccttga attaccttga ttttgccctc
5151  caaactacca atagctgggc cgaaaattgg catcatttaa aatcaccaac
5201  gtgtccccgg acggagctag cacaaacaga cccttaccat aggcatagct
5251  gaccacttct tggcttaaca ccatggctgc cactgcacct aaagctttaa
5301  catcccggta gcggggcata aactgtttga atttacccaa ccgttccaga
5351  tgctcgagca accgatcttt ctagaagatc tcgag (SEQ ID NO:57)
```

Figure 26E(4)

MNTAKTVVAEQRDFFRQGKTKSVQDRLTALAKLKTQIQAQEEEIIKALKQDFGKPTFESYV
NEILGVIREINYYQKHLQQWSKPQRVGTNLMVFPASAQLRPEPLGVVLIISPWNYPFYLCL
MPLIGAIAAGNCVVVKPSEYTPAISGVITRLIQNVFSPAWATVVEGDETISQQLLQEKFDH
IFFTGSPRVGRLIMAAAAEQLTPVTLELGGKSPCVVDREINLQETAKRIMWGKLVNAGQTC
VAPDYLLVEQSCLEQLLPALQQAIQMLFGENPAHSPDYTRIVNQQQWSRLVSLLSHGKVIT
RGDHNEGDRYIAPTLIIDPDLNSPLMQEEIFGPILPILTYQSLSEAIDFINIKPKPLALYF
FSNNRQKQEEILQSTSSGSVCLNDILLHLTVTDLPFGGVGESGMGRYHGKATFDTLSNYKS
ILRRPFWGETNLRYSPYGKKMNLIKKLFS (SEQ ID NO:58)

Figure 27A

```
   1  ctgcaggtcg actctagagg atccccgggt accccteate gggggctgtg
  51  ttggccgaga cggcactgag gattttactc tccatggcat tccaaggaat
 101  atctacccaa ctcacctgct ccggcggatt gttccgctca aaagtactaa
 151  tcaagtcgtc aaaatactta ttaaattttg gctgcaattg catagtccaa
 201  aagctgactt tcccctccat gctctggggg gaattgctct ggcaactgat
 251  taatccactg agcaacagcc caagacacgc aaacaaaaac caacgtcttg
 301  gcgatcgcca tcggcaccat gaaaccatcg taaagctggg gaaagaata
 351  aaaaacagtg gttcaggaat tgcattgcca tggccacttc acaaacctag
 401  ccaattttag cttgaccgca actttgacag attgtctttt gactttgcct
 451  ggaccgcctc ccataatacc ttcgcgtctt gaagacttta tccttgaaag
 501  gagaacatat gaatactgct aaaactgttg ttgctgagca aagggacttt
 551  tttcgtcagg gcaaaactaa atcagtccaa gatagattaa cagctctagc
 601  aaaattaaaa acgcaaattc aagcccagga agaggaaatt attaaggccc
 651  ttaagcaaga ttttggtaag cccacctttg aaagctatgt aaacgaaatt
 701  ttgggggtaa ttagggaaat taattattat caaaaacatc ttcagcaatg
 751  gtctaagccc caacgggtag gtacgaatct gatggttttt cctgccagtg
 801  cccagttaag accagaaccc cttggtgtag tgctaattat tagcccctgg
 851  aattatcctt tttatctttg tttaatgccc ttgatcgggg cgatcgccgc
 901  tggaaattgt gtggtggtaa agccgtcgga atatactcca gctattagtg
 951  gggtaattac cagattaatc caaaatgtat tttccccggc ttgggcaaca
1001  gtggtggagg gagatgaaac cattagccaa caattgttac aggaaaaatt
1051  tgaccatatt ttctttaccg gcagccctag ggtgggtcgg ttaattatgg
1101  cagctgcggc agagcaatta accccagtta cgttggaatt gggggggtaaa
1151  tctccctgtg tggtggatag ggaaatcaac ctccaggaaa cagccaaacg
1201  cattatgtgg ggcaagctag tcaatgctgg ccaaacctgt gtggcaccgg
1251  attatttatt ggtggagcaa tcctgcttag aacaactttt accagcttta
1301  caacaggcaa ttcagatgct tttcggggaa aatccagccc atagccctga
1351  ctacactcgc attgttaacc aacaacaatg gtcacggtta gttagtttat
1401  taagccatgg caaagtaatt acaaggggag atcataacga aggcgatcgc
1451  tacattgccc caactttaat catcgatcca gatttaaatt ctcccttaat
1501  gcaagaggaa atatttggcc caattttgcc aattttaact tatcagagtt
1551  tgtcagaagc aatagatttt attaacatca aacctaaacc attggcactt
```

Figure 27C(1)

```
1601  tatttttta  gcaataatcg  gcaaaaacag  gaggaaattt  tgcaatctac
1651  cagttccggt  agtgtttgtt  tgaacgatat  tttgcttcat  ttaactgtga
1701  cagacttacc  ctttggtggg  gtgggagaaa  gtggtatggg  acgctaccat
1751  ggcaaggcta  cttttgacac  attgagcaat  tataaaagca  ttttacgacg
1801  acccttttgg  ggggaaacta  atttacgcta  ttctccctat  ggcaaaaaaa
1851  tgaatttaat  caaaagttg   ttctcctagg  attattcatg  gccgaccgtc
1901  cccagttgag  tattattatt  cccgtgttta  atgaagcaaa  aattttacaa
1951  aagtctccga  ctgaaaatac  cagacaatat  ttgggacaat  ttaccgagga
2001  tcaacggata  gaaattttaa  ttattgatgg  gggcagtcag  gatagcacag
2051  tggagttatg  ccagacctat  gctgattctt  tacctcgag   (SEQ ID NO:59)
```

Figure 27C(2)

MNLAVPAFGLSTNWSGNGNGSNSEEESVLYQRLKMVEELWERVLQSECGQELVDLLTELR
LQGTHEAITSEISEEVIMGITQRIEHLELNDAIRAARAFALYFQLINIVEQHYEQNEQQR
NRWEASQETNFYEQAGNEEEMVPPSRLGASTEPLPVGIDQNELQASVGTFHWLMRELKRL
NVPPQHIQNLLDHLDIRLVITAHPTEIVRHTIRRKQRRVDRILRKLDQLQGSVTGRDWLN
TWDAKTAIAQLTEEIRFWWRTDELHQFKPTVLDEVDYSLHYFDEVLFDAVPELSKRLGQA
IKETFPHLRAPRANFCYFGSWVGGDRDGNPSVTPEVTWQTACYQRGLVLGKYLFSLGELV
AILSPSLHWCKVSQELLDSLERDRIQLPEIYEELSLRYRQEPYRMKLAYVTKRLENTLRR
NNRLANPEERQTMITMPAENHYRTGEELLEELRLIQRNLTETGLTCLELENLITQLEVYG
FNLAQLDFRQESSRHAEAIAEIAEYMGVLTTPYEEMAEEDKLAWLGVELQTRRPLIPQEM
PFSERTRETIETLRTLRHLQMEFGVDICQTYIISMTNDASDVLEVLLLAKEAGLYDPATA
SNSLRIVPLFETVEDLKNAPGIMDSLFSLPFYRATLAGSYHSLKELQNQPPDYYQIPTTT
ALLNPGNLQEIMVGYSDSNKDSGFLSSNWEIHKAQKSLQAVAQSHRVILRLFHGRGGSVG
RGGGPAYKAILAQPAGTVDGRIKITEQGEVLASKYSLPELALYNLETLTTAVIQASLLKS
SFDFIEPWNRIMEELACTARRAYRSLIYEEPDFLDFFLTVTPIPEISELQISSRPARRKG
GKADLSSLRAIPWVFSWTQTRFLLPAWYGVGTALKSFVDQDPVKNMKLLRYFYFKWPFFN
MVISKVEMTLSKVDLTIASHYVQELSKPEDRERFDRLFQQIKQEYQLTRDFAMEITAHPH
LLDGDRSLQRSVLLRNRTIVPLGLLQISLLKRLRQVTQEAETSGVRYRRYSKEELLRGAL
LTINGIAAGMRNTG (SEQ ID NO:60)

Figure 28A

```
   1 TCGACTCTAG AGGATCCCCG GGTACCCCTC ATCGGGGGCT GTGTTGGCCG
  51 AGACGGCACT GAGGATTTTA CTCTCCATGG CATTCCAAGG AATATCTACC
 101 CAACTCACCT GCTCCGGCGG ATTGTTCCGC TCAAAAGTAC TAATCAAGTC
 151 GTCAAAATAC TTATTAAATT TTGGCTGCAA TTGCATAGTC CAAAAGCTGA
 201 CTTTCCCCTC CATGCTCTGG GGGGAATTGC TCTGGCAACT GATTAATCCA
 251 CTGAGCAACA GCCCAAGACA CGCAAACAAA AACCAACGTC TTGGCGATCG
 301 CCATCGGCAC CATGAAACCA TCGTAAAAGC TGGGGAAAGA ATAAAAAACA
 351 GTGGTTCAGG AATTGCATTG CCATGGCCAC TTCACAAACC TAGCCAATTT
 401 TAGCTTGACC GCAACTTTGA CAGATTGTCT TTTGACTTTG CCTGGACCGC
 451 CTCCCATAAT ACCTTCGCGT CTTGAAGACT TTATCCTTGA AGGAGAACA
 501 TATGAACTTG GCAGTTCCTG CATTCGGTCT TTCCACTAAC TGGTCTGGTA
 551 ATGGCAATGG TTCCAACTCT GAAGAAGAGT CGGTGCTTTA CCAGCGGTTA
 601 AAGATGGTGG AGGAATTGTG GGAAAGGGTG CTCCAAAGCG AATGTGGCCA
 651 GGAATTGGTG GATTTGCTGA CGGAATTAAG GCTTCAGGGT ACCCATGAGG
 701 CGATCACCAG CGAAATTTCC GAAGAAGTCA TCATGGGTAT TACCCAGCGC
 751 ATTGAGCATT TAGAACTCAA TGATGCCATC CGGGCGGCTC GGGCCTTTGC
 801 CCTATATTTC CAGTTGATCA ACATCGTTGA ACAGCACTAC GAACAAAACG
 851 AGCAACAACG GAATCGTTGG GAAGCTTCCC AGGAAACCAA CTTCTATGAG
 901 CAGGCGGGCA ATGAGGAAGA AATGGTCCCC CCATCCCGAT TAGGCGCGTC
 951 AACGGAACCA TTGCCAGTGG GCATTGACCA GAATGAATTG CAAGCTTCTG
1001 TAGGTACGTT CCATTGGTTA ATGAGGGAGC TAAAACGCCT CAATGTGCCC
1051 CCCCAACATA TCCAAAATTT ATTGGATCAT CTGGACATTC GCCTGGTGAT
1101 CACCGCTCAC CCCACGGAAA TTGTCCGTCA CACCATCCGG CGCAAACAAA
1151 GAAGGGTGGA CCGCATTCTT CGTAAACTAG ATCAACTCCA GGGTTCTGTG
1201 ACCGGTCGGG ACTGGCTCAA CACCTGGGAT GCAAAACGG CGATCGCCCA
1251 ATTAACGGAG GAAATTCGCT TTGGTGGCG TACCGACGAA CTTCATCAGT
1301 TCAAACCCAC TGTGTTGGAC GAAGTGGACT ATTCCCTCCA TTATTTGAT
1351 GAAGTACTGT TCGACGCTGT ACCGGAATTG TCCAAACGGT TAGGACAAGC
1401 TATTAAAGAA ACCTTTCCCC ATCTGCGGGC CCCCGGGCT AATTTTTGTT
1451 ATTTTGGCTC CTGGGTCGGT GGCGATCGGG ACGGCAACCC TTCGGTAACC
1501 CCAGAAGTGA CCTGGCAGAC GGCCTGTTAC CAGCGGGGTT TAGTGCTGGG
1551 GAAATATTTG TTTAGTTTGG GGAACTGGT GGCCATTCTT AGCCCTTCCC
```

Figure 28C(1)

```
1601 TCCATTGGTG CAAAGTCTCC CAGGAATTGT TGGACTCTTT GGAACGGGAC
1651 CGCATTCAAT TACCGGAAAT TTACGAAGAA CTTTCTCTCC GCTATCGCCA
1701 GGAACCCTAT CGGATGAAGC TGGCCTACGT TACCAAACGG CTGGAAAACA
1751 CCCTGCGGCG TAATAATCGT CTAGCCAACC CAGAAGAACG GCAAACGATG
1801 ATCACCATGC CGGCCGAAAA TCACTATCGC ACTGGGGAAG AATTATTAGA
1851 GGAATTAAGA CTCATTCAGC GTAATCTGAC CGAAACTGGT TTAACCTGCC
1901 TGGAGTTGGA AAATTTGATT ACCCAGTTGG AAGTCTATGG CTTTAACCTA
1951 GCCCAGTTGG ATTTTCGCCA GGAATCTTCC CGCCACGCCG AGGCGATCGC
2001 CGAAATTGCT GAGTATATGG GGTACTCAC CACTCCCTAC GAAGAAATGG
2051 CCGAAGAAGA TAAATTAGCC TGGTTAGGGG TAGAACTGCA AACCCGCCGT
2101 CCTTTAATTC CCCAGGAAAT GCCCTTTTCG GAGCGGACTA GGGAAACCAT
2151 TGAAACCCTC CGCACCCTGC GCCATCTACA AATGGAATTT GGGGTGGATA
2201 TTTGCCAAAC CTACATCATC AGCATGACCA ACGATGCCAG TGATGTGTTG
2251 GAAGTATTGC TGTTAGCCAA GGAAGCCGGA TTGTATGACC CGGCCACCGC
2301 CTCCAATTCC CTCCGCATTG TGCCCCTGTT TGAAACAGTA GAAGATCTCA
2351 AAAACGCTCC GGGGATTATG GATTCTCTTT TCAGCTTGCC TTTTTACCGG
2401 GCTACATTGG CGGGCAGTTA CCATTCCTTA AAAGAGTTGC AAAATCAGCC
2451 ACCGGATTAT TACCAAATTC CCACCACCAC AGCCCTACTA AATCCCGGCA
2501 ATCTCCAGGA AATTATGGTG GGCTATTCCG ACAGCAATAA AGACTCCGGC
2551 TTTTTGAGCA GTAACTGGGA AATTCATAAG GCCCAAAAAT CACTGCAGGC
2601 AGTGGCCCAA AGCCATCGGG TAATTCTCCG GCTGTTCCAC GGTCGAGGAG
2651 GATCTGTTGG CCGGGGGGGC GGCCCGGCCT ATAAAGCCAT TTTGGCCCAG
2701 CCCGCAGGCA CCGTGGACGG TCGGATCAAA ATTACCGAAC AAGGGGAAGT
2751 GTTAGCTTCT AAATATTCCC TGCCAGAGTT GGCCCTCTAC AACCTGGAAA
2801 CTTTAACCAC GGCGGTCATC CAAGCTAGTT TACTTAAAAG TAGTTTTGAT
2851 TTCATTGAGC CCTGGAACCG GATTATGGAG GAGTTGGCCT GCACTGCCCG
2901 TCGAGCCTAC CGGAGTTTGA TTTACGAAGA ACCGGACTTT TTAGATTTCT
2951 TCCTGACGGT TACCCCCATT CCTGAAATTA GCGAGTTACA GATTAGTTCC
3001 CGCCCTGCCC GACGTAAGGG GGGTAAAGCG GATCTCAGCA GTTTGCGGGC
3051 CATTCCCTGG GTGTTCAGTT GGACCCAAAC CCGTTTCCTG CTGCCGGCTT
3101 GGTATGGGGT GGGCACGGCG TTGAAATCCT TGTGGACCA AGACCCGGTC
3151 AAAAATATGA AGTTGTTGCG TTACTTCTAT TTCAAATGGC CTTTCTTCAA
3201 CATGGTGATC TCGAAGGTGG AAATGACCCT TTCCAAGGTG GACCTCACCA
```

Figure 28C(2)

```
3251 TCGCTTCCCA CTATGTGCAA GAGCTATCTA AGCCAGAAGA CCGGGAACGA
3301 TTCGATCGCC TTTTTCAGCA GATCAAGCAA GAGTATCAAT TAACCAGGGA
3351 CTTTGCCATG GAAATTACGG CCCATCCCCA CCTCCTGGAC GGCGATCGCT
3401 CTTTGCAACG GTCGGTACTC CTACGAAATC GTACTATTGT TCCCCTGGGG
3451 CTACTGCAGA TTTCCCTGCT GAAACGTTTA CGCCAAGTAA CCCAGGAAGC
3501 GGAGACCAGC GGCGTGCGTT ACCGTCGTTA TTCCAAAGAA GAACTACTGC
3551 GGGGAGCTCT GTTAACCATT AACGGTATTG CGGCCGGAAT GCGTAATACT
3601 GGTTGATCCA GTGATATGGT GCCTAATATT GGGTAAGGAC CTGCCCTTGC (SEQ
ID NO:61)
```

Figure 28C(3)

AGATCTCAACGGCTCACAAGCCCAAC (SEQ ID NO:62)

Figure 28D

CTGCAGAATTTTCTCCATTCAACCC (SEQ ID NO:63)

Figure 28E

GAGCTCTGGAGGACTGACCTAGATGG (SEQ ID NO:64)

Figure 28F

```
AGATCT
CAACGGCTCACAAGCCCAACTAATCACCATTTGGACAAAACATCAGGAATTCTAATTAGA
AAGTCCAAAAATTGTAATTTAAAAAACAGTCAATGGAGAGCATTGCCATAAGTAAAGGCA
TCCCCTGCGTGATAAGATTACCTTCAGAAAACAGATAGTTGCTGGGTTATCGCAGATTTT
TCTCGCAACCAAATAACTGTAAATAATAACTGTCTCTGGGGCGACGGTAGGCTTTATATT
GCCAAATTTCGCCCGTGGGAGAAAGCTAGGCTATTCAAGAGCTCTGGAGGACTGACCTAG
ATGGTACAAGCCAAAGCAGGGTTTAAGGCGGGCGTACAAGATTATCGCCTGACCTACTAT
ACCCCCGACTACACCCCAAGGATACCGACCTGCTCGCCTGCTTCCGTATGACCCCCAA
CCGGGTGTACCTGCTGAAGAAGCCGCTGCTGCGGTGGCCGCTGAGTCTTCCACCGGTACC
TGGACCACCGTTTGGACTGACAACCTAACTGACTTGGACCGCTACAAAGGTCGTTGCTAT
GACCTGGAAGCTGTTCCCAACGAAGATAACCAATATTTTGCTTTTATTGCCTATCCTCTA
GATTTATTTGAAGAAGGTTCCGTCACCAACGTTTTAACCTCTTTGGTCGGTAACGTATTT
GGTTTTAAGGCTCTGCGGGCCCTCCGTTTAGAAGATATTCGTTTTCCCGTTGCTTTAATT
AAAACCTTCCAAGGCCCTCCCCACGGTATTACCGTTGAGCGGGACAAATTAAACAAATAC
GGTCGTCCTCTGCTTGGTTGTACCATCAAACCCAAACTTGGTCTGTCCGCCAAGAACTAC
GGTCGGGCTGTTTACGAATGTCTCCGGGGTGGTTTGGACTTCACCAAAGACGACGAAAAC
ATCAACTCCCAGCCCTTCATGCGTTGGCGCGATCGTTTCCTCTTCGTTCAAGAGGCGATC
GAAAAAGCCCAGGCTGAGACCAACGAAATGAAAGGTCACTACCTGAACGTCACCGCTGGC
ACCTGCGAAGAAATGATGAAACGGGCCGAGTTTGCCAAGGAAATTGGCACCCCCATCATC
ATGCATGACTTCTTCACCGGCGGTTTCACTGCCAACACCACCCTCGCTCGTTGGTGTCGG
GACAACGGCATTTTGCTCCATATTCACCGGGCAATGCACGCCGTAGTTGACCGTCAGAAA
AACCACGGGATCCACTTCCGGGTTTTGGCCAAGTGTCTGCGTCTGTCCGGCGGTGACCAC
CTCCACTCCGGTACCGTGGTTGGTAAATTGGAAGGGGAACGGGGTATCACCATGGGCTTC
GTTGACCTCATGCGCGAAGATTACGTTGAGGAAGATCGCTCCCGGGGTATTTTCTTCACC
CAAGACTATGCCTCCATGCCTGGCACCATGCCCGTAGCTTCCGGTGGTATCCACGTATGG
CACATGCCCGCGTTGGTGGAAATCTTCGGTGATGATTCCTGCTTACAGTTTGGTGGTGGT
ACTTTGGGTCACCCCTGGGGTAATGCTCCCGGTGCAACCGCTAACCGTGTTGCTTTGGAA
GCTTGTGTTCAAGCTCGGAACGAAGGTCGTAACCTGGCTCGCGAAGGTAATGACGTTATC
CGGGAAGCCTGTCGTTGGTCCCCTGAGTTGGCCGCCGCCTGCGAACTCTGGAAAGAGATC
AAGTTTGAGTTCGAGGCCATGGATACCCTCTAAACCGGTGTTTGGATTGTCGGAGTTGTA
CTCGTCCGTTAAGGATGAACAGTTCTTCGGGGTTGAGTCTGCTAACTAATTAGCCATTAA
CAGCGGCTTAACTAACAGTTAGTCATTGGCAATTGTCAAAAAATTGTTAATCAGCCAAAA
CCCACTGCTTACTGATGTTCAACTTCGACAGCAATTTACCAATTACCGGGTAGAGTGTTC
ATGCAAACTAAGCACATAGCTCAGGCAACAGTGAAAGTACTGCAAAGTTACCTCACCTAC
CAAGCCGTTCTCAGGATCCAGAGTGAACTCGGGGAAACCAACCCTCCCCAGGCCATTTGG
```
Figure 28G(1)

TTAAACCAGTATTTAGCCAGTCACAGTATTCAAAATGGAGAAACGTTTTTGACGGAACTC
CTGGATGAAAATAAAGAACTGGTACTCAGGATCCTGGCGGTAAGGGAAGACATTGCCGAA
TCAGTGTTAGATTTTTTGCCCGGTATGACCCGGAATAGCTTAGCGGAATCTAACATCGCC
CACCGCCGCCATTTGCTTGAACGTCTGACCCGTACCGTAGCCGAAGTCGATAATTTCCCT
TCGGAAACCTCCAACGGAGAATCAAACAACAACGATTCTCCCCGTCCTAACGTAGTCAT
CAGCAAGGAAAACTTTTAAATCGATGAAACTTTACCCAAAGAGCGCCGCTACGAAACCC
TTTCTTACCTGCCCCCTTTAACCGATCAACAGATTGCTAAACAGGTTGAGTTTCTGTTAG
ACCAGGGCTTTATTCCCGGCGTGGAATTTGAAGAAGACCCCCAACCCGAAACCCACTTCT
GGACCATGTGGAAACTGCCCTTCTTTGGTGGTGCCACTGCCAACGAAGTTCTAGCCGAAG
TACGGGAATGTCGTTCTGAGAATCCCAACTGCTACATTCGGGTGATTGGTTTCGACAATA
TCAAACAGTGCCAGACTGTAAGCTTTATTGTCCACAAACCCAACCAAAACCAAGGCCGTT
ACTAAGTTACAGTTTTGGCAATTACTAAAAAACTGACTTCAATTCAATGTTAGCCCGCTC
CCGCGGGTTTTTTGTTGCTTTTTCACAGTGACTATAGGTAATCAGCAACACAATACGGCC
CTGTTCTTTGGACAGTTTTTGTATAATGTTGACCGCATCCTGACCGGATTTTTTATCTAA
GTGGGGAATTGTCAATTGTCAATTAAAGCTAAGTTCTACTAATGTTTTAGAAGGCATTGT
CGATTGAAAATAAGGGTTGAATGGAGAAAATTCTGCAG (SEQ ID NO:65)

Figure 28G(2)

MVQAKAGFKAGVQDYRLTYYTPDYTPKDTDLLACFRMTPQPGVPAEEAAAAVAAESSTGT
WTTVWTDNLTDLDRYKGRCYDLEAVPNEDNQYFAFIAYPLDLFEEGSVTNVLTSLVGNVF
GFKALRALRLEDIRFPVALIKTFQGPPHGITVERDKLNKYGRPLLGCTIKPKLGLSAKNY
GRAVYECLRGGLDFTKDDENINSQPFMRWRDRFLFVQEAIEKAQAETNEMKGHYLNVTAG
TCEEMMKRAEFAKEIGTPIIMHDFFTGGFTANTTLARWCRDNGILLHIHRAMHAVVDRQK
NHGIHFRVLAKCLRLSGGDHLHSGTVVGKLEGERGITMGFVDLMREDYVEEDRSRGIFFT
QDYASMPGTMPVASGGIHVWHMPALVEIFGDDSCLQFGGGTLGHPWGNAPGATANRVALE
ACVQARNEGRNLAREGNDVIREACRWSPELAAACELWKEIKFEFEAMDTL (SEQ ID NO:66)

Figure 28H

MQTKHIAQATVKVLQSYLTYQAVLRIQSELGETNPPQAIWLNQYLASHSIQNGETFLTEL
LDENKELVLRILAVREDIAESVLDFLPGMTRNSLAESNIAHRRHLLERLTRTVAEVDNFP
SETSNGESNNNDSPPS (SEQ ID NO:67)

Figure 28I

MKTLPKERRYETLSYLPPLTDQQIAKQVEFLLDQGFIPGVEFEEDPQPETHFWTMWKLPF
FGGATANEVLAEVRECRSENPNCYIRVIGFDNIKQCQTVSFIVHKPNQNQGRY **(SEQ ID
NO:68)**

Figure 28J

```
   1 CACCTAAATT GTAAGCGTTA ATATTTTGTT AAAATTCGCG TTAAATTTTT
  51 GTTAAATCAG CTCATTTTTT AACCAATAGG CCGAAATCGG CAAAATCCCT
 101 TATAAATCAA AAGAATAGAC CGAGATAGGG TTGAGTGTTG TTCCAGTTTG
 151 GAACAAGAGT CCACTATTAA AGAACGTGGA CTCCAACGTC AAAGGGCGAA
 201 AAACCGTCTA TCAGGGCGAT GGCCCACTAC GTGAACCATC ACCCTAATCA
 251 AGTTTTTTGG GGTCGAGGTG CCGTAAAGCA CTAAATCGGA ACCCTAAAGG
 301 GAGCCCCCGA TTTAGAGCTT GACGGGGAAA GCCGGCGAAC GTGGCGAGAA
 351 AGGAAGGGAA GAAAGCGAAA GGAGCGGGCG CTAGGGCGCT GGCAAGTGTA
 401 GCGGTCACGC TGCGCGTAAC CACCACACCC GCCGCGCTTA ATGCGCCGCT
 451 ACAGGGCGCG TCCCATTCGC CATTCAGGCT GCGCAACTGT TGGGAAGGGC
 501 GATCGGTGCG GGCCTCTTCG CTATTACGCC AGCTGGCGAA AGGGGGATGT
 551 GCTGCAAGGC GATTAAGTTG GGTAACGCCA GGGTTTTCCC AGTCACGACG
 601 TTGTAAAACG ACGGCCAGTG AATTGTAATA CGACTCACTA TAGGGCGAAT
 651 TGGAGGCCAG TGCTGGAGGA ATATGATTTT GTCATCCTCG ACTGTGCCCC
 701 TGGTTATAAT CTGTTGACCC GCAGTGGCAT TGCGGCCAGC GACTTTTATC
 751 TGTTGCCGGC TCGTCCTGAA CCCCTATCGG TGGTGGGGAT GCAGTTACTG
 801 GAAAGAAGAA TTGAGAAACT GAAGGAAAGC CATAAGGCCT CCGATGATCC
 851 CCTGAATATC AATCTGATCG GAGTGGTGTT TATTCTGTCC GGCGGCGGTT
 901 TGATGAGTCG CTACTATAAC CAGGTAATGC GGCGGGTACA AACGGATTTC
 951 ACCCCGGGAC AACTTTTTCA GCAGTCCATT CCCATGGATG TCAATGTGGC
1001 TAAGGCAGTG GATAGCTTTA TGCCGGTGGT TACCTCCATG CCCAATACGG
1051 CGGGTTCAAA AGCTTTTATT AAATTAACCC AGGAATTTTT ACAGAAAGTA
1101 GAAGCTTTTG GCTAAAGCAA AGCCCCATT GATTAACAAC GGGAGGGTA
1151 CCGAGGTGCT GCTGAAGTTG CCCGCAACAG AGAGTGGAAC CAACCGGTGA
1201 TACCACGATA CTATGACTGA GAGTCAACGC CATGAGCGGC CTCATTTCTT
1251 ATTCTGAGTT ACAACAGTCC GCACCGCTGT CCGGTAGCTC CTTCCGGTGG
1301 GCGCGGGGCA TGACTATCGT CGCCGCACTT ATGACTGTCT TCTTTATCAT
1351 GCAACTCGTA GGACAGGTGC CGGCAGCGCC CAACAGTCCC CCGGCCACGG
1401 GGCCTGCCAC CATACCCACG CCGAAACAAG CGCCCTGCAC CATTATGTTC
1451 CGGATCTGCA TCGCAGGATG CTGCTGGCTA CCCTGTGGAA CACCTACATC
1501 TGTATTAACG AAGCGCTAAC CGTTTTTATC AGGCTCTGGG AGGCAGAATA
1551 AATGATCATA TCGTCAATTA TTACCTCCAC GGGGAGAGCC TGAGCAAACT
1601 GGCCTCAGGC ATTTGAGAAG CACACGGTCA CACTGCTTCC GGTAGTCAAT
1651 AAACCGGTAA ACCAGCAATA GACATAAGCG GCTATTTAAC GACCCTGCCC
1701 TGAACCGACG ACCGGGTCGA ATTTGCTTTC GAATTTCTGC CATTCATCCG
1751 CTTATTATCA CTTATTCAGG CGTAGCACCA GGCGTTTAAG GGCACCAATA
```

Figure 29B(1)

```
1801 ACTGCCTTAA AAAAATTACG CCCCGCCCTG CCACTCATCG CAGTACTGTT
1851 GTAATTCATT AAGCATTCTG CCGACATGGA AGCCATCACA GACGGCATGA
1901 TGAACCTGAA TCGCCAGCGG CATCAGCACC TTGTCGCCTT GCGTATAATA
1951 TTTGCCCATG GTGAAAACGG GGGCGAAGAA GTTGTCCATA TTGGCCACGT
2001 TTAAATCAAA ACTGGTGAAA CTCACCCAGG GATTGGCTGA GACGAAAAAC
2051 ATATTCTCAA TAAACCCTTT AGGGAAATAG GCCAGGTTTT CACCGTAACA
2101 CGCCACATCT TGCGAATATA TGTGTAGAAA CTGCCGGAAA TCGTCGTGGT
2151 ATTCACTCCA GAGCGATGAA AACGTTTCAG TTTGCTCATG GAAAACGGTG
2201 TAACAAGGGT GAACACTATC CCATATCACC AGCTCACCGT CTTTCATTGC
2251 CATACGGAAT TCCGGATGAG CATTCATCAG GCGGGCAAGA ATGTGAATAA
2301 AGGCCGGATA AAACTTGTGC TTATTTTTCT TTACGGTCTT TAAAAGGCC
2351 GTAATATCCA GCTGAACGGT CTGGTTATAG GTACATTGAG CAACTGACTG
2401 AAATGCCTCA AAATGTTCTT TACGATGCCA TTGGGATATA TCAACGGTGG
2451 TATATCCAGT GATTTTTTTC TCCATTTTAG CTTCCTTAGC TCCTGAAAAT
2501 CTCGATAACT CAAAAAATAC GCCCGGTAGT GATCTTATTT CATTATGGTG
2551 AAAGTTGGAA CCTCTTACCT CGGTACCCCT CATCGGGGGC TGTGTTGGCC
2601 GAGACGGCAC TGAGGATTTT ACTCTCCATG GCATTCCAAG GAATATCTAC
2651 CCAACTCACC TGCTCCGGCG GATTGTTCCG CTCAAAAGTA CTAATCAAGT
2701 CGTCAAAATA CTTATTAAAT TTGGCTGCA ATTGCATAGT CCAAAAGCTG
2751 ACTTTCCCCT CCATGCTCTG GGGGAATTG CTCTGGCAAC TGATTAATCC
2801 ACTGAGCAAC AGCCCAAGAC ACGCAAACAA AAACCAACGT CTTGGCGATC
2851 GCCATCGGCA CCATGAAACC ATCGTAAAAG CTGGGGAAAG AATAAAAAAC
2901 AGTGGTTCAG GAATTGCATT GCCATGGCCA CTTCACAAAC CTAGCCAATT
2951 TTAGCTTGAC CGCAACTTTG ACAGATTGTC TTTTGACTTT GCCTGGACCG
3001 CCTCCCATAA TACCTTCGCG TCTTGAAGAC TTTATCCTTG AAAGGAGAAC
3051 ATATGTTTCT CGGCAAAAAT TAATTATCGA TTGGCTGGAA CCTGGTCAAA
3101 CCAGGGCTTT TCATCCATTG GAAAAGCGAT TTTGATCATC TAGGGTCAGG
3151 AGCAAAGATC TGATCAAATA TTGATCATTT ATTAGGAAAG CTGAACTTTC
3201 ACCACTTTAT TTTTGGCTTC CTCTACTTTG GGCAAAGTCA AAGTTAGGAT
3251 ACCGGCATCG TAATTAGCTT TAACTTCTGT GTTTTGGATT GCTCCAGGTA
3301 CAGGAATAAC CCGGCGGAAA CTGCCATAGC GGAACTCTGT GCGCCGCACC
3351 CCATCTTTTT CGGTGCTATG GGTATCCTGG CGATCGCCGC TGACGGTCAC
3401 CGCATCCCTG GCGGCTTGGA TGTCCAAATT ATCGGGGTCC ATGCCAGGTA
3451 ATTCTAGTTT GAGCACATAG GCTTCTTCAG TTTCAGTTAG TTCTGCTTTA
3501 GGATTAAACC CTTGGCGATC GCCGTGGCGG TCCGTAGGGA CAAAAACTTC
3551 TTCAAACAGT TGGTTCATCT GCTGCTGGAA ATTATCCATT TCCCGCAGGG
3601 GATTGTAAAG AATGAGAGAC ATAATGTTAA CTCCTGATGT GTGGAAGGAA
```

Figure 29B(2)

```
3651 TTGATTACCC TTGAATGGTT CTATCTTAAA ATTTCCCCTT CCAGGTTAGA
3701 TTCGGTTTTC AGGAAAGAAG GTGGGGGGAT TGCCGAAATT ACATTTCTAG
3751 CCGCAATTTT TAGTAAAAAA AAGATGAGTT TTTACCTCAC CTTAAGTAAA
3801 TATTTGAGTG GCAAAACAAA ATGGTAAAAA TAGCTAAGCT TCCACCGCCC
3851 TATGGATTTT TGGAAGGAAG TCTTAGGTTG TGAAAAACTA TAAAAACCAA
3901 CCATAGGAAT GGAGACCTTT ACCCAACAAG TTGACCCCTA GGTAACAAAT
3951 CCAAACCACC GTAAAACCGC TGGCGGCCAA AATAGCGGGC TTGCGGCCTT
4001 GCCAACCTTT GGTAATGCGG GCATGGAGAT AGGCGGCAAA TACTAGCCAG
4051 GTGATTAGGG CCCGGTACCC AGCTTTTGTT CCCTTTAGTG AGGGTTAATT
4101 TCGAGCTTGG CGTAATCATG GTCATAGCTG TTTCCTGTGT GAAATTGTTA
4151 TCCGCTCACA ATTCCACACA ACATACGAGC CGGAAGCATA AAGTGTAAAG
4201 CCTGGGGTGC CTAATGAGTG AGCTAACTCA CATTAATTGC GTTGCGCTCA
4251 CTGCCCGCTT TCCAGTCGGG AAACCTGTCG TGCCAGCTGC ATTAATGAAT
4301 CGGCCAACGC GCGGGGAGAG GCGGTTTGCG TATTGGGCGC TCTTCCGCTT
4351 CCTCGCTCAC TGACTCGCTG CGCTCGGTCG TTCGGCTGCG GCGAGCGGTA
4401 TCAGCTCACT CAAAGGCGGT AATACGGTTA TCCACAGAAT CAGGGGATAA
4451 CGCAGGAAAG AACATGTGAG CAAAAGGCCA GCAAAAGGCC AGGAACCGTA
4501 AAAAGGCCGC GTTGCTGGCG TTTTTCCATA GGCTCCGCCC CCCTGACGAG
4551 CATCACAAAA ATCGACGCTC AAGTCAGAGG TGGCGAAACC CGACAGGACT
4601 ATAAAGATAC CAGGCGTTTC CCCCTGGAAG CTCCCTCGTG CGCTCTCCTG
4651 TTCCGACCCT GCCGCTTACC GGATACCTGT CCGCCTTTCT CCCTTCGGGA
4701 AGCGTGGCGC TTTCTCATAG CTCACGCTGT AGGTATCTCA GTTCGGTGTA
4751 GGTCGTTCGC TCCAAGCTGG GCTGTGTGCA CGAACCCCCC GTTCAGCCCG
4801 ACCGCTGCGC CTTATCCGGT AACTATCGTC TTGAGTCCAA CCCGGTAAGA
4851 CACGACTTAT CGCCACTGGC AGCAGCCACT GGTAACAGGA TTAGCAGAGC
4901 GAGGTATGTA GGCGGTGCTA CAGAGTTCTT GAAGTGGTGG CCTAACTACG
4951 GCTACACTAG AAGGACAGTA TTTGGTATCT GCGCTCTGCT GAAGCCAGTT
5001 ACCTTCGGAA AAAGAGTTGG TAGCTCTTGA TCCGGCAAAC AAACCACCGC
5051 TGGTAGCGGT GGTTTTTTTG TTTGCAAGCA GCAGATTACG CGCAGAAAAA
5101 AAGGATCTCA AGAAGATCCT TTGATCTTTT CTACGGGGTC TGACGCTCAG
5151 TGGAACGAAA ACTCACGTTA AGGGATTTTG GTCATGAGAT TATCAAAAAG
5201 GATCTTCACC TAGATCCTTT TAAATTAAAA ATGAAGTTTT AAATCAATCT
5251 AAAGTATATA TGAGTAAACT TGGTCTGACA GTTACCAATG CTTAATCAGT
5301 GAGGCACCTA TCTCAGCGAT CTGTCTATTT CGTTCATCCA TAGTTGCCTG
5351 ACTCCCCGTC GTGTAGATAA CTACGATACG GGAGGGCTTA CCATCTGGCC
5401 CCAGTGCTGC AATGATACCG CGAGACCCAC GCTCACCGGC TCCAGATTTA
5451 TCAGCAATAA ACCAGCCAGC CGGAAGGGCC GAGCGCAGAA GTGGTCCTGC
```

Figure 29B(3)

```
5501 AACTTTATCC GCCTCCATCC AGTCTATTAA TTGTTGCCGG GAAGCTAGAG
5551 TAAGTAGTTC GCCAGTTAAT AGTTTGCGCA ACGTTGTTGC CATTGCTACA
5601 GGCATCGTGG TGTCACGCTC GTCGTTTGGT ATGGCTTCAT TCAGCTCCGG
5651 TTCCCAACGA TCAAGGCGAG TTACATGATC CCCCATGTTG TGCAAAAAAG
5701 CGGTTAGCTC CTTCGGTCCT CCGATCGTTG TCAGAAGTAA GTTGGCCGCA
5751 GTGTTATCAC TCATGGTTAT GGCAGCACTG CATAATTCTC TTACTGTCAT
5801 GCCATCCGTA AGATGCTTTT CTGTGACTGG TGAGTACTCA ACCAAGTCAT
5851 TCTGAGAATA GTGTATGCGG CGACCGAGTT GCTCTTGCCC GGCGTCAATA
5901 CGGGATAATA CCGCGCCACA TAGCAGAACT TTAAAAGTGC TCATCATTGG
5951 AAAACGTTCT TCGGGGCGAA AACTCTCAAG GATCTTACCG CTGTTGAGAT
6001 CCAGTTCGAT GTAACCCACT CGTGCACCCA ACTGATCTTC AGCATCTTTT
6051 ACTTTCACCA GCGTTTCTGG GTGAGCAAAA ACAGGAAGGC AAAATGCCGC
6101 AAAAAAGGGA ATAAGGGCGA CACGGAAATG TTGAATACTC ATACTCTTCC
6151 TTTTTCAATA TTATTGAAGC ATTTATCAGG GTTATTGTCT CATGAGCGGA
6201 TACATATTTG AATGTATTTA GAAAAATAAA CAAATAGGGG TTCCGCGCAC
6251 ATTTCCCCGA AAAGTGC (SEQ ID NO:69)
```

Figure 29B(4)

```
   1 GATCTGTAAT CCGGGCAGCG CAACGGAACA TTCATCAGTG TAAAAATGGA
  51 ATCAATAAAG CCCTGCGCAG CGCGCAGGGT CAGCCTGAAT ACGCGTTTAA
 101 TGACCAGCAC AGTCGTGATG GCAAGGTCAG AATAGCGCTG AGGTCTGCCT
 151 CGTGAAGAAG GTGTTGCTGA CTCATACCAG GCCTGAATCG CCCCATCATC
 201 CAGCCAGAAA GTGAGGGAGC CACGGTTGAT GAGAGCTTTG TTGTAGGTGG
 251 ACCAGTTGGT GATTTTGAAC TTTTGCTTTG CCACGGAACG GTCTGCGTTG
 301 TCGGGAAGAT GCGTGATCTG ATCCTTCAAC TCAGCAAAAG TTCGATTTAT
 351 TCAACAAAGC CGCCGTCCCG TCAAGTCAGC GTAATGCTCT GCCAGTGTTA
 401 CAACCAATTA ACCAATTCTG ATTAGAAAAA CTCATCGAGC ATCAAATGAA
 451 ACTGCAATTT ATTCATATCA GGATTATCAA TACCATATTT TTGAAAAGC
 501 CGTTTCTGTA ATGAAGGAGA AAACTCACCG AGGCAGTTCC ATAGGATGGC
 551 AAGATCCTGG TATCGGTCTG CGATTCCGAC TCGTCCAACA TCAATACAAC
 601 CTATTAATTT CCCCTCGTCA AAAATAAGGT TATCAAGTGA GAAATCACCA
 651 TGAGTGACGA CTGAATCCGG TGAGAATGGC AAAAGCTTAT GCATTTCTTT
 701 CCAGACTTGT TCAACAGGCC AGCCATTACG CTCGTCATCA AAATCACTCG
 751 CATCAACCAA ACCGTTATTC ATTCGTGATT GCGCCTGAGC GAGACGAAAT
 801 ACGCGATCGC TGTTAAAAGG ACAATTACAA ACAGGAATCG AATGCAACCG
 851 GCGCAGGAAC ACTGCCAGCG CATCAACAAT ATTTTCACCT GAATCAGGAT
 901 ATTCTTCTAA TACCTGGAAT GCTGTTTTCC CGGGGATCGC AGTGGTGAGT
 951 AACCATGCAT CATCAGGAGT ACGGATAAAA TGCTTGATGG TCGGAAGAGG
1001 CATAAATTCC GTCAGCCAGT TTAGTCTGAC CATCTCATCT GTAACATCAT
1051 TGGCAACGCT ACCTTTGCCA TGTTTCAGAA ACAACTCTGG CGCATCGGGC
1101 TTCCCATACA ATCGATAGAT TGTCGCACCT GATTGCCCGA CATTATCGCG
1151 AGCCCATTTA TACCCATATA AATCAGCATC CATGTTGGAA TTTAATCGCG
1201 GCCTCGAGCA AGACGTTTCC CGTTGAATAT GGCTCATAAC ACCCCTTGTA
1251 TTACTGTTTA TGTAAGCAGA CAGTTTTATT GTTCATGATG ATATATTTTT
1301 ATCTTGTGCA ATGTAACATC AGAGATTTTG AGACACAACG TGGCTTTGTT
1351 GAATAAATCG AACTTTTGCT GAGTTGAAGG ATCAGATCAC GCATCTTCCC
1401 GACAACGCAG ACCGTTCCGT GGCAAAGCAA AAGTTCAAAA TCACCAACTG
1451 GTCCACCTAC AACAAAGCTC TCATCAACCG TGGCTCCCTC ACTTTCTGGC
1501 TGGATGATGG GGCGATTCAG GCCTGGTATG AGTCAGCAAC ACCTTCTTCA
1551 CGAGGCAGAC CTCAGCGCTA TTCTGACCTT GCCATCACGA CTGTGCTGGT
1601 CATTAAACGC GTATTCAGGC TGACCCTGCG CGCTGCGCAG GCTTTATTG
1651 ATTCCATTTT TACACTGATG AATGTTCCGT TGCGCTGCCC GGATTACAGC
1701 TGAAAGCGAC CAGGTGCTCG GCGTGGCAAG ACTCGCAGCG AACCCGTAGA
```

Figure 30B(1)

```
1751 AAGCCATGCT CCAGCCGCCC GCATTGGAGA AATTCTTCAA ATTCCCGTTG
1801 CACATAGCCC GGCAATTCCT TTCCCTGCTC TGCCATAAGC GCAGCGAATG
1851 CCGGGTAATA CTCGTCAACG ATCTGATAGA GAAGGGTTTG CTCGGGTCGG
1901 TGGCTCTGGT AACGACCAGT ATCCCGATCC CGGCTGGCCG TCCTGGCCGC
1951 CACATGAGGC ATGTTCCGCG TCCTTGCAAT ACTGTGTTTA CATACAGTCT
2001 ATCGCTTAGC GGAAAGTTCT TTTACCCTCA GCCGAAATGC CTGCCGTTGC
2051 TAGACATTGC CAGCCAGTGC CCGTCACTCC CGTACTAACT GTCACGAACC
2101 CCTGCAATAA CTGTCACGCC CCCTGCAAT AACTGTCACG AACCCCTGCA
2151 ATAACTGTCA CGCCCCCAAA CCTGCAAACC CAGCAGGGGC GGGGGCTGGC
2201 GGGGTGTTGG AAAAATCCAT CCATGATTAT CTAAGAATAA TCCACTAGGC
2251 GCGGTTATCA GCGCCCTTGT GGGGCGCTGC TGCCCTTGCC CAATATGCCC
2301 GGCCAGAGGC CGGATAGCTG GTCTATTCGC TGCGCTAGGC TACACACCGC
2351 CCCACCGCTG CGCGGCAGGG GGAAAGGCGG GCAAAGCCCG CTAAACCCCA
2401 CACCAAACCC CGCAGAAATA CGCTGGAGCG CTTTTAGCCG CTTTAGCGGC
2451 CTTTCCCCCT ACCCGAAGGG TGGGGGCGCG TGTGCAGCCC CGCAGGGCCT
2501 GTCTCGGTCG ATCATTCAGC CCGGCTCATC CTTCTGGCGT GGCGGCAGAC
2551 CGAACAAGGC GCGGTCGTGG TCGCGTTCAA GGTACGCATC CATTGCCGCC
2601 ATGAGCCGAT CCTCCGGCCA CTCGCTGCTG TTCACCTTGG CCAAAATCAT
2651 GGCCCCCACC AGCACCTTGC GCCTGTTTC GTTCTTGCGC TCTTGCTGCT
2701 GTTCCCTTGC CCGCACCCGC TGAATTTCGG CATTGATTCG CGCTCGTTGT
2751 TCTTCGAGCT TGGCCAGCCG ATCCGCCGCC TTGTTGCTCC CCTTAACCAT
2801 CTTGACACCC CATTGTTAAT GTGCTGTCTC GTAGGCTATC ATGGAGGCAC
2851 AGCGGCGGCA ATCCCGACCC TACTTTGTAG GGGAGGGCGC ACTTACCGGT
2901 TTCTCTTCGA GAAACTGGCC TAACGGCCAC CCTTCGGGCG GTGCGCTCTC
2951 CGAGGGCCAT TGCATGGAGC CGAAAAGCAA AAGCAACAGC GAGGCAGCAT
3001 GGCGATTTAT CACCTTACGG CGAAAACCGG CAGCAGGTCG GGCGGCAAT
3051 CGGCCAGGGC CAAGGCCGAC TACATCCAGC GCGAAGGCAA GTATGCCCGC
3101 GACATGGATG AAGTCTTGCA CGCCGAATCC GGGCACATGC CGGAGTTCGT
3151 CGAGCGGCCC GCCGACTACT GGGATGCTGC CGACCTGTAT GAACGCGCCA
3201 ATGGGCGGCT GTTCAAGGAG GTCGAATTTG CCCTGCCGGT CGAGCTGACC
3251 CTCGACCAGC AGAAGGCGCT GGCGTCCGAG TTCGCCCAGC ACCTGACCGG
3301 TGCCGAGCGC CTGCCGTATA CGCTGGCCAT CCATGCCGGT GGCGGCGAGA
3351 ACCCGCACTG CCACCTGATG ATCTCCGAGC GGATCAATGA CGGCATCGAG
3401 CGGCCCGCCG CTCAGTGGTT CAAGCGGTAC AACGGCAAGA CCCCGGAGAA
3451 GGGCGGGGCA CAGAAGACCG AAGCGCTCAA GCCCAAGGCA TGGCTTGAGC
3501 AGACCCGCGA GGCATGGGCC GACCATGCCA ACGGGCATT AGAGCGGGCT
3551 GGCCACGACG CCCGCATTGA CCACAGAACA CTTGAGGCGC AGGGCATCGA
```

Figure 30B(2)

```
3601 GCGCCTGCCC GGTGTTCACC TGGGGCCGAA CGTGGTGGAG ATGGAAGGCC
3651 GGGGCATCCG CACCGACCGG GCAGACGTGG CCCTGAACAT CGACACCGCC
3701 AACGCCCAGA TCATCGACTT ACAGGAATAC CGGGAGGCAA TAGACCATGA
3751 ACGCAATCGA CAGAGTGAAG AAATCCAGAG GCATCAACGA GTTAGCGGAG
3801 CAGATCGAAC CGCTGGCCCA GAGCATGGCG ACACTGGCCG ACGAAGCCCG
3851 GCAGGTCATG AGCCAGACCC AGCAGGCCAG CGAGGCGCAG GCGGCGGAGT
3901 GGCTGAAAGC CCAGCGCCAG ACAGGGGCGG CATGGGTGGA GCTGGCCAAA
3951 GAGTTGCGGG AGGTAGCCGC CGAGGTGAGC AGCGCCGCGC AGAGCGCCCG
4001 GAGCGCGTCG CGGGGGTGGC ACTGGAAGCT ATGGCTAACC GTGATGCTGG
4051 CTTCCATGAT GCCTACGGTG GTGCTGCTGA TCGCATCGTT GCTCTTGCTC
4101 GACCTGACGC CACTGACAAC CGAGGACGGC TCGATCTGGC TGCGCTTGGT
4151 GGCCCGATGA AGAACGACAG GACTTTGCAG GCCATAGGCC GACAGCTCAA
4201 GGCCATGGGC TGTGAGCGCT TCGATATCGG CGTCAGGGAC GCCACCACCG
4251 GCCAGATGAT GAACCGGGAA TGGTCAGCCG CCGAAGTGCT CCAGAACACG
4301 CCATGGCTCA AGCGGATGAA TGCCCAGGGC AATGACGTGT ATATCAGGCC
4351 CGCCGAGCAG GAGCGGCATG GTCTGGTGCT GGTGGACGAC CTCAGCGAGT
4401 TTGACCTGGA TGACATGAAA GCCGAGGGCC GGGAGCCTGC CCTGGTAGTG
4451 GAAACCAGCC CGAAGAACTA TCAGGCATGG GTCAAGGTGG CCGACGCCGC
4501 AGGCGGTGAA CTTCGGGGGC AGATTGCCCG GACGCTGGCC AGCGAGTACG
4551 ACGCCGACCC GGCCAGCGCC GACAGCCGCC ACTATGGCCG CTTGGCGGGC
4601 TTCACCAACC GCAAGGACAA GCACACCACC GCGCCGGTT ATCAGCCGTG
4651 GGTGCTGCTG CGTGAATCCA AGGGCAAGAC CGCCACCGCT GGCCCGGCGC
4701 TGGTGCAGCA GGCTGGCCAG CAGATCGAGC AGGCCCAGCG GCAGCAGGAG
4751 AAGGCCCGCA GGCTGGCCAG CCTCGAACTG CCCGAGCGGC AGCTTAGCCG
4801 CCACCGGCGC ACGGCGCTGG ACGAGTACCG CAGCGAGATG GCCGGGCTGG
4851 TCAAGCGCTT CGGTGATGAC CTCAGCAAGT GCGACTTTAT CGCCGCGCAG
4901 AAGCTGGCCA GCCGGGGCCG CAGTGCCGAG GAAATCGGCA AGGCCATGGC
4951 CGAGGCCAGC CCAGCGCTGG CAGAGCGCAA GCCCGGCCAC GAAGCGGATT
5001 ACATCGAGCG CACCGTCAGC AAGGTCATGG GTCTGCCCAG CGTCCAGCTT
5051 GCGCGGGCCG AGCTGGCACG GGCACCGGCA CCCCGCCAGC GAGGCATGGA
5101 CAGGGCGGG CCAGATTTCA GCATGTAGTG CTTGCGTTGG TACTCACGCC
5151 TGTTATACTA TGAGTACTCA CGCACAGAAG GGGGTTTTAT GGAATACGAA
5201 AAAAGCGCTT CAGGGTCGGT CTACCTGATC AAAAGTGACA AGGGCTATTG
5251 GTTGCCCGGT GGCTTTGGTT ATACGTCAAA CAAGGCCGAG GCTGGCCGCT
5301 TTTCAGTCGC TGATATGGCC AGCCTTAACC TTGACGGCTG CACCTTGTCC
5351 TTGTTCCGCG AAGACAAGCC TTTCGGCCCC GGCAAGTTTC TCGGTGACTG
5401 ATATGAAAGA CCAAAAGGAC AAGCAGACCG GCGACCTGCT GGCCAGCCCT
```

Figure 30B(3)

```
5451 GACGCTGTAC GCCAAGCGCG ATATGCCGAG CGCATGAAGG CCAAAGGGAT
5501 GCGTCAGCGC AAGTTCTGGC TGACCGACGA CGAATACGAG GCGCTGCGCG
5551 AGTGCCTGGA AGAACTCAGA GCGGCGCAGG GCGGGGGTAG TGACCCCGCC
5601 AGCGCCTAAC CACCAACTGC CTGCAAAGGA GGCAATCAAT GGCTACCCAT
5651 AAGCCTATCA ATATTCTGGA GGCGTTCGCA GCAGCGCCGC CACCGCTGGA
5701 CTACGTTTTG CCCAACATGG TGGCCGGTAC GGTCGGGGCG CTGGTGTCGC
5751 CCGGTGGTGC CGGTAAATCC ATGCTGGCCC TGCAACTGGC CGCACAGATT
5801 GCAGGCGGGC CGGATCTGCT GGAGGTGGGC GAACTGCCCA CCGGCCCGGT
5851 GATCTACCTG CCCGCCGAAG ACCCGCCCAC CGCCATTCAT CACCGCCTGC
5901 ACGCCCTTGG GGCGCACCTC AGCGCCGAGG AACGGCAAGC CGTGGCTGAC
5951 GGCCTGCTGA TCCAGCCGCT GATCGGCAGC CTGCCCAACA TCATGGCCCC
6001 GGAGTGGTTC GACGGCCTCA AGCGCGCCGC CGAGGGCCGC CGCCTGATGG
6051 TGCTGGACAC GCTGCGCCGG TTCCACATCG AGGAAGAAAA CGCCAGCGGC
6101 CCCATGGCCC AGGTCATCGG TCGCATGGAG GCCATCGCCG CCGATACCGG
6151 GTGCTCTATC GTGTTCCTGC ACCATGCCAG CAAGGGCGCG CCATGATGG
6201 GCGCAGGCGA CCAGCAGCAG GCCAGCCGGG GCAGCTCGGT ACTGGTCGAT
6251 AACATCCGCT GGCAGTCCTA CCTGTCGAGC ATGACCAGCG CCGAGGCCGA
6301 GGAATGGGGT GTGGACGACG ACCAGCGCCG GTTCTTCGTC CGCTTCGGTG
6351 TGAGCAAGGC CAACTATGGC GCACCGTTCG CTGATCGGTG GTTCAGGCGG
6401 CATGACGGCG GGGTGCTCAA GCCCGCCGTG CTGGAGAGGC AGCGCAAGAG
6451 CAAGGGGGTG CCCCGTGGTG AAGCCTAAGA ACAAGCACAG CCTCAGCCAC
6501 GTCCGGCACG ACCCGGCGCA CTGTCTGGCC CCCGGCCTGT TCCGTGCCCT
6551 CAAGCGGGGC GAGCGCAAGC GCAGCAAGCT GGACGTGACG TATGACTACG
6601 GCGACGGCAA GCGGATCGAG TTCAGCGGCC CGGAGCCGCT GGGCGCTGAT
6651 GATCTGCGCA TCCTGCAAGG GCTGGTGGCC ATGGCTGGGC CTAATGGCCT
6701 AGTGCTTGGC CCGGAACCCA AGACCGAAGG CGGACGGCAG CTCCGGCTGT
6751 TCCTGGAACC CAAGTGGGAG GCCGTCACCG CTGAATGCCA TGTGGTCAAA
6801 GGTAGCTATC GGGCGCTGGC AAAGGAAATC GGGGCAGAGG TCGATAGTGG
6851 TGGGGCGCTC AAGCACATAC AGGACTGCAT CGAGCGCCTT TGGAAGGTAT
6901 CCATCATCGC CCAGAATGGC CGCAAGCGGC AGGGGTTTCG GCTGCTGTCG
6951 GAGTACGCCA GCGACGAGGC GGACGGGCGC CTGTACGTGG CCCTGAACCC
7001 CTTGATCGCG CAGGCCGTCA TGGGTGGCGG CCAGCATGTG CGCATCAGCA
7051 TGGACGAGGT GCGGGCGCTG GACAGCGAAA CCGCCCGCCT GCTGCACCAG
7101 CGGCTGTGTG CTGGATCGA CCCCGGCAAA ACCGGCAAGG CTTCCATAGA
7151 TACCTTGTGC GGCTATGTCT GGCCGTCAGA GGCCAGTGGT TCGACCATGC
7201 GCAAGCGCCG CCAGCGGGTG CGCGAGGCGT TGCCGGAGCT GGTCGCGCTG
7251 GGCTGGACGG TAACCGAGTT CGCGGCGGGC AAGTACGACA TCACCCGGCC
```

Figure 30B(4)

```
7301 CAAGGCGGCA GGCTGACCCC CCCCACTCTA TTGTAAACAA GACATTTTTA
7351 TCTTTTATAT TCAATGGCTT ATTTTCCTGC TAATTGGTAA TACCATGAAA
7401 AATACCATGC TCAGAAAAGG CTTAACAATA TTTTGAAAAA TTGCCTACTG
7451 AGCGCTGCCG CACAGCTCCA TAGGCCGCTT TCCTGGCTTT GCTTCCAGAT
7501 GTATGCTCTT CTGCTCCTGC AGGCATCGTG GTGTCACGCT CGTCGTTTGG
7551 TATGGCTTCA TTCAGCTCCG GTTCCCAACG ATCAAGGCGA GTTACATGAT
7601 CCCCCATGTT GTGCAAAAAA GCGGTTAGCT CCTTCGGTCC TCCGATCGTT
7651 GTCAGAAGTA AGTTGGCCGC AGTGTTATCA CTCATGGTTA TGGCAGCACT
7701 GCATAATTCT CTTACTGTCA TGCCATCCGT AAGATGCTTT TCTGTGACTG
7751 GTGAGTACTC AACCAAGTCA TTCTGAGAAT AGTGTATGCG GCGACCGAGT
7801 TGCTCTTGCC CGGCGTCAAC ACGGGATAAT ACCGCGCCAC ATAGCAGAAC
7851 TTTAAAAGTG CTCATCATTG GAAAACGTTC TTCGGGGCGA AAACTCTCAA
7901 GGATCTTACC GCTGTTGAGA TCCAGTTCGA TGTAACCCAC TCGTGCACCC
7951 AACTGATCTT CAGCATCTTT TACTTTCACC AGCGTTTCTG GGTGAGCAAA
8001 AACAGGAAGG CAAAATGCCG CAAAAAAGGG AATAAGGGCG ACACGGAAAT
8051 GTTGAATACT CATACTCTTC CTTTTTCAAT ATTATTGAAG CATTTATCAG
8101 GGTTATTGTC TCATGAGCGG ATACATATTT GAATGTATTT AGAAAAATAA
8151 ACAAATAGGG GTTCCGCGCA CATTTCCCCG AAAAGTGCCA CCTGACGTCT
8201 AAGAAACCAT TATTATCATG ACATTAACCT ATAAAAATAG GCGTATCACG
8251 AGGCCCTTTC GTCTTCGAAT AAATACCTGT GACGGAAGAT CACTTCGCAG
8301 AATAAATAAA TCCTGGTGTC CCTGTTGATA CCGGGAAGCC CTGGGCCAAC
8351 TTTTGGCGAA AATGAGACGT TGATCGGCAC GTAAGAGGTT CCAACTTTCA
8401 CCATAATGAA ATAAGATCAC TACCGGGCGT ATTTTTTGAG TTATCGAGAT
8451 TTTCAGGAGC TAAGGAAGCT AAAATGGAGA AAAAAATCAC TGGATATACC
8501 ACCGTTGATA TATCCCAATG GCATCGTAAA GAACATTTTG AGGCATTTCA
8551 GTCAGTTGCT CAATGTACCT ATAACCAGAC CGTTCAGCTG GATATTACGG
8601 CCTTTTTAAA GACCGTAAAG AAAAATAAGC ACAAGTTTTA TCCGGCCTTT
8651 ATTCACATTC TTGCCCGCCT GATGAATGCT CATCCGGAAT TCCGTATGGC
8701 AATGAAAGAC GGTGAGCTGG TGATATGGGA TAGTGTTCAC CCTTGTTACA
8751 CCGTTTTCCA TGAGCAAACT GAAACGTTTT CATCGCTCTG GAGTGAATAC
8801 CACGACGATT TCCGGCAGTT TCTACACATA TATTCGCAAG ATGTGGCGTG
8851 TTACGGTGAA AACCTGGCCT ATTTCCCTAA AGGGTTATT GAGAATATGT
8901 TTTTCGTCTC AGCCAATCCC TGGGTGAGTT TCACCAGTTT TGATTTAAAC
8951 GTGGCCAATA TGGACAACTT CTTCGCCCCC GTTTTCACCA TGGGCAAATA
```

Figure 30B(5)

```
9001 TTATACGCAA GGCGACAAGG TGCTGATGCC GCTGGCGATT CAGGTTCATC
9051 ATGCCGTCTG TGATGGCTTC CATGTCGGCA GAATGCTTAA TGAATTACAA
9101 CAGTACTGCG ATGAGTGGCA GGGCGGGGCG TAATTTTTTT AAGGCAGTTA
9151 TTGGTGCCCT TAAACGCCTG GTGCTACGCC TGAATAAGTG ATAATAAGCG
9201 GATGAATGGC AGAAATTCGT CGACTCTAGA G (SEQ ID NO:70)
```

Figure 30B(6)

```
   1 GATCTGTAAT CCGGGCAGCG CAACGGAACA TTCATCAGTG TAAAAATGGA
  51 ATCAATAAAG CCCTGCGCAG CGCGCAGGGT CAGCCTGAAT ACGCGTTTAA
 101 TGACCAGCAC AGTCGTGATG GCAAGGTCAG AATAGCGCTG AGGTCTGCCT
 151 CGTGAAGAAG GTGTTGCTGA CTCATACCAG GCCTGAATCG CCCCATCATC
 201 CAGCCAGAAA GTGAGGGAGC CACGGTTGAT GAGAGCTTTG TTGTAGGTGG
 251 ACCAGTTGGT GATTTTGAAC TTTTGCTTTG CCACGGAACG GTCTGCGTTG
 301 TCGGGAAGAT GCGTGATCTG ATCCTTCAAC TCAGCAAAAG TTCGATTTAT
 351 TCAACAAAGC CGCCGTCCCG TCAAGTCAGC GTAATGCTCT GCCAGTGTTA
 401 CAACCAATTA ACCAATTCTG ATTAGAAAAA CTCATCGAGC ATCAAATGAA
 451 ACTGCAATTT ATTCATATCA GGATTATCAA TACCATATTT TTGAAAAAGC
 501 CGTTTCTGTA ATGAAGGAGA AAACTCACCG AGGCAGTTCC ATAGGATGGC
 551 AAGATCCTGG TATCGGTCTG CGATTCCGAC TCGTCCAACA TCAATACAAC
 601 CTATTAATTT CCCCTCGTCA AAAATAAGGT TATCAAGTGA GAAATCACCA
 651 TGAGTGACGA CTGAATCCGG TGAGAATGGC AAAAGCTTAT GCATTTCTTT
 701 CCAGACTTGT TCAACAGGCC AGCCATTACG CTCGTCATCA AAATCACTCG
 751 CATCAACCAA ACCGTTATTC ATTCGTGATT GCGCCTGAGC GAGACGAAAT
 801 ACGCGATCGC TGTTAAAAGG ACAATTACAA ACAGGAATCG AATGCAACCG
 851 GCGCAGGAAC ACTGCCAGCG CATCAACAAT ATTTTCACCT GAATCAGGAT
 901 ATTCTTCTAA TACCTGGAAT GCTGTTTTCC CGGGGATCGC AGTGGTGAGT
 951 AACCATGCAT CATCAGGAGT ACGGATAAAA TGCTTGATGG TCGGAAGAGG
1001 CATAAATTCC GTCAGCCAGT TTAGTCTGAC CATCTCATCT GTAACATCAT
1051 TGGCAACGCT ACCTTTGCCA TGTTTCAGAA ACAACTCTGG CGCATCGGGC
1101 TTCCCATACA ATCGATAGAT TGTCGCACCT GATTGCCCGA CATTATCGCG
1151 AGCCCATTTA TACCCATATA AATCAGCATC CATGTTGGAA TTTAATCGCG
1201 GCCTCGAGCA AGACGTTTCC CGTTGAATAT GGCTCATAAC ACCCCTTGTA
1251 TTACTGTTTA TGTAAGCAGA CAGTTTTATT GTTCATGATG ATATATTTTT
1301 ATCTTGTGCA ATGTAACATC AGAGATTTTG AGACACAACG TGGCTTTGTT
1351 GAATAAATCG AACTTTTGCT GAGTTGAAGG ATCAGATCAC GCATCTTCCC
1401 GACAACGCAG ACCGTTCCGT GGCAAAGCAA AAGTTCAAAA TCACCAACTG
1451 GTCCACCTAC AACAAAGCTC TCATCAACCG TGGCTCCCTC ACTTTCTGGC
1501 TGGATGATGG GGCGATTCAG GCCTGGTATG AGTCAGCAAC ACCTTCTTCA
1551 CGAGGCAGAC CTCAGCGCTA TTCTGACCTT GCCATCACGA CTGTGCTGGT
1601 CATTAAACGC GTATTCAGGC TGACCCTGCG CGCTGCGCAG GGCTTTATTG
1651 ATTCCATTTT TACACTGATG AATGTTCCGT TGCGCTGCCC GGATTACAGG
1701 GGTACCGAGC TCGAATTGAC ATAAGCCTGT TCGGTTCGTA AACTGTAATG
```

Figure 31B(1)

```
1751 CAAGTAGCGT ATGCGCTCAC GCAACTGGTC CAGAACCTTG ACCGAACGCA
1801 GCGGTGGTAA CGGCGCAGTG GCGGTTTTCA TGGCTTGTTA TGACTGTTTT
1851 TTTGTACAGT CTATGCCTCG GGCATCCAAG CAGCAAGCGC GTTACGCCGT
1901 GGGTCGATGT TTGATGTTAT GGAGCAGCAA CGATGTTACG CAGCAGCAAC
1951 GATGTTACGC AGCAGGGCAG TCGCCCTAAA ACAAAGTTAG GTGGCTCAAG
2001 TATGGGCATC ATTCGCACAT GTAGGCTCGG CCCTGACCAA GTCAAATCCA
2051 TGCGGGCTGC TCTTGATCTT TTCGGTCGTG AGTTCGGAGA CGTAGCCACC
2101 TACTCCCAAC ATCAGCCGGA CTCCGATTAC CTCGGGAACT TGCTCCGTAG
2151 TAAGACATTC ATCGCGCTTG CTGCCTTCGA CCAAGAAGCG GTTGTTGGCG
2201 CTCTCGCGGC TTACGTTCTG CCCAGGTTTG AGCAGCCGCG TAGTGAGATC
2251 TATATCTATG ATCTCGCAGT CTCCGGCGAG CACCGGAGGC AGGGCATTGC
2301 CACCGCGCTC ATCAATCTCC TCAAGCATGA GGCCAACGCG CTTGGTGCTT
2351 ATGTGATCTA CGTGCAAGCA GATTACGGTG ACGATCCCGC AGTGGCTCTC
2401 TATACAAAGT TGGGCATACG GGAAGAAGTG ATGCACTTTG ATATCGACCC
2451 AAGTACCGCC ACCTAACAAT TCGTTCAAGC CGAGATCGGC TTCCCGGCCG
2501 CGGAGTTGTT CGGTAAATTG TCACAACGCC GCGGCCAATT CGAGCTCGGT
2551 ACCCCTGAAA GCGACCAGGT GCTCGGCGTG GCAAGACTCG CAGCGAACCC
2601 GTAGAAAGCC ATGCTCCAGC CGCCCGCATT GGAGAAATTC TTCAAATTCC
2651 CGTTGCACAT AGCCCGGCAA TTCCTTTCCC TGCTCTGCCA TAAGCGCAGC
2701 GAATGCCGGG TAATACTCGT CAACGATCTG ATAGAGAAGG GTTTGCTCGG
2751 GTCGGTGGCT CTGGTAACGA CCAGTATCCC GATCCCGGCT GGCCGTCCTG
2801 GCCGCCACAT GAGGCATGTT CCGCGTCCTT GCAATACTGT GTTTACATAC
2851 AGTCTATCGC TTAGCGGAAA GTTCTTTTAC CCTCAGCCGA AATGCCTGCC
2901 GTTGCTAGAC ATTGCCAGCC AGTGCCCGTC ACTCCCGTAC TAACTGTCAC
2951 GAACCCCTGC AATAACTGTC ACGCCCCCCT GCAATAACTG TCACGAACCC
3001 CTGCAATAAC TGTCACGCCC CCAAACCTGC AAACCCAGCA GGGGCGGGGG
3051 CTGGCGGGGT GTTGGAAAAA TCCATCCATG ATTATCTAAG AATAATCCAC
3101 TAGGCGCGGT TATCAGCGCC CTTGTGGGGC GCTGCTGCCC TTGCCCAATA
3151 TGCCCGGCCA GAGGCCGGAT AGCTGGTCTA TTCGCTGCGC TAGGCTACAC
3201 ACCGCCCCAC CGCTGCGCGG CAGGGGGAAA GGCGGGCAAA GCCCGCTAAA
3251 CCCCACACCA AACCCGCAG AAATACGCTG GAGCGCTTTT AGCCGCTTTA
3301 GCGGCCTTTC CCCCTACCCG AAGGGTGGGG CGCGTGTGC AGCCCCGCAG
3351 GGCCTGTCTC GGTCGATCAT TCAGCCCGGC TCATCCTTCT GGCGTGGCGG
3401 CAGACCGAAC AAGGCGCGGT CGTGGTCGCG TTCAAGGTAC GCATCCATTG
```

Figure 31B(2)

```
3451 CCGCCATGAG CCGATCCTCC GGCCACTCGC TGCTGTTCAC CTTGGCCAAA
3501 ATCATGGCCC CCACCAGCAC CTTGCGCCTT GTTTCGTTCT TGCGCTCTTG
3551 CTGCTGTTCC CTTGCCCGCA CCCGCTGAAT TCGGCATTG ATTCGCGCTC
3601 GTTGTTCTTC GAGCTTGGCC AGCCGATCCG CCGCCTTGTT GCTCCCCTTA
3651 ACCATCTTGA CACCCCATTG TTAATGTGCT GTCTCGTAGG CTATCATGGA
3701 GGCACAGCGG CGGCAATCCC GACCCTACTT TGTAGGGGAG GGCGCACTTA
3751 CCGGTTTCTC TTCGAGAAAC TGGCCTAACG GCCACCCTTC GGGCGGTGCG
3801 CTCTCCGAGG GCCATTGCAT GGAGCCGAAA AGCAAAAGCA ACAGCGAGGC
3851 AGCATGGCGA TTTATCACCT TACGGCGAAA ACCGGCAGCA GGTCGGGCGG
3901 CCAATCGGCC AGGGCCAAGG CCGACTACAT CCAGCGCGAA GGCAAGTATG
3951 CCCGCGACAT GGATGAAGTC TTGCACGCCG AATCCGGGCA CATGCCGGAG
4001 TTCGTCGAGC GGCCCGCCGA CTACTGGGAT GCTGCCGACC TGTATGAACG
4051 CGCCAATGGG CGGCTGTTCA AGGAGGTCGA ATTTGCCCTG CCGGTCGAGC
4101 TGACCCTCGA CCAGCAGAAG GCGCTGGCGT CCGAGTTCGC CCAGCACCTG
4151 ACCGGTGCCG AGCGCCTGCC GTATACGCTG GCCATCCATG CCGGTGGCGG
4201 CGAGAACCCG CACTGCCACC TGATGATCTC CGAGCGGATC AATGACGGCA
4251 TCGAGCGGCC CGCCGCTCAG TGGTTCAAGC GGTACAACGG CAAGACCCCG
4301 GAGAAGGGCG GGCACAGAA GACCGAAGCG CTCAAGCCCA AGGCATGGCT
4351 TGAGCAGACC CGCGAGGCAT GGGCCGACCA TGCCAACCGG GCATTAGAGC
4401 GGGCTGGCCA CGACGCCCGC ATTGACCACA GAACACTTGA GGCGCAGGGC
4451 ATCGAGCGCC TGCCCGGTGT TCACCTGGGG CCGAACGTGG TGGAGATGGA
4501 AGGCCGGGGC ATCCGCACCG ACCGGGCAGA CGTGGCCCTG AACATCGACA
4551 CCGCCAACGC CCAGATCATC GACTTACAGG AATACCGGGA GGCAATAGAC
4601 CATGAACGCA ATCGACAGAG TGAAGAAATC CAGAGGCATC AACGAGTTAG
4651 CGGAGCAGAT CGAACCGCTG GCCCAGAGCA TGGCGACACT GGCCGACGAA
4701 GCCCGGCAGG TCATGAGCCA GACCCAGCAG GCCAGCGAGG CGCAGGCGGC
4751 GGAGTGGCTG AAAGCCCAGC GCCAGACAGG GGCGGCATGG GTGGAGCTGG
4801 CCAAAGAGTT GCGGGAGGTA GCCGCCGAGG TGAGCAGCGC CGCGCAGAGC
4851 GCCCGGAGCG CGTCGCGGGG GTGGCACTGG AAGCTATGGC TAACCGTGAT
4901 GCTGGCTTCC ATGATGCCTA CGGTGGTGCT GCTGATCGCA TCGTTGCTCT
4951 TGCTCGACCT GACGCCACTG ACAACCGAGG ACGGCTCGAT CTGGCTGCGC
5001 TTGGTGGCCC GATGAAGAAC GACAGGACTT TGCAGGCCAT AGGCCGACAG
5051 CTCAAGGCCA TGGGCTGTGA GCGCTTCGAT ATCGGCGTCA GGGACGCCAC
5101 CACCGGCCAG ATGATGAACC GGGAATGGTC AGCCGCCGAA GTGCTCCAGA
5151 ACACGCCATG GCTCAAGCGG ATGAATGCCC AGGGCAATGA CGTGTATATC
```

Figure 31B(3)

```
5201 AGGCCCGCCG AGCAGGAGCG GCATGGTCTG GTGCTGGTGG ACGACCTCAG
5251 CGAGTTTGAC CTGGATGACA TGAAAGCCGA GGGCCGGGAG CCTGCCCTGG
5301 TAGTGGAAAC CAGCCCGAAG AACTATCAGG CATGGGTCAA GGTGGCCGAC
5351 GCCGCAGGCG GTGAACTTCG GGGGCAGATT GCCCGGACGC TGGCCAGCGA
5401 GTACGACGCC GACCCGGCCA GCGCCGACAG CCGCCACTAT GGCCGCTTGG
5451 CGGGCTTCAC CAACCGCAAG GACAAGCACA CCACCCGCGC CGGTTATCAG
5501 CCGTGGGTGC TGCTGCGTGA ATCCAAGGGC AAGACCGCCA CCGCTGGCCC
5551 GGCGCTGGTG CAGCAGGCTG CCAGCAGAT CGAGCAGGCC CAGCGGCAGC
5601 AGGAGAAGGC CCGCAGGCTG GCCAGCCTCG AACTGCCCGA GCGGCAGCTT
5651 AGCCGCCACC GGCGCACGGC GCTGGACGAG TACCGCAGCG AGATGGCCGG
5701 GCTGGTCAAG CGCTTCGGTG ATGACCTCAG CAAGTGCGAC TTTATCGCCG
5751 CGCAGAAGCT GGCCAGCCGG GGCCGCAGTG CCGAGGAAAT CGGCAAGGCC
5801 ATGGCCGAGG CCAGCCCAGC GCTGGCAGAG CGCAAGCCCG GCCACGAAGC
5851 GGATTACATC GAGCGCACCG TCAGCAAGGT CATGGGTCTG CCCAGCGTCC
5901 AGCTTGCGCG GGCCGAGCTG GCACGGGCAC CGGCACCCCG CCAGCGAGGC
5951 ATGGACAGGG GCGGGCCAGA TTTCAGCATG TAGTGCTTGC GTTGGTACTC
6001 ACGCCTGTTA TACTATGAGT ACTCACGCAC AGAAGGGGGT TTTATGGAAT
6051 ACGAAAAAAG CGCTTCAGGG TCGGTCTACC TGATCAAAAG TGACAAGGGC
6101 TATTGGTTGC CCGGTGGCTT TGGTTATACG TCAAACAAGG CCGAGGCTGG
6151 CCGCTTTTCA GTCGCTGATA TGGCCAGCCT TAACCTTGAC GGCTGCACCT
6201 TGTCCTTGTT CCGCGAAGAC AAGCCTTTCG GCCCCGGCAA GTTTCTCGGT
6251 GACTGATATG AAAGACCAAA AGGACAAGCA GACCGGCGAC CTGCTGGCCA
6301 GCCCTGACGC TGTACGCCAA GCGCGATATG CCGAGCGCAT GAAGGCCAAA
6351 GGGATGCGTC AGCGCAAGTT CTGGCTGACC GACGACGAAT ACGAGGCGCT
6401 GCGCGAGTGC CTGGAAGAAC TCAGAGCGGC GCAGGGCGGG GGTAGTGACC
6451 CCGCCAGCGC CTAACCACCA ACTGCCTGCA AAGGAGGCAA TCAATGGCTA
6501 CCCATAAGCC TATCAATATT CTGGAGGCGT TCGCAGCAGC GCCGCCACCG
6551 CTGGACTACG TTTTGCCCAA CATGGTGGCC GGTACGGTCG GGGCGCTGGT
6601 GTCGCCCGGT GGTGCCGGTA AATCCATGCT GGCCCTGCAA CTGGCCGCAC
6651 AGATTGCAGG CGGGCCGGAT CTGCTGGAGG TGGGCGAACT GCCCACCGGC
6701 CCGGTGATCT ACCTGCCCGC CGAAGACCCG CCCACCGCCA TTCATCACCG
6751 CCTGCACGCC CTTGGGGCGC ACCTCAGCGC CGAGGAACGG CAAGCCGTGG
6801 CTGACGGCCT GCTGATCCAG CCGCTGATCG GCAGCCTGCC CAACATCATG
```

Figure 31B(4)

```
6851 GCCCCGGAGT GGTTCGACGG CCTCAAGCGC GCCGCCGAGG GCCGCCGCCT
6901 GATGGTGCTG GACACGCTGC GCCGGTTCCA CATCGAGGAA GAAAACGCCA
6951 GCGGCCCCAT GGCCCAGGTC ATCGGTCGCA TGGAGGCCAT CGCCGCCGAT
7001 ACCGGGTGCT CTATCGTGTT CCTGCACCAT GCCAGCAAGG GCGCGGCCAT
7051 GATGGGCGCA GGCGACCAGC AGCAGGCCAG CCGGGGCAGC TCGGTACTGG
7101 TCGATAACAT CCGCTGGCAG TCCTACCTGT CGAGCATGAC CAGCGCCGAG
7151 GCCGAGGAAT GGGGTGTGGA CGACGACCAG CGCCGGTTCT TCGTCCGCTT
7201 CGGTGTGAGC AAGGCCAACT ATGGCGCACC GTTCGCTGAT CGGTGGTTCA
7251 GGCGGCATGA CGGCGGGGTG CTCAAGCCCG CCGTGCTGGA GAGGCAGCGC
7301 AAGAGCAAGG GGGTGCCCCG TGGTGAAGCC TAAGAACAAG CACAGCCTCA
7351 GCCACGTCCG GCACGACCCG GCGCACTGTC TGGCCCCCGG CCTGTTCCGT
7401 GCCCTCAAGC GGGGCGAGCG CAAGCGCAGC AAGCTGGACG TGACGTATGA
7451 CTACGGCGAC GGCAAGCGGA TCGAGTTCAG CGGCCCGGAG CCGCTGGGCG
7501 CTGATGATCT GCGCATCCTG CAAGGGCTGG TGGCCATGGC TGGGCCTAAT
7551 GGCCTAGTGC TTGGCCCGGA ACCCAAGACC GAAGGCGGAC GGCAGCTCCG
7601 GCTGTTCCTG GAACCCAAGT GGGAGGCCGT CACCGCTGAA TGCCATGTGG
7651 TCAAAGGTAG CTATCGGGCG CTGGCAAAGG AAATCGGGGC AGAGGTCGAT
7701 AGTGGTGGGG CGCTCAAGCA CATACAGGAC TGCATCGAGC GCCTTTGGAA
7751 GGTATCCATC ATCGCCCAGA ATGGCCGCAA GCGGCAGGGG TTTCGGCTGC
7801 TGTCGGAGTA CGCCAGCGAC GAGGCGGACG GGCGCCTGTA CGTGGCCCTG
7851 AACCCCTTGA TCGCGCAGGC CGTCATGGGT GGCGGCCAGC ATGTGCGCAT
7901 CAGCATGGAC GAGGTGCGGG CGCTGGACAG CGAAACCGCC CGCCTGCTGC
7951 ACCAGCGGCT GTGTGGCTGG ATCGACCCCG GCAAAACCGG CAAGGCTTCC
8001 ATAGATACCT TGTGCGGCTA TGTCTGGCCG TCAGAGGCCA GTGGTTCGAC
8051 CATGCGCAAG CGCCGCCAGC GGGTGCGCGA GGCGTTGCCG GAGCTGGTCG
8101 CGCTGGGCTG GACGGTAACC GAGTTCGCGG CGGGCAAGTA CGACATCACC
8151 CGGCCCAAGG CGGCAGGCTG ACCCCCCCCA CTCTATTGTA AACAAGACAT
8201 TTTTATCTTT TATATTCAAT GGCTTATTTT CCTGCTAATT GGTAATACCA
8251 TGAAAAATAC CATGCTCAGA AAAGGCTTAA CAATATTTTG AAAAATTGCC
8301 TACTGAGCGC TGCCGCACAG CTCCATAGGC CGCTTTCCTG GCTTTGCTTC
8351 CAGATGTATG CTCTTCTGCT CCTGCAGGTC GACTCTAGAG (SEQ ID NO:71)
```

Figure 31B(5)

```
   1  gcgcccaata cgcaaaccgc ctctccccgc gcgttggccg attcattaat
  51  gcagctggca cgacaggttt cccgactgga aagcgggcag tgagcgcaac
 101  gcaattaatg tgagttagct cactcattag gcacccagg ctttacactt
 151  tatgcttccg gctcgtatgt tgtgtggaat tgtgagcgga taacaatttc
 201  acacaggaaa cagctatgac catgattacg ccaagcttgc atgcctgcag
 251  gtcgactcta gaggatcccc gggtacccct catcggggc tgtgttggcc
 301  gagacggcac tgaggatttt actctccatg gcattccaag gaatatctac
 351  ccaactcacc tgctccggcg gattgttccg ctcaaaagta ctaatcaagt
 401  cgtcaaaata cttattaaat tttggctgca attgcatagt ccaaaagctg
 451  actttcccct ccatgctctg gggggaattg ctctggcaac tgattaatcc
 501  actgagcaac agcccaagac acgcaaacaa aaaccaacgt cttggcgatc
 551  gccatcggca ccatgaaacc atcgtaaaag ctggggaaag aataaaaaac
 601  agtggttcag gaattgcatt gccatggcca cttcacaaac ctagccaatt
 651  ttagcttgac cgcaactttg acagattgtc ttttgacttt gcctggaccg
 701  cctcccataa taccttcgcg tcttgaagac tttatccttg aaaggagaac
 751  atatgtttct cggcaaaaat taattatcga tatctagatc tcgagctcgc
 801  gaaagcttgg cactggccgt cgttttacaa cgtcgtgact gggaaaaccc
 851  tggcgttacc caacttaatc gccttgcagc acatccccct ttcgccagct
 901  ggcgtaatag cgaagaggcc cgcaccgatc gcccttccca acagttgcgc
 951  agcctgaatg gcgaatggcg cctgatgcgg tattttctcc ttacgcatct
1001  gtgcggtatt tcacaccgca tggtgcactc tcagtacaat ctgctctgat
1051  gccgcatagt taagccagcc ccgacacccg ccaacacccg ctgacgcgcc
1101  ctgacgggct tgtctgctcc cggcatccgc ttacagacaa gctgtgaccg
1151  tctccgggag ctgcatgtgt cagaggtttt caccgtcatc accgaaacgc
1201  gcgagacgaa agggcctcgt gatacgccta ttttatagg ttaatgtcat
1251  gataataatg gtttcttaga cgtcaggtgg cacttttcgg ggaaatgtgc
1301  gcggaacccc tatttgttta ttttctaaa tacattcaaa tatgtatccg
1351  ctcatgagac aataaccctg ataaatgctt caataatatt gaaaaggaa
```

Figure 32B(1)

```
1401  gagtatgagt attcaacatt tccgtgtcgc ccttattccc ttttttgcgg
1451  cattttgcct tcctgttttt gctcacccag aaacgctggt gaaagtaaaa
1501  gatgctgaag atcagttggg tgcacgagtg ggttacatcg aactggatct
1551  caacagcggt aagatccttg agagttttcg ccccgaagaa cgttttccaa
1601  tgatgagcac ttttaaagtt ctgctatgtg gcgcggtatt atcccgtatt
1651  gacgccgggc aagagcaact cggtcgccgc atacactatt ctcagaatga
1701  cttggttgag tactcaccag tcacagaaaa gcatcttacg gatggcatga
1751  cagtaagaga attatgcagt gctgccataa ccatgagtga taacactgcg
1801  gccaacttac ttctgacaac gatcggagga ccgaaggagc taaccgcttt
1851  tttgcacaac atggggatc atgtaactcg ccttgatcgt tgggaaccgg
1901  agctgaatga agccatacca aacgacgagc gtgacaccac gatgcctgta
1951  gcaatggcaa caacgttgcg caaactatta actggcgaac tacttactct
2001  agcttcccgg caacaattaa tagactggat ggaggcggat aaagttgcag
2051  gaccacttct gcgctcggcc cttccggctg gctggtttat tgctgataaa
2101  tctggagccg gtgagcgtgg gtctcgcggt atcattgcag cactggggcc
2151  agatggtaag ccctcccgta tcgtagttat ctacacgacg gggagtcagg
2201  caactatgga tgaacgaaat agacagatcg ctgagatagg tgcctcactg
2251  attaagcatt ggtaactgtc agaccaagtt tactcatata tactttagat
2301  tgatttaaaa cttcattttt aatttaaaag gatctaggtg aagatccttt
2351  ttgataatct catgaccaaa atcccttaac gtgagttttc gttccactga
2401  gcgtcagacc ccgtagaaaa gatcaaagga tcttcttgag atccttttt
2451  tctgcgcgta atctgctgct tgcaaacaaa aaaaccaccg ctaccagcgg
2501  tggtttgttt gccggatcaa gagctaccaa ctcttttcc gaaggtaact
2551  ggcttcagca gagcgcagat accaaatact gtccttctag tgtagccgta
2601  gttaggccac cacttcaaga actctgtagc accgcctaca tacctcgctc
2651  tgctaatcct gttaccagtg gctgctgcca gtggcgataa gtcgtgtctt
```

Figure 32B(2)

```
2701  accgggttgg actcaagacg atagttaccg gataaggcgc agcggtcggg
2751  ctgaacgggg ggttcgtgca cacagcccag cttggagcga acgacctaca
2801  ccgaactgag atacctacag cgtgagctat gagaaagcgc cacgcttccc
2851  gaagggagaa aggcggacag gtatccggta agcggcaggg tcggaacagg
2901  agagcgcacg agggagcttc caggggaaa cgcctggtat ctttatagtc
2951  ctgtcgggtt tcgccacctc tgacttgagc gtcgattttt gtgatgctcg
3001  tcaggggggc ggagcctatg gaaaaacgcc agcaacgcgg cctttttacg
3051  gttcctggcc ttttgctggc cttttgctca catgttcttt cctgcgttat
3101  cccctgattc tgtggataac cgtattaccg cctttgagtg agctgatacc
3151  gctcgccgca gccgaacgac cgagcgcagc gagtcagtga gcgaggaagc
3201  ggaaga (SEQ ID NO:72)
```

Figure 32B(3)

```
   1 ATGAATTCTT ATACTGTCGG TACCTATTTA GCGGAGCGGC TTGTCCAGAT
  51 TGGTCTCAAG CATCACTTCG CAGTCGCGGG CGACTACAAC CTCGTCCTTC
 101 TTGACAACCT GCTTTTGAAC AAAAACATGG AGCAGGTTTA TTGCTGTAAC
 151 GAACTGAACT GCGGTTTCAG TGCAGAAGGT TATGCTCGTG CCAAAGGCGC
 201 AGCAGCAGCC GTCGTTACCT ACAGCGTCGG TGCGCTTTCC GCATTTGATG
 251 CTATCGGTGG CGCCTATGCA GAAAACCTTC CGGTTATCCT GATCTCCGGT
 301 GCTCCGAACA CAATGATCA CGCTGCTGGT CACGTGTTGC ATCACGCTCT
 351 TGGCAAAACC GACTATCACT ATCAGTTGGA AATGGCCAAG AACATCACGG
 401 CCGCAGCTGA AGCGATTTAC ACCCCAGAAG AAGCTCCGGC TAAAATCGAT
 451 CACGTGATTA AAACTGCTCT TCGTGAGAAG AAGCCGGTTT ATCTCGAAAT
 501 CGCTTGCAAC ATTGCTTCCA TGCCCTGCGC CGCTCCTGGA CCGGCAAGCG
 551 CATTGTTCAA TGACGAAGCC AGCGACGAAG CTTCTTTGAA TGCAGCGGTT
 601 GAAGAAACCC TGAAATTCAT CGCCAACCGC GACAAAGTTG CCGTCCTCGT
 651 CGGCAGCAAG CTGCGCGCAG CTGGTGCTGA AGAAGCTGCT GTCAAATTTG
 701 CTGATGCTCT CGGTGGCGCA GTTGCTACCA TGGCTGCTGC AAAAAGCTTC
 751 TTCCCAGAAG AAAACCCGCA TTACATCGGT ACCTCATGGG GTGAAGTCAG
 801 CTATCCGGGC GTTGAAAAGA CGATGAAAGA AGCCGATGCG GTTATCGCTC
 851 TGGCTCCTGT CTTCAACGAC TACTCCACCA CTGGTTGGAC GGATATTCCT
 901 GATCCTAAGA AACTGGTTCT CGCTGAACCG CGTTCTGTCG TCGTTAACGG
 951 CGTTCGCTTC CCCAGCGTTC ATCTGAAAGA CTATCTGACC CGTTTGGCTC
1001 AGAAAGTTTC CAAGAAAACC GGTGCTTTGG ACTTCTTCAA ATCCCTCAAT
1051 GCAGGTGAAC TGAAGAAAGC CGCTCCGGCT GATCCGAGTG CTCCGTTGGT
1101 CAACGCAGAA ATCGCCCGTC AGGTCGAAGC TCTTCTGACC CCGAACACGA
1151 CGGTTATTGC TGAAACCGGT GACTCTTGGT TCAATGCTCA GCGCATGAAG
1201 CTCCCGAACG GTGCTCGCGT TGAATATGAA ATGCAGTGGG GTCACATCGG
1251 TTGGTCCGTT CCTGCCGCCT TCGGTTATGC CGTCGGTGCT CCGGAACGTC
1301 GCAACATCCT CATGGTTGGT GATGGTTCCT TCCAGCTGAC GGCTCAGGAA
1351 GTCGCTCAGA TGGTTCGCCT GAAACTGCCG GTTATCATCT TCTTGATCAA
1401 TAACTATGGT TACACCATCG AAGTTATGAT CCATGATGGT CCGTACAACA
1451 ACATCAAGAA CTGGGATTAT GCCGGTCTGA TGGAAGTGTT CAACGGTAAC
1501 GGTGGTTATG ACAGCGGTGC TGGTAAAGGC CTGAAGGCTA AAACCGGTGG
```

Figure 33D(1)

1551 CGAACTGGCA GAAGCTATCA AGGTTGCTCT GGCAAACACC GACGGCCCAA
1601 CCCTGATCGA ATGCTTCATC GGTCGTGAAG ACTGCACTGA AGAATTGGTC
1651 AAATGGGGTA AGCGCGTTGC TGCCGCCAAC AGCCGTAAGC CTGTTAACAA
1701 GCTCCTCTAG TTTTTGGGGA TCAATTCGAG CTCGGTACCC AAACTAGTAT
1751 GTAGGGTGAG GTTATAGCTA TGGCTTCTTC AACTTTTTAT ATTCCTTTCG
1801 TCAACGAAAT GGGCGAAGGT TCGCTTGAAA AAGCAATCAA GGATCTTAAC
1851 GGCAGCGGCT TTAAAAATGC GCTGATCGTT TCTGATGCTT TCATGAACAA
1901 ATCCGGTGTT GTGAAGCAGG TTGCTGACCT GTTGAAAGCA CAGGGTATTA
1951 ATTCTGCTGT TTATGATGGC GTTATGCCGA ACCCGACTGT TACCGCAGTT
2001 CTGGAAGGCC TTAAGATCCT GAAGGATAAC AATTCAGACT TCGTCATCTC
2051 CCTCGGTGGT GGTTCTCCCC ATGACTGCGC CAAAGCCATC GCTCTGGTCG
2101 CAACCAATGG TGGTGAAGTC AAAGACTACG AAGGTATCGA CAAATCTAAG
2151 AAACCTGCCC TGCCTTTGAT GTCAATCAAC ACGACGGCTG GTACGGCTTC
2201 TGAAATGACG CGTTTCTGCA TCATCACTGA TGAAGTCCGT CACGTTAAGA
2251 TGGCCATTGT TGACCGTCAC GTTACCCCGA TGGTTTCCGT CAACGATCCT
2301 CTGTTGATGG TTGGTATGCC AAAAGGCCTG ACCGCCGCCA CCGGTATGGA
2351 TGCTCTGACC CACGCATTTG AAGCTTATTC TTCAACGGCA GCTACTCCGA
2401 TCACCGATGC TTGCGCCTTG AAGGCTGCGT CCATGATCGC TAAGAATCTG
2451 AAGACCGCTT GCGACAACGG TAAGGATATG CCAGCTCGTG AAGCTATGGC
2501 TTATGCCCAA TTCCTCGCTG GTATGGCCTT CAACAACGCT TCGCTTGGTT
2551 ATGTCCATGC TATGGCTCAC CAGTTGGGCG GCTACTACAA CCTGCCGCAT
2601 GGTGTCTGCA ACGCTGTTCT GCTTCCGCAT GTTCTGGCTT ATAACGCCTC
2651 TGTCGTTGCT GGTCGTCTGA AGACGTTGG TGTTGCTATG GGTCTCGATA
2701 TCGCCAATCT CGGTGATAAA GAAGGCGCAG AAGCCACCAT TCAGGCTGTT
2751 CGCGATCTGG CTGCTTCCAT TGGTATTCCA GCAAATCTGA CCGAGCTGGG
2801 TGCTAAGAAA GAAGATGTGC CGCTTCTTGC TGACCACGCT CTGAAAGATG
2851 CTTGTGCTCT GACCAACCCG CGTCAGGGTG ATCAGAAAGA AGTTGAAGAA
2901 CTCTTCCTGA GCGCTTTCTA ATTTCAAAAC AGGAAAACGG TTTTCCGTCC
2951 TGTCTTGATT TTCAAGCAAA CAATGCCTCC GATTTCTAAT CGGAGGCATT
3001 TGTTTTTGTT TATTGCAAAA ACAAAAAATA TTGTTACAAA TTTTTACAGG
3051 CTATTAAGCC TACCGTCATA AATAATTTGC CATTTGGGGA TCC (SEQ ID NO:73)

Figure 33D(2)

 = translation start

 = translation stop

```
MNSYTVGTYLAERLVQIGLKHHFAVAGDYNLVLLDNLLLNKNMEQVYCCN  50
ELNCGFSAEGYARAKGAAAAVVTYSVGALSAFDAIGGAYAENLPVILISG 100
APNNNDHAAGHVLHHALGKTDYHYQLEMAKNITAAAEAIYTPEEAPAKID 150
HVIKTALREKKPVYLEIACNIASMPCAAPGPASALFNDEASDEASLNAAV 200
EETLKFIANRDKVAVLVGSKLRAAGAEEAAVKFADALGGAVATMAAAKSF 250
FPEENPHYIGTSWGEVSYPGVEKTMKEADAVIALAPVFNDYSTTGWTDIP 300
DPKKLVLAEPRSVVVNGVRFPSVHLKDYLTRLAQKVSKKTGALDFFKSLN 350
AGELKKAAPADPSAPLVNAEIARQVEALLTPNTTVIAETGDSWFNAQRMK 400
LPNGARVEYEMQWGHIGWSVPAAFGYAVGAPERRNILMVGDGSFQLTAQE 450
VAQMVRLKLPVIIFLINNYGYTIEVMIHDGPYNNIKNWDYAGLMEVFNGN 500
GGYDSGAGKGLKAKTGGELAEAIKVALANTDGPTLIECFIGREDCTEELV 550
KWGKRVAAANSRKPVNKLL (SEQ ID NO:74)
```

Figure 33F

```
MASSTFYIPFVNEMGEGSLEKAIKDLNGSGFKNALIVSDAFMNKSGVVKQ  50
VADLLKAQGINSAVYDGVMPNPTVTAVLEGLKILKDNNSDFVISLGGGSP 100
HDCAKAIALVATNGGEVKDYEGIDKSKKPALPLMSINTTAGTASEMTRFC 150
IITDEVRHVKMAIVDRHVTPMVSVNDPLLMVGMPKGLTAATGMDALTHAF 200
EAYSSTAATPITDACALKAASMIAKNLKTACDNGKDMPAREAMAYAQFLA 250
GMAFNNASLGYVHAMAHQLGGYYNLPHGVCNAVLLPHVLAYNASVVAGRL 300
KDVGVAMGLDIANLGDKEGAEATIQAVRDLAASIGIPANLTELGAKKEDV 350
PLLADHALKDACALTNPRQGDQKEVEELFLSAF (SEQ ID NO:75)
```

Figure 33G

```
GTCGAC
CTTCCAGCACCACGTCAACTTTGTTTAACTGCTCCCGGAGTTGTCTTTCCGCTTTGGCAA
TGTGCCCGGGATACCATTGGATTAAAGCCATGAGTTGTTCACTTTTTTACTGACGAGGGC
TTCCGGAGGCCACGCTCCCACCCATAACAGCTTGCCACATCCCCGTCGGAAGTTACGTTA
CCCTTGGGCGATCGCCAAAAATCAGCATATATACACCAATTCTAAATAAGATCTTTTACA
CCGCTACTGCAATCAACCTCATCAACAAAATTCCCCTCTAGCATCCCTGGAGGCAAATCC
TCACCTGGCCATGGGTTCAACCCTGCTTAACATTTCTTAATAATTTTAGTTGCTATAAAT
TCTCATTTATGCCCCTATAATAATTCGGGAGTAAGTGCTAAAGATTCTCAACTGCTCCAT
CAGTGGTTTGAGCTTAGTCCTAGGGAAAGATTGGCGATCGCCGTTGTGGTTAAGCCAGAA
TAGGTCTCGGGTGGACAGAGAACGCTTTATTCTTTGCCTCCATGGCGGCATCCCACCTAG
GTTTCTCGGCACTTATTGCCATAATTTATTATTTGTCGTCTCAATTAAGGAGGCAATTCT
GTGAATTC (SEQ ID NO:76)
```

Figure 34A

```
GTCGAC
TTATGGTTGATTCGCATTGTTTTGCTCCTGAAATTTTCGGCAAATACAAATACTTCGCTC
TTCTAGCCCTATTAACCATTTTAACGACAAATTGATGGGGCAACGATTAACAAATAATGA
ATAAATTTTATGTTTTTCAAGATGAAAATTTGAAAATTTGATTTCCTTATATTTCTACTA
TAGAAGACTAATACAATTAGATCTAAAATTTGCAAGTATAAAAATCAGCAAATAGTTATA
TTGTTAATAATTCAATGACCCAATAACTCGTACTGTTATCTACGTGGTGAAAGCCAAAAA
GACGAACAGTTTAGCCTCCTCCTCCTCGGCGATCGCCAAGCGAAATGTCATGGGAGATGT
TCAGATTGAGCATTTTTTCTAAAAGCCCTTGCTAAAACAAACCACATGTGCAGGGTGTC
CCCGATGTTGACTAAATTCAGCGGACTTAAAACCTATTTTTTCCCTGGGTTGCTAGGTTT
GCCCCCCGTTTTGGGCAAGCTTGTATAAGCAGATACTGTTAATTGGGTCAACTTTTTGTT
ACATTTATTTACAATTGATTGTTTACAATTGAAAGGTAGTCGCCTTGGAGGGCAACAGCT
ATGAATTC (SEQ ID NO:77)
```

Figure 34B

```
GTCGAC
AACGACGGAGGTTTAAGGGAAAAGTGACCATGGAAGCTATATCGAGATTAATTAAAGGGG
GGGGATCAACCAAGTTGCTGGACTGGAGCAGTGGGCAAGAAACCTGAGCTAATTCTAGGC
AATTTTGTTGCCATTGCCCCCAACGTAAAGTTATTTTTTTCTCCATTACCTTTTGTTACC
TAAAATTTAATGGAGCCAACCTAGGCTGGACCTTTTGTCACCGTTGCTCTGTCCACGGGA
TGGAGGATAATCTAAACGAAATCATTAGGGACCCTGACCATGCAAAAAGCCGACGAATTT
GCCATCCATCTGTTTTTGGCCAATGGCCATCGAGAGGAAGTCCGTTTCATGACCATTCAA
GATTTCCAAAAATGGTATAGCAACGAAGTTGTGCCCAAGCACGATTCCCAGGAATTTATC
AGTGTGCCTATCAGAAATATTCAGGGCGAGTACATGGTGGTGCGACCCTCGGCGATCGTT
GCCATTCGGGTGGAACCAATTTTCTTTGGCAGTGTGGAGCGCATGTAATCCGTTGTGTAT
AATCTTGATACAGAATGGGGTTTTGCACTTCCCTTGATGCCCCCATTACCGTGAACGTGC
ATGAATTC (SEQ ID NO:78)
```

Figure 34C

```
   1 GTCGACGAAT TTCTGCCATT CATCCGCTTA TTATCACTTA TTCAGGCGTA
  51 GCACCAGGCG TTTAAGGGCA CCAATAACTG CCTTAAAAAA ATTACGCCCC
 101 GCCCTGCCAC TCATCGCAGT ACTGTTGTAA TTCATTAAGC ATTCTGCCGA
 151 CATGGAAGCC ATCACAGACG GCATGATGAA CCTGAATCGC CAGCGGCATC
 201 AGCACCTTGT CGCCTTGCGT ATAATATTTG CCCATGGTGA AAACGGGGGC
 251 GAAGAAGTTG TCCATATTGG CCACGTTTAA ATCAAAACTG GTGAAACTCA
 301 CCCAGGGATT GGCTGAGACG AAAAACATAT TCTCAATAAA CCCTTTAGGG
 351 AAATAGGCCA GGTTTTCACC GTAACACGCC ACATCTTGCG AATATATGTG
 401 TAGAAACTGC CGGAAATCGT CGTGGTATTC ACTCCAGAGC GATGAAAACG
 451 TTTCAGTTTG CTCATGGAAA ACGGTGTAAC AAGGGTGAAC ACTATCCCAT
 501 ATCACCAGCT CACCGTCTTT CATTGCCATA CGGAATTCCG GATGAGCATT
 551 CATCAGGCGG GCAAGAATGT GAATAAAGGC CGGATAAAAC TTGTGCTTAT
 601 TTTTCTTTAC GGTCTTTAAA AAGGCCGTAA TATCCAGCTG AACGGTCTGG
 651 TTATAGGTAC ATTGAGCAAC TGACTGAAAT GCCTCAAAAT GTTCTTTACG
 701 ATGCCATTGG GATATATCAA CGGTGGTATA TCCAGTGATT TTTTTCTCCA
 751 TTTTAGCTTC CTTAGCTCCT GAAAATCTCG ATAACTCAAA AAATACGCCC
 801 GGTAGTGATC TTATTTCATT ATGGTGAAAG TTGGAACCTC TTACGTGCCG
 851 ATCAACGTCT CATTTTCGCC AAAAGTTGGC CCAGGGCTTC CCGGTATCAA
 901 CAGGGACACC AGGATTTATT TATTCTGCGA AGTGATCTTC CGTCACAGGT
 951 ATTTATTCGA AGACGAAAGG GCCTCGTGAT ACGCCTATTT TTATAGGTTA
1001 ATGTCATGAT AATAATGGTT TCTTAGACGT CAGGTGGCAC TTTTCGGGGA
1051 AATGTGCGCG GAACCCCTAT TTGTTTATTT TTCTAAATAC ATTCAAATAT
1101 GTATCCGCTC ATGAGACAAT AACCCTGATA AATGCTTCAA TAATATTGAA
1151 AAAGGAAGAG TATGAGTATT CAACATTTCC GTGTCGCCCT TATTCCCTTT
1201 TTTGCGGCAT TTTGCCTTCC TGTTTTTGCT CACCCAGAAA CGCTGGTGAA
1251 AGTAAAAGAT GCTGAAGATC AGTTGGGTGC ACGAGTGGGT TACATCGAAC
1301 TGGATCTCAA CAGCGGTAAG ATCCTTGAGA GTTTTCGCCC CGAAGAACGT
1351 TTTCCAATGA TGAGCACTTT TAAAGTTCTG CTATGTGGCG CGGTATTATC
1401 CCGTGTTGAC GCCGGGCAAG AGCAACTCGG TCGCCGCATA CACTATTCTC
1451 AGAATGACTT GGTTGAGTAC TCACCAGTCA CAGAAAAGCA TCTTACGGAT
1501 GGCATGACAG TAAGAGAATT ATGCAGTGCT GCCATAACCA TGAGTGATAA
1551 CACTGCGGCC AACTTACTTC TGACAACGAT CGGAGGACCG AAGGAGCTAA
1601 CCGCTTTTTT GCACAACATG GGGGATCATG TAACTCGCCT TGATCGTTGG
```

Figure 35A(1)

```
1651 GAACCGGAGC TGAATGAAGC CATACCAAAC GACGAGCGTG ACACCACGAT
1701 GCCTGCAGGA GCAGAAGAGC ATACATCTGG AAGCAAAGCC AGGAAAGCGG
1751 CCTATGGAGC TGTGCGGCAG CGCTCAGTAG GCAATTTTTC AAAATATTGT
1801 TAAGCCTTTT CTGAGCATGG TATTTTTCAT GGTATTACCA ATTAGCAGGA
1851 AAATAAGCCA TTGAATATAA AAGATAAAAA TGTCTTGTTT ACAATAGAGT
1901 GGGGGGGGTC AGCCTGCCGC CTTGGGCCGG GTGATGTCGT ACTTGCCCGC
1951 CGCGAACTCG GTTACCGTCC AGCCCAGCGC GACCAGCTCC GGCAACGCCT
2001 CGCGCACCCG CTGGCGGCGC TTGCGCATGG TCGAACCACT GGCCTCTGAC
2051 GGCCAGACAT AGCCGCACAA GGTATCTATG GAAGCCTTGC CGGTTTTGCC
2101 GGGGTCGATC CAGCCACACA GCCGCTGGTG CAGCAGGCGG GCGGTTTCGC
2151 TGTCCAGCGC CCGCACCTCG TCCATGCTGA TGCGCACATG CTGGCCGCCA
2201 CCCATGACGG CCTGCGCGAT CAAGGGGTTC AGGGCCACGT ACAGGCGCCC
2251 GTCCGCCTCG TCGCTGGCGT ACTCCGACAG CAGCCGAAAC CCCTGCCGCT
2301 TGCGGCCATT CTGGGCGATG ATGGATACCT TCCAAAGGCG CTCGATGCAG
2351 TCCTGTATGT GCTTGAGCGC CCCACCACTA TCGACCTCTG CCCCGATTTC
2401 CTTTGCCAGC GCCCGATAGC TACCTTTGAC CACATGGCAT TCAGCGGTGA
2451 CGGCCTCCCA CTTGGGTTCC AGGAACAGCC GGAGCTGCCG TCCGCCTTCG
2501 GTCTTGGGTT CCGGGCCAAG CACTAGGCCA TTAGGCCCAG CCATGGCCAC
2551 CAGCCCTTGC AGGATGCGCA GATCATCAGC GCCCAGCGGC TCCGGGCCGC
2601 TGAACTCGAT CCGCTTGCCG TCGCCGTAGT CATACGTCAC GTCCAGCTTG
2651 CTGCGCTTGC GCTCGCCCCG CTTGAGGGCA CGGAACAGGC CGGGGGCCAG
2701 ACAGTGCGCC GGGTCGTGCC GGACGTGGCT GAGGCTGTGC TTGTTCTTAG
2751 GCTTCACCAC GGGGCACCCC CTTGCTCTTG CGCTGCCTCT CCAGCACGGC
2801 GGGCTTGAGC ACCCCGCCGT CATGCCGCCT GAACCACCGA TCAGCGAACG
2851 GTGCGCCATA GTTGGCCTTG CTCACACCGA AGCGGACGAA GAACCGGCGC
2901 TGGTCGTCGT CCACACCCCA TTCCTCGGCC TCGGCGCTGG TCATGCTCGA
2951 CAGGTAGGAC TGCCAGCGGA TGTTATCGAC CAGTACCGAG CTGCCCCGGC
3001 TGGCCTGCTG CTGGTCGCCT GCGCCCATCA TGGCCGCGCC CTTGCTGGCA
3051 TGGTGCAGGA ACACGATAGA GCACCCGGTA TCGGCGGCGA TGGCCTCCAT
3101 GCGACCGATG ACCTGGGCCA TGGGGCCGCT GGCGTTTTCT TCCTCGATGT
3151 GGAACCGGCG CAGCGTGTCC AGCACCATCA GGCGGCGGCC CTCGGCGGCG
3201 CGCTTGAGGC CGTCGAACCA CTCCGGGGCC ATGATGTTGG GCAGGCTGCC
```

Figure 35A(2)

```
3251 GATCAGCGGC TGGATCAGCA GGCCGTCAGC CACGGCTTGC CGTTCCTCGG
3301 CGCTGAGGTG CGCCCCAAGG GCGTGCAGGC GGTGATGAAT GGCGGTGGGC
3351 GGGTCTTCGG CGGGCAGGTA GATCACCGGG CCGGTGGGCA GTTCGCCCAC
3401 CTCCAGCAGA TCCGGCCCGC CTGCAATCTG TGCGGCCAGT TGCAGGGCCA
3451 GCATGGATTT ACCGGCACCA CCGGGCGACA CCAGCGCCCC GACCGTACCG
3501 GCCACCATGT TGGGCAAAAC GTAGTCCAGC GGTGGCGGCG CTGCTGCGAA
3551 CGCCTCCAGA ATATTGATAG GCTTATGGGT AGCCATTGAT TGCCTCCTTT
3601 GCAGGCAGTT GGTGGTTAGG CGCTGGCGGG GTCACTACCC CCGCCCTGCG
3651 CCGCTCTGAG TTCTTCCAGG CACTCGCGCA GCGCCTCGTA TTCGTCGTCG
3701 GTCAGCCAGA ACTTGCGCTG ACGCATCCCT TTGGCCTTCA TGCGCTCGGC
3751 ATATCGCGCT TGGCGTACAG CGTCAGGGCT GGCCAGCAGG TCGCCGGTCT
3801 GCTTGTCCTT TTGGTCTTTC ATATCAGTCA CCGAGAAACT TGCCGGGGCC
3851 GAAAGGCTTG TCTTCGCGGA ACAAGGACAA GGTGCAGCCG TCAAGGTTAA
3901 GGCTGGCCAT ATCAGCGACT GAAAAGCGGC CAGCCTCGGC CTTGTTTGAC
3951 GTATAACCAA AGCCACCGGG CAACCAATAG CCCTTGTCAC TTTTGATCAG
4001 GTAGACCGAC CCTGAAGCGC TTTTTTCGTA TTCCATAAAA CCCCCTTCTG
4051 TGCGTGAGTA CTCATAGTAT AACAGGCGTG AGTACCAACG CAAGCACTAC
4101 ATGCTGAAAT CTGGCCCGCC CCTGTCCATG CCTCGCTGGC GGGGTGCCGG
4151 TGCCCGTGCC AGCTCGGCCC GCGCAAGCTG GACGCTGGGC AGACCCATGA
4201 CCTTGCTGAC GGTGCGCTCG ATGTAATCCG CTTCGTGGCC GGGCTTGCGC
4251 TCTGCCAGCG CTGGGCTGGC CTCGGCCATG GCCTTGCCGA TTTCCTCGGC
4301 ACTGCGGCCC CGGCTGGCCA GCTTCTGCGC GGCGATAAAG TCGCACTTGC
4351 TGAGGTCATC ACCGAAGCGC TTGACCAGCC CGGCCATCTC GCTGCGGTAC
4401 TCGTCCAGCG CCGTGCGCCG GTGGCGGCTA AGCTGCCGCT CGGGCAGTTC
4451 GAGGCTGGCC AGCCTGCGGG CCTTCTCCTG CTGCCGCTGG GCCTGCTCGA
4501 TCTGCTGGCC AGCCTGCTGC ACCAGCGCCG GGCCAGCGGT GGCGGTCTTG
4551 CCCTTGGATT CACGCAGCAG CACCCACGGC TGATAACCGG CGCGGGTGGT
4601 GTGCTTGTCC TTGCGGTTGG TGAAGCCCGC CAAGCGGCCA TAGTGGCGGC
4651 TGTCGGCGCT GGCCGGGTCG GCGTCGTACT CGCTGGCCAG CGTCCGGGCA
4701 ATCTGCCCCC GAAGTTCACC GCCTGCGGCG TCGGCCACCT TGACCCATGC
4751 CTGATAGTTC TTCGGGCTGG TTTCCACTAC CAGGGCAGGC TCCCGGCCCT
```

Figure 35A(3)

```
4801 CGGCTTTCAT GTCATCCAGG TCAAACTCGC TGAGGTCGTC CACCAGCACC
4851 AGACCATGCC GCTCCTGCTC GGCGGGCCTG ATATACACGT CATTGCCCTG
4901 GGCATTCATC CGCTTGAGCC ATGGCGTGTT CTGGAGCACT TCGGCGGCTG
4951 ACCATTCCCG GTTCATCATC TGGCCGGTGG TGGCGTCCCT GACGCCGATA
5001 TCGAAGCGCT CACAGCCCAT GGCCTTGAGC TGTCGGCCTA TGGCCTGCAA
5051 AGTCCTGTCG TTCTTCATCG GGCCACCAAG CGCAGCCAGA TCGAGCCGTC
5101 CTCGGTTGTC AGTGGCGTCA GGTCGAGCAA GAGCAACGAT GCGATCAGCA
5151 GCACCACCGT AGGCATCATG GAAGCCAGCA TCACGGTTAG CCATAGCTTC
5201 CAGTGCCACC CCCGCGACGC GCTCCGGGCG CTCTGCGCGG CGCTGCTCAC
5251 CTCGGCGGCT ACCTCCCGCA ACTCTTTGGC CAGCTCCACC CATGCCGCCC
5301 CTGTCTGGCG CTGGGCTTTC AGCCACTCCG CCGCCTGCGC CTCGCTGGCC
5351 TGCTGGGTCT GGCTCATGAC CTGCCGGGCT TCGTCGGCCA GTGTCGCCAT
5401 GCTCTGGGCC AGCGGTTCGA TCTGCTCCGC TAACTCGTTG ATGCCTCTGG
5451 ATTTCTTCAC TCTGTCGATT GCGTTCATGG TCTATTGCCT CCCGGTATTC
5501 CTGTAAGTCG ATGATCTGGG CGTTGGCGGT GTCGATGTTC AGGGCCACGT
5551 CTGCCCGGTC GGTGCGGATG CCCCGGCCTT CCATCTCCAC CACGTTCGGC
5601 CCCAGGTGAA CACCGGGCAG GCGCTCGATG CCCTGCGCCT CAAGTGTTCT
5651 GTGGTCAATG CGGGCGTCGT GGCCAGCCCG CTCTAATGCC CGGTTGGCAT
5701 GGTCGGCCCA TGCCTCGCGG GTCTGCTCAA GCCATGCCTT GGGCTTGAGC
5751 GCTTCGGTCT TCTGTGCCCC GCCCTTCTCC GGGGTCTTGC CGTTGTACCG
5801 CTTGAACCAC TGAGCGGCGG GCCGCTCGAT GCCGTCATTG ATCCGCTCGG
5851 AGATCATCAG GTGGCAGTGC GGGTTCTCGC CGCCACCGGC ATGGATGGCC
5901 AGCGTATACG GCAGGCGCTC GGCACCGGTC AGGTGCTGGG CGAACTCGGA
5951 CGCCAGCGCC TTCTGCTGGT CGAGGGTCAG CTCGACCGGC AGGGCAAATT
6001 CGACCTCCTT GAACAGCCGC CCATTGGCGC GTTCATACAG GTCGGCAGCA
6051 TCCCAGTAGT CGGCGGGCCG CTCGACGAAC TCCGGCATGT GCCCGGATTC
6101 GGCGTGCAAG ACTTCATCCA TGTCGCGGGC ATACTTGCCT TCGCGCTGGA
6151 TGTAGTCGGC CTTGGCCCTG GCCGATTGGC CGCCCGACCT GCTGCCGGTT
6201 TTCGCCGTAA GGTGATAAAT CGCCATGCTG CCTCGCTGTT GCTTTTGCTT
6251 TTCGGCTCCA TGCAATGGCC CTCGGAGAGC GCACCGCCCG AAGGGTGGCC
6301 GTTAGGCCAG TTTCTCGAAG AGAAACCGGT AAGTGCGCCC TCCCCTACAA
6351 AGTAGGGTCG GGATTGCCGC CGCTGTGCCT CCATGATAGC CTACGAGACA
6401 GCACATTAAC AATGGGGTGT CAAGATGGTT AAGGGGAGCA ACAAGGCGGC
6451 GGATCGGCTG GCCAAGCTCG AAGAACAACG AGCGCGAATC AATGCCGAAA
6501 TTCAGCGGGT GCGGGCAAGG GAACAGCAGC AAGAGCGCAA GAACGAAACA
```

Figure 35A(4)

```
6551 AGGCGCAAGG TGCTGGTGGG GGCCATGATT TTGGCCAAGG TGAACAGCAG
6601 CGAGTGGCCG GAGGATCGGC TCATGGCGGC AATGGATGCG TACCTTGAAC
6651 GCGACCACGA CCGCGCCTTG TTCGGTCTGC CGCCACGCCA GAAGGATGAG
6701 CCGGGCTGAA TGATCGACCG AGACAGGCCC TGCGGGGCTG CACACGCGCC
6751 CCCACCCTTC GGGTAGGGGG AAAGGCCGCT AAAGCGGCTA AAAGCGCTCC
6801 AGCGTATTTC TGCGGGGTTT GGTGTGGGGT TTAGCGGGCT TTGCCCGCCT
6851 TTCCCCCTGC CGCGCAGCGG TGGGCGGTG TGTAGCCTAG CGCAGCGAAT
6901 AGACCAGCTA TCCGGCCTCT GGCCGGGCAT ATTGGGCAAG GGCAGCAGCG
6951 CCCCACAAGG GCGCTGATAA CCGCGCCTAG TGGATTATTC TTAGATAATC
7001 ATGGATGGAT TTTTCCAACA CCCCGCCAGC CCCCGCCCCT GCTGGGTTTG
7051 CAGGTTTGGG GGCGTGACAG TTATTGCAGG GGTTCGTGAC AGTTATTGCA
7101 GGGGGGCGTG ACAGTTATTG CAGGGGTTCG TGACAGTTAG TACGGGAGTG
7151 ACGGGCACTG GCTGGCAATG TCTAGCAACG GCAGGCATTT CGGCTGAGGG
7201 TAAAAGAACT TTCCGCTAAG CGATAGACTG TATGTAAACA CAGTATTGCA
7251 AGGACGCGGA ACATGCCTCA TGTGGCGGCC AGGACGGCCA GCCGGGATCG
7301 GGATACTGGT CGTTACCAGA GCCACCGACC CGAGCAAACC CTTCTCTATC
7351 AGATCGTTGA CGAGTATTAC CCGGCATTCG CTGCGCTTAT GGCAGAGCAG
7401 GGAAAGGAAT TGCCGGGCTA TGTGCAACGG GAATTTGAAG AATTTCTCCA
7451 ATGCGGGCGG CTGGAGCATG GCTTTCTACG GGTTCGCTGC GAGTCTTGCC
7501 ACGCCGAGCA CCTGGTCGCT TTCAGCTGTA ATCCGGGCAG CGCAACGGAA
7551 CATTCATCAG TGTAAAAATG GAATCAATAA AGCCCTGCGC AGCGCGCAGG
7601 GTCAGCCTGA ATACGCGTTT AATGACCAGC ACAGTCGTGA TGGCAAGGTC
7651 AGAATAGCGC TGAGGTCTGC CTCGTGAAGA AGGTGTTGCT GACTCATACC
7701 AGGCCTGAAT CGCCCCATCA TCCAGCCAGA AAGTGAGGGA GCCACGGTTG
7751 ATGAGAGCTT TGTTGTAGGT GGACCAGTTG GTGATTTTGA ACTTTTGCTT
7801 TGCCACGGAA CGGTCTGCGT TGTCGGGAAG ATGCGTGATC TGATCCTTCA
7851 ACTCAGCAAA AGTTCGATTT ATTCAACAAA GCCACGTTGT GTCTCAAAAT
7901 CTCTGATGTT ACATTGCACA AGATAAAAAT ATATCATCAT GAACAATAAA
7951 ACTGTCTGCT TACATAAACA GTAATACAAG GGGTGTTATG AGCCATATTC
8001 AACGGGAAAC GTCTTGCTCG AGGCCGCGAT TAAATTCCAA CATGGATGCT
8051 GATTTATATG GGTATAAATG GGCTCGCGAT AATGTCGGGC AATCAGGTGC
8101 GACAATCTAT CGATTGTATG GGAAGCCCGA TGCGCCAGAG TTGTTTCTGA
```

Figure 35A(5)

```
8151 AACATGGCAA AGGTAGCGTT GCCAATGATG TTACAGATGA GATGGTCAGA
8201 CTAAACTGGC TGACGGAATT TATGCCTCTT CCGACCATCA AGCATTTTAT
8251 CCGTACTCCT GATGATGCAT GGTTACTCAC CACTGCGATC CCCGGGAAAA
8301 CAGCATTCCA GGTATTAGAA GAATATCCTG ATTCAGGTGA AAATATTGTT
8351 GATGCGCTGG CAGTGTTCCT GCGCCGGTTG CATTCGATTC CTGTTTGTAA
8401 TTGTCCTTTT AACAGCGATC GCGTATTTCG TCTCGCTCAG GCGCAATCAC
8451 GAATGAATAA CGGTTTGGTT GATGCGAGTG ATTTTGATGA CGAGCGTAAT
8501 GGCTGGCCTG TTGAACAAGT CTGGAAAGAA ATGCATAAGC TTTTGCCATT
8551 CTCACCGGAT TCAGTCGTCA CTCATGGTGA TTTCTCACTT GATAACCTTA
8601 TTTTTGACGA GGGGAAATTA ATAGGTTGTA TTGATGTTGG ACGAGTCGGA
8651 ATCGCAGACC GATACCAGGA TCTTGCCATC CTATGGAACT GCCTCGGTGA
8701 GTTTTCTCCT TCATTACAGA AACGGCTTTT TCAAAAATAT GGTATTGATA
8751 ATCCTGATAT GAATAAATTG CAGTTTCATT TGATGCTCGA TGAGTTTTTC
8801 TAATCAGAAT TGGTTAATTG GTTGTAACAC TGGCAGAGCA TTACGCTGAC
8851 TTGACGGGAC GGCGGCTTTG TTGAATAAAT CGAACTTTTG CTGAGTTGAA
8901 GGATCAGATC ACGCATCTTC CCGACAACGC AGACCGTTCC GTGGCAAAGC
8951 AAAAGTTCAA AATCACCAAC TGGTCCACCT ACAACAAAGC TCTCATCAAC
9001 CGTGGCTCCC TCACTTTCTG GCTGGATGAT GGGGCGATTC AGGCCTGGTA
9051 TGAGTCAGCA ACACCTTCTT CACGAGGCAG ACCTCAGCGC TATTCTGACC
9101 TTGCCATCAC GACTGTGCTG GTCATTAAAC GCGTATTCAG GCTGACCCTG
9151 CGCGCTGCGC AGGGCTTTAT TGATTCCATT TTTACACTGA TGAATGTTCC
9201 GTTGCGCTGC CCGGATTACA GATCCTCTAG ATCTAGAAGA ACAGCAAGGC
9251 CGCCAATGCC TGACGATGCG TGGAGACCGA AACCTTGCGC TCGTTCGCCA
9301 GCCAGGACAG AAATGCCTCG ACTTCGCTGC TGCCCAAGGT TGCCGGGTGA
9351 CGCACACCGT GGAAACGGAT GAAGGCACGA ACCCAGTGGA CATAAGCCTG
9401 TTCGGTTCGT AAGCTGTAAT GCAAGTAGCG TATGCGCTCA CGCAACTGGT
9451 CCAGAACCTT GACCGAACGC AGCGGTGGTA ACGGCGCAGT GGCGGTTTTC
9501 ATGGCTTGTT ATGACTGTTT TTTTGGGGTA CAGTCTATGC CTCGGGCATC
9551 CAAGCAGCAA GCGCGTTACG CCGTGGGTCG ATGTTTGATG TTATGGAGCA
9601 GCAACGATGT TACGCAGCAG GCAGTCGCC CTAAAACAAA GTTAAACATC
9651 ATGAGGGAAG CGGTGATCGC CGAAGTATCG ACTCAACTAT CAGAGGTAGT
9701 TGGCGTCATC GAGCGCCATC TCGAACCGAC GTTGCTGGCC GTACATTTGT
9751 ACGGCTCCGC AGTGGATGGC GGCCTGAAGC CACACAGTGA TATTGATTTG
9801 CTGGTTACGG TGACCGTAAG GCTTGATGAA ACAACGCGGC GAGCTTTGAT
9851 CAACGACCTT TTGGAAACTT CGGCTTCCCC TGGAGAGAGC GAGATTCTCC
```

Figure 35A(6)

```
9901  GCGCTGTAGA AGTCACCATT GTTGTGCACG ACGACATCAT TCCGTGGCGT
9951  TATCCAGCTA AGCGCGAACT GCAATTTGGA GAATGGCAGC GCAATGACAT
10001 TCTTGCAGGT ATCTTCGAGC CAGCCACGAT CGACATTGAT CTGGCTATCT
10051 TGCTGACAAA AGCAAGAGAA CATAGCGTTG CCTTGGTAGG TCCAGCGGCG
10101 GAGGAACTCT TTGATCCGGT TCCTGAACAG GATCTATTTG AGGCGCTAAA
10151 TGAAACCTTA ACGCTATGGA ACTCGCCGCC CGACTGGGCT GGCGATGAGC
10201 GAAATGTAGT GCTTACGTTG TCCCGCATTT GGTACAGCGC AGTAACCGGC
10251 AAAATCGCGC CGAAGGATGT CGCTGCCGAC TGGGCAATGG AGCGCCTGCC
10301 GGCCCAGTAT CAGCCCGTCA TACTTGAAGC TAGACAGGCT TATCTTGGAC
10351 AAGAAGAAGA TCGCTTGGCC TCGCGCGCAG ATCAGTTGGA AGAATTTGTC
10401 CACTACGTGA AAGGCGAGAT CACCAAGGTA GTCGGCAAAT AATGTCTAAC
10451 AATTCGTTCA AGCCGACGCC GCTTCGCGGC GCGGCTTAAC TCAAGCTCTA
10501 GA (SEQ ID NO:79)
```

Figure 35A (7)

GTCGACGGGAATTGCTCTGGCAACTGATTAATCCACTGAGCAACAG
CCCAAGACACGCAAACAAAAACCAACGTCTTGGCGATCGCCATCGGCACCATGAAACCAT
CGTAAAAGCTGGGGAAAGAATAAAAAACAGTGGTTCAGGAATTGCATTGCCATGGCCACT
TCACAAACCTAGCCAATTTTAGCTTGACCGCAACTTTGACAGATTGTCTTTTGACTTTGC
CTGGACCGCCTCCCATAATACCTTCGCGTCTTGAAGACTTTATCCTTGAAAGGAGAACTA
ATGAATTC (SEQ ID NO:80)

Figure 36A

GTCGACTGTCCGACCAATTGGTTCATCAAAGTTGATTTACCCACATTGGGACGGCCGACA
ATGGCCACAAAGCCGGAACGAAAACCCGCAGGAGCCTGGGGAATAGTTGCAATGGTTGCG
GTGGTGTTGGGAATATCCATTGAAAAAATCAAGCCTAAAAATTCCTTAGTTTATGGAGGG
TCAAGCGGAAAAACGTTAAAAACTCCACTGAGTTAATCAACCAGAGGAAAAAGTCAAGGA
GGTAAACTATCCGCCTGGAAAACGGCTTGCCAGCTTGACAAAAAAATATGTTGGGTTAAC
CCCACTGTGCCATTCGGTAATCCTTCATCTTGGCCCTTGTGGAATCCCTTAATGATTCGT
CATCATGGTGATATTGATTTTTTGGGTATCTTTTTAGCTATGCGGCTGTAGGAGCGTGGT
ATTGGTTTCGGCGGTAACGCCCCAGCCTAGAACCACAAAAATTATTATTTATTCCCGAAC
CTTGTCACCATTTGCGGCGTCTAAAGGCCCACTCGTTAGGACACGGTGTAAAAAAAATTG
ACGACTGCACTACCCTATTCTCCACCATCAATGACTTAGTCTAAGACATTTTTGGGAAAG
ATGAATTC (SEQ ID NO:81)

Figure 36C

```
                                    GTCGACGCTGATGTGACGGTTAAGGGAGGCGGA
ATTAAACTGGGTAAGGACGTAAATTTTAACGATTTCTGAGTTGATGCAATTACTGACGGG
AATATCGATGAGGCGATACTTTCCGGCCAAGGGAACTGCGGGTTTGGCTCTGAGTTTGGT
TAAAGGATAGAGGCGGGTCCCGGCCCCACCGCCCAGGATAATCGCTAAGACACGTTTCAC
AAGCAGACCTCTCGATTGCCAACAACACACTTCGAAGTCAAGTTTAGAACCGAGGGGGAC
ATCTGGAAAGGGAATCTGGACGGAAATTCCGGCTAACCAGCGGGTTTTAATGCCCCAAGC
AAGAATGGCGATCGCCGTTGGGATTCGGAGCTGAGTTGTCAGATCACTGTGGGGGTACGG
ATAACCGAAATGGCAAAGGTCGGAAACTGCCGCTGAGTAAACTGTCCCTGGCTTCGTATG
ATGATGGGGTTACCCCCATTGCTGGGGCGCTGGGCAAATCTGGGGAGCTGACTAGGTTCC
TGGAAGTTTTGCTAATCCACTAAATTTCCTAACAATCCTAAACATTAAATCTAAAGACCT
ATGAATTC (SEQ ID NO:82)
```

Figure 36E

```
                             GTCGACCCAACAACATTAGTCCGTCCTCCCGTTGGCGATCGC
GCTGTTTGGCTCTGACCCATCGCCGCTGATATTGCCAAGCTTGGCAGTAGGGCACAAGTC
CGAACGATAATAAACGACAGGAAGGATTGGCCATGGCGCTACAAAGGAAACGGAATCAAA
CTAAAGTTCAAAGTTGGCAGAAATTAAGAAACGTAAAGAGATGCAAAGGAAAGTCAAAAT
CACCTGACCGATTAGGTCTTATTCAATACATAGTGCTAATCTGAAGATAGTCTTAGGAGT
TAATTATTTACCACCACAATTTTCTGGAAAACTTTACCTCTACCCTAGGGATGATTAAAA
GTAAACTAGAGAATAACAAGGTTGGGTTTATAATTCATCACCAAGCTCAAATTTATGGTG
TTTTTTCAATGATCCATGCTTTTGATATCTTTAGCAGAAAGGCATTTTAAGTAATGATTC
CACCTCACTGTTTCTCGGAAAAATTGCCCAATCTAACTTAGTTTTTATAACTTAAGTTTA
GATCTGCGGAAAACCAACCATTGCTCATTTTTTATTAATTTTACGAAGGGAGAATTTAGT
ATGAATTC (SEQ ID NO:83)
```

Figure 36G

GTCGACAGAATCCTTGCCCAGATG
CAGGCCTTCTGGCGATCGCCATGGTGAGCAACGATTGCGGCTTTAGCGTTCCAGTGGATA
TTTGCTGGGGGTTAATGAAACATTGTGGCGGAACCCAGGGACAATGTGACCAAAAAATTC
AGGGATATCAATAAGTATTAGGTATATGGATCATAATTGTATGCCCGACTATTGCTTAAA
CTGACTGACCACTGACCTTAAGAGTAATGGCGTGCAAGGCCCAGTGATCAATTTCATTAT
TTTTCATTATTTCATCTCCATTGTCCCTGAAAATCAGTTGTGTCGCCCCTCTACACAGCC
CAGAACTATGGTAAAGGCGCACGAAAAACCGCCAGGTAAACTCTTCTCAACCCCCAAAAC
GCCCTCTGTTTACCCATGGAAAAAACGACAATTACAAGAAAGTAAAACTTATGTCATCTA
TAAGCTTCGTGTATATTAACTTCCTGTTACAAAGCTTTACAAAACTCTCATTAATCCTTT
AGACTAAGTTTAGTCAGTTCCAATCTGAACATCGACAAATACATAAGGAATTATAACCAA
ATGAATTC (SEQ ID NO:84)

Figure 36I

```
                                    GTCGACATCAGGAATTGTAATTAGA
AAGTCCAAAAATTGTAATTTAAAAAACAGTCAATGGAGAGCATTGCCATAAGTAAAGGCA
TCCCCTGCGTGATAAGATTACCTTCAGAAAACAGATAGTTGCTGGGTTATCGCAGATTTT
TCTCGCAACCAAATAACTGTAAATAATAACTGTCTCTGGGGCGACGGTAGGCTTTATATT
GCCAAATTTCGCCCGTGGGAGAAAGCTAGGCTATTCAATGTTTATGGAGGACTGACCTAG
ATGAATTC  (SEQ ID NO:85)
```

Figure 36K

```
GTCGACATTTCTTAAAATTAAAGCTGTTATAGCAACAACATTGATTAATTTCTATCTAAT
TTTTGACGGTGCCCATTGCTATCAGTTGTAAGTTGATGAAAATGCTGTAAATTTTTGTAA
CAAAGTTCAACTTTGTCTTGACTTTTGTAAGTCTTTGCAAAATCTAGGAGCTAGAACTGG
TCAGGGCTGGGGCAATTTTTAATTATTGTTACGCAGGTCTTGCCTAGGGGGGGGAGGCC
GTATTATCTTCTAGTGATGTTTGCTGAAAACGCCTATCTGTGCAAGGTTTAACATCGTTA
TTATGAAGCGAAAACTAATTCCCTTTTTTACGCTTCCTCTATTACACTATTCTGCATAGG
AAACCCTTAATAGTTCATTGTCGAGCGAGGAGAACCCTGCATGAATTC (SEQ ID NO:86)
```

Figure 36M

```
GTCGAC
AAAAAAACTGCAAAAATTATCCTGACTGAATGGAAGTCAAAAAGACTGGAAAATGGGATC
AAACAACAAGAAAAAATCAATTTACCCTGCCCATGGCAATAGTTTTAAGGTTAACAAAAA
AAATAGAATTTACCGCAATCGACGGGTAAATTTCCAGAGGATACCCCCAACTCCAGAAGC
AGAAATCTTGCCAGAAAAGCTTTTTCTGTTACTATACTTAACAAGTAACTACTTTTTCCA
TAGTCCAGGGGCGGCTTTCCAAAAACCAGAGATTGGTGGCTTGCCGCTGCTGTTCTCCTC
TGGAGTAAGGGGAAAAGGTAATTAGTGTTACGGCATTTTACTGACGGGTTAAGTAATCTT
TAACAAAGATTTATGAGCCGTTACCGTAATTGCCCCACAGGGGAACGCGATGTCTGTGG
ACTCGCCCAGGACGTAATCAATTTTTCTGTACCGATATTAGCGGTGAAAAGTTTTATTCA
ACGTACTAAAATGCCCCGGCGGGAATTAACTTGGGTTCCGGGAAGTCGGGTGCATTAGCC
GTACTAGACTAACCCAATAGTTACTTTGTTTGATTCTTGATTTTGGAGACCGCTGATTTT
ATGAATTC (SEQ ID NO:87)
```

Figure 36O

```
GTCGAC
GGAAAACAAGCTCAGAATGCTGCGGGGAGAAGGGCAACTCCCCACCAGCCCCAAATTTTT
GCTGGCGATAAATATTTTTCGGTTTAATTGTTCACAAAGCTTTTTGAATTTGAGTTTATA
GAAATTTATTGGCTGGTAATGCTTTTTTGCCCCCCTGCAGGACTTCATTGATCCTTGCCT
ATACCATCAATATCATTGGTCAATAATGATGATGATTGACTAAAACATGTTTAACAAAAT
TTAACGCATATGCTAAATGCGTAAACTGCATATGCCTTGGCTGAGTGTAATTTACGTTAC
AAATTTTAACGAAACGGGAACCCTATATTGATCTCTATCTGGCTTGAAGCGTTGTGAATTC
```

(SEQ ID NO:88)

Figure 36Q

```
GTCGACTTTTTTGCTGAGGTACTGAGTACACAGCTAATAAAATTGGGCAATCTCCGCGCC
TCTATGACTTGAAGGAGAGTGTAGGGGTATAGGGGAAAGATATCTTTTATCTACATCACA
TAAATAAAAAATTTAATTTGTCGCTCTGGCTGCATATATTGATGTATTTTTAGCCATAAG
TTTTTTAGTGCCATGTAATTATAGTGATTTTTAGCGATCGCAGAGCATTTTTCCCTGGAT
TTATCGCGATCTCAAAAAAAATTTGCCCGAAGTATGACAGATTGTCATATTTGGTGTCGA
TTTTATTTAAAATGAAATAAGAAAAATAAAACTACAGGTTAGGAGAACGCCATGAATTC
```

(SEQ ID NO:89)

Figure 36S

```
          GTCGACACAACCTAAGACTTCCTTCCAAAAATCCATAGGGCGGTGGAAGCTTAGCTATT
TTTACCATTTTGTTTTGCCACTCAAATATTTACTTAAGGTGAGGTAAAAACTCATCTTTT
TTTTACTAAAAATTGCGGCTAGAAATGTAATTTCGGCAATCCCCCCACCTTCTTTCCTGA
AAACCGAATCTAACCTGGAAGGGGAAATTTTAAGATAGAACCATTCAAGGGTAATCAATT
CCTTCCACACATCAGGAGTTAACATTATGAATTC (SEQ ID NO:90)
```

Figure 36U

```
          GTCGACGCACTTCTGGTCAGTTTATAGCAAAAATGCTGGGGAAAGGAAGACAACT
AGGGAAAAAGAACAGGACATCAAATGGTCATTCCCCAGACCCTGGCGTCTTTGCCAGAGT
AATCTCCCTGGCGCGGATGTTACACAAATGTAACGAAAAATATTTTCCCTCTCAGAATTT
AGGCAAAGTGCCCAAACCCATCCTAGGCAAGCAATTCGTCCACCAACAAAAAGCTCTTTT
GGTCAACAGACTTGACAAAAATCTTAACAATACGTTACATTTATTTACATAAGGTTACAA
AATAAAAACCTCAAATACCCAATCAAGGAGATCAACACTATGAATTC (SEQ ID NO:91)
```

Figure 36W

```
        GTCGACAAGATTAGCCCTTAGCTTACAAGAAAGGGGCTTTG
GGGCCTAGTTGAATGGCACAAATTTTCCTTCCCTGACTGTTTTTGCGCCATTGTCTAGCT
CAAAGTCAGCCTCCGGCATCCTCTAGAAAGACTTCCATCCCCTGGTTGAGCAAGGGTAAA
CCCCACCACTGCATTGGGAAAACCCTCCTTCCTAGCTCCGGATTCCACCCCCTAAAATTG
ATTTGGTAGTCCTTACACACCCAATAGCCAATATAGAAAATTTTATGAATTC (SEQ ID NO:92)
```

Figure 36Y

```
                                                         GAGCTCT
ATATCAACAAAAGGTAGTCACCATGTCAGCCGCAGATTTGTCGACTGACC
TCTATCTCTCCGAGATATATCAACAAAAGGTAGTCACCATGAAAGCAGCC
GTCATAACTAAAGATCATACGATCGAAGTGAAAGACACCAAATTACGCCC
TCTGAAATACGGGGAAGCGCTTTTGGAAATGGAATATTGCGGGGTATGTC
ATACCGATCTCCACGTGAAAAACGGGGATTTTGGCGATGAAACCGGCAGA
ATTACCGGCCATGAAGGCATCGGTATCGTCAAGCAGGTCGGGGAAGGGGT
TACTTCTCTGAAAGTCGGTGACCGTGCCAGTGTTGCATGGTTCTTCAAAG
GCTGCGGCCATTGCGAATATTGTGTCAGTGGAAATGAAACGCTTTGCCGC
AACGTTGAAAATGCCGGTTATACGGTTGACGGCGCTATGGCAGAAGAATG
CATCGTCGTTGCCGATTACTCGGTCAAAGTGCCAGATGGTCTTGATCCTG
CGGTTGCCAGCAGCATCACTTGCGCGGGTGTAACCACCTATAAAGCAGTC
AAAGTTTCTCAGATACAGCCGGGACAATGGCTGGCTATCTATGGCTTGGG
CGGTTTAGGCAATCTAGCCCTTCAATATGCCAAGAATGTTTTCAACGCCA
AAGTGATCGCGATCGATGTCAATGATGAACAGCTCGCTTTTGCCAAAGAG
CTGGGCGCAGATATGGTCATCAATCCGAAAAACGAAGATGCTGCCAAAAT
CATTCAGGAAAAGTCGGCGGCGCACATGCGACGGTGGTGACAGCTGTTG
CCAAATCCGCCTTTAACTCGGCTGTTGAGGCTATCCGCGCGGGTGGCCGT
GTTGTCGCCGTTGGTCTGCCTCCTGAAAAAATGGATTTGAGCATTCCTCG
CTTGGTGCTTGACGGTATCGAAGTCTTAGGTTCTTTGGTCGGAACGCGGG
AAGATTTGAAAGAAGCCTTCCAGTTTGCAGCCGAAGGTAAGGTCAAACCG
AAAGTCACCAAGCGTAAAGTCGAAGAAATCAACCAAATCTTTGACGAAAT
GGAACATGGTAAATTCACAGGCCGTATGGTTGTTGATTTTACCCATCACT
AGGTTTCCGTGAAGGCGGAAGCATAAACGGAAAAAGCCTTTCTCTTACCA
GAAAGGCTTTTTCTTTGTCGTCTGATAAAAATTTTCATACAGAATTTAAT
ACACTGCAG (SEQ ID NO:93)
```

Figure 37A

MKAAVITKDHTIEVKDTKLRPLKYGEALLEMEYCGVCHTDLHVKNGDFGD
ETGRITGHEGIGIVKQVGEGVTSLKVGDRASVAWFFKGCGHCEYCVSGNE
TLCRNVENAGYTVDGAMAEECIVVADYSVKVPDGLDPAVASSITCAGVTT
YKAVKVSQIQPGQWLAIYGLGGLGNLALQYAKNVFNAKVIAIDVNDEQLA
FAKELGADMVINPKNEDAAKIIQEKVGGAHATVVTAVAKSAFNSAVEAIR
AGGRVVAVGLPPEKMDLSIPRLVLDGIEVLGSLVGTREDLKEAFQFAAEG
KVKPKVTKRKVEEINQIFDEMEHGKFTGRMVVDFTHH (SEQ ID NO:94)

Figure 37B

```
                              GAGCTCTCTGGATAAAACTAATAAACTCTATTACCC
ATGATTAAAGCCTACGCTGCCCTGGAAGCCAACGGAAAACTCCAACCCTTTGAATACGAC
CCCGGTGCCCTGGGTGCTAATGAGGTGGAGATTGAGGTGCAGTATTGTGGGGTGTGCCAC
AGTGATTTGTCCATGATTAATAACGAATGGGGCATTTCCAATTACCCCCTAGTGCCGGGT
CATGAGGTGGTGGGTACTGTGGCCGCCATGGGCGAAGGGGTGAACCATGTTGAGGTGGGG
GATTTAGTGGGGCTGGGTTGGCATTCGGGCTACTGCATGACCTGCCATAGTTGTTTATCT
GGCTACCACAACCTTTGTGCCACGGCGGAATCGACCATTGTGGGCCACTACGGTGGCTTT
GGCGATCGGGTTCGGGCCAAGGGAGTCAGCGTGGTGAAATTACCTAAAGGCATTGACCTA
GCCAGTGCCGGGCCCCTTTTCTGTGGAGGAATTACCGTTTTCAGTCCTATGGTGGAACTG
AGTTTAAAGCCCACTGCAAAAGTGGCAGTGATCGGCATTGGGGGCTTGGGCCATTTAGCG
GTGCAATTTCTCCGGGCCTGGGGCTGTGAAGTGACTGCCTTTACCTCCAGTGCCAGGAAG
CAAACGGAAGTGTTGGAATTGGGCGCTCACCACATACTAGATTCCACCAATCCAGAGGCG
ATCGCCAGTGCGGAAGGCAAATTTGACTATATTATCTCCACTGTGAACCTGAAGCTTGAC
TGGAACTTATACATCAGCACCCTGGCGCCCCAGGGACATTTCCACTTTGTTGGGGTGGTG
TTGGAGCCTTTGGATCTAAATCTTTTTCCCCTTTTGATGGGACAACGCTCCGTTTCTGCC
TCCCCAGTGGGTAGTCCCGCCACCATTGCCACCATGTTGGACTTTGCTGTGCGCCATGAC
ATTAAACCCGTGGTGGAACAATTTAGCTTTGATCAGATCAACGAGGCGATCGCCCATCTA
GAAAGCGGCAAAGCCCATTATCGGGTAGTGCTCAGCCATAGTAAAAATTAGCTCTGCAAA
GGTTGCTTCTGGGTCCGTGGAATGGTCAAACGGAGTCGATCTCAGTTTTGATACGCTCTA
TCTGGAAAGCTTGACATTCGATCTGCAG (SEQ ID NO:95)
```

Figure 38A

```
MIKAYAALEANGKLQPFEYDPGALGANEVEIEVQYCGVCHSDLSMINNEWGISNYPLVPG
HEVVGTVAAMGEGVNHVEVGDLVGLGWHSGYCMTCHSCLSGYHNLCATAESTIVGHYGGF
GDRVRAKGVSVVKLPKGIDLASAGPLFCGGITVFSPMVELSLKPTAKVAVIGIGGLGHLA
VQFLRAWGCEVTAFTSSARKQTEVLELGAHHILDSTNPEAIASAEGKFDYIISTVNLKLD
WNLYISTLAPQGHFHFVGVVLEPLDLNLFPLLMGQRSVSASPVGSPATIATMLDFAVRHD
IKPVVEQFSFDQINEAIAHLESGKAHYRVVLSHSKN (SEQ ID NO:96)
```

Figure 38B

```
                                              ATGAAT
TCTGCTGTTACTAATGTCGCTGAACTTAACGCACTCGTAGAGCGTGTAAA
AAAAGCCCAGCGTGAATATGCCAGTTTCACTCAAGAGCAAGTAGACAAAA
TCTTCCGCGCCGCCGCTCTGGCTGCTGCAGATGCTCGAATCCCACTCGCG
AAAATGGCCGTTGCCGAATCCGGCATGGGTATCGTCGAAGATAAAGTGAT
CAAAAACCACTTTGCTTCTGAATATATCTACAACGCCTATAAAGATGAAA
AAACCTGTGGTGTTCTGTCTGAAGACGACACTTTTGGTACCATCACTATC
GCTGAACCAATCGGTATTATTTGCGGTATCGTTCCGACCACTAACCCGAC
TTCAACTGCTATCTTCAAATCGCTGATCAGTCTGAAGACCCGTAACGCCA
TTATCTTCTCCCCGCACCCGCGTGCAAAAGATGCCACCAACAAAGCGGCT
GATATCGTTCTGCAGGCTGCTATCGCTGCCGGTGCTCCGAAAGATCTGAT
CGGCTGGATCGATCAACCTTCTGTTGAACTGTCTAACGCACTGATGCACC
ACCCAGACATCAACCTGATCCTCGCGACTGGTGGTCCGGGCATGGTTAAA
GCCGCATACAGCTCCGGTAAACCAGCTATCGGTGTAGGCGCGGGCAACAC
TCCAGTTGTTATCGATGAAACTGCTGATATCAAACGTGCAGTTGCATCTG
TACTGATGTCCAAAACCTTCGACAACGGCGTAATCTGTGCTTCTGAACAG
TCTGTTGTTGTTGACTCTGTTTATGACGCTGTACGTGAACGTTTTGC
AACCCACGGCGGCTATCTGTTGCAGGGTAAAGAGCTGAAAGCTGTTCAGG
ATGTTATCCTGAAAAACGGTGCGCTGAACGCGGCTATCGTTGGTCAGCCA
GCCTATAAAATTGCTGAACTGGCAGGCTTCTCTGTACCAGAAAACACCAA
GATTCTGATCGGTGAAGTGACCGTTGTTGATGAAAGCGAACCGTTCGCAC
ATGAAAAACTGTCCCCGACTCTGGCAATGTACCGCGCTAAAGATTTCGAA
GACGCGGTAGAAAAGCAGAGAAACTGGTTGCTATGGGCGGTATCGGTCA
TACCTCTTGCCTGTACACTGACCAGGATAACCAACCGGCTCGCGTTTCTT
ACTTCGGTCAGAAAATGAAAACGGCGCGTATCCTGATTAACACCCCAGCG
TCTCAGGGTGGTATCGGTGACCTGTATAACTTCAAACTCGCACCTTCCCT
GACTCTGGGTTGTGGTTCTTGGGGTGGTAACTCCATCTCTGAAAACGTTG
GTCCGAAACACCTGATCAACAAGAAAACCGTTGCTAAGCGAGCTGAAAAC
ATGTTGTGGCACAAACTTCCGAAATCTATCTACTTCCGCCGTGGCTCCCT
GCCAATCGCGCTGGATGAAGTGATTACTGATGGCCACAAACGTGCGCTCA
TCGTGACTGACCGCTTCCTGTTCAACAATGGTTATGCTGATCAGATCACT
TCCGTACTGAAAGCAGCAGGCGTTGAAACTGAAGTCTTCTTCGAAGTAGA
AGCGGACCCGACCCTGAGCATCGTTCGTAAAGGTGCAGAACTGGCAAACT
CCTTCAAACCAGACGTGATTATCGCGCTGGGTGGTGGTTCCCCGATGGAC
```

Figure 39A(1)

```
GCCGCGAAGATCATGTGGGTTATGTACGAACATCCGGAAACTCACTTCGA
AGAGCTGGCGCTGCGCTTTATGGATATCCGTAAACGTATCTACAAGTTCC
CGAAAATGGGCGTGAAAGCGAAAATGATCGCTGTCACCACCACTTCTGGT
ACAGGTTCTGAAGTCACTCCGTTTGCGGTTGTAACTGACGACGCTACTGG
TCAGAAATATCCGCTGGCAGACTATGCGCTGACTCCGGATATGGCGATTG
TCGACGCCAACCTGGTTATGGACATGCCGAAGTCCCTGTGTGCTTTCGGT
GGTCTGGACGCAGTAACTCACGCCATGGAAGCTTATGTTTCTGTACTGGC
ATCTGAGTTCTCTGATGGTCAGGCTCTGCAGGCACTGAAACTGCTGAAAG
AATATCTGCCAGCGTCCTACCACGAAGGGTCTAAAAATCCGGTAGCGCGT
GAACGTGTTCACAGTGCAGCGACTATCGCGGGTATCGCGTTTGCGAACGC
CTTCCTGGGTGTATGTCACTCAATGGCGCACAAACTGGGTTCCCAGTTCC
ATATTCCGCACGGTCTGGCAAACGCCCTGCTGATTTGTAACGTTATTCGC
TACAATGCGAACGACAACCCGACCAAGCAGACTGCATTCAGCCAGTATGA
CCGTCCGCAGGCTCGCCGTCGTTATGCTGAAATTGCCGACCACTTGGGTC
TGAGCGCACCGGGCGACCGTACTGCTGCTAAGATCGAGAAACTGCTGGCA
TGGCTGGAAACGCTGAAAGCTGAACTGGGTATTCCGAAATCTATCCGTGA
AGCTGGCGTTCAGGAAGCAGACTTCCTGGCGAACGTGGATAAACTGTCTG
AAGATGCATTCGATGACCAGTGCACCGGCGCTAACCCGCGTTACCCGCTG
ATCTCCGAGCTGAAACAGATTCTGCTGGATACCTACTACGGTCGTGATTA
TGTAGAAGGTGAAACTGCAGCGAAGAAAGAAGCTGCTCCGGCTAAAGCTG
AGAAAAAAGCGAAAAAATCCGCTTAATCAGTAGCGCTGTCTGGCAACATA
AACGGCCCCTTCTGGGCAATGCCGATCAGTTAAGGATTAGTTGACCGATC
CTTAAACTGAGGCACTATAGGATCC (SEQ ID NO:97)
```

Figure 39A(2)

```
MNSAVTNVAELNALVERVKKAQREYASFTQEQVDKIFRAAALAAADARIP
LAKMAVAESGMGIVEDKVIKNHFASEYIYNAYKDEKTCGVLSEDDTFGTI
TIAEPIGIICGIVPTTNPTSTAIFKSLISLKTRNAIIFSPHPRAKDATNK
AADIVLQAAIAAGAPKDLIGWIDQPSVELSNALMHHPDINLILATGGPGM
VKAAYSSGKPAIGVGAGNTPVVIDETADIKRAVASVLMSKTFDNGVICAS
EQSVVVVDSVYDAVRERFATHGGYLLQGKELKAVQDVILKNGALNAAIVG
QPAYKIAELAGFSVPENTKILIGEVTVVDESEPFAHEKLSPTLAMYRAKD
FEDAVEKAEKLVAMGGIGHTSCLYTDQDNQPARVSYFGQKMKTARILINT
PASQGGIGDLYNFKLAPSLTLGCGSWGGNSISENVGPKHLINKKTVAKRA
ENMLWHKLPKSIYFRRGSLPIALDEVITDGHKRALIVTDRFLFNNGYADQ
ITSVLKAAGVETEVFFEVEADPTLSIVRKGAELANSFKPDVIIALGGGSP
MDAAKIMWVMYEHPETHFEELALRFMDIRKRIYKFPKMGVKAKMIAVTTT
SGTGSEVTPFAVVTDDATGQKYPLADYALTPDMAIVDANLVMDMPKSLCA
FGGLDAVTHAMEAYVSVLASEFSDGQALQALKLLKEYLPASYHEGSKNPV
ARERVHSAATIAGIAFANAFLGVCHSMAHKLGSQFHIPHGLANALLICNV
IRYNANDNPTKQTAFSQYDRPQARRRYAEIADHLGLSAPGDRTAAKIEKL
LAWLETLKAELGIPKSIREAGVQEADFLANVDKLSEDAFDDQCTGANPRY
PLISELKQILLDTYYGRDYVEGETAAKKEAAPAKAEKKAKKSA (SEQ ID NO:98)
```

Figure 39B

```
ATGAATTCCCCAACCTTGACCAGTGACCCCCCCGTTCAAAGCCTTGCCGATCTGGAAGGG
CTGATTGAGCGCGTCCAACGGGCGCAGAGTCAGTACGCCCAATTTACCCAAGAGCAAGTG
GATCACATTTTCCACGAAGCAGCCATGGCGGCCAACCAAGCCCGGATTCCCCTGGCCAAA
CAAGCCGTAGCCGAAACGGGCATGGGGGTTGTCGAAGATAAAGTTATTAAAAATCACTTT
GCTTCGGAATACATCTACAACAAGTACAAAAATGAGAAAACCTGCGGCGTCATTGAGGAT
GACCCCATCTTTGGTATCCAAAAAATTGCTGAACCGGTGGGGATCATTGCCGGTGTGGTG
CCGGTCACGAACCCCACTTCAACGACCATCTTTAAGGCACTGATTGCCCTGAAGACTCGC
AATGGCATTATCTTTTCGCCCCACCCCGGGCAAAGGCCTGTACGGTTGCAGCGGCCAAG
GTAGTGTTGGATGCAGCGGTCGCTGCCGGCGCACCCCCGATATTATTGGCTGGATTGAT
GAGCCGACGATTGAACTCTCCCAAGCCCTGATGCAGCACCCGCAGATCAAGCTGATTTTG
GCCACGGGGGGACCAGGTATGGTCAAGGCAGCCTATTCCTCTGGCCATCCGGCGATCGGG
GTCGGGGCCGGGAATACCCCGTGCTCATTGATGCCACAGCCGATATTCCCACGGCAGTG
AGTTCGATTCTCCTCAGTAAGGCCTTTGACAATGGCATGATCTGTGCCTCGGAGCAGGCA
GTGATTGTTGTGGATGAGATTTATGACGCACTTAAAGCTGAGTTTCAACGGCGAGGGGCC
TACCTTCTCTCCCCTGAGGAACGGCAGCAGGTGGCACAACTACTGCTGAAGGATGGTCGC
CTCAATGCCGCCATTGTTGGTCAATCGGCCGCCACCATTGCCGCAATGGCCAATATCCAA
GTACCGCCAGAAACCCGGGTACTCATTGGCGAGGTGAGTGAAGTGGGGCCGCAGGAGCCA
TTTTCCTATGAGAAACTCTGTCCGGTATTGGCGTTATATCGGGCACCCCAGTTCCATAAA
GGGGTGGAGATTGCGGCCCAGTTGGTGAATTTTGGGGGCAAGGGGCATACATCTGTGCTC
TATACCGATCCCCGCAATCAAGATGATATTGCCTATTTCAAATACCGCATGCAAACGGCG
CGGGTTCTGATTAACACCCCTTCTTCCCAGGGGGCAATTGGCGATCTCTACAACTTCAAG
TTAGATCCGTCGCTAACCCTTGGTTGTGGTACGTGGGGCGGCAACGTCACATCGGAAAAT
GTTGGTCCCCGTCACTTGCTGAATATTAAAACGGTGAGCGATCGCCGGGAAAATATGCTT
TGGTTTCGGGTGCCGCCCAAGATCTACTTCAAACCCGGCTGTTTGCCCATTGCCCTGCGG
GAGCTGGCGGGGAAAAAACGCGCCTTCCTCGTGACGGATAAACCCCTCTTTGACTTGGGG
ATCACTGAACCGATTGTCCATACCCTCGAAGAACTGGGCATCAAGTATGACATCTTCCAT
GAAGTGGAACCAGATCCAACCCTCAGTACCGTTAACCGCGGTCTAGGGTTGCTGCGGCAA
TATCAGCCGGATGTGATTGTTGCTGTGGGGGGTGGCTCACCTATGGATGCAGCCAAGGTG
ATGTGGCTGTTGTATGAGCATCCGGAGGTGGAGTTTGACGGCCTTGCGATGCGCTTCATG
GATATTCGCAAGCGGGTGTATCAACTGCCTCCCTTGGGTCAAAAGGCAATCCTGGTGGCT
ATTCCCACCACCTCGGGGACGGGTTCAGAGGTGACCCCCTTTGCCGTGGTTACCGACGAT
CGCGTGGGGATTAAATATCCCTTGGCAGACTATGCCCTTACGCCAACGATGGCGATTGTG
GATCCCGACTTGGTGCTGCACATGCCCAAGAAACTGACGGCCTACGGTGGCATTGATGCG
CTGACCCATGCCCTGGAGGCCTATGTGTCGGTGCTCTCGACGGAGTTTACGGAGGGACTG
```

Figure 40A(1)

```
GCTCTAGAGGCCATTAAACTGCTCTTTACCTACCTACCCCGTGCCTATCGCTTGGGGGCG
GCGGATCCGGAGGCACGGGAGAAGGTCCACTATGCGGCGACGATCGCTGGCATGGCCTTT
GCGAATGCCTTCTTGGGGGTCTGCCACTCGCTGGCCCACAAACTAGGCTCCACCTTCCAC
GTGCCCCACGGCTTGGCGAATGCACTCATGATTTCCCATGTGATTCGCTACAATGCCACG
GATGCTCCCCTGAAGCAGGCGATTTTCCCGCAGTACAAGTATCCCCAAGCGAAGGAGCGC
TATGCCCAAATTGCCGACTTCCTCGAATTGGGGGGCACGACCCCAGAGGAAAAAGTGGAG
CGTCTCATTGCGGCAATTGAGGATTTGAAAGCCCAATTAGAAATTCCCGCCACGATTAAG
GAGGCCCTCAACAGTGAGGATCAAGCGTTCTATGAGCAGGTGGAGAGCATGGCCGAACTG
GCCTTTGACGATCAGTGCACGGGGGCCAATCCCCGCTATCCGCTGATCCAAGACCTCAAG
GAGTTGTATATCCTGGCCTATATGGGGTGTCGGCGGGATGCGGCAGCCTACTATGGGGGG
GAGGCAACGGGGAGTTGATGTGGCGTTATATTCCCCCCTTTGCAGCTCCAGCGAAGGTGC
AAATGGCGGTGGATTCCTGGCTCTGGCAGCGGAGCGATCGCCTGCAG (SEQ ID NO:99)
```

Figure 40A(2)

```
MNSPTLTSDPPVQSLADLEGLIERVQRAQSQYAQFTQEQVDHIFHEAAMA
ANQARIPLAKQAVAETGMGVVEDKVIKNHFASEYIYNKYKNEKTCGVIED
DPIFGIQKIAEPVGIIAGVVPVTNPTSTTIFKALIALKTRNGIIFSPHPR
AKACTVAAAKVVLDAAVAAGAPPDIIGWIDEPTIELSQALMQHPQIKLIL
ATGGPGMVKAAYSSGHPAIGVGAGNTPVLIDATADIPTAVSSILLSKAFD
NGMICASEQAVIVVDEIYDALKAEFQRRGAYLLSPEERQQVAQLLLKDGR
LNAAIVGQSAATIAAMANIQVPPETRVLIGEVSEVGPQEPFSYEKLCPVL
ALYRAPQFHKGVEIAAQLVNFGGKGHTSVLYTDPRNQDDIAYFKYRMQTA
RVLINTPSSQGAIGDLYNFKLDPSLTLGCGTWGGNVTSENVGPRHLLNIK
TVSDRRENMLWFRVPPKIYFKPGCLPIALRELAGKKRAFLVTDKPLFDLG
ITEPIVHTLEELGIKYDIFHEVEPDPTLSTVNRGLGLLRQYQPDVIVAVG
GGSPMDAAKVMWLLYEHPEVEFDGLAMRFMDIRKRVYQLPPLGQKAILVA
IPTTSGTGSEVTPFAVVTDDRVGIKYPLADYALTPTMAIVDPDLVLHMPK
KLTAYGGIDALTHALEAYVSVLSTEFTEGLALEAIKLLFTYLPRAYRLGA
ADPEAREKVHYAATIAGMAFANAFLGVCHSLAHKLGSTFHVPHGLANALM
ISHVIRYNATDAPLKQAIFPQYKYPQAKERYAQIADFLELGGTTPEEKVE
RLIAAIEDLKAQLEIPATIKEALNSEDQAFYEQVESMAELAFDDQCTGAN
PRYPLIQDLKELYILAYMGCRRDAAAYYGGEATGS (SEQ ID NO:100)
```

Figure 40B

```
ATGAATTCCGTTGGTATGTACTTGGCAGAACGCCTAGCCCAGATCGGCCT
GAAACACCACTTTGCCGTGGCCGGTGACTACAACCTGGTGTTGCTTGATC
AGCTCCTGCTGAACAAAGACATGGAGCAGGTCTACTGCTGTAACGAACTT
AACTGCGGCTTTAGCGCCGAAGGTTACGCTCGTGCACGTGGTGCCGCCGC
TGCCATCGTCACGTTCAGCGTAGGTGCTATCTCTGCAATGAACGCCATCG
GTGGCGCCTATGCAGAAAACCTGCCGGTCATCCTGATCTCTGGCTCACCG
AACACCAATGACTACGGCACAGGCCACATCCTGCACCACACCATTGGTAC
TACTGACTATAACTATCAGCTGGAAATGGTAAAACACGTTACCTGCGCAC
GTGAAAGCATCGTTTCTGCCGAAGAAGCACCGGCAAAAATCGACCACGTC
ATCCGTACGGCTCTACGTGAACGCAAACCGGCTTATCTGGAAATCGCATG
CAACGTCGCTGGCGCTGAATGTGTTCGTCCGGGCCCGATCAATAGCCTGC
TGCGTGAACTCGAAGTTGACCAGACCAGTGTCACTGCCGCTGTAGATGCC
GCCGTAGAATGGCTGCAGGACCGCCAGAACGTCGTCATGCTGGTCGGTAG
CAAACTGCGTGCCGCTGCCGCTGAAAAACAGGCTGTTGCCCTAGCGGACC
GCCTGGGCTGCGCTGTCACGATCATGGCTGCCGAAAAAGGCTTCTTCCCG
GAAGATCATCCGAACTTCCGCGGCCTGTACTGGGGTGAAGTCAGCTCCGA
AGGTGCACAGGAACTGGTTGAAAACGCCGATGCCATCCTGTGTCTGGCAC
CGGTATTCAACGACTATGCTACCGTTGGCTGGAACTCCTGGCCGAAAGGC
GACAATGTCATGGTCATGGACACCGACCGCGTCACTTTCGCAGGACAGTC
CTTCGAAGGTCTGTCATTGAGCACCTTCGCCGCAGCACTGGCTGAGAAAG
CACCTTCTCGCCCGGCAACGACTCAAGGCACTCAAGCACCGGTACTGGGT
ATTGAGGCCGCAGAGCCCAATGCACCGCTGACCAATGACGAAATGACGCG
TCAGATCCAGTCGCTGATCACTTCCGACACTACTCTGACAGCAGAAACAG
GTGACTCTTGGTTCAACGCTTCTCGCATGCCGATTCCTGGCGGTGCTCGT
GTCGAACTGGAAATGCAATGGGGTCATATCGGTTGGTCCGTACCTTCTGC
ATTCGGTAACGCCGTTGGTTCTCCGGAGCGTCGCCACATCATGATGGTCG
GTGATGGCTCTTTCCAGCTGACTGCTCAAGAAGTTGCTCAGATGATCCGC
TATGAAATCCCGGTCATCATCTTCCTGATCAACAACCGCGGTTACGTCAT
CGAAATCGCTATCCATGACGGCCCTTACAACTACATCAAAAACTGGAACT
ACGCTGGCCTGATCGACGTCTTCAATGACGAAGATGGTCATGGCCTGGGT
CTGAAAGCTTCTACTGGTGCAGAACTAGAAGGCGCTATCAAGAAAGCACT
CGACAATCGTCGCGGTCCGACGCTGATCGAATGTAACATCGCTCAGGACG
ACTGCACTGAAACCCTGATTGCTTGGGGTAAACGTGTAGCAGCTACCAAC
TCTCGCAAACCACAAGCGTAAGTTGAGCTC (SEQ ID NO:101)
```

Figure 41A

MNSVGMYLAERLAQIGLKHHFAVAGDYNLVLLDQLLLNKDMEQVYCCNEL
NCGFSAEGYARARGAAAAIVTFSVGAISAMNAIGGAYAENLPVILISGSP
NTNDYGTGHILHHTIGTTDYNYQLEMVKHVTCARESIVSAEEAPAKIDHV
IRTALRERKPAYLEIACNVAGAECVRPGPINSLLRELEVDQTSVTAAVDA
AVEWLQDRQNVVMLVGSKLRAAAAEKQAVALADRLGCAVTIMAAEKGFFP
EDHPNFRGLYWGEVSSEGAQELVENADAILCLAPVFNDYATVGWNSWPKG
DNVMVMDTDRVTFAGQSFEGLSLSTFAAALAEKAPSRPATTQGTQAPVLG
IEAAEPNAPLTNDEMTRQIQSLITSDTTLTAETGDSWFNASRMPIPGGAR
VELEMQWGHIGWSVPSAFGNAVGSPERRHIMMVGDGSFQLTAQEVAQMIR
YEIPVIIFLINNRGYVIEIAIHDGPYNYIKNWNYAGLIDVFNDEDGHGLG
LKASTGAELEGAIKKALDNRRGPTLIECNIAQDDCTETLIAWGKRVAATN
SRKPQA (SEQ ID NO:102)

Figure 41B

```
   1 GTCGACATAT GTTTCTCGGC AAAAATTAAT TATCGATTGG CTGGAACCTG
  51 GTCAAACCAG GGCTTTTCAT CCATTGGAAA AGCGATTTTG ATCATCTAGG
 101 GTCAGGAGCA AAGATCTGAT CAAATATTGA TCATTTATTA GGAAAGCTGA
 151 ACTTTCACCA CTTTATTTTT GGCTTCCTCT ACTTTGGGCA AAGTCAAAGT
 201 TAGGATACCG GCATCGTAAT TAGCTTTAAC TTCTGTGTTT TGGATTGCTC
 251 CAGGTACAGG AATAACCCGG CGGAAACTGC CATAGCGGAA CTCTGTGCGC
 301 CGCACCCCAT CTTTTTCGGT GCTATGGGTA TCCTGGCGAT CGCCGCTGAC
 351 GGTCACCGCA TCCCTGGCGG CTTGGATGTC CAAATTATCG GGTCCATGC
 401 CAGGTAATTC TAGTTTGAGC ACATAGGCTT CTTCAGTTTC AGTTAGTTCT
 451 GCTTTAGGAT TAAACCCTTG GCGATCGCCG TGGCGGTCCG TAGGGACAAA
 501 AACTTCTTCA AACAGTTGGT TCATCTGCTG CTGGAAATTA TCCATTTCCC
 551 GCAGGGGATT GTAAAGAATG AGAGACATAA TGTTAACTCC TGATGTGTGG
 601 AAGGAATTGA TTACCCTTGA ATGGTTCTAT CTTAAAATTT CCCCTTCCAG
 651 GTTAGATTCG GTTTTCAGGA AAGAAGGTGG GGGGATTGCC GAAATTACAT
 701 TTCTAGCCGC AATTTTTAGT AAAAAAAAGA TGAGTTTTTA CCTCACCTTA
 751 AGTAAATATT TGAGTGGCAA AACAAAATGG TAAAAATAGC TAAGCTTCCA
 801 CCGCCCTATG GATTTTTGGA AGGAAGTCTT AGGTTGTGAA AAACTATAAA
 851 AACCAACCAT AGGAATGGAG ACCTTTACCC AACAAGTTGA CCCCTAGGTA
 901 ACAAATCCAA ACCACCGTAA AACCGCTGGC GGCCAAAATA GCGGGCTTGC
 951 GGCCTTGCCA ACCTTTGGTA ATGCGGGCAT GGAGATAGGC GGCAAATACT
1001 AGCCAGGTGA TTAGGGCCCG GTACCCAGCT TTTGTTCCCT TTAGTGAGGG
1051 TTAATTTCGA GCTTGGCGTA ATCATGGTCA TAGCTGTTTC CTGTGTGAAA
1101 TTGTTATCCG CTCACAATTC CACACAACAT ACGAGCCGGA AGCATAAAGT
1151 GTAAAGCCTG GGGTGCCTAA TGAGTGAGCT AACTCACATT AATTGCGTTG
1201 CGCTCACTGC CCGCTTTCCA GTCGGGAAAC CTGTCGTGCC AGCTGCATTA
1251 ATGAATCGGC CAACGCGCGG GGAGAGGCGG TTTGCGTATT GGGCGCTCTT
1301 CCGCTTCCTC GCTCACTGAC TCGCTGCGCT CGGTCGTTCG GCTGCGGCGA
1351 GCGGTATCAG CTCACTCAAA GGCGGTAATA CGGTTATCCA CAGAATCAGG
1401 GGATAACGCA GGAAAGAACA TGTGAGCAAA AGGCCAGCAA AAGGCCAGGA
1451 ACCGTAAAAA GGCCGCGTTG CTGGCGTTTT TCCATAGGCT CCGCCCCCCT
1501 GACGAGCATC ACAAAAATCG ACGCTCAAGT CAGAGGTGGC GAAACCCGAC
1551 AGGACTATAA AGATACCAGG CGTTTCCCCC TGGAAGCTCC CTCGTGCGCT
```

Figure 42A(1)

```
1601 CTCCTGTTCC GACCCTGCCG CTTACCGGAT ACCTGTCCGC CTTTCTCCCT
1651 TCGGGAAGCG TGGCGCTTTC TCATAGCTCA CGCTGTAGGT ATCTCAGTTC
1701 GGTGTAGGTC GTTCGCTCCA AGCTGGGCTG TGTGCACGAA CCCCCCGTTC
1751 AGCCCGACCG CTGCGCCTTA TCCGGTAACT ATCGTCTTGA GTCCAACCCG
1801 GTAAGACACG ACTTATCGCC ACTGGCAGCA GCCACTGGTA ACAGGATTAG
1851 CAGAGCGAGG TATGTAGGCG GTGCTACAGA GTTCTTGAAG TGGTGGCCTA
1901 ACTACGGCTA CACTAGAAGG ACAGTATTTG GTATCTGCGC TCTGCTGAAG
1951 CCAGTTACCT TCGGAAAAAG AGTTGGTAGC TCTTGATCCG GCAAACAAAC
2001 CACCGCTGGT AGCGGTGGTT TTTTGTTTG CAAGCAGCAG ATTACGCGCA
2051 GAAAAAAGG ATCTCAAGAA GATCCTTTGA TCTTTTCTAC GGGGTCTGAC
2101 GCTCAGTGGA ACGAAAACTC ACGTTAAGGG ATTTTGGTCA TGAGATTATC
2151 AAAAAGGATC TTCACCTAGA TCCTTTTAAA TTAAAAATGA AGTTTTAAAT
2201 CAATCTAAAG TATATATGAG TAAACTTGGT CTGACAGTTA CCAATGCTTA
2251 ATCAGTGAGG CACCTATCTC AGCGATCTGT CTATTTCGTT CATCCATAGT
2301 TGCCTGACTC CCCGTCGTGT AGATAACTAC GATACGGGAG GGCTTACCAT
2351 CTGGCCCCAG TGCTGCAATG ATACCGCGAG ACCCACGCTC ACCGGCTCCA
2401 GATTTATCAG CAATAAACCA GCCAGCCGGA AGGGCCGAGC GCAGAAGTGG
2451 TCCTGCAACT TTATCCGCCT CCATCCAGTC TATTAATTGT TGCCGGGAAG
2501 CTAGAGTAAG TAGTTCGCCA GTTAATAGTT TGCGCAACGT TGTTGCCATT
2551 GCTACAGGCA TCGTGGTGTC ACGCTCGTCG TTTGGTATGG CTTCATTCAG
2601 CTCCGGTTCC CAACGATCAA GGCGAGTTAC ATGATCCCCC ATGTTGTGCA
2651 AAAAGCGGT TAGCTCCTTC GGTCCTCCGA TCGTTGTCAG AAGTAAGTTG
2701 GCCGCAGTGT TATCACTCAT GGTTATGGCA GCACTGCATA ATTCTCTTAC
2751 TGTCATGCCA TCCGTAAGAT GCTTTTCTGT GACTGGTGAG TACTCAACCA
2801 AGTCATTCTG AGAATAGTGT ATGCGGCGAC CGAGTTGCTC TTGCCCGGCG
2851 TCAATACGGG ATAATACCGC GCCACATAGC AGAACTTTAA AAGTGCTCAT
2901 CATTGGAAAA CGTTCTTCGG GGCGAAAACT CTCAAGGATC TTACCGCTGT
2951 TGAGATCCAG TTCGATGTAA CCCACTCGTG CACCCAACTG ATCTTCAGCA
3001 TCTTTTACTT TCACCAGCGT TTCTGGGTGA GCAAAAACAG GAAGGCAAAA
3051 TGCCGCAAAA AAGGGAATAA GGGCGACACG GAAATGTTGA ATACTCATAC
3101 TCTTCCTTTT TCAATATTAT TGAAGCATTT ATCAGGGTTA TTGTCTCATG
3151 AGCGGATACA TATTTGAATG TATTTAGAAA AATAAACAAA TAGGGGTTCC
3201 GCGCACATTT CCCCGAAAAG TGCCACCTAA ATTGTAAGCG TTAATATTTT
3251 GTTAAAATTC GCGTTAAATT TTTGTTAAAT CAGCTCATTT TTTAACCAAT
3301 AGGCCGAAAT CGGCAAAATC CCTTATAAAT CAAAAGAATA GACCGAGATA
3351 GGGTTGAGTG TTGTTCCAGT TTGGAACAAG AGTCCACTAT TAAAGAACGT
```

Figure 42A(2)

```
3401 GGACTCCAAC GTCAAAGGGC GAAAAACCGT CTATCAGGGC GATGGCCCAC
3451 TACGTGAACC ATCACCCTAA TCAAGTTTTT TGGGGTCGAG GTGCCGTAAA
3501 GCACTAAATC GGAACCCTAA AGGGAGCCCC CGATTTAGAG CTTGACGGGG
3551 AAAGCCGGCG AACGTGGCGA GAAAGGAAGG GAAGAAAGCG AAAGGAGCGG
3601 GCGCTAGGGC GCTGGCAAGT GTAGCGGTCA CGCTGCGCGT AACCACCACA
3651 CCCGCCGCGC TTAATGCGCC GCTACAGGGC GCGTCCCATT CGCCATTCAG
3701 GCTGCGCAAC TGTTGGGAAG GGCGATCGGT GCGGGCCTCT TCGCTATTAC
3751 GCCAGCTGGC GAAAGGGGGA TGTGCTGCAA GGCGATTAAG TTGGGTAACG
3801 CCAGGGTTTT CCCAGTCACG ACGTTGTAAA ACGACGGCCA GTGAATTGTA
3851 ATACGACTCA CTATAGGGCG AATTGGAGGC CAGTGCTGGA GGAATATGAT
3901 TTTGTCATCC TCGACTGTGC CCCTGGTTAT AATCTGTTGA CCCGCAGTGG
3951 CATTGCGGCC AGCGACTTTT ATCTGTTGCC GGCTCGTCCT GAACCCCTAT
4001 CGGTGGTGGG GATGCAGTTA CTGGAAAGAA GAATTGAGAA ACTGAAGGAA
4051 AGCCATAAGG CCTCCGATGA TCCCCTGAAT ATCAATCTGA TCGGAGTGGT
4101 GTTTATTCTG TCCGGCGGCG GTTTGATGAG TCGCTACTAT AACCAGGTAA
4151 TGCGGCGGGT ACAAACGGAT TTCACCCCGG GACAACTTTT TCAGCAGTCC
4201 ATTCCCATGG ATGTCAATGT GGCTAAGGCA GTGGATAGCT TTATGCCGGT
4251 GGTTACCTCC ATGCCCAATA CGGCGGGTTC AAAAGCTTTT ATTAAATTAA
4301 CCCAGGAATT TTTACAGAAA GTAGAAGCTT TTGGCTAAAG CAAAGCCCCC
4351 ATTGATTAAC AACGGGAGGG GTACCGAGGT GCTGCTGAAG TTGCCCGCAA
4401 CAGAGAGTGG AACCAACCGG TAGTGCATCT AACGCTTGAG TTAAGCCGCG
4451 CCGCGAAGCG GCGTCGGCTT GAACGAATTG TTAGACATTA TTTGCCGACT
4501 ACCTTGGTGA TCTCGCCTTT CACGTAGTGG ACAAATTCTT CCAACTGATC
4551 TGCGCGCGAG GCCAAGCGAT CTTCTTCTTG TCCAAGATAA GCCTGTCTAG
4601 CTTCAAGTAT GACGGGCTGA TACTGGGCCG GCAGGCGCTC CATTGCCCAG
4651 TCGGCAGCGA CATCCTTCGG CGCGATTTTG CCGGTTACTG CGCTGTACCA
4701 AATGCGGGAC AACGTAAGCA CTACATTTCG CTCATCGCCA GCCCAGTCGG
4751 GCGGCGAGTT CCATAGCGTT AAGGTTTCAT TTAGCGCCTC AAATAGATCC
4801 TGTTCAGGAA CCGGATCAAA GAGTTCCTCC GCCGCTGGAC CTACCAAGGC
4851 AACGCTATGT TCTCTTGCTT TTGTCAGCAA GATAGCCAGA TCAATGTCGA
4901 TCGTGGCTGG CTCGAAGATA CCTGCAAGAA TGTCATTGCG CTGCCATTCT
4951 CCAAATTGCA GTTCGCGCTT AGCTGGATAA CGCCACGGAA TGATGTCGTC
5001 GTGCACAACA ATGGTGACTT CTACAGCGCG GAGAATCTCG CTCTCTCCAG
5051 GGGAAGCCGA AGTTTCCAAA AGGTCGTTGA TCAAAGCTCG CCGCGTTGTT
5101 TCATCAAGCC TTACGGTCAC CGTAACCAGC AAATCAATAT CACTGTGTGG
5151 CTTCAGGCCG CCATCCACTG CGGAGCCGTA CAAATGTACG GCCAGCAACG
```

Figure 42A(3)

```
5201 TCGGTTCGAG ATGGCGCTCG ATGACGCCAA CTACCTCTGA TAGTTGAGTC
5251 GATACTTCGG CGATCACCGC TTCCCTCATG ATGTTTAACT TTGTTTTAGG
5301 GCGACTGCCC TGCTGCGTAA CATCGTTGCT GCTCCATAAC ATCAAACATC
5351 GACCCACGGC GTAACGCGCT TGCTGCTTGG ATGCCCGAGG CATAGACTGT
5401 ACCCCAAAAA AACAGTCATA ACAAGCCATG AAAACCGCCA CTGCGCCGTT
5451 ACCACCGCTG CGTTCGGTCA AGGTTCTGGA CCAGTTGCGT GAGCGCATAC
5501 GCTACTTGCA TTACAGCTTA CGAACCGAAC AGGCTTATGT CCACTGGGTT
5551 CGTGCCTTCA TCCGTTTCCA CGGTGTGCGT CACCCGGCAA CCTTGGGCAG
5601 CAGCGAAGTC GAGGCATTTC TGTCCTGGCT GGCGAACGAG CGCAAGGTTT
5651 CGGTCTCCAC GCATCGTCAG GCATTGGCGG CCTTGCTGTT CTTCTAGACA
5701 AGGCTGCAGT T (SEQ ID NO:103)
```

Figure 42A(4)

```
GTCGACTCTAGAAAGATGCCACTAGCACCAGACGACTAGTTAGCGATAGTCTATCCACCAT
TGTTCGTTTTGTAGGTTTTGCTTTTATAGCGATCGGTTTTGTATTTTGCGGTAACTTCATC
AATTTTTAGGGGCTGGTAATTTTTAACATATCTCACGGGGTGCAATCTTCGCGCCCCTAC
TAGTCCATCGAATCGTCATTTCCAACTATTAATATTAAAGTTTAGAGAAATTGGATTATAT
GTAACCTGTACTCTGTTAAGATTCACCATTGGGGTATTCGCTATCAGTCTTGGCGCTACTG
CCCATCCCGCCCCTCAAACCTTTGTCCGTCCGCCTAAGACTGATACCGCTACTGGTGACAG
GCCGATGTTATATCTGGAGTTCTATGAATTC (SEQ ID NO:104)
```

Figure 42R

GTCGACTTTTTTGCTGAGGTACTGAGTACACAGCTAATAAAATTGGGCAATCTCCGCGCCT
CTATGACTTGAAGGAGAGTGTAGGGGTATAGGGGAAAGATATCTTTTATCTACATCACATA
AATAAAAAATTTAATTTGTCGCTCTGGCTGCATATATTGATGTATTTTTAGCCATAAGTTT
TTTAGTGCCATGTAATTATAGTGATTTTTAGCGATCGCAGAGCATTTTTCCCTGGATTTAT
CGCGATCTCAAAAAAATTTGCCCGAAGTATGACAGATTGTCATATTTGGTGTCGATTTTA
TTTAAAATGAAATAAGAAAAATAAAACTACAGGTTAGGAGAACGCCATGAATTC (SEQ ID NO:105)

Figure 42S

```
   1 ATCGATAATT AATTTTTGCC GAGAAACATA TGTCGACTTT TTTGCTGAGG
  51 TACTGAGTAC ACAGCTAATA AAATTGGGCA ATCTCCGCGC CTCTATGACT
 101 TGAAGGAGAG TGTAGGGGTA TAGGGGAAAG ATATCTTTTA TCTACATCAC
 151 ATAAATAAAA AATTTAATTT GTCGCTCTGG CTGCATATAT TGATGTATTT
 201 TTAGCCATAA GTTTTTTAGT GCCATGTAAT TATAGTGATT TTTAGCGATC
 251 GCAGAGCATT TTTCCCTGGA TTTATCGCGA TCTCAAAAAA AATTTGCCCG
 301 AAGTATGACA GATTGTCATA TTTGGTGTCG ATTTTATTTA AAATGAAATA
 351 AGAAAAATAA AACTACAGGT TAGGAGAACG CCATGAATTC TTATACTGTC
 401 GGTACCTATT TAGCGGAGCG GCTTGTCCAG ATTGGTCTCA AGCATCACTT
 451 CGCAGTCGCG GGCGACTACA ACCTCGTCCT TCTTGACAAC CTGCTTTTGA
 501 ACAAAAACAT GGAGCAGGTT TATTGCTGTA ACGAACTGAA CTGCGGTTTC
 551 AGTGCAGAAG GTTATGCTCG TGCCAAAGGC GCAGCAGCAG CCGTCGTTAC
 601 CTACAGCGTC GGTGCGCTTT CCGCATTTGA TGCTATCGGT GGCGCCTATG
 651 CAGAAAACCT TCCGGTTATC CTGATCTCCG GTGCTCCGAA CAACAATGAT
 701 CACGCTGCTG GTCACGTGTT GCATCACGCT CTTGGCAAAA CCGACTATCA
 751 CTATCAGTTG GAAATGGCCA AGAACATCAC GGCCGCAGCT GAAGCGATTT
 801 ACACCCCAGA AGAAGCTCCG GCTAAAATCG ATCACGTGAT TAAAACTGCT
 851 CTTCGTGAGA AGAAGCCGGT TTATCTCGAA ATCGCTTGCA ACATTGCTTC
 901 CATGCCCTGC GCCGCTCCTG GACCGGCAAG CGCATTGTTC AATGACGAAG
 951 CCAGCGACGA AGCTTCTTTG AATGCAGCGG TTGAAGAAAC CCTGAAATTC
1001 ATCGCCAACC GCGACAAAGT TGCCGTCCTC GTCGGCAGCA AGCTGCGCGC
1051 AGCTGGTGCT GAAGAAGCTG CTGTCAAATT TGCTGATGCT CTCGGTGGCG
1101 CAGTTGCTAC CATGGCTGCT GCAAAAAGCT TCTTCCCAGA AGAAAACCCG
1151 CATTACATCG GTACCTCATG GGGTGAAGTC AGCTATCCGG GCGTTGAAAA
1201 GACGATGAAA GAAGCCGATG CGGTTATCGC TCTGGCTCCT GTCTTCAACG
1251 ACTACTCCAC CACTGGTTGG ACGGATATTC CTGATCCTAA GAAACTGGTT
1301 CTCGCTGAAC CGCGTTCTGT CGTCGTTAAC GGCGTTCGCT TCCCCAGCGT
1351 TCATCTGAAA GACTATCTGA CCCGTTTGGC TCAGAAAGTT CCAAGAAAA
1401 CCGGTGCTTT GGACTTCTTC AAATCCCTCA ATGCAGGTGA ACTGAAGAAA
1451 GCCGCTCCGG CTGATCCGAG TGCTCCGTTG GTCAACGCAG AAATCGCCCG
```

Figure 42U(1)

```
1501 TCAGGTCGAA GCTCTTCTGA CCCCGAACAC GACGGTTATT GCTGAAACCG
1551 GTGACTCTTG GTTCAATGCT CAGCGCATGA AGCTCCCGAA CGGTGCTCGC
1601 GTTGAATATG AAATGCAGTG GGGTCACATC GGTTGGTCCG TTCCTGCCGC
1651 CTTCGGTTAT GCCGTCGGTG CTCCGGAACG TCGCAACATC CTCATGGTTG
1701 GTGATGGTTC CTTCCAGCTG ACGGCTCAGG AAGTCGCTCA GATGGTTCGC
1751 CTGAAACTGC CGGTTATCAT CTTCTTGATC AATAACTATG GTTACACCAT
1801 CGAAGTTATG ATCCATGATG GTCCGTACAA CAACATCAAG AACTGGGATT
1851 ATGCCGGTCT GATGGAAGTG TTCAACGGTA ACGGTGGTTA TGACAGCGGT
1901 GCTGGTAAAG GCCTGAAGGC TAAAACCGGT GGCGAACTGG CAGAAGCTAT
1951 CAAGGTTGCT CTGGCAAACA CCGACGGCCC AACCCTGATC GAATGCTTCA
2001 TCGGTCGTGA AGACTGCACT GAAGAATTGG TCAAATGGGG TAAGCGCGTT
2051 GCTGCCGCCA ACAGCCGTAA GCCTGTTAAC AAGCTCCTCT AGTTTTTGGG
2101 GATCAATTCG AGCTCGGTAC CCAAACTAGT ATGTAGGGTG AGGTTATAGC
2151 TATGGCTTCT TCAACTTTTT ATATTCCTTT CGTCAACGAA ATGGGCGAAG
2201 GTTCGCTTGA AAAAGCAATC AAGGATCTTA ACGGCAGCGG CTTTAAAAAT
2251 GCGCTGATCG TTTCTGATGC TTTCATGAAC AAATCCGGTG TTGTGAAGCA
2301 GGTTGCTGAC CTGTTGAAAG CACAGGGTAT TAATTCTGCT GTTTATGATG
2351 GCGTTATGCC GAACCCGACT GTTACCGCAG TTCTGGAAGG CCTTAAGATC
2401 CTGAAGGATA ACAATTCAGA CTTCGTCATC TCCCTCGGTG GTGGTTCTCC
2451 CCATGACTGC GCCAAAGCCA TCGCTCTGGT CGCAACCAAT GGTGGTGAAG
2501 TCAAAGACTA CGAAGGTATC GACAAATCTA AGAAACCTGC CCTGCCTTTG
2551 ATGTCAATCA ACACGACGGC TGGTACGGCT TCTGAAATGA CGCGTTTCTG
2601 CATCATCACT GATGAAGTCC GTCACGTTAA GATGGCCATT GTTGACCGTC
2651 ACGTTACCCC GATGGTTTCC GTCAACGATC CTCTGTTGAT GGTTGGTATG
2701 CCAAAAGGCC TGACCGCCGC CACCGGTATG GATGCTCTGA CCCACGCATT
2751 TGAAGCTTAT TCTTCAACGG CAGCTACTCC GATCACCGAT GCTTGCGCCT
2801 TGAAGGCTGC GTCCATGATC GCTAAGAATC TGAAGACCGC TTGCGACAAC
2851 GGTAAGGATA TGCCAGCTCG TGAAGCTATG GCTTATGCCC AATTCCTCGC
2901 TGGTATGGCC TTCAACAACG CTTCGCTTGG TTATGTCCAT GCTATGGCTC
```

```
2951 ACCAGTTGGG CGGCTACTAC AACCTGCCGC ATGGTGTCTG CAACGCTGTT
3001 CTGCTTCCGC ATGTTCTGGC TTATAACGCC TCTGTCGTTG CTGGTCGTCT
3051 GAAAGACGTT GGTGTTGCTA TGGGTCTCGA TATCGCCAAT CTCGGTGATA
3101 AAGAAGGCGC AGAAGCCACC ATTCAGGCTG TTCGCGATCT GGCTGCTTCC
3151 ATTGGTATTC CAGCAAATCT GACCGAGCTG GGTGCTAAGA AAGAAGATGT
3201 GCCGCTTCTT GCTGACCACG CTCTGAAAGA TGCTTGTGCT CTGACCAACC
3251 CGCGTCAGGG TGATCAGAAA GAAGTTGAAG AACTCTTCCT GAGCGCTTTC
3301 TAATTTCAAA ACAGGAAAAC GGTTTTCCGT CCTGTCTTGA TTTTCAAGCA
3351 AACAATGCCT CCGATTTCTA ATCGGAGGCA TTTGTTTTTG TTTATTGCAA
3401 AAACAAAAAA TATTGTTACA AATTTTTACA GGCTATTAAG CCTACCGTCA
3451 TAAATAATTT GCCATTTGGG GATCCCGGTA GAGGGAAACC GTTGTGGTCT
3501 CCCTATAGTG AGTCGTATTA ATTTCGCGGG ATCGAGATCC TTTTTGATAA
3551 TCTCATGACC AAAATCCCTT AACGTGAGTT TTCGTTCCAC TGAGCGTCAG
3601 ACCCCGTAGA AAAGATCAAA GGATCTTCTT GAGATCCTTT TTTTCTGCGC
3651 GTAATCTGCT GCTTGCAAAC AAAAAAACCA CCGCTACCAG CGGTGGTTTG
3701 TTTGCCGGAT CAAGAGCTAC CAACTCTTTT TCCGAAGGTA ACTGGCTTCA
3751 GCAGAGCGCA GATACCAAAT ACTGTCCTTC TAGTGTAGCC GTAGTTAGGC
3801 CACCACTTCA AGAACTCTGT AGCACCGCCT ACATACCTCG CTCTGCTAAT
3851 CCTGTTACCA GTGGCTGCTG CCAGTGGCGA TAAGTCGTGT CTTACCGGGT
3901 TGGACTCAAG ACGATAGTTA CCGGATAAGG CGCAGCGGTC GGGCTGAACG
3951 GGGGGTTCGT GCACACAGCC CAGCTTGGAG CGAACGACCT ACACCGAACT
4001 GAGATACCTA CAGCGTGAGC ATTGAGAAAG CGCCACGCTT CCCGAAGGGA
4051 GAAAGGCGGA CAGGTATCCG GTAAGCGGCA GGGTCGGAAC AGGAGAGCGC
4101 ACGAGGGAGC TTCCAGGGGG AAACGCCTGG TATCTTTATA GTCCTGTCGG
4151 GTTTCGCCAC CTCTGACTTG AGCGTCGATT TTTGTGATGC TCGTCAGGGG
4201 GGCGGAGCCT ATGGAAAAAC GCCAGCAACG CGGCCTTTTT ACGGTTCCTG
4251 GCCTTTTGCT GGCCTTTTGC TCACATGTTC TTTCCTGCGT TATCCCCTGA
4301 TTCTGTGGAT AACCGTATTA CCGCCTTTGA GTGAGCTGAT ACCGCTCGCC
4351 GCAGCCGAAC GACCGAGCGC AGCGAGTCAG TGAGCGAGGA AGCGGAAGAG
4401 CGCCTGATGC GGTATTTTCT CCTTACGCAT CTGTGCGGTA TTTCACACCG
```

Figure 42U(3)

```
4451 CATATGGTGC ACTCTCAGTA CAATCTGCTC TGATGCCGCA TAGTTAAGCC
4501 AGTATACACT CCGCTATCGC TACGTGACTG GGTCATGGCT GCGCCCCGAC
4551 ACCCGCCAAC ACCCGCTGAC GCGCCCTGAC GGGCTTGTCT GCTCCCGGCA
4601 TCCGCTTACA GACAAGCTGT GACCGTCTCC GGGAGCTGCA TGTGTCAGAG
4651 GTTTTCACCG TCATCACCGA AACGCGCGAG GCAGCTGCGG TAAAGCTCAT
4701 CAGCGTGGTC GTGAAGCGAT TCACAGATGT CTGCCTGTTC ATCCGCGTCC
4751 AGCTCGTTGA GTTTCTCCAG AAGCGTTAAT GTCTGGCTTC TGATAAAGCG
4801 GGCCTGCCAC CATACCCACG CCGAAACAAG CGCTCATGAG CCCGAAGTGG
4851 CGAGCCCGAT CTTCCCCATC GGTGATGTCG GCGATATCCT CGTGATGATC
4901 AGTGATGGAA AAAGCACTGT AATTCCCTTG GTTTTTGGCT GAAAGTTTCG
4951 GACTCAGTAG ACCTAAGTAC AGAGTGATGT CAACGCCTTC AAGCTAGACG
5001 GGAGGCGGCT TTTGCCATGG TTCAGCGATC GCTCCTCATC TTCAATAAGC
5051 AGGGCATGAG CCAGCGTTAA GCAAATCAAA TCAAATCTCG CTTCTGGGCT
5101 TCAATAAATG GTTCCGATTG ATGATAGGTT GATTCATGCA AGCTTGGAGC
5151 ACAGGATGAC GCCTAACAAT TCATTCAAGC CGACACCGCT TCGCGGCGCG
5201 GCTTAATTCA GGAGTTAAAC ATCATGAGGG AAGCGGTGAT CGCCGAAGTA
5251 TCGACTCAAC TATCAGAGGT AGTTGGCGTC ATCGAGCGCC ATCTCGAACC
5301 GACGTTGCTG GCCGTACATT TGTACGGCTC CGCAGTGGAT GGCGGCCTGA
5351 AGCCACACAG TGATATTGAT TTGCTGGTTA CGGTGACCGT AAGGCTTGAT
5401 GAAACAACGC GGCGAGCTTT GATCAACGAC CTTTTGGAAA CTTCGGCTTC
5451 CCCTGGAGAG AGCGAGATTC TCCGCGCTGT AGAAGTCACC ATTGTTGTGC
5501 ACGACGACAT CATTCCGTGG CGTTATCCAG CTAAGCGCGA ACTGCAATTT
5551 GGAGAATGGC AGCGCAATGA CATTCTTGCA GGTATCTTCG AGCCAGCCAC
5601 GATCGACATT GATCTGGCTA TCTTGCTGAC AAAAGCAAGA GAACATAGCG
5651 TTGCCTTGGT AGGTCCAGCG GCGGAGGAAC TCTTTGATCC GGTTCCTGAA
5701 CAGGATCTAT TTGAGGCGCT AAATGAAACC TTAACGCTAT GGAACTCGCC
5751 GCCCGACTGG GCTGGCGATG AGCGAAATGT AGTGCTTACG TTGTCCCGCA
5801 TTTGGTACAG CGCAGTAACC GGCAAAATCG CGCCGAAGGA TGTCGCTGCC
5851 GACTGGGCAA TGGAGCGCCT GCCGGCCCAG TATCAGCCCG TCATACTTGA
```

Figure 42U(4)

```
5901 AGCTAGGCAG GCTTATCTTG GACAAGAAGA TCGCTTGGCC TCGCGCGCAG
5951 ATCAGTTGGA AGAATTTGTT CACTACGTGA AAGGCGAGAT CACCAAGGTA
6001 GTCGGCAAAT AATGTCTAAC AATTCGTTCA AGCCGACGCC GCTTCGCGGC
6051 GCGGCTTAAC TCAAGCGTTA GAGAGCTGGG GAAGACTATG CGCGATCTGT
6101 TGAAGGTGGT TCTAAGCCTC GTACTTGCGA TGGCATCGGG GCAGGCACTT
6151 GCTGACCTGC CAATTGTTTT AGTGGATGAA GCTCGTCTTC CCTATGACTA
6201 CTCCCCATCC AACTACGACA TTTCTCCAAG CAACTACGAC AACTCCATAA
6251 GCAATTACGA CAATAGTCCA TCAAATTACG ACAACTCTGA GAGCAACTAC
6301 GATAATAGTT CATCCAATTA CGACAATAGT CGCAACGGAA ATCGTAGGCT
6351 TATATATAGC GCAAATGGGT CTCGCACTTT CGCCGGCTAC TACGTCATTG
6401 CCAACAATGG GACAACGAAC TTCTTTTCCA CATCTGGCAA AAGGATGTTC
6451 TACACCCCAA AAGGGGGGCG CGGCGTCTAT GGCGGCAAAG ATGGGAGCTT
6501 CTGCGGGGCA TTGGTCGTCA TAAATGGCCA ATTTTCGCTT GCCCTGACAG
6551 ATAACGGCCT GAAGATCATG TATCTAAGCA ACTAGCCTGC TCTCTAATAA
6601 AATGTTAGGC CTCAACATCT AGTCGCAAGC TGAGGGAAC CACTAGCAGC
6651 ACGCCATAGT GACTGGCGAT GCTGTCGGAA TGGACGATAT CTAGACTTAT
6701 ATAGACACTA ATATAGACAA TAGTTTATAC TGCTATCTAT ACAAGTATAG
6751 ACATTATCTA ATCATGGCAG ACAAAACTCT AGCCACTTTT CGTATTGACT
6801 CCGAAGAATG GGAGTCTTTT AAAAACCTTG CTAGTTCTGA AAGTTCCAAC
6851 GCCTCAGCAC TGTTAACAGA ATTTGTTCGT TGGTATTTGG CAGGTAACAG
6901 GTTTAATACT CCCACTTCTC ACACTCCCAC CCATCTAGAC ACATCCCTCG
6951 AACAGCGTAT AGACAATATT GAACAACGTC TAGATAAAGT CACAACTAAT
7001 AATCTAGACA ATATAGATGA ATTTATAGAC AAGCGTATAG AAGATAATCT
7051 AGCAACACGT CTAGACAAAC TTCAATCGCA ACTGGAGGAA CTGCGGGGAA
7101 AATCGAAAGC CCGGTAGTTC AGGCAGAAGG ACAAGCTACC GGGCAAGACA
7151 GAAAGAATAT AGACAATAGT ATAGACAATC TAGACAAATT GGAGGCAACC
7201 CGCGATCGCA CCCTCAATAA GCTAAAAATG GGTAGGCAGT CAGCCGCCGG
7251 GAAAGCCATC GACGCGTTTA TCAAAGAGTT GCTTTCTTCA GGAGACAACA
7301 TAAGCTGAAG TTATCAAAAT TCTGTCCTTA CGTCGAAAGC CTGATTTTAC
```

Figure 42U(5)

```
7351 CGTGCAACGA TTGATAAGCT TGGCTAAACT AGCACTGGCT TTCAACAGAA
7401 AGCATACGAA GAATCAATAG ATATAGCCAC CAATTCCACA AAATGCAGAT
7451 AACGTGTAGA GTATTGGAAT GCTTAATCTG TAAGGGTTAT GAAGGTTAAC
7501 GGCAACGGAC GAGCCAAAAT ACTCACCTCC GACGAACTCA GGCGACTGTT
7551 TAGCGACGGA TTCACCACAC CGCGCGATCG CGTTTTGTTT GGCATCTGTC
7601 TATTCACCGG TTGCCGCGTT AGTGAAGCTC TAGCACTCCA ACAACGGAC
7651 ATTAAAGGCG AAACACTAAC CTTTAGGAAG TCTACCACCA AAGGGAAACT
7701 CAAAACCCGC GTGGTTGACA TCCAGCCAGG ACTAGCCGCA CTCATGGCTG
7751 ACTATCACCC CAAACCGGGA ACCCTGTTCC CTGGCATGAG GGGAGTCAGC
7801 GATAGGCTCA CGCGATACGC GGCGGATAAA ATCTTGCGCG ATGCAGCCAA
7851 AAGAATCGGG CTAGAAGGCA TCAGTACCCA CAGTTTCCGC CGTACTGCCC
7901 TCAACCAAAT GTCTAGCGCC GGTATCCCGT TGCGACACAT TCAAGAGATA
7951 TCCGGTCACA ATGACCTTGG CACACTGCAA CGCTATCTTG AAGTTACACC
8001 CGAACAGCGA CGCAAAGCTG TATCCGTGAT TGGCTTCTAA TGTACGCCAA
8051 CGCTGTTTAG ACCCCTATGG GTGCTAAAAA AAGACGCAGC CTAAACACAC
8101 GCTCTACACT TGAGGATACT TTTAAAGTAT CCATCGGTTC TAGAACTCTG
8151 CACACGTTCC GGACTTTGGA AACGTTATAC CTTTCCCTGT GTTGCAGAAT
8201 GCTGCAATAT TTCTTCGACA AGTTAACTTG TGACTGGTTT AATATTTTCT
8251 CAAATTGCCC CAAAACAACA CGCCTAAATC CTTAGACGTT TCTGTGGAAA
8301 CCTATTAGGT TTTTATCGCC GTTGTTTTAG TGGTAAACCC AAAGGGTTTG
8351 TATATTCTTG TATGAAGTTC GACTCTGAGG GTTAAGAAGA ATGGCTCGCC
8401 GAATTTTTTA CAAGTGGAAA CCGATTAAAG GTTAAGGGTC AATCGGGACG
8451 ATGAATATTT TCTAATTGTG ACCTTCTCCA TCTAATAAGC TTTCTTTGGG
8501 GTTAAGGTCG AAGAAAGTAC TACGCATGAT CTGCATACGA TCTCTATTGC
8551 CAAAAAGCCG CGACCCTATA GGCTCTCGGT CATGCTGCAC TAGTTCGTGT
8601 CGATCACTAT ACTGGTTGCC GCAGCATTTC ACGCTAAAAA AAAATTCTTA
8651 AAAATGTCCT TCATATCTCG CCAGAGTGGC AACCTATTAC AAAACGGTTG
8701 CCTACCCGAC CGGCTCGATT TTCGCTGAAG TGGCACTGTG ACAGTTTGAA
8751 ATGGTACTTC CGCCGTGCTG CTGACATCGT TGTTAGGGTG AATTGTTCGC
8801 GGTAGATGTT GCACCGATTC ATGAACACCT TGTCACCCAC TTTGAATAAT
```

Figure 42U (6)

```
 8851 CGACCGTCAA ATTCAGTCGC GTCAATTTGG TAAGTGTTGG GCTGTCTCTT
 8901 TTTGGCTCCA GGGGCAATGC CATCAGAAAA CACAACCGCG TCACCCATAA
 8951 CTTGATAACC GATATCAGTT TTGGTTCCAG TGAAAGCCCA AAATTCAGAC
 9001 GCGTCATTAT TCCGAGCGTG CCGGAGTTGA TTGTACTCAA TTTTGGCTTG
 9051 GCAAAGTTGA CGGCGATTCA TGCCCAGCTG CTTTTGATGT CGTCGCACTG
 9101 TGCGCTTGTG AATACCCAAC TCACAGCTGA CAGCTTTTTG AGATGTACCA
 9151 TAGTGGATGA AACTTTTTGA GACGAATATC CGCGACGAAC TAATGTGAAG
 9201 TACACAAGGT ACTTCCCCCT CTGGCGATTT AAGAGAGGAT TGCCTTGTGT
 9251 CCTTCACTAG CTCGTTCGGG TGTGGCGCTC CAAAAAGTTT TCTGTACTCT
 9301 GGTTTAAGTT GTCTGTTGGC CGCATAGCGG CTCTTTTGTT GAAAGCTTTG
 9351 TGTGACTATG CCAGTGGTCA GTGAGCGTAA ATCGCTTAAC ACTTGGACTA
 9401 AAGGCACTAC TGCAACATCA CCCCATCTTT TTAAATTTAG GTTGTAACAA
 9451 ACTTGAAACA TACCGCCCAA GTAGACGGTT ATCATTCCTG CTTTAATTTT
 9501 GTAGCGGCGG AATGCTCCTA TTTTTTTTCC ATCCTGTAAC CAACGGTAAA
 9551 CAGACTTATC ACTACAATCT AAGAACGTCT GTACTACAGG CAATGGCAAT
 9601 GTTAAATGAC CAGACCCATC CTTATCAAGC GCTCGACACA ATACCACAA
 9651 CCGCGCACAA GGTTCTCGAC CAATGCGAGT GTGTACCCTG ACCGTGTAAG
 9701 TGCCAAGAAT TATTTCAGTT TGTAGTTCCC TTGTAAGCAG GGTTAGTGAT
 9751 ACATTTGTAT TTAAGCTTTC TGGGCTGATC ATTTGGAAAT GTCTCAGTCC
 9801 AGTACCTATT GAATGTTATT TGCTTAACCT GAAGCTAAAT AAAACTTGTT
 9851 AACTACACCC ATTAATTGAT AAATTCAAAG CACGTTTTTT CTGTTGGTG
 9901 TTTGGTGTGG TAACAATTCT GTGTATGTGT GTTTTATTTA GCTTCGGTTA
 9951 AGTAGCATAA CAACCCCCAA GCACTGAACT TTTTTAATA GGTAATTTAA
10001 ACTTTGCCTA TCGGCAAAAT TTTCAATCAA TTGTACGCCA AAGTGTTGCA
10051 TGATCAACGT TTGACTTATT TTTGTATTTA CTAAATACTG AATTTCGCCG
10101 TGACGCTTTT TACAGATGGA AATTCACGGC AAAATGTTTT TTGCTAACTT
10151 TGCTATGTAA AACAAGAAAC TTGGCACTCG GTTATTACTA AATAAACTGG
10201 TAAAAAATAA CCATTAGAAC CAAAAGAAC GAAAACCAGT ACACCCTTGC
10251 CAGTTTTCAA GCTTTTGCTA TGACGACTCT AATAATCGGG TTTAACACCA
```

Figure 42U(7)

```
10301 TTCCGCTTTG AGAAAATTAT CCTTGTACAG CAAGTAACAG TCAATGCTAA
10351 ACCGCACCGC TACAAATCCT TAAGTTTTTC CAGTAGCGAT TTACCTTCTT
10401 GGTAACGCCC GCCTTGATAG CCCAAAATTT CTTTAATCAC CTTACTTTCT
10451 GAAAAACCCG CTTCCAGACA GGCTTTTACC ACTTTTGCTA GGGTTTCATC
10501 TCTTGGTTCT GGGAGGGATG AAACGGGCTG TAATGCTTGT TCTGAGGTCG
10551 GTTGAGCCGT TTGGAGTGGC TGAAAACTGG TTACAGACTG TAACCGGGGC
10601 ATAACCATTT TGTAACTGCT TACATCTGGT AACTGACACG GCATATCATC
10651 CACCATGCAG CGATATTTCC CCGACTTTAA CCACTCCACA AGGGCAAGGT
10701 CTTTTAAGGA CTTGGCGTGG CTAACTGCAA ACTTACCCAG GCGTAACATC
10751 CTAAAACACT TACGGACACC GCCTTCACCC TCGATACCTA AGGTCTTGAC
10801 ATTATCATCT TGAGTCAGCC CAATAACAAA ACGCTTGGGC TTGCGGCCGC
10851 GCCTGGCGTG TTTGATGAGC CATTCGGTTG CTATCTCGAC TTCATCTCTC
10901 AGCAGTGGCA GTTCTTCAGC AATTAAAACG CTTTCTTTTC CTGCTAGTGC
10951 CTTATCCCCA GACTCACCCC GTAGCTCAAT CCGGCGCTGC AATTCCTCCA
11001 GGTCAGCAGC CATGCCCGAC TGTATAGCCT CAAAGTCACC ACGGCGGCCA
11051 ATGACATTTA ACCCGTCCA CTCGTCCGGT GCAGCGTCAG CGTCATAGAC
11101 TGTCACCTCA CCCCGACTT GATAAGCAAG CCATTGGGCT ATGGTGCTTT
11151 TGCCAGTTCC CGTATCCCCA ACTATTAAAC AGTGCTTACC AGACAGAGCT
11201 TGCATCAAGT CGGTGATGAT TCCCTCTGGT TCGACCGCAA GGGTGACGGC
11251 GGTAGTGTCA ATGATAGCCG CGCCGTAAGT GCCAGCATAG GGCAATTGGT
11301 CGTAAACTTT GACCAAGTTG TATACAGACT GTCTACACCA CTTCACCACT
11351 GTTAACGCTG TTTGCAAAGC GTAAGACGTG GCATCAAATA AAAATATGCT
11401 GGCACTAAAA GTTAATCGCC CCAATCCCCA CAGTAAAAAC CTGCCTAGCT
11451 GTTGACGACT AGGCAAGTGC ATTTCAATCC AGTCATTTGC CATAAATCAC
11501 CCCGTCTTTA AAGCCTTGCA GTTGAGCGCG ACAGGTATTT AACTGTGCTT
11551 GTAACTCTGT TTGCTGGTTT TGATACCACA GACTGACGGC GGCGGCCGCC
11601 AGTCCTAAAA ATAGAAACTG GCGATCGCTC ATTATTGACT TACTCCCTGT
11651 TGATTAGCGT GGTAGTGAGT CATAGCCGCA TTGACCGCTT CTTGGGCTTG
```

Figure 42U(8)

```
11701 GGGTGTTCTG CCAAGATTGG GTTTTGTAGG GTCATCGTTG GCTACGACTA
11751 AGGACGCTTG TTCGGCTATC GCTTGCGGGA CACCAACTTT AGTTAACTCT
11801 GTCAAGGATA CTTGGTAAAG TCGCTCGTTC ATTAGCCGAT TCTCCGGTAC
11851 ATAAAACTGT TGCTGGCAGT CCCTTCATTG GCGACGAGTT CTTCAGCCGG
11901 AGTATCAGCG ATAATGTCAG CCCAGCCGGT GACATTATTA TTAATAATGT
11951 TTTGTTCGGC AATTGCACCC AAGCCAGGAC GCGCCGTTTC AAACTCAGAG
12001 ATGACTTGCT GCTCTTTCTC GGTGAGTGGT CTATCTGTCA TGATAATTAT
12051 GTCCTTCATT ATGTAGGCGA TTCCAGTGGG TGTTTACGAG GCAGTCCACA
12101 GGAATCAGTG CGATTCACCT TTAAGGTGAA TCGTCATCAA AAAATCACTC
12151 GGTAGCAACG ACCCGAACCG ACCAGGATTG ATTTCCGGT TCTCAGTTCG
12201 CAGGCTTTTG AGCGCGTCAC CTTGACCATT GGGTAACTGC CATCAGCCGA
12251 TAAGCTAAAC GGGCTGTATA GCGGTAAAGC ATCCCACACA GTCGGGCTGG
12301 CATCAACTTT GCAGGAATAG CTCACGTCAC TCATCTCACT CGCGCCTGGG
12351 TTGGATGGCA GCGAAGGCAG ATTACGACGC AGTTTTTTAC TGGCACTTTT
12401 ACCCGCATTA AAAACGGGTA CAGTGCCATT GTTGACGGTC TGTACTTCGG
12451 TCATATACTC GGTGTACACT TAATACACTC TATACTATTA CTGCCGATTA
12501 GTACATTTGT CAATCACTCT TTGCACAAGG TGTATGATAT GGACTCAGGA
12551 GTACACCAAA CGTCATGCCA ACCAATAAAG GGAGAATAGC AGTCACTCTA
12601 GAAGCTGAAA TTTACCAATG GATTGCTAAC CGAGCGTCTG AGGAAGGAAG
12651 ACCGTTGGCT AATCTTGCCG CTTTCTTACT CACACGAGTT GTTAAAGAAC
12701 AAATGGAACA AGAAGCCAAG GACAACCAAG ACAAGCAGGG GGCAGCATGA
12751 GCGAAGACAG ACTAGCCAGA ATAGAAGCTG CGTTAGACAG CCAAGTTGCA
12801 GTGAATGCCG ACCTCCGCAC ATCGGTTACA GAACTCCGCG CAACCGCAGA
12851 AGCATTGTTG CAAACAGTTC AAATCCATCA GCAGAACTTT GAAATTCTTA
12901 CCGCTAGGCA ATTACAAACC GAAGCACGGC TTGATGAGTA CCAACGTACC
12951 ACTAGCGCGG CACTCGACAG AATTGGCGCG GTCTTAGACT ACCTCGTTAG
13001 GCAGCAAAAC GGTTGAGGTG AGGGATGAGC GATGACTATC TAGACGGATA
13051 TCCCGCAAGA GGCCCTTTCG TCTTCAAGAA TTCTCATGTT TGACAGCTTA
13101 TC (SEQ ID NO:106)
```

Figure 42U(9)

```
   1 CTAGCGCTAT ATGCGTTGAT GCAATTTCTA TGCGCACCCG TTCTCGGAGC
  51 ACTGTCCGAC CGCTTTGGCC GCCGCCCAGT CCTGCTCGCT TCGCTACTTG
 101 GAGCCACTAT CGACTACGCG ATCATGGCGA CCACACCCGT CCTGTGGATC
 151 ACTACCGGGC GTATTTTTTG AGTTATCGAG ATTTTCAGGA GCTAAGGAAG
 201 CTAAAATGGA GAAAAAATC ACTGGATATA CCACCGTTGA TATATCCCAA
 251 TGGCATCGTA AAGAACATTT TGAGGCATTT CAGTCAGTTG CTCAATGTAC
 301 CTATAACCAG ACCGTTCAGC TGGATATTAC GGCCTTTTTA AAGACCGTAA
 351 AGAAAAATAA GCACAAGTTT TATCCGGCCT TTATTCACAT TCTTGCCCGC
 401 CTGATGAATG CTCATCCGGA ATTCCGTATG GCAATGAAAG ACGGTGAGCT
 451 GGTGATATGG GATAGTGTTC ACCCTTGTTA CACCGTTTTC CATGAGCAAA
 501 CTGAAACGTT TTCATCGCTC TGGAGTGAAT ACCACGACGA TTTCCGGCAG
 551 TTTCTACACA TATATTCGCA AGATGTGGCG TGTTACGGTG AAAACCTGGC
 601 CTATTTCCCT AAAGGGTTTA TTGAGAATAT GTTTTCGTC TCAGCCAATC
 651 CCTGGGTGAG TTTCACCAGT TTTGATTTAA ACGTGGCCAA TATGGACAAC
 701 TTCTTCGCCC CCGTTTTCAC CATGGGCAAA TATTATACGC AAGGCGACAA
 751 GGTGCTGATG CCGCTGGCGA TTCAGGTTCA TCATGCCGTT TGTGATGGCT
 801 TCCATGTCGG CAGAATGCTT AATGAATTAC AACAGTACTG CGATGAGTGG
 851 CAGGGCGGGG CGTAATTTTT TTAAGGCAGT TATTGGTGCC CTTAAACGCC
 901 TGGTGCTACG CCTGAATAAG TGATAATAAG CGGATGAATG GCAGAAATTC
 951 GAAAGCAAAT TCGACCCGGT CGTCGGTTCA GGGCAGGGTC GTTAAATAGC
1001 CGCTTATGTC TATTGCTGGT TTACCGGTTT ATTGACTACC GGAAGCAGTG
1051 TGACCGTGTG CTTCTCAAAT GCCTGAGGCC AGTTTGCTCA GGCTCTCCCC
1101 GTGGAGGTAA TAATTGACGA TATGATCCTC TACGCCGGAC GCATCGTGGC
1151 CGGCATCACC GGCGATAAGC TTCACGCTGC CGCAAGCACT CAGGGCGCAA
1201 GGGCTGCTAA AGGAAGCGGA ACACGTAGAA AGCCAGTCCG CAGAAACGGT
1251 GCTGACCCCG GATGAATGTC AGCTACTGGG CTATCTGGAC AAGGGAAAAC
1301 GCAAGCGCAA AGAGAAAGCA GGTAGCTTGC AGTGGGCTTA CATGGCGATA
1351 GCTAGACTGG GCGGTTTTAT GGACAGCAAG CGAACCGGAA TTGCCAGCTG
1401 GGGCGCCCTC TGGTAAGGTT GGGAAGCCCT GCAAAGTAAA CTGGATGGCT
```

Figure 42W(1)

```
1451 TTCTTGCCGC CAAGGATCTG ATGGCGCAGG GGATCAAGAT CTGATCAAGA
1501 GACAGGATGA GGATCGTTTC GCATGATTGA ACAAGATGGA TTGCACGCAG
1551 GTTCTCCGGC CGCTTGGGTG GAGAGGCTAT TCGGCTATGA CTGGGCACAA
1601 CAGACAATCG GCTGCTCTGA TGCCGCCGTG TTCCGGCTGT CAGCGCAGGG
1651 GCGCCCGGTT CTTTTTGTCA AGACCGACCT GTCCGGTGCC CTGAATGAAC
1701 TGCAGGACGA GGCAGCGCGG CTATCGTGGC TGGCCACGAC GGGCGTTCCT
1751 TGCGCAGCTG TGCTCGACGT TGTCACTGAA GCGGGAAGGG ACTGGCTGCT
1801 ATTGGGCGAA GTGCCGGGGC AGGATCTCCT GTCATCTCAC CTTGCTCCTG
1851 CCGAGAAAGT ATCCATCATG GCTGATGCAA TGCGGCGGCT GCATACGCTT
1901 GATCCGGCTA CCTGCCCATT CGACCACCAA GCGAAACATC GCATCGAGCG
1951 AGCACGTACT CGGATGGAAG CCGGTCTTGT CGATCAGGAT GATCTGGACG
2001 AAGAGCATCA GGGGCTCGCG CCAGCCGAAC TGTTCGCCAG GCTCAAGGCG
2051 CGCATGCCCG ACGGCGAGGA TCTCGTCGTG ACCCATGGCG ATGCCTGCTT
2101 GCCGAATATC ATGGTGGAAA ATGGCCGCTT TTCTGGATTC ATCGACTGTG
2151 GCCGGCTGGG TGTGGCGGAC CGCTATCAGG ACATAGCGTT GGCTACCCGT
2201 GATATTGCTG AAGAGCTTGG CGGCGAATGG GCTGACCGCT TCCTCGTGCT
2251 TTACGGTATC GCCGCTCCCG ATTCGCAGCG CATCGCCTTC TATCGCCTTC
2301 TTGACGAGTT CTTCTGAGCG GGACTCTGGG GTTCGAAATG ACCGACCAAG
2351 CGACGCCCAA CCTGCCATCA CGAGATTTCG ATTCCACCGC CGCCTTCTAT
2401 GAAAGGTTGG GCTTCGGAAT CGTTTTCCGG GACGCCGGCT GGATGATCCT
2451 CCAGCGCGGG GATCTCATGC TGGAGTTCTT CGCCCACCCC AACGATCTGA
2501 TAGAGAAGGG TTTGCTCGGG TCGGTGGCTC TGGTAACGAC CAGTATCCCG
2551 ATCCGGCTG GCCGTCCTGG CCGCCACATG AGGCATGTTC CGCGTCCTTG
2601 CAATACTGTG TTTACATACA GTCTATCGCT TAGCGGAAAG TTCTTTTACC
2651 CTCAGCCGAA ATGCCTGCCG TTGCTAGACA TTGCCAGCCA GTGCCCGTCA
2701 CTCCCGTACT AACTGTCACG AACCCCTGCA ATAACTGTCA CGCCCCCTG
2751 CAATAACTGT CACGAACCCC TGCAATAACT GTCACGCCCC CAAACCTGCA
2801 AACCCAGCAG GGGCGGGGGC TGGCGGGGTG TTGGAAAAAT CCATCCATGA
2851 TTATCTAAGA ATAATCCACT AGGCGCGGTT ATCAGCGCCC TTGTGGGGCG
```

Figure 42W(2)

```
2901 CTGCTGCCCT TGCCCAATAT GCCCGGCCAG AGGCCGGATA GCTGGTCTAT
2951 TCGCTGCGCT AGGCTACACA CCGCCCCACC GCTGCGCGGC AGGGGGAAAG
3001 GCGGGCAAAG CCCGCTAAAC CCCACACCAA ACCCCGCAGA AATACGCTGG
3051 AGCGCTTTTA GCCGCTTTAG CGGCCTTTCC CCCTACCCGA AGGGTGGGGG
3101 CGCGTGTGCA GCCCCGCAGG GCCTGTCTCG GTCGATCATT CAGCCCGGCT
3151 CATCCTTCTG GCGTGGCGGC AGACCGAACA AGGCGCGGTC GTGGTCGCGT
3201 TCAAGGTACG CATCCATTGC CGCCATGAGC CGATCCTCCG GCCACTCGCT
3251 GCTGTTCACC TTGGCCAAAA TCATGGCCCC CACCAGCACC TTGCGCCTTG
3301 TTTCGTTCTT GCGCTCTTGC TGCTGTTCCC TTGCCCGCTC CCGCTGAATT
3351 TCGGCATTGA TTCGCGCTCG TTGTTCTTCG AGCTTGGCCA GCCGATCCGC
3401 CGCCTTGTTG CTCCCCTTAA CCATCTTGAC ACCCCATTGT TAATGTGCTG
3451 TCTCGTAGGC TATCATGGAG GCACAGCGGC GGCAATCCCG ACCCTACTTT
3501 GTAGGGGAGG GCGCACTTAC CGGTTTCTCT TCGAGAAACT GGCCCTAACG
3551 GCCACCCTTC GGGCGGTGCG CTCTCCGAGG GCCATTGCAT GGAGCCGAAA
3601 AGCAAAAGCA ACAGCGAGGC AGCATGGCGA TTTATCACCT TACGGCGAAA
3651 ACCGGCAGCA GGTCGGGCGG CCAATCGGCC AGGGCCAAGG CCGACTACAT
3701 CCAGCGCGAA GGCAAGTATG CCCGCGACAT GGATGAAGTC TTGCACGCCG
3751 AATCCGGGCA CATGCCGGAG TTCGTCGAGC GGCCCGCCGA CTACTGGGAT
3801 GCTGCCGACC TGTATGAACG CGCCAATGGG CGGCTGTTCA AGGAGGTCGA
3851 ATTTGCCCTG CCGGTCGAGC TGACCCTCGA CCAGCAGAAG GCGCTGGCGT
3901 CCGAGTTCGC CCAGCACCTG ACCGGTGCCG AGCGCCTGCC GTATACGCTG
3951 GCCATCCATG CCGGTGGCGG CGAGAACCCG CACTGCCACC TGATGATCTC
4001 CGAGCGGATC AATGACGGCA TCGAGCGGCC CGCCGCTCAG TGGTTCAAGC
4051 GGTACAACGG CAAGACCCCG GAGAAGGGCG GGCACAGAA GACCGAAGCG
4101 CTGAAGCCCA AGGCATGGCT TGAGCAGACC CGCGAGGCAT GGGCCGACCA
4151 TGCCAACCGG GCATTAGAGC GGGCTGGCCA CGACGCCCGC ATTGACCACA
4201 GAACACTTGA GGCGCAGGGC ATCGAGCGCC TGCCCGGTGT TCACCTGGGG
4251 CCGAACGTGG TGGAGATGGA AGGCCGGGGC ATCCGCACCG ACCGGGCAGA
4301 CGTGGCCCTG AACATCGACA CCGCCAACGC CCAGATCATC GACTTACAGG
```

Figure 42W(3)

```
4351 AATACCGGGA GGCAATAGAC CATGAACGCA ATCGACAGAG TGAAGAAATC
4401 CAGAGGCATC AACGAGTTAG CGGAGCAGAT CGAACCGCTG GCCCAGAGCA
4451 TGGCGACACT GGCCGACGAA GCCCGGCAGG TCATGAGCCA GACCAAGCAG
4501 GCCAGCGAGG CGCAGGCGGC GGAGTGGCTG AAAGCCCAGC GCCAGACAGG
4551 GGCGGCATGG GTGGAGCTGG CCAAAGAGTT GCGGGAGGTA GCCGCCGAGG
4601 TGAGCAGCGC CGCGCAGAGC GCCCGGAGCG CGTCGCGGGG GTGGCACTGG
4651 AAGCTATGGC TAACCGTGAT GCTGGCTTCC ATGATGCCTA CGGTGGTGCT
4701 GCTGATCGCA TCGTTGCTCT TGCTCGACCT GACGCCACTG ACAACCGAGG
4751 ACGGCTCGAT CTGGCTGCGC TTGGTGGCCC GATGAAGAAC GACAGGACTT
4801 TGCAGGCCAT AGGCCGACAG CTCAAGGCCA TGGGCTGTGA GCGCTTCGAT
4851 ATCGGCGTCA GGGACGCACC CACCGGCCAG ATGATGAACC GGGAATGGTC
4901 AGCCGCCGAA GTGCTCCAGA ACACGCCATG GCTCAAGCGG ATGAATGCCC
4951 AGGGCAATGA CGTGTATATC AGGCCCGCCG AGCAGGAGCG GCATGGTCTG
5001 GTGCTGGTGG ACGACCTCAG CGAGTTTGAC CTGGATGACA TGAAAGCCGA
5051 GGGCCGGGAG CCTGCCCTGG TAGTGGAAAC CAGCCCGAAG AACTATCAGG
5101 CATGGGTCAA GGTGGCCGAC GCCGCAGGCG GTGAACTTCG GGGGCAGATT
5151 GCCCGGACGC TGGCCAGCGA GTACGACGCC GACCCGGCCA GCGCCGACAG
5201 CCGCCACTAT GGCCGCTTGG CGGGCTTCAC CAACCGCAAG GACAAGCACA
5251 CCACCCGCGC CGGTTATCAG CCGTGGGTGC TGCTGCGTGA ATCCAAGGGC
5301 AAGACCGCCA CCGCTGGCCC GGCGCTGGTG CAGCAGGCTG CCAGCAGAT
5351 CGAGCAGGCC CAGCGGCAGC AGGAGAAGGC CCGCAGGCTG GCCAGCCTCG
5401 AACTGCCCGA GCGGCAGCTT AGCCGCCACC GGCGCACGGC GCTGGACGAG
5451 TACCGCAGCG AGATGGCCGG GCTGGTCAAG CGCTTCGGTC ATGACCTCAG
5501 CAAGTGCGAC TTTATCGCCG CGCAGAAGCT GGCCAGCCGG GGCCGCAGTG
5551 CCGAGGAAAT CGGCAAGGCC ATGGCCGAGG CCAGCCCAGC GCTGGCAGAG
5601 CGCAAGCCCG GCCACGAAGC GGATTACATC GAGCGCACCG TCAGCAAGGT
5651 CATGGGTCTG CCCAGCGTCC AGCTTGCGCG GGCCGAGCTG GCACGGGCAC
5701 CGGCACCCCG CCAGCGAGGC ATGGACAGGG GCGGGCCAGA TTTCAGCATG
5751 TAGTGCTTGC GTTGGTACTC ACGCCTGTTA TACTATGAGT ACTCACGCAC
```

Figure 42W(4)

```
5801 AGAAGGGGGT TTTATGGAAT ACGAAAAAAG CGCTTCAGGG TCGGTCTACC
5851 TGATCAAAAG TGACAAGGGC TATTGGTTGC CCGGTGGCTT TGGTTATACG
5901 TCAAACAAGG CCGAGGCTGG CCGCTTTTCA GTCGCTGATA TGGCCAGCCT
5951 TAACCTTGAC GGCTGCACCT TGTCCTTGTT CCGCGAAGAC AAGCCTTTCG
6001 GCCCCGGCAA GTTTCTCGGT GACTGATATG AAAGACCAAA AGGACAAGCA
6051 GACCGGCGAC CTGCTGGCCA GCCCTGACGC TGTACGCCAA GCGCGATATG
6101 CCGAGCGCAT GAAGGCCAAA GGGATGCGTC AGCGCAAGTT CTGGCTGACC
6151 GACGACGAAT ACGAGGCGCT GCGCGAGTGC CTGGAAGAAC TCAGAGCGGC
6201 GCAGGGCGGG GGTAGTGACC CCGCCAGCGC CTAACCACCA ACTGCCTGCA
6251 AAGGAGGCAA TCAATGGCTA CCCATAAGCC TATCAATATT CTGGAGGCGT
6301 TCGCAGCAGC GCCGCCACCG CTGGACTACG TTTTGCCCAA CATGGTGGCC
6351 GGTACGGTCG GGGCGCTGGT GTCGCCCGGT GGTGCCGGTA AATCCATGCT
6401 GGCCCTGCAA CTGGCCGCAC AGATTGCAGG CGGGCCGGAT CTGCTGGAGG
6451 TGGGCGAACT GCCCACCGGC CCGGTGATCT ACCTGCCCGC CGAAGACCCG
6501 CCCACCGCCA TTCATCACCG CCTGCACGCC CTTGGGGCGC ACCTCAGCGC
6551 CGAGGAACGG CAAGCCGTGG CTGACGGCCT GCTGATCCAG CCGCTGATCG
6601 GCAGCCTGCC CAACATCATG GCCCCGGAGT GGTTCGACGG CCTCAAGCGC
6651 GCCGCCGAGG CCGCCGCCT GATGGTGCTG ACACGCTGC GCCGGTTCCA
6701 CATCGAGGAA GAAAACGCCA GCGGCCCCAT GGCCCAGGTC ATCGGTCGCA
6751 TGGAGGCCAT CGCCGCCGAT ACCGGGTGCT CTATCGTGTT CCTGCACCAT
6801 GCCAGCAAGG GCGCGGCCAT GATGGGCGCA GGCGACCAGC AGCAGGCCAG
6851 CCGGGGCAGC TCGGTACTGG TCGATAACAT CCGCTGGCAG TCCTACCTGT
6901 CGAGCATGAC CAGCGCCGAG GCCGAGGAAT GGGGTGTGGA CGACGACCAG
6951 CGCCGGTTCT TCGTCCGCTT CGGTGTGAGC AAGGCCAACT ATGGCGCACC
7001 GTTCGCTGAT CGGTGGTTCA GGCGGCATGA CGGCGGGGTG CTCAAGCCCG
7051 CCGTGCTGGA GAGGCAGCGC AAGAGCAAGG GGGTGCCCCG TGGTGAAGCC
7101 TAAGAACAAG CACAGCCTCA GCCACGTCCG GCACGACCCG GCGCACTGTC
7151 TGGCCCCCGG CCTGTTCCGT GCCCTCAAGC GGGGCGAGCG CAAGCGCAGC
7201 AAGCTGGACG TGACGTATGA CTACGGCGAC GGCAAGCGGA TCGAGTTCAG
7251 CGGCCCGGAG CCGCTGGGCG CTGATGATCT GCGCATCCTG CAAGGGCTGG
```
Figure 42W(5)

```
7301 TGGCCATGGC TGGGCCTAAT GGCCTAGTGC TTGGCCCGGA ACCCAAGACC
7351 GAAGGCGGAC GGCAGCTCCG GCTGTTCCTG GAACCCAAGT GGGAGGCCGT
7401 CACCGCTGAA TGCCATGTGG TCAAAGGTAG CTATCGGGCG CTGGCAAAGG
7451 AAATCGGGGC AGAGGTCGAT AGTGGTGGGG CGCTCAAGCA CATACAGGAC
7501 TGCATCGAGC GCCTTTGGAA GGTATCCATC ATCGCCCAGA ATGGCCGCAA
7551 GCGGCAGGGG TTTCGGCTGC TGTCGGAGTA CGCCAGCGAC GAGGCGGACG
7601 GGCGCCTGTA CGTGGCCCTG AACCCCTTGA TCGCGCAGGC CGTCATGGGT
7651 GGCGGCCAGC ATGTGCGCAT CAGCATGGAC GAGGTAGCGG GCGCTGGACA
7701 GCGAAACCGC CCGCCTGCTG CACCAGCGGC TGTGTGGCTG GATCGACCCC
7751 GGCAAAACCG GCAAGGCTTC CATAGATACC TTGTGCGGCT ATGTCTGGCC
7801 GTCAGAGGCC AGTGGTTCGA CCATGCGCAA GCGCCGCAAG CGGGTGCGCG
7851 AGCGTTGCCG GAGCTGGTCG CGCTGGGCTG GACGGTAACC GAGTTCGCGG
7901 CGGGCAAGTA CGACATCACC CGGCCCAAGG CGGCAGGCTG ACCCCCCCCA
7951 CTCTATTGTA AACAACACAT TTTTATCTTT TATATTCAAT GGCTTATTTT
8001 CCTGCTAATT GGTAATACCA TGAAAAATAC CATGCTCAGA AAAGGCTTAA
8051 CAATATTTTG AAAAATTGCC TACTGAGCGC TGCCGCACAG CTCCATAGGC
8101 CGCTTTCCAG GCTTTGCTTC CAGATGTATG CTCTTCTGCT CCTGCAGTTC
8151 ATTCAGGGCA CCGGACAGGT CGGTCTTGAC AAAAAGAACC GGGCGCCCCT
8201 GCGCTGACAG CCGGAACACG GCGGCATCAG AGCAGCCGAT TGTCTGTTGT
8251 GCCCAGTCAT AGCCGAATAG CCTCTCCACC CAAGCGGCCG GAGAACCTGC
8301 GTGCAATCCA TCTTGTTCAA TCATGCGAAA CGATCCTCAT CCTGTCTCTT
8351 GATCATTGAT CCCCTGCGCC ATCAGATCCT TGGCGGCAAG AAAGCCATCC
8401 AGTTTACTTT GCAGGGCTTC CCAACCTTAC CAGAGGGCGC CCCAGCTGGC
8451 AATTCCGGTT CGCTTGCTGT CCATAAAACC GCCCAGTCTA GCTATCGCCA
8501 TGTAAGCCCA CTGCAAGCTA CCTGCTTTCT CTTTGCGCTT GCGTTTTCCC
8551 TTGTCCAGAT AGCCCAGTAG CTGACATTCA TCCGGGGTCA GCACCGTTTC
8601 TGCGGACTGG CTTTCTACGT GTTCCGCTTC CTTTAGCAGC CCTTGCGCCC
8651 TGAGTGCTTG CGGCAGCGTG AAGCTTATCG ATTCACAAAA AATAGGCACA
8701 CGAAAAACAA GTTAAGGGAT GCAGTTTATG CACTAGCCTA GGCTCGAGAA
8751 GCTTGTCGAC CTTCCAGCAC CACGTCAACT TGTTTAACT GCTCCCGGAG
```

```
8801  TTGTCTTTCC GCTTTGGCAA TGTGCCCGGG ATACCATTGG ATTAAAGCCA
8851  TGAGTTGTTC ACTTTTTTAC TGACGAGGGC TTCCGGAGGC CACGCTCCCA
8901  CCCATAACAG CTTGCCACAT CCCCGTCGGA AGTTACGTTA CCCTTGGGCG
8951  ATCGCCAAAA ATCAGCATAT ATACACCAAT TCTAAATAAG ATCTTTTACA
9001  CCGCTACTGC AATCAACCTC ATCAACAAAA TTCCCCTCTA GCATCCCTGG
9051  AGGCAAATCC TCACCTGGCC ATGGGTTCAA CCCTGCTTAA CATTTCTTAA
9101  TAATTTTAGT TGCTATAAAT TCTCATTTAT GCCCTATAA TAATTCGGGA
9151  GTAAGTGCTA AAGATTCTCA ACTGCTCCAT CAGTGGTTTG AGCTTAGTCC
9201  TAGGGAAAGA TTGGCGATCG CCGTTGTGGT TAAGCCAGAA TAGGTCTCGG
9251  GTGGACAGAG AACGCTTTAT TCTTTGCCTC CATGGCGGCA TCCCACCTAG
9301  GTTTCTCGGC ACTTATTGCC ATAATTTATT ATTTGTCGTC TCAATTAAGG
9351  AGGCAATTCT GTGAATTCTT ATACTGTCGG TACCTATTTA GCGGAGCGGC
9401  TTGTCCAGAT TGGTCTCAAG CATCACTTCG CAGTCGCGGG CGACTACAAC
9451  CTCGTCCTTC TTGACAACCT GCTTTTGAAC AAAAACATGG AGCAGGTTTA
9501  TTGCTGTAAC GAACTGAACT GCGGTTTCAG TGCAGAAGGT TATGCTCGTG
9551  CCAAAGGCGC AGCAGCAGCC GTCGTTACCT ACAGCGTCGG TGCGCTTTCC
9601  GCATTTGATG CTATCGGTGG CGCCTATGCA GAAAACCTTC CGGTTATCCT
9651  GATCTCCGGT GCTCCGAACA ACAATGATCA CGCTGCTGGT CACGTGTTGC
9701  ATCACGCTCT TGGCAAAACC GACTATCACT ATCAGTTGGA AATGGCCAAG
9751  AACATCACGG CCGCAGCTGA AGCGATTTAC ACCCCAGAAG AAGCTCCGGC
9801  TAAAATCGAT CACGTGATTA AAACTGCTCT TCGTGAGAAG AAGCCGGTTT
9851  ATCTCGAAAT CGCTTGCAAC ATTGCTTCCA TGCCCTGCGC CGCTCCTGGA
9901  CCGGCAAGCG CATTGTTCAA TGACGAAGCC AGCGACGAAG CTTCTTTGAA
9951  TGCAGCGGTT GAAGAAACCC TGAAATTCAT CGCCAACCGC GACAAAGTTG
10001 CCGTCCTCGT CGGCAGCAAG CTGCGCGCAG CTGGTGCTGA AGAAGCTGCT
10051 GTCAAATTTG CTGATGCTCT CGGTGGCGCA GTTGCTACCA TGGCTGCTGC
10101 AAAAAGCTTC TTCCCAGAAG AAACCCGCA TTACATCGGT ACCTCATGGG
10151 GTGAAGTCAG CTATCCGGGC GTTGAAAAGA CGATGAAAGA AGCCGATGCG
10201 GTTATCGCTC TGGCTCCTGT CTTCAACGAC TACTCCACCA CTGGTTGGAC
10251 GGATATTCCT GATCCTAAGA AACTGGTTCT CGCTGAACCG CGTTCTGTCG
```

Figure 42W(7)

```
10301 TCGTTAACGG CGTTCGCTTC CCCAGCGTTC ATCTGAAAGA CTATCTGACC
10351 CGTTTGGCTC AGAAAGTTTC CAAGAAAACC GGTGCTTTGG ACTTCTTCAA
10401 ATCCCTCAAT GCAGGTGAAC TGAAGAAAGC CGCTCCGGCT GATCCGAGTG
10451 CTCCGTTGGT CAACGCAGAA ATCGCCCGTC AGGTCGAAGC TCTTCTGACC
10501 CCGAACACGA CGGTTATTGC TGAAACCGGT GACTCTTGGT TCAATGCTCA
10551 GCGCATGAAG CTCCCGAACG GTGCTCGCGT TGAATATGAA ATGCAGTGGG
10601 GTCACATCGG TTGGTCCGTT CCTGCCGCCT TCGGTTATGC CGTCGGTGCT
10651 CCGGAACGTC GCAACATCCT CATGGTTGGT GATGGTTCCT TCCAGCTGAC
10701 GGCTCAGGAA GTCGCTCAGA TGGTTCGCCT GAAACTGCCG GTTATCATCT
10751 TCTTGATCAA TAACTATGGT TACACCATCG AAGTTATGAT CCATGATGGT
10801 CCGTACAACA ACATCAAGAA CTGGGATTAT GCCGGTCTGA TGGAAGTGTT
10851 CAACGGTAAC GGTGGTTATG ACAGCGGTGC TGGTAAAGGC CTGAAGGCTA
10901 AAACCGGTGG CGAACTGGCA GAAGCTATCA AGGTTGCTCT GGCAAACACC
10951 GACGGCCCAA CCCTGATCGA ATGCTTCATC GGTCGTGAAG ACTGCACTGA
11001 AGAATTGGTC AAATGGGGTA AGCGCGTTGC TGCCGCCAAC AGCCGTAAGC
11051 CTGTTAACAA GCTCCTCTAG TTTTTGGGGA TCAATTCGAG CTCGGTACCC
11101 AAACTAGTAT GTAGGGTGAG GTTATAGCTA TGGCTTCTTC AACTTTTTAT
11151 ATTCCTTTCG TCAACGAAAT GGGCGAAGGT TCGCTTGAAA AAGCAATCAA
11201 GGATCTTAAC GGCAGCGGCT TTAAAAATGC GCTGATCGTT TCTGATGCTT
11251 TCATGAACAA ATCCGGTGTT GTGAAGCAGG TTGCTGACCT GTTGAAAGCA
11301 CAGGGTATTA ATTCTGCTGT TTATGATGGC GTTATGCCGA ACCCGACTGT
11351 TACCGCAGTT CTGGAAGGCC TTAAGATCCT GAAGGATAAC AATTCAGACT
11401 TCGTCATCTC CCTCGGTGGT GGTTCTCCCC ATGACTGCGC CAAAGCCATC
11451 GCTCTGGTCG CAACCAATGG TGGTGAAGTC AAAGACTACG AAGGTATCGA
11501 CAAATCTAAG AAACCTGCCC TGCCTTTGAT GTCAATCAAC ACGACGGCTG
11551 GTACGGCTTC TGAAATGACG CGTTTCTGCA TCATCACTGA TGAAGTCCGT
11601 CACGTTAAGA TGGCCATTGT TGACCGTCAC GTTACCCCGA TGGTTTCCGT
11651 CAACGATCCT CTGTTGATGG TTGGTATGCC AAAAGGCCTG ACCGCCGCCA
11701 CCGGTATGGA TGCTCTGACC CACGCATTTG AAGCTTATTC TTCAACGGCA
11751 GCTACTCCGA TCACCGATGC TTGCGCCTTG AAGGCTGCGT CCATGATCGC
```

Figure 42W(8)

```
11801 TAAGAATCTG AAGACCGCTT GCGACAACGG TAAGGATATG CCAGCTCGTG
11851 AAGCTATGGC TTATGCCCAA TTCCTCGCTG GTATGGCCTT CAACAACGCT
11901 TCGCTTGGTT ATGTCCATGC TATGGCTCAC CAGTTGGGCG GCTACTACAA
11951 CCTGCCGCAT GGTGTCTGCA ACGCTGTTCT GCTTCCGCAT GTTCTGGCTT
12001 ATAACGCCTC TGTCGTTGCT GGTCGTCTGA AAGACGTTGG TGTTGCTATG
12051 GGTCTCGATA TCGCCAATCT CGGTGATAAA GAAGGCGCAG AAGCCACCAT
12101 TCAGGCTGTT CGCGATCTGG CTGCTTCCAT TGGTATTCCA GCAAATCTGA
12151 CCGAGCTGGG TGCTAAGAAA GAAGATGTGC CGCTTCTTGC TGACCACGCT
12201 CTGAAAGATG CTTGTGCTCT GACCAACCCG CGTCAGGGTG ATCAGAAAGA
12251 AGTTGAAGAA CTCTTCCTGA GCGCTTTCTA ATTTCAAAAC AGGAAAACGG
12301 TTTTCCGTCC TGTCTTGATT TTCAAGCAAA CAATGCCTCC GATTTCTAAT
12351 CGGAGGCATT TGTTTTTGTT TATTGCAAAA ACAAAAAATA TTGTTACAAA
12401 TTTTTACAGG CTATTAAGCC TACCGTCATA AATAATTTGC CATTTGGGGA
12451 TCCGATACGT AACGCGTCTG CA (SEQ ID NO:107)
```

Figure 42W(9)

ZmPDC and ZmADHII ezymatic activity in *Synechocystis* pVZ transconjugants

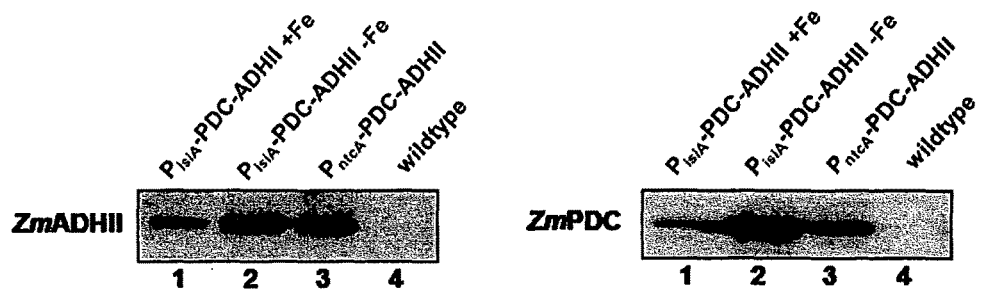

| ADH activity: | 40,0 nmol/min*mg protein (1) |
| | 297,7 nmol/min*mg protein (2) |
| | 165,5 nmol/min*mg protein (3) |
| | 0,0 nmol/min*mg protein (4) |

(Deng & Coleman, 1999: ~170 nmol/min*mg protein)

| PDC activity: | 11,5 nmol/min*mg protein (1) |
| | 2917,0 nmol/min*mg protein (2) |
| | 154,2 nmol/min*mg protein (3) |
| | 0,0 nmol/min*mg protein (4) |

(Deng & Coleman, 1999: ~230 nmol/min*mg protein)

➡ The estimated ADHII and PDC protein amounts from Western blot analysis correlate well with the measured ADH and PDC activities, respectively.

Figure 43B

| node | organism | taxanomy | accession | protein |
|---|---|---|---|---|
| Subclade A | | | | |
| Aca.ma_YP_001519107 | Acaryochloris marina MBIC11017 | Cyanobacteria | YP_001519107.1 | Zinc-containing alcohol dehydrogenase family protein |
| Cce7424_YP_002380432 | Cyanothece sp. PCC 7424 | Cyanobacteria | YP_002380432.1 | Alcohol dehydrogenase GroES domain protein |
| Cce7424_ZP_02976085 | Cyanothece sp. PCC 7424 | Cyanobacteria | ZP_02976085.1 | Alcohol dehydrogenase GroES domain protein |
| Cce7822_ZP_03154326 | Cyanothece sp. PCC 7822 | Cyanobacteria | ZP_03154326.1 | Alcohol dehydrogenase GroES domain protein |
| Cce8801_YP_002371662 | Cyanothece sp. PCC 8801 | Cyanobacteria | YP_002371662.1 | Alcohol dehydrogenase GroES domain protein |
| Cce8801_ZP_02941996 | Cyanothece sp. PCC 8801 | Cyanobacteria | ZP_02941996.1 | Alcohol dehydrogenase GroES domain protein |
| Cce8802_ZP_03143898 | Cyanothece sp. PCC 8802 | Cyanobacteria | ZP_03143898.1 | Alcohol dehydrogenase GroES domain protein |

Figure 47B(1)

| | | | |
|---|---|---|---|
| Mic.ch7420_EDX77810 | Microcoleus chthonoplastes PCC 7420 | Cyanobacteria | EDX77810.1 | Alcohol dehydrogenase GroES-like domain family |
| Mic.aeNIES843_YP_001659961 | Microcystis aeruginosa NIES-843 | Cyanobacteria | YP_001659961.1 | uncharacterized zinc-type alcohol dehydrogenase-like protein |
| Mic.ae7806_CAO90817 | Microcystis aeruginosa PCC 7806 | Cyanobacteria | CAO90817.1 | unnamed protein product |

Figure 47B(1) (Continued)

Subclade B

| | | | |
|---|---|---|---|
| LimnoMED105_ZP_01914609 | Limnobacter sp. MED105 | Betaproteobacteria | ZP_01914609.1 | Alcohol dehydrogenase, zinc-binding protein |
| Syn6803_NP_443028 | Synechocystis sp. PCC 6803 | Cyanobacteria | NP_443028.1 | zinc-containing alcohol dehydrogenase family protein |
| Alt.ma_YP_002126870 | Alteromonas macleodii 'Deep ecotype' | Gammaproteobacteria | YP_002126870.1 | zinc-containing alcohol dehydrogenase |
| OceanRED65_ZP_01306627 | Oceanobacter sp. RED65 | Gammaproteobacteria | ZP_01306627.1 | family protein zinc- |

Figure 47B(2)

| | | | |
|---|---|---|---|
| Psy.crK5_yp_581659 | Psychrobacter cryohalolentis K5 | Gammaproteobacteria YP_581659.1 | containing alcohol dehydrogenase family protein |
| Sac.de_YP_529423 | Saccharophagus degradans 2-40 | Gammaproteobacteria YP_529423.1 | alcohol dehydrogenase GroES-like protein zinc-containing alcohol dehydrogenase family protein |
| Ver.ba_EDY84203 | Verrucomicrobiae bacterium DG1235 | Verrucomicrobia EDY84203.1 | Alcohol dehydrogenase GroES-like domain family |

Figure 47B(2) (Continued)

Subclade C

| | | | |
|---|---|---|---|
| ScoRS9916_ZP_01472751 | Synechococcus | Cyanobacteria | ZP_01472751.1 zinc- |

Figure 47B(3)

| | | |
|---|---|---|
| Sco9917_ZP_01079933 | Synechococcus sp. RS9916 | zinc-containing alcohol dehydrogenase superfamily protein |
| Sco9917_ZP_01079933 | Synechococcus sp. RS9917 | zp_01079933.1 zinc-containing alcohol dehydrogenase superfamily protein |
| Sco5701_ZP_01085101 | Synechococcus sp. WH 5701 | zp_01085101.1 zinc-containing alcohol dehydrogenase superfamily protein |
| Sco7803_YP_001224538 | Synechococcus sp. WH 7803 | YP_001224538.1 Zn-dependent alcohol dehydrogenases |
| Sco7805_ZP_01125148 | Synechococcus sp. WH 7805 | zp_01125148.1 zinc-containing alcohol dehydrogenase superfamily protein |

Figure 47B(3) (Continued)

```
MIKAYAALEANGKLQPFEYDPGALGANEVEIEVQYCGVCHSDLSMINNEWGISNYPLVPGH
EVVGTVAAMGEGVNHVEVGDLVGLGWHSGYCMTCHSCLSGYHNLCATAESTIVGHYGGFGD
RVRAKGVSVVKLPKGIDLASAGPLFCGGITVFSPMVELSLKPTAKVAVIGIGGLGHLAVQF
LRAWGCEVTAFTSSARKQTEVLELGAHHILDSTNPEAIASAEGKFDYIISTVNLKLDWNLY
ISTLAPQGHFHFVGVVLEPLDLNLFPLLMGQRSVSASPVGSPATIATMLDFAVRHDIKPVV
EQFSFDQINEAIAHLESGKAHYRVVLSHSKN    (SEQ ID NO:108)
```

Figure 47C

MIKAFAADTAKGELKPFEYEVGELGSQEVEIEVHYCGVCHSDISMLDNEWGMTQYPFVPGH
EVAGLIKQVGAEVNHLKVGDRVGLGWQSGYCNHCENCMSGDHNLCGTAEMTIVGRHGGFAD
HVRAQASSVVKLPDDIHMADAGPLFCGGVTVYNPMKQFDLKPTAKVAVIGIGGLGHMALQF
LNSWGCEVTAFTSTEEKRKEAIALGAHKTLNSRDEGELKGAAGSFDMIISTVNVSLNWEAY
INTLKAKGRLHFVGAVLEPIQVGVFPLMMGQRSISASPVGSPSTISQMLEFTARHQIKPQV
ELFQKDQINDAINHVREGKARYRAVIQFKATSDNSA    (SEQ ID NO:109)

Figure 47D

```
MELIMINAYAAFEAKGPLKPFQYDPGELNAFDIEIDVDHCGICHSDVSMLDNDWGRAKYPM
VAGHEIIGRVSQVGSHVSHLAIGDVVGLGWHSGYCESCRMCMGGDHNLCSTAKGTIVGRHG
GFADKVRAQAVSAVKIPAGVNPATAGPLLCGGITVYNPLVQFNISPQSKVAVIGVGGLGHM
AVMFLKAWGCEVTAFSSNVSKTDELLGMGAHHVLNSKDPDALKKAAGSFDLILSTVNVKLD
WNAYIGTLAPKGRLHFLGAVLEPLDIGVFGLMGQQRSISSSPVGSPRVIADMLKFAALHNI
QPIVETYSFDQINEAVDKVRNGSPRFRVVLSR   (SEQ ID NO:110)
```

Figure 47E

```
MINAYAAKEKGGEFVPYQYDPGTLGDHEVEIEVHSCGICHSDLSMWQNEWGMTQYPFVGGH
EVAGKVLAKGKHVKHLELGDKVGLGWHKGYCNVCDLCIGGDHNLCPEQEGTIIGNHGGFAD
KVRAKDTSVIKIPEGLDFNAVGPLLCGGVTVFNPLMQYDITPTSRVAVIGIGGLGHLALQF
ANAWGCEVTAFTSESKMEEAKEMGAHHSLNSREDSEIEKAAGSFDLIISTVNVDMNWDVVI
KTLRPKGKLHFVGLLEAPLEISAAPMIMAQNSLSGSPVGSPSTLRKMLDFAARHNIQPVTE
TYKMSEINEAFERLESGNARYRVVLERD    (SEQ ID NO:111)
```

Figure 47F

MIKAYATHTPGGKLEPFEYDPGELAPTDVEINVEHCGICHSDLSMLNNEWGMTTYPFVPGH
EVVGTIGAIGSDVKNLAPGQRVGLGWHSSYCTTCPSCLSGDHNLCQAAAGTIVGRHGGFAD
KVRASALSVIPLPDSIDAAKAGPLFCGGITVFNPLIQYEVSPTAKVAVIGIGGLGHMALAF
LNAWGCEVTAFTTSEAKRQEALKLGAHHTLNSRDAAEIEAAAGRFDLILSTVNVGLDWNGY
VNTLKPKGRLHFLGAALEPIQIGAFSLIMAQRQISGSPVGSPATIAKMIEFAALHKIEPVT
EHFKFDQANEALAHLESGQARYRIVLSH    (SEQ ID NO:112)

Figure 47G

```
MIKAYAAMEPGAALVPFEYEPGPLANNEVELKVESCGICHSDLSMLDNEWGFTQYPFVGGH
EVIGIVEAVGSSVNNVAVGQRVGLGWHSGYCNTCASCQSGDQNLCNSAQPTIAGHHGGFAD
KVRADANAVVALPEGVNPDSAGPLFCGGITVFNPLVQFGIKPTSKVGVIGIGGLGHIALQF
LNAWGCEVTAFTSSESKKEEALKLGAHHVLNSSDAAQLEAAAGRFDFIISTVNVKLDWNEY
LATLAPKGRLHFVGATLAPLDINVFQLIGSQREISGSPVGSPGTISQMLDFAALHNIQPVT
EYFRFDQINEALTKLREGKAHYRIVLTNK   (SEQ ID NO:113)
```

Figure 47H

MIYAYAAKEAGGKLEKFEYDPGELGAHDVEIDVESCGICHSDLSMLDNEWGITEFPFVPGH
EVVGTVSKIGDHVTSLKVGQRVGLGWHASYCNSCRTCEAGDHNLCAGATMTIGGRHGGFAD
KVRAQARAVIPLPESIDSTKAGPLFCGGITVFNPLVQFNISPTSEVGVVGIGGLGHLALQF
LNAWGCKVVAFTSSESKEKEALSLGASETINSRDEDEIKKAQGRFDLIISTVNVKLDWNLY
LSTLAPKGRLHFVGATLEPLDIGAFNLIGGQKSVSGSPVGSPATIKTMLDFAAHHDIEPVT
ETFKFEDVNKAIDRLREGKAHYRIVLTR   (SEQ ID NO:114)

Figure 47I

```
MVNAYAAFEQGGVLQPFEYDPGPLGRQQVDIQVEYCGICHSDLSMIKNEWGMTQYPFVPGH
EIVGIVAEIGSEVTTLRVGQRVGLGWYSSSCMHCEWCMGGDHHLCLSAEGTIVGRPGGFAD
QVRADQSWIVPIPESIDSAVAGPLFCAGITVFQPIIQCGVQPTDRVAVIGIGGLGHLALQF
LNAWGCEVTALSTQPDKEAEARRLGAHHFVNTRDPAALQAIANSCDYIISTVNVSLEWSIY
LNALRPKGRLHLVGVAPDLSLPVFPLLAGQRSISGSPVGSPATITKMLNFVARHGLAPQTE
VFPLAQVNEALEKLRSQHPPYRLALKC    (SEQ ID NO:115)
```

Figure 47J

```
MIRAYAAHEPGGKLEPFEYEPGSLGDEEVDIKVEYCGICHSDLSMLKNDWGMTQYPFVPGH
EVVGVVEAVGSKVKNLQIGQKVGLGWYSRSCMTCEFCMSGNHNLCQDAEGTIVGRYGGFAE
KVRAHQGWVIPLPEGVNPVTAGPLFCGGITVFNPIVQFNIKPTDQVGVIGIGGLGHMALGF
LRAWGCEITAFSTSPDKEAEAKALGATHFVNSRDPEALKALTNSFDVILSTVNADLDWPTY
IKLLRPQGRLHLVGVIPNPLSVPIFPMILGQKSVSASPLGSPTTIAQMLNFAGRHHLEPIV
EFFPLEQVNEALERLQSNKARYRIILKMDH   (SEQ ID NO:116)
```

Figure 47K

```
MIRAYAAHEPGGKLEPFEYEPGSLGDEEVDIKVEYCGICHSDLSMLKNDWGMTQYPFVPGH
EVVGVVEAVGSKVKNLQIGQKVGLGWYSRSCMTCEFCMSGNHNLCQDAEGTIVGRYGGFAE
KVRAHQGWVIPLPEGVNPVTAGPLFCGGITVFNPIVQFNIKPTDQVGVIGIGGLGHMALGF
LRAWGCEITAFSTSPDKEAEAKALGATHFVNSRDPEALKALTNSFDVILSTVNADLDWPTY
IKLLRPQGRLHLVGVIPNPLSVPIFPMILGQKSVSASPLGSPTTIAQMLNFAGRHHLEPIV
EFFPLEQVNEALERLQSNKARYRIILKMDH    (SEQ ID NO:117)
```

Figure 47L

```
MIRAYAAHEPGGKLEPFEYDPGSLGDEDVEIQVEYCGICHSDLSMLNNEWGMTRYPFVPGH
EVVGTINAVGERVKHLQVGQRVGLGWYSRSCMTCEWCLSGNQNLCPQAEGTIVGRYGGFAE
KVRAHQGWVLPLPEKLNPLTAGPLFCGGITVFNPIVQFDVKPTDRVGVIGIGGLGHMALGF
LAAWGCEITAFSTSPDKEIEAKNLGANHFVNSRDPQALKALANSLDLILSTVNADLDWDTY
ISLLRPKGRLHFVGVIPNPLSVQLFPLIGGQKSVSGSPLGSPVTLAQMLNFAGRHHVEPVV
EFYPIEQVNEAMERLKANKARYRIVLTFKNS    (SEQ ID NO:118)
```

Figure 47M

```
MIKAYAASEPGKELNSFEYDPGLLGEEDVEINVQYCGICHSDLSMLDNEWGITQYPFVPGH
EVVGTIGAVGSKVTTFQVGQTVGLGWFSRSCFDCEWCLSGDQNLCQTAEGTIVGRPGGFAD
KVRAHHRWVVPLPSGVNPETAGPLFCGGITVFNPIIQCGVKSTDRVGVIGIGGLGHLAIEF
LHAWGCEVTAFSSNPEKESEVKQLGADYFVNSRDPEAIKAVENSFDFIISTVNVSLDWNSY
ILALRPRGTLHFVGAVLNPISTQIFPLLMGQKTISGSPTGSPTTIAQMLDFAARHQIEPVT
EIFPFEQVNEAIDKLRHGQPRYRLVLKM   (SEQ ID NO:119)
```

Figure 47N

```
MRGERIVRSGVKEDILCNNAINTTIEVKVVIKAYAASEPGKELNSFEYDPGLLGEEDVEIN
VQYCGICHSDLSMLDNEWGITQYPFVPGHEVVGTIGAVGSKVTTFQVGQTVGLGWFSRSCF
DCEWCLSGDQNLCQTAEGTIVGRPGGFADKVRAHHRWVVPLPSGVNPETAGPLFCGGITVF
NPIIQCGVKSTDRVGVIGIGGLGHLAIEFLHAWGCEVTAFSSNPEKESEVKQLGADYFVNS
RDPEAIKAVENSFDFIISTVNVSLDWNSYILALRPRGTLHFVGAVLNPISTQIFPLLMGQK
TISGSPTGSPTTIAQMLDFAARHQIEPVTEIFPFEQVNEAIDKLRHGQPRYRLVLKM
(SEQ ID NO:120)
```

Figure 470

```
MRGERIVRSGVKEDILCNNAINTTIEVKVVIKAYAASEPGKELNSFEYDPGLLGEEDVEIN
VQYCGICHSDLSMLDNEWGITQYPFVPGHEVVGTIGAVGSKVTTFQVGQTVGLGWFSRSCF
DCEWCLSGDQNLCQTAEGTIVGRPGGFADKVRAHHRWVVPLPSGVNPETAGPLFCGGITVF
NPIIQCGVKSTDRVGVIGIGGLGHLAIEFLHAWGCEVTAFSSNPEKESEVKQLGADYFVNS
RDPEAIKAVENSFDFIISTVNVSLDWNSYILALRPRGTLHFVGAVLNPISTQIFPLLMGQK
TISGSPTGSPTTIAQMLDFAARHQIEPVTEIFPFEQVNEAIDKLRHGQPRYRLVLKM
(SEQ ID NO:121)
```

Figure 47P

```
MIKAYAAHEPGGQLQPFEYDPGTLGDEEVEIKVEYCGICHSDLSMLDNEWGMTDYPFVPGH
EVVGTIAALGDKVTTLNLGQRVGLGWFSGSCMTCEWCMSGNHNLCSNAEGTIVSRHGGFAD
KVRADYSWVVPLPDGINPATAGPLFCGGITVFNPIVQFDIKPSDRVGVIGIGGLGHIALGF
LQAWGCEITAFSSSPDKEAEARELGATHFINSGDVNALESVQNSFDFILATANADLDWNAY
IAALRPKGRLHFVGVIPNPLSTPIFPLILGQKSISASPVGSPATISQMINFAARQGVEPIT
ETFSFEQVNEAMEKLRHGKPRYRLVLKHS   (SEQ ID NO:122)
```

Figure 47Q

```
MIRAYAAREKGGKLEPFDYDPGILADEDVEIAVEYCGICHSDLSMLDNDWGLTTYPFVPGH
EVVGTIAALGAKVKELKLGQRVGLGWFSRSCSTCETCMSGDQNLCATAEGTIVGRHGGFAD
RVRAHHSWLVPLGNQLDAAKAGPLFCGGITVFNPIVQFNIKPTARVGVIGIGGLGHIALKF
LKAWGCEVTAFSSSPDKETEAKELGATHFINSRDPEALQSVQNYFDFIISTVNVNLDWGLY
IACLRPKGRLHIVGAVLEPMATYAFPLIMGQKSISGSPLGSPSTINKMIEFASRHGIEPVT
EIYPISQVNEAMEKLRTGQPKYRLVLQIK    (SEQ ID NO:123)
```

Figure 47R

```
MIRAYAAQEKGGKLEPFDYDPGILADEDVEIAVEYCGICHSDLSMLDNDWGLTTYPFVPGH
EVVGTIAALGAKVKELKLGQRVGLGWFSRSCSTCETCMSGDQNLCATAEGTIVGRHGGFAE
RVRAHHSWLVPLPDQLDAAKAGPLFCGGITVFNPIVQFNIKPTARVGVIGIGGLGHIALKF
LKAWGCEVTAFSSSPDKETEAKELGATHFINSRDPEALQSVQNYFDFIISTVNVNLDWGLY
IACLRPKGRLHIVGAVLEPMATYAFPLIMGQKSISGSPLGSPSTVSKMIEFASRHGIEPVT
ETYPISRVNEAMEKLRTGQPKYRLVLQIK   (SEQ ID NO:124)
```

Figure 47S

```
MQITVWQALAKGGRLERSQATLLDPGPDEVLLEVLHCGLCHSDLSMLDNSWGISTYPLVPG
HEVVGRVAAVGAGVDSGLLGSIQGLGWIAGSCRHCDWCLGGNANLCPSLEASVVGRHGGFA
SHVMAHQDWIVAIPDGVSAADAGPLFCGGITVFAPLFDEAVSPTSRVAVIGIGGLGHMALQ
FARAWGCEVTAVTTSPAKADEARRLGAHRVLALSELGDHPGVFDLIINTSNHDLDWPALIG
SLAPLGRLHQLGVPLSPLQIPAFPLIAGRRSVTGSPTSSPASLRRMVEFCARHGIAPLVEH
LPMAEINTAIERLRQGDVRYRFVLDGPA    (SEQ ID NO:125)
```

Figure 47T

```
MVVTITVWQAREAGAPLERAERAMLEPAAGELVLEVLHCGLCHSDLSMLDNNWGLSAYPLV
PGHEVVGRVVRVGEGVDPGVIGELRGLGWISGSCMHCALCLGGTANLCGSLEATIVGRQGG
FASHVTARQDWAIRLPEGMDPAAAGPLFCGGITVFAPLVDEVVSPTAHVAVIGIGGLGHMA
LQFARAWGCEVTALTTHLAKAEEAKRFGAHHVESLEELPDLAGRFDLVINTVNHALDWGAV
MGSLAPLGRLHQLGAVLEPLQVSAFDLIMARRSITGSPTSSPASLMKMVEFCVRHNIRPQV
EHLPMDRLNEAIDRLRRGDVRYRFVLDSVAD     (SEQ ID NO:126)
```

Figure 47U

```
MQITVWQALAKGGRLERSQATLLDPGPDEVLLEVLHCGLCHSDLSMLDNSWGISTYPLVPG
HEVVGRVAAVGAGVDSGLLGSIQGLGWIAGSCRHCDWCLGGNANLCPSLEASVVGRHGGFA
SHVMAHQDWIVAIPDGVSAADAGPLFCGGITVFAPLFDEAVSPTSRVAVIGIGGLGHMALQ
FARAWGCEVTAVTTSPAKADEARRLGAHRVLALSELGDHPGVFDLIINTSNHDLDWPALIG
SLAPLGRLHQLGVPLSPLQIPAFPLIAGRRSVTGSPTSSPASLRRMVEFCARHGIAPLVEH
LPMAEINTAIERLRQGDVRYRFVLDGPA    (SEQ ID NO:127)
```

Figure 47V

```
MISVWQAPSAGAPLECGQRPAPEPAADELVLEVMHCGLCHSDLSMIGNHWGVSRYPLVPGH
EVIGRVTAVGEGVDPGLIGDVRGLGWISGSCNHCSLCLGGDQNLCTSLEATIVGRQGGFAS
HVVARQDWAIPLPPGLDPADAGPLFCGGITVFAPLVDEAVSPTAHVAVVGIGGLGHIALQF
ARAWGCEVTAITTNLAKAEQARRFGAHHVEELEMLPDLQSRFDLVINTVNHPLDWSAVMAS
LRPRGRLHQLGAVLEPIQVGAFDLIPARRSITGSPTSSPASLQKMVEFCVRHNILPLVEHL
PMDQVNVAIQRLAKGDVRYRFVLDA    (SEQ ID NO:128)
```

Figure 47W

```
MISVWQAPSAGAPLECAQRPALQPVADELVLEVMHCGLCHSDLSMIGNHWGVSRYPLVPGH
EVIGRVTAVGEGVDPGVIGEVRGLGWISGSCNHCSLCLGGDQNLCSSLEATIVGRQGGFAS
HVVARQDWTIPLPTGLDPAEAGPLFCGGVTVFAPLVDEAVSPTAHVAVVGIGGLGHIALQF
ARAWGCEVTAITTNPAKTEQARRFGAHHVEELEALSDLQRRFDLVINTVNHPLDWSAVMAS
LKPRGRLHQLGAVLEPIQVGAFDLISARRSITGSPTSSPASLLKMVEFCVRHNILPLVEHL
PMDQVNVAIERLAKGDVRYRFVLDA   (SEQ ID NO:129)
```

Figure 47X

| shaked Erlenmeyer flask (time course in days) | 0 | 5 | 6 | 7 | 9 | 12 | 13 | 14 | 15 | 16 | 19 |
|---|---|---|---|---|---|---|---|---|---|---|---|
| EtOH % (v/v) | | | | | | | | | | | |
| 6803-PisiA-ZmPDC-ADHII | 0 | 0,0172 | 0,021 | 0,026 | 0,0384 | 0,0429 | 0,0407 | 0,0401 | 0,0401 | 0,0354 | 0,0304 |
| 6803-PisiA-ZmPDC | 0 | 0,0216 | 0,0247 | 0,0303 | 0,0422 | 0,0541 | 0,057 | 0,0596 | 0,072 | 0,0733 | 0,0882 |
| 6803-PisiA-ZpPDC-ADHII | 0 | 0,0189 | 0,0224 | 0,029 | 0,043 | 0,0522 | 0,0497 | 0,0527 | 0,0549 | 0,0511 | 0,0459 |
| 6803-PisiA-ZpPDC | 0 | 0,0258 | 0,0303 | 0,0355 | 0,0504 | 0,0688 | 0,0682 | 0,0749 | 0,0826 | 0,0833 | 0,0911 |

Figure 48C

| shaked Erlenmeyer flask (time course in days) | 0 | 5 | 8 | 9 | 10 | 11 | 15 | 19 |
|---|---|---|---|---|---|---|---|---|
| EtOH % (v/v) | | | | | | | | |
| PpetJ-PDC | 0 | 0,0145 | 0,0191 | 0,0218 | 0,0225 | 0,0273 | 0,0323 | 0,0418 |
| PpetJ-PDC/SynADH | 0 | 0,0174 | 0,022 | 0,0267 | 0,0265 | 0,0306 | 0,0362 | 0,0426 |

Figure 48E

| aerated with 0,5% CO2 | | | | | | | | |
|---|---|---|---|---|---|---|---|---|
| EtOH % (v/v) | 0 | 3 | 4 | 7 | 10 | 12 | 14 | 17 |
| PisiA-PDC/ADHII | 0 | 0,020 | 0,047 | 0,066 | 0,086 | 0,118 | 0,133 | 0,116 |
| PisiA-PDC | 0 | 0,012 | 0,031 | 0,052 | 0,087 | 0,108 | 0,134 | 0,127 |

Figure 48G

| aerated with 0,5% CO2 | | | | | | | | | | | | | | |
|---|---|---|---|---|---|---|---|---|---|---|---|---|---|---|
| EtOH % (v/v) | 0 | 1 | 2 | 3 | 4 | 7 | 8 | 10 | 11 | 14 | 15 | 16 | 17 | 18 |
| PpetJ-PDC/ADHII | 0 | 0,0028 | 0,0101 | 0,0208 | 0,0338 | 0,0655 | 0,0752 | 0,0896 | 0,1005 | 0,1096 | 0,1186 | 0,1169 | 0,126 | 0,1198 |
| PpetJ-PDC/SynADH | 0 | 0,0051 | 0,0126 | 0,0279 | 0,0456 | 0,0985 | 0,1325 | 0,1543 | 0,1726 | 0,2023 | 0,2194 | 0,2241 | 0,241 | 0,2494 |

Figure 48 I

| promoter | constitutive | light conditions | stationary phase | nutrient status | heat stress | cold stress | salt/osmotic stress | oxidative stress |
|---|---|---|---|---|---|---|---|---|
| isiA | | high light | X | iron↓ | | | | X |
| nblA | | | | nitrogen↓ | | | | X |
| nicA | (X) | | | nitrogen↓ | | | | |
| nirA | | | | NH₄⁺ → NO₃⁻ | | | | |
| petJ | | | | copper↓ | | | | |
| petE | | | | copper↑ | | | | |
| psaA | X | low light | | | | | | |
| psbA2 | (X) | high light | | | | | | X |
| rbcL | X | | | | | | | |
| lrtA | | darkness | | | | | | |
| crhC | | | | | | X | | |
| sigB | | | X | | X | | X | |
| ggpS | | | | | | | X | |
| htpG | | | | | X | | X | |
| hspA | | | | | X | X | X | X |
| clpB1 | | | | | X | X | X | X |
| hliB | | | | | X | X | X | X |

Figure 49A

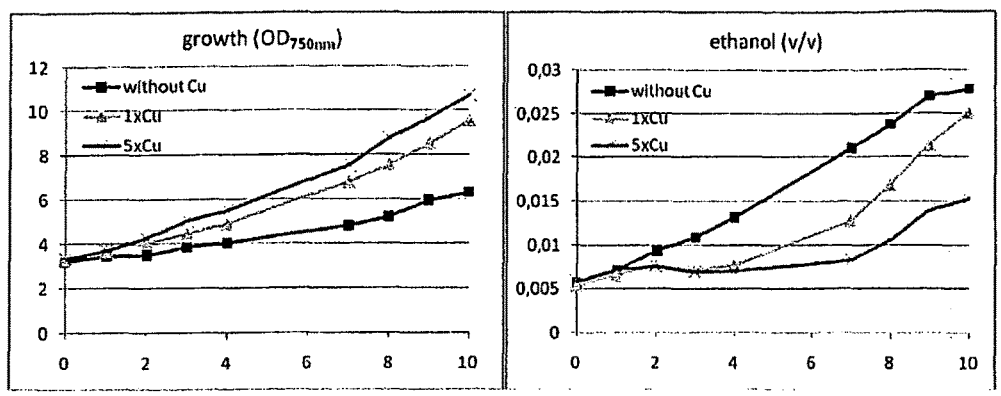
Figure 49H                    Figure 49I

SEQUENCE LISTING

```
<160> NUMBER OF SEQ ID NOS: 212

<210> SEQ ID NO 1
<211> LENGTH: 477
<212> TYPE: PRT
<213> ORGANISM: Synechocystis PCC6803

<400> SEQUENCE: 1

Met Lys Ile Leu Phe Val Ala Ala Glu Val Ser Pro Leu Ala Lys Val
1               5                   10                  15

Gly Gly Met Gly Asp Val Val Gly Ser Leu Pro Lys Val Leu His Gln
            20                  25                  30

Leu Gly His Asp Val Arg Val Phe Met Pro Tyr Tyr Gly Phe Ile Gly
        35                  40                  45

Asp Lys Ile Asp Val Pro Lys Glu Pro Val Trp Lys Gly Glu Ala Met
    50                  55                  60

Phe Gln Gln Phe Ala Val Tyr Gln Ser Tyr Leu Pro Asp Thr Lys Ile
65                  70                  75                  80

Pro Leu Tyr Leu Phe Gly His Pro Ala Phe Asp Ser Arg Arg Ile Tyr
                85                  90                  95

Gly Gly Asp Asp Glu Ala Trp Arg Phe Thr Phe Phe Ser Asn Gly Ala
```

```
                100             105             110
Ala Glu Phe Ala Trp Asn His Trp Lys Pro Glu Ile Ile His Cys His
            115             120             125
Asp Trp His Thr Gly Met Ile Pro Val Trp Met His Gln Ser Pro Asp
130             135             140
Ile Ala Thr Val Phe Thr Ile His Asn Leu Ala Tyr Gln Gly Pro Trp
145             150             155             160
Arg Gly Leu Leu Glu Thr Met Thr Trp Cys Pro Trp Tyr Met Gln Gly
            165             170             175
Asp Asn Val Met Ala Ala Ile Gln Phe Ala Asn Arg Val Thr Thr
            180             185             190
Val Ser Pro Thr Tyr Ala Gln Gln Ile Gln Thr Pro Ala Tyr Gly Glu
            195             200             205
Lys Leu Glu Gly Leu Leu Ser Tyr Leu Ser Gly Asn Leu Val Gly Ile
            210             215             220
Leu Asn Gly Ile Asp Thr Glu Ile Tyr Asn Pro Ala Glu Asp Arg Phe
225             230             235             240
Ile Ser Asn Val Phe Asp Ala Asp Ser Leu Asp Lys Arg Val Lys Asn
                245             250             255
Lys Ile Ala Ile Gln Glu Gly Thr Gly Leu Glu Ile Asn Arg Asn Ala
            260             265             270
Met Val Val Gly Ile Val Ala Arg Leu Val Glu Gln Lys Gly Ile Asp
            275             280             285
Leu Val Ile Gln Ile Leu Asp Arg Phe Met Ser Tyr Thr Asp Ser Gln
290             295             300
Leu Ile Ile Leu Gly Thr Gly Asp Arg His Tyr Glu Thr Gln Leu Trp
305             310             315             320
Gln Met Ala Ser Arg Phe Pro Gly Arg Met Ala Val Gln Leu Leu His
            325             330             335
Asn Asp Ala Leu Ser Arg Arg Val Tyr Ala Gly Ala Asp Val Phe Leu
            340             345             350
Met Pro Ser Arg Phe Glu Pro Cys Gly Leu Ser Gln Leu Met Ala Met
            355             360             365
Arg Tyr Gly Cys Ile Pro Ile Val Arg Arg Thr Gly Gly Leu Val Asp
            370             375             380
Thr Val Ser Phe Tyr Asp Pro Ile Asn Glu Ala Gly Thr Gly Tyr Cys
385             390             395             400
Phe Asp Arg Tyr Glu Pro Leu Asp Cys Phe Thr Ala Met Val Arg Ala
                405             410             415
Trp Glu Gly Phe Arg Phe Lys Ala Asp Trp Gln Lys Leu Gln Gln Arg
            420             425             430
Ala Met Arg Ala Asp Phe Ser Trp Tyr Arg Ser Ala Gly Glu Tyr Ile
            435             440             445
Lys Val Tyr Lys Gly Val Val Gly Lys Pro Glu Glu Leu Ser Pro Met
            450             455             460
Glu Glu Glu Lys Ile Ala Glu Leu Thr Ala Ser Tyr Arg
465             470             475

<210> SEQ ID NO 2
<211> LENGTH: 491
<212> TYPE: PRT
<213> ORGANISM: Synechocystis PCC6803

<400> SEQUENCE: 2
```

```
Met Tyr Ile Val Gln Ile Ala Ser Glu Cys Ala Pro Val Ile Lys Ala
1               5                   10                  15
Gly Gly Leu Gly Asp Val Ile Tyr Gly Leu Ser Arg Glu Leu Glu Leu
            20                  25                  30
Arg Gly His Cys Val Glu Leu Ile Leu Pro Met Tyr Asp Cys Met Arg
        35                  40                  45
Tyr Asp His Ile Trp Gly Leu His Asp Ala Tyr Arg Asn Leu Glu Val
    50                  55                  60
Pro Trp Tyr Gly Ser Ser Ile Phe Cys Asp Val Phe Cys Gly Trp Val
65                  70                  75                  80
His Gly Arg Leu Cys Phe Phe Ile Gln Pro Lys Ser Ser Asp Asn Phe
            85                  90                  95
Phe Asn Arg Gly His Tyr Tyr Gly Ala Leu Asp Asp His Met Arg Phe
            100                 105                 110
Ala Phe Phe Ser Lys Ala Ala Met Glu Phe Leu Leu Arg Ser Asn Lys
            115                 120                 125
Arg Pro Asp Ile Ile His Cys His Asp Trp Gln Thr Gly Leu Val Pro
    130                 135                 140
Val Leu Leu Tyr Glu Ile Tyr Arg Phe His Gly Met Asp His Gln Arg
145                 150                 155                 160
Val Cys Tyr Thr Ile His Asn Phe Lys His Gln Gly Ile Ala Gly Ala
                165                 170                 175
Asn Ile Leu His Ala Thr Gly Leu Asn Asn Asp Ser Tyr Tyr Phe Ser
            180                 185                 190
Tyr Asp Arg Leu Gln Asp Asn Phe Asn Pro Asn Ala Ile Asn Phe Met
            195                 200                 205
Lys Gly Gly Ile Val Tyr Ser Asn Tyr Val Asn Thr Val Ser Pro His
    210                 215                 220
His Ala Trp Glu Ala Arg Phe Ser Asp Ile Ser Cys Gly Leu Gly His
225                 230                 235                 240
Thr Leu Glu Ile His Gln Gln Lys Phe Gly Gly Ile Leu Asn Gly Leu
                245                 250                 255
Asp Tyr Glu Val Trp Asn Pro Glu Ile Asp Pro Leu Leu Ala Ser Asn
            260                 265                 270
Phe Ser Val Lys Thr Phe Gly Asp Lys Ala Lys Asn Lys Gln Ala Leu
            275                 280                 285
Arg Glu Arg Leu Leu Leu Glu Thr Asp Asp Lys Lys Pro Met Leu Cys
    290                 295                 300
Phe Ile Gly Arg Leu Asp Gly Gln Lys Gly Val His Leu Val His His
305                 310                 315                 320
Ser Ile Tyr Tyr Ala Leu Ser Gln Gly Ala Gln Phe Val Leu Leu Gly
                325                 330                 335
Ser Ala Thr Glu Pro Asn Leu Ser Lys Trp Phe Trp His Glu Lys Gln
            340                 345                 350
His Leu Asn Asp Asn Pro Asn Val His Leu Glu Leu Gly Phe Asp Glu
            355                 360                 365
Glu Leu Ala His Leu Ile Tyr Gly Ala Ala Asp Ile Ile Val Val Pro
    370                 375                 380
Ser Asn Tyr Glu Pro Cys Gly Leu Thr Gln Met Ile Gly Leu Arg Tyr
385                 390                 395                 400
Gly Ala Val Pro Val Val Arg Gly Val Gly Gly Leu Val Asn Thr Val
                405                 410                 415
Phe Asp Arg Asp Tyr Asp Gln Asn His Pro Pro Glu Lys Arg Asn Gly
```

```
                420             425              430
Phe Val Phe Tyr Gln Pro Asp Glu Tyr Ala Leu Glu Thr Ala Leu Ser
            435                 440                 445

Arg Ala Ile Ala Leu Tyr Lys Asp Asp Pro Val Ala Phe Lys Thr Leu
    450                 455                 460

Ala Leu Gln Gly Met Ala Tyr Asp Tyr Ser Trp Asn Lys Pro Gly Leu
465             470                 475                 480

Gln Tyr Val Glu Ala Tyr Glu Tyr Ile Arg Ala
                485                 490

<210> SEQ ID NO 3
<211> LENGTH: 5069
<212> TYPE: DNA
<213> ORGANISM: Artificial Sequence
<220> FEATURE:
<223> OTHER INFORMATION: synthetic combined bacterial sequences

<400> SEQUENCE: 3
```

| | | | | | |
|---|---|---|---|---|---|
| tcgcgcgttt | cggtgatgac | ggtgaaaacc | tctgacacat | gcagctcccg | gagacggtca | 60 |
| cagcttgtct | gtaagcggat | gccgggagca | gacaagcccg | tcagggcgcg | tcagcgggtg | 120 |
| ttggcgggtg | tcggggctgg | cttaactatg | cggcatcaga | gcagattgta | ctgagagtgc | 180 |
| accatatgcg | gtgtgaaata | ccgcacagat | gcgtaaggag | aaaataccgc | atcaggcgcc | 240 |
| attcgccatt | caggctgcgc | aactgttggg | aagggcgatc | ggtgcgggcc | tcttcgctat | 300 |
| tacgccagct | ggcgaaaggg | ggatgtgctg | caaggcgatt | aagttgggta | acgccagggt | 360 |
| tttcccagtc | acgacgttgt | aaaacgacgg | ccagtgaatt | cgagctcggt | accaactaaa | 420 |
| gtctgcccgc | atggcccgtt | gctgtaattt | ttgccaatct | gccttgaaac | ggaaaccctc | 480 |
| ccaggcccga | accatggccg | taaagcaatc | caggggttca | taacggtcaa | agcaatagcc | 540 |
| ggtgccggct | tcattgatag | gatcgtagaa | ggataccgta | tccaccaaac | cccctgtccg | 600 |
| ccgcacaatg | gggatacagc | cataacgcat | ggccatcaat | tgactcagcc | cacgggctc | 660 |
| aaagcgagaa | ggcattaaaa | acacatccgc | cccggcatag | actcgacggg | aaagggcatc | 720 |
| gttgtggagt | aattgcaccg | ccatccgccc | aggaaatcgg | gaagccatct | gccaaagttg | 780 |
| ggtttcgtaa | tggcgatcgc | cagtgccgag | gataattaac | tgggaatcgg | tgtaggacat | 840 |
| gaagcggtca | aggatctgaa | tcaccaaatc | aatccccttt | tgttccacca | agcgagccac | 900 |
| tatacccacg | taagaggttc | caactttcac | cataatgaaa | taagatcact | accgggcgta | 960 |
| tttttttgagt | tatcgagatt | ttcaggagct | aaggaagcta | aaatggagaa | aaaaatcact | 1020 |
| ggatatacca | ccgttgatat | atcccaatgg | catcgtaaag | aacattttga | ggcatttcag | 1080 |
| tcagttgctc | aatgtaccta | taaccagacc | gttcagctgg | atattacggc | cttttttaaag | 1140 |
| accgtaaaga | aaaataagca | caagttttat | ccggccttta | ttcacattct | tgcccgcctg | 1200 |
| atgaatgctc | atccggaatt | ccgtatggca | atgaaagacg | gtgagctggt | gatatgggat | 1260 |
| agtgttcacc | cttgttacac | cgttttccat | gagcaaactg | aaacgttttc | atcgctctgg | 1320 |
| agtgaatacc | acgacgattt | ccggcagttt | ctacacatat | attcgcaaga | tgtggcgtgt | 1380 |
| tacggtgaaa | acctggccta | tttccctaaa | gggtttattg | agaatatgtt | tttcgtctca | 1440 |
| gccaatccct | gggtgagttt | caccagtttt | gatttaaacg | tggccaatat | ggacaacttc | 1500 |
| ttcgccccg | ttttcaccat | gggcaaatat | tatacgcaag | gcgacaaggt | gctgatgccg | 1560 |
| ctggcgattc | aggttcatca | tgccgtctgt | gatggcttcc | atgtcggcag | aatgcttaat | 1620 |
| gaattacaac | agtactgcga | tgagtggcag | ggcggggcgt | aatttttta | aggcagttat | 1680 |

```
tggtgccctt aaacgcctgg tgctacgcct gaataagtga taataagcgg atgaatggca    1740
gaaattcgaa agcaaattcg acccggtcgt cggttcaggg cagggtcgtt aaatagccgc    1800
ttatgtctat tgctggttta ccggtttatt gactaccgga agcagtgtga ccgtgtgctt    1860
ctcaaatgcc tgaggccagt ttgctcaggc tctccccgtg gaggtaataa ttgacgatat    1920
gatcatttat tctgcctccc agagcctgat aaaaacggtt agcgcttcgt taatacagat    1980
gtaggtgttc cacagggtag ccagcagcat cctgcgatgc atggcattac gattaatttc    2040 taacccgtt tcctcctgga tggcaatttt atttttcacc cgcttgtcca aactgtccgc    2100
atcgaaaaca ttgctgataa agcggtcttc cgccgggttg taaatctccg tatcaatacc    2160
gttgagaata ccgactaaat taccactcag gtaggacaat aaccctttcca gcttttcccc    2220 ataggccggg gtttggatct gttgggcata ggtgggagaa acggtagtca cccgattggc    2280
aaattgaatc gccgccgcca tcacattgtc tccctgcatg taccaaggac accaagtcat    2340
agtttcaagc aagccccgcc agggcccttg gtaagcaaga ttatggatgg tgaaaacggt    2400
ggcgatgtct ggggactgat gcatccaaac agggatcatg ccagtgtgcc aatcatggca    2460
atggataatt tccggcttcc aatggttcca ggcaaattca gctgcccgt tagaaaaaaa     2520 agtgaaccgc cacgcctcgt catctccgcc atagatcctt cgggagtcga agctggatg    2580 gccgaacaag tagagaggaa ttttggtgtc cggtagatag gactggtaaa cagcaaactg    2640
ctggaacatg gcttcccctt tccagaccgg ctccttgggc acatcaatct tgtcgccgat    2700
gaaaccgtag tagggcatga agacacggac atcatggccc aactgatgca gaactttagg    2760
cagggaaccc accacatccc ccatgccacc tacctttgct aggggggata cttccgccgc    2820
cacaaataaa agcttggcgt aatcatggtc atagctgttt cctgtgtgaa attgttatcc    2880
gctcacaatt ccacacaaca tacgagccgg aagcataaag tgtaaagcct ggggtgccta    2940
atgagtgagc taactcacat taattgcgtt gcgctcactg cccgctttcc agtcgggaaa    3000
cctgtcgtgc cagctgcatt aatgaatcgg ccaacgcgcg gggagaggcg gtttgcgtat    3060
tgggcgctct tccgcttcct cgctcactga ctcgctgcgc tcggtcgttc ggctgcggcg    3120
agcggtatca gctcactcaa aggcggtaat acggttatcc acagaatcag gggataacgc    3180
aggaaagaac atgtgagcaa aaggccagca aaaggccagg aaccgtaaaa aggccgcgtt    3240
gctggcgttt ttccataggc tccgcccccc tgacgagcat cacaaaaatc gacgctcaag    3300
tcagaggtgg cgaaacccga caggactata aagataccag gcgtttcccc ctggaagctc    3360
cctcgtgcgc tctcctgttc cgaccctgcc gcttaccgga tacctgtccg cctttctccc    3420
ttcgggaagc gtggcgcttt ctcatagctc acgctgtagg tatctcagtt cggtgtaggt    3480
cgttcgctcc aagctgggct gtgtgcacga accccccgtt cagcccgacc gctgcgcctt    3540
atccggtaac tatcgtcttg agtccaaccc ggtaagacac gacttatcgc cactggcagc    3600
agccactggt aacaggatta gcagagcgag gtatgtaggc ggtgctacag agttcttgaa    3660
gtggtggcct aactacggct acactagaag gacagtattt ggtatctgcg ctctgctgaa    3720
gccagttacc ttcggaaaaa gagttggtag ctcttgatcc ggcaaacaaa ccaccgctgg    3780
tagcggtggt ttttttgttt gcaagcagca gattacgcgc agaaaaaaag gatctcaaga    3840
agatcctttg atcttttcta cggggtctga cgctcagtgg aacgaaaact cacgttaagg    3900
gattttggtc atgagattat caaaaaggat cttcacctag atccttttaa attaaaaatg    3960
aagttttaaa tcaatctaaa gtatatatga gtaaacttgg tctgacagtt accaatgctt    4020
```

```
aatcagtgag gcacctatct cagcgatctg tctatttcgt tcatccatag ttgcctgact    4080
ccccgtcgtg tagataacta cgatacggga gggcttacca tctggcccca gtgctgcaat    4140
gataccgcga gacccacgct caccggctcc agatttatca gcaataaacc agccagccgg    4200
aagggccgag cgcagaagtg gtcctgcaac tttatccgcc tccatccagt ctattaattg    4260
ttgccgggaa gctagagtaa gtagttcgcc agttaatagt ttgcgcaacg ttgttgccat    4320
tgctacaggc atcgtggtgt cacgctcgtc gtttggtatg gcttcattca gctccggttc    4380
ccaacgatca aggcgagtta catgatcccc catgttgtgc aaaaaagcgg ttagctcctt    4440
cggtcctccg atcgttgtca gaagtaagtt ggccgcagtg ttatcactca tggttatggc    4500
agcactgcat aattctctta ctgtcatgcc atccgtaaga tgcttttctg tgactggtga    4560
gtactcaacc aagtcattct gagaatagtg tatgcggcga ccgagttgct cttgcccggc    4620
gtcaatacgg gataataccg cgccacatag cagaacttta aaagtgctca tcattggaaa    4680
acgttcttcg gggcgaaaac tctcaaggat cttaccgctg ttgagatcca gttcgatgta    4740
acccactcgt gcacccaact gatcttcagc atcttttact ttcaccagcg tttctgggtg    4800
agcaaaaaca ggaaggcaaa atgccgcaaa aagggaata agggcgacac ggaaatgttg    4860
aatactcata ctcttccttt ttcaatatta ttgaagcatt tatcagggtt attgtctcat    4920
gagcggatac atatttgaat gtatttagaa aaataaacaa ataggggttc gcgcacatt    4980 tccccgaaaa gtgccacctg acgtctaaga accattatt atcatgacat aacctataa    5040 aaataggcgt atcacgaggc cctttcgtc                                      5069

<210> SEQ ID NO 4
<211> LENGTH: 5533
<212> TYPE: DNA
<213> ORGANISM: Artificial Sequence
<220> FEATURE:
<223> OTHER INFORMATION: synthetic combined bacterial sequences

<400> SEQUENCE: 4
tcgcgcgttt cggtgatgac ggtgaaaacc tctgacacat gcagctcccg gagacggtca      60
cagcttgtct gtaagcggat gccgggagca gacaagcccg tcagggcgcg tcagcgggtg     120
ttggcgggtg tcgggctggc ttaactatg cggcatcaga gcagattgta ctgagagtgc     180
accatatgcg gtgtgaaata ccgcacagat gcgtaaggag aaaataccgc atcaggcgcc     240
attcgccatt caggctgcgc aactgttggg aagggcgatc ggtgcgggcc tcttcgctat     300
tacgccagct ggcgaaaggg ggatgtgctg caaggcgatt aagttgggta acgccagggt     360
tttcccagtc acgacgttgt aaaacgacgg ccagtgaatt ctcctccagt gcttgcaagg     420 gagggggcaat ataggaaaat acaatcaact cgatcgccgt cgagccgaag tcgagtaaaa    480
accgctatca ggagcctcta tgtacatcgt tcaaattgcc tcagaatgcg ccccgtcat     540 taaggctggg ggattggggg atgttattta cggcctaagc cgtgaattgg aactgcgggg    600
ccattgcgtc gagctaatcc tacccatgta cgattgcatg cgctatgacc acatctgggg    660
tttacacgat gcttaccgca acctagaggt gccctggtat ggaagctcaa tcttctgtga    720
tgttttttgt ggctgggttc acggtaggct ctgcttcttc attcagccca atcttctga    780 taacttttc aatcggggtc attattatgg cgctctagac gaccatatgc gctttgcctt    840
tttctccaag gcggccatgg agttttttgct acgcagtaac aaacgccag acattatcca    900 ctgccacgat tggcaaacgg gactggtgcc ggtgttgttg tatgaaattt accgtttcca    960
tggcatggac catcaacggg tttgttacac catccacaat ttcaaacacc agggtattgc    1020
```

-continued

```
tggagccaat attctccacg ccactgggct caataatgac agttattatt tcagctacga      1080
tcgcctgcag gataatttca atcccaatgc gattaacttc atgaaggggg gcattgtcga      1140
cctgcagggg ggggggggaa agccacgttg tgtctcaaaa tctctgatgt tacattgcac      1200
aagataaaaa tatatcatca tgaacaataa aactgtctgc ttacataaac agtaatacaa      1260
ggggtgttat gagccatatt caacgggaaa cgtcttgctc gaggccgcga ttaaattcca      1320
acatggatgc tgatttatat gggtataaat gggctcgcga taatgtcggg caatcaggtg      1380
cgacaatcta tcgattgtat gggaagcccg atgcgccaga gttgtttctg aaacatggca      1440
aaggtagcgt tgccaatgat gttacagatg agatggtcag actaaactgg ctgacggaat      1500
ttatgcctct tccgaccatc aagcatttta tccgtactcc tgatgatgca tggttactca      1560
ccactgcgat ccccgggaaa acagcattcc aggtattaga agaatatcct gattcaggtg      1620
aaaatattgt tgatgcgctg gcagtgttcc tgcgccggtt gcattcgatt cctgtttgta      1680
attgtccttt taacagcgat cgcgtatttc gtctcgctca ggcgcaatca cgaatgaata      1740
acggtttggt tgatgcgagt gattttgatg acgagcgtaa tggctggcct gttgaacaag      1800
tctggaaaga aatgcataag cttttgccat tctcaccgga ttcagtcgtc actcatggtg      1860
atttctcact tgataacctt atttttgacg aggggaaatt aataggttgt attgatgttg      1920
gacgagtcgg aatcgcagac cgataccagg atcttgccat cctatggaac tgcctcggtg      1980
agttttctcc ttcattacag aaacggcttt ttcaaaaata tggtattgat aatcctgata      2040
tgaataaatt gcagtttcat ttgatgctcg atgagttttt ctaatcagaa ttggttaatt      2100
ggttgtaaca ctggcagagc attacgctga cttgacggga cggcggcttt gttgaataaa      2160
tcgaactttt gctgagttga aggatcagat cacgcatctt cccgacaacg cagaccgttc      2220
cgtggcaaag caaaagttca aaatcaccaa ctggtccacc tacaacaaag ctctcatcaa      2280
ccgtggctcc ctcactttct ggctggatga tggggcgatt caggcctggt atgagtcagc      2340
aacaccttct tcacgaggca gacctcagcg ccccccccccc cctgcaggtc tactccaact      2400
atgtcaacac cgtttccccc caccatgctt gggaagcccg ttttccgat atttcctgtg      2460
gcttgggcca taccctggaa atccatcagc aaaaattcgg cggtattttg aacggtttgg      2520
attacgaagt gtggaaccca gaaattgatc ctttactggc gagtaacttc agtgtcaaaa      2580
cctttggcga taaggcaaaa aataagcaag cgttacggga agattactg ttagaaacgg      2640
atgataaaaa acccatgctc tgctttattg gccgcttgga tggacaaaaa ggtgtgcact      2700
tggtgcatca ctccatctac tacgccctca gccaggagc gcaatttgtc ctgctcggct      2760
ccgccaccga acccaatctg agcaaatggt tctggcatga aaacaacat ctcaacgata      2820
accccaatgt ccatctagag ttgggctttg acgaggagct ggcccactta atttacggag      2880
cggcggacat tattgtggtg cccagtaact acgaaccctg tggtttgacc caaatgattg      2940
gtctgcgtta tgggccgtt ccggtggtgc ggggagtagg cggttggta aatactgttt      3000
tcgaccggga ttatgaccag aaccatcccc cggagaaacg taatggtttt gttttctatc      3060
aaccggatga gtatgccctg gaaacggccc tcagtcgggc gatcgccttg tataaggatg      3120
atcccgtggc ttttaaaacc ttggccttgc agggcatggc ctacgactac tcttggaata      3180
aaccagggct ccaatatgtg gaagcctacg aatacatccg ggcttaacac ctcgggtttg      3240
taacagtttc gttacactag ttcagaggcg gagtcaaagc agttggtcag aataagcttg      3300
gcgtaatcat ggtcatagct gtttcctgtg tgaaattgtt atccgctcac aattccacac      3360
```

```
aacatacgag ccggaagcat aaagtgtaaa gcctggggtg cctaatgagt gagctaactc    3420
acattaattg cgttgcgctc actgcccgct ttccagtcgg gaaacctgtc gtgccagctg    3480
cattaatgaa tcggccaacg cgcggggaga ggcggtttgc gtattgggcg ctcttccgct    3540
tcctcgctca ctgactcgct gcgctcggtc gttcggctgc ggcgagcggt atcagctcac    3600
tcaaaggcgg taatacggtt atccacagaa tcagggata acgcaggaaa gaacatgtga    3660
gcaaaaggcc agcaaaaggc caggaaccgt aaaaaggccg cgttgctggc gttttttccat    3720
aggctccgcc cccctgacga gcatcacaaa aatcgacgct caagtcagag gtggcgaaac    3780
ccgacaggac tataaagata ccaggcgttt ccccctggaa gctccctcgt gcgctctcct    3840
gttccgaccc tgccgcttac cggatacctg tccgcctttc tcccttcggg aagcgtggcg    3900
ctttctcata gctcacgctg taggtatctc agttcggtgt aggtcgttcg ctccaagctg    3960
ggctgtgtgc acgaaccccc cgttcagccc gaccgctgcg ccttatccgg taactatcgt    4020
cttgagtcca acccggtaag acacgactta tcgccactgg cagcagccac tggtaacagg    4080
attagcagag cgaggtatgt aggcggtgct acagagttct tgaagtggtg gcctaactac    4140
ggctacacta aaggacagt atttggtatc tgcgctctgc tgaagccagt taccttcgga    4200
aaaagagttg gtagctcttg atccggcaaa caaaccaccg ctggtagcgg tggtttttttt    4260
gtttgcaagc agcagattac gcgcagaaaa aaggatctc aagaagatcc tttgatcttt    4320
tctacggggt ctgacgctca gtggaacgaa aactcacgtt aagggatttt ggtcatgaga    4380
ttatcaaaaa ggatcttcac ctagatcctt ttaaattaaa aatgaagttt taaatcaatc    4440
taaagtatat atgagtaaac ttggtctgac agttaccaat gcttaatcag tgaggcacct    4500
atctcagcga tctgtctatt tcgttcatcc atagttgcct gactccccgt cgtgtagata    4560
actacgatac gggagggctt accatctggc cccagtgctg caatgatacc gcgagaccca    4620
cgctcaccgg ctccagattt atcagcaata aaccagccag ccggaagggc cgagcgcaga    4680
agtggtcctg caactttatc cgcctccatc cagtctatta attgttgccg ggaagctaga    4740
gtaagtagtt cgccagttaa tagtttgcgc aacgttgttg ccattgctac aggcatcgtg    4800
gtgtcacgct cgtcgtttgg tatggcttca ttcagctccg gttcccaacg atcaaggcga    4860
gttacatgat cccccatgtt gtgcaaaaaa gcggttagct ccttcggtcc tccgatcgtt    4920
gtcagaagta agttggccgc agtgttatca ctcatggtta tggcagcact gcataattct    4980
cttactgtca tgccatccgt aagatgcttt tctgtgactg gtgagtactc aaccaagtca    5040
ttctgagaat agtgtatgcg gcgaccgagt tgctcttgcc cggcgtcaat acgggataat    5100
accgcgccac atagcagaac tttaaaagtg ctcatcattg gaaaacgttc ttcggggcga    5160
aaactctcaa ggatcttacc gctgttgaga tccagttcga tgtaacccac tcgtgcaccc    5220
aactgatctt cagcatcttt tactttcacc agcgtttctg ggtgagcaaa aacaggaagg    5280
caaaatgccg caaaaaaggg aataagggcg acacggaaat gttgaatact catactcttc    5340
cttttttcaat attattgaag catttatcag ggttattgtc tcatgagcgg atacatattt    5400
gaatgtattt agaaaaataa acaaataggg gttccgcgca catttccccg aaaagtgcca    5460
cctgacgtct aagaaaccat tattatcatg acattaacct ataaaaatag gcgtatcacg    5520
aggccctttc gtc                                                      5533

<210> SEQ ID NO 5
<211> LENGTH: 360
<212> TYPE: PRT
<213> ORGANISM: Synechocystis PCC6803
```

<400> SEQUENCE: 5

```
Met Glu Ile Gly Val Pro Lys Glu Ile Lys Asp Gln Glu Phe Arg Val
1               5                   10                  15

Gly Leu Thr Pro Ser Ser Val Arg Ala Leu Leu Ser Gln Gly His Gln
            20                  25                  30

Val Phe Val Glu Glu Gly Ala Gly Val Gly Ser Gly Phe Pro Asp Gly
        35                  40                  45

Ala Tyr Ala Lys Ala Gly Ala Glu Leu Val Ala Thr Ala Lys Glu Ala
    50                  55                  60

Trp Asn Arg Glu Leu Val Val Lys Val Lys Glu Pro Leu Pro Glu Glu
65                  70                  75                  80

Tyr Glu Tyr Leu Thr Leu Pro Lys Leu Leu Phe Thr Tyr Leu His Leu
                85                  90                  95

Ala Ala Glu Arg Thr Leu Thr Glu Ala Leu Ile Lys Ser Gly Ile Thr
            100                 105                 110

Ala Ile Ala Tyr Glu Thr Val Gly Leu Ala Asp Gly Gln Leu Pro Leu
        115                 120                 125

Leu Ala Pro Met Ser Arg Ile Ala Gly Arg Leu Ala Val Gln Met Gly
130                 135                 140

Ala His Tyr Leu Glu Lys Gln Gln Gly Arg Gly Val Leu Leu Gly
145                 150                 155                 160

Gly Val Pro Gly Val Lys Ala Gly Gln Val Thr Ile Leu Gly Gly Gly
                165                 170                 175

Val Val Gly Thr Glu Ala Ala Lys Met Ala Ile Gly Leu Gly Ala Met
            180                 185                 190

Val Thr Ile Leu Asp Ile Asn Val Asp Arg Leu Asn Gln Leu Gly Glu
        195                 200                 205

Leu Phe Gly Ser Arg Val Asp Leu Arg Tyr Ser Asn Ala Ser Gln Ile
    210                 215                 220

Glu Asp Leu Leu Pro His Thr Asp Leu Leu Ile Gly Ala Val Leu Ile
225                 230                 235                 240

Thr Gly Lys Arg Ala Pro Val Leu Val Ser Arg Gln Glu Val Glu Gln
                245                 250                 255

Met Leu Pro Gly Ala Val Ile Met Asp Val Ala Ile Asp Gln Gly Gly
            260                 265                 270

Cys Val Glu Thr Leu Arg Val Thr Ser His Ser Gln Pro Ser Tyr Ile
        275                 280                 285

Glu Ala Glu Val Val His Val Gly Ile Pro Asn Met Pro Gly Ala Thr
    290                 295                 300

Pro Trp Thr Ala Thr Gln Ala Leu Asn Asn Ser Thr Leu Arg Tyr Val
305                 310                 315                 320

Leu Lys Leu Ala Asn Leu Gly Glu Gln Ala Trp Glu Asn Asp Leu Pro
                325                 330                 335

Leu Ala Lys Gly Val Asn Val Gln Ala Gly Lys Leu Val Gln Gly Ala
            340                 345                 350

Val Lys Thr Val Phe Pro Asp Leu
        355                 360
```

<210> SEQ ID NO 6
<211> LENGTH: 2292
<212> TYPE: DNA
<213> ORGANISM: Artificial Sequence
<220> FEATURE:
<223> OTHER INFORMATION: synthetic combined bacterial sequences

<400> SEQUENCE: 6

```
gggattggct gacccccagt agtgtacggg cattgctgag ccagggccat caagtatttg      60
tggaagaagg ggccggagtc gggtctggct tccccgatgg agcctacgca aaggcgggag     120
ctgagttagt tgccactgcc aaagaggctt ggaacaggga attggtggtg aaagtgaaag     180
agcctctccc tgaagagtat gaatatttaa ctttgcctaa gttgttgttc acttatctcc     240
atttggcagc ggaacgtacc ctcaccgaag ctctaattaa atctggcatt acggcgatcg     300
cctatgaaac ggtggaattg gctgatggtc aattgccatt gttggccccc atgagccgca     360
ttgccggacg attggcggtg cagatgggtg cccattattt ggaaaaacaa cagggaggcc     420
ggggagttct gttgggaggc gtacccggag tcaaggccgg acaagtaact atcctcggcg     480
gtggcgtagt cggtacagag gcggccaaaa tggcgatcgg actggggggcc atggtgacca     540
tcctagacat caatgtagac cgtttaaacc aattgggaga actgttcggt tcccgaattc     600
cccggatccg tcgacctgca ggggggggggg ggcgctgagg tctgcctcgt gaagaaggtg     660
ttgctgactc ataccaggcc tgaatcgccc catcatccag ccagaaagtg agggagccac     720
ggttgatgag agctttgttg taggtggacc agttggtgat tttgaacttt tgctttgcca     780
cggaacggtc tgcgttgtcg ggaagatgcg tgatctgatc cttcaactca gcaaaagttc     840
gatttattca acaaagccgc cgtcccgtca agtcagcgta atgctctgcc agtgttacaa     900
ccaattaacc aattctgatt agaaaaactc atcgagcatc aaatgaaact gcaatttatt     960
catatcagga ttatcaatac catattttttg aaaaagccgt ttctgtaatg aaggagaaaa    1020
ctcaccgagg cagttccata ggatggcaag atcctggtat cggtctgcga ttccgactcg    1080
tccaacatca atacaaccta ttaatttccc ctcgtcaaaa ataaggttat caagtgagaa    1140
atcaccatga gtgacgactg aatccggtga gaatggcaaa agcttatgca tttctttcca    1200
gacttgttca acaggccagc cattacgctc gtcatcaaaa tcactcgcat caaccaaacc    1260
gttattcatt cgtgattgcg cctgagcgag acgaaatacg cgatcgctgt taaaaggaca    1320
attacaaaca ggaatcgaat gcaaccggcg caggaacact gccagcgcat caacaatatt    1380
ttcacctgaa tcaggatatt cttctaatac ctggaatgct gttttcccgg ggatcgcagt    1440
ggtgagtaac catgcatcat caggagtacg gataaaatgc ttgatggtcg gaagaggcat    1500
aaattccgtc agccagttta gtctgaccat ctcatctgta acatcattgg caacgctacc    1560
tttgccatgt ttcagaaaca actctggcgc atcgggcttc ccatacaatc gatagattgt    1620
cgcacctgat tgcccgacat tatcgcgagc ccatttatac ccatataaat cagcatccat    1680
gttggaattt aatcgcggcc tcgagcaaga cgtttcccgt tgaatatggc tcataacacc    1740
ccttgtatta ctgtttatgt aagcagacag ttttattgtt catgatgata tatttttatc    1800
ttgtgcaatg taacatcaga gattttgaga cacaacgtgg ctttcccccc cccccctgca    1860
ggtcgacgga tccggggaat tcgggtggat ctgcgctaca gcaatgccag ccaaatcgaa    1920
gacctgttgc cccatacaga tttgctcatc ggcgcagtat tgatcacagg caagcgggcc    1980
ccagtgttgg tttcccgcca ggaagtggag caaatgttgc caggggcggt gattatggat    2040
gtggcgatca accaaggggg ctgtgtggag actttgcggg taacttctca tagtcaaccc    2100
agttacatcg aagcagaagt agttcatgtg ggcattccca atatgccagg agccactccc    2160
tggacagcaa cccaagcgtt gaataatagt acattgcgct atgtgttgaa attggccaat    2220
ctgggggaac aggcttggga aaatgatttg ccgttggcga aaggagtcaa tgttcaagcc    2280
``` gga aaataat ca                                                                                                                2292

<210> SEQ ID NO 7
<211> LENGTH: 439
<212> TYPE: PRT
<213> ORGANISM: Synechocystis PCC6803

<400> SEQUENCE: 7

```
Met Cys Cys Trp Gln Ser Arg Gly Leu Leu Val Lys Arg Val Leu Ala
1               5                   10                  15

Ile Ile Leu Gly Gly Gly Ala Gly Thr Arg Leu Tyr Pro Leu Thr Lys
            20                  25                  30

Leu Arg Ala Lys Pro Ala Val Pro Leu Ala Gly Lys Tyr Arg Leu Ile
        35                  40                  45

Asp Ile Pro Val Ser Asn Cys Ile Asn Ser Glu Ile Val Lys Ile Tyr
    50                  55                  60

Val Leu Thr Gln Phe Asn Ser Ala Ser Leu Asn Arg His Ile Ser Arg
65                  70                  75                  80

Ala Tyr Asn Phe Ser Gly Phe Gln Glu Gly Phe Val Glu Val Leu Ala
                85                  90                  95

Ala Gln Gln Thr Lys Asp Asn Pro Asp Trp Phe Gln Gly Thr Ala Asp
            100                 105                 110

Ala Val Arg Gln Tyr Leu Trp Leu Phe Arg Glu Trp Asp Val Asp Glu
        115                 120                 125

Tyr Leu Ile Leu Ser Gly Asp His Leu Tyr Arg Met Asp Tyr Ala Gln
    130                 135                 140

Phe Val Lys Arg His Arg Glu Thr Asn Ala Asp Ile Thr Leu Ser Val
145                 150                 155                 160

Val Pro Val Asp Asp Arg Lys Ala Pro Glu Leu Gly Leu Met Lys Ile
                165                 170                 175

Asp Ala Gln Gly Arg Ile Thr Asp Phe Ser Glu Lys Pro Gln Gly Glu
            180                 185                 190

Ala Leu Arg Ala Met Gln Val Asp Thr Ser Val Leu Gly Leu Ser Ala
        195                 200                 205

Glu Lys Ala Lys Leu Asn Pro Tyr Ile Ala Ser Met Gly Ile Tyr Val
    210                 215                 220

Phe Lys Lys Glu Val Leu His Asn Leu Leu Glu Lys Tyr Gly Ala
225                 230                 235                 240

Thr Asp Phe Gly Lys Glu Ile Ile Pro Asp Ser Ala Ser Asp His Asn
                245                 250                 255

Leu Gln Ala Tyr Leu Phe Asp Asp Tyr Trp Glu Asp Ile Gly Thr Ile
            260                 265                 270

Glu Ala Phe Tyr Glu Ala Asn Leu Ala Leu Thr Lys Gln Pro Ser Pro
        275                 280                 285

Asp Phe Ser Phe Tyr Asn Glu Lys Ala Pro Ile Tyr Thr Arg Gly Arg
    290                 295                 300

Tyr Leu Pro Pro Thr Lys Met Leu Asn Ser Thr Val Thr Glu Ser Met
305                 310                 315                 320

Ile Gly Glu Gly Cys Met Ile Lys Gln Cys Arg Ile His His Ser Val
                325                 330                 335

Leu Gly Ile Arg Ser Arg Ile Glu Ser Asp Cys Thr Ile Glu Asp Thr
            340                 345                 350

Leu Val Met Gly Asn Asp Phe Tyr Glu Ser Ser Ser Glu Arg Asp Thr
        355                 360                 365
```

```
Leu Lys Ala Arg Gly Glu Ile Ala Ala Gly Ile Gly Ser Gly Thr Thr
    370                 375                 380

Ile Arg Arg Ala Ile Ile Asp Lys Asn Ala Arg Ile Gly Lys Asn Val
385                 390                 395                 400

Met Ile Val Asn Lys Glu Asn Val Gln Glu Ala Asn Arg Glu Glu Leu
                405                 410                 415

Gly Phe Tyr Ile Arg Asn Gly Ile Val Val Val Ile Lys Asn Val Thr
                420                 425                 430

Ile Ala Asp Gly Thr Val Ile
            435

<210> SEQ ID NO 8
<211> LENGTH: 2522
<212> TYPE: DNA
<213> ORGANISM: Artificial Sequence
<220> FEATURE:
<223> OTHER INFORMATION: synthetic combined bacterial sequences

<400> SEQUENCE: 8
gggattgttg ttggcaatcg agaggtctgc ttgtgaaacg tgtcttagcg attatcctgg      60
gcggtggggc cgggacccgc ctctatcctt aaccaaaact cagagccaaa cccgcagttc     120
ccttggccgg aaagtatcgc ctcatcgata ttcccgtcag taattgcatc aactcagaaa     180
tcgttaaaat ttacgtcctt acccagttta attccgcctc ccttaaccgt cacatcagcc     240
gggcctataa tttttccggc ttccaagaag gatttgtgga agtcctcgcc gcccaacaaa     300
ccaaagataa tcctgattgg tttcagggca ctgctgatgc ggtacggcaa tacctctggt     360
tgtttaggga atgggacgta gatgaatatc ttattctgtc cggcgaccat ctctaccgca     420
tggattacgc ccaatttgtt aaaagacacc gggaaaccaa tgccgacata ccctttccg     480 ttgtgcccgt ggatgacaga aaggcacccg agctgggctt aatgaaaatc gacgcccagg     540
gcagaattac tgacttttct gaaaagcccc aggggaagc cctccgggcc atgcaggtgg     600
acaccagcgt tttgggccta agtgcggaga aggctaagct taatccttac attgcctcca     660
tgggcattta cgttttcaag aaggaagtat tgcacaacct cctggaaaaa tatgaagggg     720
caacggactt tggcaaagaa atcattcctg attcagccag tgatcacaat ctgcaagcct     780
atctctttga tgactattgg gaagacattg gtaccattga agccttctat gaggctaatt     840
tagccctgac caaacaacct agtcccgact ttagttttta taacgaaaaa gcccccatct     900
ataccagggg tcgttatctt cccccccacca aaatgttgaa ttccccggat ccgtcgacct     960 gcagggggg ggggcgctg aggtctgcct cgtgaagaag gtgttgctga ctcataccag     1020
gcctgaatcg ccccatcatc cagccagaaa gtgagggagc cacggttgat gagagctttg     1080
ttgtaggtgg accagttggt gattttgaac ttttgctttg ccacggaacg gtctgcgttg     1140
tcgggaagat gcgtgatctg atccttcaac tcagcaaaag ttcgatttat tcaacaaagc     1200
cgccgtcccg tcaagtcagc gtaatgctct gccagtgtta caaccaatta accaattctg     1260
attagaaaaa ctcatcgagc atcaaatgaa actgcaattt attcatatca ggattatcaa     1320
taccatattt tgaaaaagc cgtttctgta atgaaggaga aaactcaccg aggcagttcc     1380
ataggatggc aagatcctgg tatcggtctg cgattccgac tcgtccaaca tcaatacaac     1440
ctattaattt ccctcgtca aaataaggt tatcaagtga aaatcacca tgagtgacga     1500 ctgaatccgg tgagaatggc aaaagctat gcatttcttt ccagacttgt tcaacaggcc     1560
agccattacg ctcgtcatca aaatcactcg catcaaccaa accgttattc attcgtgatt     1620
```

```
gcgcctgagc gagacgaaat acgcgatcgc tgttaaaagg acaattacaa acaggaatcg    1680
aatgcaaccg gcgcaggaac actgccagcg catcaacaat attttcacct gaatcaggat    1740
attcttctaa tacctggaat gctgttttcc cggggatcgc agtggtgagt aaccatgcat    1800
catcaggagt acggataaaa tgcttgatgg tcggaagagg cataaattcc gtcagccagt    1860
ttagtctgac catctcatct gtaacatcat tggcaacgct acctttgcca tgtttcagaa    1920
acaactctgg cgcatcgggc ttcccataca atcgatagat tgtcgcacct gattgcccga    1980
cattatcgcg agcccattta tacccatata aatcagcatc catgttggaa tttaatcgcg    2040
gcctcgagca agacgtttcc cgttgaatat ggctcataac accccttgta ttactgttta    2100
tgtaagcaga cagtttttatt gttcatgatg atatattttt atcttgtgca atgtaacatc    2160
agagattttg agacacaacg tggctttccc cccccccct gcaggtcgac ggatccgggg    2220
aattccaccg tgacggaatc catgatcggg gaaggttgca tgattaagca atgtcgcatc    2280
caccactcag ttttaggcat tcgcagtcgc attgaatctg attgcaccat tgaggatact    2340
ttggtgatgg gcaatgattt ctacgaatct tcatcagaac gagacaccct caaagcccgg    2400
ggggaaattg ccgctggcat aggttccggc accactatcc gccgagccat catcgacaaa    2460
aatgcccgca tcggcaaaaa cgtcatgatt gtcaacaagg aaaatgtcca ggaggctaat    2520
ca                                                                   2522

<210> SEQ ID NO 9
<211> LENGTH: 2586
<212> TYPE: DNA
<213> ORGANISM: Artificial Sequence
<220> FEATURE:
<223> OTHER INFORMATION: synthetic combined bacterial sequences

<400> SEQUENCE: 9
aattcgtgat taccccatca tcatacgaag ccagggacag tttactcagc ggcagtttcc      60
gacctttgcc atttcggtta tccgtacccc cacagtgatc tgacaactca gctccgaatc     120
ccaacggcga tcgccattct tgcttggggc attaaaaccc gctggttagc cggaatttcc     180
gtccagattc cctttccaga tgtccccctc ggttctaaac ttgacttcga agtgtgttgt     240
tggcaatcga gaggtctgct tgtgaaacgt gtcttagcga ttatcctggg cggtggggcc     300
gggacccgcc tctatccttt aaccaaactc agagccaaac ccgcagttcc cttggccgga     360
aagtatcgcc tcatcgatat tcccgtcagt aattgcatca actcagaaat cgttaaaatt     420
tacgtcctta cccagtttaa ttccgcctcc cttaaccgtc acatcagccg ggcctataat     480
ttttccggct tccaagaagg atttgtggaa gtcctcgccg cccaacaaac caaagataat     540
cctgattggt tcagggcac tgctgatgcg gtacggcaat acctctggtt gtttagggaa     600
tgggacgtag atgatacgtg ctgctgaagt tgcccgcaac agagagtgga accaaccggt     660
gataccacga tactatgact gagagtcaac gccatgagcg gcctcatttc ttattctgag     720
ttacaacagt ccgcaccgct gtccggtagc tccttccggt gggcgcgggg catgactatc     780
gtcgccgcac ttatgactgt cttctttatc atgcaactcg taggacaggt gccggcagcg     840
cccaacagtc cccggccac ggggcctgcc accataccca cgccgaaaca agcgccctgc     900
accattatgt tccggatctg catcgcagga tgctgctggc tacctgtgg aacacctaca     960 tctgtattaa cgaagcgcta accgttttta tcaggctctg ggaggcagaa taaatgatca    1020
tatcgtcaat tattacctcc acggggagag cctgagcaaa ctggcctcag gcatttgaga    1080
agcacacggt cacactgctt ccggtagtca ataaaccggt aaaccagcaa tagacataag    1140
```

```
cggctattta acgaccctgc cctgaaccga cgaccgggtc gaatttgctt tcgaatttct    1200
gccattcatc cgcttattat cacttattca ggcgtagcac caggcgttta agggcaccaa    1260
taactgcctt aaaaaaatta cgccccgccc tgccactcat cgcagtactg ttgtaattca    1320
ttaagcattc tgccgacatg gaagccatca cagacggcat gatgaacctg aatcgccagc    1380
ggcatcagca ccttgtcgcc ttgcgtataa tatttgccca tggtgaaaac gggggcgaag    1440
aagttgtcca tattggccac gtttaaatca aactggtgaa aactcaccca gggattggct    1500
gagacgaaaa acatattctc aataaaccct ttagggaaat aggccaggtt ttcaccgtaa    1560
cacgccacat cttgcgaata tatgtgtaga aactgccgga aatcgtcgtg gtattcactc    1620
cagagcgatg aaaacgtttc agtttgctca tggaaaacgg tgtaacaagg gtgaacacta    1680
tcccatatca ccagctcacc gtctttcatt gccatacgga attccggatg agcattcatc    1740
aggcgggcaa gaatgtgaat aaaggccgga taaaacttgt gcttattttt ctttacggtc    1800
tttaaaaagg ccgtaatatc cagctgaacg gtctggttat aggtacattg agcaactgac    1860
tgaaatgcct caaaatgttc tttacgatgc cattgggata tatcaacggt ggtatatcca    1920
gtgatttttt tctccatttt agcttcctta gctcctgaaa atctcgataa ctcaaaaaat    1980
acgcccggta gtgatcttat ttcattatgg tgaaagttgg aacctcttac gtgatatctt    2040
attctgtccg gcgaccatct ctaccgcatg gattacgccc aatttgttaa agacaccgg     2100 gaaaccaatg ccgacataac cctttccgtt gtgcccgtgg atgacagaaa ggcacccgag    2160
ctgggcttaa tgaaaatcga cgcccagggc agaattactg actttctga aaagccccag    2220 ggggaagccc tccgggccat gcaggtggac accagcgttt tgggcctaag tgcggagaag    2280
gctaagctta atccttacat tgcctccatg ggcatttacg ttttcaagaa ggaagtattg    2340
cacaacctcc tggaaaaata tgaaggggca acggactttg gcaaagaaat cattcctgat    2400
tcagccagtg atcacaatct gcaagcctat ctctttgatg actattggga agacattggt    2460
accattgaag ccttctatga ggctaattta gccctgacca acaacctag tcccgacttt    2520 agttttata cgaaaaagc cccatctat accagggtc gttatcttcc ccccaccaaa        2580
atgttg                                                               2586
```

<210> SEQ ID NO 10
<211> LENGTH: 818
<212> TYPE: PRT
<213> ORGANISM: Synechocystis PCC6803

<400> SEQUENCE: 10

Met Val Ser Ser Val Glu Lys Thr Ser Val Ala His Lys Glu Thr
1               5                   10                  15

Ala Leu Ile Leu Trp Phe Glu Glu Val Gly Thr His Asp Val Gly Leu
            20                  25                  30

Val Gly Gly Lys Asn Ser Ser Leu Gly Glu Met Ile Gln Gln Leu Thr
        35                  40                  45

Asn Lys Gly Val Asn Val Pro Ser Gly Phe Ala Thr Thr Ala Tyr Ala
    50                  55                  60

Tyr Arg Tyr Phe Ile Gln Glu Ala Gly Leu Glu Gln Lys Leu Arg Asp
65                  70                  75                  80

Leu Phe Thr Asp Leu Asp Val Asn Asp Met Ala Asn Leu Gln Glu Arg
                85                  90                  95

Gly His Leu Ala Arg Gln Leu Ile Leu Asp Thr Pro Phe Pro Gln Asn
            100                 105                 110

```
Leu Gln Thr Ala Ile Ala Glu Ala Tyr Gly Ala Met Cys Glu Arg Tyr
            115                 120                 125

Gly Gln Lys Met Gly Arg Thr Gly Val Asp Val Ala Val Arg Ser Ser
130                 135                 140

Ala Thr Ala Glu Asp Leu Pro Glu Ala Ser Phe Ala Gly Gln Gln Glu
145                 150                 155                 160

Thr Tyr Leu Asn Val His Ser Leu Ser Cys Val Leu Glu Ser Cys His
                165                 170                 175

Lys Cys Phe Ala Ser Leu Phe Thr Asp Arg Ala Ile Ser Tyr Arg His
                180                 185                 190

His Asn Gly Phe Asp His Phe Ala Val Ala Leu Ser Val Gly Val Gln
                195                 200                 205

Lys Met Val Arg Ser Asp Leu Ala Thr Ser Gly Val Met Phe Ser Ile
        210                 215                 220

Asp Thr Glu Thr Gly Phe Lys Asn Ala Ala Leu Ile Thr Ala Ala Tyr
225                 230                 235                 240

Gly Leu Gly Glu Asn Val Val Gln Gly Ala Val Asn Pro Asp Glu Tyr
                245                 250                 255

Phe Val Phe Lys Pro Thr Leu Lys Glu Gly Phe Lys Pro Ile Leu Glu
                260                 265                 270

Lys Arg Leu Gly Ser Lys Ala Ile Lys Met Val Tyr Asp Val Gly Gly
        275                 280                 285

Ser Lys Leu Thr Lys Asn Val Glu Val Ala Glu Pro Glu Arg Glu Lys
        290                 295                 300

Tyr Cys Ile Asn Asp Glu Glu Ile Leu Gln Leu Ala Arg Trp Ala Cys
305                 310                 315                 320

Ile Ile Glu Asp His Tyr Ser Gly Val Arg Gly Val Tyr Thr Pro Met
                325                 330                 335

Asp Ile Glu Trp Ala Lys Asp Gly Gln Thr Gly Glu Leu Phe Ile Val
                340                 345                 350

Gln Ala Arg Pro Glu Thr Val Gln Ser Gln Lys Ser Ala Asn Val Ile
        355                 360                 365

Lys Thr Tyr Glu Leu Lys Asp His Ser Gln Val Leu Ala Thr Gly Arg
        370                 375                 380

Ser Val Gly Ala Ala Ile Gly Gln Gly Lys Ala Gln Val Ile Arg Asn
385                 390                 395                 400

Val Ser Gln Ile Asn Gln Phe Arg Pro Gly Glu Val Leu Ile Thr Asn
                405                 410                 415

Arg Thr Asp Pro Asp Trp Glu Pro Ile Met Lys Gln Ala Ser Ala Ile
                420                 425                 430

Val Thr Asn Gln Gly Gly Lys Thr Cys His Ala Ala Ile Ile Ala Arg
        435                 440                 445

Glu Met Gly Ile Pro Ala Ile Val Gly Cys Gly Asp Ala Thr Asp Thr
        450                 455                 460

Ile Lys Thr Gly Glu Asp Val Thr Ile Cys Cys Ser Glu Gly Asp Glu
465                 470                 475                 480

Gly Ser Val Tyr Ser Gly Ile Leu Asn Tyr Glu Val His Glu Thr Glu
                485                 490                 495

Leu Ser Asn Leu Pro Arg Thr Lys Thr Gln Ile Leu Met Asn Val Gly
                500                 505                 510

Asn Pro Glu Gln Ala Phe Gly Phe Ala Ser Tyr Pro Ala Asp Gly Val
                515                 520                 525
```

```
Gly Leu Ala Arg Leu Glu Phe Ile Ile Ala Asn His Ile Lys Ala His
        530                 535                 540

Pro Leu Ala Leu Met Lys Phe Asp Glu Leu Glu Asp Pro Leu Ala Lys
545                 550                 555                 560

Ala Glu Ile Ala Glu Leu Thr Lys Leu Tyr Ala Gly Asp Arg Pro Arg
                565                 570                 575

Phe Phe Val Asp Lys Leu Ala His Gly Ile Ala Met Ile Ala Ala Ala
                580                 585                 590

Phe Tyr Pro Lys Pro Val Val Arg Met Ser Asp Phe Lys Ser Asn
                595                 600                 605

Glu Tyr Ala Asn Leu Leu Gly Gly Arg Gln Phe Glu Pro Lys Glu Glu
                610                 615                 620

Asn Pro Met Ile Gly Trp Arg Gly Ala Ser Arg Tyr Tyr Asp Pro Asn
625                 630                 635                 640

Tyr Arg Glu Ala Tyr Ala Leu Glu Cys Gln Ala Leu Lys Arg Val Arg
                645                 650                 655

Asp Glu Met Gly Leu Thr Asn Val Ile Pro Met Ile Pro Phe Cys Arg
                660                 665                 670

Thr Pro Asp Glu Gly Arg Lys Val Ile Ala Glu Met Ala Lys His Gly
                675                 680                 685

Leu Lys Gln Gly Lys Asn Gly Leu Glu Ile Tyr Val Met Cys Glu Leu
690                 695                 700

Pro Ser Asn Val Ile Leu Ala Asp Glu Phe Ser Glu Val Phe Asp Gly
705                 710                 715                 720

Phe Ser Ile Gly Ser Asn Asp Leu Thr Gln Leu Thr Leu Gly Leu Asp
                725                 730                 735

Arg Asp Ser Ser Leu Val Ala His Leu Phe Asp Glu Arg Asn Leu Gly
                740                 745                 750

Val Lys Arg Met Val Lys Met Ala Ile Glu Thr Ala Lys Ala Asn Gly
                755                 760                 765

Arg Lys Ile Gly Ile Cys Gly Gln Ala Pro Ser Asp Tyr Pro Glu Phe
770                 775                 780

Ala Glu Phe Leu Val Glu Leu Gly Ile Asp Ser Ile Ser Leu Asn Pro
785                 790                 795                 800

Asp Ser Val Leu Lys Thr Val Leu Arg Ile Ala Glu Val Glu Lys Ala
                805                 810                 815

Leu Gly

<210> SEQ ID NO 11
<211> LENGTH: 3082
<212> TYPE: DNA
<213> ORGANISM: Artificial Sequence
<220> FEATURE:
<223> OTHER INFORMATION: synthetic combined bacterial sequences

<400> SEQUENCE: 11
gggattttca ctgaccgggc tatttcctat cgccatcaca atggttttga ccattttgcg    60
gtggccctat cggtgggcgt acaaaagatg gtgcgttctg atctggccac ctccggggtg   120
atgttttcca ttgatacgga aacgggtttc aaaaatgccg ctctgattac tgccgcctat   180
ggcctagggg aaaatgtggt gcaaggggcg gttaaccccg atgaatattt tgtgtttaaa   240
cctactttga agagggttt taaccaattc tggaaaaac gtttgggtag taaagctatc   300
aaaatggtct atgacgtggg cggttccaaa ctgaccaaaa atgtggaagt agcggagccg   360
gaacgggaaa atattgcat taatgatgaa gaaattctcc aattagcccg ctgggcctgc   420
```

```
atcattgaag accattattc tggggtgcgg ggagtttata ccccccatgga tattgaatgg    480
gctaaggatg ggcaaacggg ggaattgttc attgtccaag cccgcccaga aacggtgcag    540
tcgcaaaaat ccgccaatgt gattaaaacc tatgagttaa aagatcacag ccaagtgtta    600
gccacgggcc gcagtgtggg ggcggcgatc ggccagggta aagcccaggt aattcgcaat    660
gtgtcccaaa tcaatcagtt tcgtcccggc gaggtgttaa tcaccaaccg cactgacccg    720
gattgggaac cgattatgaa acaggcttcg gcgatcgtca ctaaccaggg ggggaaaacc    780
tgccacgccg caattattgc ccgaattccc cggatccgtc gacctgcagg gggggggggg    840
cgctgaggtc tgcctcgtga agaaggtgtt gctgactcat accaggcctg aatcgcccca    900
tcatccagcc agaaagtgag ggagccacgg ttgatgagag ctttgttgta ggtggaccag    960
ttggtgattt tgaacttttg ctttgccacg gaacggtctg cgttgtcggg aagatgcgtg   1020
atctgatcct tcaactcagc aaaagttcga tttattcaac aaagccgccg tcccgtcaag   1080
tcagcgtaat gctctgccag tgttacaacc aattaaccaa ttctgattag aaaaactcat   1140
cgagcatcaa atgaaactgc aatttattca tatcaggatt atcaatacca tatttttgaa   1200
aaagccgttt ctgtaatgaa ggagaaaact caccgaggca gttccatagg atggcaagat   1260
cctggtatcg gtctgcgatt ccgactcgtc caacatcaat acaacctatt aatttcccct   1320
cgtcaaaaat aaggttatca agtgagaaat caccatgagt gacgactgaa tccggtgaga   1380
atggcaaaag cttatgcatt tctttccaga cttgttcaac aggccagcca ttacgctcgt   1440
catcaaaatc actcgcatca accaaaccgt tattcattcg tgattgcgcc tgagcgagac   1500
gaaatacgcg atcgctgtta aaaggacaat tacaaacagg aatcgaatgc aaccggcgca   1560
ggaacactgc cagcgcatca acaatatttt cacctgaatc aggatattct tctaatacct   1620
ggaatgctgt tttcccgggg atcgcagtgg tgagtaacca tgcatcatca ggagtacgga   1680
taaaatgctt gatggtcgga gaggcataa attccgtcag ccagtttagt ctgaccatct   1740
catctgtaac atcattggca acgctacctt tgccatgttt cagaaacaac tctggcgcat   1800
cgggcttccc atacaatcga tagattgtcg cacctgattg cccgacatta tcgcgagccc   1860
atttataccc atataaatca gcatccatgt tggaattaa tcgcggcctc gagcaagacg   1920
tttcccgttg aatatggctc ataacacccc ttgtattact gtttatgtaa gcagacagtt   1980
ttattgttca tgatgatata ttttatctt gtgcaatgta acatcagaga ttttgagaca   2040
caacgtggct ttccccccccc cccctgcagg tcgacggatc cggggaattc gggaaatggg   2100
tattccggcg attgtgggtt gtggagatgc caccgacaca atcaaaaccg gggaagatgt   2160
caccatctgt tgctccgaag gggatgaagg ttcggtttac agcggcattt tgaactatga   2220
agttcacgaa acgaactgt ccaatttgcc ccgcaccaag actcaaattt tgatgaatgt   2280
gggtaaccca gaacaggcct ttggattttgc tagttatccc gccgatggcg tgggtctagc   2340
ccggttggaa tttatcattg ctaaccacat taaggctcac cccctcgccc tgatgaaatt   2400
tgatgagttg gaagatccct tggccaaggc agaaattgcc gaactaacca aactctatgc   2460
tggcgatcgc ccccggttct tgtggacaa attggcccat ggtattgcca tgattgcggc   2520
ggcgttctat cccaaacctg tggtggtgcg gatgtcggat tttaaatcca atgaatacgc   2580
taacctcctg ggtggtcgtc agtttgagcc gaaggaagaa aaccccatga tcggttggcg   2640
gggcgcttcc cgttactacg atcccaatta ccgagaagcc tacgctttgg aatgccaagc   2700
tctgaaacga gtgcgggacg aaatgggttt aaccaacgtc attcccatga ttcccttctg   2760
```

-continued

```
tcgtacccce gatgaaggtc gcaaagttat tgcggaaatg gctaaacatg gcttgaaaca   2820
agggaaaaac ggcttggaaa tctacgttat gtgtgaattg cccagtaacg tcattctggc   2880
cgatgaattt agcgaggtat ttgacggctt ctccattggc tccaatgatt taacccaatt   2940
aactttaggt ttagaccggg attcttccct cgttgcccat ctgtttgatg aacgcaatct   3000
aggggtcaaa cggatggtca aaatggccat tgaaacggcg aaagctaacg gtcgcaaaat   3060
cggtatctgt ggccaagaat ca                                            3082
```

<210> SEQ ID NO 12
<211> LENGTH: 333
<212> TYPE: PRT
<213> ORGANISM: Synechocystis PCC6803

<400> SEQUENCE: 12

```
Met Lys Ile Ala Phe Phe Ser Ser Lys Ala Tyr Asp Arg Gln Phe Phe
1               5                   10                  15

Gln Gln Ala Asn His Pro His Gln Arg Glu Met Val Phe Phe Asp Ala
            20                  25                  30

Gln Leu Asn Leu Asp Thr Ala Ile Leu Ala Glu Asp Cys Pro Val Ile
        35                  40                  45

Cys Leu Phe Val Asn Asp Gln Ala Pro Ala Pro Val Leu Glu Lys Leu
    50                  55                  60

Ala Ala Gln Gly Thr Lys Leu Ile Ala Leu Arg Ser Ala Gly Tyr Asn
65                  70                  75                  80

Asn Val Asp Leu Lys Thr Ala Ala Asp Leu Gly Leu Lys Val His
                85                  90                  95

Val Pro Ser Tyr Ser Pro His Ala Val Ala Glu His Thr Val Gly Leu
            100                 105                 110

Ile Leu Ala Leu Asn Arg Lys Leu Tyr Arg Ala Tyr Asn Arg Val Arg
        115                 120                 125

Asp Asp Asn Phe Ser Leu Glu Gly Leu Leu Gly Phe Asp Leu His Gly
    130                 135                 140

Thr Thr Val Gly Val Ile Gly Thr Gly Lys Ile Gly Leu Ala Phe Ala
145                 150                 155                 160

Gln Ile Met Asn Gly Phe Gly Cys His Leu Leu Gly Tyr Asp Ala Phe
                165                 170                 175

Pro Asn Asp Lys Phe Thr Ala Ile Gly Gln Ala Leu Tyr Val Ser Leu
            180                 185                 190

Asn Glu Leu Leu Ala His Ser Asp Ile Ile Ser Leu His Cys Pro Leu
        195                 200                 205

Leu Pro Glu Thr His Tyr Leu Ile Asn Thr Asn Thr Ile Ala Gln Met
    210                 215                 220

Lys Pro Gly Val Met Leu Ile Asn Thr Ser Arg Gly His Leu Ile Asp
225                 230                 235                 240

Thr Gln Ala Val Ile Gln Gly Ile Lys Ser His Lys Ile Gly Phe Leu
                245                 250                 255

Gly Ile Asp Val Tyr Glu Glu Glu Glu Leu Phe Phe Thr Asp His
            260                 265                 270

Ser Asp Thr Ile Ile Gln Asp Asp Thr Phe Gln Leu Leu Gln Ser Phe
        275                 280                 285

Pro Asn Val Met Ile Thr Ala His Gln Gly Phe Phe Thr His Asn Ala
    290                 295                 300

Leu Gln Thr Ile Ala Ala Thr Leu Ala Asn Ile Ala Glu Phe Glu
305                 310                 315                 320
```

```
Gln Asn Lys Pro Leu Thr Tyr Gln Val Ile Cys Pro His
            325                 330

<210> SEQ ID NO 13
<211> LENGTH: 2520
<212> TYPE: DNA
<213> ORGANISM: Artificial Sequence
<220> FEATURE:
<223> OTHER INFORMATION: synthetic combined bacterial sequences

<400> SEQUENCE: 13 cgggccccc  ctcgaggtcg  acggtatcga  taagcttgat  atccctggga  gcggagacct    60
ttaagctcaa  atttggtcat  cgagggctca  atcaaccctg  tggcctggag  caacaggtgg   120
aaattaccag  ccagaaccat  ggttttgcgg  tgacggaagg  ttccctggcc  gaagaagtgg   180
aaattaccca  tttcaacctc  aacgataaaa  cggtggcggg  gctacgccat  aaagaattgc   240 ccttttctc   ggtgcagtac  cacccggagg  ccagccctgg  accccatgat  gccgattatc   300
tgttcgagaa  gttcgtcaag  ttgatgcgac  aacaaaaggc  agaagtcgcc  ggttagtaaa   360
acctagtaac  agctacgatt  tatcgtacta  tcgatcacca  aggtagtgcc  gttaatacta   420
tcgttgcttc  attttaggaa  aaatatctg   taataaaag   gctaaaaaat  ttaacgttat   480
ctttagttaa  cattgatatt  ttctaacctt  aatggggaca  gattacttgg  taagttaaag   540
gtttattctg  ctcaaattca  gcaatatttg  ccagtgtcgt  tgcggcaatg  gtttgcagag   600
cgttgtgggt  aaagaatccc  tgatgagctg  tgatccgtcg  acctgcaggg  ggggggggc   660 gctgaggtct  gcctcgtgaa  gaaggtgttg  ctgactcata  ccaggcctga  atcgccccat   720
catccagcca  gaaagtgagg  gagccacggt  tgatgagagc  tttgttgtag  gtggaccagt   780
tggtgatttt  gaacttttgc  tttgccacgg  aacggtctgc  gttgtcggga  agatgcgtga   840
tctgatcctt  caactcagca  aaagttcgat  ttattcaaca  aagccgccgt  cccgtcaagt   900
cagcgtaatg  ctctgccagt  gttacaacca  attaaccaat  tctgattaga  aaaactcatc   960
gagcatcaaa  tgaaactgca  atttattcat  atcaggatta  tcaataccat  attttgaaa   1020 aagccgtttc  tgtaatgaag  gagaaaactc  accgaggcag  ttccatagga  tgcaagatc   1080 ctggtatcgg  tctgcgattc  cgactcgtcc  aacatcaata  caacctatta  atttcccctc   1140
gtcaaaaata  aggttatcaa  gtgagaaatc  accatgagtg  acgactgaat  ccggtgagaa   1200
tggcaaaagc  ttatgcattt  cttttccagac  ttgttcaaca  ggccagccat  tacgctcgtc   1260
atcaaaatca  ctcgcatcaa  ccaaaccgtt  attcattcgt  gattgcgcct  gagcgagacg   1320
aaatacgcga  tcgctgttaa  aaggacaatt  acaaacagga  atcgaatgca  accggcgcag   1380
gaacactgcc  agcgcatcaa  caatattttc  acctgaatca  ggatattctt  ctaatacctg   1440
gaatgctgtt  ttcccgggga  tcgcagtggt  gagtaaccat  gcatcatcag  gagtacggat   1500
aaaatgcttg  atggtcggaa  gaggcataaa  ttccgtcagc  cagtttagtc  tgaccatctc   1560
atctgtaaca  tcattggcaa  cgctacccttt  gccatgtttc  agaaacaact  ctggcgcatc   1620
gggcttccca  tacaatcgat  agattgtcgc  acctgattgc  ccgacattat  cgcgagccca   1680 tttatacccca  tataaatcag  catccatgtt  ggaatttaat  cgcggcctcg  agcaagacgt   1740
ttcccgttga  atatggctca  taacacccct  tgtattactg  tttatgtaag  cagacagttt   1800
tattgttcat  gatgatatat  ttttatcttg  tgcaatgtaa  catcagagat  tttgagacac   1860
aacgtggctt  tcccccccc   ccctgcaggt  cgacggatct  gcggctgttt  tgaggtcaac   1920
attattatag  cccgcactgc  gcagagcgat  taatttgtg   ccctgggcag  ctaacttttc   1980
```

```
tagcaccggg gcaggagctt ggtcattaac gaagaggcaa ataacggggc aatcctccgc    2040
taaaatagcg gtatcaaggt tgagttgggc atcaaaaaag accatttccc gttgatgggg    2100
gtggtttgct tgttggaaaa attgacgatc ataggcttta ctgctaaaaa aagcgatttt    2160
catgacgatt atgggaagta gtttagaacg tgtttggaaa gttttattcc gcccccctaaa   2220 tcccccaata atgggtact ttcacccagc ttcaccccaa atttggggc caggggggct      2280 tgttaaacag gctcttagag cactatttag tcaagggtat ttttccaat cttaaaagaa     2340 attttctgat tcttcctgca tttgtattat ttaatactcc cctagctctg gcgattgccg    2400
tagcggtaga tattgactca cactgggggca actgtagggt ttggcctcca actcctgtgt   2460
ttggctgtga tgcattttca gcttcccttt agctagagcg gccgccaccg cggtggagct    2520
```

<210> SEQ ID NO 14
<211> LENGTH: 413
<212> TYPE: PRT
<213> ORGANISM: Synechocystis PCC6803

<400> SEQUENCE: 14

```
Met Lys Phe Leu Ile Leu Asn Ala Gly Ser Ser Gln Lys Ser Cys
1               5                   10                  15

Leu Tyr Glu Leu Thr Gly Asp Arg Leu Pro Glu Thr Ile Pro Glu Pro
            20                  25                  30

Leu Trp Glu Ala Phe Ile Asp Trp Thr Val Leu Ala Asn Gln Gly Arg
        35                  40                  45

Leu Thr Val Glu Thr Ala Gly Gln Lys Gln Val Ile Ile Leu Glu Thr
    50                  55                  60

Gly Asp Arg Gln Gln Gly Ile Ala Arg Met Leu Asp Thr Leu Val Thr
65                  70                  75                  80

Gly Asp Asp Ala Val Leu Lys Ser Leu Ala Glu Ile Asp Leu Val Gly
                85                  90                  95

His Arg Val Val His Gly Gly Thr Asp His Ala Glu Ala Thr Leu Ile
            100                 105                 110

Thr Pro Glu Val Gln Gln Ala Ile Ala Asp Leu Ile Pro Leu Ala Pro
        115                 120                 125

Ala His Asn Pro Ala His Leu Glu Gly Ile Glu Ala Ile Ser Ala Leu
    130                 135                 140

Leu Val Leu Gly Glu Val Pro Gln Ile Ala Val Phe Asp Thr Ala Phe
145                 150                 155                 160

His Arg Thr Ile Pro Thr Pro Ala Ala Glu Tyr Pro Ile Pro Gln Ala
                165                 170                 175

Trp Thr Asn Leu Gly Ile Arg Arg Tyr Gly Phe His Gly Thr Ser His
            180                 185                 190

Lys Tyr Cys Ala Gln Lys Thr Ala Glu Ile Leu Gly Lys Pro Leu Ala
        195                 200                 205

Asp Leu Lys Leu Ile Thr Cys His Ile Gly Asn Gly Ala Ser Leu Thr
    210                 215                 220

Ala Ile Lys Asn Gly Val Ser Ile Asp Thr Thr Met Gly Phe Thr Pro
225                 230                 235                 240

Leu Glu Gly Leu Met Met Gly Ala Arg Ser Gly Ser Ile Asp Pro Ala
                245                 250                 255

Ile Leu Leu Phe Leu Gln Glu Thr Gln Gly Leu Thr Pro Ala Glu Ile
            260                 265                 270

Asn Thr Thr Leu Asn Lys Lys Ser Gly Leu Leu Gly Val Ser Gly Leu
```

```
                275                 280                 285
Ser Ala Asp Leu Arg Thr Ile Leu Gln Ala Lys Ala Glu Gly Asn Glu
            290                 295                 300
Gln Ala Gln Leu Ala Tyr Val Met Tyr Ile His Arg Phe Arg Ser Cys
305                 310                 315                 320
Leu Gly Gln Met Ile Ala Ser Leu Glu Gly Leu Asp Thr Leu Val Phe
                325                 330                 335
Thr Ala Gly Val Gly Glu Asn Ala Ala Thr Val Arg Ala Asp Val Cys
            340                 345                 350
Gln Ala Phe Glu Phe Leu Gly Leu Lys Leu Asp Pro Glu Leu Asn Asn
                355                 360                 365
Arg Ser Pro Arg Asp Thr Val Ile Ser His Ser Asp Ser Leu Val Thr
            370                 375                 380
Val Leu Ile Val His Thr Glu Glu Asp Trp Ala Ile Ala Gln Asp Cys
385                 390                 395                 400
Trp His Trp Trp His Ser Gln Gly Gln Arg Lys Gln Ser
                405                 410
```

<210> SEQ ID NO 15
<211> LENGTH: 2754
<212> TYPE: DNA
<213> ORGANISM: Artificial Sequence
<220> FEATURE:
<223> OTHER INFORMATION: synthetic combined bacterial sequences

<400> SEQUENCE: 15

```
ctagtagtgc agaaattttg agcgatctgg aagccaccat tgcctacgcc caaactttac      60
ccaacgttaa accggaagaa gtaggattaa ttggtttttg ttttggtggt tggattgtct     120
atttaggggc tagtttaccc acagtcaagg ccacggcttc cttttacggc gcgggtattc     180
cccattgggc tccagggaca gcggaaccgc ccattaccta taccgataaa attcagggca     240
ctttatacgc cttcttcggc ttggaagata ccagcattcc catggcagat acggagcaga     300
ttgaacaggc tttaaccaag tatcaggtga accataaaat tttccgttac ccaggcgcag     360
accatggctt tttctgtgac caagggcta gctataacgc cgaagcggcc gccgatgctt     420
ggcaaaaagt gaaacaactt ttccaaaccg aattgaaatg aaattcctga ttctcaatgc     480
cggttccagc agtcaaaaaa gttgtcttta tgagctgact ggcgatcgcc taccggagac     540
gataccggag ccccttatgg gaggctttca tgattggacg gtgttggcaa atcagggacg     600
gttgacctgc agggggggggg gggcgctgag gtctgcctcg tgaagaaggt gttgctgact     660
cataccaggc ctgaatcgcc ccatcatcca gccagaaagt gagggagcca cggttgatga     720
gagctttgtt gtaggtggac cagttggtga ttttgaactt ttgctttgcc acggaacggt     780
ctgcgttgtc gggaagatgc gtgatctgat ccttcaactc agcaaaagtt cgatttattc     840
aacaaagccg ccgtcccgtc aagtcagcgt aatgctctgc cagtgttaca accaattaac     900
caattctgat tagaaaaact catcgagcat caaatgaaac tgcaatttat tcatatcagg     960
attatcaata ccatattttt gaaaaagccg tttctgtaat gaaggagaaa actcaccgag    1020
gcagttccat aggatggcaa gatcctggta tcggtctgcg attccgactc gtccaacatc    1080
aatacaacct attaatttcc cctcgtcaaa ataaggtta tcaagtgaga atcaccatg     1140
agtgacgact gaatccggtg agaatggcaa aagcttatgc atttctttcc agacttgttc    1200
aacaggccag ccattacgct cgtcatcaaa atcactcgca tcaaccaaac cgttattcat    1260
tcgtgattgc gcctgagcga gacgaaatac gcgatcgctg ttaaaaggac aattacaaac    1320
```

```
aggaatcgaa tgcaaccggc gcaggaacac tgccagcgca tcaacaatat tttcacctga   1380
atcaggatat tcttctaata cctggaatgc tgttttcccg gggatcgcag tggtgagtaa   1440
ccatgcatca tcaggagtac ggataaaatg cttgatggtc ggaagaggca taaattccgt   1500
cagccagttt agtctgacca tctcatctgt aacatcattg caacgctac ctttgccatg    1560 tttcagaaac aactctggcg catcgggctt cccatacaat cgatagattg tcgcacctga   1620 ttgccccgaca ttatcgcgag cccatttata cccatataaa tcagcatcca tgttggaatt  1680
taatcgcggc ctcgagcaag acgtttcccg ttgaatatgg ctcataacac cccttgtatt   1740
actgtttatg taagcagaca gttttattgt tcatgatgat atattttat cttgtgcaat    1800 gtaacatcag agattttgag acacaacgtg ctttcccccc cccccctgc aggtcaaccc    1860 cggcggaaat taacaccacc ctcaataaaa aatccggttt gctcggagtc tctgggctgt   1920
cggcggatct tcgtaccatt ttgcaggcca agcagaggg taatgaacaa gctcaattgg    1980
cttatgtcat gtatatccat cgcttccgga gttgtttggg gcaaatgatt gcttccttgg   2040
aaggtttgga tacgttggtg tttaccgccg gggtggggga aaatgccgcc actgtgcggg   2100
cagatgtttg ccaagctttt gaatttctag gtttaaaact tgatccagag ttgaataacc   2160
gatcgccaag ggatactgtc atttctcact ccgactcctt ggtgacggtg ttgattgtcc   2220
acaccgaaga agattgggcg atcgcccagg attgttggca ctggtggcat agccagggac   2280
agagaaagca atcgtaaatt gcgaaaatgt tagaaaatgg ctgtgaagat aaatgttgaa   2340
ttaggctaaa tttccttggc tagagtccgc atccgccaac acgtcaaccc cctcagtgaa   2400
aaatatcggc aggtgttggc ctgtcccgat tgggccaccg tttatgacga tgtccaacga   2460
ccattgcatc tagatattgg ctgtgccgg ggtcgctttc ccctcaaaat ggctcaacaa    2520
caccccgact ggaatttttt aggggtggaa atccgtcaac ccttggtgct agaggccaac   2580
gaaaccggcg atcgtctggg gttaaaaaat ctccattacc tgtttggcaa catcaatgtg   2640
gagccagaaa aattcttttc cgcctttccc cccactctgc aacgggtcag catccaattt   2700
cccgatccct ggtttaagca acgacataat aaacgccgag tggcccaacc agaa         2754
```

<210> SEQ ID NO 16
<211> LENGTH: 697
<212> TYPE: PRT
<213> ORGANISM: Synechocystis PCC6803

<400> SEQUENCE: 16

Met Thr Ser Ser Leu Tyr Leu Ser Thr Thr Glu Ala Arg Ser Gly Lys
1               5                   10                  15

Ser Leu Val Val Leu Gly Ile Leu Asp Leu Ile Leu Lys Lys Thr Thr
            20                  25                  30

Arg Ile Ala Tyr Phe Arg Pro Ile Ile Gln Asp Pro Val Asn Gly Lys
        35                  40                  45

His Asp Asn Asn Ile Ile Leu Val Leu Glu Asn Phe Arg Leu Gln Gln
    50                  55                  60

Thr Tyr Thr Asp Ser Phe Gly Leu Tyr Phe His Glu Ala Val Ser Leu
65                  70                  75                  80

Ala Ser Asp Gly Ala Ile Asp Gln Val Leu Asp Arg Ile Leu Ala Lys
                85                  90                  95

Tyr Arg His Leu Ala Asp Gln Val Asp Phe Ile Leu Cys Glu Gly Ser
            100                 105                 110

Asp Tyr Leu Gly Glu Glu Ser Ala Phe Glu Phe Asp Leu Asn Thr Thr

```
            115                 120                 125
Ile Ala Lys Met Leu Asn Cys Pro Ile Leu Leu Gly Asn Ala Met
            130                 135                 140
Gly Asn Thr Ile Ala Asp Ser Leu Gln Pro Ile Asp Met Ala Leu Asn
145                 150                 155                 160
Ser Tyr Asp Gln Glu Ser Cys Gln Val Val Gly Val Ile Ile Asn Arg
                165                 170                 175
Val Gln Pro Glu Leu Ala Thr Glu Ile Gln Ala Gln Leu Glu Gln Arg
            180                 185                 190
Tyr Gly Asp Arg Pro Met Val Leu Gly Thr Ile Pro Gln Asp Ile Met
            195                 200                 205
Leu Lys Ser Leu Arg Leu Arg Glu Ile Val Ser Gly Leu Asn Ala Gln
210                 215                 220
Val Leu Ser Gly Ala Asp Leu Leu Asp Asn Leu Val Tyr His His Leu
225                 230                 235                 240
Val Val Ala Met His Ile Ala His Ala Leu His Trp Leu His Glu Lys
                245                 250                 255
Asn Thr Leu Ile Ile Thr Pro Gly Asp Arg Gly Asp Ile Ile Leu Gly
            260                 265                 270
Val Met Gln Ala His Arg Ser Leu Asn Tyr Pro Ser Ile Ala Gly Ile
            275                 280                 285
Leu Leu Thr Ala Asp Tyr His Pro Glu Pro Ala Ile Met Lys Leu Ile
            290                 295                 300
Glu Gly Leu Pro Asp Ala Pro Pro Leu Leu Thr Ser Thr His Thr
305                 310                 315                 320
His Glu Thr Ser Ala Arg Leu Glu Thr Leu His Pro Ala Leu Ser Pro
                325                 330                 335
Thr Asp Asn Tyr Lys Ile Arg His Ser Ile Ala Leu Phe Gln Gln Gln
            340                 345                 350
Ile Asp Gly Glu Lys Leu Leu Asn Tyr Leu Lys Thr Ile Arg Ser Lys
            355                 360                 365
Gly Ile Thr Pro Lys Leu Phe Leu Tyr Asn Leu Val Gln Ala Ala Thr
            370                 375                 380
Ala Ala Gln Arg His Ile Val Leu Pro Glu Gly Glu Glu Ile Arg Ile
385                 390                 395                 400
Leu Lys Ala Ala Ala Ser Leu Ile Asn His Gly Ile Val Arg Leu Thr
                405                 410                 415
Leu Leu Gly Asn Ile Glu Ala Ile Glu Gln Thr Val Lys Ile Asn His
            420                 425                 430
Ile Asp Leu Asp Leu Ser Lys Val Arg Leu Ile Asn Pro Lys Thr Ser
            435                 440                 445
Pro Asp Arg Glu Arg Tyr Ala Glu Thr Tyr Gln Leu Arg Lys His
            450                 455                 460
Lys Gly Val Thr Leu Ala Met Ala Arg Asp Ile Leu Thr Asp Ile Ser
465                 470                 475                 480
Tyr Phe Gly Thr Met Met Val His Leu Gly Glu Ala Asp Gly Met Val
                485                 490                 495
Ser Gly Ser Val Asn Thr Thr Gln His Thr Val Arg Pro Ala Leu Gln
            500                 505                 510
Ile Ile Lys Thr Gln Pro Gly Phe Ser Leu Val Ser Ser Val Phe Phe
            515                 520                 525
Met Cys Leu Glu Asp Arg Val Leu Val Tyr Gly Asp Cys Ala Val Asn
            530                 535                 540
```

```
Pro Asp Pro Asn Ala Glu Gln Leu Ala Glu Ile Ala Leu Thr Ser Ala
545                 550                 555                 560

Ala Thr Ala Lys Asn Phe Gly Ile Glu Pro Arg Val Ala Leu Leu Ser
            565                 570                 575

Tyr Ser Ser Gly Ser Ser Gly Gln Gly Ala Asp Val Glu Lys Val Arg
        580                 585                 590

Gln Ala Thr Ala Ile Ala Lys Glu Arg Glu Pro Asp Leu Ala Leu Glu
            595                 600                 605

Gly Pro Ile Gln Tyr Asp Ala Ala Val Asp Ser Thr Val Ala Ala Gln
610                 615                 620

Lys Met Pro Gly Ser Ala Val Ala Gly Lys Ala Thr Val Phe Ile Phe
625                 630                 635                 640

Pro Asp Leu Asn Thr Gly Asn Asn Thr Tyr Lys Ala Val Gln Arg Glu
                645                 650                 655

Thr Lys Ala Ile Ala Ile Gly Pro Ile Leu Gln Gly Leu Asn Lys Pro
                660                 665                 670

Val Asn Asp Leu Ser Arg Gly Cys Leu Val Glu Asp Ile Ile Asn Thr
                675                 680                 685

Val Val Ile Thr Ala Leu Gln Val Lys
    690                 695
```

<210> SEQ ID NO 17
<211> LENGTH: 3654
<212> TYPE: DNA
<213> ORGANISM: Artificial Sequence
<220> FEATURE:
<223> OTHER INFORMATION: synthetic combined bacterial sequences

<400> SEQUENCE: 17

| | |
|---|---:|
| ttggccaaaa aacaaggttt actgggtttt accgctgatg tttttactgga aaatcgagcc | 60 |
| atgttgcatc tatttgagaa gatgaacttt cgcatggaac gacgtatgag cgaaggggtt | 120 |
| tacgaattaa aaatgttttt tagttgagcc gtcttctttc tgctaattta ttgaaggaat | 180 |
| ttttgatgct ggcgttagta atttttaccgc ttcttagatt tattaaaatc tcgtcataaa | 240 |
| actttactga ctagcggttt atttttctggc taaaagcgct atcacttaag taggtggaat | 300 |
| tggcagattt gtagtagttg atacttaact ttttagggaa tatcgctgtg ggaaaaatcg | 360 |
| agatcatttt cccagaaaaa tcattgctgg atacgttgag gttatttaaa ttatgacgag | 420 |
| ttccctttat ttaagcacca ccgaagcccg cagcggtaaa tctctagtag tattgggcat | 480 |
| tttagactta attctcaaaa aaaccacccg tattgcctat tttcgtccca ttattcaaga | 540 |
| cccagttaat ggcaaacatg ataacaacat tattctggtg ctggaaaatt tcgtctcca | 600 |
| acaaacctat accgattcct ttggtttgta tttccatgaa gcggtgagtt tagcctccga | 660 |
| tggagctatt gatcaggtat tagaccgaat tttggctaaa tatcgccatt tggcagatca | 720 |
| agtagatttt attctctgtg aaggctcaga ctatttgggg gaggaatcgg cttttgaatt | 780 |
| tgatctcaac accacgatcg ccaagatgtt gaactgcccc atttttgctgt tgggcaatgc | 840 |
| catgggcaac accattgccg atagtttgca acccatcgat tttccatggc agctgagaat | 900 |
| attgtaggag atcttctaga aagatcctgt gacggaagtt aacttcgcag aataataaa | 960 |
| tcctggtgtc cctgttgata ccgggaagcc ctgggccaac ttttggcgaa atgagacgt | 1020 |
| tgatcggcac gtaagaggtt ccaactttca ccataatgaa ataagatcac taccgggcgt | 1080 |
| atttttgag ttatcgagat tttcaggagc taaggaagct aaaatggaga aaaaaatcac | 1140 |

| | |
|---|---|
| tggatatacc accgttgata tatcccaatg gcatcgtaaa gaacattttg aggcatttca | 1200 |
| gtcagttgct caatgtacct ataaccagac cgttcagctg gatattacgg ccttttaaa | 1260 |
| gaccgtaaag aaaaataagc acaagtttta tccggccttt attcacattc ttgcccgcct | 1320 |
| gatgaatgct catccggaat tccgtatggc aatgaaagac ggtgagctgg tgatatggga | 1380 |
| tagtgttcac ccttgttaca ccgttttcca tgagcaaact gaaacgtttt catcgctctg | 1440 |
| gagtgaatac cacgacgatt tccggcagtt tctacacata tattcgcaag atgtggcgtg | 1500 |
| ttacggtgaa aacctggcct atttccctaa agggtttatt gagaatatgt ttttcgtctc | 1560 |
| agccaatccc tgggtgagtt tcaccagttt tgatttaaac gtggccaata tggacaactt | 1620 |
| cttcgccccc gttttcacca tgggcaaata ttatacgcaa ggcgacaagg tgctgatgcc | 1680 |
| gctggcgatt caggttcatc atgccgtttg tgatggcttc catgtcggca gaatgcttaa | 1740 |
| tgaattacaa cagtactgcg atgagtggca gggcggggcg taatttttt aaggcagtta | 1800 |
| ttggtgccct aaacgcctg gttgctacgc ctgaataagt gataataagc ggttgactgg | 1860 |
| cagaaattcg atcttgctga aaactcgag ccatccggaa gatctggcgg ccgctctccc | 1920 |
| tatagtgagt cgtattacgc cggatggata tggtgttcag gcacaagtgt taaagcagtt | 1980 |
| gattttattc actatgatga aaaaacaat gaatggaacc tgctccaagt taaaaataga | 2040 |
| gataataccg aaaactcatc gagtagtaag attagagata atacaacaat aaaaaatgg | 2100 |
| tttagaactt actcacagcg tgatgctact aattgggaca attttccaga tgaagtatca | 2160 |
| tctaagaatt taaatgaaga agacttcaga gcttttgtta aaaattattt ggcaaaaata | 2220 |
| atataattcg gctgcagatt accatcccga accggccatt atgaaactaa ttgaagggct | 2280 |
| acccgacgcc cctcccctgt tgctgactag cacccacacc catgaaactt ccgcccgttt | 2340 |
| ggaaactctc caccctgccc tgagccctac ggataattat aaaattcgcc acagtattgc | 2400 |
| gctgtttcaa caacaaattg atggggagaa attactcaat taccttaaaa ccatccgcag | 2460 |
| taaaggtatt accccaaac tgtttctcta caatttagtt caagccgcca ccgccgccca | 2520 |
| acgacatatt gtcctaccgg aaggggaaga aattcgtatt ctcaaggcgg ccgctagctt | 2580 |
| aattaaccac ggcattgtcc gtttgacttt actcggtaac attgaggcga tcgagcaaac | 2640 |
| ggtaaaaatt aatcacattg acttagattt gagcaaagtt cgcctcatta atcctaaaac | 2700 |
| tagcccagac cgagagcgct acgccgaaac ctattaccag ctacgtaaac ataaggggt | 2760 |
| aaccctggcc atggctcggg atatcctcac cgatatttcc tattttggaa cgatgatggt | 2820 |
| gcatttggga gaggccgatg gcatggttc tggctccgtc aataccaccc aacataccgt | 2880 |
| gcgtcctgct ttacaaatta ttaaaaccca gccaggtttt tccttggttt cttcagtctt | 2940 |
| ttttatgtgt ttagaagacc gagttttggt ctatggagat tgtgctgtta atcccgatcc | 3000 |
| caatgcagaa cagttagcag aaattgccct tacttctgcg gctacggcca agaattttgg | 3060 |
| cattgagccc agggtagctc tattgtccta ttcttccggt tcttctgggc aaggggccga | 3120 |
| tgtggaaaaa gtgcggcaag ccacggcgat cgccaaggaa agagagccag atttagcatt | 3180 |
| ggaagggccg atccagtatg atgcggcggt ggattccaca gtggcggccc aaaaaatgcc | 3240 |
| tgggtcagcg gtgcgggta agcaacggt gtttatttt cccgatttaa ataccggtaa | 3300 |
| caatacttac aaggcagtgc aaagagaaac aaaggcgatc gccattggcc ccatttaca | 3360 |
| aggattaaat aaaccagtta atgatctaag tcggggttgt ttagtggagg atattattaa | 3420 |
| tacggtggta attacagctt tgcaagttaa ataattttac tcttaattag ttaaaatgat | 3480 |
| cccttgaatt accttgattt tgccctccaa actaccaata gctgggccga aaattggcat | 3540 |

```
catttaaaat caccaacgtg tccccggacg gagctagcac aaacagaccc ttaccatagg    3600
catagctgac cacttcttgg cttaacacca tggctgccac tgcacctaaa gctt          3654
```

<210> SEQ ID NO 18
<211> LENGTH: 378
<212> TYPE: PRT
<213> ORGANISM: Synechocystis PCC6803

<400> SEQUENCE: 18

```
Met Phe Leu Leu Phe Phe Ile Val His Trp Leu Lys Ile Met Leu Pro
1               5                   10                  15

Phe Phe Ala Gln Val Gly Leu Glu Glu Asn Leu His Glu Thr Leu Asp
            20                  25                  30

Phe Thr Glu Lys Phe Leu Ser Gly Leu Glu Asn Leu Gln Gly Leu Asn
        35                  40                  45

Glu Asp Asp Ile Gln Val Gly Phe Thr Pro Lys Glu Ala Val Tyr Gln
50                  55                  60

Glu Asp Lys Val Ile Leu Tyr Arg Phe Gln Pro Val Val Glu Asn Pro
65                  70                  75                  80

Leu Pro Ile Pro Val Leu Ile Val Tyr Ala Leu Val Asn Arg Pro Tyr
                85                  90                  95

Met Val Asp Leu Gln Glu Gly Arg Ser Leu Val Ala Asn Leu Leu Lys
            100                 105                 110

Leu Gly Leu Asp Val Tyr Leu Ile Asp Trp Gly Tyr Pro Ser Arg Gly
        115                 120                 125

Asp Arg Trp Leu Thr Leu Glu Asp Tyr Leu Ser Gly Tyr Leu Asn Asn
130                 135                 140

Cys Val Asp Ile Ile Cys Gln Arg Ser Gln Gln Glu Lys Ile Thr Leu
145                 150                 155                 160

Leu Gly Val Cys Gln Gly Gly Thr Phe Ser Leu Cys Tyr Ala Ser Leu
                165                 170                 175

Phe Pro Asp Lys Val Lys Asn Leu Val Val Met Val Ala Pro Val Asp
            180                 185                 190

Phe Glu Gln Pro Gly Thr Leu Leu Asn Ala Arg Gly Gly Cys Thr Leu
        195                 200                 205

Gly Ala Glu Ala Val Asp Ile Asp Leu Met Val Asp Ala Met Gly Asn
210                 215                 220

Ile Pro Gly Asp Tyr Leu Asn Leu Glu Phe Leu Met Leu Lys Pro Leu
225                 230                 235                 240

Gln Leu Gly Tyr Gln Lys Tyr Leu Asp Val Pro Asp Ile Met Gly Asp
                245                 250                 255

Glu Ala Lys Leu Leu Asn Phe Leu Arg Met Glu Lys Trp Ile Phe Asp
            260                 265                 270

Ser Pro Asp Gln Ala Gly Glu Thr Tyr Arg Gln Phe Leu Lys Asp Phe
        275                 280                 285

Tyr Gln Gln Asn Lys Leu Ile Lys Gly Glu Val Met Ile Gly Asp Arg
290                 295                 300

Leu Val Asp Leu His Asn Leu Thr Met Pro Ile Leu Asn Leu Tyr Ala
305                 310                 315                 320

Glu Lys Asp His Leu Val Ala Pro Ser Ser Leu Ala Leu Gly Asp
                325                 330                 335

Tyr Leu Pro Glu Asn Cys Asp Tyr Thr Val Gln Ser Phe Pro Val Gly
            340                 345                 350
```

His Ile Gly Met Tyr Val Ser Gly Lys Val Gln Arg Asp Leu Pro Pro
    355                 360                 365

Ala Ile Ala His Trp Leu Ser Glu Arg Gln
    370                 375

<210> SEQ ID NO 19
<211> LENGTH: 2121
<212> TYPE: DNA
<213> ORGANISM: Artificial Sequence
<220> FEATURE:
<223> OTHER INFORMATION: synthetic combined bacterial sequences

<400> SEQUENCE: 19

| | | | | | |
|---|---|---|---|---|---|
| tctagataat | tcaccatcaa | tgtttttact | atttttttatc | gttcattggt | taaaaattat | 60 |
| gttgccttt | tttgctcagg | tggggttaga | agaaaatctc | catgaaaccc | tagattttac | 120 |
| tgaaaaattt | ctctctggct | tggaaaattt | gcagggtttg | aatgaagatg | acatccaggt | 180 |
| gggctttacc | cccaaagaag | cagtttacca | ggaagataag | gttattcttt | accgtttcca | 240 |
| accggtggtg | gaaaatccct | tacctatccc | ggttttaatt | gttacgccc | tggtaaatcg | 300 |
| cccctacatg | gtggatttgc | aggaaggacg | ctccctggtg | gccaacctcc | tcaaactggg | 360 |
| tttggacgtg | tatttaattg | attggggtta | tccctcccgg | ggcgatcgtt | ggatccgtcg | 420 |
| acctgcaggg | gggggggggc | gctgaggtct | gcctcgtgaa | gaaggtgttg | ctgactcata | 480 |
| ccaggcctga | atcgccccat | catccagcca | gaaagtgagg | gagccacggt | tgatgagagc | 540 |
| tttgttgtag | gtggaccagt | tggtgatttt | gaacttttgc | tttgccacgg | aacggtctgc | 600 |
| gttgtcggga | agatgcgtga | tctgatcctt | caactcagca | aaagttcgat | ttattcaaca | 660 |
| aagccgccgt | cccgtcaagt | cagcgtaatg | ctctgccagt | gttacaacca | attaaccaat | 720 |
| tctgattaga | aaaactcatc | gagcatcaaa | tgaaactgca | atttattcat | atcaggatta | 780 |
| tcaataccat | attttttgaaa | agccgtttc | tgtaatgaag | gagaaaactc | accgaggcag | 840 |
| ttccatagga | tggcaagatc | ctggtatcgg | tctgcgattc | cgactcgtcc | aacatcaata | 900 |
| caacctatta | atttcccctc | gtcaaaaata | aggttatcaa | gtgagaaatc | accatgagtg | 960 |
| acgactgaat | ccggtgagaa | tggcaaaagc | ttatgcattt | ctttccagac | ttgttcaaca | 1020 |
| ggccagccat | tacgctcgtc | atcaaaatca | ctcgcatcaa | ccaaaccgtt | attcattcgt | 1080 |
| gattgcgcct | gagcgagacg | aaatacgcga | tcgctgttaa | aaggacaatt | acaaacagga | 1140 |
| atcgaatgca | accggcgcag | gaacactgcc | agcgcatcaa | caatatttc | acctgaatca | 1200 |
| ggatattctt | ctaatacctg | gaatgctgtt | ttcccgggga | tcgcagtggt | gagtaaccat | 1260 |
| gcatcatcag | gagtacggat | aaaatgcttg | atggtcggaa | gaggcataaa | ttccgtcagc | 1320 |
| cagtttagtc | tgaccatctc | atctgtaaca | tcattggcaa | cgctaccttt | gccatgtttc | 1380 |
| agaaacaact | ctggcgcatc | gggcttccca | tacaatcgat | agattgtcgc | acctgattgc | 1440 |
| ccgacattat | cgcgagccca | tttataccca | tataaatcag | catccatgtt | ggaatttaat | 1500 |
| cgcggcctcg | agcaagacgt | ttcccgttga | atatggctca | taacaccct | tgtattactg | 1560 |
| tttatgtaag | cagacagttt | tattgttcat | gatgatatat | ttttatcttg | tgcaatgtaa | 1620 |
| catcagagat | tttgagacac | aacgtggctt | tcccccccc | ccctgcaggt | cgacggatcc | 1680 |
| tcttaaccta | gaatttctca | tgcttaaacc | cctgcaatta | ggttaccaaa | agtatcttga | 1740 |
| tgtgcccgat | attatggggg | atgaagcgaa | attgttaaac | tttctacgca | tggaaaaatg | 1800 |
| gatttttgat | agtcccgatc | aagcggggga | aacttaccgt | caattcctca | aggatttta | 1860 |
| tcaacaaaat | aaattgatca | aaggggaagt | gatgattggc | gatcgcctgg | tggatctgca | 1920 |

```
taatttgacc atgcccatat tgaatttata tgcggaaaaa gaccacttgg tggcccctgc    1980 ttcttccta gctttggggg actatttgcc ggaaaactgt gactacaccg tccaatcttt    2040
ccccgtgggt catattggca tgtatgtcag tggtaaagta caacgggatc tgcccccggc    2100
gatcgcccat tggctatcga t                                              2121

<210> SEQ ID NO 20
<211> LENGTH: 426
<212> TYPE: PRT
<213> ORGANISM: Anabaena PCC7120

<400> SEQUENCE: 20

Met Lys Lys Val Leu Ala Ile Ile Leu Gly Gly Gly Ala Gly Thr Arg
1               5                   10                  15

Leu Tyr Pro Leu Thr Lys Leu Arg Ala Lys Pro Ala Val Pro Val Ala
            20                  25                  30

Gly Lys Tyr Arg Leu Ile Asp Ile Pro Val Ser Asn Cys Ile Asn Ser
        35                  40                  45

Glu Ile Phe Lys Ile Tyr Val Leu Thr Gln Phe Asn Ser Ala Ser Leu
    50                  55                  60

Asn Arg His Ile Ala Arg Thr Tyr Asn Phe Ser Gly Phe Ser Glu Gly
65                  70                  75                  80

Phe Val Glu Val Leu Ala Ala Gln Gln Thr Pro Glu Asn Pro Asn Trp
                85                  90                  95

Phe Gln Gly Thr Ala Asp Ala Val Arg Gln Tyr Leu Trp Met Leu Gln
            100                 105                 110

Glu Trp Asp Val Asp Glu Phe Leu Ile Leu Ser Gly Asp His Leu Tyr
        115                 120                 125

Arg Met Asp Tyr Arg Leu Phe Ile Gln Arg His Arg Glu Thr Asn Ala
    130                 135                 140

Asp Ile Thr Leu Ser Val Ile Pro Ile Asp Asp Arg Arg Ala Ser Asp
145                 150                 155                 160

Phe Gly Leu Met Lys Ile Asp Asn Ser Gly Arg Val Ile Asp Phe Ser
                165                 170                 175

Glu Lys Pro Lys Gly Glu Ala Leu Thr Lys Met Arg Val Asp Thr Thr
            180                 185                 190

Val Leu Gly Leu Thr Pro Glu Gln Ala Ala Ser Gln Pro Tyr Ile Ala
        195                 200                 205

Ser Met Gly Ile Tyr Val Phe Lys Lys Asp Val Leu Ile Lys Leu Leu
    210                 215                 220

Lys Glu Ala Leu Glu Arg Thr Asp Phe Gly Lys Glu Ile Ile Pro Asp
225                 230                 235                 240

Ala Ala Lys Asp His Asn Val Gln Ala Tyr Leu Phe Asp Asp Tyr Trp
                245                 250                 255

Glu Asp Ile Gly Thr Ile Glu Ala Phe Tyr Asn Ala Asn Leu Ala Leu
            260                 265                 270

Thr Gln Gln Pro Met Pro Pro Phe Ser Phe Tyr Asp Glu Glu Ala Pro
        275                 280                 285

Ile Tyr Thr Arg Ala Arg Tyr Leu Pro Pro Thr Lys Leu Leu Asp Cys
    290                 295                 300

His Val Thr Glu Ser Ile Ile Gly Glu Gly Cys Ile Leu Lys Asn Cys
305                 310                 315                 320

Arg Ile Gln His Ser Val Leu Gly Val Arg Ser Arg Ile Glu Thr Gly
                325                 330                 335
```

```
Cys Met Ile Glu Glu Ser Leu Leu Met Gly Ala Asp Phe Tyr Gln Ala
            340                 345                 350

Ser Val Glu Arg Gln Cys Ser Ile Asp Lys Gly Asp Ile Pro Val Gly
            355                 360                 365

Ile Gly Pro Asp Thr Ile Ile Ile Asp Lys Asn Ala Arg Ile Gly
            370                 375                 380

His Asp Val Lys Ile Ile Asn Lys Asp Asn Val Gln Glu Ala Asp Arg
385                 390                 395                 400

Glu Ser Gln Gly Phe Tyr Ile Arg Ser Gly Ile Val Val Val Leu Lys
            405                 410                 415

Asn Ala Val Ile Thr Asp Gly Thr Ile Ile
            420                 425

<210> SEQ ID NO 21
<211> LENGTH: 5916
<212> TYPE: DNA
<213> ORGANISM: Artificial Sequence
<220> FEATURE:
<223> OTHER INFORMATION: synthetic combined bacterial sequences

<400> SEQUENCE: 21
gagctctgtt aacagtcaac agtcatttca caaattaagg caagattaag aaaatactgt    60
aaccattaac atatctaata tttttaatca tgagtgcaaa ttaatacagt ggaaattgtt   120
ttctgatcaa tggctgcacg atacgtcacc agtaaggttt tttaaaattc attcaagata   180
atctttgatc ccccccttacc agctgccaca gacagtccta aactgtaggt gggagttgaa   240
aggcagttgg gagaaatctt gtgaaaaaag tcttagcaat tattcttggt ggtggtgcgg   300
gtactcgcct ttacccacta accaaactcc gcgctaaacc ggcagtacca gtggcaggga   360
aataccgcct aatagatatc cctgtcagta actgcattaa ttcggaaatt tttaaaatct   420
acgtattaac acaatttaac tcagcttctc tcaatcgcca cattgcccgt acctacaact   480
ttagtggttt tagcgagggt tttgtggaag tgctggccgc ccagcagaca ccagagaacc   540
ctaactggtt ccaaggtaca gccgatgctg tacgtcagta tctctggatg ttacaagagt   600
gggacgtaga tgaattttg atcctgtcgg gggatcacct gtaccggatg gactatcgcc   660
tatttatcca gcgccatcta gaggatcccc aaatggcaaa ttatttatga cggtaggctt   720
aatagcctgt aaaaatttgt aacaatattt tttgttttg caataaacaa aaacaaatgc   780
ctccgattag aaatcggagg cattgtttgc ttgaaaatca agacaggacg gaaaaccgtt   840
ttcctgtttt gaaattagaa agcgctcagg aagagttctt caacttcttt ctgatcaccc   900
tgacgcgggt tggtcagagc acaagcatct tcagagcgt ggtcagcaag agcggcaca    960 tcttctttct tagcacccag ctcggtcaga tttgctggaa taccaatgga agcagccaga  1020
tcgcgaacag cctgaatggt ggcttctgcg ccttctttat caccgagatt ggcgatatcg  1080
agacccatag caacaccaac gtctttcaga cgaccagcaa cgacagaggc gttataagcc  1140
agaacatgcg gaagcagaac agcgttgcag acaccatgcg gcaggttgta gtagccgccc  1200
aactggtgag ccatagcatg gacataacca agcgaagcgt tgttgaaggc cataccagcg  1260
aggaattggg cataagccat agcttcacga gctggcatat ccttaccgtt gtcgcaagcg  1320
gtcttcagat tcttagcgat catggacgca gccttcaagg cgcaagcatc ggtgatcgga  1380
gtagctgccg ttgaagaata agcttcaaat gcgtgggtca gagcatccat accggtggcg  1440
gcggtcaggc ctttttggcat accaaccatc aacagaggat cgttgacgga aaccatcggg  1500
```

```
gtaacgtgac ggtcaacaat ggccatctta acgtgacgga cttcatcagt gatgatgcag    1560
aaacgcgtca tttcagaagc cgtaccagcc gtcgtgttga ttgacatcaa aggcagggca    1620
ggtttcttag atttgtcgat accttcgtag tctttgactt caccaccatt ggttgcgacc    1680
agagcgatgg cttttggcgca gtcatgggga gaaccaccac cgaggagat gacgaagtct    1740 gaattgttat ccttcaggat cttaaggcct tccagaactg cggtaacagt cgggttcggc    1800
ataacgccat cataaacagc agaattaata ccctgtgctt tcaacaggtc agcaacctgc    1860
ttcacaacac cggatttgtt catgaaagca tcagaaacga tcagcgcatt tttaaagccg    1920
ctgccgttaa gatccttgat tgcttttca gcgaacctt cgcccatttc gttgacgaaa       1980
ggaatataaa aagttgaaga agccatagct ataacctcac cctacatact agtttgggta    2040
ccgagctcga attgatcccc aaaaactaga ggagcttgtt aacaggctta cggctgttgg    2100
cggcagcaac gcgcttaccc catttgacca attcttcagt gcagtcttca cgaccgatga    2160
agcattcgat cagggttggg ccgtcggtgt tgccagagc aaccttgata gcttctgcca      2220
gttcgccacc ggttttagcc ttcaggcctt taccagcacc gctgtcataa ccaccgttac    2280
cgttgaacac ttccatcaga ccggcataat cccagttctt gatgttgttg tacggaccat    2340 catgatcat aacttcgatg gtgtaaccat agttattgat caagaagatg ataaccggca     2400
gtttcaggcg aaccatctga gcgacttcct gagccgtcag ctggaaggaa ccatcaccaa    2460
ccatgaggat gttgcgacgt tccggagcac cgacggcata accgaaggcg gcaggaacgg    2520
accaaccgat gtgaccccac tgcatttcat attcaacgcg agcaccgttc gggagcttca    2580
tgcgctgagc attgaaccaa gagtcaccgg tttcagcaat aaccgtcgtg ttcggggtca    2640
gaagagcttc gacctgacgg gcgatttctg cgttgaccaa cggagcactc ggatcagccg    2700
gagcggcttt cttcagttca cctgcattga gggatttgaa gaagtccaaa gcaccggttt    2760
tcttggaaac tttctgagcc aaacgggtca gatagtcttt cagatgaacg ctggggaagc    2820
gaacgccgtt aacgacgaca gaacgcggtt cagcgagaac cagtttctta ggatcaggaa    2880
tatccgtcca accagtggtg gagtagtcgt tgaagacagg agccagagcg ataaccgcat    2940
cggcttcttt catcgtcttt tcaacgcccg gatagctgac ttcacccat gaggtaccga     3000 tgtaatgcgg gttttcttct gggaagaagc ttttttgcagc agccatggta gcaactgcgc    3060
caccgagagc atcagcaaat ttgacagcag cttcttcagc accagctgcg cgcagcttgc    3120
tgccgacgag gacggcaact tgtcgcggt tggcgatgaa tttcagggtt tcttcaaccg     3180
ctgcattcaa agaagcttcg tcgctggctt cgtcattgaa caatgcgctt gccggtccag    3240
gagcggcgca gggcatggaa gcaatgttgc aagcgatttc gagataaacc ggcttcttct    3300
cacgaagagc agttttaatc acgtgatcga ttttagccgg agcttcttct ggggtgtaaa    3360
tcgcttcagc tgcggccgtg atgttcttgg ccatttccaa ctgatagtga tagtcggttt    3420
tgccaagagc gtgatgcaac acgtgaccag cagcgtgatc attgttgttc ggagcaccgg    3480
agatcaggat aaccggaagg ttttctgcat aggcgccacc gatagcatca aatgcggaaa    3540
gcgcaccgac gctgtaggta acgacggctg ctgctgcgcc tttggcacga gcataacctt    3600
ctgcactgaa accgcagttc agttcgttac agcaataaac ctgctccatg ttttttgttca    3660 aaagcaggtt gtcaagaagg acgaggttgt agtcgcccgc gactgcgaag tgatgcttga    3720
gaccaatctg gacaagccgc tccgctaaat aggtaccgac agtataagaa ttcatggcgt    3780
tctcctaacc tgtagttta tttttcttat ttcattttaa ataaaatcga caccaaatat    3840
gacaatctgt catacttcgg gcaaattttt tttgagatcg cgataaatcc agggaaaaat    3900
```

```
gctctgcgat cgctaaaaat cactataatt acatggcact aaaaaactta tggctaaaaa    3960
tacatcaata tatgcagcca gagcgacaaa ttaaattttt tatttatgtg atgtagataa    4020
aagatatctt tccccctatac ccctacactc tccttcaagt catagaggcg cggagattgc   4080
ccaattttat tagctgtgta ctcagtacct cagcaaaaaa gtcgacatat gtttctcggc   4140
aaaaattaat tatcgattgg ctggaacctg gtcaaaccag gcttttcat ccattggaaa    4200
agcgattttg atcatctagg gtcaggagca aagatccccg gtgggcgaag aactccagca   4260
tgagatcccc gcgctggagg atcatccagc cggcgtcccg gaaaacgatt ccgaagccca   4320
accttttcata gaaggcggcg gtggaatcga atctcgtga tggcaggttg ggcgtcgctt   4380
ggtcggtcat ttcgaacccc agagtcccgc tcagaagaac tcgtcaagaa ggcgatagaa   4440
ggcgatgcgc tgcgaatcgg gagcggcgat accgtaaagc acgaggaagc ggtcagccca   4500
ttcgccgcca agctcttcag caatatcacg ggtagccaac gctatgtcct gatagcggtc   4560
cgccacaccc agccggccac agtcgatgaa tccagaaaag cggccatttt ccaccatgat   4620
attcggcaag caggcatcgc catgggtcac gacgagatcc tcgccgtcgg catgcgcgc    4680
cttgagcctg gcgaacagtt cggctggcgc gagcccctga tgctcttcgt ccagatcatc   4740
ctgatcgaca agaccggctt ccatccgagt acgtgctcgc tcgatgcgat gtttcgcttg   4800
gtggtcgaat gggcaggtag ccggatcaag cgtatgcagc cgccgcattg catcagccat   4860
gatggatact ttctcggcag gagcaaggtg agatgacagg agatcctgcc ccggcacttc   4920
gcccaatagc agccagtccc ttcccgcttc agtgacaacg tcgagcacag ctgcgcaagg   4980
aacgcccgtc gtggccagcc acgatagccg cgctgcctcg tcctgcagtt cattcagggc   5040
accgacagg tcggtcttga caaaaagaac cgggcgcccc tgcgctgaca gccgaacac    5100
ggcggcatca gagcagccga ttgtctgttg tgcccagtca tagccgaata gcctctccac   5160
ccaagcggcc ggagaacctg cgtgcaatcc atcttgttca atcatgcgaa acgatcctca   5220
tcctgtctct tgatcagatc cgtccttgtt attcaacagt ataacatgtc ttatacgccc   5280
gtgtcaacca atattcattg agatcctcta gacgagtcat tgatttcagt gaaaaaccca   5340
agggcgaagc cttaaccaaa atgcgtgttg ataccacggt tttaggcttg acaccagaac   5400
aggcggcatc acagccttac attgcctcga tggggattta cgtatttaaa aaagacgttt   5460
tgatcaagct gttgaaggaa gctttagaac gtactgattt cggcaaagaa attattcctg   5520
atgccgccaa agatcacaac gttcaagctt acctattcga tgactactgg gaagatattg   5580
ggacaatcga agctttttat aacgccaatt tagcgttaac tcagcagccc atgccgccct   5640
ttagcttcta cgatgaagaa gcacctattt atacccgcgc tcgttactta ccacccacaa   5700
aactattaga ttgccacgtt acagaatcaa tcattggcga aggctgtatt ctgaaaaact   5760
gtcgcattca acactcagta ttgggagtgc gatcgcgtat tgaaactggc tgcatgatcg   5820
aagaatcttt actcatgggt gccgacttct accaagcttc agtggaacgc cagtgcagca   5880
tcgataaagg agacatccct gtaggcatcg ctcgag                             5916
```

<210> SEQ ID NO 22
<211> LENGTH: 429
<212> TYPE: PRT
<213> ORGANISM: Anabaena variabilis

<400> SEQUENCE: 22

Met Lys Lys Val Leu Ala Ile Ile Leu Gly Gly Gly Ala Gly Thr Arg
1               5                   10                  15

-continued

```
Leu Tyr Pro Leu Thr Lys Leu Arg Ala Lys Pro Ala Val Pro Val Ala
         20                  25                  30

Gly Lys Tyr Arg Leu Ile Asp Ile Pro Val Ser Asn Cys Ile Asn Ser
         35                  40                  45

Glu Ile Phe Lys Ile Tyr Val Leu Thr Gln Phe Asn Ser Ala Ser Leu
 50                  55                  60

Asn Arg His Ile Ala Arg Thr Tyr Asn Phe Ser Gly Phe Ser Glu Gly
 65                  70                  75                  80

Phe Val Glu Val Leu Ala Ala Gln Gln Thr Pro Glu Asn Pro Asn Trp
                 85                  90                  95

Phe Gln Gly Thr Ala Asp Ala Val Arg Gln Tyr Leu Trp Met Leu Gln
            100                 105                 110

Glu Trp Asp Val Asp Glu Phe Leu Ile Leu Ser Gly Asp His Leu Tyr
        115                 120                 125

Arg Met Asp Tyr Arg Leu Phe Ile Gln Arg His Arg Glu Thr Asn Ala
    130                 135                 140

Asp Ile Thr Leu Ser Val Ile Pro Ile Asp Asp Arg Arg Ala Ser Asp
145                 150                 155                 160

Phe Gly Leu Met Lys Ile Asp Asn Ser Gly Arg Val Ile Asp Phe Ser
                165                 170                 175

Glu Lys Pro Lys Gly Glu Ala Leu Thr Lys Met Arg Val Asp Thr Thr
            180                 185                 190

Val Leu Gly Leu Thr Pro Glu Gln Ala Ala Ser Gln Pro Tyr Ile Ala
        195                 200                 205

Ser Met Gly Ile Tyr Val Phe Lys Lys Asp Val Leu Ile Lys Leu Leu
    210                 215                 220

Lys Glu Ser Leu Glu Arg Thr Asp Phe Gly Lys Glu Ile Ile Pro Asp
225                 230                 235                 240

Ala Ser Lys Asp His Asn Val Gln Ala Tyr Leu Phe Asp Asp Tyr Trp
                245                 250                 255

Glu Asp Ile Gly Thr Ile Glu Ala Phe Tyr Asn Ala Asn Leu Ala Leu
            260                 265                 270

Thr Gln Gln Pro Met Pro Pro Phe Ser Phe Tyr Asp Glu Glu Ala Pro
        275                 280                 285

Ile Tyr Thr Arg Ala Arg Tyr Leu Pro Pro Thr Lys Leu Leu Asp Cys
    290                 295                 300

His Val Thr Glu Ser Ile Ile Gly Glu Gly Cys Ile Leu Lys Asn Cys
305                 310                 315                 320

Arg Ile Gln His Ser Val Leu Gly Val Arg Ser Arg Ile Glu Thr Gly
                325                 330                 335

Cys Val Ile Glu Glu Ser Leu Leu Met Gly Ala Asp Phe Tyr Gln Ala
            340                 345                 350

Ser Val Glu Arg Gln Cys Ser Ile Asp Lys Gly Asp Ile Pro Val Gly
        355                 360                 365

Ile Gly Pro Asp Thr Ile Ile Arg Arg Ala Ile Ile Asp Lys Asn Ala
    370                 375                 380

Arg Ile Gly His Asp Val Lys Ile Ile Asn Lys Asp Asn Val Gln Glu
385                 390                 395                 400

Ala Asp Arg Glu Ser Gln Gly Phe Tyr Ile Arg Ser Gly Ile Val Val
                405                 410                 415

Val Leu Lys Asn Ala Val Ile Thr Asp Gly Thr Ile Ile
            420                 425
```

```
<210> SEQ ID NO 23
<211> LENGTH: 324
<212> TYPE: PRT
<213> ORGANISM: Synechocystis PCC6803

<400> SEQUENCE: 23

Met Ala Glu Thr Leu Leu Phe Ala Ala Leu Arg Gln Ala Leu Asp Glu
1               5                   10                  15

Glu Met Gly Arg Asp Val Asn Val Leu Val Leu Gly Glu Asp Val Gly
            20                  25                  30

Leu Tyr Gly Gly Ser Tyr Lys Val Thr Lys Asp Leu Tyr Glu Lys Tyr
        35                  40                  45

Gly Glu Met Arg Val Leu Asp Thr Pro Ile Ala Glu Asn Ser Phe Thr
    50                  55                  60

Gly Met Ala Val Gly Ala Ala Met Thr Gly Leu Arg Pro Val Ile Glu
65                  70                  75                  80

Gly Met Asn Met Gly Phe Leu Leu Leu Ala Phe Asn Gln Ile Ala Asn
                85                  90                  95

Asn Ala Gly Met Leu Arg Tyr Thr Ser Gly Gly Asn Tyr Gln Ile Pro
            100                 105                 110

Met Val Ile Arg Gly Pro Gly Gly Val Gly Arg Gln Leu Gly Ala Glu
        115                 120                 125

His Ser Gln Arg Leu Glu Ala Tyr Phe His Ala Val Pro Gly Leu Lys
    130                 135                 140

Ile Val Ala Cys Ser Thr Pro Tyr Asn Ala Lys Gly Leu Leu Lys Ala
145                 150                 155                 160

Ala Ile Arg Asp Asn Asn Pro Val Leu Phe Phe Glu His Val Leu Leu
                165                 170                 175

Tyr Asn Leu Lys Glu Asn Leu Pro Asp Tyr Gly Tyr Ile Val Pro Leu
            180                 185                 190

Asp Lys Ala Glu Val Val Arg Pro Gly Lys Asp Val Thr Ile Leu Thr
        195                 200                 205

Tyr Ser Arg Met Arg His His Cys Leu Gln Ala Leu Lys Thr Leu Glu
    210                 215                 220

Lys Glu Gly Tyr Asp Pro Glu Ile Ile Asp Leu Ile Ser Leu Lys Pro
225                 230                 235                 240

Phe Asp Met Glu Thr Ile Ser Ala Ser Val Lys Lys Thr His Arg Val
                245                 250                 255

Ile Ile Val Glu Glu Cys Met Lys Thr Gly Gly Ile Gly Ala Glu Leu
            260                 265                 270

Ile Ala Leu Ile Asn Asp His Leu Phe Asp Glu Leu Asp Gly Pro Val
        275                 280                 285

Val Arg Leu Ser Ser Gln Asp Ile Pro Thr Pro Tyr Asn Gly Met Leu
    290                 295                 300

Glu Arg Leu Thr Ile Val Gln Pro Pro Gln Ile Val Asp Ala Val Lys
305                 310                 315                 320

Ala Ile Ile Gly

<210> SEQ ID NO 24
<211> LENGTH: 257
<212> TYPE: DNA
<213> ORGANISM: Artificial Sequence
<220> FEATURE:
<223> OTHER INFORMATION: synthetic combined bacterial sequences

<400> SEQUENCE: 24
```

```
cgatataatt tccgggtcgt agccttcttt ttccaaagtt tttagtgcct gtaaacaatg      60
gtgacgcatg cgggaatagg tcaaaatagt gacatcctta ccggggcgca ccacttcggc     120
tttatccaga ggcacaatat attcgtagtc gggtaagttt tctttcaagt tgtacaaaag     180
tacgtgctca aaaaataaca ctgggttatt atcccgaatg gctgccgctc ggttgccgcc     240
gggcgttttt tattcca                                                    257
```

<210> SEQ ID NO 25
<211> LENGTH: 1128
<212> TYPE: DNA
<213> ORGANISM: Artificial Sequence
<220> FEATURE:
<223> OTHER INFORMATION: synthetic combined bacterial sequences

<400> SEQUENCE: 25

```
atatggctga gaccctactg tttgccgccc tacgccaagc ccttgacgaa gaaatgggac      60
gggatgtcaa cgtccttgtg ctgggagaag atgtgggact ctatggcggt tcctataagg     120
taaccaagga tttgtacgag aagtatggcg aaatgcgggt gctggatacg cccatcgccg     180
aaaacagttt taccggcatg gcggtggggg cggccatgac aggattgcgc ccagtcattg     240
aaggcatgaa tatgggtttt cttctgctgg cgtttaacca aattgccaat aatgcgggga     300
tgttgcgcta tacctccggc ggcaattacc aaattcccat ggttatccgt ggtcctgggg     360
gcgtaggtcg gcaattaggg gcagaacatt cccaacggtt ggaggcctat tccatgcgg     420 tgccggggtt aaaaattgtg gcttgctcca cccctataa cgccaaggga ttgctcaaag     480
cagccattcg ggataataac ccagtgttat tttttgagca cgtacttttg tacaacttga     540
aagaaaactt acccgactac gaatatattg tgcctctgga taaagccgaa gtggtgcgcc     600
ccggtaagga tgtcactatt ttgacctatt cccgcatgcg tcaccattgt ttacaggcac     660
taaaaacttt ggaaaagaa ggctacgacc cggaaattat tgatttgatt tccctcaagc     720
cttttgacat ggaaaccatc agcgcttcgg tgaagaaaac ccatcgggtc attattgtcg     780
aagaatgtat gaaaaccgga ggcatcggcg ctgagctcat tgccctaatc aatgatcatc     840
tctttgatga gttagatggg ccggtggtgc gcctttcttc ccaagatatt cccactccct     900
acaacggtat gttggaacga ctgaccattg tgcaaccgcc ccaaattgtg gacgcagtta     960
aggcgatcat cggctaattg gcctcaaaac agtacccctt gccgtaaacg gaattaatca    1020 ggcgggggc attgggctgt tcaatttttgc gccgcagtaa tcgcaccagg gccgccagca    1080
cgttactact ggggggcgctt tcgccgggcc aaaggtggga atagatct                1128
```

<210> SEQ ID NO 26
<211> LENGTH: 2441
<212> TYPE: DNA
<213> ORGANISM: Artificial Sequence
<220> FEATURE:
<223> OTHER INFORMATION: synthetic combined bacterial sequences

<400> SEQUENCE: 26

```
gggattaatc gacatccacc cttgtccct gactaaaatc tccgctatgg tggccagcca      60
gtgtgtcaaa atactagatt gttgtgcccc gatcgcccct gcttggtttg cctacaccgg     120
accaacaagg agagatgcgg cggcggtcta aattgttatt aaaaactaag ttttcccca     180 gaaatcatgg ctgagaccct actgtttgcc gccctacgcc aagcccttga cgaagaaatg     240
ggacgggatg tcaacgtcct tgtgctggga gaagatgtgg gactctatgg cggttcctat     300
```

```
aaggtaacca aggatttgta cgagaagtat ggcgaaatgc gggtgctgga tacgcccatc      360
gccgaaaaca gttttaccgg catggcggtg ggggcggcca tgacaggatt gcgcccagtc      420
attgaaggca tgaatatggg ttttcttctg ctggcgttta accaaattgc caataatgcg      480
gggatgttgc gctataccctc cggcggcaat taccaaattc ccatggttat ccgtggtcct     540
gggggcgtag gtcggcaatt aggggcagaa cattcccaac ggttggaggg aattccccgg      600
atccgtcgac ctgcaggggg ggggggggcgc tgaggtctgc ctcgtgaaga aggtgttgct     660
gactcatacc aggcctgaat cgccccatca tccagccaga aagtgaggga gccacggttg      720
atgagagctt tgttgtaggt ggaccagttg gtgattttga acttttgctt tgccacggaa      780
cggtctgcgt tgtcgggaag atgcgtgatc tgatccttca actcagcaaa agttcgattt      840
attcaacaaa gccgccgtcc cgtcaagtca gcgtaatgct ctgccagtgt tacaaccaat      900
taaccaattc tgattagaaa aactcatcga gcatcaaatg aaactgcaat ttattcatat      960
caggattatc aataccatat ttttgaaaaa gccgtttctg taatgaagga gaaaactcac     1020
cgaggcagtt ccataggatg gcaagatcct ggtatcggtc tgcgattccg actcgtccaa     1080
catcaataca acctattaat ttcccctcgt caaaaataag gttatcaagt gagaaatcac     1140
catgagtgac gactgaatcc ggtgagaatg gcaaaagctt atgcatttct ttccagactt     1200
gttcaacagg ccagccatta cgctcgtcat caaaatcact cgcatcaacc aaaccgttat     1260
tcattcgtga ttgcgcctga gcgagacgaa atacgcgatc gctgttaaaa ggacaattac     1320
aaacaggaat cgaatgcaac cggcgcagga acactgccag cgcatcaaca atattttcac     1380
ctgaatcagg atattcttct aatacctgga atgctgtttt cccggggatc gcagtggtga     1440
gtaaccatgc atcatcagga gtacggataa aatgcttgat ggtcggaaga ggcataaatt     1500
ccgtcagcca gtttagtctg accatctcat ctgtaacatc attggcaacg ctacctttgc     1560
catgtttcag aaacaactct ggcgcatcgg gcttcccata caatcgatag attgtcgcac     1620
ctgattgccc gacattatcg cgagcccatt tatacccata taaatcagca tccatgttgg     1680
aatttaatcg cggcctcgag caagacgttt cccgttgaat atggctcata cacccccttg     1740
tattactgtt tatgtaagca gacagttttta ttgttcatga tgatatattt ttatcttgtg     1800
caatgtaaca tcagagattt tgagacacaa cgtggctttc ccccccccc ctgcaggtcg     1860 acggatccgg ggaattccct atttccatgc ggtgccgggg ttaaaaattg tggcttgctc     1920
caccccctat aacgccaagg gattgctcaa agcagccatt cgggataata cccagtgtt     1980 atttttttgag cacgtacttt tgtacaactt gaaagaaaac ttacccgact acgaatatat   2040
tgtgcctctg gataaagccg aagtggtgcg ccccggtaag gatgtcacta ttttgaccta    2100
ttcccgcatg cgtcaccatt gtttacaggc actaaaaact ttggaaaaag aaggctacga   2160
cccggaaatt attgatttga tttccctcaa gccttttgac atggaaacca tcagcgcttc   2220
ggtgaagaaa acccatcggg tcattattgt cgaagaatgt atgaaaaccg gaggcatcgg   2280
cgctgagctc attgccctaa tcaatgatca tctctttgat gagttagatg ggccggtggt   2340
gcgcctttct tcccaagata ttcccactcc ctacaacggt atgttggaac gactgaccat   2400
tgtgcaaccg ccccaaattg tggacgcagt taaggcaatc a                         2441
```

<210> SEQ ID NO 27
<211> LENGTH: 3000
<212> TYPE: DNA
<213> ORGANISM: Artificial Sequence
<220> FEATURE:
<223> OTHER INFORMATION: synthetic combined bacterial sequences

<400> SEQUENCE: 27

```
gggcgaattg ggcccgacgt cgcatgctcc cggccgccat ggccgcggga tatcactagt    60
gcggccgcct gcaggtcgac catatgggag agctcccaac gcgttggatg catagcttga   120
gtattctata gtgtcaccta aatagcttgg cgtaatcatg gtcatagctg tttcctgtgt   180
gaaattgtta tccgctcaca attccacaca acatacgagc cggaagcata agtgtaaag    240
cctggggtgc ctaatgagtg agctaactca cattaattgc gttgcgctca ctgcccgctt   300
tccagtcggg aaacctgtcg tgccagctgc attaatgaat cggccaacgc gcgggggagag  360
gcggtttgcg tattgggcgc tcttccgctt cctcgctcac tgactcgctg cgctcggtcg   420
ttcggctgcg gcgagcggta tcagctcact caaaggcggt aatacggtta ccacagaat    480
caggggataa gcaggaaag aacatgtgag caaaaggcca gcaaaaggcc aggaaccgta    540
aaaaggccgc gttgctggcg ttttttccata ggctccgccc cctgacgag catcacaaaa   600
atcgacgctc aagtcagagg tggcgaaacc cgacaggact ataaagatac caggcgttc    660
cccctggaag ctccctcgtg cgctctcctg ttccgaccct gccgcttacc ggatacctgt   720
ccgcctttct cccttcggga agcgtggcgc tttctcatag ctcacgctgt aggtatctca   780
gttcggtgta ggtcgttcgc tccaagctgg gctgtgtgca cgaaccccc gttcagcccg    840
accgctgcgc cttatccggt aactatcgtc ttgagtccaa cccggtaaga cacgacttat   900
cgccactggc agcagccact ggtaacagga ttagcagagc gaggtatgta ggcggtgcta   960
cagagttctt gaagtggtgg cctaactacg gctacactag aagaacagta tttggtatct  1020
gcgctctgct gaagccagtt accttcggaa aaagagttgg tagctcttga tccggcaaac  1080
aaaccaccgc tggtagcggt ggtttttttg tttgcaagca gcagattacg cgcagaaaaa  1140
aaggatctca agaagatcct ttgatctttt ctacggggtc tgacgctcag tggaacgaaa  1200
actcacgtta agggattttg gtcatgagat tatcaaaaag gatcttcacc tagatccttt  1260
taaattaaaa atgaagtttt aaatcaatct aaagtatata tgagtaaact tggtctgaca  1320
gttaccaatg cttaatcagt gaggcaccta tctcagcgat ctgtctattt cgttcatcca  1380
tagttgcctg actccccgtc gtgtagataa ctacgatacg ggagggctta ccatctggcc  1440
ccagtgctgc aatgataccg cgagacccac gctcaccggc tccagattta tcagcaataa  1500
accagccagc cggaagggcc gagcgcagaa gtggtcctgc aactttatcc gcctccatcc  1560
agtctattaa ttgttgccgg gaagctagag taagtagttc gccagttaat agtttgcgca  1620
acgttgttgc cattgctaca ggcatcgtgg tgtcacgctc gtcgtttggt atggcttcat  1680
tcagctccgg ttcccaacga tcaaggcgag ttacatgatc ccccatgttg tgcaaaaaag  1740
cggttagctc cttcggtcct ccgatcgttg tcagaagtaa gttggccgca gtgttatcac  1800
tcatggttat ggcagcactg cataattctc ttactgtcat gccatccgta agatgctttt  1860
ctgtgactgg tgagtactca accaagtcat tctgagaata gtgtatgcgg cgaccgagtt  1920
gctcttgccc ggcgtcaata cgggataata ccgcgccaca tagcagaact ttaaaagtgc  1980
tcatcattgg aaaacgttct tcggggcgaa aactctcaag gatcttaccg ctgttgagat  2040
ccagttcgat gtaacccact cgtgcaccca actgatcttc agcatctttt actttcacca  2100
gcgtttctgg gtgagcaaaa acaggaaggc aaaatgccgc aaaaaaggga ataagggcga  2160
cacggaaatg ttgaatactc atactcttcc tttttcaata ttattgaagc atttatcagg  2220
gttattgtct catgagcgga tacatatttg aatgtattta gaaaaataaa caaatagggg  2280
```

| | |
|---|---|
| ttccgcgcac atttccccga aaagtgccac ctgatgcggt gtgaaatacc gcacagatgc | 2340 |
| gtaaggagaa ataccgcat caggaaattg taagcgttaa tattttgtta aaattcgcgt | 2400 |
| taaattttg ttaaatcagc tcattttta accaataggc cgaaatcggc aaaatccctt | 2460 |
| ataaatcaaa agaatagacc gagatagggt tgagtgttgt tccagtttgg aacaagagtc | 2520 |
| cactattaaa gaacgtggac tccaacgtca aagggcgaaa aaccgtctat cagggcgatg | 2580 |
| gcccactacg tgaaccatca ccctaatcaa gttttttggg gtcgaggtgc cgtaaagcac | 2640 |
| taaatcggaa ccctaaaggg agccccgat ttagagcttg acggggaaag ccggcgaacg | 2700 |
| tggcgagaaa ggaagggaag aaagcgaaag gagcgggcgc tagggcgctg gcaagtgtag | 2760 |
| cggtcacgct gcgcgtaacc accacacccg ccgcgcttaa tgccgcgcta cagggcgcgt | 2820 |
| ccattcgcca ttcaggctgc gcaactgttg ggaagggcga tcggtgcggg cctcttcgct | 2880 |
| attacgccag ctggcgaaag ggggatgtgc tgcaaggcga ttaagttggg taacgccagg | 2940 |
| gttttcccag tcacgacgtt gtaaaacgac ggccagtgaa ttgtaatacg actcactata | 3000 |

<210> SEQ ID NO 28
<211> LENGTH: 3851
<212> TYPE: DNA
<213> ORGANISM: Artificial Sequence
<220> FEATURE:
<223> OTHER INFORMATION: synthetic combined bacterial sequences

<400> SEQUENCE: 28

| | |
|---|---|
| gcgcccaata cgcaaaccgc ctctccccgc gcgttggccg attcattaat gcagctggca | 60 |
| cgacaggttt cccgactgga aagcgggcag tgagcgcaac gcaattaatg tgagttagct | 120 |
| cactcattag gcaccccagg ctttacactt tatgcttccg gctcgtatgt tgtgtggaat | 180 |
| tgtgagcgga taacaatttc acacaggaaa cagctatgac catgattacg ccaagctcta | 240 |
| atacgactca ctatagggaa agctcggtac cacgcatgct gcagacgcgt tacgtatcgg | 300 |
| atccagaatt cgtgatatct gaattcgtcg acaagcttct cgagcctagg ctagctctag | 360 |
| accacacgtg tgggggcccg agctcgcggc cgctgtattc tatagtgtca cctaaatggc | 420 |
| cgcacaattc actggccgtc gttttacaac gtcgtgactg gaaaaccct ggcgttaccc | 480 |
| aacttaatcg ccttgcagca catccccctt tcgccagctg gcgtaatagc gaagaggccc | 540 |
| gcaccgatcg cccttcccaa cagttgcgca gcctgaatgg cgaatggaaa ttgtaagcgt | 600 |
| taatattttg ttaaaattcg cgttaaattt ttgttaaatc agctcatttt ttaaccaata | 660 |
| ggccgaaatc ggcaaaatcc cttataaatc aaaagaatag accgagatag ggttgagtgt | 720 |
| tgttccagtt tggaacaaga gtccactatt aaagaacgtg gactccaacg tcaaagggcg | 780 |
| aaaaaccgtc tatcagggcg atggcccact acgtgaacca tcaccctaat caagtttttt | 840 |
| ggggtcgagg tgccgtaaag cactaaatcg gaaccctaaa gggagccccc gatttagagc | 900 |
| ttgacgggga agccggcga acgtggcgag aaaggaaggg aagaaagcga aggagcggg | 960 |
| cgctagggcg ctggcaagtg tagcggtcac gctgcgcgta accaccacac ccgccgcgct | 1020 |
| taatgcgccg ctacagggcg cgtcaggtgg cacttttcgg ggaaatgtgc gcggaacccc | 1080 |
| tatttgttta ttttttctaaa tacattcaaa tatgtatccg ctcatgagac aataaccctg | 1140 |
| ataaatgctt caataatatt gaaaaaggaa gagtatgagt attcaacatt tccgtgtcgc | 1200 |
| ccttattccc ttttttgcgg cattttgcct tcctgttttt gctcacccag aaacgctggt | 1260 |
| gaaagtaaaa gatgctgaag atcagttggg tgcacgagtg ggttacatcg aactggatct | 1320 |
| caacagcggt aagatccttg agagttttcg ccccgaagaa cgttttccaa tgatgagcac | 1380 |

```
ttttaaagtt ctgctatgtg gcgcggtatt atcccgtatt gacgccgggc aagagcaact   1440
cggtcgccgc atacactatt ctcagaatga cttggttgag tactcaccag tcacagaaaa   1500
gcatcttacg gatggcatga cagtaagaga attatgcagt gctgccataa ccatgagtga   1560
taacactgcg gccaacttac ttctgacaac gatcggagga ccgaaggagc taaccgcttt   1620
tttgcacaac atggggatc  atgtaactcg ccttgatcgt tgggaaccgg agctgaatga   1680
agccatacca aacgacgagc gtgacaccac gatgcctgta gcaatggcaa caacgttgcg   1740
caaactatta actggcgaac tacttactct agcttcccgg caacaattaa tagactggat   1800
ggaggcggat aaagttgcag gaccacttct gcgctcggcc cttccggctg gctggtttat   1860
tgctgataaa tctggagccg gtgagcgtgg gtctcgcggt atcattgcag cactggggcc   1920
agatggtaag ccctcccgta tcgtagttat ctacacgacg gggagtcagg caactatgga   1980
tgaacgaaat agacagatcg ctgagatagg tgcctcactg attaagcatt ggtaactgtc   2040
agaccaagtt tactcatata ctttagat  tgatttaaaa cttcattttt aatttaaaag   2100
gatctaggtg aagatccttt ttgataatct catgaacaat aaaactgtct gcttacataa   2160
acagtaatac aaggggtgtt atgagccata ttcaacggga acgtcttgc  tctaggccgc   2220
gattaaattc caacatggat gctgatttat atgggtataa atgggctcgc gataatgtcg   2280
ggcaatcagg tgcgacaatc tatcgattgt atgggaagcc cgatgcgcca gagttgtttc   2340
tgaaacatgg caaaggtagc gttgccaatg atgttacaga tgagatggtc agactaaact   2400
ggctgacgga atttatgcct cttccgacca tcaagcattt tatccgtact cctgatgatg   2460
catggttact caccactgcg atccccggga aaacagcatt ccaggtatta gaagaatatc   2520
ctgattcagg tgaaaatatt gttgatgcgc tggcagtgtt cctgcgccgg ttgcattcga   2580
ttcctgtttg taattgtcct tttaacagcg atcgcgtatt tcgtctcgct caggcgcaat   2640
cacgaatgaa taacggtttg gttgatgcga gtgattttga tgacgagcgt aatggctggc   2700
ctgttgaaca agtctggaaa gaaatgcata actttttgcc attctcaccg gattcagtcg   2760
tcactcatgg tgatttctca cttgataacc ttatttttga cgaggggaaa ttaataggtt   2820
gtattgatgt tggacgagtc ggaatcgcag accgatacca ggatcttgcc atcctatgga   2880
actgcctcgg tgagttttct ccttcattac agaaacggct tttcaaaaa  tatggtattg   2940
ataatcctga tatgaataaa ttgcagtttc atttgatgct cgatgagttt ttctaagaat   3000
taattcatga ccaaaatccc ttaacgtgag ttttcgttcc actgagcgtc agaccccgta   3060
gaaaagatca aaggatcttc ttgagatcct ttttttctgc gcgtaatctg ctgcttgcaa   3120
acaaaaaaac caccgctacc agcggtggtt tgtttgccgg atcaagagct accaactctt   3180
tttccgaagg taactggctt cagcagagcg cagataccaa atactgtcct tctagtgtag   3240
ccgtagttag gccaccactt caagaactct gtagcaccgc ctacatacct cgctctgcta   3300
atcctgttac cagtggctgc tgccagtggc gataagtcgt gtcttaccgg gttggactca   3360
agacgatagt taccggataa ggcgcagcgg tcgggctgaa cggggggttc gtgcacacag   3420
cccagcttgg agcgaacgac ctacaccgaa ctgagatacc tacagcgtga gctatgagaa   3480
agcgccacgc ttcccgaagg gagaaaggcg gacaggtatc cggtaagcgg cagggtcgga   3540
acaggagagc gcacgaggga gcttccaggg ggaaacgcct ggtatcttta tagtcctgtc   3600
gggtttcgcc acctctgact tgagcgtcga ttttgtgat  gctcgtcagg ggggcggagc   3660
ctatggaaaa acgccagcaa cgcggccttt ttacggttcc tggccttttg ctggcctttt   3720
```

-continued

```
gctcacatgt tctttcctgc gttatcccct gattctgtgg ataaccgtat taccgccttt    3780
gagtgagctg ataccgctcg ccgcagccga acgaccgagc gcagcgagtc agtgagcgag    3840
gaagcggaag a                                                        3851
```

<210> SEQ ID NO 29
<211> LENGTH: 2961
<212> TYPE: DNA
<213> ORGANISM: Artificial Sequence
<220> FEATURE:
<223> OTHER INFORMATION: synthetic combined bacterial sequences

<400> SEQUENCE: 29

```
ctaaattgta agcgttaata ttttgttaaa attcgcgtta aattttttgtt aaatcagctc      60 attttttaac caataggccg aaatcggcaa atcccttat aaatcaaaag aatagaccga     120
gatagggttg agtgttgttc cagtttggaa caagagtcca ctattaaaga acgtggactc     180
caacgtcaaa gggcgaaaaa ccgtctatca gggcgatggc ccactacgtg aaccatcacc     240
ctaatcaagt tttttggggt cgaggtgccg taaagcacta atcggaacc ctaaagggag      300 cccccgattt agagcttgac ggggaaagcc ggcgaacgtg gcgagaaagg aagggaagaa     360
agcgaaagga gcgggcgcta gggcgctggc aagtgtagcg gtcacgctgc gcgtaaccac     420
cacacccgcc gcgcttaatg cgccgctaca gggcgcgtcc cattcgccat tcaggctgcg     480
caactgttgg aagggcgat cggtgcgggc ctcttcgcta ttacgccagc tggcgaaagg      540
gggatgtgct gcaaggcgat taagttgggt aacgccaggg ttttcccagt cacgacgttg     600
taaaacgacg gccagtgagc gcgcgtaata cgactcacta tagggcgaat tgggtaccgg     660
gccccccctc gaggtcgacg gtatcgataa gcttgatatc gaattcctgc agcccggggg    720
atccactagt tctagagcgg ccgccaccgc ggtggagctc cagcttttgt tcccttagt      780 gagggttaat tgcgcgcttg gcgtaatcat ggtcatagct gtttcctgtg tgaaattgtt     840
atccgctcac aattccacac aacatacgag ccggaagcat aaagtgtaaa gcctggggtg     900
cctaatgagt gagctaactc acattaattg cgttgcgctc actgcccgct ttccagtcgg     960
gaaacctgtc gtgccagctg cattaatgaa tcggccaacg cgcggggaga ggcggtttgc    1020
gtattgggcg ctcttccgct tcctcgctca ctgactcgct gcgctcggtc gttcggctgc    1080
ggcgagcggt atcagctcac tcaaaggcgg taatacggtt atccacagaa tcaggggata    1140
acgcaggaaa gaacatgtga gcaaaaggcc agcaaaaggc caggaaccgt aaaaaggccg    1200
cgttgctggc gttttttccat aggctccgcc cccctgacga gcatcacaaa aatcgacgct    1260
caagtcagag gtggcgaaac ccgacaggac tataaagata ccaggcgttt ccccctggaa    1320
gctccctcgt gcgctctcct gttccgaccc tgccgcttac cggatacctg tccgcctttc    1380
tcccttcggg aagcgtggcg ctttctcata gctcacgctg taggtatctc agttcggtgt    1440
aggtcgttcg ctccaagctg ggctgtgtgc acgaaccccc cgttcagccc gaccgctgcg    1500
ccttatccgg taactatcgt cttgagtcca acccggtaag acacgactta tcgccactgg    1560
cagcagccac tggtaacagg attagcagag cgaggtatgt aggcggtgct acagagttct    1620
tgaagtggtg gcctaactac ggctacacta aaggacagt atttggtatc tgcgctctgc    1680
tgaagccagt taccttcgga aaaagagttg gtagctcttg atccggcaaa caaaccaccg    1740
ctggtagcgg tggttttttt gtttgcaagc agcagattac gcgcagaaaa aaaggatctc    1800
aagaagatcc tttgatcttt tctacggggt ctgacgctca gtggaacgaa aactcacgtt    1860
aagggatttt ggtcatgaga ttatcaaaaa ggatcttcac ctagatcctt ttaaattaaa    1920
```

```
aatgaagttt taaatcaatc taaagtatat atgagtaaac ttggtctgac agttaccaat    1980
gcttaatcag tgaggcacct atctcagcga tctgtctatt tcgttcatcc atagttgcct    2040
gactccccgt cgtgtagata actacgatac gggagggctt accatctggc cccagtgctg    2100
caatgatacc gcgagaccca cgctcaccgg ctccagattt atcagcaata aaccagccag    2160
ccggaagggc cgagcgcaga agtggtcctg caactttatc cgcctccatc cagtctatta    2220
attgttgccg ggaagctaga gtaagtagtt cgccagttaa tagtttgcgc aacgttgttg    2280
ccattgctac aggcatcgtg gtgtcacgct cgtcgtttgg tatggcttca ttcagctccg    2340
gttcccaacg atcaaggcga gttacatgat cccccatgtt gtgcaaaaaa gcggttagct    2400
ccttcggtcc tccgatcgtt gtcagaagta agttggccgc agtgttatca ctcatggtta    2460
tggcagcact gcataattct cttactgtca tgccatccgt aagatgcttt tctgtgactg    2520
gtgagtactc aaccaagtca ttctgagaat agtgtatgcg gcgaccgagt tgctcttgcc    2580
cggcgtcaat acgggataat accgcgccac atagcagaac tttaaaagtg ctcatcattg    2640
gaaaacgttc ttcggggcga aaactctcaa ggatcttacc gctgttgaga tccagttcga    2700
tgtaacccac tcgtgcaccc aactgatctt cagcatcttt tactttcacc agcgtttctg    2760
ggtgagcaaa aacaggaagg caaaatgccg caaaaaaggg aataagggcg acacggaaat    2820
gttgaatact catactcttc ctttttcaat attattgaag catttatcag ggttattgtc    2880
tcatgagcgg atacatattt gaatgtattt agaaaaataa acaaataggg gttccgcgca    2940
catttccccg aaaagtgcca c                                              2961

<210> SEQ ID NO 30
<211> LENGTH: 2686
<212> TYPE: DNA
<213> ORGANISM: Artificial Sequence
<220> FEATURE:
<223> OTHER INFORMATION: synthetic combined bacterial sequences

<400> SEQUENCE: 30
tcgcgcgttt cggtgatgac ggtgaaaacc tctgacacat gcagctcccg gagacggtca      60
cagcttgtct gtaagcggat gccgggagca gacaagcccg tcagggcgcg tcagcgggtg     120
ttggcgggtg tcggggctgg cttaactatg cggcatcaga gcagattgta ctgagagtgc     180
accatatgcg gtgtgaaata ccgcacagat gcgtaaggag aaaataccgc atcaggcgcc     240
attcgccatt caggctgcgc aactgttggg aagggcgatc ggtgcgggcc tcttcgctat     300
tacgccagct ggcgaaaggg ggatgtgctg caaggcgatt aagttgggta acgccagggt     360
tttcccagtc acgacgttgt aaaacgacgg ccagtgaatt cgagctcggt acccggggat     420
cctctagagt cgacctgcag gcatgcaagc ttggcgtaat catggtcata gctgtttcct     480
gtgtgaaatt gttatccgct cacaattcca cacaacatac gagccggaag cataaagtgt     540
aaagcctggg gtgcctaatg agtgagctaa ctcacattaa ttgcgttgcg ctcactgccc     600
gctttccagt cgggaaacct gtcgtgccag ctgcattaat gaatcggcca acgcgcgggg     660
agaggcggtt tgcgtattgg gcgctcttcc gcttcctcgc tcactgactc gctgcgctcg     720
gtcgttcggc tgcggcgagc ggtatcagct cactcaaagg cggtaatacg ttatccaca     780 gaatcagggg ataacgcagg aaagaacatg tgagcaaaag gccagcaaaa ggccaggaac     840
cgtaaaaagg ccgcgttgct ggcgtttttc cataggctcc gcccccctga cgagcatcac     900
aaaaatcgac gctcaagtca gaggtggcga aacccgacag gactataaag ataccaggcg     960
```

```
tttcccctg gaagctccct cgtgcgctct cctgttccga ccctgccgct taccggatac    1020
ctgtccgcct ttctcccttc gggaagcgtg gcgctttctc atagctcacg ctgtaggtat    1080
ctcagttcgg tgtaggtcgt tcgctccaag ctgggctgtg tgcacgaacc ccccgttcag    1140
cccgaccgct gcgccttatc cggtaactat cgtcttgagt ccaacccggt aagacacgac    1200
ttatcgccac tggcagcagc cactggtaac aggattagca gagcgaggta tgtaggcggt    1260
gctacagagt tcttgaagtg gtggcctaac tacggctaca ctagaaggac agtatttggt    1320
atctgcgctc tgctgaagcc agttaccttc ggaaaaagag ttggtagctc ttgatccggc    1380
aaacaaacca ccgctggtag cggtggtttt tttgtttgca agcagcagat tacgcgcaga    1440
aaaaaaggat ctcaagaaga tcctttgatc ttttctacgg ggtctgacgc tcagtggaac    1500
gaaaactcac gttaagggat tttggtcatg agattatcaa aaaggatctt cacctagatc    1560
cttttaaatt aaaaatgaag ttttaaatca atctaaagta tatatgagta aacttggtct    1620
gacagttacc aatgcttaat cagtgaggca cctatctcag cgatctgtct atttcgttca    1680
tccatagttg cctgactccc cgtcgtgtag ataactacga tacgggaggg cttaccatct    1740
ggccccagtg ctgcaatgat accgcgagac ccacgctcac cggctccaga tttatcagca    1800 ataaccagc cagccggaag ggccgagcgc agaagtggtc ctgcaacttt atccgcctcc    1860
atccagtcta ttaattgttg ccgggaagct agagtaagta gttcgccagt taatagtttg    1920
cgcaacgttg ttgccattgc tacaggcatc gtggtgtcac gctcgtcgtt tggtatggct    1980
tcattcagct ccggttccca acgatcaagg cgagttacat gatccccccat gttgtgcaaa    2040 aaagcggtta gctccttcgg tcctccgatc gttgtcagaa gtaagttggc cgcagtgtta    2100
tcactcatgg ttatggcagc actgcataat tctcttactg tcatgccatc cgtaagatgc    2160
ttttctgtga ctggtgagta ctcaaccaag tcattctgag aatagtgtat gcggcgaccg    2220
agttgctctt gcccggcgtc aatacgggat aataccgcgc cacatagcag aactttaaaa    2280
gtgctcatca ttggaaaacg ttcttcgggg cgaaaactct caaggatctt accgctgttg    2340
agatccagtt cgatgtaacc cactcgtgca cccaactgat cttcagcatc ttttactttc    2400
accagcgttt ctgggtgagc aaaaacagga aggcaaaatg ccgcaaaaaa gggaataagg    2460
gcgacacgga aatgttgaat actcatactc ttccttttc aatattattg aagcatttat    2520
cagggttatt gtctcatgag cggatacata tttgaatgta tttagaaaaa taaacaaata    2580
ggggttccgc gcacatttcc ccgaaaagtg ccacctgacg tctaagaaac cattattatc    2640
atgacattaa cctataaaaa taggcgtatc acgaggccct ttcgtc    2686
```

<210> SEQ ID NO 31
<211> LENGTH: 6267
<212> TYPE: DNA
<213> ORGANISM: Artificial Sequence
<220> FEATURE:
<223> OTHER INFORMATION: synthetic combined bacterial sequences

<400> SEQUENCE: 31

```
cacctaaatt gtaagcgtta atattttgtt aaaattcgcg ttaaattttt gttaaatcag      60
ctcatttttt aaccaatagg ccgaaatcgg caaaatccct tataaatcaa agaatagac     120 cgagataggg ttgagtgttg ttccagtttg gaacaagagt ccactattaa agaacgtgga    180
ctccaacgtc aaagggcgaa aaaccgtcta tcagggcgat ggcccactac gtgaaccatc    240 acctaatca gttttttggg ggtcgaggtg ccgtaaagca ctaaatcgga acctaaagg     300 gagccccga tttagagctt gacggggaaa gccggcgaac gtggcgagaa aggaagggaa    360
```

```
gaaagcgaaa ggagcgggcg ctagggcgct ggcaagtgta gcggtcacgc tgcgcgtaac    420
caccacaccc gccgcgctta atgcgccgct acagggcgcg tcccattcgc cattcaggct    480
gcgcaactgt tgggaagggc gatcggtgcg ggcctcttcg ctattacgcc agctggcgaa    540 aggggatgt gctgcaaggc gattaagttg ggtaacgcca gggttttccc agtcacgacg    600
ttgtaaaacg acggccagtg aattgtaata cgactcacta tagggcgaat tggaggccag    660
tgctggagga atatgatttt gtcatcctcg actgtgcccc tggttataat ctgttgaccc    720
gcagtggcat tgcggccagc gacttttatc tgttgccggc tcgtcctgaa cccctatcgg    780
tggtggggat gcagttactg gaaagaagaa ttgagaaact gaaggaaagc cataaggcct    840
ccgatgatcc cctgaatatc aatctgatcg gagtggtgtt tattctgtcc ggcggcggtt    900
tgatgagtcg ctactataac caggtaatgc ggcgggtaca aacggatttc accccgggac    960 aacttttca gcagtccatt cccatggatg tcaatgtggc taaggcagtg gatagcttta   1020
tgccggtggt tacctccatg cccaatacgg cgggttcaaa agcttttatt aaattaaccc   1080 aggaatttt acagaaagta gaagcttttg gctaaagcaa agcccccatt gattaacaac   1140
gggaggggta ccgaggtgct gctgaagttg cccgcaacag agagtggaac caaccggtga   1200
taccacgata ctatgactga gagtcaacgc catgagcggc ctcatttctt attctgagtt   1260
acaacagtcc gcaccgctgt ccggtagctc cttccggtgg gcgcggggca tgactatcgt   1320
cgccgcactt atgactgtct tctttatcat gcaactcgta ggacaggtgc cggcagcgcc   1380
caacagtccc ccggccacgg ggcctgccac catacccacg ccgaaacaag cgccctgcac   1440
cattatgttc cggatctgca tcgcaggatg ctgctggcta ccctgtggaa cacctacatc   1500
tgtattaacg aagcgctaac cgttttatc aggctctggg aggcagaata atgatcata    1560 tcgtcaatta ttacctccac ggggagagcc tgagcaaact ggcctcaggc atttgagaag   1620
cacacggtca cactgcttcc ggtagtcaat aaaccggtaa accagcaata gacataagcg   1680
gctatttaac gaccctgccc tgaaccgacg accgggtcga atttgctttc gaatttctgc   1740
cattcatccg cttattatca cttattcagg cgtagcacca ggcgtttaag ggcaccaata   1800
actgccttaa aaaaattacg ccccgccctg ccactcatcg cagtactgtt gtaattcatt   1860
aagcattctg ccgacatgga agccatcaca gacggcatga tgaacctgaa tcgccagcgg   1920
catcagcacc ttgtcgcctt gcgtataata tttgcccatg gtgaaaacgg gggcgaagaa   1980
gttgtccata ttggccacgt ttaaatcaaa actggtgaaa ctcacccagg gattggctga   2040
gacgaaaaac atattctcaa taaacccttt agggaaatag gccaggtttt caccgtaaca   2100
cgccacatct tgcgaatata tgtgtagaaa ctgccggaaa tcgtcgtggt attcactcca   2160
gagcgatgaa aacgtttcag tttgctcatg gaaaacggtg taacaagggt gaacactatc   2220
ccatatcacc agctcaccgt ctttcattgc catacggaat tccggatgag cattcatcag   2280
gcgggcaaga atgtgaataa aggccggata aaacttgtgc ttattttct ttacggtctt   2340 taaaaaggcc gtaatatcca gctgaacggt ctggttatag gtacattgag caactgactg   2400
aaatgcctca aaatgttctt tacgatgcca ttgggatata tcaacggtgg tatatccagt   2460 gattttttc tccattttag cttccttagc tcctgaaaat ctcgataact caaaaaatac   2520
gcccggtagt gatcttattt cattatggtg aaagttggaa cctcttacct cggtacccct   2580 catcggggc tgtgttggcc gagacggcac tgaggatttt actctccatg gcattccaag   2640
gaatatctac ccaactcacc tgctccggcg gattgttccg ctcaaaagta ctaatcaagt   2700
```

```
cgtcaaaata cttattaaat tttggctgca attgcatagt ccaaaagctg actttcccct   2760
ccatgctctg gggggaattg ctctggcaac tgattaatcc actgagcaac agcccaagac   2820
acgcaaacaa aaaccaacgt cttggcgatc gccatcggca ccatgaaacc atcgtaaaag   2880
ctggggaaag aataaaaaac agtggttcag gaattgcatt gccatggcca cttcacaaac   2940
ctagccaatt ttagcttgac cgcaactttg acagattgtc ttttgacttt gcctggaccg   3000
cctcccataa taccttcgcg tcttgaagac tttatccttg aaaggagaac atatgtttct   3060
cggcaaaaat taattatcga ttggctggaa cctggtcaaa ccagggcttt tcatccattg   3120
gaaaagcgat tttgatcatc tagggtcagg agcaaagatc tgatcaaata ttgatcattt   3180
attaggaaag ctgaactttc accactttat ttttggcttc ctctactttg ggcaaagtca   3240
aagttaggat accggcatcg taattagctt taacttctgt gttttggatt gctccaggta   3300
caggaataac ccggcggaaa ctgccatagc ggaactctgt gcgccgcacc ccatcttttt   3360
cggtgctatg ggtatcctgg cgatcgccgc tgacggtcac cgcatccctg gcggcttgga   3420
tgtccaaatt atcggggtcc atgccaggta attctagttt gagcacatag gcttcttcag   3480
tttcagttag ttctgcttta ggattaaacc cttggcgatc gccgtggcgg tccgtaggga   3540
caaaaacttc ttcaaacagt tggttcatct gctgctggaa attatccatt ccccgcaggg   3600
gattgtaaag aatgagagac ataatgttaa ctcctgatgt gtggaaggaa ttgattaccc   3660
ttgaatggtt ctatcttaaa atttccccct tccaggttaga ttcggttttc aggaaagaag   3720
gtgggggat tgccgaaatt acatttctag ccgcaatttt tagtaaaaaa aagatgagtt   3780
tttacctcac cttaagtaaa tatttgagtg gcaaaacaaa atggtaaaaa tagctaagct   3840
tccaccgccc tatggatttt tggaaggaag tcttaggttg tgaaaaacta taaaaaccaa   3900
ccataggaat ggagacctt acccaacaag ttgaccccta ggtaacaaat ccaaaccacc   3960
gtaaaaccgc tggcggccaa aatagcgggc ttgcggcctt gccaacctt ggtaatgcgg   4020
gcatggagat aggcggcaaa tactagccag gtgattaggg cccggtaccc agcttttgtt   4080
cccttagtg agggttaatt tcgagcttgg cgtaatcatg gtcatagctg tttcctgtgt   4140
gaaattgtta tccgctcaca attccacaca acatacgagc cggaagcata agtgtaaag   4200
cctggggtgc ctaatgagtg agctaactca cattaattgc gttgcgctca ctgcccgctt   4260
tccagtcggg aaacctgtcg tgccagctgc attaatgaat cggccaacgc gcggggagag   4320
gcggtttgcg tattgggcgc tcttccgctt cctcgctcac tgactcgctg cgctcggtcg   4380
ttcggctgcg gcgagcggta tcagctcact caaaggcggt aatacggtta tccacagaat   4440
caggggataa cgcaggaaag aacatgtgag caaaaggcca gcaaaaggcc aggaaccgta   4500
aaaaggccgc gttgctggcg ttttttccata ggctccgccc ccctgacgag catcacaaaa   4560
atcgacgctc aagtcagagg tggcgaaacc cgacaggact ataaagatac caggcgtttc   4620
cccctggaag ctccctcgtg cgctctcctg ttccgaccct gccgcttacc ggatacctgt   4680
ccgcctttct cccttcggga agcgtggcgc tttctcatag ctcacgctgt aggtatctca   4740
gttcggtgta ggtcgttcgc tccaagctgg gctgtgtgca cgaaccccc gttcagcccg   4800
accgctgcgc cttatccggt aactatcgtc ttgagtccaa cccggtaaga cacgactat   4860
cgccactggc agcagccact ggtaacagga ttagcagagc gaggtatgta ggcggtgcta   4920
cagagttctt gaagtggtgg cctaactacg gctacactag aaggacagta tttggtatct   4980
gcgctctgct gaagccagtt accttcggaa aaagagttgg tagctcttga tccggcaaac   5040
aaaccaccgc tggtagcggt ggtttttttg tttgcaagca gcagattacg cgcagaaaaa   5100
```

-continued

```
aaggatctca agaagatcct ttgatctttt ctacggggtc tgacgctcag tggaacgaaa      5160
actcacgtta agggattttg gtcatgagat tatcaaaaag gatcttcacc tagatccttt      5220
taaattaaaa atgaagtttt aaatcaatct aaagtatata tgagtaaact tggtctgaca      5280
gttaccaatg cttaatcagt gaggcaccta tctcagcgat ctgtctattt cgttcatcca      5340
tagttgcctg actccccgtc gtgtagataa ctacgatacg ggagggctta ccatctggcc      5400
ccagtgctgc aatgataccg cgagacccac gctcaccggc tccagattta tcagcaataa      5460
accagccagc cggaagggcc gagcgcagaa gtggtcctgc aactttatcc gcctccatcc      5520
agtctattaa ttgttgccgg gaagctagag taagtagttc gccagttaat agtttgcgca      5580
acgttgttgc cattgctaca ggcatcgtgg tgtcacgctc gtcgtttggt atggcttcat      5640
tcagctccgg ttcccaacga tcaaggcgag ttacatgatc ccccatgttg tgcaaaaaag      5700
cggttagctc cttcggtcct ccgatcgttg tcagaagtaa gttggccgca gtgttatcac      5760
tcatggttat ggcagcactg cataattctc ttactgtcat gccatccgta agatgctttt      5820
ctgtgactgg tgagtactca accaagtcat tctgagaata gtgtatgcgg cgaccgagtt      5880
gctcttgccc ggcgtcaata cgggataata ccgcgccaca tagcagaact ttaaaagtgc      5940
tcatcattgg aaaacgttct cgggggcgaa aactctcaag gatcttaccg ctgttgagat      6000
ccagttcgat gtaacccact cgtgcaccca actgatcttc agcatctttt actttcacca      6060
gcgtttctgg gtgagcaaaa acaggaaggc aaaatgccgc aaaaaaggga ataagggcga      6120
cacggaaatg ttgaatactc atactcttcc ttttcaata ttattgaagc atttatcagg      6180
gttattgtct catgagcgga tacatatttg aatgtattta gaaaaataaa caaatagggg      6240
ttccgcgcac atttccccga aaagtgc                                         6267
```

<210> SEQ ID NO 32
<211> LENGTH: 463
<212> TYPE: PRT
<213> ORGANISM: Synechocystis PCC6803

<400> SEQUENCE: 32

```
Met Val Ser Leu Thr Pro Asn Pro Ser Tyr Ser Val Ser Leu Leu Leu
1               5                   10                  15

Glu Leu Pro Asn His Ala Gly Thr Leu Ala Ser Val Thr Gln Ala Ile
            20                  25                  30

Ala Asp Ala Gly Gly Ser Phe Gly Gln Ile Ser Leu Ile Glu Ser Asn
        35                  40                  45

Leu Lys Leu Thr Arg Arg Glu Ile Ala Val Asp Ala Ser Ser Ser Glu
    50                  55                  60

His Ala Glu Lys Ile Ile Gly Ala Val Lys Ala Leu Asp Asn Val Lys
65                  70                  75                  80

Leu Leu Lys Val Ser Asp Arg Thr Phe Asp Leu His Arg Gln Gly Lys
                85                  90                  95

Ile Ser Val Val Ser Arg Ile Pro Leu Thr Ser Gln Ser Asp Leu Ala
            100                 105                 110

Met Ala Tyr Thr Pro Gly Val Gly Arg Ile Cys Arg Ala Ile Ala Glu
        115                 120                 125

Asp Pro Glu Lys Val Tyr Ser Leu Thr Ile Lys Ser Asn Thr Val Ala
    130                 135                 140

Val Val Thr Asp Gly Ser Ala Val Leu Gly Leu Gly Asn Leu Gly Pro
145                 150                 155                 160
```

```
Glu Ala Ala Leu Pro Val Met Glu Gly Lys Ala Met Leu Phe Lys Glu
            165                 170                 175

Phe Ala Gln Leu Asp Ala Phe Pro Ile Cys Leu Asp Thr Gln Asp Thr
        180                 185                 190

Glu Glu Ile Ile Arg Thr Val Lys Ala Ile Ala Pro Val Phe Gly Gly
    195                 200                 205

Val Asn Leu Glu Asp Ile Ala Ala Pro Arg Cys Phe Glu Ile Glu Ala
210                 215                 220

Arg Leu Lys Lys Glu Leu Asn Ile Pro Val Phe His Asp Asp Gln His
225                 230                 235                 240

Gly Thr Ala Ile Val Thr Leu Ala Ala Leu Leu Asn Ala Leu Lys Phe
                245                 250                 255

Val Gly Lys Ala Met Ala Ala Val Arg Ile Val Ile Asn Gly Ala Gly
            260                 265                 270

Ala Ala Gly Leu Ala Ile Ala Glu Leu Leu Lys Glu Ser Gly Ala Thr
        275                 280                 285

Asp Ile Trp Ile Cys Asp Ser Lys Gly Ile Val Gly Lys His Arg Thr
    290                 295                 300

Asp Leu Asn Ser Lys Lys Gln Ser Phe Ala Val Asp Ala Glu Gly Thr
305                 310                 315                 320

Leu Ala Asp Ala Met Ala Gly Ala Asp Val Phe Leu Gly Val Ser Ala
                325                 330                 335

Pro Gly Val Val Thr Lys Glu Met Val Gln Ser Met Ala Lys Asp Pro
            340                 345                 350

Ile Val Phe Ala Met Ala Asn Pro Ile Pro Glu Ile Gln Pro Glu Leu
        355                 360                 365

Ile Gln Glu Asp Ala Ala Val Ile Ala Thr Gly Arg Ser Asp Tyr Pro
    370                 375                 380

Asn Gln Ile Asn Asn Val Leu Ala Phe Pro Gly Val Phe Arg Gly Ala
385                 390                 395                 400

Ile Asp Cys Arg Ala Ser Ile Ile Thr Thr Thr Met Cys Ile Glu Ala
                405                 410                 415

Ala Lys Ala Ile Ala Ser Leu Val His Ser Asn Thr Leu Asp Ser Glu
            420                 425                 430

His Ile Ile Pro Ser Val Phe Asp Asn Arg Val Ala Thr Thr Val Ala
        435                 440                 445

Ser Ala Val Gln Leu Ala Ala Arg Asn Glu Gly Val Ala Gly Gln
    450                 455                 460

<210> SEQ ID NO 33
<211> LENGTH: 1545
<212> TYPE: DNA
<213> ORGANISM: Artificial Sequence
<220> FEATURE:
<223> OTHER INFORMATION: synthetic combined bacterial sequences

<400> SEQUENCE: 33
tatggttagc ctcaccccca atccgagtta tagcgtcagc ctactgttgg aactccccaa      60
ccacgccgga actttggcca gcgttaccca ggcgatcgcc gatgcggggg gcagttttgg     120
gcaaatttcc ctgattgaga gtaacttaaa actcacccgg cgggaaattg cgtggatgc     180 ttccagcagt gagcacgccg aaaaaattat tggggcagtg aaagctctgg ataatgtcaa     240
attgctgaag gtgtccgatc gcacctttga tttacaccgt cagggcaaaa ttagcgtggt     300
tagtcgcatt cccctcacct cccaatcgga tttggccatg gcctataccc caggggtggg     360
```

-continued

```
gcgcatctgt cgggcgatcg ccgaagatcc ggaaaaggtt tattccctga ccattaaaag    420
caatacggtg gcggtggtga ccgatggcag tgcggtgttg gggttgggta acctggggcc    480
ggaagcggct ttaccagtga tggaaggcaa ggccatgtta ttcaaggaat tgcccaact    540
ggacgctttt cccatctgtt tggatacca ggatacggag gaaattattc gcaccgtcaa     600
ggcgatcgcc ccggtgtttg gcggcgtaaa tttggaagac attgccgctc cccggtgttt    660
tgaaattgaa gcccggctga aaaagaatt aaatattcct gtatttcacg atgatcagca     720
cggcaccgcc attgttaccc tggccgcttt gttaaatgcc ctcaaatttg ttggtaaagc    780
catggccgct gtccgcattg tcatcaacgg cgctgggggct gctgggttgg cgatcgccga   840
attgctcaag gaatccggag ccaccgatat ttggatttgc gactccaagg gcattgtggg    900
caaacatcgc accgatttaa acagcaaaaa acagagcttt gcggtggatg cggaagggac    960
tttagccgat gctatggctg gagctgatgt gttttttaggg gtgagtgcgc cggggggtagt 1020
gaccaaggaa atggtgcaat ccatggccaa ggacccgatt gtgtttgcca tggccaaccc   1080
tatccccgaa attcagccgg aattaatcca agaggatgcg gcggttattg ccacggggcg   1140
cagtgattac cccaaccaaa ttaacaatgt gcttgccttt ccgggggttt tccggggagc   1200
cattgactgt agagctagca ttattaccac caccatgtgc atcgaagcgg ccaaggcgat   1260
cgcctctttg gtgcacagca acaccctaga tagtgagcat attattcctt cggttttga    1320
caatcgggtc gccactaccg tagccagtgc agtgcagttg gccgcccgca atgaaggggt    1380
ggccggtcaa tagttaatcg ggaattgtta aacctttact ggtcaaccat tcctgattgt   1440
aaagacggga ttggtaacgg gctcctccgt cacaaagtac ggtaacaatg gtatgccccg   1500
gcccaagttt tttggccaat tggtaagccg ctcccacatt aatat                  1545
```

<210> SEQ ID NO 34
<211> LENGTH: 324
<212> TYPE: PRT
<213> ORGANISM: Synechocystis PCC6803

<400> SEQUENCE: 34

```
Met Asn Ile Leu Glu Tyr Ala Pro Ile Ala Cys Gln Ser Trp Gln Val
1               5                   10                  15

Thr Val Val Gly Ala Gly Asn Val Gly Arg Thr Leu Ala Gln Arg Leu
            20                  25                  30

Val Gln Gln Asn Val Ala Asn Val Leu Leu Asp Ile Val Pro Gly
        35                  40                  45

Leu Pro Gln Gly Ile Ala Leu Asp Leu Met Ala Ala Gln Ser Val Glu
    50                  55                  60

Glu Tyr Asp Ser Lys Ile Ile Gly Thr Asn Glu Tyr Glu Ala Thr Ala
65                  70                  75                  80

Gly Ser Asp Val Val Ile Thr Ala Gly Leu Pro Arg Arg Pro Gly
                85                  90                  95

Met Ser Arg Asp Asp Leu Leu Gly Lys Asn Ala Asn Ile Val Ala Gln
            100                 105                 110

Gly Ala Arg Glu Ala Leu Arg Tyr Ser Pro Asn Ala Ile Leu Ile Val
        115                 120                 125

Val Thr Asn Pro Leu Asp Val Met Thr Tyr Leu Ala Trp Lys Val Thr
    130                 135                 140

Gly Leu Pro Ser Gln Arg Val Met Gly Met Ala Gly Val Leu Asp Ser
145                 150                 155                 160

Ala Arg Leu Lys Ala Phe Ile Ala Met Lys Leu Gly Ala Cys Pro Ser
```

```
                    165                 170                 175
Asp Ile Asn Thr Leu Val Leu Gly Gly His Gly Asp Leu Met Leu Pro
                180                 185                 190

Leu Pro Arg Tyr Cys Thr Val Ser Gly Val Pro Ile Thr Glu Leu Ile
            195                 200                 205

Pro Pro Gln Thr Ile Glu Glu Leu Val Glu Arg Thr Arg Asn Gly Gly
        210                 215                 220

Ala Glu Ile Ala Ala Leu Leu Gln Thr Gly Thr Ala Tyr Tyr Ala Pro
225                 230                 235                 240

Ala Ser Ser Ala Ala Val Met Val Glu Ser Ile Leu Arg Asn Gln Ser
                245                 250                 255

Arg Ile Leu Pro Ala Ala Thr Tyr Leu Asp Gly Ala Tyr Gly Leu Lys
            260                 265                 270

Asp Ile Phe Leu Gly Val Pro Cys Arg Leu Gly Cys Arg Gly Val Glu
        275                 280                 285

Asp Ile Leu Glu Val Gln Leu Thr Pro Glu Glu Lys Ala Ala Leu His
    290                 295                 300

Leu Ser Ala Glu Ala Val Arg Leu Asn Ile Asp Val Ala Leu Ala Met
305                 310                 315                 320

Val Ser Asp Gly

<210> SEQ ID NO 35
<211> LENGTH: 1027
<212> TYPE: DNA
<213> ORGANISM: Artificial Sequence
<220> FEATURE:
<223> OTHER INFORMATION: synthetic combined bacterial sequences

<400> SEQUENCE: 35
tatgaatatt ttggagtatg ctccgatcgc ctgtcagtcc tggcaggtta ccgtggtcgg     60
cgctggcaat gtggggcgga cccttgccca gaggttagtg cagcaaaatg tcgccaacgt    120
agttttgttg acattgtgc caggcttacc ccagggcatt gccttggatt tgatggccgc     180
ccagagcgtg gaggaatacg acagcaaaat cattggcacc aatgaatacg aggccaccgc    240
cggctccgat gtggtggtaa ttaccgctgg tctaccccgc aggcccggca tgagtcggga    300
tgatttgttg ggcaaaaacg ccaacattgt ggcccagggg gcccgggaag cattgcgtta    360
ttcccccaac gccattttga ttgtggtcac caatcccctg gatgtaatga cctatttggc    420
ctggaaagta actggtttac cttcccaacg ggttatgggc atggcggggg tgttggactc    480
ggctcggctc aaggccttca ttgcgatgaa attaggggcc tgtccttctg atatcaacac    540
cttagtgctg gcgggcacg gagatttgat gctgcccttg ccacgatact gcaccgtcag    600
cggggttccc attaccgaat taatacccccc ccaaaccatt gaagagttgg tggagcgtac    660
ccgtaacggt ggggctgaaa ttgccgcctt actacaaacg ggcacagcct attatgcgcc    720
ggcctcttcc gctgcggtga tggtggagtc catttacgc aatcagtcta gaattctccc    780
cgccgccacc taccttgatg gtgcctatgg attgaaggac attttccttg gagtgccctg    840
ccgtttgggg tgtcgaggag tggaagatat tctcgaagtg caattaaccc ctgaagaaaa    900
agctgccctc catctttctg cagaagcagt tcgccttaat attgatgtgg cgttggccat    960
ggttagcgac ggttaacacg ataacggaca gtgccaatac cgttttttca ccgaggttag   1020
ggcttat                                                             1027

<210> SEQ ID NO 36
```

```
<211> LENGTH: 2606
<212> TYPE: DNA
<213> ORGANISM: Artificial Sequence
<220> FEATURE:
<223> OTHER INFORMATION: synthetic combined bacterial sequences

<400> SEQUENCE: 36
tatggttagc ctcacccccca atccgagtta tagcgtcagc ctactgttgg aactccccaa      60
ccacgccgga actttggcca gcgttaccca ggcgatcgcc gatgcggggg cagttttgg      120
gcaaatttcc ctgattgaga gtaacttaaa actcacccgg cgggaaattg cggtggatgc      180
ttccagcagt gagcacgccg aaaaaattat tggggcagtg aaagctctgg ataatgtcaa      240
attgctgaag gtgtccgatc gcacctttga tttacaccgt cagggcaaaa ttagcgtggt      300
tagtcgcatt ccctcacct cccaatcgga tttggccatg gcctataccc aggggtggg      360
gcgcatctgt cgggcgatcg ccgaagatcc ggaaaaggtt tattccctga ccattaaaag      420
caatacggtg gcggtggtga ccgatggcag tgccgtgttg gggttgggta acctggggcc      480
ggaagcggct ttaccagtga tggaaggcaa ggccatgtta ttcaaggaat ttgcccaact      540
ggacgctttt cccatctgtt tggatacccca ggatacggag gaaattattc gcaccgtcaa      600
ggcgatcgcc ccggtgtttg gcggcgtaaa tttggaagac attgccgctc cccggtgttt      660
tgaaattgaa gcccggctga aaaaagaatt aaatattcct gtatttcacg atgatcagca      720
cggcaccgcc attgttaccc tggccgcttt gttaaatgcc ctcaaatttg ttggtaaagc      780
catggccgct gtccgcattg tcatcaacgg cgctggggct gctgggttgg cgatcgccga      840
attgctcaag gaatccggag ccaccgatat tggatttgc gactccaagg gcattgtggg      900
caaacatcgc accgattta acagcaaaaa acagagctt gcggtggatg cggaagggac      960
tttagccgat gctatggctg gagctgatgt gttttaggg gtgagtgcgc cggggtagt     1020
gaccaaggaa atggtgcaat ccatggccaa ggacccgatt gtgtttgcca tggccaaccc     1080
tatccccgaa attcagccgg aattaatcca agaggatgcg gcggttattg ccacggggcg     1140
cagtgattac cccaaccaaa ttaacaatgt gcttgccttt ccgggggttt tccggggagc     1200
cattgactgt agagctagca ttattaccac caccatgtgc atcgaagcgg ccaaggcgat     1260
cgcctctttg gtgcacagca caccctaga tagtgagcat attattcctt cggttttga     1320
caatcgggtc gccactaccg tagccagtgc agtgcagttg gccgcccgca atgaagggt     1380
ggccggtcaa tagttaatcg ggaattgtta aaccttact ggtcaaccat tcctgattgt     1440
aaagacggga ttggtaacgg gctcctccgt cacaaagtac ggtaacaatg gtatgccccg     1500
gcccaagttt tttggccaat tggtaagccg ctcccacatt aatatcgatt tttctccacc     1560
atcaacaccc cggagggtgc catgaatatt ttggagtatg ctccgatcgc ctgtcagtcc     1620
tggcaggtta ccgtggtcgg cgctggcaat gtgggggcgga cccttgccca gaggttagtg     1680
cagcaaaatg tcgccaacgt agttttgttg gacattgtgc caggcttacc ccagggcatt     1740
gccttggatt tgatggccgc ccagagcgtg gaggaatacg acagcaaaat cattggcacc     1800
aatgaatacg aggccaccgc cggctccgat gtggtggtaa ttaccgctgg tctaccccgc     1860
aggcccggca tgagtcggga tgatttgttg ggcaaaaacg ccaacattgt ggcccagggg     1920
gcccgggaag cattgcgtta ttccccccaac gccatttga ttgtggtcac caatccctg     1980
gatgtaatga cctatttggc ctggaaagta actggtttac cttcccaacg ggttatgggc     2040
atggcggggg tgttgactc ggctcggctc aaggccttca ttgcgatgaa attagggcc     2100
tgtccttctg atatcaacac cttagtgctg ggcgggcacg gagatttgat gctgcccttg     2160
```

```
ccacgatact gcaccgtcag cggggttccc attaccgaat taataccccc ccaaaccatt    2220
gaagagttgg tggagcgtac ccgtaacggt ggggctgaaa ttgccgcctt actacaaacg    2280
ggcacagcct attatgcgcc ggcctcttcc gctgcggtga tggtggagtc cattttacgc    2340
aatcagtcta gaattctccc cgccgccacc taccttgatg gtgcctatgg attgaaggac    2400
attttccttg gagtgccctg ccgtttgggg tgtcgaggag tggaagatat tctcgaagtg    2460
caattaaccc ctgaagaaaa agctgccctc catctttctg cagaagcagt tcgccttaat    2520
attgatgtgg cgttggccat ggttagcgac ggttaacacg ataacggaca gtgccaatac    2580
cgttttttca ccgaggttag ggctta                                         2606
```

<210> SEQ ID NO 37
<211> LENGTH: 473
<212> TYPE: PRT
<213> ORGANISM: Synechocystis PCC6803

<400> SEQUENCE: 37

```
Met Arg Pro Leu Ser His Arg Thr Lys Ile Val Ala Thr Ile Gly Pro
 1               5                  10                  15

Ala Ser Ser Val Glu Val Ile Arg Gln Met Val Asp Ala Gly Met
            20                  25                  30

Asn Val Ala Arg Leu Asn Phe Ser His Gly Ser Tyr Glu Asp His Ala
        35                  40                  45

Thr Met Val Arg Leu Leu Arg Ser Val Glu Gln Met Asp Thr Pro
    50                  55                  60

Ile Thr Leu Leu Gln Asp Leu Gln Gly Pro Lys Ile Arg Ile Gly Gln
65                  70                  75                  80

Leu Pro Gly Gly Glu Lys Gln Leu Arg Glu Gly Glu Lys Val Ser Leu
                85                  90                  95

Val Pro Val Glu Ile Gly Asp Arg His Pro Gly Ala Val Gly Ile Asp
            100                 105                 110

Tyr Pro His Leu Ala Thr Glu Ala Lys Val Gly Glu Arg Ile Leu Leu
        115                 120                 125

Asp Asp Gly Leu Leu Glu Met Lys Val Val Ser Ile Gln Asp Pro Glu
    130                 135                 140

Val Ile Cys Glu Val Val Thr Gly Gly Ile Leu Lys Ser Arg Lys Gly
145                 150                 155                 160

Val Asn Leu Pro Gly Leu Val Leu Thr Leu Pro Ser Met Thr Thr Lys
                165                 170                 175

Asp Lys Gln Asp Leu Glu Phe Gly Leu Ser Gln Gly Ile Asp Trp Val
            180                 185                 190

Ser Leu Ser Phe Val Arg Lys Gly Glu Asp Ile His Thr Leu Lys Gln
        195                 200                 205

Phe Leu Ala Glu Arg Gly His Pro Asp Leu Pro Val Ile Ala Lys Ile
    210                 215                 220

Glu Lys Pro Gln Ala Ile Asp Asn Leu Glu Glu Ile Val Ala Val Ser
225                 230                 235                 240

Asn Gly Ile Met Val Ala Arg Gly Asp Leu Gly Val Glu Val Asn Pro
                245                 250                 255

Glu Lys Val Pro Arg Leu Gln Lys Glu Ile Ile Arg Arg Cys Asn Val
            260                 265                 270

Arg Ala Ile Pro Val Ile Thr Ala Thr Gln Met Leu Asp Ser Met Ile
        275                 280                 285
```

| | | | | | | | | | | | | |
|---|---|---|---|---|---|---|---|---|---|---|---|---|
|Gln|Asn|Ser|Arg|Pro|Thr|Arg|Ala|Glu|Ala|Ser|Asp|Val|Ala|Asn|Ala|
| |290| | | |295| | | |300| | | | | | |

Ile Leu Asp Gly Thr Asp Ala Val Met Leu Ser Gly Glu Ser Ala Val
305                 310                 315                 320

Gly Gln Tyr Pro Val Lys Ser Val Gln Met Leu Arg Lys Ile Ala Glu
            325                 330                 335

Glu Thr Glu Val Gly Leu His Leu Val Asn Asn Pro Pro Ile Glu Asn
        340                 345                 350

Thr Glu Thr His Ala Leu Ser Glu Ala Leu Val Val Ile Asp Gly Ile
    355                 360                 365

Leu Asp Leu Lys Tyr Ile Val Thr Phe Thr Thr Ser Gly Phe Thr Ser
370                 375                 380

Leu Leu Ala Ser Asn Gln Arg Pro Ser Val Pro Val Ile Ala Phe Thr
385                 390                 395                 400

Pro Ser Glu Lys Val Tyr His Ser Leu Asn Leu Val Trp Gly Ile Ile
            405                 410                 415

Pro Phe Leu Ile Asn Glu Phe Asp Thr Phe Glu Asp Leu Ile Gln
            420                 425                 430

Gln Ala Glu Val Leu Leu Arg Asp Arg Lys Met Val Glu Lys Gly Asp
435                 440                 445

Gln Leu Leu Ile Met Ala Gly Ile Pro Thr Lys Ile Pro Arg Gly Thr
450                 455                 460

Asn Phe Leu Lys Ile His Arg Ile Ser
465                 470

<210> SEQ ID NO 38
<211> LENGTH: 2350
<212> TYPE: DNA
<213> ORGANISM: Artificial Sequence
<220> FEATURE:
<223> OTHER INFORMATION: synthetic combined bacterial sequences

<400> SEQUENCE: 38

```
tcgactaccc attgggggct gagcggccca gcggtgttaa agctatctgc ctggggagca      60
agacaattac aggcatcggg ttatgaccat tccctctgga tcaactggct gcctaaagtg     120
actcccctgg aatccatggc ccaatggcga gcaacaaagc aaagccatcc ccgcaaacaa     180
atcgctaact ttaccgccac tgctttacct aaacgacttt ggcagaggtt gacgacccag     240
gctggtatta accggggca atgttgggcc gattttttcca aggttcagga gcgacaacta     300
acagagaata tccaccgcta ccactgtcag atcaaaggta aagggggtgtt caaagaagaa     360
tttgtcacct gtgggggcat taccctcaag gaagtggatt ttaagaccat ggctagccgt     420
tgttgccctg gattatattt tgccggggaa atcctcgacg tagatggtat taccggcggt     480
tttaattttc aaaatgcctg gactacggct tggttggcgg cccaggggat ggcggctcca     540
taacattccc ttaattcctc ctcagtaagt tggactaaaa ttccagtgcc agccctgatt     600
aacccggtga agtttatgag accctaagt catcgcacca aaattgtggc caccattggc     660
cccgccagta gttcggtaga ggtgatacgt cagatggtgg atgcgggcat gaatgtggcc     720
cggctgaatt tttcccacgg tagttatgag gaccatgcca ccatggttcg cctactacgg     780
tcagtggagc aggaaatgga cacccccatt acccttttgc aagatttaca ggggcccaaa     840
attcggattg gtcagttgcc gggggagaa aagcaactgc gggaagggga aaaagtttct     900
ttggtgccgg tggaaattgg cgatcgccat cctggagcgg tggcattga ctatcccat     960
ttggcgacgg aggcaaaagt aggggaaaga atttatttgg acgatggttt actggaaatg    1020
```

```
aaagttgtgt ccattcaaga tccagaggta atttgtgaag tggtgaccgg gggcatcctc      1080
aaaagtcgca aaggggtcaa tctaccgggt ttagtcctaa ccctaccttc catgacgacc      1140
aaagacaagc aagacttaga atttggtttg agccaaggca ttgactgggt ttcccttagt      1200
tttgtccgca aaggggaaga tatccacacc cttaaacaat ttctcgctga acggggccat      1260
cctgatctgc cggtcattgc caaaattgaa aaccccagg cgatcgataa tctagaagaa       1320
atcgtggcag tttccaacgg cattatggtg gccaggggg atctgggggt ggaagtaaac       1380
ccagaaaagg ttccccgttt gcaaaaggaa attattcggc gctgtaacgt gcgggccatt      1440
ccggtcatca ccgctaccca atgctagat agcatgattc aaaattcccg acccaccagg       1500
gcggaagcca gtgacgtggc caacgctatt ttggacggca ccgatgcggt gatgttatcg      1560
ggggaatcgg cagtgggaca atatcccgtt aaatcagtgc aaatgttgcg aaaaattgcc      1620
gaagagacgg aagtgggtct acatcttgtt aataatcccc caatagaaaa tacggaaacc      1680
catgccctaa gtgaagcgtt agtggtaatt gacggaattc tagatttaaa atacattgtc      1740
acgttcacca cctcaggttt tacttctctc ctcgcttcca accaaagacc gtcggtgccg      1800
gtgattgctt tcactccctc agaaaaggtt taccatagcc tcaacttagt ttggggtatt      1860
attccctttt taattaacga agaatttgac accttttgagg atttaatcca acaggcggag     1920
gtactactgc gggatagaaa aatggtggaa aagggcgatc agttgctaat catggcggga     1980
attcccacta aaatacccag gggcactaat ttcctcaaga ttcaccgtat ttcttaaaac      2040
ctatgcctca aatccatagt tgctggacaa ggattctaca ctactgtttt caggaagtat      2100
acttggaata atttctagaa aatagcaaaa ttatgtcatt attccctctt ttaaccgctt      2160
tgttagggat tatgcccgca aacaccattg aacaagttcc tgctgttgtt gaagctgaag      2220
ctcgtccttt tctggttagc caagctaaca gcgcagatat tttggtgaaa ctcccccgac      2280
cccagggtag tcccaagaat gtaggtagca tgttcatggc caatgcctat ggacaacagg      2340
gcctaaattc                                                              2350
```

<210> SEQ ID NO 39
<211> LENGTH: 2236
<212> TYPE: DNA
<213> ORGANISM: Artificial Sequence
<220> FEATURE:
<223> OTHER INFORMATION: synthetic combined bacterial sequences

<400> SEQUENCE: 39

```
tcgactctag aggatccccg ggtacccctc atcgggggct gtgttggccg agacggcact       60
gaggatttta ctctccatgg cattccaagg aatatctacc caactcacct gctccggcgg      120
attgttccgc tcaaaagtac taatcaagtc gtcaaaatac ttattaaatt ttggctgcaa      180
ttgcatagtc caaaagctga ctttcccctc catgctctgg ggggaattgc tctggcaact      240
gattaatcca ctgagcaaca gcccaagaca cgcaaacaaa aaccaacgtc ttggcgatcg      300
ccatcggcac catgaaacca tcgtaaaagc tggggaaaga ataaaaaaca gtggttcagg      360
aattgcattg ccatggccac ttcacaaacc tagccaattt tagcttgacc gcaactttga      420
cagattgtct tttgactttg cctggaccgc ctcccataat accttcgcgt cttgaagact      480
ttatccttga aaggagaaca tatgagaccc ctaagtcatc gcaccaaaat tgtggccacc      540
attggccccg ccagtagttc ggtagaggtg atacgtcaga tggtgatgc gggcatgaat       600 gtggcccggc tgaattttc ccacggtagt tatgaggacc atgccaccat ggttcgccta       660
```

-continued

```
ctacggtcag tggagcagga aatggacacc cccattaccc ttttgcaaga tttacagggg    720
cccaaaattc ggattggtca gttgccgggg ggagaaaagc aactgcggga aggggaaaaa    780
gtttctttgg tgccggtgga aattggcgat cgccatcctg gagcggtggg cattgactat    840
ccccatttgg cgacggaggc aaaagtaggg gaaagaattt tattggacga tggtttactg    900
gaaatgaaag ttgtgtccat tcaagatcca gaggtaattt gtgaagtggt gaccgggggc    960
atcctcaaaa gtcgcaaagg ggtcaatcta ccgggtttag tcctaaccct accttccatg   1020
acgaccaaag acaagcaaga cttagaattt ggtttgagcc aaggcattga ctgggtttcc   1080
cttagttttg tccgcaaagg ggaagatatc cacacccta aacaatttct cgctgaacgg   1140
ggccatcctg atctgccggt cattgccaaa attgaaaaac cccaggcgat cgataatcta   1200
gaagaaatcg tggcagtttc caacggcatt atggtggcca gggggatct gggggtggaa    1260 gtaaacccag aaaaggttcc ccgttttgcaa aaggaaatta ttcggcgctg taacgtgcgg   1320
gccattccgg tcatcaccgc tacccaaatg ctagatagca tgattcaaaa ttcccgaccc   1380
accagggcgg aagccagtga cgtggccaac gctattttgg acggaccga tgcggtgatg    1440 ttatcggggg aatcggcagt gggacaatat cccgttaaat cagtgcaaat gttgcgaaaa   1500
attgccgaag acggaagt gggtctacat cttgttaata atcccccaat agaaaatacg     1560
gaaacccatg ccctaagtga agcgttagtg gtaattgacg gaattctaga tttaaaatac   1620
attgtcacgt tcaccacctc aggttttact tctctcctcg cttccaacca agaccgtcg    1680 gtgccggtga ttgctttcac tccctcagaa aaggtttacc atagcctcaa cttagtttgg   1740
ggtattattc ccttttttaat taacgaagaa tttgacacct tgaggatttt aatccaacag   1800
gcggaggtac tactgcggga tagaaaaatg gtggaaaagg gcgatcagtt gctaatcatg   1860
gcgggaattc ccactaaaat acccaggggc actaatttcc tcaagattca ccgtatttct   1920
taaaacctat gcctcaaatc catagttgct ggacaaggat tctacactac tgttttcagg   1980
aagtatactt ggaataattt ctagaaaata gcaaaattat gtcattattc cctcttttaa   2040
ccgctttgtt agggattatg cccgcaaaca ccattgaaca agttcctgct gttgttgaag   2100
ctgaagctcg tccttttctg gttagccaag ctaacagcgc agatattttg gtgaaactcc   2160 cccgaccca gggtagtccc aagaatgtag gtagcatgtt catggccaat gcctatggac    2220
aacagggcct aaattc                                                    2236
```

<210> SEQ ID NO 40
<211> LENGTH: 591
<212> TYPE: PRT
<213> ORGANISM: Synechocystis PCC6803

<400> SEQUENCE: 40

```
Met Gln Thr Ser Pro Leu Pro Arg Arg Thr Lys Ile Val Ala Thr Ile
 1               5                  10                  15

Gly Pro Ala Thr Gln Ser Lys Glu Val Leu Arg Gln Leu Ile Gln Ala
            20                  25                  30

Gly Ala Thr Thr Phe Arg Leu Asn Phe Ser His Gly Asp His Ala Tyr
        35                  40                  45

His Gln Gln Ser Ile Arg Leu Ile Arg Gln Ile Ala Phe Glu Leu Asn
    50                  55                  60

Gln Pro Val Gly Ile Leu Gln Asp Leu Gln Gly Pro Lys Ile Arg Val
65                  70                  75                  80

Gly Lys Phe Leu Asn Asp Ala Gly Ser Val Gln Leu Lys Asn Gly Asp
                85                  90                  95
```

```
Pro Tyr Thr Leu Thr Ser Arg Pro Val Glu Cys Thr Glu Thr Ile Ser
            100                 105                 110

Ser Ile Ser Tyr Glu Tyr Leu Ala Asp Glu Val Pro Ser Gly Ala Arg
            115                 120                 125

Ile Leu Leu Asp Asp Gly Lys Leu Glu Met Leu Val Glu Glu Val Asp
            130                 135                 140

Thr Val Ala Arg Asp Leu His Cys Arg Val Ile Val Gly Gly Thr Leu
145                 150                 155                 160

Ser Ser Asn Lys Gly Val Asn Phe Pro Gly Val Cys Leu Ser Val Lys
                165                 170                 175

Ala Met Thr Asp Lys Asp Lys Glu Asp Leu Met Phe Gly Leu Asp Gln
            180                 185                 190

Gly Val Asp Trp Val Ala Leu Ser Phe Val Arg Asn Pro Gln Asp Ile
            195                 200                 205

Asp Glu Ile Lys Gly Leu Ile Ala Ala Gly Lys Ser Val Pro Val
            210                 215                 220

Ile Ala Lys Ile Glu Lys His Glu Ala Ile Lys Asp Met Gln Ala Val
225                 230                 235                 240

Leu Glu Lys Cys Asp Gly Val Met Val Ala Arg Gly Asp Leu Gly Val
                245                 250                 255

Glu Leu Pro Ala Glu Asp Val Pro Ile Leu Gln Lys Lys Leu Ile Ala
            260                 265                 270

Thr Ala Asn Arg Leu Gly Ile Pro Val Ile Thr Ala Thr Gln Met Leu
            275                 280                 285

Asp Ser Met Val Asn Ser Pro Arg Pro Thr Arg Ala Glu Val Ser Asp
            290                 295                 300

Val Ala Asn Ala Ile Leu Asp Gly Thr Asp Ala Val Met Leu Ser Asn
305                 310                 315                 320

Glu Thr Ala Ile Gly Lys Phe Pro Val Glu Ala Val Ala Ile Met Ala
                325                 330                 335

Lys Ile Ala Glu Arg Ile Glu Gln Glu Asp Ile Asn Pro Ser Gln Ala
            340                 345                 350

Glu Ala Ser Arg Thr Ser Ile Pro Asn Ala Ile Ser Ser Ala Val Ser
            355                 360                 365

Gln Ile Ala Glu Thr Leu Asn Ala Ala Ala Ile Met Ser Leu Thr Lys
            370                 375                 380

Thr Gly Ser Thr Ala Arg His Val Ser Lys Phe Arg Pro Lys Thr Pro
385                 390                 395                 400

Ile Leu Ala Val Thr Pro His Val Asp Val Ser Arg Gln Leu Gln Leu
                405                 410                 415

Val Trp Gly Val Lys Pro Leu Leu Val Leu Asp Leu Pro Ser Thr Ser
            420                 425                 430

Gln Thr Phe Gln Ala Ala Ile Asn Val Ala Gln Glu Asn His Phe Leu
            435                 440                 445

Arg Asp Gly Asp Leu Val Val Met Thr Ala Gly Thr Leu Gln Gly Val
            450                 455                 460

Ala Gly Ser Thr Asp Leu Ile Lys Val Glu Val Val Lys Ala Ile Leu
465                 470                 475                 480

Gly Arg Gly Val Gly Ile Gly Gln Gly Ala Val Ser Gly Arg Ala Arg
                485                 490                 495

Val Ala Ser Arg Pro Gln Ala Ile Ala Gln Phe Thr Gln Gly Glu Ile
            500                 505                 510
```

| | | | | | | | | | | | |
|---|---|---|---|---|---|---|---|---|---|---|---|
| Leu | Val | Val | Pro | Ser | Thr | Asn | Ala | Asp | Cys | Val | Asp | Met | Met | Arg | Arg |
| | | 515 | | | | 520 | | | | 525 | | | | | |

Ala Ala Gly Ile Ile Thr Glu Glu Ser Leu Thr Ser His Ala Ala
    530                    535                  540

Ile Ile Gly Leu Arg Leu Gly Val Pro Val Ile Val Gly Phe Lys Gly
545                        550                    555                    560

Ala Thr Gln Lys Ile Arg Asp Gly Ala Ile Val Thr Ile Asp Ala Gln
                565                    570                    575

Lys Gly Leu Ile Tyr Ser Gly Ala Leu Pro Pro Val Ser Lys Gly
                580                    585                    590

<210> SEQ ID NO 41
<211> LENGTH: 2620
<212> TYPE: DNA
<213> ORGANISM: Artificial Sequence
<220> FEATURE:
<223> OTHER INFORMATION: synthetic combined bacterial sequences

<400> SEQUENCE: 41

```
tcgaccggca aacaaatcca gcggaaaata accgtaggtt cccgctaagg tatcatcctc      60
cgcctgacag gaaattaata ctccccgata atccccgtca taactgtcga gataaaagcg     120
cagggattgg ctctggcatt tcaaatacac tggcccttca atggttttac ctggttccat     180
ggcgatcgcc tctccgtaat ccaacccctg tagatattgc cccaaagcat tttccgcact     240
agcttggtcg tcggcacaaa tgccaaaatt ttccgcttca ctctggccac aaatccagac     300
aatggcttgg cgtaaatctt ccctttcctg gtcattctgg ggaatacgga tttctaaacg     360
actgtaatcc tttaacaacg tcaactgagc ggaagcattc atagcaaacc catcaaactg     420
tgcagactat tgggaaaaat tgcccaaagc ccagcctacc atcgttggcc ctgtaagccg     480
atgcaactga acggcgatcg tgcggata atgagaatat tccctaaca ccgcttaaaa     540 gcagacggcc ttaactatta tatttaactg cccctaattt cagcccatta tgcaaacgtc     600
tccccttccc cgtcgtacca aaatcgtcgc taccattggc cccgcgaccc aaagcaagga     660
agtgctgaga caactgatcc aagccggtgc taccactttc cgcctcaatt ttttcccacgg     720 agaccacgct taccaccaac aaagtatccg tttgattcgc cagattgcct ttgaactgaa     780
ccaaccagtg ggcattctcc aggatttaca ggggccaaag attcgggtgg gcaaatttct     840
caatgatgcc ggctctgtgc aactcaaaaa cggtgatccc tataccctca ccagtcgccc     900
ggtggaatgt acggaaacca ttagttccat tagctacgaa tatttagccg acgaagtacc     960
ttctggggca agaattttgc tcgacgacgg caaactggaa atgttggtgg aggaagtgga    1020
cactgttgcc cgggatctcc actgtcgggt gattgtgggg ggaacccttt ccagcaataa    1080
agggggtaat tttcccgggg tctgcctttc cgttaaggcc atgaccgata agataagga    1140 agatttgatg ttcgggctgg accaaggggt ggactgggtg ccctgagtt ttgttcgtaa    1200 tccccaggat attgatgaga ttaagggggtt aattgcggcg gcagggaaat ccgtgccggt    1260
aatcgccaaa attgagaagc acgaagcgat taaggatatg caggcggtgc tggaaaaatg    1320
tgacggtgtc atggtggccc gggggggactt gggggtagaa ctaccgcag aagatgtacc    1380 tattttgcaa agaaaactca ttgccactgc taaccggttg gcattcctg tcattactgc    1440 tacccaaatg ttggacagta tggtcaacag cccccgacct actagggctg aagtgtccga    1500
cgtggccaat gccatcctcg atggtaccga tgccggtgatg ctctccaacg aaacggcgat    1560
cggtaaattt cccgtggaag cagtggctat tatggccaaa attgcggagc gcattgaaca    1620
```

```
ggaagatatc aatccttccc aagcggaagc cagtcgcact tctattccca atgctatttc    1680
cagcgccgtt agccagattg cggaaaccct caacgcggcg gctattatgt ctttgactaa    1740
gaccggatcc accgcccgcc atgtgtcaaa gttccgcccc aaaaccccca ttctggccgt    1800
tacgccccat gtggatgtgt cccgtcagtt gcagttggtg tggggagtta agcccctgtt    1860
ggtattggat ttaccttcca ccagccaaac gttccaagcc gccattaacg tggcccagga    1920
aaaccatttt ctccgggatg gagatttggt ggtgatgacc gccgggacat tgcagggagt    1980
tgccggttcg acggatttaa tcaaagtgga agtggtcaag gccattcttg gtcggggtgt    2040
aggtattggc caaggagctg taagtggccg ggccagggtt gccagtcgtc cccaggcgat    2100
cgcccaattt acccagggag aaattttagt agttccctct accaacgctg attgtgtgga    2160
catgatgcga cgggcggcgg gcattatcac cgaagaagaa agcctgacta gccatgcggc    2220
cattattggt ttgcggctgg gggtgccggt cattgtgggt tttaaaggcg ctacccaaaa    2280
gattcgagat ggagccattg tcaccatcga tgcccaaaaa ggactgattt attccggtgc    2340 attaccccg gtgtccaaag gatagggaat aattaggac ccagtaacag ggcgagaaca    2400
ggaagcatca tcccaatgga gttcccattc ccaccccct ggaacagtaa cattttggta    2460
gaatcaacgg ggttctttc ccgacgtaat ttagtccttt gcagaaaaaa tcttcccta    2520 aatcccgcta ctggctgtta atccctata ttcgtccca tcggcggact attgggctgg    2580 cttcctctg tactctgcta ttcactgttt tttggcccac                          2620

<210> SEQ ID NO 42
<211> LENGTH: 2532
<212> TYPE: DNA
<213> ORGANISM: Artificial Sequence
<220> FEATURE:
<223> OTHER INFORMATION: synthetic combined bacterial sequences

<400> SEQUENCE: 42
tcgactctag aggatccccg ggtacccctc atcgggggct gtgttggccg agacggcact      60 gaggattta ctctccatgg cattccaagg aatatctacc caactcacct gctccggcgg     120
attgttccgc tcaaaagtac taatcaagtc gtcaaaatac ttattaaatt ttggctgcaa     180
ttgcatagtc caaaagctga cttttcccctc catgctctgg ggggaattgc tctggcaact     240
gattaatcca ctgagcaaca gcccaagaca cgcaaacaaa aaccaacgtc ttggcgatcg     300
ccatcggcac catgaaacca tcgtaaaagc tggggaaaga ataaaaaaca gtggttcagg     360
aattgcattg ccatggccac ttcacaaacc tagccaattt tagcttgacc gcaactttga     420
cagattgtct tttgactttg cctggaccgc ctcccataat accttcgcgt cttgaagact     480
ttatccttga aaggagaaca tatgcaaacg tctcccctc cccgtcgtac caaaatcgtc     540
gctaccattg gccccgcgac ccaaagcaag gaagtgctga caaactgat ccaagccggt     600 gctaccactt tccgcctcaa ttttcccac ggagaccacg cttaccacca acaaagtatc     660
cgtttgattc gccagattgc ctttgaactg aaccaaccag tggcattct ccaggattta     720 cagggggccaa agattcgggt gggcaaattt ctcaatgatg ccggctctgt gcaactcaaa     780
aacggtgatc cctatacct caccagtcgc ccggtggaat gtacgaaac cattagttcc     840 attagctacg aatatttagc cgacgaagta ccttctgggg caagaatttt gctcgacgac     900
ggcaaactgg aaatgttggt ggaggaagtg acactgttg cccgggatct ccactgtcgg     960
gtgattgtgg ggggaaccct ttccagcaat aaagggggtta attttcccgg ggtctgcctt    1020
tccgttaagg ccatgaccga taaagataag gaagatttga tgttcgggct ggaccaaggg    1080
```

```
gtggactggg tggccctgag ttttgttcgt aatccccagg atattgatga gattaagggg    1140
ttaattgcgg cggcagggaa atccgtgccg gtaatcgcca aaattgagaa gcacgaagcg    1200
attaaggata tgcaggcggt gctggaaaaa tgtgacggtg tcatggtggc ccggggggac    1260
ttgggggtag aactacccgc agaagatgta cctatttttgc aaaagaaact cattgccact    1320
gctaaccggt tgggcattcc tgtcattact gctacccaaa tgttggacag tatggtcaac    1380
agcccccgac ctactagggc tgaagtgtcc gacgtggcca atgccatcct cgatggtacc    1440
gatgcggtga tgctctccaa cgaaacggcg atcggtaaat tcccgtgga agcagtggct    1500 attatggcca aaattgcgga gcgcattgaa caggaagata tcaatccttc caagcggaa    1560 gccagtcgca cttctattcc caatgctatt ccagcgccg ttagccagat tgcggaaacc    1620
ctcaacgcgg cggctattat gtctttgact aagaccggat ccaccgcccg ccatgtgtca    1680
aagttccgcc ccaaaacccc cattctggcc gttacgcccc atgtggatgt gtcccgtcag    1740
ttgcagttgg tgtggggagt taagcccctg ttggtattgg atttaccttc caccagccaa    1800
acgttccaag ccgccattaa cgtggcccag gaaaaccatt ttctccggga tggagatttg    1860
gtggtgatga ccgccgggac attgcaggga gttgccggtt cgacggattt aatcaaagtg    1920
gaagtggtca aggccattct tggtcggggt gtaggtattg gccaaggagc tgtaagtggc    1980
cgggccaggg ttgccagtcg tccccaggcg atcgcccaat ttacccaggg agaaatttta    2040
gtagttccct ctaccaacgc tgattgtgtg gacatgatgc gacgggcggc gggcattatc    2100
accgaagaag aaagcctgac tagccatgcg gccattattg gtttgcggct gggggtgccg    2160
gtcattgtgg gttttaaagg cgctacccaa aagattcgag atggagccat tgtcaccatc    2220
gatgcccaaa aaggactgat ttattccggt gcattacccc cggtgtccaa aggatagga    2280 ataattaggg acccagtaac agggcgagaa caggaagcat catcccaatg gagttcccat    2340
tccccacccc ctggaacagt aacatttttg tagaatcaac ggggttcttt tcccgacgta    2400
atttagtcct ttgcagaaaa aatcttccct taaatcccgc tactggctgt taatccccta    2460
tattcgtccc catcggcgga ctattgggct ggctttcctc tgtactctgc tattcactgt    2520
tttttggccc ac                                                       2532
```

<210> SEQ ID NO 43
<211> LENGTH: 470
<212> TYPE: PRT
<213> ORGANISM: Escherichia coli

<400> SEQUENCE: 43

```
Met Lys Lys Thr Lys Ile Val Cys Thr Ile Gly Pro Lys Thr Glu Ser
1               5                   10                  15

Glu Glu Met Leu Ala Lys Met Leu Asp Ala Gly Met Asn Val Met Arg
            20                  25                  30

Leu Asn Phe Ser His Gly Asp Tyr Ala Glu His Gly Gln Arg Ile Gln
        35                  40                  45

Asn Leu Arg Asn Val Met Ser Lys Thr Gly Lys Thr Ala Ala Ile Leu
    50                  55                  60

Leu Asp Thr Lys Gly Pro Glu Ile Arg Thr Met Lys Leu Glu Gly Gly
65                  70                  75                  80

Asn Asp Val Ser Leu Lys Ala Gly Gln Thr Phe Thr Phe Thr Asp
                85                  90                  95

Lys Ser Val Ile Gly Asn Ser Glu Met Val Ala Val Thr Tyr Glu Gly
                100                 105                 110
```

```
Phe Thr Thr Asp Leu Ser Val Gly Asn Thr Val Leu Val Asp Asp Gly
        115                 120                 125
Leu Ile Gly Met Glu Val Thr Ala Ile Glu Gly Asn Lys Val Ile Cys
    130                 135                 140
Lys Val Leu Asn Asn Gly Asp Leu Asp Glu Asn Lys Gly Val Asn Leu
145                 150                 155                 160
Pro Gly Val Ser Ile Ala Leu Pro Ala Leu Ala Glu Lys Asp Lys Gln
                165                 170                 175
Asp Leu Ile Phe Gly Cys Glu Gln Gly Val Asp Phe Val Ala Ala Ser
            180                 185                 190
Phe Ile Arg Lys Arg Ser Asp Val Ile Glu Ile Arg Glu His Leu Lys
        195                 200                 205
Ala His Gly Gly Glu Asn Ile His Ile Ile Ser Lys Ile Glu Asn Gln
    210                 215                 220
Glu Gly Leu Asn Asn Phe Asp Glu Ile Leu Glu Ala Ser Asp Gly Ile
225                 230                 235                 240
Met Val Ala Arg Gly Asp Leu Gly Val Glu Ile Pro Val Glu Glu Val
                245                 250                 255
Ile Phe Ala Gln Lys Met Met Ile Glu Lys Cys Ile Arg Ala Arg Lys
            260                 265                 270
Val Val Ile Thr Ala Thr Gln Met Leu Asp Ser Met Ile Lys Asn Pro
        275                 280                 285
Arg Pro Thr Arg Ala Glu Ala Gly Asp Val Ala Asn Ala Ile Leu Asp
    290                 295                 300
Gly Thr Asp Ala Val Met Leu Ser Gly Glu Ser Ala Lys Gly Lys Tyr
305                 310                 315                 320
Pro Leu Glu Ala Val Ser Ile Met Ala Thr Ile Cys Glu Arg Thr Asp
                325                 330                 335
Arg Val Met Asn Ser Arg Leu Glu Phe Asn Asn Asp Asn Arg Lys Leu
            340                 345                 350
Arg Ile Thr Glu Ala Val Cys Arg Gly Ala Val Glu Thr Ala Glu Lys
        355                 360                 365
Leu Asp Ala Pro Leu Ile Val Val Ala Thr Gln Gly Gly Lys Ser Ala
    370                 375                 380
Arg Ala Val Arg Lys Tyr Phe Pro Asp Ala Thr Ile Leu Ala Leu Thr
385                 390                 395                 400
Thr Asn Glu Lys Thr Ala His Gln Leu Val Leu Ser Lys Gly Val Val
                405                 410                 415
Pro Gln Leu Val Lys Glu Ile Thr Ser Thr Asp Asp Phe Tyr Arg Leu
            420                 425                 430
Gly Lys Glu Leu Ala Leu Gln Ser Gly Leu Ala His Lys Gly Asp Val
        435                 440                 445
Val Val Met Val Ser Gly Ala Leu Val Pro Ser Gly Thr Thr Asn Thr
    450                 455                 460
Ala Ser Val His Val Leu
465                 470

<210> SEQ ID NO 44
<211> LENGTH: 429
<212> TYPE: PRT
<213> ORGANISM: Zymomonas mobilis

<400> SEQUENCE: 44

Met Thr Ala Ile Val Ser Ile His Gly Arg Gln Val Val Asp Ser Arg
```

-continued

```
1               5                   10                  15
Gly Asn Pro Thr Val Glu Val Asp Val Thr Leu Glu Asp Gly Ser Phe
                20                  25                  30
Gly Arg Ala Ala Val Pro Ser Gly Ala Ser Thr Gly Val His Glu Ala
                35                  40                  45
Val Glu Leu Arg Asp Gly Asp Lys Thr Arg Trp Gly Lys Gly Val
 50                  55                  60
Thr Lys Ala Val His Ala Val Asn Asn Glu Ile Ala Asn Ala Ile Ile
 65                  70                  75                  80
Gly Leu Glu Ala Glu Asp Gln Glu Leu Ile Asp Gln Thr Met Ile Lys
                85                  90                  95
Leu Asp Gly Thr Pro Asn Lys Gly Lys Phe Gly Ala Asn Ala Ile Leu
                100                 105                 110
Gly Val Ser Leu Ala Val Ala Lys Ala Ala Ala Glu Ala Arg Gly Leu
                115                 120                 125
Pro Leu Tyr Arg Tyr Val Gly Gly Thr Ala Ala His Val Leu Pro Val
                130                 135                 140
Pro Met Met Asn Ile Val Asn Gly Gly Met His Ala Asp Asn Pro Ile
145                 150                 155                 160
Asp Phe Gln Glu Phe Met Ile Ala Pro Val Gly Ala Ser Ser Ile Asn
                165                 170                 175
Glu Ala Val Arg Ile Gly Thr Glu Val Phe His Thr Leu Lys Lys Glu
                180                 185                 190
Leu Ser Ala Lys Gly Met Asn Thr Asn Val Gly Asp Glu Gly Gly Phe
                195                 200                 205
Ala Pro Ser Leu Asp Ser Ala Ser Ala Leu Asp Phe Ile Val Asp
                210                 215                 220
Ser Ile Ser Lys Ala Gly Tyr Lys Pro Gly Glu Asp Val Phe Ile Ala
225                 230                 235                 240
Leu Asp Ala Ala Ser Ser Glu Phe Tyr Asn Lys Asp Gln Asn Ile Tyr
                245                 250                 255
Asp Leu Lys Gly Glu Gly Arg Lys Leu Thr Ser Ala Gln Leu Val Asp
                260                 265                 270
Tyr Tyr Val Glu Leu Cys Gly Lys Tyr Pro Ile Tyr Ser Ile Glu Asp
                275                 280                 285
Gly Leu Ala Glu Asp Asp Phe Glu Gly Trp Lys Ile Leu Thr Glu Lys
                290                 295                 300
Leu Gly Asp Lys Val Gln Leu Val Gly Asp Asp Leu Phe Val Thr Asn
305                 310                 315                 320
Val Lys Arg Leu Ser Asp Gly Ile Glu Arg Gly Ile Ala Asn Ser Leu
                325                 330                 335
Leu Val Lys Phe Asn Gln Ile Gly Ser Leu Ser Glu Thr Leu Ala Ala
                340                 345                 350
Val Asn Met Ala Asn Asp Ala Ser Tyr Thr Ala Val Met Ser His Arg
                355                 360                 365
Ser Gly Glu Thr Glu Asp Thr Thr Ile Ala Asp Leu Ala Val Ala Thr
                370                 375                 380
Asn Cys Gly Gln Ile Lys Thr Gly Ser Leu Cys Arg Ser Glu Arg Ile
385                 390                 395                 400
Ala Lys Tyr Asn Gln Leu Met Arg Ile Glu Glu Leu Gly Ser Val
                405                 410                 415
Ala Lys Tyr Ala Gly Arg Ser Val Leu Arg Lys Ala Lys
                420                 425
```

<210> SEQ ID NO 45
<211> LENGTH: 228
<212> TYPE: PRT
<213> ORGANISM: Zymomonas mobilis

<400> SEQUENCE: 45

```
Met Pro Thr Leu Val Leu Ser Arg His Gly Gln Ser Glu Trp Asn Leu
1               5                   10                  15

Glu Asn Arg Phe Thr Gly Trp Trp Asp Val Asn Leu Thr Glu Gln Gly
            20                  25                  30

Val Gln Glu Ala Thr Ala Gly Gly Lys Ala Leu Ala Glu Lys Gly Phe
        35                  40                  45

Glu Phe Asp Ile Ala Phe Thr Ser Val Leu Thr Arg Ala Ile Lys Thr
    50                  55                  60

Thr Asn Leu Ile Leu Glu Ala Gly Lys Thr Leu Trp Val Pro Thr Glu
65                  70                  75                  80

Lys Asp Trp Arg Leu Asn Glu Arg His Tyr Gly Gly Leu Thr Gly Leu
                85                  90                  95

Asn Lys Ala Glu Thr Ala Ala Lys His Gly Glu Glu Gln Val His Ile
            100                 105                 110

Trp Arg Arg Ser Tyr Gly Val Pro Pro Pro Met Glu Lys Gly Ser
        115                 120                 125

Lys Phe Asp Leu Ser Gly Asp Arg Arg Tyr Asp Gly Val Lys Ile Pro
    130                 135                 140

Glu Thr Glu Ser Leu Lys Asp Thr Val Ala Arg Val Leu Pro Tyr Trp
145                 150                 155                 160

Glu Glu Arg Ile Ala Pro Glu Leu Lys Ala Gly Lys Arg Val Leu Ile
                165                 170                 175

Gly Ala His Gly Asn Ser Leu Arg Ala Leu Val Lys His Leu Ser Lys
            180                 185                 190

Leu Ser Asp Glu Glu Ile Val Lys Phe Glu Leu Pro Thr Gly Gln Pro
        195                 200                 205

Leu Val Tyr Glu Leu Asn Asp Asp Leu Thr Pro Lys Asp Arg Tyr Phe
    210                 215                 220

Leu Asn Glu Arg
225
```

<210> SEQ ID NO 46
<211> LENGTH: 4274
<212> TYPE: DNA
<213> ORGANISM: Artificial Sequence
<220> FEATURE:
<223> OTHER INFORMATION: synthetic combined bacterial sequences

<400> SEQUENCE: 46

```
cccgggatct ctagaaagtt tcggactcag tagacctaag tacagagtga tgtcaacgcc      60
ttcaagctag acgggaggcg gcttttgcca tggttcagcg atcgctcctc atcttcaata     120
agcagggcat gagccagcgt taagcaaatc aaatcaaatc tcgcttctgg gcttcaataa     180
atggttccga ttgatgatag gttgattcat gaggaatcta aggcttaatt ctccacaaaa     240
gaattaagcg tccgtcgcaa cggaatgctc cgctggactt gcgctgtggg actgcagctt     300
tacaggctcc ccctgccaga aatcctgaat cgtcgagcat atctgacata tctctaggga     360
gagacgacat gtcgacgatt aatttcagcg tataatgcgc gccaattgac tcttgaatgg     420
tttcagcact ttggactgta gaactcaacg actcaaaaac aggcactcac gttgggctga     480
```

```
gacacaagca cacattcctc tgcacgcttt ttcgatgtca cctatcctta gagcgaggca    540
ccaccacttt cgtaataccg gattcgcttt ccggcagtgc gcccagaaag caagtttctc    600
ccatccttct caacttaaag actaagactg tcatgaaaaa gaccaaaatt gtttgcacca    660
tcggaccgaa aaccgaatct gaagagatgt tagctaaaat gctggacgct ggcatgaacg    720
ttatgcgtct gaacttctct catggtgact atgcagaaca cggtcagcgc attcagaatc    780
tgcgcaacgt gatgagcaaa actggtaaaa ccgccgctat cctgcttgat accaaaggtc    840
cggaaatccg caccatgaaa ctggaaggcg gtaacgacgt ttctctgaaa gctggtcaga    900
cctttacttt caccactgat aaatctgtta tcggcaacag cgaaatggtt gcggtaacgt    960
atgaaggttt cactactgac ctgtctgttg gcaacaccgt actggttgac gatggtctga   1020
tcggtatgga agttaccgcc attgaaggta acaaagttat ctgtaaagtg ctgaacaacg   1080
gtgacctgga cgaaaacaaa ggtgtgaacc tgcctggcgt ttccattgct ctgccagcac   1140
tggctgaaaa agacaaacag gacctgatct ttggttgcga acaaggcgta gactttgttg   1200
ctgcttcctt tattcgtaag cgttctgacg ttatcgaaat ccgtgagcac ctgaaagcgc   1260
acggcggcga aaacatccac atcatctcca aaatcgaaaa ccaggaaggc ctcaacaact   1320
tcgacgaaat cctcgaagcc tctgacggca tcatggttgc gcgtggcgac ctgggtgtag   1380
aaatcccggt agaagaagtt atcttcgccc agaagatgat gatcgaaaaa tgtatccgtg   1440
cacgtaaagt cgttatcact gcgacccaga tgctggattc catgatcaaa acccacgcc   1500 cgactcgcgc agaagccggt gacgttgcaa acgccatcct cgacggtact gacgcagtga   1560
tgctgtctgg tgaatccgca aaaggtaaat acccgctgga agcggtttct atcatggcga   1620
ccatctgcga acgtaccgac cgcgtgatga acagccgtct cgagttcaac aatgacaacc   1680
gtaaactgcg cattaccgaa gcggtatgcc gtggtgccgt cgaaactgct gaaaaactgg   1740
atgctccgct gatcgtggtt gctactcagg gcggtaaatc tgctcgcgca gtacgtaaat   1800
acttcccgga tgccaccatc ctggcactga ccactaacga aaaaacggct catcagttgg   1860
tactgagcaa aggcgttgtg ccgcagcttg ttaaagagat cacttctact gatgatttct   1920
accgtctggg taaagaactg gctctgcaga gcggtctggc acacaaaggt gacgttgtag   1980
ttatggtttc tggtgcactg gtaccgagcg gcactactaa caccgcatct gttcacgtcc   2040
tgtaataagc ttcattgacg gactgagttc aaaaagagac tcgtctaaaa gattttaaga   2100
aaggtttcga tatgacagct attgtcagta tccatggccg tcaggttgtc gacagccgcg   2160
gtaacccgac cgttgaagtt gatgttacgc ttgaagatgg cagcttcggc cgcgccgcag   2220
tgccgtcagg tgcttctacc ggcgttcatg aagctgttga acttcgtgat ggcgacaaaa   2280
cccgttgggg tggtaaaggc gttaccaaag ctgttcacgc tgtaaacaac gaaattgcta   2340
acgcaattat tggtctggaa gccgaagatc aggaactgat cgaccagacg atgatcaagc   2400
tcgatggcac cccgaacaag ggtaaattcg gtgctaacgc tatcctcggt gtcagcttgg   2460
ctgttgctaa agctgctgct gaagctcgcg gtctcccgct ttaccgttat gttggtggta   2520
cggcagctca cgttcttccg gttccgatga tgaacatcgt taacggtggt atgcacgctg   2580 acaacccccat cgatttccag gaattcatga ttgctccggt tggcgccagc tctatcaatg   2640
aagctgtccg catcggtacc gaagtttttcc atacccctgaa aaagaactg tctgctaaag   2700 gcatgaacac caacgtcggt gacgaaggtg gtttcgctcc tagccttgac agtgcttctt   2760
ctgctctgga cttcatcgtc gattccatct ccaaagccgg ttataagccg ggcgaagatg   2820
```

```
tgttcatcgc tctcgatgca gcttcctccg agttctacaa caaagatcag aacatctacg   2880
atcttaaggg tgaaggccgt aaactgacct ccgctcagct cgttgattac tatgtcgaac   2940
tctgcggcaa atatccgatc tattccatcg aagatggtct ggccgaagat gacttcgaag   3000
gctggaagat ccttaccgaa aagctcggtg acaaagttca gttggtcggt gacgatctgt   3060
tcgtgaccaa cgtgaagcgt cttactgatg gtatcgaacg cggtatcgcc aactcgctgc   3120
tcgtgaagtt taaccagatc ggttctttgt ctgaaacgct cgcagccgtt aacatggcta   3180
acgacgcttc ttacacggct gttatgtctc accgttccgg tgaaaccgaa gacaccacga   3240
ttgctgacct cgctgttgcc accaactgcg gtcagatcaa gaccggtagc ctttgccgtt   3300
ccgaacgtat cgctaaatac aatcagctga tgcgcatcga agaagaactg ggttcggttg   3360
ctaaatatgc tggccgttcg gttcttagaa aagccaaata agaatcacag ctagaaccga   3420
gctcacataa cgaagagata ttgaaaagga gtggaatatg cccacgctcg ttttgtcccg   3480
tcacggacag tccgaatgga accttgaaaa ccgtttcacc ggttggtggg atgttaacct   3540
gactgaacag ggtgttcagg aagcaacggc cggtggtaaa gctctggctg aaaagggttt   3600
tgaattcgat atcgctttca ccagcgttct gacccgcgcc atcaaaacca ccaatcttat   3660
tctcgaagcc ggtaaaaccc tttgggttcc gaccgaaaaa gattggcgtt tgaatgaacg   3720
tcactatggt ggtctgaccg gtctgaacaa ggctgaaacc gccgctaaac atggtgaaga   3780
acaggttcat atttggcgcc gttcttatgg cgttccgccg cccccgatgg aaaaaggcag   3840
caagttcgat ctgtctggcg atcgccgtta tgatggtgtc aagattcctg aaacggaaag   3900
cctgaaagac accgttgctc gcgtgctgcc ttattgggaa gaacgcattg cccctgaact   3960
gaaggctggc aagcgcgtcc tgatcggtgc gcatggtaac tcactgcgcg ctctcgttaa   4020
gcatctgtcg aaattgtcgg acgaagaaat cgtcaaattc gaattgccca ccggtcagcc   4080
gttggtctac gaattgaatg atgatctgac tccgaaagat cgttacttcc ttaacgaacg   4140
ttaatagcct tgggcttta aagccttttg gtttgttaac cgtttttcg gccagagttt   4200
tctctggccg aaaatttatg tctatcccctt tgttttttcta tcccatcac ctcggtttg   4260
ttggatccac tagt                                                   4274
```

<210> SEQ ID NO 47
<211> LENGTH: 432
<212> TYPE: PRT
<213> ORGANISM: Synechocystis PCC6803

<400> SEQUENCE: 47

Met Leu Ser Lys Val Pro Ala Thr Ile Glu Glu Ile Ala Ala Arg Glu
1               5                   10                  15

Ile Leu Asp Ser Arg Gly Arg Pro Thr Ile Glu Ala Glu Val Arg Leu
            20                  25                  30

Glu Ser Gly Ala His Gly Ile Ala Gln Val Pro Ser Gly Ala Ser Thr
        35                  40                  45

Gly Ser Phe Glu Ala His Glu Leu Arg Asp Gly Asp Pro Lys Arg Tyr
    50                  55                  60

Asp Gly Lys Gly Val Glu Lys Ala Val Arg Asn Val Thr Glu Lys Ile
65                  70                  75                  80

Ala Pro Val Val Glu Gly Leu Asp Ala Phe Asp Gln Met Ala Val Asp
                85                  90                  95

Gln Ala Met Ile Asp Arg Asp Gly Thr Asp Asn Lys Lys Glu Leu Gly
            100                 105                 110

```
Ala Asn Ala Ile Leu Gly Val Ser Leu Ala Thr Ala Lys Ala Ala Ala
            115                 120                 125

Ala Glu Leu Ala Ile Pro Leu Tyr Arg Tyr Leu Gly Gly Pro Leu Ala
        130                 135                 140

Asn Val Leu Pro Val Pro Met Met Asn Val Ile Asn Gly Gly Ala His
145                 150                 155                 160

Ala Asp Asn Asn Val Asp Phe Gln Glu Phe Met Ile Met Pro Val Gly
                165                 170                 175

Ala Glu Thr Phe Lys Glu Ala Leu Arg Trp Gly Ala Glu Val Phe Ala
            180                 185                 190

Val Leu Gly Lys Val Leu Lys Glu Arg Lys Leu Leu Ser Gly Gly Val
            195                 200                 205

Gly Asp Glu Gly Gly Tyr Ala Pro Asn Leu Thr Ser Asn Gln Gln Ala
    210                 215                 220

Leu Asp Ile Leu Ile Glu Ala Ile Glu Gln Ala Gly Tyr Lys Pro Gly
225                 230                 235                 240

Ser Gln Ile Ala Leu Ala Met Asp Ile Ala Ala Ser Glu Phe Phe Lys
                245                 250                 255

Asn Gly Gln Tyr Glu Tyr Asp Gly Gly Ser His Ser Pro Gln Glu Phe
            260                 265                 270

Ile Asp Tyr Gln Ala Lys Leu Val Ser Gln Tyr Pro Ile Val Ser Ile
        275                 280                 285

Glu Asp Gly Leu His Glu Asp Asp Trp Glu Ser Trp Lys Gly Leu Thr
            290                 295                 300

Thr Ser Leu Gly Thr Lys Thr Gln Leu Val Gly Asp Asp Leu Met Val
305                 310                 315                 320

Thr Asn Pro Val Arg Leu Gln Lys Ser Ile Asp Leu Gly Val Ala Asn
                325                 330                 335

Ala Ile Leu Ile Lys Leu Asn Gln Ile Gly Thr Leu Ser Glu Thr Leu
            340                 345                 350

Glu Thr Ile Ser Leu Ala Thr Arg His Ser Tyr Arg Ser Val Ile Ser
        355                 360                 365

His Arg Ser Gly Glu Thr Glu Asp Thr Thr Ile Ala Asp Leu Ala Val
    370                 375                 380

Ala Thr Arg Val Gly Gln Ile Lys Thr Gly Ser Leu Cys Arg Ser Glu
385                 390                 395                 400

Arg Val Ala Lys Tyr Asn Arg Leu Leu Arg Ile Glu Asp Glu Leu Gly
                405                 410                 415

Asp Arg Ala Val Tyr Ala Pro Lys Ser Ile Gly Leu Gly Pro Lys His Ser
            420                 425                 430
```

<210> SEQ ID NO 48
<211> LENGTH: 2026
<212> TYPE: DNA
<213> ORGANISM: Artificial Sequence
<220> FEATURE:
<223> OTHER INFORMATION: synthetic combined bacterial sequences

<400> SEQUENCE: 48

```
gtcgactcta gaggatcccc gggtacccct catcggggc tgtgttggcc gagacggcac      60
tgaggatttt actctccatg gcattccaag gaatatctac ccaactcacc tgctccggcg    120
gattgttccg ctcaaaagta ctaatcaagt cgtcaaaata cttattaaat tttggctgca    180
attgcatagt ccaaaagctg actttcccct ccatgctctg gggggaattg ctctggcaac    240
tgattaatcc actgagcaac agcccaagac acgcaaacaa aaaccaacgt cttggcgatc    300
```

```
gccatcggca ccatgaaacc atcgtaaaag ctggggaaag aataaaaaac agtggttcag    360
gaattgcatt gccatggcca cttcacaaac ctagccaatt ttagcttgac cgcaactttg    420
acagattgtc ttttgacttt gcctggaccg cctcccataa taccttcgcg tcttgaagac    480
tttatccttg aaaggagaac atatggagct cttaagtaaa gtccccgcca ccattgaaga    540
aatcgccgcc cgggaaattt tagactccag gggtcgcccc accatcgaag cggaagtccg    600
gctggaaagt ggggcccacg gcattgccca ggtgcccagt ggtgcttcca caggcagttt    660
tgaagcccat gaattgcggg acggagaccc caaacgctat gacgggaaag ggtagaaaa     720
agcagtacgg aacgtgacag aaaaaattgc cccggtggtg gaaggcctgg atgccttcga    780
tcaaatggcg gtggatcagg ccatgattga ccgggatgga acggacaata aaaagaatt     840
gggggccaat gccattttgg gggtttcttt agccaccgct aaggccgccg ccgctgagct    900
agccattccc ctctaccgct acctgggagg cccctggct aacgtactgc cggtaccgat     960
gatgaacgtg attaacggtg gggcccatgc cgacaataac gtcgattttc aggaattcat   1020
gatcatgccg gtgggggcag aaaccttaa agaagctctg cgctggggg cggaagtttt     1080
cgctgtgttg ggcaaagtgt tgaaagaacg aaaactgctc tccggtgggg tggggacga    1140
agggggttat gctcccaatt tgacctcgaa tcaacaggcc ctagatattc tcatcgaggc   1200
gattgaacaa gctggttaca aacccggtag tcaaattgcc ttggccatgg acattgccgc   1260
cagtgaattt ttcaaaaatg gtcagtatga atacgacggt ggttcccatt ctccccagga   1320
attcatcgac tatcaggcca agctagtgag tcaatatccc attgtctcca ttgaagacgg   1380
tttgcacgaa gacgattggg aaagttggaa gggtttaacc acttccctgg caccaaaac    1440
ccagttggtg ggggatgact tgatggtgac caacccggtg cgtctgcaaa aatccattga   1500
tttgggagtt gccaacgcca ttttgatcaa actcaatcaa atcggcactt tgagcgaaac   1560
tttagagacc atttccctag ctactcgcca tagttaccgt tctgttattt cccatcgctc   1620
cggtgaaacg gaggacacca cgatcgccga cttggccgtg gccaccaggg tagggcaaat   1680
taaaaccggt tccctttgtc gttctgagcg ggttgctaaa tataaccgtt tactccgcat   1740
tgaagatgaa cttggcgatc gggccgttta tgccctaaaa attggcctgg tcccaaaca    1800
ttcttaaaaa gtgttttaaa gttccctag cccaagggtt ggggttactt cgggagataa    1860
tcaaaccatt gccaacaggt tcttttggtt aggttgttgc ttaggattgt ctaaaattcc   1920
tcagtttttt attcaagact taattttttcc catggttacc ctaccggtga actgtgggaa   1980
ttttatgcc taacccgttc taagccaagg aagcaatgac ctcgag                   2026

<210> SEQ ID NO 49
<211> LENGTH: 443
<212> TYPE: PRT
<213> ORGANISM: Synechocystis PCC6803

<400> SEQUENCE: 49

Met Ala Thr Arg Val Ile Ile Val Arg His Gly Gln Ser Thr Tyr Asn
1               5                   10                  15

Ala Glu Lys Arg Ile Gln Gly Arg Ser Asn Leu Ser Val Leu Thr Asp
                20                  25                  30

Lys Gly Lys Ala Asp Ala Gln Lys Val Gly Gln Thr Leu Asn Ser Leu
            35                  40                  45

Ala Ile Asp Lys Ile Tyr Cys Ser Pro Leu Arg Arg Ala Lys Glu Thr
        50                  55                  60
```

Ala Gln Ile Ile Gln Ala Ser Phe Ala His Pro Glu Leu Ile Pro
 65                  70                  75                  80

Ser Glu Asn Leu Leu Glu Val Asn Leu Pro Leu Trp Glu Lys Met Thr
                 85                  90                  95

Lys Asp Asp Val Ala His Gln Tyr Pro Glu Gln Tyr Arg Leu Trp His
            100                 105                 110

Glu Ala Pro Asp Gln Leu Ala Met Thr Val Asp Gly Ala Glu Tyr Tyr
        115                 120                 125

Pro Val Ala Ala Leu Tyr Ala Gln Ala Gln Arg Phe Trp Gln Asp Val
    130                 135                 140

Leu Thr Asp Ala Ala Gly Gln Thr Leu Ile Val Ala His Asn Gly
145                 150                 155                 160

Ile Asn Arg Cys Leu Leu Met Ser Ala Ile Gly Met Pro Ala Ser His
                165                 170                 175

Tyr Gln Arg Leu Gln Gln Ser Asn Cys Asn Ile Asn Val Leu Asn Phe
            180                 185                 190

Ser Gly Gly Trp Gly Asp Pro Val Gln Leu Glu Ser Leu Asn Gln Thr
        195                 200                 205

Ala His Met Gly Val Pro Leu Pro Pro Arg Lys Asp Asn Asn Arg
    210                 215                 220

Leu Arg Leu Leu Leu Ile Arg His Gly Glu Thr Gln Trp Asn Arg Glu
225                 230                 235                 240

Gly Arg Phe Gln Gly Ile Arg Asp Ile Pro Leu Asn Asp Asn Gly Arg
                245                 250                 255

His Gln Ala Gln Lys Ala Ala Glu Phe Leu Lys Asp Val Pro Ile Asn
            260                 265                 270

Leu Gly Ile Ser Ser Pro Met Ala Arg Pro Lys Glu Thr Ala Glu Ile
        275                 280                 285

Ile Leu Gln Tyr His Pro Ser Ile Glu Leu Asp Leu Gln Pro Glu Leu
    290                 295                 300

Ala Glu Ile Cys His Gly Leu Trp Glu Gly Lys Leu Glu Thr Glu Ile
305                 310                 315                 320

Glu Ala Glu Tyr Pro Gly Leu Leu Gln Gln Trp Lys Asp Ala Pro Ala
                325                 330                 335

Thr Val Gln Met Pro Glu Gly Glu Asn Leu Gln Gln Val Trp Asp Arg
            340                 345                 350

Ala Ile Ala Cys Trp Gln Asp Arg Val Lys Phe Tyr Ser Gln Gly Asp
        355                 360                 365

Gly Ser Thr Val Gly Ile Val Val Ala His Asp Ala Ile Asn Lys Val
    370                 375                 380

Ile Leu Ala Tyr Leu Leu Gly Leu Thr Pro Ala His Phe Trp Gln Val
385                 390                 395                 400

Lys Gln Gly Asn Gly Val Ser Val Ile Asp Tyr Pro Gln Gly Leu
                405                 410                 415

Asp Lys Pro Pro Val Ile Gln Ala Ile Asn Leu Met Gly His Leu Gly
            420                 425                 430

Thr Val Leu Asp Lys Thr Ala Ala Gly Ala Leu
        435                 440

<210> SEQ ID NO 50
<211> LENGTH: 1706
<212> TYPE: DNA
<213> ORGANISM: Artificial Sequence
<220> FEATURE:
<223> OTHER INFORMATION: synthetic combined bacterial sequences

<400> SEQUENCE: 50

```
gtcgactcta gaggatcccc gggtacccct catcggggc tgtgttggcc gagacggcac      60
tgaggatttt actctccatg gcattccaag gaatatctac ccaactcacc tgctccggcg    120
gattgttccg ctcaaaagta ctaatcaagt cgtcaaaata cttattaaat tttggctgca    180
attgcatagt ccaaaagctg actttcccct ccatgctctg ggggaattg ctctggcaac     240
tgattaatcc actgagcaac agcccaagac acgcaaacaa aaaccaacgt cttggcgatc    300
gccatcggca ccatgaaacc atcgtaaaag ctggggaaag aataaaaaac agtggttcag    360
gaattgcatt gccatggcca cttcacaaac ctagccaatt ttagcttgac cgcaactttg    420
acagattgtc ttttgacttt gcctggaccg cctcccataa taccttcgcg tcttgaagac    480
tttatccttg aaaggagaac atatggagct caccaaagac gatgtgggcc accaatatcc    540
cgaacaatat cgtctctggc acgaagcacc ggatcaattg gccatgaccg tagatggagc    600
ggaatattac cccgttgcgg ctctctatgc ccagcccaa agattttggc aggatgtgtt     660
aaccgatgcg gcgggacaaa ccctgctgat tgtggcccac aatggcatca atcgttgcct    720
gttaatgagc gccattggta tgcccgcttc ccattaccaa cgcctgcaac agtccaactg    780
caatattaat gtgttgaatt ttagtggtgg ctggggcgat ccggtgcaac tggaatcctt    840
gaatcaaacc gcccatatgg gggtacctct gccacctccc cgcaaggata taatcgtct     900
gcggttactg cttatccgcc atggggaaac ccaatggaat cgggaaggac ggttccaagg    960
tattcgggat attcccctca tgacaatgg ccgccatcaa gcccaaaaag cggcggaatt    1020
cctcaaagat gtgcccatta acctaggcat tagcagtccc atggctcggc ccaaggaaac   1080
ggcggagatt attctgcaat atcacccaag catagagttg gatttacagc cggaattggc   1140
ggaaatttgc catggcctgt gggaaggcaa gctagaaacg gaaattgaag cggaatatcc   1200
cggattattg caacagtgga agatgcccc cgccacagtg cagatgccgg aaggggaaaa    1260
tttacaacag gtctgggacc gggcgatcgc ctgttggcag gaccgggtca aattctatag   1320
ccagggggat ggttccacag tgggcattgt ggtggcccat gatgccatca acaaggtgat   1380
tttggcttat ttgttgggtc ttactcccgc tcacttttgg caagttaaac agggtaatgg   1440
cggggtgagc gtcattgact atccccaggg tctagataag cccccagtta ttcaagccat   1500
taatttgatg ggccatttgg gcacagtgtt ggataaaacc gccgccggag ccctatagtc   1560
ctgtccatag ccaattatcc ccccatttgt tccctaactc ttgtttgcta tgactcactt   1620
tggtttgctc tgtccagcaa cgacgggtca tctcaatacc atgttgccct tgggtaagga   1680
actgcaacag cggggtcata ctcgag                                        1706
```

<210> SEQ ID NO 51
<211> LENGTH: 4479
<212> TYPE: DNA
<213> ORGANISM: Artificial Sequence
<220> FEATURE:
<223> OTHER INFORMATION: synthetic combined bacterial sequences

<400> SEQUENCE: 51

```
ctgcaggtcg actctagagg atccccgggt acccctcatc ggggctgtg ttggccgaga     60
cggcactgag gattttactc tccatggcat tccaaggaat atctacccaa ctcacctgct    120
ccggcggatt gttccgctca aaagtactaa tcaagtcgtc aaaatactta ttaaattttg    180
gctgcaattg catagtccaa aagctgactt tcccctccat gctctggggg gaattgctct    240
```

```
ggcaactgat taatccactg agcaacagcc aagacacgc aaacaaaaac caacgtcttg      300
gcgatcgcca tcggcaccat gaaaccatcg taaaagctgg ggaaagaata aaaaacagtg      360
gttcaggaat tgcattgcca tggccacttc acaaacctag ccaattttag cttgaccgca      420
actttgacag attgtctttt gactttgcct ggaccgcctc ccataatacc ttcgcgtctt      480
gaagacttta tccttgaaag gagaacatat gagacccta agtcatcgca ccaaaattgt       540
ggccaccatt ggccccgcca gtagttcggt agaggtgata cgtcagatgg tggatgcggg      600
catgaatgtg gcccggctga atttttccca cggtagttat gaggaccatg ccaccatggt      660
tcgcctacta cggtcagtgg agcaggaaat ggacacccccc attaccccttt tgcaagattt      720 acagggcccc aaaattcgga ttggtcagtt gccgggggga gaaaagcaac tgcgggaagg      780
ggaaaaagtt tctttggtgc cggtggaaat tggcgatcgc catcctggag cggtgggcat       840
tgactatccc catttggcga cggaggcaaa agtaggggaa gaatttttat tggacgatgg      900
tttactggaa atgaaagttg tgtccattca agatccagag gtaatttgtg aagtggtgac      960
cgggggcatc ctcaaaagtc gcaagggggt caatctaccg ggtttagtcc taaccctacc     1020
ttccatgacg accaaagaca agcaagactt agaatttggt ttgagccaag gcattgactg     1080 ggtttcccctt agttttgtcc gcaaagggga agatatccac accccttaaac aatttctcgc     1140 tgaacggggc catcctgatc tgccggtcat tgccaaaatt gaaaaacccc aggcgatcga     1200
taatctagaa gaaatcgtgg cagttttcca cggcattatg gtggccaggg gggatctggg      1260
ggtggaagta aacccagaaa aggttccccg tttgcaaaag gaaattattc ggcgctgtaa      1320
cgtgcgggcc attccggtca tcaccgctac ccaaatgcta gatagcatga ttcaaaattc      1380
ccgacccacc agggcggaag ccagtgacgt ggccaacgct atttttggacg gcaccgatgc     1440 ggtgatgtta tcggggggaat cggcagtggg acaatatccc gttaaatcag tgcaaatgtt      1500
gcgaaaaatt gccgaagaga cggaagtggg tctacatctt gttaataatc ccccaataga     1560
aaatacggaa acccatgccc taagtgaagc gttagtggta attgacgaaa ttctagattt     1620
aaaatacatt gtcacgttca ccacctcagg ttttacttct ctcctcgctt ccaaccaaag      1680
accgtcggtg ccggtgattg ctttcactcc ctcagaaaag gtttaccata gcctcaactt      1740
agtttggggt attattccct ttttaattaa cgaagaattt gacacctttg aggatttaat      1800
ccaacaggcg gagtactac tgcgggatag aaaaatggtg gaaaagggcg atcagttgct      1860
aatcatggcg ggaattccca ctaaaatacc caggggcact aatttcctca agattcaccg      1920
tatttcttaa gagctcgtgt ttggagcatt acacaccgat gttaagtaaa gtccccgcca      1980
ccattgaaga aatcgccgcc cgggaaattt tagactccag gggtcgcccc accatcgaag      2040
cggaagtccg gctggaaagt ggggcccacg gcattgccca ggtgcccagt ggtgcttcca      2100
caggcagttt tgaagcccat gaattgcggg acggagaccc caaacgctat gacgggaaag      2160
gggtagaaaa agcagtacgg aacgtgacag aaaaaattgc cccggtggtg gaaggcctgg      2220
atgccttcga tcaaatggcg gtggatcagg ccatgattga ccgggatgga acggacaata      2280
aaaaagaatt gggggccaat gccatttttgg ggtttctttt agccaccgct aaggccgccg      2340
ccgctgagct agccattccc ctctaccgct acctgggagg cccctggct aacgtactgc       2400 cggtaccgat gatgaacgtg attaacggtg gggcccatgc cgacaataac gtcgattttc      2460
aggaattcat gatcatgccg gtgggggcag aaacctttaa agaagctctg cgctgggggg      2520 cggaagttttt cgctgtgttg ggcaaagtgt tgaaagaacg aaaactgctc tccggtgggg      2580
tgggggacga agggggttat gctcccaatt tgacctcgaa tcaacaggcc ctagatattc      2640
```

```
tcatcgaggc gattgaacaa gctggttaca aacccggtag tcaaattgcc ttggccatgg    2700
acattgccgc cagtgaattt ttcaaaaatg gtcagtatga atacgacggt ggttcccatt    2760
ctccccagga attcatcgac tatcaggcca agctagtgag tcaatatccc attgtctcca    2820
ttgaagacgt tttgcacgaa gacgattggg aaagttggaa gggtttaacc acttccctgg    2880
gcaccaaaac ccagttggtg ggggatgact tgatggtgac caacccggtg cgtctgcaaa    2940
aatccattga tttgggagtt gccaacgcca ttttgatcaa actcaatcaa atcggcactt    3000
tgagcgaaac tttagagacc atttccctag ctactcgcca tagttaccgt tctgttattt    3060
cccatcgctc cggtgaaacg gaggacacca cgatcgccga cttggccgtg gccaccaggg    3120
tagggcaaat taaaaccggt tccctttgtc gttctgagcg ggttgctaaa tataaccgtt    3180
tactccgcat tgaagatgaa cttggcgatc gggccgttta tgcccctaaa attggcctgg    3240
gtcccaaaca ttcttaaaaa gatctgcccc tctgggaaaa aatgaccaaa gacgatgtgg    3300
cccaccaata tcccgaacaa tatcgtctct ggcacgaagc accggatcaa ttggccatga    3360
ccgtagatgg agcggaatat accccgttg cggctctcta tgcccaggcc aaagatttt    3420 ggcaggatgt gttaaccgat gcggcgggac aaaccctgct gattgtggcc cacaatggca    3480
tcaatcgttg cctgttaatg agcgccattg gtatgcccgc ttcccattac caacgcctgc    3540
aacagtccaa ctgcaatatt aatgtgttga atttagtgg tggctgggc gatccggtgc    3600 aactggaatc cttgaatcaa accgcccata tgggggtacc tctgccacct ccccgcaagg    3660
ataataatcg tctgcggtta ctgcttatcc gccatgggga aacccaatgg aatcgggaag    3720
gacggttcca aggtattcgg gatattcccc tcaatgacaa tggccgccat caagcccaaa    3780
aagcggcgga attcctcaaa gatgtgccca ttaacctagg cattagcagt cccatggctc    3840
ggcccaagga aacggcggag attattctgc aatatcaccc aagcatagag ttggatttac    3900
agccggaatt ggcggaaatt tgccatggcc tgtgggaagg caagctagaa acggaaattg    3960
aagcggaata tcccggatta ttgcaacagt ggaaagatgc ccccgccaca gtgcagatgc    4020
cggaagggga aaatttacaa caggtctggg accgggcgat cgcctgttgg caggaccggg    4080
tcaaattcta tagccagggg gatggttcca cagtgggcat tgtggtggcc catgatgcca    4140
tcaacaaggt gatttggct tatttgttgg gtcttactcc cgctcacttt tggcaagtta    4200
aacagggtaa tggcggggtg agcgtcattg actatcccca gggtctagat aagccccag    4260 ttattcaagc cattaatttg atgggccatt tgggcacagt gttggataaa accgccgccg    4320
gagccctata gtcctgtcca tagccaatta tccccccatt tgttccctaa ctcttgtttg    4380
ctatgactca ctttggtttg ctctgtccag caacgacggg tcatctcaat accatgttgc    4440
ccttgggtaa ggaactgcaa cagcggggtc atactcgag                           4479
```

<210> SEQ ID NO 52
<211> LENGTH: 4834
<212> TYPE: DNA
<213> ORGANISM: Artificial Sequence
<220> FEATURE:
<223> OTHER INFORMATION: synthetic combined bacterial sequences

<400> SEQUENCE: 52

```
ctgcaggtcg actctagagg atccccgggt acccctcatc gggggctgtg ttggccgaga      60
cggcactgag gattttactc tccatggcat tccaaggaat atctacccaa ctcacctgct     120
ccggcggatt gttccgctca aaagtactaa tcaagtcgtc aaaatactta ttaaattttg     180
```

```
gctgcaattg catagtccaa aagctgactt tcccctccat gctctggggg gaattgctct    240
ggcaactgat taatccactg agcaacagcc aagacacgc  aaacaaaaac caacgtcttg    300
gcgatcgcca tcggcaccat gaaccatcg  taaaagctgg ggaaagaata aaaaacagtg    360
gttcaggaat tgcattgcca tggccacttc acaaacctag ccaattttag cttgaccgca    420
actttgacag attgtctttt gactttgcct ggaccgcctc ccataatacc ttcgcgtctt    480
gaagacttta tccttgaaag gagaacatat gcaaacgtct cccctttcccc gtcgtaccaa   540 aatcgtcgct accattggcc ccgcgaccca aagcaaggaa gtgctgagac aactgatcca    600
agccggtgct accactttcc gcctcaattt ttcccacgga gaccacgctt accaccaaca    660
aagtatccgt ttgattcgcc agattgcctt tgaactgaac caaccagtgg gcattctcca    720
ggatttacag gggccaaaga ttcgggtggg caaatttctc aatgatgccg gctctgtgca    780
actcaaaaac ggtgatccct ataccctcac cagtcgcccg gtggaatgta cggaaaccat    840
tagttccatt agctacgaat atttagccga cgaagtacct tctggggcaa gaattttgct    900
cgacgacggc aaactggaaa tgttggtgga ggaagtggac actgttgccc gggatctcca    960
ctgtcgggtg attgtggggg aacccttc   cagcaataaa ggggttaatt ttcccggggt   1020 ctgccttttcc gttaaggcca tgaccgataa agataaggaa gatttgatgt tcgggctgga   1080
ccaaggggtg gactgggtgg ccctgagttt tgttcgtaat ccccaggata ttgatgagat   1140
taaggggtta attgcggcgg cagggaaatc cgtgccggta atcgccaaaa ttgagaagca   1200
cgaagcgatt aaggatatgc aggcggtgct ggaaaaatgt gacggtgtca tggtggcccg   1260
gggggacttg ggggtagaac tacccgcaga agatgtacct attttgcaaa agaaactcat   1320
tgccactgct aaccggttgg gcattcctgt cattactgct acccaaatgt tggacagtat   1380
ggtcaacagc ccccgaccta ctagggctga agtgtccgac gtggccaatg ccatcctcga   1440
tggtaccgat gcggtgatgc tctccaacga aacggcgatc ggtaaattcc ccgtggaagc   1500
agtggctatt atggccaaaa ttgcggagcg cattgaacag gaagatatca atccttccca   1560
agcggaagcc agtcgcactt ctattcccaa tgctatttcc agcgccgtta gccagattgc   1620
ggaaaccctc aacgcggcgg ctattatgtc tttgactaag accggatcca ccgcccgcca   1680
tgtgtcaaag ttccgcccca aaaccccccat tctggccgtt acgcccccatg tggatgtgtc   1740 ccgtcagttg cagttggtgt ggggagttaa gccctgttg  gtattggatt taccttccac    1800
cagccaaacg ttccaagccg ccattaacgt tggcccagga aaccatttc  tccgggatgg   1860 agatttggtg gtgatgaccg ccgggacatt gcagggagtt gccggttcga cggatttaat    1920
caaagtggaa gtggtcaagg ccattcttgg tcggggtgta ggtattggcc aaggagctgt   1980
aagtggccgg gccaggggttg ccagtcgtcc ccaggcgatc gcccaattta cccagggaga   2040
aattttagta gttccctcta ccaacgctga ttgtgtggac atgatgcgac gggcggcggg   2100
cattatcacc gaagaagaaa gcctgactag ccatgcggcc attattggtt tgcggctggg   2160
ggtgccggtc attgtgggtt ttaaaggcgc tacccaaaag attcgagatg gagccattgt   2220
caccatcgat gcccaaaaag gactgattta ttccggtgca ttaccccccgg tgtccaaagg   2280 ataggggagc cgtgttttga gcattacaca ccgatgttaa gtaaagtccc cgccaccatt   2340
gaagaaatcg ccgcccggga aatttttagac tccagggggtc gccccaccat cgaagcggaa   2400
gtccggctgg aaagtggggc ccacggcatt gcccaggtgc ccagtggtgc ttccacaggc   2460
agttttgaag cccatgaatt gcgggacgga gaccccaaac gctatgacgg gaaagggta    2520 gaaaaagcag tacggaacgt gacagaaaaa attgccccgg tggtggaagg cctggatgcc   2580
```

```
ttcgatcaaa tggcggtgga tcaggccatg attgaccggg atggaacgga caataaaaaa    2640
gaattggggg ccaatgccat tttggggtt tctttagcca ccgctaaggc cgccgccgct     2700
gagctagcca ttcccctcta ccgctacctg ggaggccccc tggctaacgt actgccggta    2760
ccgatgatga acgtgattaa cggtgggcc catgccgaca taacgtcga ttttcaggaa      2820
ttcatgatca tgccggtggg ggcagaaacc tttaaagaag ctctgcgctg ggggcggaa     2880
gttttcgctg tgttgggcaa agtgttgaaa gaacgaaaac tgctctccgg tggggtgggg    2940
gacgaagggg gttatgctcc caatttgacc tcgaatcaac aggccctaga tattctcatc    3000
gaggcgattg aacaagctgg ttacaaaccc ggtagtcaaa ttgccttggc catggacatt    3060
gccgccagtg aattttcaa aaatggtcag tatgaatacg acggtggttc ccattctccc     3120
caggaattca tcgactatca ggccaagcta gtgagtcaat atcccattgt ctccattgaa    3180
gacggtttgc acgaagacga ttgggaaagt tggaagggtt taaccacttc cctgggcacc    3240
aaaacccagt tggtggggga tgacttgatg gtgaccaacc cggtgcgtct gcaaaaatcc    3300
attgatttgg gagttgccaa cgccattttg atcaaactca atcaaatcgg cactttgagc    3360
gaaactttag agaccatttc cctagctact cgccatagtt accgttctgt tatttcccat    3420
cgctccggtg aaacggagga caccacgatc gccgacttgg ccgtggccac cagggtaggg    3480
caaattaaaa ccggttccct ttgtcgttct gagcgggttg ctaaatataa ccgtttactc    3540
cgcattgaag atgaacttgg cgatcgggcc gtttatgccc ctaaaattgg cctgggtccc    3600
aaacattctt aaaagatct gccctctgg gaaaatga ccaaagacga tgtggcccac       3660
caatatcccg aacaatatcg tctctggcac gaagcaccgg atcaattggc catgaccgta    3720
gatggagcgg aatattaccc cgttgcggct ctctatgccc aggcccaaag attttggcag    3780
gatgtgttaa ccgatgcggc gggacaaacc ctgctgattg tgcccacaa tggcatcaat    3840
cgttgcctgt taatgagcgc cattggtatg cccgcttccc attaccaacg cctgcaacag    3900
tccaactgca atattaatgt gttgaatttt agtggtggct ggggcgatcc ggtgcaactg    3960
gaatccttga tcaaaccgc ccatatgggg gtacctctgc cacctccccg caaggataat    4020
aatcgtctgc ggttactgct tatccgccat ggggaaaccc aatggaatcg ggaaggacgg    4080
ttccaaggta ttcgggatat tccctcaat gacaatggcc gccatcaagc ccaaaaagcg     4140
gcggaattcc tcaaagatgt gcccattaac ctaggcatta gcagtccat ggctcggccc      4200
aaggaaacgg cggagattat tctgcaatat cacccaagca tagagttgga tttacagccg    4260
gaattggcgg aaattgcca tggcctgtgg aaggcaagc tagaacgga aattgaagcg       4320
gaatatcccg gattattgca acagtggaaa gatgcccccg ccacagtgca gatgccggaa    4380
ggggaaaatt tacaacaggt ctgggaccgg gcgatcgcct gttggcagga ccgggtcaaa    4440
ttctatagcc aggggatgg ttccacagtg ggcattgtgg tggcccatga tgccatcaac    4500
aaggtgattt tggcttattt gttgggtctt actcccgctc acttttgca agttaaacag    4560
ggtaatggcg gggtgagcgt cattgactat ccccagggtc tagataagcc cccagttatt    4620
caagccatta atttgatggg ccatttgggc acagtgttgg ataaaaccgc cgccggagcc    4680
ctatagtcct gtccatagcc aattatcccc ccatttgttc cctaactctt gtttgctatg    4740
actcactttg gtttgctctg tccagcaacg acgggtcatc tcaataccat gttgcccttg    4800
ggtaaggaac tgcaacagcg gggtcatact cgag                                 4834
```

<210> SEQ ID NO 53

```
<211> LENGTH: 821
<212> TYPE: PRT
<213> ORGANISM: Synechocystis PCC6803

<400> SEQUENCE: 53

Met Gly Ser Thr Leu Val Gly Lys Cys Thr Ser Leu Gly Val Phe Ser
1               5                   10                  15

Met Val Thr Ser Pro Phe Ser Leu Ser Pro Phe Gly Gln Ala Arg Ser
            20                  25                  30

Thr Val Thr Gly Asn Pro Leu Asp Pro Thr Glu Leu Asn Gln Met His
        35                  40                  45

Gly Phe Trp Arg Ala Ala Asn Tyr Leu Ala Val Gly Met Ile Tyr Leu
    50                  55                  60

Arg Asp Asn Pro Leu Leu Arg Glu Pro Leu Gln Pro Glu Gln Ile Lys
65                  70                  75                  80

His Arg Leu Leu Gly His Trp Gly Ser Ser Pro Gly Ile Ser Phe Leu
                85                  90                  95

Tyr Thr His Leu Asn Arg Ile Ile Arg Lys Phe Asp Gln Asp Met Leu
            100                 105                 110

Tyr Met Val Gly Pro Gly His Gly Ala Pro Gly Phe Leu Gly Pro Cys
        115                 120                 125

Tyr Leu Glu Gly Ser Tyr Ser Arg Phe Phe Ala Glu Cys Ser Glu Asp
    130                 135                 140

Glu Asp Gly Met Lys Arg Phe Phe Lys Gln Phe Ser Phe Pro Gly Gly
145                 150                 155                 160

Ile Gly Ser His Cys Thr Pro Glu Thr Pro Gly Ser Ile His Glu Gly
                165                 170                 175

Gly Glu Leu Gly Tyr Cys Leu Ser His Ala Tyr Gly Ala Ala Phe Asp
            180                 185                 190

Asn Pro Asn Leu Ile Val Val Gly Leu Ala Gly Asp Gly Glu Ser Glu
    195                 200                 205

Thr Gly Pro Leu Ala Thr Ser Trp His Ser Asn Lys Phe Ile Asn Pro
210                 215                 220

Ile Arg Asp Gly Ala Val Leu Pro Val Leu His Leu Asn Gly Tyr Lys
225                 230                 235                 240

Ile Asn Asn Pro Ser Val Leu Ser Arg Ile Ser His Glu Glu Leu Lys
                245                 250                 255

Ala Leu Phe Glu Gly Tyr Gly Tyr Thr Pro Tyr Phe Val Glu Gly Ser
            260                 265                 270

Asp Pro Glu Ser Met His Gln Ala Met Ala Ala Thr Leu Asp His Cys
    275                 280                 285

Val Ser Glu Ile His Gln Ile Gln Gln Glu Ala Arg Ser Thr Gly Ile
290                 295                 300

Ala Val Arg Pro Arg Trp Pro Met Val Val Met Arg Thr Pro Lys Gly
305                 310                 315                 320

Trp Thr Gly Pro Asp Tyr Val Asp Gly His Lys Val Glu Gly Phe Trp
                325                 330                 335

Arg Ser His Gln Val Pro Met Gly Gly Met His Glu Asn Pro Ala His
            340                 345                 350

Leu Gln Gln Leu Glu Ala Trp Met Arg Ser Tyr Lys Pro Glu Glu Leu
    355                 360                 365

Phe Asp Glu Gln Gly Thr Leu Lys Pro Gly Phe Lys Ala Ile Ala Pro
370                 375                 380

Glu Gly Asp Lys Arg Leu Gly Ser Thr Pro Tyr Ala Asn Gly Gly Leu
```

```
                385                 390                 395                 400
Leu Arg Arg Gly Leu Lys Met Pro Asp Phe Arg Gln Tyr Gly Ile Asp
                    405                 410                 415

Val Asp Gln Pro Gly Thr Ile Glu Ala Pro Asn Thr Ala Pro Leu Gly
                420                 425                 430

Val Phe Leu Arg Asp Val Met Ala Asn Asn Met Thr Asn Phe Arg Leu
            435                 440                 445

Phe Gly Pro Asp Glu Asn Ser Ser Asn Lys Leu His Ala Val Tyr Glu
        450                 455                 460

Val Ser Lys Lys Phe Trp Ile Ala Glu Tyr Leu Glu Glu Asp Gln Asp
465                 470                 475                 480

Gly Gly Glu Leu Ser Pro Asp Gly Arg Val Met Glu Met Leu Ser Glu
                485                 490                 495

His Thr Leu Glu Gly Trp Leu Glu Ala Tyr Leu Leu Thr Gly Arg His
                500                 505                 510

Gly Phe Phe Ala Thr Tyr Glu Ser Phe Ala His Val Ile Thr Ser Met
            515                 520                 525

Val Asn Gln His Ala Lys Trp Leu Asp Ile Cys Arg His Leu Asn Trp
530                 535                 540

Arg Ala Asp Ile Ser Ser Leu Asn Ile Leu Met Thr Ser Thr Val Trp
545                 550                 555                 560

Arg Gln Asp His Asn Gly Phe Thr His Gln Asp Pro Gly Phe Leu Asp
                565                 570                 575

Val Ile Leu Asn Lys Ser Pro Asp Val Val Arg Ile Tyr Leu Pro Pro
            580                 585                 590

Asp Val Asn Ser Leu Leu Ser Val Ala Asp His Cys Leu Gln Ser Lys
        595                 600                 605

Asn Tyr Ile Asn Ile Ile Val Cys Asp Lys Gln Ala His Leu Gln Tyr
    610                 615                 620

Gln Asp Met Thr Ser Ala Ile Arg Asn Cys Thr Lys Gly Val Asp Ile
625                 630                 635                 640

Trp Glu Trp Ala Ser Asn Asp Ala Gly Thr Glu Pro Asp Val Val Met
                645                 650                 655

Ala Ala Ala Gly Asp Ile Pro Thr Lys Glu Ala Leu Ala Ala Thr Ala
            660                 665                 670

Met Leu Arg Gln Phe Phe Pro Asn Leu Arg Ile Arg Phe Val Ser Val
        675                 680                 685

Ile Asp Leu Leu Lys Leu Gln Pro Glu Ser Glu His Pro His Gly Leu
    690                 695                 700

Ser Asp Arg Asp Phe Asp Ser Leu Phe Thr Thr Asp Lys Pro Ile Ile
705                 710                 715                 720

Phe Asn Phe His Ala Tyr Pro Trp Leu Ile His Arg Leu Thr Tyr Arg
                725                 730                 735

Arg Thr Asn His Gly Asn Leu His Val Arg Gly Tyr Lys Glu Lys Gly
            740                 745                 750

Asn Ile Asn Thr Pro Met Asp Leu Ala Ile Gln Asn Gln Ile Asp Arg
        755                 760                 765

Phe Ser Leu Ala Ile Asp Val Ile Asp Arg Leu Pro Gln Leu Arg Val
    770                 775                 780

Ala Gly Ala His Ile Lys Glu Met Leu Lys Asp Met Gln Ile Asp Cys
785                 790                 795                 800

Thr Asn Tyr Ala Tyr Glu His Gly Ile Asp Met Pro Glu Ile Val Asn
                805                 810                 815
```

Trp Arg Trp Pro Leu
              820

<210> SEQ ID NO 54
<211> LENGTH: 3234
<212> TYPE: DNA
<213> ORGANISM: Artificial Sequence
<220> FEATURE:
<223> OTHER INFORMATION: synthetic combined bacterial sequences

<400> SEQUENCE: 54

| | |
|---|---|
| ctgcaggtcg actctagagg atccccgggt accccctcatc ggggctgtg ttggccgaga | 60 |
| cggcactgag gattttactc tccatggcat tccaaggaat atctacccaa ctcacctgct | 120 |
| ccggcggatt gttccgctca aaagtactaa tcaagtcgtc aaaatactta ttaaattttg | 180 |
| gctgcaattg catagtccaa aagctgactt tcccctccat gctctggggg gaattgctct | 240 |
| ggcaactgat taatccactg agcaacagcc aagacacgc aaacaaaaac caacgtcttg | 300 |
| gcgatcgcca tcggcaccat gaaaccatcg taaaagctgg ggaaagaata aaaaacagtg | 360 |
| gttcaggaat tgcattgcca tggccacttc acaaacctag ccaatttag cttgaccgca | 420 |
| actttgacag attgtctttt gactttgcct ggaccgcctc ccataatacc ttcgcgtctt | 480 |
| gaagacttta tccttgaaag gagaacatat ggttacatcc ccttttccc ttagtccctt | 540 |
| tggtcaagct agatccaccg tcactggcaa tccccttgac ccgacagaac ttaaccaaat | 600 |
| gcacggtttt tggcgggcag ccaactactt ggcagtgggc atgatttatc tgcgggataa | 660 |
| tccccttttg cgggaaccgc ttcaaccgga acagatcaag catcgcctgt gggtcactg | 720 |
| gggttctagt cccggcatta gttttctcta cacccatctc aaccgcatta tcaggaaatt | 780 |
| tgaccaggat atgctgtaca tggtggggcc tggccacggc gcaccaggct ttttggggcc | 840 |
| ctgctaccta gaagggagct attctcgctt ttttgccgag tgtagtgaag atgaggacgg | 900 |
| catgaagcgc ttttcaaac aattttcctt tccccggtggc attggcagtc attgcactcc | 960 |
| cgaaacccct ggttccatcc acgagggggg agaattgggc tactgcctat cccatgccta | 1020 |
| tggcgctgcc tttgataatc ccaatttaat tgtggtcggt ttagcggggg atggggagtc | 1080 |
| ggaaacaggc cccttggcta cctcctggca ttccaataag tttattaacc cgattcggga | 1140 |
| tggggcagtt ttaccggttc tgcatctcaa tgggtacaag attaacaatc caagtgtttt | 1200 |
| atctcgcatt agccatgaag aattaaaggc tttatttgaa ggttacggtt ataccccta | 1260 |
| ctttgttgaa ggctctgacc cggaatctat gcaccaagcc atggcagcca cgttggatca | 1320 |
| ttgtgtgagc gaaattcatc aaatccaaca agaagctcgt agtacgggca ttgccgtgcg | 1380 |
| cccccgttgg cccatggttg tgatgcggac tccaagggga tggacggggc ctgactatgt | 1440 |
| tgatggccat aaggtagaag ttttttggcg atcgcaccaa gttcccatgg ggggcatgca | 1500 |
| cgagaatcca gcccatttgc aacagttgga agcttggatg cggagttata gccggaaga | 1560 |
| attgttcgac gagcaaggta ctttaaaacc gggatttaag gcgatcgccc cggagggaga | 1620 |
| taagcgttta ggctctactc cctacgccaa tggtggtttg ttacggcggg gtttgaaaat | 1680 |
| gccggacttt cgtcaatatg gtattgatgt ggaccaacca ggcaccatcg aagcccctaa | 1740 |
| tactgcaccc ctgggagtat ttctgcggga tgtgatggcc aacaacatga ccaatttccg | 1800 |
| cctgtttggc cccgatgaaa atagttccaa taactccat gccgtctacg aggttagcaa | 1860 |
| aaaattctgg attgctgaat atctagaaga agaccaggat gggggggaat taagtcccga | 1920 |
| tggtcgggtg atggaaatgt taagcgagca caccttagaa ggttggttag aggcctatct | 1980 |

-continued

```
tttaaccggg cgtcacggct ttttcgccac ctatgaatcc tttgcccatg tgatcacttc    2040
catggttaac caacacgcta aatggttgga tatttgtcga cacctcaact ggcgggcaga    2100
tatttcctcg ttaaatatct tgatgacgtc caccgtgtgg cgacaggatc acaacgggtt    2160
tacccaccaa gatcccggtt ttctcgatgt cattctcaat aaaagccccg atgtggtgcg    2220
aatttattta ccccccgatg ttaattctct gctttccgta gcggaccatt gtttacagag    2280
caaaaactac atcaacatca tcgtttgcga taagcaagcc cacctgcaat accaggacat    2340
gacttccgct atccgtaact gcactaaagg ggtggacatt tgggaatggg ccagtaatga    2400
tgccggtacg gaaccggatg tggtgatggc agcggcgggg gatattccca ccaaagaggc    2460
cttggcggcc acagccatgc taaggcaatt ttttcctaat ctgagaattc gctttgtcag    2520
cgtgattgat ttgctcaaac tgcaaccgga atcggagcat ccccatggcc tgagcgatcg    2580
ggattttgac tccctcttta ccaccgataa accgattatt tttaacttcc acgcctatcc    2640
ctggttaatt catcggttga cctatcgacg gactaaccat ggcaatctcc atgtgcgggg    2700
ctacaaggaa aagggcaaca tcaacacccc catggattta gcgattcaaa accagattga    2760
ccgtttcagc ctcgccattg atgtgatcga tcgcctgccc caattgcggg tggccggagc    2820
ccacatcaag gaaatgctca aggatatgca gattgactgc accaactacg cctacgaaca    2880
cggcattgat atgccagaaa tcgttaattg gcgctggccc ctctagacct taactaaaat    2940
ccctgacatc gttctagttt ctgttccaat aggttagcta ggccatgggg gacaacgctg    3000
gtccagcaaa attttggcag aagctagagc aaagttgggg agcttttccc gttaaagatc    3060
ggcaaaggtt tccctgcca gtaagccagc attaattttg ttggtgacca gttcccggta    3120
catggctagt tcctgggata gtaattcata ccggggcttg gagtggagtg ccaaggcctt    3180
aatgttggat tcttcttcct tggtgaccac accatcggcc acggcctgct cgag          3234
```

<210> SEQ ID NO 55
<211> LENGTH: 697
<212> TYPE: PRT
<213> ORGANISM: Synechocystis PCC6803

<400> SEQUENCE: 55

Met Thr Ser Ser Leu Tyr Leu Ser Thr Thr Glu Ala Arg Ser Gly Lys
1               5                   10                  15

Ser Leu Val Val Leu Gly Ile Leu Asp Leu Ile Leu Lys Lys Thr Thr
                20                  25                  30

Arg Ile Ala Tyr Phe Arg Pro Ile Ile Gln Asp Pro Val Asn Gly Lys
            35                  40                  45

His Asp Asn Asn Ile Ile Leu Val Leu Glu Asn Phe Arg Leu Gln Gln
        50                  55                  60

Thr Tyr Thr Asp Ser Phe Gly Leu Tyr Phe His Glu Ala Val Ser Leu
65                  70                  75                  80

Ala Ser Asp Gly Ala Ile Asp Gln Val Leu Asp Arg Ile Leu Ala Lys
                85                  90                  95

Tyr Arg His Leu Ala Asp Gln Val Asp Phe Ile Leu Cys Glu Gly Ser
            100                 105                 110

Asp Tyr Leu Gly Glu Glu Ser Ala Phe Glu Phe Asp Leu Asn Thr Thr
        115                 120                 125

Ile Ala Lys Met Leu Asn Cys Pro Ile Leu Leu Gly Asn Ala Met
    130                 135                 140

Gly Asn Thr Ile Ala Asp Ser Leu Gln Pro Ile Asp Met Ala Leu Asn

```
            145                 150                 155                 160
        Ser Tyr Asp Gln Glu Ser Cys Gln Val Gly Val Ile Ile Asn Arg
                        165                 170                 175
        Val Gln Pro Glu Leu Ala Thr Glu Ile Gln Ala Gln Leu Glu Gln Arg
                        180                 185                 190
        Tyr Gly Asp Arg Pro Met Val Leu Gly Thr Ile Pro Gln Asp Ile Met
                        195                 200                 205
        Leu Lys Ser Leu Arg Leu Arg Glu Ile Val Ser Gly Leu Asn Ala Gln
                210                 215                 220
        Val Leu Ser Gly Ala Asp Leu Leu Asp Asn Leu Val Tyr His His Leu
        225                 230                 235                 240
        Val Val Ala Met His Ile Ala His Ala Leu His Trp Leu His Glu Lys
                        245                 250                 255
        Asn Thr Leu Ile Ile Thr Pro Gly Asp Arg Gly Asp Ile Ile Leu Gly
                        260                 265                 270
        Val Met Gln Ala His Arg Ser Leu Asn Tyr Pro Ser Ile Ala Gly Ile
                        275                 280                 285
        Leu Leu Thr Ala Asp Tyr His Pro Glu Pro Ala Ile Met Lys Leu Ile
                290                 295                 300
        Glu Gly Leu Pro Asp Ala Pro Pro Leu Leu Leu Thr Ser Thr His Thr
        305                 310                 315                 320
        His Glu Thr Ser Ala Arg Leu Glu Thr Leu His Pro Ala Leu Ser Pro
                        325                 330                 335
        Thr Asp Asn Tyr Lys Ile Arg His Ser Ile Ala Leu Phe Gln Gln Gln
                        340                 345                 350
        Ile Asp Gly Glu Lys Leu Leu Asn Tyr Leu Lys Thr Ile Arg Ser Lys
                        355                 360                 365
        Gly Ile Thr Pro Lys Leu Phe Leu Tyr Asn Leu Val Gln Ala Ala Thr
                        370                 375                 380
        Ala Ala Gln Arg His Ile Val Leu Pro Glu Gly Glu Ile Arg Ile
        385                 390                 395                 400
        Leu Lys Ala Ala Ala Ser Leu Ile Asn His Gly Ile Val Arg Leu Thr
                        405                 410                 415
        Leu Leu Gly Asn Ile Glu Ala Ile Glu Gln Thr Val Lys Ile Asn His
                        420                 425                 430
        Ile Asp Leu Asp Leu Ser Lys Val Arg Leu Ile Asn Pro Lys Thr Ser
                        435                 440                 445
        Pro Asp Arg Glu Arg Tyr Ala Glu Thr Tyr Gln Leu Arg Lys His
                450                 455                 460
        Lys Gly Val Thr Leu Ala Met Ala Arg Asp Ile Leu Thr Asp Ile Ser
        465                 470                 475                 480
        Tyr Phe Gly Thr Met Met Val His Leu Gly Glu Ala Asp Gly Met Val
                        485                 490                 495
        Ser Gly Ser Val Asn Thr Thr Gln His Thr Val Arg Pro Ala Leu Gln
                        500                 505                 510
        Ile Ile Lys Thr Gln Pro Gly Phe Ser Leu Val Ser Ser Val Phe Phe
                        515                 520                 525
        Met Cys Leu Glu Asp Arg Val Leu Val Tyr Gly Asp Cys Ala Val Asn
                530                 535                 540
        Pro Asp Pro Asn Ala Glu Gln Leu Ala Glu Ile Ala Leu Thr Ser Ala
        545                 550                 555                 560
        Ala Thr Ala Lys Asn Phe Gly Ile Glu Pro Arg Val Ala Leu Leu Ser
                        565                 570                 575
```

```
Tyr Ser Ser Gly Ser Ser Gly Gln Gly Ala Asp Val Glu Lys Val Arg
            580                 585                 590

Gln Ala Thr Ala Ile Ala Lys Glu Arg Glu Pro Asp Leu Ala Leu Glu
        595                 600                 605

Gly Pro Ile Gln Tyr Asp Ala Val Asp Ser Thr Val Ala Ala Gln
    610                 615                 620

Lys Met Pro Gly Ser Ala Val Ala Gly Lys Ala Thr Val Phe Ile Phe
625                 630                 635                 640

Pro Asp Leu Asn Thr Gly Asn Asn Thr Tyr Lys Ala Val Gln Arg Glu
                645                 650                 655

Thr Lys Ala Ile Ala Ile Gly Pro Ile Leu Gln Gly Leu Asn Lys Pro
            660                 665                 670

Val Asn Asp Leu Ser Arg Gly Cys Leu Val Glu Asp Ile Ile Asn Thr
            675                 680                 685

Val Val Ile Thr Ala Leu Gln Val Lys
    690                 695

<210> SEQ ID NO 56
<211> LENGTH: 2857
<212> TYPE: DNA
<213> ORGANISM: Artificial Sequence
<220> FEATURE:
<223> OTHER INFORMATION: synthetic combined bacterial sequences

<400> SEQUENCE: 56
```

| | |
|---|---|
| gtcgactcta gaggatcccc gggtacccct catcggggcc tgtgttggcc gagacggcac | 60 |
| tgaggatttt actctccatg gcattccaag gaatatctac ccaactcacc tgctccggcg | 120 |
| gattgttccg ctcaaaagta ctaatcaagt cgtcaaaata cttattaaat tttggctgca | 180 |
| attgcatagt ccaaaagctg actttcccct ccatgctctg ggggaattg ctctggcaac | 240 |
| tgattaatcc actgagcaac agcccaagac acgcaaacaa aaaccaacgt cttggcgatc | 300 |
| gccatcggca ccatgaaacc atcgtaaaag ctggggaaag aataaaaaac agtggttcag | 360 |
| gaattgcatt gccatggcca cttcacaaac ctagccaatt ttagcttgac cgcaactttg | 420 |
| acagattgtc ttttgacttt gcctggaccg cctcccataa taccttcgcg tcttgaagac | 480 |
| tttatccttg aaaggagaac atatgacgag ttcccttat ttaagcacca ccgaagcccg | 540 |
| cagcggtaaa tctctagtag tattgggcat tttagactta attctcaaaa aaaccacccg | 600 |
| tattgcctat tttcgtccca ttattcaaga cccagttaat ggcaaacatg ataacaacat | 660 |
| tattctggtg ctggaaaatt ttcgtctcca acaaacctat accgattcct ttggtttgta | 720 |
| tttccatgaa gcggtgagtt tagcctccga tggagctatt gatcaggtat tagaccgaat | 780 |
| tttggctaaa tatcgccatt tggcagatca agtagatttt attctctgtg aaggctcaga | 840 |
| ctatttgggg gaggaatcgg cttttgaatt tgatctcaac accacgatcg ccaagatgtt | 900 |
| gaactgcccc attttgctgt gggcaatgc catgggcaac accattgccg atagtttgca | 960 |
| acccatcgat atggccctga atagctatga ccaagagtct tgtcaggtgg tgggggtaat | 1020 |
| cattaaccga gtgcagcccg aattagccac agaaattcaa gcccaactgg aacagcgtta | 1080 |
| tggcgatcgc ccgatggtgt tgggcactat tccccaggac attatgctca aaagtctgcg | 1140 |
| cctgagggaa attgtcagcg ggctcaatgc ccaagtactc agcggtgcgg atttgctcga | 1200 |
| taacttggtc tataccattt tagtggtggc gatgcacatt gcccacgccc tccattggtt | 1260 |
| gcacgaaaaa aatacccta ttattacccc tggcgatcgg ggcgacatca ttctgggggt | 1320 |

```
gatgcaggcc caccgctccc tcaactatcc cagcattgcc ggtattttgc tcactgcaga    1380
ttaccatccc gaaccggcca ttatgaaact aattgaaggg ctacccgacg cccctcccct    1440
gttgctgact agcacccaca cccatgaaac ttccgcccgt ttggaaactc tccaccctgc    1500
cctgagccct acggataatt ataaaattcg ccacagtatt gcgctgtttc aacaacaaat    1560
tgatggggag aaattactca attaccttaa aaccatccgc agtaaaggta ttaccccaa     1620 actgtttctc tacaatttag ttcaagccgc caccgccgcc aacgacata ttgtcctacc     1680 ggaaggggaa gaaattcgta ttctcaaggc ggccgctagc ttaattaacc acggcattgt    1740
ccgtttgact ttactcggta acattgaggc gatcgagcaa acggtaaaaa ttaatcacat    1800
tgacttagat ttgagcaaag ttcgcctcat taatcctaaa actagcccag accgagagcg    1860
ctacgccgaa acctattacc agctacgtaa acataagggg gtaaccctgg ccatggctcg    1920
ggatatcctc accgatattt cctattttgg aacgatgatg gtgcatttgg gagaggccga    1980
tggcatggtt tctggctccg tcaataccac ccaacatacc gtgcgtcctg ctttacaaat    2040
tattaaaacc cagccaggtt tttccttggt ttcttcagtc ttttttatgt gtttagaaga    2100
ccgagttttg gtctatggag attgtgctgt taatcccgat cccaatgcag aacagttagc    2160
agaaattgcc cttacttctg cggctacggc caagaatttt ggcattgagc ccagggtagc    2220
tctattgtcc tattcttccg gttcttctgg gcaaggggcc gatgtggaaa agtgcggca    2280 agccacggcg atcgccaagg aaagagagcc agatttagca ttggaagggc cgatccagta    2340
tgatgcggcg gtggattcca cagtggcggc ccaaaaatg cctgggtcag cggtggcggg    2400
taaagcaacg gtgtttattt ttcccgattt aaataccggt aacaatactt acaaggcagt    2460
gcaaagagaa acaaaggcga tcgccattgg ccccatttta caaggattaa ataaaccagt    2520
taatgatcta gtcgggggtt gtttagtgga ggatattatt aatacggtgg taattacagc    2580
tttgcaagtt aaataatttt actcttaatt agttaaaatg atcccttgaa ttaccttgat    2640
tttgccctcc aaactaccaa tagctgggcc gaaaattggc atcatttaaa atcaccaacg    2700
tgtccccgga cggagctagc acaaacagac ccttaccata ggcatagctg accacttctt    2760
ggcttaacac catggctgcc actgcaccta aagctttaac atcccggtag cggggcataa    2820
actgtttgaa tttacccaac cgttccagat gctcgag                             2857
```

<210> SEQ ID NO 57
<211> LENGTH: 5385
<212> TYPE: DNA
<213> ORGANISM: Artificial Sequence
<220> FEATURE:
<223> OTHER INFORMATION: synthetic combined bacterial sequences

<400> SEQUENCE: 57

```
cccgggtacc cctcatcggg ggctgtgttg gccgagacgg cactgaggat tttactctcc     60
atggcattcc aaggaatatc tacccaactc acctgctccg gcggattgtt ccgctcaaaa    120
gtactaatca agtcgtcaaa atacttatta aattttggct gcaattgcat agtccaaaag    180
ctgactttcc cctccatgct ctgggggaa ttgctctggc aactgattaa tccactgagc      240
aacagcccaa gacacgcaaa caaaaaccaa cgtcttggcg atcgccatcg gcaccatgaa    300
accatcgtaa aagctgggga aagaataaaa aacagtggtt caggaattgc attgccatgg    360
ccacttcaca aacctagcca attttagctt gaccgcaact ttgacagatt gtcttttgac    420
tttgcctgga ccgcctccca taatacctc gcgtcttgaa gactttatcc ttgaaaggag     480
aacatatggt tacatccccc ttttcccta gtccctttgg tcaagctaga tccaccgtca     540
```

```
ctggcaatcc ccttgacccg acagaactta accaaatgca cggttttttgg cgggcagcca    600
actacttggc agtgggcatg atttatctgc gggataatcc ccttttgcgg gaaccgcttc    660
aaccggaaca gatcaagcat cgcctgttgg gtcactgggg ttctagtccc ggcattagtt    720
ttctctacac ccatctcaac cgcattatca ggaaatttga ccaggatatg ctgtacatgg    780
tggggcctgg ccacggcgca ccaggctttt tggggccctg ctacctagaa gggagctatt    840
ctcgcttttt tgccgagtgt agtgaagatg aggacggcat gaagcgcttt ttcaaacaat    900
tttcctttcc cggtggcatt ggcagtcatt gcactcccga aacccctggt tccatccacg    960
aggggggaga attgggctac tgcctatccc atgcctatgg cgctgccttt gataatccca   1020
atttaattgt ggtcggttta gcggggatg gggagtcgga acaggcccc ttggctacct     1080
cctggcattc caataagttt attaacccga ttcgggatgg ggcagtttta ccggttctgc   1140
atctcaatgg gtacaagatt aacaatccaa gtgttttatc tcgcattagc catgaagaat   1200
taaaggcttt atttgaaggt tacgttata ccccctactt tgttgaaggc tctgacccgg    1260
aatctatgca ccaagccatg gcagccacgt tggatcattg tgtgagcgaa attcatcaaa   1320
tccaacaaga agctcgtagt acgggcattg ccgtgcgccc ccgttggccc atggttgtga   1380
tgcggactcc caagggatgg acggggcctg actatgttga tggccataag gtagaaggtt   1440
tttggcgatc gcaccaagtt cccatggggg gcatgcacga gaatccagcc catttgcaac   1500
agttggaagc ttggatgcgg agttataagc cggaagaatt gttcgacgag caaggtactt   1560
taaaaccggg atttaaggcg atcgccccgg agggagataa gcgtttaggc tctactccct   1620
acgccaatgg tggtttgtta cggcggggtt tgaaaatgcc ggactttcgt caatatggta   1680
ttgatgtgga ccaaccaggc accatcgaag cccctaatac tgcacccctg ggagtatttc   1740
tgcgggatgt gatggccaac aacatgacca atttccgcct gtttggcccc gatgaaaata   1800
gttccaataa actccatgcc gtctacgagg ttagcaaaaa attctggatt gctgaatatc   1860
tagaagaaga ccaggatggg ggggaattaa gtcccgatgg tcgggtgatg gaaatgttaa   1920
gcgagcacac cttagaaggt tggttagagg cctatctttt aaccgggcgt cacggcttt    1980
tcgccaccta tgaatccttt gcccatgtga tcacttccat ggttaaccaa cacgctaaat   2040
ggttggatat ttgtcgacac ctcaactggc gggcagatat ttcctcgtta aatatcttga   2100
tgacgtccac cgtgtggcga caggatcaca acgggtttac ccaccaagat cccgtttttc   2160
tcgatgtcat tctcaataaa agccccgatg tggtgcgaat ttatttaccc cccgatgtta   2220
attctctgct ttccgtagcg gaccattgtt tacagagcaa aaactacatc aacatcatcg   2280
tttgcgataa gcaagcccac ctgcaatacc aggacatgac ttccgctatc cgtaactgca   2340
ctaaaggggt ggacatttgg gaatgggcca gtaatgatgc cggtacggaa ccggatgtgg   2400
tgatggcagc ggcgggggat attcccacca agaggccttt ggcggccaca gccatgctaa   2460
ggcaattttt tcctaatctg agaattcgct ttgtcagcgt gattgatttg ctcaaactgc   2520
aaccggaatc ggagcatccc catggcctga gcgatcggga ttttgactcc ctctttacca   2580
ccgataaacc gattattttt aacttccacg cctatccctg gttaattcat cggttgacct   2640
atcgacggac taaccatggc aatctccatg tgcgggcta caaggaaaag gcaacatca    2700
acaccccat ggatttagcg attcaaaacc agattgaccg tttcagcctc gccattgatg    2760
tgatcgatcg cctgccccaa ttgcgggtgg ccggagccca tcaaggaa atgctcaagg     2820
atatgcagat tgactgcacc aactacgcct acgaacacgg cattgatatg ccagaaatcg   2880
```

```
ttaattggcg ctggcccctc tagaccttaa ctaaaatccc tgacatcgtt ctagtttctg     2940
ttccaatagg ttagctaggc catgggggac aacagatctg gatacgttga ggttatttaa     3000
attatgacga gttcccttta tttaagcacc accgaagccc gcagcggtaa atctctagta     3060
gtattgggca ttttagactt aattctcaaa aaaaccaccc gtattgccta ttttcgtccc     3120
attattcaag acccagttaa tggcaaacat gataacaaca ttattctggt gctggaaaat     3180
tttcgtctcc aacaaaccta taccgattcc tttggtttgt atttccatga agcggtgagt     3240
ttagcctccg atggagctat tgatcaggta ttagaccgaa ttttggctaa atatcgccat     3300
ttggcagatc aagtagattt tattctctgt gaaggctcag actatttggg ggaggaatcg     3360
gcttttgaat ttgatctcaa caccacgatc gccaagatgt tgaactgccc cattttgctg     3420
ttgggcaatg ccatgggcaa caccattgcc gatagtttgc aacccatcga tatgcccctg     3480
aatagctatg accaagagtc ttgtcaggtg gtgggggtaa tcattaaccg agtgcagccc     3540
gaattagcca cagaaattca agcccaactg gaacagcgtt atggcgatcg cccgatggtg     3600
ttgggcacta ttccccagga cattatgctc aaaagtctgc gcctgaggga aattgtcagc     3660
gggctcaatg cccaagtact cagcggtgcg gatttgctcg ataacttggt ctatcaccat     3720
ttagtggtgg cgatgcacat tgcccacgcc ctccattggt tgcacgaaaa aaataccctg     3780
attattaccc ctggcgatcg gggcgacatc attctggggg tgatgcaggc ccaccgctcc     3840
ctcaactatc ccagcattgc cggtattttg ctcactgcag attaccatcc cgaaccggcc     3900
attatgaaac taattgaagg gctacccgac gcccctcccc tgttgctgac tagcacccac     3960
acccatgaaa cttccgcccg tttgaaaact ctccaccctg ccctgagccc tacggataat     4020
tataaaattc gccacagtat tgcgctgttt caacaacaaa ttgatgggga gaaattactc     4080
aattaccttc aaaccatccg cagtaaaggt attacccccca aactgtttct ctacaattta     4140
gttcaagccg ccaccgccgc ccaacgacat attgtcctac cggaagggga gaaaattcgt     4200
attctcaagg cggccgctag cttaattaac cacggcattg tccgtttgac tttactcggt     4260
aacattgagg cgatcgagca acggtaaaaa attaatcaca ttgacttaga tttgagcaaa     4320
gttcgcctca ttaatcctaa aactagccca gaccgagagc gctacgccga aacctattac     4380
cagctacgta acataagggg ggtaaccctg gccatggctc gggatatcct caccgatatt     4440
tcctattttg gaacgatgat ggtgcatttg ggagaggccg atggcatggt ttctggctcc     4500
gtcaatacca cccaacatac cgtgcgtcct gctttacaaa ttattaaaac ccagccaggt     4560
ttttccttgg tttcttcagt ctttttttatg tgtttagaag accgagtttt ggtctatgga     4620
gattgtgctg ttaatcccga tcccaatgca gaacagttag cagaaattgc ccttacttct     4680
gcggctacgg ccaagaattt tggcattgag cccaggtag ctctattgtc ctattcttcc     4740
ggttcttctg ggcaagggc cgatgtggaa aaagtgcggc aagccacggc gatcgccaag     4800
gaaagagagc cagatttagc attggaaggg ccgatccagt atgatgcggc ggtggattcc     4860
acagtggcgg cccaaaaaat gcctgggtca gcggtggcgg gtaaagcaac ggtgtttatt     4920
tttcccgatt taaataccgg taacaatact tacaaggcag tgcaaagaga aacaaaggcg     4980
atcgccattg gccccatttt acaaggatta aataaaccag ttaatgatct aagtcggggt     5040
tgtttagtgg aggatattat taatacggtg gtaattacag ctttgcaagt taaataattt     5100
tactcttaat tagttaaaat gatccccttga attccttga ttttgccctc caaactacca     5160
atagctgggc cgaaaattgg catcatttaa aatcaccaac gtgtccccgg acggagctag     5220
cacaaacaga cccttaccat aggcatagct gaccacttct tggcttaaca ccatggctgc     5280
```

```
cactgcacct aaagctttaa catcccggta gcggggcata aactgtttga atttacccaa    5340
ccgttccaga tgctcgagca accgatcttt ctagaagatc tcgag                   5385
```

<210> SEQ ID NO 58
<211> LENGTH: 456
<212> TYPE: PRT
<213> ORGANISM: Synechocystis PCC6803

<400> SEQUENCE: 58

```
Met Asn Thr Ala Lys Thr Val Val Ala Glu Gln Arg Asp Phe Phe Arg
1               5                   10                  15

Gln Gly Lys Thr Lys Ser Val Gln Asp Arg Leu Thr Ala Leu Ala Lys
            20                  25                  30

Leu Lys Thr Gln Ile Gln Ala Gln Glu Glu Ile Ile Lys Ala Leu
        35                  40                  45

Lys Gln Asp Phe Gly Lys Pro Thr Phe Glu Ser Tyr Val Asn Glu Ile
    50                  55                  60

Leu Gly Val Ile Arg Glu Ile Asn Tyr Tyr Gln Lys His Leu Gln Gln
65                  70                  75                  80

Trp Ser Lys Pro Gln Arg Val Gly Thr Asn Leu Met Val Phe Pro Ala
                85                  90                  95

Ser Ala Gln Leu Arg Pro Glu Pro Leu Gly Val Val Leu Ile Ile Ser
            100                 105                 110

Pro Trp Asn Tyr Pro Phe Tyr Leu Cys Leu Met Pro Leu Ile Gly Ala
        115                 120                 125

Ile Ala Ala Gly Asn Cys Val Val Lys Pro Ser Glu Tyr Thr Pro
    130                 135                 140

Ala Ile Ser Gly Val Ile Thr Arg Leu Ile Gln Asn Val Phe Ser Pro
145                 150                 155                 160

Ala Trp Ala Thr Val Val Glu Gly Asp Glu Thr Ile Ser Gln Gln Leu
                165                 170                 175

Leu Gln Glu Lys Phe Asp His Ile Phe Phe Thr Gly Ser Pro Arg Val
            180                 185                 190

Gly Arg Leu Ile Met Ala Ala Ala Glu Gln Leu Thr Pro Val Thr
        195                 200                 205

Leu Glu Leu Gly Gly Lys Ser Pro Cys Val Val Asp Arg Glu Ile Asn
    210                 215                 220

Leu Gln Glu Thr Ala Lys Arg Ile Met Trp Gly Lys Leu Val Asn Ala
225                 230                 235                 240

Gly Gln Thr Cys Val Ala Pro Asp Tyr Leu Leu Val Glu Gln Ser Cys
                245                 250                 255

Leu Glu Gln Leu Leu Pro Ala Leu Gln Gln Ala Ile Gln Met Leu Phe
            260                 265                 270

Gly Glu Asn Pro Ala His Ser Pro Asp Tyr Thr Arg Ile Val Asn Gln
        275                 280                 285

Gln Gln Trp Ser Arg Leu Val Ser Leu Leu Ser His Gly Lys Val Ile
    290                 295                 300

Thr Arg Gly Asp His Asn Glu Gly Asp Arg Tyr Ile Ala Pro Thr Leu
305                 310                 315                 320

Ile Ile Asp Pro Asp Leu Asn Ser Pro Leu Met Gln Glu Glu Ile Phe
                325                 330                 335

Gly Pro Ile Leu Pro Ile Leu Thr Tyr Gln Ser Leu Ser Glu Ala Ile
            340                 345                 350
```

```
Asp Phe Ile Asn Ile Lys Pro Lys Pro Leu Ala Leu Tyr Phe Phe Ser
        355                 360                 365

Asn Asn Arg Gln Lys Gln Glu Glu Ile Leu Gln Ser Thr Ser Ser Gly
    370                 375                 380

Ser Val Cys Leu Asn Asp Ile Leu Leu His Leu Thr Val Thr Asp Leu
385                 390                 395                 400

Pro Phe Gly Gly Val Gly Glu Ser Gly Met Gly Arg Tyr His Gly Lys
                405                 410                 415

Ala Thr Phe Asp Thr Leu Ser Asn Tyr Lys Ser Ile Leu Arg Arg Pro
            420                 425                 430

Phe Trp Gly Glu Thr Asn Leu Arg Tyr Ser Pro Tyr Gly Lys Lys Met
        435                 440                 445

Asn Leu Ile Lys Lys Leu Phe Ser
    450                 455
```

<210> SEQ ID NO 59
<211> LENGTH: 2089
<212> TYPE: DNA
<213> ORGANISM: Artificial Sequence
<220> FEATURE:
<223> OTHER INFORMATION: synthetic combined bacterial sequences

<400> SEQUENCE: 59

```
ctgcaggtcg actctagagg atccccgggt acccctcatc ggggctgtg ttggccgaga      60
cggcactgag gattttactc tccatggcat tccaaggaat atctacccaa ctcacctgct    120
ccggcggatt gttccgctca aaagtactaa tcaagtcgtc aaaatactta ttaaattttg    180
gctgcaattg catagtccaa aagctgactt tcccctccat gctctggggg gaattgctct    240
ggcaactgat taatccactg agcaacagcc aagacacgc aaacaaaaac caacgtcttg     300
gcgatcgcca tcggcaccat gaaaccatcg taaaagctgg ggaaagaata aaaaacagtg    360
gttcaggaat tgcattgcca tggccacttc acaaacctag ccaatttag cttgaccgca     420
actttgacag attgtctttt gactttgcct ggaccgcctc ccataatacc ttcgcgtctt    480
gaagacttta tccttgaaag gagaaacatat gaatactgct aaaactgttg ttgctgagca   540
aagggacttt tttcgtcagg gcaaaactaa atcagtccaa gatagattaa cagctctagc    600
aaaattaaaa acgcaaattc aagcccagga agaggaaatt attaaggccc ttaagcaaga    660
ttttggtaag cccacctttg aaagctatgt aaacgaaatt tgggggtaa ttaggaaat     720
taattattat caaaaacatc ttcagcaatg gtctaagccc caacgggtag gtacgaatct    780
gatggttttt cctgccagtg cccagttaag accagaaccc cttggtgtag tgctaattat    840
tagcccctgg aattatcctt tttatctttg tttaatgccc ttgatcgggg cgatcgccgc    900
tggaaattgt gtggtggtaa agccgtcgga atatactcca gctattagtg gggtaattac    960
cagattaatc caaaatgtat tttccccggc ttgggcaaca gtggtggagg gagatgaaac   1020
cattagccaa caattgttac aggaaaaatt tgaccatatt tctcttaccg gcagccctag   1080
ggtgggtcgg ttaattatgg cagctgcggc agagcaatta accccagtta cgttggaatt   1140
gggggggtaaa tctcccctgtg tggtggatag ggaaatcaac ctccaggaaa cagccaaacg   1200
cattatgtgg ggcaagctag tcaatgctgg ccaaacctgt gtggcaccgg attatttatt   1260
ggtggagcaa tcctgcttag aacaactttt accagcttta caacaggcaa ttcagatgct   1320
tttcggggaa aatccagccc atagccctga ctacactcgc attgttaacc aacaacaatg   1380
gtcacggtta gttagtttat taagccatgg caaagtaatt acaaggggag atcataacga   1440
```

```
aggcgatcgc tacattgccc caactttaat catcgatcca gatttaaatt ctccctaat    1500 gcaagaggaa atatttggcc caattttgcc aattttaact tatcagagtt tgtcagaagc    1560
aatagatttt attaacatca aacctaaacc attggcactt tattttttta gcaataatcg    1620
gcaaaaacag gaggaaattt tgcaatctac cagttccggt agtgtttgtt tgaacgatat    1680
tttgcttcat ttaactgtga cagacttacc ctttggtggg gtgggagaaa gtggtatggg    1740
acgctaccat ggcaaggcta cttttgacac attgagcaat tataaaagca ttttacgacg    1800 accctttgg ggggaaacta atttacgcta ttctccctat ggcaaaaaaa tgaatttaat    1860
caaaaagttg ttctcctagg attattcatg gccgaccgtc cccagttgag tattattatt    1920
cccgtgttta atgaagcaaa aatttacaa agtctccga ctgaaaatac cagacaatat    1980
ttgggacaat ttaccgagga tcaacggata gaaattttaa ttattgatgg gggcagtcag    2040
gatagcacag tggagttatg ccagacctat gctgattctt tacctcgag              2089
```

<210> SEQ ID NO 60
<211> LENGTH: 1034
<212> TYPE: PRT
<213> ORGANISM: Synechocystis PCC6803

<400> SEQUENCE: 60

```
Met Asn Leu Ala Val Pro Ala Phe Gly Leu Ser Thr Asn Trp Ser Gly
1               5                   10                  15

Asn Gly Asn Gly Ser Asn Ser Glu Glu Ser Val Leu Tyr Gln Arg
            20                  25                  30

Leu Lys Met Val Glu Glu Leu Trp Glu Arg Val Leu Gln Ser Glu Cys
        35                  40                  45

Gly Gln Glu Leu Val Asp Leu Leu Thr Glu Leu Arg Leu Gln Gly Thr
    50                  55                  60

His Glu Ala Ile Thr Ser Glu Ile Ser Glu Glu Val Ile Met Gly Ile
65                  70                  75                  80

Thr Gln Arg Ile Glu His Leu Glu Leu Asn Asp Ala Ile Arg Ala Ala
                85                  90                  95

Arg Ala Phe Ala Leu Tyr Phe Gln Leu Ile Asn Ile Val Glu Gln His
            100                 105                 110

Tyr Glu Gln Asn Glu Gln Gln Arg Asn Arg Trp Glu Ala Ser Gln Glu
        115                 120                 125

Thr Asn Phe Tyr Glu Gln Ala Gly Asn Glu Glu Met Val Pro Pro
    130                 135                 140

Ser Arg Leu Gly Ala Ser Thr Glu Pro Leu Pro Val Gly Ile Asp Gln
145                 150                 155                 160

Asn Glu Leu Gln Ala Ser Val Gly Thr Phe His Trp Leu Met Arg Glu
                165                 170                 175

Leu Lys Arg Leu Asn Val Pro Pro Gln His Ile Gln Asn Leu Leu Asp
            180                 185                 190

His Leu Asp Ile Arg Leu Val Ile Thr Ala His Pro Thr Glu Ile Val
        195                 200                 205

Arg His Thr Ile Arg Arg Lys Gln Arg Val Asp Arg Ile Leu Arg
    210                 215                 220

Lys Leu Asp Gln Leu Gln Gly Ser Val Thr Gly Arg Asp Trp Leu Asn
225                 230                 235                 240

Thr Trp Asp Ala Lys Thr Ala Ile Ala Gln Leu Thr Glu Glu Ile Arg
                245                 250                 255

Phe Trp Trp Arg Thr Asp Glu Leu His Gln Phe Lys Pro Thr Val Leu
```

```
            260                 265                 270
Asp Glu Val Asp Tyr Ser Leu His Tyr Phe Asp Glu Val Leu Phe Asp
        275                 280                 285

Ala Val Pro Glu Leu Ser Lys Arg Leu Gly Gln Ala Ile Lys Glu Thr
    290                 295                 300

Phe Pro His Leu Arg Ala Pro Arg Ala Asn Phe Cys Tyr Phe Gly Ser
305                 310                 315                 320

Trp Val Gly Gly Asp Arg Asp Gly Asn Pro Ser Val Thr Pro Glu Val
                325                 330                 335

Thr Trp Gln Thr Ala Cys Tyr Gln Arg Gly Leu Val Leu Gly Lys Tyr
            340                 345                 350

Leu Phe Ser Leu Gly Glu Leu Ala Ile Leu Ser Pro Ser Leu His
        355                 360                 365

Trp Cys Lys Val Ser Gln Glu Leu Leu Asp Ser Leu Glu Arg Asp Arg
    370                 375                 380

Ile Gln Leu Pro Glu Ile Tyr Glu Glu Leu Ser Leu Arg Tyr Arg Gln
385                 390                 395                 400

Glu Pro Tyr Arg Met Lys Leu Ala Tyr Val Thr Lys Arg Leu Glu Asn
                405                 410                 415

Thr Leu Arg Arg Asn Asn Arg Leu Ala Asn Pro Glu Glu Arg Gln Thr
            420                 425                 430

Met Ile Thr Met Pro Ala Glu Asn His Tyr Arg Thr Gly Glu Glu Leu
        435                 440                 445

Leu Glu Glu Leu Arg Leu Ile Gln Arg Asn Leu Thr Glu Thr Gly Leu
    450                 455                 460

Thr Cys Leu Glu Leu Glu Asn Leu Ile Thr Gln Leu Glu Val Tyr Gly
465                 470                 475                 480

Phe Asn Leu Ala Gln Leu Asp Phe Arg Gln Ser Ser Arg His Ala
                485                 490                 495

Glu Ala Ile Ala Glu Ile Ala Glu Tyr Met Gly Val Leu Thr Thr Pro
            500                 505                 510

Tyr Glu Glu Met Ala Glu Glu Asp Lys Leu Ala Trp Leu Gly Val Glu
        515                 520                 525

Leu Gln Thr Arg Arg Pro Leu Ile Pro Gln Glu Met Pro Phe Ser Glu
    530                 535                 540

Arg Thr Arg Glu Thr Ile Glu Thr Leu Arg Thr Leu Arg His Leu Gln
545                 550                 555                 560

Met Glu Phe Gly Val Asp Ile Cys Gln Thr Tyr Ile Ile Ser Met Thr
                565                 570                 575

Asn Asp Ala Ser Asp Val Leu Glu Val Leu Leu Leu Ala Lys Glu Ala
            580                 585                 590

Gly Leu Tyr Asp Pro Ala Thr Ala Ser Asn Ser Leu Arg Ile Val Pro
        595                 600                 605

Leu Phe Glu Thr Val Glu Asp Leu Lys Asn Ala Pro Gly Ile Met Asp
    610                 615                 620

Ser Leu Phe Ser Leu Pro Phe Tyr Arg Ala Thr Leu Ala Gly Ser Tyr
625                 630                 635                 640

His Ser Leu Lys Glu Leu Gln Asn Gln Pro Pro Asp Tyr Tyr Gln Ile
                645                 650                 655

Pro Thr Thr Thr Ala Leu Leu Asn Pro Gly Asn Leu Gln Glu Ile Met
            660                 665                 670

Val Gly Tyr Ser Asp Ser Asn Lys Asp Ser Gly Phe Leu Ser Ser Asn
        675                 680                 685
```

Trp Glu Ile His Lys Ala Gln Lys Ser Leu Gln Ala Val Ala Gln Ser
690                 695                 700

His Arg Val Ile Leu Arg Leu Phe His Gly Arg Gly Gly Ser Val Gly
705                 710                 715                 720

Arg Gly Gly Gly Pro Ala Tyr Lys Ala Ile Leu Ala Gln Pro Ala Gly
            725                 730                 735

Thr Val Asp Gly Arg Ile Lys Ile Thr Glu Gln Gly Glu Val Leu Ala
        740                 745                 750

Ser Lys Tyr Ser Leu Pro Glu Leu Ala Leu Tyr Asn Leu Glu Thr Leu
    755                 760                 765

Thr Thr Ala Val Ile Gln Ala Ser Leu Leu Lys Ser Ser Phe Asp Phe
770                 775                 780

Ile Glu Pro Trp Asn Arg Ile Met Glu Glu Leu Ala Cys Thr Ala Arg
785                 790                 795                 800

Arg Ala Tyr Arg Ser Leu Ile Tyr Glu Glu Pro Asp Phe Leu Asp Phe
            805                 810                 815

Phe Leu Thr Val Thr Pro Ile Pro Glu Ile Ser Glu Leu Gln Ile Ser
        820                 825                 830

Ser Arg Pro Ala Arg Arg Lys Gly Gly Lys Ala Asp Leu Ser Ser Leu
    835                 840                 845

Arg Ala Ile Pro Trp Val Phe Ser Trp Thr Gln Thr Arg Phe Leu Leu
850                 855                 860

Pro Ala Trp Tyr Gly Val Gly Thr Ala Leu Lys Ser Phe Val Asp Gln
865                 870                 875                 880

Asp Pro Val Lys Asn Met Lys Leu Leu Arg Tyr Phe Tyr Phe Lys Trp
            885                 890                 895

Pro Phe Phe Asn Met Val Ile Ser Lys Val Glu Met Thr Leu Ser Lys
        900                 905                 910

Val Asp Leu Thr Ile Ala Ser His Tyr Val Gln Glu Leu Ser Lys Pro
    915                 920                 925

Glu Asp Arg Glu Arg Phe Asp Arg Leu Phe Gln Gln Ile Lys Gln Glu
930                 935                 940

Tyr Gln Leu Thr Arg Asp Phe Ala Met Glu Ile Thr Ala His Pro His
945                 950                 955                 960

Leu Leu Asp Gly Asp Arg Ser Leu Gln Arg Ser Val Leu Leu Arg Asn
            965                 970                 975

Arg Thr Ile Val Pro Leu Gly Leu Leu Gln Ile Ser Leu Leu Lys Arg
        980                 985                 990

Leu Arg Gln Val Thr Gln Glu Ala Glu Thr Ser Gly Val Arg Tyr Arg
    995                 1000                1005

Arg Tyr Ser Lys Glu Glu Leu Leu Arg Gly Ala Leu Leu Thr Ile
1010                1015                1020

Asn Gly Ile Ala Ala Gly Met Arg Asn Thr Gly
   1025                1030

<210> SEQ ID NO 61
<211> LENGTH: 3650
<212> TYPE: DNA
<213> ORGANISM: Artificial Sequence
<220> FEATURE:
<223> OTHER INFORMATION: synthetic combined bacterial sequences

<400> SEQUENCE: 61
tcgactctag aggatccccg ggtacccctc atcggggggct gtgttggccg agacggcact    60

```
gaggatttta ctctccatgg cattccaagg aatatctacc caactcacct gctccggcgg    120
attgttccgc tcaaaagtac taatcaagtc gtcaaaatac ttattaaatt ttggctgcaa    180
ttgcatagtc caaaagctga ctttcccctc catgctctgg ggggaattgc tctggcaact    240
gattaatcca ctgagcaaca gcccaagaca cgcaaacaaa aaccaacgtc ttggcgatcg    300
ccatcggcac catgaaacca tcgtaaaagc tggggaaaga ataaaaaaca gtggttcagg    360
aattgcattg ccatggccac ttcacaaacc tagccaattt tagcttgacc gcaactttga    420
cagattgtct tttgactttg cctggaccgc ctcccataat accttcgcgt cttgaagact    480
ttatccttga aaggagaaca tatgaacttg gcagttcctg cattcggtct ttccactaac    540
tggtctggta atggcaatgg ttccaactct gaagaagagt cggtgcttta ccagcggtta    600
aagatggtgg aggaattgtg ggaaagggtg ctccaaagcg aatgtggcca ggaattggtg    660
gatttgctga cggaattaag gcttcagggt acccatgagg cgatcaccag cgaaatttcc    720
gaagaagtca tcatgggtat tacccagcgc attgagcatt tagaactcaa tgatgccatc    780
cgggcggctc gggcctttgc cctatatttc cagttgatca acatcgttga acagcactac    840
gaacaaaacg agcaacaacg gaatcgttgg gaagcttccc aggaaaccaa cttctatgag    900
caggcgggca atgaggaaga atggtcccc ccatcccgat taggcgcgtc aacggaacca    960
ttgccagtgg gcattgacca gaatgaattg caagcttctg taggtacgtt ccattggtta   1020
atgagggagc taaaacgcct caatgtgccc ccccaacata tccaaaattt attggatcat   1080
ctggacattc gcctggtgat caccgctcac cccacggaaa ttgtccgtca caccatccgg   1140
cgcaaacaaa aagggtggaa ccgcattctt cgtaaactag atcaactcca gggttctgtg   1200
accggtcggg actggctcaa cacctgggat gcaaaacgg cgatcgccca attaacggag   1260
gaaattcgct tttggtggcg taccgacgaa cttcatcagt tcaaacccac tgtgttggac   1320
gaagtggact attccctcca ttattttgat gaagtactgt tcgacgctgt accggaattg   1380
tccaaacggt taggacaagc tattaaagaa acctttcccc atctgcgggc cccccgggct   1440 aattttgtt attttggctc ctgggtcggt ggcgatcggg acggcaaccc ttcggtaacc   1500
ccagaagtga cctggcagac ggcctgttac cagcggggtt tagtgctggg aaatatttg   1560 tttagtttgg gggaactggt ggccattctt agcccttccc tccattggtg caaagtctcc   1620
caggaattgt tggactcttt ggaacgggac cgcattcaat taccggaaat ttacgaagaa   1680 cttttctctcc gctatcgcca ggaaccctat cggatgaagc tggcctacgt taccaaacgg   1740
ctggaaaaca ccctgcggcg taataatcgt ctagccaacc cagaagaacg gcaaacgatg   1800
atcaccatgc cggccgaaaa tcactatcgc actggggaag aattattaga ggaattaaga   1860
ctcattcagc gtaatctgac cgaaactggt ttaacctgcc tggagttgga aaatttgatt   1920
acccagttgg aagtctatgg ctttaaccta gcccagttgg attttcgcca ggaatcttcc   1980
cgccacgccg aggcgatcgc cgaaattgct gagtatatgg gggtactcac cactccctac   2040
gaagaaatgg ccgaagaaga taaattagcc tggttagggg tagaactgca aacccgccgt   2100
cctttaattc cccaggaaat gccctttcg gagcggacta gggaaaccat tgaaaccctc   2160
cgcaccctgc gccatctaca aatgaatttg gggtggata tttgccaaac ctacatcatc   2220
agcatgacca acgatgccag tgatgtgttg aagtattgc tgttagccaa ggaagccgga   2280
ttgtatgacc cggccaccgc ctccaattcc ctccgcattg tgccctgtt tgaaacagta   2340 gaagatctca aaaacgctcc ggggattatg gattctcttt tcagcttgcc tttttaccgg   2400
gctacattgg cggcagtta ccattcctta aaagagttgc aaaatcagcc accggattat   2460
```

```
taccaaattc ccaccaccac agccctacta aatcccggca atctccagga aattatggtg      2520
ggctattccg acagcaataa agactccggc ttttgagca gtaactggga aattcataag       2580
gcccaaaaat cactgcaggc agtggcccaa agccatcggg taattctccg gctgttccac      2640
ggtcgaggag gatctgttgg ccggggggc ggcccggcct ataaagccat tttggcccag       2700
cccgcaggca ccgtggacgg tcggatcaaa attaccgaac aaggggaagt gttagcttct      2760
aaatattccc tgccagagtt ggccctctac aacctgaaaa cttaaccac ggcggtcatc       2820 caagctagtt tacttaaaag tagttttgat ttcattgagc cctggaaccg gattatggag      2880
gagttggcct gcactgcccg tcgagcctac cggagtttga tttacgaaga accggacttt      2940
ttagatttct tcctgacggt taccccatt cctgaaatta gcgagttaca gattagttcc       3000
cgccctgccc gacgtaaggg gggtaaagcg gatctcagca gtttgcgggc cattccctgg      3060
gtgttcagtt ggacccaaac ccgttcctg ctgccggctt ggtatggggt gggcacggcg       3120
ttgaaatcct ttgtggacca agacccggtc aaaaatatga agttgttgcg ttacttctat      3180
ttcaaatggc ctttcttcaa catggtgatc tcgaaggtgg aaatgaccct ttccaaggtg      3240
gacctcacca tcgcttccca ctatgtgcaa gagctatcta agccagaaga ccgggaacga      3300
ttcgatcgcc ttttcagca gatcaagcaa gagtatcaat taaccaggga ctttgccatg       3360
gaaattacgg cccatcccca cctcctggac ggcgatcgct ctttgcaacg gtcggtactc      3420
ctacgaaatc gtactattgt tccctgggg ctactgcaga tttccctgct gaaacgttta      3480
cgccaagtaa cccaggaagc ggagaccagc ggcgtgcgtt accgtcgtta ttccaaagaa      3540
gaactactgc ggggagctct gttaaccatt aacggtattg cggccggaat gcgtaatact      3600
ggttgatcca gtgatatggt gcctaatatt gggtaaggac ctgccccttgc              3650

<210> SEQ ID NO 62
<211> LENGTH: 26
<212> TYPE: DNA
<213> ORGANISM: Artificial Sequence
<220> FEATURE:
<223> OTHER INFORMATION: synthetic combined bacterial sequences

<400> SEQUENCE: 62
agatctcaac ggctcacaag cccaac                                           26

<210> SEQ ID NO 63
<211> LENGTH: 25
<212> TYPE: DNA
<213> ORGANISM: Artificial Sequence
<220> FEATURE:
<223> OTHER INFORMATION: synthetic combined bacterial sequences

<400> SEQUENCE: 63
ctgcagaatt ttctccattc aaccc                                            25

<210> SEQ ID NO 64
<211> LENGTH: 26
<212> TYPE: DNA
<213> ORGANISM: Artificial Sequence
<220> FEATURE:
<223> OTHER INFORMATION: synthetic combined bacterial sequences

<400> SEQUENCE: 64
gagctctgga ggactgacct agatgg                                           26

<210> SEQ ID NO 65
```

<211> LENGTH: 2984
<212> TYPE: DNA
<213> ORGANISM: Synechocystis PCC6803

<400> SEQUENCE: 65

| | | | | | |
|---|---|---|---|---|---:|
| agatctcaac | ggctcacaag | cccaactaat | caccatttgg | acaaaacatc | aggaattcta | 60 |
| attagaaagt | ccaaaaattg | taatttaaaa | aacagtcaat | ggagagcatt | gccataagta | 120 |
| aaggcatccc | ctgcgtgata | agattacctt | cagaaaacag | atagttgctg | ggttatcgca | 180 |
| gattttctc | gcaaccaaat | aactgtaaat | aataactgtc | tctggggcga | cggtaggctt | 240 |
| tatattgcca | aatttcgccc | gtgggagaaa | gctaggctat | tcaagagctc | tggaggactg | 300 |
| acctagatgg | tacaagccaa | agcagggttt | aaggcgggcg | tacaagatta | tcgcctgacc | 360 |
| tactataccc | ccgactacac | ccccaaggat | accgacctgc | tcgcctgctt | ccgtatgacc | 420 |
| ccccaaccgg | gtgtacctgc | tgaagaagcc | gctgctgcgg | tggccgctga | gtcttccacc | 480 |
| ggtacctgga | ccaccgtttg | gactgacaac | ctaactgact | tggaccgcta | caaaggtcgt | 540 |
| tgctatgacc | tggaagctgt | tcccaacgaa | gataaccaat | attttgcttt | tattgcctat | 600 |
| cctctagatt | tatttgaaga | aggttccgtc | accaacgttt | taacctcttt | ggtcggtaac | 660 |
| gtatttggtt | ttaaggctct | gcgggccctc | cgtttagaag | atattcgttt | tcccgttgct | 720 |
| ttaattaaaa | ccttccaagg | ccctccccac | ggtattaccg | ttgagcggga | caaattaaac | 780 |
| aaatacggtc | gtcctctgct | tggttgtacc | atcaaaccca | aacttggtct | gtccgccaag | 840 |
| aactacggtc | gggctgttta | cgaatgtctc | cggggtggtt | tggacttcac | caaagacgac | 900 |
| gaaaacatca | actcccagcc | cttcatgcgt | tggcgcgatc | gtttcctctt | cgttcaagag | 960 |
| gcgatcgaaa | aagcccaggc | tgagaccaac | gaaatgaaag | gtcactacct | gaacgtcacc | 1020 |
| gctggcacct | gcgaagaaat | gatgaaacgg | gccgagtttg | ccaaggaaat | tggcacccc | 1080 |
| atcatcatgc | atgacttctt | caccggcggt | ttcactgcca | acaccaccct | cgctcgttgg | 1140 |
| tgtcgggaca | acggcatttt | gctccatatt | caccgggcaa | tgcacgccgt | agttgaccgt | 1200 |
| cagaaaaacc | acgggatcca | cttccgggtt | ttggccaagt | gtctgcgtct | gtccggcggt | 1260 |
| gaccacctcc | actccggtac | cgtggttggt | aaattggaag | gggaacgggg | tatcaccatg | 1320 |
| ggcttcgttg | acctcatgcg | cgaagattac | gttgaggaag | atcgctcccg | gggtattttc | 1380 |
| ttcacccaag | actatgcctc | catgcctggc | accatgcccg | tagcttccgg | tggtatccac | 1440 |
| gtatggcaca | tgcccgcgtt | ggtggaaatc | ttcggtgatg | attcctgctt | acagtttggt | 1500 |
| ggtggtactt | tgggtcaccc | ctggggtaat | gctcccggtg | caaccgctaa | ccgtgttgct | 1560 |
| ttggaagctt | gtgttcaagc | tcggaacgaa | ggtcgtaacc | tggctcgcga | aggtaatgac | 1620 |
| gttatccggg | aagcctgtcg | ttggtcccct | gagttggccg | ccgcctgcga | actctggaaa | 1680 |
| gagatcaagt | ttgagttcga | ggccatggat | accctctaaa | ccggtgtttg | gattgtcgga | 1740 |
| gttgtactcg | tccgttaagg | atgaacagtt | cttcggggtt | gagtctgcta | actaattagc | 1800 |
| cattaacagc | ggcttaacta | acagttagtc | attggcaatt | gtcaaaaaat | tgttaatcag | 1860 |
| ccaaaaccca | ctgcttactg | atgttcaact | tcgacagcaa | tttaccaatt | accgggtaga | 1920 |
| gtgttcatgc | aaactaagca | catagctcag | gcaacagtga | agtactgca | aagttacctc | 1980 |
| acctaccaag | ccgttctcag | gatccagagt | gaactcgggg | aaaccaaccc | tccccaggcc | 2040 |
| atttggttaa | accagtattt | agccagtcac | agtattcaaa | atggagaaac | gttttttgacg | 2100 |
| gaactcctgg | atgaaaataa | agaactggta | ctcaggatcc | tggcggtaag | ggaagacatt | 2160 |
| gccgaatcag | tgttagattt | tttgcccggt | atgacccgga | atagcttagc | ggaatctaac | 2220 |

-continued

```
atcgcccacc gccgccattt gcttgaacgt ctgacccgta ccgtagccga agtcgataat   2280
ttcccttcgg aaacctccaa cggagaatca acaacaacg attctccccc gtcctaacgt   2340
agtcatcagc aaggaaaact tttaaatcga tgaaacttt acccaaagag cgccgctacg   2400 aaacccttc ttacctgccc cctttaaccg atcaacagat tgctaaacag gttgagtttc   2460
tgttagacca gggctttatt cccggcgtgg aatttgaaga agaccccccaa cccgaaaccc   2520 acttctggac catgtggaaa ctgcccttct ttggtggtgc cactgccaac gaagttctag   2580
ccgaagtacg ggaatgtcgt tctgagaatc ccaactgcta cattcgggtg attggtttcg   2640
acaatatcaa acagtgccag actgtaagct ttattgtcca caaacccaac caaaaccaag   2700
gccgttacta agttacagtt ttggcaatta ctaaaaaact gacttcaatt caatgttagc   2760
ccgctcccgc gggttttttg ttgcttttc acagtgacta taggtaatca gcaacacaat   2820
acggccctgt tctttggaca gttttgtat aatgttgacc gcatcctgac cggatttttt   2880
atctaagtgg ggaattgtca attgtcaatt aaagctaagt tctactaatg ttttagaagg   2940
cattgtcgat tgaaaataag ggttgaatgg agaaaattct gcag   2984
```

<210> SEQ ID NO 66
<211> LENGTH: 470
<212> TYPE: PRT
<213> ORGANISM: Synechocystis PCC6803

<400> SEQUENCE: 66

```
Met Val Gln Ala Lys Ala Gly Phe Lys Ala Gly Val Gln Asp Tyr Arg
1               5                   10                  15

Leu Thr Tyr Tyr Thr Pro Asp Tyr Thr Pro Lys Asp Thr Asp Leu Leu
                20                  25                  30

Ala Cys Phe Arg Met Thr Pro Gln Pro Gly Val Pro Ala Glu Glu Ala
            35                  40                  45

Ala Ala Val Ala Ala Glu Ser Ser Thr Gly Thr Trp Thr Thr Val
        50                  55                  60

Trp Thr Asp Asn Leu Thr Asp Leu Asp Arg Tyr Lys Gly Arg Cys Tyr
65                  70                  75                  80

Asp Leu Glu Ala Val Pro Asn Glu Asp Asn Gln Tyr Phe Ala Phe Ile
                85                  90                  95

Ala Tyr Pro Leu Asp Leu Phe Glu Glu Gly Ser Val Thr Asn Val Leu
            100                 105                 110

Thr Ser Leu Val Gly Asn Val Phe Gly Phe Lys Ala Leu Arg Ala Leu
        115                 120                 125

Arg Leu Glu Asp Ile Arg Phe Pro Val Ala Leu Ile Lys Thr Phe Gln
    130                 135                 140

Gly Pro Pro His Gly Ile Thr Val Glu Arg Asp Lys Leu Asn Lys Tyr
145                 150                 155                 160

Gly Arg Pro Leu Leu Gly Cys Thr Ile Lys Pro Lys Leu Gly Leu Ser
                165                 170                 175

Ala Lys Asn Tyr Gly Arg Ala Val Tyr Glu Cys Leu Arg Gly Gly Leu
            180                 185                 190

Asp Phe Thr Lys Asp Asp Glu Asn Ile Asn Ser Gln Pro Phe Met Arg
        195                 200                 205

Trp Arg Asp Arg Phe Leu Phe Val Gln Glu Ala Ile Glu Lys Ala Gln
    210                 215                 220

Ala Glu Thr Asn Glu Met Lys Gly His Tyr Leu Asn Val Thr Ala Gly
225                 230                 235                 240
```

```
Thr Cys Glu Glu Met Met Lys Arg Ala Glu Phe Ala Lys Glu Ile Gly
                245                 250                 255

Thr Pro Ile Ile Met His Asp Phe Phe Thr Gly Gly Phe Thr Ala Asn
            260                 265                 270

Thr Thr Leu Ala Arg Trp Cys Arg Asp Asn Gly Ile Leu Leu His Ile
        275                 280                 285

His Arg Ala Met His Ala Val Val Asp Arg Gln Lys Asn His Gly Ile
    290                 295                 300

His Phe Arg Val Leu Ala Lys Cys Leu Arg Leu Ser Gly Gly Asp His
305                 310                 315                 320

Leu His Ser Gly Thr Val Val Gly Lys Leu Glu Gly Glu Arg Gly Ile
                325                 330                 335

Thr Met Gly Phe Val Asp Leu Met Arg Glu Asp Tyr Val Glu Glu Asp
            340                 345                 350

Arg Ser Arg Gly Ile Phe Phe Thr Gln Asp Tyr Ala Ser Met Pro Gly
        355                 360                 365

Thr Met Pro Val Ala Ser Gly Gly Ile His Val Trp His Met Pro Ala
    370                 375                 380

Leu Val Glu Ile Phe Gly Asp Asp Ser Cys Leu Gln Phe Gly Gly Gly
385                 390                 395                 400

Thr Leu Gly His Pro Trp Gly Asn Ala Pro Gly Ala Thr Ala Asn Arg
                405                 410                 415

Val Ala Leu Glu Ala Cys Val Gln Ala Arg Asn Glu Gly Arg Asn Leu
            420                 425                 430

Ala Arg Glu Gly Asn Asp Val Ile Arg Glu Ala Cys Arg Trp Ser Pro
        435                 440                 445

Glu Leu Ala Ala Ala Cys Glu Leu Trp Lys Gly Ile Lys Phe Glu Phe
    450                 455                 460

Glu Ala Met Asp Thr Leu
465                 470

<210> SEQ ID NO 67
<211> LENGTH: 137
<212> TYPE: PRT
<213> ORGANISM: Synechocystis PCC6803

<400> SEQUENCE: 67

His Met Gln Thr Lys His Ile Ala Gln Ala Thr Val Lys Val Leu Gln
1               5                   10                  15

Ser Tyr Leu Thr Tyr Gln Ala Val Leu Arg Ile Gln Ser Glu Leu Gly
            20                  25                  30

Glu Thr Asn Pro Pro Gln Ala Ile Trp Leu Asn Gln Tyr Leu Ala Ser
        35                  40                  45

His Ser Ile Gln Asn Gly Glu Thr Phe Leu Thr Glu Leu Leu Asp Glu
    50                  55                  60

Asn Lys Glu Leu Val Leu Arg Ile Leu Ala Val Arg Glu Asp Ile Ala
65                  70                  75                  80

Glu Ser Val Leu Asp Phe Leu Pro Gly Met Thr Arg Asn Ser Leu Ala
                85                  90                  95

Glu Ser Asn Ile Ala His Arg Arg His Leu Leu Glu Arg Leu Thr Arg
            100                 105                 110

Thr Val Ala Glu Val Asp Asn Phe Pro Ser Glu Thr Ser Asn Gly Glu
        115                 120                 125

Ser Asn Asn Asn Asp Ser Pro Pro Ser
```

<210> SEQ ID NO 68
<211> LENGTH: 113
<212> TYPE: PRT
<213> ORGANISM: Synechocystis PCC6803

<400> SEQUENCE: 68

Met Lys Thr Leu Pro Lys Glu Arg Arg Tyr Glu Thr Leu Ser Tyr Leu
1               5                   10                  15

Pro Pro Leu Thr Asp Gln Gln Ile Ala Lys Gln Val Glu Phe Leu Leu
            20                  25                  30

Asp Gln Gly Phe Ile Pro Gly Val Glu Phe Glu Asp Pro Gln Pro
        35                  40                  45

Glu Thr His Phe Trp Thr Met Trp Lys Leu Pro Phe Phe Gly Gly Ala
    50                  55                  60

Thr Ala Asn Glu Val Leu Ala Glu Val Arg Glu Cys Arg Ser Glu Asn
65                  70                  75                  80

Pro Asn Cys Tyr Ile Arg Val Ile Gly Phe Asp Asn Ile Lys Gln Cys
                85                  90                  95

Gln Thr Val Ser Phe Ile Val His Lys Pro Gln Asn Gln Gly Arg
            100                 105                 110

Tyr

<210> SEQ ID NO 69
<211> LENGTH: 6267
<212> TYPE: DNA
<213> ORGANISM: Artificial Sequence
<220> FEATURE:
<223> OTHER INFORMATION: synthetic combined bacterial sequences

<400> SEQUENCE: 69
cacctaaatt gtaagcgtta atattttgtt aaaattcgcg ttaaattttt gttaaatcag      60
ctcatttttt aaccaatagg ccgaaatcgg caaaatccct tataaatcaa agaatagac     120 cgagataggg ttgagtgttg ttccagtttg gaacaagagt ccactattaa agaacgtgga    180
ctccaacgtc aaagggcgaa aaaccgtcta tcagggcgat ggcccactac gtgaaccatc    240
accctaatca gttttttggg gtcgaggtg ccgtaaagca ctaaatcgga accctaaagg     300
gagcccccga tttagagctt gacggggaaa gccggcgaac gtggcgagaa aggaagggaa    360
gaaagcgaaa ggagcgggcg ctagggcgct ggcaagtgta gcggtcacgc tgcgcgtaac    420
caccacaccc gccgcgctta atgcgccgct acagggcgcg tcccattcgc cattcaggct    480
gcgcaactgt tgggaagggc gatcggtgcg ggcctcttcg ctattacgcc agctggcgaa    540 aggggggatgt gctgcaaggc gattaagttg gtaacgccca gggttttccc agtcacgacg    600
ttgtaaaacg acggccagtg aattgtaata cgactcacta tagggcgaat tggaggccag    660
tgctggagga atatgatttt gtcatcctcg actgtgcccc tggttataat ctgttgaccc    720
gcagtggcat tgcggccagc gacttttatc tgttgccggc tcgtcctgaa ccctatcgg    780 tggtggggat gcagttactg gaaagaagaa ttgagaaact gaaggaaagc cataaggcct    840
ccgatgatcc cctgaatatc aatctgatcg gagtggtgtt tattctgtcc ggcggcggtt    900
tgatgagtcg ctactataac caggtaatgc ggcgggtaca aacggatttc accccgggac    960 aacttttca gcagtccatt cccatggatg tcaatgtggc taaggcagtg gatagcttta   1020
tgccggtggt tacctccatg cccaatacgg cgggttcaaa agcttttatt aaattaaccc   1080

-continued

```
aggaattttt acagaaagta gaagcttttg gctaaagcaa agcccccatt gattaacaac    1140
gggaggggta ccgaggtgct gctgaagttg cccgcaacag agagtggaac caaccggtga    1200
taccacgata ctatgactga gagtcaacgc catgagcggc ctcatttctt attctgagtt    1260
acaacagtcc gcaccgctgt ccggtagctc cttccggtgg gcgcggggca tgactatcgt    1320
cgccgcactt atgactgtct tctttatcat gcaactcgta ggacaggtgc cggcagcgcc    1380
caacagtccc ccggccacgg ggcctgccac catacccacg ccgaaacaag cgccctgcac    1440
cattatgttc cggatctgca tcgcaggatg ctgctggcta ccctgtggaa cacctacatc    1500
tgtattaacg aagcgctaac cgttttttatc aggctctggg aggcagaata aatgatcata    1560
tcgtcaatta ttacctccac ggggagagcc tgagcaaact ggcctcaggc atttgagaag    1620
cacacggtca cactgcttcc ggtagtcaat aaaccggtaa accagcaata gacataagcg    1680
gctatttaac gaccctgccc tgaaccgacg accgggtcga atttgctttc gaatttctgc    1740
cattcatccg cttattatca cttattcagg cgtagcacca ggcgtttaag ggcaccaata    1800
actgccttaa aaaaattacg ccccgccctg ccactcatcg cagtactgtt gtaattcatt    1860
aagcattctg ccgacatgga agccatcaca gacggcatga tgaacctgaa tcgccagcgg    1920
catcagcacc ttgtcgcctt gcgtataata tttgcccatg gtgaaaacgg gggcgaagaa    1980
gttgtccata ttggccacgt ttaaatcaaa actggtgaaa ctcacccagg gattggctga    2040
gacgaaaaac atattctcaa taaacccttt agggaaatag gccaggtttt caccgtaaca    2100
cgccacatct tgcgaatata tgtgtagaaa ctgccggaaa tcgtcgtggt attcactcca    2160
gagcgatgaa aacgtttcag tttgctcatg gaaaacggtg taacaagggt gaacactatc    2220
ccatatcacc agctcaccgt cttttcattgc catacggaat tccggatgag cattcatcag    2280
gcgggcaaga atgtgaataa aggccggata aaacttgtgc ttattttttct ttacggtctt    2340 taaaaaggcc gtaatatcca gctgaacggt ctggttatag gtacattgag caactgactg    2400 aaaatgcctca aaatgttctt tacgatgcca ttgggatata tcaacggtgg tatatccagt    2460
gatttttttc tccattttag cttccttagc tcctgaaaat ctcgataact caaaaaatac    2520
gcccggtagt gatcttattt cattatggtg aaagttggaa cctcttacct cggtacccct    2580 catcggggc tgtgttggcc gagacggcac tgaggatttt actctccatg gcattccaag    2640
gaatatctac ccaactcacc tgctccggcg gattgttccg ctcaaaagta ctaatcaagt    2700
cgtcaaaata cttattaaat tttggctgca attgcatagt ccaaaagctg actttcccct    2760
ccatgctctg gggggaattg ctctggcaac tgattaatcc actgagcaac agcccaagac    2820
acgcaaacaa aaaccaacgt cttggcgatc gccatcggca ccatgaaacc atcgtaaaag    2880
ctggggaaag aataaaaaac agtggttcag gaattgcatt gccatggcca cttcacaaac    2940
ctagccaatt ttagcttgac cgcaactttg acagattgtc ttttgacttt gcctggaccg    3000
cctcccataa taccttcgcg tcttgaagac tttatccttg aaaggagaac atatgtttct    3060
cggcaaaaat taattatcga ttggctggaa cctggtcaaa ccagggcttt tcatccattg    3120
gaaaagcgat tttgatcatc tagggtcagg agcaaagatc tgatcaaata ttgatcattt    3180
attaggaaag ctgaactttc accactttat ttttggcttc ctctactttg ggcaaagtca    3240
aagttaggat accggcatcg taattagctt taacttctgt gttttggatt gctccaggta    3300
caggaataac ccggcggaaa ctgccatagc ggaactctgt gcgccgcacc ccatcttttt    3360
cggtgctatg ggtatcctgg cgatcgccgc tgacggtcac cgcatccctg gcggcttgga    3420
tgtccaaatt atcggggtcc atgccaggta attctagttt gagcacatag gcttcttcag    3480
```

```
tttcagttag ttctgcttta ggattaaacc cttggcgatc gccgtggcgg tccgtaggga   3540
caaaaacttc ttcaaacagt tggttcatct gctgctggaa attatccatt tcccgcaggg   3600
gattgtaaag aatgagagac ataatgttaa ctcctgatgt gtggaaggaa ttgattaccc   3660
ttgaatggtt ctatcttaaa atttcccctt ccaggttaga ttcggttttc aggaaagaag   3720
gtgggggat tgccgaaatt acatttctag ccgcaatttt tagtaaaaaa aagatgagtt    3780
tttacctcac cttaagtaaa tatttgagtg gcaaaacaaa atggtaaaaa tagctaagct   3840
tccaccgccc tatggatttt tggaaggaag tcttaggttg tgaaaaacta taaaaaccaa   3900
ccataggaat ggagacccttt acccaacaag ttgacccctt ggtaacaaat ccaaccacc   3960
gtaaaaccgc tggcggccaa aatagcgggc ttgcggcctt gccaacccttt ggtaatgcgg  4020
gcatggagat aggcggcaaa tactagccag gtgattaggg cccggtaccc agcttttgtt   4080
cccctttagtg agggttaatt tcgagcttgg cgtaatcatg gtcatagctg tttcctgtgt  4140
gaaattgtta tccgctcaca attccacaca acatacgagc cggaagcata aagtgtaaag   4200
cctggggtgc ctaatgagtg agctaactca cattaattgc gttgcgctca ctgcccgctt   4260
tccagtcggg aaacctgtcg tgccagctgc attaatgaat cggccaacgc gcggggagag   4320
gcggtttgcg tattgggcgc tcttccgctt cctcgctcac tgactcgctg cgctcggtcg   4380
ttcggctgcg gcgagcggta tcagctcact caaaggcggt aatacggtta tccacagaat   4440
caggggataa cgcaggaaag aacatgtgag caaaaggcca gcaaaaggcc aggaaccgta   4500
aaaaggccgc gttgctggcg tttttccata ggctccgccc ccctgacgag catcacaaaa   4560
atcgacgctc aagtcagagg tggcgaaacc cgacaggact ataaagatac caggcgtttc   4620
ccctggaag ctccctcgtg cgctctcctg ttccgaccct gccgcttacc ggatacctgt    4680
ccgcctttct cccttcggga agcgtggcgc tttctcatag ctcacgctgt aggtatctca   4740
gttcggtgta ggtcgttcgc tccaagctgg gctgtgtgca cgaaccccc gttcagcccg    4800
accgctgcgc cttatccggt aactatcgtc ttgagtccaa cccggtaaga cacgacttat   4860
cgccactggc agcagccact ggtaacagga ttagcagagc gaggtatgta ggcggtgcta   4920
cagagttctt gaagtggtgg cctaactacg gctacactag aaggacagta tttggtatct   4980
gcgctctgct gaagccagtt accttcggaa aaagagttgg tagctcttga tccggcaaac   5040
aaaccaccgc tggtagcggt ggtttttttg tttgcaagca gcagattacg cgcagaaaaa   5100
aaggatctca agaagatcct ttgatctttt ctacggggtc tgacgctcag tggaacgaaa   5160
actcacgtta agggattttg gtcatgagat tatcaaaaag gatcttcacc tagatccttt   5220
taaattaaaa atgaagtttt aaatcaatct aaagtatata tgagtaaact tggtctgaca   5280
gttaccaatg cttaatcagt gaggcaccta tctcagcgat ctgtctattt cgttcatcca   5340
tagttgcctg actccccgtc gtgtagataa ctacgatacg ggagggctta ccatctggcc   5400
ccagtgctgc aatgataccg cgagacccac gctcaccggc tccagattta tcagcaataa   5460
accagccagc cggaagggcc gagcgcagaa gtggtcctgc aactttatcc gcctccatcc   5520
agtctattaa ttgttgccgg gaagctagag taagtagttc gccagttaat agtttgcgca   5580
acgttgttgc cattgctaca ggcatcgtgg tgtcacgctc gtcgtttggt atggcttcat   5640
tcagctccgg ttcccaacga tcaaggcgag ttacatgatc ccccatgttg tgcaaaaaag   5700
cggttagctc cttcggtcct ccgatcgttg tcagaagtaa gttggccgca gtgttatcac   5760
tcatggttat ggcagcactg cataattctc ttactgtcat gccatccgta agatgctttt   5820
```

| | |
|---|---|
| ctgtgactgg tgagtactca accaagtcat tctgagaata gtgtatgcgg cgaccgagtt | 5880 |
| gctcttgccc ggcgtcaata cgggataata ccgcgccaca tagcagaact ttaaaagtgc | 5940 |
| tcatcattgg aaaacgttct tcggggcgaa aactctcaag gatcttaccg ctgttgagat | 6000 |
| ccagttcgat gtaacccact cgtgcaccca actgatcttc agcatctttt actttcacca | 6060 |
| gcgtttctgg gtgagcaaaa acaggaaggc aaaatgccgc aaaaaaggga ataagggcga | 6120 |
| cacggaaatg ttgaatactc atactcttcc ttttcaata ttattgaagc atttatcagg | 6180 |
| gttattgtct catgagcgga tacatatttg aatgtattta gaaaaataaa caaataggggg | 6240 |
| ttccgcgcac atttccccga aaagtgc | 6267 |

<210> SEQ ID NO 70
<211> LENGTH: 9231
<212> TYPE: DNA
<213> ORGANISM: Artificial Sequence
<220> FEATURE:
<223> OTHER INFORMATION: synthetic combined bacterial sequences

<400> SEQUENCE: 70

| | |
|---|---|
| gatctgtaat ccgggcagcg caacggaaca ttcatcagtg taaaaatgga atcaataaag | 60 |
| ccctgcgcag cgcgcagggt cagcctgaat acgcgtttaa tgaccagcac agtcgtgatg | 120 |
| gcaaggtcag aatagcgctg aggtctgcct cgtgaagaag gtgttgctga ctcataccag | 180 |
| gcctgaatcg ccccatcatc cagccagaaa gtgagggagc cacggttgat gagagctttg | 240 |
| ttgtaggtgg accagttggt gattttgaac ttttgctttg ccacggaacg gtctgcgttg | 300 |
| tcgggaagat gcgtgatctg atccttcaac tcagcaaaag ttcgatttat tcaacaaagc | 360 |
| cgccgtcccg tcaagtcagc gtaatgctct gccagtgtta caaccaatta accaattctg | 420 |
| attagaaaaa ctcatcgagc atcaaatgaa actgcaattt attcatatca ggattatcaa | 480 |
| taccatattt ttgaaaaagc cgtttctgta atgaaggaga aaactcaccg aggcagttcc | 540 |
| ataggatggc aagatcctgg tatcggtctg cgattccgac tcgtccaaca tcaatacaac | 600 |
| ctattaattt cccctcgtca aaaataaggt tatcaagtga aaatcacca tgagtgacga | 660 |
| ctgaatccgg tgagaatggc aaaagcttat gcatttctttt ccagacttgt tcaacaggcc | 720 |
| agccattacg ctcgtcatca aaatcactcg catcaaccaa accgttattc attcgtgatt | 780 |
| gcgcctgagc gagacgaaat acgcgatcgc tgttaaaagg acaattacaa acaggaatcg | 840 |
| aatgcaaccg gcgcaggaac actgccagcg catcaacaat attttcacct gaatcaggat | 900 |
| attcttctaa tacctggaat gctgttttcc cggggatcgc agtggtgagt aaccatgcat | 960 |
| catcaggagt acgataaaa tgcttgatgg tcggaagagg cataaattcc gtcagccagt | 1020 |
| ttagtctgac catctcatct gtaacatcat tggcaacgct acctttgcca tgtttcagaa | 1080 |
| acaactctgg cgcatcgggc ttcccataca atcgatagat tgtcgcacct gattgcccga | 1140 |
| cattatcgcg agcccattta tacccatata atcagcatc catgttggaa tttaatcgcg | 1200 |
| gcctcgagca agacgtttcc cgttgaatat ggctcataac accccttgta ttactgttta | 1260 |
| tgtaagcaga cagttttatt gttcatgatg atatattttt atcttgtgca atgtaacatc | 1320 |
| agagattttg agacacaacg tggctttgtt gaataaatcg aacttttgct gagttgaagg | 1380 |
| atcagatcac gcatcttccc gacaacgcag accgttccgt ggcaaagcaa aagttcaaaa | 1440 |
| tcaccaactg gtccacctac aacaaagctc tcatcaaccg tggctccctc actttctggc | 1500 |
| tggatgatgg ggcgattcag gcctggtatg agtcagcaac accttcttca cgaggcagac | 1560 |
| ctcagcgcta ttctgacctt gccatcacga ctgtgctggt cattaaacgc gtattcaggc | 1620 |

```
tgaccctgcg cgctgcgcag ggctttattg attccatttt tacactgatg aatgttccgt    1680
tgcgctgccc ggattacagc tgaaagcgac caggtgctcg gcgtggcaag actcgcagcg    1740
aacccgtaga aagccatgct ccagccgccc gcattggaga aattcttcaa attcccgttg    1800
cacatagccc ggcaattcct ttccctgctc tgccataagc gcagcgaatg ccgggtaata    1860
ctcgtcaacg atctgataga aagggtttg ctcgggtcgg tggctctggt aacgaccagt    1920
atcccgatcc cggctggccg tcctggccgc cacatgagcg atgttccgcg tccttgcaat    1980
actgtgttta catacagtct atcgcttagc ggaaagttct tttaccctca gccgaaatgc    2040
ctgccgttgc tagacattgc cagccagtgc ccgtcactcc cgtactaact gtcacgaacc    2100
cctgcaataa ctgtcacgcc cccctgcaat aactgtcacg aaccccctgca ataactgtca    2160 cgcccccaaa cctgcaaacc cagcagggg ggggctggc ggggtgttgg aaaaatccat    2220
ccatgattat ctaagaataa tccactaggc gcggttatca gcgcccttgt ggggcgctgc    2280
tgcccttgcc caatatgccc ggccagaggc cggatagctg gtctattcgc tgcgctaggc    2340
tacacaccgc cccaccgctg cgcggcaggg ggaaaggcgg gcaaagcccg ctaaacccca    2400
caccaaaccc cgcagaaata cgctggagcg cttttagccg ctttagcggc ctttcccct    2460 acccgaaggg tggggcgcg tgtgcagccc cgcagggcct gtctcggtcg atcattcagc    2520
ccggctcatc cttctggcgt ggcggcagac cgaacaaggc gcggtcgtgg tcgcgttcaa    2580
ggtacgcatc cattgccgcc atgagccgat cctccggcca ctcgctgctg ttcaccttgg    2640
ccaaaatcat ggccccacc agcaccttgc gccttgtttc gttcttgcgc tcttgctgct    2700
gttcccttgc ccgcacccgc tgaatttcgg cattgattcg cgctcgttgt tcttcgagct    2760
tggccagccg atccgccgcc ttgttgctcc ccttaaccat cttgacaccc cattgttaat    2820
gtgctgtctc gtaggctatc atggaggcac agcggcggca atcccgaccc tactttgtag    2880
gggagggcgc acttaccggt ttctcttcga gaaactggcc taacggccac ccttcgggcg    2940
gtgcgctctc cgagggccat tgcatggagc cgaaaagcaa agcaacagc gaggcagcat    3000 ggcgatttat caccttacgg cgaaaaccgg cagcaggtcg gcggccaat cggcagggc    3060 caaggccgac tacatccagc gcgaaggcaa gtatgcccgc gacatggatg aagtcttgca    3120
cgccgaatcc gggcacatgc cggagttcgt cgagcggccc gccgactact gggatgctgc    3180
cgacctgtat gaacgcgcca atgggcggct gttcaaggag gtcgaatttg ccctgccggt    3240
cgagctgacc ctcgaccagc agaaggcgct ggcgtccgag ttcgcccagc acctgaccgg    3300
tgccgagcgc ctgccgtata cgctggccat ccatgccggt ggcggcgaga cccgcactg    3360 ccacctgatg atctccgagc ggatcaatga cggcatcgag cggcccgccg ctcagtggtt    3420
caagcggtac aacggcaaga ccccggagaa gggcgggca cagaagaccg aagcgctcaa    3480
gcccaaggca tggcttgagc agacccgcga ggcatgggcc gaccatgcca ccgggcatt    3540 agagcgggct ggccacgacg cccgcattga ccacagaaca cttgaggcgc agggcatcga    3600
gcgcctgccc ggtgttcacc tggggccgaa cgtggtggag atggaaggcc ggggcatccg    3660
caccgaccgg gcagacgtgg ccctgaacat cgacaccgcc aacgcccaga tcatcgactt    3720
acaggaatac cgggaggcaa tagaccatga acgcaatcga cagagtgaag aaatccagag    3780
gcatcaacga gttagcggag cagatcgaac cgctggccca gagcatggcg acactggccg    3840
acgaagcccg gcaggtcatg agccagaccc agcaggccag cgaggcgcag gcggcggagt    3900
ggctgaaagc ccagcgccag acaggggcgg catgggtgga gctggccaaa gagttgcggg    3960
```

```
aggtagccgc cgaggtgagc agcgccgcgc agagcgcccg gagcgcgtcg cggggggtggc    4020
actggaagct atggctaacc gtgatgctgg cttccatgat gcctacgtgt gtgctgctga    4080
tcgcatcgtt gctcttgctc gacctgacgc cactgacaac cgaggacggc tcgatctggc    4140
tgcgcttggt ggcccgatga agaacgacag gactttgcag gccataggcc gacagctcaa    4200
ggccatgggc tgtgagcgct tcgatatcgg cgtcagggac gccaccaccg gccagatgat    4260
gaaccgggaa tggtcagccg ccgaagtgct ccagaacacg ccatggctca agcggatgaa    4320
tgcccagggc aatgacgtgt atatcaggcc cgccgagcag gagcggcatg gtctggtgct    4380
ggtggacgac ctcagcgagt ttgacctgga tgacatgaaa gccgagggcc gggagcctgc    4440
cctggtagtg gaaaccagcc cgaagaacta tcaggcatgg gtcaaggtgg ccgacgccgc    4500
aggcggtgaa cttcggggc agattgcccg gacgctggcc agcgagtacg acgccgaccc    4560
ggccagcgcc gacagccgcc actatggccg cttggcgggc ttcaccaacc gcaaggacaa    4620
gcacaccacc cgcgccggtt atcagccgtg ggtgctgctg cgtgaatcca agggcaagac    4680
cgccaccgct ggcccggcgc tggtgcagca ggctggccag cagatcgagc aggcccagcg    4740
gcagcaggag aaggcccgca ggctggccag cctcgaactg cccgagcggc agcttagccg    4800
ccaccggcgc acggcgctgg acgagtaccg cagcgagatg gccgggctgg tcaagcgctt    4860
cggtgatgac ctcagcaagt gcgactttat cgccgcgcag aagctggcca gccggggccg    4920
cagtgccgag gaaatcggca aggccatggc cgaggccagc ccagcgctgg cagagcgcaa    4980
gcccggccac gaagcggatt acatcgagcg caccgtcagc aaggtcatgg gtctgcccag    5040
cgtccagctt gcgcgggccg agctggcacg ggcaccggca ccccgccagc gaggcatgga    5100
caggggcggg ccagatttca gcatgtagtg cttgcgttgg tactcacgcc tgttatacta    5160
tgagtactca cgcacagaag gggttttat ggaatacgaa aaaagcgctt cagggtcggt    5220
ctacctgatc aaaagtgaca agggctattg gttgcccggt ggctttggtt atacgtcaaa    5280
caaggccgag gctggccgct tttcagtcgc tgatatggcc agccttaacc ttgacggctg    5340
caccttgtcc ttgttccgcg aagacaagcc tttcggcccc ggcaagtttc tcggtgactg    5400
atatgaaaga ccaaaaggac aagcagaccg gcgacctgct ggccagccct gacgctgtac    5460
gccaagcgcg atatgccgag cgcatgaagg ccaaagggat gcgtcagcgc aagttctggc    5520
tgaccgacga cgaatacgag cgctgcgcg agtgcctgga agaactcaga gcggcgcagg    5580
gcgggggtag tgaccccgcc agcgcctaac caccaactgc ctgcaaagga ggcaatcaat    5640
ggctacccat aagcctatca atattctgga ggcgttcgca gcagccgcc caccgctgga    5700
ctacgttttg cccaacatgg tggccggtac ggtcggggcg ctggtgtcgc ccggtggtgc    5760
cggtaaatcc atgctggccc tgcaactggc cgcacagatt gcaggcgggc cggatctgct    5820
ggaggtgggc gaactgccca ccggcccggt gatctacctg cccgccgaag acccgcccac    5880
cgccattcat caccgcctgc acgcccttgg ggcgcacctc agcgccgagg aacggcaagc    5940
cgtggctgac ggcctgctga tccagccgct gatcggcagc ctgcccaaca tcatggcccc    6000
ggagtggttc gacggcctca agcgcgccgc cgagggccgc cgcctgatgg tgctggacac    6060
gctgcgccgt tccacatcg aggaagaaaa cgccagcggc cccatggccc aggtcatcgg    6120
tcgcatggag gccatcgccg ccgataccgg gtgctctatc gtgttcctgc accatgccag    6180
caagggcgcg gccatgatgg gcgcaggcga ccagcagcag gccagccggg gcagctcggt    6240
actggtcgat aacatccgct ggcagtccta cctgtcgagc atgaccagcg ccgaggccga    6300
ggaatggggt gtggacgacg accagcgccg gttcttcgtc cgcttcggtg tgagcaaggc    6360
```

```
caactatggc gcaccgttcg ctgatcggtg gttcaggcgg catgacgcg gggtgctcaa      6420
gcccgccgtg ctggagaggc agcgcaagag caaggggtg ccccgtggtg aagcctaaga      6480
acaagcacag cctcagccac gtccggcacg acccggcgca ctgtctggcc cccggcctgt      6540
tccgtgccct caagcggggc gagcgcaagc gcagcaagct ggacgtgacg tatgactacg      6600
gcgacggcaa gcggatcgag ttcagcggcc cggagccgct gggcgctgat gatctgcgca      6660
tcctgcaagg gctggtggcc atggctgggc taatggcct agtgcttggc ccggaaccca      6720
agaccgaagg cggacggcag ctccggctgt tcctggaacc caagtgggag gccgtcaccg      6780
ctgaatgcca tgtggtcaaa ggtagctatc gggcgctggc aaaggaaatc ggggcagagg      6840
tcgatagtgg tggggcgctc aagcacatac aggactgcat cgagcgcctt tggaaggtat      6900
ccatcatcgc ccagaatggc cgcaagcggc aggggtttcg gctgctgtcg gagtacgcca      6960
gcgacgaggc ggacgggcgc ctgtacgtgg ccctgaaccc cttgatcgcg caggccgtca      7020
tgggtggcgg ccagcatgtg cgcatcagca tggacgaggt gcgggcgctg acagcgaaa      7080
ccgcccgcct gctgcaccag cggctgtgtg ctggatcga ccccggcaaa accggcaagg      7140
cttccataga taccttgtgc ggctatgtct ggccagtggt tcgaccatgc      7200
gcaagcgccg ccagcgggtg cgcgaggcgt tgccggagct ggtcgcgctg ggctggacgg      7260
taaccgagtt cgcggcgggc aagtacgaca tcacccggcc caaggcggca ggctgacccc      7320
ccccactcta ttgtaaacaa gacatttta tcttttatat tcaatggctt attttcctgc      7380
taattggtaa taccatgaaa ataccatgc tcagaaaagg cttaacaata ttttgaaaaa      7440
ttgcctactg agcgctgccg cacagctcca taggccgctt tcctggcttt gcttccagat      7500
gtatgctctt ctgctcctgc aggcatcgtg gtgtcacgct cgtcgtttgg tatggcttca      7560
ttcagctccg gttcccaacg atcaaggcga gttacatgat cccccatgtt gtgcaaaaaa      7620
gcggttagct ccttcggtcc tccgatcgtt gtcagaagta agttggccgc agtgttatca      7680
ctcatggtta tggcagcact gcataattct cttactgtca tgccatccgt aagatgcttt      7740
tctgtgactg gtgagtactc aaccaagtca ttctgagaat agtgtatgcg gcgaccgagt      7800
tgctcttgcc cggcgtcaac acgggataat accgcgccac atagcagaac tttaaaagtg      7860
ctcatcattg gaaaacgttc ttcggggcga aaactctcaa ggatcttacc gctgttgaga      7920
tccagttcga tgtaacccac tcgtgcaccc aactgatctt cagcatcttt tactttcacc      7980
agcgtttctg ggtgagcaaa aacaggaagg caaaatgccg caaaaaggg aataagggcg      8040
acacggaaat gttgaatact catactcttc cttttcaat attattgaag catttatcag      8100
ggttattgtc tcatgagcgg atacatattt gaatgtattt agaaaaataa acaatagg      8160
gttccgcgca catttccccg aaaagtgcca cctgacgtct aagaaccat tattatcatg      8220
acattaacct ataaaaatag gcgtatcacg aggccctttc gtcttcgaat aaatacctgt      8280
gacggaagat cacttcgcag aataaataaa tcctggtgtc cctgttgata ccggaagcc      8340
ctgggccaac ttttggcgaa aatgagacgt tgatcggcac gtaagaggtt ccaactttca      8400
ccataatgaa ataagatcac taccgggcgt attttttgag ttatcgagat ttcaggagc      8460
taaggaagct aaaatggaga aaaaaatcac tggatatacc accgttgata tatcccaatg      8520
gcatcgtaaa gaacattttg aggcatttca gtcagttgct caatgtacct ataaccagac      8580
cgttcagctg gatattacgg ccttttaaa gaccgtaaag aaaaataagc acaagttta      8640
tccggccttt attcacattc ttgcccgcct gatgaatgct catccggaat tccgtatggc      8700
```

```
aatgaaagac ggtgagctgg tgatatggga tagtgttcac ccttgttaca ccgttttcca    8760
tgagcaaact gaaacgtttt catcgctctg gagtgaatac cacgacgatt tccggcagtt    8820
tctacacata tattcgcaag atgtggcgtg ttacggtgaa aacctggcct atttccctaa    8880
agggtttatt gagaatatgt ttttcgtctc agccaatccc tgggtgagtt tcaccagttt    8940
tgatttaaac gtggccaata tggacaactt cttcgccccc gttttcacca tgggcaaata    9000
ttatacgcaa ggcgacaagg tgctgatgcc gctggcgatt caggttcatc atgccgtctg    9060
tgatggcttc catgtcggca gaatgcttaa tgaattacaa cagtactgcg atgagtggca    9120
gggcggggcg taattttttt aaggcagtta ttggtgccct taaacgcctg gtgctacgcc    9180
tgaataagtg ataataagcg gatgaatggc agaaattcgt cgactctaga g             9231
```

<210> SEQ ID NO 71
<211> LENGTH: 8390
<212> TYPE: DNA
<213> ORGANISM: Artificial Sequence
<220> FEATURE:
<223> OTHER INFORMATION: synthetic combined bacterial sequences

<400> SEQUENCE: 71

```
gatctgtaat ccgggcagcg caacggaaca ttcatcagtg taaaaatgga atcaataaag      60
ccctgcgcag cgcgcagggt cagcctgaat acgcgtttaa tgaccagcac agtcgtgatg     120
gcaaggtcag aatagcgctg aggtctgcct cgtgaagaag gtgttgctga ctcataccag     180
gcctgaatcg ccccatcatc cagccagaaa gtgagggagc cacggttgat gagagctttg     240
ttgtaggtgg accagttggt gattttgaac ttttgctttg ccacggaacg gtctgcgttg     300
tcgggaagat gcgtgatctg atccttcaac tcagcaaaag ttcgatttat tcaacaaagc     360
cgccgtcccg tcaagtcagc gtaatgctct gccagtgtta caaccaatta accaattctg     420
attagaaaaa ctcatcgagc atcaaatgaa actgcaattt attcatatca ggattatcaa     480
taccatattt ttgaaaaagc cgtttctgta atgaaggaga aaactcaccg aggcagttcc     540
ataggatggc aagatcctgg tatcggtctg cgattccgac tcgtccaaca tcaatacaac     600
ctattaattt cccctcgtca aaaataaggt tatcaagtga aaatcacca tgagtgacga     660 ctgaatccgg tgagaatggc aaaagcttat gcatttcttt ccagacttgt tcaacaggcc     720
agccattacg ctcgtcatca aaatcactcg catcaaccaa accgttattc attcgtgatt     780
gcgcctgagc gagacgaaat acgcgatcgc tgttaaaagg acaattacaa acaggaatcg     840
aatgcaaccg cgcgcaggaac actgccagcg catcaacaat attttcacct gaatcaggat     900
attcttctaa tacctggaat gctgttttcc cggggatcgc agtggtgagt aaccatgcat     960
catcaggagt acggataaaa tgcttgatgg tcggaagagg cataaattcc gtcagccagt    1020
ttagtctgac catctcatct gtaacatcat tggcaacgct acctttgcca tgtttcagaa    1080
acaactctgg cgcatcgggc ttcccataca atcgatagat tgtcgcacct gattgcccga    1140
cattatcgcg agcccattta tacccatata aatcagcatc catgttggaa tttaatcgcg    1200
gcctcgagca agacgtttcc cgttgaatat ggctcataac ccccttgta ttactgttta     1260 tgtaagcaga cagtttatt gttcatgatg atatattttt atcttgtgca atgtaacatc    1320
agagattttg agacacaacg tggctttgtt gaataaatcg aacttttgct gagttgaagg    1380
atcagatcac gcatcttccc gacaacgcag accgttccgt ggcaaagcaa aagttcaaaa    1440
tcaccaactg gtccacctac aacaaagctc tcatcaaccg tggctccctc actttctggc    1500
tggatgatgg ggcgattcag gcctggtatg agtcagcaac ccttcttca cgaggcagac    1560
```

```
ctcagcgcta ttctgacctt gccatcacga ctgtgctggt cattaaacgc gtattcaggc   1620
tgaccctgcg cgctgcgcag ggctttattg attccatttt tacactgatg aatgttccgt   1680
tgcgctgccc ggattacagg ggtaccgagc tcgaattgac ataagcctgt tcggttcgta   1740
aactgtaatg caagtagcgt atgcgctcac gcaactggtc cagaaccttg accgaacgca   1800
gcggtggtaa cggcgcagtg gcggttttca tggcttgtta tgactgtttt tttgtacagt   1860
ctatgcctcg ggcatccaag cagcaagcgc gttacgccgt gggtcgatgt ttgatgttat   1920
ggagcagcaa cgatgttacg cagcagcaac gatgttacgc agcagggcag tcgccctaaa   1980
acaaagttag gtggctcaag tatgggcatc attcgcacat gtaggctcgg ccctgaccaa   2040
gtcaaatcca tgcgggctgc tcttgatctt tcggtcgtg agttcggaga cgtagccacc   2100
tactcccaac atcagccgga ctccgattac ctcgggaact tgctccgtag taagacattc   2160
atcgcgcttg ctgccttcga ccaagaagcg gttgttggcg ctctcgcggc ttacgttctg   2220
cccaggtttg agcagccgcg tagtgagatc tatatctatg atctcgcagt ctccggcgag   2280
caccggaggc agggcattgc caccgcgctc atcaatctcc tcaagcatga ggccaacgcg   2340
cttggtgctt atgtgatcta cgtgcaagca gattacggtg acgatcccgc agtggctctc   2400
tatacaaagt tgggcatacg ggaagaagtg atgcactttg atatcgaccc aagtaccgcc   2460
acctaacaat tcgttcaagc cgagatcggc ttcccggccg cggagttgtt cggtaaattg   2520
tcacaacgcc gcggccaatt cgagctcggt acccctgaaa gcgaccaggt gctcggcgtg   2580
gcaagactcg cagcgaaccc gtagaaagcc atgctccagc cgcccgcatt ggagaaattc   2640
ttcaaattcc cgttgcacat agcccggcaa ttcctttccc tgctctgcca taagcgcagc   2700
gaatgccggg taatactcgt caacgatctg atagagaagg gtttgctcgg gtcggtggct   2760
ctggtaacga ccagtatccc gatcccggct ggccgtcctg gccgccacat gaggcatgtt   2820
ccgcgtcctt gcaatactgt gtttacatac agtctatcgc ttagcggaaa gttcttttac   2880
cctcagccga aatgcctgcc gttgctagac attgccagcc agtgcccgtc actcccgtac   2940
taactgtcac gaacccctgc aataactgtc acgcccccct gcaataactg tcacgaaccc   3000
ctgcaataac tgtcacgccc ccaaacctgc aaacccagca ggggcggggg ctggcggggt   3060
gttggaaaaa tccatccatg attatctaag aataatccac taggcgcggt tatcagcgcc   3120
cttgtggggc gctgctgccc ttgcccaata tgccggcca gaggccggat agctggtcta   3180
ttcgctgcgc taggctacac accgccccac cgctgcgcgg caggggaaa ggcgggcaaa   3240
gcccgctaaa ccccacacca aacccgcag aaatacgctg gagcgctttt agccgcttta   3300
gcggcctttc ccctaccccg aagggtgggg gcgcgtgtgc agccccgcag ggcctgtctc   3360
ggtcgatcat tcagcccggc tcatccttct ggcgtggcgg cagaccgaac aaggcgcggt   3420
cgtggtcgcg ttcaaggtac gcatccattg ccgccatgag ccgatcctcc ggccactcgc   3480
tgctgttcac cttggccaaa atcatggccc ccaccagcac cttgcgcctt gtttcgttct   3540
tgcgctcttg ctgctgttcc cttgcccgca cccgctgaat tcggcattg attcgcgctc   3600
gttgttcttc gagcttggcc agccgatccg ccgccttgtt gctcccctta accatcttga   3660
cacccccattg ttaatgtgct gtctcgtagg ctatcatgga ggcacagcgg cggcaatccc   3720
gaccctactt tgtaggggag ggcgcactta ccggtttctc ttcgagaaac tggcctaacg   3780
gccacccttc gggcggtgcg ctctccgagg gccattgcat ggagccgaaa agcaaaagca   3840
acagcgaggc agcatggcga tttatcacct tacggcgaaa accggcagca ggtcgggcgg   3900
```

```
ccaatcggcc agggccaagg ccgactacat ccagcgcgaa ggcaagtatg cccgcgacat    3960
ggatgaagtc ttgcacgccg aatccgggca catgccggag ttcgtcgagc ggcccgccga    4020
ctactgggat gctgccgacc tgtatgaacg cgccaatggg cggctgttca aggaggtcga    4080
atttgccctg ccggtcgagc tgaccctcga ccagcagaag gcgctggcgt ccagttcgc     4140 ccagcacctg accggtgccg agcgcctgcc gtatacgctg gccatccatg ccggtggcgg    4200
cgagaacccg cactgccacc tgatgatctc cgagcggatc aatgacggca tcgagcggcc    4260
cgccgctcag tggttcaagc ggtacaacgg caagaccccg gagaagggcg ggcacagaa     4320 gaccgaagcg ctcaagccca aggcatggct tgagcagacc cgcgaggcat gggccgacca    4380
tgccaaccgg gcattagagc gggctggcca cgacgcccgc attgaccaca gaacacttga    4440
ggcgcagggc atcgagcgcc tgcccggtgt tcacctgggg ccgaacgtgg tggagatgga    4500
aggccggggc atccgcaccg accgggcaga cgtggccctg aacatcgaca ccgccaacgc    4560
ccagatcatc gacttacagg aataccggga ggcaatagac catgaacgca atcgacagag    4620
tgaagaaatc cagaggcatc aacgagttag cggagcagat cgaaccgctg cccagagca    4680 tggcgacact ggccgacgaa gcccggcagg tcatgagcca gacccagcag gccagcgagg    4740
cgcaggcggc ggagtggctg aaagcccagc gccagacagg ggcggcatgg gtggagctgg    4800
ccaaagagtt gcgggaggta gccgccgagg tgagcagcgc cgcgcagagc ccccggagcg    4860
cgtcgcgggg gtggcactgg aagctatggc taaccgtgat gctggcttcc atgatgccta    4920
cggtggtgct gctgatcgca tcgttgctct tgctcgacct gacgccactg acaaccgagg    4980
acggctcgat ctggctgcgc ttggtggccc gatgaagaac gacaggactt tgcaggccat    5040
aggccgacag ctcaaggcca tgggctgtga gcgcttcgat atcggcgtca gggacgccac    5100
caccggccaa atgatgaacc gggaatggtc agccgccgaa gtgctccaga acacgccatg    5160
gctcaagcgg atgaatgccc agggcaatga cgtgtatatc aggcccgccg agcaggagcg    5220
gcatggtctg gtgctggtgg acgacctcag cgagtttgac ctggatgaca tgaaagccga    5280
gggccgggag cctgccctgg tagtggaaac cagcccgaag aactatcagg catgggtcaa    5340
ggtggccgac gccgcaggcg gtgaacttcg ggggcagatt gcccggacgc tggccagcga    5400
gtacgacgcc gacccggcca gcgccgacag ccgccactat ggccgcttgg cgggcttcac    5460
caaccgcaag gacaagcaca ccacccgcgc cggttatcag ccgtgggtgc tgctgcgtga    5520
atccaagggc aagaccgcca ccgctggccc ggcgctggtg cagcaggctg gccagcagat    5580
cgagcaggcc cagcggcagc aggagaaggc ccgcaggctg gccagcctcg aactgcccga    5640
gcggcagctt agccgccacc ggcgcacggc gctggacgag taccgcagcg agatggccgg    5700
gctggtcaag cgcttcggtg atgacctcag caagtgcgac tttatcgccg cgcagaagct    5760
ggccagccgg ggccgcagtg ccgaggaaat cggcaaggcc atggccgagg ccagcccagc    5820
gctggcagag cgcaagcccg gccacgaagc ggattacatc gagcgcaccg tcagcaaggt    5880
catgggtctg cccagcgtcc agcttgcgcg ggccgagctg gcacgggcac cggcaccccg    5940
ccagcgaggc atggacaggg gcgggccaga tttcagcatg tagtgcttgc gttggtactc    6000
acgcctgtta tactatgagt actcacgcac agaaggggt tttatggaat cgaaaaaag     6060 cgcttcaggg tcggtctacc tgatcaaaag tgacaagggc tattggttgc ccggtggctt    6120
tggttatacg tcaaacaagg ccgaggctgg ccgcttttca gtcgctgata tggccagcct    6180
taaccttgac ggctgcacct tgtccttgtt ccgcgaagac aagcctttcg gcccccggcaa   6240 gtttctcggt gactgatatg aaagaccaaa aggacaagca gaccggcgac ctgctggcca    6300
```

```
gccctgacgc tgtacgccaa gcgcgatatg ccgagcgcat gaaggccaaa gggatgcgtc    6360
agcgcaagtt ctggctgacc gacgacgaat acgaggcgct gcgcgagtgc ctggaagaac    6420
tcagagcggc gcagggcggg ggtagtgacc ccgccagcgc ctaaccacca actgcctgca    6480
aaggaggcaa tcaatggcta cccataagcc tatcaatatt ctggaggcgt tcgcagcagc    6540
gccgccaccg ctggactacg ttttgcccaa catggtggcc ggtacggtcg ggcgctggt     6600 gtcgccggt ggtgccggta aatccatgct ggccctgcaa ctggccgcac agattgcagg     6660
cgggccggat ctgctggagg tgggcgaact gcccaccggc ccggtgatct acctgcccgc    6720
cgaagacccg cccaccgcca ttcatcaccg cctgcacgcc cttggggcgc acctcagcgc    6780
cgaggaacgg caagccgtgg ctgacggcct gctgatccag ccgctgatcg cagcctgcc    6840 caacatcatg gccccggagt ggttcgacgg cctcaagcgc gccgccgagg ccgccgcct     6900 gatggtgctg gacacgctgc gccggttcca catcgaggaa gaaaacgcca gcggcccat     6960 ggcccaggtc atcggtcgca tggaggccat cgccgccgat accgggtgct ctatcgtgtt    7020
cctgcaccat gccagcaagg gcgcggccat gatgggcgca ggcgaccagc agcaggccag    7080
ccggggcagc tcgtactgg tcgataacat ccgctggcag tcctacctgt cgagcatgac     7140
cagcgccgag gccgaggaat ggggtgtgga cgacgaccag cgccggttct tcgtccgctt    7200
cggtgtgagc aaggccaact atggcgcacc gttcgctgat cggtggttca ggcggcatga    7260
cggcggggtg ctcaagcccg ccgtgctgga gaggcagcgc aagagcaagg gggtgccccg    7320
tggtgaagcc taagaacaag cacagcctca gccacgtccg gcacgacccg gcgcactgtc    7380 tggccccgg cctgttccgt gccctcaagc ggggcgagcg caagcgcagc aagctggacg     7440
tgacgtatga ctacggcgac ggcaagcgga tcgagttcag cggcccggag ccgctgggcg    7500
ctgatgatct gcgcatcctg caagggctgg tggccatggc tgggcctaat ggcctagtgc    7560
ttggcccgga acccaagacc gaaggcgac ggcagctccg gctgttcctg gaacccaagt     7620
gggaggccgt caccgctgaa tgccatgtgg tcaaaggtag ctatcgggcg ctggcaaagg    7680
aaatcggggc agaggtcgat agtggtgggg cgctcaagca catacaggac tgcatcgagc    7740
gcctttggaa ggtatccatc atcgcccaga atggccgcaa gcgcagggg tttcggctgc     7800 tgtcggagta cgccagcgac gaggcggacg ggcgcctgta cgtggccctg aaccccttga    7860
tcgcgcaggc cgtcatgggt ggcggccagc atgtgcgcat cagcatggac gaggtgcggg    7920
cgctggacag cgaaaccgcc cgcctgctgc accagcggct gtgtggctgg atcgaccccg    7980
gcaaaaccgg caaggcttcc atagatacct tgtgcggcta tgtctggccg tcagaggcca    8040
gtggttcgac catgcgcaag cgccgccagc gggtgcgcga ggcgttgccg gagctggtcg    8100
cgctgggctg gacggtaacc gagttcgcgg cgggcaagta cgacatcacc cggcccaagg    8160
cggcaggctg accccccca ctctattgta aacaagacat ttttatctttt tatattcaat    8220 ggcttatttt cctgctaatt ggtaataccca tgaaaaatac catgctcaga aaaggcttaa    8280
caatattttg aaaaattgcc tactgagcgc tgccgcacag ctccataggc cgctttcctg    8340
gctttgcttc cagatgtatg ctcttctgct cctgcaggtc gactctagag                8390
```

<210> SEQ ID NO 72
<211> LENGTH: 3206
<212> TYPE: DNA
<213> ORGANISM: Artificial Sequence
<220> FEATURE:
<223> OTHER INFORMATION: synthetic combined bacterial sequences

```
<400> SEQUENCE: 72
gcgcccaata cgcaaaccgc ctctccccgc gcgttggccg attcattaat gcagctggca      60
cgacaggttt cccgactgga aagcgggcag tgagcgcaac gcaattaatg tgagttagct     120
cactcattag caccccagg ctttacactt tatgcttccg gctcgtatgt tgtgtggaat      180
tgtgagcgga taacaatttc acacaggaaa cagctatgac catgattacg ccaagcttgc     240
atgcctgcag gtcgactcta gaggatcccc gggtacccct catcggggc tgtgttggcc      300
gagacggcac tgaggatttt actctccatg gcattccaag gaatatctac ccaactcacc     360
tgctccggcg gattgttccg ctcaaaagta ctaatcaagt cgtcaaaata cttattaaat     420
tttggctgca attgcatagt ccaaaagctg actttcccct ccatgctctg gggggaattg     480
ctctggcaac tgattaatcc actgagcaac agcccaagac acgcaaacaa aaaccaacgt     540
cttggcgatc gccatcggca ccatgaaacc atcgtaaaag ctggggaaag aataaaaaac     600
agtggttcag gaattgcatt gccatggcca cttcacaaac ctagccaatt ttagcttgac     660
cgcaactttg acagattgtc ttttgacttt gcctggaccg cctcccataa taccttcgcg     720
tcttgaagac tttatccttg aaaggagaac atatgtttct cggcaaaaat taattatcga     780
tatctagatc tcgagctcgc gaaagcttgg cactggccgt cgttttacaa cgtcgtgact     840
gggaaaaccc tggcgttacc caacttaatc gccttgcagc acatcccct ttcgccagct      900
ggcgtaatag cgaagaggcc cgcaccgatc gcccttccca acagttgcgc agcctgaatg     960
gcgaatggcg cctgatgcgg tattttctcc ttacgcatct gtgcggtatt tcacaccgca    1020
tggtgcactc tcagtacaat ctgctctgat gccgcatagt taagccagcc ccgacacccg    1080
ccaacacccg ctgacgcgcc ctgacgggct tgtctgctcc cggcatccgc ttacagacaa    1140
gctgtgaccg tctccgggag ctgcatgtgt cagaggtttt caccgtcatc accgaaacgc    1200
gcgagacgaa agggcctcgt gatacgccta ttttataggt taatgtcat gataataatg     1260
gtttcttaga cgtcaggtgg cacttttcgg ggaaatgtgc gcggaacccc tatttgttta    1320
ttttctaaa tacattcaaa tatgtatccg ctcatgagac aataaccctg ataaatgctt     1380
caataatatt gaaaaggaa gagtatgagt attcaacatt tccgtgtcgc ccttattccc     1440
tttttgcgg cattttgcct tcctgttttt gctcacccag aaacgctggt gaaagtaaaa    1500
gatgctgaag atcagttggg tgcacgagtg ggttacatcg aactggatct caacagcggt    1560
aagatccttg agagttttcg ccccgaagaa cgttttccaa tgatgagcac ttttaaagtt    1620
ctgctatgtg gcgcggtatt atcccgtatt gacgccgggc aagagcaact cggtcgccgc    1680
atacactatt ctcagaatga cttggttgag tactcaccag tcacagaaaa gcatcttacg    1740
gatggcatga cagtaagaga attatgcagt gctgccataa ccatgagtga taacactgcg    1800
gccaacttac ttctgacaac gatcggagga ccgaaggagc taaccgcttt tttgcacaac    1860
atggggatc atgtaactcg ccttgatcgt tgggaaccgg agctgaatga agccatacca    1920
aacgacgagc gtgacaccac gatgcctgta gcaatggcaa caacgttgcg caaactatta    1980
actggcgaac tacttactct agcttcccgg caacaattaa tagactggat ggaggcggat    2040
aaagttgcag gaccacttct gcgctcggcc cttccggctg gctggtttat tgctgataaa    2100
tctggagccg gtgagcgtgg gtctcgcggt atcattgcag cactggggcc agatggtaag    2160
ccctcccgta tcgtagttat ctacacgacg gggagtcagg caactatgga tgaacgaaat    2220
agacagatcg ctgagatagg tgcctcactg attaagcatt ggtaactgtc agaccaagtt    2280
tactcatata ctttagat tgatttaaaa cttcattttt aatttaaaag gatctaggtg      2340
```

```
aagatccttt tgataatct catgaccaaa atcccttaac gtgagttttc gttccactga    2400
gcgtcagacc ccgtagaaaa gatcaaagga tcttcttgag atcctttttt tctgcgcgta    2460
atctgctgct tgcaaacaaa aaaaccaccg ctaccagcgg tggtttgttt gccggatcaa    2520
gagctaccaa ctcttttttcc gaaggtaact ggcttcagca gagcgcagat accaaatact    2580
gtccttctag tgtagccgta gttaggccac cacttcaaga actctgtagc accgcctaca    2640
tacctcgctc tgctaatcct gttaccagtg gctgctgcca gtggcgataa gtcgtgtctt    2700
accgggttgg actcaagacg atagttaccg gataaggcgc agcggtcggg ctgaacgggg    2760
ggttcgtgca cacagcccag cttggagcga acgacctaca ccgaactgag atacctacag    2820
cgtgagctat gagaaagcgc cacgcttccc gaagggagaa aggcggacag gtatccggta    2880
agcggcaggg tcggaacagg agagcgcacg agggagcttc caggggggaaa cgcctggtat    2940 ctttatagtc ctgtcgggtt tcgccacctc tgacttgagc gtcgattttt gtgatgctcg    3000
tcagggggcc ggagcctatg gaaaaacgcc agcaacgcgg cctttttacg gttcctggcc    3060
ttttgctggc cttttgctca catgttcttt cctgcgttat cccctgattc tgtggataac    3120
cgtattaccg cctttgagtg agctgatacc gctcgccgca gccgaacgac cgagcgcagc    3180
gagtcagtga gcgaggaagc ggaaga                                        3206

<210> SEQ ID NO 73
<211> LENGTH: 3093
<212> TYPE: DNA
<213> ORGANISM: Artificial Sequence
<220> FEATURE:
<223> OTHER INFORMATION: synthetic combined bacterial sequences

<400> SEQUENCE: 73
atgaattctt atactgtcgg tacctattta gcggagcggc ttgtccagat tggtctcaag      60
catcacttcg cagtcgcggg cgactacaac ctcgtccttc ttgacaacct gcttttgaac     120
aaaaacatgg agcaggttta ttgctgtaac gaactgaact gcggtttcag tgcagaaggt     180
tatgctcgtg ccaaaggcgc agcagcagcg gtcgttacct acagcgtcgg tgcgcttttcc    240 gcatttgatg ctatcggtgg cgcctatgca gaaaaccttc cggttatcct gatctccggt     300
gctccgaaca caatgatca cgctgctggt cacgtgttgc atcacgctct tggcaaaacc     360
gactatcact atcagttgga aatggccaag aacatcacgg ccgcagctga agcgatttac     420
accccagaag aagctccggc taaaatcgat cacgtgatta aaactgctct tcgtgagaag     480
aagccggttt atctcgaaat cgcttgcaac attgcttcca tgccctgcgc cgctcctgga     540
ccggcaagcg cattgttcaa tgacgaagcc agcgacgaag cttcttttgaa tgcagcggtt     600 gaagaaaccc tgaaattcat cgccaaccgc gacaaagttg ccgtcctcgt cggcagcaag     660
ctgcgcgcag ctggtgctga agaagctgct gtcaaatttg ctgatgctct cggtggcgca     720
gttgctacca tggctgctgc aaaaagcttc ttcccagaag aaaacccgca ttacatcggt     780
acctcatggg gtgaagtcag ctatccgggc gttgaaaaga cgatgaaaga agccgatgcg     840
gttatcgctc tggctcctgt cttcaacgac tactccacca ctggttggac ggatattcct     900
gatcctaaga aactggttct cgctgaaccg cgttctgtcg tcgttaacgg cgttcgcttc     960
cccagcgttc atctgaaaga ctatctgacc cgtttggctc agaaagtttc caagaaaacc    1020
ggtgctttgg acttcttcaa atcccctcaat gcaggtgaac tgaagaaagc cgctccggct    1080
gatccgagtg ctccgttggt caacgcagaa atcgcccgtc aggtcgaagc tcttctgacc    1140
```

-continued

```
ccgaacacga cggttattgc tgaaaccggt gactcttggt tcaatgctca gcgcatgaag   1200
ctcccgaacg gtgctcgcgt tgaatatgaa atgcagtggg gtcacatcgg ttggtccgtt   1260
cctgccgcct tcggttatgc cgtcggtgct ccggaacgtc gcaacatcct catggttggt   1320
gatggttcct tccagctgac ggctcaggaa gtcgctcaga tggttcgcct gaaactgccg   1380
gttatcatct tcttgatcaa taactatggt tacaccatcg aagttatgat ccatgatggt   1440
ccgtacaaca acatcaagaa ctgggattat gccggtctga tggaagtgtt caacggtaac   1500
ggtggttatg acagcggtgc tggtaaaggc ctgaaggcta aaaccggtgg cgaactggca   1560
gaagctatca aggttgctct ggcaaacacc gacggcccaa ccctgatcga atgcttcatc   1620
ggtcgtgaag actgcactga agaattggtc aaatggggta agcgcgttgc tgccgccaac   1680
agccgtaagc ctgttaacaa gctcctctag tttttgggga tcaattcgag ctcggtaccc   1740
aaactagtat gtagggtgag gttatagcta tggcttcttc aactttttat attcctttcg   1800
tcaacgaaat gggcgaaggt tcgcttgaaa agcaatcaa ggatcttaac ggcagcggct   1860
ttaaaaatgc gctgatcgtt tctgatgctt tcatgaacaa atccggtgtt gtgaagcagg   1920
ttgctgacct gttgaaagca cagggtatta attctgctgt ttatgatggc gttatgccga   1980
acccgactgt taccgcagtt ctggaaggcc ttaagatcct gaaggataac aattcagact   2040
tcgtcatctc cctcggtggt ggttctcccc atgactgcgc caaagccatc gctctggtcg   2100
caaccaatgg tggtgaagtc aaagactacg aaggtatcga caaatctaag aaacctgccc   2160
tgcctttgat gtcaatcaac acgacggctg gtacggcttc tgaaatgacg cgtttctgca   2220
tcatcactga tgaagtccgt cacgttaaga tggccattgt tgaccgtcac gttaccccga   2280
tggtttccgt caacgatcct ctgttgatgg ttggtatgcc aaaaggcctg accgccgcca   2340
ccggtatgga tgctctgacc cacgcatttg aagcttattc ttcaacggca gctactccga   2400
tcaccgatgc ttgcgccttg aaggctgcgt ccatgatcgc taagaatctg aagaccgctt   2460
gcgacaacgg taaggatatg ccagctcgtg aagctatggc ttatgcccaa ttcctcgctg   2520
gtatggcctt caacaacgct tcgcttggtt atgtccatgc tatggctcac cagttgggcg   2580
gctactacaa cctgccgcat ggtgtctgca acgctgttct gcttccgcat gttctggctt   2640
ataacgcctc tgtcgttgct ggtcgtctga agacgttgg tgttgctatg ggtctcgata   2700
tcgccaatct cggtgataaa gaaggcgcag aagccaccat tcaggctgtt cgcgatctgg   2760
ctgcttccat tggtattcca gcaaatctga ccgagctggg tgctaagaaa gagatgtgc   2820 cgcttcttgc tgaccacgct ctgaaagatg cttgtgctct gaccaacccg cgtcagggtg   2880
atcagaaaga agttgaagaa ctcttcctga gcgctttcta atttcaaaac aggaaaacgg   2940
ttttccgtcc tgtcttgatt ttcaagcaaa caatgcctcc gatttctaat cggaggcatt   3000 tgttttttgtt tattgcaaaa acaaaaaata ttgttacaaa tttttacagg ctattaagcc   3060
taccgtcata ataatttgc catttgggga tcc                                  3093
```

<210> SEQ ID NO 74
<211> LENGTH: 569
<212> TYPE: PRT
<213> ORGANISM: Zymomonas mobilis

<400> SEQUENCE: 74

```
Met Asn Ser Tyr Thr Val Gly Thr Tyr Leu Ala Glu Arg Leu Val Gln
1               5                   10                  15

Ile Gly Leu Lys His His Phe Ala Val Ala Gly Asp Tyr Asn Leu Val
            20                  25                  30
```

```
Leu Leu Asp Asn Leu Leu Asn Lys Asn Met Glu Gln Val Tyr Cys
         35                  40                  45

Cys Asn Glu Leu Asn Cys Gly Phe Ser Ala Glu Gly Tyr Ala Arg Ala
 50                  55                  60

Lys Gly Ala Ala Ala Val Val Thr Tyr Ser Val Gly Ala Leu Ser
 65              70                  75                  80

Ala Phe Asp Ala Ile Gly Gly Ala Tyr Ala Glu Asn Leu Pro Val Ile
                 85                  90                  95

Leu Ile Ser Gly Ala Pro Asn Asn Asp His Ala Ala Gly His Val
            100                 105                 110

Leu His His Ala Leu Gly Lys Thr Asp Tyr His Tyr Gln Leu Glu Met
        115                 120                 125

Ala Lys Asn Ile Thr Ala Ala Ala Glu Ala Ile Tyr Thr Pro Glu Glu
    130                 135                 140

Ala Pro Ala Lys Ile Asp His Val Ile Lys Thr Ala Leu Arg Glu Lys
145                 150                 155                 160

Lys Pro Val Tyr Leu Glu Ile Ala Cys Asn Ile Ala Ser Met Pro Cys
                165                 170                 175

Ala Ala Pro Gly Pro Ala Ser Ala Leu Phe Asn Asp Glu Ala Ser Asp
            180                 185                 190

Glu Ala Ser Leu Asn Ala Ala Val Glu Thr Leu Lys Phe Ile Ala
        195                 200                 205

Asn Arg Asp Lys Val Ala Val Leu Val Gly Ser Lys Leu Arg Ala Ala
    210                 215                 220

Gly Ala Glu Glu Ala Ala Val Lys Phe Ala Asp Ala Leu Gly Gly Ala
225                 230                 235                 240

Val Ala Thr Met Ala Ala Lys Ser Phe Phe Pro Glu Glu Asn Pro
                245                 250                 255

His Tyr Ile Gly Thr Ser Trp Gly Glu Val Ser Tyr Pro Gly Val Glu
            260                 265                 270

Lys Thr Met Lys Glu Ala Asp Ala Val Ile Ala Leu Ala Pro Val Phe
    275                 280                 285

Asn Asp Tyr Ser Thr Thr Gly Trp Thr Asp Ile Pro Asp Pro Lys Lys
    290                 295                 300

Leu Val Leu Ala Glu Pro Arg Ser Val Val Asn Gly Val Arg Phe
305                 310                 315                 320

Pro Ser Val His Leu Lys Asp Tyr Leu Thr Arg Leu Ala Gln Lys Val
                325                 330                 335

Ser Lys Lys Thr Gly Ala Leu Asp Phe Phe Lys Ser Leu Asn Ala Gly
            340                 345                 350

Glu Leu Lys Lys Ala Ala Pro Asp Pro Ser Ala Pro Leu Val Asn
        355                 360                 365

Ala Glu Ile Ala Arg Gln Val Glu Ala Leu Leu Thr Pro Asn Thr Thr
    370                 375                 380

Val Ile Ala Glu Thr Gly Asp Ser Trp Phe Asn Ala Gln Arg Met Lys
385                 390                 395                 400

Leu Pro Asn Gly Ala Arg Val Glu Tyr Glu Met Gln Trp Gly His Ile
                405                 410                 415

Gly Trp Ser Val Pro Ala Ala Phe Gly Tyr Ala Val Gly Ala Pro Glu
            420                 425                 430

Arg Arg Asn Ile Leu Met Val Gly Asp Gly Ser Phe Gln Leu Thr Ala
        435                 440                 445
```

```
Gln Glu Val Ala Gln Met Val Arg Leu Lys Leu Pro Val Ile Ile Phe
    450                 455                 460

Leu Ile Asn Asn Tyr Gly Tyr Thr Ile Glu Val Met Ile His Asp Gly
465                 470                 475                 480

Pro Tyr Asn Asn Ile Lys Asn Trp Asp Tyr Ala Gly Leu Met Glu Val
                485                 490                 495

Phe Asn Gly Asn Gly Gly Tyr Asp Ser Gly Ala Gly Lys Gly Leu Lys
            500                 505                 510

Ala Lys Thr Gly Gly Glu Leu Ala Glu Ala Ile Lys Val Ala Leu Ala
        515                 520                 525

Asn Thr Asp Gly Pro Thr Leu Ile Glu Cys Phe Ile Gly Arg Glu Asp
530                 535                 540

Cys Thr Glu Glu Leu Val Lys Trp Gly Lys Arg Val Ala Ala Ala Asn
545                 550                 555                 560

Ser Arg Lys Pro Val Asn Lys Leu Leu
                565

<210> SEQ ID NO 75
<211> LENGTH: 383
<212> TYPE: PRT
<213> ORGANISM: Zymomonas mobilis

<400> SEQUENCE: 75

Met Ala Ser Ser Thr Phe Tyr Ile Pro Phe Val Asn Glu Met Gly Glu
1               5                   10                  15

Gly Ser Leu Glu Lys Ala Ile Lys Asp Leu Asn Gly Ser Gly Phe Lys
            20                  25                  30

Asn Ala Leu Ile Val Ser Asp Ala Phe Met Asn Lys Ser Gly Val Val
        35                  40                  45

Lys Gln Val Ala Asp Leu Leu Lys Ala Gln Gly Ile Asn Ser Ala Val
    50                  55                  60

Tyr Asp Gly Val Met Pro Asn Pro Thr Val Thr Ala Val Leu Glu Gly
65                  70                  75                  80

Leu Lys Ile Leu Lys Asp Asn Asn Ser Asp Phe Val Ile Ser Leu Gly
                85                  90                  95

Gly Gly Ser Pro His Asp Cys Ala Lys Ala Ile Ala Leu Val Ala Thr
            100                 105                 110

Asn Gly Gly Glu Val Lys Asp Tyr Glu Gly Ile Asp Lys Ser Lys Lys
        115                 120                 125

Pro Ala Leu Pro Leu Met Ser Ile Asn Thr Thr Ala Gly Thr Ala Ser
    130                 135                 140

Glu Met Thr Arg Phe Cys Ile Ile Thr Asp Glu Val Arg His Val Lys
145                 150                 155                 160

Met Ala Ile Val Asp Arg His Val Thr Pro Met Val Ser Val Asn Asp
                165                 170                 175

Pro Leu Leu Met Val Gly Met Pro Lys Gly Leu Thr Ala Ala Thr Gly
            180                 185                 190

Met Asp Ala Leu Thr His Ala Phe Glu Ala Tyr Ser Ser Thr Ala Ala
        195                 200                 205

Thr Pro Ile Thr Asp Ala Cys Ala Leu Lys Ala Ala Ser Met Ile Ala
    210                 215                 220

Lys Asn Leu Lys Thr Ala Cys Asp Asn Gly Lys Asp Met Pro Ala Arg
225                 230                 235                 240

Glu Ala Met Ala Tyr Ala Gln Phe Leu Ala Gly Met Ala Phe Asn Asn
                245                 250                 255
```

```
Ala Ser Leu Gly Tyr Val His Ala Met Ala His Gln Leu Gly Gly Tyr
            260                 265                 270

Tyr Asn Leu Pro His Gly Val Cys Asn Ala Val Leu Leu Pro His Val
        275                 280                 285

Leu Ala Tyr Asn Ala Ser Val Val Ala Gly Arg Leu Lys Asp Val Gly
        290                 295                 300

Val Ala Met Gly Leu Asp Ile Ala Asn Leu Gly Asp Lys Glu Gly Ala
305                 310                 315                 320

Glu Ala Thr Ile Gln Ala Val Arg Asp Leu Ala Ala Ser Ile Gly Ile
                325                 330                 335

Pro Ala Asn Leu Thr Glu Leu Gly Ala Lys Lys Glu Asp Val Pro Leu
                340                 345                 350

Leu Ala Asp His Ala Leu Lys Asp Ala Cys Ala Leu Thr Asn Pro Arg
            355                 360                 365

Gln Gly Asp Gln Lys Glu Val Glu Glu Leu Phe Leu Ser Ala Phe
        370                 375                 380

<210> SEQ ID NO 76
<211> LENGTH: 614
<212> TYPE: DNA
<213> ORGANISM: Synechocystis PCC6803

<400> SEQUENCE: 76
gtcgaccttc cagcaccacg tcaactttgt ttaactgctc ccggagttgt ctttccgctt     60
tggcaatgtg cccgggatac cattggatta aagccatgag ttgttcactt ttttactgac    120
gagggcttcc ggaggccacg ctcccaccca taacagcttg ccacatcccc gtcggaagtt    180
acgttaccct tgggcgatcg ccaaaaatca gcatatatac accaattcta ataagatct    240 tttacaccgc tactgcaatc aacctcatca acaaaattcc cctctagcat ccctggaggc    300
aaatcctcac ctggccatgg gttcaaccct gcttaacatt tcttaataat tttagttgct    360
ataaattctc atttatgccc ctataataat tcgggagtaa gtgctaaaga ttctcaactg    420
ctccatcagt ggtttgagct tagtcctagg gaaagattgg cgatcgccgt tgtggttaag    480
ccagaatagg tctcgggtgg acagagaacg ctttattctt tgcctccatg gcggcatccc    540
acctaggttt ctcggcactt attgccataa tttattattt gtcgtctcaa ttaaggaggc    600
aattctgtga attc                                                     614

<210> SEQ ID NO 77
<211> LENGTH: 614
<212> TYPE: DNA
<213> ORGANISM: Synechocystis PCC6803

<400> SEQUENCE: 77
gtcgacttat ggttgattcg cattgttttg ctcctgaaat tttcggcaaa tacaaatact     60
tcgctcttct agccctatta accattttaa cgacaaattg atgggcaac gattaacaaa    120 taatgaataa atttatgtt tttcaagatg aaaatttgaa aatttgattt ccttatattt    180
ctactataga agactaatac aattagatct aaaatttgca agtataaaaa tcagcaaata    240
gttatattgt taataattca atgacccaat aactcgtact gttatctacg tggtgaaagc    300
caaaaagacg aacagtttag cctcctcctc ctcggcgatc gccaagcgaa atgtcatggg    360
agatgttcag attgagcatt ttttctaaa agcccttgct aaaacaaacc acatgtgcag    420
ggtgtccccg atgttgacta aattcagcgg acttaaaacc tatttttcc ctgggttgct    480
```

| | |
|---|---|
| aggttttgccc cccgttttgg gcaagcttgt ataagcagat actgttaatt gggtcaactt | 540 |
| tttgttacat ttatttacaa ttgattgttt acaattgaaa ggtagtcgcc ttggagggca | 600 |
| acagctatga attc | 614 |

<210> SEQ ID NO 78
<211> LENGTH: 614
<212> TYPE: DNA
<213> ORGANISM: Synechocystis PCC6803

<400> SEQUENCE: 78

| | |
|---|---|
| gtcgacaacg acggaggttt aagggaaaag tgaccatgga agctatatcg agattaatta | 60 |
| aaggggggg atcaaccaag ttgctggact ggagcagtgg gcaagaaacc tgagctaatt | 120 |
| ctaggcaatt tgttgccat tgccccaac gtaaagttat ttttttctcc attaccttt | 180 |
| gttacctaaa atttaatgga gccaacctag gctggacctt ttgtcaccgt tgctctgtcc | 240 |
| acgggatgga ggataatcta aacgaaatca ttagggaccc tgaccatgca aaaagccgac | 300 |
| gaatttgcca tccatctgtt tttggccaat ggccatcgag aggaagtccg tttcatgacc | 360 |
| attcaagatt tccaaaaatg gtatagcaac gaagttgtgc ccaagcacga ttcccaggaa | 420 |
| tttatcagtg tgcctatcag aaatattcag ggcgagtaca tggtggtgcg accctcggcg | 480 |
| atcgttgcca ttcgggtgga accaattttc tttggcagtg tggagcgcat gtaatccgtt | 540 |
| gtgtataatc ttgatacaga atggggtttt gcacttccct tgatgccccc attaccgtga | 600 |
| acgtgcatga attc | 614 |

<210> SEQ ID NO 79
<211> LENGTH: 10502
<212> TYPE: DNA
<213> ORGANISM: Synechocystis PCC6803

<400> SEQUENCE: 79

| | |
|---|---|
| gtcgacgaat tctgccatt catccgctta ttatcactta ttcaggcgta gcaccaggcg | 60 |
| tttaagggca ccaataactg ccttaaaaaa attacgcccc gccctgccac tcatcgcagt | 120 |
| actgttgtaa ttcattaagc attctgccga catggaagcc atcacagacg gcatgatgaa | 180 |
| cctgaatcgc cagcggcatc agcaccttgt cgccttgcgt ataatatttg cccatggtga | 240 |
| aaacgggggc gaagaagttg tccatattgg ccacgtttaa atcaaaactg gtgaaactca | 300 |
| cccagggatt ggctgagacg aaaaacatat tctcaataaa cccttaggg aaataggcca | 360 |
| ggttttcacc gtaacacgcc acatcttgcg aatatatgtg tagaaactgc cggaaatcgt | 420 |
| cgtggtattc actccagagc gatgaaaacg tttcagtttg ctcatggaaa acggtgtaac | 480 |
| aagggtgaac actatcccat atcaccagct caccgtcttt cattgccata cggaattccg | 540 |
| gatgagcatt catcaggcgg gcaagaatgt gaataaaggc cggataaaac ttgtgcttat | 600 |
| ttttctttac ggtctttaaa aaggccgtaa tatccagctg aacggtctgg ttataggtac | 660 |
| attgagcaac tgactgaaat gcctcaaaat gttctttacg atgccattgg gatatatcaa | 720 |
| cggtggtata tccagtgatt ttttctcca ttttagcttc cttagctcct gaaaatctcg | 780 |
| ataactcaaa aaatacgccc ggtagtgatc ttatttcatt atggtgaaag ttggaacctc | 840 |
| ttacgtgccg atcaacgtct cattttcgcc aaaagttggc ccagggcttc ccggtatcaa | 900 |
| cagggacacc aggatttatt tattctgcga agtgatcttc cgtcacaggt atttattcga | 960 |
| agacgaaagg gcctcgtgat acgcctattt ttataggtta atgtcatgat aataatggtt | 1020 |
| tcttagacgt caggtggcac ttttcgggga aatgtgcgcg gaacccctat ttgtttattt | 1080 |

```
ttctaaatac attcaaatat gtatccgctc atgagacaat aaccctgata aatgcttcaa    1140
taatattgaa aaaggaagag tatgagtatt caacatttcc gtgtcgccct tattcccttt    1200
tttgcggcat tttgccttcc tgttttgct cacccagaaa cgctggtgaa agtaaaagat     1260
gctgaagatc agttgggtgc acgagtgggt tacatcgaac tggatctcaa cagcggtaag    1320
atccttgaga gttttcgccc cgaagaacgt tttccaatga tgagcacttt taaagttctg    1380
ctatgtggcg cggtattatc ccgtgttgac gccgggcaag agcaactcgg tcgccgcata    1440
cactattctc agaatgactt ggttgagtac tcaccagtca cagaaaagca tcttacggat    1500
ggcatgacag taagagaatt atgcagtgct gccataacca tgagtgataa cactgcggcc    1560
aacttacttc tgacaacgat cggaggaccg aaggagctaa ccgcttttt gcacaacatg      1620 ggggatcatg taactcgcct tgatcgttgg gaaccggagc tgaatgaagc cataccaaac    1680
gacgagcgtg acaccacgat gcctgcagga gcagaagagc atacatctgg aagcaaagcc    1740
aggaaagcgg cctatggagc tgtgcggcag cgctcagtag gcaatttttc aaaatattgt    1800
taagcctttt ctgagcatgg tattttcat ggtattacca attagcagga aaataagcca    1860
ttgaatataa aagataaaaa tgtcttgttt acaatagagt ggggggggtc agcctgccgc   1920
cttgggccgg gtgatgtcgt acttgcccgc cgcgaactcg gttaccgtcc agcccagcgc    1980
gaccagctcc ggcaacgcct cgcgcacccg ctggcggcgc ttgcgcatgg tcgaaccact    2040
ggcctctgac ggccagacat agccgcacaa ggtatctatg gaagccttgc cggttttgcc    2100
ggggtcgatc cagccacaca gccgctggtg cagcaggcgg gcggtttcgc tgtccagcgc    2160
ccgcacctcg tccatgctga tgcgcacatg ctggccgcca cccatgacgg cctgcgcgat    2220
caaggggttc agggccacgt acaggcgccc gtccgcctcg tcgctggcgt actccgacag    2280
cagccgaaac ccctgccgct tgcggccatt ctgggcgatg atggatacct tccaaaggcg    2340
ctcgatgcag tcctgtatgt gcttgagcgc cccaccacta tcgacctctg ccccgatttc    2400
ctttgccagc gcccgatagc tacctttgac cacatggcat tcagcggtga cggcctccca    2460
cttgggttcc aggaacagcc ggagctgccg tccgccttcg tcttgggtt ccgggccaag     2520 cactaggcca ttaggcccag ccatggccac cagcccttgc aggatgcgca gatcatcagc    2580
gcccagcggc tccgggccgc tgaactcgat ccgcttgccg tcgccgtagt catacgtcac    2640
gtccagcttg ctgcgcttgc gctcgccccg cttgagggca cggaacaggc cggggggccag   2700 acagtgcgcc gggtcgtgcc ggacgtggct gaggctgtgc ttgttcttag gcttcaccac    2760
ggggcacccc cttgctcttg cgctgcctct ccagcacggc gggcttgagc accccgccgt    2820
catgccgcct gaaccaccga tcagcgaacg gtgcgccata gttggccttg ctcacaccga    2880
agcggacgaa gaaccggcgc tggtcgtcgt ccacacccca ttcctcggcc tcggcgctgg    2940
tcatgctcga caggtaggac tgccagcgga tgttatcgac cagtaccgag ctgccccggc    3000
tggcctgctg ctggtcgcct gcgcccatca tggccgcgcc cttgctggca tggtgcagga    3060
acacgataga gcaccggta tcggcggcga tggcctccat gcgaccgatg acctgggcca      3120
tggggccgct ggcgttttct tcctcgatgt ggaaccggcg cagcgtgtcc agcaccatca    3180
ggcggcggcc ctcggcggcg cgcttgaggc cgtcgaacca ctccggggcc atgatgttgg    3240
gcaggctgcc gatcagcggc tggatcagca ggccgtcagc cacggcttgc cgttcctcgg    3300
cgctgaggtg cgccccaagg gcgtgcaggc ggtgatgaat ggcggtgggc gggtcttcgg    3360
cgggcaggta gatcaccggg ccggtgggca gttcgcccac ctccagcaga tccggcccgc    3420
```

```
ctgcaatctg tgcggccagt tgcagggcca gcatggattt accggcacca ccgggcgaca    3480
ccagcgcccc gaccgtaccg gccaccatgt tgggcaaaac gtagtccagc ggtggcggcg    3540
ctgctgcgaa cgcctccaga atattgatag cttatgggt agccattgat tgcctccttt     3600
gcaggcagtt ggtggttagg cgctggcggg gtcactaccc ccgccctgcg ccgctctgag    3660
ttcttccagg cactcgcgca gcgcctcgta ttcgtcgtcg gtcagccaga acttgcgctg    3720
acgcatccct ttggccttca tgcgctcggc atatcgcgct ggcgtacag cgtcagggct     3780
ggccagcagg tcgccggtct gcttgtcctt ttggtctttc atatcagtca ccgagaaact    3840
tgccggggcc gaaaggcttg tcttcgcgga acaaggacaa ggtgcagccg tcaaggttaa    3900
ggctggccat atcagcgact gaaaagcggc cagcctcggc cttgtttgac gtataaccaa    3960
agccaccggg caaccaatag cccttgtcac ttttgatcag gtagaccgac cctgaagcgc    4020
ttttttcgta ttccataaaa ccccccttctg tgcgtgagta ctcatagtat aacaggcgtg   4080
agtaccaacg caagcactac atgctgaaat ctggcccgcc cctgtccatg cctcgctggc    4140
ggggtgccgg tgcccgtgcc agctcggccc gcgcaagctg gacgctgggc agacccatga    4200
ccttgctgac ggtgcgctcg atgtaatccg cttcgtggcc gggcttgcgc tctgccagcg    4260
ctgggctggc ctcggccatg gccttgccga tttcctcggc actgcggccc cggctggcca    4320
gcttctgcgc ggcgataaag tcgcacttgc tgaggtcatc accgaagcgc ttgaccagcc    4380
cggccatctc gctgcggtac tcgtccagcg ccgtgcgccg gtggcggcta agctgccgct    4440
cgggcagttc gaggctggcc agcctgcggg ccttctcctg ctgccgctgg gcctgctcga    4500
tctgctggcc agcctgctgc accagcgccg ggccagcggt ggcggtcttg cccttggatt    4560
cacgcagcag cacccacggc tgataaccgg cgcgggtggt gtgcttgtcc ttgcggttgg    4620
tgaagcccgc caagcggcca tagtggcggc tgtcggcgct ggccgggtcg gcgtcgtact    4680
cgctggccag cgtccgggca atctgccccc gaagttcacc gcctgcggcg tcggccacct    4740
tgacccatgc ctgatagttc ttcgggctgg tttccactac cagggcaggc tcccggccct    4800
cggctttcat gtcatccagg tcaaactcgc tgaggtcgtc caccagcacc agaccatgcc    4860
gctcctgctc ggcgggcctg atatacacgt cattgccctg gcattcatc cgcttgagcc     4920
atggcgtgtt ctggagcact tcggcggctg accattcccg gttcatcatc tggccggtgg    4980
tggcgtccct gacgccgata tcgaagcgct cacagcccat ggccttgagc tgtcggccta    5040
tggcctgcaa agtcctgtcg ttcttcatcg ggccaccaag cgcagccaga tcgagccgtc    5100
ctcggttgtc agtggcgtca ggtcgagcaa gagcaacgat gcgatcagca gcaccaccgt    5160
aggcatcatg gaagccagca tcacggttag ccatagcttc cagtgccacc ccgcgacgc     5220
gctccgggcg ctctgcgcgg cgctgctcac ctcggcggct acctcccgca actctttggc    5280
cagctccacc catgccgccc ctgtctggcg ctgggctttc agccactccg ccgcctgcgc    5340
ctcgctggcc tgctgggtct ggctcatgac ctgccgggct tcgtcggcca gtgtcgccat    5400
gctctgggcc agcggttcga tctgctccgc taactcgttg atgcctctgg atttcttcac    5460
tctgtcgatt gcgttcatgg tctattgcct cccggtattc ctgtaagtcg atgatctggg    5520
cgttggcggt gtcgatgttc agggccacgt ctgcccggtc ggtgcggatg ccccggcctt    5580
ccatctccac cacgttcggc cccaggtgaa caccgggcag gcgctcgatg ccctgcgcct    5640
caagtgttct gtggtcaatg cgggcgtcgt ggccagcccg ctctaatgcc ggttggcat    5700
ggtcggccca tgcctcgcgg gtctgctcaa gccatgcctt gggcttgagc gcttcggtct    5760
tctgtgcccc gcccttctcc ggggtcttgc cgttgtaccg cttgaaccac tgagcggcgg    5820
```

```
gccgctcgat gccgtcattg atccgctcgg agatcatcag gtggcagtgc gggttctcgc    5880
cgccaccggc atggatggcc agcgtatacg gcaggcgctc ggcaccggtc aggtgctggg    5940
cgaactcgga cgccagcgcc ttctgctggt cgagggtcag ctcgaccggc agggcaaatt    6000
cgacctcctt gaacagccgc ccattggcgc gttcatacag gtcggcagca tcccagtagt    6060
cggcgggccg ctcgacgaac tccggcatgt gcccggattc ggcgtgcaag acttcatcca    6120
tgtcgcgggc atacttgcct tcgcgctgga tgtagtcggc cttggccctg gccgattggc    6180
cgcccgacct gctgccggtt ttcgccgtaa ggtgataaat cgccatgctg cctcgctgtt    6240
gcttttgctt ttcggctcca tgcaatggcc ctcggagagc gcaccgcccg aagggtggcc    6300
gttaggccag tttctcgaag agaaaccggt aagtgcgccc tcccctacaa agtagggtcg    6360
ggattgccgc cgctgtgcct ccatgatagc ctacgagaca gcacattaac aatgggtgt     6420
caagatggtt aaggggagca caaggcggc ggatcggctg gccaagctcg aagaacaacg     6480
agcgcgaatc aatgccgaaa ttcagcgggt gcgggcaagg gaacagcagc aagagcgcaa    6540
gaacgaaaca aggcgcaagg tgctggtggg ggccatgatt ttggccaagg tgaacagcag    6600
cgagtggccg gaggatcggc tcatggcggc aatggatgcg taccttgaac gcgaccacga    6660
ccgcgccttg ttcggtctgc cgccacgcca aaggatgag ccgggctgaa tgatcgaccg     6720
agacaggccc tgcggggctg cacacgcgcc cccacccttc gggtaggggg aaaggccgct    6780
aaagcggcta aaagcgctcc agcgtatttc tgcggggttt ggtgtggggt ttagcgggct    6840
ttgcccgcct ttcccctgc cgcgcagcgg tggggcggtg tgtagcctag cgcagcgaat     6900
agaccagcta tccggcctct ggccgggcat attgggcaag ggcagcagcg ccccacaagg    6960
gcgctgataa ccgcgcctag tggattattc ttagataatc atggatggat ttttccaaca    7020
ccccgccagc ccccgcccct gctgggtttg caggtttggg ggcgtgacag ttattgcagg    7080
ggttcgtgac agttattgca gggggcgtg acagttattg caggggttcg tgacagttag     7140
tacgggagtg acgggcactg gctggcaatg tctagcaacg gcaggcattt cggctgaggg    7200
taaaagaact ttccgctaag cgatagactg tatgtaaaca cagtattgca aggacgcgga    7260
acatgcctca tgtggcggcc aggacggcca gccgggatcg ggatactggt cgttaccaga    7320
gccaccgacc cgagcaaacc cttctctatc agatcgttga cgagtattac ccggcattcg    7380
ctgcgcttat ggcagagcag ggaaaggaat tgccgggcta tgtgcaacgg gaatttgaag    7440
aatttctcca atgcgggcgg ctggagcatg gctttctacg ggttcgctgc gagtcttgcc    7500
acgccgagca cctggtcgct ttcagctgta atccgggcag cgcaacggaa cattcatcag    7560
tgtaaaaatg gaatcaataa agccctgcgc agcgcgcagg gtcagcctga atacgcgttt    7620
aatgaccagc acagtcgtga tggcaaggtc agaatagcgc tgaggtctgc ctcgtgaaga    7680
aggtgttgct gactcatacc aggcctgaat cgccccatca tccagccaga aagtgaggga    7740
gccacggttg atgagagctt tgttgtaggt ggaccagttg gtgattttga acttttgctt    7800
tgccacggaa cggtctgcgt tgtcgggaag atgcgtgatc tgatccttca actcagcaaa    7860
agttcgattt attcaacaaa gccacgttgt gtctcaaaat ctctgatgtt acattgcaca    7920
agataaaaat atatcatcat gaacaataaa actgtctgct tacataaaca gtaatacaag    7980
gggtgttatg agccatattc aacgggaaac gtcttgctcg aggccgcgat taaattccaa    8040
catggatgct gatttatatg ggtataaatg ggctcgcgat aatgtcgggc aatcaggtgc    8100
gacaatctat cgattgtatg ggaagcccga tgcgccagag ttgtttctga acatggcaa     8160
```

```
aggtagcgtt gccaatgatg ttacagatga gatggtcaga ctaaactggc tgacggaatt    8220
tatgcctctt ccgaccatca agcattttat ccgtactcct gatgatgcat ggttactcac    8280
cactgcgatc cccgggaaaa cagcattcca ggtattagaa gaatatcctg attcaggtga    8340
aaatattgtt gatgcgctgg cagtgttcct gcgccggttg cattcgattc ctgtttgtaa    8400
ttgtcctttt aacagcgatc gcgtatttcg tctcgctcag gcgcaatcac gaatgaataa    8460
cggtttggtt gatgcgagtg attttgatga cgagcgtaat ggctggcctg ttgaacaagt    8520
ctggaaagaa atgcataagc ttttgccatt ctcaccggat tcagtcgtca ctcatggtga    8580
tttctcactt gataacctta tttttgacga ggggaaatta ataggttgta ttgatgttgg    8640
acgagtcgga atcgcagacc gataccagga tcttgccatc ctatggaact gcctcggtga    8700
gttttctcct tcattacaga aacggctttt tcaaaaatat ggtattgata atcctgatat    8760
gaataaattg cagtttcatt tgatgctcga tgagttttc taatcagaat tggttaattg    8820
gttgtaacac tggcagagca ttacgctgac ttgacgggac ggcggctttg ttgaataaat    8880
cgaacttttg ctgagttgaa ggatcagatc acgcatcttc ccgacaacgc agaccgttcc    8940
gtggcaaagc aaaagttcaa aatcaccaac tggtccacct acaacaaagc tctcatcaac    9000
cgtggctccc tcactttctg gctggatgat ggggcgattc aggcctggta tgagtcagca    9060
acaccttctt cacgaggcag acctcagcgc tattctgacc ttgccatcac gactgtgctg    9120
gtcattaaac gcgtattcag gctgaccctg cgcgctgcgc agggctttat tgattccatt    9180
tttacactga tgaatgttcc gttgcgctgc ccggattaca gatcctctag atctagaaga    9240
acagcaaggc cgccaatgcc tgacgatgcg tggagaccga aaccttgcgc tcgttcgcca    9300
gccaggacag aaatgcctcg acttcgctgc tgcccaaggt tgccgggtga cgcacaccgt    9360
ggaaacggat gaaggcacga acccagtgga cataagcctg ttcggttcgt aagctgtaat    9420
gcaagtagcg tatgcgctca cgcaactggt ccagaacctt gaccgaacgc agcggtggta    9480
acggcgcagt ggcggttttc atggcttgtt atgactgttt ttttggggta cagtctatgc    9540
ctcgggcatc caagcagcaa gcgcgttacg ccgtgggtcg atgtttgatg ttatggagca    9600
gcaacgatgt tacgcagcag ggcagtcgcc ctaaaacaaa gttaaacatc atgagggaag    9660
cggtgatcgc cgaagtatcg actcaactat cagaggtagt tggcgtcatc gagcgccatc    9720
tcgaaccgac gttgctggcc gtacatttgt acggctccgc agtggatggc ggcctgaagc    9780
cacacagtga tattgatttg ctggttacgg tgaccgtaag gcttgatgaa acaacgcggc    9840
gagctttgat caacgacctt ttggaaactt cggcttcccc tggagagagc gagattctcc    9900
gcgctgtaga agtcaccatt gttgtgcacg acgacatcat tccgtggcgt tatccagcta    9960
agcgcgaact gcaatttgga gaatggcagc gcaatgacat tcttgcaggt atcttcgagc   10020
cagccacgat cgacattgat ctggctatct tgctgacaaa agcaagagaa catagcgttg   10080
ccttggtagg tccagcggcg gaggaactct ttgatccggt tcctgaacag gatctatttg   10140
aggcgctaaa tgaaacctta acgctatgga actcgccgcc cgactgggct ggcgatgagc   10200
gaaatgtagt gcttacgttg tcccgcattt ggtacagcgc agtaaccggc aaaatcgcgc   10260
cgaaggatgt cgctgccgac tgggcaatgg agcgcctgcc ggcccagtat cagcccgtca   10320
tacttgaagc tagacaggct tatcttggac aagaagaaga tcgcttggcc tcgcgcgcag   10380
atcagttgga agaatttgtc cactacgtga aaggcgagat caccaaggta gtcggcaaat   10440
aatgtctaac aattcgttca agccgacgcc gcttcgcggc gcggcttaac tcaagctcta   10500
ga                                                                  10502
```

<210> SEQ ID NO 80
<211> LENGTH: 294
<212> TYPE: DNA
<213> ORGANISM: Synechocystis PCC6803

<400> SEQUENCE: 80

```
gtcgacggga attgctctgg caactgatta atccactgag caacagccca agacacgcaa      60
acaaaaacca acgtcttggc gatcgccatc ggcaccatga aaccatcgta aaagctgggg     120
aaagaataaa aaacagtggt tcaggaattg cattgccatg gccacttcac aaacctagcc     180
aattttagct tgaccgcaac tttgacagat tgtcttttga ctttgcctgg accgcctccc     240
ataataccct tcgcgtcttga agactttatc cttgaaagga gaactaatga attc          294
```

<210> SEQ ID NO 81
<211> LENGTH: 608
<212> TYPE: DNA
<213> ORGANISM: Synechocystis PCC6803

<400> SEQUENCE: 81

```
gtcgactgtc cgaccaattg gttcatcaaa gttgatttac ccacattggg acggccgaca      60
atggccacaa agccggaacg aaaacccgca ggagcctggg gaatagttgc aatggttgcg     120
gtggtgttgg gaatatccat tgaaaaaatc aagcctaaaa attccttagt ttatggaggg     180
tcaagcggaa aaacgttaaa aactccactg agttaatcaa ccagaggaaa aagtcaagga     240
ggtaaactat ccgcctggaa aacggcttgc cagcttgaca aaaaaatatg ttgggttaac     300
cccactgtgc cattcggtaa tccttcatct tggcccttgt ggaatcccctt aatgattcgt     360
catcatggtg atattgattt tttgggtatc tttttagcta tgcggctgta ggagcgtggt     420
attggtttcg gcggtaacgc cccagcctag aaccacaaaa attattattt attcccgaac     480
cttgtcacca tttgcggcgt ctaaaggccc actcgttagg acacggtgta aaaaaaattg     540
acgactgcac taccctattc tccaccatca atgacttagt ctaagacatt tttgggaaag     600
atgaattc                                                              608
```

<210> SEQ ID NO 82
<211> LENGTH: 581
<212> TYPE: DNA
<213> ORGANISM: Synechocystis PCC6803

<400> SEQUENCE: 82

```
gtcgacgctg atgtgacggt taagggaggc ggaattaaac tgggtaagga cgtaaatttt      60
aacgatttct gagttgatgc aattactgac gggaatatcg atgaggcgat actttccggc     120
caagggaact gcgggtttgg ctctgagttt ggttaaagga tagaggcggg tcccggcccc     180
accgcccagg ataatcgcta agacacgttt cacaagcaga cctctcgatt gccaacaaca     240
cacttcgaag tcaagtttag aaccgagggg gacatctgga aagggaatct ggacggaaat     300
tccggctaac cagcgggttt taatgcccca agcaagaatg gcgatcgccg ttgggattcg     360
gagctgagtt gtcagatcac tgtgggggta cggataaccg aaatggcaaa ggtcggaaac     420
tgccgctgag taaactgtcc ctggcttcgt atgatgatgg ggttacccccc attgctgggg    480
cgctgggcaa atctggggag ctgactaggt tcctggaagt tttgctaatc cactaaattt     540
cctaacaatc ctaaacatta aatctaaaga cctatgaatt c                         581
```

<210> SEQ ID NO 83

```
<211> LENGTH: 590
<212> TYPE: DNA
<213> ORGANISM: Synechocystis PCC6803

<400> SEQUENCE: 83
gtcgacccaa caacattagt ccgtcctccc gttggcgatc gcgctgtttg gctctgaccc      60
atcgccgctg atattgccaa gcttggcagt agggcacaag tccgaacgat aataaacgac     120
aggaaggatt ggccatggcg ctacaaagga acggaatca aactaaagtt caaagttggc     180
agaaattaag aaacgtaaag agatgcaaag gaaagtcaaa atcacctgac cgattaggtc     240
ttattcaata catagtgcta atctgaagat agtcttagga gttaattatt taccaccaca     300
attttctgga aaactttacc tctaccctag ggatgattaa aagtaaacta gagaataaca     360
aggttgggtt tataattcat caccaagctc aaatttatgg tgttttttca atgatccatg     420
cttttgatat ctttagcaga aaggcatttt aagtaatgat tccacctcac tgtttctcgg     480
aaaaattgcc caatctaact tagtttttat aacttaagtt tagatctgcg gaaaaccaac     540
cattgctcat tttttattaa ttttacgaag ggagaattta gtatgaattc                590

<210> SEQ ID NO 84
<211> LENGTH: 572
<212> TYPE: DNA
<213> ORGANISM: Synechocystis PCC6803

<400> SEQUENCE: 84
gtcgacagaa tccttgccca gatgcaggcc ttctggcgat cgccatggtg agcaacgatt      60
gcggctttag cgttccagtg gatatttgct gggggtaat gaaacattgt ggcggaaccc     120
agggacaatg tgaccaaaaa attcagggat atcaataagt attaggtata tggatcataa     180
ttgtatgccc gactattgct taaactgact gaccactgac cttaagagta atggcgtgca     240
aggcccagtg atcaatttca ttattttttca ttatttcatc tccattgtcc ctgaaaatca     300
gttgtgtcgc ccctctacac agcccagaac tatggtaaag gcgcacgaaa aaccgccagg     360
taaactcttc tcaaccccca aaacgccctc tgtttaccca tggaaaaaac gacaattaca     420
agaaagtaaa acttatgtca tctataagct tcgtgtatat taacttcctg ttacaaagct     480
ttacaaaact ctcattaatc ctttagacta agtttagtca gttccaatct gaacatcgac     540
aaatacataa ggaattataa ccaaatgaat tc                                  572

<210> SEQ ID NO 85
<211> LENGTH: 273
<212> TYPE: DNA
<213> ORGANISM: Synechocystis PCC6803

<400> SEQUENCE: 85
gtcgacatca ggaattgtaa ttagaaagtc caaaaattgt aatttaaaaa acagtcaatg      60
gagagcattg ccataagtaa aggcatcccc tgcgtgataa gattaccttc agaaaacaga     120
tagttgctgg gttatcgcag attttttctcg caaccaaata actgtaaata ataactgtct     180
ctggggcgac ggtaggcttt atattgccaa atttcgcccg tgggagaaag ctaggctatt     240
caatgtttat ggaggactga cctagatgaa ttc                                 273

<210> SEQ ID NO 86
<211> LENGTH: 408
<212> TYPE: DNA
<213> ORGANISM: Synechocystis PCC6803

<400> SEQUENCE: 86
```

```
gtcgacattt cttaaaatta aagctgttat agcaacaaca ttgattaatt tctatctaat      60
ttttgacggt gcccattgct atcagttgta agttgatgaa aatgctgtaa attttttgtaa   120 caaagttcaa ctttgtcttg acttttgtaa gtctttgcaa aatctaggag ctagaactgg   180
tcagggctgg ggcaatttttt aattattgtt acgcaggtct tgcctagggg ggggggaggcc   240 gtattatctt ctagtgatgt ttgctgaaaa cgcctatctg tgcaaggttt aacatcgtta   300
ttatgaagcg aaaactaatt ccctttttta cgcttcctct attacactat tctgcatagg   360
aaacccttaa tagttcattg tcgagcgagg agaaccctgc atgaattc                408
```

<210> SEQ ID NO 87
<211> LENGTH: 614
<212> TYPE: DNA
<213> ORGANISM: Synechocystis PCC6803

<400> SEQUENCE: 87

```
gtcgacaaaa aaactgcaaa aattatcctg actgaatgga agtcaaaaag actggaaaat     60
gggatcaaac aacaagaaaa aatcaattta ccctgcccat ggcaatagtt ttaaggttaa   120
caaaaaaaat agaatttacc gcaatcgacg ggtaaatttc cagaggatac ccccaactcc   180
agaagcagaa atcttgccag aaaagctttt tctgttacta tacttaacaa gtaactactt   240
tttccatagt ccaggggcgg ctttccaaaa accagagatt ggtggcttgc cgctgctgtt   300
ctcctctgga gtaaggggaa aaggtaatta gtgttacggc attttactga cgggttaagt   360
aatctttaac aaagatttat gagccgttac cgtaattgcc cccacagggg aacgcgatgt   420
ctgtggactc gcccaggacg taatcaattt ttctgtaccg atattagcgg tgaaaagttt   480
tattcaacgt actaaaatgc cccggcggga attaacttgg gttccgggaa gtcgggtgca   540
ttagccgtac tagactaacc caatagttac tttgtttgat tcttgatttt ggagaccgct   600
gattttatga attc                                                     614
```

<210> SEQ ID NO 88
<211> LENGTH: 367
<212> TYPE: DNA
<213> ORGANISM: Synechocystis PCC6803

<400> SEQUENCE: 88

```
gtcgacggaa aacaagctca gaatgctgcg gggagaaggg caactcccca ccagccccaa     60 attttttgctg gcgataaata ttttttcggtt taattgttca caaagctttt tgaatttgag   120
tttatagaaa tttattggct ggtaatgctt ttttgccccc ctgcaggact tcattgatcc   180
ttgcctatac catcaatatc attggtcaat aatgatgatg attgactaaa acatgtttaa   240
caaaatttaa cgcatatgct aaatgcgtaa actgcatatg ccttggctga gtgtaattta   300
cgttacaaat tttaacgaaa cgggaaccct atattgatct ctatctggct tgaagcgttg   360
tgaattc                                                              367
```

<210> SEQ ID NO 89
<211> LENGTH: 359
<212> TYPE: DNA
<213> ORGANISM: Anabaena PCC7120

<400> SEQUENCE: 89

```
gtcgactttt ttgctgaggt actgagtaca cagctaataa aattgggcaa tctccgcgcc     60
tctatgactt gaaggagagt gtaggggtat aggggaaaga tatctttat ctacatcaca    120
```

```
taaataaaaa atttaatttg tcgctctggc tgcatatatt gatgtatttt tagccataag    180
ttttttagtg ccatgtaatt atagtgattt ttagcgatcg cagagcattt ttccctggat    240
ttatcgcgat ctcaaaaaaa atttgcccga agtatgacag attgtcatat ttggtgtcga    300
ttttatttaa aatgaaataa gaaaaataaa actacaggtt aggagaacgc catgaattc     359

<210> SEQ ID NO 90
<211> LENGTH: 273
<212> TYPE: DNA
<213> ORGANISM: Synechocystis PCC6803

<400> SEQUENCE: 90
gtcgacacaa cctaagactt ccttccaaaa atccataggg cggtggaagc ttagctattt     60
ttaccatttt gttttgccac tcaaatattt acttaaggtg aggtaaaaac tcatcttttt    120
tttactaaaa attgcggcta gaaatgtaat ttcggcaatc cccccacctt ctttcctgaa    180
aaccgaatct aacctggaag gggaaatttt aagatagaac cattcaaggg taatcaattc    240
cttccacaca tcaggagtta acattatgaa ttc                                 273

<210> SEQ ID NO 91
<211> LENGTH: 342
<212> TYPE: DNA
<213> ORGANISM: Synechocystis PCC6803

<400> SEQUENCE: 91
gtcgacgcac ttctggtcag tttatagcaa aaatgctggg gaaaggaaga caactaggga     60
aaaagaacag gacatcaaat ggtcattccc cagaccctgg cgtctttgcc agagtaatct    120
ccctggcgcg gatgttacac aaatgtaacg aaaaatattt tccctctcag aatttaggca    180
aagtgcccaa acccatccta ggcaagcaat tcgtccacca acaaaaagct cttttggtca    240
acagacttga caaaaatctt aacaatacgt tacatttatt tacataaggt tacaaaataa    300
aaacctcaaa tacccaatca aggagatcaa cactatgaat tc                       342

<210> SEQ ID NO 92
<211> LENGTH: 273
<212> TYPE: DNA
<213> ORGANISM: Synechocystis PCC6803

<400> SEQUENCE: 92
gtcgacaaga ttagccctta gcttacaaga aaggggcttt ggggcctagt tgaatggcac     60
aaattttcct tccctgactg ttttttgcgcc attgtctagc tcaaagtcag cctccggcat    120
cctctagaaa gacttccatc ccctggttga gcaagggtaa accccaccac tgcattggga    180
aaaccctcct tcctagctcc ggattccacc ccctaaaatt gatttggtag tccttacaca    240
cccaatagcc aatatagaaa atttttatgaa ttc                                273

<210> SEQ ID NO 93
<211> LENGTH: 1216
<212> TYPE: DNA
<213> ORGANISM: Zymomonas mobilis

<400> SEQUENCE: 93
gagctctata tcaacaaaag gtagtcacca tgtcagccgc agatttgtcg actgacctct     60
atctctccga gatatatcaa caaaaggtag tcaccatgaa agcagccgtc ataactaaag    120
atcatacgat cgaagtgaaa gacaccaaat tacgccctct gaaatacggg gaagcgcttt    180
tggaaatgga atattgcggg gtatgtcata ccgatctcca cgtgaaaaac ggggatttg     240
```

```
gcgatgaaac cggcagaatt accggccatg aaggcatcgg tatcgtcaag caggtcgggg     300
aaggggttac ttctctgaaa gtcggtgacc gtgccagtgt tgcatggttc ttcaaaggct     360
gcggccattg cgaatattgt gtcagtggaa atgaaacgct ttgccgcaac gttgaaaatg     420
ccggttatac ggttgacggc gctatggcag aagaatgcat cgtcgttgcc gattactcgg     480
tcaaagtgcc agatggtctt gatcctgcgg ttgccagcag catcacttgc gcgggtgtaa     540
ccacctataa agcagtcaaa gtttctcaga tacagccggg acaatggctg gctatctatg     600
gcttgggcgg tttaggcaat ctagcccttc aatatgccaa gaatgttttc aacgccaaag     660
tgatcgcgat cgatgtcaat gatgaacagc tcgcttttgc caaagagctg ggcgcagata     720
tggtcatcaa tccgaaaaac gaagatgctg ccaaaatcat tcaggaaaaa gtcggcggcg     780
cacatgcgac ggtggtgaca gctgttgcca atccgccctt taactcggct gttgaggcta     840
tccgcgcggg tggccgtgtt gtcgccgttg gtctgcctcc tgaaaaaatg gatttgagca     900
ttcctcgctt ggtgcttgac ggtatcgaag tcttaggttc tttggtcgga acgcgggaag     960
atttgaaaga agccttccag tttgcagccg aaggtaaggt caaaccgaaa gtcaccaagc    1020
gtaaagtcga agaaatcaac caaatctttg acgaaatgga acatggtaaa ttcacaggcc    1080
gtatggttgt tgattttacc catcactagg tttccgtgaa ggcggaagca taaacggaaa    1140 aagccttctct cttaccagaa aggcttttc tttgtcgtct gataaaaatt ttcatacaga    1200
atttaataca ctgcag                                                    1216

<210> SEQ ID NO 94
<211> LENGTH: 337
<212> TYPE: PRT
<213> ORGANISM: Zymomonas mobilis

<400> SEQUENCE: 94

Met Lys Ala Ala Val Ile Thr Lys Asp His Thr Ile Glu Val Lys Asp
1               5                   10                  15

Thr Lys Leu Arg Pro Leu Lys Tyr Gly Glu Ala Leu Leu Glu Met Glu
            20                  25                  30

Tyr Cys Gly Val Cys His Thr Asp Leu His Val Lys Asn Gly Asp Phe
        35                  40                  45

Gly Asp Glu Thr Gly Arg Ile Thr Gly His Glu Gly Ile Gly Ile Val
    50                  55                  60

Lys Gln Val Gly Glu Gly Val Thr Ser Leu Lys Val Gly Asp Arg Ala
65                  70                  75                  80

Ser Val Ala Trp Phe Phe Lys Gly Cys Gly His Cys Glu Tyr Cys Val
                85                  90                  95

Ser Gly Asn Glu Thr Leu Cys Arg Asn Val Glu Asn Ala Gly Tyr Thr
            100                 105                 110

Val Asp Gly Ala Met Ala Glu Glu Cys Ile Val Val Ala Asp Tyr Ser
        115                 120                 125

Val Lys Val Pro Asp Gly Leu Asp Pro Ala Val Ala Ser Ser Ile Thr
    130                 135                 140

Cys Ala Gly Val Thr Thr Tyr Lys Ala Val Lys Val Ser Gln Ile Gln
145                 150                 155                 160

Pro Gly Gln Trp Leu Ala Ile Tyr Gly Leu Gly Gly Leu Gly Asn Leu
                165                 170                 175

Ala Leu Gln Tyr Ala Lys Asn Val Phe Asn Ala Lys Val Ile Ala Ile
            180                 185                 190
```

```
Asp Val Asn Asp Glu Gln Leu Ala Phe Ala Lys Glu Leu Gly Ala Asp
            195                 200                 205

Met Val Ile Asn Pro Lys Asn Glu Asp Ala Ala Lys Ile Ile Gln Glu
        210                 215                 220

Lys Val Gly Gly Ala His Ala Thr Val Thr Ala Val Ala Lys Ser
225                 230                 235                 240

Ala Phe Asn Ser Ala Val Glu Ala Ile Arg Ala Gly Gly Arg Val Val
            245                 250                 255

Ala Val Gly Leu Pro Pro Glu Lys Met Asp Leu Ser Ile Pro Arg Leu
            260                 265                 270

Val Leu Asp Gly Ile Glu Val Leu Gly Ser Leu Val Gly Thr Arg Glu
        275                 280                 285

Asp Leu Lys Glu Ala Phe Gln Phe Ala Ala Glu Gly Lys Val Lys Pro
        290                 295                 300

Lys Val Thr Lys Arg Lys Val Glu Glu Ile Asn Gln Ile Phe Asp Glu
305                 310                 315                 320

Met Glu His Gly Lys Phe Thr Gly Arg Met Val Val Asp Phe Thr His
            325                 330                 335

His

<210> SEQ ID NO 95
<211> LENGTH: 1144
<212> TYPE: DNA
<213> ORGANISM: Synechocystis PCC6803

<400> SEQUENCE: 95
gagctctctg gataaaacta ataaactcta ttacccatga ttaaagccta cgctgccctg      60
gaagccaacg gaaaactcca acccttttgaa tacgaccccg gtgccctggg tgctaatgag    120
gtggagattg aggtgcagta ttgtggggtg tgccacagta atttgtccat gattaataac    180
gaatggggca tttccaatta ccccctagtc ccgggtcatg aggtggtggg tactgtggcc    240
gccatgggcg aagggggtgaa ccatgttgag gtggggggatt tagtggggct gggttggcat    300
tcgggctact gcatgacctg ccatagttgt ttatctggct accacaacct ttgtgccacg    360
gcggaatcga ccattgtggg ccactacggt ggctttggcg atcgggttcg ggccaaggga    420
gtcagcgtgg tgaaattacc taaaggcatt gacctagcca gtgccgggcc cctttttctgt    480 ggaggaatta ccgttttcag tcctatggtg gaactgagtt taaagcccac tgcaaaagtg    540
gcagtgatcg gcattggggg cttgggccat ttagcggtgc aatttctccg ggcctggggc    600
tgtgaagtga ctgcctttac ctccagtgcc aggaagcaaa cggaagtgtt ggaattgggc    660
gctcaccaca tactagattc caccaatcca gaggcgatcg ccagtgcgga aggcaaattt    720
gactatatta tctccactgt gaacctgaag cttgactgga acttatacat cagcaccctg    780
gcgccccagg gacatttcca ctttgttggg gtggtgttgg agcctttgga tctaaatctt    840
tttccccttt tgatgggaca acgctccgtt tctgcctccc cagtgggtag tcccgccacc    900
attgccacca tgttggactt tgctgtgcgc catgacatta aacccgtggt ggaacaattt    960
agctttgatc agatcaacga ggcgatcgcc catctagaaa gcggcaaagc ccattatcgg   1020
gtagtgctca gccatagtaa aaattagctc tgcaaaggtt gcttctgggt ccgtggaatg   1080
gtcaaacgga gtcgatctca gttttgatac gctctatctg gaaagcttga cattcgatct   1140
gcag                                                                 1144

<210> SEQ ID NO 96
```

<211> LENGTH: 336
<212> TYPE: PRT
<213> ORGANISM: Synechocystis PCC6803

<400> SEQUENCE: 96

| Met | Ile | Lys | Ala | Tyr | Ala | Ala | Leu | Glu | Ala | Asn | Gly | Lys | Leu | Gln | Pro |
|---|---|---|---|---|---|---|---|---|---|---|---|---|---|---|---|
| 1 | | | | 5 | | | | | 10 | | | | | 15 | |

| Phe | Glu | Tyr | Asp | Pro | Gly | Ala | Leu | Gly | Ala | Asn | Glu | Val | Glu | Ile | Glu |
|---|---|---|---|---|---|---|---|---|---|---|---|---|---|---|---|
| | | | 20 | | | | | 25 | | | | | 30 | | |

| Val | Gln | Tyr | Cys | Gly | Val | Cys | His | Ser | Asp | Leu | Ser | Met | Ile | Asn | Asn |
|---|---|---|---|---|---|---|---|---|---|---|---|---|---|---|---|
| | | 35 | | | | | 40 | | | | | 45 | | | |

| Glu | Trp | Gly | Ile | Ser | Asn | Tyr | Pro | Leu | Val | Pro | Gly | His | Glu | Val | Val |
|---|---|---|---|---|---|---|---|---|---|---|---|---|---|---|---|
| | 50 | | | | | 55 | | | | | 60 | | | | |

| Gly | Thr | Val | Ala | Ala | Met | Gly | Glu | Gly | Val | Asn | His | Val | Glu | Val | Gly |
|---|---|---|---|---|---|---|---|---|---|---|---|---|---|---|---|
| 65 | | | | | 70 | | | | | 75 | | | | | 80 |

| Asp | Leu | Val | Gly | Leu | Gly | Trp | His | Ser | Gly | Tyr | Cys | Met | Thr | Cys | His |
|---|---|---|---|---|---|---|---|---|---|---|---|---|---|---|---|
| | | | | 85 | | | | | 90 | | | | | 95 | |

| Ser | Cys | Leu | Ser | Gly | Tyr | His | Asn | Leu | Cys | Ala | Thr | Ala | Glu | Ser | Thr |
|---|---|---|---|---|---|---|---|---|---|---|---|---|---|---|---|
| | | | 100 | | | | | 105 | | | | | 110 | | |

| Ile | Val | Gly | His | Tyr | Gly | Gly | Phe | Gly | Asp | Arg | Val | Arg | Ala | Lys | Gly |
|---|---|---|---|---|---|---|---|---|---|---|---|---|---|---|---|
| | | 115 | | | | | 120 | | | | | 125 | | | |

| Val | Ser | Val | Val | Lys | Leu | Pro | Lys | Gly | Ile | Asp | Leu | Ala | Ser | Ala | Gly |
|---|---|---|---|---|---|---|---|---|---|---|---|---|---|---|---|
| | 130 | | | | | 135 | | | | | 140 | | | | |

| Pro | Leu | Phe | Cys | Gly | Gly | Ile | Thr | Val | Phe | Ser | Pro | Met | Val | Glu | Leu |
|---|---|---|---|---|---|---|---|---|---|---|---|---|---|---|---|
| 145 | | | | | 150 | | | | | 155 | | | | | 160 |

| Ser | Leu | Lys | Pro | Thr | Ala | Lys | Val | Ala | Val | Ile | Gly | Ile | Gly | Gly | Leu |
|---|---|---|---|---|---|---|---|---|---|---|---|---|---|---|---|
| | | | | 165 | | | | | 170 | | | | | 175 | |

| Gly | His | Leu | Ala | Val | Gln | Phe | Leu | Arg | Ala | Trp | Gly | Cys | Glu | Val | Thr |
|---|---|---|---|---|---|---|---|---|---|---|---|---|---|---|---|
| | | | 180 | | | | | 185 | | | | | 190 | | |

| Ala | Phe | Thr | Ser | Ser | Ala | Arg | Lys | Gln | Thr | Glu | Val | Leu | Glu | Leu | Gly |
|---|---|---|---|---|---|---|---|---|---|---|---|---|---|---|---|
| | | 195 | | | | | 200 | | | | | 205 | | | |

| Ala | His | His | Ile | Leu | Asp | Ser | Thr | Asn | Pro | Glu | Ala | Ile | Ala | Ser | Ala |
|---|---|---|---|---|---|---|---|---|---|---|---|---|---|---|---|
| | 210 | | | | | 215 | | | | | 220 | | | | |

| Glu | Gly | Lys | Phe | Asp | Tyr | Ile | Ile | Ser | Thr | Val | Asn | Leu | Lys | Leu | Asp |
|---|---|---|---|---|---|---|---|---|---|---|---|---|---|---|---|
| 225 | | | | | 230 | | | | | 235 | | | | | 240 |

| Trp | Asn | Leu | Tyr | Ile | Ser | Thr | Leu | Ala | Pro | Gln | Gly | His | Phe | His | Phe |
|---|---|---|---|---|---|---|---|---|---|---|---|---|---|---|---|
| | | | | 245 | | | | | 250 | | | | | 255 | |

| Val | Gly | Val | Val | Leu | Glu | Pro | Leu | Asp | Leu | Asn | Leu | Phe | Pro | Leu | Leu |
|---|---|---|---|---|---|---|---|---|---|---|---|---|---|---|---|
| | | | 260 | | | | | 265 | | | | | 270 | | |

| Met | Gly | Gln | Arg | Ser | Val | Ser | Ala | Ser | Pro | Val | Gly | Ser | Pro | Ala | Thr |
|---|---|---|---|---|---|---|---|---|---|---|---|---|---|---|---|
| | | 275 | | | | | 280 | | | | | 285 | | | |

| Ile | Ala | Thr | Met | Leu | Asp | Phe | Ala | Val | Arg | His | Asp | Ile | Lys | Pro | Val |
|---|---|---|---|---|---|---|---|---|---|---|---|---|---|---|---|
| | 290 | | | | | 295 | | | | | 300 | | | | |

| Val | Glu | Gln | Phe | Ser | Phe | Asp | Gln | Ile | Asn | Glu | Ala | Ile | Ala | His | Leu |
|---|---|---|---|---|---|---|---|---|---|---|---|---|---|---|---|
| 305 | | | | | 310 | | | | | 315 | | | | | 320 |

| Glu | Ser | Gly | Lys | Ala | His | Tyr | Arg | Val | Val | Leu | Ser | His | Ser | Lys | Asn |
|---|---|---|---|---|---|---|---|---|---|---|---|---|---|---|---|
| | | | | 325 | | | | | 330 | | | | | 335 | |

<210> SEQ ID NO 97
<211> LENGTH: 2781
<212> TYPE: DNA
<213> ORGANISM: Escherichia coli

<400> SEQUENCE: 97
atgaattctg ctgttactaa tgtcgctgaa cttaacgcac tcgtagagcg tgtaaaaaaa    60

```
gcccagcgtg aatatgccag tttcactcaa gagcaagtag acaaaatctt ccgcgccgcc      120
gctctggctg ctgcagatgc tcgaatccca ctcgcgaaaa tggccgttgc cgaatccggc      180
atgggtatcg tcgaagataa agtgatcaaa aaccactttg cttctgaata tatctacaac      240
gcctataaag atgaaaaaac ctgtggtgtt ctgtctgaag acgacacttt tggtaccatc      300
actatcgctg aaccaatcgg tattatttgc ggtatcgttc cgaccactaa cccgacttca      360
actgctatct tcaaatcgct gatcagtctg aagacccgta acgccattat cttctccccg      420
cacccgcgtg caaaagatgc caccaacaaa gcggctgata tcgttctgca ggctgctatc      480
gctgccggtc tccgaaaga tctgatcggc tggatcgatc aaccttctgt tgaactgtct      540
aacgcactga tgcaccaccc agacatcaac ctgatcctcg cgactggtgg tccgggcatg      600
gttaaagccg catacagctc cggtaaacca gctatcggtg taggcgcggg caacactcca      660
gttgttatcg atgaaactgc tgatatcaaa cgtgcagttg catctgtact gatgtccaaa      720
accttcgaca acggcgtaat ctgtgcttct gaacagtctg ttgttgttgt tgactctgtt      780
tatgacgctg tacgtgaacg ttttgcaacc cacggcggct atctgttgca gggtaaagag      840
ctgaaagctg ttcaggatgt tatcctgaaa acggtgcgc tgaacgcggc tatcgttggt      900
cagccagcct ataaaattgc tgaactggca ggcttctctg taccagaaaa caccaagatt      960
ctgatcggtg aagtgaccgt tgttgatgaa agcgaaccgt tcgcacatga aaaactgtcc     1020
ccgactctgg caatgtaccg cgctaaagat ttcgaagacg cggtagaaaa agcagagaaa     1080
ctggttgcta tgggcggtat cggtcatacc tcttgcctgt acactgacca ggataaccaa     1140
ccggctcgcg tttcttactt cggtcagaaa atgaaaacgg cgcgtatcct gattaacacc     1200
ccagcgtctc agggtggtat cggtgacctg tataacttca aactcgcacc ttccctgact     1260
ctgggttgtg gttcttgggg tggtaactcc atctctgaaa acgttggtcc gaaacacctg     1320
atcaacaaga aaaccgttgc taagcgagct gaaaacatgt tgtggcacaa acttccgaaa     1380
tctatctact ccgccgtgg ctccctgcca atcgcgctgg atgaagtgat tactgatggc     1440
cacaaacgtg cgctcatcgt gactgaccgc ttcctgttca acaatggtta tgctgatcag     1500
atcacttccg tactgaaagc agcaggcgtt gaaactgaag tcttcttcga agtagaagcg     1560
gacccgaccc tgagcatcgt tcgtaaaggt gcagaactgg caaactcctt caaaccagac     1620
gtgattatcg cgctgggtgg tggttccccg atggacgccg cgaagatcat gtgggttatg     1680
tacgaacatc cggaaactca cttcgaagag ctggcgctgc gctttatgga tatccgtaaa     1740 cgtatcctaca agttcccgaa aatgggcgtg aaagcgaaaa tgatcgctgt caccaccact     1800
tctggtacag gttctgaagt cactccgttt gcggttgtaa ctgacgacgc tactggtcag     1860
aaatatccgc tggcagacta tgcgctgact ccggatatgg cgattgtcga cgccaacctg     1920
gttatggaca tgccgaagtc cctgtgtgct ttcggtggtc tggacgcagt aactcacgcc     1980
atggaagctt atgtttctgt actggcatct gagttctctg atggtcaggc tctgcaggca     2040
ctgaaactgc tgaaagaata tctgccagcg tcctaccacg aagggtctaa aaatccggta     2100
gcgcgtgaac gtgttcacag tgcagcgact atcgcgggta tcgcgtttgc gaacgccttc     2160
ctgggtgtat gtcactcaat ggcgcacaaa ctgggttccc agttccatat tccgcacggt     2220
ctggcaaacg ccctgctgat ttgtaacgtt attcgctaca atgcgaacga caacccgacc     2280
aagcagactg cattcagcca gtatgaccgt ccgcaggctc gccgtcgtta tgctgaaatt     2340
gccgaccact gggtctgag cgcaccgggc gaccgtactg ctgctaagat cgagaaactg     2400
ctggcatggc tggaaacgct gaaagctgaa ctgggtattc cgaaatctat ccgtgaagct     2460
```

```
ggcgttcagg aagcagactt cctggcgaac gtggataaac tgtctgaaga tgcattcgat   2520
gaccagtgca ccggcgctaa cccgcgttac ccgctgatct ccgagctgaa acagattctg   2580
ctggatacct actacggtcg tgattatgta gaaggtgaaa ctgcagcgaa gaaagaagct   2640
gctccggcta agctgagaa aaaagcgaaa aaatccgctt aatcagtagc gctgtctggc   2700
aacataaacg gccccttctg ggcaatgccg atcagttaag gattagttga ccgatcctta   2760
aactgaggca ctataggatc c                                             2781
```

<210> SEQ ID NO 98
<211> LENGTH: 893
<212> TYPE: PRT
<213> ORGANISM: Escherichia coli

<400> SEQUENCE: 98

| Met | Asn | Ser | Ala | Val | Thr | Asn | Val | Ala | Glu | Leu | Asn | Ala | Leu | Val | Glu |
|---|---|---|---|---|---|---|---|---|---|---|---|---|---|---|---|
| 1 | | | | 5 | | | | | 10 | | | | | 15 | |

| Arg | Val | Lys | Lys | Ala | Gln | Arg | Glu | Tyr | Ala | Ser | Phe | Thr | Gln | Glu | Gln |
|---|---|---|---|---|---|---|---|---|---|---|---|---|---|---|---|
| | | | 20 | | | | | 25 | | | | | 30 | | |

| Val | Asp | Lys | Ile | Phe | Arg | Ala | Ala | Ala | Leu | Ala | Ala | Ala | Asp | Ala | Arg |
|---|---|---|---|---|---|---|---|---|---|---|---|---|---|---|---|
| | | 35 | | | | | 40 | | | | | 45 | | | |

| Ile | Pro | Leu | Ala | Lys | Met | Ala | Val | Ala | Glu | Ser | Gly | Met | Gly | Ile | Val |
|---|---|---|---|---|---|---|---|---|---|---|---|---|---|---|---|
| 50 | | | | | 55 | | | | | 60 | | | | | |

| Glu | Asp | Lys | Val | Ile | Lys | Asn | His | Phe | Ala | Ser | Glu | Tyr | Ile | Tyr | Asn |
|---|---|---|---|---|---|---|---|---|---|---|---|---|---|---|---|
| 65 | | | | | 70 | | | | | 75 | | | | | 80 |

| Ala | Tyr | Lys | Asp | Glu | Lys | Thr | Cys | Gly | Val | Leu | Ser | Glu | Asp | Asp | Thr |
|---|---|---|---|---|---|---|---|---|---|---|---|---|---|---|---|
| | | | | 85 | | | | | 90 | | | | | 95 | |

| Phe | Gly | Thr | Ile | Thr | Ile | Ala | Glu | Pro | Ile | Gly | Ile | Ile | Cys | Gly | Ile |
|---|---|---|---|---|---|---|---|---|---|---|---|---|---|---|---|
| | | | 100 | | | | | 105 | | | | | 110 | | |

| Val | Pro | Thr | Thr | Asn | Pro | Thr | Ser | Thr | Ala | Ile | Phe | Lys | Ser | Leu | Ile |
|---|---|---|---|---|---|---|---|---|---|---|---|---|---|---|---|
| | | | 115 | | | | | 120 | | | | | 125 | | |

| Ser | Leu | Lys | Thr | Arg | Asn | Ala | Ile | Ile | Phe | Ser | Pro | His | Pro | Arg | Ala |
|---|---|---|---|---|---|---|---|---|---|---|---|---|---|---|---|
| | 130 | | | | | 135 | | | | | 140 | | | | |

| Lys | Asp | Ala | Thr | Asn | Lys | Ala | Ala | Asp | Ile | Val | Leu | Gln | Ala | Ala | Ile |
|---|---|---|---|---|---|---|---|---|---|---|---|---|---|---|---|
| 145 | | | | | 150 | | | | | 155 | | | | | 160 |

| Ala | Ala | Gly | Ala | Pro | Lys | Asp | Leu | Ile | Gly | Trp | Ile | Asp | Gln | Pro | Ser |
|---|---|---|---|---|---|---|---|---|---|---|---|---|---|---|---|
| | | | | 165 | | | | | 170 | | | | | 175 | |

| Val | Glu | Leu | Ser | Asn | Ala | Leu | Met | His | His | Pro | Asp | Ile | Asn | Leu | Ile |
|---|---|---|---|---|---|---|---|---|---|---|---|---|---|---|---|
| | | | 180 | | | | | 185 | | | | | 190 | | |

| Leu | Ala | Thr | Gly | Gly | Pro | Gly | Met | Val | Lys | Ala | Ala | Tyr | Ser | Ser | Gly |
|---|---|---|---|---|---|---|---|---|---|---|---|---|---|---|---|
| | | | 195 | | | | | 200 | | | | | 205 | | |

| Lys | Pro | Ala | Ile | Gly | Val | Gly | Ala | Gly | Asn | Thr | Pro | Val | Val | Ile | Asp |
|---|---|---|---|---|---|---|---|---|---|---|---|---|---|---|---|
| | 210 | | | | | 215 | | | | | 220 | | | | |

| Glu | Thr | Ala | Asp | Ile | Lys | Arg | Ala | Val | Ala | Ser | Val | Leu | Met | Ser | Lys |
|---|---|---|---|---|---|---|---|---|---|---|---|---|---|---|---|
| 225 | | | | | 230 | | | | | 235 | | | | | 240 |

| Thr | Phe | Asp | Asn | Gly | Val | Ile | Cys | Ala | Ser | Glu | Gln | Ser | Val | Val | Val |
|---|---|---|---|---|---|---|---|---|---|---|---|---|---|---|---|
| | | | | 245 | | | | | 250 | | | | | 255 | |

| Val | Asp | Ser | Val | Tyr | Asp | Ala | Val | Arg | Glu | Arg | Phe | Ala | Thr | His | Gly |
|---|---|---|---|---|---|---|---|---|---|---|---|---|---|---|---|
| | | | | 260 | | | | | 265 | | | | | 270 | |

| Gly | Tyr | Leu | Leu | Gln | Gly | Lys | Glu | Leu | Lys | Ala | Val | Gln | Asp | Val | Ile |
|---|---|---|---|---|---|---|---|---|---|---|---|---|---|---|---|
| | | | 275 | | | | | 280 | | | | | 285 | | |

| Leu | Lys | Asn | Gly | Ala | Leu | Asn | Ala | Ala | Ile | Val | Gly | Gln | Pro | Ala | Tyr |
|---|---|---|---|---|---|---|---|---|---|---|---|---|---|---|---|
| | 290 | | | | | 295 | | | | | 300 | | | | |

| Lys | Ile | Ala | Glu | Leu | Ala | Gly | Phe | Ser | Val | Pro | Glu | Asn | Thr | Lys | Ile |
|---|---|---|---|---|---|---|---|---|---|---|---|---|---|---|---|

```
                305                 310                 315                 320
        Leu Ile Gly Glu Val Thr Val Asp Glu Ser Glu Pro Phe Ala His
                        325                 330                 335
        Glu Lys Leu Ser Pro Thr Leu Ala Met Tyr Arg Ala Lys Asp Phe Glu
                        340                 345                 350
        Asp Ala Val Glu Lys Ala Glu Lys Leu Val Ala Met Gly Ile Gly
                        355                 360                 365
        His Thr Ser Cys Leu Tyr Thr Asp Gln Asp Asn Gln Pro Ala Arg Val
                370                 375                 380
        Ser Tyr Phe Gly Gln Lys Met Lys Thr Ala Arg Ile Leu Ile Asn Thr
        385                 390                 395                 400
        Pro Ala Ser Gln Gly Gly Ile Gly Asp Leu Tyr Asn Phe Lys Leu Ala
                        405                 410                 415
        Pro Ser Leu Thr Leu Gly Cys Gly Ser Trp Gly Gly Asn Ser Ile Ser
                        420                 425                 430
        Glu Asn Val Gly Pro Lys His Leu Ile Asn Lys Lys Thr Val Ala Lys
                        435                 440                 445
        Arg Ala Glu Asn Met Leu Trp His Lys Leu Pro Lys Ser Ile Tyr Phe
                450                 455                 460
        Arg Arg Gly Ser Leu Pro Ile Ala Leu Asp Glu Val Ile Thr Asp Gly
        465                 470                 475                 480
        His Lys Arg Ala Leu Ile Val Thr Asp Arg Phe Leu Phe Asn Asn Gly
                        485                 490                 495
        Tyr Ala Asp Gln Ile Thr Ser Val Leu Lys Ala Ala Gly Val Glu Thr
                        500                 505                 510
        Glu Val Phe Phe Glu Val Glu Ala Asp Pro Thr Leu Ser Ile Val Arg
                        515                 520                 525
        Lys Gly Ala Glu Leu Ala Asn Ser Phe Lys Pro Asp Val Ile Ile Ala
                        530                 535                 540
        Leu Gly Gly Gly Ser Pro Met Asp Ala Ala Lys Ile Met Trp Val Met
        545                 550                 555                 560
        Tyr Glu His Pro Glu Thr His Phe Glu Glu Leu Ala Leu Arg Phe Met
                        565                 570                 575
        Asp Ile Arg Lys Arg Ile Tyr Lys Phe Pro Lys Met Gly Val Lys Ala
                        580                 585                 590
        Lys Met Ile Ala Val Thr Thr Thr Ser Gly Thr Gly Ser Glu Val Thr
                595                 600                 605
        Pro Phe Ala Val Val Thr Asp Asp Ala Thr Gly Gln Lys Tyr Pro Leu
                        610                 615                 620
        Ala Asp Tyr Ala Leu Thr Pro Asp Met Ala Ile Val Asp Ala Asn Leu
        625                 630                 635                 640
        Val Met Asp Met Pro Lys Ser Leu Cys Ala Phe Gly Gly Leu Asp Ala
                        645                 650                 655
        Val Thr His Ala Met Glu Ala Tyr Val Ser Val Leu Ala Ser Glu Phe
                        660                 665                 670
        Ser Asp Gly Gln Ala Leu Gln Ala Leu Lys Leu Leu Lys Glu Tyr Leu
                        675                 680                 685
        Pro Ala Ser Tyr His Glu Gly Ser Lys Asn Pro Val Ala Arg Glu Arg
                690                 695                 700
        Val His Ser Ala Ala Thr Ile Ala Gly Ile Ala Phe Ala Asn Ala Phe
        705                 710                 715                 720
        Leu Gly Val Cys His Ser Met Ala His Lys Leu Gly Ser Gln Phe His
                        725                 730                 735
```

```
Ile Pro His Gly Leu Ala Asn Ala Leu Leu Ile Cys Asn Val Ile Arg
            740                 745                 750

Tyr Asn Ala Asn Asp Asn Pro Thr Lys Gln Thr Ala Phe Ser Gln Tyr
            755                 760                 765

Asp Arg Pro Gln Ala Arg Arg Tyr Ala Glu Ile Ala Asp His Leu
770             775                 780

Gly Leu Ser Ala Pro Gly Asp Arg Thr Ala Ala Lys Ile Glu Lys Leu
785                 790                 795                 800

Leu Ala Trp Leu Glu Thr Leu Lys Ala Glu Leu Gly Ile Pro Lys Ser
                805                 810                 815

Ile Arg Glu Ala Gly Val Gln Glu Ala Asp Phe Leu Ala Asn Val Asp
            820                 825                 830

Lys Leu Ser Glu Asp Ala Phe Asp Asp Gln Cys Thr Gly Ala Asn Pro
            835                 840                 845

Arg Tyr Pro Leu Ile Ser Glu Leu Lys Gln Ile Leu Leu Asp Thr Tyr
850                 855                 860

Tyr Gly Arg Asp Tyr Val Glu Gly Glu Thr Ala Ala Lys Lys Glu Ala
865                 870                 875                 880

Ala Pro Ala Lys Ala Glu Lys Lys Ala Lys Lys Ser Ala
            885                 890

<210> SEQ ID NO 99
<211> LENGTH: 2747
<212> TYPE: DNA
<213> ORGANISM: Thermosynechococcus elongatus

<400> SEQUENCE: 99
atgaattccc caaccttgac cagtgacccc ccgttcaaa gccttgccga tctggaaggg      60
ctgattgagc gcgtccaacg ggcgcagagt cagtacgccc aatttaccca agagcaagtg    120
gatcacattt tccacgaagc agccatggcg ccaaccaag cccggattcc cctggccaaa     180
caagccgtag ccgaaacggg catgggggtt gtcgaagata agttattaa aaatcacttt     240 gcttcggaat acatctacaa caagtacaaa atgagaaaaa cctgcggcgt cattgaggat    300
gaccccatct ttggtatcca aaaaattgct gaaccggtgg ggatcattgc cggtgtggtg    360
ccggtcacga ccccacttc aacgaccatc tttaaggcac tgattgccct gaagactcgc    420
aatggcatta tcttttcgcc ccaccccgg gcaaaggcct gtacggttgc agcggccaag    480
gtagtgttgg atgcagcggt cgctgccggc gcaccccccg atattattgg ctggattgat    540
gagccgacga ttgaactctc ccaagccctg atgcagcacc gcagatcaa gctgattttg     600 gccacgggg gaccaggtat ggtcaaggca gcctattcct ctggccatcc ggcgatcggg     660
gtcggggccg ggaataccc cgtgctcatt gatgccacag ccgatattcc cacggcagtg     720
agttcgattc tcctcagtaa ggcctttgac aatggcatga tctgtgcctc ggagcaggca    780
gtgattgttg tggatgagat ttatgacgca cttaaagctg agtttcaacg gcgaggggcc    840
taccttctct cccctgagga acggcagcag gtggcacaac tactgctgaa ggatggtcgc    900
ctcaatgccg ccattgttgg tcaatcggcc gccaccattg ccgcaatggc caatatccaa    960
gtaccgccag aaacccgggt actcattggc gaggtgagtg aagtggggcc gcaggagcca   1020
ttttcctatg agaaactctg tccggtattg gcgttatatc gggcacccca gttccataaa   1080
ggggtggaga ttgcggccca gttggtgaat tttgggggca aggggcatac atctgtgctc   1140
tataccgatc ccgcaatca agatgatatt gcctatttca ataccgcat gcaaacggcg     1200
```

-continued

```
cgggttctga ttaacacccc ttcttcccag ggggcaattg gcgatctcta caacttcaag    1260
ttagatccgt cgctaaccct tggttgtggt acgtggggcg gcaacgtcac atcggaaaat    1320
gttggtcccc gtcacttgct gaatattaaa acggtgagcg atcgccggga aaatatgctt    1380
tggtttcggg tgccgcccaa gatctacttc aaacccggct gtttgcccat tgccctgcgg    1440
gagctggcgg ggaaaaaacg cgccttcctc gtgacggata aacccctctt tgacttgggg    1500
atcactgaac cgattgtcca taccctcgaa gaactgggca tcaagtatga catcttccat    1560
gaagtggaac cagatccaac cctcagtacc gttaaccgcg gtctagggtt gctgcggcaa    1620
tatcagccgg atgtgattgt tgctgtgggg ggtggctcac ctatgatgc agccaaggtg    1680 atgtggctgt tgtatgagca tccggaggtg gagtttgacg gccttgcgat gcgcttcatg    1740
gatattcgca agcgggtgta tcaactgcct cccttgggtc aaaaggcaat cctggtggct    1800
attcccacca cctcggggac gggttcagag gtgacccct tgccgtggt taccgacgat    1860 cgcgtgggga ttaaatatcc cttggcagac tatgccctta cgccaacgat ggcgattgtg    1920
gatcccgact tggtgctgca catgcccaag aaactgacgg cctacggtgg cattgatgcg    1980
ctgacccatg ccctggaggc ctatgtgtcg gtgctctcga cggagtttac ggagggactg    2040
gctctagagg ccattaaact gctctttacc tacctacccc gtgcctatcg cttggggggcg    2100 gcggatccgg aggcacggga aaggtccac tatgcggcga cgatcgctgg catggccttt    2160
gcgaatgcct tcttggggt ctgccactcg ctggcccaca aactaggctc cacctccac    2220 gtgccccacg gcttggcgaa tgcactcatg atttcccatg tgattcgcta caatgccacg    2280
gatgctcccc tgaagcaggc gattttcccg cagtacaagt atccccaagc gaaggagcgc    2340
tatgcccaaa ttgccgactt cctcgaattg gggggcacga ccccagagga aaaagtggag    2400
cgtctcattg cggcaattga ggatttgaaa gcccaattag aaattcccgc cacgattaag    2460
gaggccctca acagtgagga tcaagcgttc tatgagcagg tggagagcat ggccgaactg    2520 gccttttgacg atcagtgcac gggggccaat ccccgctatc cgctgatcca agacctcaag    2580
gagttgtata tcctggccta tatggggtgt cggcgggatg cggcagccta ctatgggggg    2640
gaggcaacgg ggagttgatg tggcgttata ttccccccctt tgcagctcca gcgaaggtgc    2700
aaatggcggt ggattcctgg ctctggcagc ggagcgatcg cctgcag             2747
```

<210> SEQ ID NO 100
<211> LENGTH: 885
<212> TYPE: PRT
<213> ORGANISM: Thermosynechococcus elongatus

<400> SEQUENCE: 100

```
Met Asn Ser Pro Thr Leu Thr Ser Asp Pro Val Gln Ser Leu Ala
1               5                  10                 15

Asp Leu Glu Gly Leu Ile Glu Arg Val Gln Arg Ala Gln Ser Gln Tyr
            20                 25                  30

Ala Gln Phe Thr Gln Glu Gln Val Asp His Ile Phe His Glu Ala Ala
        35                  40                  45

Met Ala Ala Asn Gln Ala Arg Ile Pro Leu Ala Lys Gln Ala Val Ala
    50                  55                  60

Glu Thr Gly Met Gly Val Val Glu Asp Lys Val Ile Lys Asn His Phe
65                  70                  75                  80

Ala Ser Glu Tyr Ile Tyr Asn Lys Tyr Lys Asn Glu Lys Thr Cys Gly
                85                  90                  95

Val Ile Glu Asp Asp Pro Ile Phe Gly Ile Gln Lys Ile Ala Glu Pro
```

```
              100                 105                 110
Val Gly Ile Ile Ala Gly Val Val Pro Val Thr Asn Pro Thr Ser Thr
            115                 120                 125
Thr Ile Phe Lys Ala Leu Ile Ala Leu Lys Thr Arg Asn Gly Ile Ile
            130                 135                 140
Phe Ser Pro His Pro Arg Ala Lys Ala Cys Thr Val Ala Ala Ala Lys
145                 150                 155                 160
Val Val Leu Asp Ala Ala Val Ala Ala Gly Ala Pro Pro Asp Ile Ile
                165                 170                 175
Gly Trp Ile Asp Glu Pro Thr Ile Glu Leu Ser Gln Ala Leu Met Gln
                180                 185                 190
His Pro Gln Ile Lys Leu Ile Leu Ala Thr Gly Gly Pro Gly Met Val
                195                 200                 205
Lys Ala Ala Tyr Ser Ser Gly His Pro Ala Ile Gly Val Gly Ala Gly
                210                 215                 220
Asn Thr Pro Val Leu Ile Asp Ala Thr Ala Asp Ile Pro Thr Ala Val
225                 230                 235                 240
Ser Ser Ile Leu Leu Ser Lys Ala Phe Asp Asn Gly Met Ile Cys Ala
                245                 250                 255
Ser Glu Gln Ala Val Ile Val Val Asp Glu Ile Tyr Asp Ala Leu Lys
                260                 265                 270
Ala Glu Phe Gln Arg Arg Gly Ala Tyr Leu Leu Ser Pro Glu Glu Arg
                275                 280                 285
Gln Gln Val Ala Gln Leu Leu Leu Lys Asp Gly Arg Leu Asn Ala Ala
                290                 295                 300
Ile Val Gly Gln Ser Ala Ala Thr Ile Ala Ala Met Ala Asn Ile Gln
305                 310                 315                 320
Val Pro Pro Glu Thr Arg Val Leu Ile Gly Glu Val Ser Glu Val Gly
                325                 330                 335
Pro Gln Glu Pro Phe Ser Tyr Glu Lys Leu Cys Pro Val Leu Ala Leu
                340                 345                 350
Tyr Arg Ala Pro Gln Phe His Lys Gly Val Glu Ile Ala Ala Gln Leu
                355                 360                 365
Val Asn Phe Gly Gly Lys Gly His Thr Ser Val Leu Tyr Thr Asp Pro
                370                 375                 380
Arg Asn Gln Asp Asp Ile Ala Tyr Phe Lys Tyr Arg Met Gln Thr Ala
385                 390                 395                 400
Arg Val Leu Ile Asn Thr Pro Ser Ser Gln Gly Ala Ile Gly Asp Leu
                405                 410                 415
Tyr Asn Phe Lys Leu Asp Pro Ser Leu Thr Leu Gly Cys Gly Thr Trp
                420                 425                 430
Gly Gly Asn Val Thr Ser Glu Asn Val Gly Pro Arg His Leu Leu Asn
                435                 440                 445
Ile Lys Thr Val Ser Asp Arg Arg Glu Asn Met Leu Trp Phe Arg Val
                450                 455                 460
Pro Pro Lys Ile Tyr Phe Lys Pro Gly Cys Leu Pro Ile Ala Leu Arg
465                 470                 475                 480
Glu Leu Ala Gly Lys Lys Arg Ala Phe Leu Val Thr Asp Lys Pro Leu
                485                 490                 495
Phe Asp Leu Gly Ile Thr Glu Pro Ile Val His Thr Leu Glu Glu Leu
                500                 505                 510
Gly Ile Lys Tyr Asp Ile Phe His Glu Val Glu Pro Asp Pro Thr Leu
                515                 520                 525
```

| | | | | | | | | | | | |
|---|---|---|---|---|---|---|---|---|---|---|---|
| Ser | Thr | Val | Asn | Arg | Gly | Leu | Gly | Leu | Leu | Arg | Gln | Tyr | Gln | Pro | Asp |
| | 530 | | | | 535 | | | | | 540 | | | | | |
| Val | Ile | Val | Ala | Val | Gly | Gly | Gly | Ser | Pro | Met | Asp | Ala | Ala | Lys | Val |
| 545 | | | | | 550 | | | | | 555 | | | | | 560 |
| Met | Trp | Leu | Leu | Tyr | Glu | His | Pro | Glu | Val | Glu | Phe | Asp | Gly | Leu | Ala |
| | | | | | 565 | | | | | 570 | | | | | 575 |
| Met | Arg | Phe | Met | Asp | Ile | Arg | Lys | Arg | Val | Tyr | Gln | Leu | Pro | Pro | Leu |
| | | | 580 | | | | | 585 | | | | | 590 | | |
| Gly | Gln | Lys | Ala | Ile | Leu | Val | Ala | Ile | Pro | Thr | Thr | Ser | Gly | Thr | Gly |
| | | 595 | | | | | 600 | | | | | 605 | | | |
| Ser | Glu | Val | Thr | Pro | Phe | Ala | Val | Val | Thr | Asp | Asp | Arg | Val | Gly | Ile |
| | 610 | | | | | 615 | | | | | 620 | | | | |
| Lys | Tyr | Pro | Leu | Ala | Asp | Tyr | Ala | Leu | Thr | Pro | Thr | Met | Ala | Ile | Val |
| 625 | | | | | 630 | | | | | 635 | | | | | 640 |
| Asp | Pro | Asp | Leu | Val | Leu | His | Met | Pro | Lys | Lys | Leu | Thr | Ala | Tyr | Gly |
| | | | | 645 | | | | | 650 | | | | | 655 | |
| Gly | Ile | Asp | Ala | Leu | Thr | His | Ala | Leu | Glu | Ala | Tyr | Val | Ser | Val | Leu |
| | | | 660 | | | | | 665 | | | | | 670 | | |
| Ser | Thr | Glu | Phe | Thr | Glu | Gly | Leu | Ala | Leu | Glu | Ala | Ile | Lys | Leu | Leu |
| | | 675 | | | | | 680 | | | | | 685 | | | |
| Phe | Thr | Tyr | Leu | Pro | Arg | Ala | Tyr | Arg | Leu | Gly | Ala | Ala | Asp | Pro | Glu |
| | 690 | | | | | 695 | | | | | 700 | | | | |
| Ala | Arg | Glu | Lys | Val | His | Tyr | Ala | Ala | Thr | Ile | Ala | Gly | Met | Ala | Phe |
| 705 | | | | | 710 | | | | | 715 | | | | | 720 |
| Ala | Asn | Ala | Phe | Leu | Gly | Val | Cys | His | Ser | Leu | Ala | His | Lys | Leu | Gly |
| | | | | 725 | | | | | 730 | | | | | 735 | |
| Ser | Thr | Phe | His | Val | Pro | His | Gly | Leu | Ala | Asn | Ala | Leu | Met | Ile | Ser |
| | | | 740 | | | | | 745 | | | | | 750 | | |
| His | Val | Ile | Arg | Tyr | Asn | Ala | Thr | Asp | Ala | Pro | Leu | Lys | Gln | Ala | Ile |
| | | 755 | | | | | 760 | | | | | 765 | | | |
| Phe | Pro | Gln | Tyr | Lys | Tyr | Pro | Gln | Ala | Lys | Glu | Arg | Tyr | Ala | Gln | Ile |
| | 770 | | | | | 775 | | | | | 780 | | | | |
| Ala | Asp | Phe | Leu | Glu | Leu | Gly | Gly | Thr | Thr | Pro | Glu | Glu | Lys | Val | Glu |
| 785 | | | | | 790 | | | | | 795 | | | | | 800 |
| Arg | Leu | Ile | Ala | Ala | Ile | Glu | Asp | Leu | Lys | Ala | Gln | Leu | Glu | Ile | Pro |
| | | | | 805 | | | | | 810 | | | | | 815 | |
| Ala | Thr | Ile | Lys | Glu | Ala | Leu | Asn | Ser | Glu | Asp | Gln | Ala | Phe | Tyr | Glu |
| | | | 820 | | | | | 825 | | | | | 830 | | |
| Gln | Val | Glu | Ser | Met | Ala | Glu | Leu | Ala | Phe | Asp | Asp | Gln | Cys | Thr | Gly |
| | | 835 | | | | | 840 | | | | | 845 | | | |
| Ala | Asn | Pro | Arg | Tyr | Pro | Leu | Ile | Gln | Asp | Leu | Lys | Glu | Leu | Tyr | Ile |
| | 850 | | | | | 855 | | | | | 860 | | | | |
| Leu | Ala | Tyr | Met | Gly | Cys | Arg | Arg | Asp | Ala | Ala | Ala | Tyr | Tyr | Gly | Gly |
| 865 | | | | | 870 | | | | | 875 | | | | | 880 |
| Glu | Ala | Thr | Gly | Ser | | | | | | | | | | | |
| | | | | 885 | | | | | | | | | | | |

<210> SEQ ID NO 101
<211> LENGTH: 1680
<212> TYPE: DNA
<213> ORGANISM: Zymobacter palmae

<400> SEQUENCE: 101
atgaattccg ttggtatgta cttggcagaa cgcctagccc agatcggcct gaaacaccac    60

-continued

```
tttgccgtgg ccggtgacta caacctggtg ttgcttgatc agctcctgct gaacaaagac    120
atggagcagg tctactgctg taacgaactt aactgcggct ttagcgccga aggttacgct    180
cgtgcacgtg gtgccgccgc tgccatcgtc acgttcagcg taggtgctat ctctgcaatg    240
aacgccatcg gtggcgccta tgcagaaaac ctgccggtca tcctgatctc tggctcaccg    300
aacaccaatg actacggcac aggccacatc ctgcaccaca ccattggtac tactgactat    360
aactatcagc tggaaatggt aaaacacgtt acctgcgcac gtgaaagcat cgtttctgcc    420
gaagaagcac cggcaaaaat cgaccacgtc atccgtacgg ctctacgtga acgcaaaccg    480
gcttatctgg aaatcgcatg caacgtcgct ggcgctgaat gtgttcgtcc gggcccgatc    540
aatagcctgc tgcgtgaact cgaagttgac cagaccagtg tcactgccgc tgtagatgcc    600
gccgtagaat ggctgcagga ccgccagaac gtcgtcatgc tggtcggtag caaactgcgt    660
gccgctgccg ctgaaaaaca ggctgttgcc ctagcggacc gcctgggctg cgctgtcacg    720
atcatggctg ccgaaaaagg cttcttcccg gaagatcatc cgaacttccg cggcctgtac    780
tggggtgaag tcagctccga aggtgcacag gaactggttg aaaacgccga tgccatcctg    840
tgtctggcac cggtattcaa cgactatgct accgttggct ggaactcctg ccgaaaggc     900
gacaatgtca tggtcatgga caccgaccgc gtcactttcg caggacagtc cttcgaaggt    960
ctgtcattga gcaccttcgc cgcagcactg gctgagaaag caccttctcg cccggcaacg   1020
actcaaggca ctcaagcacc ggtactgggt attgaggccg cagagcccaa tgcaccgctg   1080
accaatgacg aaatgacgcg tcagatccag tcgctgatca cttccgacac tactctgaca   1140
gcagaaacag gtgactcttg gttcaacgct ctcgcatgc cgattcctgg cggtgctcgt    1200
gtcgaactgg aaatgcaatg gggtcatatc ggttggtccg taccttctgc attcggtaac   1260
gccgttggtt ctccggagcg tcgccacatc atgatggtcg gtgatggctc tttccagctg   1320
actgctcaag aagttgctca gatgatccgc tatgaaatcc cggtcatcat cttcctgatc   1380
aacaaccgcg gttacgtcat cgaaatcgct atccatgacg gcccttacaa ctacatcaaa   1440
aactggaact acgctggcct gatcgacgtc ttcaatgacg aagatggtca tggcctgggt   1500
ctgaaagctt ctactggtgc agaactagaa ggcgctatca agaaagcact cgacaatcgt   1560
cgcggtccga cgctgatcga atgtaacatc gctcaggacg actgcactga accctgatt    1620
gcttgggta aacgtgtagc agctaccaac tctcgcaaac cacaagcgta agttgagctc   1680
```

<210> SEQ ID NO 102
<211> LENGTH: 556
<212> TYPE: PRT
<213> ORGANISM: Zymobacter palmae

<400> SEQUENCE: 102

Met Asn Ser Val Gly Met Tyr Leu Ala Glu Arg Leu Ala Gln Ile Gly
1               5                   10                  15

Leu Lys His His Phe Ala Val Ala Gly Asp Tyr Asn Leu Val Leu Leu
            20                  25                  30

Asp Gln Leu Leu Leu Asn Lys Asp Met Glu Gln Val Tyr Cys Cys Asn
        35                  40                  45

Glu Leu Asn Cys Gly Phe Ser Ala Glu Gly Tyr Ala Arg Ala Arg Gly
    50                  55                  60

Ala Ala Ala Ala Ile Val Thr Phe Ser Val Gly Ala Ile Ser Ala Met
65                  70                  75                  80

Asn Ala Ile Gly Gly Ala Tyr Ala Glu Asn Leu Pro Val Ile Leu Ile

```
                 85                  90                  95
Ser Gly Ser Pro Asn Thr Asn Asp Tyr Gly Thr Gly His Ile Leu His
            100                 105                 110

His Thr Ile Gly Thr Thr Asp Tyr Asn Tyr Gln Leu Glu Met Val Lys
            115                 120                 125

His Val Thr Cys Ala Arg Glu Ser Ile Val Ser Ala Glu Glu Ala Pro
130                 135                 140

Ala Lys Ile Asp His Val Ile Arg Thr Ala Leu Arg Glu Arg Lys Pro
145                 150                 155                 160

Ala Tyr Leu Glu Ile Ala Cys Asn Val Ala Gly Ala Glu Cys Val Arg
                165                 170                 175

Pro Gly Pro Ile Asn Ser Leu Leu Arg Glu Leu Glu Val Asp Gln Thr
            180                 185                 190

Ser Val Thr Ala Ala Val Asp Ala Ala Val Glu Trp Leu Gln Asp Arg
            195                 200                 205

Gln Asn Val Val Met Leu Val Gly Ser Lys Leu Arg Ala Ala Ala Ala
            210                 215                 220

Glu Lys Gln Ala Val Ala Leu Ala Asp Arg Leu Gly Cys Ala Val Thr
225                 230                 235                 240

Ile Met Ala Ala Glu Lys Gly Phe Phe Pro Glu Asp His Pro Asn Phe
                245                 250                 255

Arg Gly Leu Tyr Trp Gly Glu Val Ser Ser Glu Gly Ala Gln Glu Leu
            260                 265                 270

Val Glu Asn Ala Asp Ala Ile Leu Cys Leu Ala Pro Val Phe Asn Asp
            275                 280                 285

Tyr Ala Thr Val Gly Trp Asn Ser Trp Pro Lys Gly Asp Asn Val Met
            290                 295                 300

Val Met Asp Thr Asp Arg Val Thr Phe Ala Gly Gln Ser Phe Glu Gly
305                 310                 315                 320

Leu Ser Leu Ser Thr Phe Ala Ala Ala Leu Ala Glu Lys Ala Pro Ser
                325                 330                 335

Arg Pro Ala Thr Thr Gln Gly Thr Gln Ala Pro Val Leu Gly Ile Glu
            340                 345                 350

Ala Ala Glu Pro Asn Ala Pro Leu Thr Asn Asp Glu Met Thr Arg Gln
            355                 360                 365

Ile Gln Ser Leu Ile Thr Ser Asp Thr Thr Leu Thr Ala Glu Thr Gly
            370                 375                 380

Asp Ser Trp Phe Asn Ala Ser Arg Met Pro Ile Pro Gly Gly Ala Arg
385                 390                 395                 400

Val Glu Leu Glu Met Gln Trp Gly His Ile Gly Trp Ser Val Pro Ser
                405                 410                 415

Ala Phe Gly Asn Ala Val Gly Ser Pro Glu Arg Arg His Ile Met Met
            420                 425                 430

Val Gly Asp Gly Ser Phe Gln Leu Thr Ala Gln Glu Val Ala Gln Met
            435                 440                 445

Ile Arg Tyr Glu Ile Pro Val Ile Ile Phe Leu Ile Asn Asn Arg Gly
            450                 455                 460

Tyr Val Ile Glu Ile Ala Ile His Asp Gly Pro Tyr Asn Tyr Ile Lys
465                 470                 475                 480

Asn Trp Asn Tyr Ala Gly Leu Ile Asp Val Phe Asn Asp Glu Asp Gly
                485                 490                 495

His Gly Leu Gly Leu Lys Ala Ser Thr Gly Ala Glu Leu Glu Gly Ala
            500                 505                 510
```

```
Ile Lys Lys Ala Leu Asp Asn Arg Arg Gly Pro Thr Leu Ile Glu Cys
    515                 520                 525

Asn Ile Ala Gln Asp Asp Cys Thr Glu Thr Leu Ile Ala Trp Gly Lys
    530                 535                 540

Arg Val Ala Ala Thr Asn Ser Arg Lys Pro Gln Ala
545                 550                 555

<210> SEQ ID NO 103
<211> LENGTH: 5711
<212> TYPE: DNA
<213> ORGANISM: Artificial Sequence
<220> FEATURE:
<223> OTHER INFORMATION: synthetic combined bacterial sequences

<400> SEQUENCE: 103
```

| | | | | | |
|---|---|---|---|---|---|
| gtcgacatat | gtttctcggc | aaaaattaat | tatcgattgg | ctggaacctg | gtcaaaccag      60 |
| ggcttttcat | ccattggaaa | agcgattttg | atcatctagg | gtcaggagca | aagatctgat     120 |
| caaatattga | tcatttatta | ggaaagctga | actttcacca | ctttattttt | ggcttcctct     180 |
| actttgggca | aagtcaaagt | taggataccg | gcatcgtaat | tagctttaac | ttctgtgttt     240 |
| tggattgctc | caggtacagg | aataacccgg | cggaaactgc | catagcggaa | ctctgtgcgc     300 |
| cgcaccccat | cttttcggt  | gctatgggta | tcctggcgat | cgccgctgac | ggtcaccgca     360 |
| tccctggcgg | cttggatgtc | caaattatcg | gggtccatgc | caggtaattc | tagtttgagc     420 |
| acataggctt | cttcagtttc | agttagttct | gctttaggat | taaacccttg | gcgatcgccg     480 |
| tggcggtccg | tagggacaaa | aacttcttca | aacagttggt | tcatctgctg | ctggaaatta     540 |
| tccatttccc | gcaggggatt | gtaaagaatg | agagacataa | tgttaactcc | tgatgtgtgg     600 |
| aaggaattga | ttacccttga | atggttctat | cttaaaattt | ccccttccag | gttagattcg     660 |
| gttttcagga | aagaaggtgg | ggggattgcc | gaaattacat | ttctagccgc | aatttttagt     720 |
| aaaaaaaaga | tgagttttta | cctcacctta | agtaaatatt | tgagtggcaa | aacaaaatgg     780 |
| taaaaatagc | taagcttcca | ccgccctatg | gattttggga | aggaagtctt | aggttgtgaa     840 |
| aaactataaa | aaccaaccat | aggaatggag | acctttaccc | aacaagttga | cccctaggta     900 |
| acaaatccaa | accaccgtaa | aaccgctggc | ggccaaaata | gcgggcttgc | ggccttgcca     960 |
| acctttggta | atgcgggcat | ggagataggc | ggcaaatact | agccaggtga | ttagggcccg    1020 |
| gtacccagct | tttgttccct | ttagtgaggg | ttaatttcga | gcttggcgta | atcatggtca    1080 |
| tagctgtttc | ctgtgtgaaa | ttgttatccg | ctcacaattc | cacacaacat | acgagccgga    1140 |
| agcataaagt | gtaaagcctg | gggtgcctaa | tgagtgagct | aactcacatt | aattgcgttg    1200 |
| cgctcactgc | ccgctttcca | gtcgggaaac | ctgtcgtgcc | agctgcatta | atgaatcggc    1260 |
| caacgcgcgg | ggagaggcgg | tttgcgtatt | gggcgctctt | ccgcttcctc | gctcactgac    1320 |
| tcgctgcgct | cggtcgttcg | gctgcggcga | gcggtatcag | ctcactcaaa | ggcggtaata    1380 |
| cggttatcca | cagaatcagg | ggataacgca | ggaaagaaca | tgtgagcaaa | aggccagcaa    1440 |
| aaggccagga | accgtaaaaa | ggccgcgttg | ctggcgtttt | tccataggct | ccgcccccct    1500 |
| gacgagcatc | acaaaaatcg | acgctcaagt | cagaggtggc | gaaacccgac | aggactataa    1560 |
| agataccagg | cgtttccccc | tggaagctcc | ctcgtgcgct | ctcctgttcc | gaccctgccg    1620 |
| cttaccggat | acctgtccgc | ctttctccct | tcgggaagcg | tggcgctttc | tcatagctca    1680 |
| cgctgtaggt | atctcagttc | ggtgtaggtc | gttcgctcca | agctgggctg | tgtgcacgaa    1740 |
| ccccccgttc | agcccgaccg | ctgcgcctta | tccggtaact | atcgtcttga | gtccaacccg    1800 |

```
gtaagacacg acttatcgcc actggcagca gccactggta acaggattag cagagcgagg   1860
tatgtaggcg gtgctacaga gttcttgaag tggtggccta actacggcta cactagaagg   1920
acagtatttg gtatctgcgc tctgctgaag ccagttacct tcggaaaaag agttggtagc   1980
tcttgatccg gcaaacaaac caccgctggt agcggtggtt ttttgtttg caagcagcag    2040 attacgcgca gaaaaaaagg atctcaagaa gatcctttga tctttctac ggggtctgac    2100 gctcagtgga acgaaaactc acgttaaggg attttggtca tgagattatc aaaaaggatc   2160
ttcacctaga tccttttaaa ttaaaaatga agttttaaat caatctaaag tatatatgag   2220
taaacttggt ctgacagtta ccaatgctta atcagtgagg cacctatctc agcgatctgt   2280
ctatttcgtt catccatagt tgcctgactc cccgtcgtgt agataactac gatacgggag   2340
ggcttaccat ctggccccag tgctgcaatg ataccgcgag acccacgctc accggctcca   2400
gatttatcag caataaacca gccagccgga agggccgagc gcagaagtgg tcctgcaact   2460
ttatccgcct ccatccagtc tattaattgt tgccgggaag ctagagtaag tagttcgcca   2520
gttaatagtt tgcgcaacgt tgttgccatt gctacaggca tcgtggtgtc acgctcgtcg   2580
tttggtatgg cttcattcag ctccggttcc caacgatcaa ggcgagttac atgatccccc   2640
atgttgtgca aaaaagcggt tagctccttc ggtcctccga tcgttgtcag aagtaagttg   2700
gccgcagtgt tatcactcat ggttatggca gcactgcata attctcttac tgtcatgcca   2760
tccgtaagat gcttttctgt gactggtgag tactcaacca agtcattctg agaatagtgt   2820
atgcggcgac cgagttgctc ttgcccggcg tcaatacggg ataataccgc gccacatagc   2880
agaactttaa aagtgctcat cattggaaaa cgttcttcgg ggcgaaaact ctcaaggatc   2940
ttaccgctgt tgagatccag ttcgatgtaa cccactcgtg cacccaactg atcttcagca   3000
tcttttactt tcaccagcgt ttctgggtga gcaaaaacag gaaggcaaaa tgccgcaaaa   3060
aagggaataa gggcgacacg gaaatgttga atactcatac tcttcctttt tcaatattat   3120
tgaagcattt atcagggtta ttgtctcatg agcggataca tatttgaatg tatttagaaa   3180
aataaacaaa tagggggttcc gcgcacattt ccccgaaaag tgccacctaa attgtaagcg   3240
ttaatatttt gttaaaattc gcgttaaatt tttgttaaat cagctcattt tttaaccaat   3300
aggccgaaat cggcaaaatc ccttataaat caaaagaata gaccgagata gggttgagtg   3360
ttgttccagt ttggaacaag agtccactat taaagaacgt ggactccaac gtcaaagggc   3420
gaaaaaccgt ctatcagggc gatggcccac tacgtgaacc atcaccctaa tcaagttttt   3480
tggggtcgag gtgccgtaaa gcactaaatc ggaaccctaa agggagcccc cgatttagag   3540
cttgacgggg aaagccggcg aacgtggcga gaaggaagg gaagaaagcg aaaggagcgg   3600
gcgctagggc gctggcaagt gtagcggtca cgctgcgcgt aaccaccaca cccgccgcgc   3660
ttaatgcgcc gctacagggc gcgtcccatt cgccattcag gctgcgcaac tgttgggaag   3720
ggcgatcggt gcgggcctct tcgctattac gccagctggc gaaagggga tgtgctgcaa   3780 ggcgattaag ttgggtaacg ccagggtttt cccagtcacg acgttgtaaa acgacggcca   3840
gtgaattgta atacgactca ctatagggcg aattggaggc cagtgctgga ggaatatgat   3900
tttgtcatcc tcgactgtgc ccctggttat aatctgttga cccgcagtgg cattgcggcc   3960
agcgactttt atctgttgcc ggctcgtcct gaaccctat cggtggtggg gatgcagtta   4020
ctggaaagaa gaattgagaa actgaaggaa agcataagg cctccgatga tccccctgaat  4080 atcaatctga tcggagtggt gtttattctg tccggcggcg gtttgatgag tcgctactat   4140
```

```
aaccaggtaa tgcggcgggt acaaacggat ttcaccccgg acaacttttt tcagcagtcc   4200
attcccatgg atgtcaatgt ggctaaggca gtggatagct ttatgccggt ggttacctcc   4260
atgcccaata cggcgggttc aaaagctttt attaaattaa cccaggaatt tttacagaaa   4320
gtagaagctt ttggctaaag caaagccccc attgattaac aacgggaggg gtaccgaggt   4380
gctgctgaag ttgcccgcaa cagagagtgg aaccaaccgg tagtgcatct aacgcttgag   4440
ttaagccgcg ccgcgaagcg gcgtcggctt gaacgaattg ttagacatta tttgccgact   4500
accttggtga tctcgccttt cacgtagtgg acaaattctt ccaactgatc tgcgcgcgag   4560
gccaagcgat cttcttcttg tccaagataa gcctgtctag cttcaagtat gacgggctga   4620
tactgggccg gcaggcgctc cattgcccag tcggcagcga catccttcgg cgcgattttg   4680
ccggttactg cgctgtacca aatgcgggac aacgtaagca ctacatttcg ctcatcgcca   4740
gcccagtcgg gcggcgagtt ccatagcgtt aaggtttcat ttagcgcctc aaatagatcc   4800
tgttcaggaa ccggatcaaa gagttcctcc gccgctggac ctaccaaggc aacgctatgt   4860
tctcttgctt ttgtcagcaa gatagccaga tcaatgtcga tcgtggctgg ctcgaagata   4920
cctgcaagaa tgtcattgcg ctgccattct ccaaattgca gttcgcgctt agctggataa   4980
cgccacggaa tgatgtcgtc gtgcacaaca atggtgactt ctacagcgcg gagaatctcg   5040
ctctctccag gggaagccga agtttccaaa aggtcgttga tcaaagctcg ccgcgttgtt   5100
tcatcaagcc ttacgtcacc cgtaaccagc aaatcaatat cactgtgtgg cttcaggccg   5160
ccatccactg cggagccgta caaatgtacg gccagcaacg tcggttcgag atggcgctcg   5220
atgacgccaa ctacctctga tagttgagtc gatacttcgg cgatcaccgc ttccctcatg   5280
atgtttaact ttgttttagg gcgactgccc tgctgcgtaa catcgttgct gctccataac   5340
atcaaacatc gacccacggc gtaacgcgct tgctgcttgg atgcccgagg catagactgt   5400
accccaaaaa aacagtcata acaagccatg aaaaccgcca ctgcgccgtt accaccgctg   5460
cgttcggtca aggttctgga ccagttgcgt gagcgcatac gctacttgca ttacagctta   5520
cgaaccgaac aggcttatgt ccactggggtt cgtgccttca tccgtttcca cggtgtgcgt   5580
cacccggcaa ccttgggcag cagcgaagtc gaggcatttc tgtcctggct ggcgaacgag   5640
cgcaaggttt cggtctccac gcatcgtcag gcattggcgg ccttgctgtt cttctagaca   5700
aggctgcagt t                                                       5711

<210> SEQ ID NO 104
<211> LENGTH: 397
<212> TYPE: DNA
<213> ORGANISM: Anabaena PCC7120

<400> SEQUENCE: 104
gtcgactcta gaaagatgcc actagcacca gacgactagt tagcgatagt ctatccacca     60
ttgttcgttt tgtaggtttt gcttttatag cgatcggttt tgtatttgc ggtaacttca    120 tcaatttttt aggggctggt aattttttaac atatctcacg gggtgcaatc ttcgcgcccc    180
tactagtcca tcgaatcgtc atttccaact attaatatta aagtttagag aaattggatt    240
atatgtaacc tgtactctgt taagattcac cattgggta ttcgctatca gtcttggcgc    300
tactgcccat cccgcccctc aaacctttgt ccgtccgcct aagactgata ccgctactgg    360
tgacaggccg atgttatatc tggagttcta tgaattc                            397

<210> SEQ ID NO 105
<211> LENGTH: 359
```

<212> TYPE: DNA
<213> ORGANISM: Anabaena PCC7120

<400> SEQUENCE: 105

```
gtcgactttt ttgctgaggt actgagtaca cagctaataa aattgggcaa tctccgcgcc      60
tctatgactt gaaggagagt gtaggggtat aggggaaaga tatctttat ctacatcaca      120
taaataaaaa atttaatttg tcgctctggc tgcatatatt gatgtatttt tagccataag    180
ttttttagtg ccatgtaatt atagtgattt ttagcgatcg cagagcattt ttccctggat    240
ttatcgcgat ctcaaaaaaa atttgcccga agtatgacag attgtcatat ttggtgtcga    300
ttttatttaa aatgaaataa gaaaaataaa actacaggtt aggagaacgc catgaattc     359
```

<210> SEQ ID NO 106
<211> LENGTH: 13102
<212> TYPE: DNA
<213> ORGANISM: Artificial Sequence
<220> FEATURE:
<223> OTHER INFORMATION: synthetic combined bacterial sequences

<400> SEQUENCE: 106

```
atcgataatt aatttttgcc gagaaacata tgtcgacttt tttgctgagg tactgagtac      60
acagctaata aaattgggca atctccgcgc ctctatgact tgaaggagag tgtaggggta    120
taggggaaag atatctttta tctacatcac ataaataaaa aatttaattt gtcgctctgg    180
ctgcatatat tgatgtattt ttagccataa gttttttagt gccatgtaat tatagtgatt    240
tttagcgatc gcagagcatt tttccctgga tttatcgcga tctcaaaaaa aatttgcccg    300
aagtatgaca gattgtcata tttggtgtcg atttttattta aaatgaaata gaaaaataa    360
aactacaggt taggagaacg ccatgaattc ttatactgtc ggtacctatt tagcggagcg    420
gcttgtccag attggtctca agcatcactt cgcagtcgcg ggcgactaca acctcgtcct    480
tcttgacaac ctgcttttga acaaaaacat ggagcaggtt tattgctgta acgaactgaa    540
ctgcggtttc agtgcagaag gttatgctcg tgccaaaggc gcagcagcag ccgtcgttac    600
ctacagcgtc ggtgcgcttt ccgcatttga tgctatcggt ggcgcctatg cagaaaacct    660
tccggttatc ctgatctccg gtgctccgaa caacaatgat cacgctgctg gtcacgtgtt    720
gcatcacgct cttggcaaaa ccgactatca ctatcagttg gaaatggcca agaacatcac    780
ggccgcagct gaagcgattt acaccccaga agaagctccg gctaaaatcg atcacgtgat    840
taaaactgct cttcgtgaga agaagccggt ttatctcgaa atcgcttgca acattgcttc    900
catgccctgc gccgctcctg gaccggcaag cgcattgttc aatgacgaag ccagcgacga    960
agcttctttg aatgcagcgg ttgaagaaac cctgaaattc atcgccaacc gcgacaaagt   1020
tgccgtcctc gtcggcagca agctgcgcgc agctggtgct gaagaagctg ctgtcaaatt   1080
tgctgatgct ctcggtggcg cagttgctac catggctgct gcaaaaagct tcttcccaga   1140
agaaaacccg cattacatcg gtacctcatg gggtgaagtc agctatccgg cgttgaaaa    1200
gacgatgaaa gaagccgatg cggttatcgc tctggctcct gtcttcaacg actactccac   1260
cactggttgg acggatattc ctgatcctaa gaaactggtt ctcgctgaac gcgttctgt    1320
cgtcgttaac ggcgttcgct tccccagcgt tcatctgaaa gactatctga cccgtttggc   1380
tcagaaagtt tccaagaaaa ccggtgcttt ggacttcttc aaatccctca atgcaggtga   1440
actgaagaaa gccgctccgg ctgatccgag tgctccgttg gtcaacgcag aaatcgcccg   1500
tcaggtcgaa gctcttctga ccccgaacac gacggttatt gctgaaaccg gtgactcttg   1560
```

```
gttcaatgct cagcgcatga agctcccgaa cggtgctcgc gttgaatatg aaatgcagtg   1620
gggtcacatc ggttggtccg ttcctgccgc cttcggttat gccgtcggtg ctccggaacg   1680
tcgcaacatc ctcatggttg gtgatggttc cttccagctg acggctcagg aagtcgctca   1740
gatggttcgc ctgaaactgc cggttatcat cttcttgatc aataactatg gttacaccat   1800
cgaagttatg atccatgatg gtccgtacaa caacatcaag aactgggatt atgccggtct   1860
gatggaagtg ttcaacggta acggtggtta tgacagcggt gctggtaaag gcctgaaggc   1920
taaaaccggt ggcgaactgg cagaagctat caaggttgct ctggcaaaca ccgacggccc   1980
aaccctgatc gaatgcttca tcggtcgtga agactgcact gaagaattgg tcaaatgggg   2040
taagcgcgtt gctgccgcca acagccgtaa gcctgttaac aagctcctct agttttgg    2100
gatcaattcg agctcggtac ccaaactagt atgtagggtg aggttatagc tatggcttct   2160
tcaacttttt atattccttt cgtcaacgaa atgggcgaag gttcgcttga aaaagcaatc   2220
aaggatctta acggcagcgg ctttaaaaat gcgctgatcg tttctgatgc tttcatgaac   2280
aaatccggtg ttgtgaagca ggttgctgac ctgttgaaaa cacagggtat taattctgct   2340
gtttatgatg gcgttatgcc gaacccgact gttaccgcag ttctggaagg ccttaagatc   2400
ctgaaggata caattcaga cttcgtcatc tccctcggtg gtggttctcc ccatgactgc   2460
gccaaagcca tcgctctggt cgcaaccaat ggtggtgaag tcaaagacta cgaaggtatc   2520
gacaaatcta agaaacctgc cctgcctttg atgtcaatca cacgacggc tggtacggct   2580
tctgaaatga cgcgtttctg catcatcact gatgaagtcc gtcacgttaa gatggccatt   2640
gttgaccgtc acgttacccc gatggtttcc gtcaacgatc ctctgttgat ggttggtatg   2700
ccaaaaggcc tgaccgccgc caccggtatg gatgctctga cccacgcatt gaagcttat    2760
tcttcaacgg cagctactcc gatcaccgat gcttgcgcct tgaaggctgc gtccatgatc   2820
gctaagaatc tgaagaccgc ttgcgacaac ggtaaggata tgccagctcg tgaagctatg   2880
gcttatgccc aattcctcgc tggtatggcc ttcaacaacg cttcgcttgg ttatgtccat   2940
gctatggctc accagttggg cggctactac aacctgccgc atggtgtctg caacgctgtt   3000
ctgcttccgc atgttctggc ttataacgcc tctgtcgttg ctggtcgtct gaaagacgtt   3060
ggtgttgcta tgggtctcga tatcgccaat ctcggtgata agaaggcgc agaagccacc   3120
attcaggctg ttcgcgatct ggctgcttcc attggtattc cagcaaatct gaccgagctg   3180
ggtgctaaga agaagatgt gccgcttctt gctgaccacg ctctgaaaga tgcttgtgct   3240
ctgaccaacc cgcgtcaggg tgatcagaaa gaagttgaag aactcttcct gagcgctttc   3300
taatttcaaa acaggaaaac ggttttccgt cctgtcttga ttttcaagca acaatgcct    3360
ccgatttcta atcggaggca tttgttttg tttattgcaa aaacaaaaa tattgttaca    3420
aattttaca ggctattaag cctaccgtca taaataattt gccatttggg gatcccggta   3480
gagggaaacc gttgtggtct ccctatagtg agtcgtatta atttcgcggg atcgagatcc   3540
tttttgataa tctcatgacc aaaatccctt aacgtgagtt ttcgttccac tgagcgtcag   3600
accccgtaga aagatcaaa ggatcttctt gagatccttt ttttctgcgc gtaatctgct   3660
gcttgcaaac aaaaaaacca ccgctaccag cggtggtttg tttgccggat caagagctac   3720
caactctttt tccgaaggta actggcttca gcagagcgca gataccaaat actgtccttc   3780
tagtgtagcc gtagttaggc caccacttca agaactctgt agcaccgcct acatacctcg   3840
ctctgctaat cctgttacca gtggctgctg ccagtggcga taagtcgtgt cttaccgggt   3900
tggactcaag acgatagtta ccggataagg cgcagcggtc gggctgaacg ggggggttcgt  3960
```

```
gcacacagcc cagcttggag cgaacgacct acaccgaact gagataccta cagcgtgagc    4020
attgagaaag cgccacgctt cccgaaggga gaaaggcgga caggtatccg gtaagcggca    4080
gggtcggaac aggagagcgc acgagggagc ttccaggggg aaacgcctgg tatctttata    4140
gtcctgtcgg gtttcgccac ctctgacttg agcgtcgatt tttgtgatgc tcgtcagggg    4200
ggcggagcct atggaaaaac gccagcaacg cggcctttt acggttcctg gccttttgct     4260
ggccttttgc tcacatgttc tttcctgcgt tatcccctga ttctgtggat aaccgtatta    4320
ccgcctttga gtgagctgat accgctcgcc gcagccgaac gaccgagcgc agcgagtcag    4380
tgagcgagga agcggaagag cgcctgatgc ggtattttct ccttacgcat ctgtgcggta    4440
tttcacaccg catatggtgc actctcagta caatctgctc tgatgccgca tagttaagcc    4500
agtatacact ccgctatcgc tacgtgactg ggtcatggct gcgccccgac acccgccaac    4560
acccgctgac gcgccctgac gggcttgtct gctcccggca tccgcttaca gacaagctgt    4620
gaccgtctcc gggagctgca tgtgtcagag gttttcaccg tcatcaccga aacgcgcgag    4680
gcagctgcgg taaagctcat cagcgtggtc gtgaagcgat tcacagatgt ctgcctgttc    4740
atccgcgtcc agctcgttga gtttctccag aagcgttaat gtctggcttc tgataaagcg    4800
ggcctgccac catacccacg ccgaaacaag cgctcatgag cccgaagtgg cgagcccgat    4860
cttccccatc ggtgatgtcg gcgatatcct cgtgatgatc agtgatggaa aaagcactgt    4920
aattcccttg gttttggct gaaagtttcg gactcagtag acctaagtac agagtgatgt     4980
caacgccttc aagctagacg ggaggcggct tttgccatgg ttcagcgatc gctcctcatc    5040
ttcaataagc agggcatgag ccagcgttaa gcaaatcaaa tcaaatctcg cttctgggct    5100
tcaataaatg gttccgattg atgataggtt gattcatgca agcttggagc acaggatgac    5160
gcctaacaat tcattcaagc cgacaccgct tcgcggcgcg gcttaattca ggagttaaac    5220
atcatgaggg aagcggtgat cgccgaagta tcgactcaac tatcagaggt agttggcgtc    5280
atcgagcgcc atctcgaacc gacgttgctg gccgtacatt tgtacggctc cgcagtggat    5340
ggcggcctga agccacacag tgatattgat ttgctggtta cggtgaccgt aaggcttgat    5400
gaaacaacgc ggcgagcttt gatcaacgac cttttggaaa cttcggcttc ccctggagag    5460
agcgagattc tccgcgctgt agaagtcacc attgttgtgc acgacgacat cattccgtgg    5520
cgttatccag ctaagcgcga actgcaattt ggagaatggc agcgcaatga cattcttgca    5580
ggtatcttcg agccagccac gatcgacatt gatctggcta tcttgctgac aaaagcaaga    5640
gaacatagcg ttgccttggt aggtccagcg gcggaggaac tctttgatcc ggttcctgaa    5700
caggatctat ttgaggcgct aaatgaaacc ttaacgctat ggaactcgcc gcccgactgg    5760
gctggcgatg agcgaaatgt agtgcttacg ttgtcccgca tttggtacag cgcagtaacc    5820
ggcaaaatcg cgccgaagga tgtcgctgcc gactgggcaa tggagcgcct gccggcccag    5880
tatcagcccg tcatacttga agctaggcag gcttatcttg acaagaaga tcgcttggcc     5940 tcgcgcgcag atcagttgga agaatttgtt cactacgtga aggcgagat caccaaggta     6000 gtcggcaaat aatgtctaac aattcgttca agccgacgcc gcttcgcggc gcggcttaac    6060
tcaagcgtta gagagctggg gaagactatg cgcgatctgt tgaaggtggt tctaagcctc    6120
gtacttgcga tggcatcggg gcaggcactt gctgacctgc aattgttttt agtggatgaa    6180
gctcgtcttc cctatgacta ctccccatcc aactacgaca tttctccaag caactacgac    6240
aactccataa gcaattacga caatagtcca tcaaattacg acaactctga gagcaactac    6300
```

```
gataatagtt catccaatta cgacaatagt cgcaacggaa atcgtaggct tatatatagc      6360
gcaaatgggt ctcgcacttt cgccggctac tacgtcattg ccaacaatgg gacaacgaac      6420
ttcttttcca catctggcaa aaggatgttc tacaccccaa aagggggcg cggcgtctat       6480 ggcggcaaag atgggagctt ctgcggggca ttggtcgtca taaatggcca attttcgctt      6540
gccctgacag ataacggcct gaagatcatg tatctaagca actagcctgc tctctaataa     6600
aatgttaggc ctcaacatct agtcgcaagc tgagggaac cactagcagc acgccatagt      6660
gactggcgat gctgtcggaa tggacgatat ctagacttat atagacacta atatagacaa     6720
tagtttatac tgctatctat acaagtatag acattatcta atcatggcag acaaaactct     6780
agccactttt cgtattgact ccgaagaatg ggagtctttt aaaaaccttg ctagttctga     6840
aagttccaac gcctcagcac tgttaacaga atttgttcgt tggtatttgg caggtaacag     6900
gtttaatact cccacttctc acactcccac ccatctagac acatccctcg aacagcgtat     6960
agacaatatt gaacaacgtc tagataaagt cacaactaat aatctagaca atatagatga    7020
atttatagac aagcgtatag aagataatct agcaacacgt ctagacaaac ttcaatcgca    7080
actggaggaa ctgcggggaa aatcgaaagc ccggtagttc aggcagaagg acaagctacc    7140
gggcaagaca gaaagaatat agacaatagt atagacaatc tagacaaatt ggaggcaacc    7200
cgcgatcgca ccctcaataa gctaaaaatg ggtaggcagt cagccgccgg gaaagccatc    7260
gacgcgttta tcaaagagtt gctttcttca ggagacaaca taagctgaag ttatcaaaat    7320
tctgtcctta cgtcgaaagc ctgattttac cgtgcaacga ttgataagct tggctaaact    7380
agcactggct ttcaacagaa agcatacgaa gaatcaatag atatagccac caattccaca    7440
aaatgcagat aacgtgtaga gtattggaat gcttaatctg taagggttat gaaggttaac    7500
ggcaacggac gagccaaaat actcacctcc gacgaactca ggcgactgtt tagcgacgga    7560
ttcaccacac cgcgcgatcg cgttttgttt ggcatctgtc tattcaccgg ttgccgcgtt    7620
agtgaagctc tagcactcca aacaacggac attaaaggcg aaacactaac ctttaggaag    7680
tctaccacca aagggaaact caaaacccgc gtggttgaca tccagccagg actagccgca    7740 ctcatgctg actatcaccc caaaccggga accctgttcc ctggcatgag gggagtcagc     7800
gataggctca cgcgatacgc ggcggataaa atcttgcgcg atgcagccaa aagaatcggg    7860
ctagaaggca tcagtaccca cagtttccgc cgtactgccc tcaaccaaat gtctagcgcc    7920
ggtatcccgt tgcgacacat tcaagagata tccggtcaca atgaccttgg cacactgcaa    7980
cgctatcttg aagttacacc cgaacagcga cgcaaagctg tatccgtgat tggcttctaa    8040
tgtacgccaa cgctgtttag acccctatgg gtgctaaaaa aagacgcagc ctaaacacac    8100
gctctacact tgaggatact tttaaagtat ccatcggttc tagaactctg cacacgttcc    8160
ggactttgga aacgttatac ctttccctgt gttgcagaat gctgcaatat ttcttcgaca    8220
agttaacttg tgactggttt aatattttct caaattgccc caaaacaaca cgcctaaatc    8280
cttagacgtt tctgtggaaa cctattaggt ttttatcgcc gttgttttag tggtaaaccc    8340
aaagggtttg tatattcttg tatgaagttc gactctgagg gttaagaaga atggctcgcc    8400
gaatttttta caagtggaaa ccgattaaag gttaagggtc aatcgggacg atgaatattt    8460
tctaattgtg accttctcca tctaataagc tttctttggg gttaaggtcg aagaaagtac    8520
tacgcatgat ctgcatacga tctctattgc caaaaagccg cgaccctata ggctctcggt    8580
catgctgcac tagttcgtgt cgatcactat actggttgcc gcagcatttc acgctaaaaa    8640
aaaattctta aaaatgtcct tcatatctcg ccagagtggc aacctattac aaaacggttg    8700
```

```
cctacccgac cggctcgatt ttcgctgaag tggcactgtg acagtttgaa atggtacttc    8760
cgccgtgctg ctgacatcgt tgttagggtg aattgttcgc ggtagatgtt gcaccgattc    8820
atgaacacct tgtcacccac tttgaataat cgaccgtcaa attcagtcgc gtcaatttgg    8880
taagtgttgg gctgtctctt tttggctcca ggggcaatgc catcagaaaa cacaaccgcg    8940
tcacccataa cttgataacc gatatcagtt ttggttccag tgaaagccca aaattcagac    9000
gcgtcattat tccgagcgtg ccggagttga ttgtactcaa ttttggcttg caaagttga     9060 cggcgattca tgcccagctg cttttgatgt cgtcgcactg tgcgcttgtg aatacccaac    9120
tcacagctga cagcttttg agatgtacca tagtggatga aacttttga dacgaatatc     9180 cgcgacgaac taatgtgaag tacacaaggt acttccccct ctggcgattt aagagaggat    9240
tgccttgtgt cctcactag ctcgttcggg tgtggcgctc caaaaagttt tctgtactct     9300
ggtttaagtt gtctgttggc cgcatagcgg ctcttttgtt gaaagctttg tgtgactatg    9360
ccagtggtca gtgagcgtaa atcgcttaac acttggacta aaggcactac tgcaacatca    9420
ccccatcttt ttaaatttag gttgtaacaa acttgaaaca taccgcccaa gtagacggtt    9480
atcattcctg ctttaatttt gtagcggcgg aatgctccta ttttttttcc atcctgtaac    9540
caacggtaaa cagacttatc actacaatct aagaacgtct gtactacagg caatggcaat    9600
gttaaatgac cagacccatc cttatcaagc gctcgacaca ataccacaa ccgcgcacaa     9660 ggttctcgac caatgcgagt gtgtaccctg accgtgtaag tgccaagaat tatttcagtt    9720
tgtagttccc ttgtaagcag ggttagtgat acatttgtat ttaagctttc tgggctgatc    9780
atttggaaat gtctcagtcc agtacctatt gaatgttatt tgcttaacct gaagctaaat    9840
aaaacttgtt aactcacccc attaattgat aaattcaaag cacgtttttt ctgtttggtg    9900
tttggtgtgg taacaattct gtgtatgtgt gtttttattta gcttcggtta agtagcataa   9960 caaccccaa gcactgaact tttttttaata ggtaattaa acttgccta tcggcaaaat     10020 tttcaatcaa ttgtacgcca aagtgttgca tgatcaacgt ttgacttatt tttgtattta   10080
ctaaatactg aatttcgccg tgacgctttt tacagatgga aattcacggc aaaatgtttt   10140
ttgctaactt tgctatgtaa aacaagaaac ttggcactcg gttattacta aataaactgg   10200
taaaaaataa ccattagaac caaaaagaac gaaaaccagt acacccttgc cagttttcaa   10260
gcttttgcta tgacgactct aataatcggg tttaacacca ttccgctttg agaaaattat   10320
ccttgtacag caagtaacag tcaatgctaa accgcaccgc tacaaatcct taagtttttc   10380
cagtagcgat ttaccttctt ggtaacgccc gccttgatag cccaaaattt ctttaatcac   10440
cttactttct gaaaacccg cttccagaca ggcttttacc acttttgcta gggtttcatc    10500
tcttggttct gggagggatg aaacgggctg taatgcttgt tctgaggtcg gttgagccgt   10560
ttggagtggc tgaaaactgg ttacagactg taaccggggc ataaccattt tgtaactgct   10620
tacatctggt aactgacacg gcatatcatc caccatgcag cgatatttcc ccgactttaa   10680
ccactccaca agggcaaggt ctttttaagga cttggcgtgg ctaactgcaa acttacccag   10740
gcgtaacatc ctaaaacact tacggacacc gccttcaccc tcgataccta aggtcttgac   10800
attatcatct tgagtcagcc caataacaaa acgcttgggc ttgcggccgc gcctggcgtg   10860
tttgatgagc cattcggttg ctatctcgac ttcatctctc agcagtggca gttcttcagc   10920
aattaaaacg ctttctttc ctgctagtgc cttatcccca gactcacccc gtagctcaat    10980
ccggcgctgc aattcctcca ggtcagcagc catgcccgac tgtatagcct caaagtcacc   11040
```

```
acggcggcca atgacattta accccgtcca ctcgtccggt gcagcgtcag cgtcatagac   11100
tgtcacctca cccccgactt gataagcaag ccattgggct atggtgcttt tgccagttcc   11160
cgtatcccca actattaaac agtgcttacc agacagagct tgcatcaagt cggtgatgat   11220
tccctctggt tcgaccgcaa gggtgacggc ggtagtgtca atgatagccg cgccgtaagt   11280
gccagcatag ggcaattggt cgtaaacttt gaccaagttg tatacagact gtctacacca   11340
cttcaccact gttaacgctg tttgcaaagc gtaagacgtg gcatcaaata aaaatatgct   11400
ggcactaaaa gttaatcgcc ccaatcccca cagtaaaaac ctgcctagct gttgacgact   11460
aggcaagtgc atttcaatcc agtcatttgc cataaatcac cccgtctttta aagccttgca   11520 gttgagcgcg acaggtattt aactgtgctt gtaactctgt ttgctggttt tgataccaca   11580
gactgacggc ggcggccgcc agtcctaaaa atagaaactg gcgatcgctc attattgact   11640
tactccctgt tgattagcgt ggtagtgagt catagccgca ttgaccgctt cttgggcttg   11700
gggtgttctg ccaagattgg gttttgtagg gtcatcgttg gctacgacta aggacgcttg   11760
ttcggctatc gcttgcggga caccaacttt agttaactct gtcaaggata cttggtaaag   11820
tcgctcgttc attagccgat ctccggtac ataaaactgt tgctggcagt cccttcattg   11880
gcgacgagtt cttcagccgg agtatcagcg ataatgtcag cccagccggt gacattatta   11940
ttaataatgt tttgttcggc aattgcaccc aagccaggac gcgccgtttc aaactcagag   12000
atgacttgct gctcttttctc ggtgagtggt ctatctgtca tgataattat gtccttcatt   12060
atgtaggcga ttccagtggg tgtttacgag gcagtccaca ggaatcagtg cgattcacct   12120
ttaaggtgaa tcgtcatcaa aaaatcactc ggtagcaacg acccgaaccg accaggattg   12180
atttcccggt tctcagttcg caggcttttg agcgcgtcac cttgaccatt gggtaactgc   12240
catcagccga taagctaaac gggctgtata gcggtaaagc atcccacaca gtcgggctgg   12300
catcaacttt gcaggaatag ctcacgtcac tcatctcact cgcgcctggg ttggatggca   12360
gcgaaggcag attcgacgc agttttttac tggcacttt accccgcatta aaaacgggta   12420 cagtgccatt gttgacggtc tgtacttcgg tcatatactc ggtgtacact taatacactc   12480
tatactatta ctgccgatta gtacatttgt caatcactct ttgcacaagg tgtatgatat   12540
ggactcagga gtacaccaaa cgtcatgcca accaataaag ggagaatagc agtcactcta   12600
gaagctgaaa tttaccaatg gattgctaac cgagcgtctg aggaaggaag accgttggct   12660
aatcttgccg ctttcttact cacacgagtt gttaaagaac aaatggaaca agaagccaag   12720
gacaaccaag acaagcaggg ggcagcatga gcgaagacag actagccaga atagaagctg   12780
cgttagacag ccaagttgca gtgaatgccg acctccgcac atcggttaca gaactccgcg   12840
caaccgcaga agcattgttg caaacagttc aaatccatca gcagaacttt gaaattctta   12900
ccgctaggca attacaaacc gaagcacggc ttgatgagta ccaacgtacc actagcgcgg   12960
cactcgacag aattggcgcg gtcttagact acctcgttag gcagcaaaac ggttgaggtg   13020
agggatgagc gatgactatc tagacggata tcccgcaaga ggccctttcg tcttcaagaa   13080
ttctcatgtt tgacagctta tc                                          13102

<210> SEQ ID NO 107
<211> LENGTH: 12472
<212> TYPE: DNA
<213> ORGANISM: Artificial Sequence
<220> FEATURE:
<223> OTHER INFORMATION: synthetic combined bacterial sequences

<400> SEQUENCE: 107
```

-continued

```
ctagcgctat atgcgttgat gcaatttcta tgcgcacccg ttctcggagc actgtccgac      60
cgctttggcc gccgcccagt cctgctcgct tcgctacttg gagccactat cgactacgcg     120
atcatggcga ccacacccgt cctgtggatc actaccgggc gtattttttg agttatcgag     180
attttcagga gctaaggaag ctaaaatgga gaaaaaatc actggatata ccaccgttga      240
tatatcccaa tggcatcgta aagaacattt tgaggcattt cagtcagttg ctcaatgtac     300
ctataaccag accgttcagc tggatattac ggccttttta aagaccgtaa agaaaaataa     360
gcacaagttt tatccggcct ttattcacat tcttgcccgc ctgatgaatg ctcatccgga     420
attccgtatg gcaatgaaag acggtgagct ggtgatatgg gatagtgttc acccttgtta     480
caccgttttc catgagcaaa ctgaaacgtt ttcatcgctc tggagtgaat accacgacga     540
tttccggcag tttctacaca tatattcgca agatgtggcg tgttacggtg aaaacctggc     600
ctatttccct aaagggttta ttgagaatat gttttttcgtc tcagccaatc cctgggtgag     660
tttcaccagt tttgatttaa acgtggccaa tatggacaac ttcttcgccc cgttttcac      720 catgggcaaa tattatacgc aaggcgacaa ggtgctgatg ccgctggcga ttcaggttca     780
tcatgccgtt tgtgatggct tccatgtcgg cagaatgctt aatgaattac aacagtactg     840
cgatgagtgg cagggcgggg cgtaatttttt ttaaggcagt tattggtgcc cttaaacgcc     900
tggtgctacg cctgaataag tgataataag cggatgaatg gcagaaattc gaaagcaaat     960
tcgacccggt cgtcggttca gggcagggtc gttaaatagc cgcttatgtc tattgctggt    1020
ttaccggttt attgactacc ggaagcagtg tgaccgtgtg cttctcaaat gcctgaggcc    1080
agtttgctca ggctctcccc gtggaggtaa taattgacga tatgatcctc tacgccggac    1140
gcatcgtggc cggcatcacc ggcgataagc ttcacgctgc cgcaagcact cagggcgcaa    1200
gggctgctaa aggaagcgga acacgtagaa agccagtccg cagaaacggt gctgaccccg    1260
gatgaatgtc agctactggg ctatctggac aagggaaaac gcaagcgcaa agagaaagca    1320
ggtagcttgc agtgggctta catggcgata gctagactgg gcggttttat ggacagcaag    1380
cgaaccggaa ttgccagctg gggcgccctc tggtaaggtt gggaagccct gcaaagtaaa    1440
ctggatggct ttcttgccgc caaggatctg atggcgcagg ggatcaagat ctgatcaaga    1500
gacaggatga ggatcgtttc gcatgattga acaagatgga ttgcacgcag gttctccggc    1560
cgcttgggtg gagaggctat tcggctatga ctgggcacaa cagacaatcg gctgctctga    1620
tgccgccgtg ttccggctgt cagcgcaggg gcgcccggtt cttttttgtca agaccgacct    1680 gtccggtgcc ctgaatgaac tgcaggacga ggcagcgcgg ctatcgtggc tggccacgac    1740
gggcgttcct tgcgcagctg tgctcgacgt tgtcactgaa gcgggaaggg actggctgct    1800
attgggcgaa gtgccgggc aggatctcct gtcatctcac cttgctcctg ccgagaaagt    1860
atccatcatg gctgatgcaa tgcggcggct gcatacgctt gatccggcta cctgcccatt    1920
cgaccaccaa gcgaaacatc gcatcgagcg agcacgtact cggatggaag ccggtcttgt    1980
cgatcaggat gatctggacg aagagcatca ggggctcgcg ccagccgaac tgttcgccag    2040
gctcaaggcg cgcatgcccg acggcgagga tctcgtcgtg acccatggcg atgcctgctt    2100
gccgaatatc atggtggaaa atggccgctt ttctggattc atcgactgtg gccggctggg    2160
tgtggcggac cgctatcagg acatagcgtt ggctacccgt gatattgctg aagagcttgg    2220
cggcgaatgg gctgaccgct tcctcgtgct ttacggtatc gccgctcccg attcgcagcg    2280
catcgccttc tatcgccttc ttgacgagtt cttctgagcg ggactctggg gttcgaaatg    2340
```

```
accgaccaag cgacgcccaa cctgccatca cgagatttcg attccaccgc cgccttctat    2400
gaaaggttgg gcttcggaat cgttttccgg gacgccggct ggatgatcct ccagcgcggg    2460
gatctcatgc tggagttctt cgcccacccc aacgatctga tagagaaggg tttgctcggg    2520
tcggtggctc tggtaacgac cagtatcccg atcccggctg ccgtcctgg ccgccacatg     2580 aggcatgttc cgcgtccttg caatactgtg tttacataca gtctatcgct tagcggaaag    2640
ttcttttacc ctcagccgaa atgcctgccg ttgctagaca ttgccagcca gtgcccgtca    2700
ctcccgtact aactgtcacg aaccctgca ataactgtca cgccccctg caataactgt      2760 cacgaacccc tgcaataact gtcacgcccc aaacctgca acccagcag gggcgggggc      2820 tggcggggtg ttggaaaaat ccatccatga ttatctaaga ataatccact aggcgcggtt    2880
atcagcgccc ttgtgggcg ctgctgccct tgcccaatat gccggccag aggccggata      2940 gctggtctat tcgctgcgct aggctacaca ccgcccacc gctgcgcggc aggggaaag      3000 gcgggcaaag cccgctaaac cccacaccaa accccgcaga aatacgctgg agcgcttta     3060 gccgctttag cggccttcc ccctacccga agggtggggg cgcgtgtgca gccccgcagg    3120
gcctgtctcg gtcgatcatt cagcccggct catccttctg gcgtggcggc agaccgaaca    3180
aggcgcggtc gtggtcgcgt tcaaggtacg catccattgc cgccatgagc cgatcctccg    3240
gccactcgct gctgttcacc ttggccaaaa tcatggcccc caccagcacc ttgcgccttg    3300
tttcgttctt gcgctcttgc tgctgttccc ttgcccgctc ccgctgaatt tcggcattga    3360
ttcgcgctcg ttgttcttcg agcttggcca gccgatccgc cgccttgttg ctccccttaa    3420
ccatcttgac accccattgt taatgtgctg tctcgtaggc tatcatggag gcacagcggc    3480
ggcaatcccg accctacttt gtaggggagg gcgcacttac cggtttctct tcgagaaact    3540
ggccctaacg gccaccttc gggcggtgcg ctctccgagg gccattgcat ggagccgaaa     3600
agcaaaagca acagcgaggc agcatggcga tttatcacct tacggcgaaa accggcagca    3660
ggtcgggcgg ccaatcggcc agggccaagg ccgactacat ccagcgcgaa ggcaagtatg    3720
cccgcgacat ggatgaagtc ttgcacgccg aatccgggca catgccggag ttcgtcgagc    3780
ggcccgccga ctactgggat gctgccgacc tgtatgaacg cgccaatggg cggctgttca    3840
aggaggtcga atttgccctg ccggtcgagc tgaccctcga ccagcagaag gcgctggcgt    3900
ccgagttcgc ccagcacctg accggtgccg agcgcctgcc gtatacgctg gccatccatg    3960
ccggtggcgg cgagaacccg cactgccacc tgatgatctc cgagcggatc aatgacggca    4020
tcgagcggcc cgccgctcag tggttcaagc ggtacaacgg caagacccg gagaagggcg     4080 gggcacagaa gaccgaagcg ctgaagccca aggcatggct tgagcagacc cgcgaggcat    4140
gggccgacca tgccaaccgg gcattagagc gggctggcca cgacgcccgc attgaccaca    4200
gaacacttga ggcgcagggc atcgagcgcc tgcccggtgt tcacctgggg ccgaacgtgg    4260
tggagatgga aggccgggc atccgcaccg accgggcaga cgtggccctg aacatcgaca    4320
ccgccaacgc ccagatcatc gacttacagg aataccggga ggcaatagac catgaacgca    4380
atcgacagag tgaagaaatc cagaggcatc aacgagttag cggagcagat cgaaccgctg    4440 gcccagcagca tggcgacact ggccgacgaa gcccggcagg tcatgagcca gaccaagcag    4500
gccagcgagg cgcaggcggc ggagtggctg aaagcccagc gccagacagg ggcggcatgg    4560
gtggagctgg ccaaagagtt gcggaggta gccgccgagg tgagcagcgc cgcgcagagc     4620
gccccggagc cgtcgcgggg gtggcactgg aagctatggc taaccgtgat gctggcttcc    4680
atgatgccta cggtggtgct gctgatcgca tcgttgctct tgctcgacct gacgccactg    4740
```

```
acaaccgagg acggctcgat ctggctgcgc ttggtggccc gatgaagaac gacaggactt    4800
tgcaggccat aggccgacag ctcaaggcca tgggctgtga gcgcttcgat atcggcgtca    4860
gggacgcacc caccggccag atgatgaacc gggaatggtc agccgccgaa gtgctccaga    4920
acacgccatg gctcaagcgg atgaatgccc agggcaatga cgtgtatatc aggcccgccg    4980
agcaggagcg gcatggtctg gtgctggtgg acgacctcag cgagtttgac ctggatgaca    5040
tgaaagccga gggccgggag cctgccctgg tagtggaaac cagcccgaag aactatcagg    5100
catgggtcaa ggtggccgac gccgcaggcg gtgaacttcg ggggcagatt gcccggacgc    5160
tggccagcga gtacgacgcc gacccggcca gcgccgacag ccgccactat ggccgcttgg    5220
cgggcttcac caaccgcaag gacaagcaca ccacccgcgc cggttatcag ccgtgggtgc    5280
tgctgcgtga atccaagggc aagaccgcca ccgctggccc ggcgctggtg cagcaggctg    5340
gccagcagat cgagcaggcc cagcggcagc aggagaaggc ccgcaggctg ccagcctcg    5400
aactgcccga gcggcagctt agccgccacc ggcgcacggc gctggacgag taccgcagcg    5460
agatggccgg gctggtcaag cgcttcggtc atgacctcag caagtgcgac tttatcgccg    5520
cgcagaagct ggccagccgg ggccgcagtg ccgaggaaat cggcaaggcc atggccgagg    5580
ccagcccagc gctggcagag cgcaagcccg ccacgaagc ggattacatc gagcgcaccg    5640
tcagcaaggt catgggtctg cccagcgtcc agcttgcgcg ggccgagctg gcacgggcac    5700
cggcaccccg ccagcgaggc atggacaggg gcgggccaga tttcagcatg tagtgcttgc    5760
gttggtactc acgcctgtta tactatgagt actcacgcac agaaggggt tttatggaat    5820
acgaaaaaag cgcttcaggg tcggtctacc tgatcaaaag tgacaagggc tattggttgc    5880
ccggtggctt tggttatacg tcaaacaagg ccgaggctgg ccgcttttca gtcgctgata    5940
tggccagcct taaccttgac ggctgcacct tgtccttgtt ccgcgaagac aagcctttcg    6000
gccccggcaa gtttctcggt gactgatatg aaagaccaaa aggacaagca gaccggcgac    6060
ctgctggcca gccctgacgc tgtacgccaa gcgcgatatg ccgagcgcat gaaggccaaa    6120
gggatgcgtc agcgcaagtt ctggctgacc gacgacgaat acgaggcgct gcgcgagtgc    6180
ctggaagaac tcagagcggc gcagggcggg ggtagtgacc ccgccagcgc ctaaccacca    6240
actgcctgca aaggaggcaa tcaatggcta cccataagcc tatcaatatt ctggaggcgt    6300
tcgcagcagc gccgccaccg ctggactacg ttttgcccaa catggtggcc ggtacggtcg    6360
gggcgctggt gtcgcccggt ggtgccggta atccatgct ggccctgcaa ctggccgcac    6420
agattgcagg cgggccggat ctgctggagg tgggcgaact gcccaccggc ccggtgatct    6480
acctgcccgc cgaagacccg cccaccgcca ttcatcaccg cctgcacgcc cttggggcgc    6540
acctcagcgc cgaggaacgg caagccgtgg ctgacggcct gctgatccag ccgctgatcg    6600
gcagcctgcc caacatcatg gcccggagt ggttcgacgg cctcaagcgc gccgccgagg    6660
gccgccgcct gatggtgctg acacgctgc gccggttcca catcgaggaa gaaaacgcca    6720
gcggcccat ggcccaggtc atcggtcgca tggaggccat cgccgccgat accgggtgct    6780
ctatcgtgtt cctgcaccat gccagcaagg gcgcggccat gatgggcgca ggcgaccagc    6840
agcaggccag ccggggcagc tcggtactgg tcgataacat ccgctggcag tcctacctgt    6900
cgagcatgac cagcgccgag gccgaggaat ggggtgtgga cgacgaccag cgccggttct    6960
tcgtccgctt cggtgtgagc aaggccaact atggcgcacc gttcgctgat cggtggttca    7020
ggcggcatga cggcggggtg ctcaagcccg ccgtgctgga gaggcagcgc aagagcaagg    7080
```

```
gggtgccccg tggtgaagcc taagaacaag cacagcctca gccacgtccg gcacgacccg    7140
gcgcactgtc tggcccccgg cctgttccgt gccctcaagc ggggcgagcg caagcgcagc    7200
aagctggacg tgacgtatga ctacggcgac ggcaagcgga tcgagttcag cggcccggag    7260
ccgctgggcg ctgatgatct gcgcatcctg caagggctgg tggccatggc tgggcctaat    7320
ggcctagtgc ttggcccgga acccaagacc gaaggcggac ggcagctccg gctgttcctg    7380
gaacccaagt ggggaggccgt caccgctgaa tgccatgtgg tcaaaggtag ctatcgggcg    7440
ctggcaaagg aaatcggggc agaggtcgat agtggtgggg cgctcaagca catacaggac    7500
tgcatcgagc gccttttggaa ggtatccatc atcgcccaga atggccgcaa gcggcagggg    7560
tttcggctgc tgtcggagta cgccagcgac gaggcggacg ggcgcctgta cgtggccctg    7620
aaccccttga tcgcgcaggc cgtcatgggg ggcggccagc atgtgcgcat cagcatggac    7680
gaggtagcgg gcgctggaca gcgaaaccgc ccgcctgctg caccagcggc tgtgtggctg    7740
gatcgacccc ggcaaaaccg gcaaggcttc catagatacc ttgtgcggct atgtctggcc    7800
gtcagaggcc agtggttcga ccatgcgcaa gcgccgcaag cgggtgcgcg agcgttgccg    7860
gagctggtcg cgctgggctg gacggtaacc gagttcgcgg cgggcaagta cgacatcacc    7920
cggcccaagg cggcaggctg accccccccca ctctattgta aacaacacat ttttatcttt    7980
tatattcaat ggcttatttt cctgctaatt ggtaatacca tgaaaaatac catgctcaga    8040
aaaggcttaa caatattttg aaaaattgcc tactgagcgc tgccgcacag ctccataggc    8100
cgcttttccag gctttgcttc cagatgtatg ctcttctgct cctgcagttc attcagggca    8160
ccggacaggt cggtcttgac aaaaagaacc gggcgcccct gcgctgacag ccggaacacg    8220
gcggcatcag agcagccgat tgtctgttgt gcccagtcat agccgaatag cctctccacc    8280
caagcggccg gagaacctgc gtgcaatcca tcttgttcaa tcatgcgaaa cgatcctcat    8340
cctgtctctt gatcattgat cccctgcgcc atcagatcct tggcggcaag aaagccatcc    8400
agttactttt gcagggcttc ccaaccttac cagagggcgc cccagctggc aattccggtt    8460
cgcttgctgt ccataaaacc gcccagtcta gctatcgcca tgtaagccca ctgcaagcta    8520
cctgctttct ctttgcgctt gcgttttccc ttgtccagat agcccagtag ctgacattca    8580
tccggggtca gcaccgtttc tgcggactgg cttttctacgt gttccgcttc ctttagcagc    8640
ccttgcgccc tgagtgcttg cggcagcgtg aagcttatcg attcacaaaa aataggcaca    8700
cgaaaaacaa gttaagggat gcagtttatg cactagccta ggctcgagaa gcttgtcgac    8760
cttccagcac cacgtcaact ttgtttaact gctcccggag ttgtctttcc gctttggcaa    8820
tgtgcccggg ataccattgg attaaagcca tgagttgttc acttttttac tgacgagggc    8880
ttccggaggc cacgctccca cccataacag cttgccacat ccccgtcgga agttacgtta    8940
cccttgggcg atcgccaaaa atcagcatat atacaccaat tctaaataag atcttttaca    9000
ccgctactgc aatcaacctc atcaacaaaa ttccccctcta gcatccctgg aggcaaatcc    9060
tcacctggcc atgggttcaa ccctgcttaa catttcttaa taattttagt tgctataaat    9120
tctcatttat gccctataa taattcggga gtaagtgcta aagattctca actgctccat    9180
cagtggtttg agcttagtcc tagggaaaga ttggcgatcg ccgttgtggt taagccagaa    9240
taggtctcgg gtggacagag aacgctttat tctttgcctc catggcggca tcccacctag    9300
gtttctcggc acttattgcc ataatttatt atttgtcgtc tcaattaagg aggcaattct    9360
gtgaattctt atactgtcgg tacctattta gcggagcggc ttgtccagat tggtctcaag    9420
catcacttcg cagtcgcggg cgactacaac ctcgtccttc ttgacaacct gcttttgaac    9480
```

-continued

```
aaaaacatgg agcaggttta ttgctgtaac gaactgaact gcggtttcag tgcagaaggt    9540
tatgctcgtg ccaaaggcgc agcagcagcc gtcgttacct acagcgtcgg tgcgctttcc    9600
gcatttgatg ctatcggtgg cgcctatgca gaaaaccttc cggttatcct gatctccggt    9660
gctccgaaca acaatgatca cgctgctggt cacgtgttgc atcacgctct tggcaaaacc    9720
gactatcact atcagttgga aatggccaag aacatcacgg ccgcagctga agcgatttac    9780
accccagaag aagctccggc taaaatcgat cacgtgatta aaactgctct tcgtgagaag    9840
aagccggttt atctcgaaat cgcttgcaac attgcttcca tgccctgcgc cgctcctgga    9900
ccggcaagcg cattgttcaa tgacgaagcc agcgacgaag cttctttgaa tgcagcggtt    9960
gaagaaaccc tgaaattcat cgccaaccgc gacaaagttg ccgtcctcgt cggcagcaag    10020
ctgcgcgcag ctggtgctga agaagctgct gtcaaatttg ctgatgctct cggtggcgca    10080
gttgctacca tggctgctgc aaaaagcttc ttcccagaag aaaacccgca ttacatcggt    10140
acctcatggg gtgaagtcag ctatccgggc gttgaaaaga cgatgaaaga agccgatgcg    10200
gttatcgctc tggctcctgt cttcaacgac tactccacca ctggttggac ggatattcct    10260
gatcctaaga aactggttct cgctgaaccg cgttctgtcg tcgttaacgg cgttcgcttc    10320
cccagcgttc atctgaaaga ctatctgacc cgtttggctc agaaagtttc caagaaaacc    10380
ggtgctttgg acttcttcaa atccctcaat gcaggtgaac tgaagaaagc cgctccggct    10440
gatccgagtg ctccgttggt caacgcagaa atcgcccgtc aggtcgaagc tcttctgacc    10500
ccgaacacga cggttattgc tgaaaccggt gactcttggt tcaatgctca gcgcatgaag    10560
ctcccgaacg gtgctcgcgt tgaatatgaa atgcagtggg gtcacatcgg ttggtccgtt    10620
cctgccgcct tcggttatgc cgtcggtgct ccggaacgtc gcaacatcct catggttggt    10680
gatggttcct tccagctgac ggctcaggaa gtcgctcaga tggttcgcct gaaactgccg    10740
gttatcatct tcttgatcaa taactatggt tacaccatcg aagttatgat ccatgatggt    10800
ccgtacaaca acatcaagaa ctgggattat gccggtctga tggaagtgtt caacggtaac    10860
ggtggttatg acagcggtgc tggtaaaggc ctgaaggcta aaaccggtgg cgaactggca    10920
gaagctatca aggttgctct ggcaaacacc gacggcccaa ccctgatcga atgcttcatc    10980
ggtcgtgaag actgcactga agaattggtc aaatggggta agcgcgttgc tgccgccaac    11040
agccgtaagc ctgttaacaa gctcctctag ttttgggga tcaattcgag ctcggtaccc    11100
aaactagtat gtagggtgag gttatagcta tggcttcttc aacttttat attcctttcg    11160 tcaacgaaat gggcgaaggt tcgcttgaaa agcaatcaa ggatcttaac ggcagcggct    11220
ttaaaaatgc gctgatcgtt tctgatgctt tcatgaacaa atccggtgtt gtgaagcagg    11280
ttgctgacct gttgaaagca cagggtatta attctgctgt ttatgatggc gttatgccga    11340
acccgactgt taccgcagtt ctggaaggcc ttaagatcct gaaggataac aattcagact    11400
tcgtcatctc cctcggtggt ggttctcccc atgactgcgc caaagccatc gctctggtcg    11460
caaccaatgg tggtgaagtc aaagactacg aaggtatcga caaatctaag aaacctgccc    11520
tgcctttgat gtcaatcaac acgacggctg gtacggcttc tgaaatgacg cgtttctgca    11580
tcatcactga tgaagtccgt cacgttaaga tggccattgt tgaccgtcac gttacccga    11640 tggtttccgt caacgatcct ctgttgatgg ttggtatgcc aaaaggcctg accgccgcca    11700
ccggtatgga tgctctgacc cacgcatttg aagcttattc ttcaacggca gctactccga    11760
tcaccgatgc ttgcgccttg aaggctgcgt ccatgatcgc taagaatctg aagaccgctt    11820
```

```
gcgacaacgg taaggatatg ccagctcgtg aagctatggc ttatgcccaa ttcctcgctg   11880
gtatggcctt caacaacgct tcgcttggtt atgtccatgc tatggctcac cagttgggcg   11940
gctactacaa cctgccgcat ggtgtctgca acgctgttct gcttccgcat gttctggctt   12000
ataacgcctc tgtcgttgct ggtcgtctga agacgttgg tgttgctatg ggtctcgata   12060
tcgccaatct cggtgataaa gaaggcgcag aagccaccat tcaggctgtt cgcgatctgg   12120
ctgcttccat tggtattcca gcaaatctga ccgagctggg tgctaagaaa gaagatgtgc   12180
cgcttcttgc tgaccacgct ctgaaagatg cttgtgctct gaccaacccg cgtcagggtg   12240
atcagaaaga agttgaagaa ctcttcctga gcgctttcta atttcaaaac aggaaaacgg   12300
ttttccgtcc tgtcttgatt ttcaagcaaa caatgcctcc gatttctaat cggaggcatt   12360 tgttttttgtt tattgcaaaa acaaaaaata ttgttacaaa ttttttacagg ctattaagcc   12420 taccgtcata aataatttgc catttgggga tccgatacgt aacgcgtctg ca           12472
```

<210> SEQ ID NO 108
<211> LENGTH: 336
<212> TYPE: PRT
<213> ORGANISM: Synechocystis PCC6803

<400> SEQUENCE: 108

```
Met Ile Lys Ala Tyr Ala Ala Leu Glu Ala Asn Gly Lys Leu Gln Pro
1               5                  10                  15

Phe Glu Tyr Asp Pro Gly Ala Leu Gly Ala Asn Glu Val Glu Ile Glu
                20                  25                  30

Val Gln Tyr Cys Gly Val Cys His Ser Asp Leu Ser Met Ile Asn Asn
            35                  40                  45

Glu Trp Gly Ile Ser Asn Tyr Pro Leu Val Pro Gly His Glu Val Val
        50                  55                  60

Gly Thr Val Ala Ala Met Gly Glu Gly Val Asn His Val Glu Val Gly
65                  70                  75                  80

Asp Leu Val Gly Leu Gly Trp His Ser Gly Tyr Cys Met Thr Cys His
                85                  90                  95

Ser Cys Leu Ser Gly Tyr His Asn Leu Cys Ala Thr Ala Glu Ser Thr
            100                 105                 110

Ile Val Gly His Tyr Gly Gly Phe Gly Asp Arg Val Arg Ala Lys Gly
        115                 120                 125

Val Ser Val Val Lys Leu Pro Lys Gly Ile Asp Leu Ala Ser Ala Gly
    130                 135                 140

Pro Leu Phe Cys Gly Gly Ile Thr Val Phe Ser Pro Met Val Glu Leu
145                 150                 155                 160

Ser Leu Lys Pro Thr Ala Lys Val Ala Val Ile Gly Ile Gly Gly Leu
                165                 170                 175

Gly His Leu Ala Val Gln Phe Leu Arg Ala Trp Gly Cys Glu Val Thr
            180                 185                 190

Ala Phe Thr Ser Ser Ala Arg Lys Gln Thr Glu Val Leu Glu Leu Gly
        195                 200                 205

Ala His His Ile Leu Asp Ser Thr Asn Pro Glu Ala Ile Ala Ser Ala
    210                 215                 220

Glu Gly Lys Phe Asp Tyr Ile Ile Ser Thr Val Asn Leu Lys Leu Asp
225                 230                 235                 240

Trp Asn Leu Tyr Ile Ser Thr Leu Ala Pro Gln Gly His Phe His Phe
                245                 250                 255

Val Gly Val Val Leu Glu Pro Leu Asp Leu Asn Leu Phe Pro Leu Leu
```

```
            260                 265                 270
Met Gly Gln Arg Ser Val Ser Ala Ser Pro Val Gly Ser Pro Ala Thr
                275                 280                 285

Ile Ala Thr Met Leu Asp Phe Ala Val Arg His Asp Ile Lys Pro Val
        290                 295                 300

Val Glu Gln Phe Ser Phe Asp Gln Ile Asn Glu Ala Ile Ala His Leu
305                 310                 315                 320

Glu Ser Gly Lys Ala His Tyr Arg Val Val Leu Ser His Ser Lys Asn
                325                 330                 335

<210> SEQ ID NO 109
<211> LENGTH: 341
<212> TYPE: PRT
<213> ORGANISM: Oceanbacter sp. RED65

<400> SEQUENCE: 109

Met Ile Lys Ala Phe Ala Ala Asp Thr Ala Lys Gly Glu Leu Lys Pro
1               5                   10                  15

Phe Glu Tyr Glu Val Gly Glu Leu Gly Ser Gln Val Glu Ile Glu
            20                  25                  30

Val His Tyr Cys Gly Val Cys His Ser Asp Ile Ser Met Leu Asp Asn
        35                  40                  45

Glu Trp Gly Met Thr Gln Tyr Pro Phe Val Pro Gly His Glu Val Ala
    50                  55                  60

Gly Leu Ile Lys Gln Val Gly Ala Glu Val Asn His Leu Lys Val Gly
65                  70                  75                  80

Asp Arg Val Gly Leu Gly Trp Gln Ser Gly Tyr Cys Asn His Cys Glu
                85                  90                  95

Asn Cys Met Ser Gly Asp His Asn Leu Cys Gly Thr Ala Glu Met Thr
            100                 105                 110

Ile Val Gly Arg His Gly Gly Phe Ala Asp His Val Arg Ala Gln Ala
        115                 120                 125

Ser Ser Val Val Lys Leu Pro Asp Asp Ile His Met Ala Asp Ala Gly
    130                 135                 140

Pro Leu Phe Cys Gly Gly Val Thr Val Tyr Asn Pro Met Lys Gln Phe
145                 150                 155                 160

Asp Leu Lys Pro Thr Ala Lys Val Ala Val Ile Gly Ile Gly Gly Leu
                165                 170                 175

Gly His Met Ala Leu Gln Phe Leu Asn Ser Trp Gly Cys Glu Val Thr
            180                 185                 190

Ala Phe Thr Ser Thr Glu Glu Lys Arg Lys Glu Ala Ile Ala Leu Gly
        195                 200                 205

Ala His Lys Thr Leu Asn Ser Arg Asp Glu Gly Glu Leu Lys Gly Ala
    210                 215                 220

Ala Gly Ser Phe Asp Met Ile Ile Ser Thr Val Asn Val Ser Leu Asn
225                 230                 235                 240

Trp Glu Ala Tyr Ile Asn Thr Leu Lys Ala Lys Gly Arg Leu His Phe
                245                 250                 255

Val Gly Ala Val Leu Glu Pro Ile Gln Val Gly Val Phe Pro Leu Met
            260                 265                 270

Met Gly Gln Arg Ser Ile Ser Ala Ser Pro Val Gly Ser Pro Ser Thr
        275                 280                 285

Ile Ser Gln Met Leu Glu Phe Thr Ala Arg His Gln Ile Lys Pro Gln
    290                 295                 300
```

```
Val Glu Leu Phe Gln Lys Asp Gln Ile Asn Asp Ala Ile Asn His Val
305                 310                 315                 320

Arg Glu Gly Lys Ala Arg Tyr Arg Ala Val Ile Gln Phe Lys Ala Thr
                325                 330                 335

Ser Asp Asn Ser Ala
            340

<210> SEQ ID NO 110
<211> LENGTH: 337
<212> TYPE: PRT
<213> ORGANISM: Limnobacter sp. MED105

<400> SEQUENCE: 110

Met Glu Leu Ile Met Ile Asn Ala Tyr Ala Ala Phe Glu Ala Lys Gly
1               5                   10                  15

Pro Leu Lys Pro Phe Gln Tyr Asp Pro Gly Glu Leu Asn Ala Phe Asp
            20                  25                  30

Ile Glu Ile Asp Val Asp His Cys Gly Ile Cys His Ser Asp Val Ser
        35                  40                  45

Met Leu Asp Asn Asp Trp Gly Arg Ala Lys Tyr Pro Met Val Ala Gly
50                  55                  60

His Glu Ile Ile Gly Arg Val Ser Gln Val Gly Ser His Val Ser His
65                  70                  75                  80

Leu Ala Ile Gly Asp Val Val Gly Leu Gly Trp His Ser Gly Tyr Cys
                85                  90                  95

Glu Ser Cys Arg Met Cys Met Gly Gly Asp His Asn Leu Cys Ser Thr
            100                 105                 110

Ala Lys Gly Thr Ile Val Gly Arg His Gly Gly Phe Ala Asp Lys Val
        115                 120                 125

Arg Ala Gln Ala Val Ser Ala Val Lys Ile Pro Ala Gly Val Asn Pro
130                 135                 140

Ala Thr Ala Gly Pro Leu Leu Cys Gly Gly Ile Thr Val Tyr Asn Pro
145                 150                 155                 160

Leu Val Gln Phe Asn Ile Ser Pro Gln Ser Lys Val Ala Val Ile Gly
                165                 170                 175

Val Gly Gly Leu Gly His Met Ala Val Met Phe Leu Lys Ala Trp Gly
            180                 185                 190

Cys Glu Val Thr Ala Phe Ser Ser Asn Val Ser Lys Thr Asp Glu Leu
        195                 200                 205

Leu Gly Met Gly Ala His His Val Leu Asn Ser Lys Asp Pro Asp Ala
210                 215                 220

Leu Lys Lys Ala Ala Gly Ser Phe Asp Leu Ile Leu Ser Thr Val Asn
225                 230                 235                 240

Val Lys Leu Asp Trp Asn Ala Tyr Ile Gly Thr Leu Ala Pro Lys Gly
                245                 250                 255

Arg Leu His Phe Leu Gly Ala Val Leu Glu Pro Leu Asp Ile Gly Val
            260                 265                 270

Phe Gly Leu Met Gly Gln Gln Arg Ser Ile Ser Ser Ser Pro Val Gly
        275                 280                 285

Ser Pro Arg Val Ile Ala Asp Met Leu Lys Phe Ala Ala Leu His Asn
290                 295                 300

Ile Gln Pro Ile Val Glu Thr Tyr Ser Phe Asp Gln Ile Asn Glu Ala
305                 310                 315                 320

Val Asp Lys Val Arg Asn Gly Ser Pro Arg Phe Arg Val Val Leu Ser
                325                 330                 335
```

Arg

<210> SEQ ID NO 111
<211> LENGTH: 333
<212> TYPE: PRT
<213> ORGANISM: Psychrobacter cryohalolentis

<400> SEQUENCE: 111

```
Met Ile Asn Ala Tyr Ala Ala Lys Glu Lys Gly Gly Glu Phe Val Pro
1               5                   10                  15

Tyr Gln Tyr Asp Pro Gly Thr Leu Gly Asp His Glu Val Glu Ile Glu
            20                  25                  30

Val His Ser Cys Gly Ile Cys His Ser Asp Leu Ser Met Trp Gln Asn
        35                  40                  45

Glu Trp Gly Met Thr Gln Tyr Pro Phe Val Gly His Glu Val Ala
    50                  55                  60

Gly Lys Val Leu Ala Lys Gly Lys His Val Lys His Leu Glu Leu Gly
65                  70                  75                  80

Asp Lys Val Gly Leu Gly Trp His Lys Gly Tyr Cys Asn Val Cys Asp
                85                  90                  95

Leu Cys Ile Gly Gly Asp His Asn Leu Cys Pro Glu Gln Glu Gly Thr
            100                 105                 110

Ile Ile Gly Asn His Gly Gly Phe Ala Asp Lys Val Arg Ala Lys Asp
        115                 120                 125

Thr Ser Val Ile Lys Ile Pro Glu Gly Leu Asp Phe Asn Ala Val Gly
    130                 135                 140

Pro Leu Leu Cys Gly Gly Val Thr Val Phe Asn Pro Leu Met Gln Tyr
145                 150                 155                 160

Asp Ile Thr Pro Thr Ser Arg Val Ala Val Ile Gly Ile Gly Gly Leu
                165                 170                 175

Gly His Leu Ala Leu Gln Phe Ala Asn Ala Trp Gly Cys Glu Val Thr
            180                 185                 190

Ala Phe Thr Ser Glu Ser Lys Met Glu Glu Ala Lys Glu Met Gly Ala
        195                 200                 205

His His Ser Leu Asn Ser Arg Glu Asp Ser Glu Ile Glu Lys Ala Ala
    210                 215                 220

Gly Ser Phe Asp Leu Ile Ile Ser Thr Val Asn Val Asp Met Asn Trp
225                 230                 235                 240

Asp Val Val Ile Lys Thr Leu Arg Pro Lys Gly Lys Leu His Phe Val
                245                 250                 255

Gly Leu Leu Glu Ala Pro Leu Glu Ile Ser Ala Ala Pro Met Ile Met
            260                 265                 270

Ala Gln Asn Ser Leu Ser Gly Ser Pro Val Gly Ser Pro Ser Thr Leu
        275                 280                 285

Arg Lys Met Leu Asp Phe Ala Ala Arg His Asn Ile Gln Pro Val Thr
    290                 295                 300

Glu Thr Tyr Lys Met Ser Glu Ile Asn Glu Ala Phe Glu Arg Leu Glu
305                 310                 315                 320

Ser Gly Asn Ala Arg Tyr Arg Val Val Leu Glu Arg Asp
                325                 330
```

<210> SEQ ID NO 112
<211> LENGTH: 333
<212> TYPE: PRT
<213> ORGANISM: Verrucommicrobiae bacterium DG1235

<400> SEQUENCE: 112

```
Met Ile Lys Ala Tyr Ala Thr His Thr Pro Gly Gly Lys Leu Glu Pro
1               5                   10                  15

Phe Glu Tyr Asp Pro Gly Glu Leu Ala Pro Thr Asp Val Glu Ile Asn
                20                  25                  30

Val Glu His Cys Gly Ile Cys His Ser Asp Leu Ser Met Leu Asn Asn
            35                  40                  45

Glu Trp Gly Met Thr Thr Tyr Pro Phe Val Pro Gly His Glu Val Val
        50                  55                  60

Gly Thr Ile Gly Ala Ile Gly Ser Asp Val Lys Asn Leu Ala Pro Gly
65                  70                  75                  80

Gln Arg Val Gly Leu Gly Trp His Ser Ser Tyr Cys Thr Thr Cys Pro
                85                  90                  95

Ser Cys Leu Ser Gly Asp His Asn Leu Cys Gln Ala Ala Gly Thr
                100                 105                 110

Ile Val Gly Arg His Gly Gly Phe Ala Asp Lys Val Arg Ala Ser Ala
                115                 120                 125

Leu Ser Val Ile Pro Leu Pro Asp Ser Ile Asp Ala Ala Lys Ala Gly
130                 135                 140

Pro Leu Phe Cys Gly Gly Ile Thr Val Phe Asn Pro Leu Ile Gln Tyr
145                 150                 155                 160

Glu Val Ser Pro Thr Ala Lys Val Ala Val Ile Gly Ile Gly Gly Leu
                165                 170                 175

Gly His Met Ala Leu Ala Phe Leu Asn Ala Trp Gly Cys Glu Val Thr
                180                 185                 190

Ala Phe Thr Thr Ser Glu Ala Lys Arg Gln Glu Ala Leu Lys Leu Gly
                195                 200                 205

Ala His His Thr Leu Asn Ser Arg Asp Ala Ala Glu Ile Glu Ala Ala
            210                 215                 220

Ala Gly Arg Phe Asp Leu Ile Leu Ser Thr Val Asn Val Gly Leu Asp
225                 230                 235                 240

Trp Asn Gly Tyr Val Asn Thr Leu Lys Pro Lys Gly Arg Leu His Phe
                245                 250                 255

Leu Gly Ala Ala Leu Glu Pro Ile Gln Ile Gly Ala Phe Ser Leu Ile
                260                 265                 270

Met Ala Gln Arg Gln Ile Ser Gly Ser Pro Val Gly Ser Pro Ala Thr
                275                 280                 285

Ile Ala Lys Met Ile Glu Phe Ala Ala Leu His Lys Ile Glu Pro Val
                290                 295                 300

Thr Glu His Phe Lys Phe Asp Gln Ala Asn Glu Ala Leu Ala His Leu
305                 310                 315                 320

Glu Ser Gly Gln Ala Arg Tyr Arg Ile Val Leu Ser His
                325                 330
```

<210> SEQ ID NO 113
<211> LENGTH: 334
<212> TYPE: PRT
<213> ORGANISM: Saccharophagus degradans

<400> SEQUENCE: 113

```
Met Ile Lys Ala Tyr Ala Ala Met Glu Pro Gly Ala Ala Leu Val Pro
1               5                   10                  15

Phe Glu Tyr Glu Pro Gly Pro Leu Ala Asn Asn Glu Val Glu Leu Lys
                20                  25                  30
```

Val Glu Ser Cys Gly Ile Cys His Ser Asp Leu Ser Met Leu Asp Asn
            35                  40                  45

Glu Trp Gly Phe Thr Gln Tyr Pro Phe Val Gly His Glu Val Ile
    50                  55                  60

Gly Ile Val Glu Ala Val Gly Ser Ser Val Asn Asn Val Ala Val Gly
65                  70                  75                  80

Gln Arg Val Gly Leu Gly Trp His Ser Gly Tyr Cys Asn Thr Cys Ala
                85                  90                  95

Ser Cys Gln Ser Gly Asp Gln Asn Leu Cys Asn Ser Ala Gln Pro Thr
            100                 105                 110

Ile Ala Gly His His Gly Gly Phe Ala Asp Lys Val Arg Ala Asp Ala
            115                 120                 125

Asn Ala Val Val Ala Leu Pro Glu Gly Val Asn Pro Asp Ser Ala Gly
130                 135                 140

Pro Leu Phe Cys Gly Gly Ile Thr Val Phe Asn Pro Leu Val Gln Phe
145                 150                 155                 160

Gly Ile Lys Pro Thr Ser Lys Val Gly Val Ile Gly Ile Gly Gly Leu
                165                 170                 175

Gly His Ile Ala Leu Gln Phe Leu Asn Ala Trp Gly Cys Glu Val Thr
            180                 185                 190

Ala Phe Thr Ser Ser Glu Ser Lys Lys Glu Ala Leu Lys Leu Gly
            195                 200                 205

Ala His His Val Leu Asn Ser Ser Asp Ala Ala Gln Leu Glu Ala Ala
            210                 215                 220

Ala Gly Arg Phe Asp Phe Ile Ile Ser Thr Val Asn Val Lys Leu Asp
225                 230                 235                 240

Trp Asn Glu Tyr Leu Ala Thr Leu Ala Pro Lys Gly Arg Leu His Phe
                245                 250                 255

Val Gly Ala Thr Leu Ala Pro Leu Asp Ile Asn Val Phe Gln Leu Ile
            260                 265                 270

Gly Ser Gln Arg Glu Ile Ser Gly Ser Pro Val Gly Ser Pro Gly Thr
            275                 280                 285

Ile Ser Gln Met Leu Asp Phe Ala Ala Leu His Asn Ile Gln Pro Val
            290                 295                 300

Thr Glu Tyr Phe Arg Phe Asp Gln Ile Asn Glu Ala Leu Thr Lys Leu
305                 310                 315                 320

Arg Glu Gly Lys Ala His Tyr Arg Ile Val Leu Thr Asn Lys
                325                 330

<210> SEQ ID NO 114
<211> LENGTH: 333
<212> TYPE: PRT
<213> ORGANISM: Alteromonas macleodii

<400> SEQUENCE: 114

Met Ile Tyr Ala Tyr Ala Ala Lys Glu Ala Gly Gly Lys Leu Glu Lys
1               5                   10                  15

Phe Glu Tyr Asp Pro Gly Glu Leu Gly Ala His Asp Val Glu Ile Asp
                20                  25                  30

Val Glu Ser Cys Gly Ile Cys His Ser Asp Leu Ser Met Leu Asp Asn
            35                  40                  45

Glu Trp Gly Ile Thr Glu Phe Pro Phe Val Pro Gly His Glu Val Val
    50                  55                  60

Gly Thr Val Ser Lys Ile Gly Asp His Val Thr Ser Leu Lys Val Gly

```
                65                  70                  75                  80
Gln Arg Val Gly Leu Gly Trp His Ala Ser Tyr Cys Asn Ser Cys Arg
                    85                  90                  95
Thr Cys Glu Ala Gly Asp His Asn Leu Cys Ala Gly Ala Thr Met Thr
                100                 105                 110
Ile Gly Gly Arg His Gly Gly Phe Ala Asp Lys Val Arg Ala Gln Ala
            115                 120                 125
Arg Ala Val Ile Pro Leu Pro Glu Ser Ile Asp Ser Thr Lys Ala Gly
130                 135                 140
Pro Leu Phe Cys Gly Gly Ile Thr Val Phe Asn Pro Leu Val Gln Phe
145                 150                 155                 160
Asn Ile Ser Pro Thr Ser Glu Val Gly Val Val Ile Gly Gly Leu
                165                 170                 175
Gly His Leu Ala Leu Gln Phe Leu Asn Ala Trp Gly Cys Lys Val Val
            180                 185                 190
Ala Phe Thr Ser Ser Glu Ser Lys Glu Lys Glu Ala Leu Ser Leu Gly
            195                 200                 205
Ala Ser Glu Thr Ile Asn Ser Arg Asp Glu Asp Ile Lys Lys Ala
        210                 215                 220
Gln Gly Arg Phe Asp Leu Ile Ile Ser Thr Val Asn Val Lys Leu Asp
225                 230                 235                 240
Trp Asn Leu Tyr Leu Ser Thr Leu Ala Pro Lys Gly Arg Leu His Phe
                245                 250                 255
Val Gly Ala Thr Leu Glu Pro Leu Asp Ile Gly Ala Phe Asn Leu Ile
                260                 265                 270
Gly Gly Gln Lys Ser Val Ser Gly Ser Pro Val Gly Ser Pro Ala Thr
            275                 280                 285
Ile Lys Thr Met Leu Asp Phe Ala Ala His His Asp Ile Glu Pro Val
            290                 295                 300
Thr Glu Thr Phe Lys Phe Glu Asp Val Asn Lys Ala Ile Asp Arg Leu
305                 310                 315                 320
Arg Glu Gly Lys Ala His Tyr Arg Ile Val Leu Thr Arg
                325                 330

<210> SEQ ID NO 115
<211> LENGTH: 332
<212> TYPE: PRT
<213> ORGANISM: Acaryochloris marina MBIC11017

<400> SEQUENCE: 115

Met Val Asn Ala Tyr Ala Ala Phe Glu Gln Gly Val Leu Gln Pro
1               5                   10                  15
Phe Glu Tyr Asp Pro Gly Pro Leu Gly Arg Gln Gln Val Asp Ile Gln
                20                  25                  30
Val Glu Tyr Cys Gly Ile Cys His Ser Asp Leu Ser Met Ile Lys Asn
            35                  40                  45
Glu Trp Gly Met Thr Gln Tyr Pro Phe Val Pro Gly His Glu Ile Val
        50                  55                  60
Gly Ile Val Ala Glu Ile Gly Ser Glu Val Thr Thr Leu Arg Val Gly
65                  70                  75                  80
Gln Arg Val Gly Leu Gly Trp Tyr Ser Ser Ser Cys Met His Cys Glu
                85                  90                  95
Trp Cys Met Gly Gly Asp His Leu Cys Leu Ser Ala Glu Gly Thr
                100                 105                 110
```

Ile Val Gly Arg Pro Gly Gly Phe Ala Asp Gln Val Arg Ala Asp Gln
            115                 120                 125

Ser Trp Ile Val Pro Ile Pro Glu Ser Ile Asp Ser Ala Val Ala Gly
    130                 135                 140

Pro Leu Phe Cys Ala Gly Ile Thr Val Phe Gln Pro Ile Ile Gln Cys
145                 150                 155                 160

Gly Val Gln Pro Thr Asp Arg Val Ala Val Ile Gly Ile Gly Gly Leu
                165                 170                 175

Gly His Leu Ala Leu Gln Phe Leu Asn Ala Trp Gly Cys Glu Val Thr
            180                 185                 190

Ala Leu Ser Thr Gln Pro Asp Lys Glu Ala Glu Ala Arg Arg Leu Gly
        195                 200                 205

Ala His His Phe Val Asn Thr Arg Asp Pro Ala Ala Leu Gln Ala Ile
    210                 215                 220

Ala Asn Ser Cys Asp Tyr Ile Ile Ser Thr Val Asn Val Ser Leu Glu
225                 230                 235                 240

Trp Ser Ile Tyr Leu Asn Ala Leu Arg Pro Lys Gly Arg Leu His Leu
                245                 250                 255

Val Gly Val Ala Pro Asp Leu Ser Leu Pro Val Phe Pro Leu Leu Ala
            260                 265                 270

Gly Gln Arg Ser Ile Ser Gly Ser Pro Val Gly Ser Pro Ala Thr Ile
        275                 280                 285

Thr Lys Met Leu Asn Phe Val Ala Arg His Gly Leu Ala Pro Gln Thr
    290                 295                 300

Glu Val Phe Pro Leu Ala Gln Val Asn Glu Ala Leu Glu Lys Leu Arg
305                 310                 315                 320

Ser Gln His Pro Pro Tyr Arg Leu Ala Leu Lys Cys
                325                 330

<210> SEQ ID NO 116
<211> LENGTH: 335
<212> TYPE: PRT
<213> ORGANISM: Cyanothece sp. PCC 7424

<400> SEQUENCE: 116

Met Ile Arg Ala Tyr Ala Ala His Glu Pro Gly Gly Lys Leu Glu Pro
1               5                   10                  15

Phe Glu Tyr Glu Pro Gly Ser Leu Gly Asp Glu Val Asp Ile Lys
                20                  25                  30

Val Glu Tyr Cys Gly Ile Cys His Ser Asp Leu Ser Met Leu Lys Asn
            35                  40                  45

Asp Trp Gly Met Thr Gln Tyr Pro Phe Val Pro Gly His Glu Val Val
    50                  55                  60

Gly Val Val Glu Ala Val Gly Ser Lys Val Lys Asn Leu Gln Ile Gly
65                  70                  75                  80

Gln Lys Val Gly Leu Gly Trp Tyr Ser Arg Ser Cys Met Thr Cys Glu
                85                  90                  95

Phe Cys Met Ser Gly Asn His Asn Leu Cys Gln Asp Ala Glu Gly Thr
            100                 105                 110

Ile Val Gly Arg Tyr Gly Gly Phe Ala Glu Lys Val Arg Ala His Gln
        115                 120                 125

Gly Trp Val Ile Pro Leu Pro Glu Gly Val Asn Pro Val Thr Ala Gly
    130                 135                 140

Pro Leu Phe Cys Gly Gly Ile Thr Val Phe Asn Pro Ile Val Gln Phe
145                 150                 155                 160

```
Asn Ile Lys Pro Thr Asp Gln Val Gly Val Ile Gly Ile Gly Gly Leu
                165                 170                 175

Gly His Met Ala Leu Gly Phe Leu Arg Ala Trp Gly Cys Glu Ile Thr
            180                 185                 190

Ala Phe Ser Thr Ser Pro Asp Lys Glu Ala Glu Ala Lys Ala Leu Gly
        195                 200                 205

Ala Thr His Phe Val Asn Ser Arg Asp Pro Glu Ala Leu Lys Ala Leu
    210                 215                 220

Thr Asn Ser Phe Asp Val Ile Leu Ser Thr Val Asn Ala Asp Leu Asp
225                 230                 235                 240

Trp Pro Thr Tyr Ile Lys Leu Leu Arg Pro Gln Gly Arg Leu His Leu
                245                 250                 255

Val Gly Val Ile Pro Asn Pro Leu Ser Val Pro Ile Phe Pro Met Ile
            260                 265                 270

Leu Gly Gln Lys Ser Val Ser Ala Ser Pro Leu Gly Ser Pro Thr Thr
        275                 280                 285

Ile Ala Gln Met Leu Asn Phe Ala Gly Arg His His Leu Glu Pro Ile
    290                 295                 300

Val Glu Phe Phe Pro Leu Glu Gln Val Asn Glu Ala Leu Glu Arg Leu
305                 310                 315                 320

Gln Ser Asn Lys Ala Arg Tyr Arg Ile Ile Leu Lys Met Asp His
                325                 330                 335

<210> SEQ ID NO 117
<211> LENGTH: 335
<212> TYPE: PRT
<213> ORGANISM: Cyanothece sp. PCC 7424

<400> SEQUENCE: 117

Met Ile Arg Ala Tyr Ala Ala His Glu Pro Gly Gly Lys Leu Glu Pro
1               5                   10                  15

Phe Glu Tyr Glu Pro Gly Ser Leu Gly Asp Glu Val Asp Ile Lys
            20                  25                  30

Val Glu Tyr Cys Gly Ile Cys His Ser Asp Leu Ser Met Leu Lys Asn
        35                  40                  45

Asp Trp Gly Met Thr Gln Tyr Pro Phe Val Pro Gly His Glu Val Val
    50                  55                  60

Gly Val Val Glu Ala Val Gly Ser Lys Val Lys Asn Leu Gln Ile Gly
65                  70                  75                  80

Gln Lys Val Gly Leu Gly Trp Tyr Ser Arg Ser Cys Met Thr Cys Glu
                85                  90                  95

Phe Cys Met Ser Gly Asn His Asn Leu Cys Gln Asp Ala Glu Gly Thr
            100                 105                 110

Ile Val Gly Arg Tyr Gly Gly Phe Ala Glu Lys Val Arg Ala His Gln
        115                 120                 125

Gly Trp Val Ile Pro Leu Pro Glu Gly Val Asn Pro Thr Ala Gly
    130                 135                 140

Pro Leu Phe Cys Gly Gly Ile Thr Val Phe Asn Pro Ile Val Gln Phe
145                 150                 155                 160

Asn Ile Lys Pro Thr Asp Gln Val Gly Val Ile Gly Ile Gly Gly Leu
                165                 170                 175

Gly His Met Ala Leu Gly Phe Leu Arg Ala Trp Gly Cys Glu Ile Thr
            180                 185                 190

Ala Phe Ser Thr Ser Pro Asp Lys Glu Ala Glu Ala Lys Ala Leu Gly
```

```
                195                 200                 205
Ala Thr His Phe Val Asn Ser Arg Asp Pro Glu Ala Leu Lys Ala Leu
        210                 215                 220

Thr Asn Ser Phe Asp Val Ile Leu Ser Thr Val Asn Ala Asp Leu Asp
225                 230                 235                 240

Trp Pro Thr Tyr Ile Lys Leu Leu Arg Pro Gln Gly Arg Leu His Leu
                245                 250                 255

Val Gly Val Ile Pro Asn Pro Leu Ser Val Pro Ile Phe Pro Met Ile
            260                 265                 270

Leu Gly Gln Lys Ser Val Ser Ala Ser Pro Leu Gly Ser Pro Thr Thr
        275                 280                 285

Ile Ala Gln Met Leu Asn Phe Ala Gly Arg His His Leu Glu Pro Ile
290                 295                 300

Val Glu Phe Phe Pro Leu Glu Gln Val Asn Glu Ala Leu Glu Arg Leu
305                 310                 315                 320

Gln Ser Asn Lys Ala Arg Tyr Arg Ile Ile Leu Lys Met Asp His
                325                 330                 335

<210> SEQ ID NO 118
<211> LENGTH: 336
<212> TYPE: PRT
<213> ORGANISM: Cyanothece sp. PCC 7822

<400> SEQUENCE: 118

Met Ile Arg Ala Tyr Ala Ala His Glu Pro Gly Gly Lys Leu Glu Pro
1               5                   10                  15

Phe Glu Tyr Asp Pro Gly Ser Leu Gly Asp Glu Asp Val Glu Ile Gln
                20                  25                  30

Val Glu Tyr Cys Gly Ile Cys His Ser Asp Leu Ser Met Leu Asn Asn
            35                  40                  45

Glu Trp Gly Met Thr Arg Tyr Pro Phe Val Pro Gly His Glu Val Val
        50                  55                  60

Gly Thr Ile Asn Ala Val Gly Glu Arg Val Lys His Leu Gln Val Gly
65                  70                  75                  80

Gln Arg Val Gly Leu Gly Trp Tyr Ser Arg Ser Cys Met Thr Cys Glu
                85                  90                  95

Trp Cys Leu Ser Gly Asn Gln Asn Leu Cys Pro Gln Ala Glu Gly Thr
            100                 105                 110

Ile Val Gly Arg Tyr Gly Gly Phe Ala Glu Lys Val Arg Ala His Gln
        115                 120                 125

Gly Trp Val Leu Pro Leu Pro Glu Lys Leu Asn Pro Leu Thr Ala Gly
    130                 135                 140

Pro Leu Phe Cys Gly Gly Ile Thr Val Phe Asn Pro Ile Val Gln Phe
145                 150                 155                 160

Asp Val Lys Pro Thr Asp Arg Val Gly Val Ile Gly Ile Gly Gly Leu
                165                 170                 175

Gly His Met Ala Leu Gly Phe Leu Ala Ala Trp Gly Cys Glu Ile Thr
            180                 185                 190

Ala Phe Ser Thr Ser Pro Asp Lys Glu Ile Glu Ala Lys Asn Leu Gly
        195                 200                 205

Ala Asn His Phe Val Asn Ser Arg Asp Pro Gln Ala Leu Lys Ala Leu
    210                 215                 220

Ala Asn Ser Leu Asp Leu Ile Leu Ser Thr Val Asn Ala Asp Leu Asp
225                 230                 235                 240
```

Trp Asp Thr Tyr Ile Ser Leu Leu Arg Pro Lys Gly Arg Leu His Phe
            245                 250                 255

Val Gly Val Ile Pro Asn Pro Leu Ser Val Gln Leu Phe Pro Leu Ile
        260                 265                 270

Gly Gly Gln Lys Ser Val Ser Gly Ser Pro Leu Gly Ser Pro Val Thr
    275                 280                 285

Leu Ala Gln Met Leu Asn Phe Ala Gly Arg His His Val Glu Pro Val
290                 295                 300

Val Glu Phe Tyr Pro Ile Glu Gln Val Asn Glu Ala Met Glu Arg Leu
305                 310                 315                 320

Lys Ala Asn Lys Ala Arg Tyr Arg Ile Val Leu Thr Phe Lys Asn Ser
                325                 330                 335

<210> SEQ ID NO 119
<211> LENGTH: 333
<212> TYPE: PRT
<213> ORGANISM: Cyanothece sp. PCC 8801

<400> SEQUENCE: 119

Met Ile Lys Ala Tyr Ala Ala Ser Glu Pro Gly Lys Glu Leu Asn Ser
1               5                   10                  15

Phe Glu Tyr Asp Pro Gly Leu Leu Gly Glu Asp Val Glu Ile Asn
            20                  25                  30

Val Gln Tyr Cys Gly Ile Cys His Ser Asp Leu Ser Met Leu Asp Asn
        35                  40                  45

Glu Trp Gly Ile Thr Gln Tyr Pro Phe Val Pro Gly His Glu Val Val
    50                  55                  60

Gly Thr Ile Gly Ala Val Gly Ser Lys Val Thr Thr Phe Gln Val Gly
65                  70                  75                  80

Gln Thr Val Gly Leu Gly Trp Phe Ser Arg Ser Cys Phe Asp Cys Glu
                85                  90                  95

Trp Cys Leu Ser Gly Asp Gln Asn Leu Cys Gln Thr Ala Glu Gly Thr
            100                 105                 110

Ile Val Gly Arg Pro Gly Gly Phe Ala Asp Lys Val Arg Ala His His
        115                 120                 125

Arg Trp Val Val Pro Leu Pro Ser Gly Val Asn Pro Glu Thr Ala Gly
    130                 135                 140

Pro Leu Phe Cys Gly Gly Ile Thr Val Phe Asn Pro Ile Ile Gln Cys
145                 150                 155                 160

Gly Val Lys Ser Thr Asp Arg Val Gly Val Ile Gly Ile Gly Gly Leu
                165                 170                 175

Gly His Leu Ala Ile Glu Phe Leu His Ala Trp Gly Cys Glu Val Thr
            180                 185                 190

Ala Phe Ser Ser Asn Pro Glu Lys Glu Ser Glu Val Lys Gln Leu Gly
        195                 200                 205

Ala Asp Tyr Phe Val Asn Ser Arg Asp Pro Glu Ala Ile Lys Ala Val
    210                 215                 220

Glu Asn Ser Phe Asp Phe Ile Ile Ser Thr Val Asn Val Ser Leu Asp
225                 230                 235                 240

Trp Asn Ser Tyr Ile Leu Ala Leu Arg Pro Arg Gly Thr Leu His Phe
                245                 250                 255

Val Gly Ala Val Leu Asn Pro Ile Ser Thr Gln Ile Phe Pro Leu Leu
            260                 265                 270

Met Gly Gln Lys Thr Ile Ser Gly Ser Pro Thr Gly Ser Pro Thr Thr
        275                 280                 285

```
Ile Ala Gln Met Leu Asp Phe Ala Ala Arg His Gln Ile Glu Pro Val
    290                 295                 300

Thr Glu Ile Phe Pro Phe Glu Gln Val Asn Glu Ala Ile Asp Lys Leu
305                 310                 315                 320

Arg His Gly Gln Pro Arg Tyr Arg Leu Val Leu Lys Met
                325                 330

<210> SEQ ID NO 120
<211> LENGTH: 362
<212> TYPE: PRT
<213> ORGANISM: Cyanothece sp. PCC 8801

<400> SEQUENCE: 120

Met Arg Gly Glu Arg Ile Val Arg Ser Gly Val Lys Glu Asp Ile Leu
1               5                   10                  15

Cys Asn Asn Ala Ile Asn Thr Thr Ile Glu Val Lys Val Val Ile Lys
                20                  25                  30

Ala Tyr Ala Ala Ser Glu Pro Gly Lys Glu Leu Asn Ser Phe Glu Tyr
            35                  40                  45

Asp Pro Gly Leu Leu Gly Glu Glu Asp Val Glu Ile Asn Val Gln Tyr
        50                  55                  60

Cys Gly Ile Cys His Ser Asp Leu Ser Met Leu Asp Asn Glu Trp Gly
65                  70                  75                  80

Ile Thr Gln Tyr Pro Phe Val Pro Gly His Glu Val Val Gly Thr Ile
                85                  90                  95

Gly Ala Val Gly Ser Lys Val Thr Thr Phe Gln Val Gly Gln Thr Val
            100                 105                 110

Gly Leu Gly Trp Phe Ser Arg Ser Cys Phe Asp Cys Glu Trp Cys Leu
        115                 120                 125

Ser Gly Asp Gln Asn Leu Cys Gln Thr Ala Glu Gly Thr Ile Val Gly
130                 135                 140

Arg Pro Gly Gly Phe Ala Asp Lys Val Arg Ala His His Arg Trp Val
145                 150                 155                 160

Val Pro Leu Pro Ser Gly Val Asn Pro Glu Thr Ala Gly Pro Leu Phe
                165                 170                 175

Cys Gly Gly Ile Thr Val Phe Asn Pro Ile Ile Gln Cys Gly Val Lys
            180                 185                 190

Ser Thr Asp Arg Val Gly Val Ile Gly Ile Gly Gly Leu Gly His Leu
        195                 200                 205

Ala Ile Glu Phe Leu His Ala Trp Gly Cys Glu Val Thr Ala Phe Ser
210                 215                 220

Ser Asn Pro Glu Lys Glu Ser Glu Val Lys Gln Leu Gly Ala Asp Tyr
225                 230                 235                 240

Phe Val Asn Ser Arg Asp Pro Glu Ala Ile Lys Ala Val Glu Asn Ser
                245                 250                 255

Phe Asp Phe Ile Ile Ser Thr Val Asn Val Ser Leu Asp Trp Asn Ser
            260                 265                 270

Tyr Ile Leu Ala Leu Arg Pro Arg Gly Thr Leu His Phe Val Gly Ala
        275                 280                 285

Val Leu Asn Pro Ile Ser Thr Gln Ile Phe Pro Leu Leu Met Gly Gln
290                 295                 300

Lys Thr Ile Ser Gly Ser Pro Thr Gly Ser Pro Thr Thr Ile Ala Gln
305                 310                 315                 320

Met Leu Asp Phe Ala Ala Arg His Gln Ile Glu Pro Val Thr Glu Ile
```

```
                    325                 330                 335
Phe Pro Phe Glu Gln Val Asn Glu Ala Ile Asp Lys Leu Arg His Gly
                340                 345                 350

Gln Pro Arg Tyr Arg Leu Val Leu Lys Met
            355                 360

<210> SEQ ID NO 121
<211> LENGTH: 362
<212> TYPE: PRT
<213> ORGANISM: Cyanothece sp. PCC 8802

<400> SEQUENCE: 121

Met Arg Gly Glu Arg Ile Val Arg Ser Gly Val Lys Glu Asp Ile Leu
1               5                   10                  15

Cys Asn Asn Ala Ile Asn Thr Thr Ile Glu Val Lys Val Val Ile Lys
                20                  25                  30

Ala Tyr Ala Ala Ser Glu Pro Gly Lys Glu Leu Asn Ser Phe Glu Tyr
            35                  40                  45

Asp Pro Gly Leu Leu Gly Glu Glu Asp Val Glu Ile Asn Val Gln Tyr
        50                  55                  60

Cys Gly Ile Cys His Ser Asp Leu Ser Met Leu Asp Asn Glu Trp Gly
65                  70                  75                  80

Ile Thr Gln Tyr Pro Phe Val Pro Gly His Glu Val Val Gly Thr Ile
                85                  90                  95

Gly Ala Val Gly Ser Lys Val Thr Thr Phe Gln Val Gly Gln Thr Val
            100                 105                 110

Gly Leu Gly Trp Phe Ser Arg Ser Cys Phe Asp Cys Glu Trp Cys Leu
        115                 120                 125

Ser Gly Asp Gln Asn Leu Cys Gln Thr Ala Glu Gly Thr Ile Val Gly
130                 135                 140

Arg Pro Gly Gly Phe Ala Asp Lys Val Arg Ala His Arg Trp Val
145                 150                 155                 160

Val Pro Leu Pro Ser Gly Val Asn Pro Glu Thr Ala Gly Pro Leu Phe
                165                 170                 175

Cys Gly Gly Ile Thr Val Phe Asn Pro Ile Ile Gln Cys Gly Val Lys
            180                 185                 190

Ser Thr Asp Arg Val Gly Val Ile Gly Ile Gly Gly Leu Gly His Leu
        195                 200                 205

Ala Ile Glu Phe Leu His Ala Trp Gly Cys Glu Val Thr Ala Phe Ser
210                 215                 220

Ser Asn Pro Glu Lys Glu Ser Glu Val Lys Gln Leu Gly Ala Asp Tyr
225                 230                 235                 240

Phe Val Asn Ser Arg Asp Pro Glu Ala Ile Lys Ala Val Glu Asn Ser
                245                 250                 255

Phe Asp Phe Ile Ile Ser Thr Val Asn Val Ser Leu Asp Trp Asn Ser
            260                 265                 270

Tyr Ile Leu Ala Leu Arg Pro Arg Gly Thr Leu His Phe Val Gly Ala
        275                 280                 285

Val Leu Asn Pro Ile Ser Thr Gln Ile Phe Pro Leu Leu Met Gly Gln
290                 295                 300

Lys Thr Ile Ser Gly Ser Pro Thr Gly Ser Pro Thr Thr Ile Ala Gln
305                 310                 315                 320

Met Leu Asp Phe Ala Ala Arg His Gln Ile Glu Pro Val Thr Glu Ile
                325                 330                 335
```

```
Phe Pro Phe Glu Gln Val Asn Glu Ala Ile Asp Lys Leu Arg His Gly
            340                 345                 350

Gln Pro Arg Tyr Arg Leu Val Leu Lys Met
            355                 360

<210> SEQ ID NO 122
<211> LENGTH: 334
<212> TYPE: PRT
<213> ORGANISM: Microcoleus chthonoplastes PCC 7420

<400> SEQUENCE: 122

Met Ile Lys Ala Tyr Ala Ala His Glu Pro Gly Gly Gln Leu Gln Pro
1               5                   10                  15

Phe Glu Tyr Asp Pro Gly Thr Leu Gly Asp Glu Val Glu Ile Lys
            20                  25                  30

Val Glu Tyr Cys Gly Ile Cys His Ser Asp Leu Ser Met Leu Asp Asn
            35                  40                  45

Glu Trp Gly Met Thr Asp Tyr Pro Phe Val Pro Gly His Glu Val Val
50                  55                  60

Gly Thr Ile Ala Ala Leu Gly Asp Lys Val Thr Thr Leu Asn Leu Gly
65                  70                  75                  80

Gln Arg Val Gly Leu Gly Trp Phe Ser Gly Ser Cys Met Thr Cys Glu
                85                  90                  95

Trp Cys Met Ser Gly Asn His Asn Leu Cys Ser Asn Ala Glu Gly Thr
            100                 105                 110

Ile Val Ser Arg His Gly Gly Phe Ala Asp Lys Val Arg Ala Asp Tyr
            115                 120                 125

Ser Trp Val Val Pro Leu Pro Asp Gly Ile Asn Pro Ala Thr Ala Gly
            130                 135                 140

Pro Leu Phe Cys Gly Gly Ile Thr Val Phe Asn Pro Ile Val Gln Phe
145                 150                 155                 160

Asp Ile Lys Pro Ser Asp Arg Val Gly Val Ile Gly Ile Gly Gly Leu
                165                 170                 175

Gly His Ile Ala Leu Gly Phe Leu Gln Ala Trp Gly Cys Glu Ile Thr
            180                 185                 190

Ala Phe Ser Ser Ser Pro Asp Lys Glu Ala Glu Ala Arg Glu Leu Gly
            195                 200                 205

Ala Thr His Phe Ile Asn Ser Gly Asp Val Asn Ala Leu Glu Ser Val
            210                 215                 220

Gln Asn Ser Phe Asp Phe Ile Leu Ala Thr Ala Asn Ala Asp Leu Asp
225                 230                 235                 240

Trp Asn Ala Tyr Ile Ala Ala Leu Arg Pro Lys Gly Arg Leu His Phe
                245                 250                 255

Val Gly Val Ile Pro Asn Pro Leu Ser Thr Pro Ile Phe Pro Leu Ile
            260                 265                 270

Leu Gly Gln Lys Ser Ile Ser Ala Ser Pro Val Gly Ser Pro Ala Thr
            275                 280                 285

Ile Ser Gln Met Ile Asn Phe Ala Ala Arg Gln Gly Val Glu Pro Ile
290                 295                 300

Thr Glu Thr Phe Ser Phe Glu Gln Val Asn Glu Ala Met Glu Lys Leu
305                 310                 315                 320

Arg His Gly Lys Pro Arg Tyr Arg Leu Val Leu Lys His Ser
                325                 330

<210> SEQ ID NO 123
```

<211> LENGTH: 334
<212> TYPE: PRT
<213> ORGANISM: Microsystis aeruginosa NIES-843

<400> SEQUENCE: 123

Met Ile Arg Ala Tyr Ala Ala Arg Glu Lys Gly Gly Lys Leu Glu Pro
1               5                   10                  15

Phe Asp Tyr Asp Pro Gly Ile Leu Ala Asp Glu Asp Val Glu Ile Ala
            20                  25                  30

Val Glu Tyr Cys Gly Ile Cys His Ser Asp Leu Ser Met Leu Asp Asn
        35                  40                  45

Asp Trp Gly Leu Thr Thr Tyr Pro Phe Val Pro Gly His Glu Val Val
    50                  55                  60

Gly Thr Ile Ala Ala Leu Gly Ala Lys Val Lys Glu Leu Lys Leu Gly
65                  70                  75                  80

Gln Arg Val Gly Leu Gly Trp Phe Ser Arg Ser Cys Ser Thr Cys Glu
                85                  90                  95

Thr Cys Met Ser Gly Asp Gln Asn Leu Cys Ala Thr Ala Glu Gly Thr
            100                 105                 110

Ile Val Gly Arg His Gly Gly Phe Ala Asp Arg Val Arg Ala His His
        115                 120                 125

Ser Trp Leu Val Pro Leu Gly Asn Gln Leu Asp Ala Ala Lys Ala Gly
    130                 135                 140

Pro Leu Phe Cys Gly Gly Ile Thr Val Phe Asn Pro Ile Val Gln Phe
145                 150                 155                 160

Asn Ile Lys Pro Thr Ala Arg Val Gly Val Ile Gly Ile Gly Gly Leu
                165                 170                 175

Gly His Ile Ala Leu Lys Phe Leu Lys Ala Trp Gly Cys Glu Val Thr
            180                 185                 190

Ala Phe Ser Ser Ser Pro Asp Lys Glu Thr Glu Ala Lys Glu Leu Gly
        195                 200                 205

Ala Thr His Phe Ile Asn Ser Arg Asp Pro Gly Ala Leu Gln Ser Val
    210                 215                 220

Gln Asn Tyr Phe Asp Phe Ile Ile Ser Thr Val Asn Val Asn Leu Asp
225                 230                 235                 240

Trp Gly Leu Tyr Ile Ala Cys Leu Arg Pro Lys Gly Arg Leu His Ile
                245                 250                 255

Val Gly Ala Val Leu Glu Pro Met Ala Thr Tyr Ala Phe Pro Leu Ile
            260                 265                 270

Met Gly Gln Lys Ser Ile Ser Gly Ser Pro Leu Gly Ser Pro Ser Thr
        275                 280                 285

Ile Asn Lys Met Ile Glu Phe Ala Ser Arg His Gly Ile Glu Pro Val
    290                 295                 300

Thr Glu Ile Tyr Pro Ile Ser Gln Val Asn Glu Ala Met Glu Lys Leu
305                 310                 315                 320

Arg Thr Gly Gln Pro Lys Tyr Arg Leu Val Leu Gln Ile Lys
                325                 330

<210> SEQ ID NO 124
<211> LENGTH: 334
<212> TYPE: PRT
<213> ORGANISM: Microcystis aeruginosa PCC 7806

<400> SEQUENCE: 124

Met Ile Arg Ala Tyr Ala Ala Gln Glu Lys Gly Gly Lys Leu Glu Pro
1               5                   10                  15

```
Phe Asp Tyr Asp Pro Gly Ile Leu Ala Asp Glu Asp Val Glu Ile Ala
            20                  25                  30

Val Glu Tyr Cys Gly Ile Cys His Ser Asp Leu Ser Met Leu Asp Asn
        35                  40                  45

Asp Trp Gly Leu Thr Thr Tyr Pro Phe Val Pro Gly His Glu Val Val
    50                  55                  60

Gly Thr Ile Ala Ala Leu Gly Ala Lys Val Lys Glu Leu Lys Leu Gly
65                  70                  75                  80

Gln Arg Val Gly Leu Gly Trp Phe Ser Arg Ser Cys Ser Thr Cys Glu
                85                  90                  95

Thr Cys Met Ser Gly Asp Gln Asn Leu Cys Ala Thr Ala Glu Gly Thr
            100                 105                 110

Ile Val Gly Arg His Gly Gly Phe Ala Glu Arg Val Arg Ala His His
        115                 120                 125

Ser Trp Leu Val Pro Leu Pro Asp Gln Leu Asp Ala Ala Lys Ala Gly
130                 135                 140

Pro Leu Phe Cys Gly Gly Ile Thr Val Phe Asn Pro Ile Val Gln Phe
145                 150                 155                 160

Asn Ile Lys Pro Thr Ala Arg Val Gly Val Ile Gly Ile Gly Gly Leu
                165                 170                 175

Gly His Ile Ala Leu Lys Phe Leu Lys Ala Trp Gly Cys Glu Val Thr
            180                 185                 190

Ala Phe Ser Ser Ser Pro Asp Lys Glu Thr Glu Ala Lys Glu Leu Gly
        195                 200                 205

Ala Thr His Phe Ile Asn Ser Arg Asp Pro Glu Ala Leu Gln Ser Val
    210                 215                 220

Gln Asn Tyr Phe Asp Phe Ile Ile Ser Thr Val Asn Val Asn Leu Asp
225                 230                 235                 240

Trp Gly Leu Tyr Ile Ala Cys Leu Arg Pro Lys Gly Arg Leu His Ile
                245                 250                 255

Val Gly Ala Val Leu Glu Pro Met Ala Thr Tyr Ala Phe Pro Leu Ile
            260                 265                 270

Met Gly Gln Lys Ser Ile Ser Gly Ser Pro Leu Gly Ser Pro Ser Thr
        275                 280                 285

Val Ser Lys Met Ile Glu Phe Ala Ser Arg His Gly Ile Glu Pro Val
    290                 295                 300

Thr Glu Thr Tyr Pro Ile Ser Arg Val Asn Glu Ala Met Glu Lys Leu
305                 310                 315                 320

Arg Thr Gly Gln Pro Lys Tyr Arg Leu Val Leu Gln Ile Lys
                325                 330

<210> SEQ ID NO 125
<211> LENGTH: 333
<212> TYPE: PRT
<213> ORGANISM: Synechococcus sp. WH 5701

<400> SEQUENCE: 125

Met Gln Ile Thr Val Trp Gln Ala Leu Ala Lys Gly Gly Arg Leu Glu
1               5                   10                  15

Arg Ser Gln Ala Thr Leu Leu Asp Pro Gly Pro Asp Glu Val Leu Leu
                20                  25                  30

Glu Val Leu His Cys Gly Leu Cys His Ser Asp Leu Ser Met Leu Asp
            35                  40                  45

Asn Ser Trp Gly Ile Ser Thr Tyr Pro Leu Val Pro Gly His Glu Val
```

Val Gly Arg Val Ala Ala Val Gly Ala Gly Val Asp Ser Gly Leu Leu
65                  70                  75                  80

Gly Ser Ile Gln Gly Leu Gly Trp Ile Ala Gly Ser Cys Arg His Cys
                85                  90                  95

Asp Trp Cys Leu Gly Gly Asn Ala Asn Leu Cys Pro Ser Leu Glu Ala
            100                 105                 110

Ser Val Val Gly Arg His Gly Gly Phe Ala Ser His Val Met Ala His
        115                 120                 125

Gln Asp Trp Ile Val Ala Ile Pro Asp Gly Val Ser Ala Ala Asp Ala
    130                 135                 140

Gly Pro Leu Phe Cys Gly Gly Ile Thr Val Phe Ala Pro Leu Phe Asp
145                 150                 155                 160

Glu Ala Val Ser Pro Thr Ser Arg Val Ala Val Ile Gly Ile Gly Gly
                165                 170                 175

Leu Gly His Met Ala Leu Gln Phe Ala Arg Ala Trp Gly Cys Glu Val
            180                 185                 190

Thr Ala Val Thr Thr Ser Pro Ala Lys Ala Asp Glu Ala Arg Arg Leu
        195                 200                 205

Gly Ala His Arg Val Leu Ala Leu Ser Glu Leu Gly Asp His Pro Gly
    210                 215                 220

Val Phe Asp Leu Ile Ile Asn Thr Ser Asn His Asp Leu Asp Trp Pro
225                 230                 235                 240

Ala Leu Ile Gly Ser Leu Ala Pro Leu Gly Arg Leu His Gln Leu Gly
                245                 250                 255

Val Pro Leu Ser Pro Leu Gln Ile Pro Ala Phe Pro Leu Ile Ala Gly
            260                 265                 270

Arg Arg Ser Val Thr Gly Ser Pro Thr Ser Pro Ala Ser Leu Arg
        275                 280                 285

Arg Met Val Glu Phe Cys Ala Arg His Gly Ile Ala Pro Leu Val Glu
    290                 295                 300

His Leu Pro Met Ala Glu Ile Asn Thr Ala Ile Glu Arg Leu Arg Gln
305                 310                 315                 320

Gly Asp Val Arg Tyr Arg Phe Val Leu Asp Gly Pro Ala
                325                 330

<210> SEQ ID NO 126
<211> LENGTH: 336
<212> TYPE: PRT
<213> ORGANISM: Synechococcus sp. RS9917

<400> SEQUENCE: 126

Met Val Val Thr Ile Thr Val Trp Gln Ala Arg Glu Ala Gly Ala Pro
1               5                   10                  15

Leu Glu Arg Ala Glu Arg Ala Met Leu Glu Pro Ala Ala Gly Glu Leu
            20                  25                  30

Val Leu Glu Val Leu His Cys Gly Leu Cys His Ser Asp Leu Ser Met
        35                  40                  45

Leu Asp Asn Asn Trp Gly Leu Ser Ala Tyr Pro Leu Val Pro Gly His
    50                  55                  60

Glu Val Val Gly Arg Val Val Arg Val Gly Glu Gly Val Asp Pro Gly
65                  70                  75                  80

Val Ile Gly Glu Leu Arg Gly Leu Gly Trp Ile Ser Gly Ser Cys Met
                85                  90                  95

His Cys Ala Leu Cys Leu Gly Gly Thr Ala Asn Leu Cys Gly Ser Leu
                100                 105                 110

Glu Ala Thr Ile Val Gly Arg Gln Gly Gly Phe Ala Ser His Val Thr
            115                 120                 125

Ala Arg Gln Asp Trp Ala Ile Arg Leu Pro Glu Gly Met Asp Pro Ala
        130                 135                 140

Ala Ala Gly Pro Leu Phe Cys Gly Gly Ile Thr Val Phe Ala Pro Leu
145                 150                 155                 160

Val Asp Glu Val Val Ser Pro Thr Ala His Val Ala Val Ile Gly Ile
                165                 170                 175

Gly Gly Leu Gly His Met Ala Leu Gln Phe Ala Arg Ala Trp Gly Cys
            180                 185                 190

Glu Val Thr Ala Leu Thr Thr His Leu Ala Lys Ala Glu Glu Ala Lys
        195                 200                 205

Arg Phe Gly Ala His His Val Glu Ser Leu Glu Glu Leu Pro Asp Leu
    210                 215                 220

Ala Gly Arg Phe Asp Leu Val Ile Asn Thr Val Asn His Ala Leu Asp
225                 230                 235                 240

Trp Gly Ala Val Met Gly Ser Leu Ala Pro Leu Gly Arg Leu His Gln
                245                 250                 255

Leu Gly Ala Val Leu Glu Pro Leu Gln Val Ser Ala Phe Asp Leu Ile
            260                 265                 270

Met Ala Arg Arg Ser Ile Thr Gly Ser Pro Thr Ser Pro Ala Ser
        275                 280                 285

Leu Met Lys Met Val Glu Phe Cys Val Arg His Asn Ile Arg Pro Gln
    290                 295                 300

Val Glu His Leu Pro Met Asp Arg Leu Asn Glu Ala Ile Asp Arg Leu
305                 310                 315                 320

Arg Arg Gly Asp Val Arg Tyr Arg Phe Val Leu Asp Ser Val Ala Asp
                325                 330                 335

<210> SEQ ID NO 127
<211> LENGTH: 333
<212> TYPE: PRT
<213> ORGANISM: Synechococcus sp. WH 5701

<400> SEQUENCE: 127

Met Gln Ile Thr Val Trp Gln Ala Leu Ala Lys Gly Gly Arg Leu Glu
1               5                   10                  15

Arg Ser Gln Ala Thr Leu Leu Asp Pro Gly Pro Asp Glu Val Leu Leu
            20                  25                  30

Glu Val Leu His Cys Gly Leu Cys His Ser Asp Leu Ser Met Leu Asp
        35                  40                  45

Asn Ser Trp Gly Ile Ser Thr Tyr Pro Leu Val Pro Gly His Glu Val
    50                  55                  60

Val Gly Arg Val Ala Ala Val Gly Ala Gly Val Asp Ser Gly Leu Leu
65                  70                  75                  80

Gly Ser Ile Gln Gly Leu Gly Trp Ile Ala Gly Ser Cys Arg His Cys
                85                  90                  95

Asp Trp Cys Leu Gly Gly Asn Ala Asn Leu Cys Pro Ser Leu Glu Ala
            100                 105                 110

Ser Val Val Gly Arg His Gly Gly Phe Ala Ser His Val Met Ala His
        115                 120                 125

Gln Asp Trp Ile Val Ala Ile Pro Asp Gly Val Ser Ala Ala Asp Ala
    130                 135                 140

```
Gly Pro Leu Phe Cys Gly Gly Ile Thr Val Phe Ala Pro Leu Phe Asp
145                 150                 155                 160

Glu Ala Val Ser Pro Thr Ser Arg Val Ala Val Ile Gly Ile Gly Gly
            165                 170                 175

Leu Gly His Met Ala Leu Gln Phe Ala Arg Ala Trp Gly Cys Glu Val
        180                 185                 190

Thr Ala Val Thr Thr Ser Pro Ala Lys Ala Asp Glu Ala Arg Arg Leu
            195                 200                 205

Gly Ala His Arg Val Leu Ala Leu Ser Glu Leu Gly Asp His Pro Gly
        210                 215                 220

Val Phe Asp Leu Ile Ile Asn Thr Ser Asn His Asp Leu Asp Trp Pro
225                 230                 235                 240

Ala Leu Ile Gly Ser Leu Ala Pro Leu Gly Arg Leu His Gln Leu Gly
            245                 250                 255

Val Pro Leu Ser Pro Leu Gln Ile Pro Ala Phe Pro Leu Ile Ala Gly
            260                 265                 270

Arg Arg Ser Val Thr Gly Ser Pro Thr Ser Pro Ala Ser Leu Arg
            275                 280                 285

Arg Met Val Glu Phe Cys Ala Arg His Gly Ile Ala Pro Leu Val Glu
290                 295                 300

His Leu Pro Met Ala Glu Ile Asn Thr Ala Ile Glu Arg Leu Arg Gln
305                 310                 315                 320

Gly Asp Val Arg Tyr Arg Phe Val Leu Asp Gly Pro Ala
            325                 330

<210> SEQ ID NO 128
<211> LENGTH: 330
<212> TYPE: PRT
<213> ORGANISM: Synechococcus sp. WH 7803

<400> SEQUENCE: 128

Met Ile Ser Val Trp Gln Ala Pro Ser Ala Gly Ala Pro Leu Glu Cys
1               5                   10                  15

Gly Gln Arg Pro Ala Pro Glu Pro Ala Ala Asp Glu Leu Val Leu Glu
            20                  25                  30

Val Met His Cys Gly Leu Cys His Ser Asp Leu Ser Met Ile Gly Asn
        35                  40                  45

His Trp Gly Val Ser Arg Tyr Pro Leu Val Pro Gly His Glu Val Ile
    50                  55                  60

Gly Arg Val Thr Ala Val Gly Glu Gly Val Asp Pro Gly Leu Ile Gly
65                  70                  75                  80

Asp Val Arg Gly Leu Gly Trp Ile Ser Gly Ser Cys Asn His Cys Ser
                85                  90                  95

Leu Cys Leu Gly Gly Asp Gln Asn Leu Cys Thr Ser Leu Glu Ala Thr
            100                 105                 110

Ile Val Gly Arg Gln Gly Gly Phe Ala Ser His Val Val Ala Arg Gln
        115                 120                 125

Asp Trp Ala Ile Pro Leu Pro Pro Gly Leu Asp Pro Ala Asp Ala Gly
    130                 135                 140

Pro Leu Phe Cys Gly Gly Ile Thr Val Phe Ala Pro Leu Val Asp Glu
145                 150                 155                 160

Ala Val Ser Pro Thr Ala His Val Ala Val Gly Ile Gly Gly Leu
            165                 170                 175

Gly His Ile Ala Leu Gln Phe Ala Arg Ala Trp Gly Cys Glu Val Thr
```

```
            180                 185                 190
Ala Ile Thr Thr Asn Leu Ala Lys Ala Glu Gln Ala Arg Arg Phe Gly
            195                 200                 205

Ala His His Val Glu Glu Leu Glu Met Leu Pro Asp Leu Gln Ser Arg
            210                 215                 220

Phe Asp Leu Val Ile Asn Thr Val Asn His Pro Leu Asp Trp Ser Ala
225                 230                 235                 240

Val Met Ala Ser Leu Arg Pro Arg Gly Arg Leu His Gln Leu Gly Ala
                245                 250                 255

Val Leu Glu Pro Ile Gln Val Gly Ala Phe Asp Leu Ile Pro Ala Arg
            260                 265                 270

Arg Ser Ile Thr Gly Ser Pro Thr Ser Pro Ala Ser Leu Gln Lys
            275                 280                 285

Met Val Glu Phe Cys Val Arg His Asn Ile Leu Pro Leu Val Glu His
    290                 295                 300

Leu Pro Met Asp Gln Val Asn Val Ala Ile Gln Arg Leu Ala Lys Gly
305                 310                 315                 320

Asp Val Arg Tyr Arg Phe Val Leu Asp Ala
                325                 330

<210> SEQ ID NO 129
<211> LENGTH: 330
<212> TYPE: PRT
<213> ORGANISM: Synechococcus sp. WH 7805

<400> SEQUENCE: 129

Met Ile Ser Val Trp Gln Ala Pro Ser Ala Gly Ala Pro Leu Glu Cys
1               5                   10                  15

Ala Gln Arg Pro Ala Leu Gln Pro Val Ala Asp Glu Leu Val Leu Glu
            20                  25                  30

Val Met His Cys Gly Leu Cys His Ser Asp Leu Ser Met Ile Gly Asn
        35                  40                  45

His Trp Gly Val Ser Arg Tyr Pro Leu Val Pro Gly His Glu Val Ile
    50                  55                  60

Gly Arg Val Thr Ala Val Gly Glu Gly Val Asp Pro Gly Val Ile Gly
65                  70                  75                  80

Glu Val Arg Gly Leu Gly Trp Ile Ser Gly Ser Cys Asn His Cys Ser
                85                  90                  95

Leu Cys Leu Gly Gly Asp Gln Asn Leu Cys Ser Ser Leu Glu Ala Thr
            100                 105                 110

Ile Val Gly Arg Gln Gly Gly Phe Ala Ser His Val Val Ala Arg Gln
        115                 120                 125

Asp Trp Thr Ile Pro Leu Pro Thr Gly Leu Asp Pro Ala Glu Ala Gly
    130                 135                 140

Pro Leu Phe Cys Gly Gly Val Thr Val Phe Ala Pro Leu Val Asp Glu
145                 150                 155                 160

Ala Val Ser Pro Thr Ala His Val Ala Val Val Gly Ile Gly Gly Leu
                165                 170                 175

Gly His Ile Ala Leu Gln Phe Ala Arg Ala Trp Gly Cys Glu Val Thr
            180                 185                 190

Ala Ile Thr Thr Asn Pro Ala Lys Thr Glu Gln Ala Arg Arg Phe Gly
        195                 200                 205

Ala His His Val Glu Glu Leu Glu Ala Leu Ser Asp Leu Gln Arg Arg
    210                 215                 220
```

```
Phe Asp Leu Val Ile Asn Thr Val Asn His Pro Leu Asp Trp Ser Ala
225                 230                 235                 240

Val Met Ala Ser Leu Lys Pro Arg Gly Arg Leu His Gln Leu Gly Ala
            245                 250                 255

Val Leu Glu Pro Ile Gln Val Gly Ala Phe Asp Leu Ile Ser Ala Arg
        260                 265                 270

Arg Ser Ile Thr Gly Ser Pro Thr Ser Ser Pro Ala Ser Leu Leu Lys
    275                 280                 285

Met Val Glu Phe Cys Val Arg His Asn Ile Leu Pro Leu Val Glu His
290                 295                 300

Leu Pro Met Asp Gln Val Asn Val Ala Ile Glu Arg Leu Ala Lys Gly
305                 310                 315                 320

Asp Val Arg Tyr Arg Phe Val Leu Asp Ala
                325                 330

<210> SEQ ID NO 130
<211> LENGTH: 23
<212> TYPE: DNA
<213> ORGANISM: Artificial Sequence
<220> FEATURE:
<223> OTHER INFORMATION: synthetic combined bacterial sequences

<400> SEQUENCE: 130
cgacggtatg aagcttttat ttg                                            23

<210> SEQ ID NO 131
<211> LENGTH: 19
<212> TYPE: DNA
<213> ORGANISM: Artificial Sequence
<220> FEATURE:
<223> OTHER INFORMATION: synthetic combined bacterial sequences

<400> SEQUENCE: 131
ccggcggaac ggtaccaac                                                 19

<210> SEQ ID NO 132
<211> LENGTH: 22
<212> TYPE: DNA
<213> ORGANISM: Artificial Sequence
<220> FEATURE:
<223> OTHER INFORMATION: synthetic combined bacterial sequences

<400> SEQUENCE: 132
ggccagggga attctcctcc ag                                             22

<210> SEQ ID NO 133
<211> LENGTH: 25
<212> TYPE: DNA
<213> ORGANISM: Artificial Sequence
<220> FEATURE:
<223> OTHER INFORMATION: synthetic combined bacterial sequences

<400> SEQUENCE: 133
gcggataata ctgaacgaag ctttg                                          25

<210> SEQ ID NO 134
<211> LENGTH: 20
<212> TYPE: DNA
<213> ORGANISM: Artificial Sequence
<220> FEATURE:
<223> OTHER INFORMATION: synthetic combined bacterial sequences

<400> SEQUENCE: 134
```

```
ggctgacsccc cagtagtgta                                              20
```

<210> SEQ ID NO 135
<211> LENGTH: 20
<212> TYPE: DNA
<213> ORGANISM: Artificial Sequence
<220> FEATURE:
<223> OTHER INFORMATION: synthetic combined bacterial sequences

<400> SEQUENCE: 135

```
attttccggc ttgaacattg                                               20
```

<210> SEQ ID NO 136
<211> LENGTH: 20
<212> TYPE: DNA
<213> ORGANISM: Artificial Sequence
<220> FEATURE:
<223> OTHER INFORMATION: synthetic combined bacterial sequences

<400> SEQUENCE: 136

```
gttgttggca atcgagaggt                                               20
```

<210> SEQ ID NO 137
<211> LENGTH: 20
<212> TYPE: DNA
<213> ORGANISM: Artificial Sequence
<220> FEATURE:
<223> OTHER INFORMATION: synthetic combined bacterial sequences

<400> SEQUENCE: 137

```
gtctgccggt ttgaaacaat                                               20
```

<210> SEQ ID NO 138
<211> LENGTH: 11
<212> TYPE: DNA
<213> ORGANISM: Artificial Sequence
<220> FEATURE:
<223> OTHER INFORMATION: synthetic BsaBI restriction enzyme recognition
      sequence
<220> FEATURE:
<221> NAME/KEY: misc_feature
<222> LOCATION: (4)..(5)
<223> OTHER INFORMATION: n is a, c, g, or t
<220> FEATURE:
<221> NAME/KEY: misc_feature
<222> LOCATION: (7)..(8)
<223> OTHER INFORMATION: n is a, c, g, or t

<400> SEQUENCE: 138

```
gatnntnnat c                                                        11
```

<210> SEQ ID NO 139
<211> LENGTH: 20
<212> TYPE: DNA
<213> ORGANISM: Artificial Sequence
<220> FEATURE:
<223> OTHER INFORMATION: synthetic combined bacterial sequences

<400> SEQUENCE: 139

```
accccatcat catacgaagc                                               20
```

<210> SEQ ID NO 140
<211> LENGTH: 20
<212> TYPE: DNA
<213> ORGANISM: Artificial Sequence
<220> FEATURE:
<223> OTHER INFORMATION: synthetic combined bacterial sequences

```
<400> SEQUENCE: 140
agcctcctgg acattttcct                                                   20

<210> SEQ ID NO 141
<211> LENGTH: 20
<212> TYPE: DNA
<213> ORGANISM: Artificial Sequence
<220> FEATURE:
<223> OTHER INFORMATION: synthetic combined bacterial sequences

<400> SEQUENCE: 141
ttcactgacc gggctatttc                                                   20

<210> SEQ ID NO 142
<211> LENGTH: 20
<212> TYPE: DNA
<213> ORGANISM: Artificial Sequence
<220> FEATURE:
<223> OTHER INFORMATION: synthetic combined bacterial sequences

<400> SEQUENCE: 142
cttggccaca gataccgatt                                                   20

<210> SEQ ID NO 143
<211> LENGTH: 23
<212> TYPE: DNA
<213> ORGANISM: Artificial Sequence
<220> FEATURE:
<223> OTHER INFORMATION: synthetic combined bacterial sequences

<400> SEQUENCE: 143
gcgaactacc caacgctgac cgg                                               23

<210> SEQ ID NO 144
<211> LENGTH: 26
<212> TYPE: DNA
<213> ORGANISM: Artificial Sequence
<220> FEATURE:
<223> OTHER INFORMATION: synthetic combined bacterial sequences

<400> SEQUENCE: 144
gcatcaagtg ttgggggata tccctg                                            26

<210> SEQ ID NO 145
<211> LENGTH: 23
<212> TYPE: DNA
<213> ORGANISM: Artificial Sequence
<220> FEATURE:
<223> OTHER INFORMATION: synthetic combined bacterial sequences

<400> SEQUENCE: 145
ccgggacgtg acagaacggg tgg                                               23

<210> SEQ ID NO 146
<211> LENGTH: 23
<212> TYPE: DNA
<213> ORGANISM: Artificial Sequence
<220> FEATURE:
<223> OTHER INFORMATION: synthetic combined bacterial sequences

<400> SEQUENCE: 146
gcgttggcga tcgccgtcac tag                                               23

<210> SEQ ID NO 147
<211> LENGTH: 21
```

```
<212> TYPE: DNA
<213> ORGANISM: Artificial Sequence
<220> FEATURE:
<223> OTHER INFORMATION: synthetic combined bacterial sequences

<400> SEQUENCE: 147
gccattgtgg gggtgggtca g                                         21

<210> SEQ ID NO 148
<211> LENGTH: 22
<212> TYPE: DNA
<213> ORGANISM: Artificial Sequence
<220> FEATURE:
<223> OTHER INFORMATION: synthetic combined bacterial sequences

<400> SEQUENCE: 148
cagtttatgc cccgctaccg gg                                        22

<210> SEQ ID NO 149
<211> LENGTH: 24
<212> TYPE: DNA
<213> ORGANISM: Artificial Sequence
<220> FEATURE:
<223> OTHER INFORMATION: synthetic combined bacterial sequences

<400> SEQUENCE: 149
ccgatgtcta gataattcac catc                                      24

<210> SEQ ID NO 150
<211> LENGTH: 21
<212> TYPE: DNA
<213> ORGANISM: Artificial Sequence
<220> FEATURE:
<223> OTHER INFORMATION: synthetic combined bacterial sequences

<400> SEQUENCE: 150
tctaggggga tccaacgatc g                                         21

<210> SEQ ID NO 151
<211> LENGTH: 22
<212> TYPE: DNA
<213> ORGANISM: Artificial Sequence
<220> FEATURE:
<223> OTHER INFORMATION: synthetic combined bacterial sequences

<400> SEQUENCE: 151
ccaggggatc ctcttaacct ag                                        22

<210> SEQ ID NO 152
<211> LENGTH: 21
<212> TYPE: DNA
<213> ORGANISM: Artificial Sequence
<220> FEATURE:
<223> OTHER INFORMATION: synthetic combined bacterial sequences

<400> SEQUENCE: 152
tgtcgtatcg atagccaatg g                                         21

<210> SEQ ID NO 153
<211> LENGTH: 23
<212> TYPE: DNA
<213> ORGANISM: Artificial Sequence
<220> FEATURE:
<223> OTHER INFORMATION: synthetic combined bacterial sequences

<400> SEQUENCE: 153
```
catccatcat gagctctgtt aac                                              23

<210> SEQ ID NO 154
<211> LENGTH: 23
<212> TYPE: DNA
<213> ORGANISM: Artificial Sequence
<220> FEATURE:
<223> OTHER INFORMATION: synthetic combined bacterial sequences

<400> SEQUENCE: 154
gtatctcgag cgatgcctac agg                                              23

<210> SEQ ID NO 155
<211> LENGTH: 22
<212> TYPE: DNA
<213> ORGANISM: Artificial Sequence
<220> FEATURE:
<223> OTHER INFORMATION: synthetic combined bacterial sequences

<400> SEQUENCE: 155
cgcattggtt tctagatggc gc                                               22

<210> SEQ ID NO 156
<211> LENGTH: 23
<212> TYPE: DNA
<213> ORGANISM: Artificial Sequence
<220> FEATURE:
<223> OTHER INFORMATION: synthetic combined bacterial sequences

<400> SEQUENCE: 156
cgataactct agacgagtca ttg                                              23

<210> SEQ ID NO 157
<211> LENGTH: 23
<212> TYPE: DNA
<213> ORGANISM: Artificial Sequence
<220> FEATURE:
<223> OTHER INFORMATION: synthetic combined bacterial sequences

<400> SEQUENCE: 157
gaggcaatga gctccactgg acg                                              23

<210> SEQ ID NO 158
<211> LENGTH: 22
<212> TYPE: DNA
<213> ORGANISM: Artificial Sequence
<220> FEATURE:
<223> OTHER INFORMATION: synthetic combined bacterial sequences

<400> SEQUENCE: 158
ctggcgttcc actcgagctt gg                                               22

<210> SEQ ID NO 159
<211> LENGTH: 22
<212> TYPE: DNA
<213> ORGANISM: Artificial Sequence
<220> FEATURE:
<223> OTHER INFORMATION: synthetic combined bacterial sequences

<400> SEQUENCE: 159
cgcattggtt tctagatggc gc                                               22

<210> SEQ ID NO 160
<211> LENGTH: 23
<212> TYPE: DNA
<213> ORGANISM: Artificial Sequence

```
<220> FEATURE:
<223> OTHER INFORMATION: synthetic combined bacterial sequences

<400> SEQUENCE: 160
cgataactct agacgagtca tcg                                              23

<210> SEQ ID NO 161
<211> LENGTH: 26
<212> TYPE: DNA
<213> ORGANISM: Artificial Sequence
<220> FEATURE:
<223> OTHER INFORMATION: synthetic combined bacterial sequences

<400> SEQUENCE: 161
atcgatataa tttccgggtc gtagcc                                           26

<210> SEQ ID NO 162
<211> LENGTH: 56
<212> TYPE: DNA
<213> ORGANISM: Artificial Sequence
<220> FEATURE:
<223> OTHER INFORMATION: synthetic combined bacterial sequences

<400> SEQUENCE: 162
gatctggaat aaaaaacgcc cggcggcaac cgagcggcag ccattcggga taataa          56

<210> SEQ ID NO 163
<211> LENGTH: 24
<212> TYPE: DNA
<213> ORGANISM: Artificial Sequence
<220> FEATURE:
<223> OTHER INFORMATION: synthetic combined bacterial sequences

<400> SEQUENCE: 163
catatggctg agaccctact gttt                                             24

<210> SEQ ID NO 164
<211> LENGTH: 26
<212> TYPE: DNA
<213> ORGANISM: Artificial Sequence
<220> FEATURE:
<223> OTHER INFORMATION: synthetic combined bacterial sequences

<400> SEQUENCE: 164
atcgatctta caagctcccg gacaaa                                           26

<210> SEQ ID NO 165
<211> LENGTH: 20
<212> TYPE: DNA
<213> ORGANISM: Artificial Sequence
<220> FEATURE:
<223> OTHER INFORMATION: synthetic combined bacterial sequences

<400> SEQUENCE: 165
aatcgacatc cacccttgtc                                                  20

<210> SEQ ID NO 166
<211> LENGTH: 20
<212> TYPE: DNA
<213> ORGANISM: Artificial Sequence
<220> FEATURE:
<223> OTHER INFORMATION: synthetic combined bacterial sequences

<400> SEQUENCE: 166
gccttaactg cgtccacaat                                                  20
```

<210> SEQ ID NO 167
<211> LENGTH: 24
<212> TYPE: DNA
<213> ORGANISM: Artificial Sequence
<220> FEATURE:
<223> OTHER INFORMATION: synthetic combined bacterial sequences

<400> SEQUENCE: 167
catatggtta gcctcacccc caat                                      24

<210> SEQ ID NO 168
<211> LENGTH: 25
<212> TYPE: DNA
<213> ORGANISM: Artificial Sequence
<220> FEATURE:
<223> OTHER INFORMATION: synthetic combined bacterial sequences

<400> SEQUENCE: 168
atcgatcggg atggcctatt tatgg                                     25

<210> SEQ ID NO 169
<211> LENGTH: 26
<212> TYPE: DNA
<213> ORGANISM: Artificial Sequence
<220> FEATURE:
<223> OTHER INFORMATION: synthetic combined bacterial sequences

<400> SEQUENCE: 169
catatgaata ttttggagta tgctcc                                    26

<210> SEQ ID NO 170
<211> LENGTH: 23
<212> TYPE: DNA
<213> ORGANISM: Artificial Sequence
<220> FEATURE:
<223> OTHER INFORMATION: synthetic combined bacterial sequences

<400> SEQUENCE: 170
atcgataagc cctaacctcg gtg                                       23

<210> SEQ ID NO 171
<211> LENGTH: 24
<212> TYPE: DNA
<213> ORGANISM: Artificial Sequence
<220> FEATURE:
<223> OTHER INFORMATION: synthetic combined bacterial sequences

<400> SEQUENCE: 171
catatggtta gcctcacccc caat                                      24

<210> SEQ ID NO 172
<211> LENGTH: 30
<212> TYPE: DNA
<213> ORGANISM: Artificial Sequence
<220> FEATURE:
<223> OTHER INFORMATION: synthetic combined bacterial sequences

<400> SEQUENCE: 172
atcgatacaa ttcccgatta actattgacc                                30

<210> SEQ ID NO 173
<211> LENGTH: 26
<212> TYPE: DNA
<213> ORGANISM: Artificial Sequence
<220> FEATURE:
<223> OTHER INFORMATION: synthetic combined bacterial sequences

```
<400> SEQUENCE: 173
atcgattttt ctccaccatc aacacc                                        26

<210> SEQ ID NO 174
<211> LENGTH: 23
<212> TYPE: DNA
<213> ORGANISM: Artificial Sequence
<220> FEATURE:
<223> OTHER INFORMATION: synthetic combined bacterial sequences

<400> SEQUENCE: 174
agatctaagc cctaacctcg gtg                                           23

<210> SEQ ID NO 175
<211> LENGTH: 23
<212> TYPE: DNA
<213> ORGANISM: Artificial Sequence
<220> FEATURE:
<223> OTHER INFORMATION: synthetic combined bacterial sequences

<400> SEQUENCE: 175
cctgttattg gccacgggca gta                                           23

<210> SEQ ID NO 176
<211> LENGTH: 27
<212> TYPE: DNA
<213> ORGANISM: Artificial Sequence
<220> FEATURE:
<223> OTHER INFORMATION: synthetic combined bacterial sequences

<400> SEQUENCE: 176
ggtttaccct gggctcgaga atttagg                                       27

<210> SEQ ID NO 177
<211> LENGTH: 24
<212> TYPE: DNA
<213> ORGANISM: Artificial Sequence
<220> FEATURE:
<223> OTHER INFORMATION: synthetic combined bacterial sequences

<400> SEQUENCE: 177
cccggtgaag catatgagac ccct                                          24

<210> SEQ ID NO 178
<211> LENGTH: 27
<212> TYPE: DNA
<213> ORGANISM: Artificial Sequence
<220> FEATURE:
<223> OTHER INFORMATION: synthetic combined bacterial sequences

<400> SEQUENCE: 178
ggtttaccct gggctcgaga atttagg                                       27

<210> SEQ ID NO 179
<211> LENGTH: 25
<212> TYPE: DNA
<213> ORGANISM: Artificial Sequence
<220> FEATURE:
<223> OTHER INFORMATION: synthetic combined bacterial sequences

<400> SEQUENCE: 179
cctaaattca ggtcgaccgg caaac                                         25

<210> SEQ ID NO 180
```

```
<211> LENGTH: 21
<212> TYPE: DNA
<213> ORGANISM: Artificial Sequence
<220> FEATURE:
<223> OTHER INFORMATION: synthetic combined bacterial sequences

<400> SEQUENCE: 180
caccaaccag gctcgagtgg g                                        21

<210> SEQ ID NO 181
<211> LENGTH: 26
<212> TYPE: DNA
<213> ORGANISM: Artificial Sequence
<220> FEATURE:
<223> OTHER INFORMATION: synthetic combined bacterial sequences

<400> SEQUENCE: 181
cctaatttca gccccatatg caaacg                                   26

<210> SEQ ID NO 182
<211> LENGTH: 31
<212> TYPE: DNA
<213> ORGANISM: Artificial Sequence
<220> FEATURE:
<223> OTHER INFORMATION: synthetic combined bacterial sequences

<400> SEQUENCE: 182
tagagctctt aagtaaagtc cccgccacca t                             31

<210> SEQ ID NO 183
<211> LENGTH: 31
<212> TYPE: DNA
<213> ORGANISM: Artificial Sequence
<220> FEATURE:
<223> OTHER INFORMATION: synthetic combined bacterial sequences

<400> SEQUENCE: 183
tagagctctt aagtaaagtc cccgccacca t                             31

<210> SEQ ID NO 184
<211> LENGTH: 32
<212> TYPE: DNA
<213> ORGANISM: Artificial Sequence
<220> FEATURE:
<223> OTHER INFORMATION: synthetic combined bacterial sequences

<400> SEQUENCE: 184
tactcgaggt cattgcttcc ttggcttaga ac                            32

<210> SEQ ID NO 185
<211> LENGTH: 32
<212> TYPE: DNA
<213> ORGANISM: Artificial Sequence
<220> FEATURE:
<223> OTHER INFORMATION: synthetic combined bacterial sequences

<400> SEQUENCE: 185
tagagctcac caaagacgat gtggcccacc aa                            32

<210> SEQ ID NO 186
<211> LENGTH: 30
<212> TYPE: DNA
<213> ORGANISM: Artificial Sequence
<220> FEATURE:
<223> OTHER INFORMATION: synthetic combined bacterial sequences

<400> SEQUENCE: 186
```
tactcgagta tgaccccgct gttgcagttc                                      30

<210> SEQ ID NO 187
<211> LENGTH: 24
<212> TYPE: DNA
<213> ORGANISM: Artificial Sequence
<220> FEATURE:
<223> OTHER INFORMATION: synthetic combined bacterial sequences

<400> SEQUENCE: 187
cccggtgaag catatgagac ccct                                            24

<210> SEQ ID NO 188
<211> LENGTH: 30
<212> TYPE: DNA
<213> ORGANISM: Artificial Sequence
<220> FEATURE:
<223> OTHER INFORMATION: synthetic combined bacterial sequences

<400> SEQUENCE: 188
tagagctctt aagaaatacg gtgaatcttg                                      30

<210> SEQ ID NO 189
<211> LENGTH: 26
<212> TYPE: DNA
<213> ORGANISM: Artificial Sequence
<220> FEATURE:
<223> OTHER INFORMATION: synthetic combined bacterial sequences

<400> SEQUENCE: 189
cctaatttca gccccatatg caaacg                                          26

<210> SEQ ID NO 190
<211> LENGTH: 25
<212> TYPE: DNA
<213> ORGANISM: Artificial Sequence
<220> FEATURE:
<223> OTHER INFORMATION: synthetic combined bacterial sequences

<400> SEQUENCE: 190
tagagctccc tatcctttgg acacc                                           25

<210> SEQ ID NO 191
<211> LENGTH: 33
<212> TYPE: DNA
<213> ORGANISM: Artificial Sequence
<220> FEATURE:
<223> OTHER INFORMATION: synthetic combined bacterial sequences

<400> SEQUENCE: 191
tagagctcgt gtttggagca ttacacaccg atg                                  33

<210> SEQ ID NO 192
<211> LENGTH: 31
<212> TYPE: DNA
<213> ORGANISM: Artificial Sequence
<220> FEATURE:
<223> OTHER INFORMATION: synthetic combined bacterial sequences

<400> SEQUENCE: 192
taagatcttt ttaagaatgt ttgggaccca g                                    31

<210> SEQ ID NO 193
<211> LENGTH: 31
<212> TYPE: DNA

```
<213> ORGANISM: Artificial Sequence
<220> FEATURE:
<223> OTHER INFORMATION: synthetic combined bacterial sequences

<400> SEQUENCE: 193
tcagatctgc ccctctggga aaaaatgacc a                                31

<210> SEQ ID NO 194
<211> LENGTH: 30
<212> TYPE: DNA
<213> ORGANISM: Artificial Sequence
<220> FEATURE:
<223> OTHER INFORMATION: synthetic combined bacterial sequences

<400> SEQUENCE: 194
tactcgagta tgaccccgct gttgcagttc                                  30

<210> SEQ ID NO 195
<211> LENGTH: 33
<212> TYPE: DNA
<213> ORGANISM: Artificial Sequence
<220> FEATURE:
<223> OTHER INFORMATION: synthetic combined bacterial sequences

<400> SEQUENCE: 195
gtgtctcata tggttacatc ccccttttcc ctt                              33

<210> SEQ ID NO 196
<211> LENGTH: 20
<212> TYPE: DNA
<213> ORGANISM: Artificial Sequence
<220> FEATURE:
<223> OTHER INFORMATION: synthetic combined bacterial sequences

<400> SEQUENCE: 196
cgagccctgc tcgagcaggc                                             20

<210> SEQ ID NO 197
<211> LENGTH: 35
<212> TYPE: DNA
<213> ORGANISM: Artificial Sequence
<220> FEATURE:
<223> OTHER INFORMATION: synthetic combined bacterial sequences

<400> SEQUENCE: 197
gtgcctcata tgacgagttc cctttattta agcac                            35

<210> SEQ ID NO 198
<211> LENGTH: 34
<212> TYPE: DNA
<213> ORGANISM: Artificial Sequence
<220> FEATURE:
<223> OTHER INFORMATION: synthetic combined bacterial sequences

<400> SEQUENCE: 198
cggttgctcg agcatctgga acggttgggt aaat                             34

<210> SEQ ID NO 199
<211> LENGTH: 33
<212> TYPE: DNA
<213> ORGANISM: Artificial Sequence
<220> FEATURE:
<223> OTHER INFORMATION: synthetic combined bacterial sequences

<400> SEQUENCE: 199
gtgtctcata tggttacatc ccccttttcc ctt                              33
```

<210> SEQ ID NO 200
<211> LENGTH: 34
<212> TYPE: DNA
<213> ORGANISM: Artificial Sequence
<220> FEATURE:
<223> OTHER INFORMATION: synthetic combined bacterial sequences

<400> SEQUENCE: 200
ggtcacagat ctgttgtccc ccatggccta gcta        34

<210> SEQ ID NO 201
<211> LENGTH: 40
<212> TYPE: DNA
<213> ORGANISM: Artificial Sequence
<220> FEATURE:
<223> OTHER INFORMATION: synthetic combined bacterial sequences

<400> SEQUENCE: 201
ccttgcagat ctggatacgt tgaggttatt taaattatga        40

<210> SEQ ID NO 202
<211> LENGTH: 34
<212> TYPE: DNA
<213> ORGANISM: Artificial Sequence
<220> FEATURE:
<223> OTHER INFORMATION: synthetic combined bacterial sequences

<400> SEQUENCE: 202
cggttgctcg agcatctgga acggttgggt aaat        34

<210> SEQ ID NO 203
<211> LENGTH: 35
<212> TYPE: DNA
<213> ORGANISM: Artificial Sequence
<220> FEATURE:
<223> OTHER INFORMATION: synthetic combined bacterial sequences

<400> SEQUENCE: 203
gtgcctcata tgaatactgc taaaactgtt gttgc        35

<210> SEQ ID NO 204
<211> LENGTH: 35
<212> TYPE: DNA
<213> ORGANISM: Artificial Sequence
<220> FEATURE:
<223> OTHER INFORMATION: synthetic combined bacterial sequences

<400> SEQUENCE: 204
gatctcctcg aggtaaagaa tcagcatagg tctgg        35

<210> SEQ ID NO 205
<211> LENGTH: 23
<212> TYPE: DNA
<213> ORGANISM: Artificial Sequence
<220> FEATURE:
<223> OTHER INFORMATION: synthetic combined bacterial sequences

<400> SEQUENCE: 205
ctagaggttc atatgaactt ggc        23

<210> SEQ ID NO 206
<211> LENGTH: 20
<212> TYPE: DNA
<213> ORGANISM: Artificial Sequence
<220> FEATURE:

```
<223> OTHER INFORMATION: synthetic combined bacterial sequences

<400> SEQUENCE: 206
gtaagcaggc tcgaggcaag                                              20

<210> SEQ ID NO 207
<211> LENGTH: 25
<212> TYPE: DNA
<213> ORGANISM: Artificial Sequence
<220> FEATURE:
<223> OTHER INFORMATION: synthetic combined bacterial sequences

<400> SEQUENCE: 207
gtcgaccttc cagcaccacg tcaac                                        25

<210> SEQ ID NO 208
<211> LENGTH: 29
<212> TYPE: DNA
<213> ORGANISM: Artificial Sequence
<220> FEATURE:
<223> OTHER INFORMATION: synthetic combined bacterial sequences

<400> SEQUENCE: 208
gaattcacag aattgcctcc ttaattgag                                    29

<210> SEQ ID NO 209
<211> LENGTH: 29
<212> TYPE: DNA
<213> ORGANISM: Artificial Sequence
<220> FEATURE:
<223> OTHER INFORMATION: synthetic combined bacterial sequences

<400> SEQUENCE: 209
acgcgtcgac ttatggttga ttcgcattg                                    29

<210> SEQ ID NO 210
<211> LENGTH: 27
<212> TYPE: DNA
<213> ORGANISM: Artificial Sequence
<220> FEATURE:
<223> OTHER INFORMATION: synthetic combined bacterial sequences

<400> SEQUENCE: 210
cggaattcat agctgttgcc ctccaag                                      27

<210> SEQ ID NO 211
<211> LENGTH: 25
<212> TYPE: DNA
<213> ORGANISM: Artificial Sequence
<220> FEATURE:
<223> OTHER INFORMATION: synthetic combined bacterial sequences

<400> SEQUENCE: 211
gtcgacaacg acggaggttt aaggg                                        25

<210> SEQ ID NO 212
<211> LENGTH: 26
<212> TYPE: DNA
<213> ORGANISM: Artificial Sequence
<220> FEATURE:
<223> OTHER INFORMATION: synthetic combined bacterial sequences

<400> SEQUENCE: 212
gaattcatgc acgttcacgg taatgg                                       26
```

US 9,650,642 B2

GENETICALLY MODIFIED CYANOBACTERIA FOR THE PRODUCTION OF ETHANOL

CROSS-REFERENCE TO RELATED APPLICATIONS

The present application claims priority to U.S. provisional application 61/065,292, filed Feb. 8, 2008, which is incorporated by reference in its entirety. The present application is related to a PCT application titled "GENETICALLY MODIFIED PHOTOAUTOTROPHIC ETHANOL PRODUCING HOST CELLS, METHOD FOR PRODUCING THE HOST CELLS, CONSTRUCTS FOR THE TRANSFORMATION OF THE HOST CELLS, METHOD FOR TESTING A PHOTOAUTOTROPHIC STRAIN FOR A DESIRED GROWTH PROPERTY AND METHOD OF PRODUCING ETHANOL USING THE HOST CELLS," filed on even the same day with the present application and claiming priority to U.S. provisional application 61/065,292, which PCT application is incorporated by reference in its entirety.

FIELD OF THE INVENTION

This invention is related to the field of direct production of ethanol from carbon dioxide and water using genetically modified cyanobacteria.

This application refers to a "Sequence Listing" listed below, which is provided as a text document. The document is entitled "12368060SeqList2.txt" (506,402 bytes, created Nov. 13, 2009) and is hereby incorporated by reference in its entirety herein.

BACKGROUND OF THE INVENTION

There is a current need to find alternate energy sources to substitute for the use of fossil fuels for transportation applications. Biologically produced ethanol has been proposed as an alternative to petroleum-derived liquid fuels. There are different ways to generate ethanol through biological means. Obtaining ethanol from grains and seeds has been criticized for contributing to rising food prices and leading to deforestation. The disadvantages of obtaining ethanol from grain and cellulosic sources are further explained in paragraph [0007] of published U.S. patent application 20090017512. The present invention is addressed to the direct production of ethanol from carbon dioxide and water using genetically-modified cyanobacteria and overcomes problems associated with grain or cellulosic sources of ethanol.

Further, the present invention discloses the capability to produce ethanol using desert lands and salt water and resolves problems associated with demand on food-producing land and water resources. Moreover, the ethanol productivity of the present invention is higher than for corn-based ethanol. The present invention has projected productivity of 6,000 gallons (22,700 liter) ethanol per acre compared to 370 gallons (1,400 liter) ethanol for corn ethanol. [Bryan Walsh, "Biofuels: the New Alchemy," TIME magazine, http://www.time.com/time/specials/packages/article/0,28804,18 72110_1872133_1872143-1,00.html; see also Emily Waltz, "Biotech's Green Gold," 27 Nature Biotechnology 15-18 (2009)].

The present invention improves upon work disclosed by Woods et al. in U.S. Pat. Nos. 6,306,639 and 6,699,696, which taught the genetic modification of Cyanobacteria by incorporating the genetic information encoding for pyruvate decarboxylase (pdc) and alcohol dehydrogenase (adh). Specifically, the coding sequences of pyruvate decarboxylase (pdc) and alcohol dehydrogenase II (adh) from the bacterium *Zymomonas mobilis* were cloned into the shuttle vector pCB4 and then used to transform the cyanobacterium *Synechococcus* sp. strain PCC 7942. The pdc and adh genes were expressed at high levels, and the transformed cyanobacterium synthesized ethanol, which diffused from the cells into the culture medium.

Methods to improve ethanol production in such ethanologenic organisms are needed to facilitate commercial implementation of this ethanol source. The ability to modify the genetics of specific species has been stated to be currently limiting progress. E. T. Johnson and C. Schmidt-Dannert, "Light Energy Conversion in Engineered Microorganisms," Trends in Biotechnology, Volume 26, Issue 12, December 2008, Pages 682-689. The problem of genetic engineering is complicated. Some of the obstacles to achieving high yields of products are a result of the interdependence of metabolic networks, which are strongly influenced by the global levels of a handful of metabolites: ATP/ADP, NAD+/NADH, NADP+/NADPH, and acyl-CoAs. ( . . . ) The incorporation of new pathways for biofuel synthesis can destabilize the balance of these important metabolites, leading to the production of undesirable byproducts and a decrease in yield. Sung Kuk Lee, Howard Chou, Timothy S Ham, Taek Soon Lee, Jay D Keasling, Current Opinion in Biotechnology, Volume 19, Issue 6, December 2008, Pages 556-563. [Generally, see also Biochemistry. Fifth Edition. Berg J M, Tymoczko J L, and Stryer L. New York. W.H. Freeman and Company. 2002.]

One way to increase ethanol production in a microbial host cell is to down-regulate and/or disrupt genes encoding enzymes involved in metabolic pathways that may compete for substrates, intermediates, and/or co-factors that influence ethanol production. The present invention discloses how this can be successfully done to increase ethanol production.

SUMMARY OF THE INVENTION

The present invention discloses genetically-modified cyanobacteria with ethanol-production capabilities enhanced over the currently-reported art, and methods of making such cyanobacteria.

The genetically modified photoautotrophic ethanol producing host cell comprises at least two different genetic modifications, a first and a second genetic modification.

The first genetic modification changes the enzymatic activity or affinity of an endogenous host enzyme, resulting in a higher level of biosynthesis of acetyl-CoA, acetaldehyde, pyruvate or precursors thereof. The endogenous host enzyme is already present in an unmodified wild type host cell and its activity or affinity is changed by the first genetic modification in order to increase the level of biosynthesis of metabolic intermediates, which are also present in the wild type host cell and which can be used to form ethanol. Suitable endogenous host enzymes are selected from the group consisting of phosphoglycerate mutase, enolase, pyruvate kinase, ribulose-1,5-bisphosphate carboxylase/oxygenase (RubisCO), malic enzyme, phosphoenolpyruvate [PEP]carboxylase, malic enzyme, and malate dehydrogenase. The enhanced level of metabolic intermediates can arise through an increase in the rate of synthesis of the metabolic intermediate or elimination or reduction of the rate of use of the metabolic intermediate by a competing reaction. Examples of the latter include knockout of alanine dehydrogenase, phosphotransacetylase, acetate kinase, lactate dehydrogenase, and a knock-down of pyruvate dehydrogenase activity, in which we are attempting to reduce the turnover and thus keep the metabolite pools higher.

The second genetic modification is in the form of at least one overexpressed enzyme, which can form ethanol, for example from the above-mentioned important metabolic intermediates. In a further embodiment the overexpressed enzyme for ethanol formation can catalyze the last step of ethanol formation leading to the final product ethanol. The overexpressed enzyme for ethanol formation can also catalyze the penultimate step of ethanol formation resulting in a metabolic intermediate, which can further be converted by another enzyme for ethanol formation into the final product ethanol. The second genetic modification can take the form of overexpression of pdc or the form of overexpression of adh and pdc.

Enhanced ethanol production has been obtained by identifying a variety of genes as targets for downregulation, which are set forth more fully in the examples below. The fermentative pathway is impacted in the double mutant Δack/Δpta and the carbohydrate storage pathway is impacted in the ΔglgA1/ΔglgA2 double mutant.

In one aspect the invention provides a method for the production of ethanol comprising the steps
a) providing an ethanologenic cyanobacterial host cell, having genetic modifications relative to the corresponding wild type cell comprising
i) changing the enzymatic activity or affinity of an endogenous host cell enzyme
ii) creating an ethanologenic biosynthetic pathway comprising an overexpressed first enzyme for the formation of ethanol,
b) growing the host cell of (a) under conditions whereby ethanol is produced; and
c) isolating the ethanol produced at step (b).

BRIEF DESCRIPTION OF THE DRAWINGS

FIG. 4a presents the amino acid sequence of a glycogen synthase gene of *Synechocystis* sp. PCC 6803 that is encoded by the gene sll0945 (glgA1). (SEQ ID NO:1)

FIG. 4B presents the amino acid sequence of a second glycogen synthase of *Synechocystis* sp. PCC 6803 that is encoded by the gene sll1393 (glgA2). (SEQ ID NO:2)

FIG. 4E presents the nucleotide sequence of the construct pUC 19-glgA1-Cm. (SEQ ID NO:3)

FIG. 4H presents the nucleotide sequence of the construct pUC 19-glgA2-Kan. (SEQ ID NO:4)

FIG. 5A presents the amino acid sequence of the open reading frame sll1682, which encodes alanine dehydrogenase (EC 1.4.1.1) (Genbank No BAA16790) of *Synechocystis* sp. strain PCC6803. (SEQ ID NO:5)

FIG. 5C presents the nucleotide sequence of the insert of construct pGEM-T/ald-KManti. (SEQ ID NO:6)

FIG. 6A presents the amino acid sequence of the open reading frame slr1176, which encodes ADP-glucose pyrophosphorylase (EC 2.7.7.27) (Genbank No BAA18822) of *Synechocystis* sp. strain PCC6803. (SEQ ID NO:7)

FIG. 6C presents the nucleotide sequence of the insert of construct pGEM-T/glgC-KManti. (SEQ ID NO:8)

FIG. 6E presents the nucleotide sequence of the insert of construct pDrive/glgC-CMantisense. (SEQ ID NO:9)

FIG. 7A presents the amino acid sequence of the open reading frame slr0301 that encodes pyruvate water dikinase/PEP synthase (EC 2.7.9.2) (Genbank No BAA10668) of *Synechocystis* sp. strain PCC6803. (SEQ ID NO:10)

FIG. 7C presents the nucleotide sequence of the insert of construct pGEM-T/ppsA-anti. (SEQ ID NO:11)

FIG. 8A presents the amino acid sequence of open reading frame slr 1556 that encodes a putative lactate dehydrogenase (EC 1.1.1.28), (annotated as 2-hydroxyaciddehydrogenase homolog) (GenBank No. P74586) of *Synechocystis* sp. strain PCC6803. (SEQ ID NO:12)

FIG. 8D presents the nucleotide sequence of the insert contained in the construct pBlue ldh-Kan-a. (SEQ ID NO:13)

FIG. 9A presents the amino acid sequence of the open reading frame sll 1299 that encodes a putative acetate kinase (EC 2.7.2.1) (Genbank No. P73162). (SEQ ID NO:14)

FIG. 9D presents the nucleotide sequence of the insert of construct pBlue-ack-Kan-b. (SEQ ID NO:15)

FIG. 10A presents the amino acid sequence of the open reading frame slr2132 that encodes a phosphoacetyltransacetylase (EC 2.3.1.8) (Genbank No. P73662) of *Synechocystis* sp. strain PCC6803. (SEQ ID NO:16)

FIG. 10D presents the nucleotide sequence of the insert of construct pUC pta-Cm. (SEQ ID NO:17)

FIG. 11A presents the amino acid sequence of open reading frame slr1830 that encodes poly(3-hydroxyalkanoate) synthase [EC:2.3.1.] (Genbank No BAA17430) of *Synechocystis* sp. strain PCC6803. (SEQ ID NO:18)

FIG. 11C presents the nucleotide sequence of the insert of construct as pIC2OH/ΔphaC-KM. (SEQ ID NO:19)

FIG. 11D presents the amino acid sequence of ORF all4645 for PCC 7120 (SEQ ID NO:20).

FIG. 11F presents the sequence of the insert of pRL271 agp (all4645)::C.K3-PpetE-pdc-adhII (SEQ ID NO:21).

FIG. 11G presents the amino acid sequence of Glucose-1-phosphate adenylyltransferase (ADP-glucose-pyrophosphorylase, agp, glgC), EC 2.7.7.27, of *Anabaena variabilis* ATCC29314 (SEQ ID NO:22).

FIG. 12A presents the amino acid sequence of open reading frame sll1721 that encodes the β-subunit of the E1 component of the pyruvate dehydrogenase (EC 1.2.4.1) (Genbank No BAA17445) of *Synechocystis* sp. strain PCC6803. (SEQ ID NO:23)

FIG. 12C presents the nucleotide sequence of the insert for pSK9/pdhBanti. (SEQ ID NO:24)

FIG. 12E presents the nucleotide sequence of the insert for the construct pSK9/pdhB. (SEQ ID NO:25)

FIG. 12G presents the nucleotide sequence of the insert of construct pGEM-T/ΔpdhB-KMantisense. (SEQ ID NO:26)

FIG. 13B presents the nucleotide sequence of vector pGEM-T. (SEQ ID NO:27)

FIG. 14B presents the nucleotide sequence of vector pDrive. (SEQ ID NO:28)

FIG. 15B presents the nucleotide sequence of the vector pBluescript II SK (+). (SEQ ID NO:29)

FIG. 16B presents the nucleotide sequence of the vector pUC 19. (SEQ ID NO:30)

FIG. 17B presents the nucleotide sequence of the vector pSK9. (SEQ ID NO:31)

FIG. 18A presents the amino acid sequence of open reading frame slr0721 that encodes malic enzyme 1 (EC 1.1.1.38) (Genbank No P72661) of *Synechocystis* sp. strain PCC6803. (SEQ ID NO:32)

FIG. 18C presents the nucleotide sequence of the insert of construct pSK9/me-long. (SEQ ID NO:33)

FIG. 19A presents the amino acid sequence of open reading frame sll0891 that encodes malate dehydrogenase (EC 1.1.1.37) (Genbank No Q55383) of *Synechocystis* sp. strain PCC6803. (SEQ ID NO:34)

FIG. 19C presents the nucleotide sequence of the insert of construct pSK9-mdh. (SEQ ID NO:35)

FIG. 19E presents the nucleotide sequence of the insert of construct pSK9/me-mdh. (SEQ ID NO:36)

FIG. 20A presents the amino acid sequence of open reading frame sll0587 that encodes a pyruvate kinase 1 (EC 2.7.1.40 (PK1)) (Genbank No Q55863) of *Synechocystis* sp. strain PCC6803. (SEQ ID NO:37)

FIG. 20C presents the nucleotide sequence of the insert of construct pVZ321-pyk1. (SEQ ID NO:38)

FIG. 20E presents the nucleotide sequence of the insert found in construct pVZ321 PpetJ pyk1. (SEQ ID NO:39)

FIG. 21A presents the amino acid sequence of open reading frame sll1275 that encodes pyruvate kinase 2 (EC 2.7.1.40 (PK2)) (Genbank No P73534) of *Synechocystis* sp. strain PCC6803. (SEQ ID NO:40)

FIG. 21C presents the nucleotide sequence of the insert of pVZ321pyk2. (SEQ ID NO:41)

FIG. 21E presents the nucleotide sequence for the insert of the construct pVZ321 PpetJ pyk2. (SEQ ID NO:42)

FIG. 22B presents the amino acid sequence of pyruvate kinase I (*E. coli* K12). (SEQ ID NO:43)

FIG. 22C presents the amino acid sequence of enolase (*Zymomonas mobilis*). (SEQ ID NO:44)

FIG. 22D presents the amino acid sequence of phosphoglycerate mutase (*Zymomonas mobilis*). (SEQ ID NO:45)

FIG. 22E presents the nucleotide sequence of the insert of plasmid #67. (SEQ ID NO:46)

FIG. 23A presents the amino acid sequence of open reading frame slr0752 that encodes the enolase (eno, 2-phosphoglycerate dehydratase) (EC 4.2.1.11) (Genbank No. BAA18749) of *Synechocystis* sp. strain PCC6803. (SEQ ID NO:47)

FIG. 23C presents the nucleotide sequence of the insert of construct pVZ321-PpetJ-eno. (SEQ ID NO:48)

FIG. 24A presents the amino acid sequence of open reading frame slr1124 that encodes the phosphoglycerate mutase (pgm or gpmB) (EC 5.4.2.1) (Genbank No. BAA16651) of *Synechocystis* sp. strain PCC6803. (SEQ ID NO:49)

FIG. 24C presents the nucleotide sequence of the insert of construct pVZ321-PpetJ-pgm. (SEQ ID NO:50)

FIG. 24F presents the nucleotide sequence of the insert of construct pVZ322-PpetJ-pyk1-eno-pgm. (SEQ ID NO:51)

24G presents the nucleotide sequence of the insert of construct pVZ322-PpetJ-pyk2-eno-pgm. (SEQ ID NO:52)

FIG. 25A presents the amino acid sequence for open reading frame slr0453 that encodes the probable phosphoketolase (phk), (EC 4.1.2.-) (Genbank No. P74690) of *Synechocystis* sp. strain PCC6803. (SEQ ID NO:53)

Figure 25B:
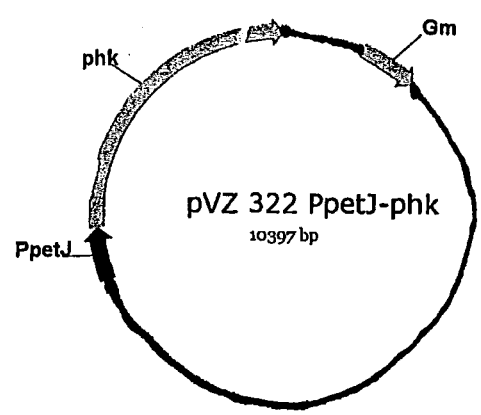

FIG. 25B presents a schematic representation of the gene organization for the construct pVZ322 PpetJ-phk.

FIG. 25C presents the nucleotide sequence of the insert of the construct pVZ322 PpetJ-phk. (SEQ ID NO:54)

FIG. 26A presents the amino acid sequence of open reading frame slr2132 that encodes a phosphoacetyltransacetylase (pta) (EC 2.3.1.8) (Genbank No. P73662) of *Synechocystis* sp. strain PCC6803. (SEQ ID NO:55)

Figure 26B:
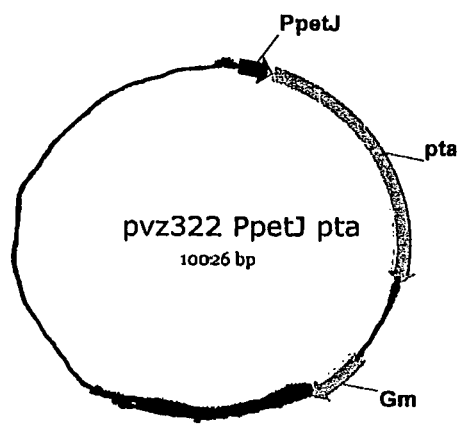

FIG. 26B presents a schematic representation of gene organization in the construct pVZ322 PpetJ pta.

FIG. 26C presents the nucleotide sequence of the insert of construct pVZ322 PpetJ pta. (SEQ ID NO:56)

Figure 26D:
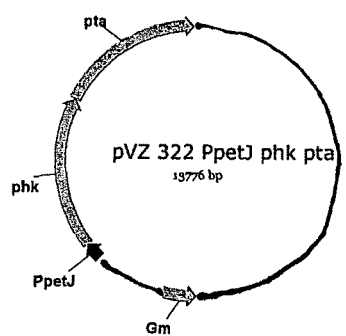

FIG. 26D presents a schematic representation of gene organization in construct pVZ322 PpetJ phk pta.

FIG. 26E presents the nucleotide sequence of the insert of construct pVZ322 PpetJ phk pta. (SEQ ID NO:57)

FIG. 27A presents the amino acid sequence of open reading frame slr0091 encodes a aldehyde dehydrogenase (aldh) (EC 1.2.1.3) (Genbank No. BAA10564) of *Synechocystis* sp. strain PCC6803. (SEQ ID NO:58)

Figure 27B:
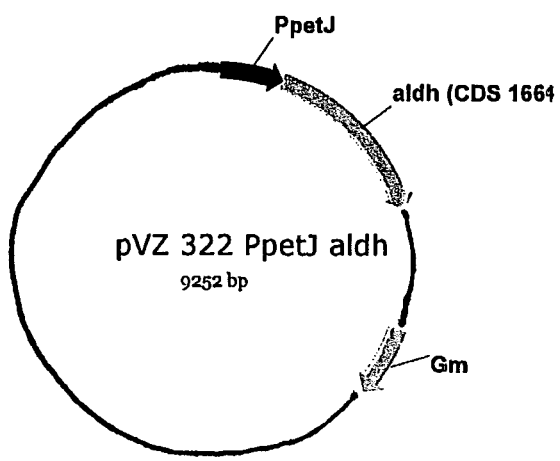

FIG. 27B is a schematic representation of gene organization in construct pVZ 322 PpetJ aldh.

FIG. 27C presents the nucleotide sequence of construct pvc 322 PpetJ aldh. (SEQ ID NO:59)

FIG. 28A presents the amino acid sequence of open reading frame sll0920 that encodes phosphoenolpyruvate carboxylase (EC 4.1.1.31) (Genbank No. BAA18393) of *Synechocystis* sp. strain PCC6803. (SEQ ID NO:60)

Figure 28B:
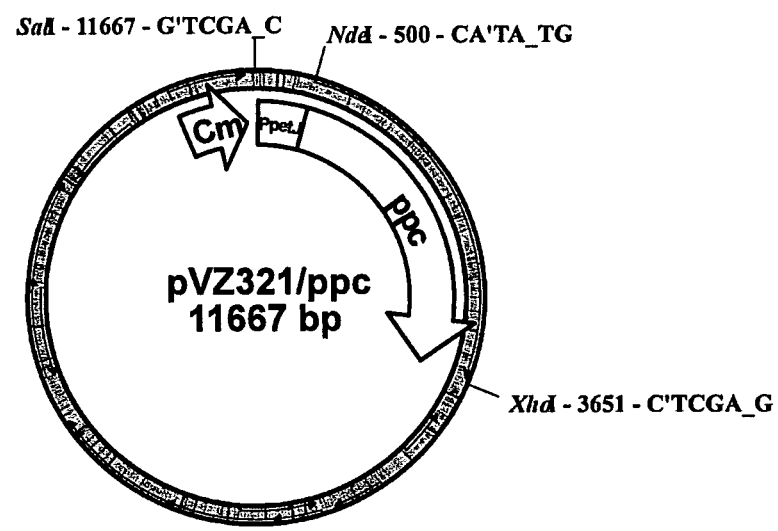

FIG. 28B is a schematic representation of gene organization in pVZ321-PpetJ-ppc.

FIG. 28C presents the nucleotide sequence of the insert of construct pVZ321-PpetJ-ppc. (SEQ ID NO:61)

FIG. 28D presents the nucleotide sequence of primer SynRbc-BglII-fw (SEQ ID NO:62).

FIG. 28E presents the nucleotide sequence of primer SynRbc-PstI-rev (SEQ ID NO:63).

FIG. 28F presents the nucleotide sequence of primer SynRbc-SacI-fw (SEQ ID NO:64).

FIG. 28G presents the nucleotide sequence of the rbcLXS operon of *Synechocystis* PCC 6803 (SEQ ID NO:65).

FIG. 28H presents the amino acid sequence of the rbcL large subunit of *Synechocystis* PCC 6803 (SEQ ID NO:66).

FIG. 28I presents the amino acid sequence of the rbcX Rubisco chaperonin protein of *Synechocystis* PCC 6803 (SEQ ID NO:67).

FIG. 28J presents the amino acid sequence of the ribulose bisphosphate carboxylase small subunit (rbcS) of *Synechocystis* PCC 6803 (SEQ ID NO:68).

Figure 28K:
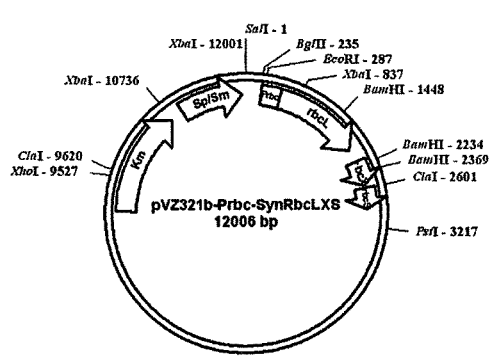

FIG. 28K is a schematic presentation of gene organization for plasmid pVZ321b-Prbc-SynRbcLXS.

Figure 28L:
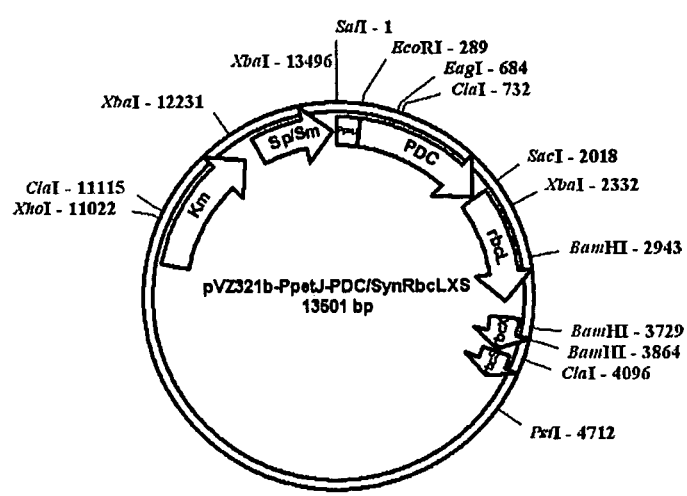

FIG. 28L is a schematic presentation of gene organization for plasmid pVZ321b-PpetJ-PDC/SynRbcLXS.

Figure 29A:
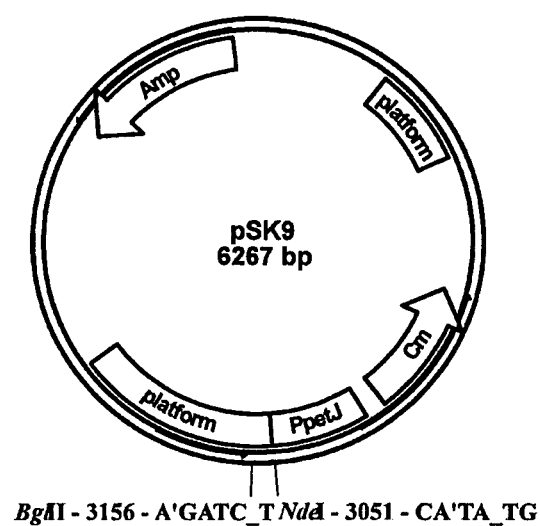

FIG. 29A is a schematic representation of the structure of the vector pSK9.

FIG. 29B presents the nucleotide sequence of the vector pSK9. (SEQ ID NO:69)

Figure 30A:
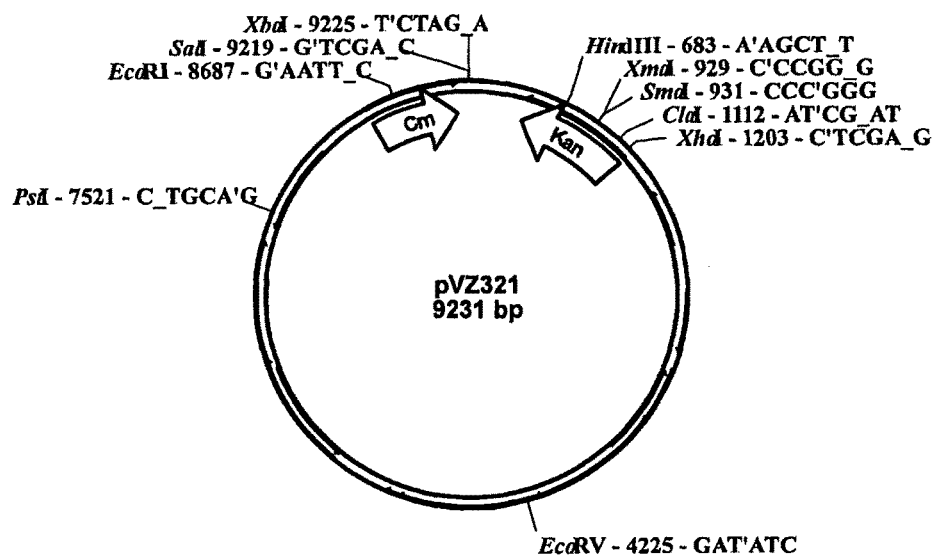

FIG. 30A is a schematic representation of gene organization in construct pVZ321. (GenBank No. AF100176).

FIG. 30B presents the nucleotide sequence of the pVZ321 vector. (SEQ ID NO:70)

Figure 31A:
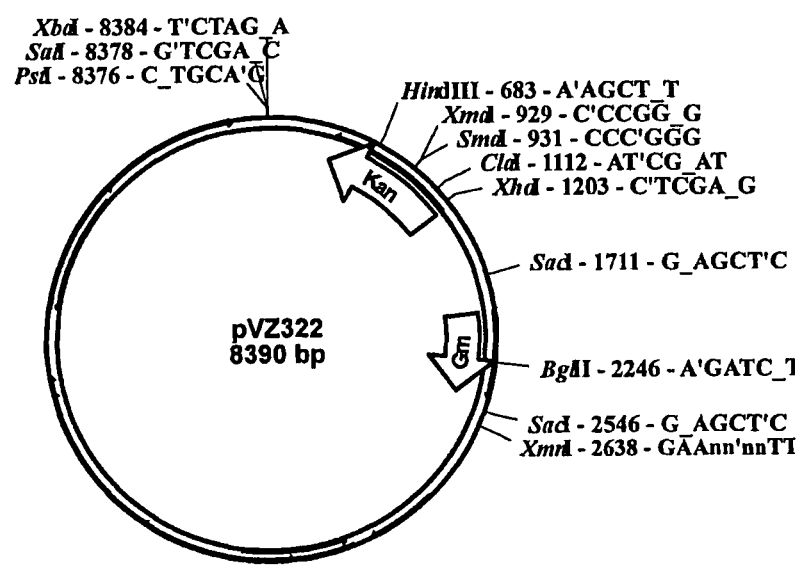

FIG. 31A is a schematic representation of gene organization for construct pVZ322.

FIG. 31B presents the nucleotide sequence of the pVZ322 vector (SEQ ID NO:71).

Figure 32A:
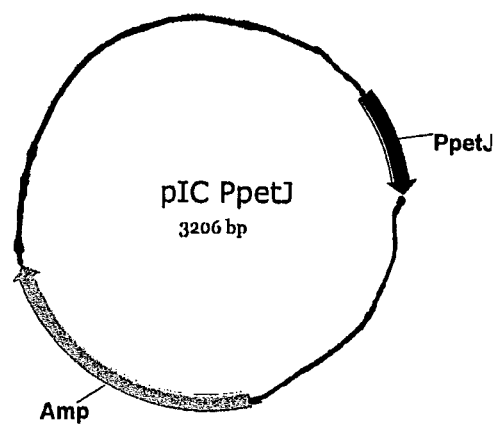

FIG. 32A is a schematic representation of gene organization of construct pIC PpetJ.

FIG. 32B presents the nucleotide sequence of the construct pIC PpetJ. (SEQ ID NO:72)

Figure 32C:
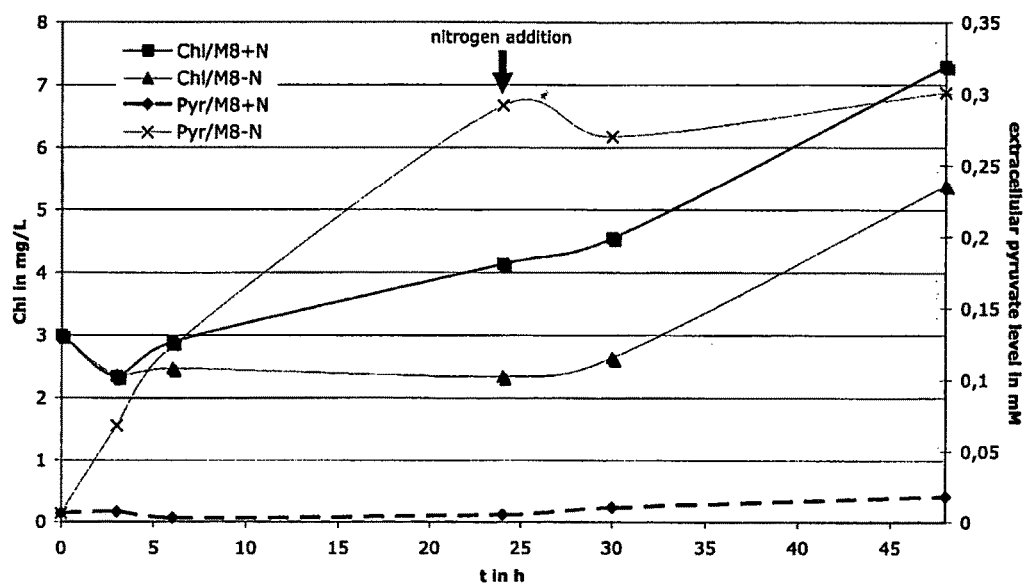

FIG. 32C is a graphic presentation demonstrating growth properties and extracellular pyruvate levels of the ΔglgA1/ΔglgA2 double mutant (M8) under nitrogen replete and nitrogen starved conditions.

Figure 32D:
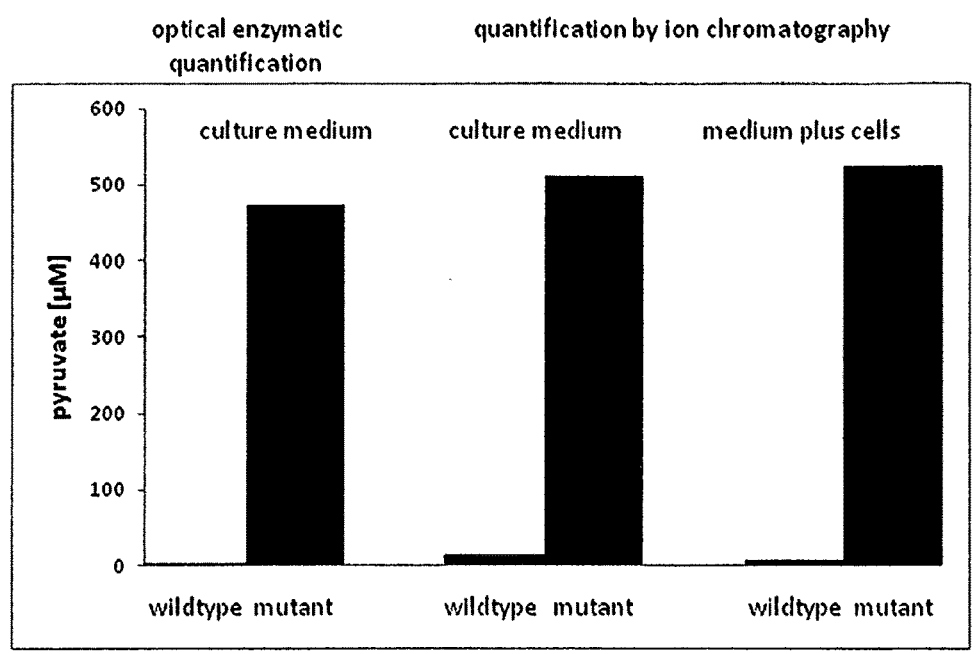

FIG. 32D is a graphic presentation of pyruvate levels in wildtype and mutant (ΔglgA1/ΔglgA2) media/cells as determined enzymatically and by ion chromatography.

Figure 32E:
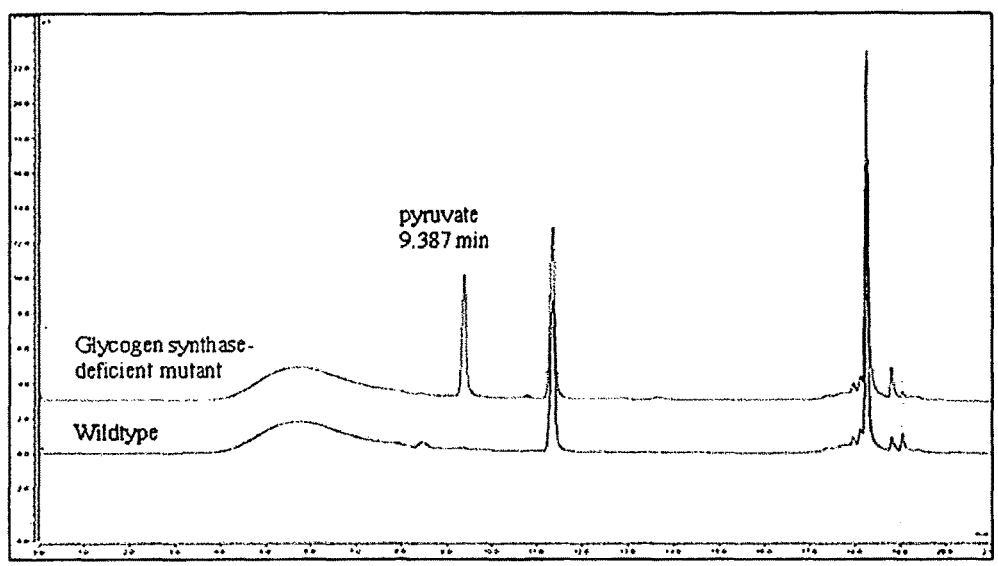

FIG. 32E is a graphic presentation of the conductimetric detection of pyruvate in methanol extracts (snapshot) of cultures of wildtype and a glycogen synthase deficient mutant after 24 h under N-deficient conditions.

Figure 32F:
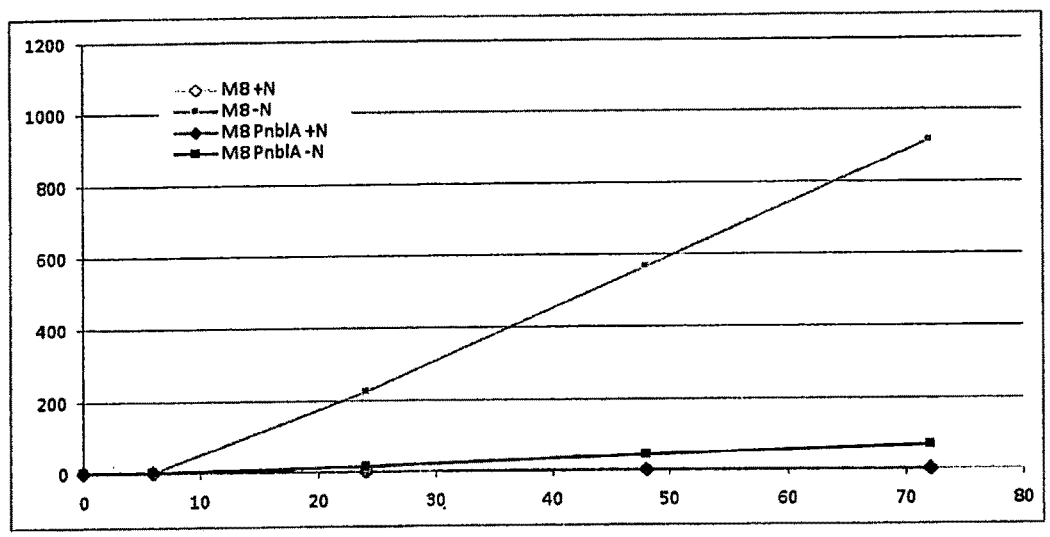

FIG. 32F is a graphic depiction showing the that the pyruvate concentration in the growth medium is higher for the M8 mutant without Adh and Pdc enzymes than for the M8 mutant including both ethanol forming enzymes under the conditions of nitrogen starvation.

Figure 32G:
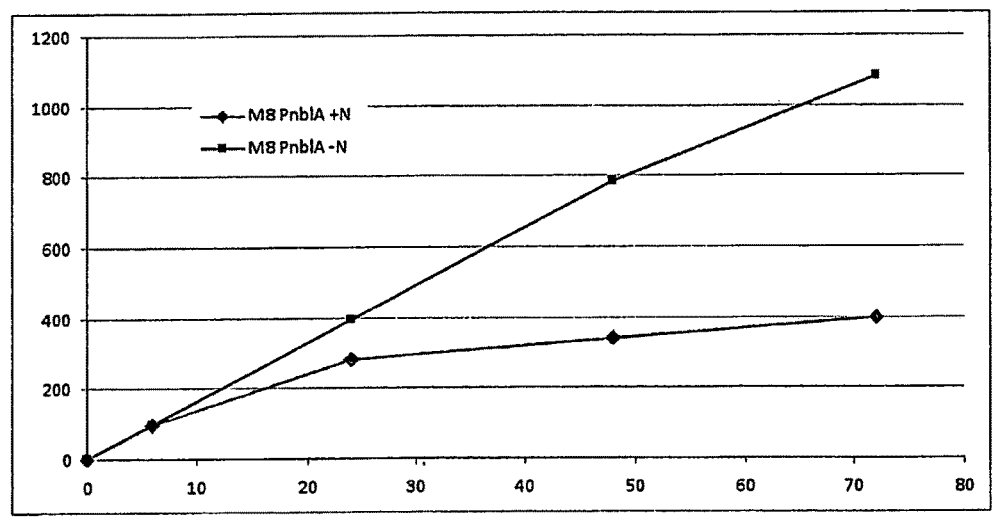

FIG. 32G is a graphic depiction of the ethanol concentration determined in the growth medium for the M8 mutant with the Adh and Pdc enzymes under the conditions of nitrogen starvation and without nitrogen starvation.

Figure 32H:
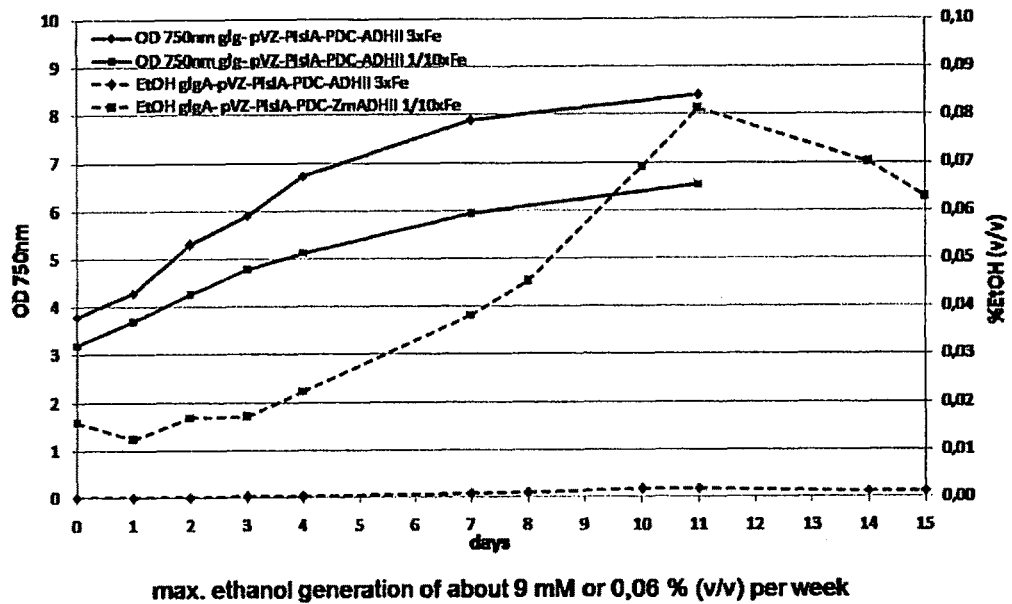

FIG. 32H is a graphic depiction of ethanol generation in glycogen deficient *Synechocystis* pVC mutants with ZmPDC and ZmADHII under the control of the iron-dependent isiA promoter.

Figure 32I:
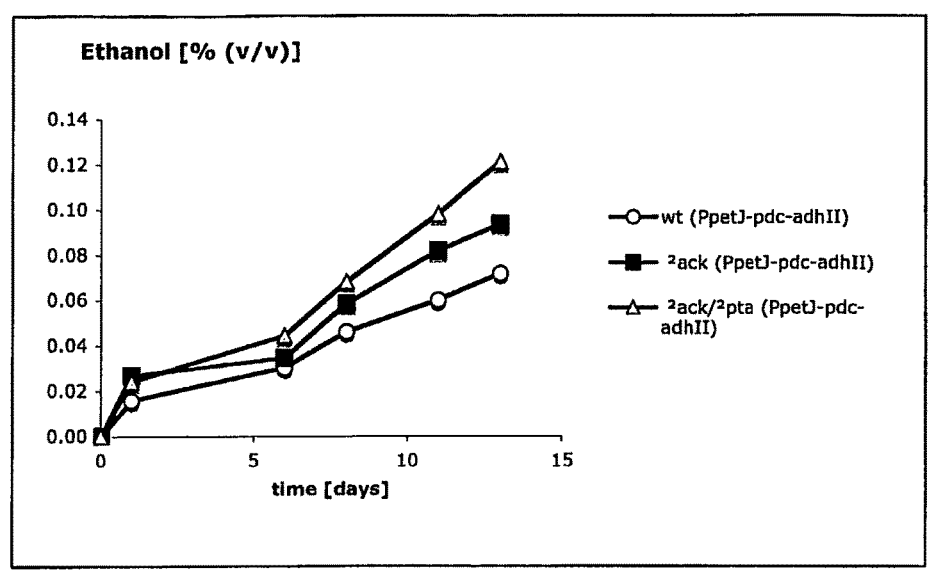

FIG. 32I is a graphic presentation of ethanol production in wildtype, ack and ack/pta double mutant cells.

Figure 32J:
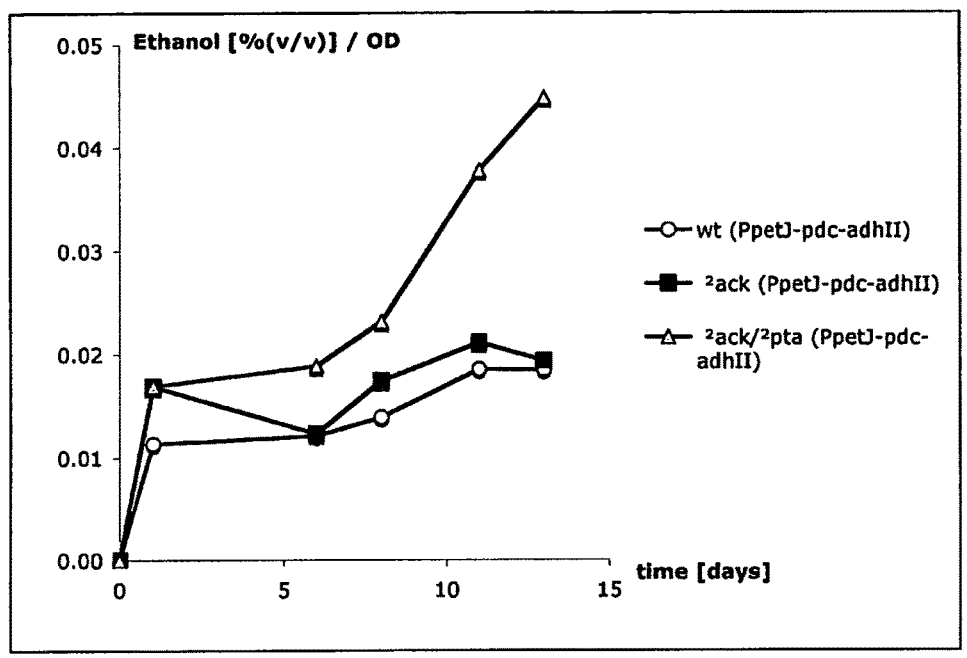

FIG. 32J is a graphic presentation of ethanol production in wildtype, ack and ack/pta double mutant cells when normalized for optical density.

Figure 32K:
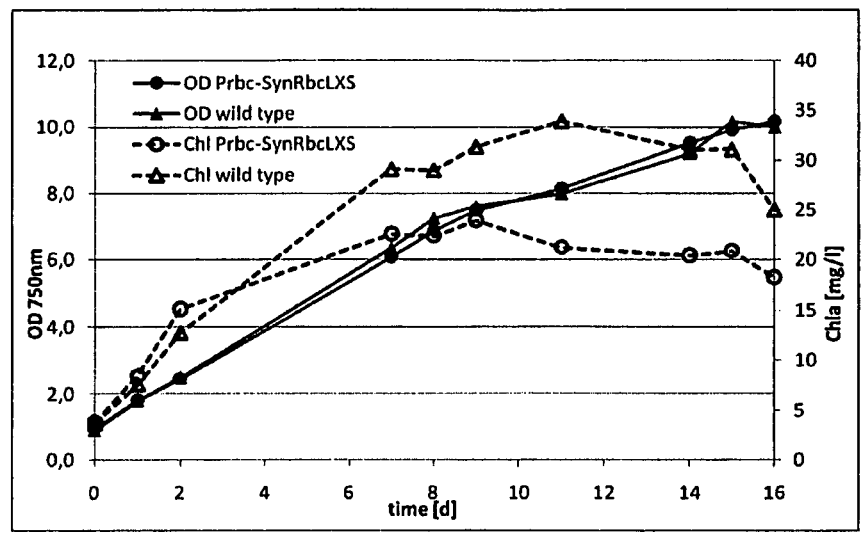

FIG. 32K is a graphic presentation of demonstrating that pVZ321b-Prbc-SynRbcLXS grows as fast as the *Synechocystis* wild type and shows no phenotypical differences except for the chlorophyll content that is reduced by 20-30% compared to wild type.

Figure 32L:
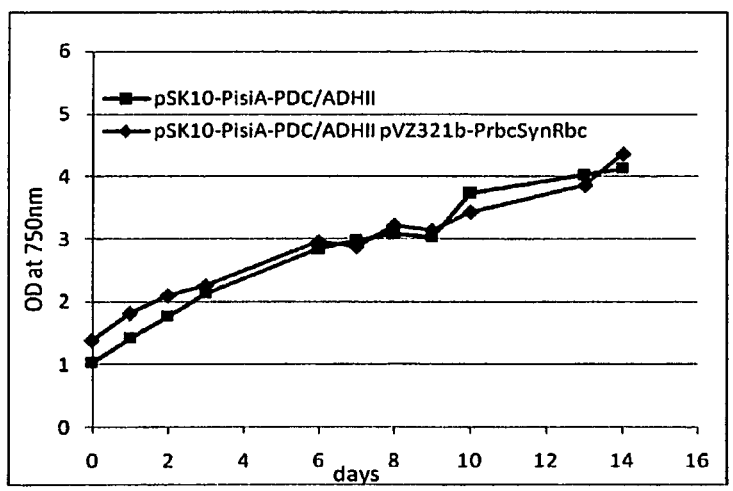

FIG. 32L is a graphic presentation of demonstrating the growth parameter (OD at 750 nm and Chlorophyll content) of *Synechocystis* wild type and a mutant that over-express the endogenous RuBisCO operon.

Figure 32M:
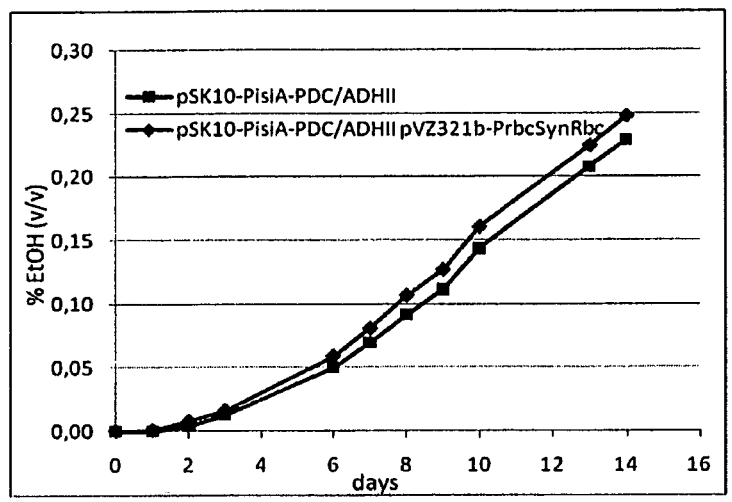

FIG. 32M is a graphic presentation of ethanol production for the mutant *Synechocystis* PCC6803 harboring the pSK10-PisiA-PDC/ADHII plasmid and the mutant additionally containing the vector pVZ321b-Prbc-SynRbc.

Figure 32N:
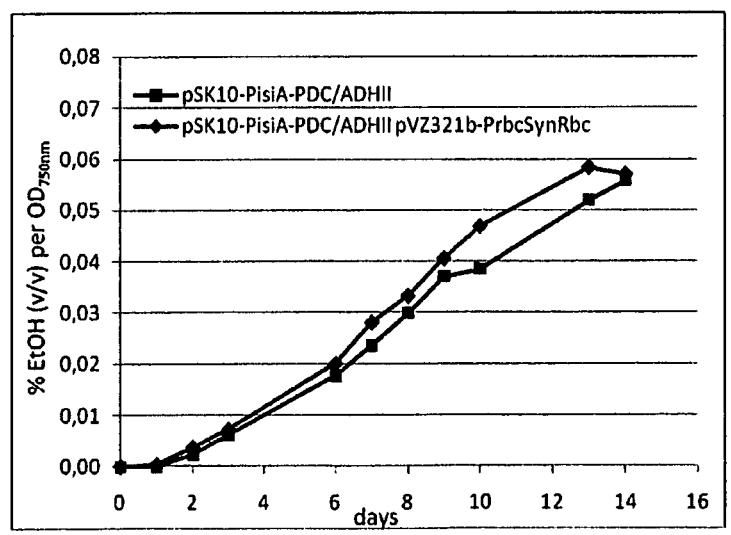
Figure 33A:
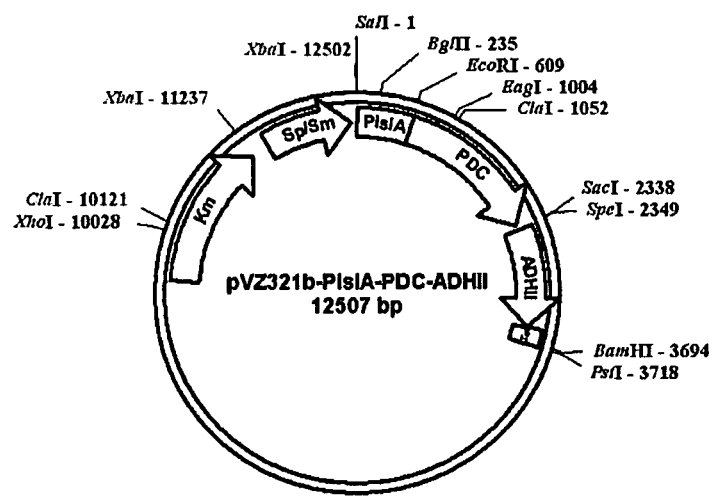

FIG. 32N is a graphic presentation of ethanol production normalized to the $OD_{750}$ for the mutant *Synechocystis* PCC6803 harboring the pSK10-PisiA-PDC/ADHII plasmid and the mutant additionally containing the vector pVZ321b-Prbc-SynRbc FIG. 33A is a schematic representation of gene organization for the construct pVZ-PisiA-pdc/adh.

Figure 33B:
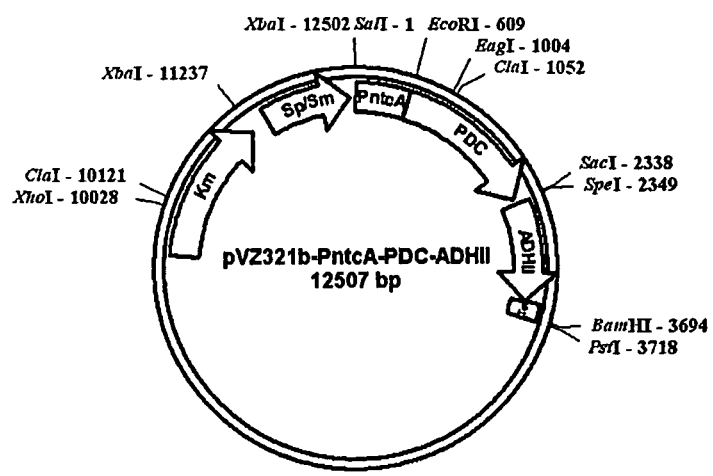

FIG. 33B is a schematic representation of gene organization for the construct pVZ-PntcA-pdc/adh.

Figure 33C:
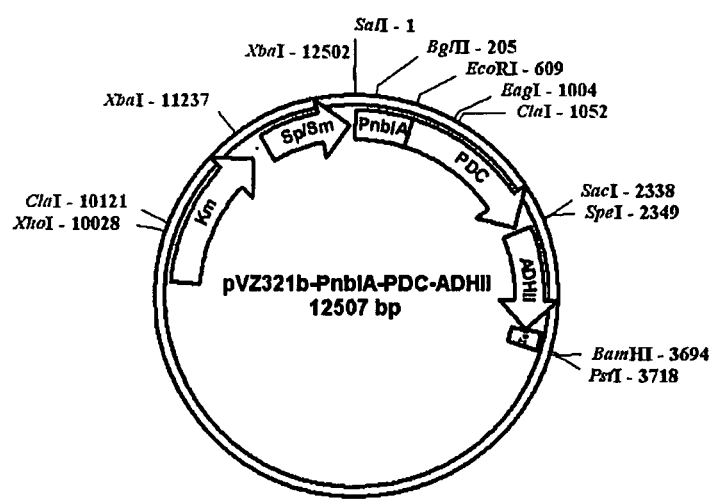

FIG. 33C is a schematic representation of gene organization for the construct pVZ-PnblA-pdc/adh.

FIG. 33D presents the nucleotide sequence of the insert of the vector pCB4-LR(TF)pa that encodes *Z. mobilis* adhII and pdc genes. (SEQ ID NO:73)

Figure 33E:
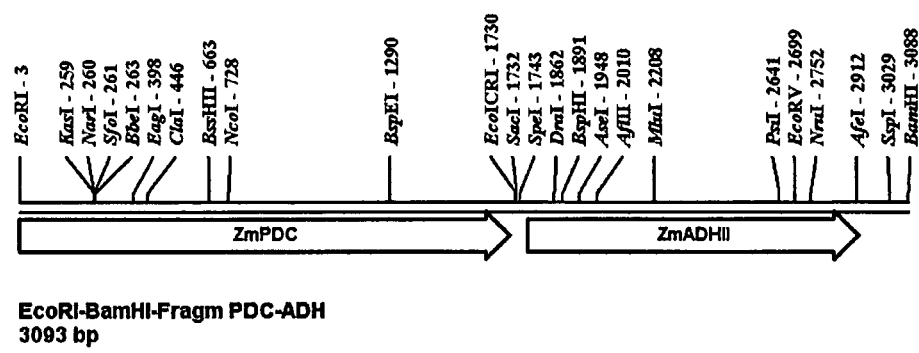

FIG. 33E is a schematic representation of restriction sites present in the *Z. mobilis* adhII and pdc fragment.

FIG. 33F presents the amino acid sequence of *Z. mobilis* pdc protein. (SEQ ID NO:74)

FIG. 33G presents the amino acid sequence of the *Z. mobilis* adhII protein. (SEQ ID NO:75)

FIG. 34A presents the nucleotide sequence for the isiA promoter (*Synechocystis* sp. PCC6803) (isiA gene: sll0247), which is induced under iron starvation conditions. (SEQ ID NO:76)

FIG. 34B presents the nucleotide sequence for the nblA promoter (*Synechocystis* sp. PCC6803) (nblA gene: ssll10452), which is induced under nitrogen starvation conditions. (SEQ ID NO:77)

FIG. 34C presents the nucleotide sequence for the ntcA promoter (*Synechocystis* sp. PCC6803) (ntcA gene: sll1423), which is induced under nitrogen starvation. (SEQ ID NO:78)

FIG. 35A presents the nucleotide sequence of the cloning vector pVZ321b, a derivative of pVZ321. (SEQ ID NO:79)

Figure 35B:
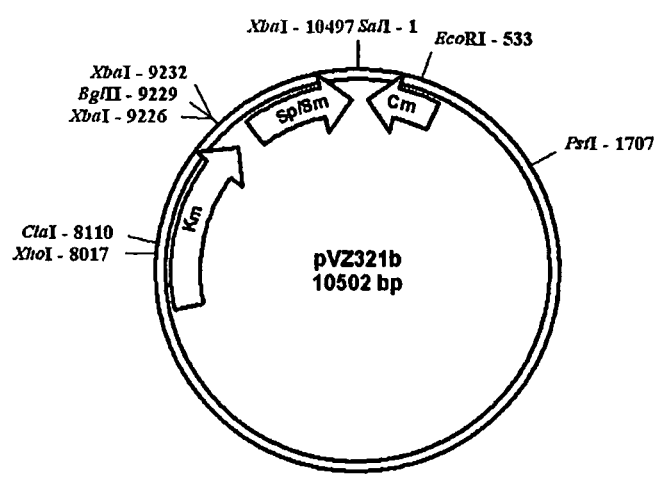

FIG. 35B is a schematic representation of gene organization for the cloning vector pVZ321b.

FIG. 36A presents the nucleotide sequence for the petJ promoter (*Synechocystis* sp. PCC 6803) (petJ gene: sll1796) (encoding for cytochrome c553), which is induced under copper starvation conditions. (SEQ ID NO:80)

Figure 36B:
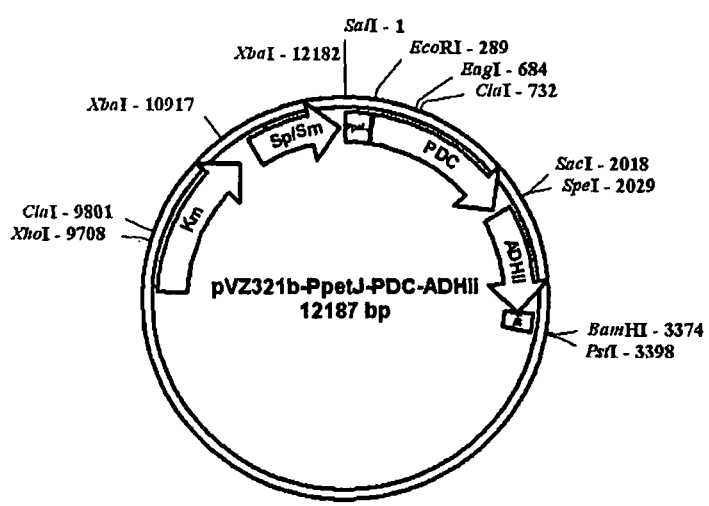

FIG. 36B is a schematic representation of gene organization for the construct pVZ321b-PpetJ-PDC-ADHII.

FIG. 36C presents the nucleotide sequence of the sigB promoter (*Synechocystis* sp. PCC 6803) (sigB gene: sll0306) (encoding for RNA polymerase group 2 sigma factor), which is induced after heat shock, in stationary growth phase/nitrogen starvation and darkness. (SEQ ID NO:81)

Figure 36D:
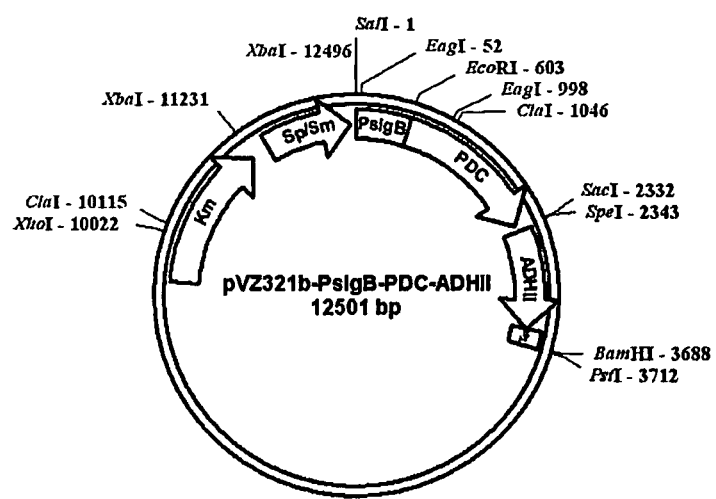

FIG. 36D is a schematic representation of gene organization for the construct pVZ321b-PsigB-PDC-ADHII.

FIG. 36E presents the nucleotide sequence of the htpG promoter (*Synechocystis* sp. PCC 6803) (htpG gene: sll0430) (encoding for heat shock protein 90, molecular chaperone), which is induced after heat shock. (SEQ ID NO:82)

Figure 36F:
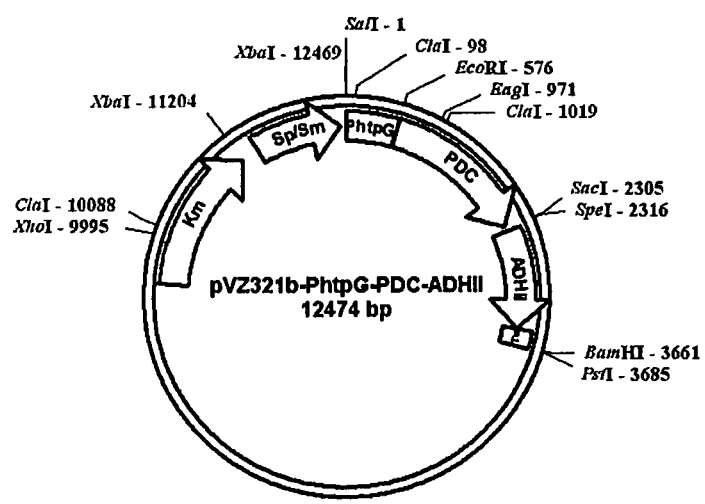

FIG. 36F is a schematic representation of gene organization for the construct pVZ321b-PhtpG-PDC-ADHII.

FIG. 36G presents the nucleotide sequence of the lrtA promoter (*Synechocystis* sp. PCC 6803) (lrtA gene: sll0947) (encoding the light repressed protein A homolog), which is induced after light to dark transition. (SEQ ID NO:83)

Figure 36H:
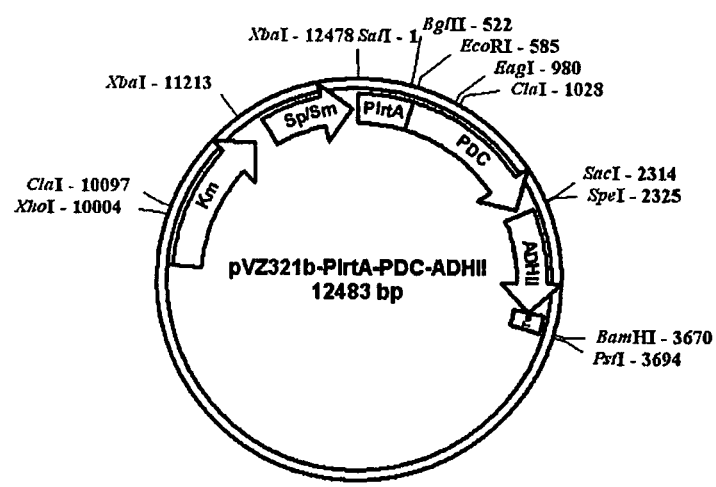

FIG. 36H is a schematic representation of gene organization in the construct pVZ321b-PlrtA-PDC-ADHII.

FIG. 36I presents the nucleotide sequence of the psbA2 promoter (*Synechocystis* sp. PCC 6803) (psbA2 gene: slr1311) (encoding the photosystem II D1 protein), which is induced after dark to light transition. (SEQ ID NO:84)

Figure 36J:
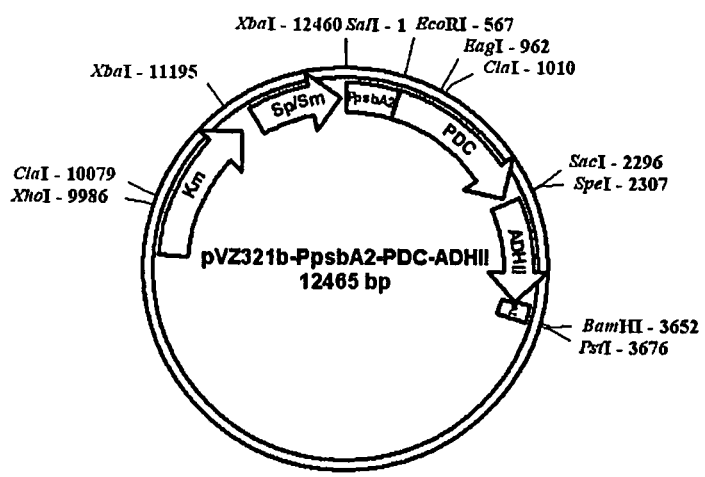

FIG. 36J is a schematic representation of gene organization for the construct pVZ321b-PpsbA2-PDC-ADHII.

FIG. 36K presents the nucleotide sequence of the rbcL promoter (*Synechocystis* sp. PCC 6803) (rbcL gene: slr0009) (encoding the ribulose biphosphate carboxylase/oxygenase large subunit), which is a constitutive and strong promoter under continuous light conditions. (SEQ ID NO:85)

Figure 36L:
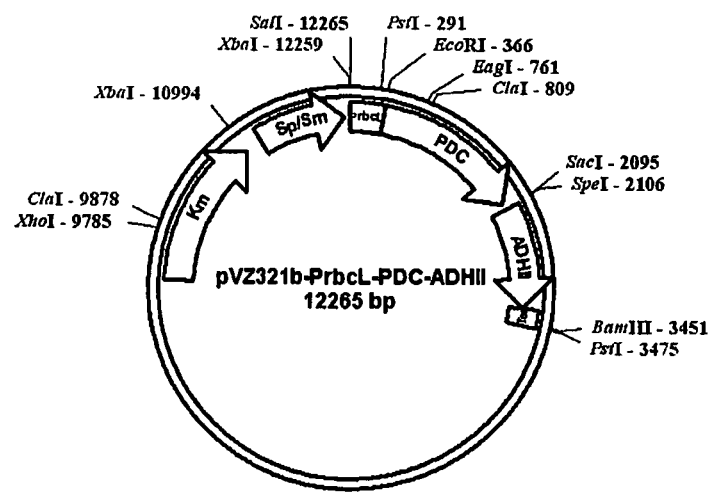

FIG. 36L is a schematic representation of gene organization for the construct pVZ321b-PrbcL-PDC-ADHII.

FIG. 36M presents the nucleotide sequence for the psaA promoter (*Synechocystis* sp. PCC6803) (psaA gene: slr1834) (encoding P700 apoprotein subunit Ia), which is induced under low white light and orange light, low expression level under high light and red light, and repressed in darkness. (SEQ ID NO:86)

Figure 36N:
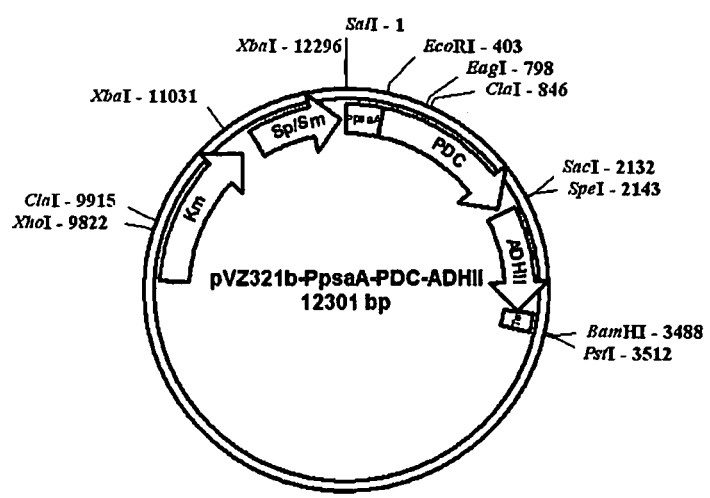

FIG. 36N is a schematic representation of the gene organization of the construct pVZ321b-PpsaA-PDC-ADHII.

FIG. 36O presents the nucleotide sequence of the ggpS promoter (*Synechocystis* sp. PCC6803) (ggpS gene: sll1566) (encoding glucosylglycerolphosphate synthase), which is induced after salt stress. (SEQ ID NO:87)

Figure 36P:
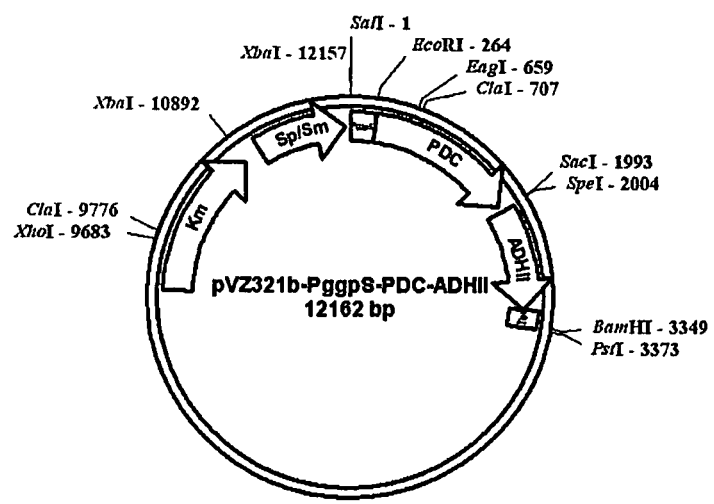

FIG. 36P is a schematic representation of the gene organization of the construct pVZ321b-PggpS-PDC-ADHII.

FIG. 36Q presents the nucleotide sequence of the nirA promoter (*Synechocystis* sp. PCC6803) (nirA gene: slr0898) (encoding ferredoxin-nitrite reductase), which is induced after transition from ammonia to nitrate. (SEQ ID NO:88)

Figure 36R:
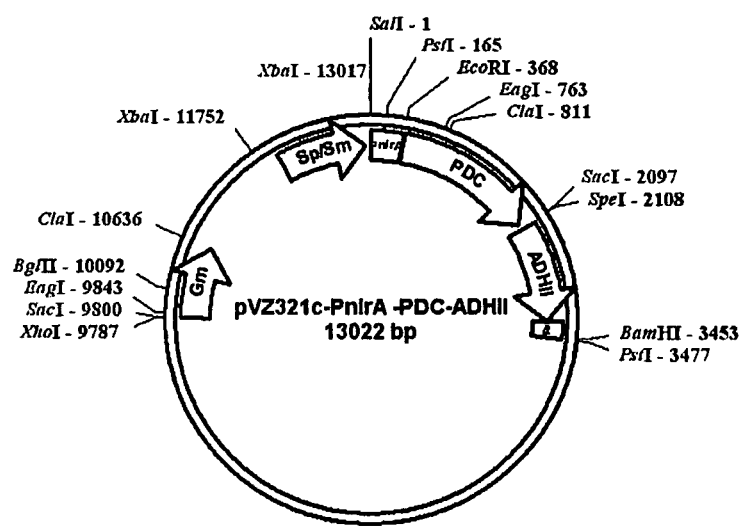

FIG. 36R is a schematic representation of the gene organization of the construct pVZ321c-PnirA-PDC-ADHII.

FIG. 36S presents the nucleotide sequence of the petE promoter (*Anabaena* sp. PCC7120) (petE gene: all0258) (encoding plastocyanin precursor), which is induced at elevated copper concentrations. (SEQ ID NO:89)

Figure 36T:
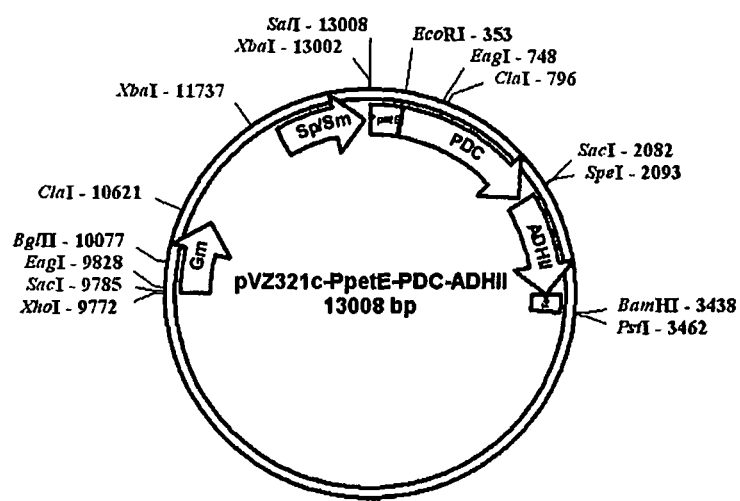

FIG. 36T is a schematic representation of gene organization for the construct pVZ321c-PpetE-PDC-ADHII.

FIG. 36U presents the nucleotide sequence of the hspA promoter (*Synechocystis* sp. PCC6803) (hspA gene: sll1514) 16.6 kDa small heat shock protein, molecular chaperone multi-stress responsive promoter (heat, cold, salt and oxidative stress). (SEQ ID NO:90)

Figure 36V:
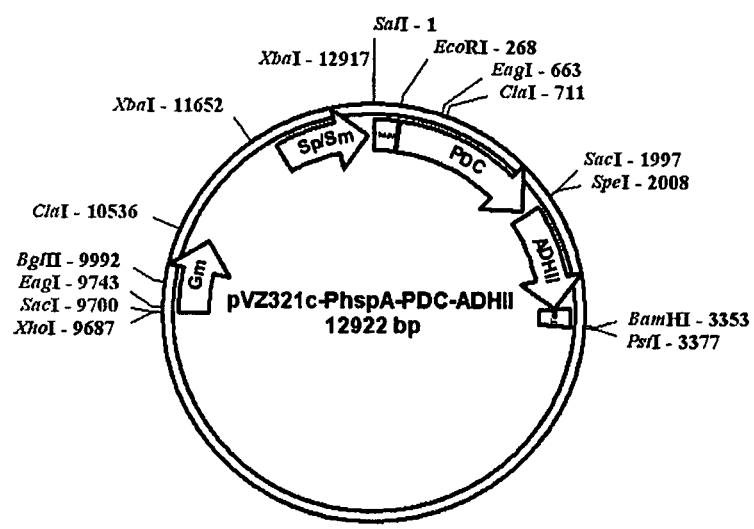

FIG. 36V is a schematic representation of gene organization for the construct pVZ321c-PhspA-PDC-ADHII.

FIG. 36W presents the nucleotide sequence for the hliB promoter (*Synechocystis* sp. PCC6803) (hliB gene: ssr2595) high light-inducible polypeptide HliB, CAB/ELIP/HLIP superfamily) (multi-stress responsible promoter (heat, cold, salt and oxidative stress). (SEQ ID NO:91)

Figure 36X:
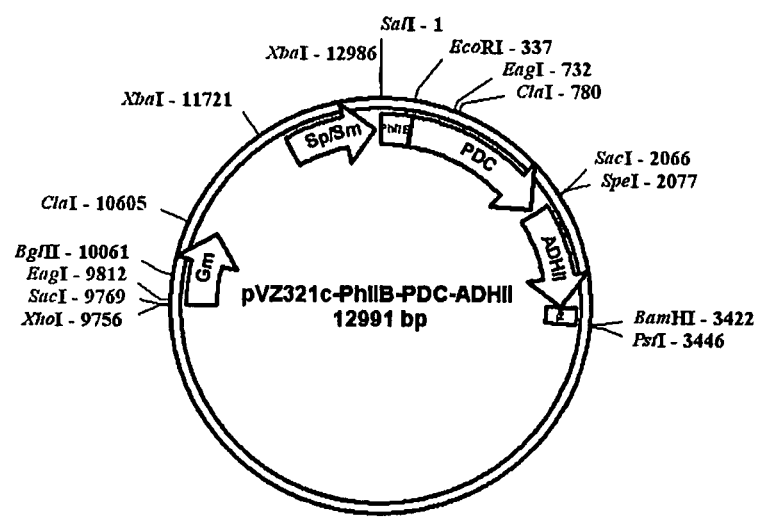

FIG. 36X is a schematic representation of gene organization of the construct pVZ321c-PhliB-PDC-ADHII.

FIG. 36Y presents the nucleotide sequence of the clpB1 promoter (*Synechocystis* sp. PCC6803) (clpB1 gene: slr1641) ATP-dependent Clp protease, Hsp 100, ATP-binding subunit ClpB multi-stress responsible promoter (heat, cold, salt and oxidative stress). (SEQ ID NO:92)

Figure 36Z:
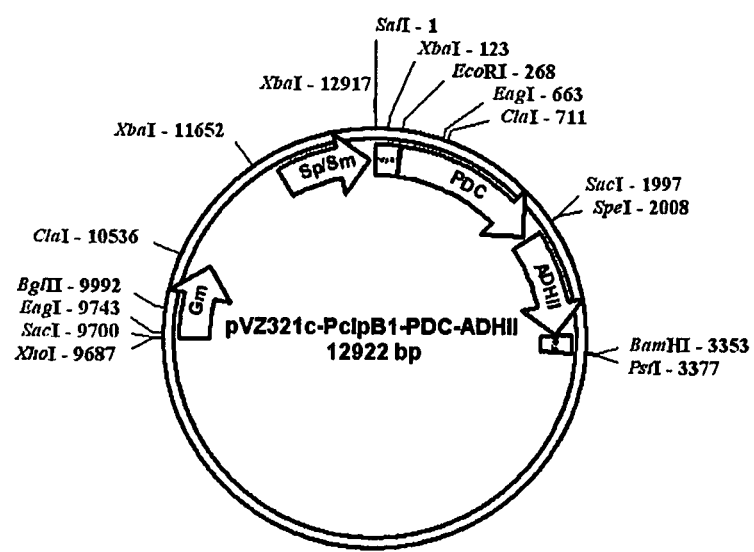

FIG. 36Z is a schematic representation of the gene organization for the construct pVZ321c-PclpB1-PDC-ADHII.

FIG. 37A presents the nucleotide sequence of the adhA gene from *Zymomonas mobilis* ZM4. (SEQ ID NO:93)

FIG. 37B presents the amino acid sequence for the ZmAdhI protein sequence (AAV89860). (SEQ ID NO:94)

Figure 37C:
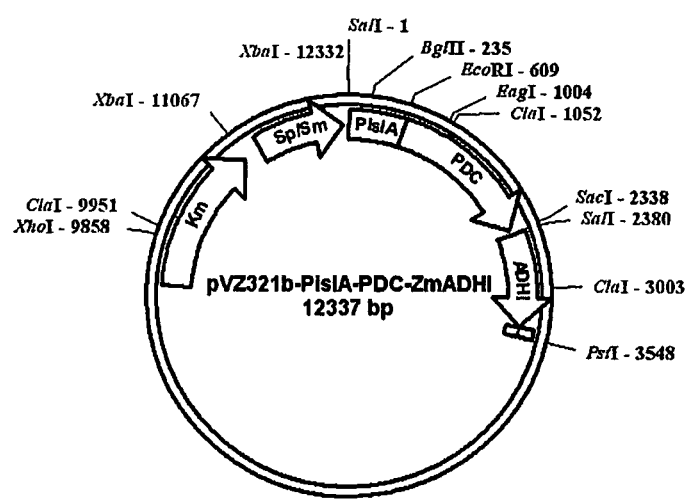

FIG. 37C is a schematic presentation of the gene organization for construct pVZ321b-PisiA-PDC-ADHI.

Figure 37D:
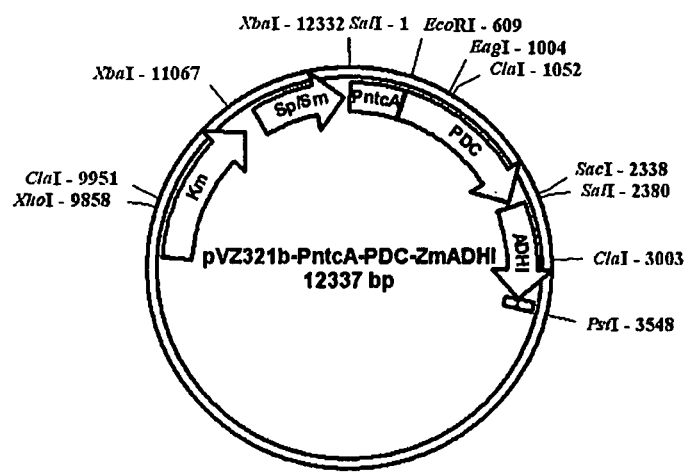

FIG. 37D is a schematic presentation of the gene organization for construct pVZ321b-PntcA-PDC-ZmADHI.

Figure 37E:
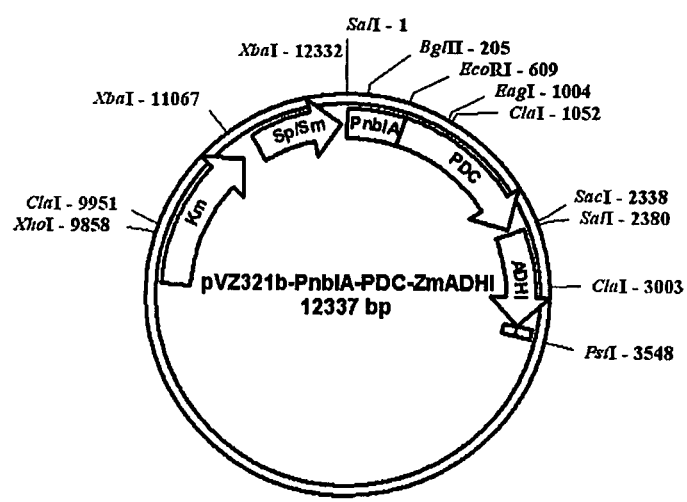

FIG. 37E is a schematic presentation of the gene organization for construct pVZ321b-PnblA-PDC-ZmADHI.

FIG. 38A presents the nucleotide sequence of SynAdh, the adh gene (slr1192) of *Synechocystis* sp. PCC 6803. (SEQ ID NO:95)

FIG. 38B presents the amino acid sequence of SynAdh (protein sequence BAA18840) of *Synechocystis* sp. PCC 6803. (SEQ ID NO:96)

Figure 38C:
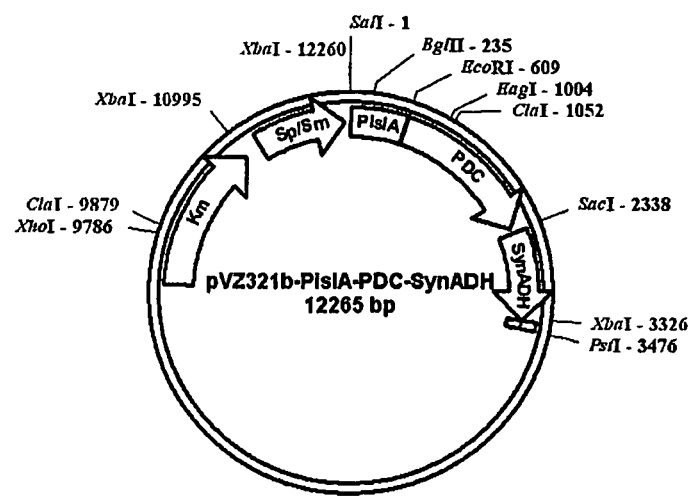

FIG. 38C is a schematic representation of the gene organization for construct pVZ321b-PisiA-PDC-SynADH.

Figure 38D:
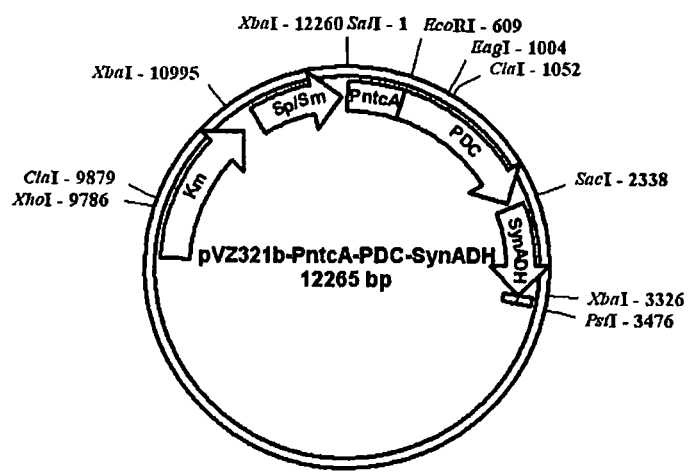

FIG. 38D is a schematic representation of the gene organization for construct pVZ321b-PntcA-PDC-SynADH.

Figure 38E:
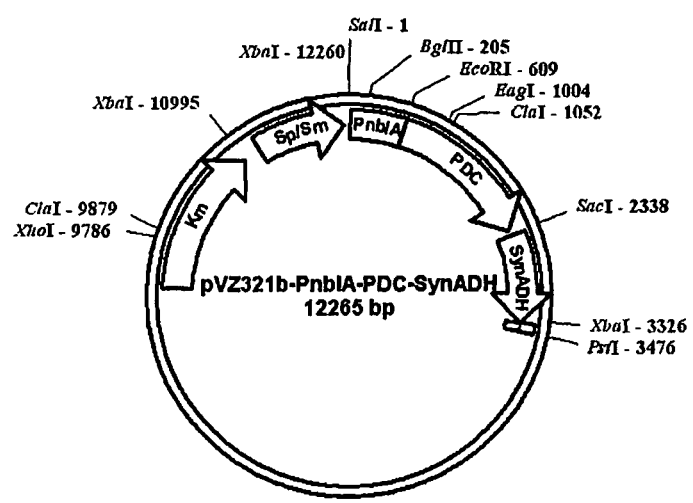

FIG. 38E is a schematic representation of the gene organization for construct pVZ321b-PnblA-PDC-SynADH.

FIG. 39A presents the nucleotide sequence of EcAdhE, the adhE gene from *E. coli* K12. (SEQ ID NO:97)

FIG. 39B presents the amino acid sequence of EcAdhE (protein sequence NP_415757). (SEQ ID NO:98)

Figure 39C:
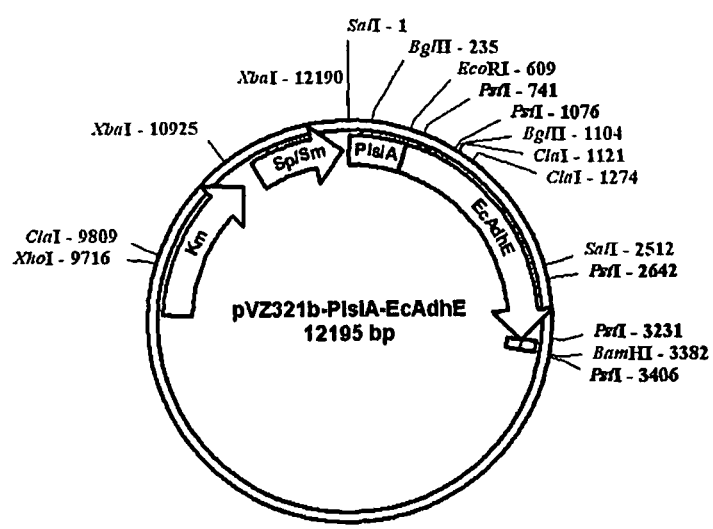

FIG. 39C is a schematic representation of the gene organization for construct pVZ321b-PisiA-PDC-EcAdhE.

Figure 39D:
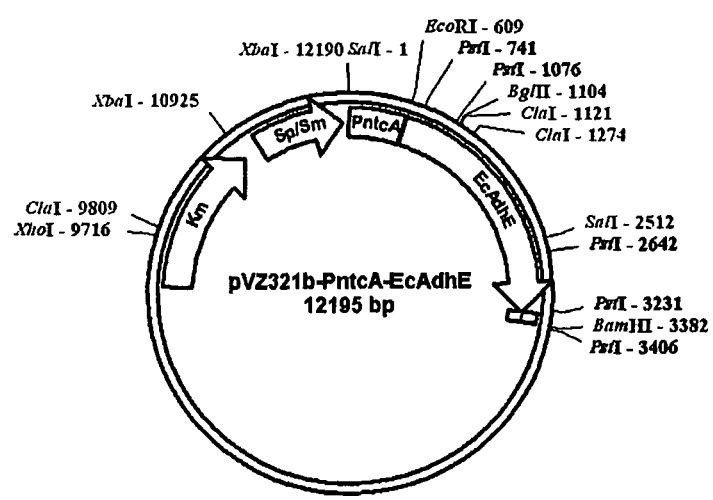

FIG. 39D is a schematic representation of the gene organization for construct pVZ321b-PntcA-PDC-EcAdhE.

Figure 39E:
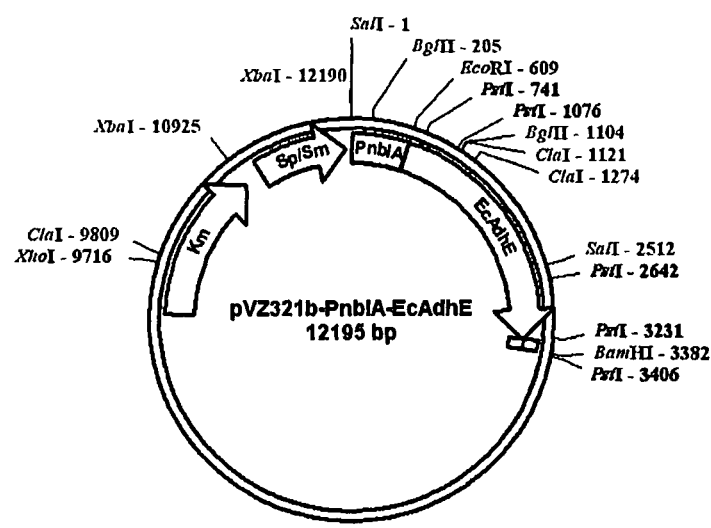

FIG. 39E is a schematic representation of the gene organization for construct pVZ321b-PnblA-PDC-EcAdhE.

FIG. 40A presents the nucleotide sequence of ThAdhE, the adhE gene (tlr0227) from *Thermosynechococcus elongatus* BP-1. (SEQ ID NO:99)

FIG. 40B presents the amino acid sequence of ThAdhE (protein sequence BAC07780). (SEQ ID NO:100)

Figure 40C:
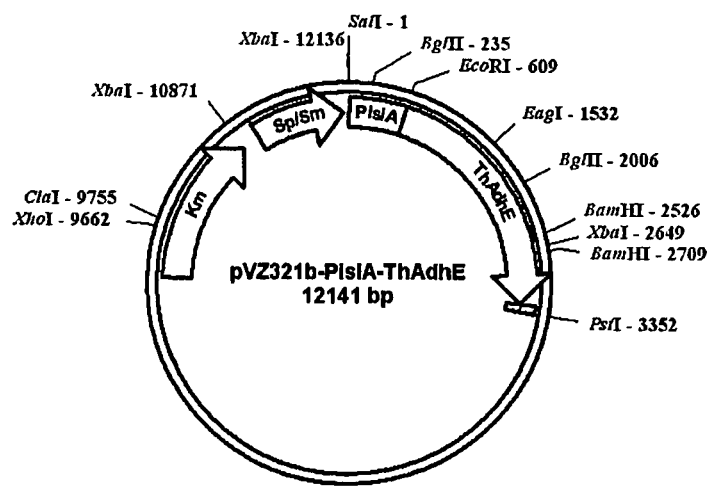

FIG. 40C is a schematic representation of the gene organization for the construct pVZ321b-PisiA-ThAdhE.

Figure 40D:
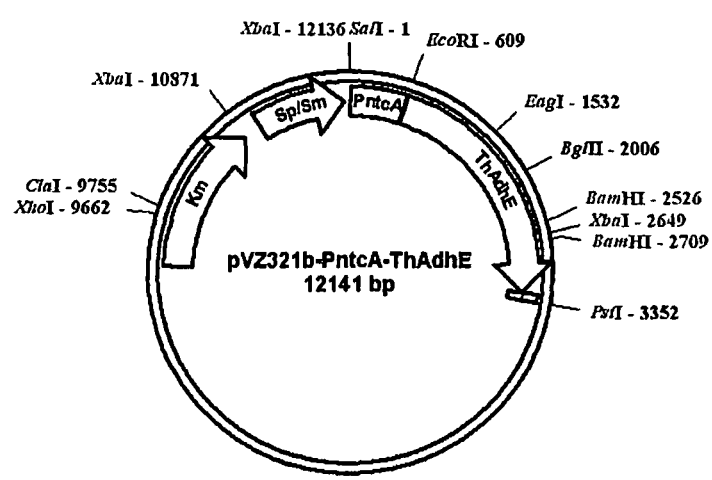

FIG. 40D is a schematic representation of the gene organization for the construct pVZ321b-PntcA-ThAdhE.

Figure 40E:
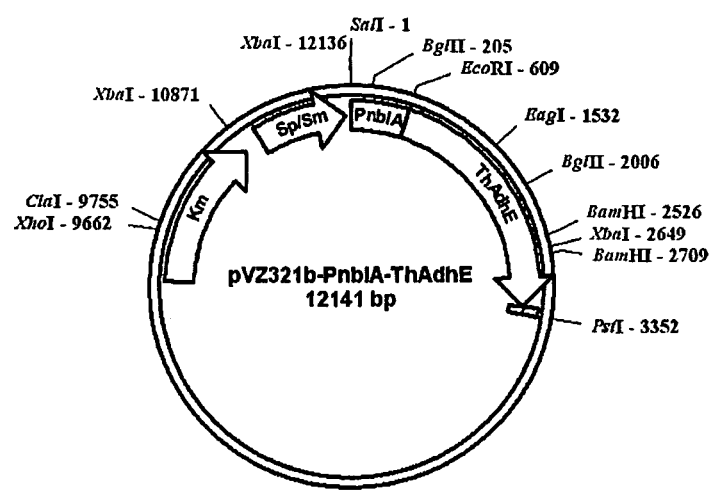

FIG. 40E is a schematic representation of the gene organization for the construct pVZ321b-PnblA-ThAdhE.

FIG. 41A presents the nucleotide sequence of ZpPdcpdc gene from *Zymobacter palmae* ATCC 51623 (SEQ ID NO:101)

FIG. 41B presents the amino acid sequence of ZpPdc (protein sequence AAM49566). (SEQ ID NO:102)

FIG. 42A presents the nucleotide sequence of pSK10 cloning vector (derivate of pSK9 [V. V. Zinchenko, Moscow, Russia; unpublished]). (SEQ ID NO:103)

Figure 42B:
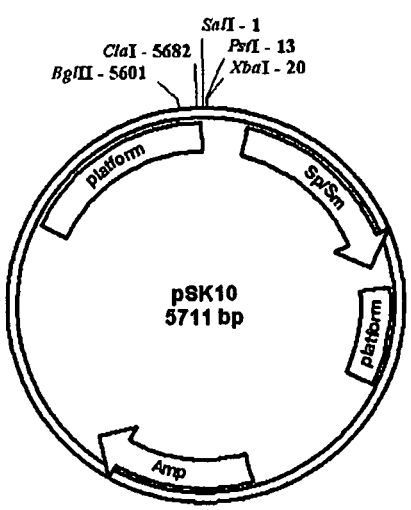

FIG. 42B is a schematic representation of the gene organization for the plasmid pSK10.

Figure 42C:
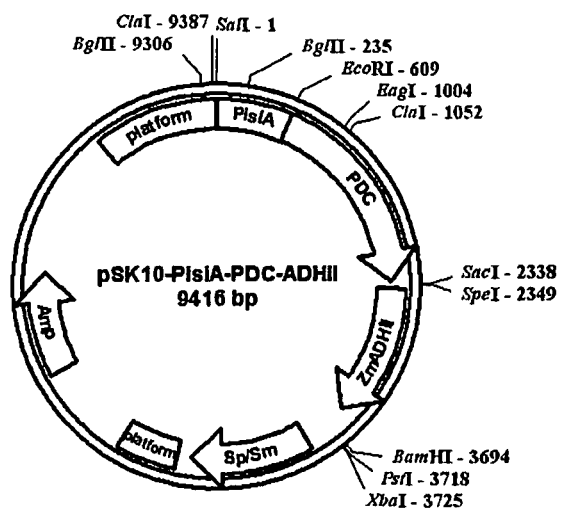

FIG. 42C is a schematic representation of the gene organization of the construct pSK10-PisiA-PDC-ADHII.

Figure 42D:
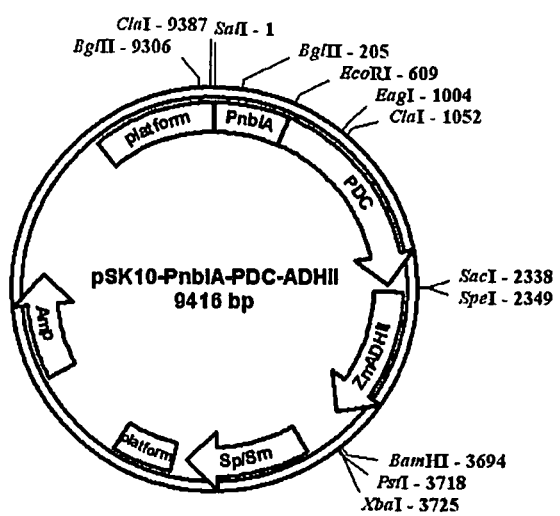

FIG. 42D is a schematic representation of the gene organization of the construct pSK10-PnblA-PDC-ADHII.

Figure 42E:
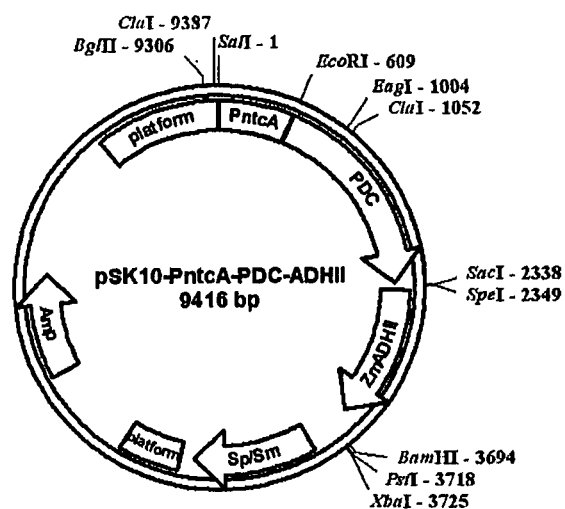

FIG. 42E is a schematic representation of the gene organization of the construct pSK10-PntcA-PDC-ADHII.

Figure 42F:
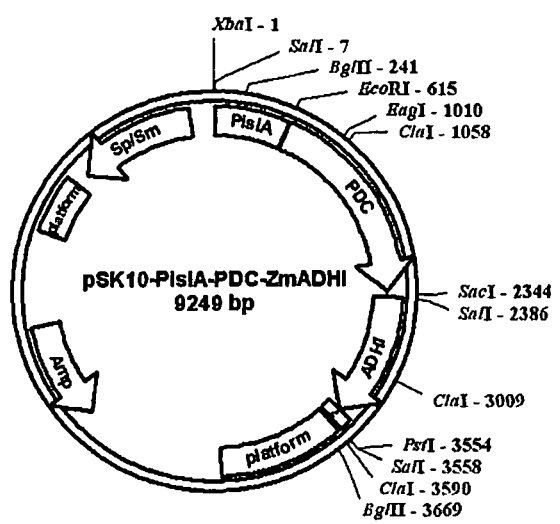

FIG. 42F is a schematic representation of the gene organization of the construct pSK10-PisiA-PDC-ADHI.

Figure 42G:
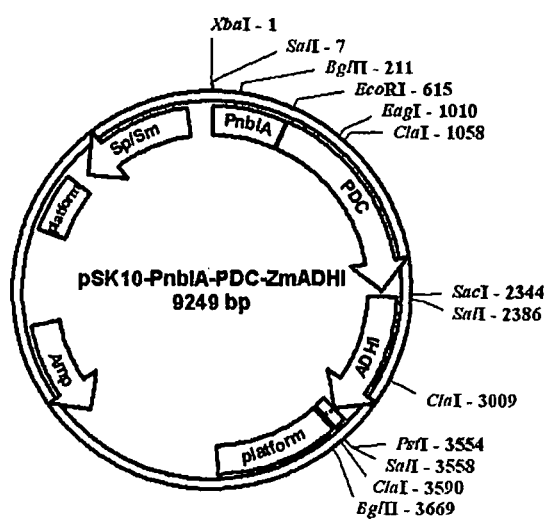

FIG. 42G is a schematic representation of the gene organization of the construct pSK10-PnblA-PDC-ADHI.

Figure 42H:
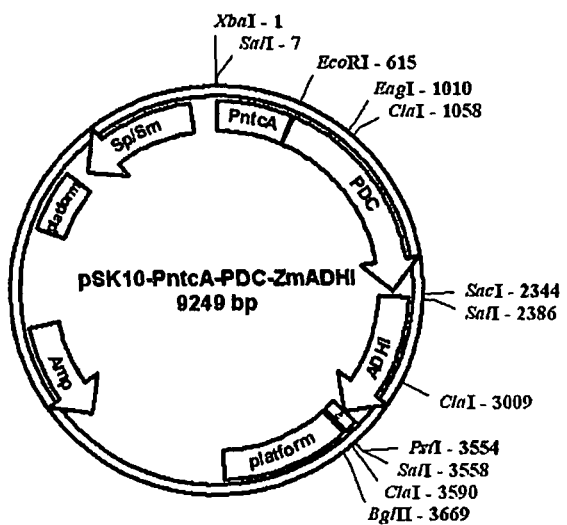

FIG. 42H is a schematic representation of the gene organization of the construct pSK10-PntcA-PDC-ADHI.

Figure 42I:
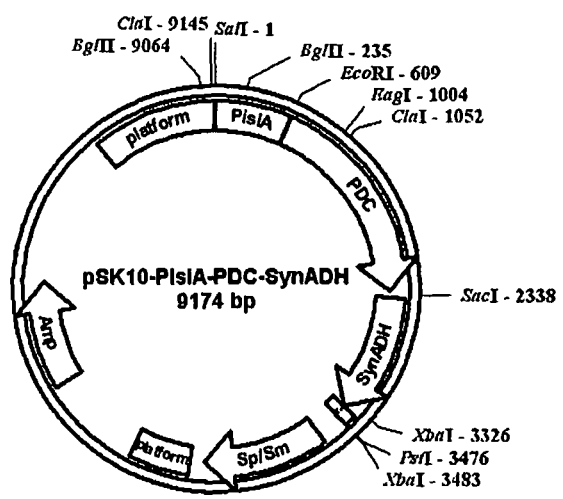

FIG. 42I is a schematic representation of the gene organization of the construct pSK10-PisiA-PDC-SynADH.

Figure 42J:
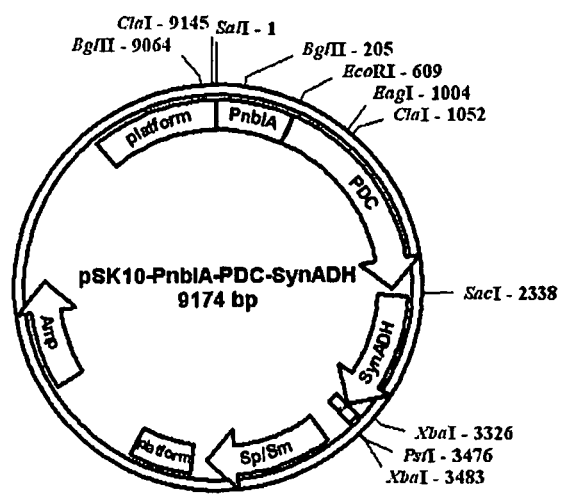

FIG. 42J is a schematic representation of the gene organization of the construct pSK10-PnblA-PDC-SynADH.

Figure 42K:
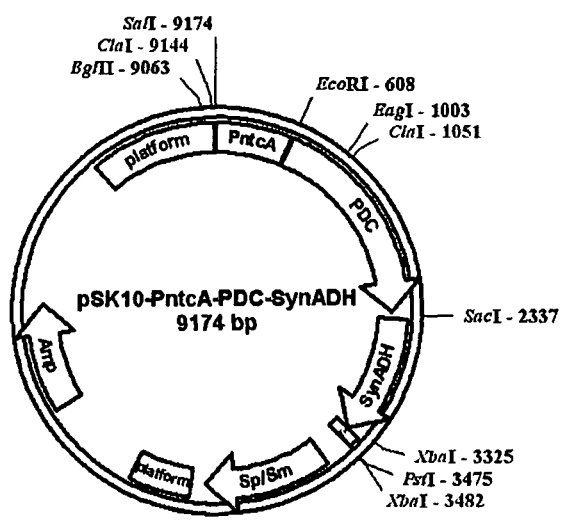

FIG. 42K is a schematic representation of the gene organization of the construct pSK10-PntcA-PDC-SynADH.

Figure 42L:
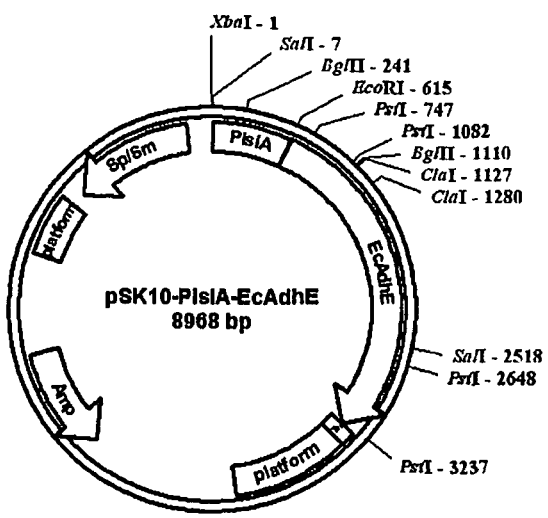

FIG. 42L is a schematic representation of the gene organization of the construct pSK10-PisiA-PDC-EcAdhE.

Figure 42M:
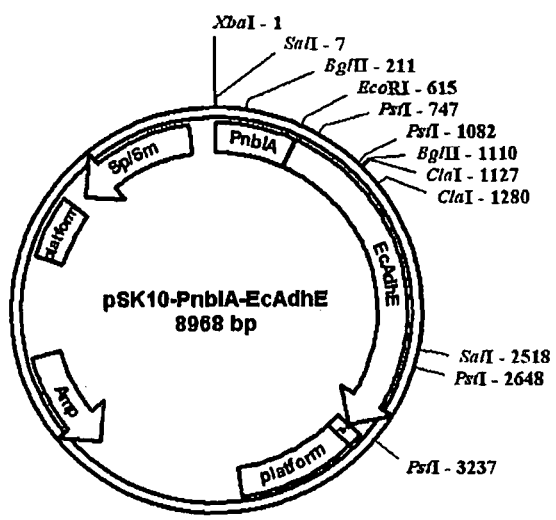

FIG. 42M is a schematic representation of the gene organization of the construct pSK10-PnblA-PDC-EcAdhE.

Figure 42N:
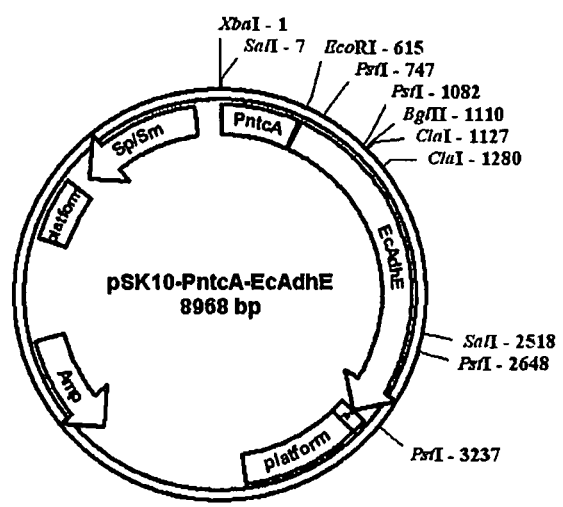
Figure 420:
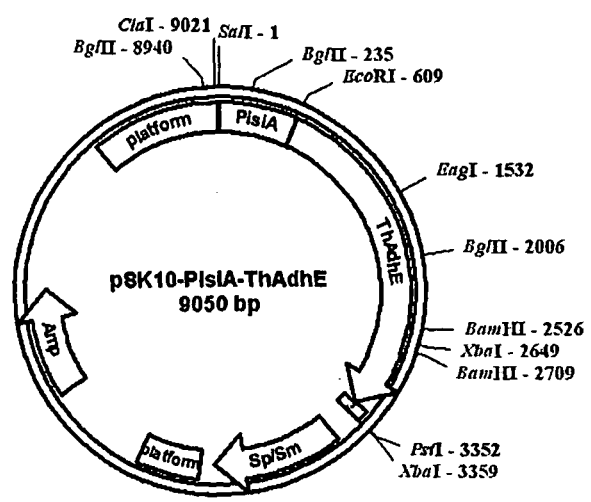

FIG. 42N is a schematic representation of the gene organization of the construct pSK10-PntcA-PDC-EcAdhE.

FIG. 42O is a schematic representation of the gene organization of the construct pSK10-PisiA-PDC-ThAdhE.

Figure 42P:
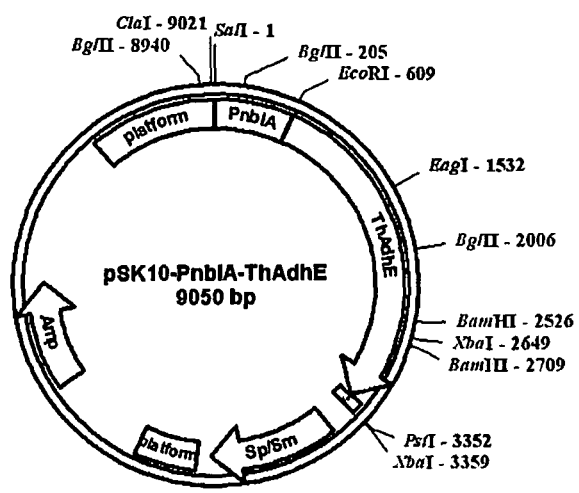

FIG. 42P is a schematic representation of the gene organization of the construct pSK10-PnblA-PDC-ThAdhE.

Figure 42Q:
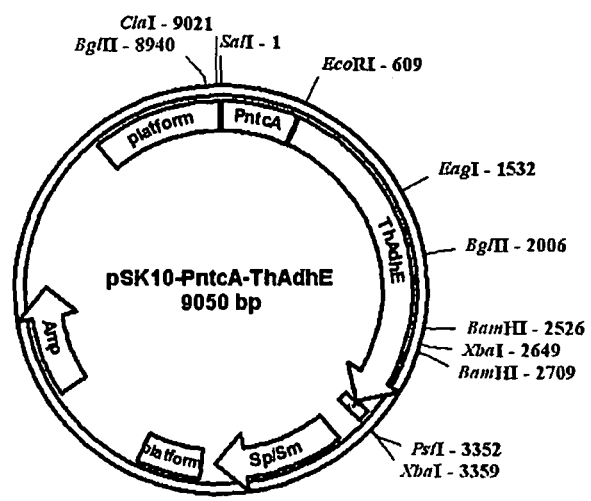

FIG. 42Q is a schematic representation of the gene organization of the construct pSK10-PntcA-PDC-ThAdhE.

FIG. 42R presents the nucleotide sequence of the crhC promoter (*Anabaena* sp. PCC7120) (crhC gene: alr4718, RNA helicase crhC cold shock inducible) (SEQ ID NO:104).

FIG. 42S presents the nucleotide sequence of the petE promoter (*Anabaena* sp. PCC7120) petE gene: all0258, plastocyanin precursor (petE) induced by addition of Cu (SEQ ID NO:X). (SEQ ID NO:105)

Figure 42T:
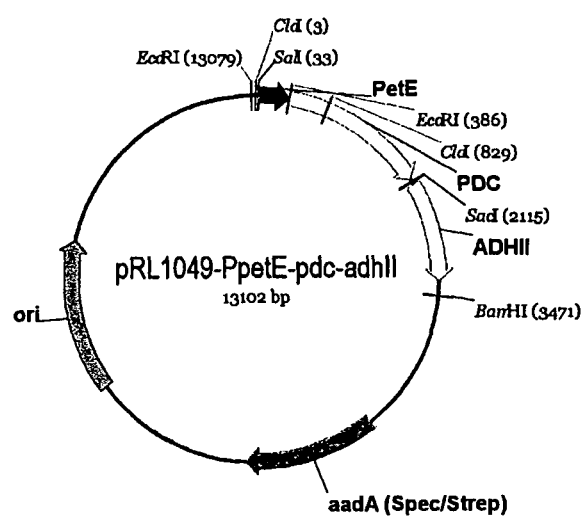

FIG. 42T presents the gene organization of plasmid pRL1049-PpetE-PDC-ADHII.

FIG. 42U presents the nucleotide sequence of plasmid pRL1049-PpetE-PDC-ADHII (SEQ ID NO:106).

Figure 42V:
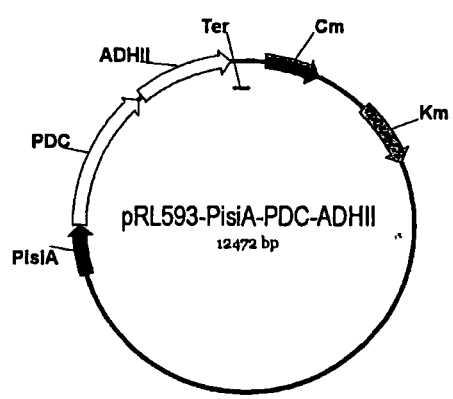

FIG. 42V depicts the gene organization of plasmid pRL593-PisiA-PDC-ADHII.

FIG. 42W presents the nucleotide sequence of plasmid pRL593-PisiA-PDC-ADHII (SEQ ID NO:107).

Figure 42X:
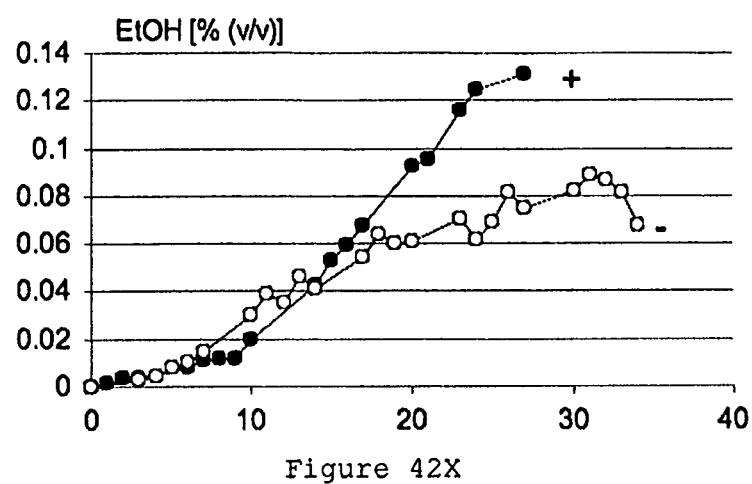

FIG. 42X is a graphic depiction of ethanol production rate in *Anabaena* PCC7120 harboring pRL593-PisiA-PDC-ADHII following induction by iron starvation was measured in BG11 medium (+N) and in medium lacking combined nitrogen (−N) in day (12 h)/night (12 h) cycle.

Figure 42Y:
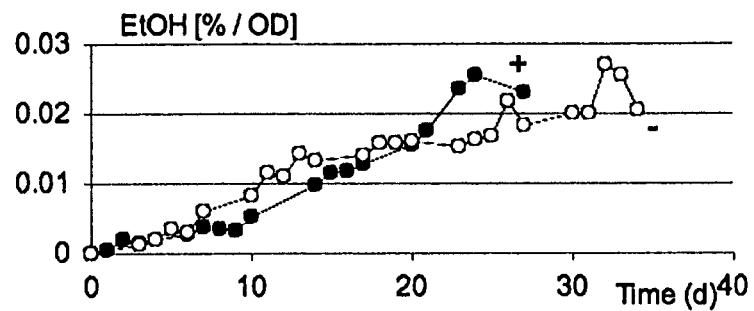

FIG. 42Y is a graphic depiction of ethanol production rate in *Anabaena* PCC7120 harboring pRL593-PisiA-PDC-ADHII following induction by iron starvation was measured in BG11 medium (+N) and in medium lacking combined nitrogen (−N) in day (12 h)/night (12 h) cycle, wherein values are normalized for optical density.

Figure 43A:
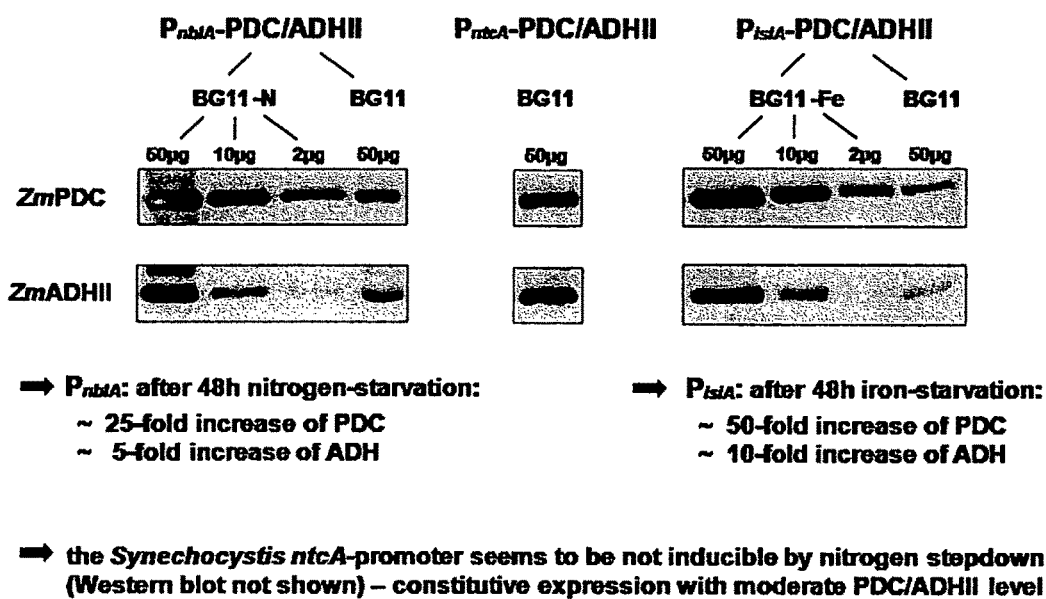

FIG. 43A is a photographic depiction of a Western Blot that was used to quantify the induction rate of the used promoters by determining the relative abundance of the *Z. mobilis* ADHII and PDC enzymes expressed in *Synechocystis* with and without nutrient starvation.

FIG. 43B is a photograph of a Western Blot that was used to determine the relative abundance of the *Z. mobilis* ADHII and PDC enzymes expressed in *Synechocystis* with and without nutrient starvation.

Figure 44A:
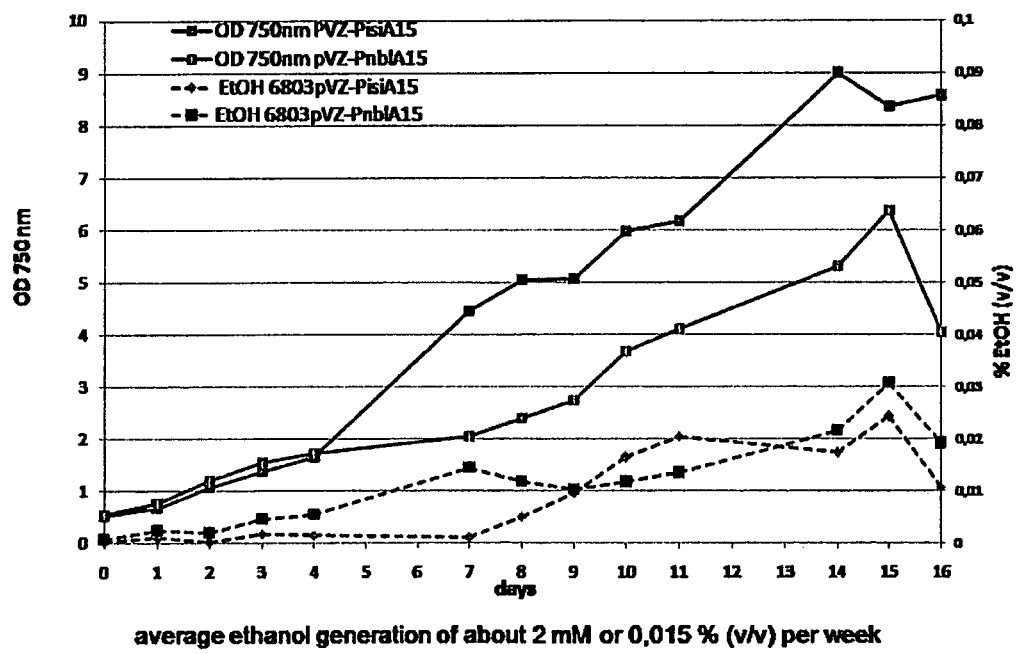

FIG. 44A is a graphic representation of ethanol production rates of genetically modified photoautotrophic host cells containing *Zymomonas mobilis* PDC and ADHII as a second genetic modification.

Figure 44B:
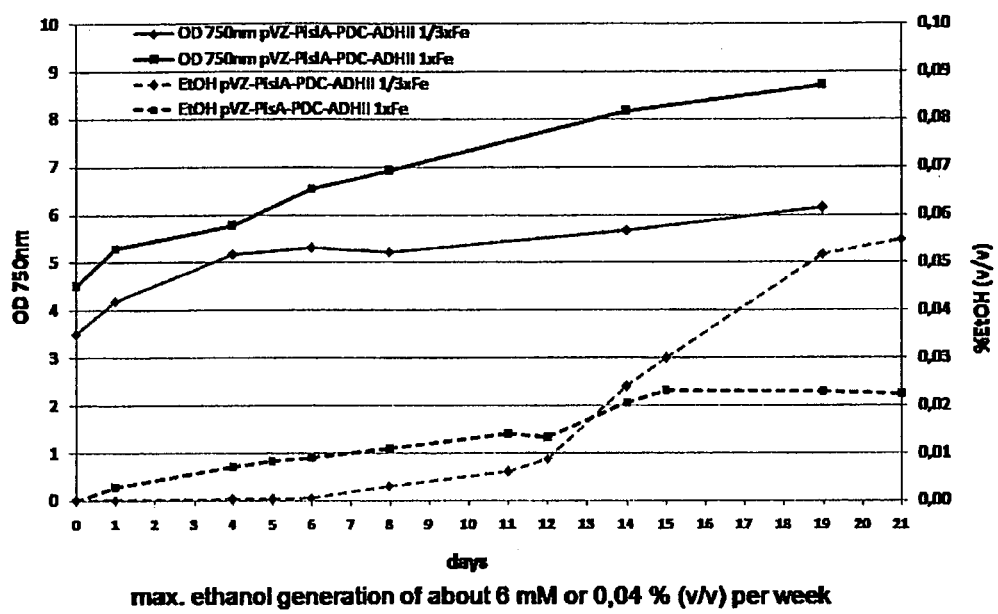

FIG. 44B is a graphic representation of ethanol production in *Synechocystis* pVZ mutants having ZmPdC and ZmADHII under the control of isiA, and iron-dependent promoter.

Figure 44C:
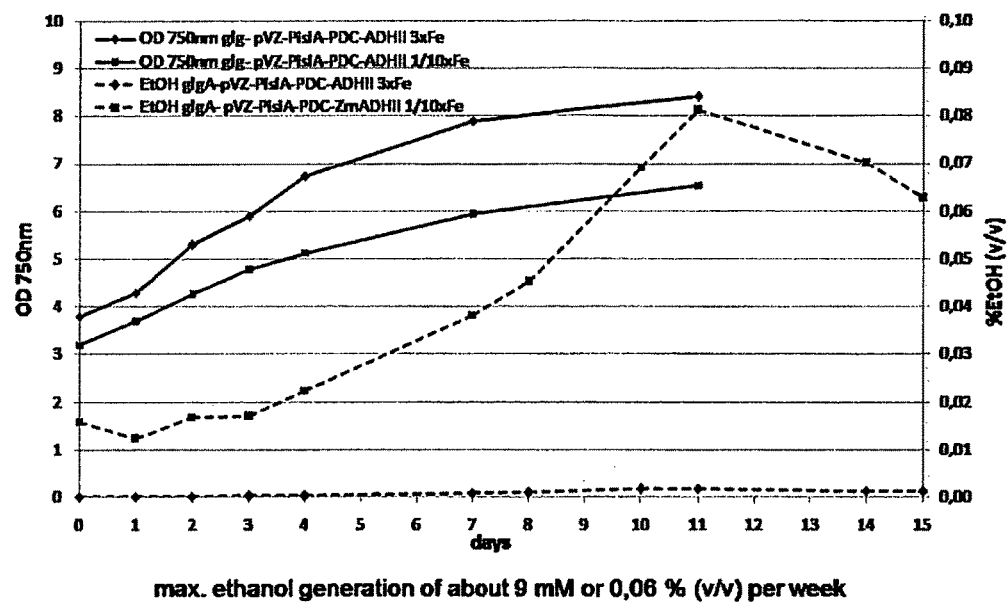

FIG. 44C is a graphic presentation of ethanol production in glycogen deficient *Synechocystis* pVZ mutants having ZmPdC and ZmADHII under the control of isiA, an iron-dependent promoter.

Figure 44D:
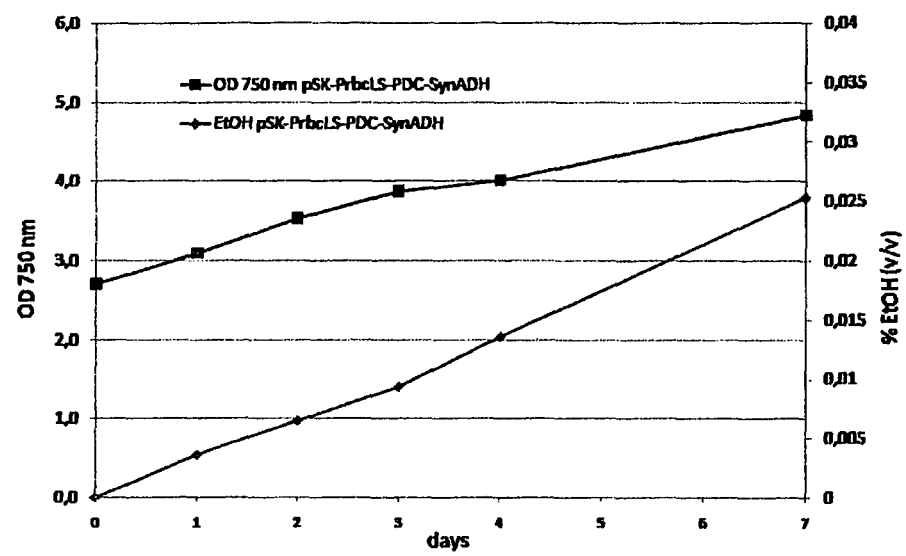

FIG. 44D is a graphic presentation of ethanol production in *Synechocystis* pVZ mutants having ZmPdC and SynADH under the control of rbcLS, a constitutive promoter.

Figure 45:
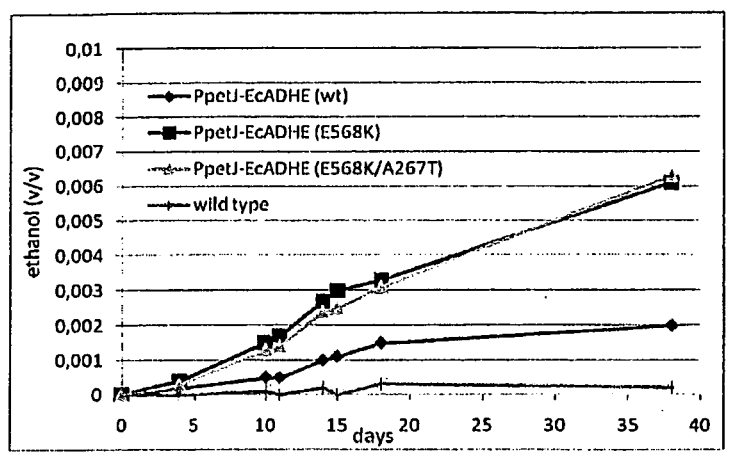

FIG. 45 is a graphic presentation of ethanol production in *Synechocystis* expressing different 3 variants of *E. coli* AdhE compared to wild-type.

Figure 46A:
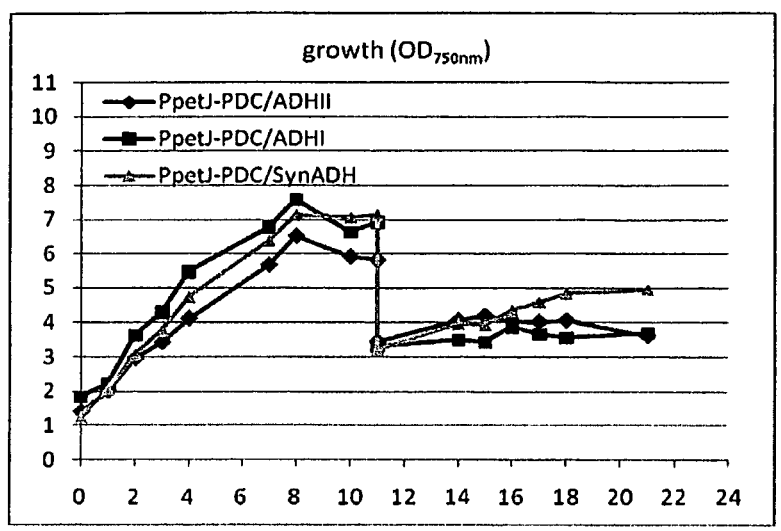

FIG. 46A is a graphic representation of growth over time for the captioned mutant strains.

Figure 46B:
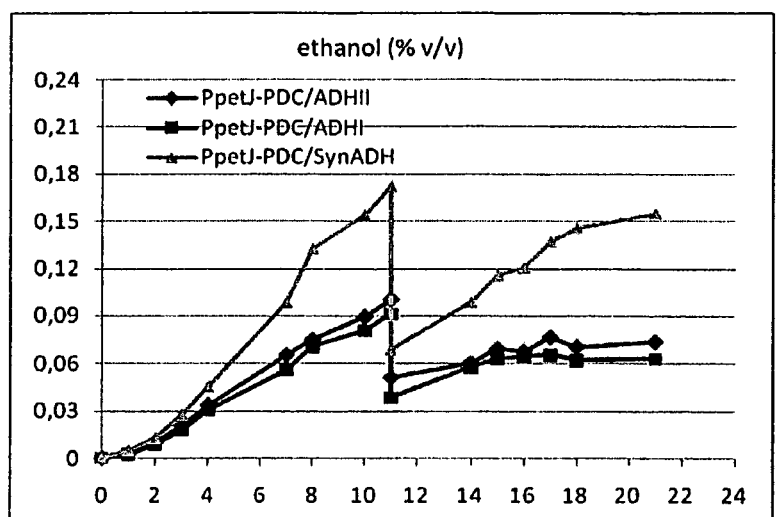

FIG. 46B is a graphic representation of ethanol production over time (% v/v) for the captioned mutant strains.

Figure 46C:
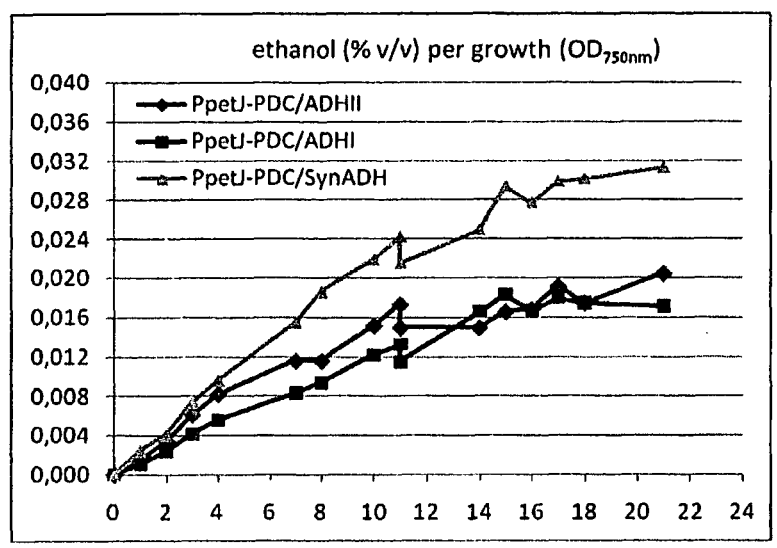

FIG. 46C is a graphic representation of ethanol production per growth for the captioned mutant strains.

Figure 46D:
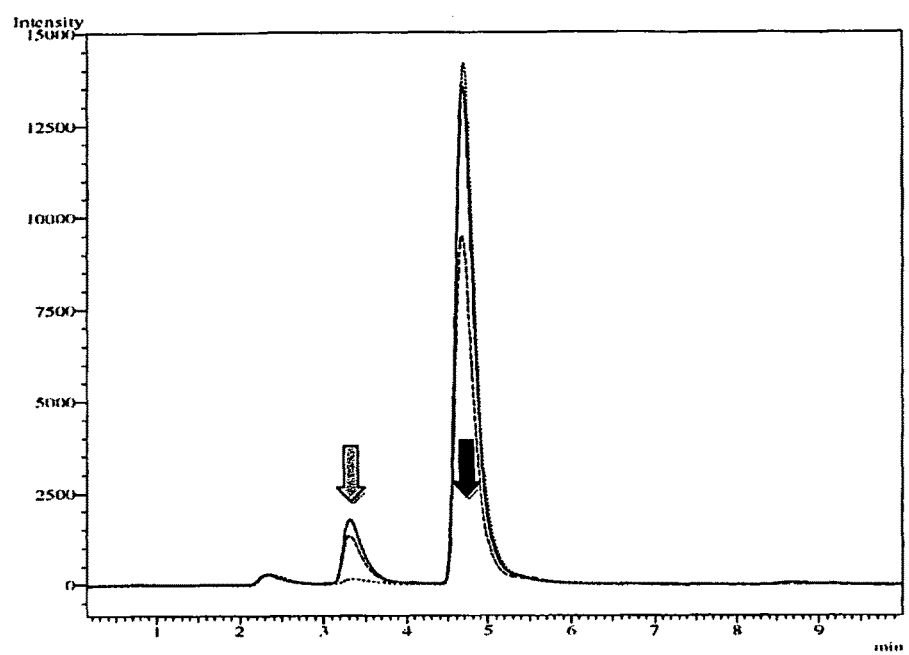

FIG. 46D is a graphic representation of measurements on outgas samples of *Synechocystis* mutants that express ZmPdc/ZmAdhI (dashed line), ZmPdc/ZmAdhII (solid line) and ZmPdc/SynAdh (dotted line) analysed by gas chromatography. The grey arrow indicates the acetaldehyde, and the black arrow indicates the ethanol peak.

Figure 46E:
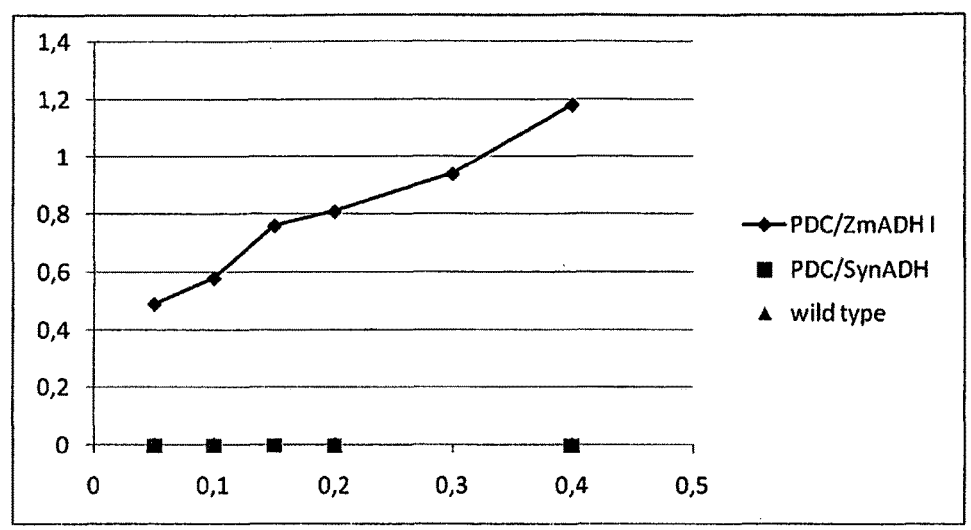

FIG. 46E is a graphic depiction of acetaldehyde production after addition of ethanol in different concentrations. Wild type and ethanol producing transgenic cells are presented.

Figure 46F:
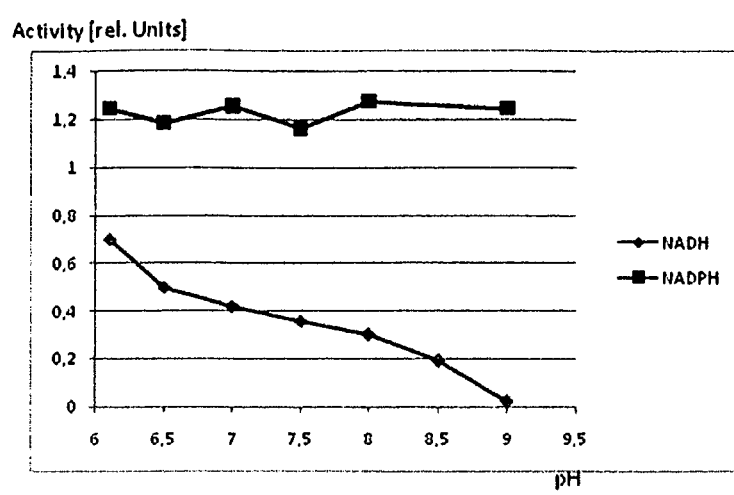

FIG. 46F is a graphic depiction of the pH-dependency of acetaldehyde reduction by crude extracts containing the *Synechocystis* Adh.

Figure 46G:
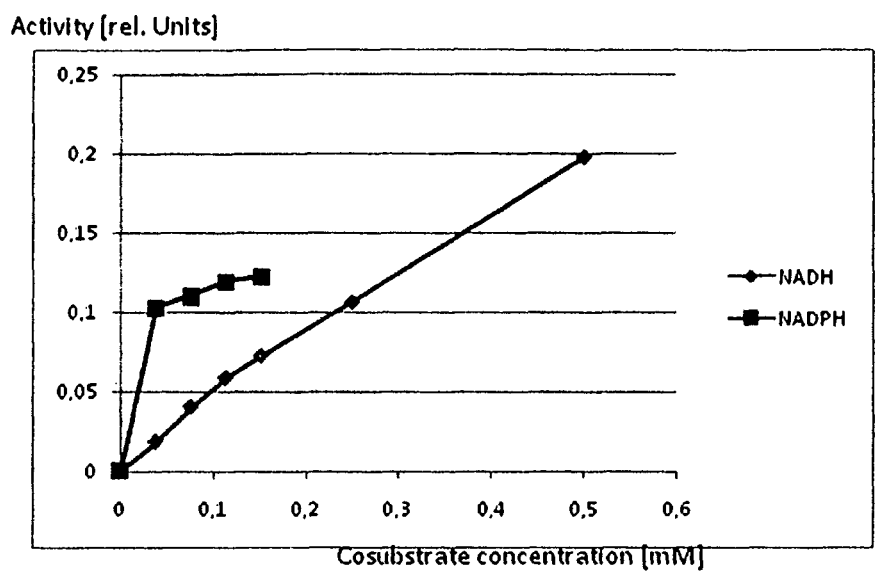

FIG. 46G is a graphic depiction summarizing the acetaldehyde reduction rates at different cosubstrate concentrations. Measurements were performed at pH 6.1

Figure 46H:
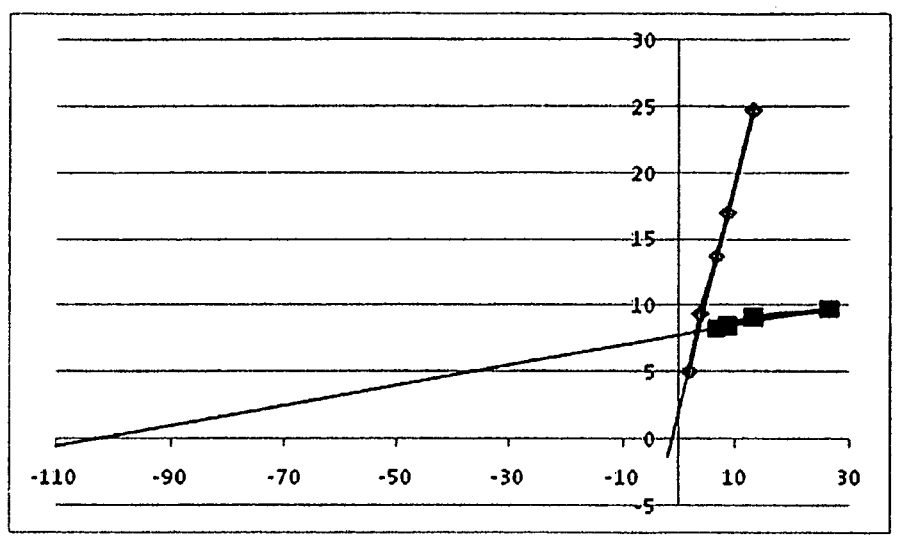
Figure 46I:
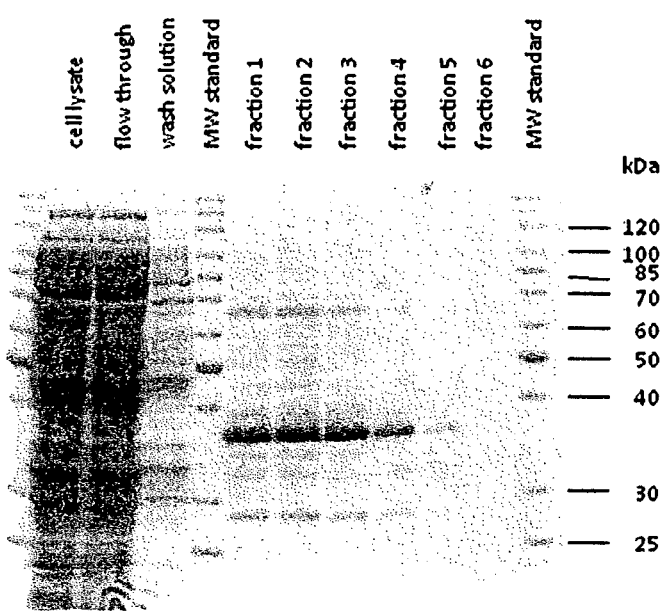

FIG. 46H is a graphic depiction of Lineweaver-Burk plots, which depict the reciprocal of the rate of acetaldehyde reduction versus the reciprocal of the concentration of NADH (squares) or NADPH (rhombi), respectively. $K_m$ and $v_{max}$ values are discussed in the text.

46-I is a photographic depiction of SDS/PAGE analysis of recombinantly expressed SynADH showing that SynADH was enriched, but not purified to homogeneity.

Figure 47A:
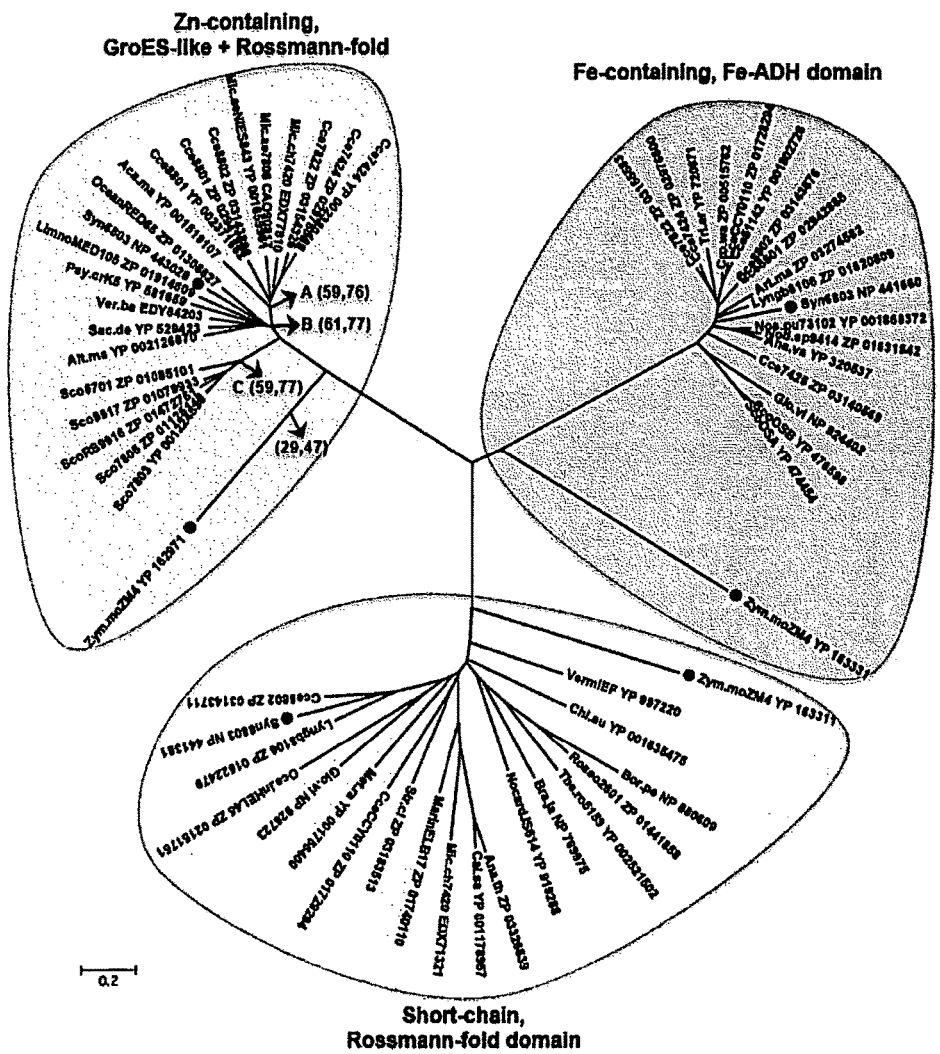

FIG. 47A is a clade analysis of alcohol dehydrogenase enzymes.

FIG. 47B(1) is a table of several alcohol dehydrogenase genes from subclade A, indicating the originating organism, the accession number, gene information, and protein designation.

FIG. 47B(2) is a table of several alcohol dehydrogenase genes from subclade B, indicating the originating organism, the accession number, gene information, and protein designation.

FIG. 47B(3) is a table of several alcohol dehydrogenase genes from subclade C, indicating the originating organism, the accession number, gene information, and protein designation.

FIGS. 47C through 47X depict the amino acid sequences of several proteins described herein, which are also present in the sequence listing.

Figure 48A:
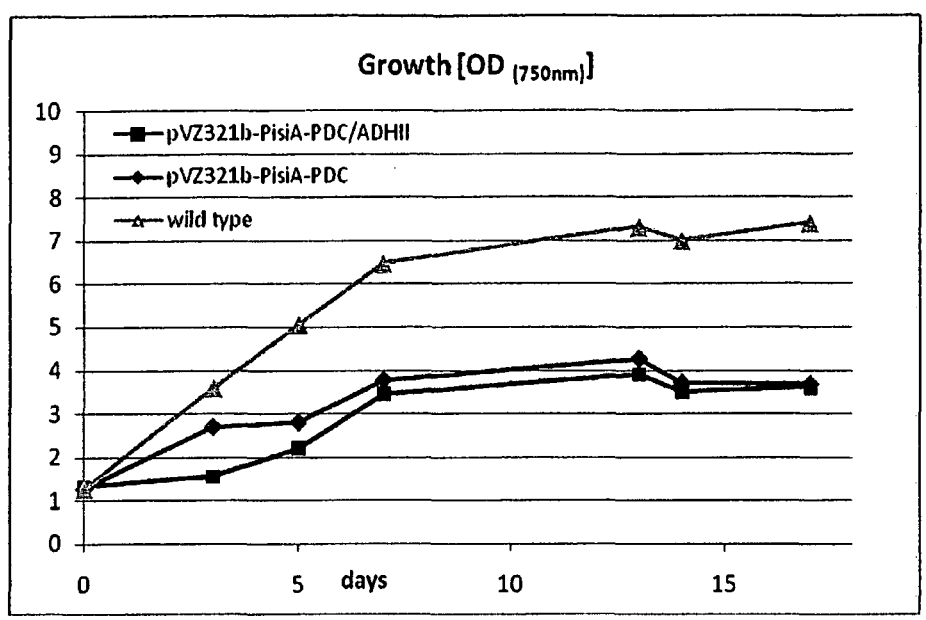

FIG. 48A is a graphic depiction of the $OD_{750}$ growth properties of Synechocystis wild type and mutants that express Pdc/Adh enzyme and Pdc enzyme alone.

Figure 48B:
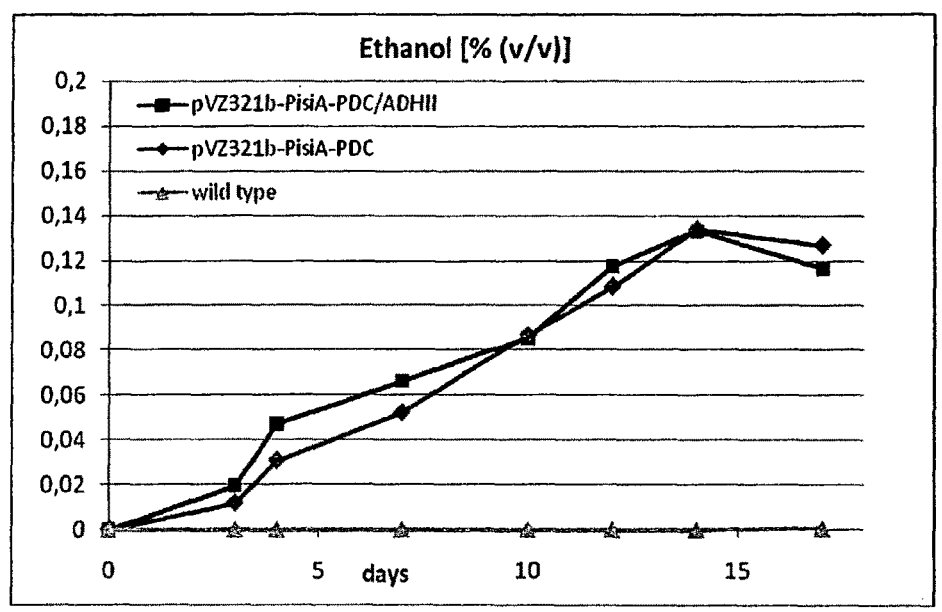

FIG. 48B is a graphic depiction of ethanol production for Synechocystis wild type and mutants that express Pdc/Adh enzyme and Pdc enzyme alone.

Figure 48D:
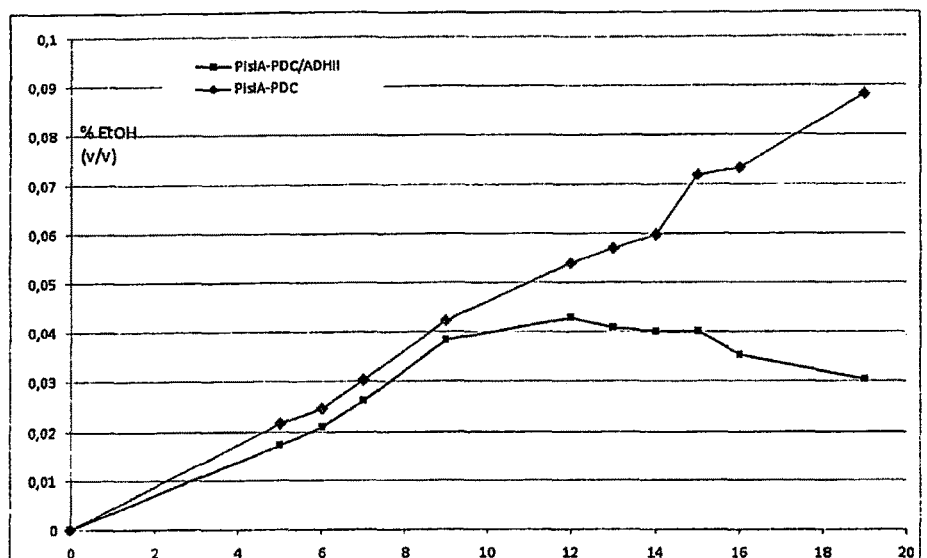

FIG. 48C is a tabular presentation of data for an ethanol concentration time course under limiting CO2 conditions; these data are presented graphically in FIG. 48D.

FIG. 48D is a graphical presentation of data for an ethanol concentration time course under limiting CO2 conditions; these data are presented in tabular form in FIG. 48C.

Figure 48F:
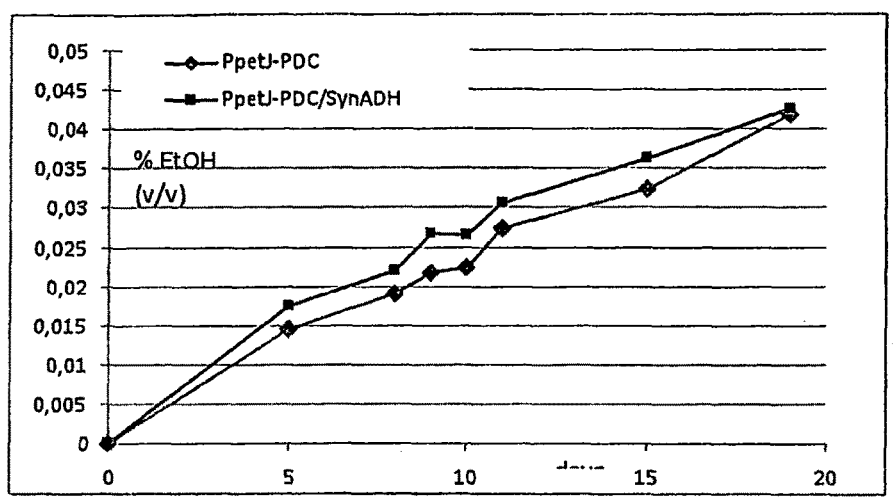

FIG. 48E is a tabular presentation of data for an ethanol concentration time course under limiting CO2 conditions; these data are presented graphically in FIG. 48F.

FIG. 48F is a graphical presentation of data for an ethanol concentration time course under limiting CO2 conditions; these data are presented in tabular form in FIG. 48E.

Figure 48H:
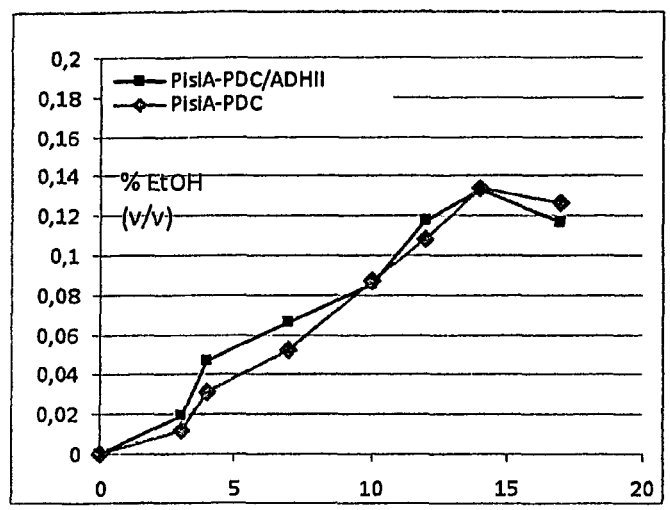

FIG. 48G is a tabular presentation of data for an ethanol concentration time course under limiting CO2 conditions; these data are presented graphically in FIG. 48H.

FIG. 48H is a graphical presentation of data for an ethanol concentration time course under limiting CO2 conditions; these data are presented in tabular form in FIG. 48G.

Figure 48J:
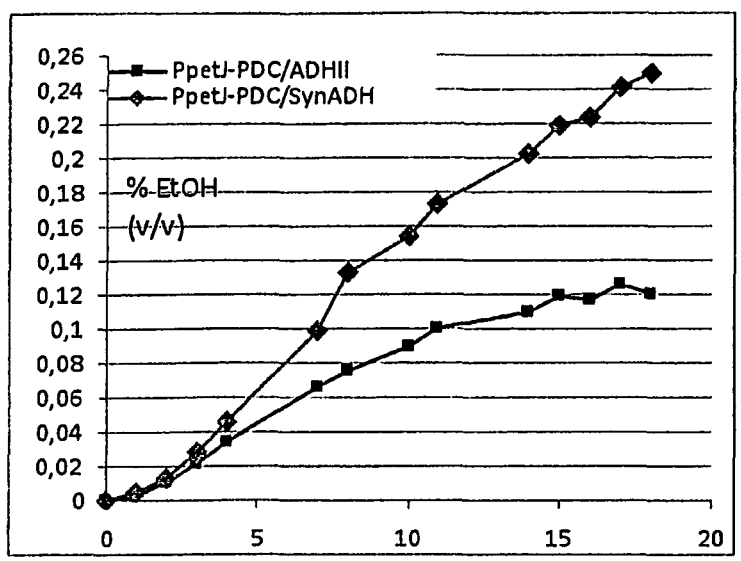

FIG. 48I is a tabular presentation of data for an ethanol concentration time course under limiting CO2 conditions; these data are presented graphically in FIG. 48J.

FIG. 48J is a graphical presentation of data for an ethanol concentration time course under limiting CO2 conditions; these data are presented in tabular form in FIG. 48I.

FIG. 49A is a tabular presentation of cyanobacterial promoters used to express ethanologenic enzymes in Synechocystis 6803.

Figures 49B, 49C:
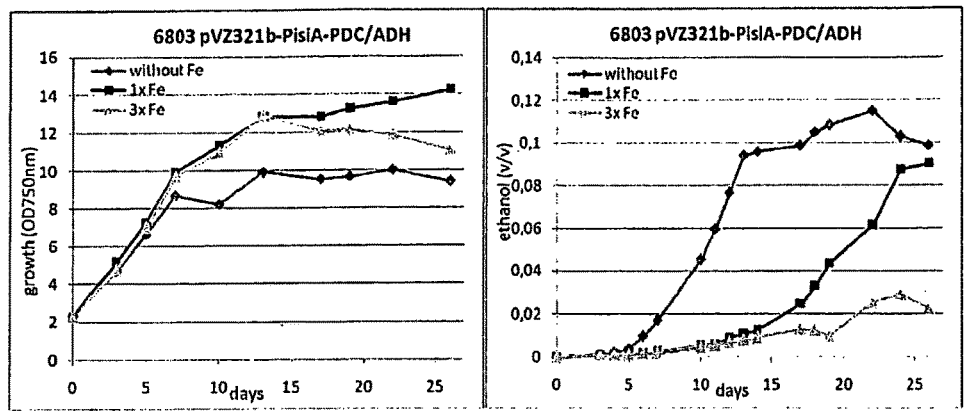

FIG. 49B is a graphic depiction of growth properties of 6803 transformed with pVZ321b-PisiA-PDC/ADH as monitored by determining the $OD_{750}$.

FIG. 49C is a graphic depiction of iron-induced ethanol production of 6803 transformed with pVZ321b-PisiA-PDC/ADH.

Figure 49D:
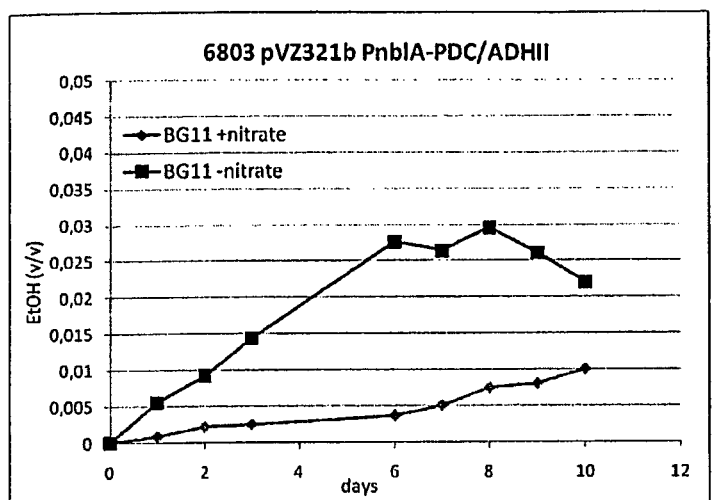

FIG. 49D is a graphic depiction of ethanol production of Synechocystis 6803 pVZ321b-PnblA-PDC/ADH that express Pdc/Adc enzymes under the control of the nitrogen dependent nblA-promoter.

Figures 49E, 49F:
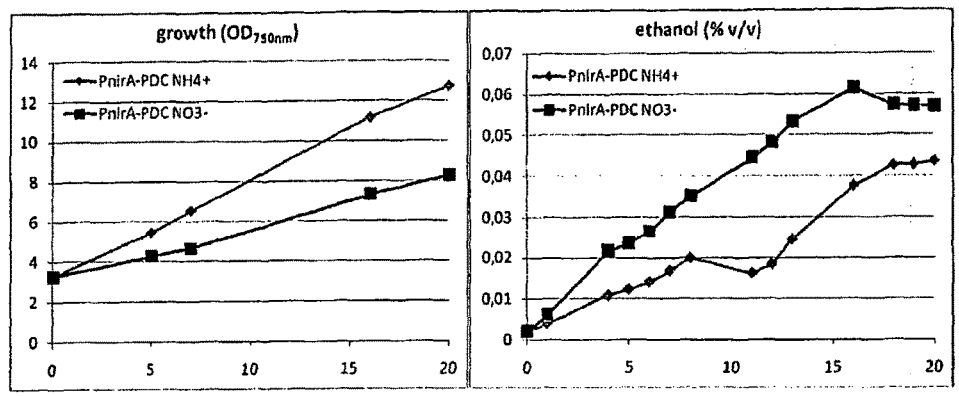

FIG. 49E is a graphic depiction of the growth properties of cells with PnirA-PDC when nitrogen is provided by ammonia or nitrate.

FIG. 49F is a graphic depiction of ethanol production of cells with PnirA-PDC when nitrogen is provided by ammonia or nitrate.

Figure 49G:
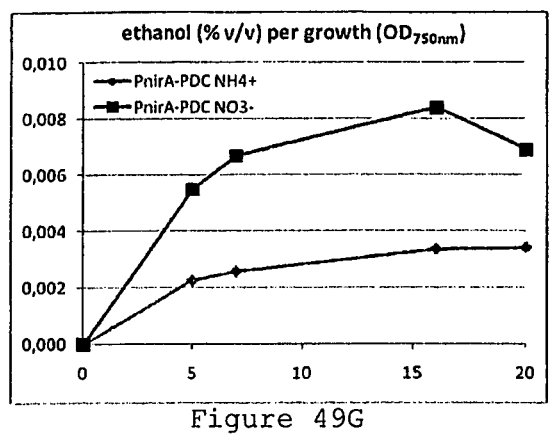

FIG. 49G is a graphic depiction of ethanol production normalized for culture optical density of cells with PnirA-PDC when nitrogen is provided by ammonia or nitrate.

FIG. 49H is a graphic depiction of growth of Synechocystis 6803 pVZ321b-PpetJ-PDC/ADH.

FIG. 49I is a graphic depiction of ethanol production of Synechocystis 6803 pVZ321b-PpetJ-PDC/ADH.

Figure 49J:
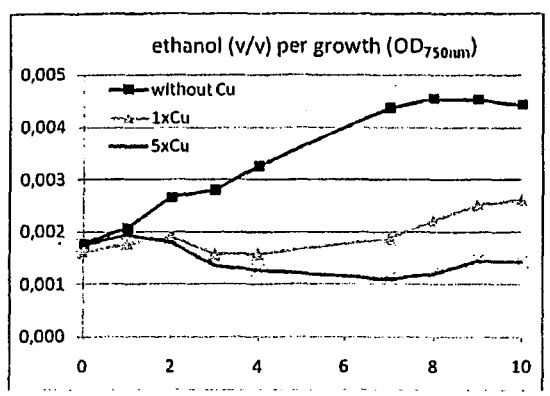

FIG. 49J is a graphic depiction ethanol productivity per growth of Synechocystis 6803 pVZ321b-PpetJ-PDC/ADH.

Figures 49K, 49L:
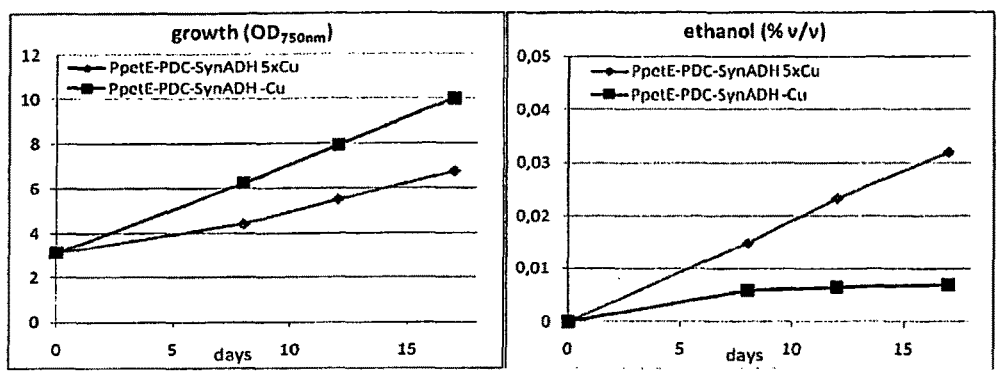

FIG. 49K is a graphic depiction of the growth of Synechocystis 6803 pVZ321b-PpetE-PDC/ADH.

FIG. 49L is a graphic depiction ethanol production of Synechocystis 6803 pVZ321b-PpetE-PDC/ADH.

Figure 49M:
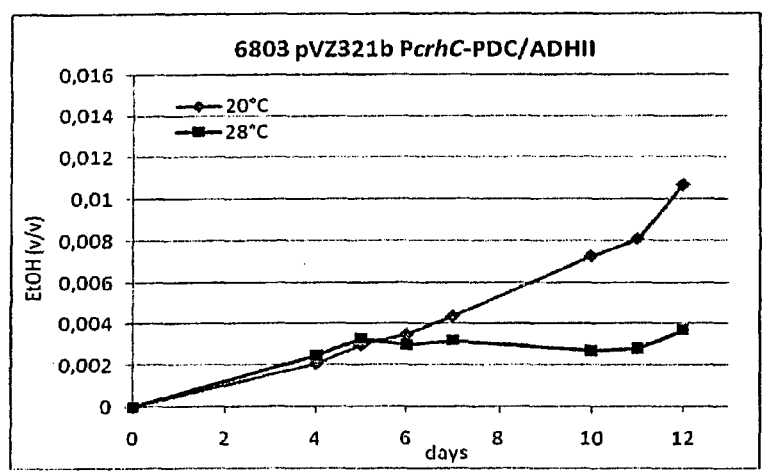

FIG. 49M is a graphic depiction of ethanol production of Synechocystis 6803 pVZ321b-PcrhC-PDC/ADH.

Figures 49N, 49O:
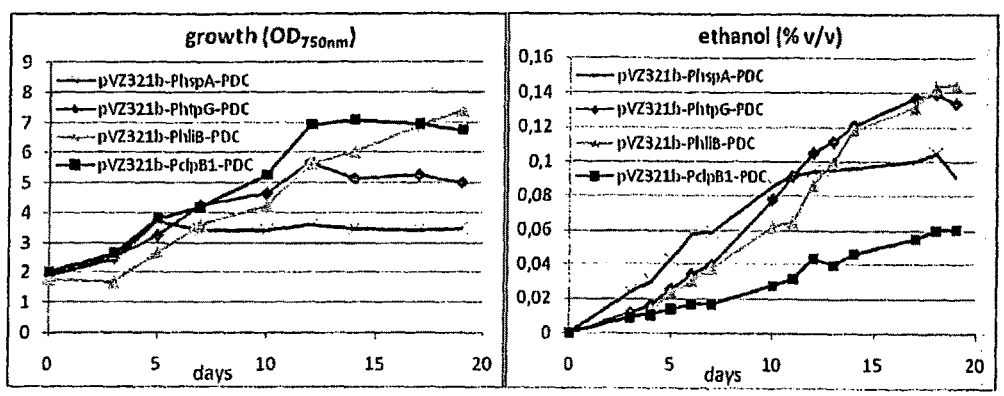

FIG. 49N is a graphic depiction of growth properties of Synechocystis 6803 pVZ321b-PhspA-PDC, pVZ321b-PhtpG-PDC, pVZ321b-PhliB-PDC and pVZ321b-PclpB1-PDC.

FIG. 49O is a graphic depiction of ethanol production of Synechocystis 6803 pVZ321b-PhspA-PDC, pVZ321b-PhtpG-PDC, pVZ321b-PhliB-PDC and pVZ321b-PclpB1-PDC.

Figure 49P:
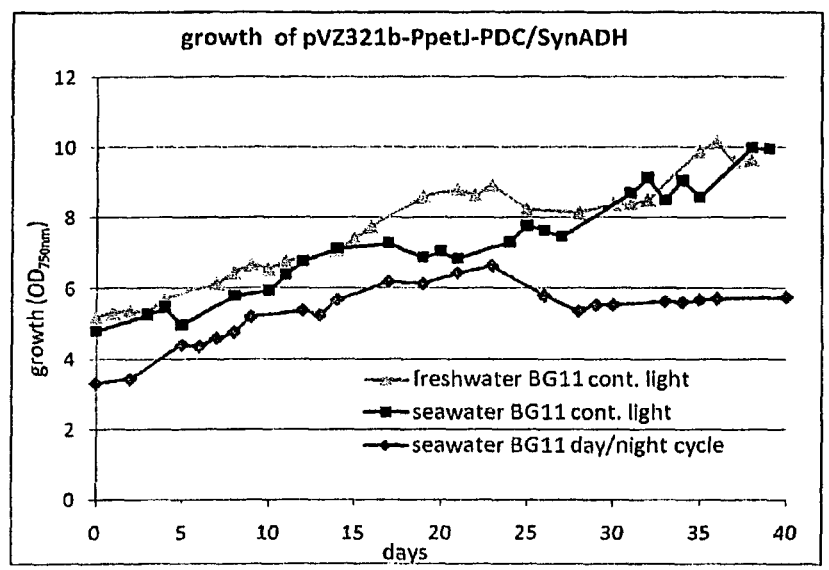

FIG. 49P is a graphic presentation of growth properties under different conditions of cells containing pVZ321b-PpetJ-PDC/SynADH.

Figure 49Q:
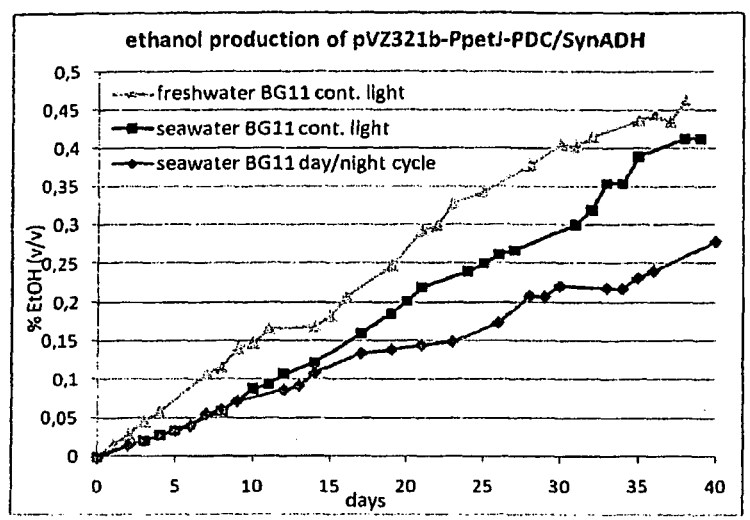

FIG. 49Q is a graphic presentation of ethanol production under different growth conditions of cells containing pVZ321b-PpetJ-PDC/SynADH.

Figure 49R:
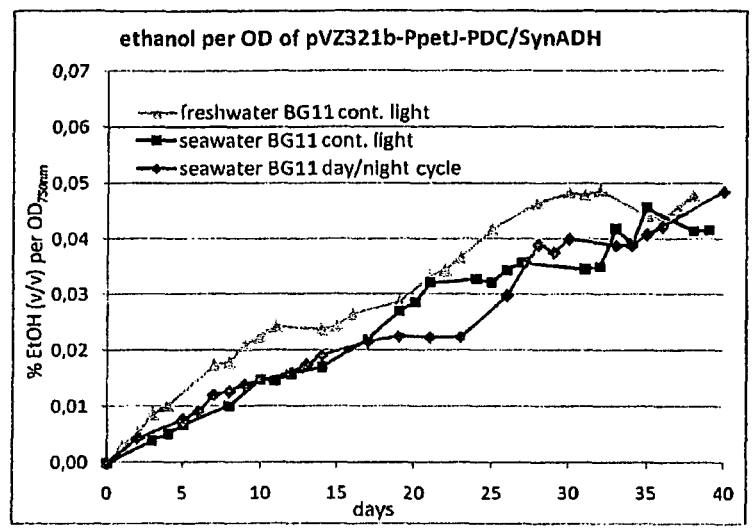

FIG. 49R is a graphic presentation of ethanol production per OD under different growth conditions of cells containing pVZ321b-PpetJ-PDC/SynADH.

DETAILED DESCRIPTION OF EMBODIMENTS

Definitions

As used herein, the term "genetically modified" refers to any change in the endogenous genome of a wild type cell or to the addition of non-endogenous genetic code to a wild type cell, e.g., the introduction of a heterologous gene. More specifically, such changes are made by the hand of man through the use of recombinant DNA technology or mutagenesis. The changes can involve protein coding sequences or non-protein coding sequences such as regulatory sequences as promoters or enhancers.

The term "nucleic acid" is intended to include nucleic acid molecules, e.g., polynucleotides which include an open reading frame encoding a polypeptide, and can further include non-coding regulatory sequences, and introns. In addition, the terms are intended to include one or more genes that map to a functional locus. In addition, the terms are intended to include a specific gene for a selected purpose. The gene can be endogenous to the host cell or can be recombinantly introduced into the host cell.

The phrase "operably linked" means that the nucleotide sequence of the nucleic acid molecule or gene of interest is linked to the regulatory sequence(s) in a manner which allows for expression (e.g., enhanced, increased, constitutive, basal, attenuated, decreased or repressed expression) of the nucleotide sequence and expression of a gene product encoded by the nucleotide sequence (e.g., when the recombinant nucleic acid molecule is included in a recombinant vector, as defined herein, and is introduced into a microorganism).

The term "recombinant nucleic acid molecule" includes a nucleic acid molecule (e.g., a DNA molecule) that has been altered, modified or engineered such that it differs in nucleotide sequence from the native or natural nucleic acid molecule from which the recombinant nucleic acid molecule was derived (e.g., by addition, deletion or substitution of one or more nucleotides). Advantageously, a recombinant nucleic acid molecule (e.g., a recombinant DNA molecule) includes an isolated nucleic acid molecule or gene of the present invention The terms "host cell" and "recombinant host cell" are intended to include a cell suitable for genetic manipulation, e.g., which can incorporate heterologous polynucleotide sequences, e.g., which can be transfected. The cell can be a prokaryotic or a eukaryotic cell. The term is intended to include progeny of the cell originally transfected. In particular embodiments, the cell is a prokaryotic cell, e.g., a cyanobacterial cell. Particularly, the term recombinant host cell is intended to include a cell that has already been selected or engineered to have certain desirable properties and suitable for further modification using the compositions and methods of the invention.

The term "promoter" is intended to include a polynucleotide segment that can transcriptionally control a gene-of-interest, e.g., a pyruvate decarboxylase gene, that it does or does not transcriptionally control in nature. In one embodiment, the transcriptional control of a promoter results in an increase in expression of the gene-of-interest. In another embodiment, a promoter is placed 5' to the gene-of-interest. A promoter can be used to replace the natural promoter, or can be used in addition to the natural promoter. A promoter can be endogenous with regard to the host cell in which it is used or it can be a heterologous polynucleotide sequence introduced into the host cell, e.g., exogenous with regard to the host cell in which it is used. Promoters of the invention may also be inducible, meaning that certain exogenous stimuli (e.g., nutrient starvation, heat shock, mechanical stress, light exposure, etc.).

The term "about" is used herein to mean approximately, in the region of, roughly, or around. When the term "about" is used in conjunction with a numerical value/range, it modifies that value/range by extending the boundaries above and below the numerical value(s) set forth. In general, the term "about" is used herein to modify a numerical value(s) above and below the stated value(s) by a variance of 20%.

As used herein, the phrase "increased activity" refers to any genetic modification resulting in increased levels of enzyme in a host cell. As known to one of ordinary skill in the art, enzyme activity may be increased by increasing the level of transcription, either by modifying promoter function or by increasing gene copy number, increasing translational efficiency of an enzyme messenger RNA, e.g., by modifying ribosomal binding, or by increasing the stability of a enzyme protein, which because the half-life of the protein is increased, will lead to more enzyme molecules in the cell. All of these represent non-limiting examples of increasing the activity of an enzyme. (mRNA Processing and Metabolism: Methods and Protocols, Edited by Daniel R. Schoenberg, Humana Press Inc., Totowa, N.J.; 2004; ISBN 1-59259-750-5; Prokaryotic Gene Expression (1999) Baumberg, S., Oxford University Press, ISBN 0199636036; The Structure and Function of Plastids (2006) Wise, R. R. and Hoober J. K., Springer, ISBN 140203217X; The Biomedical Engineering Handbook (2000) Bronzino, J. D., Springer, ISBN 354066808X).

Genetic knockdown includes techniques by which the expression of one or more of the organism's genes is reduced. In genetic knockout, the gene is made inoperative.

In one aspect the invention also provides nucleic acids, which are at least 60%, 70%, 80% 90% or 95% identical to the promoter nucleic acids disclosed therein and to the nucleic acids, which encode proteins, for example enzymes for ethanol formation or host cell enzymes involved in the conversion or formation of acetyl CoA, acetaldehyde or pyruvate or for formation of reserve compounds. The invention also provides amino acid sequences for enzymes for ethanol formation or host cell enzymes involved in the conversion or formation of acetyl-CoA, acetaldehyde or pyruvate or for formation of reserve compounds, which are at least 60%, 70%, 80% 90% or 95% identical to the amino acid sequences disclosed therein.

The percentage of identity of two nucleic acid sequences or two amino acid sequences can be determined using the algorithm of Thompson et al. (CLUSTALW, 1994 Nucleic Acid Research 22: 4673-4,680). A nucleotide sequence or an amino acid sequence can also be used as a so-called "query sequence" to perform against public nucleic acid or protein sequence databases in order, for example, to identify further unknown homologous promoters, which can also be used in embodiments of this invention. In addition, any nucleic acid sequences or protein sequences disclosed in this patent application can also be used as a "query sequence" in order to identify yet unknown sequences in public databases, which can encode for example new enzymes, which could be useful in this invention. Such searches can be performed using the algorithm of Karlin and Altschul (1999 Proceedings of the National Academy of Sciences U.S.A. 87: 2,264 to 2,268), modified as in Karlin and Altschul (1993 Proceedings of the National Academy of Sciences U.S.A. 90: 5,873 to 5,877). Such an algorithm is incorporated in the NBLAST and XBLAST programs of Altschul et al. (1999 Journal of Molecular Biology 215: 403 to 410). Suitable parameters for these database searches with these programs are, for example, a score of 100 and a word length of 12 for BLAST nucleotide searches as performed with the NBLAST program. BLAST protein searches are performed with the XBLAST program with a score of 50 and a word length of 3. Where gaps exist between two sequences, gapped BLAST is utilized as described in Altschul et al. (1997 Nucleic Acid Research, 25: 3,389 to 3,402).

Database entry numbers given in the following are for the CyanoBase, the genome database for cyanobacteria (http://bacteria.kazusa.or.jp/cyanobase/index.html); Yazukazu et al. "CyanoBase, the genome database for *Synechocystis* sp. Strain PCC6803: status for the year 2000", Nucleic Acid Research, 2000, Vol. 18, page 72.

Embodiments

It is one object of embodiments of the invention to provide a genetically modified host cell, which can be used for production of ethanol.

This object is reached by providing a genetically modified host cell according to base claim 1. Further embodiments of the genetically modified host cell, as well as constructs for producing the genetically modified host cells and a method for producing ethanol using the genetically modified host cells are subject matters of further claims.

Embodiment of genetic knockout and/or overexpression of metabolic pathway enzymes In a first aspect the invention provides a genetically modified photoautotrophic, ethanol producing host cell comprising:
- at least one first genetic modification changing the enzymatic activity or affinity of an endogenous host cell enzyme,
- the first genetic modification resulting in an enhanced level of biosynthesis of acetaldehyde, pyruvate, acetyl-CoA or precursors thereof compared to the respective wild type host cell,
- at least one second genetic modification different from the first genetic modification comprising an overexpressed enzyme for the formation of ethanol.

Acetaldehyde, pyruvate and acetyl-coA or their precursors are important metabolic intermediates for energy production in cells. In photoautotrophic cells, which use light, $CO_2$, and water as a source of energy to produce carbohydrates via photosynthesis, acetaldehyde, pyruvate, acetyl-CoA and their precursors can be formed by conversion of organic molecules obtained via $CO_2$ fixation in the Calvin-cycle, for example 3-phosphoglycerate. Pyruvate, acetyl-CoA and their precursors are important metabolic intermediates obtained e.g. by photosynthetic $CO_2$ fixation in photoautotrophic cells. Acetaldehyde is a metabolic intermediate of the anoxygenic fermentation pathway in many photoautotrophic cells. Precursors of pyruvate and acetyl-CoA are organic compounds, which can be converted into these important metabolic intermediates via the enzymatic action of enzymes of the photoautotrophic cell. For example the organic compounds 2-phosphoglycerate, 3-phosphoglycerate or phosphoenolpyruvate can be converted into pyruvate by enzymes of the glycolytic pathway in photoautotrophic cells.

The genetically modified photoautotrophic ethanol producing host cell comprises at least two different genetic modifications, a first and a second genetic modification. The first genetic modification changes the enzymatic activity or affinity of an endogenous host enzyme, resulting in a higher level of biosynthesis of acetyl-CoA, acetaldehyde, pyruvate or precursors thereof. The endogenous host enzyme is already present in an unmodified wild type host cell and its activity or affinity is changed by the first genetic modification in order to increase the level of biosynthesis of metabolic intermediates, which are also present in the wild type host cell and which can be used to form ethanol.

Furthermore the genetically modified photoautotrophic ethanol producing host cell comprises a second genetic modification in the form of at least one overexpressed enzyme, which can form ethanol, for example from the above-mentioned important metabolic intermediates. In a further embodiment the overexpressed enzyme for ethanol formation can catalyze the last step of ethanol formation leading to the final product ethanol. The overexpressed enzyme for ethanol formation can also catalyze the penultimate step of ethanol formation resulting in a metabolic intermediate, which can further be converted by another enzyme for ethanol formation into the final product ethanol.

The enzyme for ethanol formation can, for example, be an endogenous enzyme already present in a wild type photoautotrophic host cell, which is not genetically modified. In this case the activity or affinity of the enzyme for ethanol formation can be enhanced by the second genetic modification, for example by genetic engineering or random mutagenesis. This can, for example, be done by genetically modifying the amino acid sequence of the enzyme by site directed or random mutagenesis of the gene encoding this endogenous enzyme, thereby enhancing its activity for formation of ethanol. Another possibility is to increase the number of gene copies encoding for the enzyme in the host cell or simply by enhancing the rate of transcription of the gene already present in the wild type cell to increase the abundance of its messenger RNA in the second genetic modification. This can be done for example by replacing or mutating the endogenous promoter controlling the transcription of the endogenous gene encoding the enzyme for ethanol formation.

Alternatively or additionally a heterologous enzyme for ethanol formation can be introduced into the host cell by the second genetic modification, if that enzyme is not present in an genetically unmodified wild type host cell. This can be done, for example, by introducing a construct, for example a DNA vector into the host cell including a heterologous gene encoding the overexpressed enzyme for ethanol formation. In the case that an endogenous enzyme for ethanol formation is already present in a photoautotrophic wild type host cell, the heterologous enzyme for ethanol formation can enhance the activity of the endogenous enzyme resulting in a higher rate of ethanol formation.

The enzymatic activity and the affinity of an enzyme for its substrate are important kinetic constants. The enzymatic activity is given by the parameter $V_{max}$, which reflects the maximal velocity of an enzymatic reaction occurring at high substrate concentrations when the enzyme is saturated with its substrate. The affinity is given by the Michaelis-Menten constant $K_m$ which is the substrate concentration required for an enzyme to reach one-half its maximum velocity. In order to increase the enzymatic activity $V_{max}$ has to be increased, whereas for increasing the affinity $K_m$ has to be reduced. Regarding a further explanation of enzyme kinetics we refer to the chapter "enzyme kinetics" in the textbook "Biochemistry" by Donald Voet and Judith Voet (John Wiley & Sons, 1990, pages 335 to 340).

The higher level of biosynthesis of acetyl-CoA, acetaldehyde, pyruvate or precursors thereof results in a change of the flux of the acetyl-CoA, acetaldehyde, pyruvate or precursors thereof in the direction of the at least one overexpressed enzyme for ethanol formation so that formation of ethanol can be increased in comparison to a photoautotrophic ethanol producing host cell harboring only the second genetic modification, but lacking the first genetic modification.

Acetyl-CoA, acetaldehyde, pyruvate or precursors thereof are transient metabolic intermediates, which are often rapidly processed into other metabolites by the photoautotrophic host cell and therefore a change in the level of biosynthesis of these metabolic intermediates can be hard to detect in photoautotrophic host cells featuring the first genetic modification but lacking the second genetic modification.

A first genetic modification therefore results in a higher level of biosynthesis of acetyl-CoA, acetaldehyde, pyruvate or precursors thereof compared to the respective wild type host cell, if after introduction of the second genetic modification a high level of ethanol formation can be detected, even if a change in the level of biosynthesis of these metabolic intermediates could not be detected in the photoautotrophic host cell harboring the first genetic modification but lacking the second genetic modification.

The genetically modified photoautotrophic host cell can comprise more than one first genetic modification and also more than one second genetic modification. For example the first genetic modification can comprise at least two genetic modifications, one first genetic modification (a), which is a down-regulation or a knock out of gene expression of a metabolic enzyme and at least one further first genetic modification (b), which is an increase in metabolic enzyme activity and/or substrate affinity for a endogenous enzyme for formation of acetyl-CoA, pyruvate or acetaldehyde or precursors thereof.

In a further embodiment thereof, the total number of possible one first genetic modifications (a) is represented by N, wherein N is a number from 0 to 50, and N indicates the number of genetic modifications resulting in the down-regulation or knockout of metabolic enzyme activity and/or substrate affinity, and the number of further first genetic modifications (b) is represented by P, wherein P is a number from 0 to 50, resulting in an increase in metabolic enzyme activity and/or substrate affinity for a endogenous enzyme for formation of acetyl-CoA, pyruvate or acetaldehyde or precursors thereof. The numerical values for genetic modification (a) N and genetic modification (b) P are selected independently from one another as long as the sum of P+N is at least one. By way of non-limiting example, (a) N may have a numerical value of 1, indicating a single genetic modification, and (b) P may have a numerical value of 2, indicating two genetic modifications. Alternatively (a) N may have numerical value of 2, indicating two genetic modifications, and (b) P may have a numerical value of 1, indicating a single genetic modification. Thus, as will be understood to those skilled in the art, the invention provides herein for a wide variety of genetically modified, photoautotrophic ethanol producing host cells comprising a multitude of genetic modifications, the combination of which result in an enhanced level of biosynthesis of acetaldehyde, pyruvate, acetyl-CoA or precursors thereof.

The genetically modified photoautotrophic host cell shows a high production of ethanol due to the fact that the ethanol forming enzyme is overexpressed due to the second genetic modification leading to a high enzymatic activity or activity for ethanol formation and that at the same time a higher level of biosynthesis of acetaldehyde, pyruvate, acetyl-CoA or their precursors is formed in the cells compared to the respective wild type cells due to the first genetic modification. Acetaldehyde, pyruvate, acetyl-CoA or their precursors serve as substrates for the ethanol production. These metabolic intermediates can either be a direct substrate for the overexpressed enzyme for the formation of ethanol or for another second overexpressed enzyme for ethanol formation, which then catalyzes the formation of a substrate for the first overexpressed enzyme for ethanol formation.

In yet another embodiment of the genetically modified host cell
the at least one endogenous host cell enzyme is selected from enzymes of the glycolysis pathway, Calvin-cycle, intermediate steps of metabolism, amino acid metabolism, the fermentation pathway and the citric acid cycle, wherein the activity of at least one of these enzymes is enhanced compared to the respective wild type host cell.
Enzymes of intermediate steps of metabolism are enzymes which connect different metabolic pathways. For example the glycolysis and the citric acid cycle are connected via the enzyme malic enzyme converting malate into pyruvate.

In particular the endogenous host cell enzyme can be selected from only one of the above pathways or in the case that more than one endogenous host cell enzyme is mutated in a first genetic modification can be selected from any possible combination of the above pathways.

The Calvin-cycle is an important part of photosynthesis and includes the light-independent reactions, where $CO_2$ is captured from the environment of the cell and converted into organic compounds, for example three-carbon compounds such as 3-phosphoglycerate. $CO_2$ may also be captured by alternative routes into four-carbon compounds such as oxaloacetate. These processes are also referred to as C3-carbon fixation and C4-carbon fixation.

Photosynthetic $CO_2$ fixation can lead to the production of carbon storage compounds such as reserve carbohydrates like glycogen, starch or sucrose.

The glycolysis pathway is normally the first step of carbohydrate catabolism in order to generate adenosine triphosphate (ATP) and reductants such as nicotinamide adenine dinucleotide (NADH). Glycolysis furthermore can produce pyruvate which is an important compound for the citric acid cycle that generates reductant for aerobic respiration and intermediates for biosynthesis. Furthermore, glycolysis serves to synthesize various 6- and 3-carbon intermediate compounds which can be used for other cellular processes such as amino acid biosynthesis.

Pyruvate produced via glycolysis is one of the major sources for the citric acid cycle, which is an important part of a metabolic pathway for the chemical conversion of carbo-hydrates, fat and proteins into carbon dioxide and water to generate energy for the host cell. Pyruvate can, for example, be fed into the citric acid cycle via acetyl-CoA (acetyl-CoA). Furthermore, pyruvate can also be metabolized to acetaldehyde via other enzymes. Therefore, enhancing the activity or affinity of at least one of the endogenous host cell enzymes of the Calvin-cycle or glycolysis pathway or the citric acid cycle in a first genetic modification can result in a higher level of biosynthesis of pyruvate, or acetyl-CoA or their precursors, respectively. This in turn can result in a higher ethanol production due to the fact that these metabolic intermediates can be ultimately converted to ethanol via the at least one overexpressed enzyme for the formation of ethanol provided by the second genetic modification.

In certain aspects and embodiments of the invention the enzymatic activity or affinity of any of these enzymes can be enhanced, for example, by increasing the activity or affinity of the enzymes present in the wild type host cell. Non-limiting examples contemplated by the invention include site directed mutagenesis or random mutagenesis and by increasing the amount of enzymes in the host cell. The latter is achieved, for example by introducing mutations in the promoter regions controlling the transcriptional activity of the genes encoding the enzymes or by introducing additional gene copies coding for these enzymes into the host cell.

In a further embodiment at least one enzyme of the glycolysis pathway, the citric acid cycle, the intermediate steps of metabolism, the amino acid metabolism, the fermentation pathway or the Calvin-cycle of the host cell is overexpressed. Overexpression of an enzyme already present in a wild type host cell is an effective method to enhance the enzymatic activity of enzymes in a cell. Overexpression can also be achieved by introducing a heterologous enzyme into the host cell, which exhibits the same enzymatic activity as the host cell enzyme, which should be overexpressed. For example if 3-phosphoglycerate mutase should be overexpressed in the cyanobacterium *Synechocystis* a plasmid comprising a heterologous gene encoding 3-phosphoglycerate mutase from *Zymomonas mobilis* can be introduced into the host cell. Another non-limiting example is the overexpression of pyruvate kinase from E. coli in Synechocystis, thereby raising the enzymatic activity of the endogenous host cell enzyme pyruvate kinase in Synechocystis.

In the case that the enzymatic activity of malate dehydrogenase, an enzyme of the citric acid cycle and malic enzyme, an enzyme of the intermediate steps of metabolism is enhanced, malate dehydrogenase can stimulate the conversion of oxaloacetate to pyruvate via malate. Malate dehydrogenase catalyzes the conversion of oxaloacetate to malate using NADH:

$$\text{Oxaloacetate} + \text{NADH} + \text{H}^+ \rightarrow \text{malate} + \text{NAD}^+$$

Malic enzyme catalyzes the conversion of malate into pyruvate using NADP$^+$:

$$\text{malate} + \text{NADP}^+ \rightarrow \text{pyruvate} + \text{CO}_2 + \text{NADPH}$$

In C4-plants the released $CO_2$ can be fixed by ribulose-1,5-bisphosphate carboxylase/oxygenase (RubisCO) and NADPH can be used for $CO_2$-fixation in the Calvin-cycle. The enzymatic activity or affinity of RubisCO can be enhanced in a first genetic modification in order to increase the $CO_2$-fixation and direct more carbon towards ethanol formation. This can be done for example by overexpressing only the small and the large subunits of RubisCO or a complete RubisCO operon also including a RubisCO Chaperonin in the photoautotrophic host cells such as prokaryotic cells. The RubisCO Chaperonin can assist in the folding of the RubisCO enzyme, which is a complex of eight large and eight small subunits in cyanobacteria and algae. The binding sites for the substrate ribulose 1,5-bisphosphate are located on the large subunits, whereas the small subunits have regulatory functions. RubisCO catalyzes bifunctional the initial step in the carbon dioxide assimilatory pathway and photorespiratory pathway in photosynthetic organisms. The enzyme catalyzes the carboxylation of ribulose-1,5-bisphosphate into two molecules of 3-phosphoglycerate (3-PGA) in the carbon dioxide assimilatory pathway, but also the oxygenation of ribulose-1,5-bisphosphate resulting in 3-PGA and 2-Phosphoglycolate (2-PG) in the photorespiratory pathway. In order to direct the carbon provided by the $CO_2$-fixation into ethanol formation, the carbon dioxide assimilatory pathway has to be enhanced and the activity of the photorespiratory pathway has to be reduced. Some photoautotrophic cells such as cyanobacteria have mechanisms to actively uptake $CO_2$ and $HCO_3^-$ and to raise the $CO_2$-concentration in the proximity of RubisCO (Badger M. R., and Price, G. D. (2003) J. Exp. Bot. 54, 609-622). This reduces the oxygenase activity of the enzyme. Nevertheless the cyanobacterial photosynthesis is not efficient enough to completely abolish the formation of 2-PG. Cyanobacteria produce significant amounts of 2-PG, particularly at elevated oxygen concentrations or after a change to low $CO_2$-concentrations.

In order to enhance the carbon dioxide fixating activity of RubisCO random or side directed mutagenesis can be performed to achieve higher $CO_2$ fixation according to some embodiments of the invention. Efforts to select RubisCO enzymes with improved activity using random mutagenesis were successful when the large subunit of RubisCO from Synechococcus PCC 7942 was mutagenized and co-expressed with the small subunit of RubisCO and phosphoribulokinase (prkA) in E. coli (Directed evolution of RubisCO hypermorphs through genetic selection in engineered E. coli, Parikh et al, Protein Engineering, Design & Selection vol. 19 no. 3 pp. 113-119, 2006). This strategy was also successful in the case of the similar enzymes from Synechococcus PCC 6301 in E. coli (Artificially evolved Synechococcus PCC 6301 RubisCO variants exhibit improvements in folding and catalytic efficiency, Greene et al., Biochem J. 404 (3): 517-24, 2007).

Another way of increasing the enzymatic activity of RubisCO according to the invention involves overexpressing heterologous RubisCO in order to increase the $CO_2$ fixation as it was shown in case of the heterologous expression of RubisCO from Allochromatium vinosum in Synechococcus PCC 7942 (Expression of foreign type I ribulose-1,5-bisphosphate carboxylase/oxygenase (EC 4.1.1.39) stimulates photosynthesis in cyanobacterium Synechococcus PCC 7942 cells, Iwaki et al, Photosynthesis Research 88: 287-297, 2006).

Overexpression of RubisCO in photoautotrophic host cells such as cyanobacteria also harboring at least one overexpressed enzyme for the formation of ethanol surprisingly not just results in an increased activity of RubisCO, but also leads to an increased biomass of the cells and a higher growth rate accompanied by a slight increase in the rate of ethanol production.

In addition the photorespiration activity of RubisCO can be reduced or eliminated by random or side directed mutagenesis.

Certain embodiments of the invention relate to the overexpression of at least one enzyme from the glycolysis pathway. Non-limiting examples are phosphoglycerate mutase, enolase and pyruvate kinase.

Phosphoglycerate mutase catalyzes the reversible reaction leading from 3-phosphoglycerate formed in the Calvin-cycle to 2-phosphoglycerate. 2-phosphoglycerate in turn can then, in a reversible reaction catalyzed by the enzyme enolase, be converted to phosphoenolpyruvate. Phosphoenolpyruvate can further be converted to pyruvate via the enzymatic action of pyruvate kinase. Therefore, enhancing the activity of any or all of these enzymes enhances the pyruvate pool in the host cell by enhancing the conversion of 3-phosphoglycerate formed in the Calvin-cycle to pyruvate. Pyruvate itself can then either be a direct substrate for the at least one overexpressed enzyme for ethanol formation or it can further be converted into another intermediate, which then can be further metabolized by the enzyme for ethanol formation in order to form high amounts of ethanol.

An enzyme of the fermentation pathway, which can be overexpressed is for example the acetaldehyde dehydrogenase enzyme, which can convert acetyl-CoA to acetaldehyde, thereby increasing the level of biosynthesis of acetaldehyde in the host cell. Alternatively other aldehyde dehydrogenases enzymes could be expressed in order to increase the level of biosynthesis of acetaldehyde in the host cell.

Enzymes of the intermediate steps of metabolism, which can be overexpressed are for example pyruvate dehydrogenase enzyme converting pyruvate into acetyl-CoA, increasing the level of biosynthesis of acetyl-CoA in the host cell. In addition or alternatively phosphotransacetylase converting acetyl-CoA to acetylphosphate can be overexpressed in the host cell, thereby increasing the level of biosynthesis of acetaldehyde in the host cell.

Another non-limiting example of an enzyme, whose activity or affinity can be increased is the enzyme PEP-carboxylase (phosphoenolpyruvate carboxylase). This enzyme catalyzes the addition of $CO_2$ to phosphoenolpyruvate (PEP) to form the four-carbon compound oxaloacetate (OAA). This PEP-carboxylase catalyzed reaction is used for $CO_2$ fixation and can enhance the photosynthetic activity leading to higher $CO_2$ fixation, which can be used for ethanol formation.

In particular the enzymatic activity or affinity of PEP-carboxylase, malate dehydrogenase and malic enzyme can be enhanced concomitantly. This leads to a higher $CO_2$ fixation and an enhanced level of biosynthesis of pyruvate. In addition the decarboxylation of malate to pyruvate catalyzed by the enzyme malic enzyme, enhances the $CO_2$ partial pressure leading to an increased efficiency of the Calvin cycle. PEP-carboxylase is used for $CO_2$ fixation in C4-plants and can also be found in cyanobacteria.

Furthermore it is possible to overexpress enzymes of the amino acid metabolism of the host cell, which for example convert certain amino acids into pyruvate leading to an enhanced biosynthesis of pyruvate in the host cell. For example serine can directly be converted to pyruvate in the cyanobacterium Synechocystis PCC 6803. The open reading frame slr 2072, which is annotated as ilvA (threonine dehydratase), EC 4.3.1.19, can catalyze the deamination of serine to pyruvate.

According to a further aspect of the invention the enzymatic activity or affinity of the enzyme phosphoketolase (EC 4.1.2.-, putative phosphoketolase in Synechocystis PCC 6803 slr 0453) is enhanced in a first genetic modification in order to increase the level of biosynthesis of precursor molecules for the generation of acetyl-CoA and acetaldehyde. Phosphoketolase catalyses the formation of acetyl phosphate and glyceraldehyde 3-phosphate, a precursor of 3-phosphoglycerate from xylulose-5-phosphate which is an intermediate of the Calvin cycle.

According to another embodiment of the invention in combination with enhancing the enzymatic activity or affinity of phosphoketolase enzyme, the polyhydroxybutyrate (PHB) pathway is knocked out in order to avoid PHB accumulation due to an increased level of acetyl-CoA biosynthesis (Control of Poly-β-Hydroxybutyrate Synthase Mediated by Acetyl Phosphate in Cyanobacteria, Miyake et al., Journal of Bacteriology, p. 5009-5013, 1997). Additionally AdhE can be overexpressed at the same time to convert the acetyl-CoA to ethanol.

Endogenous host enzymes of the glycolysis pathway, the Calvin-cycle, the intermediate steps of metabolism, the amino acid metabolism pathways, the fermentation pathways or the citric acid cycle, can be dependent upon a cofactor. The invention also provides an enhanced level of biosynthesis of this cofactor compared to the respective wild type host cell, thereby increasing the activity of these enzymes. Such an enhanced level of biosynthesis of this cofactor can be provided in a first genetic modification.

An enhanced level of the cofactor biosynthesis also results in an enhanced enzymatic activity or affinity of these above mentioned enzymes and therefore in an enhanced level of biosynthesis of pyruvate, acetyl-CoA, acetaldehyde or their precursors in the cell.

For example, alcohol dehydrogenase enzymes are often $NAD^+/NADH$ cofactor dependent enzymes. In this case, their enzymatic activity can be enhanced by raising the level of NADH biosynthesis in the host cell. This can, for example, be done by overexpressing $NAD(P)^+$ transhydrogenases, which transfer reduction equivalents between NADP(H) to NAD(H). These $NAD(P)^+$ transhydrogenases are oxidoreductases.

Furthermore the host cell can comprise a host NADH dehydrogenase converting NADH to $NAD^+$ wherein the activity of the NADH dehydrogenase is reduced compared to the wild type host cell.

For example, point mutations can be introduced into the gene encoding the NADH dehydrogenase in order to reduce the activity or affinity of this enzyme or alternatively the gene encoding the NADH dehydrogenase can be knocked-out by inserting for example heterologous nucleic acid sequences into the gene, thereby disrupting it.

Alternatively, in order to enhance the enzymatic activity of an enzyme, which is $NADP^+/NADPH$ cofactor dependent as, for example the malic enzyme, the level of $NADP^+/NADPH$ in the host cell also can be increased.

In many of photoautotrophic cells the level of $NAD^+$ plus NADH to $NADP^+$ plus NADPH is around 1:10. Due to this high imbalance of NADH to NADPH, the conversion of an $NADP^+/NADH$ cofactor specific enzyme via site directed mutagenesis or random mutagenesis of the enzyme into an $NADP^+/NADPH$ dependent enzyme can increase its activity. The changing of the cofactor specificity of alcohol dehydrogenase via in vitro random mutagenesis is for example described in the publication "Alteration of Substrate Specificity of Zymomonas mobilis Alcohol Dehydrogenase-2 Using in Vitro Random Mutagenesis" (Protein Expression and Purification Volume 9, Issue 1, February 1997, Pages 83-90).

A further embodiment of the invention provides a genetically modified host cell
wherein the at least one endogenous host cell enzyme is for the conversion of pyruvate or acetyl-CoA or for the formation of reserve compounds, wherein its activity or affinity is reduced.

Alternatively or in addition to enhancing the activity of enzymes forming pyruvate, acetaldehyde, acetyl-CoA or precursors thereof, the activity of the enzymes converting the above-mentioned important intermediate metabolic compounds into other compounds can be reduced by the way of the first genetic modification. The inventors found out that by reducing the activity of at least one of these enzymes the level of biosynthesis of pyruvate, acetyl-CoA, acetaldehyde or their precursors can be risen compared to a wild type host cell. In addition, the inventors made the observation that by reducing the activity of host enzymes forming reserve compounds, for example glycogen, more carbohydrates formed via photosynthesis in the photoautotrophic host cells are shuffled into the glycolysis pathway and the citric acid cycle, thereby enhancing the level of biosynthesis of pyruvate, acetaldehyde, acetyl-CoA or their precursors. Due to the fact that these metabolic intermediates are used by at least one overexpressed enzyme for the formation of ethanol, a higher ethanol production of such a genetically modified host cell can be observed.

The enzymatic activity of at least one of these enzymes can be reduced, for example by introducing point mutations into the genes encoding these enzymes, thereby reducing the activity of these enzymes. Alternatively or in addition, the promoter regions controlling the transcriptional activity of these genes can be mutated, resulting in a lower transcriptional activity and therefore a reduced level of protein translation in the genetically modified host cell.

A point mutation, or single base substitution, is a type of mutation that causes the replacement of a single base nucleotide with another nucleotide.

A "promoter" is an array of nucleic acid control sequences that direct transcription of an associated nucleic acid sequence, which may be a heterologous or endogenous nucleic acid sequence. A promoter includes nucleic acid sequences near the start site of transcription, such as a polymerase binding site for a RNA polymerase used for the synthesis of messenger RNA. The promoter also optionally includes distal enhancer or repressor elements which can be located as much as several thousand base pairs from the start site of transcription.

Furthermore, it is possible that the host cell comprises disruptions in the host gene encoding at least one of the enzymes of the host cell converting pyruvate, acetyl-CoA, the precursors thereof or for forming reserve compounds. In this case, the enzymatic activity of the enzymes can be eliminated to a full extent due to the fact that the disrupted gene does not encode for a functional protein anymore.

The disruption of the gene can be furthermore caused by an insertion of a biocide resistance gene into the respective gene. This has the advantage that so-called "knockout mutants" containing the insertions in the respective genes can easily be selected by culturing the genetically modified host cells in selective medium containing the biocide to which the genetically modified host cell is resistant.

The term "biocide" refers to a chemical substance, which is able to inhibit the growth of cells or even kill cells, which are not resistant to this biocide. Biocides can include herbicides, algaecides and antibiotics, which can inhibit the growth of plants, algae or microorganisms such as bacteria, for example cyanobacteria.

Alternatively or in addition for disrupting the gene encoding one of the enzymes converting pyruvate, acetyl-CoA or acetaldehyde or forming reserve compounds, the enzymatic activity of one of these enzymes can also be reduced by using the antisense messenger RNA concept.

A wild type cell normally comprises at least one host gene encoding for the host enzyme or protein, wherein transcription of this gene results in a sense messenger RNA (mRNA), which codes for the functional protein and is translated into the protein via translation mediated by the ribosomes, ribonucleoprotein complexes present in cells. The messenger RNA is normally a single stranded RNA molecule encoding the amino acid sequence of the enzyme in the form of the genetic code. Specifically, the genetic code defines a mapping between tri-nucleotide sequences called codons in the messenger RNA and the amino acids of the amino acid sequence; every triplet of nucleotides in a nucleic acid sequence of the mRNA specifies a single amino acid. This messenger RNA molecule is normally called sense RNA. In order to reduce or even eliminate the enzymatic activity of the enzyme encoded by this gene a nucleic acid sequence can be introduced into the host cell, which upon transcription results in a RNA strand complementary to the sense messenger RNA strand, the so-called antisense RNA. This antisense RNA can then interact with the sense RNA, forming a double-stranded RNA species which cannot be translated by the ribosomes into a functional protein anymore. Depending on the ratio of the sense RNA to the antisense RNA in the host cell, the level of enzymatic activity of the enzyme can be reduced or even eliminated. Different antisense RNA approaches for the regulation of gene expression are described in the following publications:

Dühring U, Axmann I M, Hess W R, Wilde A.
"An internal antisense RNA regulates expression of the photosynthesis gene isiA" (*Proc Natl Acad Sci USA*. 2006 May 2; 103(18):7054-8).

Udekwu K I, Darfeuille F, Vogel J, Reimegård J, Holmqvist E, Wagner E G.
"Hfq-dependent regulation of OmpA synthesis is mediated by an antisense RNA" (*Genes Dev.* 2005 Oct. 1; 19(19): 2355-66)

Prime enzyme targets for down regulation of enzymatic activity or for elimination of enzymatic activity are ADP-glucose-pyrophosphorylase, glycogen synthase, alanine dehydrogenase, lactate dehydrogenase, pyruvate water dikinase, phosphotransacetylase, and acetate kinase as well as pyruvate dehydrogenase.

ADP-glucose-pyrophosphorylase catalyzes the conversion of glucose-1-phosphate into ADP-glucose, which is a precursor for the reserve polysaccharide glycogen in many photoautotrophic host cells. The enzyme glycogen synthase catalyzes the addition of further glucose monomers donated by ADP glucose to the ends of glycogen primers.

The inventors found out that by reducing or even eliminating the formation of reserve carbohydrates such as starch or glycogen, the level of biosynthesis of pyruvate, acetyl-CoA or acetaldehyde can be raised compared to the level of biosynthesis a wild type host cell. This finding was particularly true for the reduction of the enzymatic affinity and activity of glycogen synthase and ADP-glucose-pyrophosphorylase. A knock out of both enzymes in photoautotrophic host cells lacking at least one overexpressed enzyme for ethanol production as a second genetic modification resulted in a big increase of pyruvate secreted into the growth medium. Further introducing a second genetic modification into these photoautotrophic host cells resulted in an increased fraction of fixed carbon being diverted to ethanol production.

Alanine dehydrogenase catalyzes the reversible reductive amination of pyruvate to alanine using NADH as a reductant. A reduction of activity of alanine dehydrogenase can result in a higher level of pyruvate.

The enzyme lactate dehydrogenase catalyzes the interconversion of pyruvate to the fermentative end product lactate using NADH as a reductant. Reducing or inhibiting the enzymatic action of lactate dehydrogenase can result in an increase of the level of biosynthesis of pyruvate in the genetically modified host cell.

The enzyme pyruvate water dikinase catalyzes the ATP-dependent conversion of pyruvate, ATP and water to adenosine monophosphate (AMP), phosphoenolpyruvate and phosphate. Due to that a reduction of the enzymatic activity of pyruvate water dikinase can also result in an increased level of pyruvate in the host cell.

The enzyme phosphotransacetylase catalyzes the reversible transfer of an acetyl group from acetyl-CoA to a phosphate thereby forming acetylphosphate. A reduction of the enzymatic activity of this enzyme can also result in an increased level of acetyl-CoA as well as of its precursor pyruvate.

The enzyme acetate kinase catalyzes the conversion of acetylphosphate to the fermentative end product acetate whereas the phosphate group is transferred from acetylphosphate to adenosine diphosphate (ADP) so adenosine triphosphate (ATP) is formed. An inactivation or a reduction of the enzymatic activity of this enzyme can therefore result in a higher level of acetylphosphate and maybe acetyl-CoA in the cell.

Reducing the enzymatic activity or knocking out of the gene encoding phosphotransacetylase (PTA) can be important, since this enzyme is at the branch point of acetate generation via acetylphosphate. Acetylphosphate itself is an important intermediate, because it is needed for ADP regeneration to ATP and it stimulates the activity of polyhydroxybutyrate (PHB) synthase. Knock out of the PTA therefore can avoid loss of acetyl-CoA into the acetate branch and additionally can minimize PHB generation. Thus acetyl-CoA can be channeled to the ethanol generating branch.

The inventors found out that a reduction in the enzymatic affinity or activity of the enzymes of the complete acetate fermentation pathway, in particular phosphotransacetylase and acetate kinase can lead to an increase in the ethanol production rate without reducing the photosynthetic capacity of the photoautotrophic host cells. For example a knock out of both genes coding for phosphotransacetylase and acetate kinase can enhance the ethanol production rate compared to a photoautotrophic host cell harboring only at least one overexpressed enzyme for ethanol formation as a second genetic modification but lacking the first genetic modification, the knock out mutations of both enzymes.

On the other hand acetylphosphate is the natural precursor of fermentative EtOH synthesis via acetaldehyde and therefore overexpressing the phosphotransacetylase together with the acetaldehyde forming enzyme and knocking-out or reducing the enzymatic activity of the PHB synthase can also increase the level of biosynthesis of acetaldehyde in the genetically modified host cell.

In some bacterial cells both enzymes phosphotransacetylase and acetate kinase can also catalyze the reverse reaction from acetate to acetylphosphate and from acetylphosphate to acetyl-CoA. In the case that the level of biosynthesis of acetyl-CoA should be raised compared to the wild type cells the activity or affinity of both enzymes can be enhanced for example via overexpression in different first genetic modifications. Alternatively only acetate kinase can be overexpressed in a first genetic modification in the case that the second genetic modification comprises at least acetaldehyde dehydrogenase converting the acetylphosphate to acetaldehyde and further Adh, such as AdhI and/or AdhII converting the acetaldehyde into ethanol.

Another possible target enzyme for down-regulation to increase the level of biosynthesis of pyruvate is pyruvate dehydrogenase, which catalyzes the thiamine pyrophosphate (TPP) cofactor dependent decarboxylation of pyruvate resulting in acetyl-CoA, NADH and $CO_2$.

With regard to the enzymes forming reserve compounds for the cell, the gene for glycogen synthase can be disrupted, for example by inserting a heterologous nucleic acid sequence encoding for a biocide resistance cassette into the gene. The inventors found out that such a knockout of both glycogen synthase genes glgA1 and glgA2 in the phototropic genetically modified host cell of the genera *Synechocystis* results in an enhanced pyruvate level of up to 50-fold compared to the unmodified wild type host cell.

In particular, the enzymes forming one of the following reserve compounds can be a prime target for a reduction of their enzymatic activity of even for knockout: Glycogen, polyhydroxyalkanoates like, for example poly-3-hydroxybutyrate or poly-4-hydroxybutyrate, polyhydroxyvalerate, polyhydroxyhexanoate, polyhydroxy-octanoate, amylopectin, starch, cyanophycin and their copolymers, glucosyl glycerol and bacterial extracellular polymeric substances such as extracellular polysaccharides. Enzymes which are involved in the synthesis of these reserve compounds are for example beta-ketothiolase, acetoacetyl-CoA reductase, polyhydroxybutyrate synthase, glucosylglycerolphosphate synthase.

Polyhydroxybutyrate is synthesized from acetyl-CoA via three enzymatic reactions: 3-thiolase (EC 2.3.1.9) converts two acetyl-CoA molecules to an acetoacetyl-CoA molecule, NADPH-dependent acetoacetyl-CoA reductase (EC 1.1.1.36) converts acetoacetyl-CoA to D-3-hydroxybutyryl-CoA with NADPH oxidation, and the last enzyme, PHB synthase, catalyzes the linkage of the D-3-hydroxybutyryl moiety to an existing PHB molecule by an ester bond.

The biosynthetic pathway of glucosyl glycerol begins with ADP-glucose and glycerol-3-phosphate (G3P), which are used by the GG-phosphate synthase (GGPS), and proceeds via the intermediate GG-phosphate (GGP), which is dephosphorylated to GG by the GGphosphate phosphatase (GGPP).

Hydrolyzed EPSs (bacterial extracellular polymeric substances) showed the compositional involvement of four sugar moieties viz. mannose, glucose, xylose and ribose in varying combinations. Chemical analysis of EPS revealed a heteropolysaccharidic nature, with xylose, glucose, galactose, and mannose the main neutral sugars found.

In the case that a genetically modified host cell exhibits a reduced enzymatic activity for the formation of any of the above-mentioned reserve compounds, it is expected that the precursors for these reserve compounds are fed into the glycolysis pathway or the citric acid cycle, thereby resulting in an enhanced level of, pyruvate, acetyl-CoA, acetaldehyde or their precursors. This in turn can result in a higher ethanol production in the case that pyruvate, acetyl-CoA or acetaldehyde are used by the at least one overexpressed enzyme for ethanol formation in order to produce ethanol.

In yet a further embodiment of the host cell of the invention, the at least one overexpressed enzyme for the formation of ethanol is an alcohol dehydrogenase.

An alcohol dehydrogenase catalyzes the reduction of a substrate to ethanol. This reaction is normally dependent on the cofactor NADH. Alternatively there are alcohol dehydrogenases which are NADPH-dependent.

Furthermore, the alcohol dehydrogenase can be a thermophilic alcohol dehydrogenase. Thermophilic alcohol dehydrogenase can, for example, be obtained from a host cell which can normally grow well at temperatures above 45° C. Thermophilic alcohol dehydrogenases can be more stable and probably more active than alcohol dehydrogenases obtained from mesophilic host cells, which normally grow at temperatures below 45° C. One possible example for such a thermophilic alcohol dehydrogenase is the alcohol dehydrogenase AdhE obtained from the thermophilic cyanobacterium *Thermosynechococcus* sp. or from *E. coli*.

One possible substrate for alcohol dehydrogenase can be acetyl-CoA, which for example can be directly converted to ethanol by the above-mentioned alcohol dehydrogenase AdhE from *Thermosynechococcus* or *E. coli*. Overexpressing such an alcohol dehydrogenase in a genetically modified host cell has the advantage that only one enzyme has to be overexpressed in order to enhance the level of ethanol production. In the case that the level of biosynthesis of acetyl-CoA of the host cell is increased due to overexpression of acetyl-coenzyme A forming enzymes and due to the reduction of enzymatic activity of acetyl-CoA converting enzymes, a high level of ethanol formation can result.

In addition the enzymatic activity or affinity of AdhE can be increased by introducing mutations, in particular point mutations into the protein via site directed or random mutagenesis. The AdhE is an iron-dependent, bifunctional enzyme containing a CoA-depending aldehyde dehydrogenase and an alcohol dehydrogenase activity. One characteristic of iron-dependent alcohol dehydrogenases (AdhII) is the sensitivity to oxygen. In the case of the AdhE from *E. coli* a mutant was described that shows in contrast to the wildtype also Adh activity under aerobic conditions. The site of the mutation was determined in the coding region at the codon position 568. The G to A nucleotide transition in this codon results in an amino acid exchange from glutamate to lysine (E568K). The E568K derivate of the *E. coli* AdhE is active both aerobically and anaerobically. This mutation is therefore a solution for the use of this oxygen-sensitive enzyme in an oxygen-producing photosynthetic host cell. [Holland-Staley et al., Aerobic activity of *Escherichia coli* alcohol dehydrogenase is determined by a single amino acid, J. Bacteriol. 2000 November; 182(21):6049-54].

In a further embodiment of the invention, a genetically modified host cell can be provided, which further comprises:
pyruvate decarboxylase converting pyruvate to acetaldehyde, wherein
the alcohol dehydrogenase converts the acetaldehyde to ethanol.

In this case, the substrate for the alcohol dehydrogenase is provided by a further overexpressed enzyme, for example pyruvate decarboxylase, which is introduced into the host cell via a further second genetic modification. Due to the fact that the level of biosynthesis of pyruvate of the host cell is increased due to the above-mentioned modifications of the pyruvate forming and converting enzymatic activities by way of the first genetic modification, more acetaldehyde is formed via the enzymatic activity of pyruvate decarboxylase. Therefore there is an increased synthesis of acetaldehyde, which is then further converted by alcohol dehydrogenase to ethanol resulting in a higher intracellular or extracellular ethanol level in the host cell. The alcohol dehydrogenase, as well as the pyruvate decarboxylase can be obtained from alcohol-fermenting organisms such as *Zymomonas mobilis, Zymobacter palmae* or the yeast *Saccharomyces cerevisiae*.

In another embodiment of the invention the genetically modified host cell comprises two second genetic modifications, one comprising alcohol dehydrogenases Adh converting acetaldehyde into ethanol and another second genetic modification comprising a CoA-dependent acetaldehyde dehydrogenase converting acetyl-CoA into acetaldehyde. One example of such an acetylating CoA-dependent acetaldehyde dehydrogenase is mhpF from *E. coli*.

In yet a further embodiment of the invention the genetically modified host cell harbors a pyruvate decarboxylase enzyme as the only second genetic modification. Such a single second genetic modification is particularly advantageous in genetically modified host cells, which already have an endogenous alcohol dehydrogenase enzyme. The inventors surprisingly found that the activity of such an endogenous alcohol dehydrogenase enzyme can be high enough in order to convert all or almost all of the acetaldehyde formed by the overexpressed pyruvate decarboxylase enzyme into ethanol.

For example all cyanobacterial host cells harbor at least one endogenous alcohol dehydrogenase enzyme. A preferred example is the cyanobacterium *Synechocystis* in particular *Synechocystis* PCC6803 or nitrogen fixing cyanobacteria such as *Nostoc/Anabaena* spec. PCC7120 and *Anabaena variabilis* ATCC 29413.

The alcohol dehydrogenase can be a zinc-dependent dehydrogenase. In comparison to iron-dependent dehydrogenases, a zinc-dependent dehydrogenase is less oxygen-sensitive and therefore can exhibit a higher enzymatic activity in a photoautotrophic host cell compared to an iron-dependent alcohol dehydrogenase. For example, the alcohol dehydrogenase AdhI obtained from *Zymomonas mobilis* is a zinc-dependent alcohol dehydrogenase, which can convert acetaldehyde to ethanol by using NADH as a reductant. Alternatively a zinc-dependent alcohol dehydrogenase can be obtained from the cyanobacterium *Synechocystis*, which also depends on the cofactor NADH.

Alternatively or additionally the alcohol dehydrogenase can comprise AdhII for example from *Zymomonas mobilis*, which is a $Fe^{2+}$ dependent alcohol dehydrogenase converting acetaldehyde into ethanol.

In one embodiment, the photoautotrophic ethanol producing host cell comprises at least three second genetic modifications, wherein the at least three overexpressed enzymes for ethanol production have at least three different substrate specificities.

In one embodiment thereof, the three substrate specificities are for the substrates pyruvate, acetaldehyde and acetyl-CoA. For example the three different overexpressed enzymes for ethanol formation can be AdhE converting acetyl-CoA to ethanol, Pdc converting pyruvate to acetaldehyde and AdhI or AdhII converting the acetaldehyde to ethanol. In another embodiment the three different overexpressed enzymes for ethanol formation can be a CoA-dependent acetaldehyde dehydrogenase converting acetyl-CoA to acetaldehyde and Pdc converting pyruvate to acetaldehyde and AdhI or AdhII converting the acetaldehyde to ethanol.

In a further embodiment thereof, the three substrate specificities are for the substrates pyruvate, acetaldehyde and acetylphosphate. In this case the three different overexpressed enzymes for ethanol formation can be acetaldehyde dehydrogenase converting acetylphosphate to acetaldehyde, Pdc converting pyruvate to acetaldehyde and AdhI or AdhII converting the acetaldehyde to ethanol.

In another embodiment, the photoautrophic ethanol producing host cell comprises at least four second genetic modifications, wherein the at least four overexpressed enzymes for ethanol production have at least four different substrate specificities. In one embodiment thereof, the four substrate specificities are for the substrates pyruvate, acetaldehyde and acetyl-CoA and acetylphosphate.

A further embodiment of the invention provides a genetically modified host cell further comprising:
a host cell genome, wherein
a gene encoding the at least overexpressed enzyme for the formation of ethanol is integrated into the host cell genome. The host cell genome can be arranged in at least one chromosome containing coding as well as non-coding sequences. The coding sequences of the genome encode all the proteins and nucleic acids present in a wild type host cell. The gene encoding the at least one overexpressed enzyme for the formation of ethanol can be integrated into the host cell genome, for example via homologous recombination. Integration of the gene coding for the at least one overexpressed enzyme for ethanol formation into the host cell genome can be advantageous for host cells, which exhibit a natural competence for homologous recombination, for example the cyanobacterium *Synechocystis* sp.

Yet another embodiment of the invention provides a genetically modified host cell further comprising:
at least one host gene encoding the enzyme converting pyruvate or acetyl-CoA or acetaldehyde or forming reserve compounds,
wherein a heterologous or endogenous gene encoding the at least one overexpressed enzyme for the formation of ethanol is integrated into that host gene thereby disrupting the host gene.

Such a genetically modified host cell can be produced in just one genetic engineering step, by simply inserting the heterologous or endogenous gene, encoding the at least one overexpressed enzyme for ethanol formation into the host genome into a gene encoding an enzyme converting pyruvate or Acetyl-CoA or forming reserve compounds. Such a procedure knocks out the gene for the enzyme with the undesired activity and at the same time provides a genetic modification introducing an ethanol producing enzyme into a host cell. These genetically modified host cells are therefore easier to obtain than other genetically modified host cells wherein the reduction of enzymatic activity of the enzymes converting pyruvate, acetyl-CoA or acetaldehyde and the introduction of a gene encoding the overexpressed enzyme for ethanol formation is done in two separate steps.

Furthermore, the gene encoding the heterologously or endogenously expressed enzyme can be under the transcriptional control of a promoter endogenous to the host cell. This have the advantage that no exogenous promoter has to be introduced into the host cell. In the case that an exogenous promoter is introduced into a genetically modified host cell a further heterologous gene encoding a transcription factor which recognizes the heterologous promoter, can be introduced into the host cell as well, which complicates the genetic engineering step. Therefore, the introduction of an endogenous promoter, which is also present in an genetically unmodified wild type host cell, has the advantage that this promoter is easily recognized by the genetically modified host cell without the need to introduce further genetic modifications. For example, an inducible promoter such as isiA, which can be induced under iron starvation and stationary growth phase conditions for the host cells can be introduced into *Synechocystis* PCC 6803 as an endogenous promoter. Further non-limiting examples for suitable promoters will be explained later on.

The gene encoding the heterologously or endogenously expressed enzyme for ethanol formation can also be under the transcriptional control of a heterologous promoter, which is not present in a wild type host cell. For example, heat inducible promoters such as the CI-PL promoter from the bacteriophage lambda can be used to control the transcription of genes.

According to another embodiment of the invention the gene encoding the heterologously or endogenously expressed enzyme for ethanol formation is under the transcriptional control of an inducible promoter.

Such a genetically modified host cell can accumulate large amounts of acetyl-CoA, pyruvate, acetaldehyde or their precursors in the uninduced state due to the abovementioned modifications and can then, after induction of the promoter, produce high amounts of ethanol via the enzymatic action of the enzyme for ethanol formation, which is now induced. Ethanol can be harmful to the cell. Therefore, larger amounts of ethanol can be produced by first accumulating the substrate necessary for ethanol formation without producing ethanol (uninduced state of the host cell) and then after induction directly converting these substrates into large amounts of ethanol. Therefore inducible promoters can be a good genetic tool in order to decouple the accumulation of acetyl-CoA, pyruvate, acetaldehyde or their precursors in host cells from the ethanol production.

Inducible promoters can be induced for example by nutrient starvation of the host cell, by stationary phase growth of the host cell culture or by subjecting the host cell to stressful conditions.

These kind of promoters are useful, because a genetically modified host cell culture can grow and reach a certain density, thereby leading to a nutrient starvation of the host cell and also increasing the stress for the host cell culture in the case that the growth medium is not continuously supplemented with nutrients. In this case a genetically modified cell culture can accumulate for example acetyl-CoA, pyruvate or their precursors in the exponential growth phase in the non-induced state without producing ethanol, and upon having reached the stationary growth phase can convert these metabolic products into ethanol due to induction of the promoters. For example, the inducible promoters can be inducible by nitrogen starvation or by trace element starvation, such as iron or copper. Examples of such kinds of promoters are the ntcA promoter, the nblA promoter as well as the sigB promoter from *Synechocystis*, which are inducible by nitrogen starvation and the isiA promoter which is inducible upon iron starvation. The petJ promoter is inducible by copper starvation. In addition, the isiA or sigB promoter can be also inducible by stationary growth phase of the host cell culture. The sigB promoter can also be induced by subjecting the host cell culture to darkness. Further stressful conditions can be heat shock for induction (sigB promoter or the htpG promoter) and cold shock, which induces for example the crhC promoter. Heat shock can be induced, for example by raising the growth temperature of the host cell culture from 30° C. to 40° C. In contrast to that, a cold shock can be induced by reducing the growth temperature of the cell culture from 30° C. to 20° C. A further example of an inducible promoter is the nirA promoter, which can be induced by nitrate starvation or light.

Further relevant promoters are a promoter of a gene encoding light repressed protein A homolog (lrtA promoter), which can be induced by a transition from light to dark conditions. In addition the promoter of gene of P700 apoprotein subunit Ia (psaA promoter), which can be induced under low white light and orange light and repressed in darkness.

Alternatively the gene encoding the heterologously or endogenously expressed enzyme for ethanol formation can be under the transcriptional control of a constitutive promoter, which allows a certain level of transcription and therefore enzymatic activity of the overexpressed enzyme for ethanol formation during the whole period of cultivation even without induction. This can be advantageous in the case that the metabolic intermediate converted by the overexpressed enzyme for ethanol formation is harmful to the cell, as for example acetaldehyde. In this case the acetaldehyde is continuously converted to ethanol and is not present in the genetically modified host cell in high amounts.

A further embodiment of the invention provides a genetically modified photoautotrophic, ethanol producing host cell comprising:
- at least one first genetic modification changing the enzymatic activity or affinity of an endogenous host enzyme of the host cell,
- the first genetic modification resulting in a level of biosynthesis of a first metabolic intermediate for energy production of the host cell, which is enhanced compared to the level of biosynthesis in the respective wild type host cell,
- at least one second genetic modification different from the first genetic modification comprising an overexpressed first enzyme for the formation of ethanol from the first metabolic intermediate.

The first metabolic intermediate can be any metabolic intermediate involved in the energy production of the host cell or in the formation of reserve compounds in the claim, for example starch, glycogen or polyhydroxybutyrate. This first metabolic intermediate can, for example, be formed during the Calvin-cycle, the light-independent part of photosynthesis, the glycolysis, the fermentation pathway, the amino acid metabolism or the citric acid cycle. Some non-limiting examples for the first metabolic intermediate are pyruvate, acetyl-CoA or acetaldehyde.

Due to the fact that the level of biosynthesis of this first metabolic intermediate is enhanced compared to the wild type host cell and due to the fact that this first intermediate is used by the first enzyme for ethanol formation in order to produce ethanol, these genetically modified photoautotrophic host cells can produce a high amount of ethanol.

For example, the first metabolic intermediate can comprise acetyl-CoA and the at least one overexpressed first enzyme can comprise the alcohol dehydrogenase AdhE directly converting acetyl-CoA to ethanol. In this case only one overexpressed enzyme is necessary in order to produce a increased amount of ethanol.

It is also possible that the genetically modified host cell further comprises:
- at least one overexpressed second enzyme, converting the first metabolic intermediate into a second metabolic intermediate, wherein
- the at least one overexpressed first enzyme converts the second metabolic intermediate into ethanol.

In this case, the first enzyme uses another metabolic intermediate provided by a second overexpressed enzyme in order to produce ethanol.

For example, the first metabolic intermediate can comprise pyruvate and the second metabolic intermediate can comprise acetaldehyde and the at least one overexpressed second enzyme can comprise pyruvate decarboxylase converting pyruvate into acetaldehyde and the at least one overexpressed first enzyme can comprise alcohol dehydrogenase Adh, converting acetaldehyde into ethanol.

Some host cells, for example, cyanobacteria, normally do not have a pyruvate decarboxylase. Therefore, the transformation of cyanobacteria with a pyruvate decarboxylase and in addition the overexpression of an alcohol dehydrogenase which already can be present in the wild type cyanobacterial cell can result in increased amounts of ethanol.

Another embodiment of the invention provides a genetically modified host cell, which further comprises:
- at least one host enzyme for conversion of the first metabolic intermediate, wherein
- the activity of said host enzyme is reduced compared to the respective wild type host cell by genetic engineering.

As mentioned above, the activity of host enzymes can be reduced, for example by site directed mutagenesis or random mutagenesis of the gene encoding the host enzyme, which results in a protein with a lower activity. Alternatively or additionally the promoter sequences controlling the transcriptional activity of the genes encoding this host enzyme also can be genetically modified in order to reduce the transcriptional activity. Another example is to disrupt the gene encoding the host enzyme for conversion of the first metabolic intermediate with a heterologous nucleic acid sequence. The host enzyme, for example, can be any enzyme of the Calvin-cycle, the glycolysis pathway, the intermediate steps of metabolism, the amino acid metabolism or the citric acid cycle converting the first metabolic intermediate, which for example, can be pyruvate. In this case the host enzymes whose activity is reduced can, for example, be selected from a group consisting of pyruvate water dikinase, pyruvate dehydrogenase, phosphotransacetylase, acetate kinase, lactate dehydrogenase or alanine dehydrogenase.

In addition or alternatively the genetically modified host cell can further comprise:
- at least one host enzyme for forming the first metabolic intermediate, wherein
- the activity of said host enzyme is enhanced compared to the respective wild type host cell by genetic engineering.

In the case that the first metabolic intermediate is, for example, pyruvate the at least one host enzyme can be selected from the above-mentioned enzymes, which are: malate dehydrogenase, malic enzyme, pyruvate kinase, enolase, and phosphoglycerate mutase.

In the case that the first metabolic intermediate is, for example, acetyl-CoA the at least one host enzyme in addition to the above latter mentioned enzymes also can be selected from pyruvate dehydrogenase.

There are several methods for genetic engineering, which are useful in enhancing the enzymatic activity or affinity of an enzyme, for example introducing point mutations (site directed mutagenesis or random mutagenesis) into a gene encoding the host enzyme for forming the first metabolic intermediate in order to enhance the enzymatic activity of this enzyme. Furthermore, additional gene copies encoding the host enzyme can be introduced into the host cell therefore enhancing the amount of protein in the host cell. Alternatively or in addition, the promoter region controlling the transcriptional activity of the gene encoding the enzyme can be mutated in order to enhance the transcriptional activity of the gene. Overexpression can also be achieved by introducing a heterologous enzyme into the host cell, which exhibits the same enzymatic activity as the host cell enzyme, which should be overexpressed. For example if PGA mutase should be overexpressed in the cyanobacterium *Synechocystis* a plasmid comprising a heterologous gene encoding PGA mutase from *Zymomonas mobilis* can be introduced into the host cell. Another non-limiting example is the overexpression of pyruvate kinase from *E. coli* in *Synechocystis*, thereby raising the enzymatic activity of the endogenous host cell enzyme pyruvate kinase in *Synechocystis*. In addition homologous genes from other cyanobacterial sources such as *Synechocystis* can be overexpressed in photoautotrophic host cells. Non-limiting examples for overexpression are: PGA mutase genes slr1124, slr1945, sll0395 and slr1748 and the enolase homolog slr0752 from *Synechocystis* PCC 6803.

Yet another embodiment of the invention provides a construct for the transformation of a photoautotrophic host cell by disrupting a host gene sequence encoding a host enzyme in order to increase the biosynthetic level of pyruvate, acetyl-CoA, acetaldehyde or precursors thereof in the host cell comprising:
- a heterologous nucleic acid sequence comprising a promoter and a biocide resistance conferring gene under the transcriptional control of the promoter, wherein
- the heterologous nucleic sequence is flanked at its 5' and 3' end by nucleic acid sequences that bind to the host gene sequence encoding a host enzyme.

Such a construct can, for example, be used in order to knock out unwanted host enzymes which convert an important first metabolic intermediate into another metabolic compound. Due to the biocide resistance conferring gene, genetically modified host cells resulting from the transformation with such a construct can be selected by exposing the transformed host cells to a growth medium containing the biocide. The 5' and 3' flanking nucleic acid sequences are preferably homologous to the nucleic acid sequence of the host gene encoding the host enzyme for conversion of the first metabolic intermediate.

The term "binds to" is used herein to refer to the annealing or hydrogen bonding of one nucleic acid (polynucleotide) to another nucleic acid (polynucleotide) In a particularly preferred embodiment, binding occurs in vivo or within a cell between a heterologous nucleic acid sequence and a genomic or chromosomal nucleic acid sequence. This is particularly useful in promoting homologous recombination. In other circumstances, the term may refer to hybridization in a non-natural environment, particularly under stringent conditions in the laboratory. "Hybridization stringency" is a term well understood to those of ordinary skill in the art. A particular, non-limiting example of stringent (e.g. high stringency) hybridization conditions are hybridization in 6× sodium chloride/sodium citrate (SSC) buffer at about 45 degrees Celsius, followed by one or more washes in 0.2× SSC, 0.1% SDS at 50-65 degrees Celsius. Hybridization stringency may also be varied and used to identify and isolate nucleic acid sequences having different percent identity with the probe sequence.

In various embodiments of the invention, 5' and 3' flanking sequences of the invention are selected from a host cell enzyme gene sequence described herein. Moreover, in the Examples section provided herewith, the construction of various nucleic acid constructs is provided. As one of ordinary skill in the art would recognize, the invention is not limited to only those sequences disclosed herein because these examples provide ample teaching to select similar 5' and 3' sequences from host cell enzyme identified in sequence databases.

These sequences can, for example, have an identity at least 80%, 85%, 90%, 95% and 100% to the corresponding nucleic acid sequences of the host cell enzyme gene.

Another embodiment of the invention provides a construct for the transformation of a photoautotrophic host cell by disrupting a host cell gene sequence encoding a host cell enzyme in order to increase the biosynthetic level of pyruvate, acetyl-CoA, acetaldehyde or precursors thereof in the host cell, comprising:
  a heterologous nucleic acid sequence comprising a promoter and a first gene encoding at least one overexpressed first enzyme for the formation of ethanol from the first metabolic intermediate under the transcriptional control of the promoter, wherein
  the heterologous nucleic acid sequence is flanked at its 5' and 3' end by nucleic acid sequences that bind to said host gene.

Such a construct can, for example, be used in order to knock out a gene encoding a host enzyme for conversion of a first metabolic intermediate, which can be pyruvate, acetyl-CoA, acetaldehyde or precursors thereof and at the same time, introduce via genetic engineering a gene encoding a first enzyme for the formation of ethanol. Such a construct can therefore be used in order to enhance the level of a first metabolic intermediate in a genetically modified host cell and at the same time use this first metabolic intermediate as a substrate for ethanol production.

The 5' and 3' flanking nucleic acid sequences are preferably highly identical, more preferably completely identical, to the corresponding parts of the host cell gene encoding the host cell enzyme. Such a construct is integrated into the host genome of a host cell via homologous recombination.

Homologous recombination involves the alignment of similar sequences, preferably homologous nucleic acid sequences located in different nucleic acid strands, for example a recombinant integrative plasmid and the chromosome of a host cell. After a crossover between the aligned nucleic acid strands, the nucleic acid strands are broken and repaired in order to produce an exchange of nucleic acid material between the chromosome and the recombinant integrative plasmid. The process of homologous recombination naturally occurs in many host cells, for example cyanobacteria such as *Synechocystis* and can be utilized as a molecular biology technique for genetically engineering organisms and introducing genetic changes into the organisms. The 5' and 3' flanking nucleic acid sequences each can have a length of a few hundred base pairs, preferably at least around 500 base pairs or more, in order to enable homologous recombination. The length can be up to 1.5 kilobases or even 2 kilobases.

In various embodiments of the invention, the heterologous nucleic acid sequence further comprises a second gene encoding at least one overexpressed second enzyme converting the first metabolic intermediate into a second metabolic intermediate, wherein the at least one overexpressed first enzyme converts the second metabolic intermediate into ethanol.

In such a case the first metabolic intermediate can comprise pyruvate and the second metabolic intermediate can comprise acetaldehyde and the second gene can encode pyruvate decarboxylase converting pyruvate into acetaldehyde, and the first gene can encode alcohol dehydrogenase converting acetaldehyde into ethanol.

Alternatively, the first metabolic intermediate can comprise pyruvate and the second metabolic intermediate can, for example, comprise acetyl-CoA. In this case the first gene can encode pyruvate dehydrogenase, pyruvate formate lyase or pyruvate-ferredoxin-oxidoreductase which can convert pyruvate to acetyl-CoA. The second gene then can encode a coenzyme A dependent aldehyde dehydrogenase which can convert acetyl-CoA to acetaldehyde. In this case a third gene can be introduced into the construct which encodes alcohol dehydrogenase which can convert acetaldehyde to ethanol. Therefore, constructs according to certain embodiments of the inventions can comprise more than two or even more than three genes encoding more than two or three enzymes involved in ethanol formation.

Alternatively the first metabolic intermediate can comprise acetyl-CoA and the first gene can be alcohol dehydrogenase AdhE directly converting acetyl-CoA into ethanol. In this case one enzyme can be sufficient to trigger ethanol formation in a genetically modified host cell.

Furthermore a co-expression of the enzymes AdhE, Adh and Pdc in parallel is also able to convert acetyl-CoA into ethanol (e.g. in combination with a blocked or reduced acetate and lactate pathway) and to convert pyruvate into ethanol in parallel. This could avoid that pathways are shifted to acetyl-CoA in case of Pdc and Adh expression or to pyruvate in case of AdhE expression.

A further embodiment of the invention is directed to a genetically modified photoautotrophic, ethanol producing host cell comprising:
  a first genetic modification comprising at least one genetic modification of at least one host cell enzyme that is not pyruvate decarboxylase or alcohol dehydrogenase, wherein the first genetic modification results in an enhanced level of biosynthesis of acetaldehyde, pyruvate, acetyl-CoA or precursors thereof compared to the respective wild type host cell, and
  a second genetic modification comprising at least one overexpressed enzyme for the formation of ethanol.

The subject matter of a further embodiment of the invention is a construct for the transformation of a host cell by disrupting a host gene encoding a host enzyme for conversion of a first metabolic intermediate for energy production of the host cell or forming reserve compounds, comprising:
  a heterologous nucleic acid sequence comprising an inducible promoter and a gene encoding the host enzyme for conversion of the first metabolic intermediate for energy production of the host cell or forming the reserve compounds under the transcriptional control of the inducible promoter, wherein the heterologous nucleic acid sequence is flanked at its 5' and 3' end by nucleic acid sequences which are able to bind to at least parts of said host gene.

As mentioned above, the 5' and 3' flanking nucleic acid sequences are necessary in order to ensure the insertion of this construct into the host cell genome, for example via homologous recombination. Such a construct can be useful in the case that the host enzyme for conversion of the first metabolic intermediate or for forming reserve compounds is a very crucial enzyme for the metabolism of the host cell so that it might not be possible to completely knock out this enzyme without killing the host cells during this process. Such a construct can be used in order to replace the uncontrollable wild type host gene by a copy of the gene which is under the control of an inducible promoter. Such a construct enables the controlling of the enzymatic activity of an important metabolic enzyme of the host cell without completely knocking out the enzymatic activity of this enzyme.

The host gene, for example, can encode glycogen synthase. Due to the fact that two copies are sometimes present in the genome of a host cell, two different constructs have to be designed in order to knock out both glycogen synthase coding genes.

The above-mentioned constructs can be part of a recombinant plasmid which further can comprise other genes, which for example encode biocide resistance conferring genes.

Subject matter of a further embodiment of the invention is a method for producing genetically modified host cells comprising the method steps:
A) Providing a wild type host cell showing a wild type level of biosynthesis of a first metabolic intermediate for energy production of the host cell,
B) enhancing the level of biosynthesis of the first metabolic intermediate in comparison to the wild type level by genetic engineering,
C) introducing a first heterologous or endogenous gene into the host cell, the first gene encoding at least one overexpressed first enzyme for the formation of ethanol from the first metabolic intermediate.

Such a method enhances in method step B) the level of biosynthesis of a useful first metabolic intermediate and then introduces in method step C) a gene into the host cell encoding a protein which can use the first metabolic intermediate for ethanol synthesis.

Alternatively first method step C) then method step B) can be carried out. Such a method, can be healthier for the cell due to the fact that the metabolic intermediate, which can be harmful would not accumulate in the cells, e.g. in case of acetaldehyde.

According to a further embodiment of the method of the invention in step C) a second heterologous or endogenous gene can be introduced into the host cell, the second heterologous or endogenous gene encoding at least one overexpressed second enzyme converting the first metabolic intermediate into a second metabolic intermediate, wherein the at least overexpressed first enzyme converts the second metabolic intermediate into ethanol.

As mentioned above, the first metabolic intermediate can comprise pyruvate and the second metabolic intermediate can comprise acetaldehyde so that the second gene can encode pyruvate decarboxylase converting pyruvate into acetaldehyde and the first gene can encode alcohol dehydrogenase converting acetaldehyde into ethanol.

Alternatively the first metabolic intermediate can comprise acetyl-CoA and the first gene can encode the alcohol dehydrogenase AdhE, which directly converts acetyl-CoA into ethanol.

In a further modification of the method of the invention in step A) a wild type host cell can be provided which further comprises a first host gene encoding at least one first host enzyme for conversion of the first metabolic intermediate or for forming reserve compounds, the first host gene is under the transcriptional control of a first host promoter.

Then in step B) the activity of the at least one first host enzyme can be reduced by genetic engineering.

In particular, in step B) the activity of the at least one host enzyme can be reduced by mutating either the first host promoter or the first host gene or by disrupting the first host gene by introducing a heterologous nucleic acid sequence into the first host gene.

According to a further embodiment of the method of the invention, in step A) a wild type host cell can be provided which further comprises a second host gene encoding at least one second host enzyme for forming the first metabolic intermediates or precursors thereof, the second host gene is under the transcriptional control of a second host promoter, and then in step B) the activity of the at least one second host enzyme is enhanced by genetic engineering. The activity of the at least one second host gene can be enhanced by mutating either the second host promoter or the second host gene or by overexpressing the second host enzyme.

A further embodiment of the invention provides a genetically modified photoautotrophic ethanol-producing host cell comprising:
  a heterologous or endogenous nucleic acid sequence comprising a promoter and a gene encoding at least one overexpressed enzyme for the formation of ethanol under the transcriptional control of the promoter, wherein
  the promoter can be induced by nutrient starvation, oxidative stress, light, darkness, heat shock, cold shock, salt stress, by a change of the nutrient source, by an increase in the concentration of one nutrient or stationary growth of the host cell.

Figure 1A:
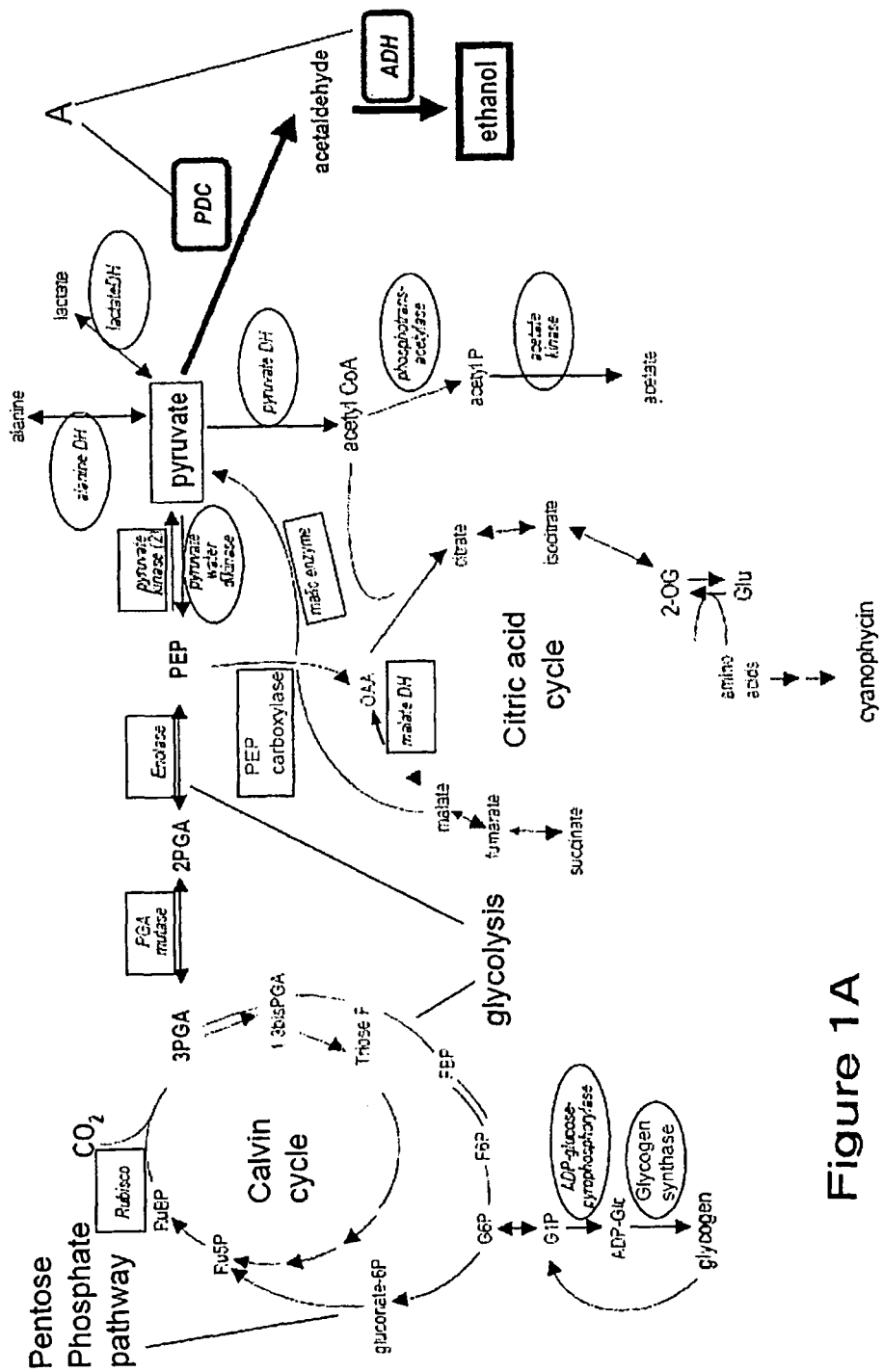
FIG. 1, comprising 1A, 1B, 1C, 1D, 1E, and 1F illustrates some relevant metabolic pathways
Figure 1B:
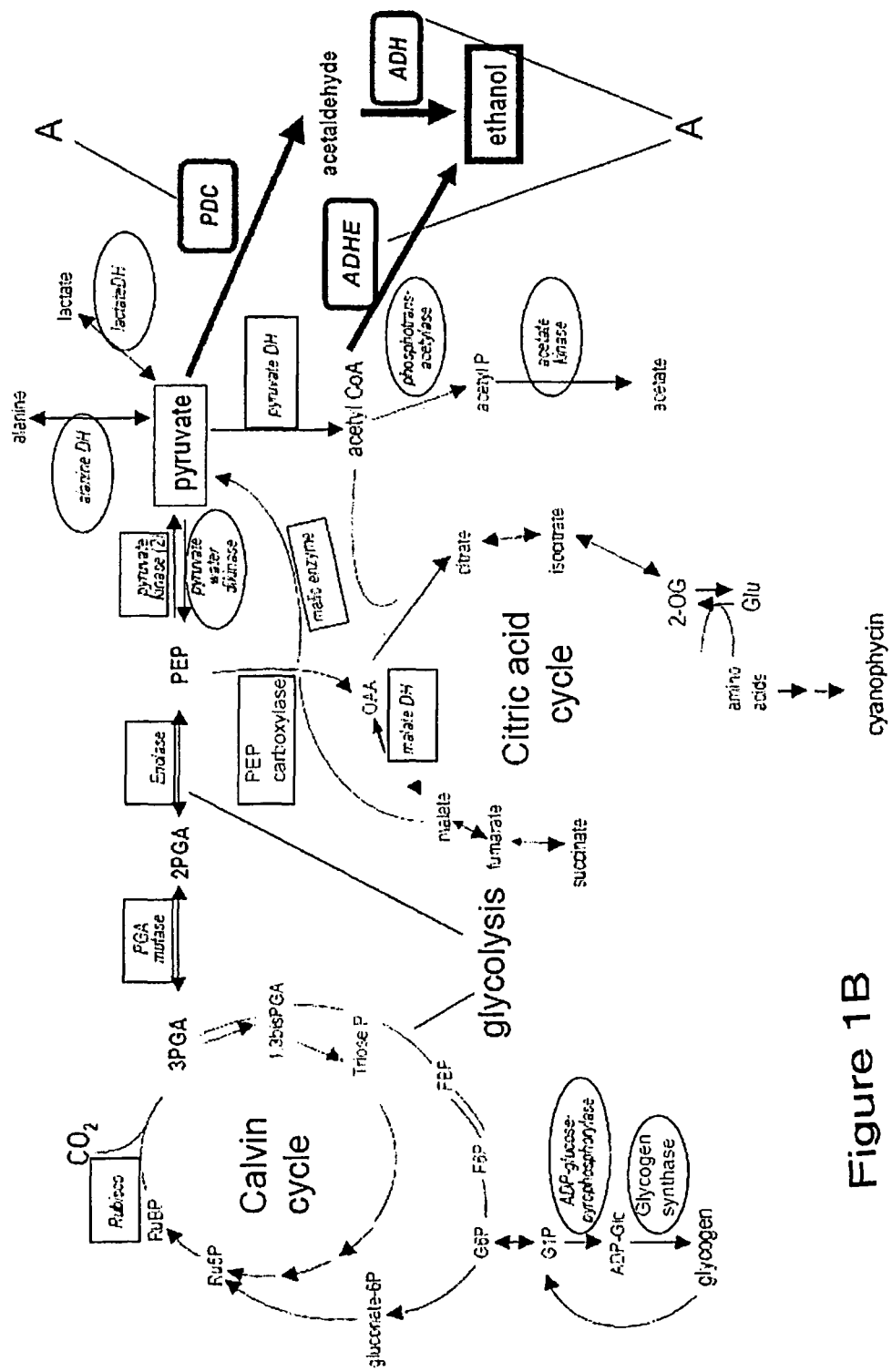
Figure 1C:
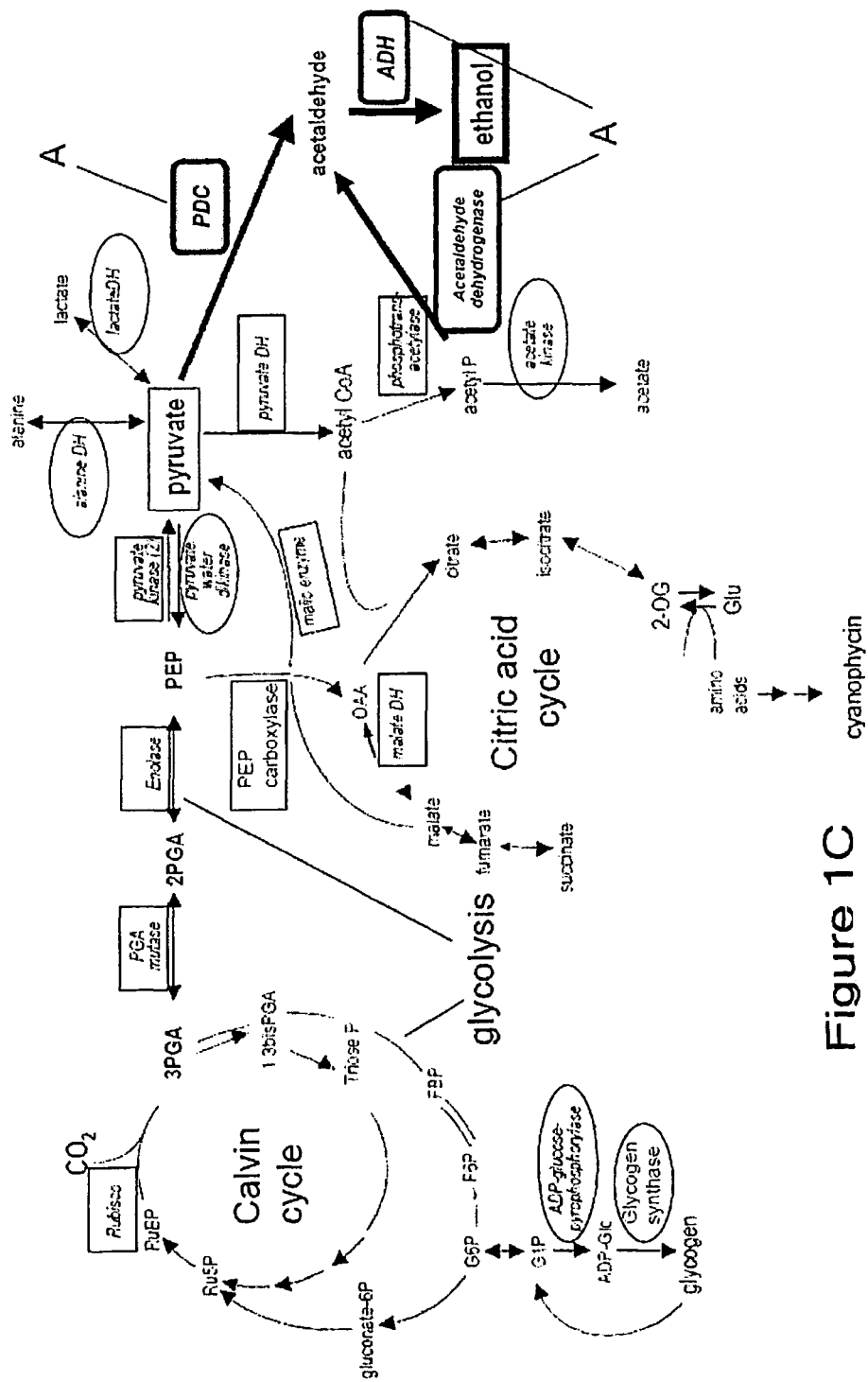

In the following the inventions will be explained in more detail with reference to figures and certain embodiments:

FIGS. 1A to C depict general schemes of metabolic pathways in Cyanobacteria with marked enzymes for overexpression and down-regulation or knock-out for the increase of biosynthesis of different metabolic intermediates.

Figure 2:
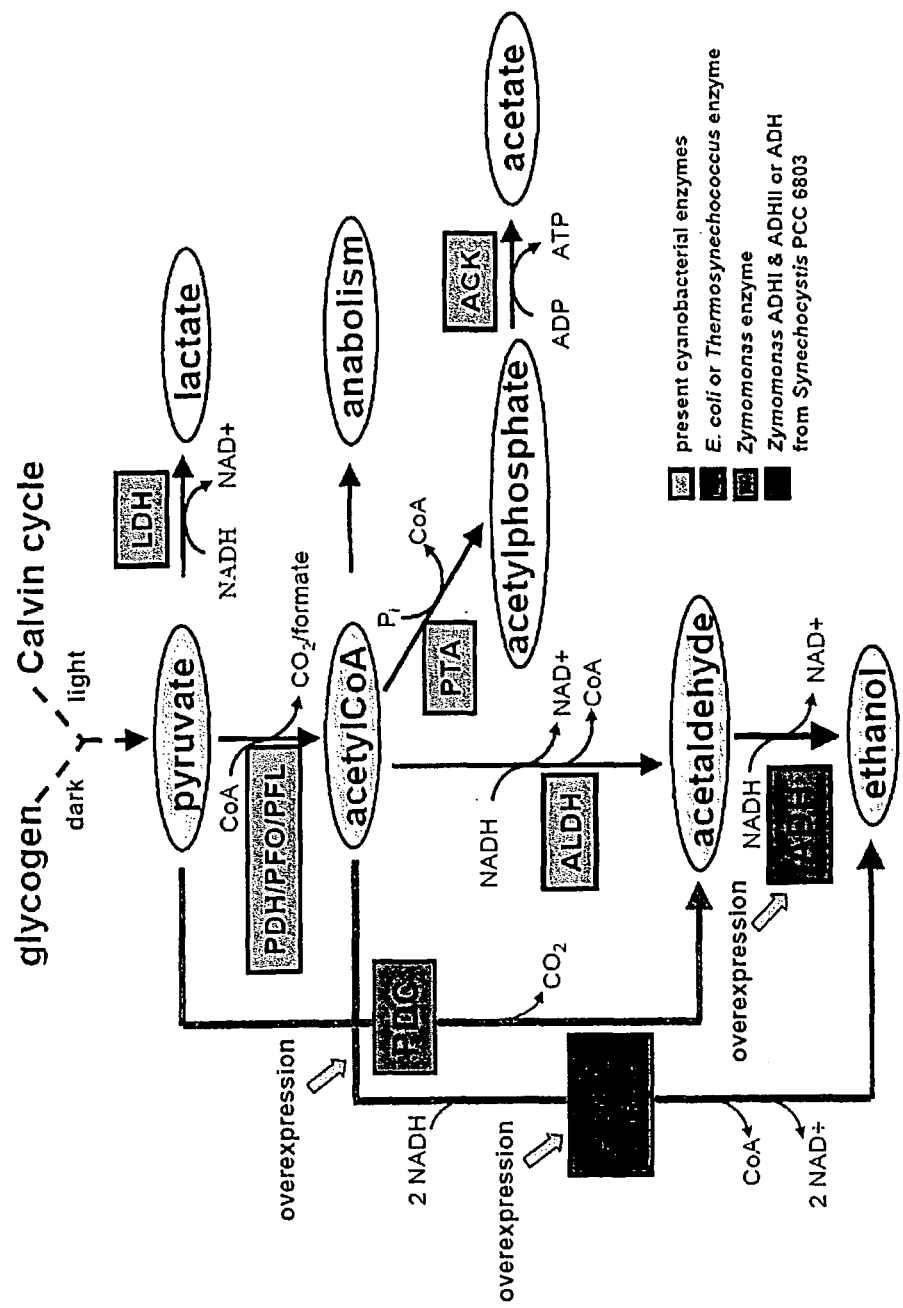
FIG. 2 illustrates possible pathways leading to ethanol production.

FIG. 2 shows a flow chart including some ethanologenic enzymes for ethanol production.

FIG. 1A shows some general metabolic pathways in cyano-bacteria as a non-limiting example. In particular the Calvin cycle as the light independent part of the photosynthesis is shown starting with the carbon dioxide fixation reaction catalyzed by the enzyme RubisCO. Further the glycolysis pathway, the pentose phosphate pathway and the citric acid cycle are shown. The general metabolic pathways depict boxed and circled enzymes, whose activity or affinity can be changed as part of at least one first genetic modification of an endogenous host enzyme of the cyanobacterial host cell. Boxed enzymes either have been overexpressed compared to the respective wild type cyanobacterial cells or are prime candidates for overexpression. Circled enzymes either have been knocked out or down regulated or are prime targets for knock-out or down-regulation. The main reason for the knock-out or overexpression is to enhance the level of pyruvate biosynthesis in the genetically modified cell by knocking-out or reducing the activity or affinity of enzymes consuming pyruvate or its metabolites and to enhance the enzymatic activity of enzymes producing pyruvate or its precursors such as phosphoenolpyruvate (PEP). The cyanobacterial host cell can comprise more than one first genetic modification. For example enzymes enhancing the level of pyruvate biosynthesis such as enolase or malic enzyme can be overexpressed and the activity or affinity of enzymes consuming pyruvate, such as lactate dehydrogenase or alanine dehydrogenase can be reduced or abolished by knock-out of the respective genes in one cyanobacterial host cell.

In addition two second genetic modifications resulting in an overexpression of enzymes for ethanol formation have been introduced into the metabolic cyanobacterial pathways shown in FIG. 1A. These enzymes are indicated by the thickly framed boxes denoted with the reference sign "A". In particular these enzymes are alcohol dehydrogenase (abbreviated as Adh) and pyruvate decarboxylase (abbreviated as Pdc), which also have to be introduced into most cyano-bacteria via genetic engineering.

FIG. 1B shows the same general metabolic pathways in cyano-bacteria as already presented in FIG. 1A for the case that the level of biosynthesis of acetyl-CoA is raised compared to a wildtype cyanobacterial cell. The enzymes, which are part of the first and second genetic modification are marked in the same way as in FIG. 1A. In addition the direct conversion of acetyl-CoA to ethanol catalyzed by the enzyme aldehyde-alcohol dehydrogenase AdhE, which has to be introduced into most cyanobacteria via a second genetic modification is denoted. AdhE is for example an endogenous enzyme in the cyanobacterium *Thermosynechococcus* or an heterologous enzyme from *E. coli*. In this case the expression of AdhE can be enhanced in a second genetic modification in *Thermosynechococcus*, for example by introducing additional gene copies into the cell or by mutating the promoter of the wildtype gene encoding AdhE in order to enhance transcription and translation. In the case of overexpression of AdhE the enzyme pyruvate dehydrogenase can be overexpressed (shown as a boxed enzyme). In addition to overexpression of AdhE it is still possible to overexpress Pdc and Adh simultaneously. Alternatively only AdhE can be overexpressed.

FIG. 1C gives an overview of metabolic enzymes in cyanobacteria, which can be overexpressed (boxed enzymes) or knocked out or downregulated (circled enzymes) in the case that the level of biosynthesis of acetaldehyde is to be increased in the cell. In this case the enzymes phosphotransacetylase and acetaldehyde dehydrogenase are overexpressed in comparison to the situation shown in FIG. 1B. The enzyme acetaldehyde dehydrogenase converting acetylphosphate to acetaldehyde is for example disclosed in the publication Stal (Stal, Moezelaar, "Fermentation in cyanobacteria", FEMS Microbiology Reviews 21, (1997), pages 179-211). The enzymes, which are part of the first and second genetic modification are marked in the same way as in FIGS. 1A and 1B.

Figure 1D:
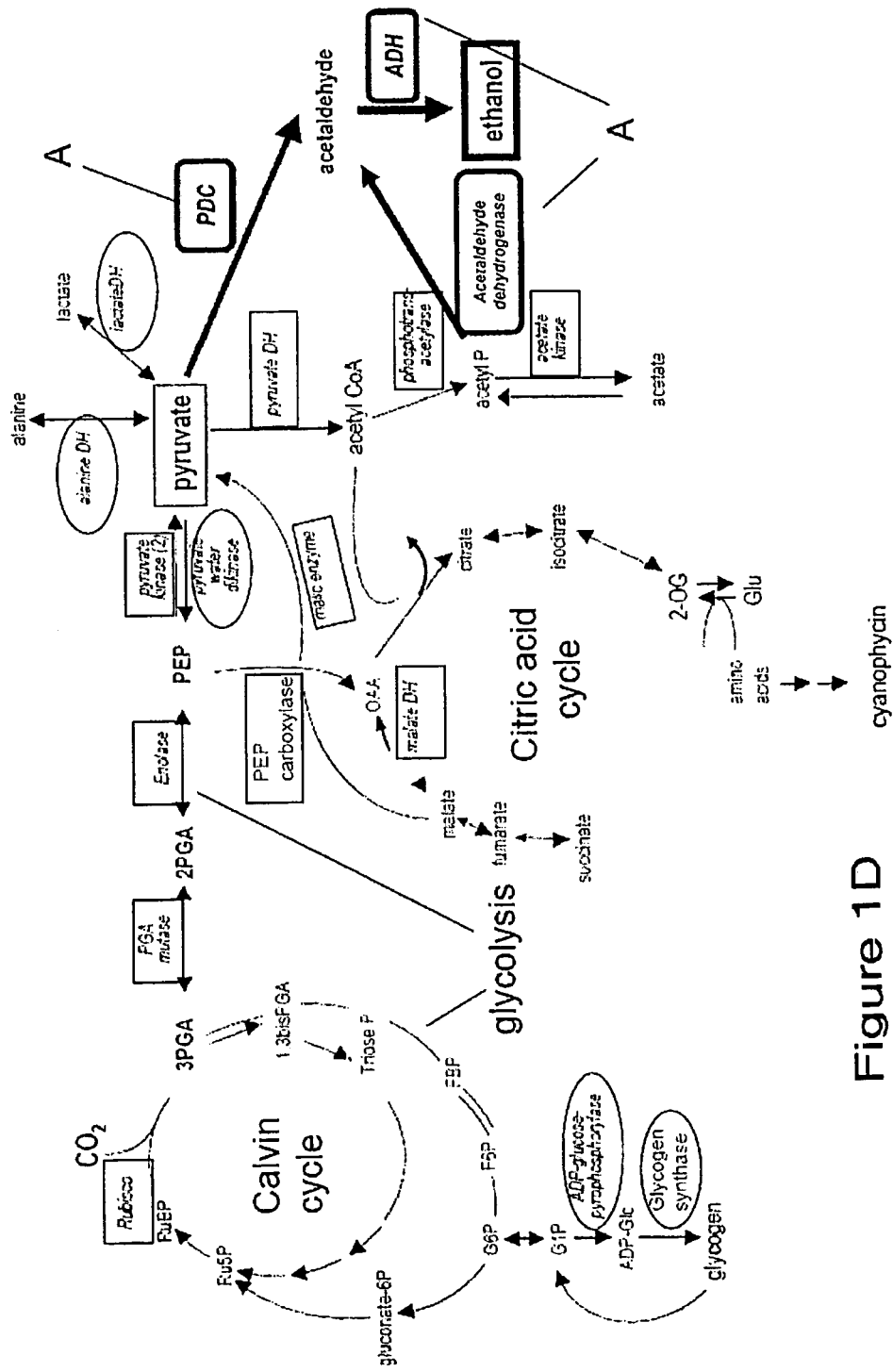

FIG. 1D depicts the exemplary metabolic pathway of other bacteria. In contrast to the metabolic pathways shown in the FIGS. 1A to 1C, the enzyme acetate kinase in addition also catalyzes the reaction in the other direction from acetate to acetylphosphate. In the case that the enzyme acetaldehyde dehydrogenase is overexpressed or its affinity or activity is enhanced in other ways described in this patent application, Overexpression of acetate kinase enzyme can enhance the level of biosynthesis of acetylphosphate, thereby enhancing ethanol formation by Adh. In addition the other ethanol forming enzyme AdhE can also be overexpressed.

Figure 1E:
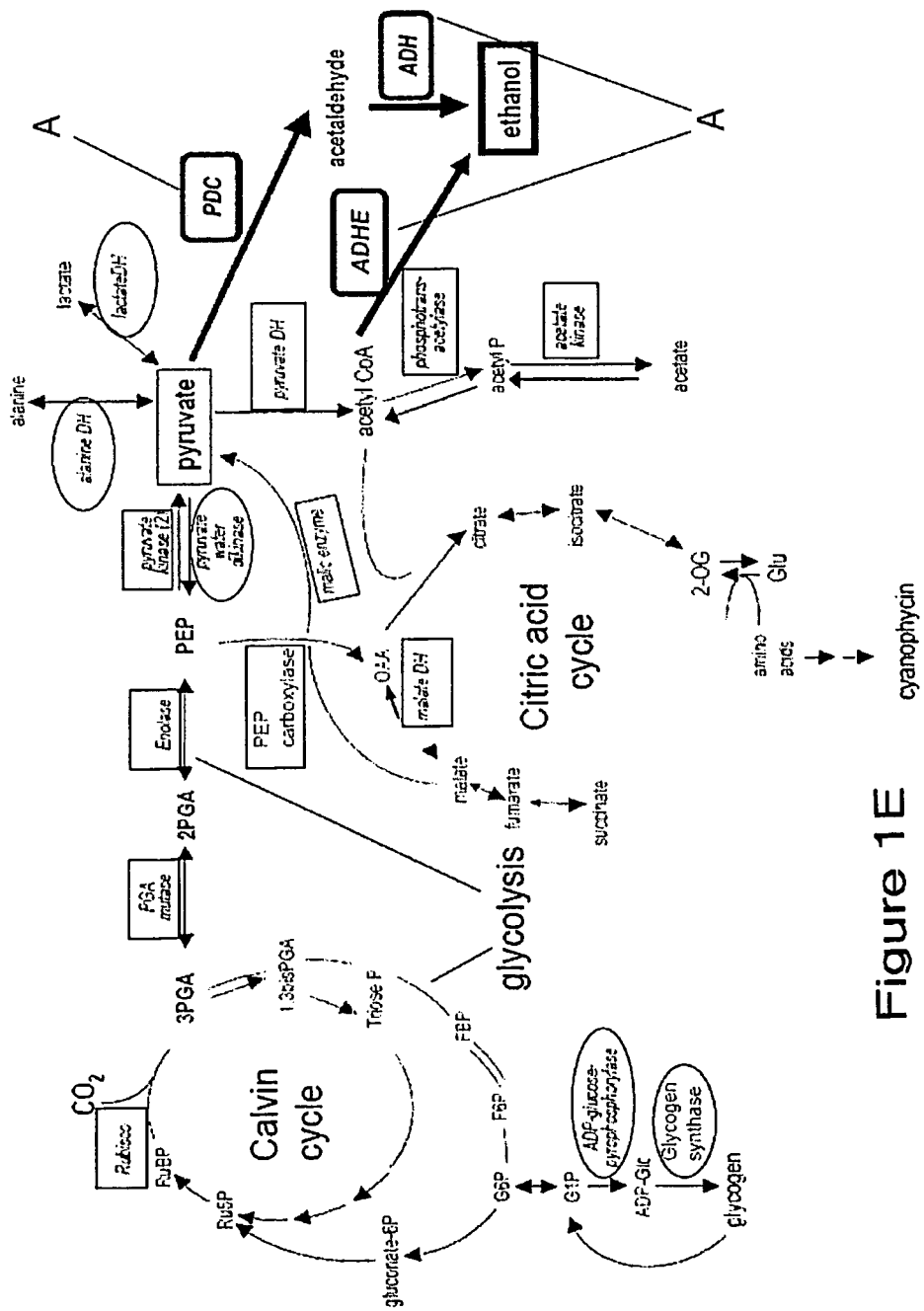

FIG. 1E shows the same metabolic pathway as depicted in FIG. 1D with the exception that in addition to the acetate kinase enzyme the phosphotransacetylase enzyme also catalyzes the reverse reaction from acetylphosphate to acetyl-CoA. In this case phosphotransacetylase can be overexpressed in addition to acetate kinase enzyme in order to enhance the level of biosynthesis of acetyl-CoA in a first genetic modification. The second genetic modification comprises overexpression of AdhE, which converts the acetyl-CoA into ethanol. In addition the second genetic modification also can comprise overexpression of Adh and Pdc.

Figure 1F:
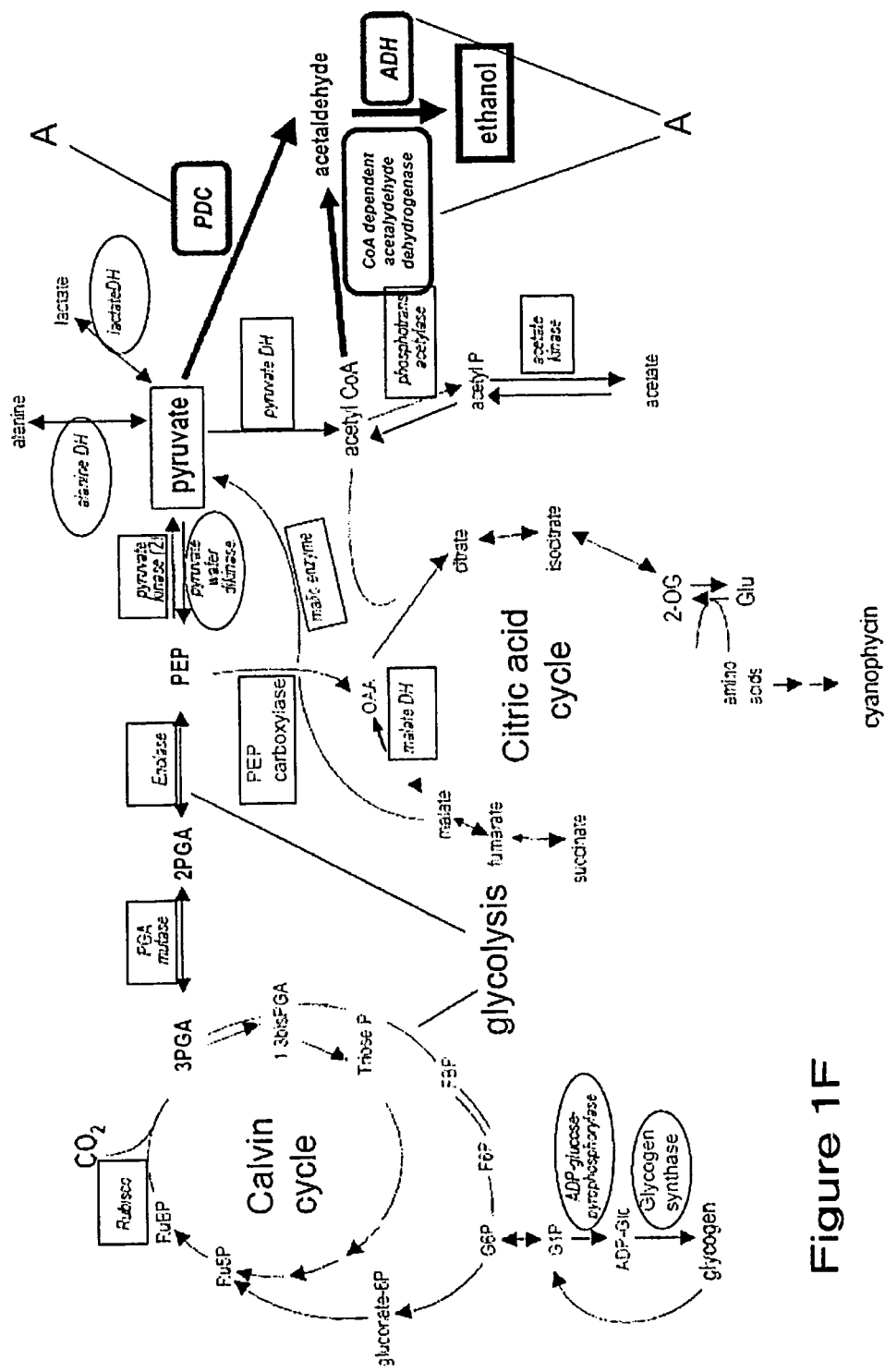

FIG. 1F shows some relevant metabolic pathways of cyanobacteria with different overexpressed enzymes for ethanol formation, which can be introduced into a photoautotrophic cyanobacterial host cell by second genetic modifications. In one aspect of the invention a CoA-dependent acetaldehyde dehydrogenase can be overexpressed in the host cell, which converts acetyl-CoA into acetaldehyde. The acetaldehyde can then further be converted to ethanol by a further enzyme for ethanol formation Adh, which can be AdhI enzyme or AdhII enzyme or a combination of both enzymes.

In addition or alternatively Pdc enzyme can be present in the host cell as a further overexpressed enzyme for ethanol formation introduced via a second genetic modification, which can convert pyruvate into acetaldehyde.

FIG. 2 shows in a more detailed way the last steps of ethanol synthesis in genetically modified cyanobacteria.

Figure 3:
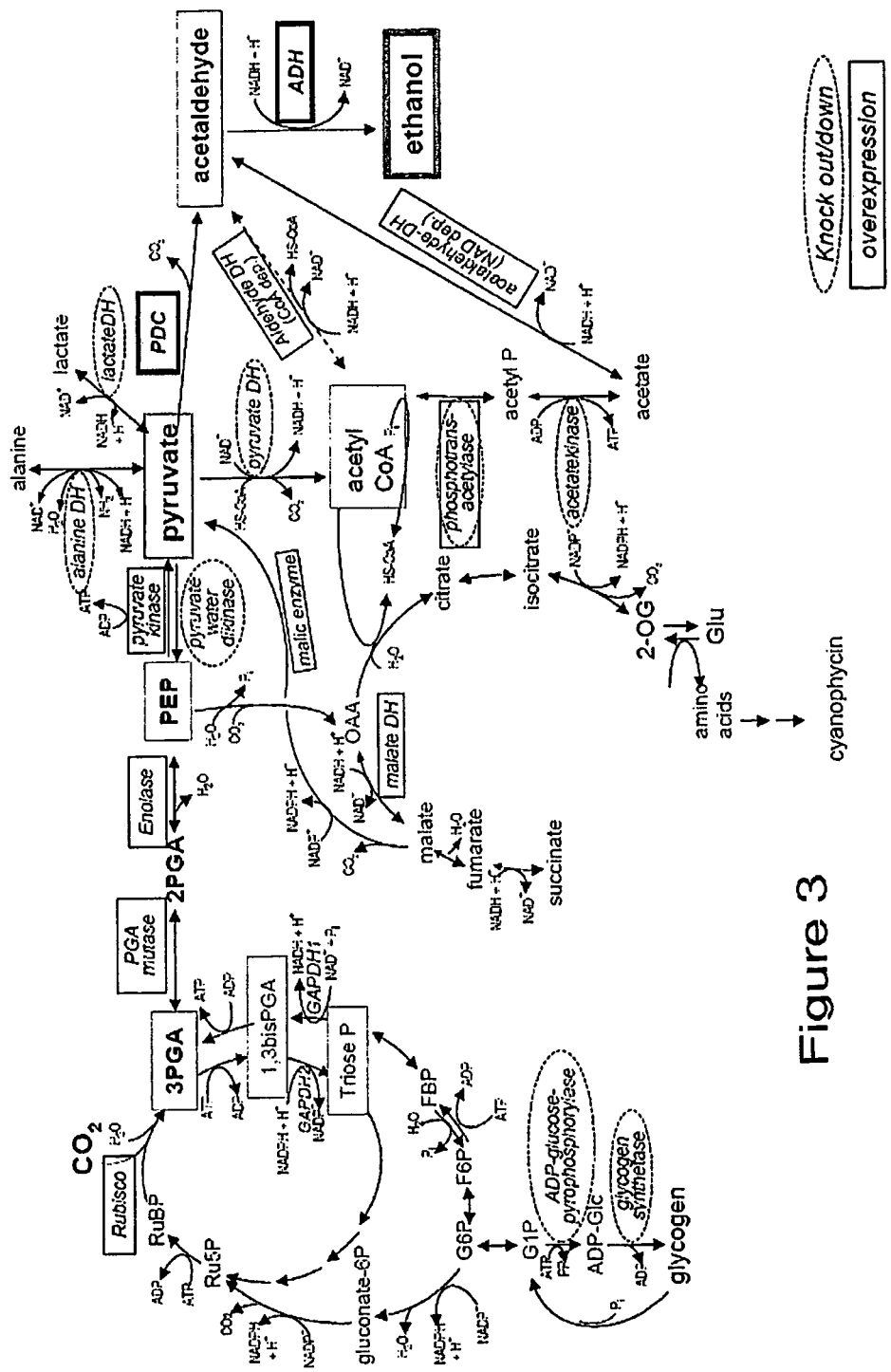
FIG. 3 illustrates possible pathways leading to ethanol production

FIG. 3 depicts a further non-limiting representation of metabolic pathways of a cyanobacterium. In contrast to the FIGS. 1A to 1F a NAD dependent acetaldehyde dehydrogenase is shown, which can convert acetate into acetaldehyde, which then can be converted into ethanol by Adh enzyme.

Working Example of Genetic Knockout

In the following one embodiment of the invention, in particular a genetically modified host cell comprising a host enzyme forming reserve compounds, wherein the gene encoding this enzyme is disrupted by genetic engineering, is explained in more detail with reference to a working example. The host enzyme is glycogen synthase, which is encoded by two genes in the host cell *Synechocystis* sp. PCC 6803. In order to knock-out both genes a double knock-out mutant has to be generated.

Laboratory Protocols

Protocols for the Generation of a Glycogen Synthase Double Mutant of *Synechocystis* sp. PCC 6803

In the genome database of *Synechocystis* sp. PCC 6803 two genes encoding glycogen synthases are annotated (http://bacteria.kazusa.or.jp/cyano).

One glycogen synthase of *Synechocystis* sp. PCC 6803 is encoded by the gene sll0945 (glgA1), annotated as glycogen synthase 1 (GlgA1). The Accession number of the protein is P74521 (EC 2.4.1.21), its amino acid sequence is presented in FIG. 4A.

A second glycogen synthase of *Synechocystis* sp. PCC 6803 is encoded by the gene sll1393 (glgA2), annotated as glycogen (starch) synthase 2 (GlgA2). The Accession number of the protein is P72623 (EC 2.4.1.21), its amino acid sequence is presented in FIG. 4B.

Construction of DNA-Vectors (Knock-Out-Constructs) for the Two Glycogen Synthase Encoding Genes (glgA1 and glgA2) of *Synechocystis* sp. PCC 6803

In General:

DNA sequences encoding genes of interest are amplified by polymerase chain reaction (PCR) using specific primers. When the genomic sequence does not contain appropriate restriction sites for cloning, primers are designed containing restriction sites. Genomic DNA from *Synechocystis* sp. PCC 6803 are used as template. The amplified PCR fragments are digested with the appropriate restriction enzymes and ligated into a cloning vector.

An antibiotic resistance cassette is then inserted into selected sites of the cloned genes. Upstream and downstream on each site of the antibiotic resistance cassette at least 500 bps remain for homologous recombination.

Genetic engineering of constructs as well as PCRs, ligations into cloning vectors, insertions of antibiotic resistance cassettes and transformations into *E. coli* are done using standard procedures (state of the art) or according to the manufacturers instructions.

To generate a glycogen deficient mutant in *Synechocystis* sp. PCC 6803, constructs were created for inactivation both glycogen synthase genes. The resulting glycogen deficient mutant described below is named mutant M8.

For creating a knock-out construct to inactivate glgA1, a 1341 bp fragment containing the major part of the coding sequence from glycogen synthase 1 (sll0945) was amplified by PCR using the following primers:

```
#glgA-1fw:
5'-CGACGGTATGAAGCTTTTATTTG-3',;  (SEQ ID NO: 130)
``` primer contains a HindIII restriction site for cloning (marked in bold letters).

```
#glgA-1rv:
  5'-CCGGCGGAACGGTACCAAC-3',,  (SEQ ID NO: 131)
``` primer contains a KpnI restriction site for cloning (marked in bold letters).

The PCR fragment was digested with HindIII and KpnI and cloned into plasmid pUC19 (Ac. No M77789). A single BstXI site present in the middle of glgA1 gene was used to insert a chloramphenicol resistance cassette (named Cm). The chloramphenicol resistance cassette, encoding a chloramphenicolacetyltransferase (cat) gene, was cut out of plasmid pACYC184 (Ac. No X06403) using BsaAI and BsaBI. The orientation of the antibiotic cassette was analyzed by digestion with HindIII and EcoRI; a restriction map is presented in FIG. 4C.

Figure 4C:
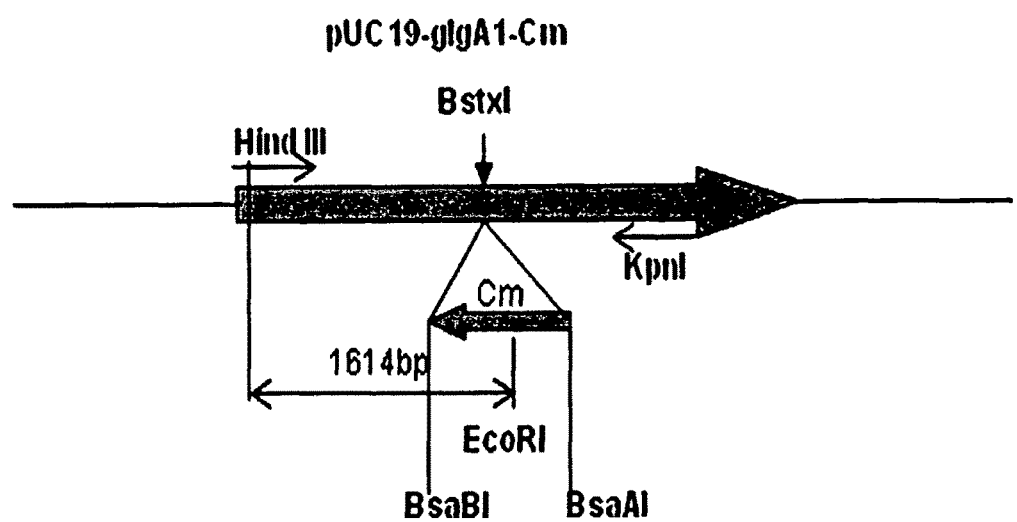
FIG. 4C presents a schematic representation of restriction sites used in the cloning strategy for pUC 19-glgA1-Cm.
Figure 4D:
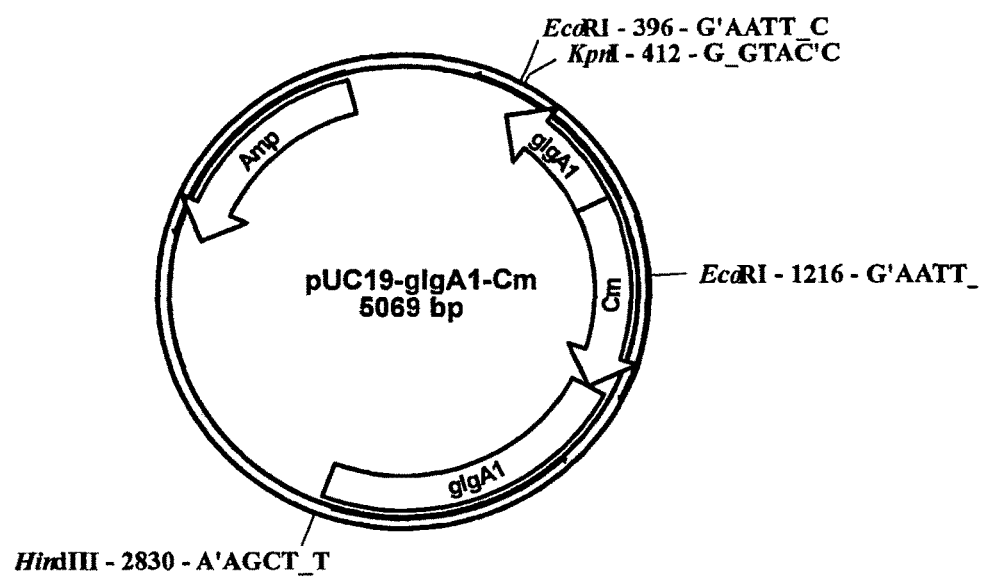
FIG. 4D is a schematic representation of gene organization for the plasmid pUC 19-glgA1-Cm.
Figure 4F:
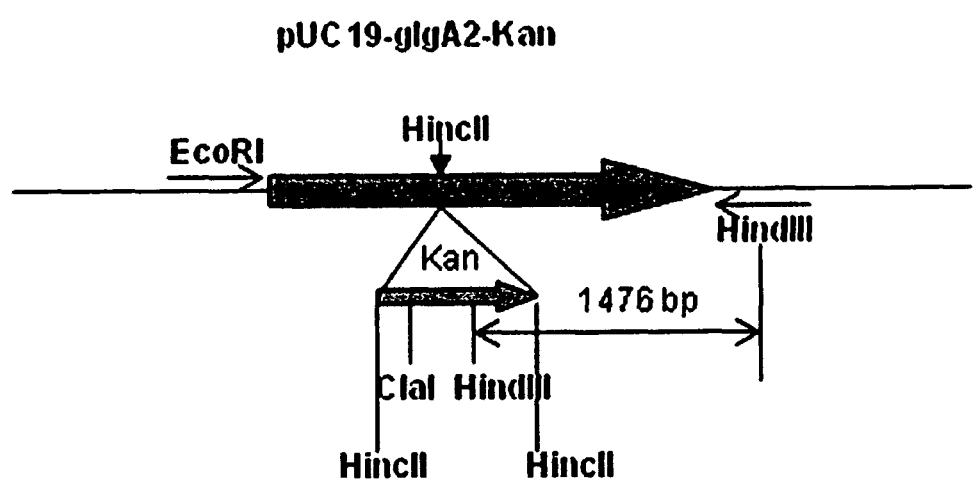
FIG. 4F presents a schematic representation of restriction sites used in the cloning strategy for pUC 19-glgA2-Kan.

A knock-out-construct, named pUC-glgA1-Cm, has the structure presented in FIG. 4D, and the nucleotide sequence of the construct pUC-glgA1-Cm is presented in FIG. 4E.

For creating a knock-out construct to inactivate glgA2, a 1673 bp fragment containing the entire coding sequence from glycogen synthase 2 (sll1393) was amplified by PCR using the following primers:

```
#glgA-2fw:
  5'-GGCCAGGGGAATTCTCCTCCAG-3',  (SEQ ID NO: 132)
``` primer contains an EcoRI restriction site for cloning (marked in bold letters).

```
#glgA-2rv:
5'-GCGGATAATACTGAACGAAGCTTTG-3',  (SEQ ID NO: 133)
``` primer contains a HindIII restriction site for cloning (marked in bold letters).

The PCR fragment was digested with EcoRI and HindIII and cloned into plasmid pUC19. A single HincII site present in the middle of glgA2 gene was used to insert a kanamycin resistance cassette (named Kan). The kanamycin resistance cassette, encoding an aminoglycoside 3'-phosphotransferase (aph) gene, was cut out of plasmid pUC4K (Ac. No X06404) using HincII. The orientation of antibiotic cassette was analyzed with the restriction enzyme HindIII. A restriction map of this clone is presented schematically in FIG. 4G.

Figure 4G:
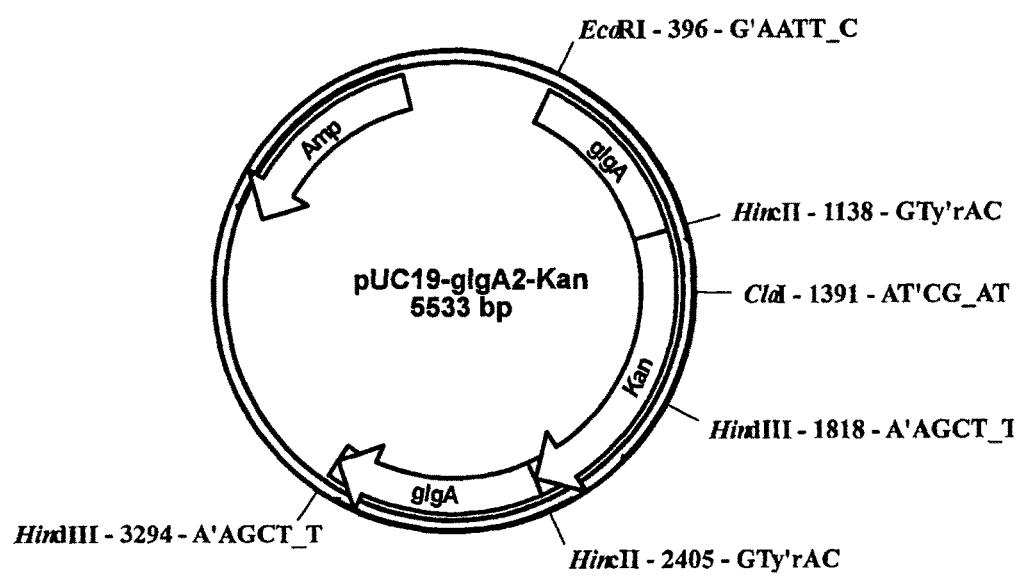
FIG. 4G is a schematic representation of gene organization for the plasmid pUC 19-glgA2-Kan.

The knock-out-construct used, named pUC-glgA2-Kan, has the structure presented in FIG. 4G and the nucleotide sequence presented in FIG. 4H.

Mutagenesis by transformation of the DNA-vectors (knock-out-constructs) using the natural competence of *Synechocystis* sp. PCC 6803 for DNA uptake and its system for homologous recombination.

The transformation was done in two steps. The first transformation knocks out gene sll0945 (glgA1) in the wild type of *Synechocystis*, and the corresponding mutant ΔglgA1 was selected. In a second step, gene sll1393 (glgA2) was knocked out in the ΔglgA1 mutant and the double mutant ΔglgA1/ΔglgA2 was selected.

General Transformation Protocol:
  Spin down 10 ml of exponentially growing culture of *Synechocystis* sp. at room temperature (RT) and remove the supernatant
  Resuspend the pellet in 0.5-1.0 ml of BG11 medium (media recipe:
    $NaNO_3$: 1.5 g
    $K_2HPO_4$: 0.04 g
    $MgSO_4.7H_2O$: 0.075 g
    $CaCl_2.2H_2O$: 0.036 g
    Citric acid: 0.006 g
    Ferric ammonium citrate: 0.006 g
    EDTA (disodium salt): 0.001 g
    $NaCO_3$: 0.02 g
    Trace metal mix A5_ 1.0 ml
    Agar (if needed): 10.0 g
    Distilled water: 1.0 L
    The pH should be 7.1 after sterilization
    Trace Metal Mix A5:
    $H_3BO_3$: 2.86 g
    $MnCl_2.4H_2O$: 1.81 g
    $ZnSO_4.7H_2O$: 0.222 g
    $NaMoO_4.2H_2O$: 0.39 g
    $CuSO_4.5H_2O$: 0.079 g
    $Co(NO_3)_2.6H_2O$: 49.4 mg
    Distilled water: 1.0 L)
  Add 1-10 µg plasmid DNA (knock-out-construct carrying gene of interest and an antibiotic cassette for screening for homologous recombination)
  Incubate on a table top shaker for 5-6 hours in the light at RT
  Plate 500 it of a 1/100 dilution of the transformation mixture on a BG11 agar plate. Plate the remainder of the cell suspension on another plate. Include control plate (transformation mixture with water instead of plasmid DNA).
  Incubate 48 h in the light at room temperature (RT) when chloramphenicol is used for selection or over night when kanamycin is used for selection.
  Pipet 500 µl of the corresponding antibiotic in a suitable concentration under the agar for the selection of mutant clones (initial concentration for chloramphenicol: 1 µg/ml BG11 agar; initial concentration for kanamycin: 5 µg/ml)
  Incubate for approx. 2 weeks in the light at RT
  Transfer individual colonies to plates containing the corresponding antibiotic Thereafter, the concentrations of antibiotics were increased stepwise when the cells were transferred onto another agar plate or into liquid culture (for kanamycin from initially 5 to 15 μg/ml BG11, for chloramphenicol from initially 1 to 15 μg/ml BG11 medium) in order to get fully segregated (homozygous) mutants. Transfers were done every 2 weeks. In case of kanamycin, the concentration in the range from 50 to 150 μg/ml agar was increased gradually over the course of 4 weeks.

Cultivation of Cyanobacterial Wild Type and Mutant Strains

Wild type and mutant strains of *Synechocystis* PCC 6803 were grown as batch cultures in BG11 medium at 29° C. under continuous illumination with white light (intensity: 40 μE m$^{-2}$ s$^{-1}$) and aeration with air. For cultivation of mutants, the appropriate antibiotics were added to the medium (kanamycin 75 mg/l; chloramphenicol 15 mg/l).

Samples were analyzed briefly before the nitrogen step down ("+N"), directly after resuspension of the cells in BG11 medium lacking a nitrogen source ("−N", 0 h) and after 3, 6 and 24 hours.

Generation of Knock-Out Mutants of *Synechocystis* sp. PCC 6803 Affecting the Following Genes:
a) alanine dehydrogenase (ald)
b) ADP-glucose pyrophosphorylase (glgC)
c) pyruvate water dikinase (ppsA)
d) lactate dehydrogenase (ldh)
e) acetate kinase (ack)
f) phosphoacetyltransacetylase (pta)
g) PHB knockout mutant (ΔphaC)
h) knockout mutant of ADP-glucose-pyrophosphorylase, agp, glgC in the filamentous, diazotrophic cyanobacteria *Nostoc/Anabaena* spec. PCC7120 and *Anabaena variabilis* ATCC 29413

Protocols for Generation of Knock-Down Mutants of *Synechocystis* sp. PCC 6803 Affecting the Following Gene:
a) pyruvate dehydrogenase (pdhB)
Description of the here Used Cloning Vectors Protocols for the Generation of Knock-Out Mutants of *Synechocystis* sp. PCC 6803

Construction of DNA-Vectors for Generation of Knock-Out Mutants
In General:

DNA sequences encoding genes of interest were amplified by polymerase chain reaction (PCR) using specific primers. When the genomic sequence did not contain appropriate restriction sites for cloning, primers were designed containing restriction sites. Genomic DNA from *Synechocystis* sp. PCC 6803 was used as template. The amplified PCR fragments were digested with the appropriate restriction enzymes and ligated into a cloning vector.

An antibiotic resistance cassette was then inserted into selected sites of the cloned genes. Upstream and downstream on each site of the antibiotic resistance cassette at least 500 bps remained for homologous recombination. The following antibiotic resistance cartridges were used: kanamycin resistance cassette (named Kan) from pUC4K vector (Ac. No X06404) from the NCBI database under: http://www.ncbi.nlm.nih.gov/sites/entrez?term=X06404& cmd= Search&db=nuccore&QueryKey=1 encoding aminoglycoside 3'-phosphotransferase (aph) gene or chloramphenicol resistance cartridge (named Cm) from pACYC184 vector (Biolabs, Ac No. X06403) encoding chloramphenicolacyltransferase (cat) gene. Genetic engineering of constructs as well as PCRs, ligations into cloning vectors, insertions of antibiotic resistance cassettes and transformations into *E. coli* were done using standard procedures (state of the art) or according to the manufacturer instructions.

Sequences and structures of the used cloning and expression plasmids are described below (see 3).

Knock-outs were generated via homologous recombination of the wild type gene with the mutant genes. The method of transformation of the DNA-vectors (knock-out-constructs) using the natural competence of *Synechocystis* sp. PCC 6803 for DNA uptake was already described in detail for the generation of the glycogen deficient mutant.

a) Construction of a DNA-Vector for Generation of an Alanine Dehydrogenase Knock-Out Mutant (Δald)

The open reading frame (ORF) sll1682 encodes alanine dehydrogenase (EC 1.4.1.1), Ac. No BAA16790. The amino acid sequence of this protein is presented in FIG. 5A.

Two constructs were generated for knock-out of alanine dehydrogenase differing in orientation of the inserted kanamycin resistance cartridge (in sense and in antisense orientation to the ald ORF) using the following primers:

```
#Ald50.fw:
5'-GGCTGACCCCCAGTAGTGTA-3    (SEQ ID NO: 134)

#Ald1042.rv:
5'-ATTTTCCGGCTTGAACATTG-3'   (SEQ ID NO: 135)
```

A 993 bp ald PCR fragment was amplified by a BIO-TAQ™ DNA Polymerase (BIOLINE), cloned into the pGEM-T vector (Promega) and restricted with SmaI (blunt ends; Fermentas). The kanamycin cartridge was remained by a restriction of the pUC4K vector with EcoRI (5'overhangs; Fermentas) and a following "fill in reaction" via the T4 DNA Polymerase (Promega). Plasmids were analyzed by restriction digest in order to select constructs with both orientations of the inserted kanamycin cartridge.

Figure 5B:
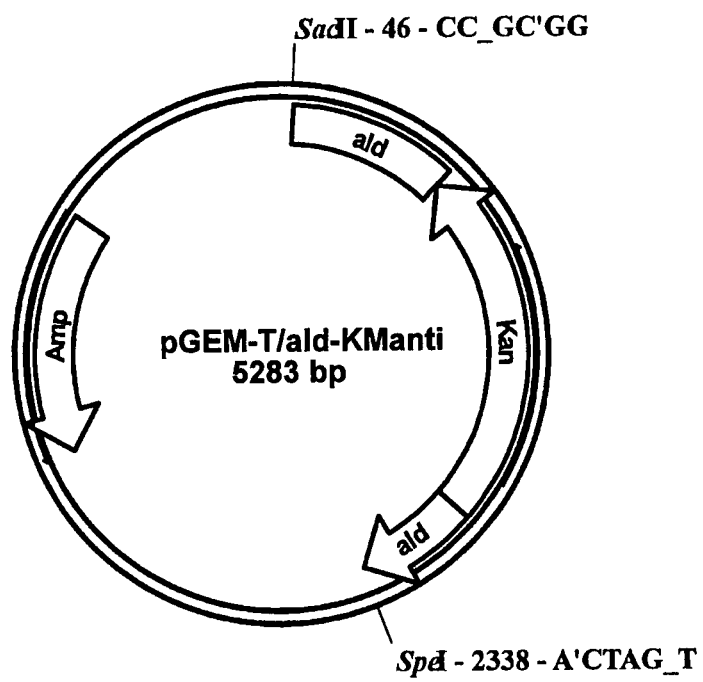
FIG. 5B presents a schematic representation of gene organization for the plasmid pGEM-T/ald-KManti.

A construct designated as pGEM-T/Δald-antisense has the structure presented schematically in FIG. 5B.

The sequence of the insert for this construct (pGEM-T/Δald-antisense) is presented in FIG. 5C.

In the other construct, designated as pGEM-T/Δald-sense the kanamycin resistance cartridge is inserted in the other direction.

b) Construction of DNA-Vector for Generation of an ADP-Glucose Pyrophosphorylase Knock-Out Mutant (ΔglgC)

The open reading frame (ORF) slr1176 encodes ADP-glucose pyrophosphorylase (EC 2.7.7.27), Ac. No BAA18822. The amino acid sequence of this protein is presented in FIG. 6A.

Four constructs were generated for knock out of ADP-glucose pyrophosphorylase differing in the locus of insertion (EcoRI, BsaBI) and in orientation of the resistance (kanamycin-Km, chloramphenicol-Cm) cartridge (in sense and in antisense orientation to the glgC gene). Both insertion sites were tested because of a putative small non-coding RNA at the 5'-terminus of the glgC gene (in antisense orientation). Therefore, the insertion of the chloramphenicol cartridge at the BsaBI-site might affect the expression of the putative small non-coding RNA.

The following primers were used for PCR

```
#GglC5.fw:
5'-GTTGTTGGCAATCGAGAGGT-3'   (SEQ ID NO: 136)

#GlgCiR.rv:
5'-GTCTGCCGGTTTGAAACAAT-3'   (SEQ ID NO: 137)
```

-continued

```
BsaBI:
GATNNtNNATC                         (SEQ ID NO: 138)

#GlgCiR.fw:
5'-ACCCCATCATCATACGAAGC-3'          (SEQ ID NO: 139)

#GlgC1233.rv:
5'-AGCCTCCTGGACATTTTCCT-3'          (SEQ ID NO: 140)
```

The first 1579 bp glgC PCR fragment was amplified by a BIOTAQ™ DNA Polymerase (BIOLINE), cloned into the pGEM-T vector (Promega) and restricted with EcoRI (5'overhangs; Fermentas). The kanamycin cartridge was remained by a restriction of the pUC4K vector with EcoRI (5'overhangs; Fermentas).

Plasmids were analyzed by restriction digest in order to select constructs with both orientations of the inserted kanamycin cartridge, respectively.

Figure 6B:
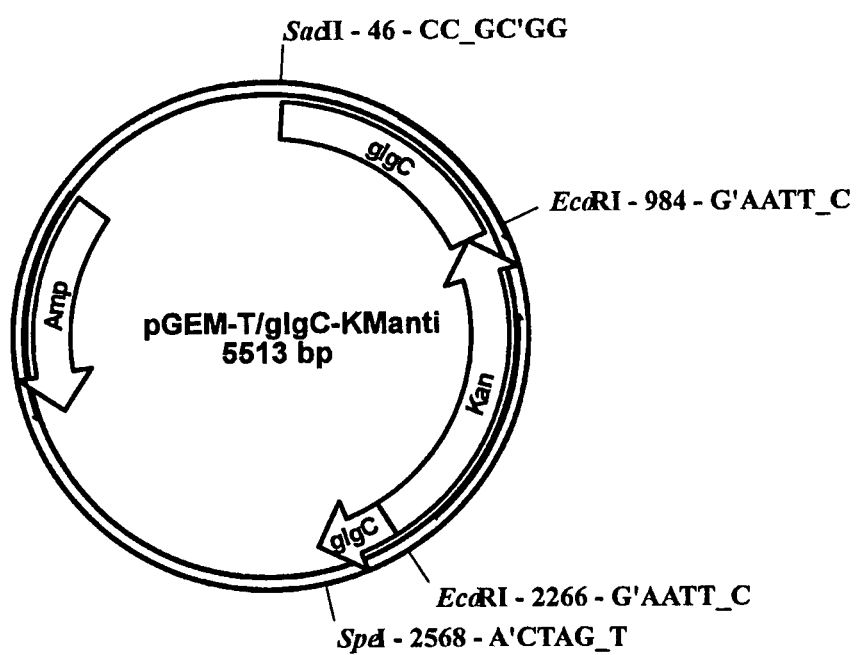
FIG. 6B presents a schematic representation of gene organization for the plasmid pGEM-T/glgC-KManti.

The construct pGEM-T/ΔglgC-KMantisense has the structure shown in FIG. 6B, and its insert the nucleotide sequence presented in FIG. 6C.

In the other construct, designated as pGEM-T/ΔglgC-KMsense the kanamycin resistance cartridge is inserted in the other direction.

The second 1453 bp glgC PCR fragment was amplified by a BIOTAQ™ DNA Polymerase (BIOLINE), cloned into the pDrive vector (Qiagen) and restricted with BsaBI (blunt ends; Biolabs). The chloramphenicol cartridge was remained by restriction of the pACYC184 vector (Biolabs, Ac No. X06403) with BsaAI (blunt ends; Biolabs).

Plasmids were analyzed by restriction digest in order to select constructs with both orientations of the inserted chloramphenicol resistance (Cm) cartridge, respectively.

Figure 6D:
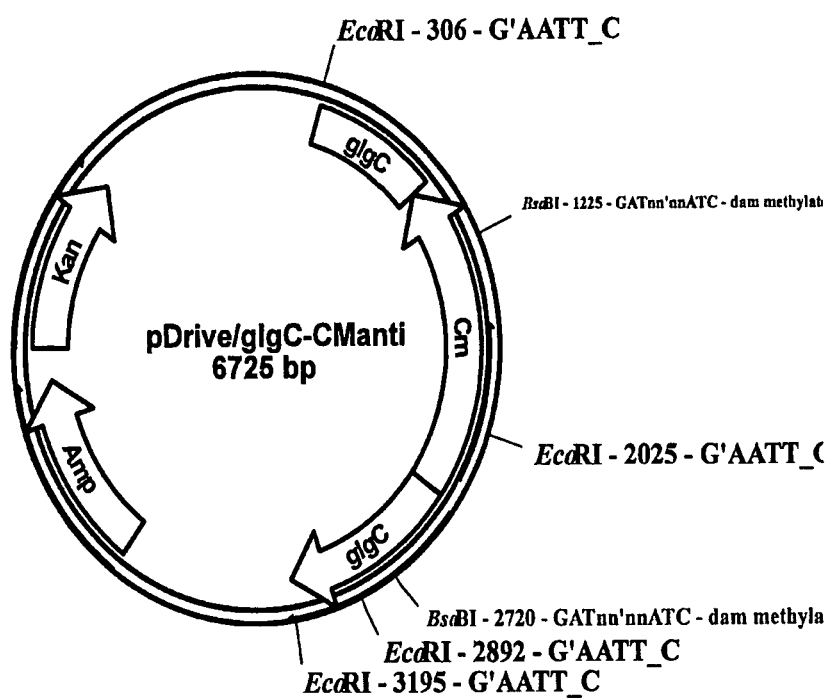
FIG. 6D presents a schematic representation of gene organization for the plasmid pDrive/glgC-CMantisense.

A construct designated as pDrive/ΔglgC-CMantisense was selected; its structure is presented schematically in FIG. 6D and the nucleotide sequence of the insert is presented in FIG. 6E.

In the other construct, designated as pDrive/ΔglgC-CMsense the chloramphenicol resistance cartridge is inserted in the other direction.

c) Construction of DNA-Vector for Generation of a Pyruvate Water Dikinase Knock-Out Mutant (ΔppsA)

The open reading frame (ORF) slr0301 encodes pyruvate water dikinase/PEP synthase (EC 2.7.9.2), Ac. No BAA10668. This protein has the amino acid sequence that is presented in FIG. 7A.

Two constructs were generated for knock-out of pyruvate water dikinase differing in orientation of the inserted kanamycin resistance cartridge (in sense and in antisense orientation to the ppsA ORF) using the following primers:

```
#PpsA547.fw:
5'-TTCACTGACCGGGCTATTTC-3'          (SEQ ID NO: 141)

#PpsA2329.rv:
5'-CTTGGCCACAGATACCGATT-3'          (SEQ ID NO: 142)
```

A 1783 bp ppsA PCR fragment was amplified by a BIOTAQ™ DNA Polymerase (BIOLINE), cloned into the pGEM-T vector (Promega) and restricted with SmaI (blunt ends; Fermentas). The kanamycin cartridge was remained by a restriction of the pUC4K vector with EcoRI (5' overhangs; Fermentas) and a following "fill in reaction" via the T4 DNA Polymerase (Promega). Plasmids were analyzed by restriction digest in order to select constructs with both orientations of the inserted kanamycin cartridge.

Figure 7B:
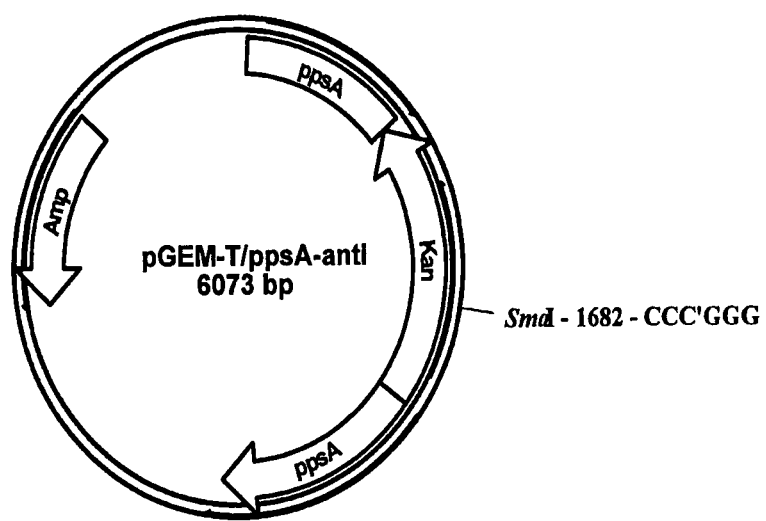
FIG. 7B presents a schematic of gene organization for the plasmid pGEM-T/ppsA-anti.

The construct used, designated as pGEM-T/ΔppsA-antisense, has the structure presented in FIG. 7B. The nucleotide sequence of it insert is presented in FIG. 7C.

In the other construct, designated as pGEM-T/ΔppsA-sense the kanamycin resistance cartridge is inserted in the other direction.

d) Construction of a DNA-Vector for Generation of a Lactate Dehydrogenase Knock-Out Mutant (Δldh)

Figure 8B:
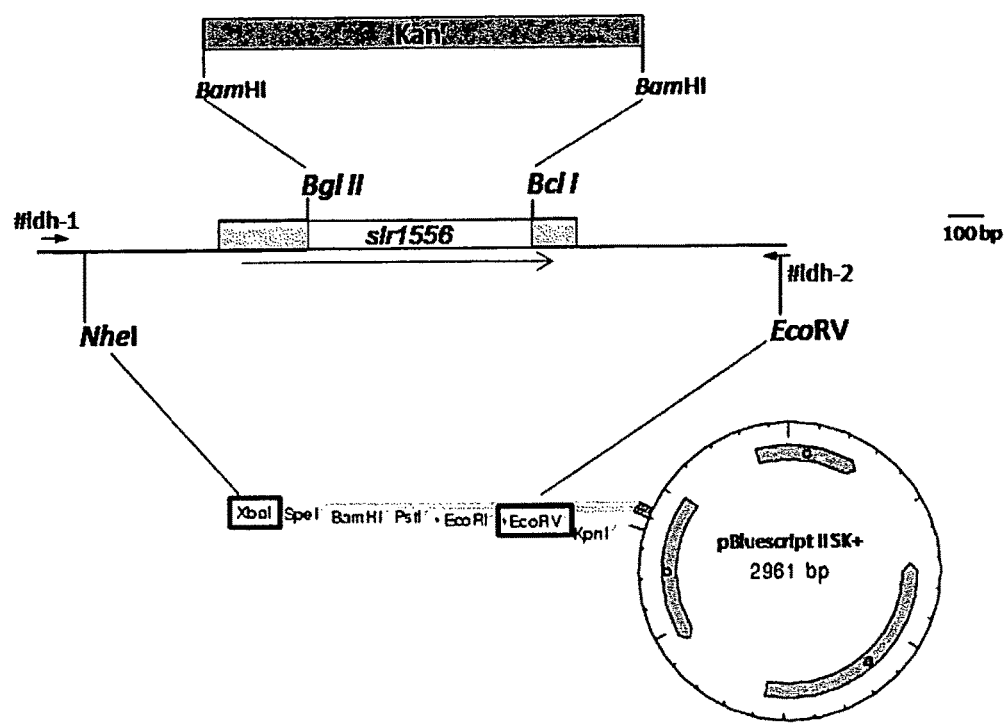
FIG. 8B presents a schematic representation of restriction sites used in the cloning strategy for pBlue ldh-Kan-a.

The open reading frame (ORF) slr 1556 encodes a putative lactate dehydrogenase (EC 1.1.1.28), annotated as 2-hydroxyaciddehydrogenase homolog (P74586). This amino acid sequence for this protein is presented in FIG. 8A.

A 1931 bp fragment containing the entire coding sequence from lactate dehydrogenase (slr1556) was amplified by PCR using the following primer:

```
#lhd-1fw:
5'-GCGAACTACCCAACGCTGACCGG-3'       (SEQ ID NO: 143)

#ldh-2rv:
5'-GCATCAAGTGTTGGGGGATATCCCTG-3',   (SEQ ID NO: 144)
``` primer contains a EcoRV restriction site (GATATC) for cloning (marked in bold letters).

The PCR fragment was digested with NheI/EcoRV (NheI site is present in the genomic sequence) and cloned into pBluescript SK+ vector using XbaI/EcoRV. The kanamycin resistance cassette was used from the DNA vector pUC4K and ligated into the BglII/BclI restriction sites of slr1556. A restriction map of this is presented in FIG. 8B.

Figure 8C:
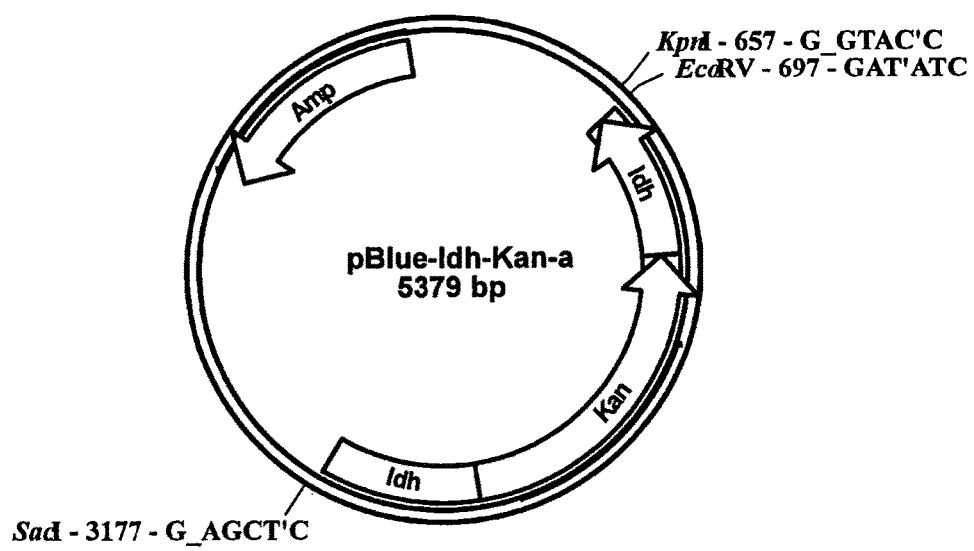
FIG. 8C presents a schematic for the gene organization of the plasmid pBlue ldh-Kan-a.

The knock-out-construct used, named pBlue ldh-Kan-a, has the structure presented in FIG. 8C, and the nucleotide sequence for its insert is presented in FIG. 8D.

e) Construction of a DNA-Vector for Generation of an Acetate Kinase Knock-Out Mutant (Δack)

Figure 9B:
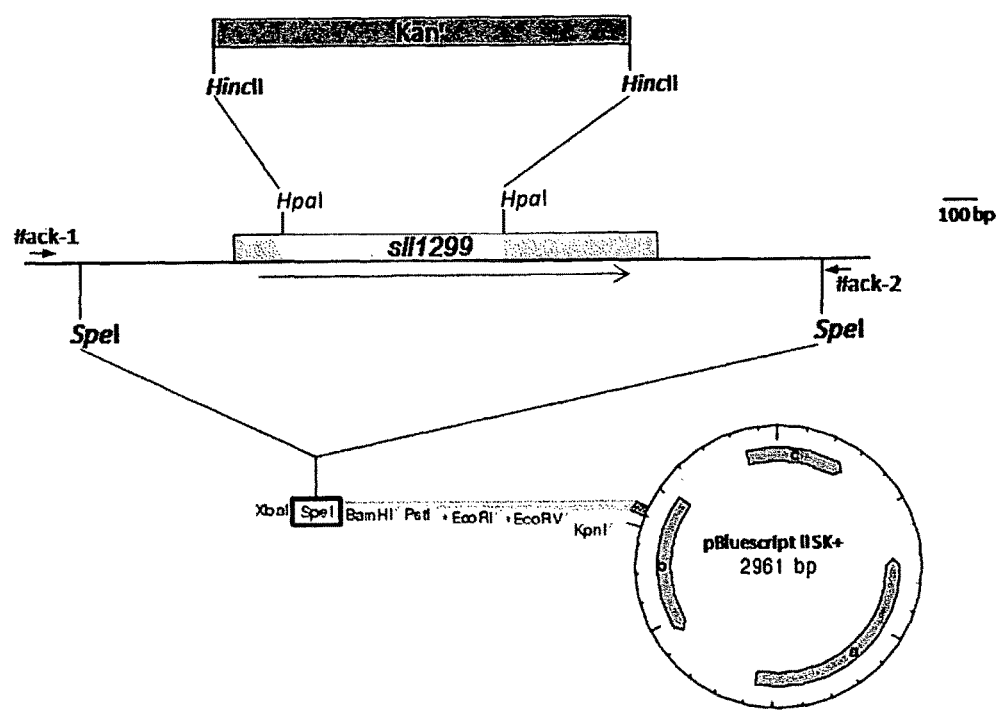
FIG. 9B presents a schematic representation of restriction sites used in the cloning strategy for pBlue-ack-Kan-b.

The open reading frame (ORF) sll 1299 encodes a putative acetate kinase (EC 2.7.2.1), Ac No. P73162. The amino acid sequence for this protein is presented in FIG. 9A.

A 2316 bp fragment containing the entire coding sequence from acetate kinase (sll1299) was amplified by PCR using the following primer:

```
#ack-1 fw:
5'-CCGGGACGTGACAGAACGGGTGG-3'       (SEQ ID NO: 145)

#ack-2 rv:
5'-GCGTTGGCGATCGCCGTCACTAG-3'       (SEQ ID NO: 146)
```

The PCR fragment was digested with SpeI (both sites are located in the genomic sequence) and cloned into pBluescript SK+ vector. The kanamycin resistance cassette was used from the DNA vector pUC4K and ligated into the HpaI restriction sites of slr1299. A restriction enzyme map of this region is presented in FIG. 9B.

The orientation of the kanamycin resistance cassette was either in the same direction as sll1299 (designed "a") or in the opposite direction (designed "b").

Figure 9C:
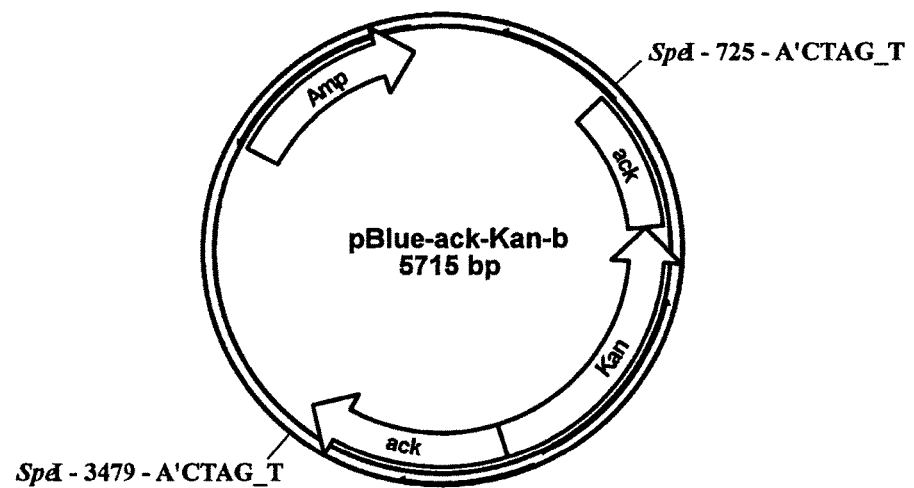
FIG. 9C presents a schematic for the gene organization of the plasmid pBlue-ack-Kan-b.

The knock-out-construct used, named pBlue ack-Kan-b, has the structure presented in FIG. 9C, and the nucleotide sequence of its insert is presented in FIG. 9D.

f) Construction of a DNA-Vector for Generation of a Phosphoacetyltransacetylase (Phosphoacyltransferase) Knock-Out Mutant (Δpta)

Figure 10B:
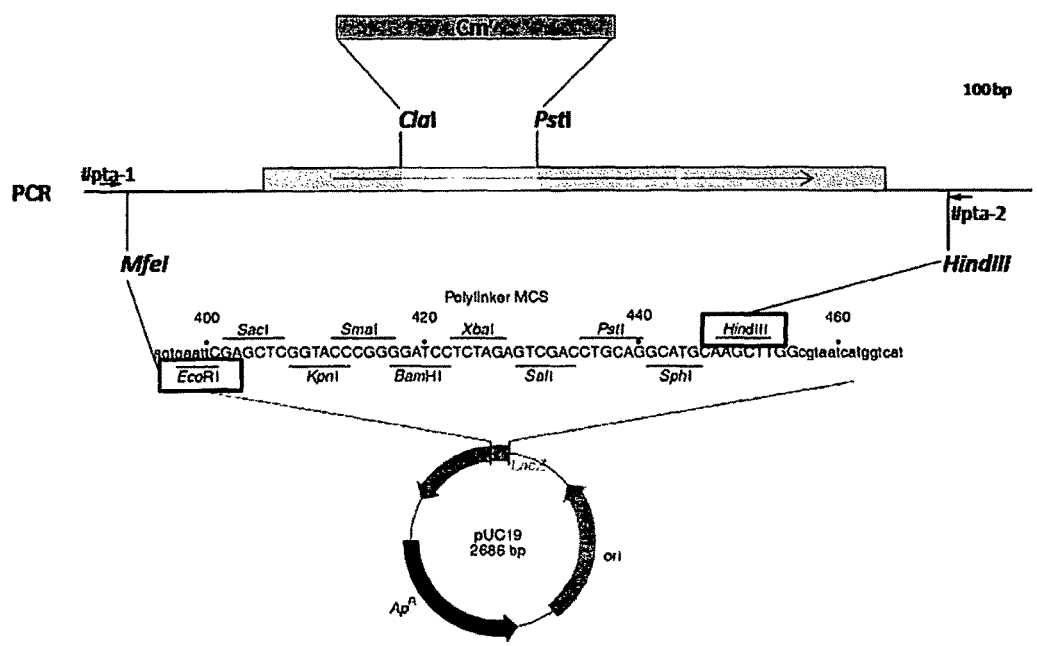
FIG. 10B presents a schematic representation of restriction sites used in the cloning strategy for pUC pta-Cm.

The open reading frame (ORF) slr2132 encodes a phosphoacetyltransacetylase (EC 2.3.1.8), Ac No. P73662. The amino acid sequence for this protein is presented in FIG. 10A.

A 2869 bp fragment containing the entire coding sequence from phosphoacetyl-transacetylase (slr2132) was amplified by PCR using the following primer:

```
#pta-1fw:
5'-GCCATTGTGGGGGTGGGTCAG-3'      (SEQ ID NO: 147)

#pta-2rv:
5'-CAGTTTATGCCCCGCTACCGGG-3'     (SEQ ID NO: 148)
```

The PCR fragment was digested with MfeI/HindIII (both sites present in the genomic sequence) and cloned into pUC19 (EcoRI/HindIII) vector. The chloramphenicol resistance cassette was used from plasmid pACYC184 and ligated into the ClaI/PstI restriction sites of slr2132. A restriction map of this region is presented in FIG. 10B.

Figure 10C:
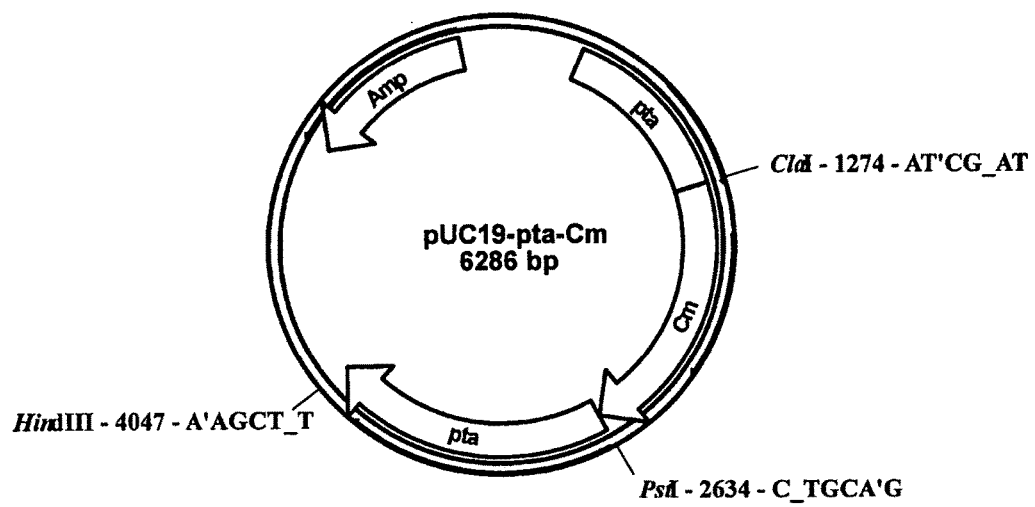
FIG. 10C presents a schematic for the gene organization of the plasmid pUC pta-Cm.

The knock-out-construct selected is named pUC pta-Cm. It's structure is presented schematically in FIG. 10C, and the nucleotide sequence of the insert for this clone is presented in FIG. 10D.

g) Construction of DNA-Vector for Generation of PHB Knockout Mutant (ΔphaC)

The open reading frame (ORF) slr1830 encodes poly(3-hydroxyalkanoate) synthase [EC:2.3.1.], Ac. No BAA17430. The amino acid sequence for this protein is presented in FIG. 11A.

One construct was generated for knock out of poly(3-hydroxyalkanoate) synthase by deletion/insertion (resistance cartridge: kanamycin) mutagenesis.

```
# phaC-25'HD -XbaI.fw:
5'-CCGATGtcTAGaTAATTCACCATC-3'   (SEQ ID NO: 149)

# phaC404_BamHI.rv:
5'-TCTAGGGggAtCCAACGATCG-3'      (SEQ ID NO: 150)

# phaC711_BamHI.fw:
5'-CCAGGGGATccTCTTAACCTAG-3'     (SEQ ID NO: 151)

# phaC1133'HD -ClaI.rv:
5'-TGTCGTatCGATAGCCAATGG-3'      (SEQ ID NO: 152)
```

Two PCR products (pos. 24 to pos. 404; pos. 711 to pos. 1133) of the phaC fragment were amplified by a BIOTAQ™ DNA Polymerase (BIOLINE), ligated via BamHI sites and cloned into the pIC2OH vector. The kanamycin cartridge was remained by a restriction of the pUC vector (http://seq.yeastgenome.org/vectordb/vector_descrip/COMPLETE/PUC4K.SEQ.html) with BamHI (Fermentas). Plasmids were analyzed by restriction digest. Knockouts were generated via homologous recombination of the wild type gene with the mutant genes.

Figure 11B:
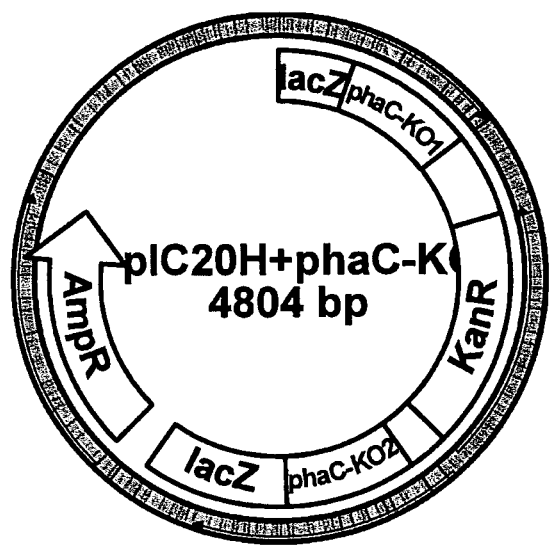
FIG. 11B presents a schematic representation of gene structure for the plasmid as pIC2OH/ΔphaC-KM.

The construct selected is pIC2OH/ΔphaC-KM and has the structure presented schematically in FIG. 11B. The nucleotide sequence for the insert of this clone is presented in FIG. 11C.

h) Construction of DNA-Vectors for Generation of Knock-out Mutants of ADP-Glucose-Pyrophosphorylase, agp (glgC) in the Filamentous, Diazotrophic Cyanobacteria Nostoc/Anabaena spec. PCC7120 and Anabaena variabilis ATCC 29413

In order to generate ethanol producing Anabaena strains, different constructs were created for conjugation into Anabaena PCC7120 and Anabaena variabilis ATCC29413. Constructs for genome integration of ethanologenic genes were created for both Anabaena strains. As integration site into the genome the glucose-1-phosphate adenylyltransferase gene (ADP-glucose-pyrophosphorylase, agp, glgC) was chosen. Thus, by integration of the ethanologenic genes simultaneously an agp knock-out mutant was created.

Glucose-1-phosphate adenylyltransferase (ADP-glucose-pyrophosphorylase, agp, glgC), EC 2.7.7.27, of Anabaena spec. PCC7120 is encoded by ORF all4645, Ac. No. P30521. The amino acid sequence of ORF all4645 is shown in FIG. 11D.

Constructs for conjugation into Anabaena PCC7120 were cloned as followed:

Two fragments representing the 5' and 3' part of the ADP-glucose-pyrophosphorylase (agp) gene, ORF all4645, were amplified by PCR using the following primers:

```
#agp1.1
5'-CATCCATCATGAGCTCTGTTAAC-3'    (SEQ ID NO: 153)
(SacI site inserted)

#agp2.1
5'-GTATCTCGAGCGATGCCTACAGG-3'    (SEQ ID NO: 154)
(XhoI site inserted)

#agp3.1
5'-CGCATTGGTTTCTAGATGGCGC-3'     (SEQ ID NO: 155)
(XbaI site inserted)

#agp4.1
5'-CGATAACTCTAGACGAGTCATTG-3'    (SEQ ID NO: 156)
(XbaI site inserted)
```

Inserted Restriction Sites in Primer Sequences are Marked in Bold Letters

Figure 11E:
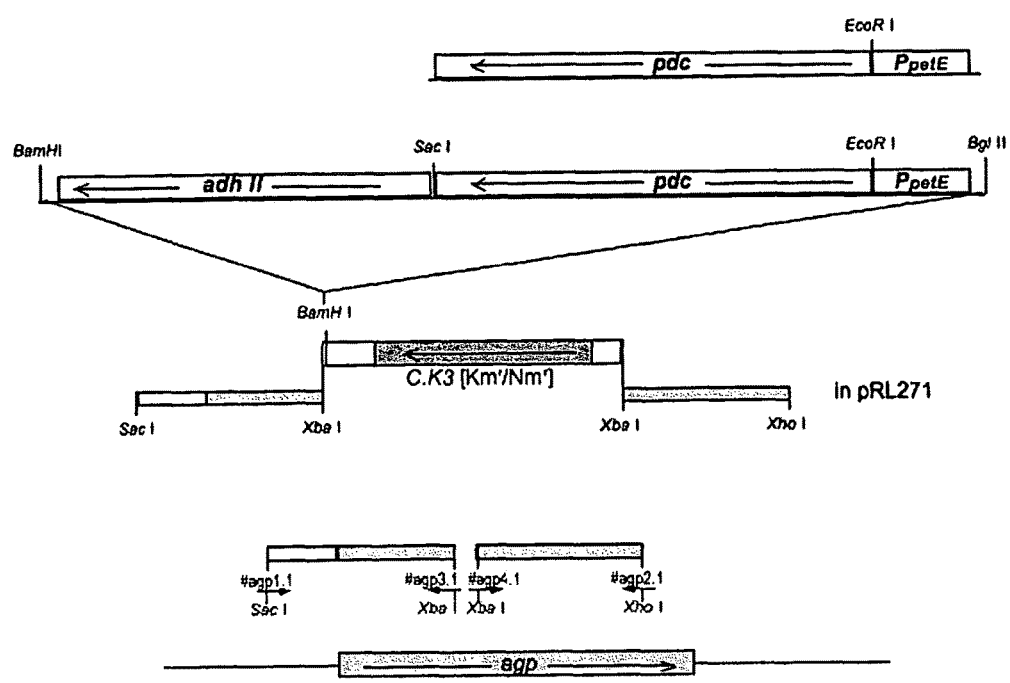
FIG. 11E presents a schematic representation of restriction sites and gene organization for the PCC 7120 glgC knockout.

As indicated in FIG. 11E, in between these agp fragments a C.K3 cassette (coding for kanamycin/neomycin resistance) was ligated into the XbaI site. [C.K3 cassette is described in Elhai, J. & Wolk, C. P. (1988) Gene, 68, 119-138.]

The entire "agp knock-out" fragment was cloned into suicide vector pRL271 (Ac. No. L05081). The pdc/adh genes, or only pdc, were cloned downstream of the inducible promoter PpetE and integrated into the "agp-C.K3" construct.

The following constructs have been generated:
pRL271 agp (all4645)::C.K3
pRL271 agp (all4645)::C.K3-PpetE-pdc-adhII
pRL271 agp (all4645)::C.K3-PpetE-pdc The structures of the constructs are depicted in FIG. 11-2.

The sequence of the insert of pRL271 agp (all4645):: C.K3-PpetE-pdc-adhII is shown in FIG. 11F.

The same strategy was used to create constructs for expression in Anabaena variabilis ATCC29413. The nucleotide sequences of the agp genes from both strains are 97%, their protein sequences are 99.3% identical.

Glucose-1-phosphate adenylyltransferase (ADP-glucose-pyrophosphorylase, agp, glgC), EC 2.7.7.27, of Anabaena variabilis ATCC29314 is encoded by ORF Ava_2020, Ac. No. Q3MBJ4, and has the amino acid sequence as shown in FIG. 11G.

For PCR amplification of the genomic fragments of Anabaena variabilis the following primers were used:

```
#agp1.2
5'-GAGGCAATGAGCTCCACTGGACG-3'    (SEQ ID NO: 157)
(SacI site inserted)

#agp2.2
5'-CTGGCGTTCCACTCGAGCTTGG-3'     (SEQ ID NO: 158)
(XhoI site inserted)

#agp3.1
5'-CGCATTGGTTTCTAGATGGCGC-3'     (SEQ ID NO: 159)
(XbaI site inserted)
```

-continued agp4.2
5'-CGATAACTCTAGACGAGTCATCG-3' (SEQ ID NO: 160)
(XbaI site inserted)

Inserted restriction sites in primer sequences are marked in bold letters.

Generation of the constructs was exactly as described for the constructs of *Anabaena* PCC7120.

The following constructs have been generated:
pRL271 agp::C.K3
pRL271 agp::C.K3-PpetE-pdc-adhII
pRL271 agp::C.K3-PpetE-pdc All described plasmids were conjugated into *Anabaena* strains according the following method:

Conjugation of *Nostoc* spec. PCC7120/*Anabaena variabilis*
Cargoplasmids

Cargoplasmids (pRL593, pRL1049 or pRL271) were transformed into competent *E. coli* HB101 (pRL528$_{helperplasmid}$).

In Preparation for Conjugation

*E. coli* Cultures:
  inoculation of overnight cultures in LB with the appropriate antibiotics from
    Cargoplasmid in *E. coli* HB101 (pRL528$_{helperplasmid}$)
    Helperstrain *E. coli* J53 (RP4)
  preparation of well growing culture (for each conjugation/plate 10 ml of HB101 (pRL528+cargo plasmid) and 10 ml of J53 (RP4) is needed): inoculate 0.25 ml overnight culture in 10 ml LB+antibiotic, grow for 2.5 h/37° C.
  spin down the well grown *E. coli* cultures in "Falcons" 10 min 4800 rpm.
  (for J53 culture: take 2 Falcons).
  "wash"/resuspend cells in equal volume of LB without antibiotics.
  for each conjugation spin 10 ml of resuspended HB101 (culture carrying pRL528+cargo plasmid) in 15 ml Falcon tube, remover supernatant
  add on the cell pellets 10 ml resuspended J53 (RP4) culture, spin down, remove supernatant and resuspend combined cells in 1 ml LB, transfer cells in Eppi tubes, resuspend again in 100 µl and incubate for 2 h at 30° C.

Cyanos
  determine the chlorophyll concentration of well grown *Anabaena* cultures
  for each conjugation, culture corresponding to about 10 µg Chlorophyll is needed.
  spin down the equivalent volume of *Anabaena* culture and resuspend to a volume corresponding to 10 µg Chlorophyll/100 µl BG11 medium.

Conjugation
  for each conjugation place one HATF filter on a plate (BG11)
  mix 100 µl *E. coli* suspension=100 µl *Anabaena* culture and plate on filter
  incubate plates at 30° C. overnight wrapped in paper
  next day remove paper
  after one day transfer filter on plates containing antibiotics.

Construction of DNA-Vectors for Generation of Knock-Down Mutants a) Construction of a DNA-Vector for Generation of a Pyruvate Dehydrogenase (pdhB) Knock-Down Mutant The open reading frame (ORF) sll1721 encodes the β-subunit of the E1 component of the pyruvate dehydrogenase, (EC 1.2.4.1), Ac. No BAA17445. This protein has the amino acid sequence presented in FIG. 12A.

Two strategies were considered for knock-down of the pyruvate dehydrogenase. A knock-down could be achieved by regulation of the expression of the adequate antisense RNA (i) or by insertion of a controllable wild type gene copy accompanied by a knock-out of the original wild type gene (ii). Therefore, four constructs were generated to knock-down the pyruvate dehydrogenase.

The PCR fragments for the expression of the adequate antisense RNA as well as for the controllable wild type gene copy were amplified by a High-Fidelity DNA Polymerase (Phusion™; Finnzymes), adenylated (BIOTAQ™ DNA Polymerase; BIOLINE), cloned into the pDrive vector (Qiagen) and restricted with ClaI/BglII (i) or NdeI/BglII[1] (ii) (Fermentas). These fragments were cloned into the pSK9

[1] BglII was used instead of ClaI because this inserted ClaI cleavage side was affected by Dam-methylation. The BglII cleavage side is part of the 3' end of the amplified PCR product and do not affect the translation termination loop.

vector, digested with ClaI/BglII (i) or NdeI/BglII (ii). The non-public pSK9 vector was generated in the lab of V. V. Zinchenko (Moscow, Russia). The gene is incorporated into a non-coding genome region via the integrated platform. The expression of the enzyme and the antisense RNA is under the control of the copper inducible promoter petJ. The termination of transcription is achieved either by the gene-specific terminator loop (ii) or by the oop-terminator of the lambda phage (i) (Toop is part of the reverse-Primer), both amplified by PCR reaction.

PdhBantiClaI.fw:
(SEQ ID NO: 161)
5'-ATCGATATAATTTCCGGGTCGTAGCC-3', this primer contains a ClaI restriction site for cloning (marked in bold letters)

PdhBantioopBglII.rv:

(SEQ ID NO: 162)
5'GATCTGGAATAAAAAACGCCCGGCGGCAACCGAGCGGCAGCCATTCGG

GATAATAA-3', this primer contains a BglII restriction site for cloning (marked in bold letters) and the oop terminator region of the lambda phage (underlined)

(SEQ ID NO: 163)
PdhBNdeI.fw: 5'-CATATGGCTGAGACCCTACTGTTT-3', this primer contains a NdeI restriction site for cloning (marked in bold letters)

(SEQ ID NO: 164)
PdhB1061ClaI.rv 5'-ATCGATCTTACAAGCTCCCGGACAAA-3', this primer contains a ClaI restriction site for cloning (marked in bold letters)

The 1142 bp pdhB PCR fragment for the knock-out of the original wild type gene was amplified by a BIOTAQ™ DNA Polymerase (BIOLINE), cloned into the pGEM-T vector (Promega) and restricted with Eco147I (blunt ends; Fermentas). The kanamycin cartridge was remained by a restriction of the pUC4K vector with EcoRI (5' overhangs; Fermentas) and a following "fill in reaction" via the T4 DNA Polymerase (Promega) and ligated into the Eco147I site. Resulting plasmids were analyzed by restriction digest in order to select constructs with both orientations of the inserted kanamycin cartridge. Knock-outs were generated via homologous recombination of the wild type gene with the mutant genes. The following primers were used for PCR:

PdhB.fw: 5'-AATCGACATCCACCCTTGTC-3' (SEQ ID NO: 165)
PdhB.rv: 5'-GCCTTAACTGCGTCCACAAT-3' (SEQ ID NO: 166)

(i) Knock-Down by Regulation of the Expression of the Adequate Antisense RNA

Figure 12B:
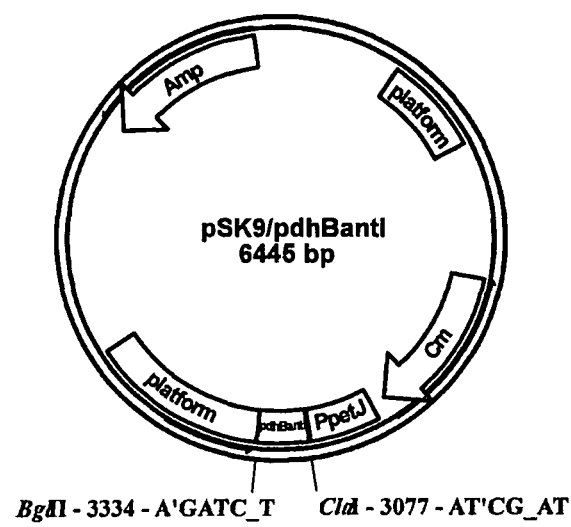
FIG. 12B presents a schematic of gene organization for the plasmid pSK9/pdhBanti.

The construct used, designated as pSK9/pdhBanti, has the structure presented in FIG. 12B, and the nucleotide sequence of its insert is presented in FIG. 12C.

Figure 12D:
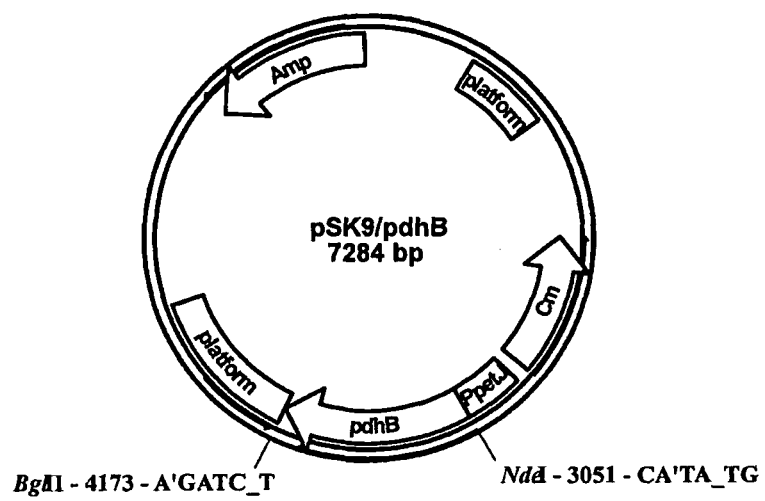
FIG. 12D presents a schematic representation of gene organization for the plasmid pSK9/pdhB.

(ii) Knock-Down by Insertion of a Controllable Wild Type Gene Copy Accompanied by a Knock-Out of the Original Wild Type Gene The construct used, designated as pSK9/pdhB, has the structure presented in FIG. 12D, and the nucleotide sequence of the insert for this clone is presented in FIG. 12E.

Figure 12F:
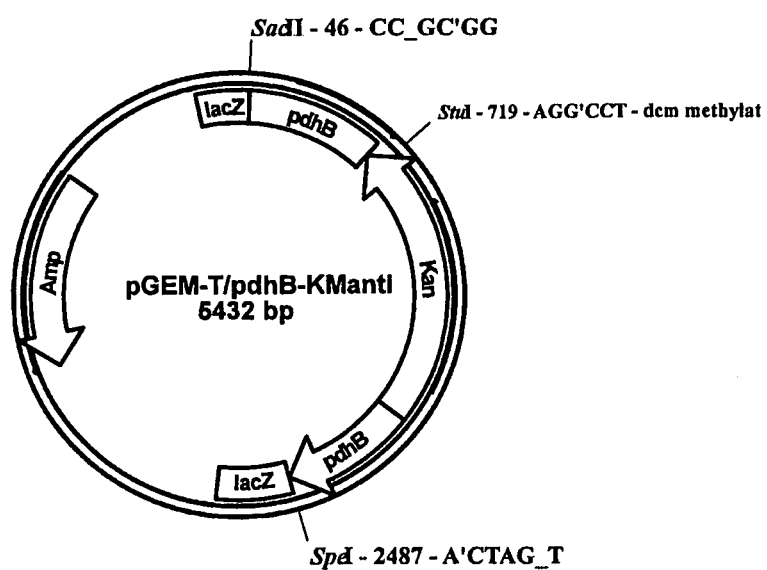
FIG. 12F presents a schematic of gene organization for the plasmid pGEM-T/ΔpdhB-KMantisense.

The knock-out construct used, designated as pGEM-T/ΔpdhB-KMantisense, has the structure presented in FIG. 12F. The sequence for the insert in this clone is presented in FIG. 12G.

In the other construct, designated as pGEM-T/ΔpdhB-KMsense the kanamycin resistance cartridge is inserted in the other direction.

In the following the cloning vectors, which were used are described.

a) Cloning Vector pGEM®-T Structure and Sequence

Figure 13A:
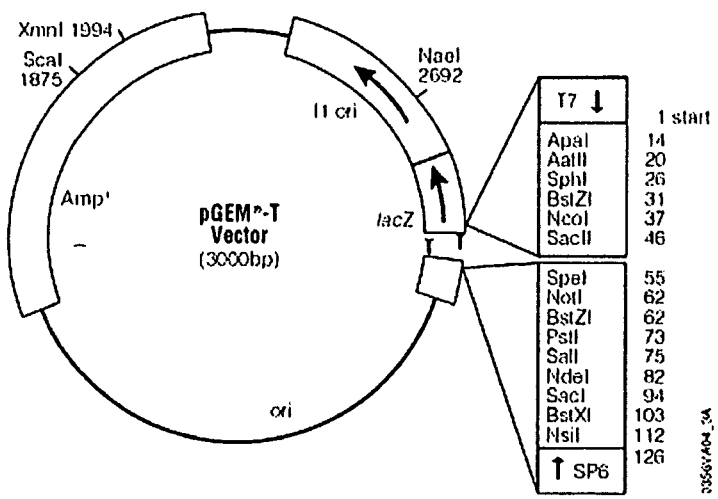
FIG. 13A presents a schematic representation of the cloning vector pGEM-T.

PCR cloning vector pGEM®-T was from Promega corp., Madison Wis., USA. The structure of the plasmid is presented in FIG. 13A, and its nucleotide sequence is presented in FIG. 13B.

b) Cloning Vector pDrive Structure and Sequence

Figure 14A:
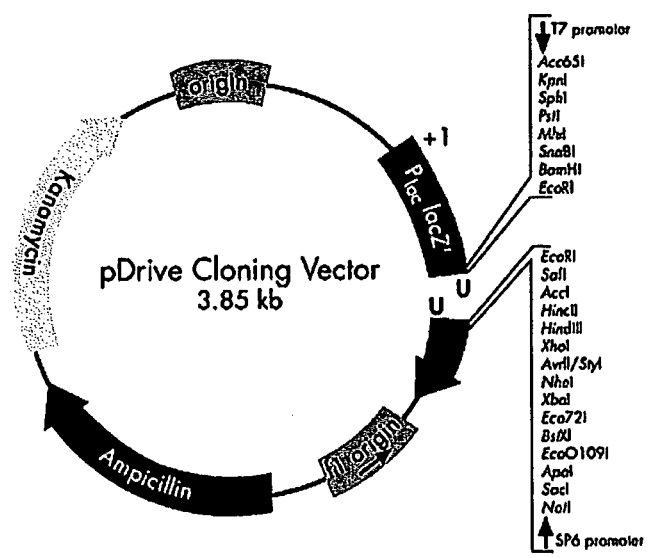
FIG. 14A presents a schematic representation of the cloning vector pDrive.

Cloning vector pDrive was from Qiagen, Hilden, Germany. The structure of this plasmid is presented in FIG. 14A and its nucleotide sequence in FIG. 14B.

c) Cloning Vector pBlueSK+ Structure and Sequence

Cloning vector pBluescript II® SK+ (Ac. No X52328) was from Stratagene, La Jolla, Calif., USA.

Figure 15A:
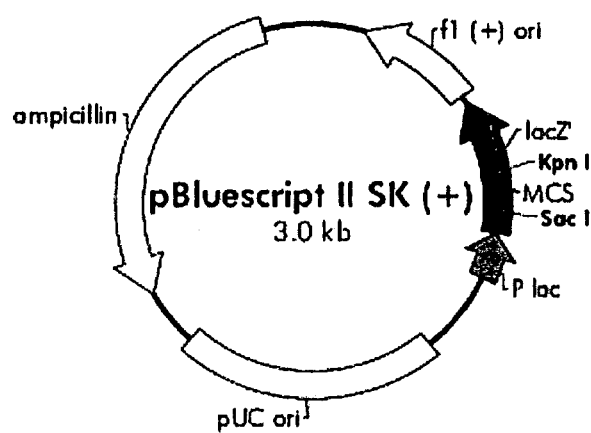
FIG. 15A presents a schematic representation of the cloning vector pBluescript II SK (+).

The structure of this plasmid is presented in FIG. 15A and, its nucleotide sequence is presented in FIG. 15B.

d) Cloning Vector pUC19 Structure and Sequence

Figure 16A:
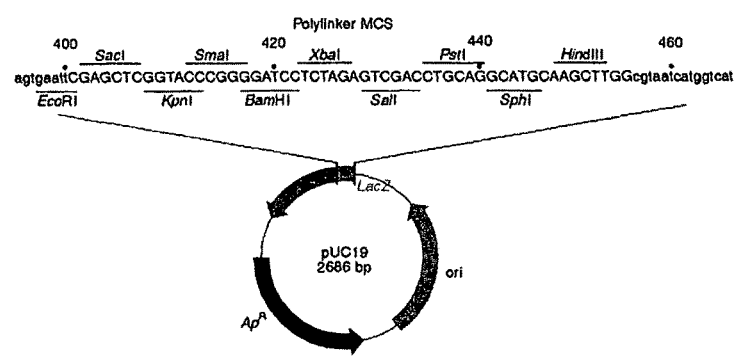
FIG. 16A presents a schematic representation of the cloning vector pUC 19.

Cloning vector pUC19 (Ac. No M77789) is presented schematically in FIG. 16A, and its nucleotide sequence is presented in FIG. 16B.

e) Plasmid pSK9 Structure and Sequence

Figure 17A:
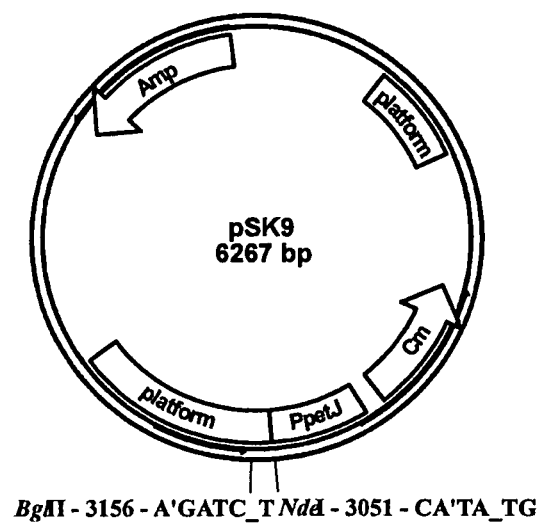
FIG. 17A presents a schematic representation of genes organized in the vector pSK9.

The non-public pSK9 vector was generated in the lab of V. V. Zinchenko (Moscow, Russia). A schematic of pSK9 structure is presented in FIG. 17A, and its nucleotide sequence is presented in FIG. 17B.

Protocols for Generation of *Synechocystis* sp. PCC 6803 Mutants Overexpressing the Following Genes:
a) malic enzyme
b) malate dehydrogenase
c) malic enzyme and malate dehydrogenase
d) pyruvate kinase 1
e) pyruvate kinase 2
f) pyruvate kinase, enolase and phosphoglycerate mutase
g) enolase
h) phosphoglycerate mutase
i) pyruvate kinase (1 or 2)/enolase/phosphoglycerate mutase
j) phosphoketolase
k) phosphoacetyltransacetylase
l) phosphoketolase/phosphoacetyltransacetylase
m) acetaldehyde dehydrogenase
n) PEP carboxylase
o) ribulose-1,5-bisphosphate carboxylase/oxygenase (RubisCO)

Construction of DNA-Vectors for Overexpression

In General:

DNA sequences encoding genes of interest were amplified by polymerase chain reaction (PCR) using specific primers. When the genomic sequence did not contain appropriate restriction sites for cloning, primers were designed containing restriction sites. Genomic DNA from *Synechocystis* sp. PCC 6803 was used as template. The amplified PCR fragments were digested with the appropriate restriction enzymes and cloned into either a self replicating plasmid (pVZ series) or an integrative plasmid (pSK series). As promoters either the genomic 5'region of the specific gene itself was used or alternative an inducible promoter like PpetJ. (PpetJ, pVZ, pSK, for description see below mentioned adh/pdc constructs). An antibiotic resistance cassette for selection of positive clones is present on the appropriate plasmid. The structures and sequences of all used DNA-vectors are described below (see 2).

Genetic engineering of constructs as well as PCRs, ligations into cloning vectors, insertions of antibiotic resistance cassettes and transformations into *E. coli* were done using standard procedures (state of the art) or according to the manufacturer instructions.

All pVZ plasmids were transferred to *Synechocystis* sp. PCC 6803 bp conjugation. This method is described for the below mentioned adh/pdc constructs. The pSK constructs were transferred to *Synechocystis* sp. PCC 6803 by transformation. The method of transformation using the natural competence of *Synechocystis* sp. PCC 6803 for DNA uptake was already described in detail for the generation of the glycogen synthase mutant.

a) Construction of DNA-Vectors for Overexpression of Malic Enzyme

The open reading frame (ORF) slr0721 encodes malic enzyme 1 (EC 1.1.1.38), Ac. No P72661. The amino acid sequence for this protein is presented in FIG. 18A.

For overexpression of malic enzyme, the encoding me gene together with its gene-specific terminator region was PCR-amplified using the following primer:
Mae-NdeI.fw: 5'-CATATGGTTAGCCTCACCCCCAAT-3, (SEQ ID NO:167), primer contains a NdeI restriction site for cloning (marked in bold letters)
MeLongClaI.rv: 5'-ATCGATCGGGATGGCCTATTTATGG 3' (SEQ ID NO:168), primer contains a ClaI restriction site for cloning (marked in bold letters)

The PCR fragment was amplified by a High-Fidelity DNA Polymerase (Phusion™; Finnzymes), adenylated (BIOTAQ™ DNA-Polymerase; BIOLINE), cloned into the pDrive vector (Qiagen) and restricted with NdeI/ClaI (Fermentas). This fragment was cloned into the pSK9 vector, digested with NdeI/ClaI. The gene is incorporated into a non-coding genome region of *Synechocystis* sp. PCC 6803 via the integrated platform. The expression of the enzyme is under control of the copper dependent promoter PpetJ.

Figure 18B:
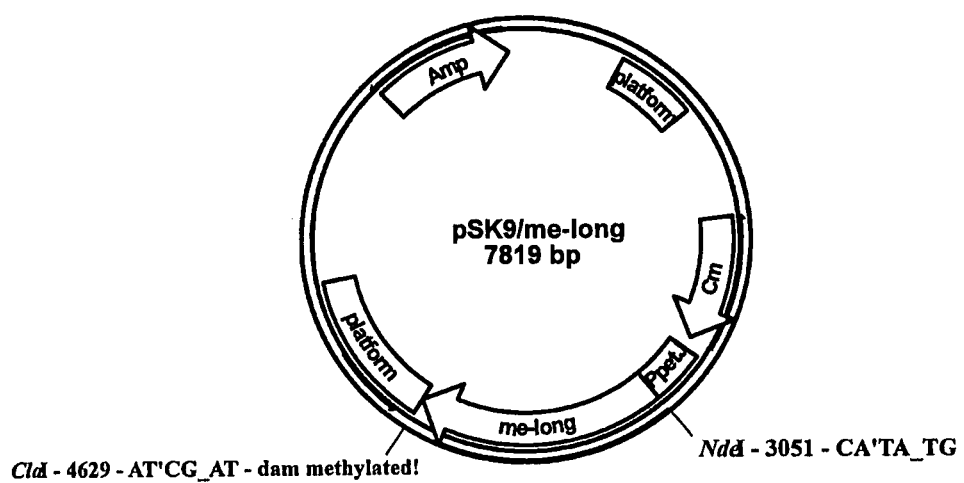
FIG. 18B presents a schematic of genes organized in the construct of *Synechocystis* sp. strain PCC6803.

The construct used, designated as pSK9/me-long, has the structure presented in FIG. 18B. The insert for this clone has the nucleotide sequence presented in FIG. 18C b) Construction of DNA-Vector for Overexpression of Malate Dehydrogenase An open reading frame (ORF) sll0891 encodes malate dehydrogenase (EC 1.1.1.37), Ac. No Q55383. The amino acid sequence for this protein is presented in FIG. 19A.

For overexpression of malate dehydrogenase a construct was generated including start-codon and the gene specific termination loop of the mdh gene using the following primers:

```
                                                       (SEQ ID NO: 169)
Mdh-NdeI.fw:  5'-CATATGAATATTTTGGAGTATGCTCC-3',
``` primer contains a NdeI restriction site for cloning (marked in bold letters)

```
                                                       (SEQ ID NO: 170)
   Mdh-ClaI.rv  5'-ATCGATAAGCCCTAACCTCGGTG-3',
``` primer contains a ClaI restriction site for cloning (marked in bold letters)

The PCR fragment was amplified by a High-Fidelity DNA Polymerase (Phusion™; Finnzymes), adenylated (BIOTAQ™ DNA-Polymerase; BIOLINE), cloned into the pDrive vector (Qiagen) and restricted with NdeI/ClaI (Fermentas). This fragment was cloned into the pSK9 vector, digested with NdeI/ClaI. The expression of the enzyme is under the control of the copper dependent promoter PpetJ.

Figure 19B:
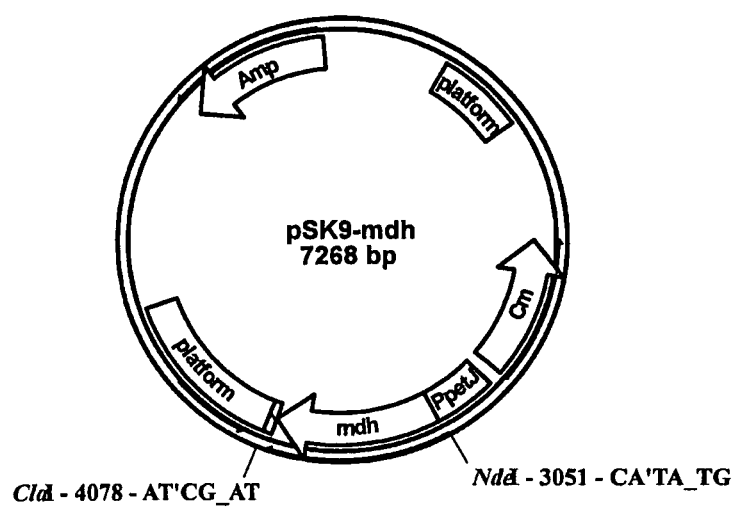
FIG. 19B presents a schematic representation of gene organization for the construct pSK9-mdh.

The construct used, designated as pSK9/mdh, has the structure presented in FIG. 19B; the nucleotide sequence for the insert of this clone is presented in 19C.

c) Construction of DNA-Vector for Co-Overexpression of Malic Enzyme and Malate Dehydrogenase This construct was generated for co-overexpression of malic enzyme and malate dehydrogenase. These genes were amplified by PCR using primers including the start and stop-codon of the me gene (PCR fragment I) and including the ribosome binding site (RBS) and termination loop of the mdh gene (PCR fragment II). The co-expression of the enzymes is under the control of the copper dependent promoter PpetJ.

The following primers were used for amplification
PCR Fragment I:

```
                                                       (SEQ ID NO: 171)
   Mae-NdeI.fw:  5'-CATATGGTTAGCCTCACCCCCAAT-3',
``` primer contains a 'NdeI restriction site for cloning (marked in bold letters)

```
   MeShortClaI.rv:
                                                       (SEQ ID NO: 172)
   5'-ATCGATACAATTCCCGATTAACTATTGACC-3',
``` primer contains a ClaI restriction site for cloning (marked in bold letters)

PCR fragment II:

```
                                                       (SEQ ID NO: 173)
MdhRBSClaI.fw:  5'-ATCGATTTTTCTCCACCATCAACACC-3',
``` primer contains a ClaI restriction site for cloning (marked in bold letters)

```
                                                       (SEQ ID NO: 174)
   MdhBglII.rv:  5'-AGATCTAAGCCCTAACCTCGGTG-3',
``` primer contains a BglII restriction site for cloning (marked in bold letters)

The PCR fragments were amplified by a High-Fidelity DNA Polymerase (Phusion™; Finnzymes), adenylated (BIOTAQ™ DNA-Polymerase; BIOLINE), cloned into the pDrive vector (Qiagen) and restricted with NdeI/ClaI and ClaI/BglII (Fermentas), respectively. These fragments were cloned into the pSK9 vector, first digested with NdeI/ClaI for integration of malic enzyme and secondly with ClaI/BglII for integration of malate dehydrogenase.

Figure 19D:
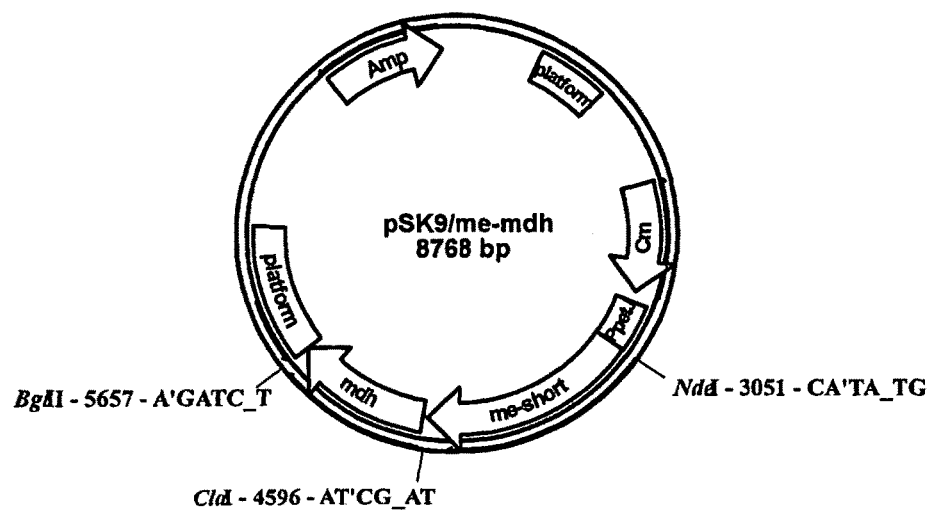
FIG. 19D presents a schematic representation of gene organization for the construct pSK9/me-mdh.

The construct used, designated as pSK9/me-mdh, has the structure presented in FIG. 19D, and the nucleotide sequence of its insert is presented in FIG. 19E.

d) Construction of DNA-Vectors for Overexpression of Pyruvate Kinase 1

The open reading frame (ORF) sll0587 encodes a pyruvate kinase 1 (EC 2.7.1.40 (PK1)), Ac. No Q55863. The amino acid sequence of this protein is presented in FIG. 20A.

Two constructs were generated in order to overexpress pyruvate kinase 1. One, harboring the own pyruvate kinase promoter region, and another construct on which pyruvate kinase 1 is under control of the inducible promoter PpetJ.

For the construct with the genomic 5'-region of the pyruvate kinase gene itself serving as promoter, a 2376 bp fragment containing the entire coding sequence from pyruvate kinase 1 (sll 0587) plus 770 bp upstream of the gene (promoter region) and 320 bp downstream of the gene (terminator region) was amplified by PCR using the following primer:

```
                                                       (SEQ ID NO: 175)
   #pykA-5fw:  5'-CCTGTTATTGGCCACGGGCAGTA-3', (SEQ ID NO: 176)
   #pykA-2rv:  5'-GGTTTACCCTGGGCTCGAGAATTTAGG-3',
``` primer contains a XhoI restriction site (CTCGAG) for cloning (marked in bold letters).

The PCR fragment was digested with MfeI/XhoI (MfeI site was present in the genomic sequence; MfeI shares compatible cohesive ends with EcoRI), subcloned into pIC20H (using EcoRI/XhoI), cut out of this plasmid with SalI/XhoI and ligated into the E. coli-Synechocystis shuttle vector pVZ321 (self replicating plasmid).

Figure 20B:
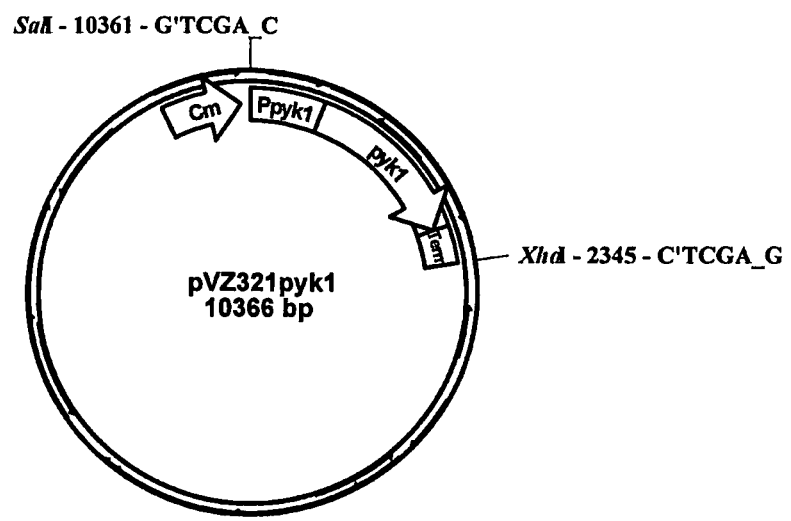
FIG. 20B presents a schematic representation of gene organization for the construct pVZ321-pyk1.

The construct used, named pVZ321-pyk1, has the structure presented in FIG. 20B, and its insert nucleotide sequence is presented in FIG. 20C.

For the construct on which pyruvate kinase 1 is under control of the inducible promoter PpetJ, a 1763 bp fragment containing the entire coding sequence from pyruvate kinase 1 (sll 0587) plus 320 bp downstream of the gene (terminator region) was amplified by PCR using the following primer:

```
                                                       (SEQ ID NO: 177)
   #pykA-3fw:  5'-CCCGGTGAAGCATATGAGACCCCT-3',
``` primer contains a NdeI restriction site (CATATG) for cloning (marked in bold letters). ATG in the restriction site represents the start codon of the gene.

```
                                                       (SEQ ID NO: 178)
   #pykA-2rv:  5'-GGTTTACCCTGGGCTCGAGAATTTAGG-3',
``` primer contains a XhoI restriction site (CTCGAG) for cloning (marked in bold letters).

The PCR fragment was digested with NdeI/XhoI, ligated to PpetJ (SalI/NdeI) and cloned into the E. coli-Synechocystis shuttle vector pVZ321 (self replicating plasmid).

Figure 20D:
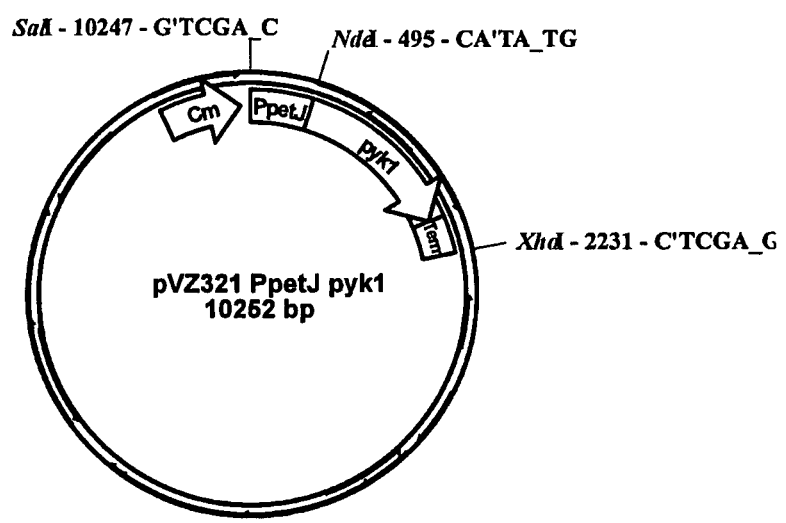
FIG. 20D presents a schematic representation of gene organization for the construct pVZ321 PpetJ pyk1.

The construct used, named pVZ321-PpetJ-pyk1, has the structure presented in FIG. 20D, and the nucleotide sequence of its insert is presented in FIG. 20E.

e) Construction of DNA-Vectors for Overexpression of Pyruvate Kinase 2

The open reading frame (ORF) sll1275 encodes pyruvate kinase 2 (EC 2.7.1.40 (PK2)), Ac. No P73534. The amino acid sequence for this protein is presented in FIG. 21A.

Two constructs were generated in order to overexpress pyruvate kinase 2. One, harboring the own pyruvate kinase promoter region, and another construct on which pyruvate kinase 2 is under control of the inducible promoter PpetJ.

For the construct with the genomic 5' region of the pyk2 gene itself serving as promoter, a 2647 bp fragment containing the entire coding sequence from pyk 2 (sll 1275) plus 600 bp upstream of the gene (promoter region) and 280 bp downstream of the gene (terminator region) was amplified by PCR using the following primer:

```
                                        (SEQ ID NO: 179)
#pykB-1fw: 5'-CCTAAATTCAGGTCGACCGGCAAAC-3',
``` primer contains a SalI restriction site (GTCGAC) for cloning (marked in bold letters).

```
# pykB-2rv:
5'-CACCAACCAGGCTCGAGTGGG-3',     (SEQ ID NO: 180)
``` primer contains a XhoI restriction site (CTCGAG) for cloning (marked in bold letters).

The PCR fragment was digested with SalI/XhoI and ligated into the *E. coli-Synechocystis* shuttle vector pVZ321 (self replicating plasmid).

Figure 21B:
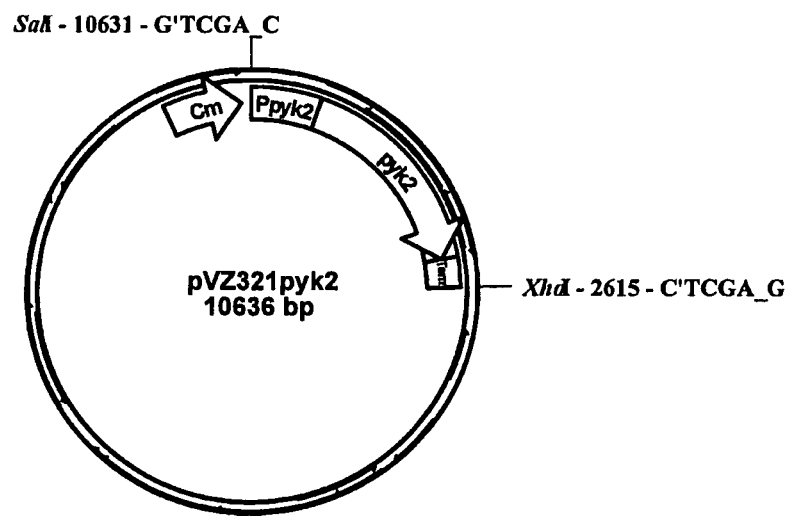
FIG. 21B presents a schematic representation of gene organization for the construct pVZ321pyk2.

The construct used, named pVZ321-pyk2, has the structure presented in FIG. 21B, and the nucleotide sequence of its insert is presented in FIG. 21C.

For the construct on which pyruvate kinase 2 is under control of the inducible promoter PpetJ, a 2057 bp fragment containing the entire coding sequence from pyruvate kinase 2 (sll 1275) plus 280 bp downstream of the gene (terminator region) was amplified by PCR using the following primer:

```
# pykB-3fw:
5'-CCTAATTTCAGCCCCATATGCAAACG-3',   (SEQ ID NO: 181)
``` primer contains a NdeI restriction site (CATATG) for cloning (marked in bold letters). ATG in the restriction site represents the start codon of the gene.

```
# pykB-2rv:
5'-CACCAACCAGGCTCGAGTGGG-3',    (SEQ ID NO: 182)
``` primer contains a XhoI restriction site (CTCGAG) for cloning (marked in bold letters).

The PCR fragment was digested with NdeI/XhoI, ligated to PpetJ (SalI/NdeI) and cloned into the *E. coli-Synechocystis* shuttle vector pVZ321 (self replicating plasmid).

Figure 21D:
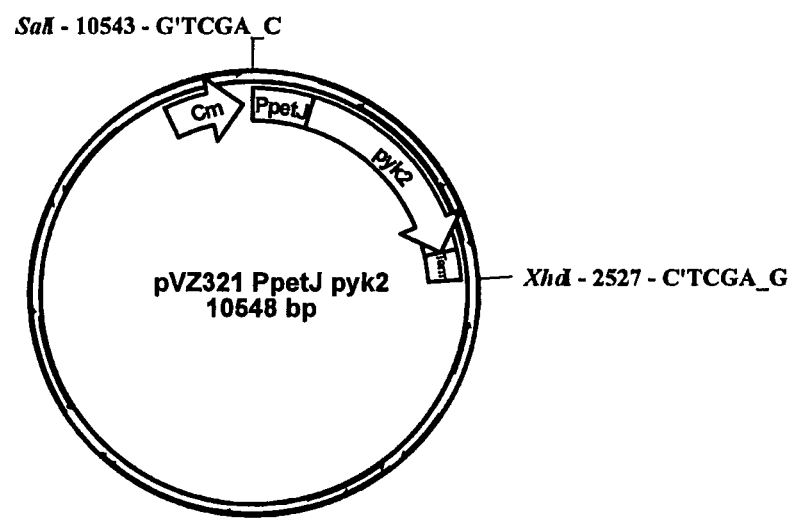
FIG. 21D presents a schematic representation of gene organization for the construct. pVZ321 PpetJ pyk2.

The resulting construct, pVZ321-PpetJ-pyk2, has the structure presented in FIG. 21D, and the nucleotide sequence of its insert is presented in FIG. 21E.

f) Construction of DNA-Vector for Overexpression of Pyruvate Kinase, Enolase and Phosphoglycerate Mutase A DNA-vector was constructed in order to express additional genes coding for pyruvate kinase, phosphoglycerate mutase and enolase. A DNA fragment encoding these genes was cut out of plasmid #67. This plasmid was constructed by Dr. John Coleman, University of Toronto, Toronto, Canada.

Figure 22A:
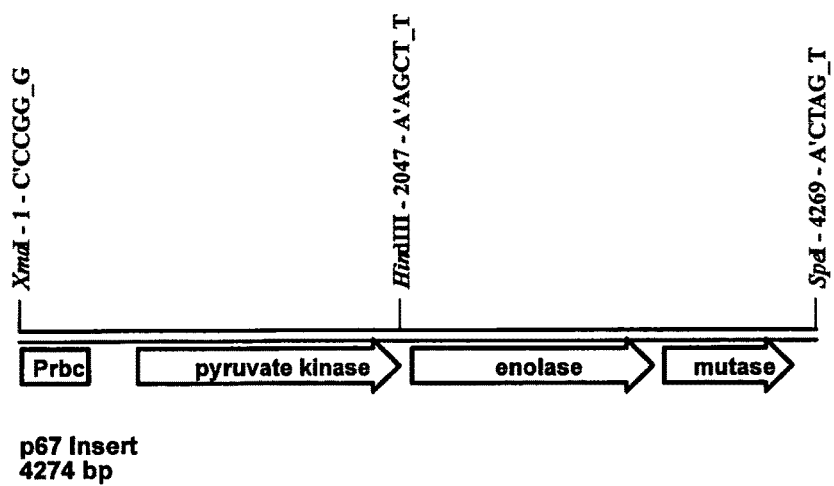
FIG. 22A presents a schematic representation of the gene organization for the p67 insert.

The insert of plasmid #67 has the structure presented in FIG. 22A.

The insert of plasmid #67 contains a 357 bases long cyanobacterial ribulose-1,5-bisphosphate carboxylase/oxygenase (RubisCO) promoter (Prbc) from *Synechococcus* PCC 7942. Downstream of this promoter there are three inserted open reading frames, the first is pyruvate kinase 1 from *E. coli*, the second enolase and the third phosphoglycerate mutase both from *Zymomonas mobilis*. The pyruvate kinase region differs from *E. coli* K-12 pyruvate kinase 1 (Ac. No AAC74746) by 3 nucleotides and one amino acid. (G to D mutation, underlined in the sequence below). The enolase gene from *Zymomonas mobilis* (Ac. No YP_163343) is a 100% amino acid match. The nucleotide sequence differs by two synonymous substitutions in the enolase region. The phosphoglycerate mutase gene is one amino acid different from *Zymomonas* (Ac. No YP_162975), from G to D at 118th amino acid (underlined in the sequence below). A HindIII site links the *E. coli* pyruvate kinase and the *Zymomonas* enolase genes.

The amino acid sequences of the enzymes encoded by the described insert are presented in FIG. 22B for pyruvate kinase I (*E. coli* K12); in FIG. 22C for enolase (*Zymomonas mobilis*); and in FIG. 22D for phosphoglycerate mutase (*Zymomonas mobilis*).

The nucleotide sequence of the described insert of plasmid #67 is presented in FIG. 22E.

The insert of plasmid #67 was cut out the vector using restriction enzymes XmaI and SpeI and cloned into the *E. coli-Synechocystis* shuttle vector pVZ321 and pVZ322 (self replicating plasmids) (XmaI/XbaI); XbaI and SpeI share compatible cohesive ends.

Figure 22F:
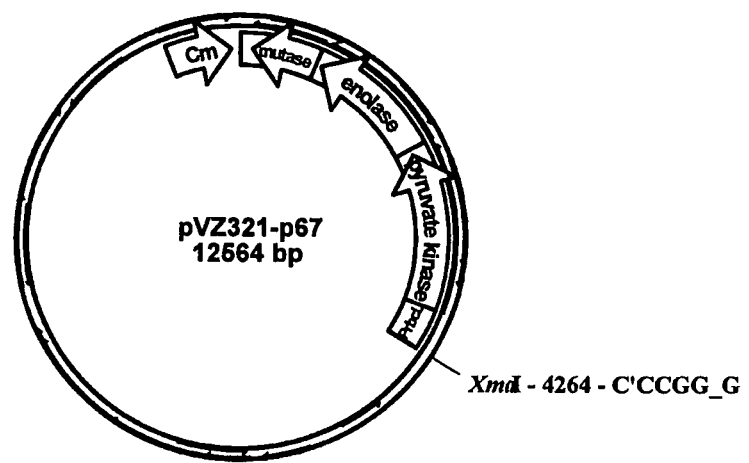
FIG. 22F presents a schematic representation of gene organization for the construct pVZ321-p67.
Figure 22G:
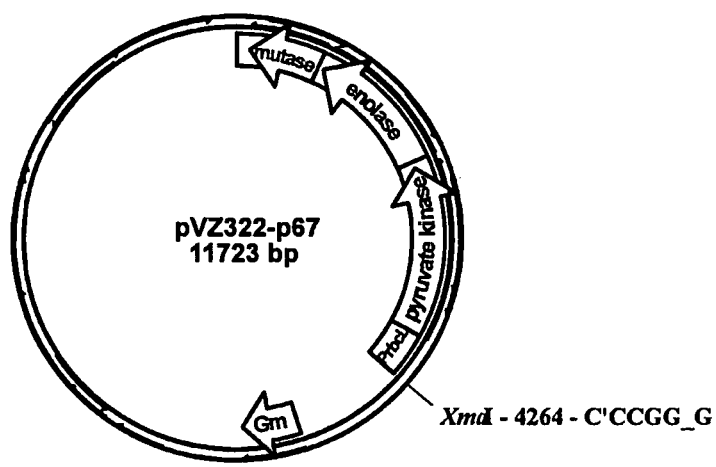
FIG. 22G presents a schematic representation of gene organization for construct pVZ322-p67.

Plasmid pVZ321-p67 has the structure presented in FIG. 22F, and plasmid pVZ322-p67 has the structure presented in FIG. 22G.

g) Construction of DNA-Vectors for Overexpression of Enolase

Figure 23B:
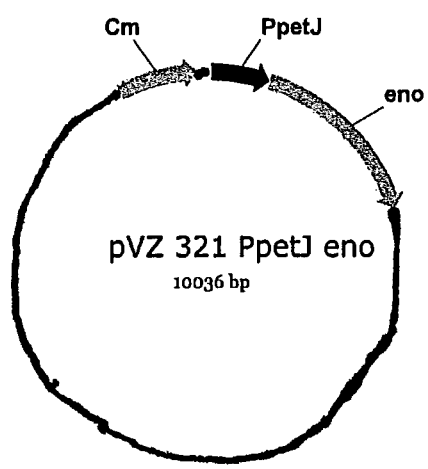
FIG. 23B presents a schematic representation of gene organization for construct pVZ321 PpetJ eno.

The open reading frame (ORF) slr0752 encodes the enolase (eno, 2-phosphoglycerate dehydratase) (EC 4.2.1.11), Ac. No BAA18749. The amino acid sequence for this protein is presented in FIG. 23A.

A construct was generated for overexpression of enolase under control of the inducible promoter PpetJ.

The construct includes the petJ promoter, the 1299 bp coding sequence for enolase (slr0752) and 214 bp downstream of the gene (terminator region). The enolase gene was amplified by PCR using the following primer:

```
# Eno-SacI-ATG
                                    (SEQ ID NO: 183)
5'-TAGAGCTCTTAAGTAAAGTCCCCGCCACCAT-3',

# Eno-XhoI-rev
                                    (SEQ ID NO: 184)
5'-TACTCGAGGTCATTGCTTCCTTGGCTTAGAAC-3',
```

Primers contain a SacI or XhoI restriction site, respectively, for cloning (marked in bold letters).

The PCR fragment was digested with SacI/XhoI and ligated downstream of the PpetJ promoter into pJet-PpetJ. The entire PpetJ-enolase fragment was cut out of this plasmid with SalI/XhoI and ligated into the *E. coli-Synechocystis* shuttle vector pVZ321 (self replicating plasmid).

The construct used, named pVZ321-PpetJ-eno, has the structure presented in 23B, and the nucleotide sequence of its insert is presented in 23C.

h) Construction of DNA-Vectors for Overexpression of Phosphoglycerate Mutase

The open reading frame (ORF) slr1124 encodes the phosphoglycerate mutase (pgm or gpmB) (EC 54.2.1), Ac. No BAA16651. The amino acid sequence for this protein is presented in FIG. 24A.

A construct was generated for overexpression of phosphoglycerate mutase under control of the inducible promoter PpetJ.

The construct includes the petJ promoter, the 1047 bp coding sequence for phosphoglycerate mutase (slr1124) and 143 bp downstream of the gene (terminator region). The phosphoglycerate mutase gene was amplified by PCR using the following primer:

```
# Pgm-SacI-ATG
                                        (SEQ ID NO: 185)
5'-TAGAGCTCACCAAAGACGATGTGGCCCACCAA-3'

# Pgm-XhoI-rev
                                        (SEQ ID NO: 186)
5'-TACTCGAGTATGACCCCGCTGTTGCAGTTC-3'
```

Primers contain a SacI or XhoI restriction site, respectively, for cloning (marked in bold letters).

The PCR fragment was digested with SacI/XhoI and ligated downstream of the PpetJ promoter into pJet-PpetJ. The entire PpetJ-phosphoglycerate mutase fragment was cut out of this plasmid with SalI/XhoI and ligated into the *E. coli-Synechocystis* shuttle vector pVZ321 (self replicating plasmid).

Figure 24B:
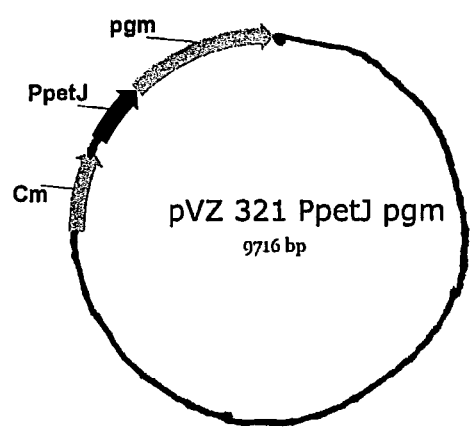
FIG. 24B presents a schematic representation of the gene organization of construct pVZ321-PpetJ-pgm.

The construct used, named pVZ321-PpetJ-pgm, has the structure presented in FIG. 24B, the nucleotide sequence of its insert is presented in FIG. 24C.

i) Construction of DNA-Vectors for Co-Overexpression of Pyruvate Kinase 1 or 2, Enolase and Phosphoglycerate Mutase Further plasmids were generated in order to overexpress the three glycolytic enzymes pyruvate kinase 1 or 2, enolase and phosphoglycerate mutase from one transcript.

One construct was generated for overexpression of pyruvate kinase 1 (ORF sll0587), enolase (ORF slr0752) and phosphoglycerate mutase (ORF slr1124); the second construct encodes pyruvate kinase 2 (ORF sll1275), enolase (ORF slr0752) and phosphoglycerate mutase (ORF slr1124). The protein sequences, EC and Accession numbers of the enzymes are already described herein.

In both constructs the overexpression of the three genes is under control of the inducible promoter PpetJ.

The glycolytic genes were amplified by PCR using the following primers:

```
pyruvate kinase 1 (pyk1):
# pykA-3fw
                                        (SEQ ID NO: 187)
5'-CCCGGTGAAGCATATGAGACCCCT-3'

(NdeI-site inserted)
# Pyk1-SacI-rev
                                        (SEQ ID NO: 188)
5'-TAGAGCTCTTAAGAAATACGGTGAATCTTG-3' pyruvate kinase 2 (pyk2):
pykB-3fw:
                                        (SEQ ID NO: 189)
5'-CCTAATTTCAGCCCCATATGCAAACG-3'

(NdeI-site inserted)
# Pyk2-SacI-rev
                                        (SEQ ID NO: 190)
5'-TAGAGCTCCCTATCCTTTGGACACC-3' enolase (eno):
Eno-SacI-fw
                                        (SEQ ID NO: 191)
5'-TAGAGCTCGTGTTTGGAGCATTACACACCGATG-3'

# Eno-BglII-rev
                                        (SEQ ID NO: 192)
5'-TAAGATCTTTTTAAGAATGTTTGGGACCCAG-3' phospgoglycerate mutase (pgm):
Pgm-BglII-fw
                                        (SEQ ID NO: 193)
5'-TCAGATCTGCCCCTCTGGGAAAAAATGACCA-3'

# Pgm-XhoI-rev
                                        (SEQ ID NO: 194)
5'-TACTCGAGTATGACCCCGCTGTTGCAGTTC-3'
```

All primers contain restriction sites for cloning (marked in bold letters).

PCR fragments were subcloned into PCR cloning plasmid pJet1.2 blunt. The genes were cut out of these plasmids with the appropriate restriction enzymes and ligated downstream of the PpetJ promoter into pIC-PpetJ as followed:

```
5'-XhoI-pIC-PpetJ-NdeI-3'
           5'-NdeI-pyk1-SacI-3'
                      5'-SacI-eno-BglII-3'
                                  5'-BglII-pgm-
                                         XhoI-3'
```

The same construct was generated using fragment 5'-NdeI-pyk2-SacI-3' instead of 5'-NdeI-pyk1-SacI-3'.

The entire PpetJ-pyk1-eno-pgm or PpetJ-pyk2 eno-pgm fragments were cut out of the cloning plasmid with PstI/XhoI and ligated into the *E. coli-Synechocystis* shuttle vector pVZ322 (self replicating plasmid).

Figure 24D:
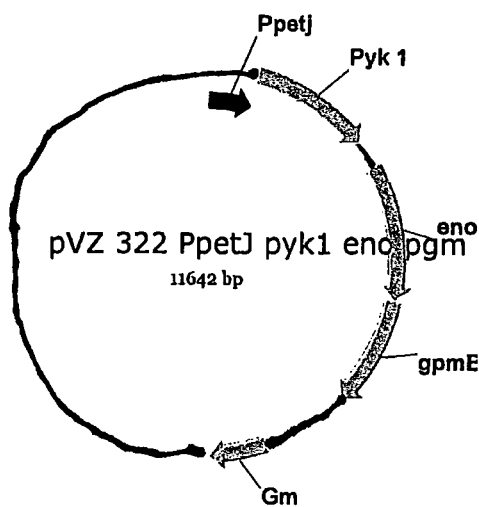
FIG. 24D presents a schematic representation of gene organization for the construct pVZ322-PpetJ-pyk1-eno-pgm.
Figure 24E:
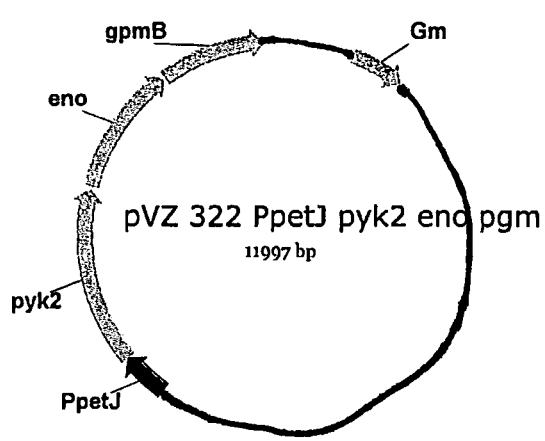
FIG. 24E presents a schematic representation of gene organization for the construct pVZ322-PpetJ-pyk2-eno-pgm.

The construct named pVZ322-PpetJ-pyk1-eno-pgm has the structure presented in FIG. 24D and the construct pVZ322-PpetJ-pyk2-eno-pgm has the structure presented in FIG. 24E. The sequence of the insert of pVZ322-PpetJ-pyk1-eno-pgm is presented in the FIG. 24F and the sequence of the insert of pVZ322-PpetJ-pyk2-eno-pgm is presented in FIG. 24G.

j) Construction of DNA-Vector for Overexpression of Phosphoketolase

The open reading frame (ORF) slr0453 encodes the probable phosphoketolase (phk), (EC 4.1.2.-), Ac. No P74690. The amino acid sequence of the protein is presented in FIG. 25A.

A construct was generated for overexpression of phosphoketolase under control of the inducible promoter PpetJ.

The construct includes the petJ promoter, the 2418 bp coding sequence for phosphoketolase (slr0453) and 307 bp downstream of the gene (terminator region). The phosphoketolase gene was amplified by PCR using the following primer:

```
                                        (SEQ ID NO: 195)
# phk1-NdeI 5'-GTGTCTCATATGGTTACATCCCCCTTTTCCCTT-3'

(SEQ ID NO: 196)
# phk2-XhoI 5'-CGAGCCCTGCTCGAGCAGGC-3'
```

Primers contain a NdeI or XhoI restriction site, respectively, for cloning (marked in bold letters).

The PCR fragment was digested with NdeI/XhoI and ligated downstream of the PpetJ promoter into pIC-PpetJ. The entire PpetJ-phosphoketolase fragment was cut out of this plasmid with PstI/XhoI and ligated into the *E. coli-Synechocystis* shuttle vector pVZ322 (self replicating plasmid).

The construct used, named pVZ321-PpetJ-phk, has the structure presented in FIG. 25B, and the nucleotide sequence of its insert is presented in FIG. 25C.

k) Construction of DNA-Vector for Overexpression of Phosphoacetyltransacetylase

The open reading frame (ORF) slr2132 encodes a phosphoacetyltransacetylase (pta), EC 2.3.1.8, Ac No. P73662. The amino acid sequence of this protein is presented in FIG. 26A.

A construct was generated for overexpression of phosphoacetyltransacetylase under control of the inducible promoter PpetJ.

The construct includes the petJ promoter, the 2094 bp coding sequence from ORF slr2132 and 258 bp downstream of the gene (terminator region). The phosphoacetyltransacetylase gene was amplified by PCR using the following primer:

```
# pta_pPETJ1-NdeI
                                          (SEQ ID NO: 197)
5'-GTGCCTCATATGACGAGTTCCCTTTATTTAAGCAC-3' pta_pPETJ2-XhoI
                                          (SEQ ID NO: 198)
5'-CGGTTGCTCGAGCATCTGGAACGGTTGGGTAAAT-3'
```

Primers contain a NdeI or XhoI restriction site, respectively, for cloning (marked in bold letters).

The PCR fragment was digested with NdeI/XhoI and ligated downstream of the PpetJ promoter into pIC-PpetJ. The entire PpetJ-phosphoacetyltransacetylase fragment was cut out of this plasmid with PstI/XhoI and ligated into the *E. coli-Synechocystis* shuttle vector pVZ322 (self replicating plasmid).

The construct used, named pVZ322-PpetJ-pta, has the structure presented in FIG. 26B, and the nucleotide sequence of the insert for construct pVZ322-PpetJ-pta is presented in FIG. 26C.

l) Construction of DNA-Vector for Co-Overexpression of Phosphoketolase and Phosphoacetyltransacetylase One further construct was created in order to co-overexpress the phosphoketolase and phosphoacetyltransacetylase from one transcript. The protein sequences, EC and Accession numbers of the enzymes are already described above. The expression of the genes is under control of the inducible promoter PpetJ. The phosphoketolase and phosphoacetyltransacetylase genes were amplified by PCR using the following primers:

```
# phk1
                                          (SEQ ID NO: 199)
5'-GTGTCTCATATGGTTACATCCCCCTTTTCCCTT-3' phk-BgIII-rev
                                          (SEQ ID NO: 200)
5'-GGTCACAGATCTGTTGTCCCCCATGGCCTAGCTA-3' phosphoacetyltransacetylase (pta)
pta-BgIII-fw
                                          (SEQ ID NO: 201)
5'-CCTTGCAGATCTGGATACGTTGAGGTTATTTAAATTATGA-3' pta_pPETJ2-XhoI
                                          (SEQ ID NO: 202)
5'-CGGTTGCTCGAGCATCTGGAACGGTTGGGTAAAT-3'
```

All primers contain restriction sites for cloning (marked in bold letters).

PCR fragments were cut with the appropriate restriction enzymes and ligated downstream of the PpetJ promoter into pIC-PpetJ as followed:

```
5'-XhoI-pIC-PpetJ-NdeI-3'
            5'-NdeI-phk-BglII-3'
                        5'-BglII-pta-XhoI-3'
```

The entire PpetJ-phk-pta fragment was cut out of the cloning plasmid pIC20H with SmaI/NruI and ligated into SmaI site of the *E. coli-Synechocystis* shuttle vector pVZ322 (self replicating plasmid).

The construct named pVZ322-PpetJ-phk-pta has the structure presented in FIG. 26D, and the nucleotide sequence of the insert of pVZ322-PpetJ-phk-pta is presented in FIG. 26E.

m) Construction of DNA-Vector for Overexpression of Aldehyde Dehydrogenase

The open reading frame (ORF) slr0091 encodes a aldehyde dehydrogenase (aldh), EC 1.2.1.3, Ac No. BAA10564 Q55811. The amino acid sequence for the protein is presented in FIG. 27A.

A construct was generated for overexpression of aldehyde dehydrogenase under control of the inducible promoter PpetJ. The construct includes the petJ promoter, the 1369 bp aldehyde dehydrogenase fragment containing the entire coding sequence from ORF slr0091 and 205 bp downstream of the gene (terminator region). The aldehyde dehydrogenase (aldh) gene was amplified by PCR using the following primer:

```
# aldh1-NdeI-fw
                                          (SEQ ID NO: 203)
5'-GTGCCTCATATGGAATACTGCTAAAACTGTTGTTGC-3' aldh2-XhoI-rev
                                          (SEQ ID NO: 204)
5'-GATCTCCTCGAGGTAAAGAATCAGCATAGGTCTGG-3'
```

Primers contain a NdeI or XhoI restriction site, respectively, for cloning (marked in bold letters).

The PCR fragment was digested with NdeI/XhoI and ligated downstream of the PpetJ promoter into pIC-PpetJ. The entire PpetJ-aldehyde dehydrogenase fragment was cut out of this plasmid with PstI/XhoI and ligated into the *E. coli-Synechocystis* shuttle vector pVZ322 (self replicating plasmid).

The construct used, named pVZ322-PpetJ-aldh, has the structure presented in FIG. 27B, and the nucleotide sequence of the insert of construct pVZ322-PpetJ-aldh is presented in FIG. 27C.

n) Construction of DNA-Vectors for Overexpression of PEP Carboxylase

The open reading frame (ORF) sll0920 encodes the phosphoenolpyruvate carboxylase (EC 4.1.1.31), BAA18393. The amino acid sequence for this protein is presented in FIG. 28A.

One construct was generated for overexpression of phosphoenolpyruvate carboxylase under control of the inducible promoter PpetJ.

The construct includes the petJ promoter, the 3105 bp ppc-fragment containing the entire coding sequence from phosphoenolpyruvate carboxylase (sll 0920) and 59 bp downstream of the gene (terminator region) was amplified by PCR using the following primer:

```
# ppc.NdeI.fw:
5'-CTAGAGGTTCATATGAACTTGGC-3',    (SEQ ID NO: 205)
``` this primer contains a NdeI restriction site (CATATG) for cloning (marked in bold letters)

```
# ppc.XhoI.rv:
5'-GTAAGCAGGCTCGAGGCAAG-3',    (SEQ ID NO: 206)
``` this primer contains a XhoI restriction site (CTCGAG) for cloning (marked in bold letters).

The PCR fragment was digested with NdeI/XhoI, subcloned into K8 (using NdeI/XhoI), cut out of this plasmid with SalI/XhoI and ligated into the E. coli/Synechocystis shuttle vector pVZ321 (self replicating plasmid). The pVZ321 vector has the GenBank accession number AF100176.

The construct used, named pVZ321-PpetJ-ppc, has the structure presented in FIG. 28B, and the nucleotide sequence for the pVZ321-PpetJ-ppc insert is presented in FIG. 28C.

o) Construction of DNA-Vectors for Overexpression of Ribulose-1,5-bisphosphate Carboxylase/Oxygenase (RubisCO)

Overexpression of the Synechocystis RuBisCO was reached by integration of a conjugative, self-replicating pVZ plasmid into Synechocystis containing either the rbcLXS operon alone or the rbcLXS operon as transcriptional fusion together with the pyruvate decarboxylase from Zymomonas mobilis.

The entire rbc operon from Synechocystis sp. PCC6803 was amplified by PCR using the primer pairs:
SynRbc-BglII-fw and SynRbc-PstI-rev for the over-expression from the rbcL-promoter, which are shown in FIGS. 28D and 28E, respectively.
SynRbc-SacI-fw and SynRbc-PstI-rev for the over-expression as transcriptional fusion with the Pdc from Zymomonas mobilis. The sequence of SynRbc-SacI-fw is shown in FIG. 28F.

The database entry numbers for the CyanoBase, the genome database for cyanobacteria (http://bacteria.kazusa.or.jp/cyanobase/index.html) for the Synechocystis rbcL-rbcX-rbcS coding sequences are slr0009 for the ribulose bisphosphate carboxylase large subunit (rbcL), slr0011 for the possible Rubisco chaperonin (rbcX) and slr0012 for the ribulose bisphosphate carboxylase small subunit (rbcS). The DNA sequence coding for the rbcLXS operon is depicted in FIG. 28G. The protein sequence obtained by translation of the protein coding DNA sequence is depicted in FIG. 28H for the rbcL large subunit; the rbcX Rubisco chaperonin protein sequence is shown in FIG. 28I and the protein sequence of the ribulose bisphosphate carboxylase small subunit (rbcS) is shown in FIG. 28J.

Mutants were selected on streptomycin plates and grown in BG11 medium containing the appropriate antibiotics (kanamycin 100 mg/l; streptomycin 10 mg/l).

In Synechocystis sp. PCC6803 mutants were generated by transforming the cells with two different plasmids, pVZ321b-Prbc-SynRbcLXS (FIG. 28K) and pVZ321b-PpetJ-PDC/SynRbcLXS (FIG. 28L).

In the following the vectors, which were used are described.

a) Plasmid pSK9 Structure and Sequence

The non-public pSK9 vector was generated in the lab of V. V. Zinchenko (Moscow, Russia). The structure of this plasmid is schematically represented in FIG. 29A, and its nucleotide sequence is presented in FIG. 29B.

b) Self-Replicating Synechocystis Plasmid pVZ321 Structure and Sequence

The pVZ321 vector has the GenBank accession number AF100176. This vector is presented schematically in FIG. 30A, and the pVZ321 nucleotide sequence is presented in FIG. 30B.

c) Self-Replicating Synechocystis Plasmid pVZ322 Structure and Sequence

The pVZ322 vector has the GenBank accession number AF100175. FIG. 31A presents a schematic of its structure, and FIG. 31B presents its nucleotide sequence.

d) construction of the Cloning Vector pIC20H

For cloning procedures a plasmid was constructed harboring promoter PpetJ in the multi-cloning site of cloning vector pIC20H, Ac. No. L08912, (Marsh J. L., Erfle M., Wykes E. J.; "The pIC plasmid and phage vectors with versatile cloning sites for recombinant selection by insertional inactivation"; Gene 32:481-485 (1984)). Promoter PpetJ was cut out of the herein described pSK9 plasmid with ClaI and KpnI and ligated into pIC20H (ClaI/KpnI), resulting in plasmid pIC-PetJ.

The plasmid pIC-PpetJ has the structure presented schematically in FIG. 32A, and the nucleotide sequence of pIC PpetJ is presented in FIG. 32B.

Generation of Additional Knock-Out/Knock-Down Mutants of Synechocystis Sp. PCC 6803: Methods and Results The following Knock-Out construct sequences have been conveniently described and provided herein: (a) alanine dehydrogenase (ald), (b) ADP-glucose pyrophosphorylase (glgC), (c) pyruvate water dikinase (ppsA), (d) lactate dehydrogenase (ldh), (e) acetate kinase (ack) and (f) phosphoacetyltransacetylase (pta). The following Knock-Down construct sequence is described and provided pyruvate dehydrogenase (pdhB). These constructs may be used singly or sequentially in order to provide one or more mutations.

Mutagenesis

Host cells are mutagenized by transformation of the DNA-vectors (knock-out-constructs) using the natural competence of Synechocystis sp. PCC 6803 for DNA uptake and its system for homologous recombination as previously described herein. The transformation may comprise one or more steps in order to create mutant cells having a single, double, triple, etc. knockout and/or knockdown mutations. Additionally, knockdown/knockout mutants may additionally be mutagenized by introducing one or more overexpressing DNA constructs as described herein. As noted previously herein, the concentration of the appropriate antibiotic(s) is increased stepwise when the cells are transferred onto another agar plate or into liquid culture (for kanamycin from initially 5 to 150 μg/ml BG11, for chloramphenicol from initially 1 to 15 μg/ml BG11 medium) in order to get fully segregated (homozygous) mutants. Transfers are done every 2 weeks. In case of kanamycin, the concentration in the range from 50 to 150 μg/ml agar is increased gradually over the course of 4 weeks.

Molecular Analysis of Mutant Host Cells

In order to clearly demonstrate that a targeted homologous recombination event occurred in the selected mutant(s)

cell, a variety of methods well known to one of ordinary skill in the art may be utilized. A test for successful knockout mutagenesis will be done initially by PCR amplifying a DNA fragment from the inserted antibiotic resistance cassette into the gene that should be knocked out. In addition, knockout mutants as well as knock-down mutants will be also checked by the detection and non-detection respectively of the target enzyme mRNA level in the mutant and wild type cells by using different techniques known in the art, e.g. RT-PCR, Northern blot or RNase protection assays. These recombinant DNA/molecular biology methods are well known to one of ordinary skill in the art; For example see: Methods in Enzymology, Vol. 167, (L. Packer, A. N. Glazer, eds); For extraction of genomic DNA: Franche C, Damerval T. in Methods of Enzymology, Vol. 167 p. 803-808; for extraction of total RNA: David l. Lane, Katherine G. Field, Gary J. Olsen, and Norman R. Pace in Methods of Enzymology, Vol. 167 p. 138-144; for Extraction of plasmid DNA: Grant R. Lambert and Noel G. Carr, Rapid Small-Scale Plasmid Isolation by Several Methods from Filamentous Cyanobacteria, Arch Microbiol (1982) 133: 122-125; for Northern Blots: Axmann, I. M., Kensche, P., Vogel, J., Kohl, S., Herzel, H. & Hess, W. R. (2005) Genome Biol 6, R73; for RT-PCR: Emanuel C, von Groll U, Müller M, Börner T, Weihe A. Development- and tissue-specific expression of the RpoT gene family of *Arabidopsis* encoding mitochondrial and plastid RNA polymerases. Planta. 2006 April; 223(5):998-1009; for RNase protection assay: W. R. Hess, B. Hoch, P. Zeltz, T. Hübschmann, H. Kössel and T. Bürner. Plant Cell 6 (1994), pp. 1455-1465. Academic Press, Inc., 1988), which are incorporated herein by reference.

Also, sufficient nucleotide sequence information for all enzymes is provided herein or available from known nucleotide sequence databases for the selection of the appropriate probes/primers for these analyses. With Northern Blot analysis, the abundance and relative amount of a mRNA will be detected. The same would be the case using a RNase protection assay but with a much higher sensitivity. The abundance and also the absolute amount of a mRNA can be determined with a high sensitivity using the RT-PCR.

With the PCR analysis, one forward primer is derived from the genetic sequence of the targeted enzyme and one reverse primer is derived from the biocide gene sequence; the amplified hybrid DNA fragment will be characterized and analyzed for predicted size and/or nucleotide sequence content. Mutant(s) cells found not to be expressing wildtype mRNA and found to have the above noted characteristics will be selected for further analysis.

Characterization of Knock-Out/Knock-Down Mutants
Cultivation of Cyanobacterial Wild Type and Mutant Strains For a knock-out or knock-down mutant(s) related to the formation of reserve compounds such as glycogen, e.g., mutants of further reserve metabolites syntheses as PHB or cyanophycin, wild type and mutant strains of *Synechocystis* PCC 6803 are grown as batch cultures in BG11 medium at 29° C. under continuous illumination with white light (intensity: 40 µE m$^{-2}$ s$^{-1}$) and aeration with air. For cultivation of mutants, the appropriate antibiotics are added to the medium (kanamycin 75 mg/l; chloramphenicol 15 mg/l). Samples are analyzed briefly before the nitrogen step down ("+N"), directly after resuspension of the cells in BG11 medium lacking a nitrogen source ("−N", 0 h) and after 3, 6 and 24 hours.

All other knock-out or knock-down mutants will be grown under standard culture conditions known in the art.

As provided below, mutants and wild type cells will be characterized regarding their intra- and extracellular pyruvate content using optical enzymatic tests and their profile of all relevant metabolites respectively. (incl. 3-PGA, PEP, pyruvate, acetyl-CoA, glycogen, PHB, cyanophycin, malate, oxaloacetate, 2-oxoglutarate, acetate, lactate, etc.) using appropriate techniques for example, spectroscopic methods, chromatographic methods such ion chromatography or optical or enzymatic methods or combinations thereof. The analysis will always be done in comparison to the wild type.

Also the growth and pigmentation properties of mutant(s) will be compared to the wild type cell using standard protocols well known in the art.

The example presented here will provide a graphic depiction of growth properties for wild type and mutant cells as change in X vs. time, wherein X is ideally dry weight or biovolume. Alternatively, optical density, cell count and chlorophyll could be used as reference parameters. Alternatively, pigmentation could be quantified spectrophotometrically as another parameter.

Protocol for Characterization of Metabolic Mutants Containing at Least One First and/or One First and One Second Genetic Modification Generation of knock-out and over-expression mutants with single, double, triple, etc. knock-out and/or knock-down and/or over-expression mutations as a first genetic modification and the molecular analysis of such mutant cells in general is already described above.

Characterization of Metabolic Mutants

Metabolic mutant strains having a first genetic modification were characterized regarding their growth properties and certain extra- and intracellular metabolites in comparison to wild type strains. In addition the afore described metabolic mutants were also transformed with PDC and ADH as a second genetic modification and were characterized regarding growth properties, extra- and intracellular metabolites and ethanol production rates in comparison to the appropriate reference strain(s) expressing PDC and ADH, but lacking the metabolic mutation (first genetic modification).

Cultivation of Cyanobacterial Wild Type and Mutant Strains

Wild type and mutant strains of *Synechocystis* PCC 6803 were grown as batch cultures in BG11 medium at 28-29° C. For cultivation of mutants the appropriate antibiotics were added to the medium (kanamycin 75 mg/l; chloramphenicol 10 mg/l; gentamycin 3 mg/l or streptomycin 10 mg/l). In order to avoid premature induction of gene expression in mutants having constructs with PpetJ or PisiA promoter, these mutants were grown in culture medium supplemented with excess copper or iron (5× Cu for PpetJ; 3× Fe for PisiA).

Prior to characterization experiments, pre-cultures were grown in BG11 medium (no excess of Cu or Fe) and aeration with 0.5% CO2 in air.

For characterization experiments, wild type and mutant strains were grown in BG11 medium. Mutants having constructs with PpetJ or PisiA (overexpression, knock-down mutants or mutants expressing PDC and ADH) were transferred to BG11 lacking Cu (PpetJ) or Fe (PisiA), respectively, in order to induce gene expression (described in detail for PDC/ADH expressing mutants).

The total culture volume in characterization experiments was 300 mL in a 500 mL Schott-Flask; the initial OD750 was 1. Cultures were aerated with 0.5% CO2 in air.

All mutants were characterized under constant light conditions (75-100 µE m-2 s-1). In fast growing cultures, the light intensity was increased during the growth experiment (75-100 μE m-2 s-1 up to OD5; then light intensity was increased to 200 μE m-2 s-1).

Knock-out mutants related to fermentative pathways such as lactate dehydrogenase, acetate kinase or phosphoacetyl-transacetylase were additionally characterized under day/night conditions (12 h 100 μE m-2 s-1/12 h dark). Knock-out mutants related to the formation of reserve compounds such as glycogen or PHB were additionally examined after transferring the cells in BG11 medium lacking a nitrogen source (nitrogen starvation conditions) as previously described herein.

Principle of Ethanol Quantification:

Ethanol is oxidized by nicotinamide-adenine dinucleotide (NAD$^+$) to acetaldehyde in a reaction, which is catalyzed by the enzyme alcohol dehydrogenase (ADH) (reaction 1). The acetaldehyde, which is formed in the reaction, is quantitatively oxidized to acetic acid by the enzyme aldehyde dehydrogenase (Al-DH) (reaction 2).

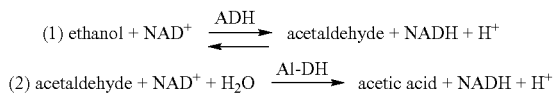

$$(1)\ \text{ethanol} + \text{NAD}^+ \xrightleftharpoons{\text{ADH}} \text{acetaldehyde} + \text{NADH} + \text{H}^+$$

$$(2)\ \text{acetaldehyde} + \text{NAD}^+ + \text{H}_2\text{O} \xrightarrow{\text{Al-DH}} \text{acetic acid} + \text{NADH} + \text{H}^+$$

In reactions (1) and (2) reduced nicotinamide-adenine dinucleotide (NADH) is formed. The amount of NADH formed is proportionate to the amount of ethanol in the sample. NADH is easily quantified by means of its light absorbance. The absorbance is usually measured at 340 nm, Hg 365 nm or Hg 334 nm.

Procedure:

Preparation of solutions: Solution 1: 1.3 mg/ml NAD and 0.27 U aldehyde dehydrogenase in potassium diphosphate buffer, pH 9.0. Solution 2: Suspension of alcohol dehydrogenase (ADH) with approx. 4000 U/ml. Alternatively, the chemicals and solutions of the ethanol determination kit of Boehringer Mannheim/R-Biopharm (Cat. No. 10 176 290 035) can be used. Sample and solution 1 are mixed in a ratio of 3 ml solution 1 and 0.1 ml sample (if necessary the sample is diluted with water). After approx. 3 min the absorbance is measured ($A_1$). The reaction is then started by the addition of ADH suspension (solution 2, 0.050 ml for 3 ml solution 1 and 0.1 ml sample). After completion of the reaction (approx. 5 to 10 min) the absorbance is measured again ($A_2$). The absorption measurements can be performed using a photometer or a microplate reader. For plate reader measurements all volumes are downscaled.

From the measured absorbance difference $\Delta A = (A_2 - A_1)$ the ethanol concentration in the sample is calculated with the equation:

$$c = \frac{V \times MG}{\varepsilon \times d \times v \times 2 \times 1000} \times \Delta A$$

c, ethanol concentration [g/L]; V, total volume [mL]; MG, molecular weight of ethanol (46.07 g/mol); e, extinction coefficient (6.3 L×mmol$^{-1}$×cm$^{-1}$ at 340 nm); d, light path [cm]; v, sample volume [mL]

LITERATURE

Protocol of the kit Ethanol, UV method for the determination of ethanol in foodstuff and other materials, Cat. No. 10176290035, R-Biopharm AG, Darmstadt, Germany.

H.-O. Beutler (1984) in: Methods in Enzymatic Analysis (Bergmeyer, H. U. ed.) 3$^{rd}$ ed. Vol. VI, pp. 598-606, Verlag Chemie, Weinheim, Germany.

Growth Properties

For characterization experiments, metabolic mutant and the appropriate reference strains were cultured as described. Growth was followed for about 14 days by measuring optical density (daily) and chlorophyll (every second day). Photosynthetic O$_2$ production was determined several times during exponential growth phase using a Clark electrode as followed:

Measurement of Photosynthetic Oxygen Evolution

Cell are washed 2× with fresh growth medium by centrifugation (3000×g, 10 min, room temperature) and resuspension. The cells are finally resuspended in growth medium to a chlorophyll concentration of 10 to 15 μg chlorophyll/ml. Chlorophyll is measured as described by [N. Tandeau De Marsac and J. Houmard]. The cells are filled into the chamber of a Rank Brothers oxygen electrode (Digital Model 10, Rank Brothers, Cambridge, England) and sodium bicarbonate is added to a final concentration of 25 mM.

The excitation light for photosynthesis experiments is provided by a slide projector with a 150-watt lamp (Osram, Xenophot HLX Germany).

The oxygen concentration in the chamber is recorded continuously with chart recorder (REC 112, Amersham Pharmacia Biotech) connected to the electrode. The chamber of the oxygen electrode is maintained at 25° C. with a circulating, temperature-controlled water bath (RM6, Lauda Brinkmann). For the calibration of the electrode the signal difference of air-saturated water (100% saturation) and oxygen free water (zero point) is measured. Oxygen free water is obtained by adding sodium dithionite (approximately 1 mg/ml). The measured amplitude is equated with the solubility of oxygen in water at 25° C. and a pressure of 1 bar (8.11 mg oxygen/L).

Literature: N. Tandeau De Marsac and J. Houmard in: Methods in Enzymology, Vol. 169, 318-328. L. Packer, ed., Academic Press, 1988

Determination of Ethanol Production

For characterization of mutants expressing PDC and ADH or only PDC or other ethanologenic enzymes as a second genetic modification, ethanol was measured daily during the growth experiment according to the afore described optical enzymatic method ("Ethanol UV method" test kit by Boehringer Mannheim/R-Biopharm, Darmstadt, Germany). Ethanol production of metabolic mutants expressing PDC and ADH were compared to the appropriate reference strain expressing PDC and ADH as a second genetic modification, but lacking the respective metabolic mutation, the first genetic modification.

The cells were cultured over a period of time of 14 days. These cell cultures were further characterized during their logarithmic growth phase at certain time points with regard to their ethanol production rate, their chlorophyll content and photosynthetic capacity (oxygen evolution in μmol O$_2$/mg Chl*h). These three values were measured in a period of time of approximately 2 hours as described below. In the following these measurements are referred to as "short term measurements" or "short term experiments".

Simultaneous Measurement of Photosynthetic Oxygen Evolution and Ethanol Production (Short Term Experiment)

For the comparison of ethanol production and photosynthesis, ethanol production rates and rates of photosynthetic oxygen evolution are measured simultaneous in a single assay.

Cells are washed 2× with fresh growth medium by centrifugation (3000×g, 10 min, room temperature) and resuspension. Cells are resuspended in growth medium to a chlorophyll concentration of 10 to 15 µg chlorophyll/mL. Chlorophyll is measured as described in [N. Tandeau De Marsac and J. Houmard in: Methods in Enzymology, Vol. 169, 318-328. L. Packer, ed., Academic Press, 1988]. 1.9 mL of the cells and 0.1 mL of 500 mM sodium bicarbonate are filled into the chamber of the oxygen electrode and the rate of the photosynthetic oxygen evolution is measured as described herein (Measurement of photosynthetic oxygen evolution). The oxygen concentration in the sample in the chamber is constantly measured and plotted by a flat bed reecorder [REC 112, Amersham Pharmacia Biotech] that runs with a constant speed (1 cm/min). When the light is switched on one observes an increase of the oxygen concentration. Within several minutes (2-5 min) the plotted curve becomes linear. The change of the oxygen concentration is observed for the next minutes to make sure, that the increase of the oxygen concentration remains linear. The amount of oxygen evolved as a result of photosynthesis per unit time is calculated. The chamber of the oxygen electrode is maintained at 25° C. with a circulating, temperature-controlled water bath (RM6, Lauda Brinkmann. For the calibration of the electrode the signal difference of air-saturated water (100% saturation) and oxygen free water (zero point) is measured. Oxygen free water is obtained by adding sodium dithionite (approximately 1 mg/ml). The measured amplitude is equated with the solubility of oxygen in water at 25° C. and a pressure of 1 bar (8.11 mg oxygen/L). [See also: N. Tandeau De Marsac and J. Houmard in: Methods in Enzymology, Vol. 169, 318-328. L. Packer, ed., Academic Press, 1988.]

After completion of this measurement illumination of the sample in the chamber is continued under unchanged conditions. Over a period of one hour samples of 0.15 ml are taken in defined intervals (in most cases every 10 minutes). Immediately after removal samples are centrifuged (14,000× g, 10 min, 4° C.) and the supernatant is stored on ice. After completion of the sampling, the ethanol concentration in the supernatants is measured as described herein. The ethanol concentration versus time is plotted. Using the linear equation the rate of the increase of the ethanol content in v/v in the assay per hour is calculated. The rate of ethanol production is usually given in the dimension µmol ethanol*$h^{-1}$*mg chlorophyll$^{-1}$, the chlorophyll content measured at the beginning of the experiment is then used.

Determination of Intra- and Extracellular Metabolites

Two different methods were used to determine the level of intracellular metabolites in particular pyruvate and acetaldehyde.

Protocol for Extraction of Intracellular Metabolites
  use 5 ml culture.
  Centrifuge for 10 min, 4500 rpm.
  Resuspend the pellet in 1 ml dd water.
  Centrifuge 5 min with 14000 rpm. Discard the supernatant.
  Resuspend the pellet in 1 ml double distilled water.
  Centrifuge 5 min, 14000 rpm, 4° C. Discard the complete supernatant.
  Continue or store the pellet by −20° C. under Argon atmosphere.
  Add 600 ml of extraction buffer.
    Extraction buffer: 10:3:1—methanol:chloroform:water
  Vortex briefly.
  Shake at 4 degrees for 10 min.
  Centrifuge 5 min with 14000 rpm.
  Transfer 500 µl to a new tube.
  Add 200 µl chloroform and 200 µl water.
  Centrifuge 5 min with 14000 rpm.
  Transfer 500 µl of the upper phase to a new tube and speed vac to dry.
  Resuspend the pellet in 100 µl double distilled water.
  Shake at 4 degrees for ≥20 min. Centrifuge 5 min with 14000 rpm.
  Transfer 95 µl to a vial for IC.

Extraction and Analysis of Extracellular Metabolites
Extraction of Metabolites Using a Retsch Mill:

The protocol for extraction of intracellular metabolites was designed by Dr. M. Gründel.

Protocol:

Cells (150 ml cell culture) are harvested by centrifugation and resuspended in 400 µl buffer (100 mM Tris/HCl, pH 7.5) to which 200 µl of glass beads (0.1 mm diameter) are added. Cell lysis is performed using a Retsch mill model MM 301 (treatment for 10 minutes, 4° C.). After removal of glass beads, remaining intact cells and cell debris was removed by centrifugation (10 minutes, 4° C.). The whole procedure is repeated once. Proteins in the combined supernatants are precipitated by deoxycholate/trichloroacetic acid treatment (Bensadoun and Weinstein. 1976. Anal. Biochem. 70:241-250) and removed by centrifugation. The supernatant, containing the soluble metabolites, is neutralized with 2 M $K_2CO_3$ and adjusted to a volume of 1.5 ml with 100 mM Tris/HCl buffer, pH 7.5. In order to determine the concentration of metabolites, aliquots of 100-500 µl are used in the optical tests.

Extraction of Metabolites Using Ice Cold Methanol (Snap Shot Extraction):
Literature Describing the Method:

According to R. P. Maharjan, T. Ferenci. 2002. Global metabolite analysis: the influence of extraction methodology on metabolome profiles of *Escherichia coli*. Anal. Biochem. 313:145-154.

This method allows for the immediate freezing of intracellular metabolite pools and the extraction of numerous intra- and extracellular metabolites at the same time.

Protocol:

Batches of cyanobacterial cultures are dropped into an equal volume of methanol, cooled by dry ice, and incubated on dry ice until completely frozen. After thawing in ice/water (10 min) the samples are centrifuged for 5 min (>=17.000×g, temperature as low as possible). The pellet is extracted a second time with cold 50% methanol (−20° C.). Supernatants are combined. Methanol is removed by evaporation at 35° C. under vacuum using a rotavapor apparatus. The remaining solution is lyophilized, the residue is resuspended in a minimal volume of water.

The efficiency of extraction of bacterial cells with cold methanol is similar to that with hot ethanol or hot methanol. But the method is very simple, rapid and changes in the stability and reactivity in metabolites are minimized.

When extracellular pyruvate and oxoglutarate are assayed, an extraction is not necessary since both metabolites are detectable directly in the media. Quantification of intracellular and extracellular pyruvate and oxoglutarate levels before and after nitrogen deprivation is done as previously described herein.

Pyruvate and phosphoenolpyruvate are quantified using an optic enzymatic test of Häusler et al. (2000), Anal. Biochem, 281:1-8. This method allows for the quantification of pyruvate and phosphoenolpyruvate in one test.

Protocol:

The quantifications are based on the reduction of pyruvate to lactate by lactate dehydrogenase (LDH) at the expense of NADH which is oxidized to NAD+. In the first step, pyruvate was assayed. After completion of this reaction, pyruvate kinase is added. Pyruvate kinase converts phosphoenolpyruvate to pyruvate and thus allows for determination of phosphoenolpyruvate.

To 450 µl master mix (9 µl 20 mM NADH, 12 µl 1 M MgCl2, 46 µl 1 M KCl, 12 µl 100 mM ADP, 360 µl 100 mM HEPES, 10 µl H2O) 520 µl sample (if necessary diluted with H2O) are added. Add 2 µl LDH to start the reaction. The oxidation of NADH is observed as decrease of absorbance at 340 nm. Either the difference of the absorbances at 340 nm minus 380 nm is measured by difference spectroscopy (turbid or colored samples; ε340-380=4.83 l×cm×mmol-1) or the absorbance at 340 nm is measured against water (ε340=6.28 l×cm×mmol-1). After complete reaction of pyruvate, 2 µl pyruvate kinase are added to the assay. NADH oxidation is measured as before. From the differences of the absorbances at the start and the end of the reactions, the amount of oxidized NADH (=amount of pyruvate, and phosphoenolpyruvate, respectively) is calculated.

Chemicals and Solutions:
1. Lactate dehydrogenase suspension from bovine heart (L-LDH, Sigma L2625-2.5 KU, suspension with 5629.5 U/ml), diluted 1:10
2. Pyruvate Kinase from rabbit muscle (PK, Serva 34085, suspension with 4000 U/ml), diluted 1:20
3. 100 mM HEPES/NaOH (pH 7.5)
4. 1 M MgCl2
5. 100 mM ADP
6. NADH (Sigma, N6005) 20 mM in H2O
7. 1 M KCl Photometric Quantification of Pyruvate (and/or Lactate) in an Enzymatic Cycling System
Method:

According to E. Valero & F. Garcia-Carmona. 1996. Optimizing Enzymatic Cycling Assays: Spectrophotometric Determination of Low Levels of Pyruvate and L-Lactate. Anal. Biochem. 239:47-52

This method allows for the quantification of pyruvate (and/or lactate) with a 10-fold higher sensitivity than the pyruvate quantification method described before.

Protocol:

In a cyclic reaction pyruvate is reduced to lactate under consumption of NADH, the lactate is oxidized by lactate oxidase to pyruvate. The rate of NADH consumption, monitored spectrophotometrically at 340 nm is proportional to the amount of pyruvate (plus lactate if present) in the sample. For calibration curves, different amounts of pyruvate are added to the master mix (end volume 1000 µl) consisting of 50 mM TRIS-buffer, pH 7.5, 256 µM NADH, 1.8 µg lactate dehydrogenase and 60 µg lactate oxidase. The reaction is started by addition of lactate dehydrogenase and the time course of the reaction at 340 nm is followed for some minutes. Samples with unknown amounts of pyruvate and lactate are treated identically and quantified using the calibration curve. Detection limit is about 1 nmol pyruvate and/or lactate.

Chemicals and Solutions:
1. 50 mM TRIS/HCl (pH 7.5)
2. 20 mM NADH in H2O
3. 0.25 mg/ml lactate dehydrogenase in 50 mM TRIS/HCl (pH 7.5)
4. 2.6 mg/ml lactate oxidase in 50 mM TRIS/HCl (pH 7.5).

Spectrophotometric Quantification of 2-oxoglutarate Using an Enzymatic Test
Method:

The method used is an adaptation of a fluorimetric method (P. J. Senior. (1975). J. Bacteriol. 123:407-418) for spectrophotometry. The oxidation of NADH, followed by the absorption change at 340 nm, is proportional to the concentration of 2-oxoglutarate.

Protocol:

Cuvettes contained a final volume of 1000 µl: 100-500 µl sample; 10 µl ammonium sulfate; 10 µl NADH; 10 µl ADP; 10 µl glutamate dehydrogenase solution; TRIS buffer added to a final volume of 1000 µl. The reaction is started by the addition of glutamate dehydrogenase.

Chemicals and Solutions:
1. 1 M ammonium sulfate
2. 20 mM NADH
3. 0.1 M ADP
4. 2.6 enzyme units per ml glutamate dehydrogenase (from bovine liver; 104
   enzyme units per mg; Serva lot no. 22904)
5. 0.1 M TRIS/HCl pH 8.0

Acetaldehyde was quantified by a modification of the protocol of a kit for ethanol quantification (Ethanol kit, R-Biopharm AG). Acetaldehyde is converted by aldehyde dehydrogenase under formation of NADH, which is quantified by its absorption at 340 nm. The amount is proportionate to the acetaldehyde content of the sample.

All mutant strains were characterized regarding their profile of relevant intracellular metabolites using ion chromatography always in comparison to the wild type or appropriate reference strain, respectively.

Short description of the UV-method for the determination of acetic acid in foodstuff and other materials from Boehringer Mannheim/R-Biopharm, Darmstadt, Germany Principle: Acetic acid (acetate) is converted to acetyl-CoA in the presence of the acetyl-CoA synthetase (ACS), adenosine-5'-triphosphate (ATP) and coenzyme A (CoA) (1).

Acetate+ATP+CoAACS acetyl-CoA+AMP+PP (1)

Acetyl-CoA reacts with oxaloacetate to citrate in the presence of citrate synthase (CS) (2).

Acetyl-CoA+oxaloacetate+H2OCS citrate+CoA (2)

The oxaloacetate required for reaction (2) is formed from L-malate and nicotinamide-adenine dinucleotide (NAD) in the presence of L-malate dehydrogenase (L-MDH) (3). In this reaction NAD is reduced to NADH.

L-malate+NAD+L-MDH oxaloacetate+NADH+H+ (3)

The determination is based on the formation of NADH measured by the increase in light absorbance at 340, 334 or 365 nm. Because of the equilibrium of the preceding indicator reaction, the amount of NADH formed is not linearly (directly) proportional to the acetic acid concentration (this fact is been taken into consideration in the calculation of acetic acid concentrations).

The above described methods for the quantification of acetate, pyruvate, acetaldehyde and 2-oxoglutarate can detect changes in the static steady state levels of these metabolic intermediates. As mentioned above the first genetic modification can result in a change of the metabolic flux of these metabolic intermediates, which is hard to detect by assays, which are able to detect the steady state level of a metabolite, but not the changes in the flux of the metabolite. In particular, these enzymatic assays might not properly show the changes in the metabolic activity of a photoautotrophic host cell, induced by the first genetic modification.

An overview of alternative assay methods, which can be used to detect the change in the metabolic activity of a photoautotrophic host cell of this invention is shown in the Review of Shimizu, "Metabolic Engineering-Integrating Methodologies of Molecular Breeding and Bioprocess Systems Engineering", Journal of Bioscience and Bioengineering, Vol. 94, No. 6: 563-573 (2002), which is hereby incorporated by reference. These methods are more time-consuming and complex than the above described enzymatic assays and are for example metabolic flux analysis (MFA), cell capability analysis, metabolic control analysis (MCA) or $^{13}C$-NMR and gas chromatography. Mass spectroscopy (GCMS) measurements.

Wild type (WT) and mutant metabolite (pyruvate, acetaldehyde or acetyl-CoA or precursors thereof) measurements will be obtained as previously described herein and presented in the tables below.

| $OD_{750}$ | | Metabolite Intracellular level in mmol per liter | | Metabolite Extracellular level in mmol per liter | |
|---|---|---|---|---|---|
| | | wt | mutant | wt | mutant |
| 1.0 | +N | A | A + Δ | F | F + Δ |
| | −N, 0 h | B | B + Δ | G | G + Δ |
| | −N, 3.5 h | C | C + Δ | H | H + Δ |
| | −N, 6 h | D | D + Δ | I | I + Δ |
| | −N, 24 h | E | E + Δ | J | J + Δ |

Data will be verified by repetitions.
A-J represent wild type values for the indicated conditions
Δ represents an increment relative to the wt measurement The table shows an example for such an experiment. In other experiments the optical density ($OD_{750}$) at the beginning of the experiment and the time points can be different

| Time of cultivation | Metabolite Intracellular level in mmol per liter (calculated per packed cell volume[1]) | | Metabolite Extracellular level in mmol per liter culture volume | |
|---|---|---|---|---|
| | wt | mutant | wt | Mutant |
| T1 | A | A + Δ | E | E + Δ |
| T2 | B | B + Δ | F | F + Δ |
| T3 | C | C + Δ | G | G + Δ |
| T4 | D | D + Δ | H | H + Δ |

Data will be verified by repetitions.
A-H represent wild type values
Δ represents an increment relative to the wt measurement Parameters such as $OD_{750nm}$, Chlorophyll content, protein content and cell number will also be measured in standardizing and evaluating metabolite values at different time points.

In addition, measurements can be obtained for variations in culture conditions such as light intensity, growth in darkness and in day/night cycles respectively, $CO_2$ supplementation and temperature. Also, further variations might concern the composition of the growth medium (e.g. concentration of nitrate, ammonium, phosphate, sulfate or microelements (e.g. Cu, Fe)). All these variations in culture conditions are known to one of ordinary skill in the art.

The data will be analyzed and presented graphically as previously described herein.

Analysis of Ethanol Production

In order to discover whether the enhanced level of biosynthesis of pyruvate, acetaldehyde or acetyl-CoA in the mutant(s) cells also leads to a higher production of ethanol, *Synechocystis* sp. PCC 6803, both wildtype as well as the mutant(s) cells are transformed with the plasmid pVZ containing the *Zymomonas mobilis* Pdc and AdhII enzymes or other plasmids encoding ethanologenic genes under the control of the iron dependent isiA promoter or other promoters.

Analysis of ethanol production is done as previously described herein. *Synechocystis* sp. PCC 6803 with and without Pdc and Adh and *Synechocystis* sp. PCC 6803 mutant(s) cells with and without Pdc and Adh will be compared. This example will present a graphic depiction of these results that clearly demonstrate that increased ethanol production is provided by the mutant(s) cells when compared to the wild type cell.

Generation of Overexpression Mutants of *Synechocystis* Sp. PCC 6803: Methods and Results The following overexpression construct sequences have been conveniently described and provided herein: (a) malic enzyme, (b) malate dehydrogenase, (c) pyruvate kinase 1, (d) pyruvate kinase 2, and (e) pyruvate kinase, enolase and phospho-glycerate mutase. These constructs may be used singly or sequentially in order to provide one or more mutations. Also, constructs contain either the natural promoter for the enzyme gene of interest or an inducible promoter.

Mutagenesis

Host cells are mutagenized by transformation of the overexpression DNA-vectors using the natural competence of *Synechocystis* sp. PCC 6803 for DNA uptake. In case of integrative overexpression mutants, the system of *Synechocystis* sp. PCC 6803 for homologous recombination as previously described herein is used. In addition, self-replicating constructs may also be used. The transformation may comprise one or more steps in order to create mutant cells having a single, double, triple, etc. overexpression mutations. Additionally, one or more knockdown/knockout mutations (as described herein) may be introduced. As noted previously herein, the concentration of the appropriate antibiotic(s) is increased stepwise when the cells are transferred onto another agar plate or into liquid culture (for kanamycin from initially 5 to 150 µg/ml Bg11, for chloramphenicol from initially 1 to 15 µg/ml BG11 medium) in order to get fully segregated (homozygous) mutants. Transfers are done every 2 weeks. In case of kanamycin, the concentration in the range from 50 to 150 µg/ml agar is increased gradually over the course of 4 weeks.

Molecular Analysis of Mutant Host Cell

In order to establish that the selected mutant(s) cell is overexpressing the target enzyme, RNA will be extracted from wild type and mutant cells and will be examined by using different techniques known in the art, e.g. RT-PCR, Northern blot or RNase protection assays. These recombinant DNA/molecular biology methods are well known to one of ordinary skill in the art; For example see: Methods in Enzymology, Vol. 167, (L. Packer, A. N. Glazer, eds) Academic Press, Inc., 1988); For extraction of genomic DNA: Franche C, Damerval T. in Methods of Enzymology, Vol. 167 p. 803-808; for extraction of total RNA: David 1. Lane, Katherine G. Field, Gary J. Olsen, and Norman R. Pace in Methods of Enzymology, Vol. 167 p. 138-144; for Extraction of plasmid DNA: Grant R. Lambert and Noel G. Carr, Rapid Small-Scale Plasmid Isolation by Several Methods from Filamentous Cyanobacteria, Arch Microbiol (1982)

133: 122-125; for Northern Blots: Axmann, I. M., Kensche, P., Vogel, J., Kohl, S., Herzel, H. & Hess, W. R. (2005) Genome Biol 6, R73; for RT-PCR: Emanuel C, von Groll U, Müller M, Börner T, Weihe A. Development- and tissue-specific expression of the RpoT gene family of *Arabidopsis* encoding mitochondrial and plastid RNA polymerases. Planta. 2006 April; 223(5):998-1009; for RNase protection assay: W. R. Hess, B. Hoch, P. Zeltz, T. Hübschmann, H. Kössel and T. Börner. Plant Cell 6 (1994), pp. 1455-1465., which are incorporated herein by reference.

Also, sufficient nucleotide sequence information for all enzymes is provided herein or available from known nucleotide sequence databases for the selection of the appropriate probes/primers for these analyses. With Northern Blot analysis, the abundance and relative amount of a mRNA will be detected. The same would be the case using a RNase protection assay but with a much higher sensitivity. The abundance and also the absolute amount of a mRNA can be determined with a high sensitivity using the RT-PCR. Mutant(s) cells found to be overexpressing the target mRNA will be selected for further analysis.

Characterization of Overexpression Mutants

Cultivation of Cyanobacterial Wild Type and mutant Strains wild type (WT) and mutant strains will be grown under standard culture conditions.

Nitrogen step-down conditions will be as previously described herein.

Conditions for the induction of inducible promoters is provided herein through the teachings of the specification and by way of reference to specific publications. See also D. A. Los, M. K. Ray and M. Murata, Differences in the control of the temperature-dependent expression of four genes for desaturases in *Synechocystis* sp. PCC 6803, Mol. Microbiol. 25 (1997), pp. 1167-1175.

As provided below, mutants and wild type cells will be characterized regarding their intra- and extracellular pyruvate content using optical enzymatic tests and their profile of all relevant metabolites respectively. (incl. 3-PGA, PEP, pyruvate, acetyl-CoA, glycogen, PHB, cyanophycin, malate, oxaloacetate, 2-oxoglutarate, acetate, lactate, etc.) using ion chromatography always in comparison to the wild type.

Also the growth and pigmentation properties of mutant(s) will be compared to the wild type cell using standard protocols well known in the art.

The example presented here will provide a graphic depiction of growth properties for wild type and mutant cells as change in X vs. time, wherein X is ideally dry weight or biovolume. Alternatively, optical density, cell count and chlorophyll could be used as reference parameters. Alternatively, pigmentation could be quantified spectrophotometrically as another parameter.

Wild type (WT) and mutant metabolite (pyruvate, acetaldehyde or acetyl-CoA or precursors thereof) measurements will be obtained as previously described herein and presented in the table below.

| $OD_{750}$ | | Metabolite Intracellular level in mmol per liter | | Metabolite Extracellular level in mmol per liter | |
|---|---|---|---|---|---|
| | | wt | mutant | wt | mutant |
| 1.0 | +N | A | A + Δ | F | F + Δ |
| | −N, 0 h | B | B + Δ | G | G + Δ |
| | −N, 3.5 h | C | C + Δ | H | H + Δ |
| | −N, 6 h | D | D + Δ | I | I + Δ |
| | −N, 24 h | E | E + Δ | J | J + Δ |

Data will be verified by repetitions.
A-J represent wild type values for the indicated conditions
Δ represents an increment relative to the wt measurement The table shows an example for such an experiment. In other experiments the optical density ($OD_{750}$) at the beginning of the experiment and the time points can be different

| Time of cultivation | Metabolite Intracellular level in mmol per liter (calculated per packed cell volume[1]) | | Metabolite Extracellular level in mmol per liter culture volume | |
|---|---|---|---|---|
| | wt | mutant | wt | mutant |
| T1 | A | A + Δ | E | E + Δ |
| T2 | B | B + Δ | F | F + Δ |
| T3 | C | C + Δ | G | G + Δ |
| T4 | D | D + Δ | H | H + Δ |

Data will be verified by repetitions.
A-H represent wild type values
Δ represents an increment relative to the wt measurement Parameters such as $OD_{750nm}$, Chlorophyll content, protein content and cell number will also be measured in standardizing and evaluating metabolite values at different time points.

In addition, measurements can be obtained for variations in culture conditions such as light intensity, growth in darkness and in day/night cycles respectively, CO2 supplementation and temperature. Also, further variations might concern the composition of the growth medium (e.g. concentration of nitrate, ammonium, phosphate, sulfate or microelements (e.g. Cu, Fe)). All these variations in culture conditions are known to one of ordinary skill in the art.

The data will be analyzed and presented graphically as previously described herein.

Analysis of Ethanol Production

In order to discover whether the enhanced level of biosynthesis of pyruvate, acetaldehyde or acetyl-CoA in the mutant(s) cells also leads to a higher production of ethanol, *Synechocystis* sp. PCC 6803, both wildtype as well as the mutant(s) cells are transformed with the plasmid pVZ containing the *Zymomonas mobilis* Pdc and AdhII enzymes or other plasmids encoding ethanologenic genes under the control of the iron dependent isiA promoter or other promoters.

Analysis of ethanol production is done as previously described herein. *Synechocystis* sp. PCC 6803 with and without Pdc and Adh and *Synechocystis* sp. PCC 6803 mutant(s) cells with and without Pdc and Adh will be compared. This example will present a graphic depiction of these results that clearly demonstrate that increased ethanol production is provided by the mutant(s) cells when compared to the wild type cell.

X. Experimental Data for Characterization of Metabolic Mutants Containing at Least One First or One First and One Second Genetic Modification In the following available experimental data regarding pyruvate secretion are discussed for photoautotrophic cells harboring at least one first genetic modification. Furthermore ethanol production rate, if available, are also discussed for photoautotrophic cells containing in addition to the at least one first genetic modification at least one second genetic modification.

X.1 Metabolic Mutant Harbouring a Glycogen Synthase Double Knock Out Mutation as a First Genetic Modification Characterization of the glycogen deficient glycogen synthase double knock out mutants of *Synechocystis* PCC 6803:
Nomenclature:

| Enzyme: | Glycogen synthase 1 | Glycogen (starch) synthase 2 |
|---|---|---|
| EC no.: | EC 2.4.1.21 | EC 2.4.1.21 |
| Gene name: | glgA1 | glgA2 |
| Gene in | sll0945 | sll1393 |

*Synechocystis* PCC 6803:
Theoretical background: Diverting the production of storage reserves into an enhanced production of pyruvate/ethanol
Genetic Manipulation: double knockout by insertion of a chloramphenicol cassette (ΔglgA1) and kanamycin cassette (ΔglgA2)
  M8-mutant: Cm, Km
  Complete segregation: yes
Characterization of the Mutants Harboring the Glycogen Synthase Double Knock Out Mutation as a the First Genetic Modification, but Lacking the Second Genetic Modification (Ethanologenic Enzymes).
Determination of Intracellular Glycogen Before and After a N Step Down
The procedure is an adaptation of the method described by Ernst et al. (A. Ernst, H. Kirschenloher, J. Diez, P. Boger. 1984. Arch. Microbiol. 140:120-125). Glycogen is isolated by alkaline hydrolysis of cells followed by precipitation of glycogen with ethanol. Isolated glycogen is digested with amylolytic enzymes to glucose, which is quantified in a standard optical test.
Protocol:
  Spin down 1-4 ml of *Synechocystis* culture before and after N step down resp. at RT and remove the supernatant
  Add 200 µl KOH (30% w/v) to the pellet and incubate 90 minutes at 95° C. in a heating block
  Add 600 µl cold ethanol (96%) and incubate 90 min on ice
  Spin down and discard the supernatant
  Wash once with ethanol (70%) and once with ethanol (96%)
  Dry the pellet in a vacuum centrifuge
  Dissolve the pellet in 45-90 µl acetate buffer
  5-10 µl enzyme mix (amyloglucosidase+alpha-amylase from *Bacillus amyloliquefaciens*, purchased from Roche) and incubate 90 min at 45° C.
  Use 10-40 µl of the resulting sample for the determination of glucose after manufacturer's instruction (Infinity glucose hexokinase liquid stable reagent for optical test at 340 nm; Cat No. TR15421 Thermo Electron Corporation)
Reaction:

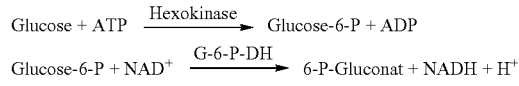

Chemicals and Solutions:
1. aqueous solution of KOH (30% w/v)
2. ethanol 96% v/v
3. 100 mM acetate buffer, adjusted to pH 5.0 with NaOH
4. enzyme mixture of amylo glucosidase (26.7 mg/ml; Boehringer, lot 1490306) plus alpha-amylase (1.0 mg/ml; Boehringer, lot 84874220-34) in 100 mM acetate buffer pH 5.0)

Quantification of Intracellular and Extracellular Pyruvate and Oxoglutarate Levels Before and After Nitrogen Deprivation ("N Step Down")
Explanation for "N Step Down":
This means sedimentation of cyanobacterial cells by centrifugation, decantation of the nitrate-containing (+N) medium and resuspension of the culture in nitrate-free (−N) medium.
Cultivation Under Continuous Light (40 µE m$^{-2}$ s$^{-1}$), BG11, 29° C.:
Growth properties: no difference between wild type (wt) and mutant (M8)
  (the growth of M8 is impaired under High Light conditions [130 µE m$^{-2}$ s$^{-1}$] and low inoculi [initial OD$_{750}$<0.1])
Pigmentation: no difference between wt and mutant
Storage substances: no glycogen production by the mutants in contrast to the wt
Continuous Light (40 µEm$^{-2}$ s$^{-1}$), BG11 without Nitrogen (24 h, 48 h), 29° C.: (N Starvation)
Growth properties: wt and mutant stopped growing. After passage to BG11 medium containing nitrogen, wt started to grow again whereas the mutant M8 gradually lost the ability to grow, depending on duration of nitrogen depletion.
Pigmentation: After withdrawal of nitrogen, wt started to degrade phycobilisomes (measured as absorbance at 625 nm): yellow color; M8-mutant did not degrade phycobilisomes: still blue-green color; unchanged chlorophyll levels (absorbance at 681 nm) in both wt and mutant M8
Pyruvate Level:

| | | Intracellular level in mmol per liter (calculated per packed cell volume[1]) | | Extracellular level in mmol per liter culture volume | |
|---|---|---|---|---|---|
| OD$_{750}$ | | wt | M8 | wt | M8 |
| 1.0 | +N | 0.8 | 0.8 | 0.007 | 0.018 |
| | −N, 0 h | | | nd | nd |
| | −N, 3.5 h | | | 0.005 | 0.038 |
| | −N, 6 h | | | 0.004 | 0.08 |
| | −N, 24 h | 0.9 | 1.6 | 0.007 | 0.470 |

Data were verified by repetitions.
nd, not detectable
The packed cell volume is less than 1% of the culture volume Growth properties and extracellular pyruvate levels of the ΔglgA1/ΔglgA2 double mutant (M8) under nitrogen replete and nitrogen starved conditions are presented in FIG. 32C.
The glycogen deficient mutant M8 was grown up to an OD$_{750}$ of 0.6. After a centrifugation step, the cells were washed twice with nitrogen deficient BG11 medium and transferred to medium with nitrogen (+N, control) and without nitrogen (−N), respectively. After 24 h incubation, nitrogen was added to the nitrogen deficient cultures (black arrow). The growth of the cultures was estimated by measurement of chlorophyll. Abbreviations: Chl, chlorophyll a; Pyr, pyruvate Oxoglutarate Level:

| Hours after nitrogen step down | Intracellular level in mmol per liter (calculated per packed cell volume[1]) | | Extracellular level in mmol per liter culture volume | |
|---|---|---|---|---|
| | wt | M8 | wt | M8 |
| 0.5 | 0.036 | 0.038 | nd | nd |
| 2 | 0.17 | 0.22 | nd | nd |
| 5 | 0.18 | 0.26 | nd | 0.01 |
| 24 | 0.22 | 0.53 | nd | 0.14 |

[1]The packed cell volume is less than 1% of the culture volume
nd, not detectable Light/Dark Cycle (16 h/8 h), BG11, 29° C.:
  Growth properties: no difference between wt and mutants M1 and M8
  Further mutant characterization of the glycogen deficient mutant M8 in comparison with the wild type strain of *Synechocystis* sp. PCC6803
Culture Conditions:
Continuous light (150 $\mu m^{-2}\ s^{-1}$), 28° C.:
Aeration with air (no additional $CO_2$ supplementation)
Culturing in glass flasks with 5 cm diameter, 400 ml culture volume
Media: BG11 buffered with TES buffer (Sigma-Aldrich Inc.) at pH 8
Storage Substances:
No glycogen production by the mutants in contrast to the wild type.
Pyruvate Concentrations in the Media Determined by Using an Optical Enzymatic Test:

| | $OD_{750}$ | Chlorophyll | Pyruvate 0 h after N step down | Pyruvate 3.5 h after N step down | Pyruvate 6 h after N step down | Pyruvate 24 h after N step down |
|---|---|---|---|---|---|---|
| WT | 1.2 | 6.18 µg/ml | 0 µM | 5.1 µM | 4.0 µM | 2.5 µM |
| M8 mutant | 1.1 | 3.60 µg/ml | 0 µM | 37 µM | 79 µM | 473 µM |

Pyruvate Concentrations in the Media Determined by Ion Chromatography:

| | $OD_{750}$ | Chlorophyll | Pyruvate 0 h after N step down | Pyruvate 24 h after N step down |
|---|---|---|---|---|
| WT | 1.2 | 6.18 µg/ml | 0 µM | 13.4 µM |
| M8 mutant | 1.1 | 3.60 µg/ml | 0 µM | 511 µM |

Pyruvate Concentrations in the Media Plus Cells (Snap Shot Extraction) Determined by Ion Chromatography:

| | $OD_{750}$ | Chlorophyll | Pyruvate 0 h after N step down | Pyruvate 24 h after N step down |
|---|---|---|---|---|
| WT | 1.2 | 6.18 µg/ml | 0 µM | 6.12 µM |
| M8 mutant | 1.1 | 3.60 µg/ml | 0 µM | 523 µM |

Wildtype and mutant were transferred into a medium without combined nitrogen and grown for 24 hours. Subsequently the amount of pyruvate in the culture medium was determined in with an optical enzymatic method and by ion chromatography. The sum of intra- and extracellular pyruvate was determined by ion chromatography after snapshot extraction Shown is the conductimetric detection of pyruvate in methanol extracts (snapshot) of cultures of wildtype and a glycogen synthase deficient mutant after 24 h under N-deficient conditions. The area of the pyruvate peak corresponds to 523 pmoles.

Data results are presented graphically in FIGS. 32D and 32E.

Summary Pertaining to Ethanol Production:
  The loss of the two functional glycogen synthases in *Synechocystis* PCC 6803 mutant M8 resulted in a two-times increased intracellular pyruvate level and an at least 10-times increased extracellular pyruvate level after nitrogen depletion (24 h). In dense cultures ($OD_{750}$ 1.0), the extracellular pyruvate level is actually increased up to 500 times. In the wild type, these concentrations remained unchanged and much lower. The enhanced pyruvate level is used for ethanol production.
  Glycogen is made during the day and would therefore compete with ethanol production in the light. It is degraded during the night and may thus support ethanol production by a quasi continuous production.
Possible Advantages of Glycogen Deficiency:
  Glycogen Synthesis Requires Energy (ATP):
  Photosynthesis→glucose phosphate
  glucose phosphate+ATP→ADP-glucose+pyrophosphate
  n ADP-glucose→glycogen+n ADP
  During the night, glycogen will be degraded:
  glycogen+n phosphate→n glucose phosphate
  glucose phosphate→→pentose phosphate+$CO_2$↑
  pentose phosphate→→pyruvate
  pyruvate→→ethanol+$CO_2$↑
Conclusions:
  Ethanol production via glycogen requires more energy and releases 50% more $CO_2$ than direct production.
  A further advantage may be that glycogen-deficient mutants degrade photosynthetic pigments at a much lower rate than the wild type under conditions of nitrogen deficiency. Thus, growth could be retarded during ethanol production by lowering nitrogen supply.
  In order to find out whether the pyruvate produced by the glycogen synthase double knock out mutant in *Synechocystis* can be used for ethanol production, the glycogen synthase double knock out mutant cells (denoted as M8 in the below two graphs) were transformed with the plasmid pVZ321b-PnblA-pdc/adh containing the alcohol dehydrogenase and pyruvate decarboxylase genes under the transcriptional control of the nblA promoter inducible by nitrogen starvation (denoted as M8 PnblA in the below two graphs). The concentration of pyruvate in the growth medium was determined for the M8 mutant without the pVZ321b-PnblA-pdc/adh plasmid after having induced pyruvate secretion into the medium by nitrogen starvation (indicated by M8-N in the below graphs). In addition the concentration of pyruvate and ethanol in the growth medium was also determined for the M8 mutant including the pVZ321b-PnblA-pdc/adh plasmid after having induced pyruvate production by nitrogen starvation (indicated by M8 PnblA-N in the below graphs). For the reason of comparison the respective pyruvate concentrations are also shown for the uninduced cells (denoted with M8 PnblA+N and M8+N, respectively).

Both graphs depict on the Y-axis the concentrations of pyruvate and ethanol in μM normalized to the cell density measured at 750 nm ($OD_{750nm}$). The x-axes denote the course of the experiments in hours.

As can be seen in FIG. 32F the graph shows the pyruvate concentrations. It can clearly be seen that the pyruvate concentration in the growth medium is higher for the M8 mutant without Adh and Pdc enzymes than for the M8 mutant including both ethanol forming enzymes under the conditions of nitrogen starvation. In the case that the cells are not subjected to nitrogen starvation pyruvate could not be detected in the growth medium.

FIG. 32G depicts the ethanol concentration determined in the growth medium for the M8 mutant with the Adh and Pdc enzymes under the conditions of nitrogen starvation and without nitrogen starvation. The graph shows that the ethanol concentration is higher for the M8 mutant under the conditions of nitrogen starvation than without nitrogen starvation. By comparing both graphs it can be observed that nearly all pyruvate produced by the M8 mutant can be converted into ethanol by the Adh and Pdc enzymes: The M8 mutant without the Adh and Pdc enzymes secretes high amounts of pyruvate into the growth medium, but the M8 including both enzymes only excretes small amounts of pyruvate but a high amount of ethanol into the growth medium.

Furthermore the glycogen deficient glycogen synthase double knock out mutants of *Synechocystis* PCC 6803 were transformed with the plasmid pVZ containing ZmPDC and ADHII under the control of the iron starvation inducible promoter isiA using the standard protocols described above. Ethanol production rates and the $OD_{750nm}$ were determined over the course of 15 days. Results are depicted graphically in FIG. 32H.

Further, short term measurements of ethanol production rates were carried out for the glycogen synthase double knock out mutant in *Synechocystis* PCC 6803 with and without a second genetic modification of at least one overexpressed enzyme for ethanol formation and these production rates were compared to the ethanol production rates of the corresponding *Synechocystis* cells only harboring the second genetic modification.

| ΔglgA1/ΔglgA2 mutant | | | | |
|---|---|---|---|---|
| | μmol $O_2$/ mg Chl* h | μmol EtOH/ mg Chl* h | μmol EtOH/ μmol $O_2$ | % of theoretical fixed CO2 |
| S. PCC6803 pVZ321b-PisiA-PDC-ADHII | 98.3 | 5.0 | 0.051 | 15.3 |

| ΔglgA1/ΔglgA2 mutant | | | | |
|---|---|---|---|---|
| | μmol $O_2$/ mg Chl* h | μmol EtOH/ mg Chl* h | μmol EtOH/ μmol $O_2$ | % of theoretical fixed CO2 |
| ΔglgA1/A2 pVZ321b-PisiA-PDC-ADHII | 34.8 | 5.4 | 0.200 | 60.1 |

The above table shows the ethanol production rates normalized either to the chlorophyll content, the maximal photosynthetic capacity as determined by the oxygen evolution and the percentage of theoretical fixed CO2 which is diverted to ethanol production for a *Synechocystis* strain without the glycogen synthase double knock out mutation, the first genetic modification (S. PCC6803 pVZ321b-PisiA-PDC-ADHII), and for *Synechocystis* strains having both the first and second genetic modification (ΔglgA1/A2 pVZ321b-PisiA-PDC-ADHII). The data show that the overall photosynthetic capacity of the cells harboring the double knock out mutation is reduced. The results also indicate that a higher percentage of carbon fixed via photosynthesis can be diverted to ethanol production via a reduction of the enzymatic affinity or activity of glycogen synthase for example by introducing a knock out mutation of both genes glgA1/glgA2 coding for glycogen synthase into cyanobacteria) cells such as *Synechocystis*.

X.2 Metabolic Mutant Harbouring a Knock Out of ADP-Glucose-Pyrophosphorylase (ΔGLGC) as a First Genetic Modification Construction of the DNA-vector pGEM-T/ΔglgC-KM, which was used for generation of ΔglgC mutant, was already described herein. The obtained ΔglgC mutant was partially segregated and was grown in BG11 medium containing 75 mg/l kanamycin. The segregation status was checked by southern blot analysis using a radio-labeled glgC probe. Approximately 80% of the wild-type gene copies were replaced by the introduced mutant gene copy.

The partially segregated mutant ΔglgC was examined in comparison to *Synechocystis* wild-type strain under constant light conditions as described herein.

Growth Characteristics Under Constant Light Conditions

The ΔglgC mutant is generally more sensitive to light at low concentrated inoculi than the wild type strain (*Synechocystis* PCC6803). During further batch culturing no significant differences were detected in cell growth and chlorophyll content between the mutant and the *Synechocystis* PCC6803 wild type. However, the photosynthetic capacity of the ΔglgC mutant was about 35% lower compared to the *Synechocystis* PCC6803 wild type. This finding is consistent with data reported by Miao et al., 2003 (Miao, X., Wu, Q., Wu, G. & Zhao, N. (2003) Changes in photosynthesis and pigmentation in an agp deletion mutant of the cyanobacterium *Synechocystis* sp.; Biotechnol Lett. 25, 391-396).

Like in the ΔglgA mutant described above, in the ΔglgC mutant the extracellular pyruvate level is strongly increased. Data from one representative experiment are shown in the following table:

| | 4 days | | 7 days | | 9 days | |
|---|---|---|---|---|---|---|
| | $OD_{750}$ | pyruvate [mM] | $OD_{750}$ | pyruvate [mM] | $OD_{750}$ | pyruvate [mM] |
| PCC6803 Wt | 1.7 | 0.009 | 2.0 | 0.001 | 2.4 | 0.003 |
| ΔglgC | 1.1 | 0.087 | 2.0 | 0.093 | 2.2 | 0.199 |

In wild type cells glycogen synthesis is increased during nitrogen starvation. Therefore, in the ΔglgC mutant, that is not able to produce glycogen, an additional increase of the pyruvate level was achieved by a nitrogen step down.

After 9 days of culturing under standard conditions, the culture was split into two parts. With one half of the culture a nitrogen step down was performed (as described for the ΔglgA mutant) and cells were grown on BG11 lacking combined nitrogen (−N) for two days. The second half of the culture was grown in full BG11 medium (+N) as a control. Two days after the nitrogen step-down, the excretion of pyruvate into the medium was measured.

|  | +N | | −N | |
|---|---|---|---|---|
|  | $OD_{750}$ | pyruvate [mM] | $OD_{750}$ | pyruvate [mM] |
| PCC 6803 Wt | 1.7 | 0.012 | 1.2 | 0.010 |
| ΔglgC | 1.3 | 0.295 | 1.2 | 0.361 |

ADP Glucose Pyrophosphorylase (GlgC) Knock-Out Mutant Expressing PDC and ADH

The DNA-vector pGEM-T/ΔglgC-KM was transformed into the PDC-ADHII expressing mutant Synechocystis PCC6803 pSK10-PpetJ-PDC-ADHII. The obtained mutant ΔglgC pSK10-PpetJ-PDC-ADHII was fully segregated and was grown in BG11 medium containing 100 mg/l kanamycin and 10 mg/l streptomycin.

Ethanol production was induced by copper starvation and compared to that of Synechocystis wild-type pSK10-PpetJ-PDC-ADHII.

In short term experiments under optimal conditions (light, $CO_2$) the overall as well as the relative (to photosynthetic activity) ethanol production rate of the ΔglgC pSK-PpetJ-PDC-ADHII mutant was higher compared to that of the reference strain S. PCC6803 pSK-PpetJ-PDC-ADHII. Therefore the short term experiments performed at the beginning of the log phase (day 5 and 6 during the growth experiment) indicate a higher potential for ethanol production for the ΔglgC pSK-PpetJ-PDC-ADHII mutant. (Data are the mean of 2 measurements)

| ΔglgC mutant | | | | |
|---|---|---|---|---|
|  | µmol $O_2$/ mg Chl* h | µmol EtOH/ mg Chl* h | µmol EtOH/ µmol $O_2$ | % of theoretical fixed CO2 |
| S. PCC6803 pSK-PpetJ-PDC-ADHII | 250 | 4 | 0.016 | 4.8 |
| ΔglgC pSK-PpetJ-PDC-ADHII | 125 | 9 | 0.072 | 21.6 |

Similar to the glycogen synthase double knock out mutation, these results indicate that by reducing the enzymatic affinity or activity of ADP-glucose-pyrophosphorylase for example by a knock out mutation of the gene encoding ADP-glucose-pyrophosphorylase a higher percentage of carbon fixed via photosynthesis can be redirected to ethanol production. In the case that the photoautotrophic host cells do not have a second genetic modification, a drastic increase of pyruvate secretion into the growth medium can be detected.

X.3 Metabolic Mutant Harbouring a Knock Out of Pyruvate Water Dikinase (ΔppsA) as a First Genetic Modification Knock out of phosphoenolpyruvate synthase or pyruvate water-dikinase (PpsA) was accomplished by insertion of a kanamycin resistance cassette into gene slr0301. Construction of the DNA-vector pGEM-T/ΔppsA, which was used for generation of the ppsA knock-out mutant, was already described herein. The obtained ppsA knock-out mutant was fully segregated and cultivated in BG11 medium containing 75 mg/l kanamycin.

The mutant ΔppsA was characterized in comparison to the Synechocystis wild-type strain under constant light conditions as described herein.

No significant differences could be detected in cell growth, chlorophyll content and photosynthetic oxygen production between Synechocystis PCC6803 wild-type and the ΔppsA mutant. However, in several independent growth experiments the extracellular pyruvate level of the ΔppsA mutant was increased at the end of the log-phase. Data from one representative experiment are shown in the following table:

|  | 4 days | | 10 days | | 14 days | |
|---|---|---|---|---|---|---|
|  | $OD_{750}$ | pyruvate [mM] | $OD_{750}$ | pyruvate [mM] | $OD_{750}$ | pyruvate [mM] |
| PCC6803 Wt | 2.0 | 0 | 12.8 | 0.009 | 13.3 | 0.010 |
| ΔppsA | 1.8 | 0.014 | 8 | 0.010 | 10.8 | 0.073 |

X.4 Metabolic Mutant Harbouring a Knock Out of Either Acetatekinase (ΔACK) or a Double Knock Out of Acetatekinase and Phosphoacetyltransacetylase (ΔACK/PTA) as a First Genetic Modification The following knock-out mutants were generated: the single-mutants Δack and Δpta and the double mutant Δack/Δpta. Knock-out of acetatekinase (ack) was accomplished by replacement of a 0.65 kb fragment of slr1299 (ack gene) by a kanamycin resistance cassette. As described herein, plasmid pBlue-ack-Kan was used to generate the Δack mutant. Knock-out of phosphoacetyltrans-acetylase (pta) was accomplished by replacement of a 0.45 kb fragment of slr2132 (pta gene) by a chloramphenicol resistance cassette. The construction of plasmid pUC-pta-Cm, which was used for generation of Δpta mutant is described above. The double knock-out mutant Δack/Δpta was generated by transformation of pBlue-ack-Kan into the Δpta mutant.

All mutants were fully segregated. Mutants were grown in BG11 medium containing the appropriate antibiotics (kanamycin 75 mg/l; chloramphenicol 10 mg/l).

Mutants Δack, Δpta, Δack/pta and Synechocystis wild-type strains were examined under constant light conditions as described.

Results:

No significant differences could be detected in cell growth, chlorophyll content and photosynthetic oxygen production between the Synechocystis PCC6803 wild type and mutants Δack, Δpta and double mutant Δack/Δpta.

Excretion of pyruvate into the medium could be detected at the end of the log phase and was increased in the mutants compared to the wild type. Data from representative experiments are shown in the following tables. The optical density at 750 nm ($OD_{750nm}$) and the concentration of pyruvate in the medium are given at two time points at the end of the log phase.

|  | 10 days | | 14 days | |
| --- | --- | --- | --- | --- |
|  | $OD_{750\ nm}$ | pyruvate [mM] | $OD_{750\ nm}$ | pyruvate [mM] |
| PCC6803 wt | 4.6 | 0.006 | 6.2 | 0.012 |
| Δack | 6.6 | 0.009 | 7.0 | 0.025 |
| Δpta | 6.7 | 0.010 | 6.3 | 0.019 |

|  | 10 days | | 12 days | |
| --- | --- | --- | --- | --- |
|  | $OD_{750\ nm}$ | pyruvate [mM] | $OD_{750\ nm}$ | pyruvate [mM] |
| PCC6803 wt | 8 | 0.003 | 8 | 0.011 |
| Δack/Δpta | 6 | 0.004 | 7 | 0.026 |

Acetatekinase (ack) and Acetatekinase (ack)/Phosphoacetyl-transacetylase (pta) Knock-Out Mutants Expressing PDC and ADH The self-replicating plasmid pVZ321b-PpetJ-PDC-ADHII was conjugated into each of the mutants: Δack, and double mutant Δack/pta, resulting in mutants Δack pVZ321b-PpetJ-PDC-ADHII, and Δack/pta pVZ321b-PpetJ-PDC-ADHII. Mutants were grown in BG11 medium containing the appropriate antibiotics (kanamycin 75 mg/l; chloramphenicol 10 mg/l; streptomycin 10 mg/l). Ethanol production was induced by copper starvation under constant light and compared to *Synechocystis* wild-type harboring pVZ321b-PpetJ-PDC-ADHII as described above.

Results:

In several independent growth experiments, the double mutant Δack/pta, harboring pVZ321b-PpetJ-PDC-ADHII, exhibited significantly higher ethanol production rates compared to the reference strain S. PCC6803 pVZ321b-PpetJ-PDC-ADHII. In the single mutant Δack, harboring pVZ321b-PpetJ-PDC-ADHII, ethanol production was increased compared to the reference strain S. PCC6803 pVZ321b-PpetJ-PDC-ADHII. However, this effect was not apparent, when given relative to cell growth.

Data from one representative experiment are shown in the following table. FIGS. 32I and 32J depict a graphical presentation of these data.

|  | time [days] | 0 | 6 d | 11 d | 13 d |
| --- | --- | --- | --- | --- | --- |
| PCC6803 pVZ321b-PpetJ-PDC-ADHII | $OD_{750\ nm}$ | 1.2 | 2.5 | 3.2 | 3.9 |
|  | EtOH [%] | 0.000 | 0.030 | 0.060 | 0.072 |
| Δack/pta pVZ321b-PpetJ-PDC-ADHII | $OD_{750\ nm}$ | 1.2 | 2.3 | 2.6 | 2.7 |
|  | EtOH [%] | 0.000 | 0.044 | 0.098 | 0.121 |
| Δack pVZ321b-PpetJ-PDC-ADHII | $OD_{750\ nm}$ | 1.3 | 2.8 | 3.9 | 4.8 |
|  | EtOH [%] | 0.000 | 0.034 | 0.082 | 0.094 |

The following table shows the ethanol concentration in the medium at the end of a growth experiment and the ethanol production rate relative to cell growth (given as the slope of ethanol production [%] per $OD_{750nm}$ and day.

|  | EtOH [%] after 13 days of growth | EtOH production rate [%/$OD_{750\ nm}$*d] |
| --- | --- | --- |
| PCC6803 pVZ321b-PpetJ-PDC-ADHII | 0.072 | 0.001 |
| Δack/pta pVZ321b-PpetJ-PDC-ADHII | 0.121 | 0.0039 |
| Δack pVZ321b-PpetJ-PDC-ADHII | 0.094 | 0.001 |

When mutants Δack pVZ321b-PpetJ-PDC-ADHII, and Δack/pta pVZ321b-PpetJ-PDC-ADHII and the reference strain S. PCC6803 pVZ321b-PpetJ-PDC-ADHII were grown under day/night cycle conditions, similar results were obtained. After induction of PDC and ADHII by copper starvation, strains Δack/pta pVZ321b-PpetJ-PDC-ADHII and Δack pVZ321b-PpetJ-PDC-ADHII showed higher ethanol production rates compared to the reference strain S. PCC6803 pVZ321b-PpetJ-PDC.

At three consecutive days during the logarithmic growth phase, photosynthetic capacity and ethanol production was measured in the oxygen electrode as described.

In these short-term measurements photosynthetic activity is measured under optimized conditions (saturating light and carbon supply). Results represent the maximal photosynthetic capacity of cells rather than the real photosynthetic activity during cultivation.

Following the reaction equation of photosynthesis $6\ CO_2 + 12H_2O \rightarrow C_6H_{12}O_6 + 6O_2 + 6H_2O$, the photosynthetic capacity [μmol $O_2$/mg Chl*h] is equivalent to the maximal carbon fixation [μmol $CO_2$/mg Chl*h]. Therefore the factor (μmol EtOH per/μmol $O_2$) given in the following table puts EtOH production into perspective of carbon fixation/photosynthesis.

Values are the mean of three consecutive measurements.

|  | PS capacity [μmol $O_2$/ mg Chl* h] | EtOH production [μmol EtOH/ mg Chl* h] | μmol EtOH/ μmol $O_2$ |
| --- | --- | --- | --- |
| PCC6803 pVZ321b-PpetJ-PDC-ADHII | 221 | 3.6 | 0.016 |
| Δack/pta pVZ321b-PpetJ-PDC-ADHII | 241 | 6.1 | 0.025 |
| Δack pVZ321b-PpetJ-PDC-ADHII | 301 | 7.2 | 0.024 |

Conclusions:

Ethanol production in the double mutant Δack/pta, harboring pVZ321b-PpetJ-PDC-ADHII, was significantly enhanced compared to the reference strain (wt) and also in comparison to the single mutant Δack pVZ321b-PpetJ-PDC-ADHII. For the single mutant Δack pVZ321b-PpetJ-PDC-ADHII, high ethanol production rates were obtained in short term experiments.

X.5 Metabolic Mutant Harbouring a Knock Down of Pyruvate Dehydrogenase E1 Component (Beta Subunit) (Pdh-Banti) as a First Genetic Modification Knock-down of Pyruvate dehydrogenase (PdhB) was accomplished by regulated expression (PpetJ) of the corresponding antisense RNA (sll1721-pdhB). Construction of the DNA-vector pSK9/PpetJ-pdhB$_{anti}$, which was used for the generation of a pdhB knock down mutant, was already described herein. The obtained pdhB knock-down mutant was fully segregated and was grown in BG11 medium containing 14 mg/l chloramphenicol. The mutant pdhB$_{anti}$ was characterized in comparison to the *Synechocystis* wild-type strain under constant light conditions as described herein. Expression of anti-sense RNA was induced by copper starvation as described for induction experiments with the promoter PpetJ. Expression of anti-sense RNA was verified by northern blot analysis.

Results:

No significant differences could be detected in cell growth, chlorophyll content and photosynthetic oxygen production between *Synechocystis* PCC6803 wild type and pdhB$_{anti}$ mutant. After induction of the petJ promoter, the level of extracellular pyruvate was slightly increased in the pdhB$_{anti}$ mutant compared to the wild-type. This effect was verified in three independent growth experiments, data from one representative experiment are shown.

|  | 7 days | | 9 days | |
|---|---|---|---|---|
|  | OD$_{750}$ | pyruvate [mM] | OD$_{750}$ | pyruvate [mM] |
| PCC6803 wt | 3.6 | 0 | 5.3 | 0.004 |
| pdhB$_{anti}$ | 3.9 | 0.004 | 6.1 | 0.015 |

X.6 Metabolic Mutant Harbouring an Overexpressed Ribulose-1,5-Bisphosphate Carboxylase/Oxygenase (Rubisco) as a First Genetic Modification Mutant and *Synechocystis* wild-type strains were grown at 28° C., under constant light (70 µE m$^{-2}$ s$^{-1}$) and aerated with $CO_2$-enriched air (0.5% $CO_2$). The initial OD$_{750}$ was about 1 in a total culture volume of 200 ml in a 250 ml Schott-flask. For comparison of the ethanol production ethanol producing mutants pVZ321b-PpetJ-PDC and pVZ321b-PpetJ-PDC/SynRbcLXS and wild type were cultivated in BG11 without copper in continuous light (75-200 µE m$^{-2}$ s$^{-1}$) and a culture volume of 300 ml in a 500 ml Schott-flask.

Methods:

The rate of oxygen evolution was measured with a Clark-type oxygen electrode (Rank Brothers, UK). Prior to the measurement cells were washed 2× and resuspended in BG-11 medium supplemented with 25 mM NaHCO$_3$. Light intensity was saturating with approx. 500 µE/s*m$^2$.

For preparation of cell extracts, cells were pelleted, washed two times with 20 mM HEPES/KOH, pH 7.5, 5 mM EDTA, 2 mM DTT, dissolved in this buffer and broken with a beadbeater (2×10 min). The supernatant of a centrifugation (15 min, 14000 rpm, 4° C., Micro 200R, Hettich) was used for the experiments. The protein content of cell extracts was measured with the method of Lowry.

RuBisCO activity was measured similar as described in Iwaki et al. (2006) Photosynth Res. 2006 June; 88(3):287-97. Epub 2006 May 12. Expression of foreign type I ribulose-1,5-bisphosphate carboxylase/oxygenase stimulates photosynthesis in cyanobacterium *Synechococcus* PCC7942 cells:

5 µl to 15 µl of cell extracts were mixed with 750 µl of 50 mM HEPES/KOH, pH 7.5, 20 mM MgCl$_2$, 50 mM KHCO$_3$, 0.15 mM NADH, 5 mM ATP, 2.5 mM Phosphocreatine, 1.5 µl carbonic anhydrase (10 U/µl in 50 mM HEPES, pH 7.5), 7.5 µl creatine kinase (0.5 U/µl) 3.75 µl of glyceraldehyde-3-phosphate dehydrogenase (12.5 mg/ml), phosphoglycerate kinase (suspension with 10 mg/ml). The assay was incubated at 30° C. for 10 min. Then the reaction was started by the addition of 7.5 µl of 250 mM ribulose-1,5-bisphosphate and the absorption of 340 nm was monitored.

Results and Conclusions:

The mutant with RuBisCO over-expression (6803 pVZ321b-Prbc-SynRbcLXS) grows as fast as the *Synechocystis* wild type and shows no phenotypical differences except for the chlorophyll content that is reduced by 20-30% compared to wild type (see FIG. 32K). Interestingly, at the same time the mutant produces significant more biomass observed by dry weight determination at several time points during the cultivation experiment (Tab. 1). At the end point the difference in dry weight accounts to about 30%. This means although both cultures are indistinguishable by the optical density the mutant seems to build up more biomass. Either the cells are larger in size or the cells are denser packed by biomass (eg. with carbohydrates like glycogen or fatty acids).

FIG. 32L shows the growth parameter (OD at 750 nm and Chlorophyll content) of *Synechocystis* wild type and a mutant that over-express the endogenous RuBisCO operon.

TABLE 1

Biomass (dry weight, mean value of triplicates) during the (in FIG. 50-1A shown) cultivation experiment of *Synechocystis* wild type cells and cells overexpressing RuBisCO.

|  | Prbc-SynRbcLXS | | | WT 6803 | | |
|---|---|---|---|---|---|---|
| time [d] | OD$_{750\,nm}$ | Chl a [mg/l] | Dryweight [g/l] | OD$_{750\,nm}$ | Chl a [mg/l] | Dryweight [g/l] |
| 0 | 0.96 | 3.82 | 0.23 | 0.91 | 3.69 | 0.18 |
| 7 | 6.09 | 22.60 | 1.01 | 6.36 | 29.07 | 1.02 |
| 11 | 8.14 | 21.22 | 1.51 | 7.99 | 33.89 | 1.30 |
| 16 | 10.17 | 18.30 | 1.70 | 10.01 | 24.97 | 1.32 |

Measurements of the RuBisCO activity from the mutant with RuBisCO over-expression revealed an about 2-fold increase in the activity compared to the wild type (see Tab. 2). This was confirmed by semi-quantitative Western blot analyses, too (data not shown). Furthermore for this mutant and the wild type the oxygen evolution was determined. Based on the wild-type level a slight increase (about 15%) in the oxygen evolution was detectable for the cells over-expressing the *Synechocystis* RuBisCO.

TABLE 2

RuBisCO activity and photosynthetic oxygen evolution of *Synechocystis* wild type and a mutant overexpressing the endogenous RuBisCO operon.

|  | RuBisCO activity [µmol RBP/min * mg protein] | oxygen evolution [µmol O$_2$/h * mg chl] |
|---|---|---|
| PCC6803 wild type | 0.23 (100%) | 107.8 (100%) |
| pVZ321b-Prbc-SynRbcLXS | 0.48 (209%) | 124.6 (115%) |

In a further experiment the potential positive effect of the detected increased RuBisCO activity for the ethanol production was analyzed. For this purpose growth and ethanol production of an integrative ethanol producing mutant (6803 pSK10-PisiA-PDC/ADHII) was compared to the isogenic, ethanologenic mutant containing moreover the RuBisCO overexpressing plasmid (pVZ321b-Prbc-SynRbc).

FIGS. 32L, 32M and 32N, respectively show the OD$_{750}$, the ethanol production and the ethanol production normalized to the OD$_{750}$ for the mutant *Synechocystis* PCC6803 harboring the pSK10-PisiA-PDC/ADHII plasmid and the mutant additionally containing the vector pVZ321b-Prbc-SynRbc.

Both ethanologenic *Synechocystis* mutants exhibit a similar ethanol production rate of about 0.017% (v/v) per day for 14 days under continuous light illumination (see FIG. 32-4C). Over the whole time-scale the mutant with the RubisCO over-expression produces a bit more ethanol (about 8% compared to the reference). Also when the ethanol production is normalized to the cell density (OD at 750 nm as indicator for the growth) this difference in the ethanol production remains. This indicates that an elevated RuBisCO activity can lead to an increased ethanol formation. The potential to direct additional carbon fixed via photosynthesis into ethanol production might be further improvable by optimization of the RubisCO expression level as well as by combination with other metabolic mutations, enhancing the level of substrates for the ethanologenic enzymes.

X.7 Metabolic Mutant Harbouring an Overexpressed Pyruvate Kinase 2 as a First Genetic Modification Construction of the DNA-vector pVZ321-PpetJ-pyk2, which was used for the generation of a pyk2 overexpression mutant, was already described herein.

The obtained mutant Synechocystis PCC6803 pVZ321-PpetJ-pyk2 was cultivated in BG11 medium containing 14 mg/l chloramphenicol and characterized in comparison to the Synechocystis wild-type strain under constant light conditions as described herein. Expression of pyruvate kinase gene was induced by copper starvation.

Results:

No significant differences could be detected in cell growth, chlorophyll content and photosynthetic oxygen production between Synechocystis PCC6803 wild type and mutant PCC6803 PpetJ-pyk2.

After induction of the petJ promoter, the level of extracellular pyruvate was slightly increased in the PCC6803 PpetJ-pyk2 mutant compared to the wild-type.

|  | 6 days | | 9 days | | 14 days | |
| --- | --- | --- | --- | --- | --- | --- |
|  | $OD_{750}$ | pyruvate [mM] | $OD_{750}$ | pyruvate [mM] | $OD_{750}$ | pyruvate [mM] |
| PCC6803 Wt | 1.3 | 0.018 | 1.9 | 0.005 | 2.5 | 0.009 |
| PpetJ-pyk2 | 0.8 | 0.016 | 1.3 | 0.051 | 1.9 | 0.064 |

Pyruvatekinase 2 Overexpression Mutant Expressing PDC and ADH

Pyruvate kinase 2 was also expressed from self-replicating plasmid pVZ321 under control of its endogeneous promoter Ppyk2 in the ethanol producing strain S. PCC6803 pSK-PisiA-PDC-ADHII. Generation of plasmid pVZ-Ppyk2-pyk2, which was conjugated into Synechocystis pSK-PisiA-PDC-ADHII, was already described herein.

The ethanol production rates and the oxygen evolution for the photosynthetic capacity of Synechocystis strains S. PCC6803 pSK-PisiA-PDC-ADHII harboring plasmid pVZ-Ppyk2-pyk2 and reference strain S. PCC6803 pSK-PisiA-PDC-ADHII were determined as mentioned above.

| (data are mean of two measurements) | | | |
| --- | --- | --- | --- |
|  | µmol $O_2$/ mg Chl* h | µmol EtOH/ mg Chl* h | µmol EtOH/ µmol $O_2$ |
| S. PCC6803 pSK-PisiA-PDC-ADHII | 164.5 | 9.5 | 0.058 |
| Ppyk2-pyk2 pSK-PisiA-PDC-ADHII | 134.3 | 10.0 | 0.074 |

X.8 Metabolic Mutant Photoautotrophic Cells Harbouring an Overexpressed Pyruvate Kinase (pyk) Enolase (eno) and Phosphoglycerate Mutase (Pgm) as First Genetic Modifications Two mutants have been created for overexpression of the three glycolytic genes pyruvate kinase (pyk), enolase (eno) and phosphoglycerate mutase (pgm).

In one mutant expression of pyruvate kinase 1 (from E. coli), enolase and phosphoglycerate mutase (both from Zymomonas mobilis) is controlled by the ribulose-1,5-bis-phosphate carboxylase/oxygenase (RubisCO) promoter (Prbc) from Synechococcus PCC7942. Construction of the DNA-vector pVZ321-p67, which was conjugated into Synechocystis PCC6803 to generate mutant PCC6803 Prbc-pyk-eno-pgm, was already described herein.

In the other mutant the expression of additional copies of the endogenous genes pyruvate kinase 2, enolase and phosphoglycerate mutase from Synechocystis PCC6803 is controlled by the PpetJ promoter. DNA-vector pVZ322-PpetJ-pyk2-eno-pgm, which was conjugated into Synechocystis PCC6803 to generate mutant PCC6803 PpetJ-pyk2-eno-pgm, was already described herein.

The obtained mutants PCC6803 pVZ321-Prbc-pyk-eno-pgm and PCC6803 pVZ322-PpetJ-pyk2-eno-pgm were cultivated in BG11 medium containing 14 mg/l chloramphenicol or 3 mg/l gentamycin, respectively, and characterized in comparison to the Synechocystis wild-type strain under constant light conditions as described herein.

Results:

No significant differences could be detected in cell growth, chlorophyll content and photosynthetic oxygen production between Synechocystis PCC6803 wild type and mutants PCC6803 Prbc-pyk-eno-pgm and PCC6803 PpetJ-pyk2-eno-pgm.

Excretion of pyruvate was increased in mutant PCC6803 Prbc-pyk-eno-pgm compared to wild-type, as shown in the following table:

|  | 10 days | | 14 days | |
| --- | --- | --- | --- | --- |
|  | $OD_{750}$ | pyruvate [mM] | $OD_{750}$ | pyruvate [mM] |
| PCC6803 (BG11) | 4.6 | 0.006 | 6.2 | 0.012 |
| PCC6803 Prbc-pyk-eno-pgm | 3.0 | 0.017 | 6.1 | 0.032 |

In mutant PCC6803 PpetJ-pyk2-eno-pgm the level of extracellular pyruvate was increased after induction of the glycolytic genes by copper starvation.

|  | 7 days | | 14 days | |
| --- | --- | --- | --- | --- |
|  | $OD_{750}$ | pyruvate [mM] | $OD_{750}$ | pyruvate [mM] |
| PCC6803 (BG11-Cu) | 1.6 | 0 | 3 | 0.006 |
| PCC6803 PpetJ-pyk2-eno-pgm | 3.1 | 0.013 | 3.7 | 0.024 |

Expression of Pyruvate Kinase, Enolase and Phospho-Glycerate Mutase in Synechocystis Strains Expressing Pdc Enzyme Alone as a Second Genetic Modification.

Plasmids pVZ321-p67 and pVZ322-PpetJ-pyk2-eno-pgm were each conjugated into the ethanol producing strain Synechocystis PCC6803 pSK10-PpetJ-pdc expressing only PDC. (Construct pSK10-PpetJ-pdc is a derivate of pSK10-PpetJ-pdc-adhII, from that the adhII gene was cut out with SacI and PstI.)

The resulting mutants were cultured in BG11 containing 10 mg/l streptomycin and 7 mg/l chloramphenicol or 2 mg/l gentamycin, respectively. Expression of pdc (and in mutant PpetJ-pyk2-eno-pgm also of the glycolytic genes) was induced by copper starvation (PpetJ).

In short term measurements both mutants expressing the glycolytic enzymes showed a better ethanol production rate (relative to photosynthetic activity) than the reference strains. Data in the following table are means of two consecutive measurements within one cultivation.

|  | μmol $O_2$/ mg Chl* h | μmol EtOH/ mg Chl* h | μmol EtOH/ μmol $O_2$ |
|---|---|---|---|
| PCC6803 pSK-PpetJ-PDC | 130 | 1.8 | 0.014 |
| PCC6803 pSK-PpetJ-PDC pVZ-Prbc-pyk-eno-pgm | 148 | 3.2 | 0.022 |
| PCC6803 pSK-PpetJ-PDC | 197 | 2.5 | 0.012 |
| PCC6803 pSK-PpetJ-PDC pVZ-Ppet J-pyk2-eno-pgm | 104 | 2.8 | 0.028 |

Conclusions

These data suggest that overexpression of the glycolytic enzymes pyruvate kinase, enolase and phosphoglycerate mutase leads to a higher flux from $CO_2$ towards pyruvate which results in a higher ethanol production rate, relative to the photosynthetic capacity.

X.9 Metabolic Mutant Photoautotrophic Cells Harbouring an Overexpressed Malic Enzyme (Me) and Malate Dehydrogenase (Mdh) as First Genetic Modifications Overexpression of malic enzyme (Me) and malate dehydrogenase (Mdh) were accomplished by regulated expression of the corresponding genes (slr0721-me; sll0891-mdh) via the PpetJ promoter. Construction of DNA-vectors pSK9/PpetJ-me and pSK9/PpetJ-me-mdh, which were used for generation of me- and me/mdh-overexpression mutants, was already described herein. The obtained overexpression mutants were fully segregated and were grown in BG11 medium containing 14 mg/l chloramphenicol. Mutants PpetJ-me and PpetJ-me/mdh were examined in comparison to the Synechocystis wild-type strain under constant light conditions as described herein. Expression of me and mdh genes was induced by copper starvation and successfully proven by northern blot analysis via a radio-labeled me- and mdh-probe, respectively (data not shown).

Results:

No significant differences could be detected in cell growth, chlorophyll content and photosynthetic oxygen production between Synechocystis PCC6803 wild type and PpetJ-me and PpetJ-me/mdh mutant, respectively.

An enhanced extracellular pyruvate level was detected in the medium of the PpetJ-me and the PpetJ-me/mdh mutants after induction by copper starvation. The following table shows the extracellular pyruvate concentrations measured 10 days after induction in comparison with values measured in medium from non-induced cells.

|  | Not induced (BG11) 10 days | | Induced (BG11 —Cu) 10 days | |
|---|---|---|---|---|
|  | $OD_{750}$ | pyruvate [mM] | $OD_{750}$ | pyruvate [mM] |
| PCC6803 Wt | 8.3 | 0.010 | 9.3 | 0.011 |
| PpetJ-me | 10.1 | 0.005 | 8.3 | 0.032 |
| PpetJ-me-mdh | 7.8 | 0.005 | 8.5 | 0.024 |

The higher extracellular pyruvate levels measured in the induced PpetJ-me and PpetJ-me/mdh mutants (compared to wildtype and non-induced cells) suggest, that overexpression of malic enzyme or malic enzyme in combination with malate dehydrogenase leads to a higher pyruvate level within the cyanobacterial cells.

X.10 Metabolic Mutant Cells of Nostoc/Anabaena PCC7120 and Anabaena Variabilis ATCC 29413 Harbouring a Knockout of the ADP-Glucose-Pyrophosphorylase as a First Genetic Modification In the following the EtOH production in Anabaena PCC7120 transformed with the integrative PpetE-PDC-ADHII and PpetE-PDC constructs will be discussed.

In a first test experiment EtOH production in Anabaena PCC7120 with PpetE-pdc-adhII or PpetE-pdc inserted in ADP-glucose-pyrophosphorylase gene, agp, was measured of the following mutants: A.7120 Δagp (all4645)::C.K3-PpetE-pdc-adhII, named "PpetE-pdc-adhII" and A.7120 Δagp (all4645)::C.K3-PpetE-pdc, named "PpetE-pdc". Mutant A.7120 Δagp (all4645)::C.K3, named Δagp, served as control.

Cultures of all mutants were grown at 28° C., under continuous light conditions (40 μE/$m^2$ $s^1$) in batches of 50 ml in 100 ml Erlenmeyer flasks with shaking. Precultures were grown in BG11 medium lacking copper sulfate (BG11–Cu), supplemented with neomycin (100 μg/ml). It should be noted here, that the petE promoter might not be fully repressed under this BG11–Cu conditions, as the glassware was not treated to remove trace amounts of copper from it. The petE promoter seems to be smoothly regulated in Anabaena PCC7120 [Buikema, W. J., and R. Haselkorn. 2001. Expression of the Anabaena hetR gene from a copper-regulated promoter leads to heterocyst differentiation under repressing conditions. PNAS USA 98:2729-2734], therefore trace amounts of copper coming from the glassware might be sufficient to induce expression.

Expression of the ethanologenic genes was induced by addition of 1× copper (0.32 μM $CuSO_4$). This corresponds to the copper concentration present in BG11 medium.

As a measure of growth, chlorophyll was determined at several time points and ethanol was measured using the already described enzymatic method.

TABLE 1

Growth and ethanol production of Anabaena mutants expressing ethanologenic genes under control of petE promoter.

| | time | | | | | | | |
|---|---|---|---|---|---|---|---|---|
| | 0 (start) | | 5 days | | 9 days | | 14 days | |
| | Chl | EtOH | Chl | EtOH | Chl | EtOH | Chl | EtOH |
| "PpetE-pdc-adhII" | 1 | 0.002 | 3 | 0.014 | 6 | 0.022 | 8 | 0.037 |

TABLE 1-continued

Growth and ethanol production of Anabaena mutants expressing ethanologenic genes under control of petE promoter.

| | time | | | | | | | |
|---|---|---|---|---|---|---|---|---|
| | 0 (start) | | 5 days | | 9 days | | 14 days | |
| | Chl | EtOH | Chl | EtOH | Chl | EtOH | Chl | EtOH |
| "PpetE-pdc" | 3 | 0.006 | 5 | 0.015 | 6 | 0.028 | 8 | 0.044 |
| Δagp (control) | 8 | 0 | 16 | 0.0001 | 20 | 0.0001 | 25 | 0.0001 |

Chl, chlorophyll in [µg/ml] and EtOH [%].

Ethanol was produced by both integrative mutants, while in the control strain (mutant Δagp) no ethanol production was detected. The similar ethanol production rates obtained in mutants "PpetE-pdc-adhII" and "PpetE-pdc" clearly indicate that also in *Anabaena* PCC7120 expression of PDC alone is sufficient for ethanol production. Thus it appears that this strain constitutively expresses an endogenous ADH enzyme converting acetaldehyde into ethanol. Several open reading frames are annotated as alcohol dehydrogenases in *Anabaena* PCC7120 (http://bacteria.kazusa.or.jp/cyanobase/), however all genes show only little similarity (less than 30% identical amino acids) to SynADH.

Detailed Discussion of the Embodiments Involving Overexpressed $Zn^{2+}$ Dependent Alcohol Dehydrogenase and Pdc and/or Adh Enzymes Under the Control of Various Inducible Promoters In the following further embodiments of the invention related to for example an overexpressed $Zn^{2+}$ dependent alcohol dehydrogenase, an overexpressed alcohol dehydrogenase, directly converting acetyl-CoA to ethanol, or promoters that can be induced by nutrient starvation, cold shock, heat shock, salt stress, light exposure or stationary growth of the host cell will be explained in more detail.

Construction of selfreplicating (extrachromosomal) and chromosome-integrative vectors for the inducible overexpression of ethanologenic enzymes in cyanobacteria Construction of extrachromosomal pVZ-vectors for inducible overexpression of pyruvate decarboxylase (ZmPdc) and alcohol dehydrogenase (ZmAdhII) from *Zymomonas mobilis*

The construction of the certain vectors including the different promoters were done by using the following general protocol:

- EcoRI/BamHI restriction of the pCB4-LR(TF)pa shuttle vector in order to cut off the pdc and adh genes. This shuttle vector was constructed by Dr. John Coleman, University of Toronto, Toronto, Canada.
- ligation of the pdc/adh containing EcoRI/BamHI fragment into the cloning vector pDrive (EcoRI/BamHI). The pDrive vector (Qiagen, Hilden, Germany, GenBank no.: DQ996013) was already described above.
- amplification of the isiA-, nblA- and ntcA-promoter using chromosomal DNA from *Synechocystis* sp. PCC 6803 and the following primers (all amplified promoters have a length of about 600 bp and include the ribosome binding site of the corresponding genes):

```
                                      (SEQ ID NO: 207)
isiA-fw-SalI    5'-GTCGACCTTCCAGCACCACGTCAAC-3'

(SEQ ID NO: 208)
isiA-rev-EcoRI  5'-GAATTCACAGAATTGCCTCCTTAATTGAG-3'
```

-continued
```
                                      (SEQ ID NO: 209)
nblA-fw-SalI    5'-ACGCGTCGACTTATGGTTGATTCGCATTG-3'

(SEQ ID NO: 210)
nblA-rev-EcoRI  5'-CGGAATTCATAGCTGTTGCCCTCCAAG-3'

(SEQ ID NO: 211)
ntcA-fw-SalI    5'-GTCGACAACGACGGAGGTTTAAGGG-3'

(SEQ ID NO: 212)
ntcA-rev-EcoRI  5'-GAATTCATGCACGTTCACGGTAATGG-3'
```

All forward primer included the SalI restriction site, all reverse primer included a EcoRI restriction site for cloning (marked bold).

ligation of the SalI/EcoRI cut promoter fragments into the pDrive-pdc/adh (SalI/EcoRI) generating the constructs pDrive-PisiA-pdc/adh, pDrive-PnblA-pdc/adh and pDrive-PntcA-pdc/adh SalI/PstI restriction of pDrive-PisiA-pdc/adh, pDrive-PnblA-pdc/adh and pDrive-PntcA-pdc/adh and ligation of the corresponding promoter-pdc/adh fusions into the self replicating broad-host range vector pVZ321b (SalI/PstI), a derivate of the pVZ321 (constructed by V. V. Zinchenko Moscow, Russia; described above) with an additional streptomycin resistance cassette/cartridge introduced into the XbaI site of pVZ321. The pVZ321b vector was constructed by Anne Karradt, Humboldt-Universitaet Berlin, Plant Biochemistry Department (Prof. Lockau) and was used as a cargo plasmid for conjugation.

pVZ321 Gen Bank no.: AF100176.

End products of the cloning procedure are the pVZ-vectors: FIG. 33A presents a schematic diagram of pVZ-PisiA-pdc/adh; FIG. 33B presents a schematic diagram of pVZ-PnblA-pdc/adh; and FIG. 33C presents a schematic diagram of pVZ-PntcA-pdc/.

FIG. 33D presents the nucleotide sequence of adhII and pdc genes from *Zymomonas mobilis*. The source of this polynucleotide is the shuttle vector pCB4-LR(TF)pa, a kind gift from John Coleman. FIG. 33E presents a schematic diagram of some restriction sites occurring within the adhII and pdc gene sequences. FIGS. 33F and 33G presents the amino acid sequence of ZmPdc and ZmAdhII, respectively. Various gene promoter elements were utilized to control constitutive and/or induced gene expression. Sequences for these elements are presented herein. As known to those skilled in the art, other genetic elements may serve the same purpose.

Remark: In all following nucleotide sequences of promoters restriction sites for clonings are marked (colored).

The isiA promoter (*Synechocystis* sp. PCC6803) element nucleotide sequence is presented in FIG. 34A. This genetic element induces gene expression under conditions of iron starvation.

The nblA promoter (*Synechocystis* sp. PCC6803) element nucleotide sequence is presented in FIG. 34B. This genetic element induces gene expression under conditions of nitrogen starvation.

The ntcA promoter (*Synechocystis* sp. PCC6803) element nucleotide sequence is presented in FIG. 34C. This genetic element induces gene expression under conditions of nitrogen starvation.

The pVZ321b cloning vector (derivate of pVZ321) was constructed by Anne Karradt, Humboldt-Universitaet Berlin, Plant Biochemistry Department (Prof. Lockau), Berlin. The nucleotide sequence for pVZ321b is presented in FIG. 35A, and the structure of this plasmid is presented schematically in FIG. 35B.

Introduction of further well suited inducible promoters into the existing pVZ-expression constructs (point 1).

In order to create expression constructs as described above (point 1) but under control of a different promoter, the promoter sequence was cut out by SalI/EcoRI digestion of the corresponding pVZ-Pxxx-pdc/adh construct (xxx for isiA, ntcA, nblA). The new promoter sequence containing the restriction sites SalI/EcoRI as described for the isiA-, nblA- and ntcA-promoter was ligated into the "promoter free" pVZ construct resulting in a pdc/adh expression construct under control of the new promoter.

Representative new promoters include, but are not limited to, the following:

(1) FIG. 36A depicts the nucleotide sequence of the petJ promoter (*Synechocystis* sp. PCC 6803) (petJ gene: sll1796 (encoding for cytochrome c553; induced expression under copper starvation);

REFERENCE

J Biol Chem. 2004 Feb. 20; 279(8):7229-33. Epub 2003 December
  The efficient functioning of photosynthesis and respiration in *Synechocystis* sp. PCC 6803 strictly requires the presence of either cytochrome c6 or plastocyanin.
  Durán R V, Hervas M, De La Rosa M A, Navarro J A.
  A plasmid created with this promoter element is presented schematically in FIG. 36B.

(2) FIG. 36 C depicts the nucleotide sequence of the sigB promoter (*Synechocystis* sp. PCC 6803)
  sigB gene: sll0306 (encoding for RNA polymerase group 2 sigma factor) induced expression after heat shock, in stationary growth phase/nitrogen starvation and darkness)

REFERENCES

Arch Microbial. 2006 October; 186(4):273-86. Epub 2006 Jul. 26.
  The heat shock response in the cyanobacterium *Synechocystis* sp. Strain PCC 6803 and regulation of gene expression by HrcA and SigB.
  Singh A K, Summerfield T C, Li H, Sherman L A
FEBS Lett. 2003 Nov. 20; 554(3):357-62.
  Antagonistic dark/light-induced SigB/SigD, group 2 sigma factors, expression through redox potential and their roles in cyanobacteria.
  Imamura S, Asayama M, Takahashi H., Tanaka K, Takahashi H, Shirai M
J Biol. Chem. 2006 Feb. 3; 281(5):2668-75. Epub 2005 Nov. 21.
  Growth phase-dependent activation of nitrogen-related genes by a control network of group 1 and group 2 sigma factors in a cyanobacterium.
  Imamura S, Tanaka K, Shirai M, Asayama M.
  A plasmid created with this promoter element is presented schematically in FIG. 36D.

(3) FIG. 36 E depicts the nucleotide sequence of the htpG promoter (*Synechocystis* sp. PCC 6803) htpG gene: sll0430: (encoding for heat shock protein 90, molecular chaperone) induced expression after heat shock

REFERENCE

Plant Physiol. 1998 May; 117(1):225-34.
  Transcriptional and posttranscriptional control of mRNA from lrtA, a light-repressed transcript in *Synechococcus* sp. PCC 7002.
  Samartzidou H, Widger W R
  A plasmid created with this promoter element is presented schematically in FIG. 36F.

(4) FIG. 36 G shows the nucleotide sequence of the lrtA promoter (*Synechocystis* sp. PCC 6803) lrtA gene:sll0947 (encoding the light repressed protein A homolog induced expression after light to dark transition)

REFERENCE

Plant Physiol. 1998 May; 117(1):225-34.
  Transcriptional and posttranscriptional control of mRNA from lrtA, a light-repressed transcript in *Synechococcus* sp. PCC 7002.
  Samartzidou H, Widger W R
  A plasmid created with this promoter element is presented schematically in FIG. 36H.

(5) the nucleotide sequence of the psbA2 promoter (*Synechocystis* sp. PCC 6803) (FIG. 36I) psbA2 gene: slr1311 (encoding the photosystem II D1 protein) induced expression after dark to light transition

REFERENCE

Biochem Biophys Res Commun. 1999 Feb. 5; 255(1):47-53.
  Light-dependent and rhythmic psbA transcripts in homologous/heterologous cyanobacterial cells.
  Agrawal G K, Asayama M, Shirai M.
  A plasmid created with this promoter element is presented schematically in FIG. 36J.

(6) FIG. 36K shows the nucleotide sequence of the rbcL promoter (*Synechocystis* sp. PCC 6803) rbcL gene: slr0009 (encoding the ribulose biphosphate carboxylase/oxygenase large subunit constitutive strong expression under continuous light conditions

REFERENCE

Plant Mol. Biol. 1989 December; 13(6):693-700
  Influence of light on accumulation of photosynthesis-specific transcripts in the cyanobacterium *Synechocystis* 6803.
  Mohamed A, Jansson C.
  A plasmid created with this promoter element is presented schematically in FIG. 36L.

(7) FIG. 36M depicts the nucleotide sequence of the psaA promoter (*Synechocystis* sp. PCC6803); PsaA gene: slr1334 (encoding P700 apoprotein subunit Ia) induced expression under low white light and orange light, low expression level under high light and red light, repressed in darkness

REFERENCES

Plant Cell Physiol. 2005 September; 46(9):1484-93. Epub 2005 Jun. 24.

Regulation of photosystem I reaction center genes in *Synechocystis* sp. strain PCC 6803 during Light acclimation.

Herranen M, Tyystjärvi T, Aro E M.

*Plant Cell Physiol.* 2006 July; 47(7):878-90. Epub 2006 May 16.

Characterization of high-light-responsive promoters of the psaAB genes in *Synechocystis* sp. PCC 6803.

Muramatsu M, Hihara Y.

A plasmid created with this promoter element is presented schematically in FIG. 36N.

(8) FIG. 36O shows the nucleotide sequence of the ggpS promoter (*Synechocystis* sp. PCC6803); ggpS gene: sll1566 (encoding glucosylglycerolphosphate synthase) induced expression after salt stress

REFERENCE

*Plant Physiol.* 2004 October; 136(2):3290-300. Epub 2004 Sep. 10.

Gene expression profiling reflects physiological processes in salt acclimation of *Synechocystis* sp. strain PCC 6803.

Malin K, Kanesaki Y, Los D A, Murata N, Suzuki Hagemann M.

*J Bacteriol.* 2002 June; 184(11):2870-7.

Salt-dependent expression of glucosylglycerol-phosphate synthase, involved in osmolyte synthesis in the cyanobacterium *Synechocystis* sp. strain PCC 6803.

Marin K, Huckauf J, Fulda S, Hagemann M.

A plasmid created with this promoter element is presented schematically in FIG. 36P.

(9) FIG. 36Q depicts the nucleotide sequence of the nirA promoter (*Synechocystis* sp. PCC6803); nirA gene: slr0898 (encoding ferredoxin-nitrite reductase) induced expression after transition from ammonia to nitrate

REFERENCE

*Appl Environ Microbial.* 2005 October; 71(10):5678-84.

Application of the *Synechococcus* nirA promoter to establish an inducible expression system for engineering the *Synechocystis* tocopherol pathway.

Qi Q, Hao M, Ng W O, Slater S C, Baszis S R, Weiss J D, Valentin H E.

*J. Bacterial.* 1998 August; 180(16):4080-8 cis-acting sequences required for NtcB-dependent, nitrite-responsive positive regulation of the nitrate assimilation operon in the cyanobacterium *Synechococcus* sp. strain PCC 7942.

Maeda S, Kawaguchi Y, Ohe T A, Omata T.

A plasmid created with this promoter element is presented schematically in FIG. 36R.

(10) FIG. 36S depicts the nucleotide sequence of the petE promoter (*Anabaena* sp. PCC7120); petE gene: all0258 (encoding plastocyanin precursor) induced expression at elevated copper concentrations

REFERENCE

*Microbiology.* 1994 May; 140 (Pt 5):1151-9.

Cloning, sequencing and transcriptional studies of the genes for cytochrome c-553 and plastocyanin from *Anabaena* sp. PCC 7120.

Ghassemian M, Wong B, Ferreira F, Markley J L, Straus N A.

*Proc Natl Acad Sci USA.* 2001 Feb. 27; 98(5):2729-34. Epub 2001 Feb. 20.

Expression of the *Anabaena* hetR gene from a copper-regulated promoter leads to heterocyst differentiation under repressing conditions.

Buikema W J, Haselkorn R.

A plasmid created with this promoter element is presented schematically in FIG. 36T.

(11) FIG. 36U shows the nucleotide sequence of the hspA promoter (*Synechocystis* sp. PCC6803); hspA gene: sll154 16.6 kDa small heat shock protein, molecular chaperone multi-stress responsible promoter (heat, cold, salt and oxidative stress)

REFERENCE

*Curr Microbial.* 2004 September; 49(3):192-8.

Expression of the heat shock gene hsp16.6 and promoter analysis in the cyanobacterium, *Synechocystis* sp. PCC 6803.

Fang F, Barnum S R.

*J Exp Bat.* 2006; 57(7):1573-8. Epub 2006 Mar. 30.

The heat shock response of *Synechocystis* sp. PCC 6803 analysed by transcriptomics and proteomics.

Suzuki I, Simon W J, Slabas A R.

A plasmid created with this promoter element is presented schematically in FIG. 36V.

(12) FIG. 36W depicts the nucleotide sequence of the hliB promoter (*Synechocystis* sp. PCC6803); hliB gene: ssr2595: high light-inducible polypeptide HliB, CAB/ELIP/HLIP superfamily multi-stress responsible promoter (heat, cold, salt and oxidative stress)

REFERENCE

*J Biol Chem.* 2001 Jan. 5; 276(1):306-14.

The high light-inducible polypeptides in *Synechocystis* PCC6803. Expression and function in high light.

He Q, Dolganov N, Bjorkman O, Grossman A R.

*Arch Microbial.* 2007 April; 187(4):337-42. Epub 2007 Feb. 10.

The response regulator RpaB binds the high light regulatory 1 sequence upstream of the high-light-inducible hliB gene from the cyanobacterium *Synechocystis* PCC 6803.

Kappell A D, van Waasbe en L G.

A plasmid created with this promoter element is presented schematically in FIG. 36X.

(13) FIG. 36Y shows the nucleotide sequence of the clpB1 promoter (*Synechocystis* sp. PCC6803); clpB1 gene: slr1641: ATP-dependent Clp protease, Hsp 100, ATP-binding subunit ClpB multi-stress responsible promoter (heat, cold, salt and oxidative stress)

REFERENCE

*Microbiology.* 2004 May; 150 (Pt 5):1271-81.

Effects of high light on transcripts of stress-associated genes for the cyanobacteria *Synechocystis* sp. PCC 6803 and Prochlorococcus MED4 and MIT9313.

Mary I, Tu C J, Grossman A, Vaulot D.

*J Exp Bot.* 2006; 57(7):1573-8. Epub 2006 Mar. 30.

The heat shock response of *Synechocystis* sp. PCC 6803 analysed by transcriptomics and proteomics.

Suzuki I, Simon W J, Slabas A R.

A plasmid created with this promoter element is presented schematically in FIG. 36Z.

Introduction of Alternative Ethanologenic Genes to ZmPdc and ZmAdhII into the Existing pVZ-Expression Constructs (point 1)

In order to create expression constructs as described above (point 1) but with different alcohol dehydrogenases, the adh encoding sequence was cut out by SacI/PstI digestion of the corresponding pVZ-Pxxx-pdc/adh construct (xxx for isiA, nblA, ntcA). The new adh sequence containing the restriction sites SacI/PstI (introduced by used primer) was ligated into the "adh free" pVZ construct resulting in a construct that expresses the ZmPdc together with new Adh.

Remark: In all following nt sequences of genes restriction sites are marked for clonings as well as translation starts (start codons) and translation stops (stop codons).

In this context, new alcohol dehydrogenases include the following:

(1) FIG. 37A presents the nucleotide sequence for ZmADHI (adhA gene from *Zymomonas mobilis* ZM4) and FIG. 37B presents the amino acid sequence for ZmAdhI AAV89860

FIG. 37C presents a schematic representation of the plasmid pVZ321b-PisiA-PDC-ZmADH1. FIG. 37D presents a schematic representation of the plasmid pVZ321b-PntcA-PDC-ZmAH1. FIG. 37E presents a schematic representation of the plasmid pVZ321b-PnblA-PDC-ZmADH1.

(2) The nucleotide sequence of SynAdh (adh gene (slr1192) *Synechocystis* sp. PCC 6803) is presented in FIG. 38A. The amino acid sequence of this protein (SynAdh protein sequence BAA18840) is presented in FIG. 38B.

FIG. 38C presents a schematic representation of the plasmid pVZ321b-PisiA-PDC-SynADH. FIG. 38D presents a schematic representation of the plasmid pVZ321b-PntcA-PDC-SynADH. FIG. 38E presents a schematic representation of the plasmid pVZ321b-PnblA-PDC*SynADH.

In order to create expression constructs as described above (point 1) but with AdhE-type alcohol dehydrogenases, the pdc/adh encoding sequence was cut out by EcoRI/BamHI and EcoRI/PstI digestion resp. of the corresponding pVZ-Pxxx-pdc/adh construct (xxx for isiA, ntcA, nblA). The adhE sequence of *E. coli* and *Thermosynechococcus elongatus* resp. containing the restriction sites EcoRI/BamHI and EcoRI/PstI resp. (introduced by used primer) were ligated into the "pdc/adh free" pVZ construct resulting in constructs that express the AdhE-type alcohol dehydrogenases.

(3) The nucleotide sequence for EcAdhE (adhE gene from *E. coli* K12) is presented in FIG. 39A. The amino acid sequence for this protein (EcAdhE protein sequence NP_415757) is presented in FIG. 39B.

FIG. 39C presents a schematic representation of the plasmid pVZ321b-PisiA-PDC-EcAdhE. FIG. 39D depicts a schematic representation of the plasmid pVZ321b-PntcA-PDC-EcAdhE. FIG. 39E presents a schematic representation of the plasmid pVZ321b-PnblA-PDC-EcAdhE.

(4) The nucleotide sequence for the ThAdhE gene (adhE gene (tlr0227) from *Thermosynechococcus elongatus* BP-1) is presented in FIG. 40A, and the amino acid sequence for this protein (ThAdhE protein sequence BAC07780) is presented in FIG. 40B.

FIG. 40C presents a schematic representation of the plasmid pVZ321b-PisiA-PDC-ThAdhE. FIG. 40D presents a schematic representation of the plasmid pVZ321b-PntcA-PDC-ThAdhE. FIG. 40E presents a schematic representation of the plasmid pVZ321b-PnblA-PDC-ThAdhE.

In order to create expression constructs as described above (point 1) but with an alternative pyruvate decarboxylase to the *Zymomonas mobilis* enzyme, the Pdc encoding sequence was cut out by EcoRI/SacI digestion of the corresponding pVZ-Pxxx-pdc/adh construct (xxx for isiA, ntcA, nblA). The pdc sequence from *Zymobacter palmae* containing the restriction sites EcoRI/SacI (introduced by used primer) was ligated into the "pdc free" pVZ construct resulting in a construct that express the Pdc from *Zymobacter palmae* together with the preexisting Adh.

FIG. 41A presents the nucleotide sequence for ZpPdc (pdc gene from *Zymobacter palmae* ATCC 51623), and the amino acid sequence for this protein (ZpPdc protein sequence AAM49566) is presented in FIG. 41B.

Construction of Chromosome Integrative pSK-Vectors

In order to create plasmids for stable chromosome integration in cyanobacteria the whole inserts from the described pVZ constructs (point 1 and 3) containing the promoter sequence and the coding region of the ethanologenic enzymes (Pdc and Adh) were cut out by SalI/PstI digestion. The resulting inserts were ligated into the pSK10, a derivate of the pSK9 (a kind gift of V. V. Zinchenko and described in Dühring et al., submitted 16th of December 2007, Plant Physiology) using the SalI/PstI restriction sites. In some cases other restriction sites were used, e.g. in case of pVZ321b-Pxxx-pdc-adhI the restriction sites XbaI/PstI were used, in case of pVZ321b-Pxxx-Ecdhe the restriction sites XbaI/BamHI were used.

FIG. 42A presents the nucleotide sequence of the pSK10 cloning vector (derivate of pSK9 [V. V. Zinchenko, Moscow, Russia; unpublished]). FIG. 42B presents a schematic representation of this plasmid.

Several pSK10 constructs with ZmPdc/ZmAdhII were obtained.

FIG. 42C presents a schematic diagram of pSK10-PisiA-PDC-ADHII.

FIG. 42D presents a schematic diagram of pSK10-PnblA-PDC-ADHII.

FIG. 42E presents a schematic diagram of pSK10-PntcA-PDC-ADHII.

Several pSK10 constructs with ZmPdc/ZmAdhI were obtained.

FIG. 42F presents a schematic diagram of pSK10-PisiA-PDC-ADHI.

FIG. 42G presents a schematic diagram of pSK10-PnblA-PDC-ADHI.

FIG. 42H presents a schematic diagram of pSK10-PntcA-PDC-ADHI.

Several pSK10 constructs with ZmPdc/SynAdh were obtained.

FIG. 42I presents a schematic diagram of pSK10-PisiA-PDC-SynADH.

FIG. 42J presents a schematic diagram of pSK10-PnblA-PDC-SynADH.

FIG. 42K presents a schematic diagram of pSK10-PntcA-PDC-SynADH.

Several pSK10 constructs with EcAdhE were obtained.

FIG. 42L presents a schematic diagram of pSK10-PisiA-PDC-EcAdhE.

FIG. 42M presents a schematic diagram of pSK10-PnblA-PDC-EcAdhE.

FIG. 42N presents a schematic diagram of pSK10-PntcA-PDC-EcAdhE.

Several pSK10 constructs with ThAdhE were obtained.

FIG. 42O presents a schematic diagram of pSK10-PisiA-PDC-ThAdhE.

FIG. 42P presents a schematic diagram of pSK10-PnblA-PDC-ThAdhE.

FIG. 42Q presents a schematic diagram of pSK10-PntcA-PDC-ThAdhE.

Expression of Pdc and Adh in the Filamentous; Diazotropic Cyanobacteria Nostoc/Anabaena Spec. PCC7120 and Anabaena variabilis ATCC 29413

In order to generate ethanol producing Anabaena strains, different constructs were created for conjugation into Anabaena PCC7120 and Anabaena variabilis ATCC29413.

Nostoc/Anabaena spec. PCC7120 and Anabaena variabilis ATCC 29413 were transformed using Self-replicating plasmids.

The ethanologenic genes were cloned into self-replicating plasmids for conjugation into Anabaena PCC7120. In these constructs different promoters were used to control expression of pdc and adhII.

pRL1049 Constructs

Genes encoding pdc and adhII from Zymomonas mobilis were cloned into the self-replicating plasmid pRL1049, which is known to replicate in Nostoc strains. Nucleotide and amino acid sequences of adhII and pdc genes from Zymomonas mobilis are already described herein.

The promoter-pdc-adhII fragment was cut out of the herein described pSK10-PpetJ-pdc-adhII plasmid with ClaI and BamHI and ligated into pRL1049. Promoter sequences were exchanged via EcoRI and SalI. Different promoters were used: promoters originating from PCC 6803: PisiA, PpetJ and PrbcL (nucleotide sequences are already described herein) and promoters originating from PCC 7120: PcrhC and PpetE.

Promoter sequences of PcrhC and PpetE are shown in FIGS. 42R and 42S, respectively (SalI and EcoRI restriction sites for cloning are marked in bold letters):

FIG. 42R depicts the crhC promoter (Anabaena sp. PCC7120) (crhC gene: alr4718, RNA helicase crhC cold shock inducible)

FIG. 42S shows the petE promoter (Anabaena sp. PCC7120) petE gene: all0258, plastocyanin precursor (petE) induced by addition of Cu The structure of plasmid pRL1049-PpetE-PDC-ADHII is shown in FIG. 42T.

The sequence of the plasmid pRL1049-PpetE-PDC-ADHII is shown in FIG. 42U.

pRL593 Construct

In addition to pRL1049 the broad range plasmid pRL593 was used for expression of pdc and adhII in Anabaena PCC7120. The structure of plasmid pRL593-PisiA-PDC-ADHII is presented in FIG. 42V and the DNA sequence is depicted in FIG. 42W.

EtOH Production in Anabaena PCC7120 Harboring Self-Replicating Plasmid pRL593-PisiA-PDC-ADHII EtOH production in Anabaena PCC7120 harboring pRL593-PisiA-PDC-ADHII following induction by iron starvation was measured in BG11 medium (+N) and in medium lacking combined nitrogen (−N) in day (12 h)/night (12 h) cycle. The results of this measurement is presented in FIGS. 42X and 42Y.

Ethanol production in medium +N appeared higher than under condition lacking combined nitrogen (−N); but this effect was not very pronounced when calculated per OD750 nm.

The best EtOH production rate in Anabaena PCC7120/pRL593-PisiA-pdc-adhII achieved was 0.0076% EtOH per day, constant for 19 days. This rate is lower compared to Synechocystis strains expressing pdc-adhII under control of PisiA, but continues for a longer time.

Characterization of Generated Ethanologenic Synechocystis cyanobacteria

P.1 Experimental Data for Characterization of Genetically Modified Photoautotrophic Host Cells Containing at Least One Second Genetic Modification Expression Levels of ZmPdc/ZmAdhII in Generated Synechocystis Cyanobacterial Mutants:

In order to quantify the induction rate of the used promoters, Pdc/AdhII protein levels in cultures with and without nutrient starvation were estimated by Western blot analysis.

In the case of the mutant with the isiA-promoter cultures were grown with and without addition of iron for about 48 hours. In the case of the mutants with the ntcA- and nblA-promoter cultures were grown with and without addition of nitrogen to the media. To get more comparable signals in the immunodetection, from the cultures under induced conditions, different dilutions of the prepared crude extracts were used.

Activities of ZmPdc/ZmAdhII in Cyanobacterial Mutants:

In order to compare the enzymatic activities of Pdc/AdhII with the estimated expression level, activities of Adh and Pdc were measured in crude extracts of the corresponding cultures.

In the case of the mutant with the isiA-promoter, cultures were grown with and without addition of iron for about 48 hours. The mutant with the ntcA-promoter was grown in standard BG11. Estimated activities were calculated on the corresponding protein concentration of the used crude extracts. It should be noted that Pdc activities were estimated in the presence of added thiamine pyrophosphate (cofactor for Pdc enzyme).

Results are presented in FIGS. 43A and 43B.

Ethanol Generation Rates in Cyanobacterial Mutants:

In general the inducible promoters used therein can be induced by medium exchange or by letting the cyanobacterial mutants grow into starvation conditions in the case of promoters which are inducible by nutrient starvation for example iron or copper starvation.

The use of inducible promoters for the over-expression of ethanologenic enzymes in cyanobacteria allow for switch on or switch off ethanol production on demand. Several promoters that are used for this purpose are inducible by the nutrient status, e.g. iron or copper availability. To reach these inducible conditions either a medium exchange or growth into these starvation conditions are possible.

Induction by Medium Exchange:

Mutants and Synechocystis wild-type strains were grown at 28° C., under constant light (50 µE m-2 s-1) either on a shaker (100 rpm) or in aerated culture vessels, bubbled with $CO_2$-enriched air (0.5% $CO_2$). The initial $OD_{750}$ was between 2 and 3 in a total culture volume of 50 ml in Erlenmeyer flasks or 100 ml in the aerated culture vessels.

When an optical density of 2-3 was reached the culture was harvested by centrifugation and the supernatant was discarded. The cell pellet was washed with the new medium (e.g. without iron, without copper, without nitrate and thereafter resuspended in the respective medium for promoter induction. If iron starvation is needed (isiA-promoter) the ferric ammonium citrate in the BG11 was omitted, in the case of copper starvation (petJ-promoter) the trace metal mix used was prepared without addition of copper sulfate, for nitrogen starvation the sodium nitrate in the BG11 was omitted.

Induction by Letting the Cultures Grow into Starvation Conditions:

Promoter induction by growing into starvation is based on the consumption of nutrients due to the nutrient demand of a culture. After nutrients are consumed the culture enters the starvation condition which leads to the induction of the appropriate promoter. The duration to reach such a starvation condition can be influenced/limited by reduction of the amount of the respective nutrient in the BG11 medium, e.g. ⅓ of the Ferric ammonium citrate or copper sulfate concentration.

Furthermore, for repression of the nirA-promoter ammonia (0.265 g/l corresponds to 5 mM $NH_4Cl$) was added to the BG11 medium, which already contains nitrate. The culture induces itself by consuming the ammonia as a preferred nitrogen source at first (nirA promoter not induced) and upon complete consumption of ammonia starts consuming the nitrate accompanied with induction of the nirA-promoter.

BG11 Media Recipe:
 $NaNO_3$: 1.5 g
 $K_2HPO_4$: 0.04 g
 $MgSO_4.7H_2O$: 0.075 g
 $CaCl_2.2H_2O$: 0.036 g
 Citric acid: 0.006 g
 Ferric ammonium citrate: 0.006 g
 EDTA (disodium salt): 0.001 g
 $NaCO_3$: 0.02 g
 Trace metal mix A5 1.0 ml (see below)
 Distilled water: 1.0 L Trace Metal Mix A5:
 $H_3BO_3$: 2.86 g
 $MnCl_2.4H_2O$: 1.81 g
 $ZnSO_4.7H_2O$: 0.222 g
 $NaMoO_4.2H_2O$: 0.39 g
 $CuSO_4.5H_2O$: 0.079 g
 $Co(NO_3)_2.6H_2O$: 49.4 mg
 Distilled water: 1.0 L P.8 Ethanol Production Rates of Genetically Modified Photoautotrophic Host Cells Containing Ethanologenic Enzymes Under the Transcriptional Control of Various Inducible Promoters In this section several natural occurring promoters from *Synechocystis* were analyzed for their suitability to express the Pdc enzyme in *Synechocystis*. In Tab. 1 an overview of the chosen promoters with their characteristics is shown. For all these promoters corresponding mutants in *Synechocystis* PCC6803 were already created and characterized. This section reports only a summary of the best embodiments.

FIG. 49A shows a summary of the cyanobacterial promoters used to express ethanologenic enzymes in *Synechocystis* 6803. Characteristics were taken from the literature, mainly analyzed and described for the cyanobacterium *Synechocystis* 6803.

Mutant Generation:
From a preexisting pVZ plasmid (pVZ321b-PisiA-PDC/ADHII) containing Pdc/Adh genes from *Zymomonas mobilis* the respective promoter fragment (PisiA) was cut out by SalI/EcoRI digestion and subsequent ligation of a new promoter fragment into the residual plasmid leading to a new pVZ321b-Pxxx-PDC/ADHII derivate with exchanged promoter xxx. Mutants were selected on streptomycin plates and grown in BG11 medium containing the appropriate antibiotics (kanamycin 100 mg/l; streptomycin 10 mg/l).

Growth Conditions:
Cultures were grown in BG11 in continuous light (50-100 µE) either on a shaker in 100 ml Erlenmeyer flasks (100 rpm) or in bubbling flasks (200 ml) aerated with $CO_2$-enriched air (0.5%). Depending on the current promoter BG11 without iron or copper was used as well as BG11 without nitrogen or supplemented with 5 mM $NH_4Cl$. Pre-cultures were harvested by centrifugation, the supernatant discarded and the cell pellet resuspended in new medium with or without the specific nutrient, needed for the regarding promoter mutant.

The growth of the cultures was monitored by photodensitometrical measurements at 750 nm. The ethanol production was determined in the culture supernatant by an optical enzymatic test (Boehringer Mannheim).

Results and Conclusions:
Transconjugants with the isiA-promoter are well growing and as pigmented in the same way as the wild type. Growth experiments reveal that the ethanol formation in the culture strongly depends on the availability of iron (FIG. 1). If iron is present the ethanol production is lower and time-shifted compared to the sub-culture without iron. As described in the literature iron starvation leads to very strong induction of the isiA-promoter. After transition of the cells to iron-free BG11 it needs usual 3-5 days until ethanol formation starts. Western blot analyses revealed that Pdc accumulates within 48 hours past iron depletion (up to 50-fold), but it strongly depends on the growth phase and the iron availability of the pre-culture. By supplementation the growth medium with additional iron (3× Fe) the ethanol production can be disabled for long time and starts very late with a low rate as depicted in FIG. 49C. FIG. 49B shoes the growth of the same culture monitored by determining the $OD_{750}$. Thus, ethanol production in *Synechocystis* is excellent adjustable by using the iron depending isiA-promoter.

Until now best production rates were observed for the isiA-promoter. In continuous light about 0.02% (v/v) ethanol and in day/night cycle about 0.014% (v/v) ethanol was produced per day, respectively (for at least 10 days). Since longer iron deficiency limits the photosynthesis rate it is imaginable to use this promoter in a biphasic manner in which after a production period iron is added to regenerate the cells for the next production period. Furthermore autoinduction by stationary growth is a possibility for the application of the isiA-promoter, too.

Transconjugants with the nblA-promoter appear more slowly growing compared to transconjugants with the isiA-promoter and are also a bit more yellowish pigmented than the wild type. Growth experiments reveal that the ethanol formation in the culture depends on the availability of nitrogen as described in the literature for the nblA-promoter. If nitrogen is absent the ethanol production is significant higher compared to the control culture with nitrogen (FIG. 49D). Western blot analyses revealed a fast and strong induction of the Pdc expression after nitrogen starvation. Within 48 hours the Pdc accumulates up to 25-fold compared to control cells (with nitrogen). But the ethanol accumulation in the culture stops after 5-6 days (see FIG. 49D) most likely due to the nitrogen deficiency. Since *Synechocystis* is not able to fix nitrogen from the atmosphere, nitrogen deprivation leads to a reduction of photosynthesis because of the deficiency of amino acid biosynthesis in the absence of an utilizable nitrogen source. Within some days of nitrogen deprivation photosynthesis decreases significantly. But by using of nitrogen-fixing cyanobacterial species (e.g. *Anabaena* sp. PCC7120) the application of a nitrogen-dependent promoter like the nblA-promoter might be well suited.

FIG. 49D shows the ethanol production of *Synechocystis* 6803 pVZ321b-PnblA-PDC/ADH that express Pdc/Adc enzymes under the control of the nitrogen dependent nblA-promoter. Cultures were grown on a shaker in Erlenmeyer flasks in BG11 under continuous light. A pre-culture was divided into 2 sub-cultures (start OD750 nm=2), one with and the other without nitrate.

The next set of promoters consists of three promoters inducible by the nutrient status. Two of them, PpetJ and PpetE are inducible by the copper availability and the third one, PnirA, depending from the nitrogen source, ammonia or nitrate.

According to the literature the nirA-promoter is repressed if ammonia is present and turned on if nitrate is the sole nitrogen source. Furthermore this promoter is described as tight regulated and was already successful used for heterologous gene expression in *Synechocystis* PCC6803. Transconjugants with the nirA-promoter appear more yellowish compared to the wild type and grow very slowly, if grown on usual BG11 plates. This phenotype is common for strong ethanol producers and is not surprising since the sole nitrogen source of BG11 is nitrate, which switches the nirA-promoter on.

Growth experiments revealed that the ethanol accumulation depends from the nitrogen source (FIGS. 49F and 49G). Without supplementation of ammonia to the BG11, the culture grows more slowly as shown in FIG. 49E and produces at the same time more ethanol. If ammonia is present the ethanol production was significant lower. At the 8th day new ammonia was added to the culture to take care that enough ammonia is present for repression of the nirA-promoter. Due to this elevated ammonia availability the ethanol formation was transiently blocked whereas the reference culture (BG11 without ammonia) continues accumulating ethanol with a similar rate anymore. But already 5 days later most of the new supplemented ammonia is consumed by the cells and the promoter becomes activated and reaches ethanol production rates similar to the reference culture. If the produced ethanol in each sub-culture is normalized to the cell growth (optical density) a clear difference in the ethanol productivity is visible (FIGS. 49F and 49G). The reference culture without ammonia produces at least two times more ethanol per cell compared to the culture supplemented with ammonia.

FIGS. 49E to 49G depict the growth, ethanol production and productivity per growth of *Synechocystis* 6803 pVZ325PnirA-PDC. Cultures were grown in Erlenmeyer flasks with BG11 medium in continuous light. A pre-culture was divided into two sub-cultures (start $OD_{750nm}$=3), one with and the other without ammonia supplementation. At the 8th day new ammonia (again 5 mM) was added to the subculture that already contained ammonia.

Thus, in general the nirA-promoter is applicable but in contrast to the literature no tight repression seems to be possible. If the leakiness of the nirA-promoter can be somehow reduced, it is imaginable that in the up-scaling process ammonia can be added to the BG11 to reach fast growth rates and reduced activity of the nirA-promoter. By consuming the ammonia over the time the culture induces itself, but can still grow by using the second nitrogen source, the nitrate that will stimulate the ethanol production. Thus, no medium exchange will be necessary.

Since copper is not essential for photosynthetic growth of *Synechocystis* (in contrast to iron) promoters of copper-responsible genes are very promising. Well described in the literature are the petJ- and the petE-promoter. The petJ-promoter is switched off if copper is present whereas the petE promoter is switched on. Both promoters have been already applied for heterologous expression in cyanobacteria, the petJ mainly in *Synechocystis*, whereas the petE was mainly used in *Anabaena* sp. PCC7120.

Transconjugants with the petJ-promoter show a reduced growth rate compared to wild type and appear also a bit yellowish. This is not surprising, since it is known that the limited copper availability in BG11 medium (0.3 µM) already activates the petJ-promoter to some extent. Growth experiments revealed that the ethanol formation in the culture with different concentrations of copper strongly depends on the availability of copper (see FIG. 49H to 49J). If copper is absent the ethanol production is significant higher compared to the control cultures with 0.3 µM (1×) or 1.5 µM copper (5×) but at the same time the culture without copper grows more slowly. Between 1× and 5× copper also a significant difference in growth and ethanol accumulation is detectable. If copper is added to the culture the growth rate is increased depending on the amount. A control experiment with the wild type was performed in which the growth was documented in dependence of the copper availability. Neither growth improvement nor retardation was detectable for the wild type by various copper concentrations (data not shown). Therefore the faster growth of the mutant at elevated copper concentration is not due to a growth stimulating effect of copper, it is a consequence of the lower ethanol production. The higher the ethanol production rate the lower the growth rate of corresponding mutants. If the ethanol accumulation is calculated per cell (ethanol per $OD_{750nm}$) strong differences in the productivity were obvious depending on the copper availability (see FIG. 47-6C). Thus, it is possible to adjust the ethanol production and the growth rate by copper supplementation. The petJ-promoter seems to be therefore well suited. Till now best production rates for this promoter are 0.014% (v/v) ethanol per day in continuous light (for about 4 weeks) and about 0.007% (v/v) ethanol in day/night cycles (for about 3 weeks).

FIG. 49H to 49J show the growth, ethanol production and productivity per growth of *Synechocystis* 6803 pVZ321b-PpetJ-PDC/ADH. Cultures were grown on a shaker in Erlenmeyer flasks in BG11 in continuous light. A pre-culture (1× copper) was divided into 3 sub-cultures (start $OD_{750nm}$=3) and different concentrations of copper were added.

Since in contrast to *Synechocystis* PCC6803 for the nitrogen-fixing cyanobacterium *Anabaena* PCC7120 it was shown that the *Anabaena* petE-promoter responds to different copper concentrations. Therefore, instead of the *Synechocystis* promoter the petE-promoter from *Anabaena* PCC7120 was chosen for the over-expression of Pdc/Adh in *Synechocystis*. Transconjugants with the petE-promoter are well growing and as pigmented as the wild type when grown on copper-free BG11-plates. Growth experiments reveal that the ethanol formation in the culture depends on the availability of copper (FIG. 49L). If the copper concentration is elevated (5× copper corresponds 1.5 µM) the ethanol production is significant higher and the culture grows more slowly at the same time (compared to the reference culture in copper-free BG11). Thus, the petE-promoter from *Anabaena* works well for the over-expression of Pdc/Adh in *Synechocystis*.

FIGS. 49K and 49L show the growth, ethanol production of *Synechocystis* 6803 pVZ321b-PpetE-PDC/ADH. Cultures were grown on a shaker in Erlenmeyer flasks with BG11 in continuous light. A pre-culture (1× copper) was divided into 2 sub-cultures (start $OD_{750nm}$=3) with different concentrations of copper (without and 5× Cu).

The crhC-promoter (cold shock induced RNA helicase) was amplified from the genome of *Anabaena* PCC7120, since the chrC-gene from *Synechocystis* seems to be not regulated by the temperature or alternatively exhibit no induction by cold-shock. The Pdc enzyme expression level of the corresponding mutants is relatively low, also when induced by cold-chock. But at least a 3-fold increase in Pdc expression, verified by Western blot analysis, and also an elevated ethanol formation was detectable if the culture was grown at 20° C. (compared to reference culture at 28° C.). Although the crhC-promoter works in general and seems to be adjustable by temperature, this promoter allows only low expression level of ethanologenic enzymes in *Synechocystis*. However for *Anabaena* it was shown that the crhC-promoter works well. Therefore it might be possible that the crhC-promoter works more efficient by using other cyanobacterial species.

FIG. 49M shows the ethanol production of *Synechocystis* 6803 pVZ321b-PcrhC-PDC/ADH. Cultures were grown on a shaker in Erlenmeyer flasks in BG11 under continuous light conditions at 20° C. and 28° C.

Further multi-stress responsible promoters, the htpG-promoter (heat shock protein 90), the hspA-promoter (small heat shock protein A), the clpB1-promoter (clp protease, HSP100) and the hliB-promoter (high-light inducible protein B, HLIP) were analyzed in order to test their suitability for over-expression of ethanologenic ORFs in *Synechocystis* 6803.

All four mutants showed different degrees in growth retardation and yellow pigmentation if grown on a plate. Strongest yellow pigmentation and most slowly growth were observed for the mutants with the hspA-promoter, followed by the htpG, the hliB and the clpB1-promoter.

The growth experiment revealed that the mutant with the hspA-promoter was most productive till the 10$^{th}$ day concerning the ethanol formation, but grows more slowly compared to the three other mutants (FIGS. 49N and 49O). But after 10 days of cultivation the ethanol accumulation decreases compared to mutants with the htpG- and the hliB-promoter which show a comparable ethanol accumulation.

FIGS. 49N and 49O show the growth, ethanol production and productivity per growth of *Synechocystis* 6803 pVZ321b-PhspA-PDC, pVZ321b-PhtpG-PDC, pVZ321b-PhliB-PDC and pVZ321b-PclpB1-PDC. Cultures were grown in a culture vessel in BG11 in continuous light, bubbled with $CO_2$ enriched air (0.5%).

If for these four mutants the ethanol production is normalized to the culture growth the first observation or rather the first assumption about the strength of each promoter (different degree of yellow pigmentation and growth retardation indicates) can be clearly confirmed. The hspA-promoter seems to be most active in this set of multi-stress responsible promoters. The htpG- and the hliB-promoter exhibit a quite similar expression level, but the expression level of hliB-promoter can be additional elevated by increasing the light intensity. The clpB1-promoter exhibit the lowest expression in this selection of promoters, probably too low for commercial application. Further tests are necessary to elucidate the full performance of these kind of promoters, since no stress conditions were tested which might increase the observed expression level additionally. It is noteworthy that cultivation of the mutant with the hspA-promoter revealed production rates of about 0.015% (v/v) ethanol per day in continuous light and about 0.01% (v/v) ethanol in day/night cycles (both for about 2 weeks) that is comparable to the maximal expression level of mutants with the isiA- and petJ-promoter.

Multi-stress inducible promoters are especially of interest because of their potential to respond to ethanol or side effects the ethanol production (probably indirect). In this case some kind of auto-induction or self-enhancement is imaginable, which might be advantageous, e.g. in combination with other promoters.

It can be summarized that the genome of *Synechocystis* contains several promoters useful for the ethanol production process. Well working examples are the isiA-, petJ- and the petE-promoter as well as the nirA-promoter, which are all adjustable by the nutrient status. Furthermore the hspA and the htpG as well as the hliB-promoter appear to be suited for the production process.

We claim:

1. A genetically modified cyanobacterial host cell which produces ethanol ($C_2H_5OH$) and oxygen ($O_2$) comprising:
   (a) a first genetic modification which comprises transforming the cyanobacterial host cell with a nucleic acid encoding a protein with ribulose-1,5-bisphosphate carboxylase/oxygenase (RubisCO) activity; and
   (b) a second genetic modification which comprises transforming the cyanobacterial host cell with a nucleic acid encoding a pyruvate decarboxylase enzyme associated with the formation of ethanol.

2. The genetically modified cyanobacterial host cell of claim 1 wherein the production of $C_2H_5OH$ per $O_2$ produced with the first and second modifications is higher than without the first genetic modification but with the second modification.

3. The genetically modified cyanobacterial host cell of claim 1 wherein the protein with RubisCO activity comprises a large subunit, a small subunit and a RubisCO chaperonin.

4. A genetically modified cyanobacterial host cell which produces $C_2H_5OH$ and $O_2$ comprising:
   (a) a first genetic modification which comprises transforming the cyanobacterial host cell with a nucleic acid encoding a protein with RubisCO activity; and
   (b) a second genetic modification which comprises transforming the cyanobacterial host cell with an alcohol dehydrogenase gene and a pyruvate decarboxylase gene.

5. A genetically modified cyanobacterial host cell which produces ethanol and oxygen comprising:
   (a) at least one first genetic modification which results in an increase in the level of a first metabolic intermediate in the genetically modified cyanobacterial host cell compared to the level of said first metabolic intermediate in the corresponding cyanobacterial host cell lacking the first genetic modification, wherein said first genetic modification comprises transforming the cyanobacterial host cell with a nucleic acid encoding a protein with RubisCO activity; and
   (b) at least a second genetic modification which comprises transforming the cyanobacterial host cell with a nucleic acid encoding a pyruvate decarboxylase enzyme for the formation of ethanol.

6. The genetically modified cyanobacterial host cell of claim 5 wherein the first metabolic intermediate is pyruvate.

7. The genetically modified cyanobacterial host cell of claim 1, wherein:
   (a) the nucleic acid encoding the protein with RubisCO activity encodes a small subunit and a large subunit of a RubisCO;
   (b) the nucleic acid encoding the protein with RubisCO activity encodes a small subunit, a large subunit and a chaperonin of a RubisCO; or
   (c) the cyanobacterial host cell has been transformed with a conjugative, self-replicating pVZ plasmid containing a RubisCO (rbcLXS) operon and a *Z. mobilis* pyruvate decarboxylase gene.

8. The genetically modified cyanobacterial host cell of claim 1, wherein the protein with RubisCO activity is from a cyanobacterial cell.

9. The genetically modified cyanobacterial host cell of claim 8, wherein the nucleic acid encoding the protein with RubisCO activity has at least 95% sequence identity to the *Synechocystis* rbcL-rbcX-rbcS operon of SEQ ID NO: 65.

10. The genetically modified cyanobacterial host cell of claim 9, wherein the rbcL gene encodes a RubisCO large subunit having an amino acid sequence at least 95% identical to SEQ ID NO: 66; the rbcS gene encodes a RubisCO small subunit having an amino acid sequence at least 95% identical to SEQ ID NO: 68; and the rbcX gene encodes a RubisCO chaperonin having an amino acid sequence at least 95% identical to SEQ ID NO: 67.

11. A method for the production of ethanol comprising:
   (a) providing the genetically modified cyanobacterial host cell of claim 1;
   (b) growing the genetically modified cyanobacterial host cell of (a) under conditions whereby ethanol is produced; and
   (c) isolating the ethanol produced in step (b).

12. A method for the production of ethanol comprising:
   (a) providing the genetically modified cyanobacterial host cell of claim 4;
   (b) growing the genetically modified cyanobacterial host cell of (a) under conditions whereby ethanol is produced; and
   (c) isolating the ethanol produced in step (b).

* * * * *